US012661410B2

(12) United States Patent
Henderson et al.

(10) Patent No.: US 12,661,410 B2
(45) Date of Patent: Jun. 23, 2026

(54) COMPOUNDS FOR TARGETED DEGRADATION OF RET

(71) Applicant: C4 Therapeutics, Inc., Watertown, MA (US)

(72) Inventors: James A. Henderson, Weston, MA (US); Christopher G. Nasveschuk, Stoneham, MA (US); Kiel Lazarski, Boston, MA (US); Victoria Garza, San Antonio, TX (US); Moses Moustakim, Brighton, MA (US); Jae Young Ahn, Somerville, MA (US); Gesine Kerstin Veits, Somerville, MA (US); Morgan Welzel O'Shea, Walthan, MA (US); Ryan E. Michael, Erie, CO (US); Jeremy L. Yap, Sudbury, MA (US); Yanke Liang, Belmont, MA (US); Andrew Charles Good, Watertown, MS (US); Mark E. Fitzgerald, Newton, MA (US); Robert T. Yu, Arlington, VA (US)

(73) Assignee: C4 Therapeutlcs, Inc., Watertown, MA (US)

( * ) Notice: Subject to any disclaimer, the term of this patent is extended or adjusted under 35 U.S.C. 154(b) by 669 days.

(21) Appl. No.: 18/105,735

(22) Filed: Feb. 3, 2023

(65) Prior Publication Data

US 2023/0233692 A1 Jul. 27, 2023

Related U.S. Application Data

(63) Continuation of application No. PCT/US2021/044838, filed on Aug. 5, 2021.

(60) Provisional application No. 63/061,741, filed on Aug. 5, 2020, provisional application No. 63/136,586, filed on Jan. 12, 2021.

(51) Int. Cl.
*A61K 47/55* (2017.01)

(52) U.S. Cl.
CPC .................................... *A61K 47/55* (2017.08)

(58) Field of Classification Search
CPC ....... A61K 47/55; A61P 35/00; C07D 471/04; C07D 487/04; C07D 519/00
See application file for complete search history.

(56) References Cited

U.S. PATENT DOCUMENTS

| | | | |
|---|---|---|---|
| 5,635,517 | A | 6/1997 | Muller et al. |
| 6,306,663 | B1 | 10/2001 | Kenten et al. |
| 8,008,332 | B2 | 8/2011 | Cao et al. |
| 10,023,570 | B2 | 7/2018 | Andrews et al. |
| 10,112,942 | B2 | 10/2018 | Andrews et al. |
| 10,137,124 | B2 | 11/2018 | Andrews et al. |
| 10,138,243 | B2 | 11/2018 | Andrews et al. |
| 10,144,734 | B2 | 12/2018 | Andrews et al. |
| 10,172,845 | B2 | 1/2019 | Andrews et al. |
| 10,172,851 | B2 | 1/2019 | Andrews et al. |
| 10,174,027 | B2 | 1/2019 | Andrews et al. |
| 10,174,028 | B2 | 1/2019 | Andrews et al. |
| 10,441,581 | B2 | 10/2019 | Andrews et al. |
| 10,555,944 | B2 | 2/2020 | Andrews et al. |
| 2014/0302523 | A1 | 10/2014 | Crews et al. |
| 2014/0356322 | A1 | 12/2014 | Crews et al. |
| 2015/0291562 | A1 | 10/2015 | Crew et al. |
| 2016/0022642 | A1 | 1/2016 | Crews et al. |
| 2016/0045607 | A1 | 2/2016 | Crew et al. |
| 2016/0046661 | A1 | 2/2016 | Gray et al. |
| 2016/0058872 | A1 | 3/2016 | Crew et al. |
| 2016/0176916 | A1 | 6/2016 | Bradner et al. |
| 2016/0272639 | A1 | 9/2016 | Crew et al. |
| 2018/0085465 | A1 | 3/2018 | Bradner et al. |
| 2019/0106438 | A1 | 4/2019 | Eary et al. |
| 2019/0262322 | A1 | 8/2019 | Reynolds et al. |

FOREIGN PATENT DOCUMENTS

| | | | |
|---|---|---|---|
| WO | WO 2016/065139 | A1 | 4/2016 |
| WO | WO 2016/105518 | A1 | 6/2016 |
| WO | WO 2016/197032 | A1 | 12/2016 |
| WO | WO 2017/011776 | A1 | 1/2017 |
| WO | WO 2017/024317 | A2 | 2/2017 |

(Continued)

OTHER PUBLICATIONS

U.S. Pat. No. 10,646,575, B2, U.S. Appl. No. 16/186,339, Phillips et al., May 12, 2020.

(Continued)

*Primary Examiner* — Jeffrey H Murray
*Assistant Examiner* — Daniel John Burkett
(74) *Attorney, Agent, or Firm* — Knowles Intellectual Property Strategies, LLC

(57) ABSTRACT

Compounds of Formula (I) which act as protein degradation inducing moieties for proto-oncogene tyrosine-protein kinase receptor (RET), which may be either wild type RET or a mutant form of RET, are described. The compounds can be used to treat a disorder mediated by RET protein, for example a cancer or a tumor.

(I)

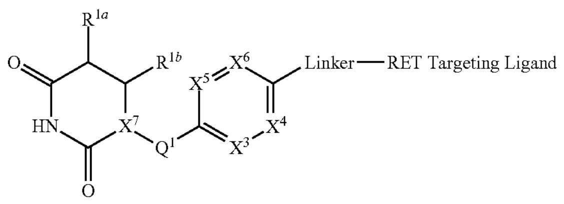

27 Claims, 13 Drawing Sheets

(56) References Cited

FOREIGN PATENT DOCUMENTS

| | | | |
|---|---|---|---|
| WO | WO 2017/079267 | A1 | 5/2017 |
| WO | WO 2017/161119 | A1 | 9/2017 |
| WO | WO 2017/197051 | A1 | 11/2017 |
| WO | WO 2017/197055 | A1 | 11/2017 |
| WO | WO 2017/201069 | A1 | 11/2017 |
| WO | WO 2018/071447 | A1 | 4/2018 |
| WO | WO 2018/118947 | A1 | 6/2018 |
| WO | WO 2018/119357 | A1 | 6/2018 |
| WO | WO 2018/119441 | A1 | 6/2018 |
| WO | WO 2018/119448 | A1 | 6/2018 |
| WO | WO 2018/136661 | A1 | 7/2018 |
| WO | WO 2018/144649 | A1 | 8/2018 |
| WO | WO 2018/237026 | A1 | 12/2018 |
| WO | WO 2019/060742 | A1 | 3/2019 |
| WO | WO 2019/140387 | A1 | 7/2019 |
| WO | WO 2019/143977 | A1 | 7/2019 |
| WO | WO 2019/143991 | A1 | 7/2019 |
| WO | WO 2019/143994 | A1 | 7/2019 |
| WO | WO 2020/033838 | A2 | 2/2020 |
| WO | WO 2020/055672 | A1 | 3/2020 |
| WO | WO 2020/114487 | A1 | 6/2020 |
| WO | WO 2020/248972 | A1 | 12/2020 |

OTHER PUBLICATIONS

U.S. Pat. No. 10,660,968, B2, U.S. Appl. No. 16/186,334, Phillips et al., May 26, 2020.
U.S. Pat. No. 10,849,982, B2, U.S. Appl. No. 16/186,341, Phillips et al., Dec. 1, 2020.
U.S. Pat. No. 10,905,768, B1, U.S. Appl. No. 16/872,225, Phillips et al., Feb. 2, 2021.
U.S. Pat. No. 11,185,592, B2, U.S. Appl. No. 16/882,236, Phillips et al., Nov. 30, 2021.
U.S. Pat. No. 11,254,672, B2, U.S. Appl. No. 16/809,325, Norcross et al., Feb. 22, 2022.
U.S. Pat. No. 11,401,256, B2, U.S. Appl. No. 16/809,345, Norcross et al., Aug. 2, 2022.
U.S. Pat. No. 11,407,732, B1, U.S. Appl. No. 17/498,617, Henderson et al., Aug. 9, 2022.
U.S. Pat. No. 11,459,335, B2, U.S. Appl. No. 16/721,650, Phillips et al., Oct. 4, 2022.
U.S. Pat. No. 11,524,949, B2, U.S. Appl. No. 16/874,475, Phillips et al., Dec. 13, 2022.
U.S. Pat. No. 11,584,748, B2, U.S. Appl. No. 17/072,896, Nasveschuk et al., Feb. 21, 2023.
U.S. Pat. No. 11,623,929, B2, U.S. Appl. No. 17/103,621, Nasveschuk et al., Apr. 11, 2023.
U.S. Pat. No. 11,673,902, B2, U.S. Appl. No. 17/843,769, Nasveschuk et al., Jun. 13, 2023.
U.S. Pat. No. 11,691,972, B2, U.S. Appl. No. 17/541,035, Nasveschuk et al., Jul. 4, 2023.
U.S. Pat. No. 11,753,397, B2, U.S. Appl. No. 17/031,550, Henderson et al., Sep. 12, 2023.
U.S. Pat. No. 11,787,802, B2, U.S. Appl. No. 17/576,582, Norcross et al., Oct. 17, 2023.
U.S. Pat. No. 11,802,131, B2, U.S. Appl. No. 16/809,336, Norcross et al., Oct. 31, 2023.
US, 2021/0198256, A1, U.S. Appl. No. 17/192,634, Nasveschuk et al., Jul. 1, 2021.
US, 2022/0313827, A1, U.S. Appl. No. 17/121,389, Phillips et al., Oct. 6, 2022.
US, 2022/0313826, A1, U.S. Appl. No. 17/107,781, Phillips et al., Oct. 6, 2022.
US, 2022/0372016, A1, U.S. Appl. No. 17/351,935, Phillips et al., Nov. 24, 2022.
US, 2023/0002367, A1, U.S. Appl. No. 17/771,127, Gaufreteau et al., Jan. 5, 2023.
US, 2023/0014124, A1, U.S. Appl. No. 17/164,446, Phillips et al., Jan. 19, 2023.
US, 2023/0019060, A1, U.S. Appl. No. 17/465,583, Nasveschuk et al., Jan. 19, 2023.
US, 2023/0024096, A1, U.S. Appl. No. 17/771,204, Duplessis et al., Jan. 26, 2023.
US, 2023/0060334, A1, U.S. Appl. No. 17/901,775, Nasveschuk et al., Mar. 2, 2023.
US, 2023/0082430, A1, U.S. Appl. No. 17/723,199, Henderson et al., Mar. 16, 2023.
US, 2023/0095223, A1, U.S. Appl. No. 17/524,558, Phillips et al., Mar. 30, 2023.
US, 2023/0145336, A1, U.S. Appl. No. 18/084,380, Nasveschuk et al., May 11, 2023.
US, 2023/0192643, A1, U.S. Appl. No. 17/878,753, Norcross et al., Jun. 22, 2023.
US, 2023/0190760, A1, U.S. Appl. No. 18/106,893, Proia et al., Jun. 22, 2023.
US, 2023/0279023, A1, U.S. Appl. No. 17/959,144, Phillips et al., Sep. 7, 2023.
US, 2023/0339902, A1, U.S. Appl. No. 18/134,985, Nasveschuk et al., Oct. 26, 2023.
US, 2023/0357180, A1, U.S. Appl. No. 18/079,815, Phillips et al., Nov. 9, 2023.
US, 2023/0372496, A1, U.S. Appl. No. 18/134,971, Nasveschuk et al., Nov. 23, 2023.
US, 2023/0416251, A1, U.S. Appl. No. 18/100,992, Nasveschuk et al., Dec. 28, 2023.
US, 2024/0018156, A1, U.S. Appl. No. 18/117,978, Nasveschuk et al., Jan. 18, 2024.
US, 2024/0018118, A1, U.S. Appl. No. 18/134,990, Nasveschuk et al., Jan. 18, 2024.
US, 2024/0051953, A1, U.S. Appl. No. 17/965,569, Nasveschuk et al., Feb. 15, 2024.
U.S. Appl. No. 18/144,800, Nasveschuk et al., May 8, 2023.
U.S. Appl. No. 18/240,231, Henderson et al., Aug. 30, 2023.
U.S. Appl. No. 18/370,186, Norcross et al., Sep. 19, 2023.
U.S. Appl. No. 18/385,277, Norcross et al., Oct. 30, 2023.
U.S. Appl. No. 18/516,589, Nasveschuk et al., Nov. 21, 2023.
U.S. Appl. No. 18/534,395, Nasveschuk et al., Dec. 8, 2023.
Bartlett, et al. "The evolution of thalidomide and its IMiD derivatives as anticancer agents," Nat Rev Cancer, Apr. 2004, 4(4):314-322.
Berndsen et al. "New insights into ubiquitin E3 ligase mechanism," Nat. Struct. Mol. Biol. Nature America, Inc. Apr. 2014, 21:4, 301-307.
Bondeson et al. "Catalytic in vivo protein knockdown by small-molecule PROTACs" Nature Chemical Biology Jun. 10, 2015, 11:611-617.
C4 Therapeutics Presentation Phillips—"Small Molecule Driven Targeted Protein Degradation", ChemBio in the Hub 47, Cambridge, MA, 47 pages (Oct. 22, 2018).
C4 Therapeutics Presentation Fisher—"Targeted Protein Degradation", Targeted Protein Degradation Summit, Boston, MA, 39 pages, Oct. 24-25, 2018.
C4 Therapeutics Presentation Fisher—"Degrader Drugs: From cellular activity to in vivo pharmacology Discovery on Target," Boston, MA, 21 pages, Sep. 18, 2019.
C4 Therapeutics Presentation Nasveschuk—"Degrader Drug Space: What Rules?" HT-ADME Conference Cambridge, MA, Jun. 20, 2019; 20 pages.
Chamberlain et al. "Structure of the human cereblon-DDB1-lenalidomide complex reveals basis for responsiveness to thalidomide analogs" Nature Structural and Molecule Biology, Nature American, Inc., Sep. 2014, 21(9):803-809.
Corson et al. "Design and applications of bifunctional small molecules: Why two heads are better than one" ACS Chemical Biology Nov. 21, 2008, 3(11): 677-692.
Fischer et al. "Structure of the DDB1-CRBN E3 ubiquitin ligase in complex with thalidomide" Nature Aug. 7, 2014, Macmillan Publisher Limited, 512:49-53.
Fischer et al. "The Molecular Basis of $CRL4^{DDB2/CSA}$ Ubiquitin Ligase Architecture, Targeting, and Activation," Cell Nov. 23, 2011, 147:1024-1039.

(56) References Cited

OTHER PUBLICATIONS

Hatcher et al. “Development of highly potent and selective steroidal inhibitors and degraders of CDK8” ACS Med. Chem. Lett., Mar. 18, 2018; 9(6): 540-545. doi: 10.1021/acsmedchemlett.8b00011.
Mologni et al. “RET kinase inhibitors: a review of recent patents (2012-2015)” Expert Opinion on therapeutic Patents, Sep. 26, 2016, vol. 27, 2017, pp. 91-99.
PubChem SID 151451671; Modify date: Jun. 2, 2019.
International Search Report and Written Opinion for PCT/US2021/044838, filed Aug. 5, 2021.

COMPOUNDS FOR TARGETED DEGRADATION OF RET

CROSS-REFERENCE TO RELATED APPLICATIONS

This application is a continuation of International Application No. PCT/US2021/044838, filed Aug. 5, 2021, which claims the benefit of U.S. Provisional Application No. 63/061,741, which was filed on Aug. 5, 2020, and U.S. Provisional Application No. 63/136,586, which was filed on Jan. 12, 2021. The entirety of each of these applications is hereby incorporated by reference herein for all purposes.

FIELD OF THE INVENTION

This invention provides rearranged during transfection (RET) proto-oncogene tyrosine-protein kinase receptor degrading compounds for therapeutic applications as described further herein.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of disorders including cancer and others.

The drug thalidomide and its analogs lenalidomide and pomalidomide have garnered interest as immunomodulators and antineoplastics, especially in multiple myeloma (Kim S A et. al., “A novel cereblon modulator for targeted protein degradation”, Eur J Med Chem. 2019 Mar. 15; 166:65-74; R. Verma et. al., “Identification of a Cereblon-Independent Protein Degradation Pathway in Residual Myeloma Cells Treated with Immunomodulatory Drugs” Blood (2015) 126 (23): 913. Liu Y, et al., “A novel effect of thalidomide and its analogs: suppression of cereblon ubiquitination enhances ubiquitin ligase function” FASEB J. 2015 December; 29(12):4829-39; Martiniani, R. et al., “Biological activity of lenalidomide and its underlying therapeutic effects in multiple myeloma” Adv Hematol, 2012, 2012:842945; and Terpos, E. et al., “Pomalidomide: a novel drug to treat relapsed and refractory multiple myeloma” Oncotargets and Therapy, 2013, 6:531).

There are also clinical and preclinical studies with thalidomide and its analogs related to the treatment of renal cell carcinoma, glioblastoma, prostate cancer, melanoma, colorectal cancer, crohns disease, rheumatoid arthritis, Behcet’s syndrome, breast cancer, head and neck cancer, ovarian cancer, chronic heart failure, graft-versus-host disease, and tuberculous meningitis.

Thalidomide and its analogues have been found to bind to the ubiquitin ligase cereblon and redirect its ubiquitination activity (see Ito, T. et al. “Identification of a primary target of thalidomide teratogenicity” Science, 2010, 327:1345). Cereblon forms part of an E3 ubiquitin ligase complex which interacts with damaged DNA binding protein 1, forming an E3 ubiquitin ligase complex with Cullin 4 and the E2-binding protein ROC1 (known as RBX1) where it functions as a substrate receptor to select proteins for ubiquitination. The binding of lenalidomide to cereblon facilitates subsequent binding of cereblon to Ikaros and Aiolos, leading to their ubiquitination and degradation by the proteasome (see Lu, G. et al. “The myeloma drug lenalidomide promotes the cereblon-dependent destruction of Ikaros proteins” Science, 2014, 343:305-309; Kronke, J. et al. “Lenalidomide causes selective degradation of IKZF1 and IKZF3 in multiple myeloma cells” Science, 2014, 343:301-305).

Celgene has also disclosed imides for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; 9,101,622, 9,587,281, 9,857,359, and 10,092,555.

The disclosure that thalidomide binds to the cereblon E3 ubiquitin ligase led to research to investigate incorporating thalidomide and certain derivatives into compounds for the targeted destruction of proteins. This research led to a patent application filed by Proteinex, Inc. in February 1999 that issued as U.S. Pat. No. 6,306,663 claiming a method of generating a compound for activating the ubiquitination of a Target Protein which comprises covalently linking a Target Protein binding element able to bind specifically to the Target Protein via a ubiquitination recognition element. Proteinex described that the invention can be used to control protein levels in eukaryotes. While the ’663 patent may have been based on the first patent application to describe the high level concept of how to manipulate the UPP system to degrade selected proteins in vivo, the patent did not provide sufficient detail to allow persons of skill to easily construct the range of proposed compounds. For example, for the 25 ubiquitination recognition elements, the skilled person was told among other things to use standard methods for drug discovery and screen for appropriate small molecules that would bind to the ligase. Proteinex also emphasized the use of peptides as ubiquitination recognition elements, which can pose significant difficulties for oral drug administration.

Patent applications filed by C4 Therapeutics, Inc., that describe compounds capable of binding to an E3 ubiquitin ligase and a target protein for degradation include: WO/2021/127561 titled “Isoindolinone And Indazole Compounds For The Degradation Of EGFR”; WO/2021/086785 titled “Bifunctional Compounds”; WO/2021/083949 titled “Bifunctional Compounds for the Treatment of Cancer”; WO/2020/210630 titled “Tricyclic Degraders of Ikaros and Aiolos”; WO/2020/181232 titled “Heterocyclic Compounds for Medical Treatment”; WO/2020/132561 titled “Targeted Protein Degradation”; WO/2019/236483 titled “Spirocyclic Compounds”; WO2020/051235 titled “Compounds for the degradation of BRD9 or MTH1”; WO/2019/191112 titled “Cereblon binders for the Degradation of Ikaros”; WO/2019/204354 titled “Spirocyclic Compounds”; WO/2019/099868 titled “Degraders and Degrons for Targeted Protein Degradation”; WO/2018/237026 titled “N/O-Linked Degrons and Degronimers for Protein Degradation”; WO 2017/197051 titled “Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 titled "C3-Carbon Linked Glutarimide Degronimers for Target Protein Degradation"; and WO 2017/197056 titled "Bromodomain Targeting Degronimers for Target Protein Degradation."

Other patent applications that describe protein degrading compounds include: WO 2015/160845; WO 2016/105518; WO 2016/118666; WO 2016/149668; WO 2016/197032; WO 2016/197114; WO 2017/007612; WO 2017/011371; WO 2017/011590; WO 2017/030814; WO 2017/046036; WO 2017/176708; WO 2017/176957; WO 2017/180417; WO 2018/053354; WO 2018/071606; WO 2018/102067; WO 2018/102725; WO 2018/118598; WO 2018/119357; WO 2018/119441; WO 2018/119448; WO 2018/140809; WO2018/144649; WO 2018/119448; WO 2018/226542; WO 2019/023553; WO/2019/195201; WO2019/199816; WO/2019/099926; WO 2019/195609; WO 2020/041331; WO 2020/051564; and WO 2020/023851.

The rearranged during transfection (RET) proto-oncogene tyrosine-protein kinase receptor, a cell surface tyrosine kinase receptor, is widely known for its essential role in cell survival, differentiation, proliferation, migration and chemotaxis. RET germline missense and somatic mutations cause medullary thyroid cancer (MTC) and neuroendocrine tumors, whereas RET fusion proteins, overexpression, and copy number gains are present in a broad spectrum of additional cancers such as papillary thyroid cancer, pancreatic cancer, melanoma, leukemia, lung adenocarcinomas, and breast cancer. (Liu Xuan et al., "RET kinase alterations in targeted cancer therapy", Cancer Drug Resist, 2020; and Mulligan L M., "RET revisited: expanding the oncogenic portfolio", Nat Rev Cancer., 2014, 14(3), 173-186).

RET forms a complex with its natural ligands, a family of glial-derived neurotrophic factors, and with glycosyl phosphatidylinositol-linked co-receptors, resulting in dimerization and subsequent activation of the kinase domain through the formation of a multimeric signaling complex consisting of RET's soluble ligand glial derived neurotrophic factor (GDNF) and a membrane-bound coreceptor (GDNF family receptor α1). This complex causes autophosphorylation of tyrosine residues. As a result of this mechanism, glial family ligand mediated activation of wildtype RET is an increasingly recognized mechanism related to tumor growth and dissemination of a much broader group of cancers. (Mulligan L M., "GDNF and the RET Receptor in Cancer: New Insights and Therapeutic Potential", Front. Physiol., 2019, 9(1873), 1-13; and Airaksinen M S, and Saarma M., "The GDNF family: signaling, biological functions and therapeutic value", Nat Rev Neurosci., 2002, 3(5), 383-94).

There are multiple protein isoforms of RET including RET9, RET51 and RET43 each of which differs in the lengths of carboxyl-terminal tails and their ability to bind SHC, GRB2, c-CBL, and SHANK3. Each RET isoform has a unique C-terminal tail sequence that recruits distinct protein complexes to mediate signals, thereby exhibiting different abilities to recruit E3 ubiquitin ligases to their unique C-termini. (Lorenzo M J, et al., "RET alternative splicing influences the interaction of activated RET with the SH2 and PTB domains of Shc, and the SH2 domain of Grb2", Oncogene, 1997, 14, 763-771). Studies on acute myeloid leukemia (AML) have shown that AML subtypes are dependent on expression of the RET receptor tyrosine kinase (RTK), and that depletion of RET by shRNA knockdown or CRISPR/Cas9-mediated knockout leads to cell cycle arrest in the G0/G1 phase, increased apoptosis, and reduced clonogenic activity. Analysis of known RET ligand/co-receptor pairs (GDNF/GFRA1, NRTN/GFRA2, ARTN/GFRA3, PSPN/GFRA4) by quantitative real-time PCR and shRNA knockdown indicates that RET signaling is facilitated mainly through NTRN/GFRA2 or ARTN/GFRA3. (Rudat S., et al., "The RET Receptor Tyrosine Kinase Promotes Acute Myeloid Leukemia through Protection of FLT3-ITD Mutants from Autophagic Degradation", Blood, 2016, 128(22), 2849). The RET fusions genes are mutually exclusive with other known drivers in LAD (e.g. KRAS, epidermal growth factor receptor (EGFR), EML4-anaplastic lymphoma kinase (ALK)), further supporting a role for RET as a unique driver of malignancy in these tumors.

Selpercatinib (formerly LOXO-292) is a clinically approved highly selective, small molecule RET tyrosine kinase inhibitor with nanomolar potency against diverse RET alterations. Patent applications and publications describing selpercatinib include: US20190106438; US20190262322; US20180133222 LOXO-292 Reins In RET-Driven Tumors, Cancer discovery, 2018, 8(8), 904-905; Markham, Anthony, "Selpercatinib: First Approval", Drugs (2020), 80(11), 1119-1124; Brandhuber B B, et al, "ENA-0490 The development of LOXO-292, a potent, KDR/VEGFR$^2$-sparing RET kinase inhibitor for treating patients with RET-dependent cancers", AACR-NCI-EORTC International Conference on Molecular Targets and Cancer Therapeutics, Munich, Germany, Nov. 29-Dec. 2, 2016; and "Selective RET kinase inhibition for patients with RET-altered cancers," Ann Oncol., 2018, 29(8), 1869-1876).

The academic and clinical interest in RET has led to the identification of several RET mutations that are clinically relevant including RET G810R, RET G810S, and RET G810C. (Solomon, et al., "RET Solvent Front Mutations Mediated Acquired Resistance to Selective RET Inhibition in RET-driven malignancies", J Thoracic Oncolog., 2020). Treatment of patients with non small cell lung cancer selpercatinib has been shown to cause RET mutations that infer resistances including the RET G810R, RET G810S, and RET G810C mutations.

Other approved tyrosine kinase inhibitors such as sunitinib, sorafenib, ponatinib and lenvatinib have also shown some RET activity in pre-clinical trials and are currently under investigation in numerous phase II clinical trials for treatment of RET fusion positive lung adenocarcinoma (LAD). (Song M., "Progress in Discovery of KIF5B-RET Kinase Inhibitors for the Treatment of Non-Small-Cell Lung Cancer", J Med Chem., 2015, 58(9), 3672-3681; Watson A J., et al., "Identification of selective inhibitors of RET and comparison with current clinical candidates through development and validation of a robust screening cascade", F1000Research 2016, 5:1005).

Examples of RET inhibitor patent applications include U.S. Pat. Nos. 10,138,243; 10,172,851; 10,441,581; 10,174,028; 10,137,124; 10,172,845; 10,555,944; 10,023,570; 10,112,942; 10,144,734; 10,174,027; WO 2017/011776; WO 2018/136661; WO2018/071447; WO/2018/136663; WO 2019/126121; WO 2019/143991; WO 2019/143994; WO 2019/143977; and WO 2020/055672.

Despite these efforts, there remains a need for new RET modulators to treat disorders mediated by RET in hosts in need thereof, including humans.

SUMMARY OF THE INVENTION

Compounds and their uses and manufacture are provided that degrade the proto-oncogene tyrosine-protein kinase receptor (RET) via the ubiquitin proteasome pathway (UPP). The present invention provides compounds of Formula I, Formula II, Formula III, Formula IV, Formula V, Formula VI, and Formula VII or a pharmaceutically acceptable salt thereof that include a Targeting Ligand that binds to RET, an E3 Ligase binding portion (typically via a cereblon subunit), and a Linker that covalently links the Targeting Ligand to the E3 Ligase binding portion. In certain embodiments the Targeting Ligand is a moiety of B of the Formulas described below, the Linker is a moiety L1, and the remainder of the molecule is the E3 Ligase binding portion.

RET is widely known for its essential role in cell survival, differentiation, proliferation, migration and chemotaxis. Thus, by degrading RET the compounds of the present invention can be used to treat RET mediated disorders such as Hirschsprung disease, medullary thyroid cancer (MTC), thyroid carcinoma, familial medullary thyroid carcinoma, multiple endocrine neoplasia, multiple endocrine neoplasia type 2 (MEN-2, MEN-2A, MEN-2B), neuroendocrine tumors, central nervous system tumors, central hypoventilation syndrome, renal agenesis, pheochromocytoma and parathyroid hyperplasia. In another embodiment, a compound of the present invention is used to treat a disorder mediated by RET fusion proteins, overexpression, or copy number gains, such as papillary thyroid cancer, pancreatic cancer, melanoma, leukemia, acute myeloid leukemia (AML), chronic myelomonocytic leukemia, lung adenocarcinomas, lung cancer, non-small cell lung cancer (NSCLC), nonsyndromic paraganglioma, breast cancer, nonhereditary (sporadic) cancers, colorectal, or a hematologic malignancy.

A compound of the present invention provided herein or its pharmaceutically acceptable salt and/or its pharmaceutically acceptable composition can be used to treat a disorder which is mediated by RET. In some embodiments a method to treat a patient with a disorder mediated by RET is provided that includes administering an effective amount of one or more compounds as described herein, or a pharmaceutically acceptable salt thereof, to the patient, typically a human, optionally in a pharmaceutically acceptable composition.

In certain aspects, the present invention provides a compound of Formula I, Formula II, Formula III, or Formula IV:

(I)

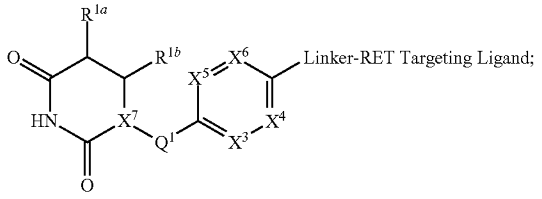

(II)

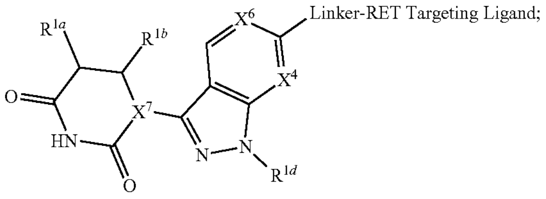

-continued (III)

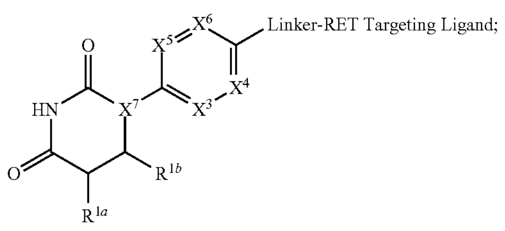

(IV)

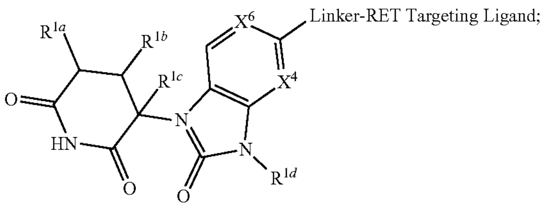

or a pharmaceutically acceptable salt thereof;

wherein $X^3$, $X^4$, $X^5$, and $X^6$ are selected from the group consisting of N, CH and $CR^3$, wherein no more than 3 of $X^3$, $X^4$, $X^5$, and $X^6$ are N;

$X^7$ is N or $CR^{1c}$;

$Q^1$ is —$NR^6$—, —$CH_2$—, or —O—, wherein if $X^7$ is N then $Q^1$ is $CH_2$;

$R^{1a}$, $R^{1b}$, $R^{1c}$, and $R^{1d}$ are each independently hydrogen, $C_1$-$C_4$alkyl, $C_1$-$C_4$haloalkyl, or cycloalkyl; or $R^{1a}$ and $R^{1c}$ are combined to form a 1 or 2 atom bridge, for example

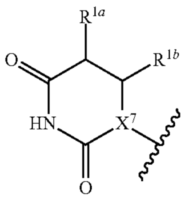

includes

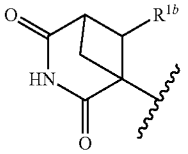 and 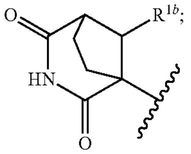;

$R^3$ is independently at each occurrence selected from the group consisting of hydrogen, hydroxyl, alkoxy, $C_1$-$C_4$alkyl, $C_1$-$C_4$haloalkyl, cycloalkyl, fluorine, chlorine, bromine, and iodine;

RET Targeting Ligand is selected from
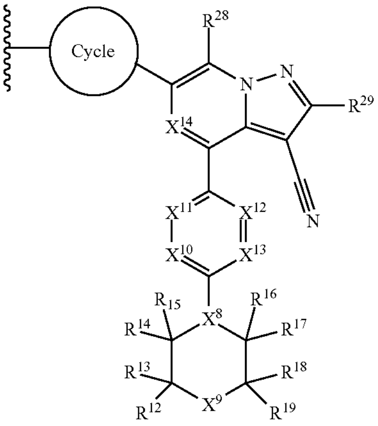
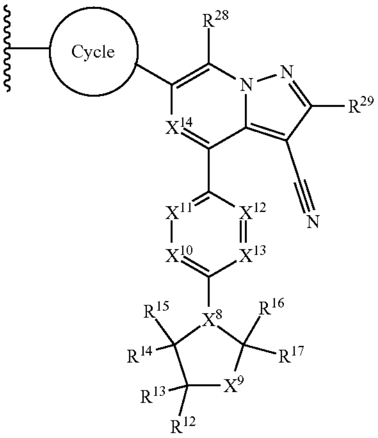
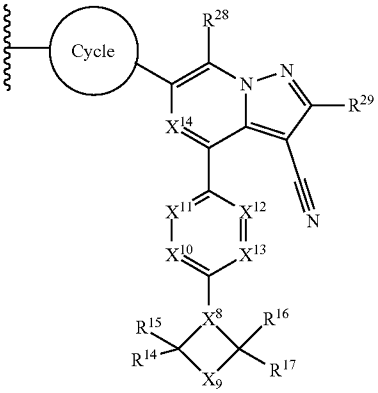
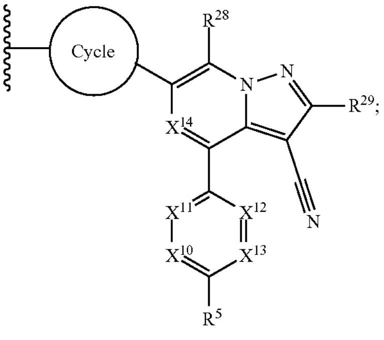
-continued
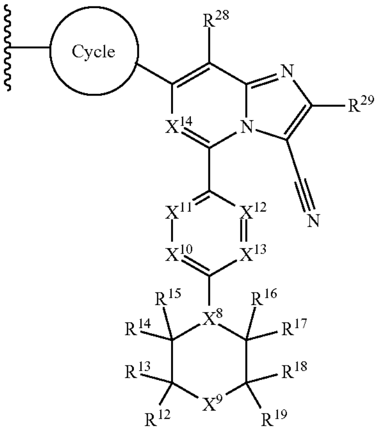
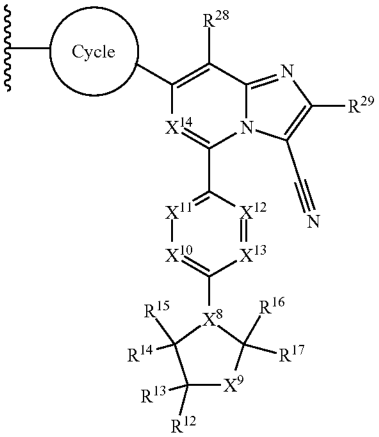
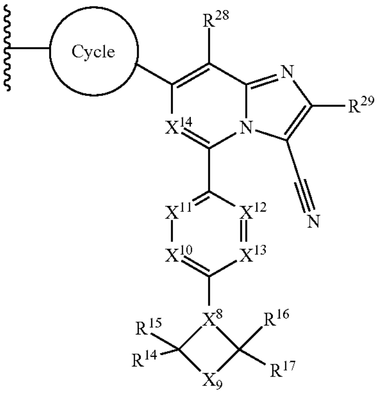
and
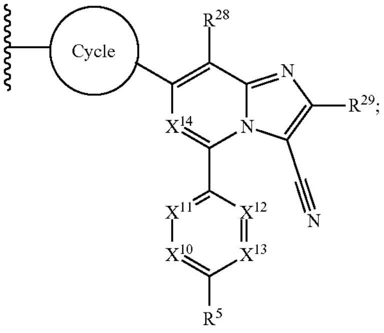

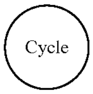

is a heteroaryl, heterocycle, aryl, or cycloalkyl, each of which is optionally substituted with 0, 1, 2, 3, or 4 substituents independently selected from $R^9$, wherein

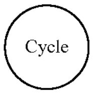

is directly bonded to Linker and to

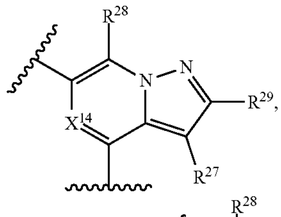,
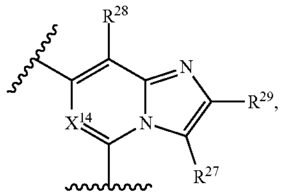,

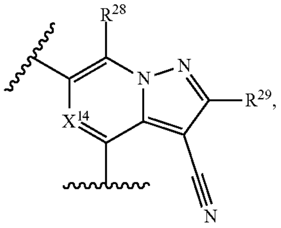, or

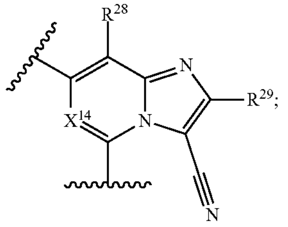; or 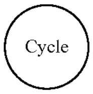

is a heteroaryl, heterocycle, aryl, or cycloalkyl, each of which is optionally substituted with 0, 1, 2, 3, or 4 substituents independently selected from $R^9$, wherein

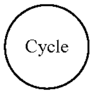

is directly bonded to Linker and to

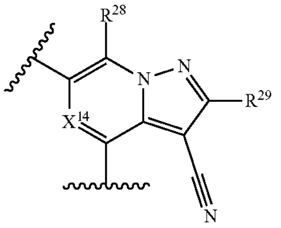 or

-continued

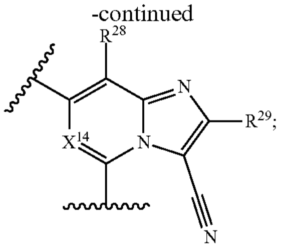;

N or N;

$X^8$ is N or $CR^4$;

$X^9$ is $NR^4$, $CR^4R^{11}$, or O;

$X^{10}$, $X^{11}$, $X^{12}$, and $X^{13}$ are selected from the group consisting of N, CH and CR, wherein no more than 3 of $X^{10}$, $X^{11}$, $X^{12}$, and $X^{13}$ are N;

$X^{14}$ is $CR^{27}$ or N;

each $R^4$ is independently hydrogen, $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, -alkyl-heterocycle, —C(O)$R^5$, -alkyl-C(O)$R^5$, —OC(O)$R^5$, or —$NR^6C(O)R^5$, each of which $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, and -alkyl-heterocycle groups is optionally substituted with 0, 1, 2, or 3 substituents independently selected from $R^8$;

$R^5$ is hydrogen, $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, bicycle, -alkyl-heteroaryl, -alkyl-aryl, -alkyl-heterocycle, —$OR^6$, or —$NR^6R^7$, each of which $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, and -alkyl-heterocycle groups is optionally substituted with 0, 1, 2, or 3 substituents independently selected from $R^9$;

$R^6$ and $R^7$ are independently selected at each instance from the group consisting of hydrogen, $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, and -alkyl-heterocycle, each of which $R^6$ and $R^7$ groups other than hydrogen is optionally substituted with 0, 1, 2, or 3 substituents independently selected from $R^{10}$;

$R^8$ is independently at each occurrence selected from the group consisting of hydrogen, $C_1$-$C_4$haloalkyl, $C_1$-$C_4$alkyl, halogen, —$OR^6$, —$NR^6R^7$, —OC(O)$R^5$, —$NR^6C(O)R^5$, —C(O)$R^5$, and -alkyl-C(O)$R^5$;

$R^9$ is independently at each occurrence selected from the group consisting of hydrogen, aryl, heteroaryl, heterocycle, cycloalkyl, $C_1$-$C_4$haloalkyl, $C_1$-$C_4$alkyl, halogen, —$OR^6$, —$NR^6R^7$, —C(O)$OR^6$, —C(O)$NR^6R^7$, -alkyl-C(O)$OR^6$, and -alkyl-C(O)$NR^6R^7$, each of which aryl, heteroaryl, heterocycle, and cycloalkyl groups is optionally substituted with 0, 1, 2, or 3 substituents selected from $C_1$-$C_4$haloalkyl, $C_1$-$C_4$alkyl, halogen, —$OR^6$, —$NR^6R^7$, —C(O)$OR^6$, —C(O)$NR^6R^7$, -alkyl-C(O)$OR^6$, and -alkyl-C(O)$NR^6R^7$;

or $R^9$ is independently at each occurrence selected from the group consisting of hydrogen, aryl, -alkyl-aryl, heteroaryl, alkyl-heteroaryl, heterocycle, alkyl-heterocycle, cycloalkyl, -alkyl-cycloalkyl, $C_1$-$C_4$haloalkyl, $C_1$-$C_4$alkyl, halogen, —$OR^6$, —$NR^6R^7$, —C(O)$OR^6$, —C(O)$NR^6R^7$, -alkyl-C(O)$OR^6$, and -alkyl-C(O)$NR^6R^7$, each of which aryl, -alkyl-aryl, heteroaryl, -alkyl-heteroaryl, heterocycle, -alkyl-heterocycle, -alkyl-cycloalkyl, and cycloalkyl groups is optionally substituted with 0, 1, 2, or 3 substituents selected from —$S(O)_2$alkyl, $C_1$-$C_4$haloalkyl, $C_1$-$C_4$alkyl, halogen, —$OR^6$, —$NR^6R^7$, —$C(O)OR^6$, —$C(O)NR^6R^7$, -alkyl-$C(O)OR^6$, and -alkyl-$C(O)NR^6R^7$;

$R^{10}$ is independently at each occurrence selected from the group consisting $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, and -alkyl-heterocycle;

or $R^{10}$ is independently at each occurrence selected from the group consisting $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, halogen, and -alkyl-heterocycle;

$R^{11}$ is hydrogen, $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, -alkyl-heterocycle, -alkyl-$OR^6$, —$OC(O)R^6$, —$OR^6$, -alkyl-$NR^6R^7$, —$NR^6C(O)R^7$ or —$NR^6R^7$;

R, $R^{27}$, $R^{28}$, and $R^{29}$ are independently at each occurrence selected from the group consisting of hydrogen, $C_1$-$C_4$haloalkyl, $C_1$-$C_4$alkyl, halogen, cyano, nitro, —$OR^6$, —$NR^6R^7$, —$C(O)OR^6$, and —$C(O)NR^6R^7$;

$R^{12}$, $R^{13}$, $R^{14}$, $R^{15}$, $R^{16}$, $R^{17}$, $R^{18}$, and $R^{19}$ are independently at each occurrence selected from the group consisting of hydrogen, $C_1$-$C_4$haloalkyl, $C_1$-$C_4$alkyl, and halogen; or $R^{12}$ and $R^{13}$ are combined to form a carbonyl or 3 to 6-membered spirocycle, for example

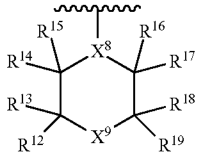

includes

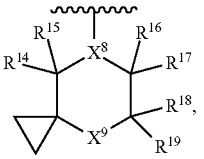 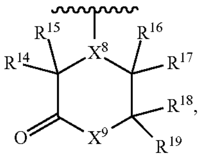 and

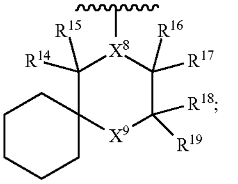

or $R^{14}$ and $R^{15}$ are combined to form a carbonyl or 3 to 6-membered spirocycle; or $R^{16}$ and $R^{17}$ are combined to form a carbonyl or 3 to 6-membered spirocycle; or $R^{18}$ and $R^{19}$ are combined to form a carbonyl or 3 to 6-membered spirocycle; or $R^{12}$ and $R^{14}$ are combined to form a 3 to 6-membered fused ring, for example

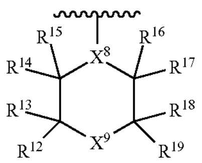

includes

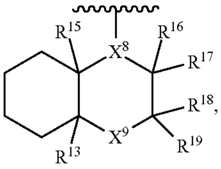 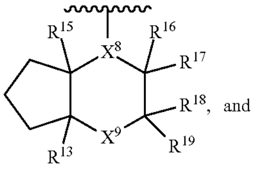 and

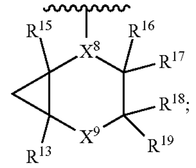

or $R^{12}$ and $R^4$ are combined to form a 3 to 6-membered fused ring; or $R^{16}$ and $R^{18}$ are combined to form a 3 to 6-membered fused ring; or $R^{12}$ and $R^{17}$ are combined to form a 1 or 2 atom bridge for example

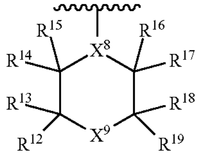

includes

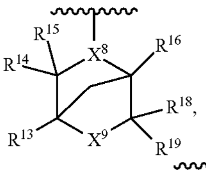 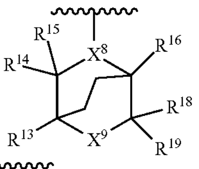 and

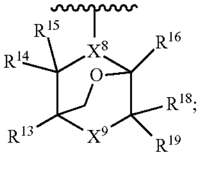

or $R^{12}$ and $R^{19}$ are combined to form a 1 or 2 atom bridge; or $R^{14}$ and $R^{17}$ are combined to form a 1 or 2 atom bridge; or $R^{14}$ and $R^{19}$ are combined to form a 1 or 2 atom bridge; and Linker is a bivalent linking group, for example a bivalent linking group of Formula LI.

In certain embodiments Linker is of formula:

(LI)

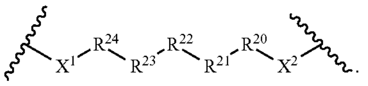

wherein, $X^1$ and $X^2$ are independently at each occurrence selected from bond, heterocycle, $NR^2$, $C(R^2)_2$, O, C(O), and S;

$R^2$ is independently at each occurrence selected from the group consisting of hydrogen, alkyl, aliphatic, heteroaliphatic, heterocycle, aryl, heteroaryl, —C(O)H, —C(O)OH, —C(O)alkyl, —C(O)Oalkyl, —C(O)(aliphatic, aryl, heteroaliphatic or heteroaryl), —C(O)O (aliphatic, aryl, heteroaliphatic, or heteroaryl), alkene, and alkyne;

$R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —$SO_2$—, —S(O)—, —C(S)—, —C(O)$NR^2$—, —$NR^2$C(O)—, —O—, —S—, —$NR^2$—, —$C(R^{40}R^{40})$—, —P(O)($OR^{26}$)O—, —P(O)($OR^{26}$)—, bicycle, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from $R^{40}$;

$R^{26}$ is independently at each occurrence selected from the group consisting of hydrogen, alkyl, arylalkyl, heteroarylalkyl, alkene, alkyne, aryl, heteroaryl, heterocycle, aliphatic and heteroaliphatic; and $R^{40}$ is independently at each occurrence selected from the group consisting of hydrogen, alkyl, alkene, alkyne, fluoro, bromo, chloro, hydroxyl, alkoxy, azide, amino, cyano, —NH(aliphatic, including alkyl), —N(aliphatic, including alkyl)$_2$, —$NHSO_2$(aliphatic, including alkyl), —N(aliphatic, including alkyl)$SO_2$alkyl, —$NHSO_2$(aryl, heteroaryl or heterocycle), —N(alkyl)$SO_2$(aryl, heteroaryl or heterocycle), —$NHSO_2$alkenyl, —N(alkyl)$SO_2$alkenyl, —$NHSO_2$alkynyl, —N(alkyl)$SO_2$alkynyl, haloalkyl, aliphatic, heteroaliphatic, aryl, heteroaryl, heterocycle, and cycloalkyl.

In other aspects, the present invention provides a compound of Formula V, Formula VI, or Formula VII:

(V)

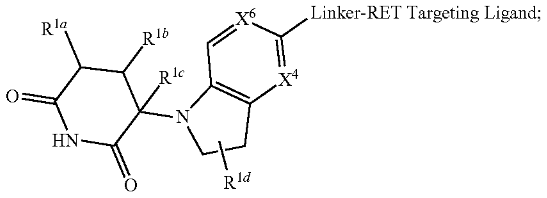

-continued (VI)

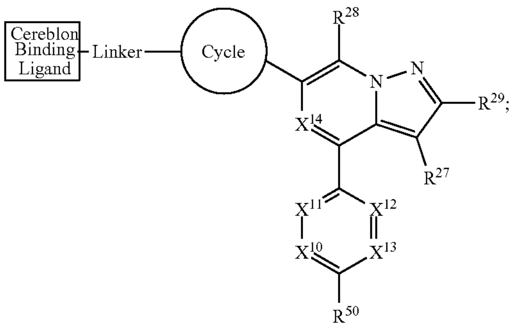

(VII)

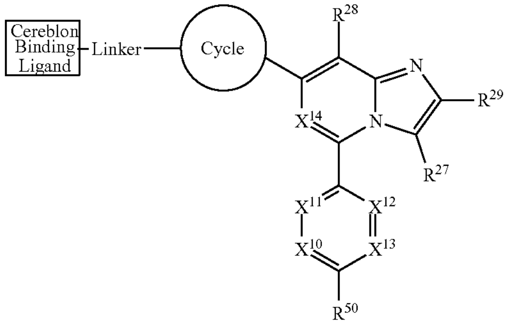

wherein

Cereblon Binding Ligand is selected from:

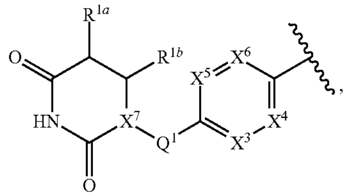

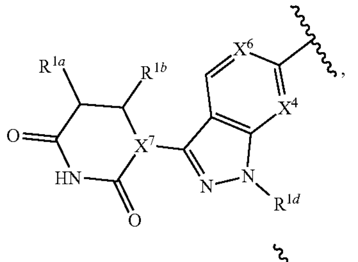

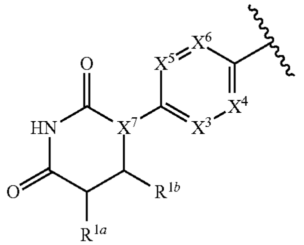

-continued

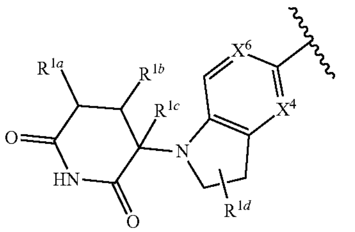

or

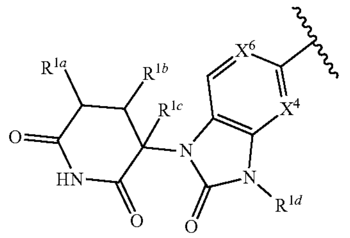

$R^{50}$ is selected from $R^5$ and $R^{51}$ $R^{51}$ is selected from

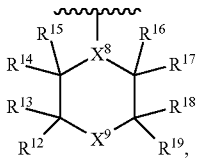

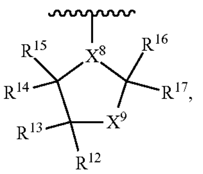

and

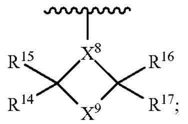

and all other variables are as defined herein.

Every combination of variables, substituents, embodiments, and the compounds that result from these combinations, is deemed specifically and individually disclosed, as such depiction is for convenience of space only and not intended to describe only a genus or even a subgenus of compounds.

In certain embodiments a compound of the present invention penetrates the blood brain barrier and can be used for the treatment of a cancer that has metastasized to the brain or a CNS involved cancer.

In certain embodiments, a method of treatment is provided comprising administering an effective amount of a compound of Formula I, Formula II, Formula III, Formula IV, Formula V, Formula VI, or Formula VII, or a pharmaceutically acceptable salt thereof to a patient in need thereof, for example a human, optionally in a pharmaceutically acceptable carrier. For example, in one embodiment, a compound of Formula I, Formula II, Formula III, Formula IV, Formula V, Formula VI, or Formula VII, is administered to a human to treat a cancer.

In certain embodiments a compound of the present invention is used to treat sporadic medullary thyroid cancer. In certain embodiments a compound of the present invention is used to treat non-sporadic medullary thyroid cancer. In certain embodiments a compound of the present invention is used to treat lung cancer, for example non-small cell lung cancer.

In certain embodiments, the compound of the present invention provides one or more, and even may provide multiple advantages over traditional treatment with a RET ligand. For example, the RET degrading compound of the present invention may a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; and/or d) have increased potency compared to inhibitors due to the possibility of the small molecule acting catalytically.

In certain embodiments, a compound of the present invention is used to treat a tumor or cancer with a RET protein that has mutated. In certain embodiments, a compound of the present invention is used to treat a tumor or cancer with a RET protein solvent front mutation, for example G810R, G810S, or G810C. In certain embodiments, a compound of the present invention is used to treat a tumor or cancer with a RET G810R mutation. In certain embodiments, a compound of the present invention is used to treat a tumor or cancer with a RET G810S mutation. In certain embodiments, a compound of the present invention is used to treat a tumor or cancer with a RET G810C mutation.

In certain embodiments, a compound of the present invention is used to treat a tumor or cancer in the CNS with a RET protein that has mutated. In certain embodiments, a compound of the present invention is used to treat a tumor or cancer in the CNS with a RET protein solvent front mutation, for example G810R, G810S, or G810C. In certain embodiments, a compound of the present invention is used to treat a tumor or cancer in the CNS with a RET G810R mutation. In certain embodiments, a compound of the present invention is used to treat a tumor or cancer in the CNS with a RET G810S mutation. In certain embodiments, a compound of the present invention is used to treat a tumor or cancer in the CNS with a RET G810C mutation. In certain embodiments the tumor or cancer in the CNS metastasized from a primary cancer elsewhere in the body. In other embodiments the tumor or cancer in the CNS is a primary cancer such as glioblastoma or head and neck cancer.

In certain embodiments, a compound of the present invention is used to treat a tumor or cancer with a RET protein gatekeeper mutation, for example V804L or V804M.

In certain embodiments, a compound of the present invention is used to treat a tumor or cancer with a RET protein activating mutation. In one aspect the RET activating mutation is M918T.

In certain embodiments, a compound of the present invention is used to treat a drug resistant RET altered tumor or cancer. In certain embodiments the tumor is resistant to a drug selected from selpercatinib, pralsetinib, TPX-0046, and/or selumetinib.

In certain embodiments, a compound of the present invention is used to treat a tumor or cancer with a RET protein fused to another protein, for example KIF5B-RET fusion, CCDC6-RET fusion, or NCOA4-RET fusion. In certain embodiments, a compound of the present invention is used to treat a tumor or cancer with a KIF5B-RET fusion. In certain embodiments, a compound of the present invention is used to treat a tumor or cancer with a CCDC6-RET fusion or NCOA4-RET fusion. In certain embodiments, a compound of the present invention is used to treat a tumor or cancer with a CCDC6-RET fusion. In certain embodiments, a compound of the present invention is used to treat a tumor or cancer with a NCOA4-RET fusion In certain embodiments, a compound of the present invention is used to treat a tumor cancer that is resistant to RET inhibitors, for example selpercatinib, pralsetinib, and/or TPX-0046. In certain embodiments, a compound of the present invention is used to treat a tumor or cancer that has acquired resistance to a RET inhibitor, for example selpercatinib, pralsetinib, and/or TPX-0046.

In certain embodiments, the compound of the present invention provides an improved efficacy and/or safety profile relative to known RET inhibitors.

In certain embodiments, the compound of the present invention has one or more advantages in the treatment of a RET mediated disorders than using the targeting ligand portion alone.

In certain embodiments, less of the compounds described herein is needed for the treatment of a RET mediated disorder, than by mole of the targeting ligand portion alone.

In certain embodiments, the compound of the present invention has less of at least one side-effect in the treatment of a RET mediated disorder, than by mole of the targeting ligand portion alone.

In certain embodiments, a less frequent dose regimen of a selected compounds described herein is needed for the treatment of a RET mediated disorders, than the dose by mole of the targeting ligand portion alone.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for inhibiting or preventing a disorder mediated by RET or for modulating or decreasing the amount of RET.

Another aspect of the present invention provides a compound as described herein, or an enantiomer, diastereomer, or stereoisomer thereof, or pharmaceutically acceptable salt, hydrate, or solvate thereof, or its pharmaceutical composition, for use in the manufacture of a medicament for treating or preventing a disease mediated by RET.

In certain embodiments, a selected compound as described herein is useful to treat a disorder comprising an abnormal cellular proliferation, such as a tumor or cancer, wherein RET is an oncogenic protein or a signaling mediator of the abnormal cellular proliferative pathway and its degradation decreases abnormal cell growth.

In certain embodiments, the selected compound of Formula I, Formula II, Formula III, Formula IV, Formula V, Formula VI, or Formula VII, or its pharmaceutically acceptable salt thereof, has at least one desired isotopic substitution of an atom, at an amount above the natural abundance of the isotope, i.e., enriched.

In one embodiment, the compound of Formula I, Formula II, Formula III, Formula IV, Formula V, Formula VI, or Formula VII, or its pharmaceutically acceptable salt thereof, includes a deuterium atom or multiple deuterium atoms.

Other features and advantages of the present application will be apparent from the following detailed description.

The present invention thus includes at least the following features:

(a) A compound of Formula I, Formula II, Formula III, Formula IV, Formula V, Formula VI, or Formula VII, as described herein, or a pharmaceutically acceptable salt or isotopic derivative (including a deuterated derivative) thereof, (b) A method to treat a RET mediated disorder, such as an abnormal cellular proliferation, including cancer, comprising administering an effective amount of a compound of Formula I, Formula II, Formula III, Formula IV, Formula V, Formula VI, or Formula VII, or pharmaceutically acceptable salt thereof, as described herein, to a patient in need thereof;

(c) A compound of Formula I, Formula II, Formula III, Formula IV, Formula V, Formula VI, or Formula VII, or a pharmaceutically acceptable salt, or isotopic derivative (including a deuterated derivative) thereof for use in the treatment of a disorder that is mediated by RET, for example an abnormal cellular proliferation such as a tumor or cancer;

(d) Use of a compound of Formula I, Formula II, Formula III, Formula IV, Formula V, Formula VI, or Formula VII, or a pharmaceutically acceptable salt thereof, in an effective amount in the treatment of a patient in need thereof, typically a human, with a RET mediated disorder, for example an abnormal cellular proliferation such as a tumor or cancer;

(e) Use of a compound of Formula I, Formula II, Formula III, Formula IV, Formula V, Formula VI, or Formula VII, or a pharmaceutically acceptable salt or isotopic derivative (including a deuterated derivative) thereof in the manufacture of a medicament for the treatment of a RET mediated disorder, for example an abnormal cellular proliferation such as a tumor or cancer;

(f) A pharmaceutical composition comprising an effective patient-treating amount of a compound of Formula I, Formula II, Formula III, Formula IV, Formula V, Formula VI, or Formula VII, or a pharmaceutically acceptable salt, isotopic derivative thereof, and optionally a pharmaceutically acceptable carrier or diluent;

(g) A compound of Formula I, Formula II, Formula III, Formula IV, Formula V, Formula VI, or Formula VII, as described herein as a mixture of enantiomers or diastereomers (as relevant), including as a racemate;

(h) A compound of Formula I, Formula II, Formula III, Formula IV, Formula V, Formula VI, or Formula VII, as described herein in enantiomerically or diastereomerically (as relevant) enriched form, including an isolated enantiomer or diastereomer (i.e., greater than about 85, 90, 95, 97, or 99% pure); and (i) A process for the preparation of therapeutic products that contain an effective amount of a compound of Formula I, Formula II, Formula III, Formula IV, Formula V, Formula VI, or Formula VII, or a pharmaceutically acceptable salt thereof, as described herein.

DETAILED DESCRIPTION OF THE INVENTION

I. Definitions

Figure 1:
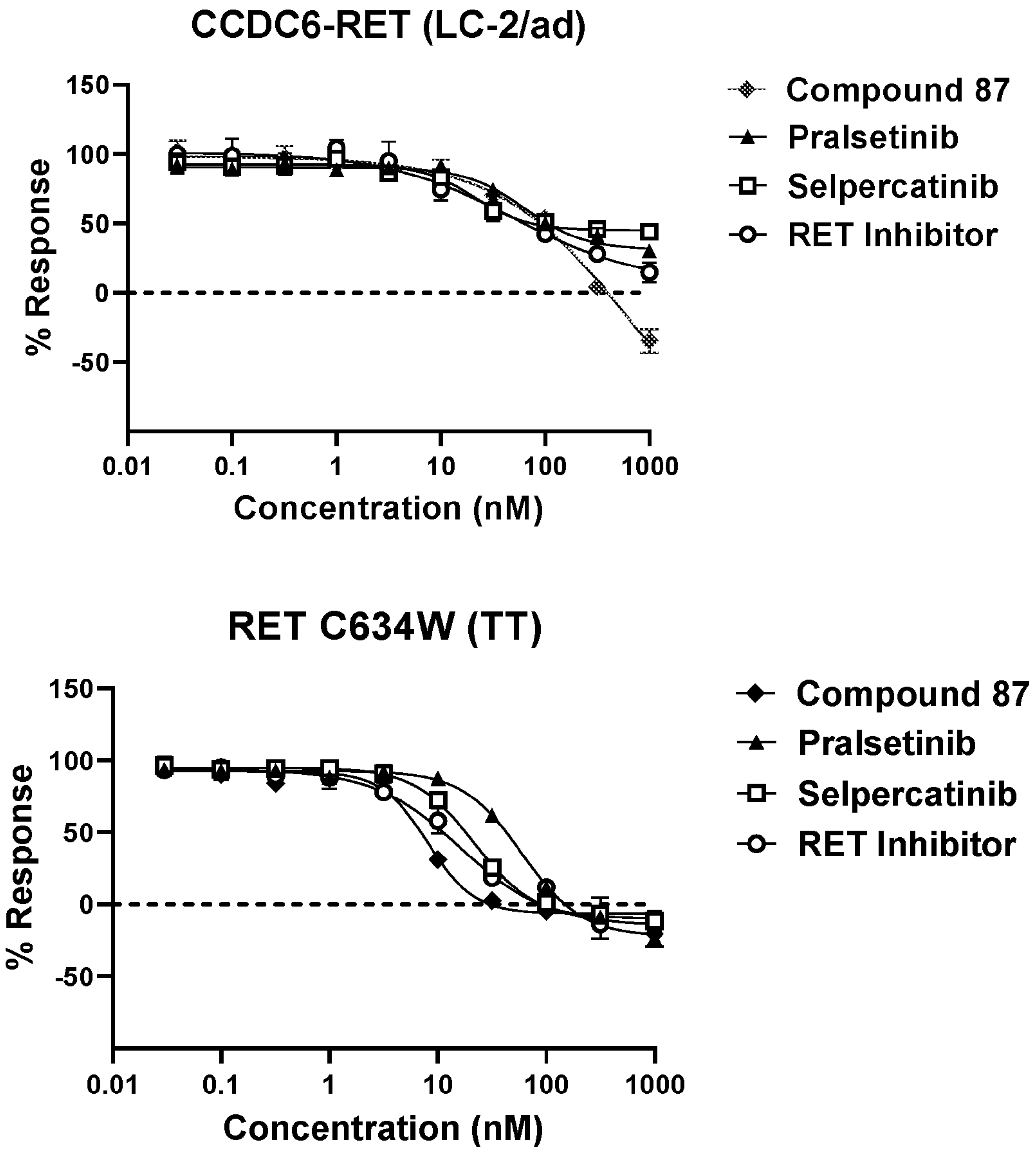
FIG. 1 provides dose-response curves describing the effect of Compound 87 (diamonds) on the viability of the lung cancer cell line LC-2/ad, which endogenously harbors the CCDC6-RET fusion and the thyroid cancer cell line TT, which endogenously harbors the C634W mutation. RET-selective inhibitors pralsetinib (triangles), selpercatinib (squares), and compound 5 of WO2019/126121 which is labeled "RET inhibitor" (circles) were tested in parallel. The x-axis is the concentration of the compounds in nM and the y-axis is the % cell viability after 120 hours. The experimental procedure is provided in Example 224.
Figure 2A:
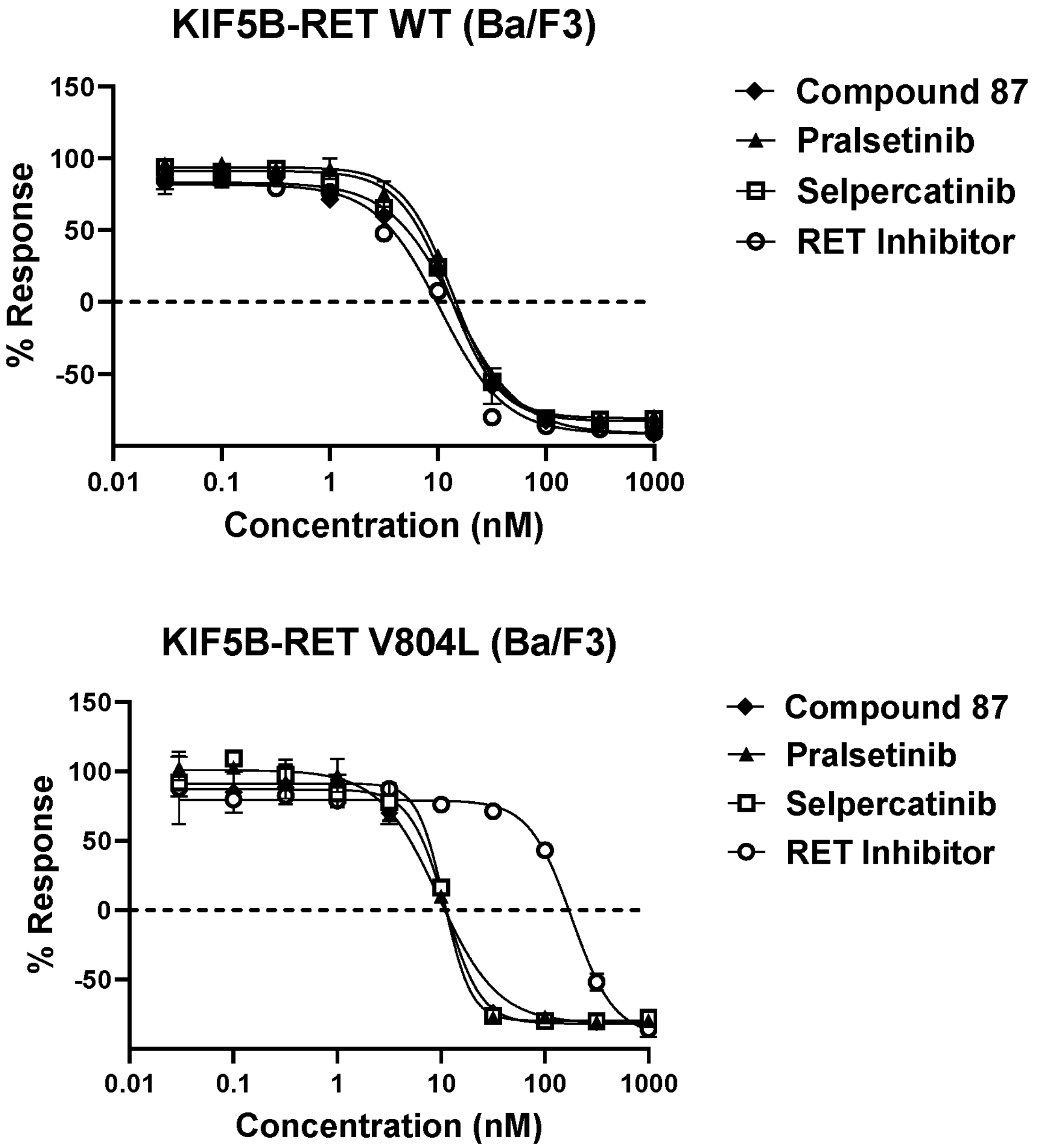
FIGS. 2A, 2B, 2C, 2D, and 2E provide dose-response curves describing the effect of Compound 87 (diamonds) on the viability of Ba/F3 cell lines engineered to express various RET alterations. RET-selective inhibitors pralsetinib (triangles), selpercatinib (squares), and compound 5 of WO2019/126121 which is labeled "RET inhibitor" (circles) were tested in parallel. The x-axis is the concentration of the compounds in nM and the y-axis is the % cell viability after 72 hours. The experimental procedure is provided in Example 224.
Figure 2B:
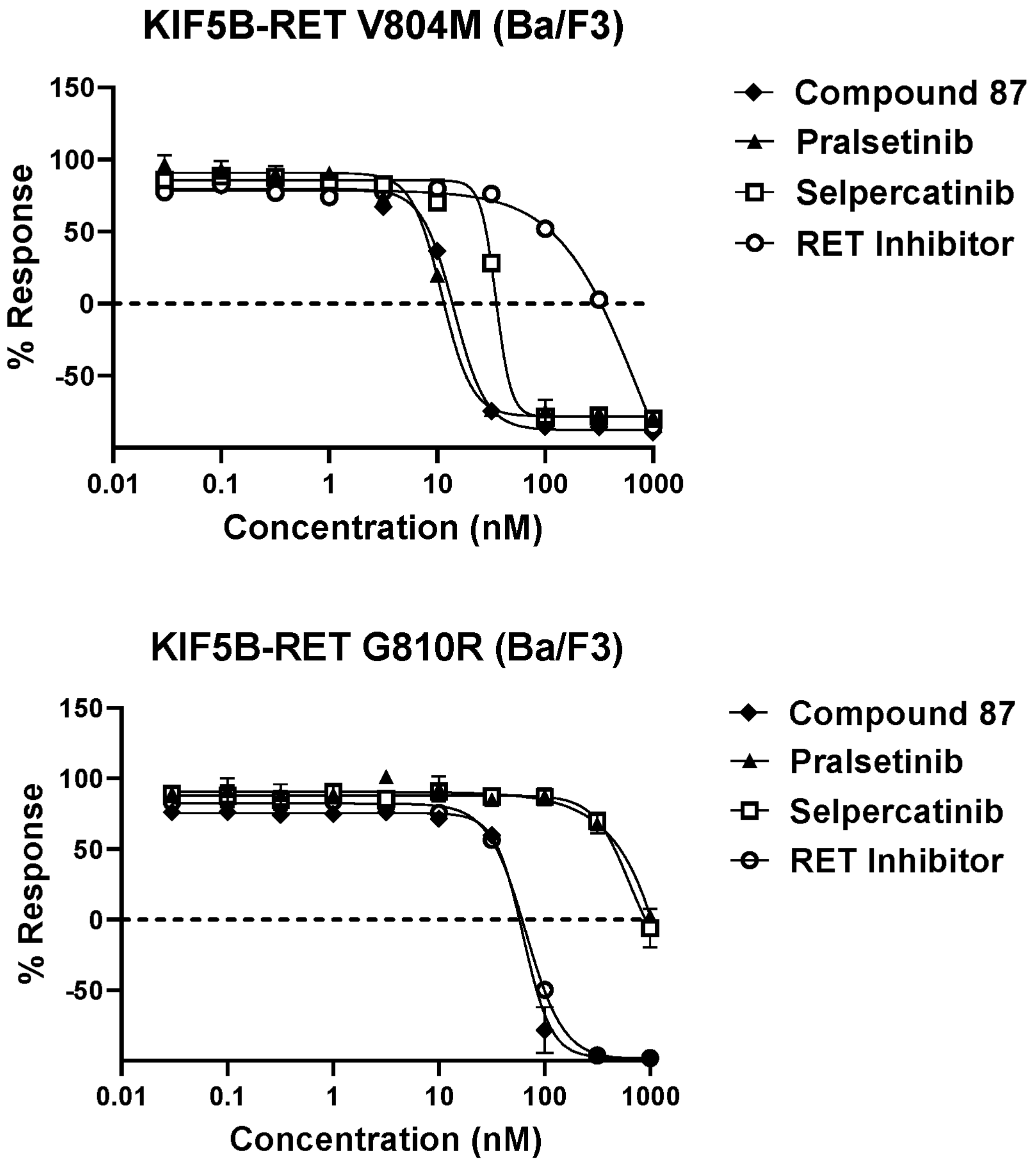
Figure 2C:
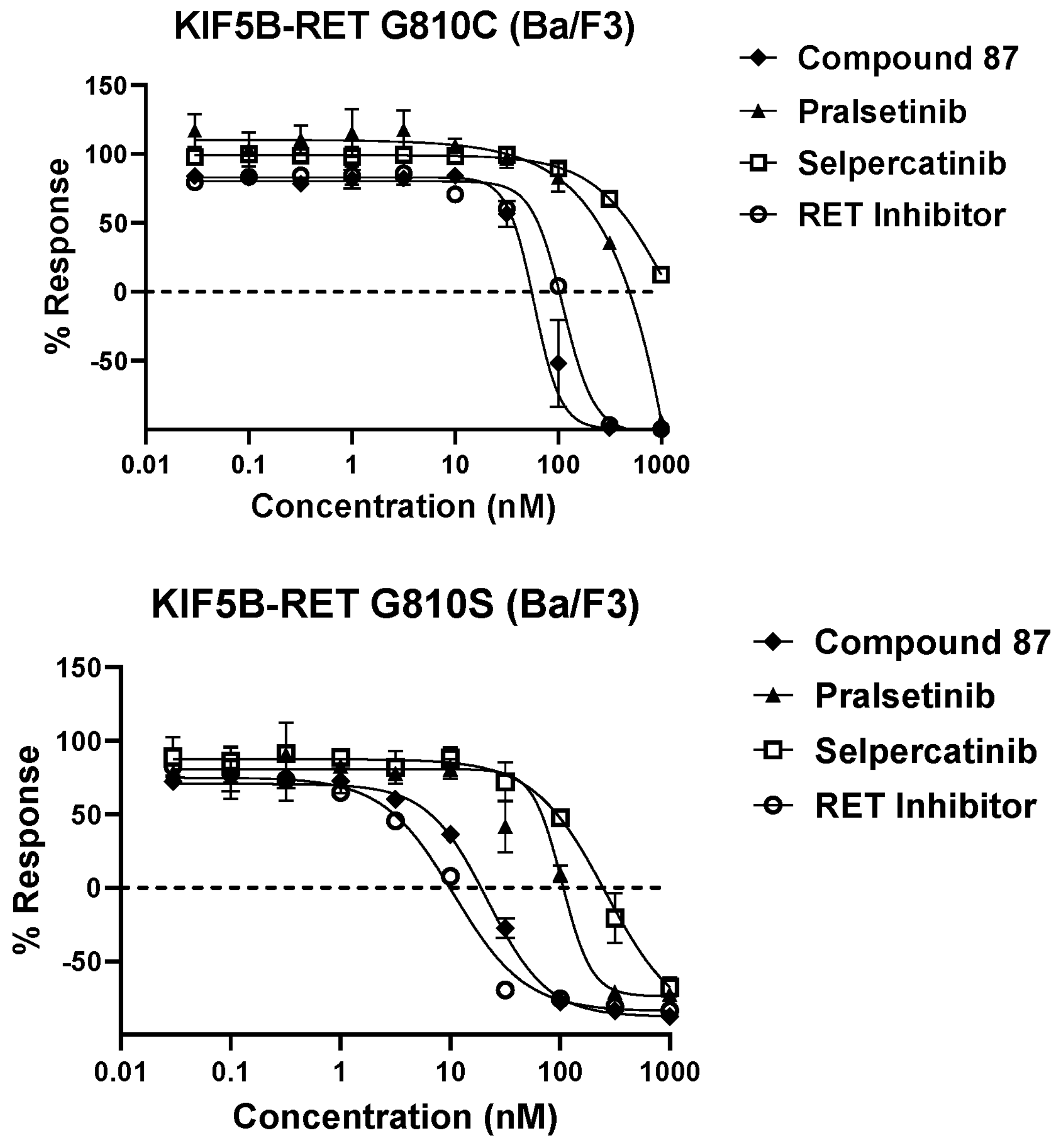
Figure 2D:
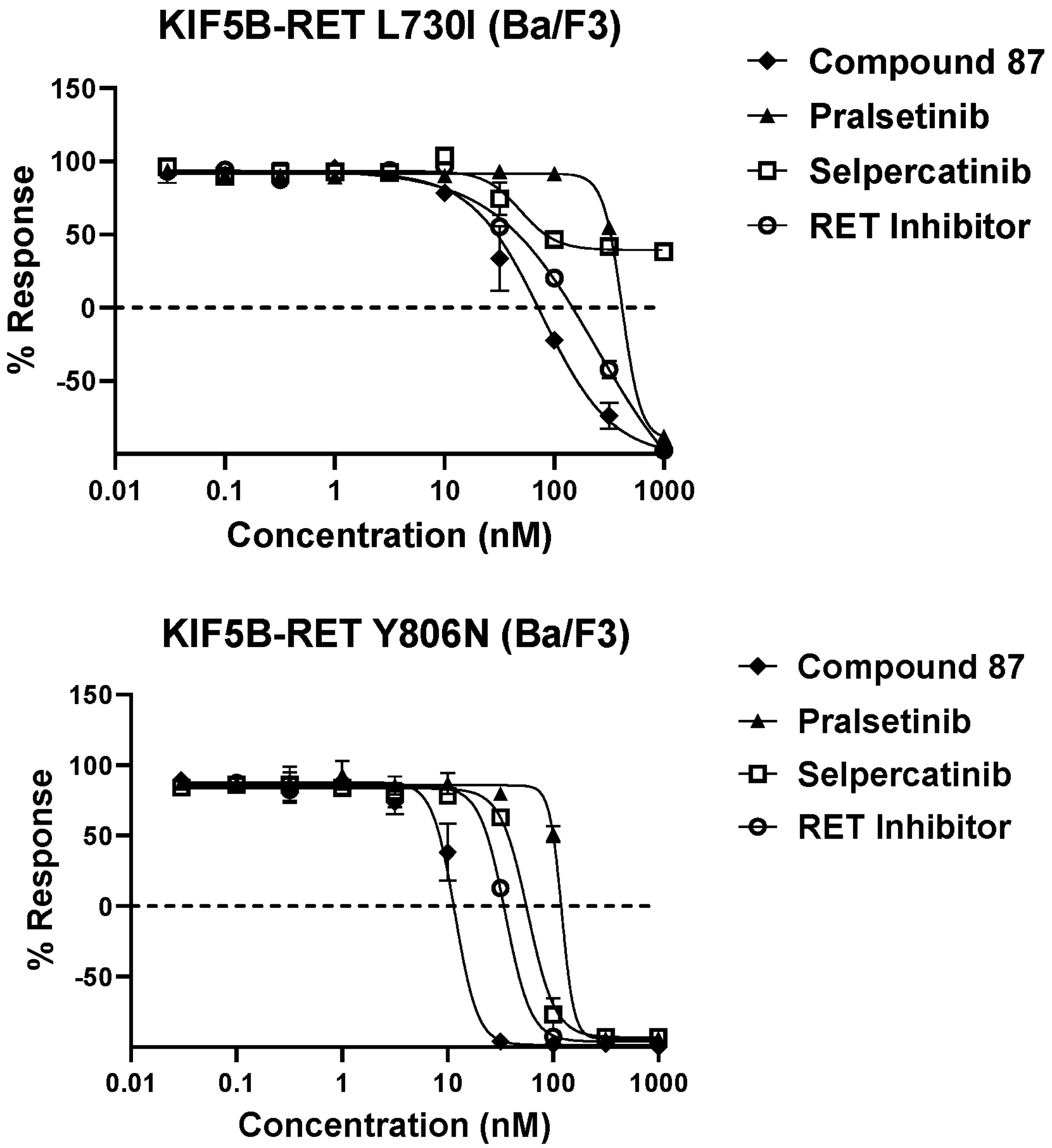
Figure 2E:
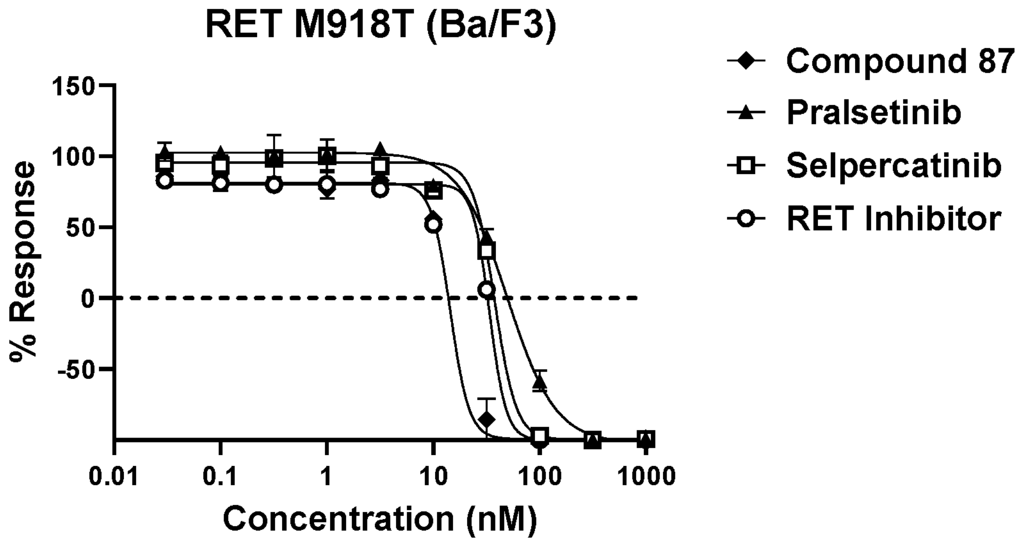

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula III, Formula IV, Formula V, Formula VI, or Formula VII, or its pharmaceutically acceptable salt thereof, with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^{2}H$, $^{3}H$, $^{11}C$, $^{13}C$, $^{14}C$, $^{15}N$, $^{17}O$, $^{18}O$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound of Formula I, Formula II, Formula III, Formula IV, Formula V, Formula VI, or Formula VII, or a pharmaceutically acceptable salt thereof. In one non-limiting embodiment, the substitution of a hydrogen atom for a deuterium atom occurs within one or more groups selected from any of R's or variables described herein, Linker, and Targeting Ligand. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO (dimethyl sulfoxide). A solvate can be in a liquid or solid form.

A dash ("-") that is not between two letters or symbols is used to indicate a point of attachment for a substituent. For example, —(C═O)$NH_2$ is attached through carbon of the carbonyl (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, alkoxy, haloalkyl, etc., can all be considered to include the cyclic forms of alkyl, unless unambiguously excluded by context.

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.

In one embodiment "alkyl" has two carbons.

In one embodiment "alkyl" has three carbons.

In one embodiment "alkyl" has four carbons.

In one embodiment "alkyl" has five carbons.

In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In an alternative embodiment "alkyl" is "optionally substituted" with 1, 2, 3, or 4 substituents.

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.

In one embodiment "cycloalkyl" has four carbons.

In one embodiment "cycloalkyl" has five carbons.

In one embodiment "cycloalkyl" has six carbons.

In one embodiment "cycloalkyl" has seven carbons.

In one embodiment "cycloalkyl" has eight carbons.

In one embodiment "cycloalkyl" has nine carbons.

In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example:

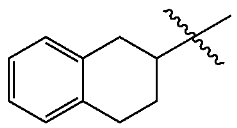 [SMILES: *C1CCc2ccccc2C1]

is an "cycloalkyl" group.

However,

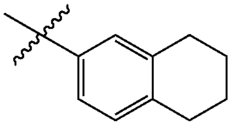 [SMILES: *c1ccc2c(c1)CCCC2]

is an "aryl" group.

In an alternative embodiment "cycloalkyl" is a "optionally substituted" with 1, 2, 3, or 4 substituents.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or cycloalkyl groups possessing at least one point of unsaturation. In an alternative embodiment "alkenyl" is "optionally substituted" with 1, 2, 3, or 4 substituents.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or cycloalkyl groups possessing at least one triple bond. In an alternative embodiment "alkynyl" is "optionally substituted" with 1, 2, 3, or 4 substituents.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond.

Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, a 2 to 6 carbon moiety, or an indicated number of carbon atoms, for example $C_2$-$C_4$alkynylene.

"Halo" and "Halogen" refers independently to fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

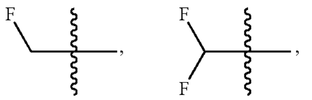

and

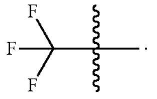

Additional non-limiting examples of "haloalkyl" include:

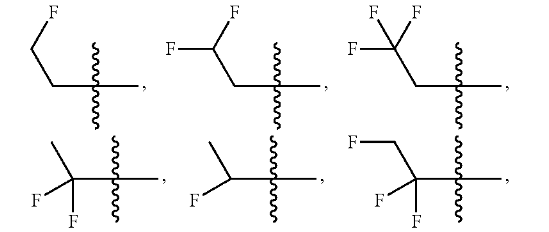

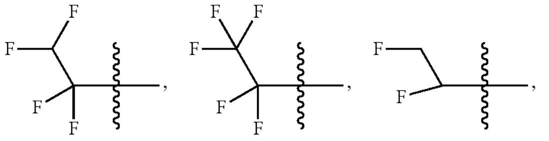

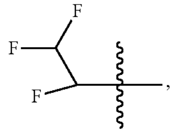

and

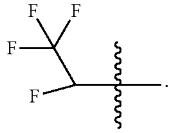

Additional non-limiting examples of "haloalkyl" include:

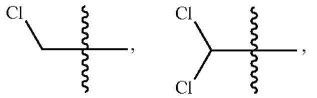

and

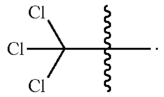

Additional non-limiting examples of "haloalkyl" include:

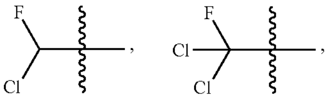

and

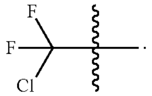

"Chain" indicates a linear chain to which all other chains, long or short or both, may be regarded as being pendant. Where two or more chains could equally be considered to be the main chain, "chain" refers to the one which leads to the simplest representation of the molecule.

"Haloalkoxy" indicates a haloalkyl group as described herein attached through an oxygen bridge (oxygen of an alcohol radical).

"Heterocycloalkyl" is an alkyl group as described herein substituted with a heterocyclo group as described herein.

"Arylalkyl" is an alkyl group as described herein substituted with an aryl group as described herein.

Non-limiting examples of "arylalkyl" include:

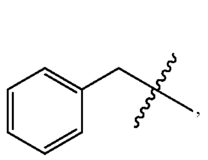

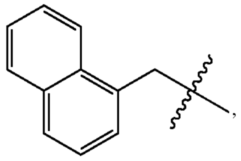

-continued

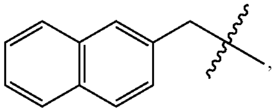, 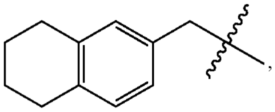,

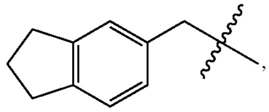, or 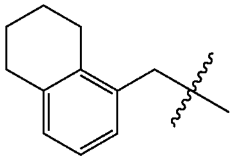.

In one embodiment "arylalkyl" is

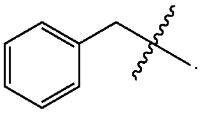 [SMILES: *Cc1ccccc1].

In one embodiment the "arylalkyl" refers to a 2 carbon alkyl group substituted with an aryl group.

Non-limiting examples of "arylalkyl" include:

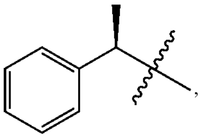, 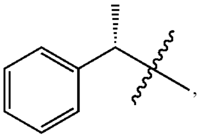,

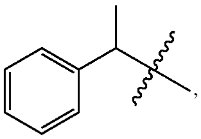, or

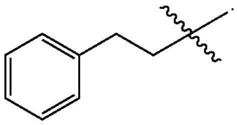.

In one embodiment the "arylalkyl" refers to a 3 carbon alkyl group substituted with an aryl group.

"Heteroarylalkyl" is an alkyl group as described herein substituted with a heteroaryl group as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocycle groups wherein the radical or point of attachment is on the aryl ring, and in such instances, the number of carbon atoms continue to designate the number of carbon atoms in the aryl ring system. The one or more fused carbocyclyl or heterocycle groups can be 4 to 7 or 5 to 7-membered saturated or partially unsaturated carbocyclyl or heterocycle groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

In one embodiment "aryl" is a 6 carbon aromatic group (phenyl).

In one embodiment "aryl" is a 10 carbon aromatic group (napthyl).

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example,

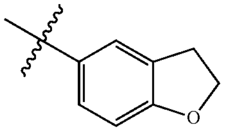 [SMILES: *c1ccc2c(c1)CCO2]

is an "aryl" group.

However,

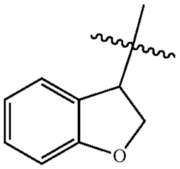 [SMILES: *C1COc2ccccc21]

is a "heterocycle" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example,

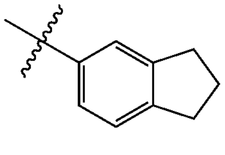 [SMILES: *c1ccc2c(c1)CCC2]

is an "aryl" group.

However,

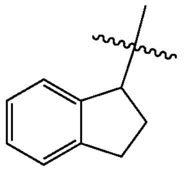 [SMILES: *C1CCc2ccccc21]

is a "cycloalkyl" group.

In an alternative embodiment "aryl" is "optionally substituted" with 1, 2, 3, or 4 substitutents.

The term "heterocyclyl", "heterocycle", and "heterocyclo" includes saturated, and partially saturated heteroatom-containing ring radicals, where the heteroatoms may be selected from nitrogen, sulfur and oxygen. Heterocyclic rings comprise monocyclic 3, 4, 5, 6, 7, 8, 9, or 10 membered rings, as well as 5, 6, 7, 8, 9, 10, 11, 12, 13, 14, 15, or 16 membered bicyclic ring systems (which can include bridged fused and spiro-fused bicyclic ring systems). It does not include rings containing —O—O—.—O—S— or —S—S— portions. Examples of saturated heterocyclo groups include saturated 3, 4, 5, or 6-membered heteromonocyclic groups containing 1, 2, 3, or 4 nitrogen atoms [e.g. pyrrolidinyl, imidazolidinyl, piperidinyl, pyrrolinyl, piperazinyl]; saturated 3, 4, 5, or 6-membered heteromonocyclic group containing 1 or 2 oxygen atoms and 1, 2, or 3 nitrogen atoms [e.g. morpholinyl]; saturated 3, 4, 5, or 6-membered heteromonocyclic group containing 1 or 2 sulfur atoms and 1, 2, or 3 nitrogen atoms [e.g., thiazolidinyl]. Examples of partially saturated heterocycle radicals include, but are not limited to, dihydrothienyl, dihydropyranyl, dihydrofuryl, and dihydrothiazolyl. Examples of partially saturated and saturated heterocyclo groups include, but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl, isoquinolin-1(2H)-onyl, benzo[d]oxazol-2(3H)-onyl, 1,3-dihydro-2H-benzo[d]midazol-2-onyl, benzo[d]thiazole-2(3H)-onyl, 1,2-dihydro-3H-pyrazol-3-onyl, 2(1H)-pyridinonyl, 2-piperazinonyl, indolinyl, and dihydrothiazolyl. In certain embodiments said "heterocycle" group may be optionally substituted, for example, with 1, 2, 3, 4 or more substituents that include but are not limited to, hydroxyl, Boc, halo, haloalkyl, cyano, alkyl, aralkyl, oxo, alkoxy, and amino.

The term"heterocyclyl", "heterocycle", and "heterocyclo" groups also include moieties where heterocycle radicals are fused/condensed with aryl or heteroaryl radicals: such as unsaturated condensed heterocycle group containing 1, 2, 3, 4, or 5 nitrogen atoms, for example, indoline, isoindoline, unsaturated condensed heterocycle group containing 1 or 2 oxygen atoms and 1, 2, or 3 nitrogen atoms, unsaturated condensed heterocycle group containing 1 or 2 sulfur atoms and 1, 2, or 3 nitrogen atoms, and saturated, partially unsaturated and unsaturated condensed heterocycle group containing 1 or 2 oxygen or sulfur atoms.

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocycle ring.

For example,

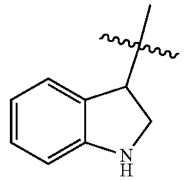 [SMILES: *C1CNc2ccccc21]

is a "heterocycle" group.

However,

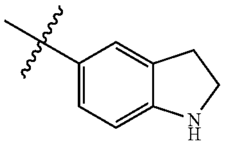 [SMILES: *c1ccc2c(c1)CCN2]

is an "aryl" group.

Non-limiting examples of "heterocycle" also include:

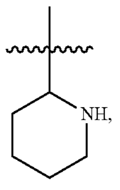
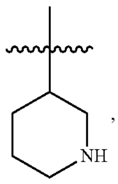
,
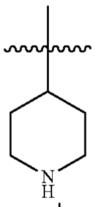
,
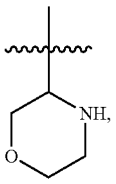
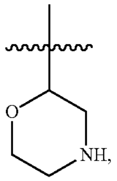
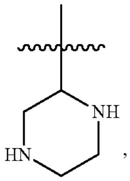
,
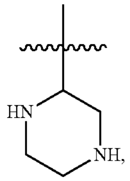
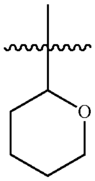
, -continued

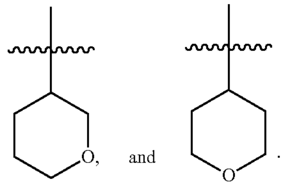

and

Additional non-limiting examples of "heterocycle" include:

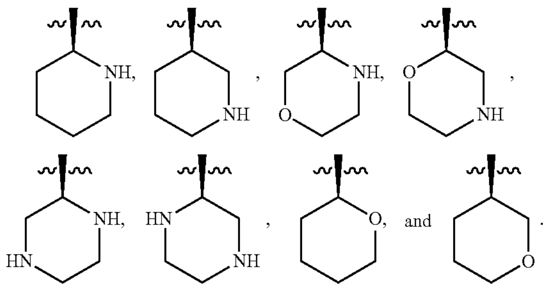

, , , and .

Additional non-limiting examples of "heterocycle" include:

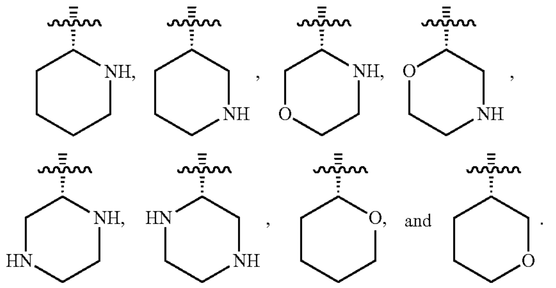

, , , and .

Non-limiting examples of "heterocycle" also include:

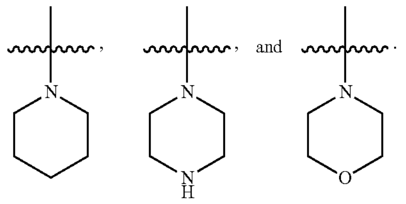 [SMILES: *N1CCCCC1 ; *N1CCNCC1 ; *N1CCOCC1]

, and .

Non-limiting examples of "heterocycle" also include:

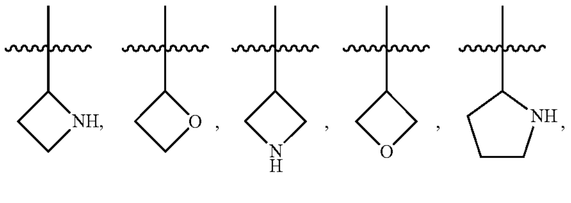

-continued

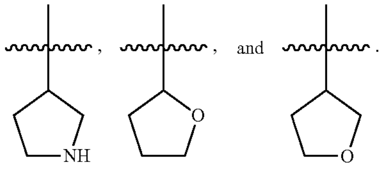

, , and .

Additional non-limiting examples of "heterocycle" include:

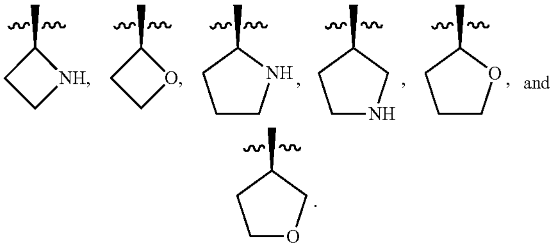

, , and .

Additional non-limiting examples of "heterocycle" include:

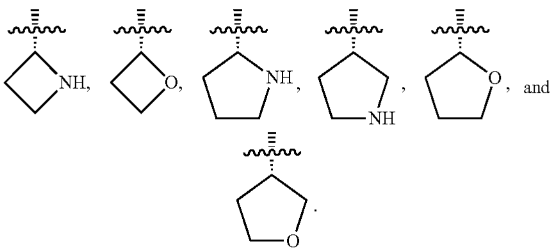

, , and .

In an alternative embodiment "heterocycle" is "optionally substituted" with 1, 2, 3, or 4 substituents.

The term "heteroaryl" denotes a monocyclic or polycyclic (e.g., bicyclic or tricyclic) 4n+2 aromatic ring system (e.g., having 6, 10, or 14 π electrons shared in a cyclic array) and 1, 2, 3, 4, 5, or 6, heteroatoms independently selected from O, N, and S, wherein the ring nitrogen and sulfur atom(s) are optionally oxidized, and nitrogen atom(s) are optionally quarternized. Examples include, but are not limited to, unsaturated 5 to 6 membered heteromonocyclyl groups containing 1, 2, 3, or 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- or 6-membered heteromonocyclic groups containing an oxygen atom, for example, pyranyl, 2-furyl, 3-furyl, etc.; unsaturated 5- or 6-membered heteromonocyclic groups containing a sulfur atom, for example, 2-thienyl, 3-thienyl, etc.; unsaturated 5- or 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 or 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. Additional examples include 8-, 9-, or 10-membered heteroaryl bicyclic groups such as indazolyl, indolyl, imidazo[1,5-a]pyridinyl, benzimidazolyl, 4(3H)-quinazolinonyl, quinolinyl, isoquinolinyl, isoindolyl, thienothienyl, indolizinyl, benzofuranyl, isobenzofuranyl, benzothienyl, isobenzothienyl, benzoxazolyl, benzothiazolyl, purinyl, coumarinyl, cinnolinyl, and triazolopyridinyl.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

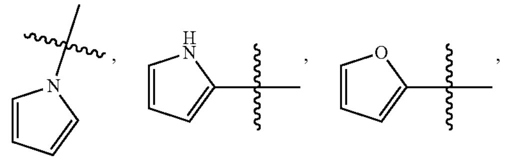

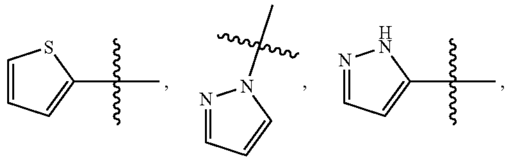

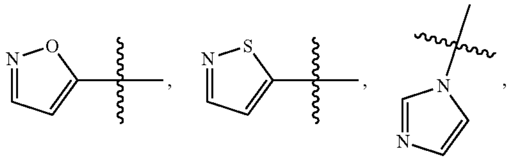

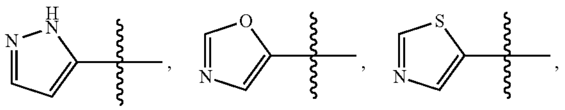

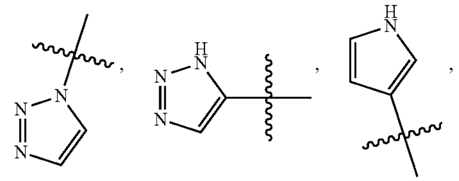

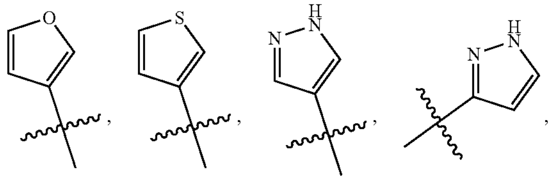

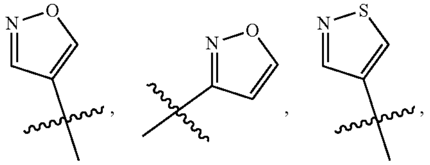

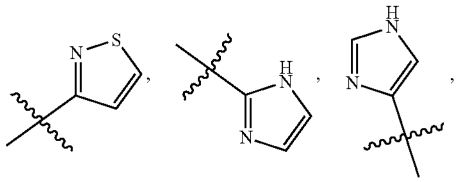

-continued

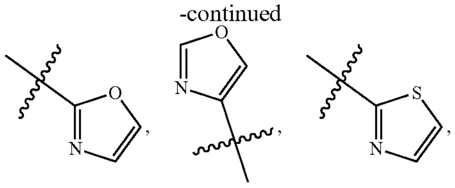

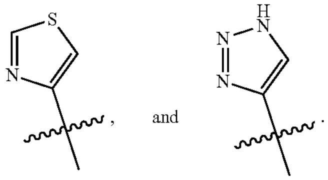

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

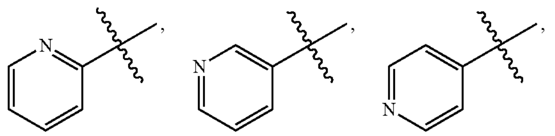

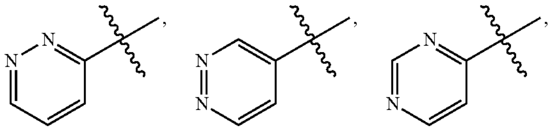

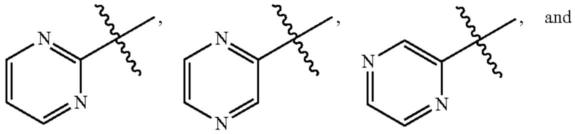

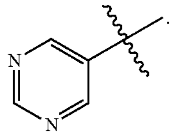

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

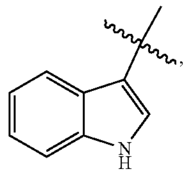

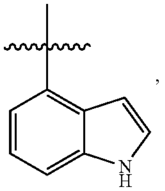

-continued

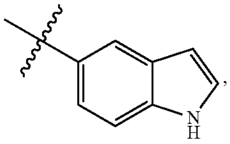, 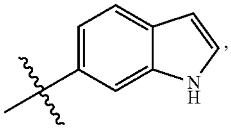,

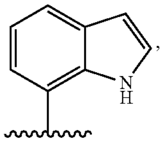, 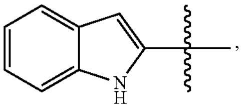, and

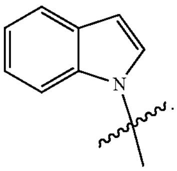.

Additional non-limiting examples of "heteroaryl" groups that are bicyclic include:

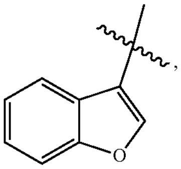, 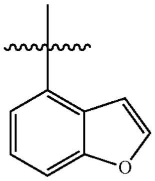,

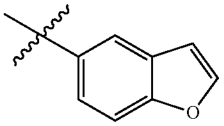, 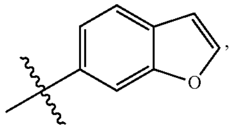,

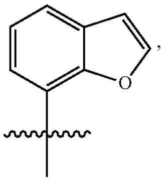, and 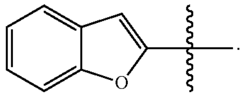.

Additional non-limiting examples of "heteroaryl" groups that are bicyclic include:

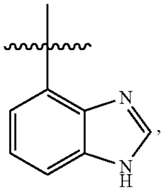, 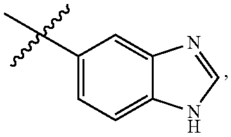,

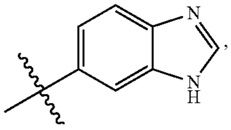, 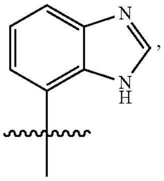,

-continued

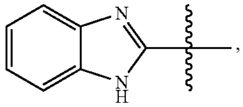, and 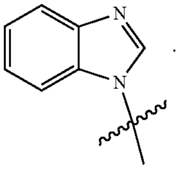.

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

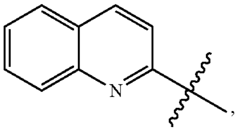, 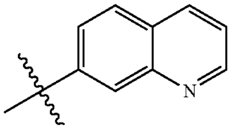,

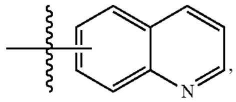, 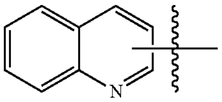,

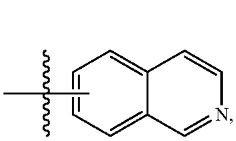, and 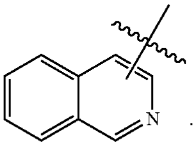.

In an alternative embodiment "heteroaryl" is "optionally substituted" with 1, 2, 3, or 4 substituents.

The term "bicycle" refers to a ring system wherein two rings are fused together and each ring is independently selected from carbocycle, heterocycle, aryl, and heteroaryl. Non-limiting examples of bicycle groups include:

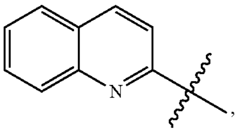, 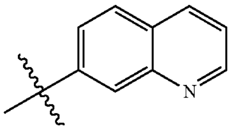,

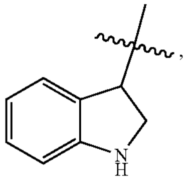, 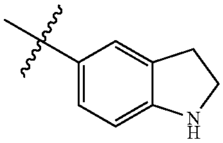,

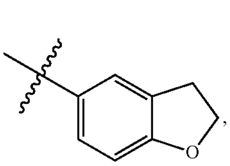, 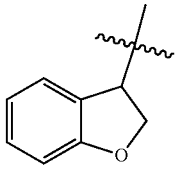,

-continued

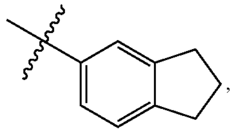
, and
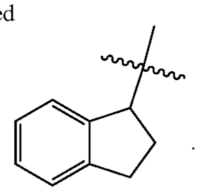
.

When the term "bicycle" is used in the context of a bivalent residue such as Linker the attachment points can be on separate rings or on the same ring. In certain embodiments both attachment points are on the same ring. In certain embodiments both attachment points are on different rings. Non-limiting examples of bivalent bicycle groups include:

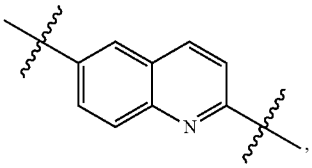
,
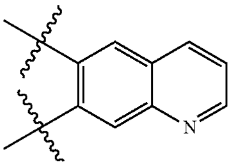
,
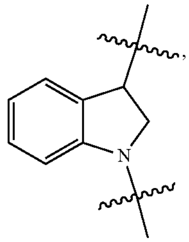
,
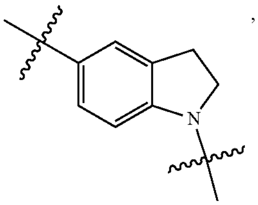
,
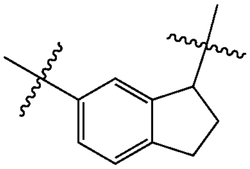
, and
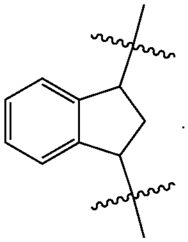
.

In an alternative embodiment "bicycle" is "optionally substituted" with 1, 2, 3, or 4 substituents.

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino.

In certain embodiments "optionally substituted" includes one or more substituents independently selected from halogen, hydroxyl, amino, cyano, —CHO, —COOH, —$CONH_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl (heterocyclo), $C_1$-$C_6$alkyl(heteroaryl), —$C_1$-$C_6$alkyl($C_3$-$C_7$cycloalkyl), 0-$C_1$-$C_6$alkyl($C_3$-$C_7$cycloalkyl), $B(OH)_2$, phosphate, phosphonate and haloalkoxy including $C_1$-$C_6$haloalkoxy.

In some embodiments, the suitable group present on a "substituted" or "optionally substituted" is divalent including, but not limited to, oxo (=O), =S, $=CH_2$, etc. The suitable group on a "substituted" or "optional substituted" position may be monovalent, divalent, or trivalent such that it forms a stable molecule and meets the desired purpose of the invention.

In one embodiment a group described herein that can be substituted with 1, 2, 3, or 4 substituents is substituted with one substituent.

In one embodiment a group described herein that can be substituted with 1, 2, 3, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a patient compared with the level of a response in the patient in the absence of a treatment or compound, and/or compared with the level of a response in an otherwise identical but untreated patient. The term encompasses perturbing and/or affecting a native signal or response thereby mediating a beneficial therapeutic response in a patient, preferably, a human.

"Parenteral" administration of a pharmaceutical composition includes, e.g., subcutaneous (s.c.), intravenous (i.v.), intramuscular (i.m.), intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and the maximum number of amino acids present within the protein or peptide's sequence is typically comparable to up to that found in nature. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

To "treat" a disease as the term is used herein, means to reduce the frequency or severity of at least one sign or symptom of a disease or disorder experienced by a patient (i.e. palliative treatment) or to decrease a cause or effect of the disease or disorder (i.e. disease-modifying treatment).

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable carrier" means a carrier or excipient that is useful in preparing a pharmaceutical composition/combination that is generally safe, non-toxic and neither biologically nor otherwise inappropriate for administration to a patient, typically a human. In one embodiment, an excipient is used that is acceptable for veterinary use.

A "patient" or "subject" is a human or domesticated animal in need of treatment for any of the disorders as specifically described herein, for example, a disorder that is modulated by a natural (wild-type) or modified (non-wild type)RET protein that can be degraded according to the present invention, resulting in a therapeutic effect. Non-limiting examples of domesticated animals include dogs, cats, horses, and livestock. As described further herein, the words patient or subject typically refers to a human patient or subject, and unless otherwise indicated by the text is assumed to refer to a human. In an alternative embodiment, the patient or subject is a domesticated animal in need of such therapy and responsive thereto.

"Livestock" refers to animals that are generally kept for agricultural purposes, including, for example, cows, sheep, goats, pigs, and poultry.

A "therapeutically effective amount" of a pharmaceutical composition/combination of this invention means an amount effective, when administered to a patient, to provide a therapeutic benefit such as an amelioration of symptoms or reduction or diminution of the disease itself.

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

II. Compounds of Formula I, Formula II, Formula III, Formula IV, Formula V, Formula VI, or Formula VII In one aspect, the present invention provides a compound of Formula I, Formula II, Formula III, or Formula IV:

(I)

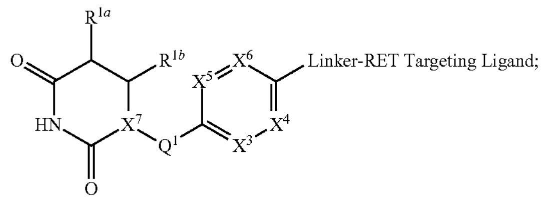

(II)

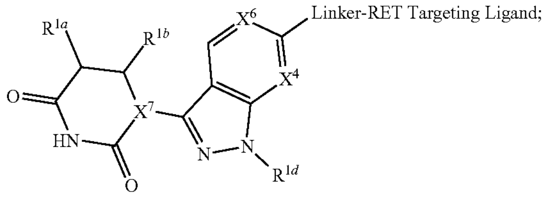

(III)

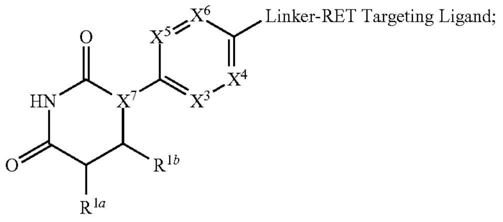

(IV)

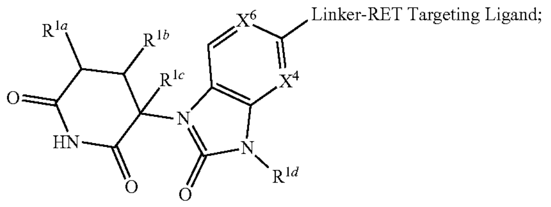

or a pharmaceutically acceptable salt thereof;

wherein all variables are defined as above.

In certain embodiments the compound of the present invention is selected from:

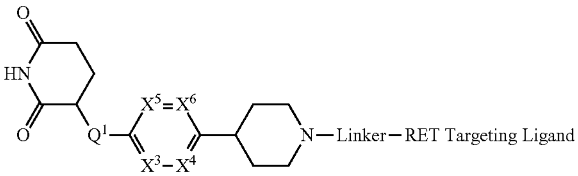

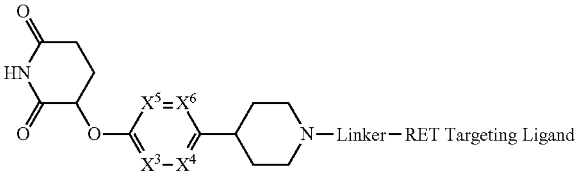

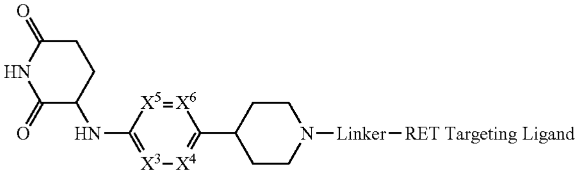

-continued
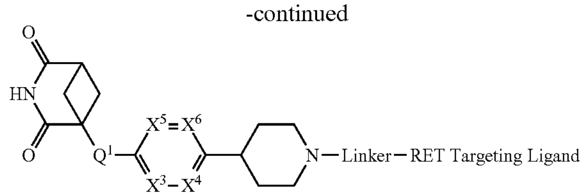
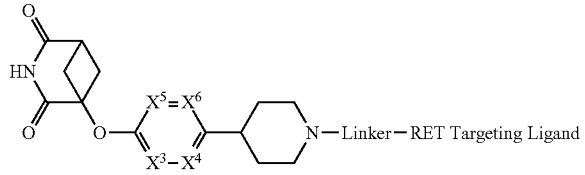
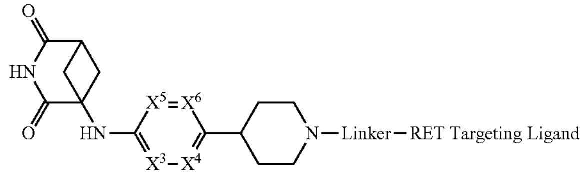
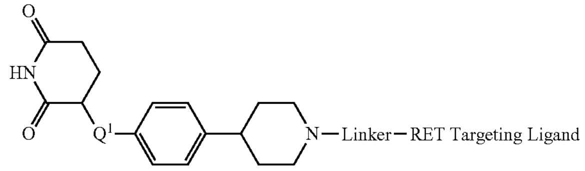
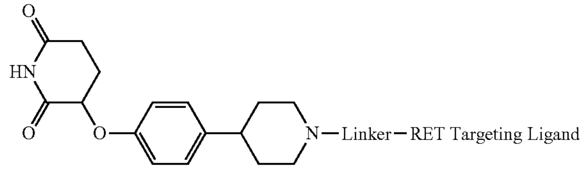
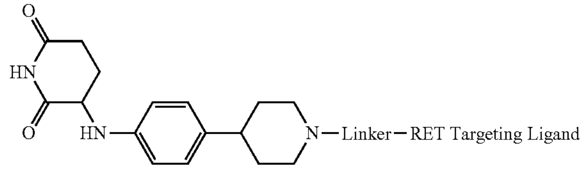
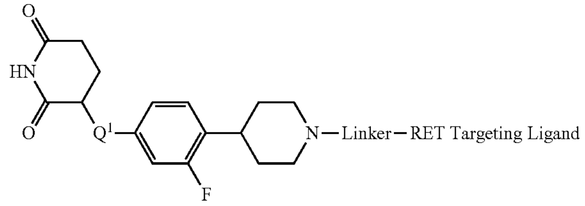
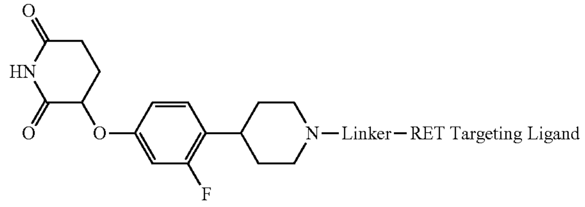
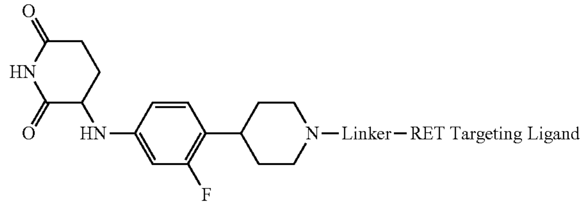
or a pharmaceutically acceptable salt thereof.
In certain embodiments the compound of the present invention is selected from:
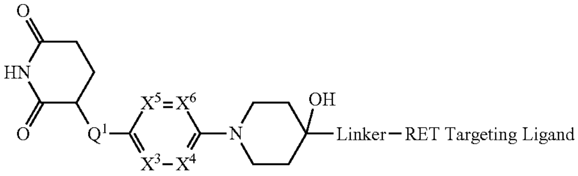
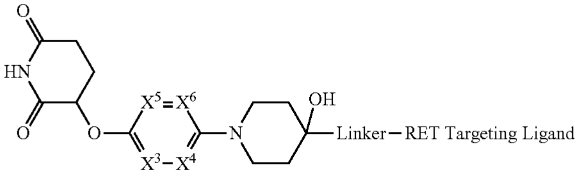
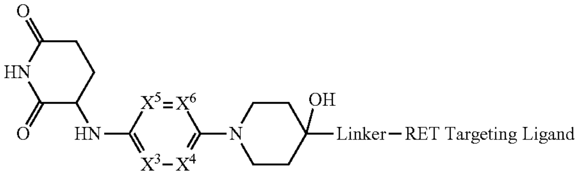
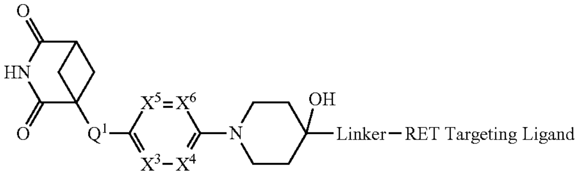
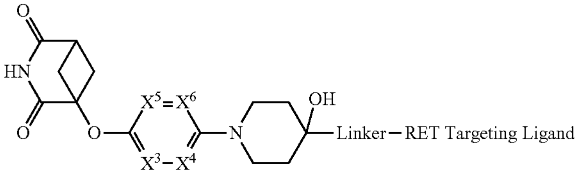
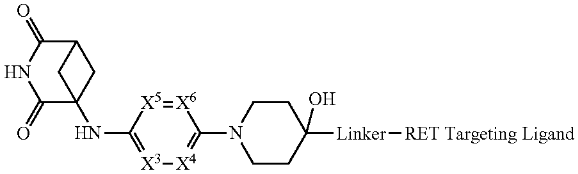
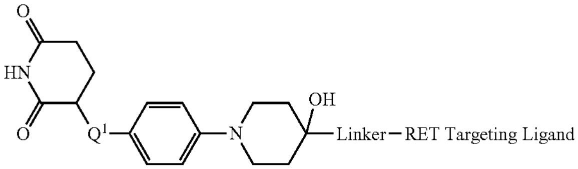
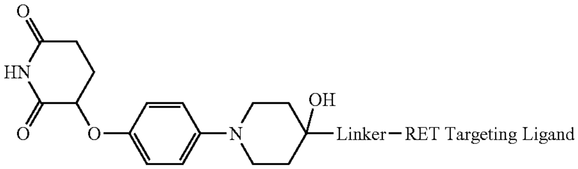
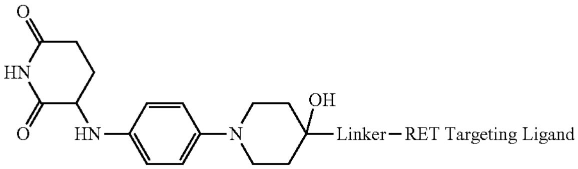
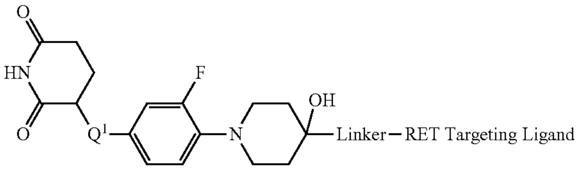

-continued

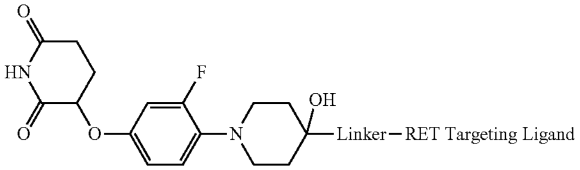

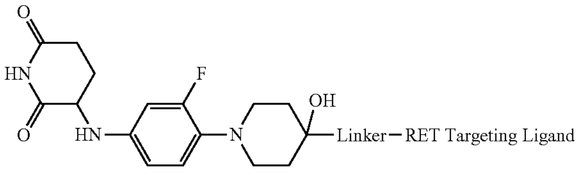

or a pharmaceutically acceptable salt thereof.

In certain embodiments the compound of the present invention is selected from:

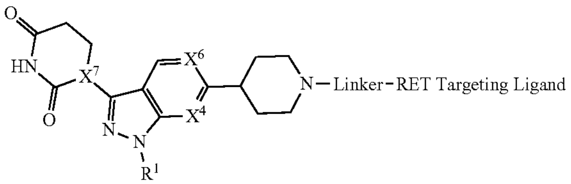

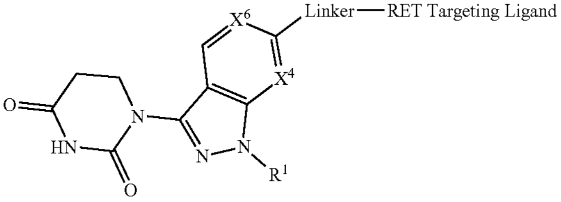

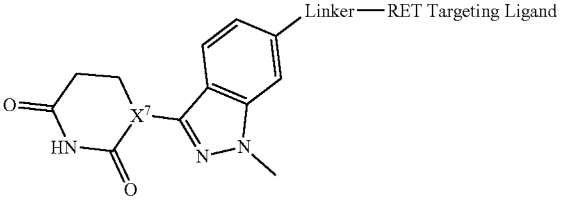

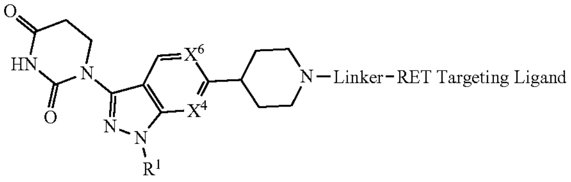

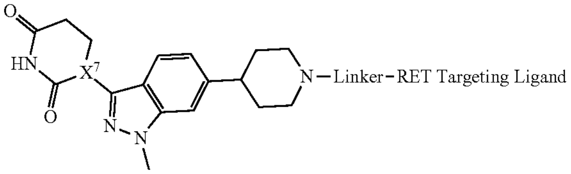

or a pharmaceutically acceptable salt thereof.

In certain embodiments the compound of the present invention is selected from:

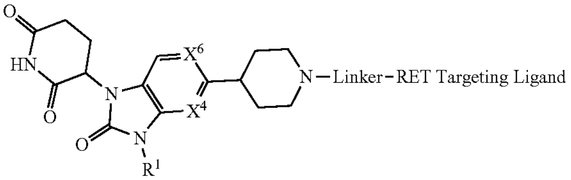

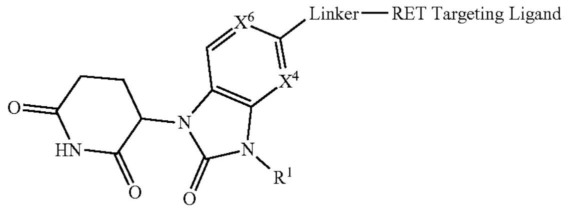

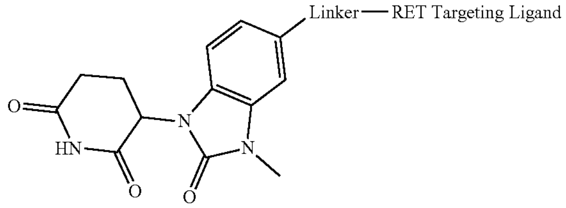

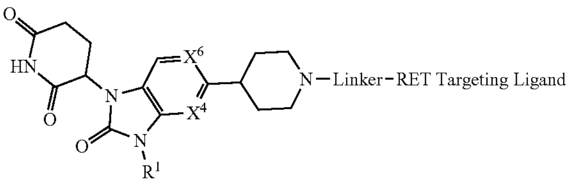

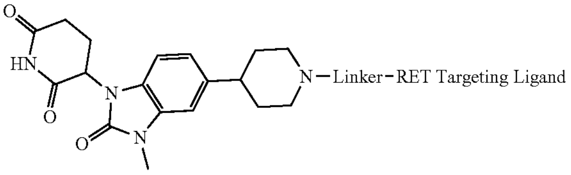

or a pharmaceutically acceptable salt thereof.

In certain embodiments the compound of the present invention is selected from:

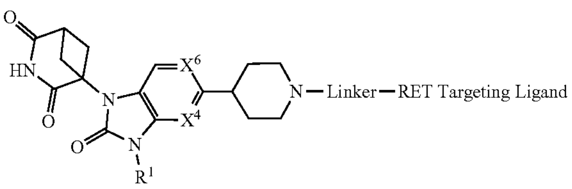

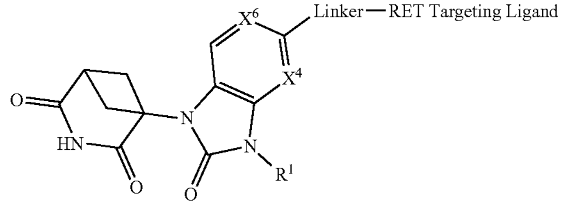

or a pharmaceutically acceptable salt thereof.

In certain embodiments the compound of the present invention is:

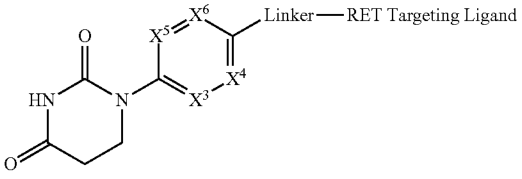

or a pharmaceutically acceptable salt thereof.

In certain embodiments the compound of the present invention is:

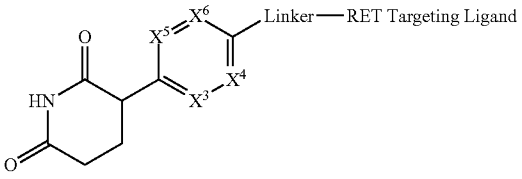

or a pharmaceutically acceptable salt thereof.

In certain embodiments the compound of the present invention is:

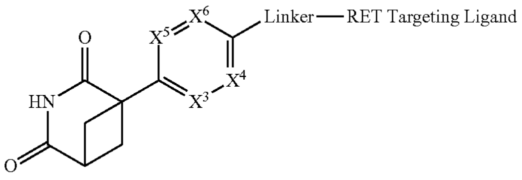

or a pharmaceutically acceptable salt thereof.

In certain embodiments the compound of the present invention is selected from:

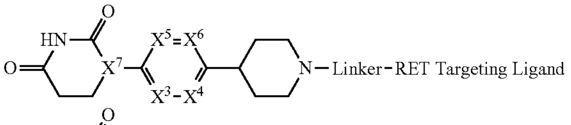

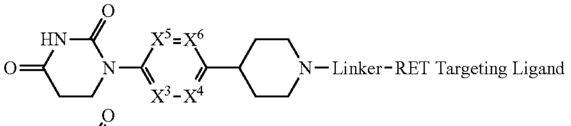

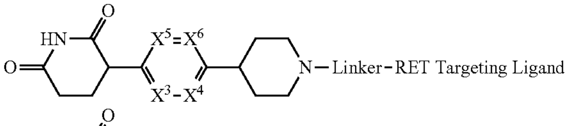

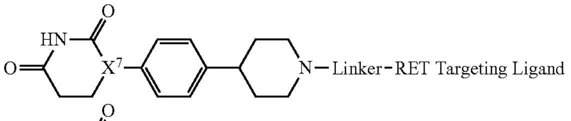

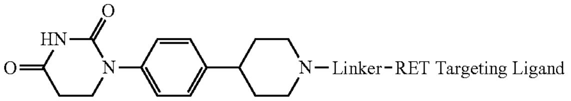

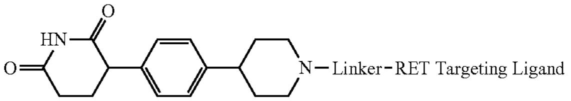

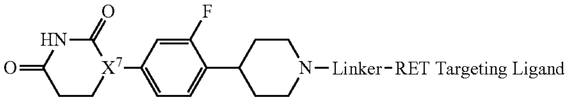

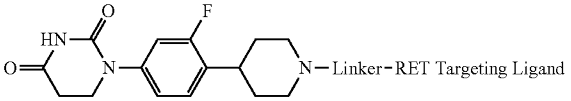

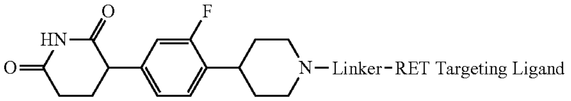

or a pharmaceutically acceptable salt thereof.

In certain embodiments, the compound of the present invention is selected from

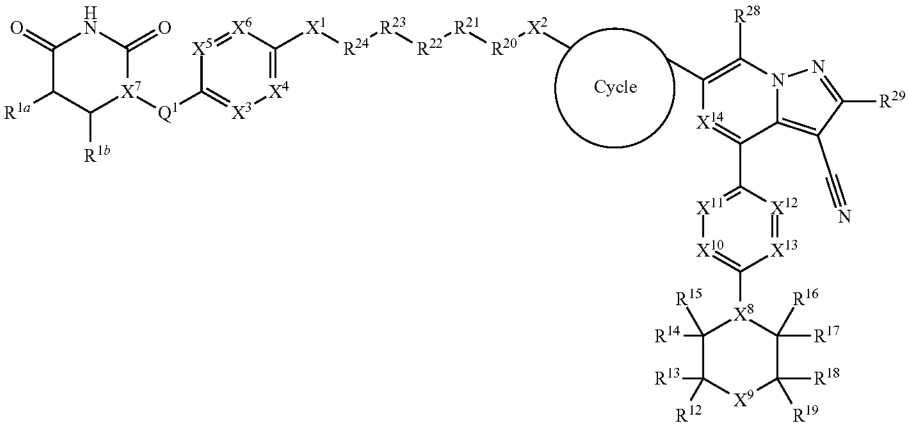

-continued
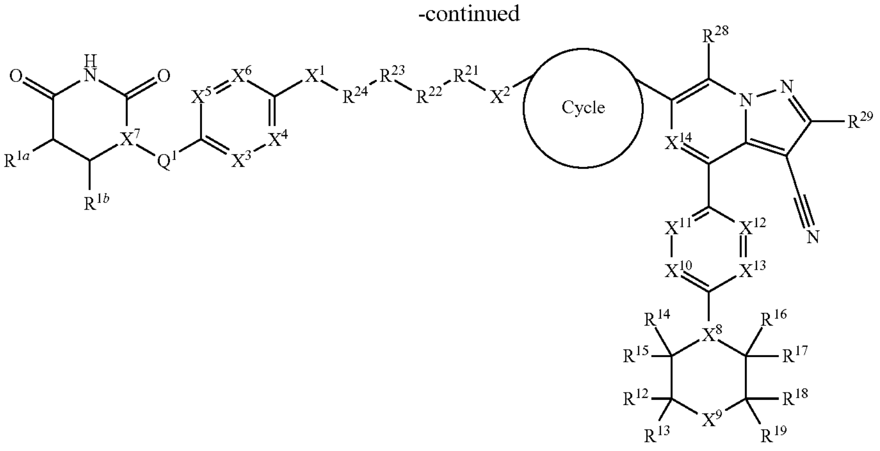
and
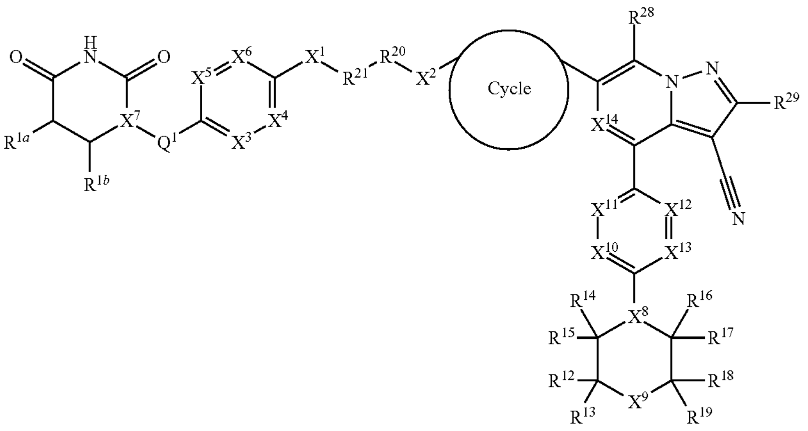
or a pharmaceutically acceptable salt thereof.
In certain embodiments, the compound of the present invention is selected from
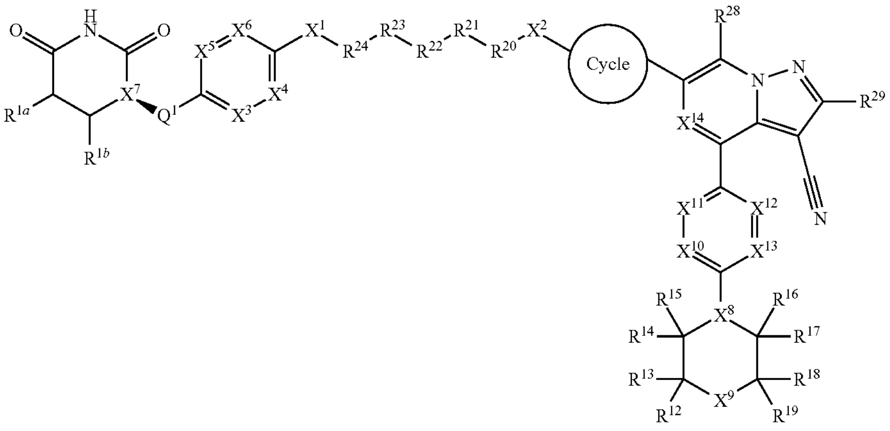

-continued
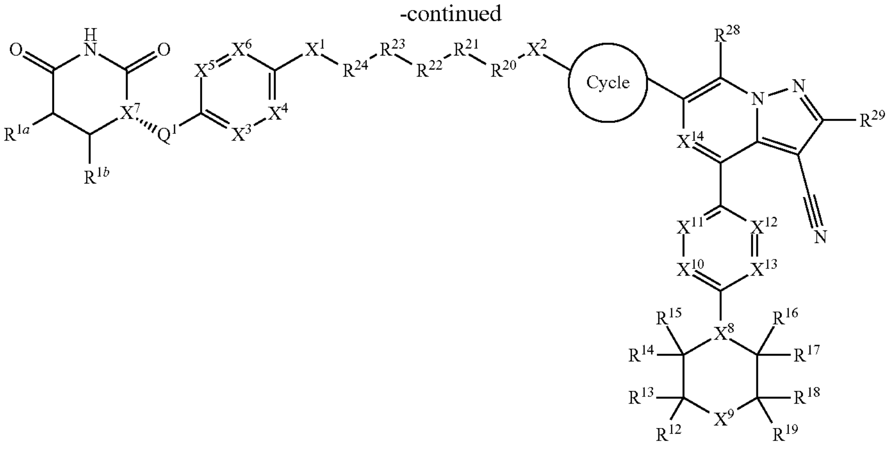
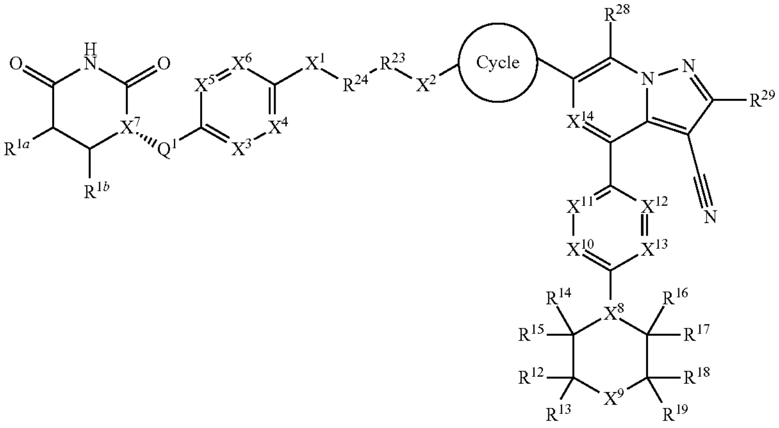
and
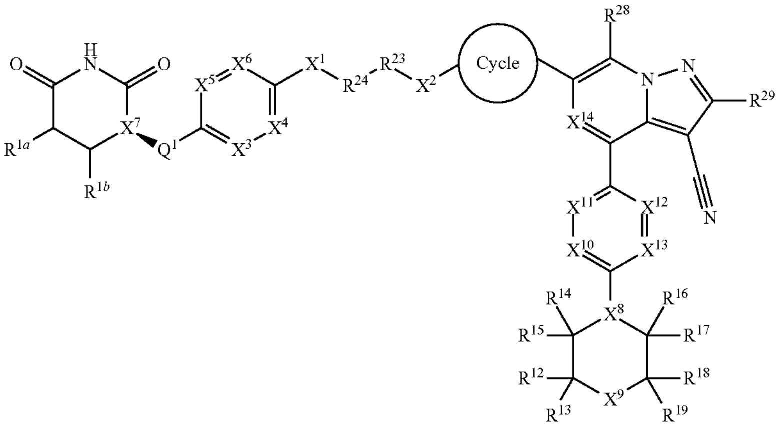
or a pharmaceutically acceptable salt thereof.
In certain embodiments, the compound of the present invention is selected from

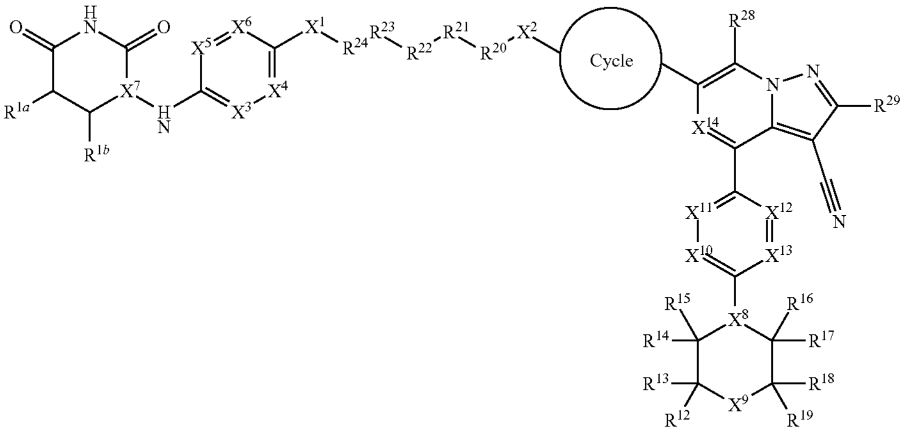
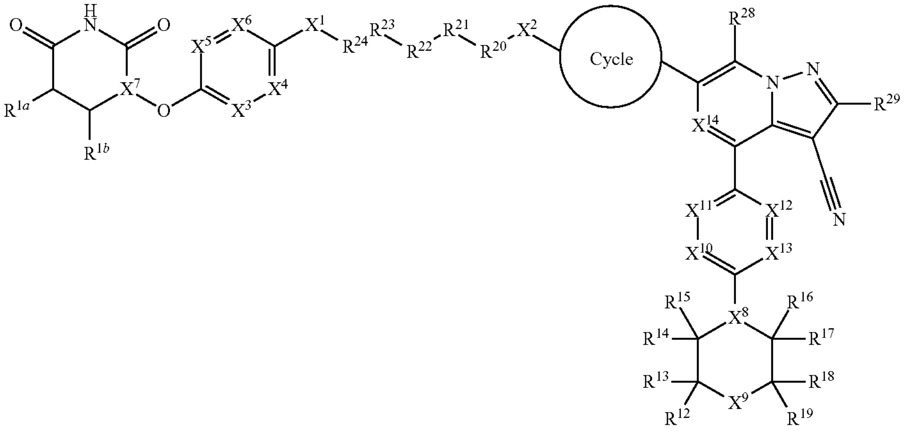
or a pharmaceutically acceptable salt thereof.
In certain embodiments, the compound of the present invention is selected from
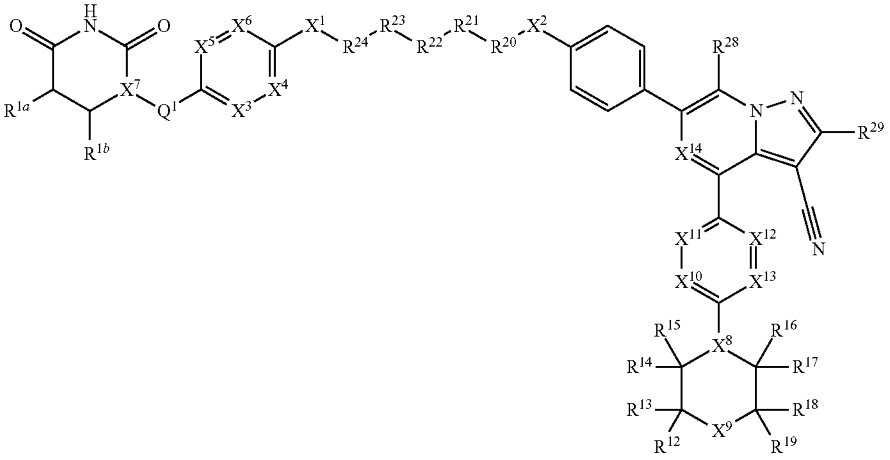

-continued
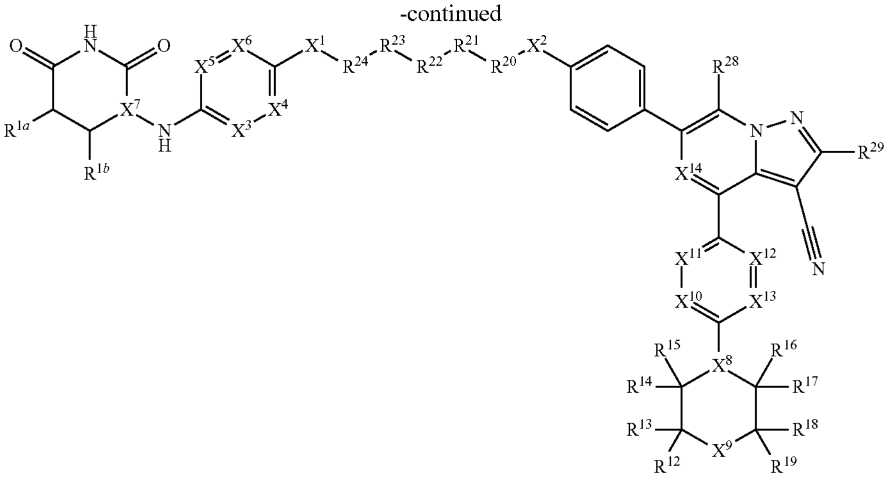
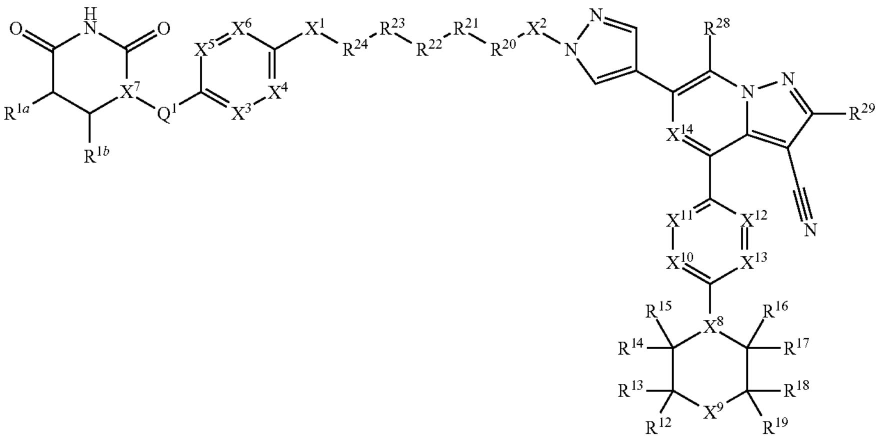
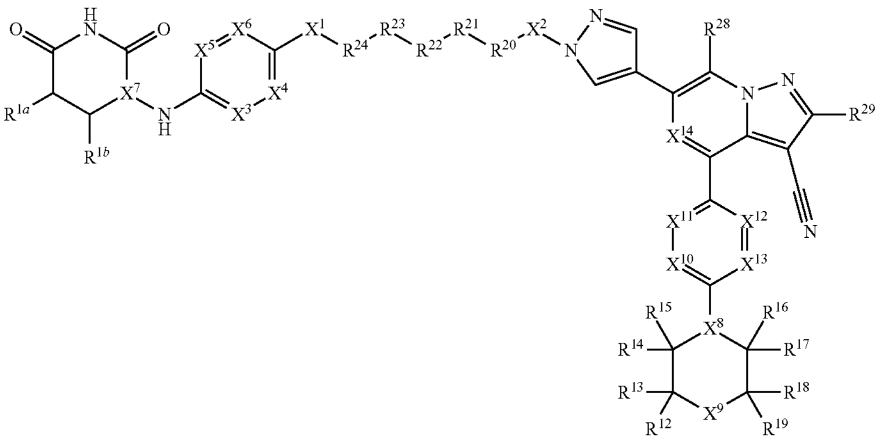
or a pharmaceutically acceptable salt thereof.
In certain embodiments, the compound of the present invention is selected from

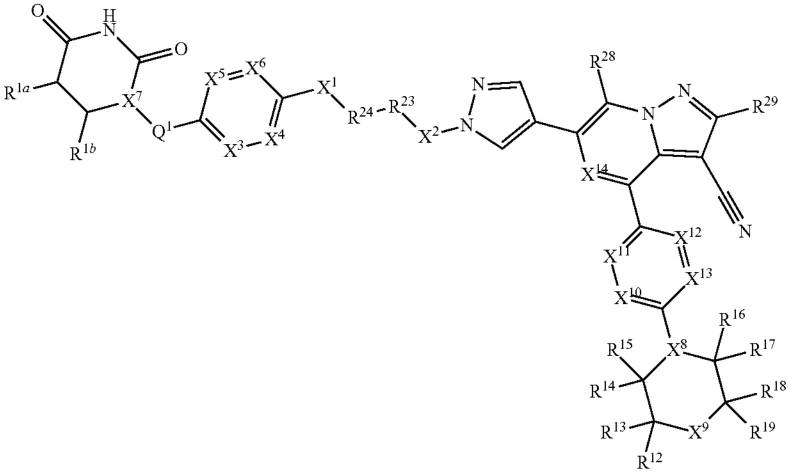
and
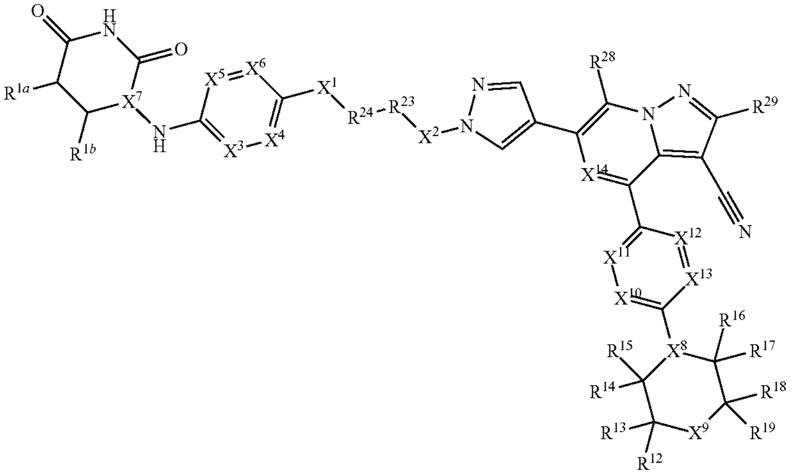
or a pharmaceutically acceptable salt thereof.
In certain embodiments, the compound of the present invention is selected from
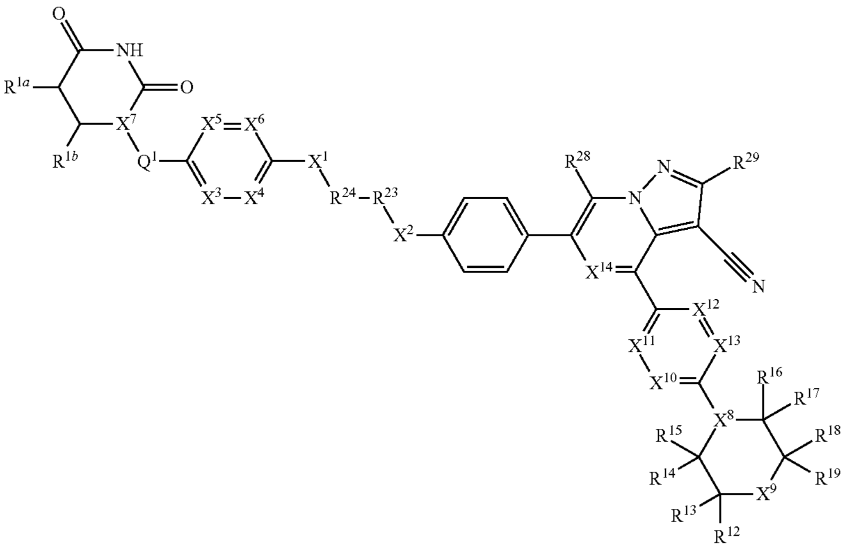

-continued
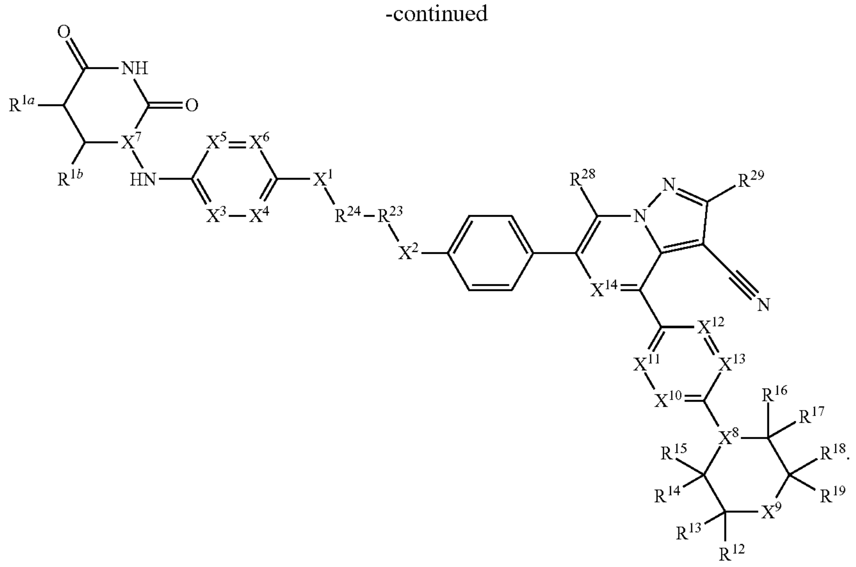
In certain embodiments, the compound of the present invention is selected from
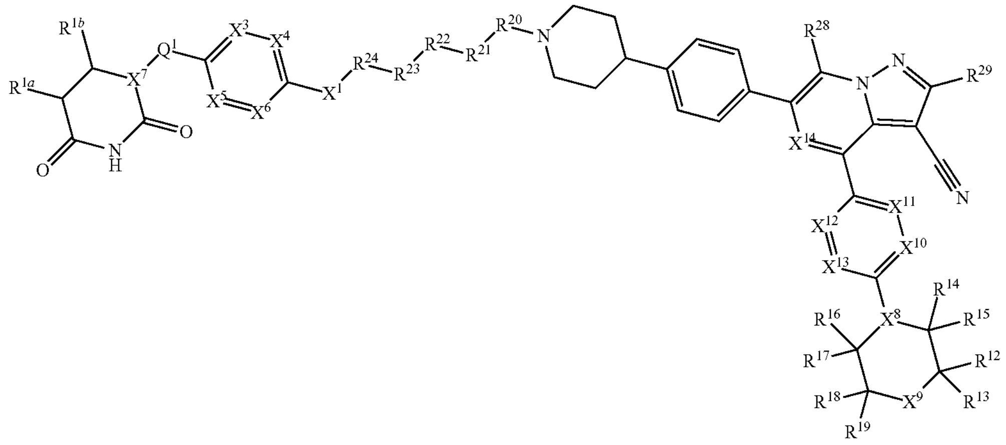
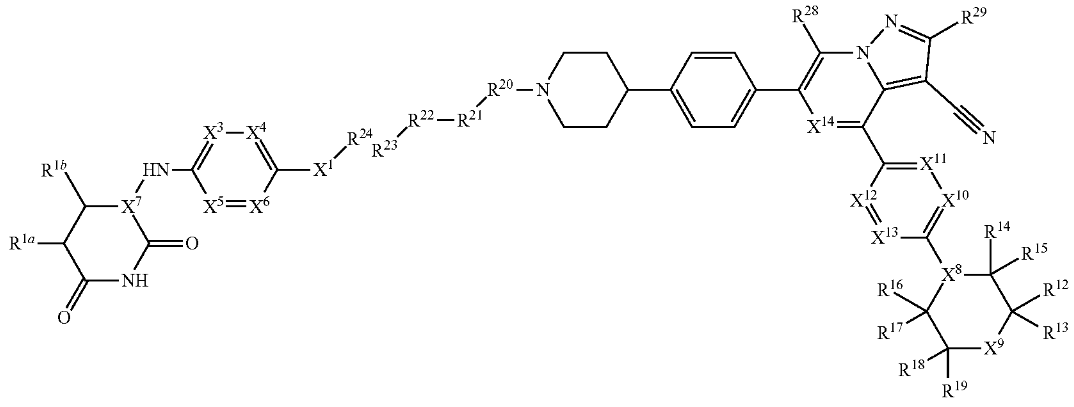
or a pharmaceutically acceptable salt thereof.
In certain embodiments, the compound of the present invention is selected from

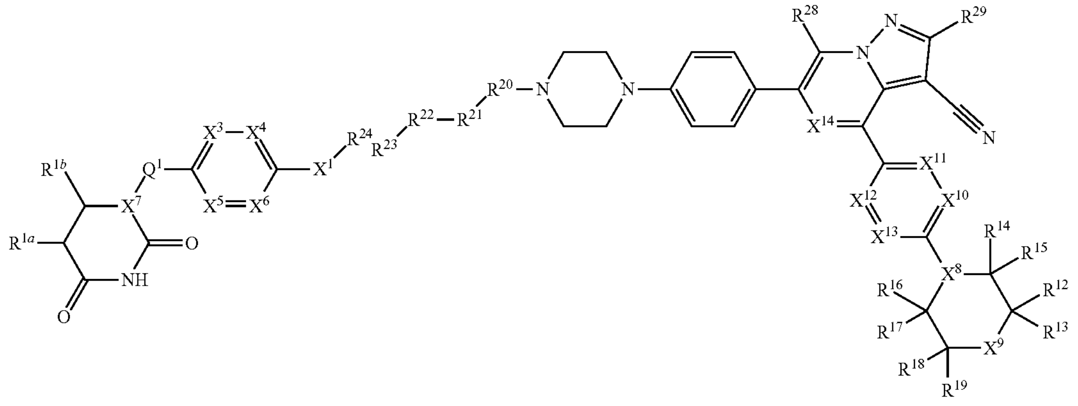
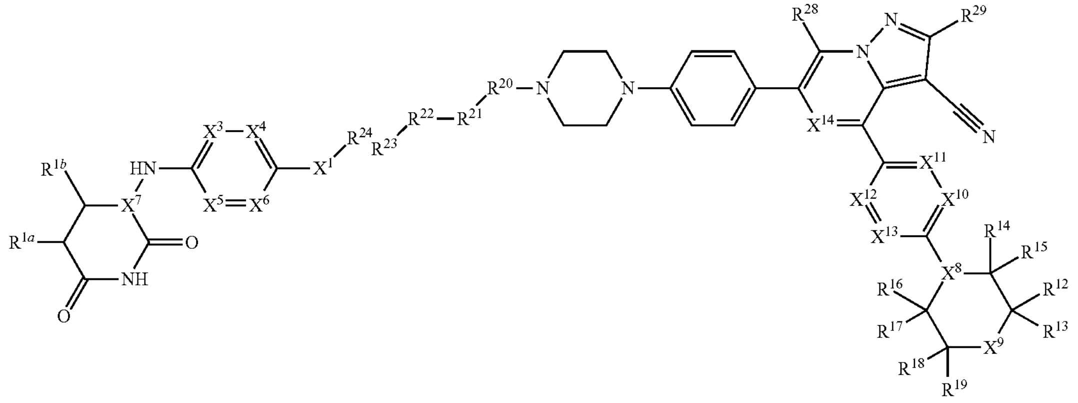
or a pharmaceutically acceptable salt thereof
In certain embodiments, the compound of the present invention is selected from
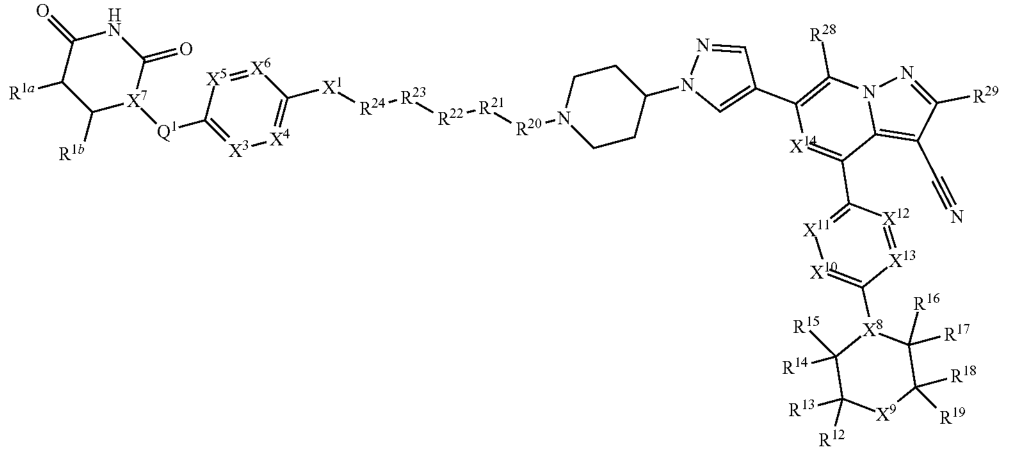

-continued
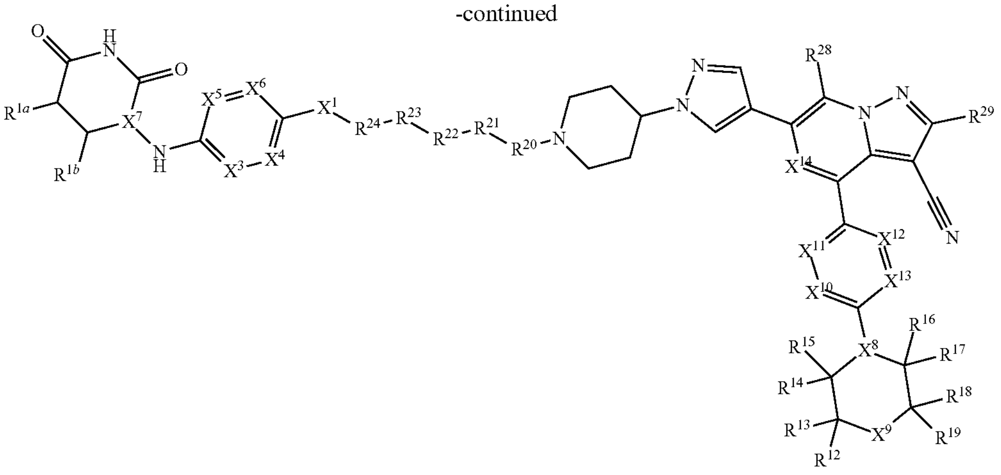
or a pharmaceutically acceptable salt thereof.
In certain embodiments, the compound of the present invention is selected from
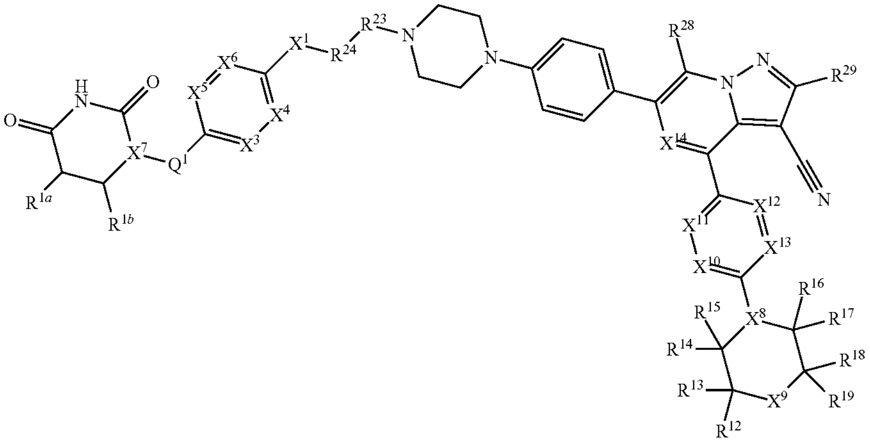
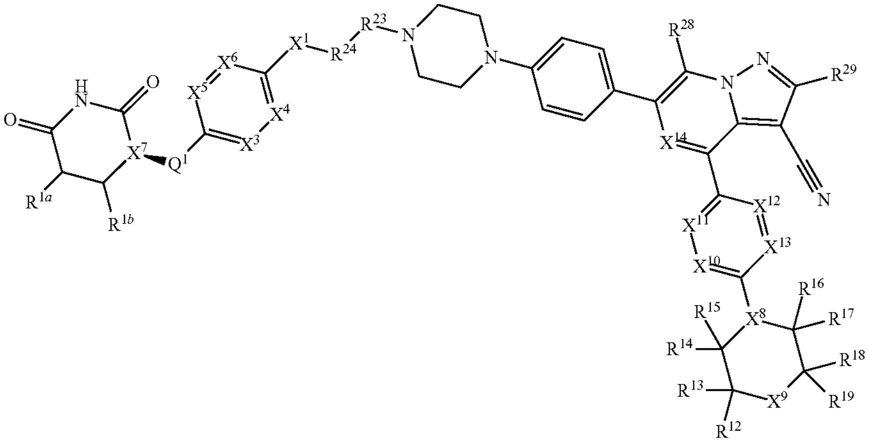
and -continued
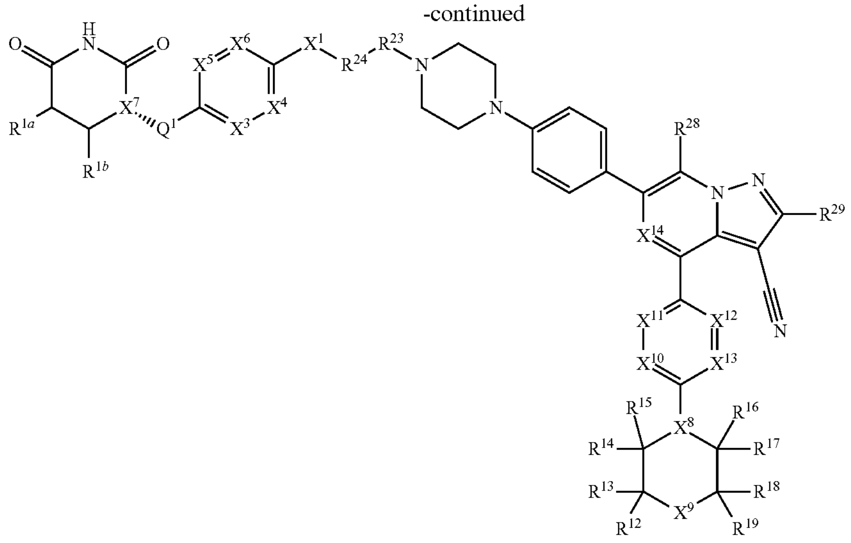
or a pharmaceutically acceptable salt thereof.
In certain embodiments, the compound of the present invention is selected from
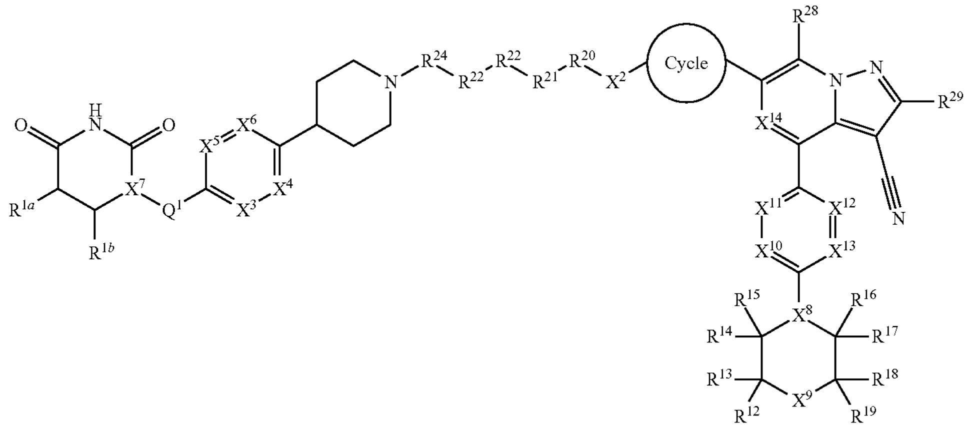
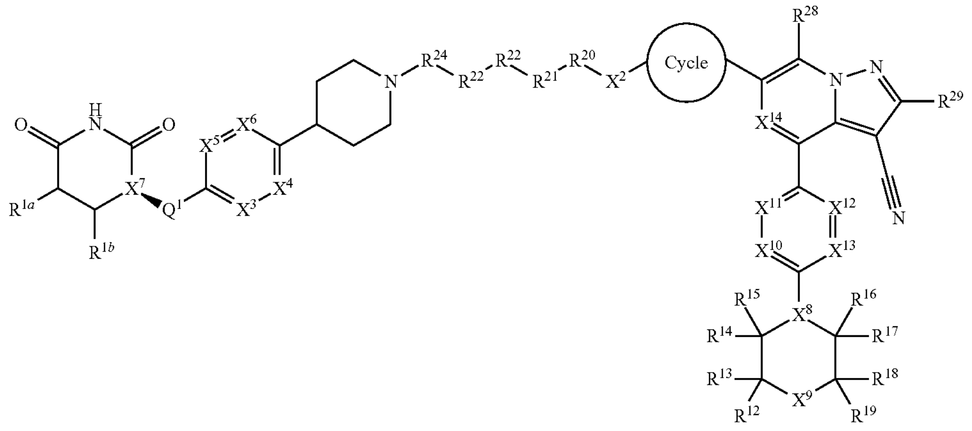

-continued
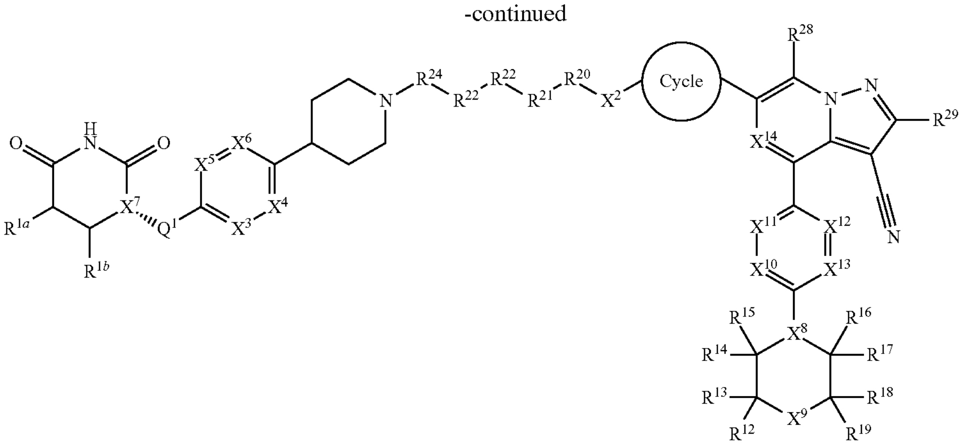
and
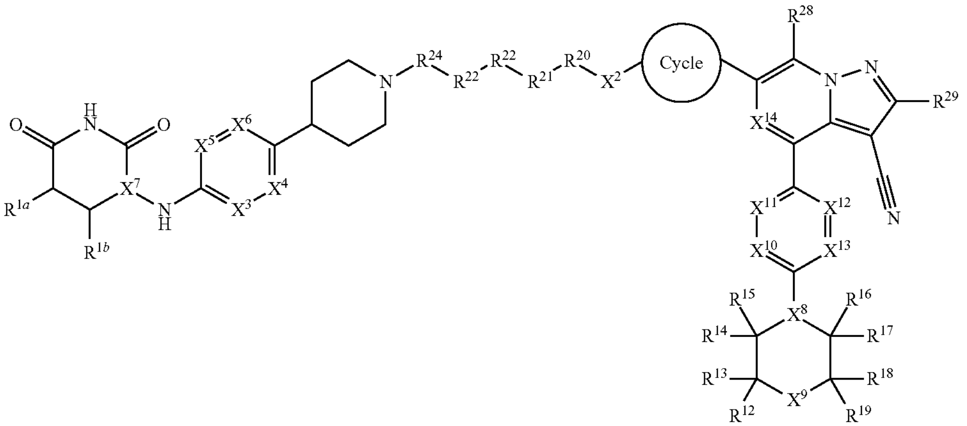
or a pharmaceutically acceptable salt thereof.
In certain embodiments, the compound of the present invention is selected from
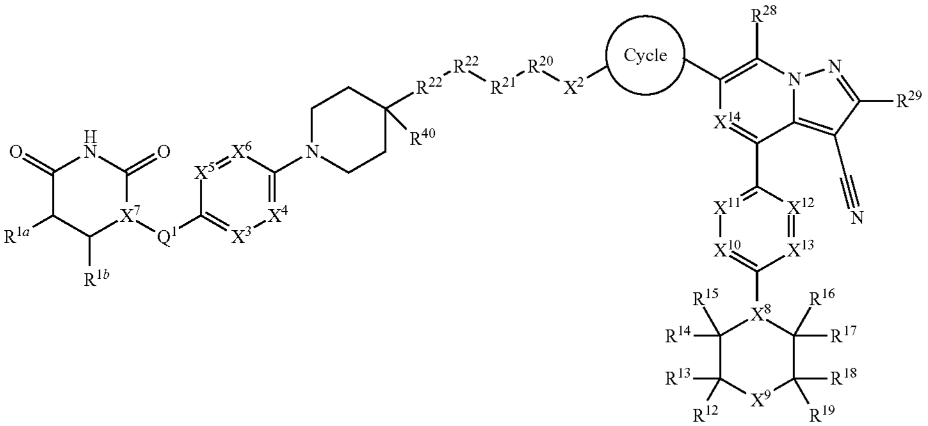

-continued
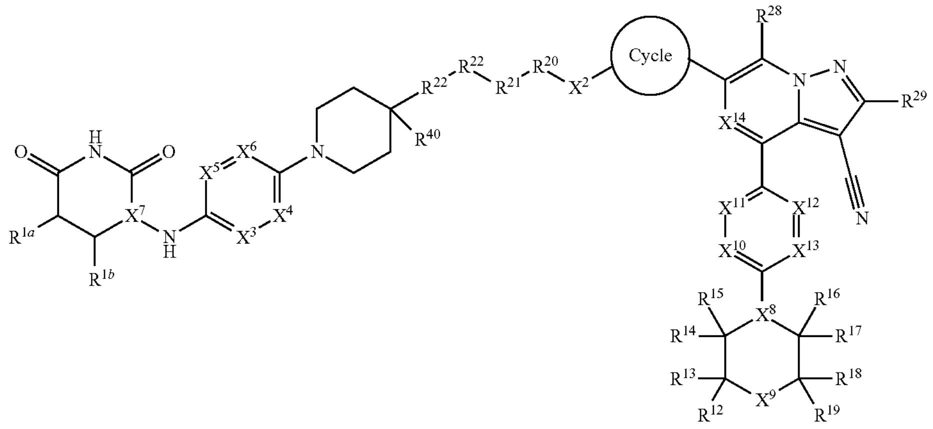
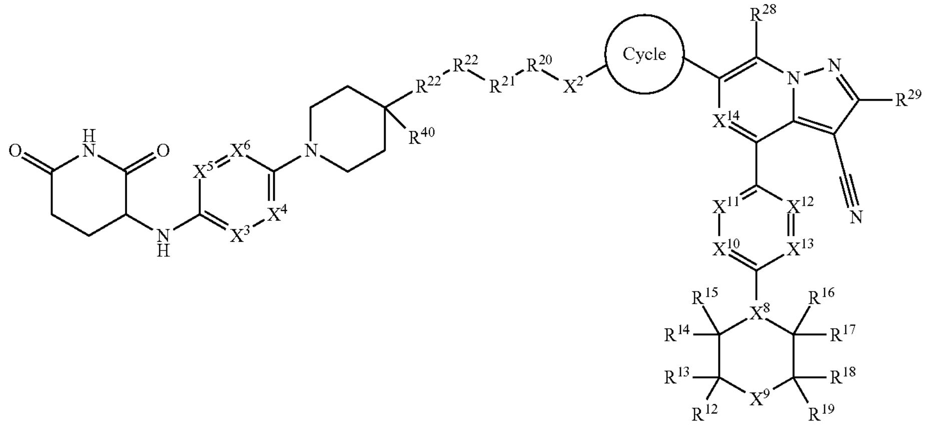
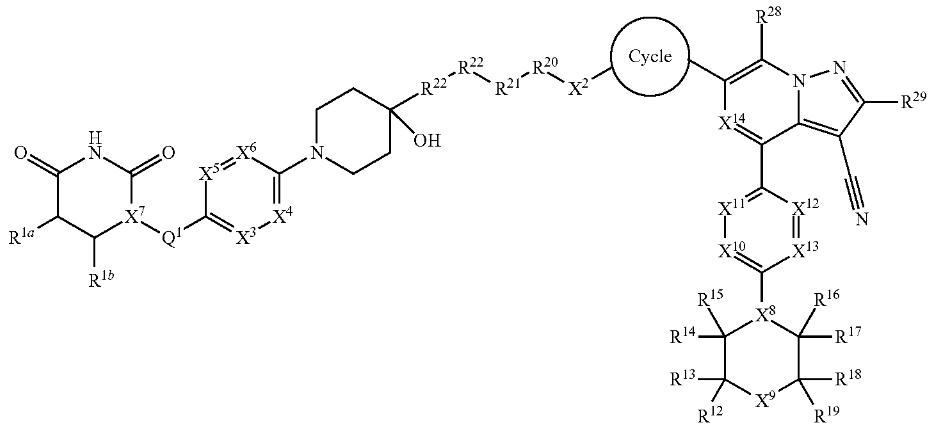
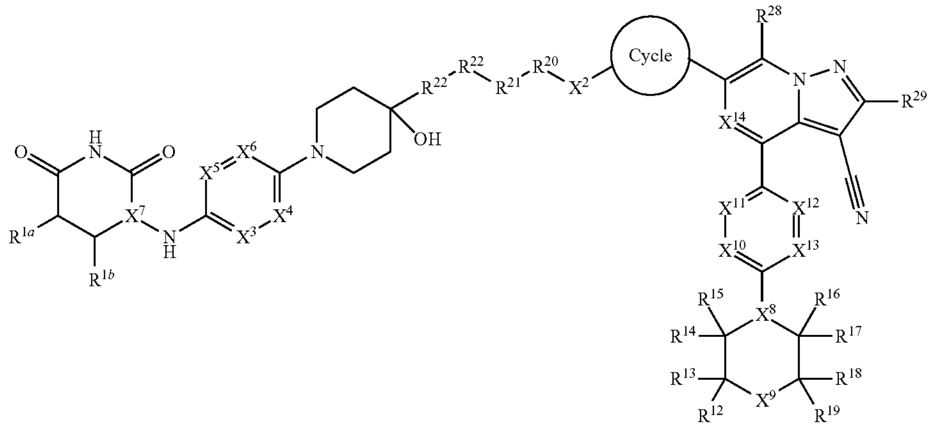

-continued
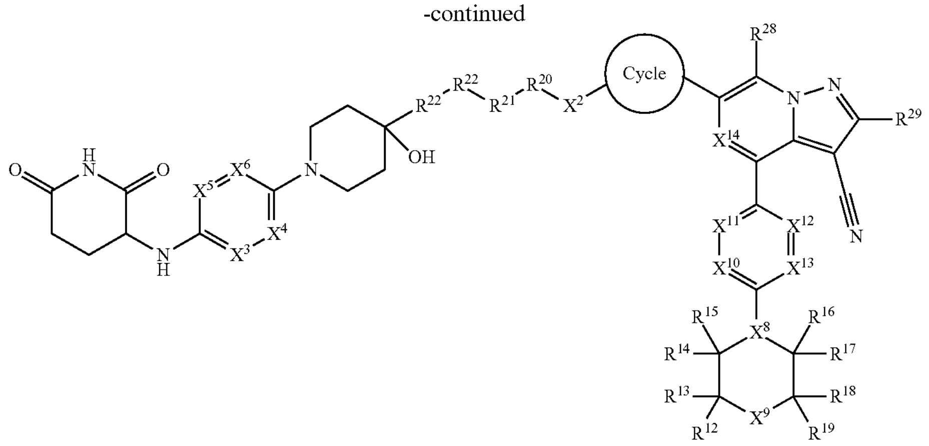
In certain embodiments, the compound of the present invention is selected from
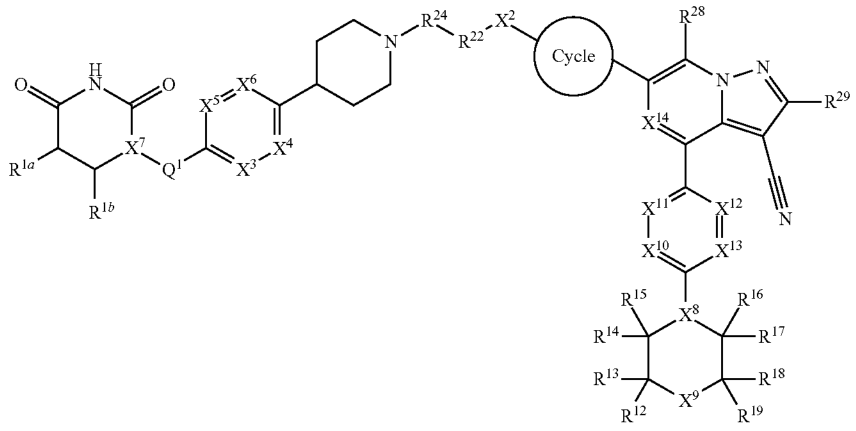
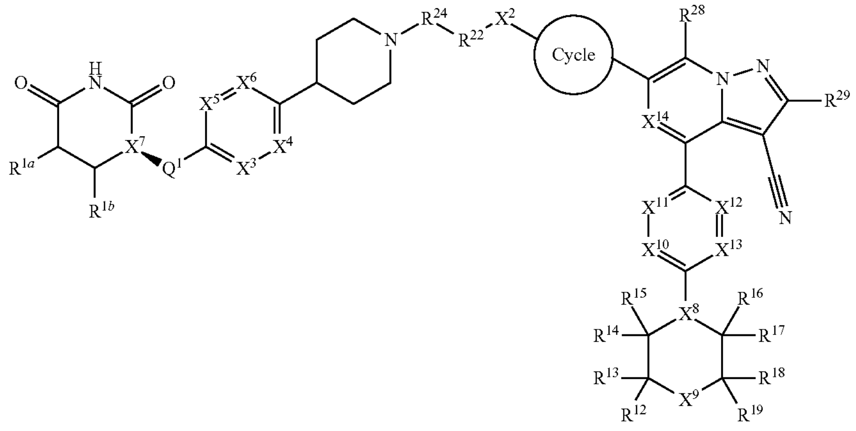

-continued
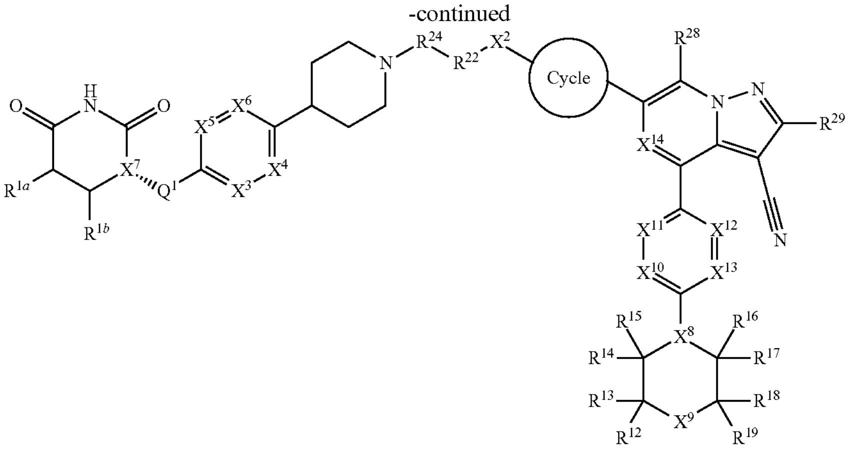
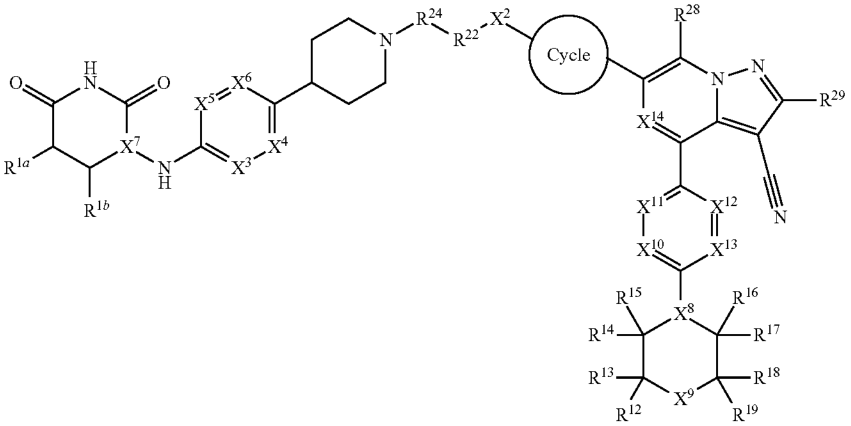
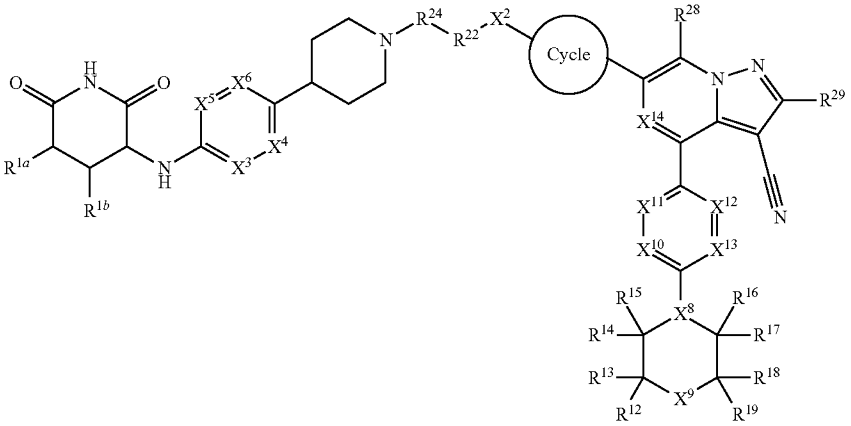
and
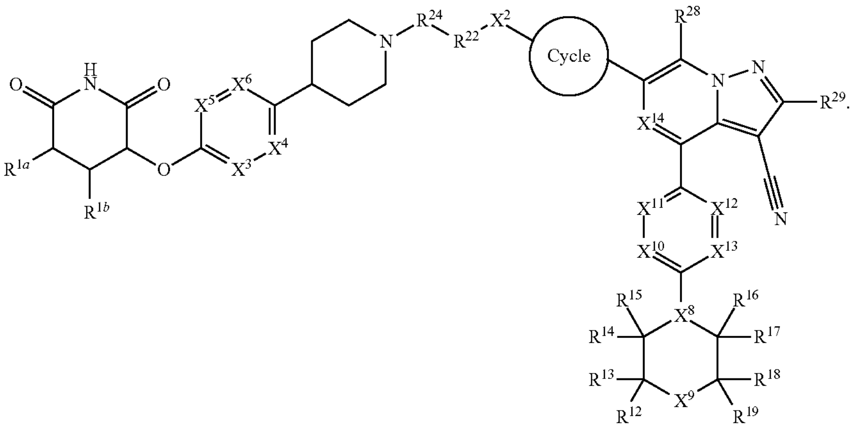

In certain embodiments the compound of the present invention is selected from:
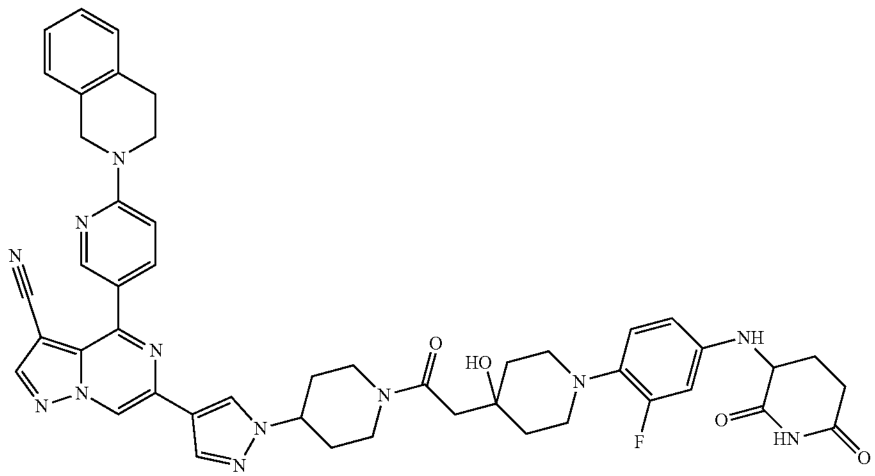
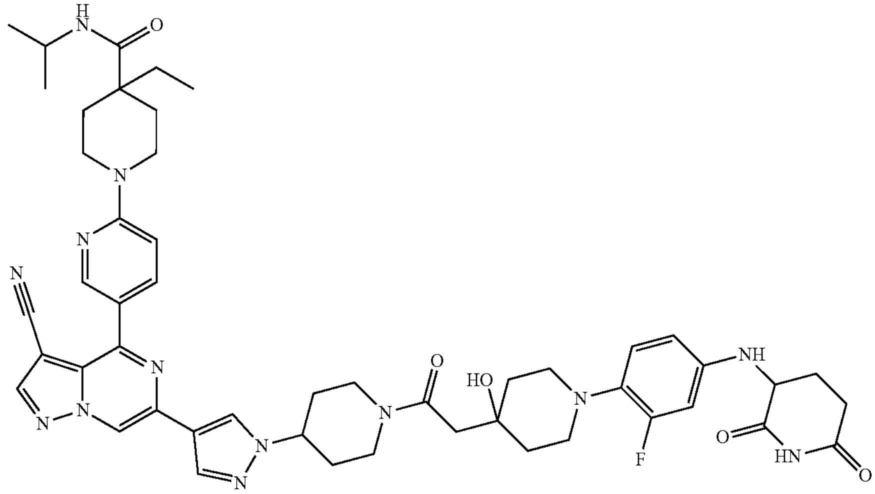
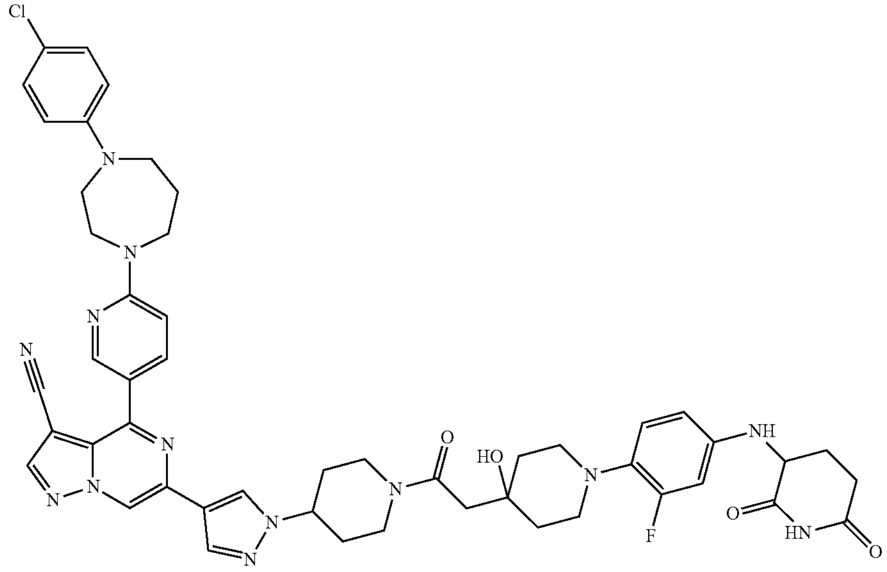
or a pharmaceutically acceptable salt thereof.
In certain embodiments the compound of the present invention is selected from:

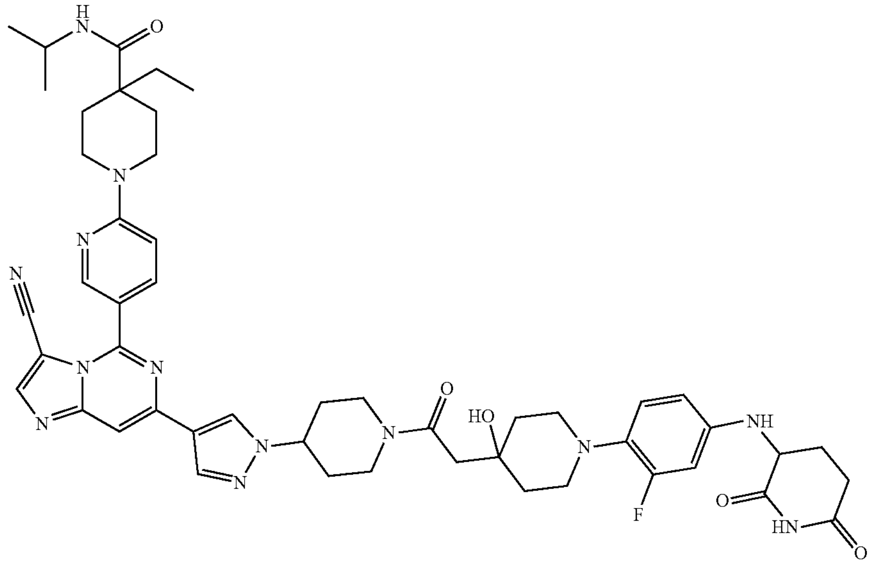 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7F)CC6)CC5)c4)cc4ncc(C#N)n34)cn2)CC1]
or a pharmaceutically acceptable salt thereof.
Embodiments of the Present Invention
In certain embodiments is
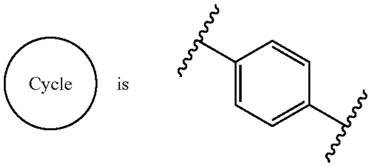 [SMILES: *c1ccc(*)cc1]
In certain embodiments
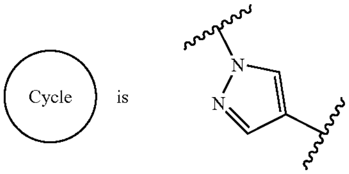 [SMILES: *c1cnn(*)c1]
In certain embodiments
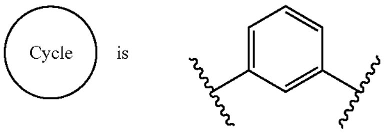 [SMILES: *c1cccc(*)c1]
In certain embodiments
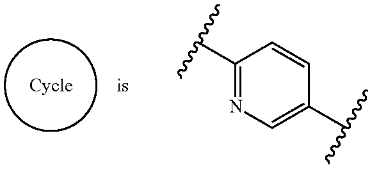 [SMILES: *c1ccc(*)nc1]
In certain embodiments
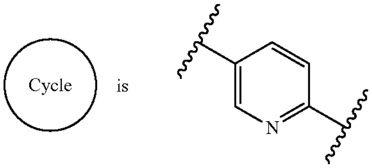 [SMILES: *c1ccc(*)nc1]
In certain embodiments
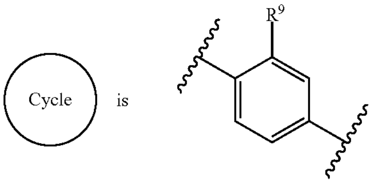
In certain embodiments
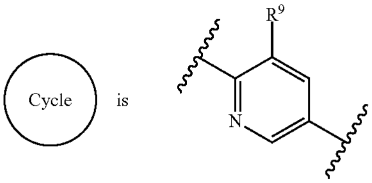

In certain embodiments

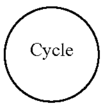 is 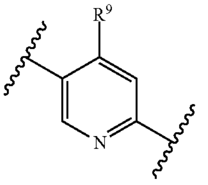

In certain embodiments

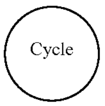 is 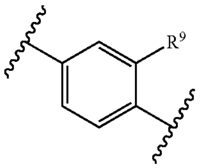

In certain embodiments

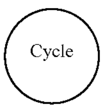 is 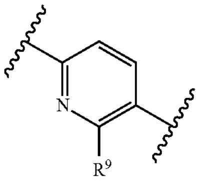

In certain embodiments

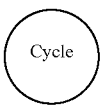 is 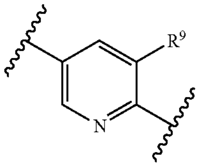

In certain embodiments at most two of $X^3$, $X^4$, $X^5$ and $X^6$ is N.

In certain embodiments all of $X^3$, $X^4$, $X^5$ and $X^6$ are CH.

In certain embodiments one of $X^3$, $X^4$, $X^5$ and $X^6$ is $CR^3$; wherein $R^3$ is selected from the group consisting of fluoro, chloro, and bromo. In certain embodiments $R^3$ is $C_1$-$C_4$haloalkyl. In certain embodiments $R^3$ is $C_1$-$C_4$alkyl.

In certain embodiments one of $X^3$, $X^4$, $X^5$ and $X^6$ is $CR^3$, wherein $R^3$ is $C_1$-$C_4$alkyl.

In certain embodiments $X^4$ or $X^6$ is N. In certain embodiments $X^4$ and $X^6$ are both N. In certain embodiments $X^4$ or $X^6$ is CH. In certain embodiments $X^4$ and $X^6$ are both CH.

In certain embodiments $X^4$ or $X^6$ is $CR^3$; wherein $R^3$ is selected from the group consisting of fluoro, chloro, and bromo.

In certain embodiments $X^4$ or $X^6$ is $CR^3$, wherein $R^3$ is selected from the group consisting of $C_1$-$C_4$haloalkyl, $CH_2F$, $CHF_2$, $CF_3$, $CH_2Cl$, $CHCl_2$, $CCl_3$, $CH_2Br$, $CHBr_2$, and $CBr_3$.

In certain embodiments $X^4$ or $X^6$ is $CR^3$; wherein $R^3$ is $C_1$-$C_4$alkyl.

In certain embodiments, $X^7$ is N and $Q^1$ is $CH_2$. In certain embodiments, $X^7$ is CH. In certain embodiments, $X^7$ is $C_1$-$C_4$alkyl. In certain embodiments, $X^7$ is $C_1$-$C_4$haloalkyl.

In certain embodiments $X^8$ is CH.

In certain embodiments $X^8$ is N.

In certain embodiments $X^9$ is $NR^4$.

In certain embodiments $X^9$ is O.

In certain embodiments $X^9$ is $CR^4R^{11}$.

In certain embodiments, $Q^1$ is NH. In certain embodiments, $Q^1$ is O. In certain embodiments, $Q^1$ is S. In certain embodiments, $Q^1$ is $CH_2$. In certain embodiments, $Q^1$ is N(alkyl) wherein the alkyl is a $C_1$-$C_4$alkyl, or $C_1$-$C_4$haloalkyl. In certain embodiments, $Q^1$ is N(haloalkyl) wherein the haloalkyl is a $C_1$-$C_4$haloalkyl.

In certain embodiments, R is hydrogen. In certain embodiments R is selected from the group consisting of fluoro, chloro, and bromo. In certain embodiments, R is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments, R is $C_1$-$C_4$alkyl.

In certain embodiments, $R^{1a}$ is hydrogen. In certain embodiments $R^{1a}$ is selected from the group consisting of fluoro, chloro, and bromo. In certain embodiments $R^{1a}$ is $C_1$-$C_4$haloalkyl, $CH_2F$, $CHF_2$, $CF_3$, $CH_2Cl$ $CHCl_2$, $CCl_3$, $CH_2Br$, $CHBr_2$, or $CBr_3$. In certain embodiments $R^{1a}$ is cycloalkyl.

In certain embodiments, $R^{1b}$ is hydrogen. In certain embodiments $R^{1b}$ is selected from the group consisting of fluoro, chloro, and bromo. In certain embodiments $R^{1b}$ is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^{1b}$ is cycloalkyl.

In certain embodiments, $R^{1c}$ is hydrogen. In certain embodiments $R^{1c}$ is selected from the group consisting of fluoro, chloro, and bromo. In certain embodiments $R^{1c}$ is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^{1c}$ is cycloalkyl.

In certain embodiments, $R^{1d}$ is hydrogen. In certain embodiments $R^{1d}$ is selected from the group consisting of fluoro, chloro, and bromo. In certain embodiments $R^{1d}$ is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^{1d}$ is cycloalkyl.

In certain embodiments, $R^3$ is hydrogen. In certain embodiments $R^3$ is selected from the group consisting of fluoro, chloro, and bromo. In certain embodiments $R^3$ is a $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^3$ is $C_1$-$C_4$alkoxy. In certain embodiments, $R^4$ is $C_1$-$C_4$alkyl. In certain embodiments $R^3$ is cycloalkyl.

In certain embodiments, $R^4$ is hydrogen. In certain embodiments $R^4$ is selected from the group consisting of fluoro, chloro, and bromo. In certain embodiments $R^4$ is a $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^4$ is $C_1$-$C_4$alkoxy. In certain embodiments, $R^4$ is $C_1$-$C_4$alkyl. In certain embodiments, $R^4$ is C1-$C_4$haloalkoxy.

In certain embodiments, $R^5$ is hydrogen. In certain embodiments $R^5$ is a $C_1$-$C_4$alkyl. In certain embodiments, $R^5$ is allyl. In certain embodiments, $R^5$ is crotyl. In certain embodiments, $R^5$ is alkenyl. In certain embodiments, $R^5$ is alkynyl. In certain embodiments, $R^5$ is haloalkyl. In certain embodiments, $R^5$ is cycloalkyl.

In alternative embodiments, $R^5$ is a bicycle substituted with —$OR^6$, —$NR^6R^7$, —$OC(O)R^{5'}$, —$NR^6C(O)R^{5'}$, —$C(O)R^{5'}$, -alkyl-$OR^6$, -alkyl-$NR^6R^7$, -alkyl-$OC(O)R^{5'}$, -alkyl-$NR^6C(O)R^{5'}$, or -alkyl-$C(O)R^{5'}$, and optionally substituted with 1, 2, or 3 substituents selected from $R^8$; wherein $R^{5'}$ is hydrogen, $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, bicycle, -alkyl-heteroaryl, -alkyl-aryl, -alkyl-heterocycle, —$OR^6$, or —$NR^6R^7$, each of which $C_1$-$C_4$alkyl, $C_2$-$C_4$alkenyl, $C_2$-$C_4$alkynyl, $C_1$-$C_4$haloalkyl, cycloalkyl, heteroaryl, aryl, heterocycle, -alkyl-heteroaryl, -alkyl-aryl, and -alkyl-heterocycle groups is optionally substituted with 0, 1, 2, or 3 substituents independently selected from $R^9$.

In certain embodiments, $R^6$ is hydrogen. In certain embodiments $R^6$ is selected from the group consisting of fluoro, chloro, and bromo. In certain embodiments $R^6$ is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^6$ is $C_1$-$C_4$alkyl.

In certain embodiments, $R^7$ is hydrogen. In certain embodiments $R^7$ is selected from the group consisting of fluoro, chloro, and bromo. In certain embodiments $R^7$ is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^7$ is $C_1$-$C_4$alkyl.

In certain embodiments, $R^8$ is hydrogen. In certain embodiments $R^8$ is a $C_1$-$C_4$alkyl. In certain embodiments, $R^8$ is haloalkyl. In certain embodiments, $R^8$ is cycloalkyl.

In certain embodiments

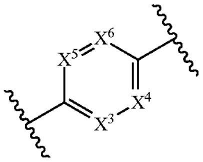

is selected from the group consisting of:

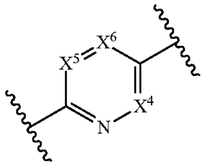
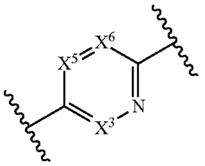
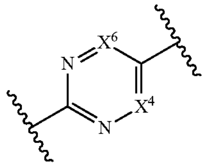
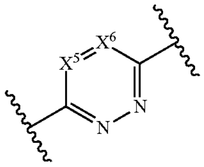
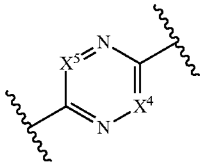
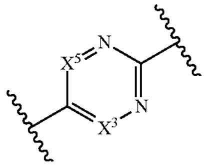
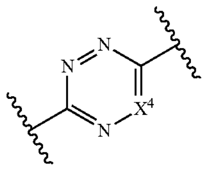
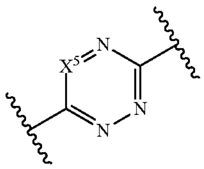

-continued

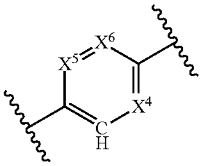
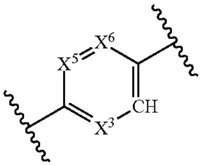
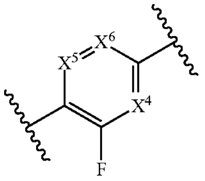
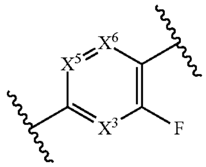
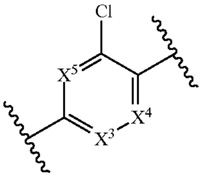
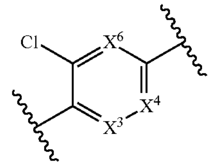
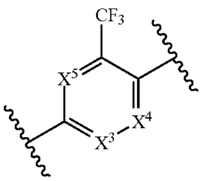

and

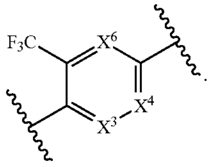

In an alternative embodiment the para-connected structures in the embodiments herein are in the meta configuration.

In certain embodiments

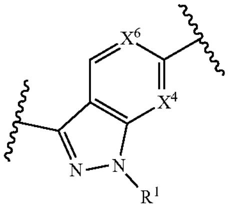

is selected from the group consisting of:

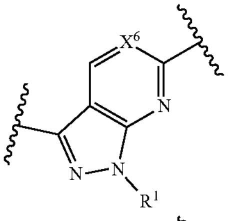
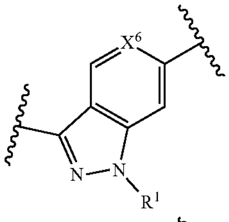
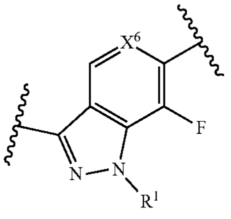
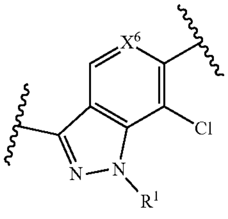

-continued
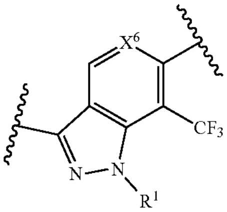 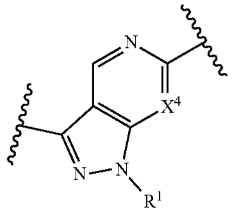
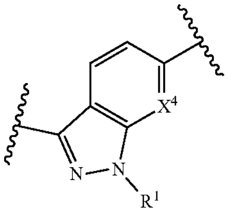 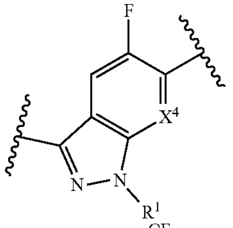
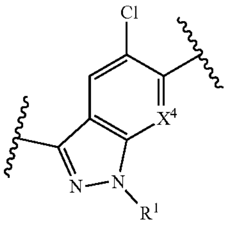 and 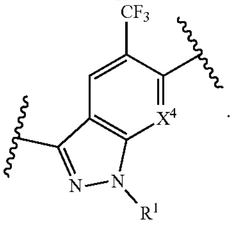.
In certain embodiments
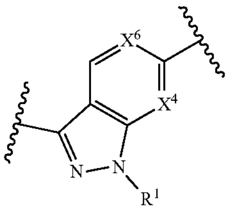
is selected from the group consisting of:
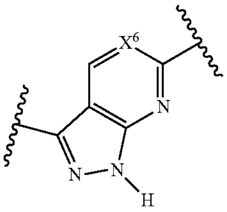 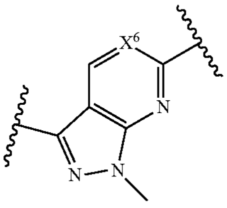
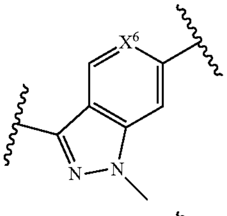 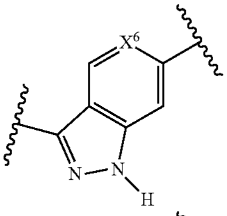
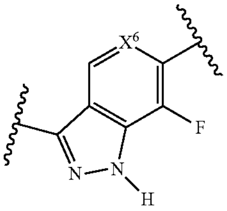 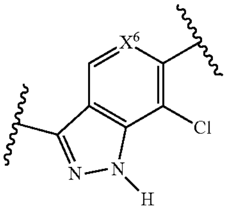
-continued
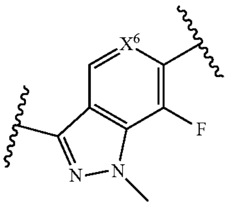 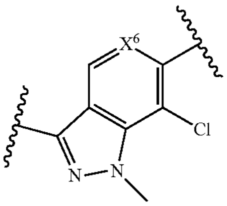
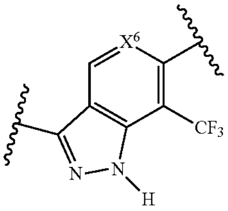 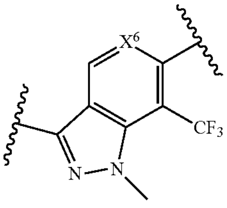
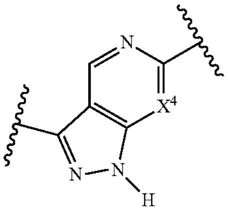 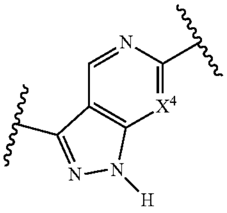
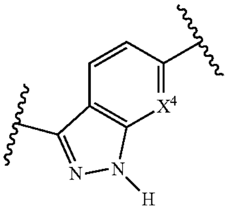 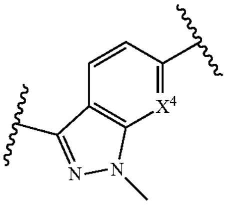
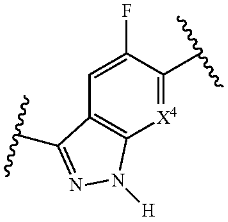 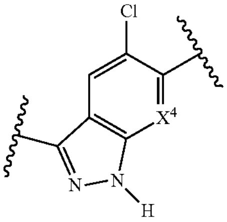
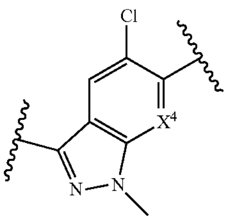 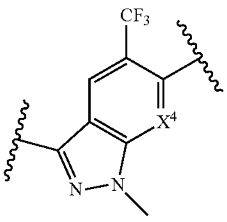 and
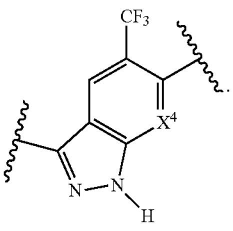.

In certain embodiments
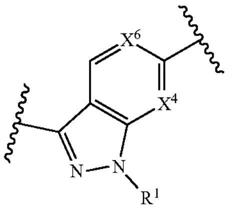
is selected from the group consisting of:
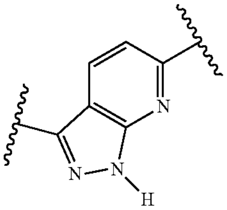
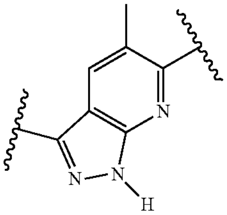
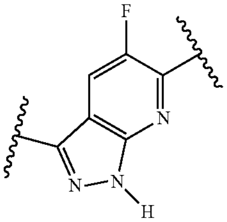
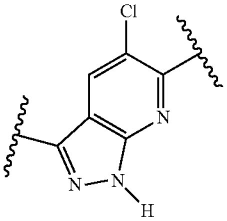
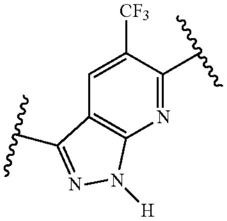
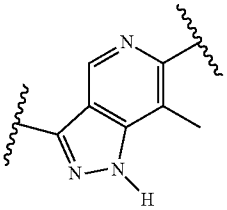
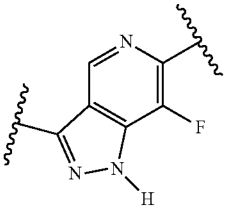
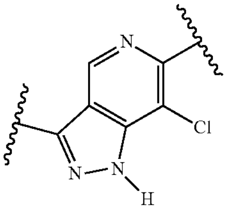
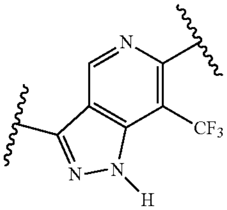
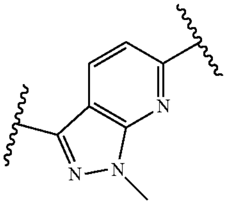
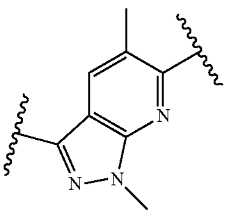
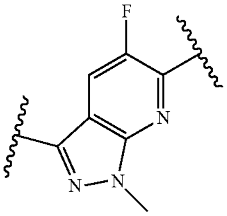
-continued
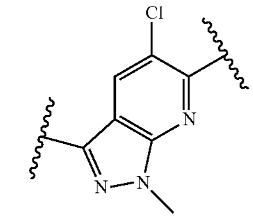
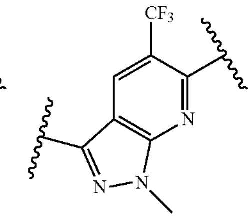
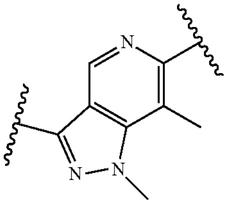
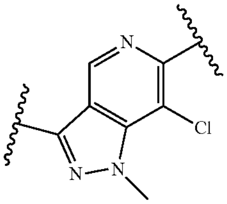
and
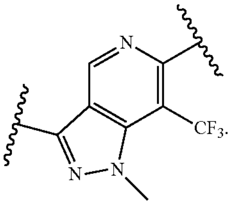
In certain embodiments,
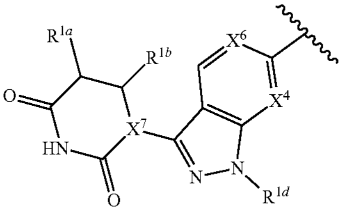
is selected from
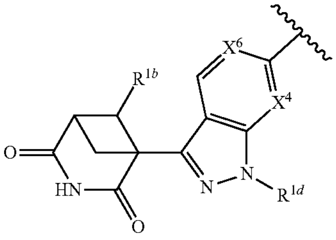
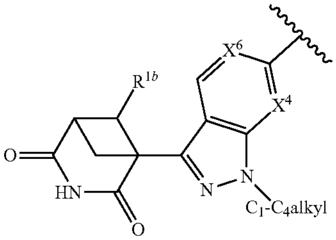

-continued
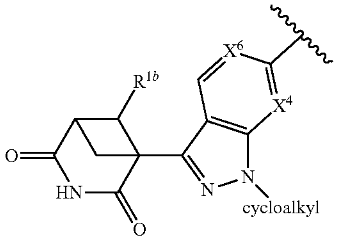
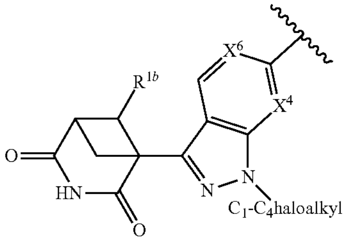
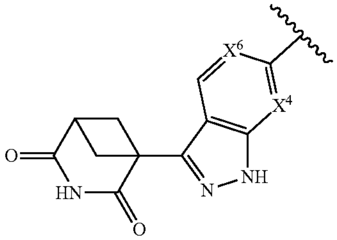
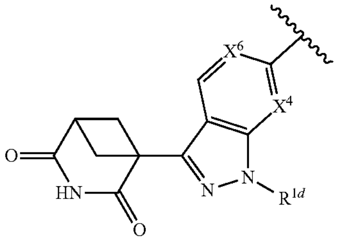
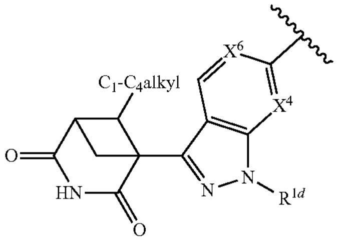
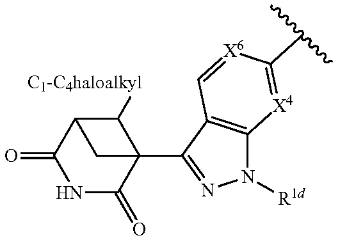
and
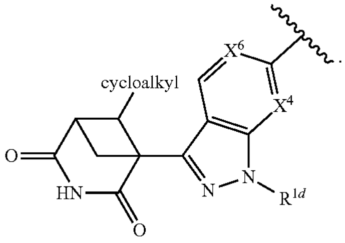
.
In certain embodiments,
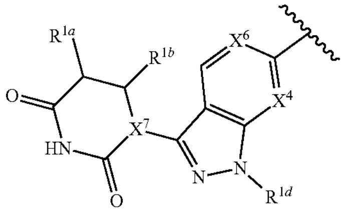
is selected from
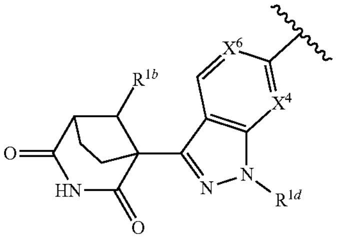
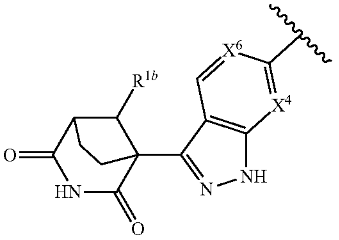
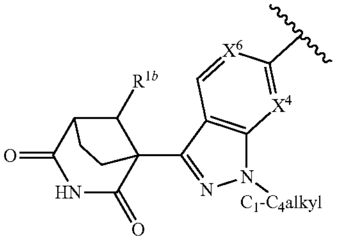
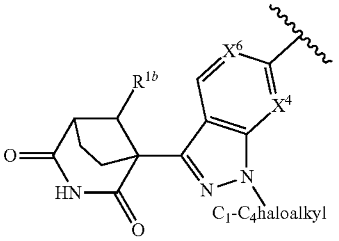
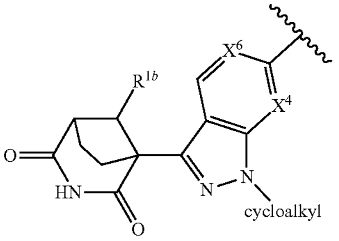

-continued
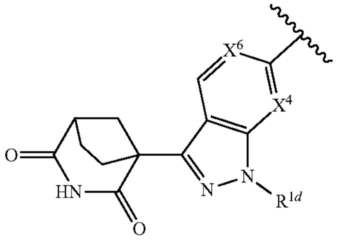
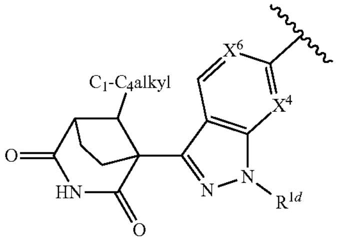
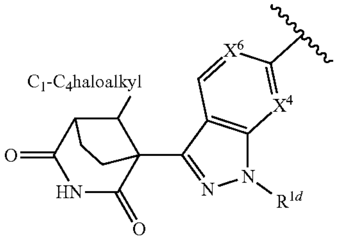
and
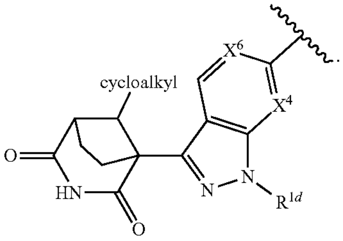
.
In certain embodiments,
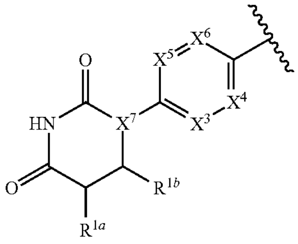
is selected from
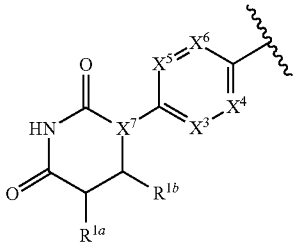
-continued
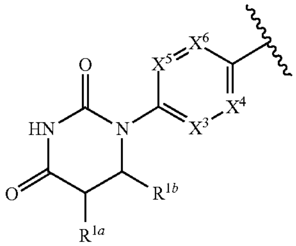
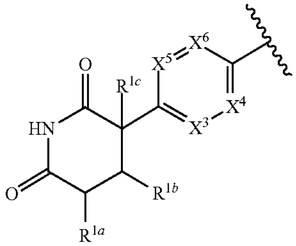
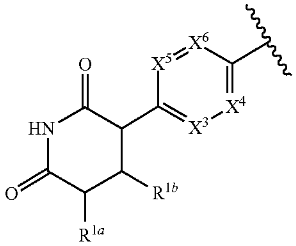
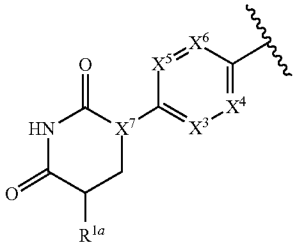
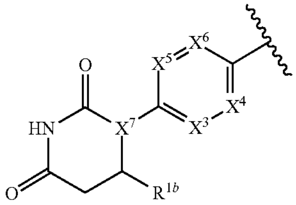
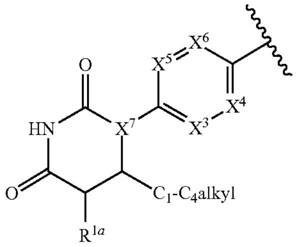
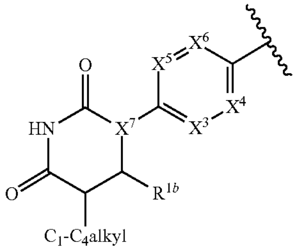

-continued
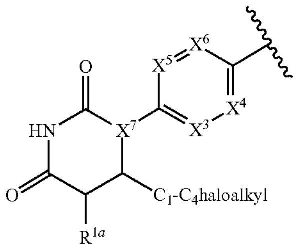
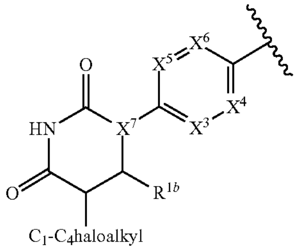
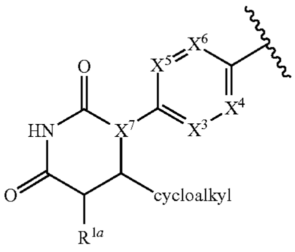
and
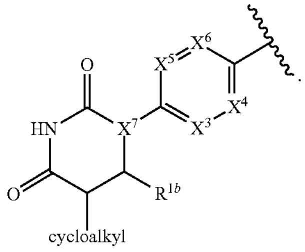
In certain embodiments,
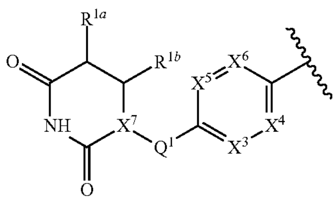
is selected from
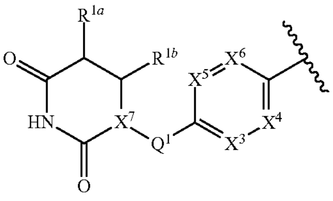
-continued
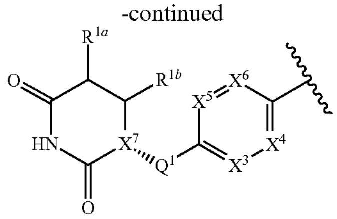
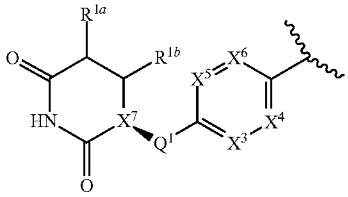
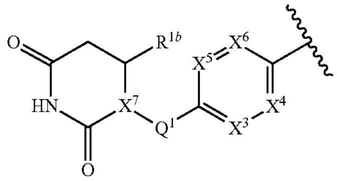
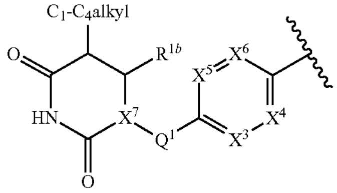
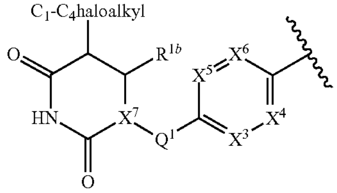
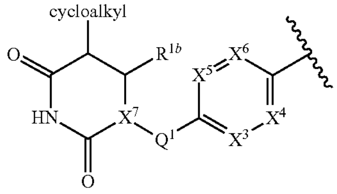
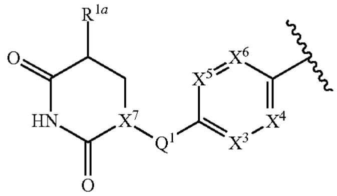
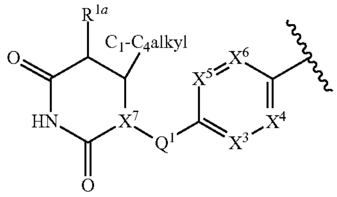
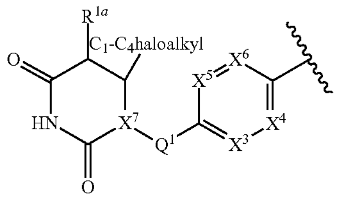

-continued
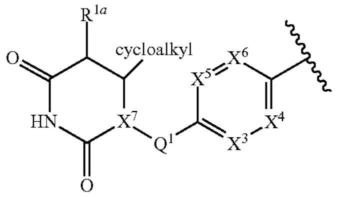
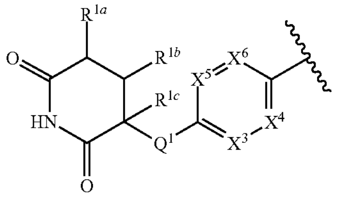
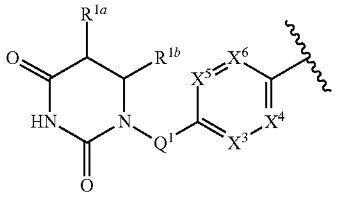
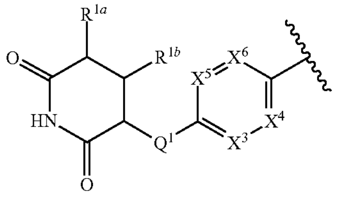
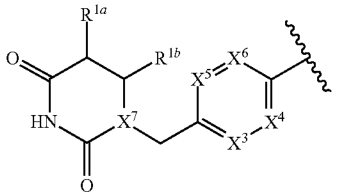
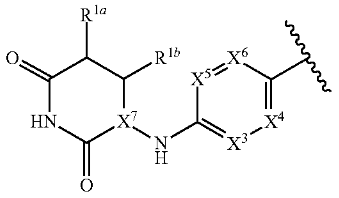
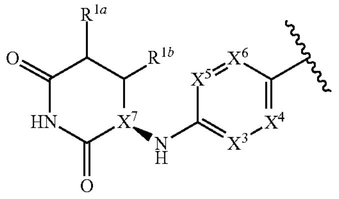
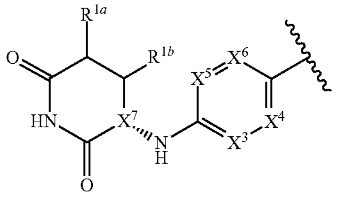
-continued
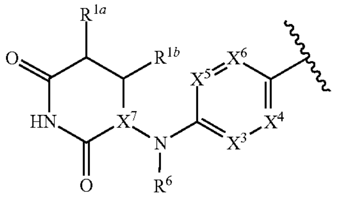
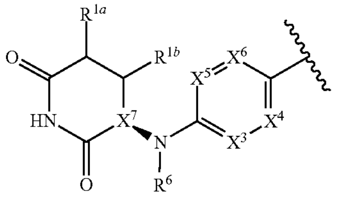
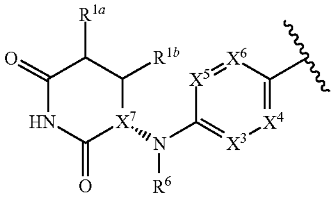
and
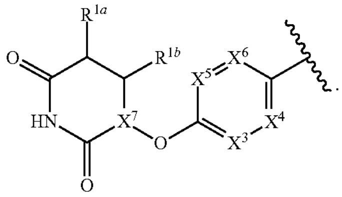
.
In certain embodiments,
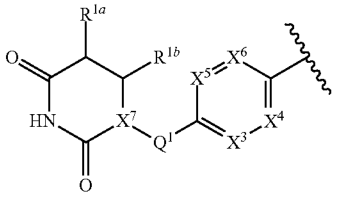
is selected from
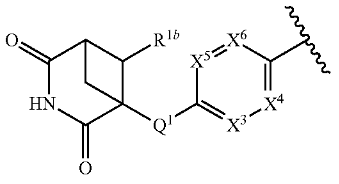
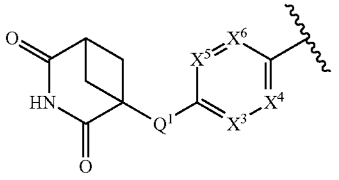

-continued
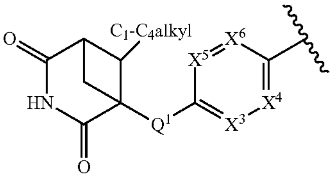
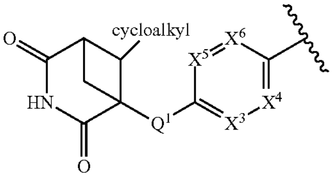
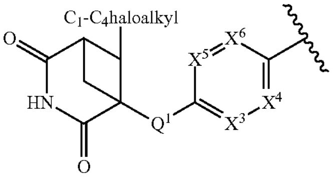
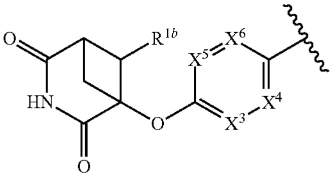
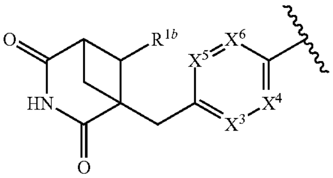
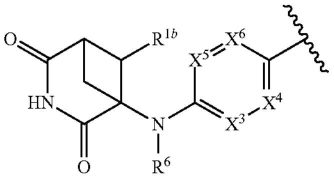
and
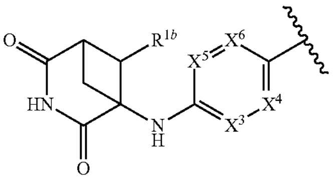
.
In certain embodiments,
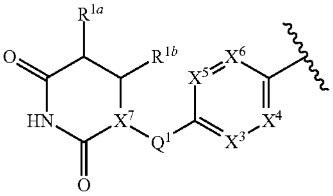
is selected from
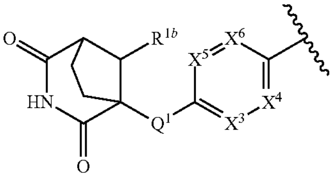
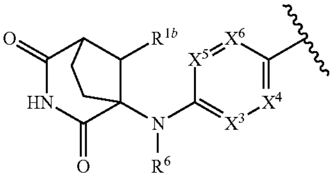
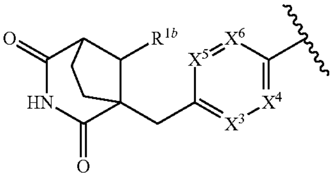
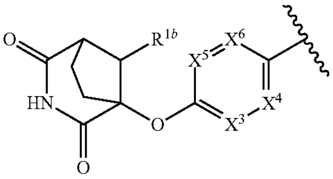
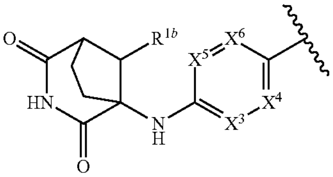
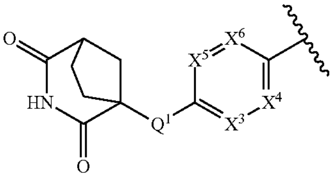
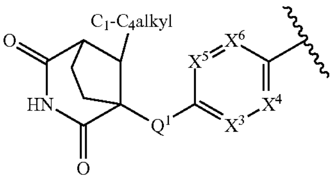
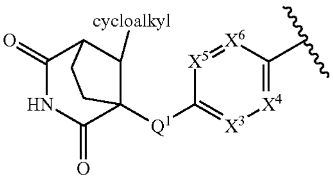
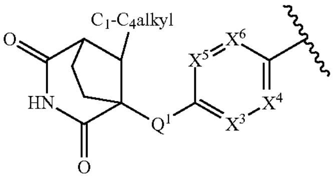
and -continued

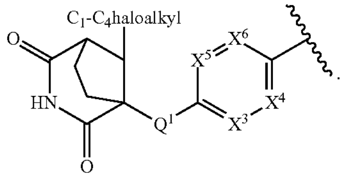

In certain embodiments,

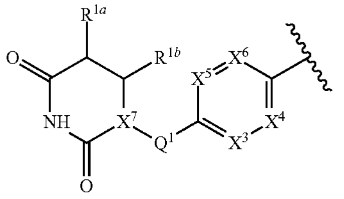

is selected from

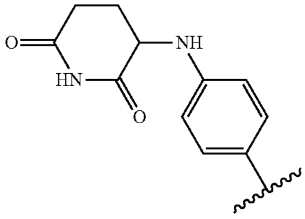

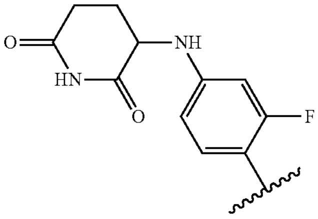

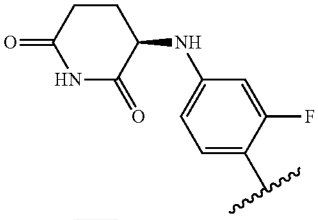

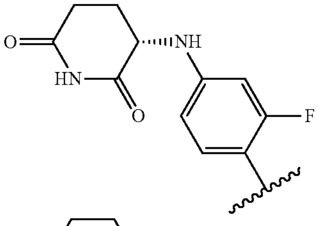

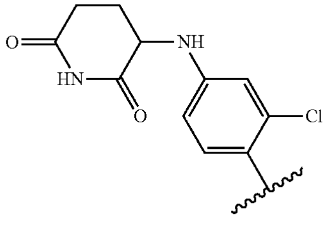

-continued

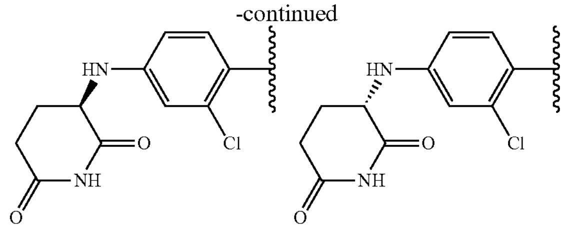

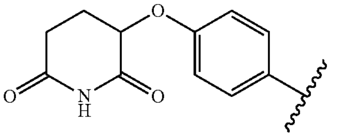

and

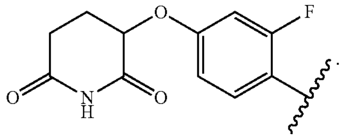

In certain embodiments, the structure of the compound is typically selected such that it is sufficiently stable to sustain a shelf life of at least two, three, four, or five months under ambient conditions. To accomplish this, each of the variables described herein must be sufficiently stable to sustain the corresponding desired shelf life of at least two, three, four, or five months under ambient conditions. One of ordinary skill in the art is well aware of the stability of chemical moieties and can avoid those that are not stable or are too reactive under appropriate conditions.

In certain alternative embodiments, the compound of the present invention including any of the variable groups described herein, may be optionally substituted as described below in Section I. Definitions, if desired to achieve the target effect, results in a stable moiety and final compound that makes chemical sense to the routineer, and if a final compound for therapy, is pharmaceutically acceptable. Also, all variables, with or without optional substituents, should be interpreted in a manner that does not include redundancy (i.e., as known in the art, alkyl substituted with alkyl is redundant; however, for example, alkoxy substituted with alkoxy is not redundant).

III. Targeting Ligands

RET forms a complex with its natural ligands, a family of glial-derived neurotrophic factors, and with glycosyl phosphatidylinositol-linked co-receptors, resulting in dimerization and subsequent activation of the kinase domain through the formation of a multimeric signaling complex consisting of RET's soluble ligand glial derived neurotrophic factor (GDNF) and a membrane-bound coreceptor (GDNF family receptor al). This complex causes autophosphorylation of tyrosine residues. As a result of this mechanism glial family ligand mediated activation of wildtype RET is an increasingly recognized mechanism related to tumor growth and dissemination of a much broader group of cancers. (Mulligan L M., "GDNF and the RET Receptor in Cancer: New Insights and Therapeutic Potential", Front. Physiol., 2019, 9(1873), 1-13; and Airaksinen M S, and Saarma M., "The GDNF family: signaling, biological functions and therapeutic value", Nat Rev Neurosci., 2002, 3(5), 383-94).

There are multiple protein isoforms of RET including RET9, RET51 and RET43 each of which differs in the lengths of carboxyl-terminal tails and their ability to bind SHC, GRB2, c-CBL, and SHANK3. Each RET isoform has a unique C-terminal tail sequences that recruits distinct protein complexes to mediate signals, thereby exhibiting different abilities to recruit E3 ubiquitin ligases to their unique C-termini. (Lorenzo M J, et al., "RET alternative splicing influences the interaction of activated RET with the SH2 and PTB domains of Shc, and the SH2 domain of Grb2", Oncogene, 1997, 14, 763-771). Studies on Acute myeloid leukemia (AML) have shown that AIL subtypes were dependent on expression of the RET receptor tyrosine kinase (RTK), and that depletion of RET by shRNA knockdown or CRISPR/Cas9-mediated knockout led to cell cycle arrest in the G0/G1 phase, increased apoptosis, and reduced clonogenic activity. Analysis of known RET ligand/co-receptor pairs (GDNF/GFRA1, NRTN/GFRA2, ARTN/GFRA3, PSPN/GFRA4) by quantitative real-time PCR and shRNA knockdown indicated that RET signaling is facilitated mainly through NTRN/GFRA2 or ARTN/GFRA3. (Rudat S., et al., "The RET Receptor Tyrosine Kinase Promotes Acute Myeloid Leukemia through Protection of FLT3-ITD Mutants from Autophagic Degradation", Blood, 2016, 128(22), 2849). The RET fusions genes are mutually exclusive with other known drivers in LAD (e.g. KRAS, epidermal growth factor receptor (EGFR), EML4-anaplastic lymphoma kinase (ALK)), further supporting a role for RET as a unique driver of malignancy in these tumors.

In certain embodiments, the RET Targeting Ligand is selected from

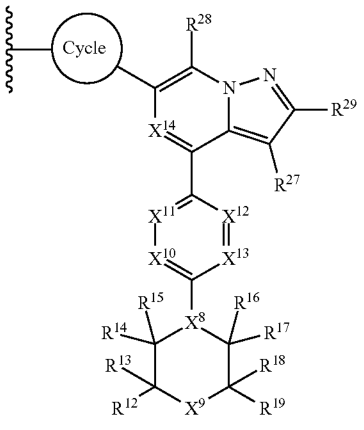

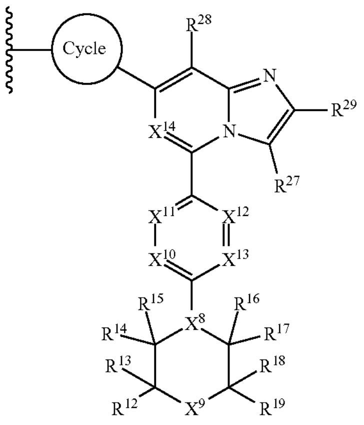

-continued

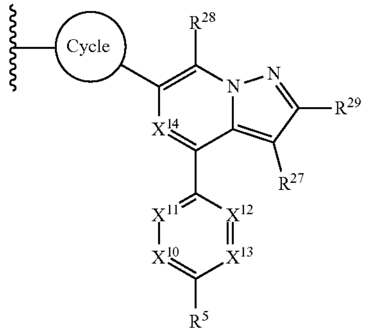

and

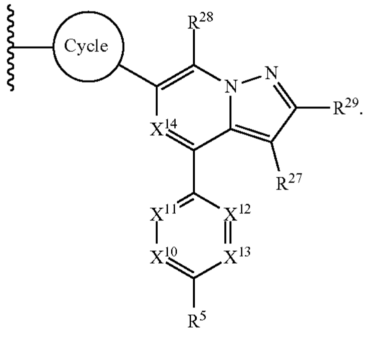

In certain embodiments, the RET Targeting Ligand is selected from

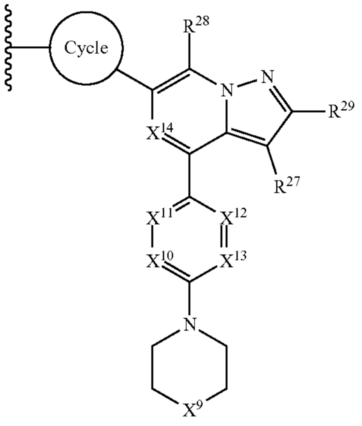

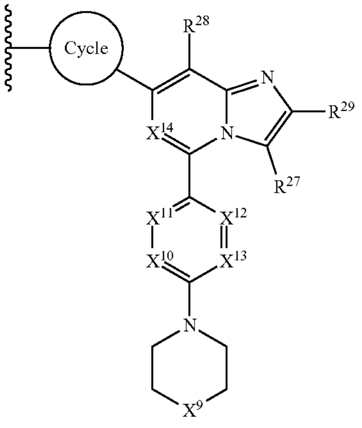

-continued
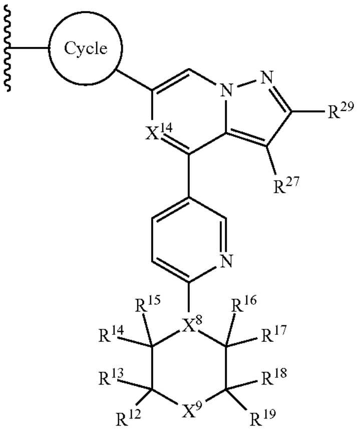
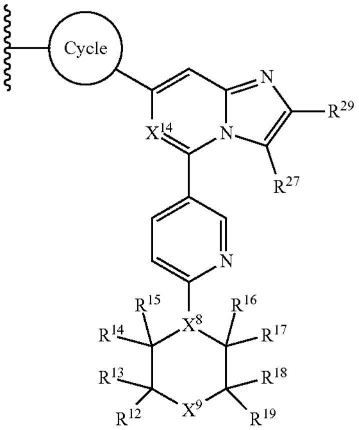
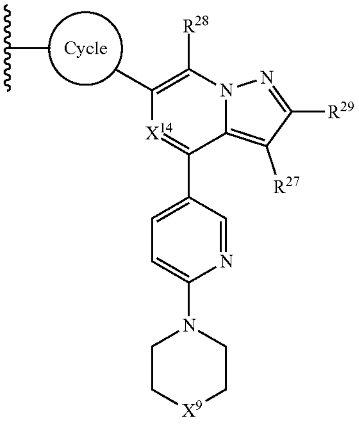
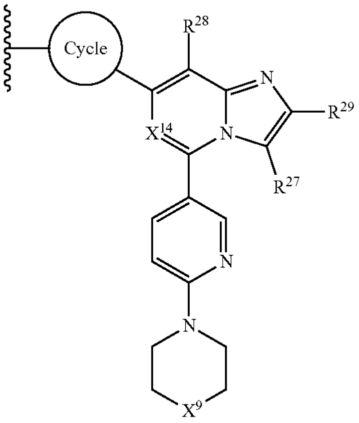
In certain embodiments, the RET Targeting Ligand is selected from
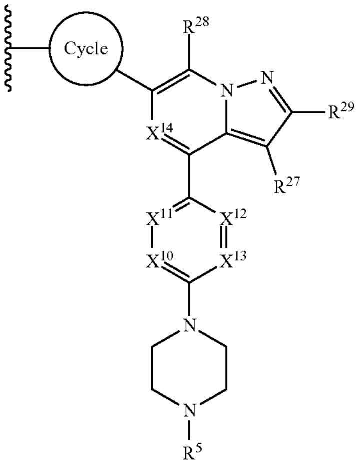
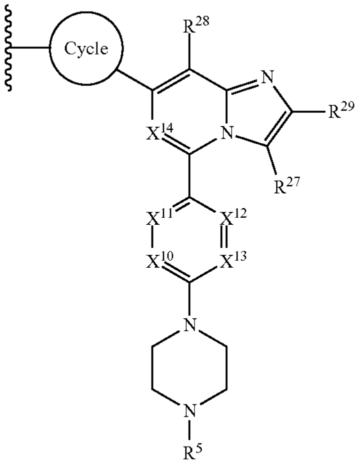
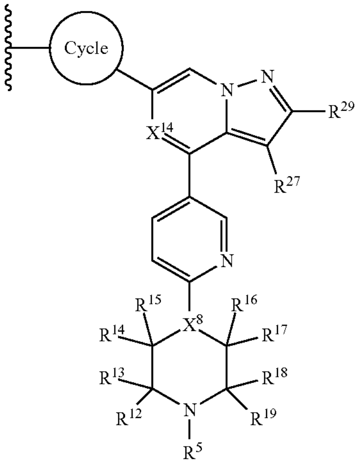

-continued
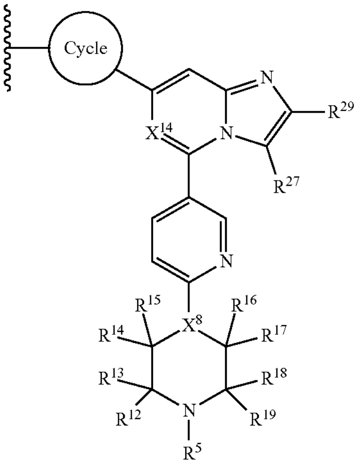
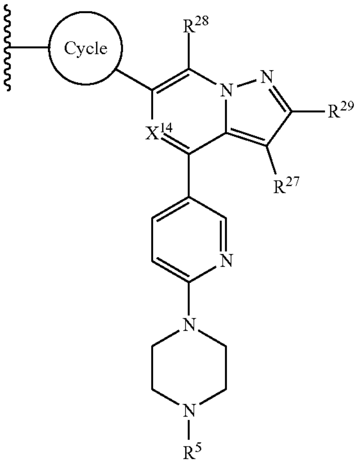
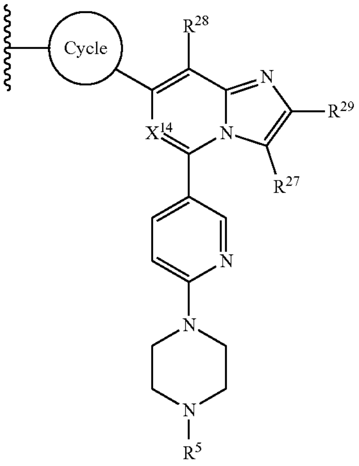
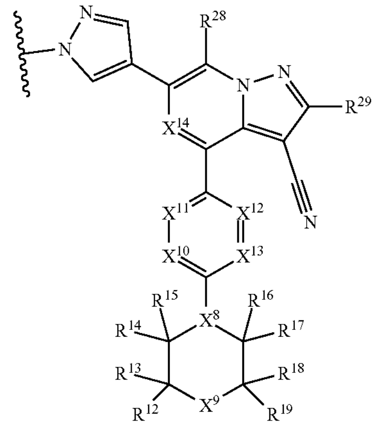
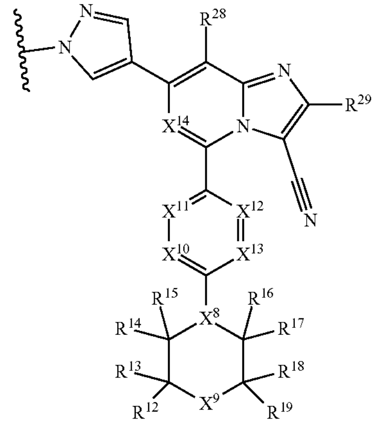
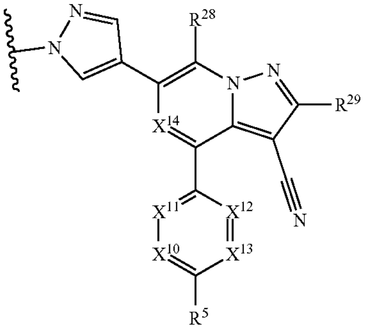
and
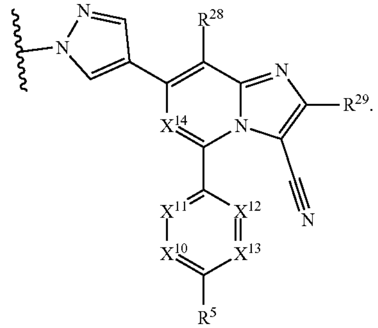
In certain embodiments, the RET Targeting Ligand is selected from
In certain embodiments, the RET Targeting Ligand is selected from -continued
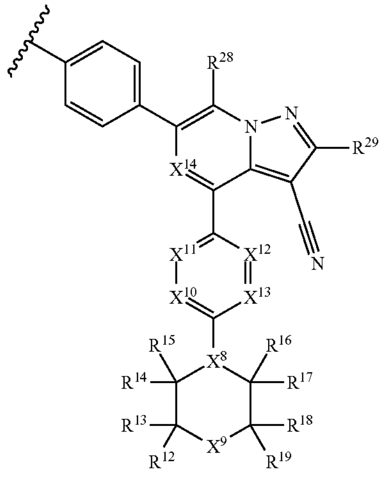
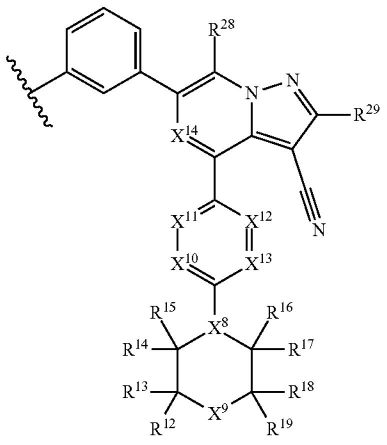
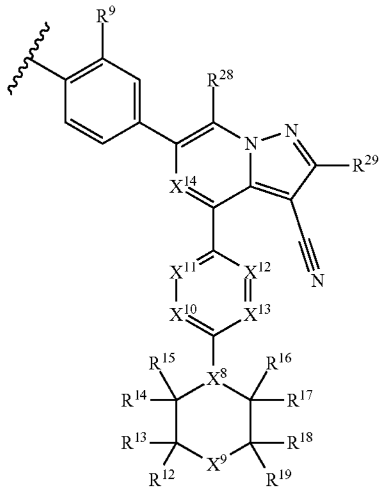
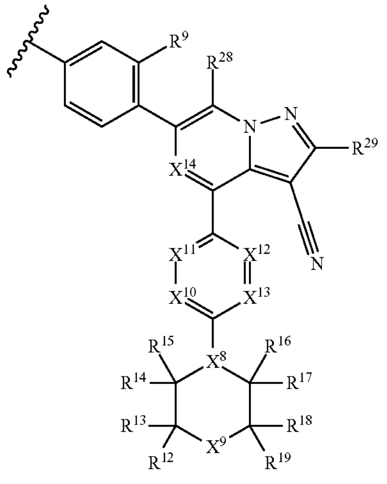
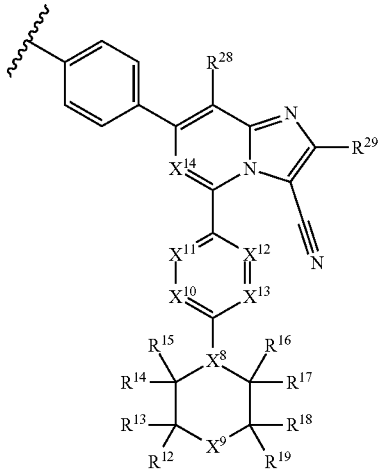
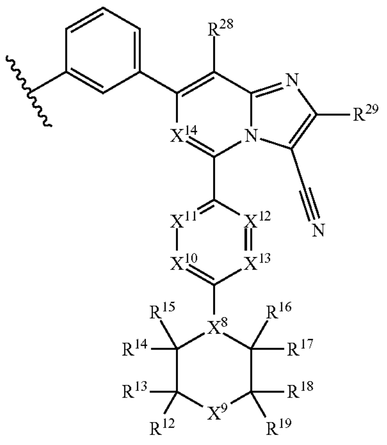

-continued
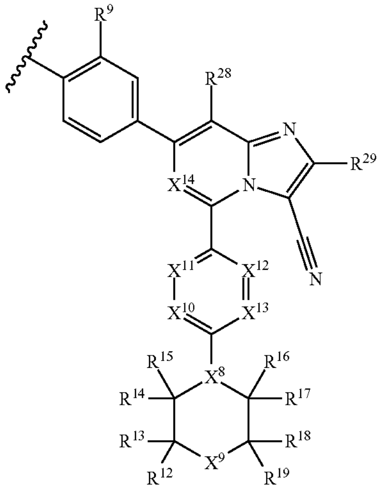
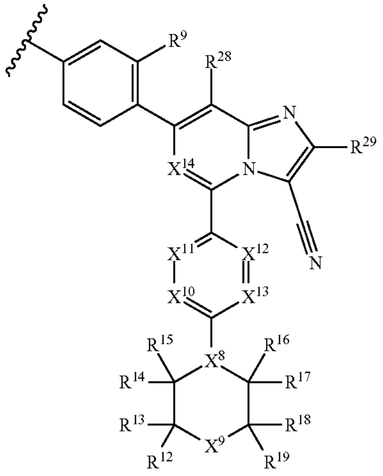
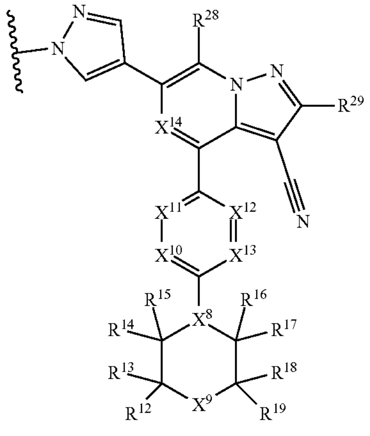
-continued
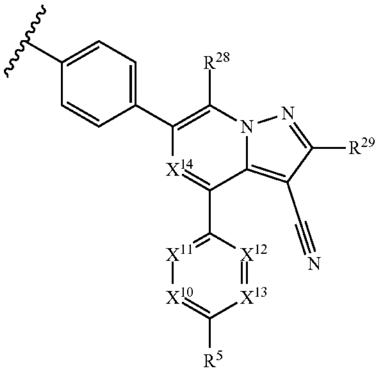
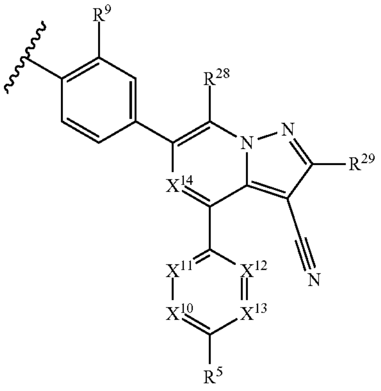
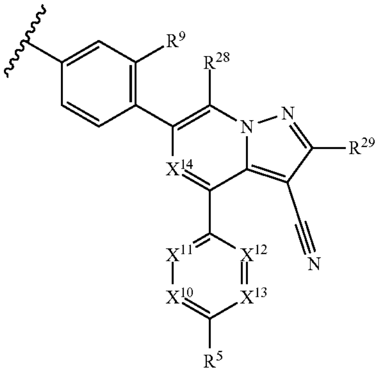
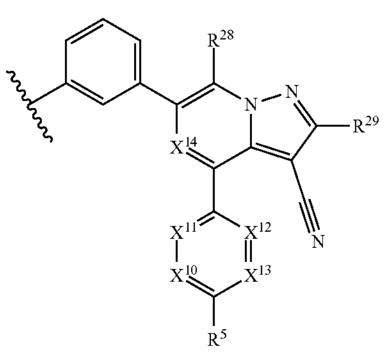
and -continued
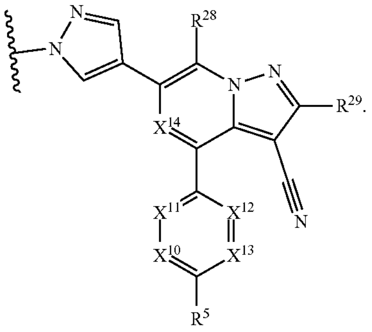
In certain embodiments, the RET Targeting Ligand is selected from
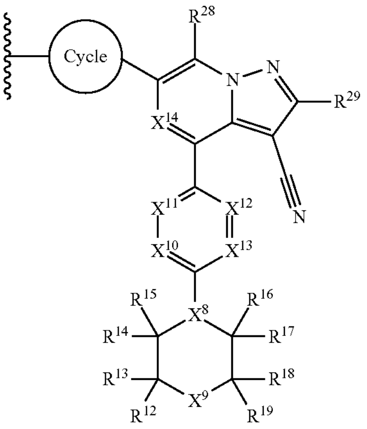
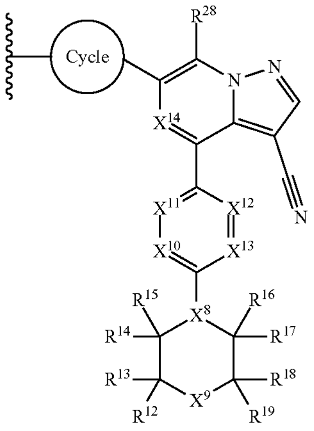
-continued
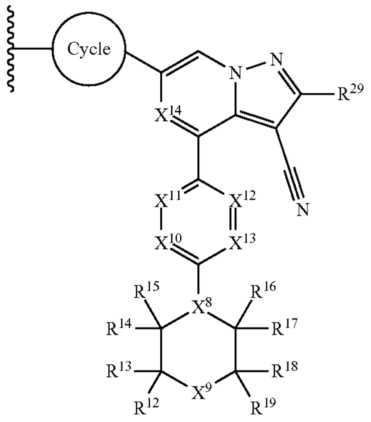
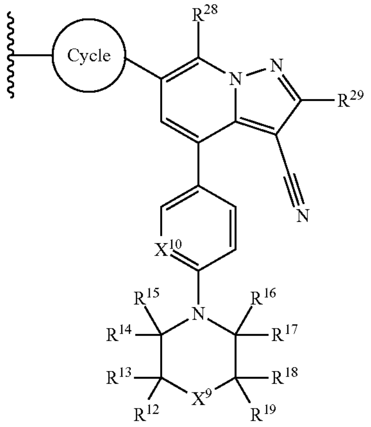
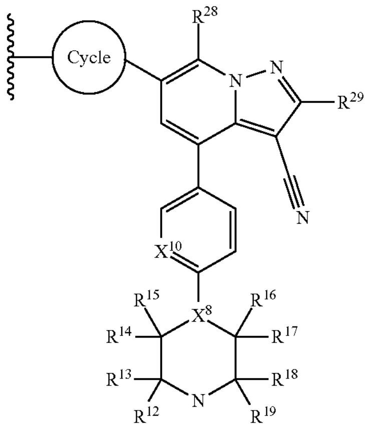
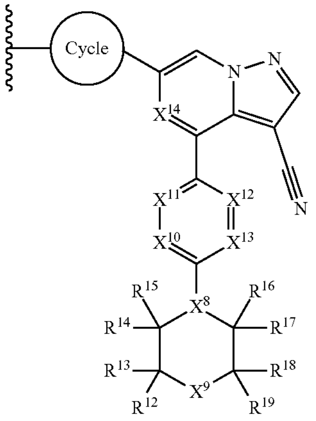

-continued
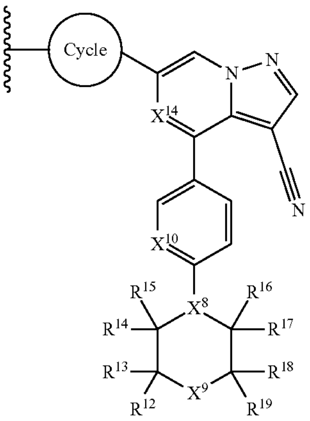
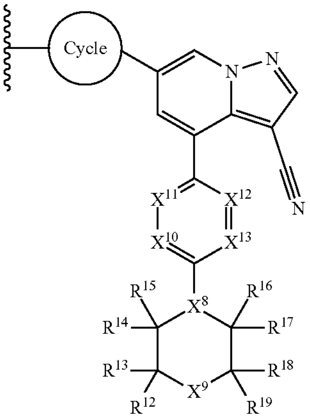
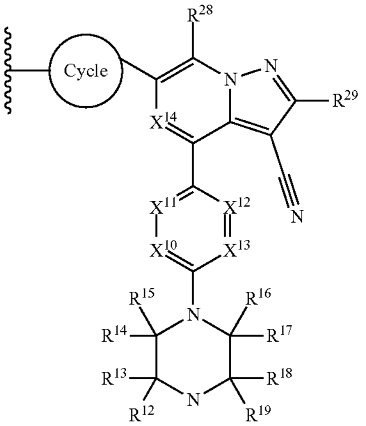
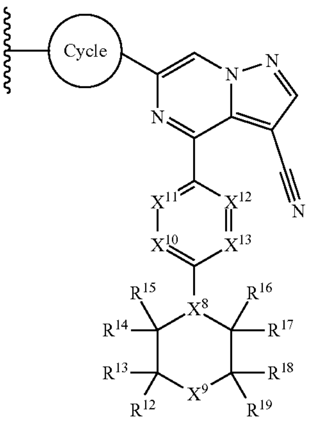
-continued
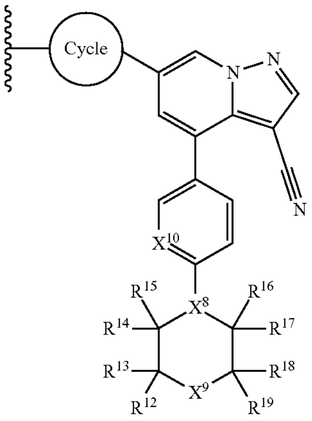
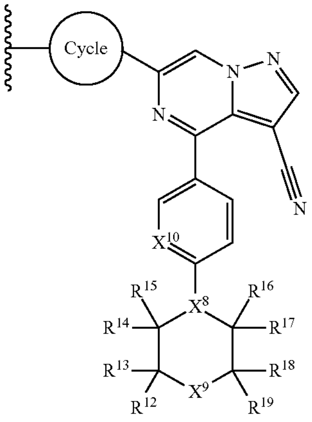
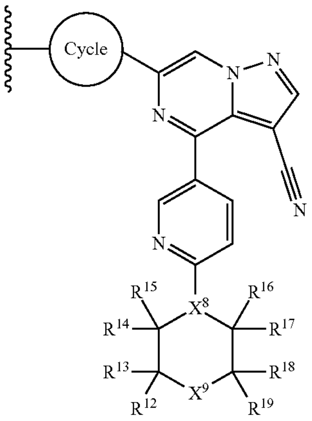
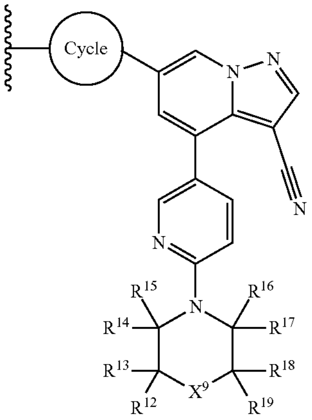

-continued
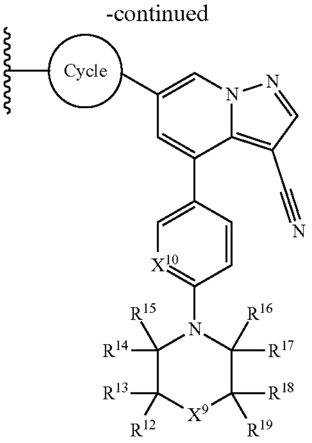
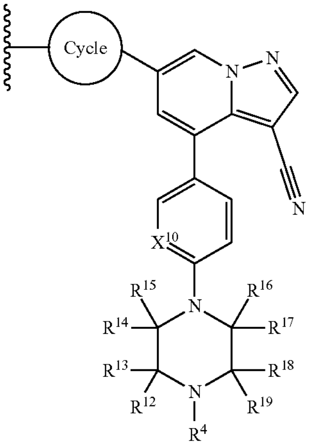
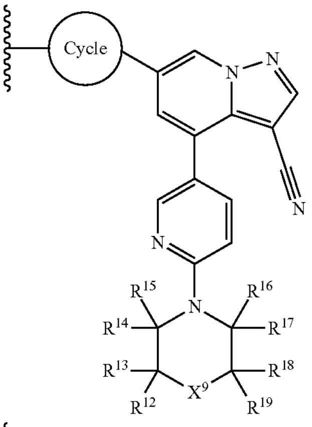
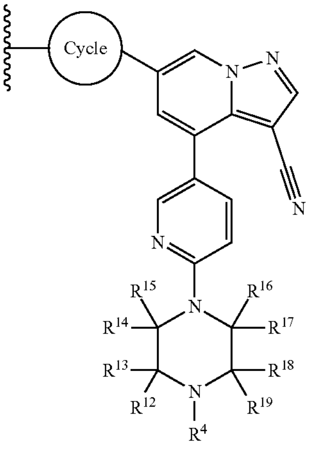
-continued
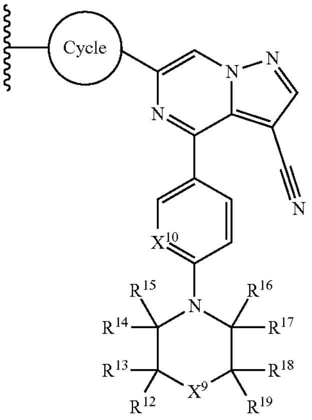
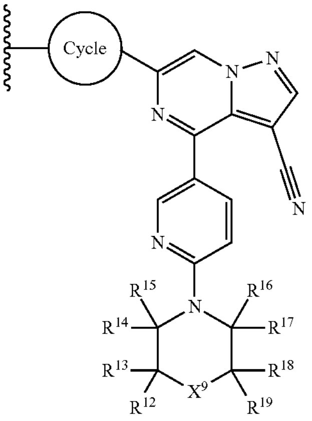
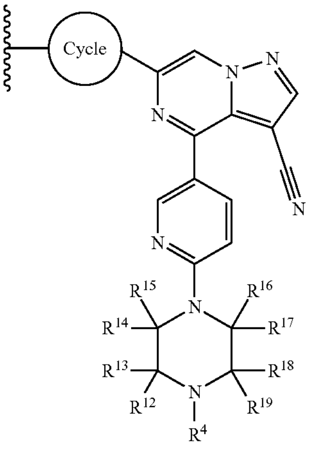
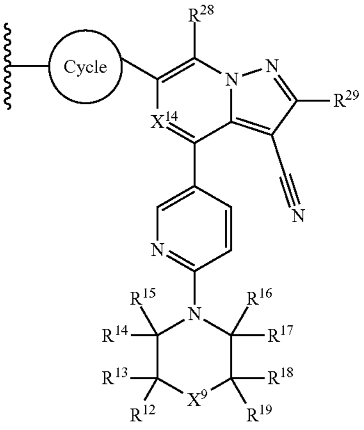

-continued
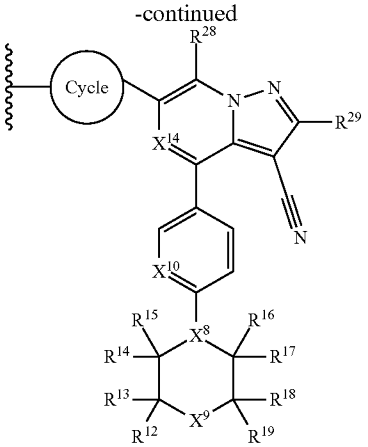
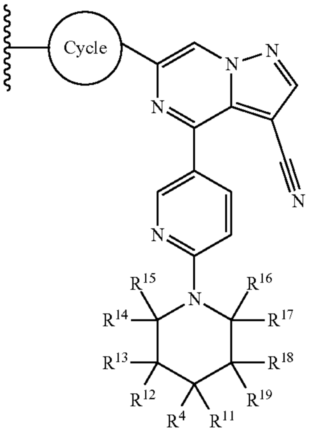
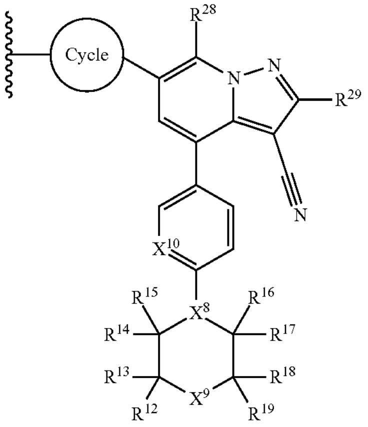
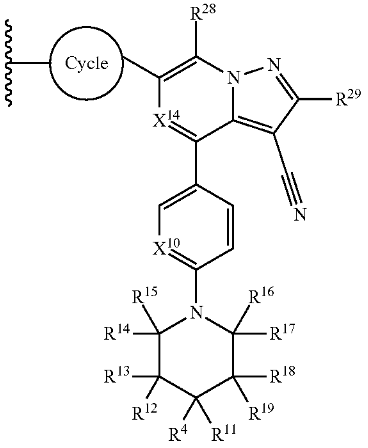
-continued
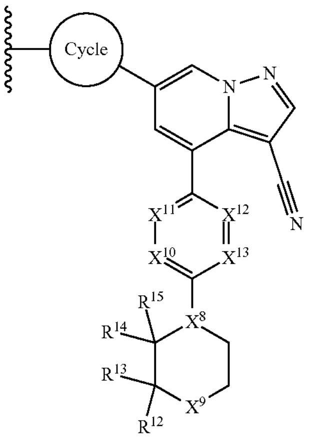
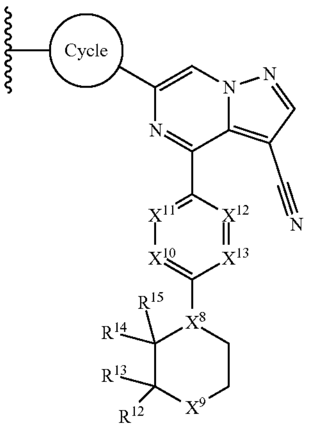
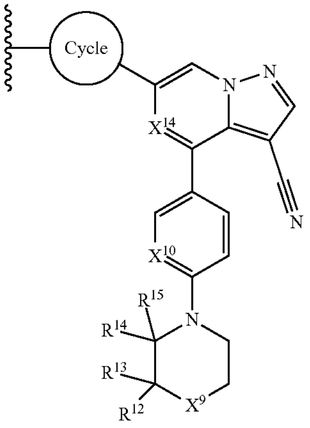

-continued
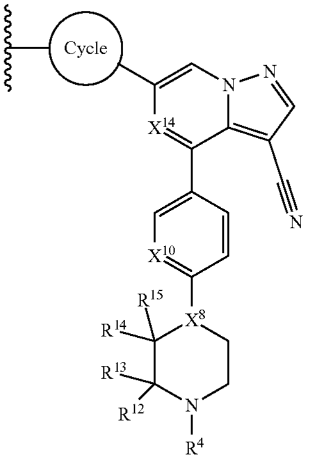
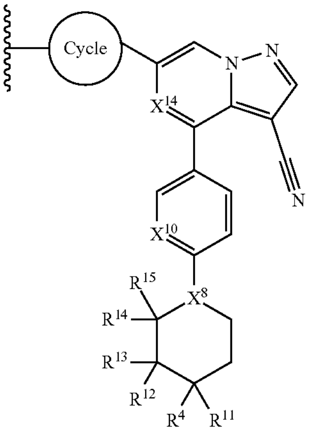
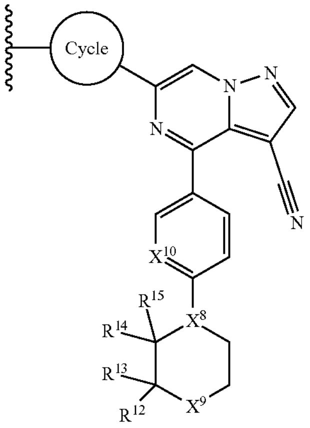
-continued
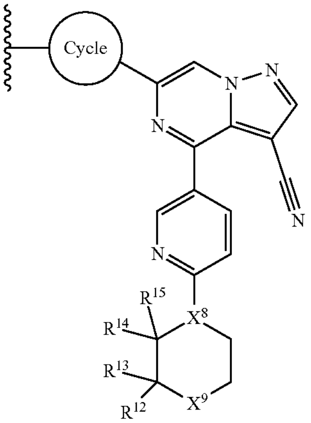
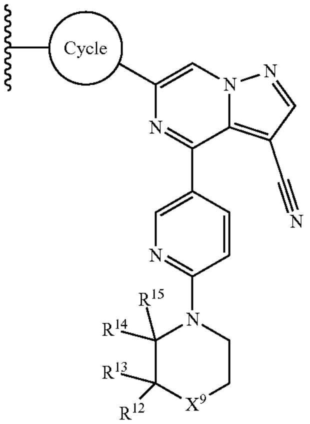
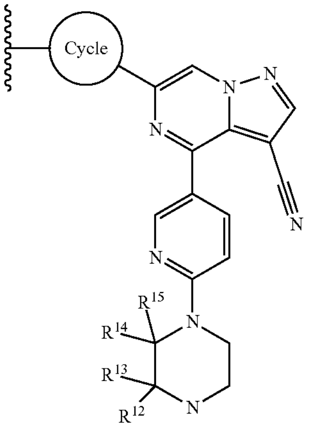
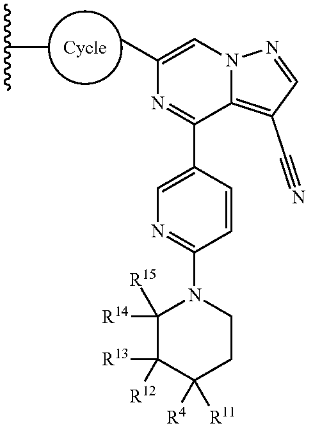

-continued
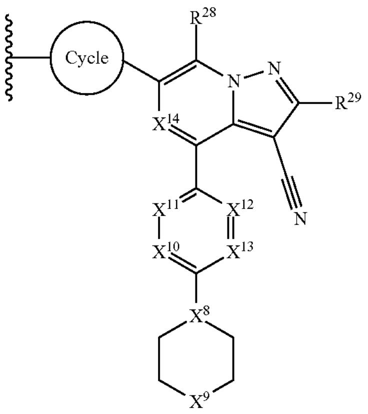
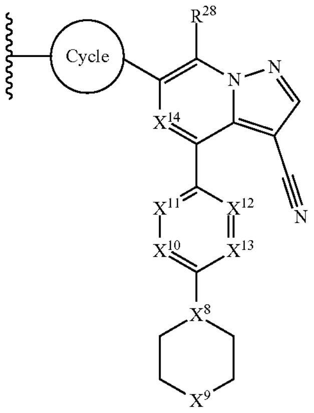
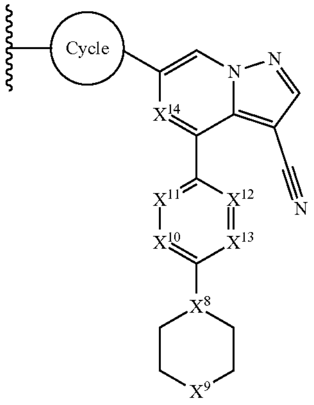
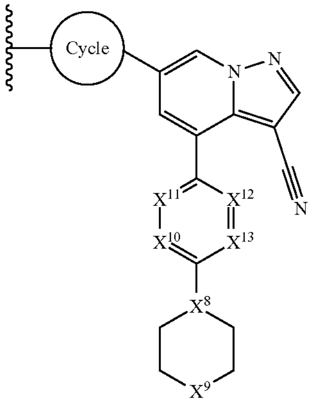
-continued
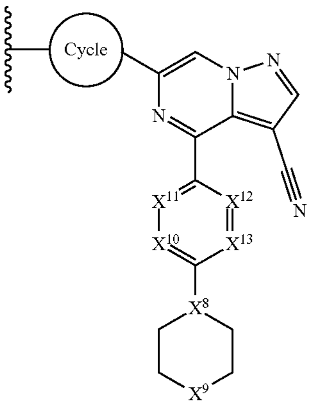
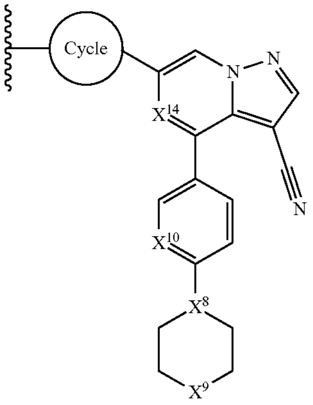
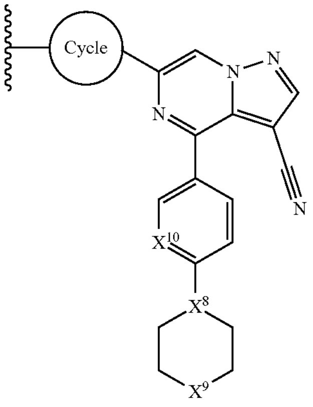
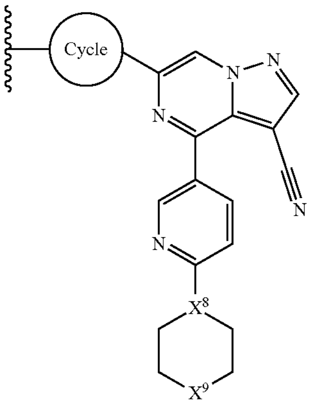

-continued
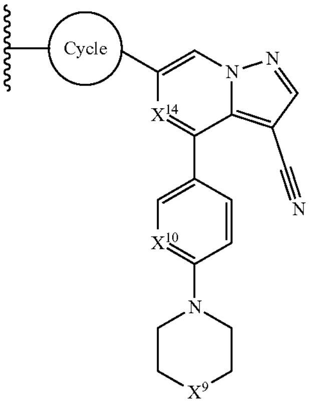
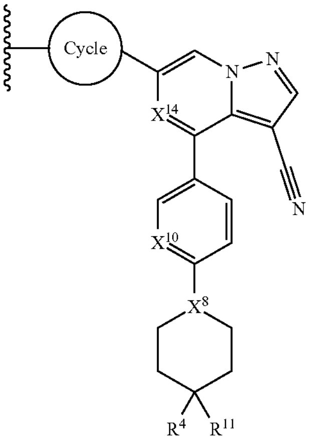
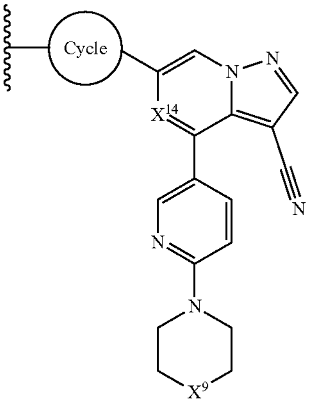
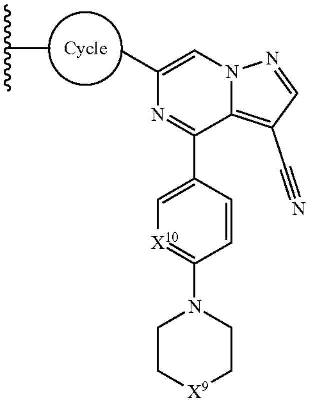
-continued
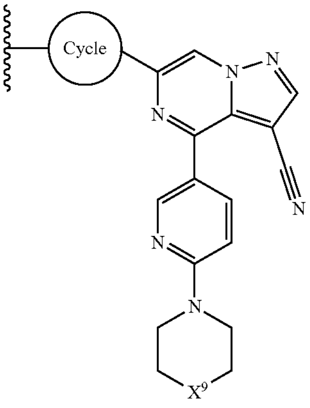
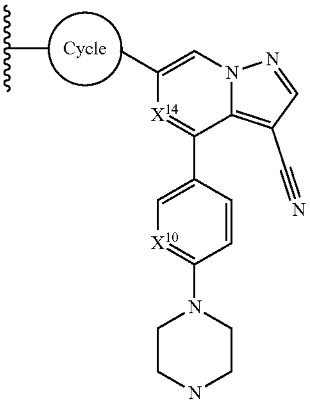
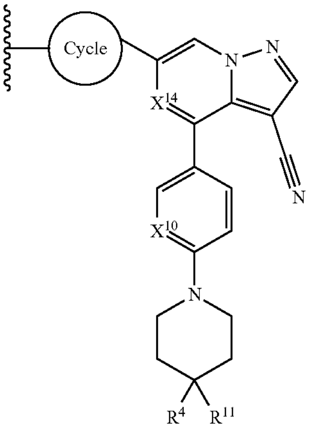
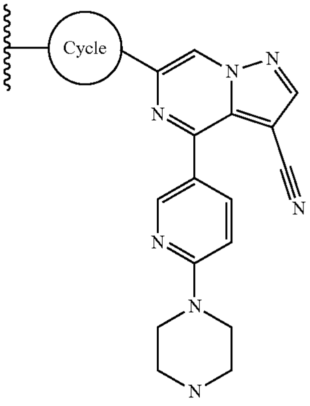

-continued
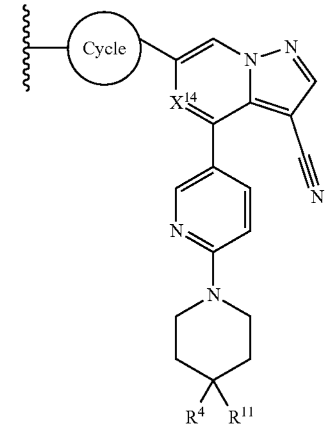
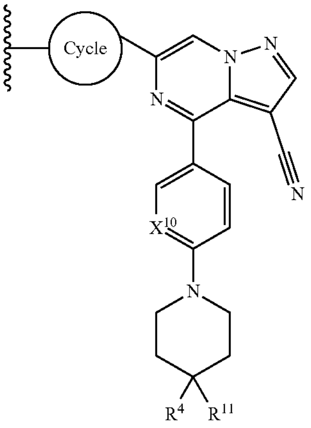
and
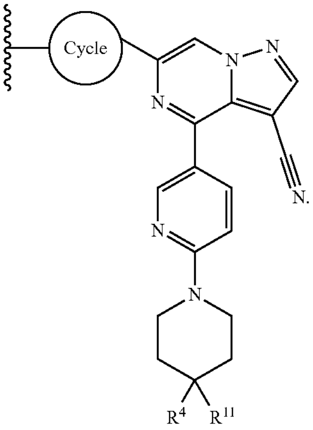
In certain embodiments, the RET Targeting Ligand is selected from:
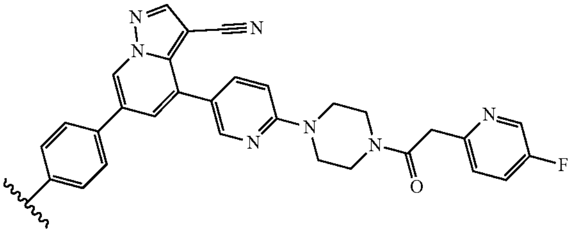
-continued
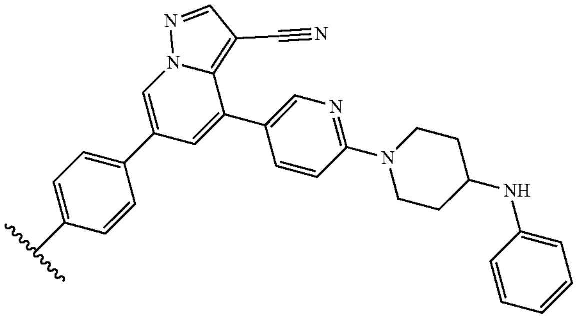
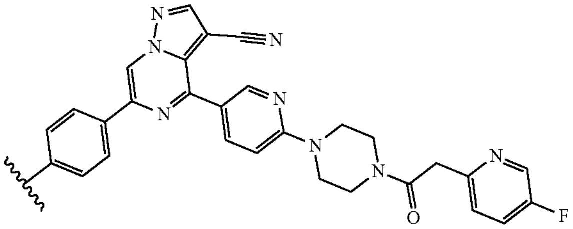
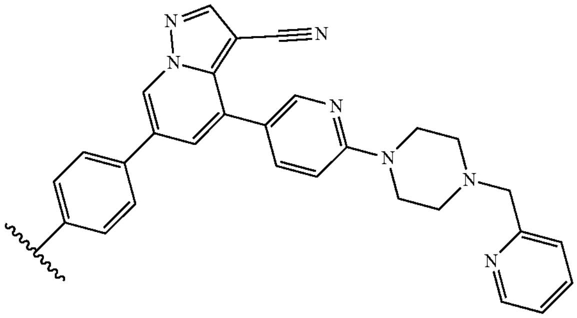
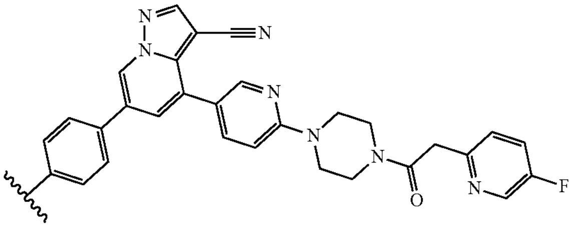
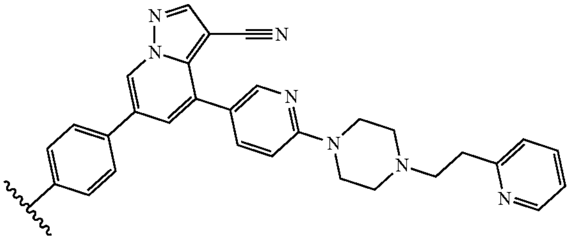
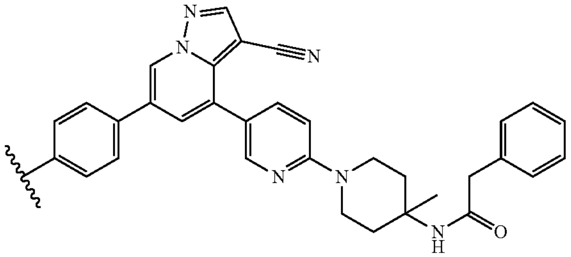

-continued
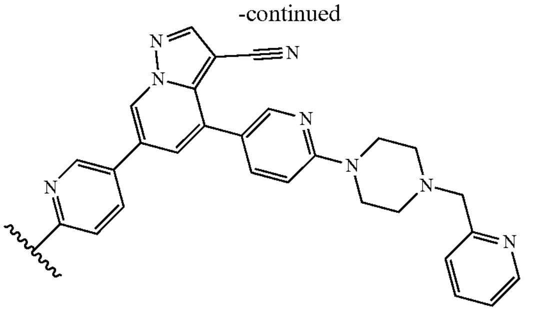
and
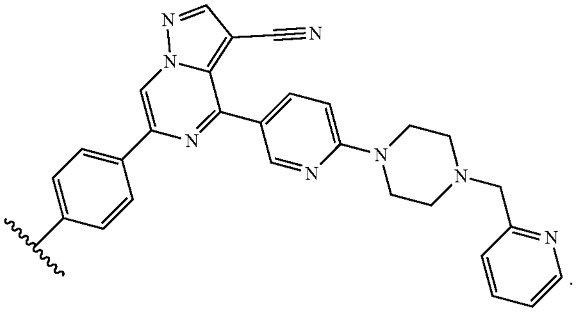
In certain embodiments, the RET Targeting Ligand is selected from:
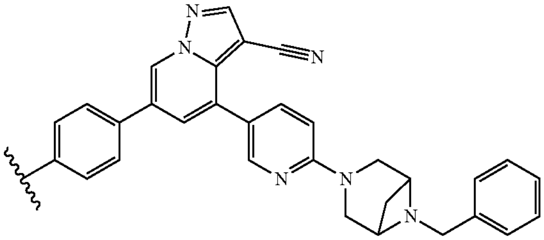
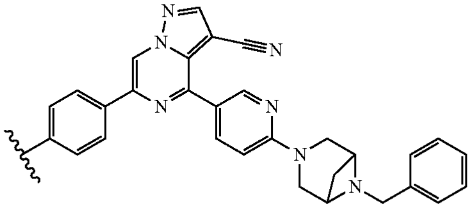
and
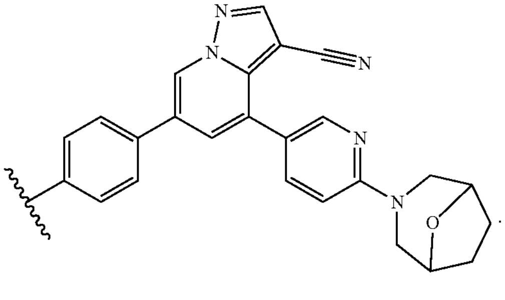
In certain embodiments, the RET Targeting Ligand is selected from:
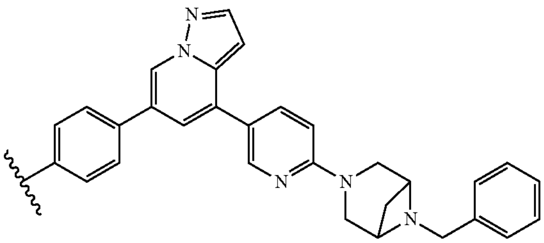
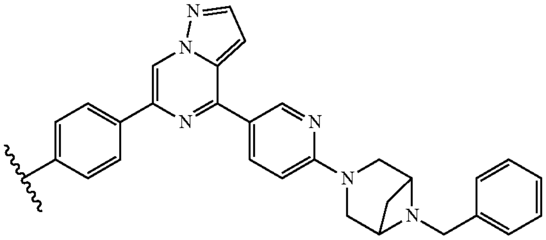
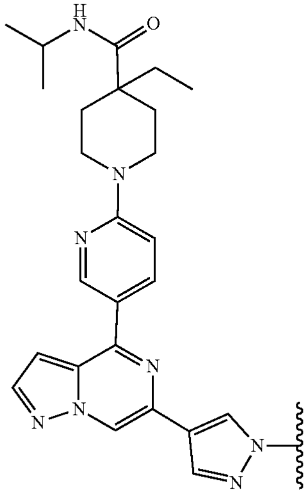
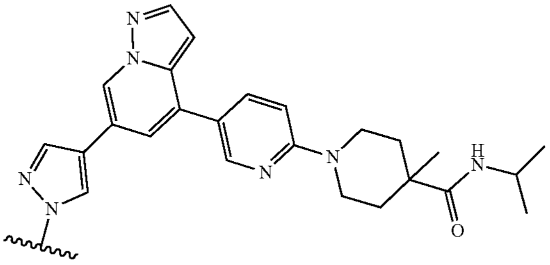
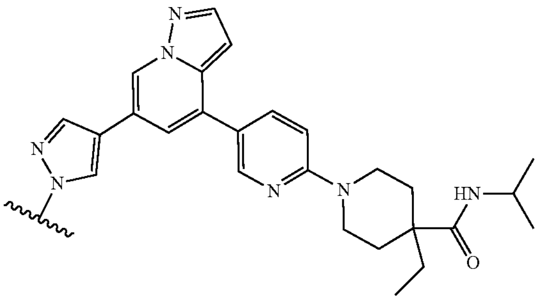

-continued
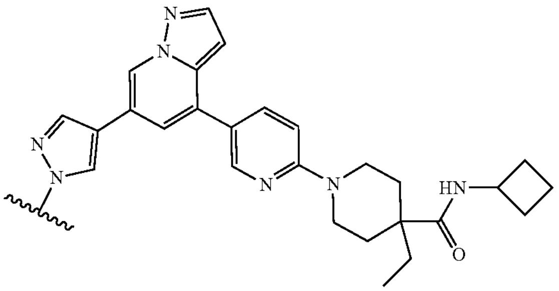
In certain embodiments, the RET Targeting Ligand is selected from:
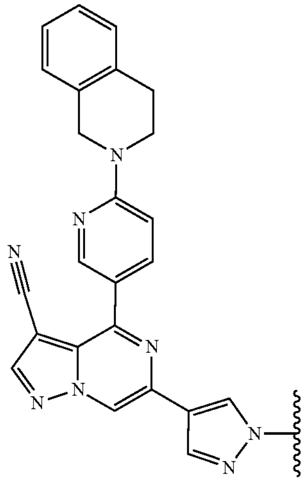
,
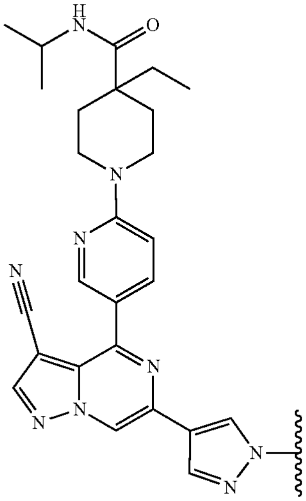
, and
-continued
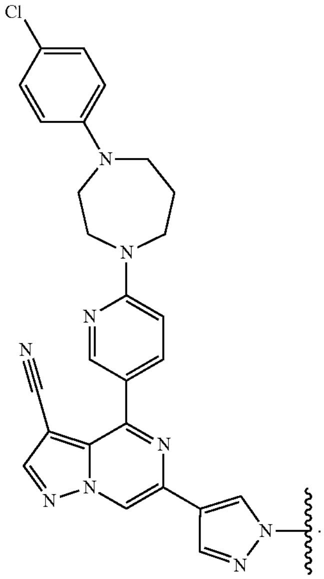
.
In certain embodiments, the RET Targeting Ligand is selected from:
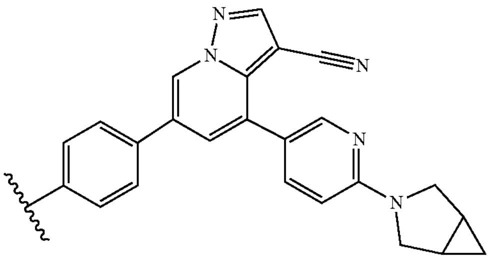
and
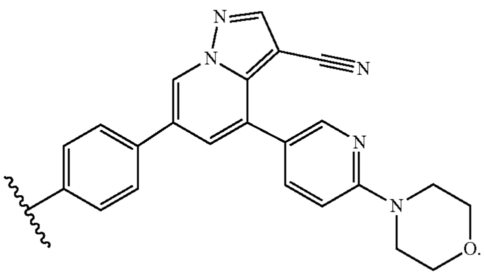
.

In certain embodiments, the RET Targeting Ligand is:
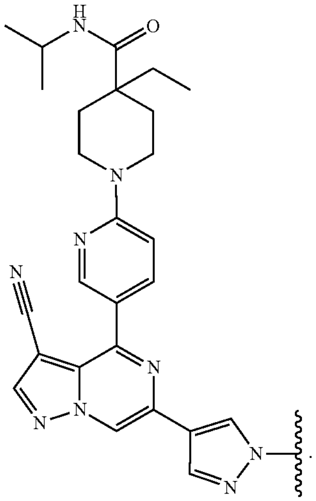 [SMILES: *n1cc(-c2cn3ncc(C#N)c3c(-c3ccc(N4CCC(CC)(C(=O)NC(C)C)CC4)nc3)n2)cn1]
In certain embodiments, the RET Targeting Ligand is selected from:
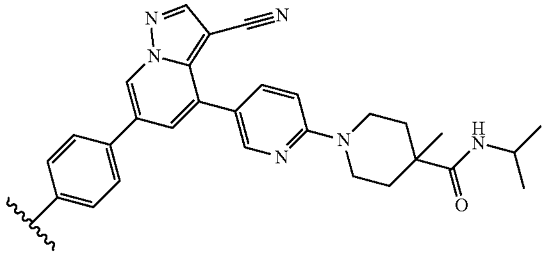
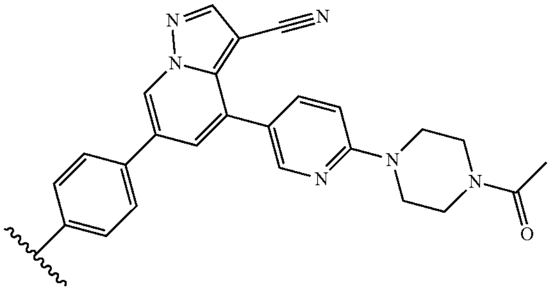
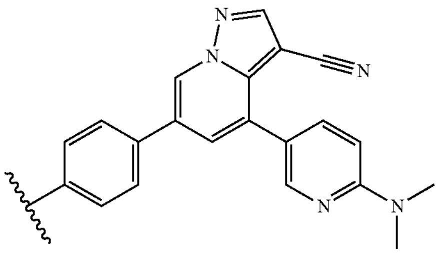
-continued
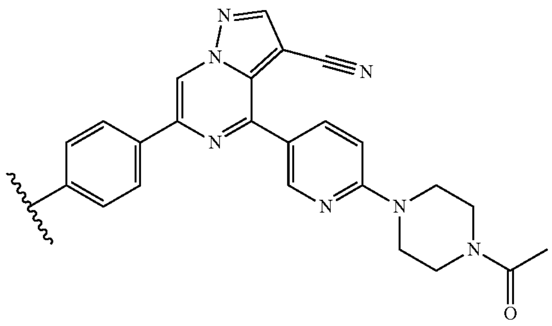
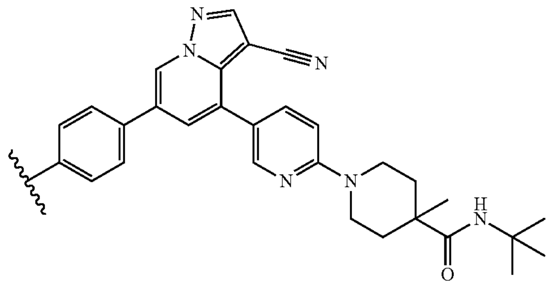
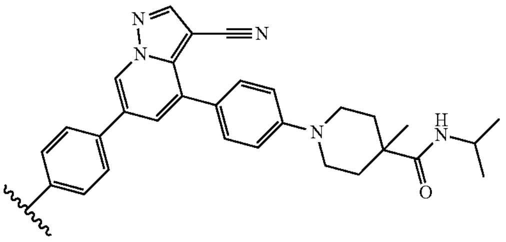
and
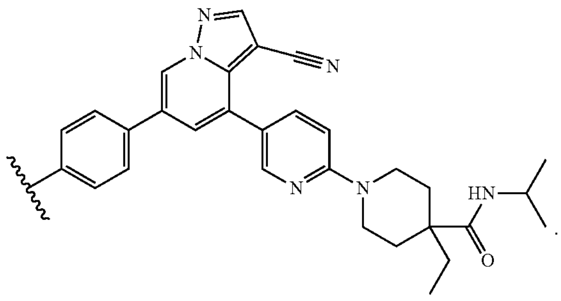 [SMILES: *c1ccc(-c2cc(-c3ccc(N4CCC(CC)(C(=O)NC(C)C)CC4)nc3)c3c(C#N)cnn3c2)cc1]
In certain embodiments, the RET Targeting Ligand is selected from:
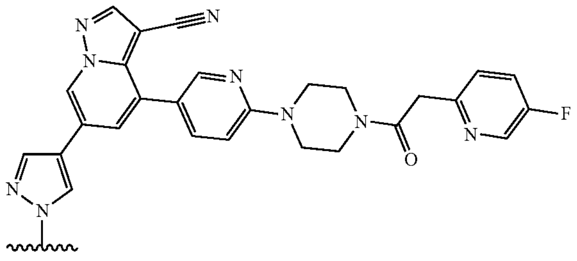

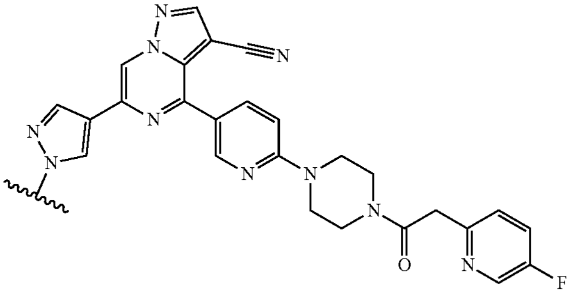
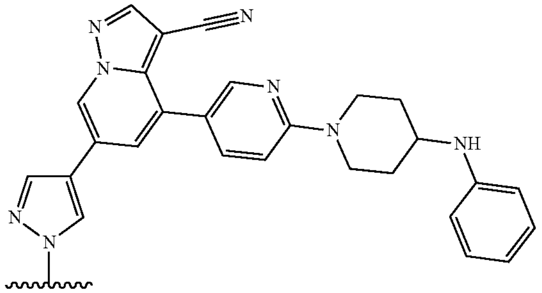
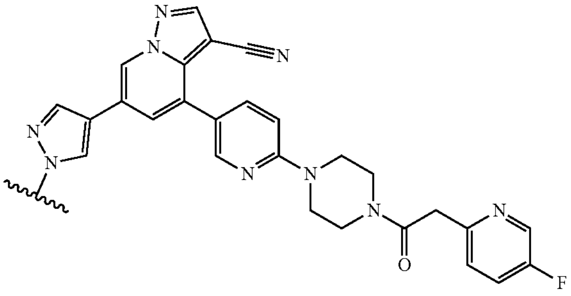
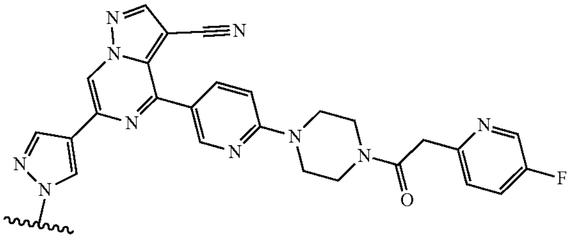
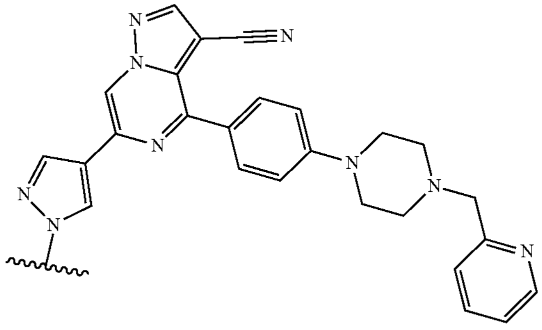
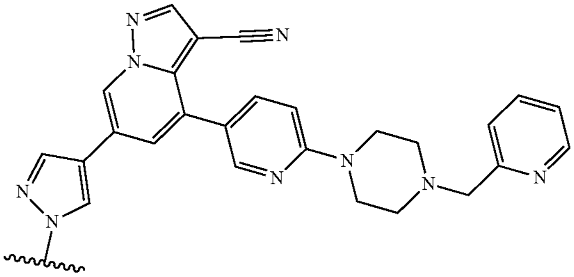
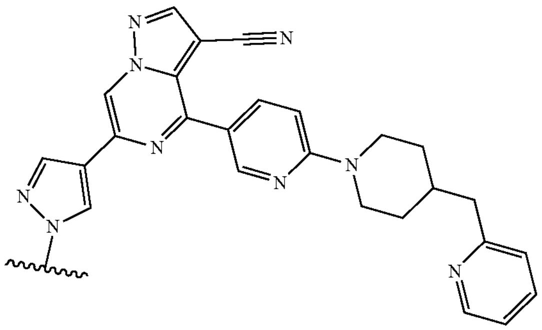
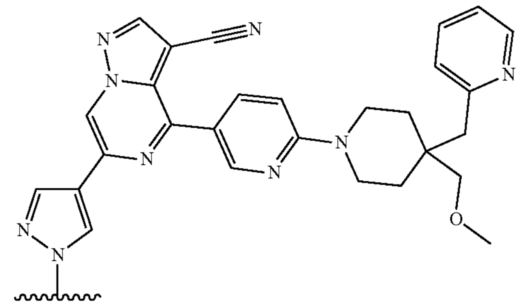
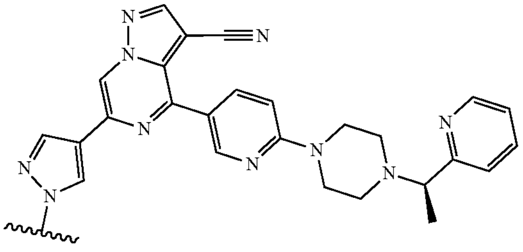
and
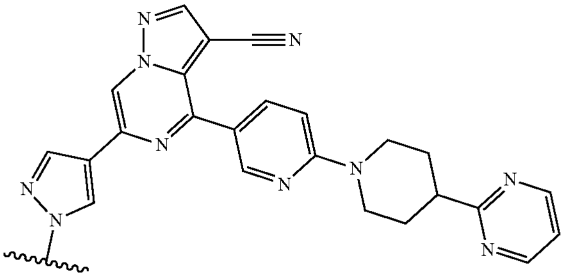
.
In certain embodiments, the RET Targeting Ligand is selected from:
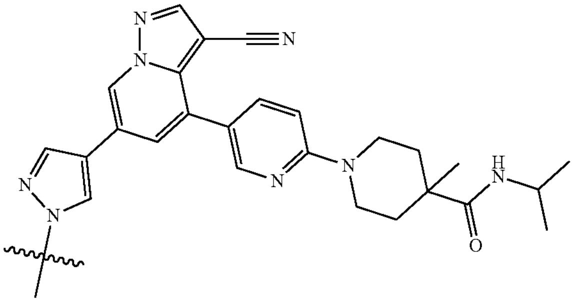

-continued
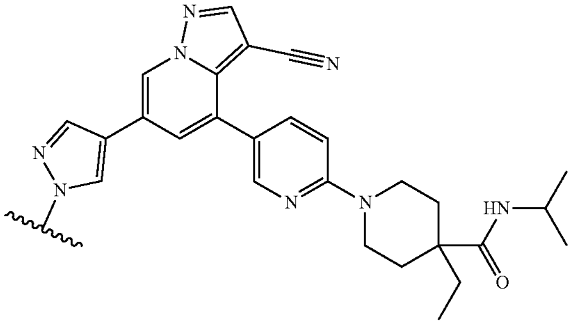
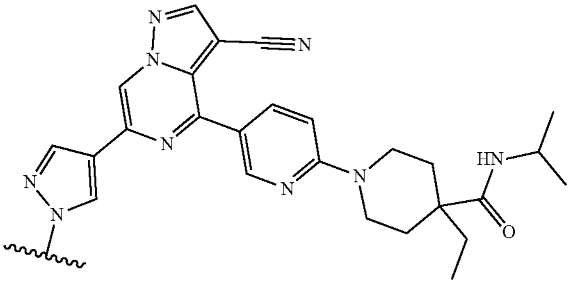
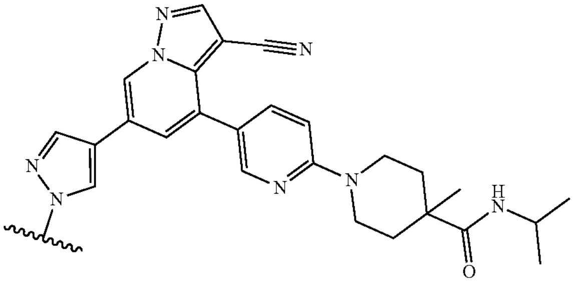
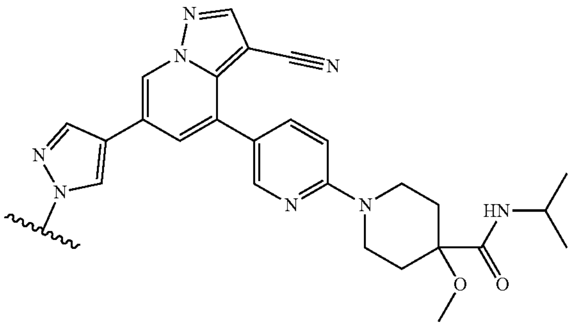
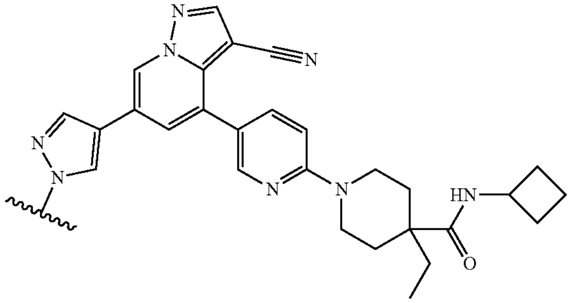
-continued
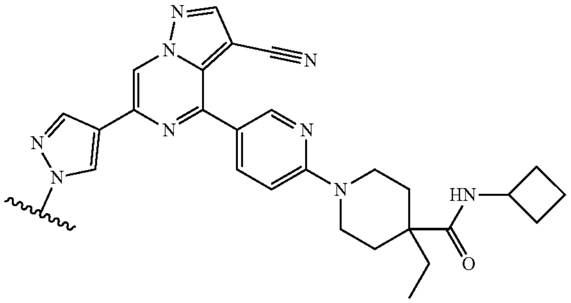
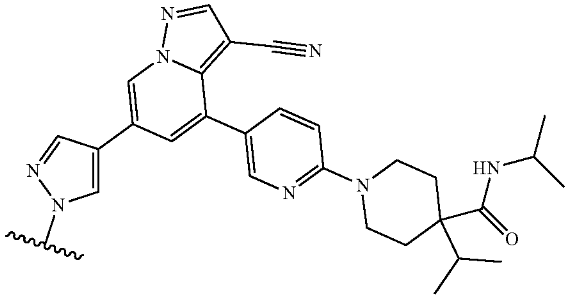
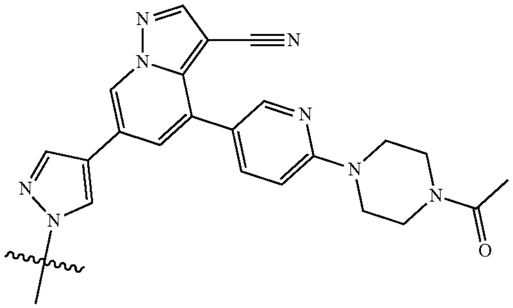
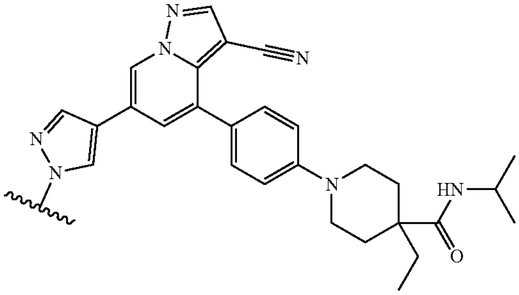
and
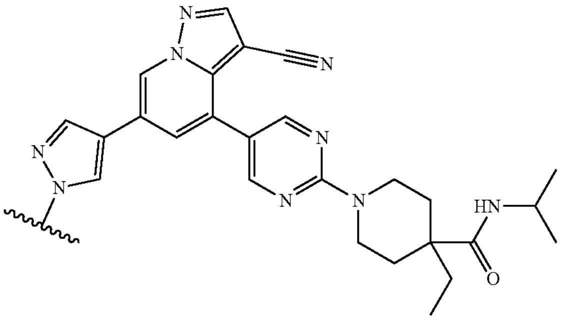
.
In certain embodiments, the RET Targeting Ligand is selected from:

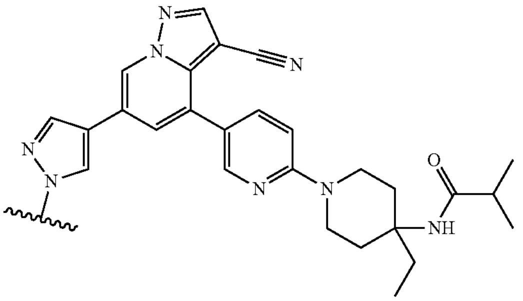
and
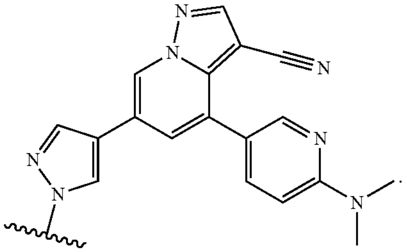
In certain embodiments, the RET Targeting Ligand is selected from:
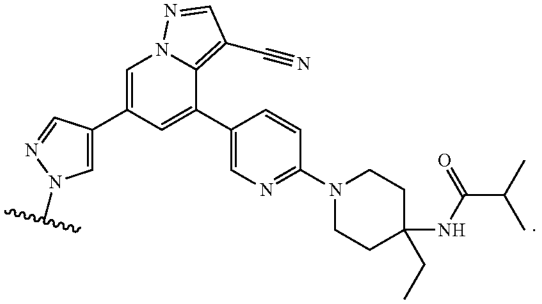 [SMILES: *n1cc(-c2cc(-c3ccc(N4CCC(CC)(NC(=O)C(C)C)CC4)nc3)c3c(C#N)cnn3c2)cn1]
In certain embodiments, the RET Targeting Ligand is selected from:
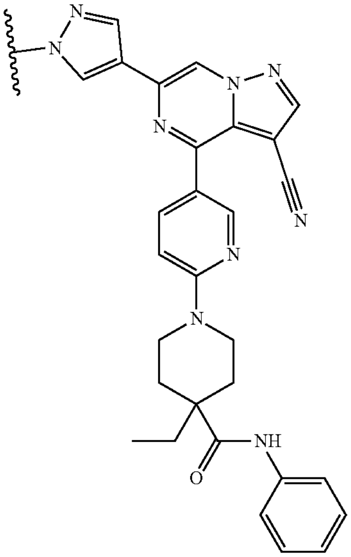
-continued
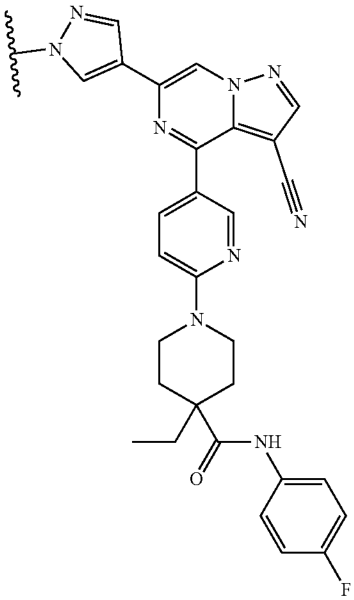
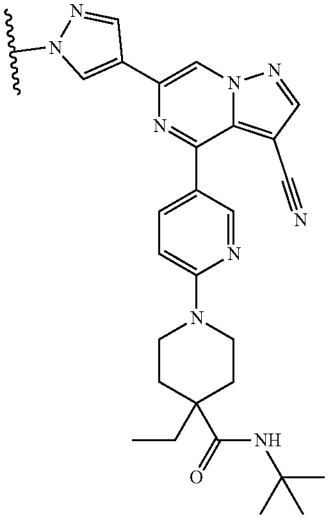
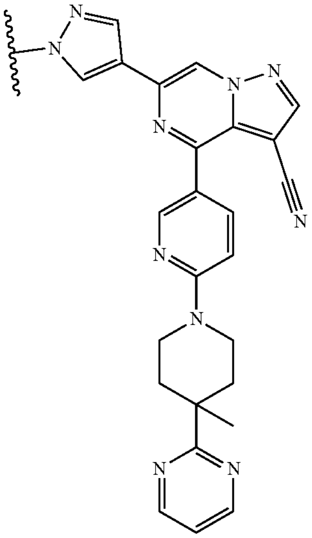

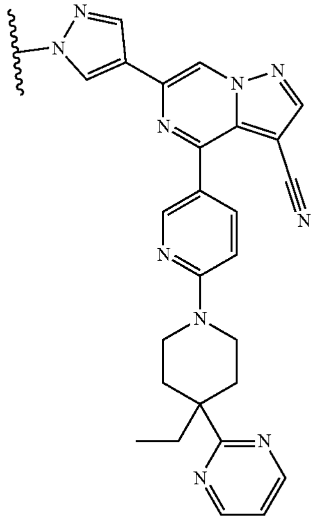
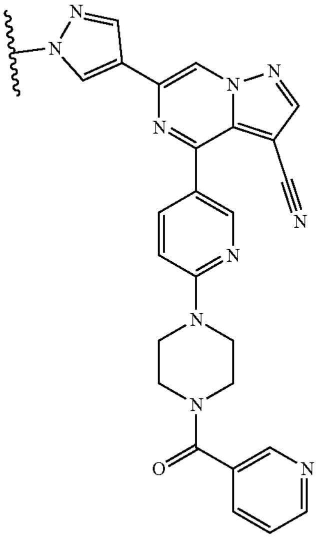
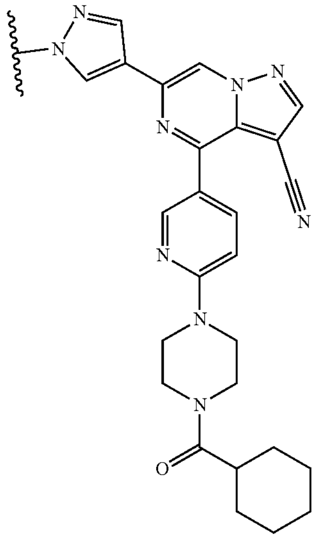
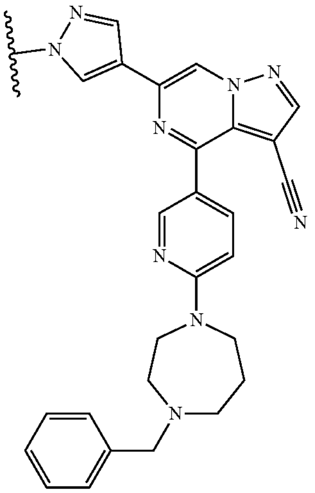
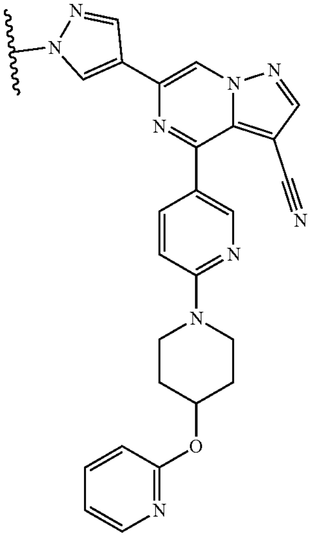
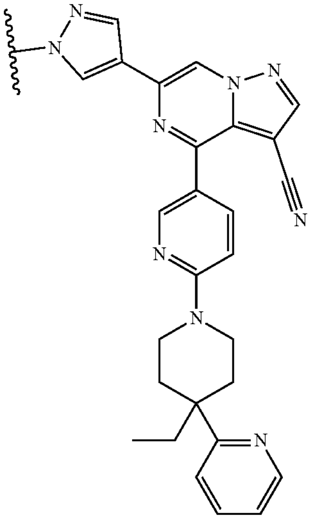

-continued
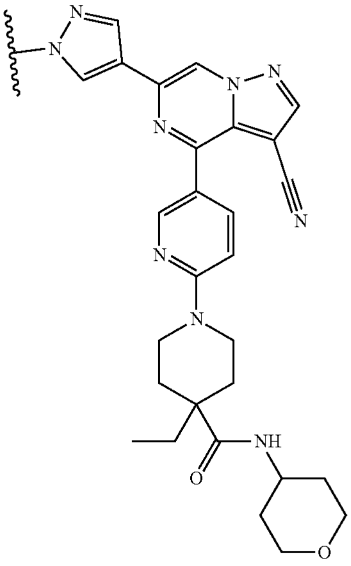
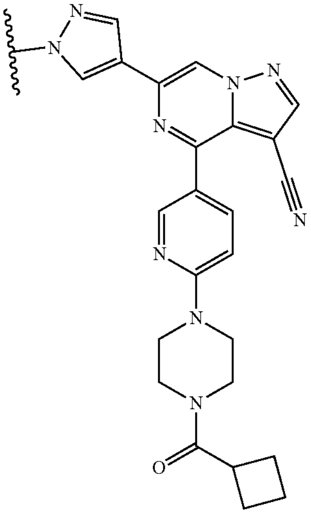
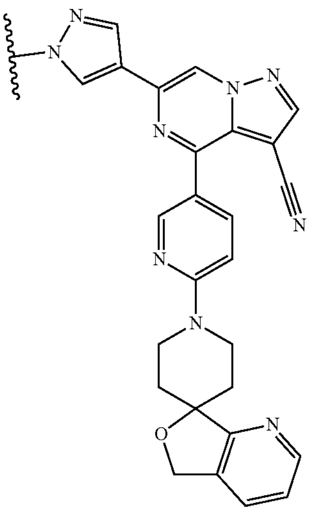
-continued
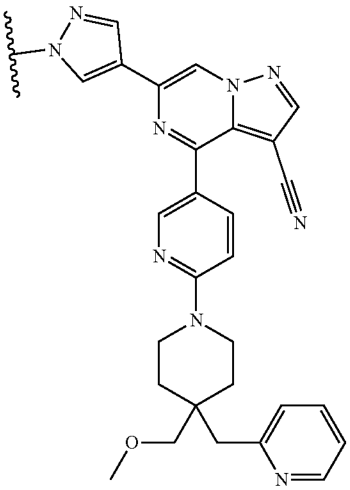
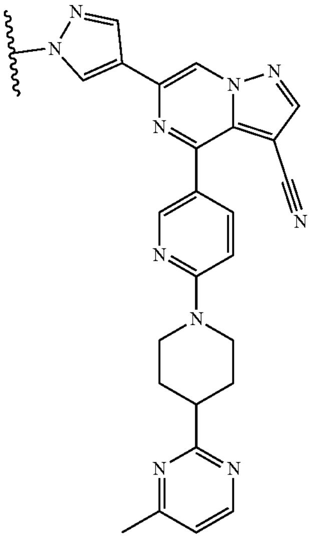
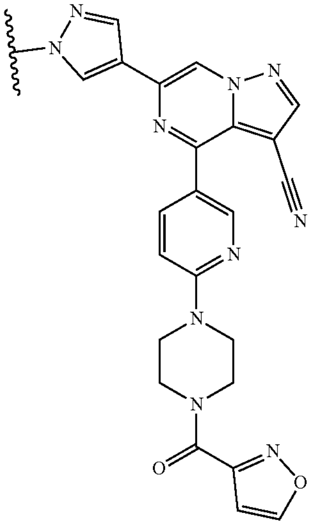

-continued
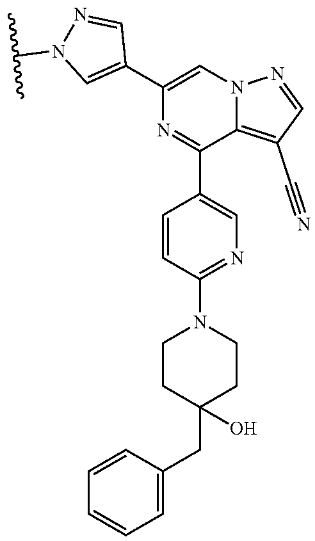
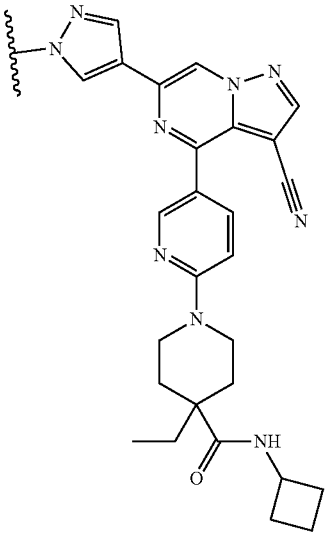
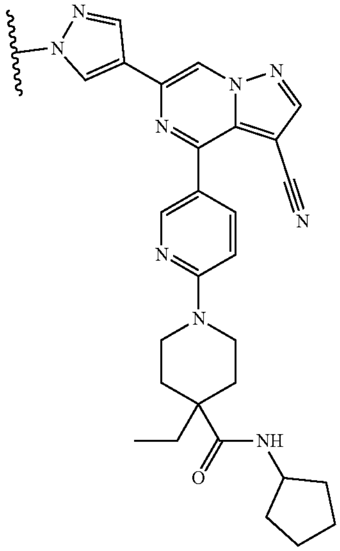
-continued
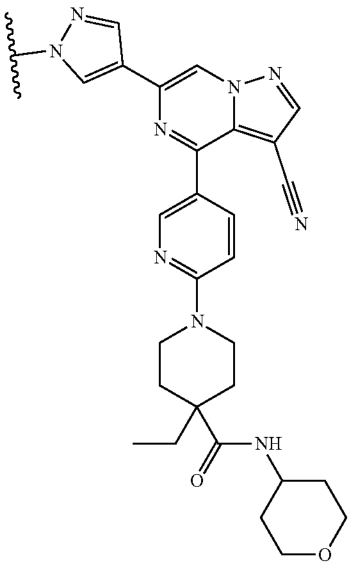
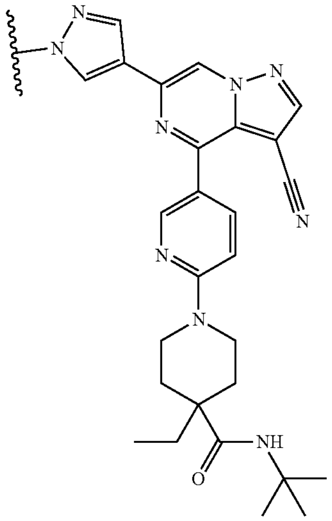
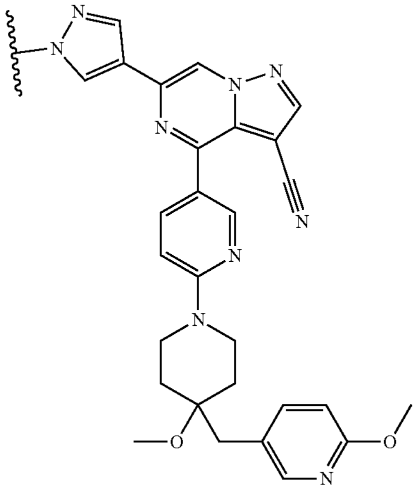

-continued
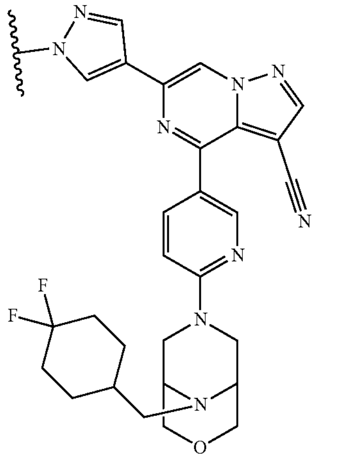
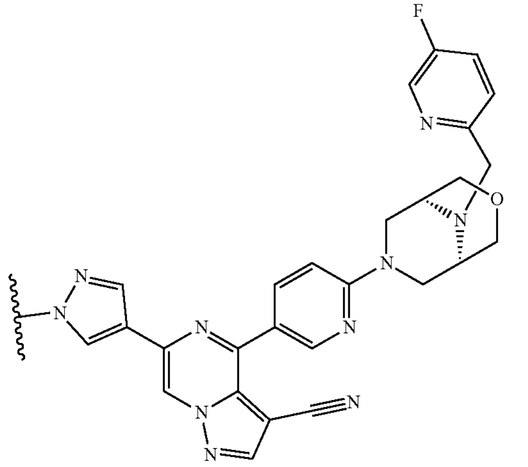
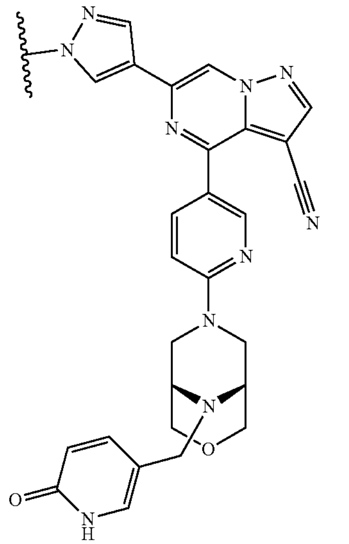
-continued
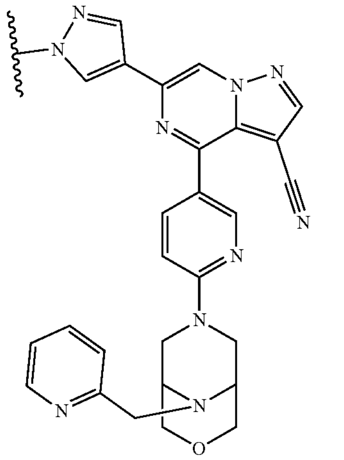
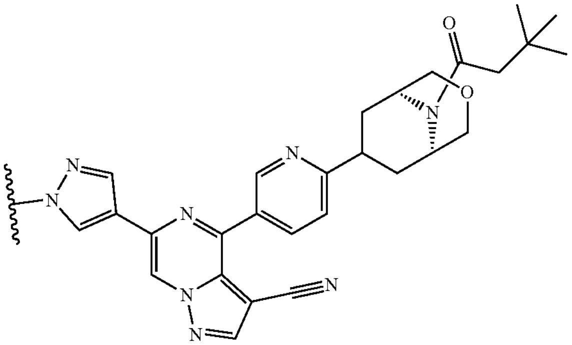
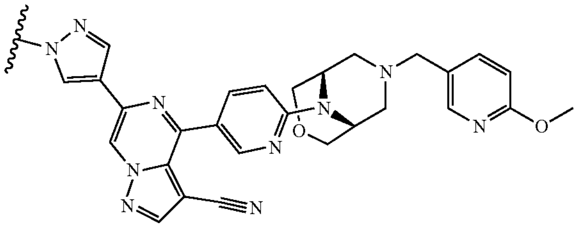
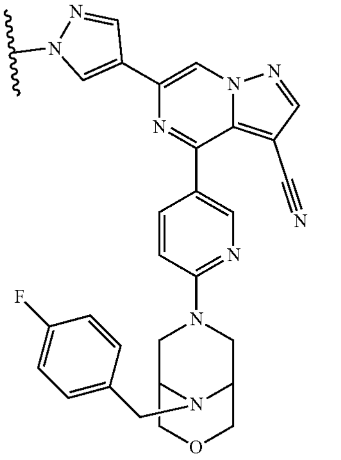

-continued
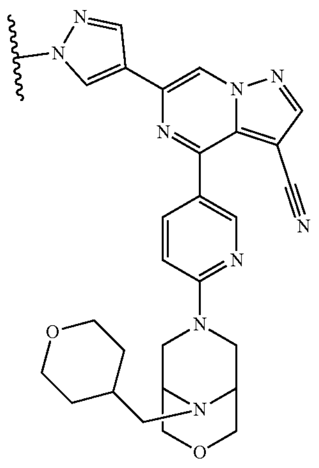
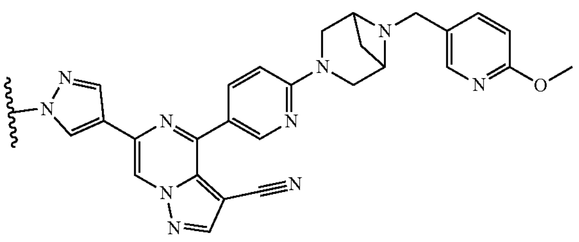
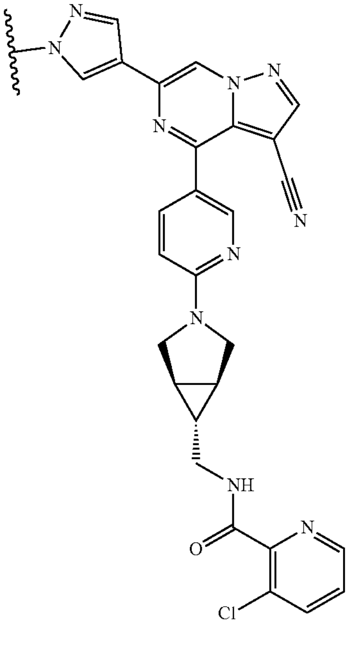
-continued
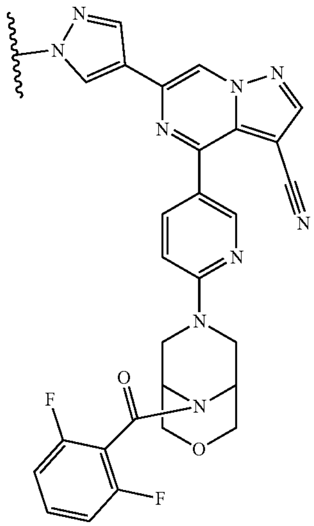
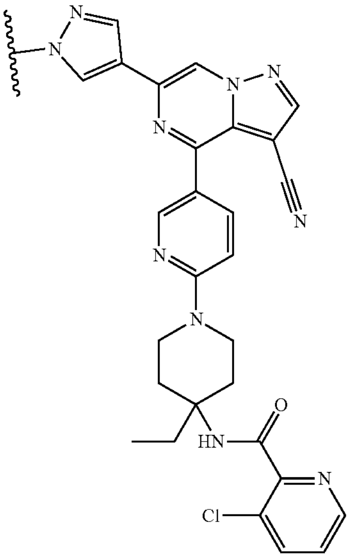
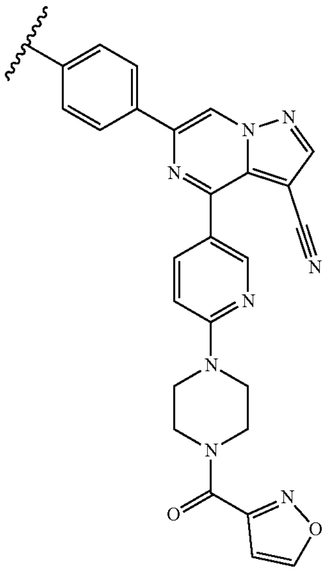

-continued
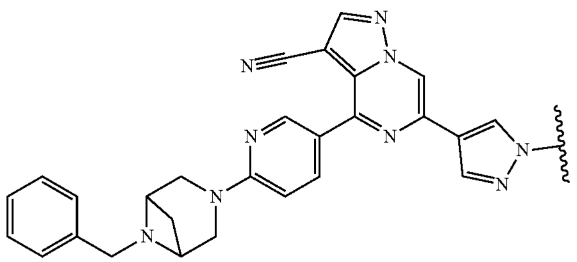
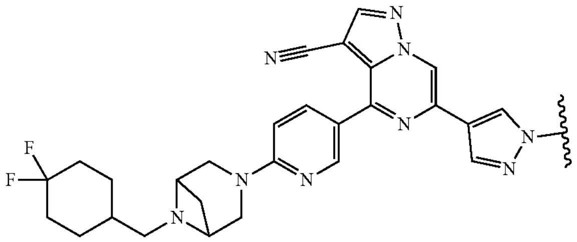
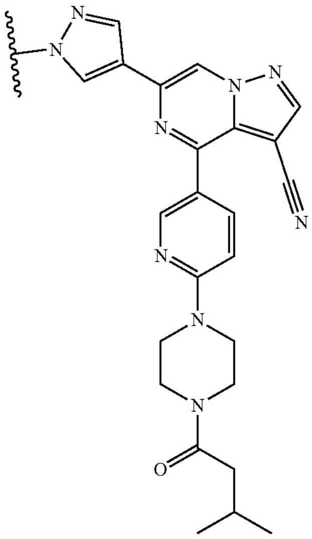
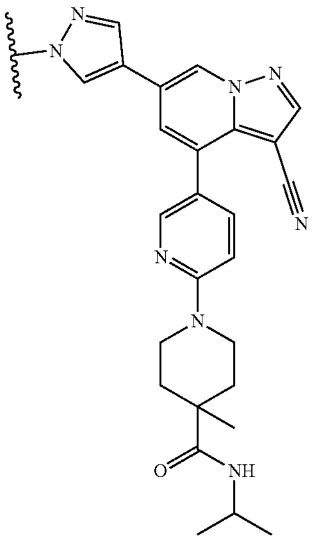
-continued
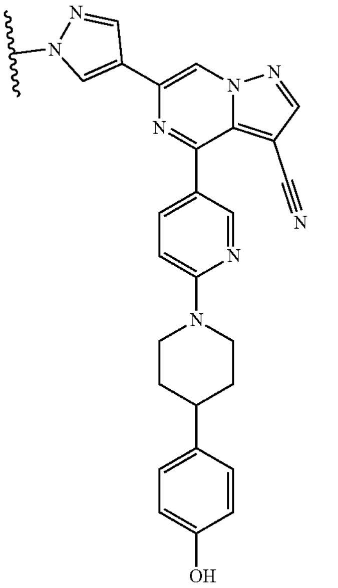
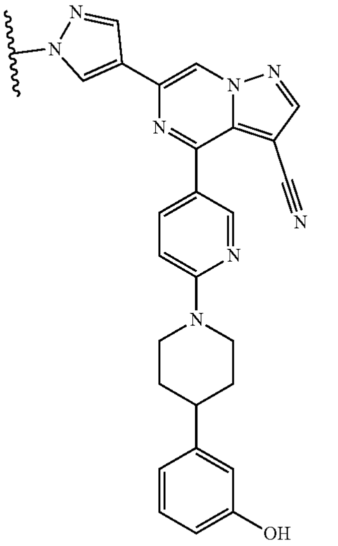
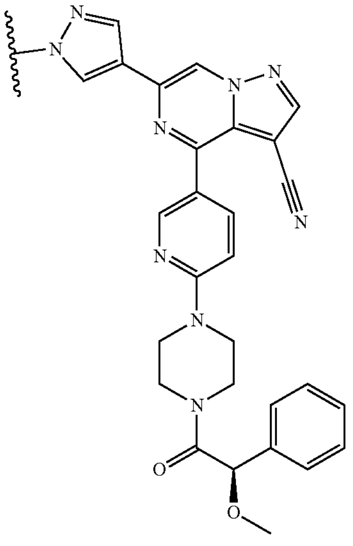

-continued
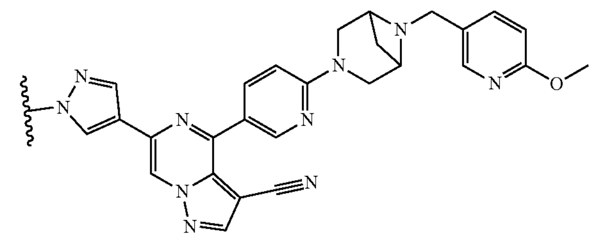
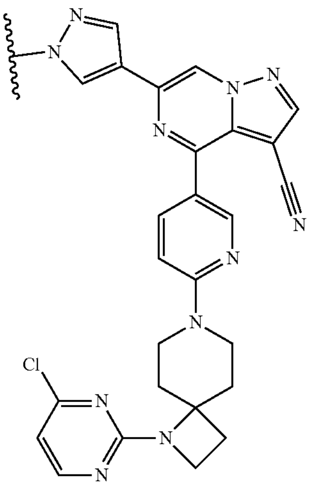
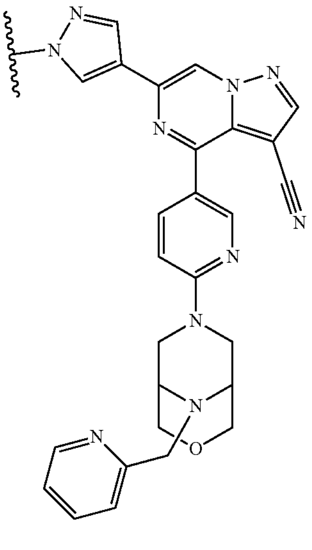
-continued
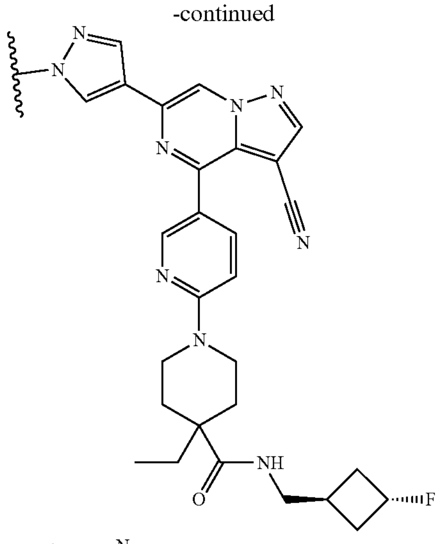
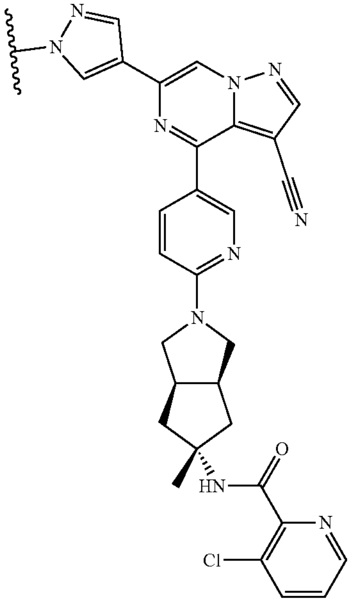
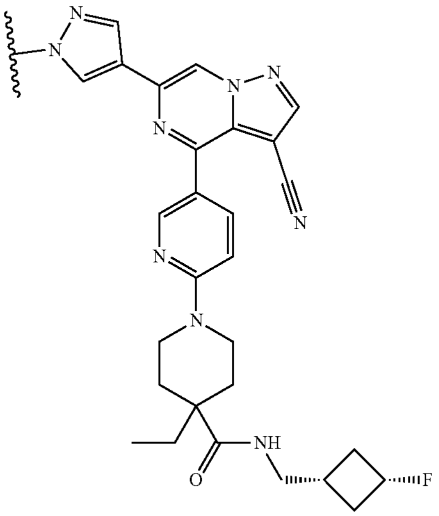

-continued
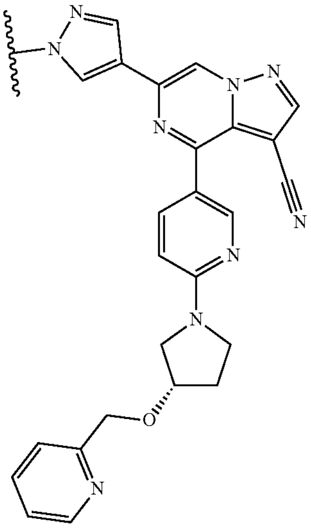
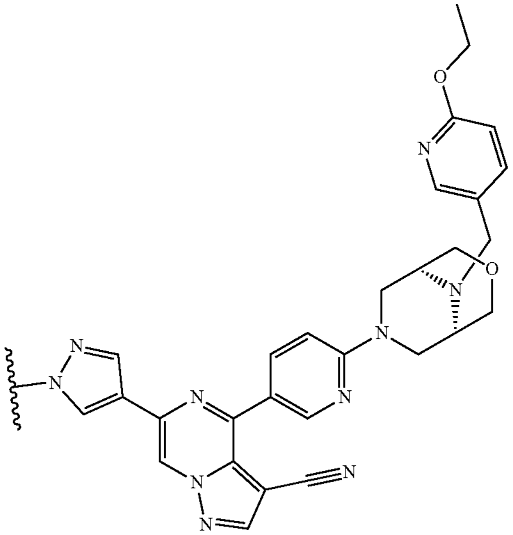
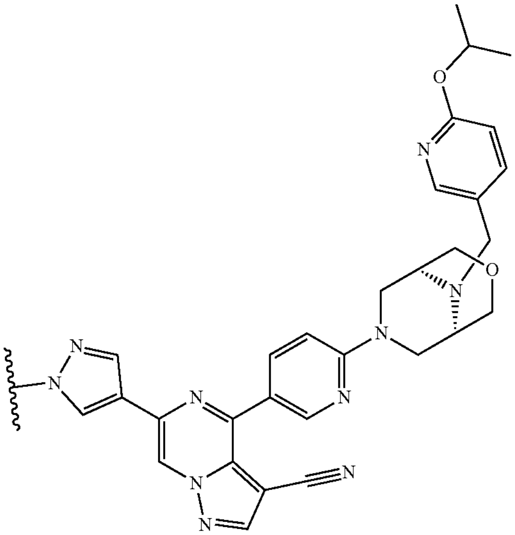
-continued
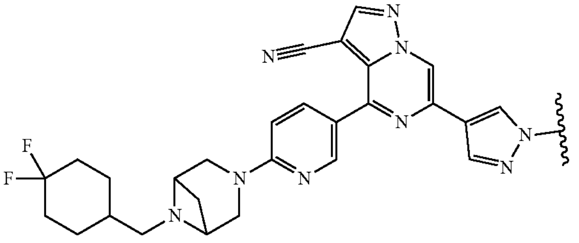
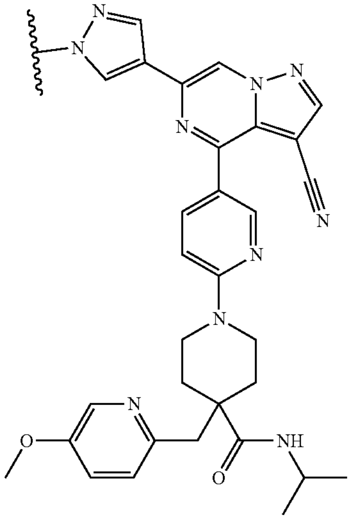
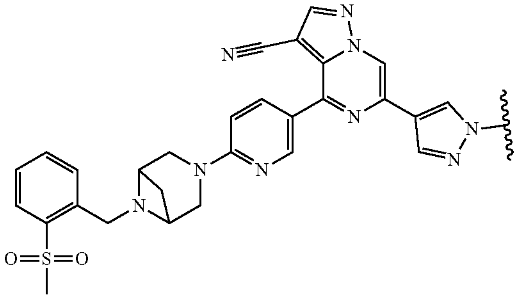
and
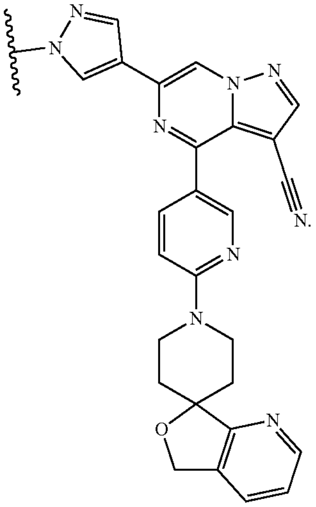 [SMILES: *n1cc(-c2cn3ncc(C#N)c3c(-c3ccc(N4CCC5(CC4)OCc4cccnc45)nc3)n2)cn1]
In certain embodiments, the RET Targeting Ligand is selected from:

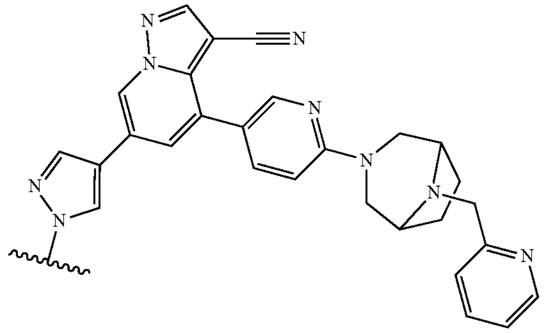

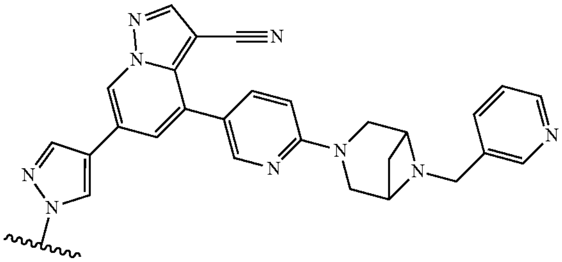

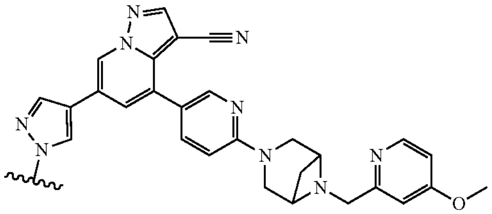

and

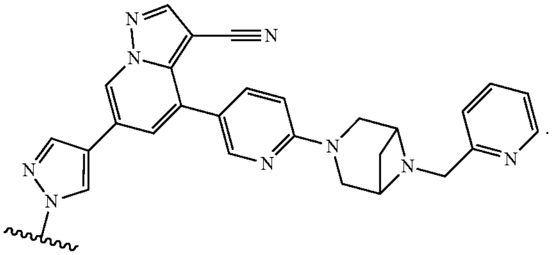

In certain alternative embodiments a compound is provided wherein the compound is a structure drawn herein wherein the cyano group is replaced with an $R^{27}$ group. For example, in this alternative embodiment when the RET targeting ligand is

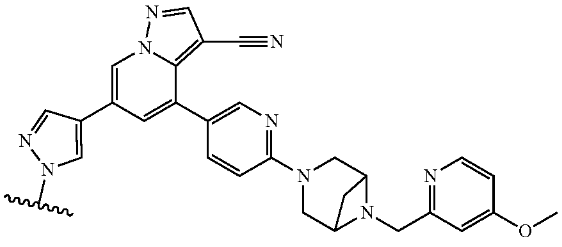 [SMILES: *n1cc(-c2cc(-c3ccc(N4CC5CC(C4)N5Cc4cc(OC)ccn4)nc3)c3c(C#N)cnn3c2)cn1]

the compound of the present invention is

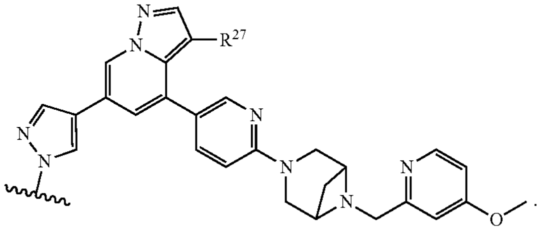

In certain embodiments the compound of the present invention is selected from:

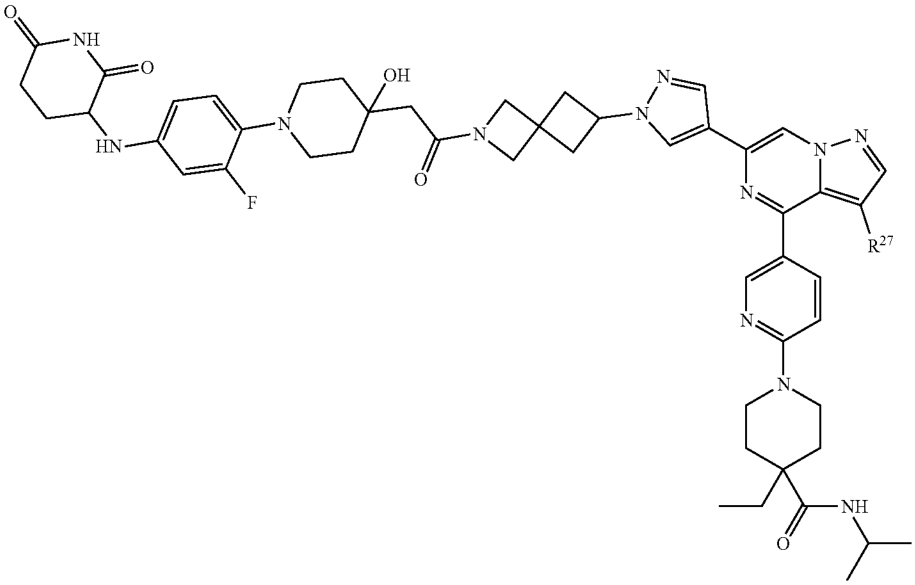

-continued
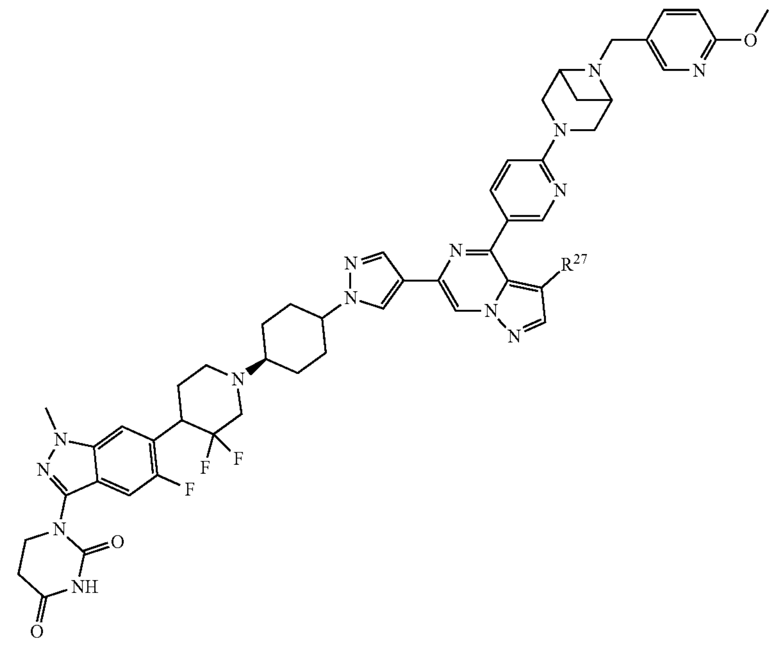
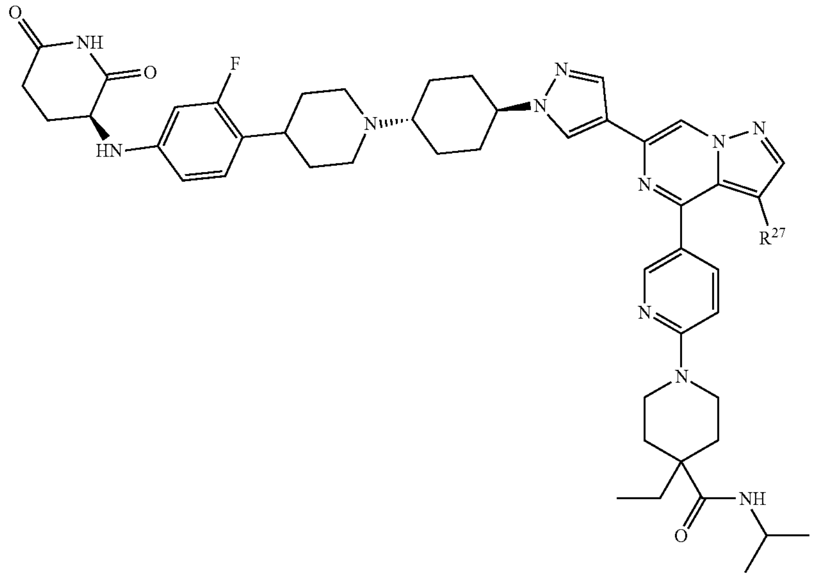

-continued
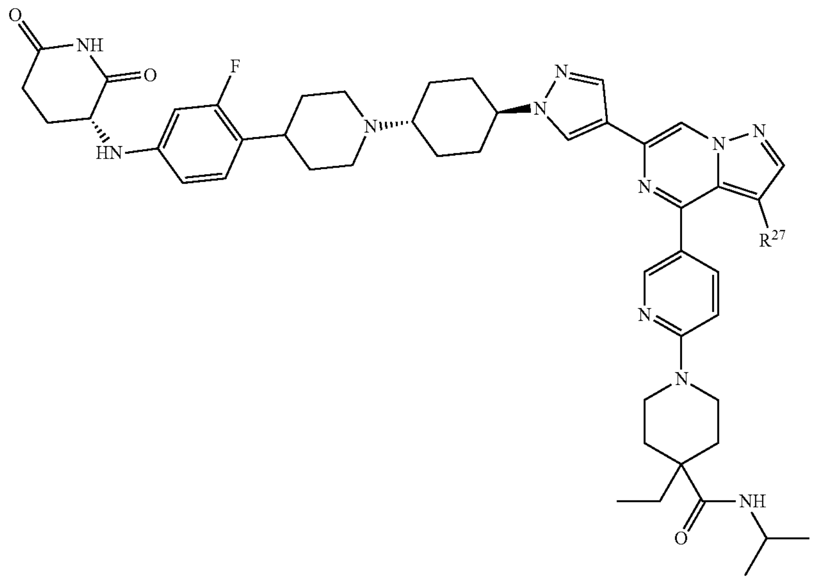
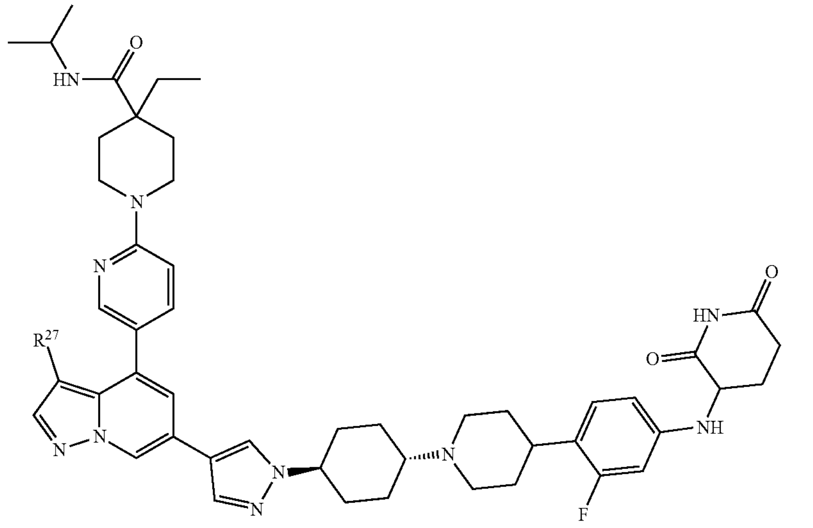
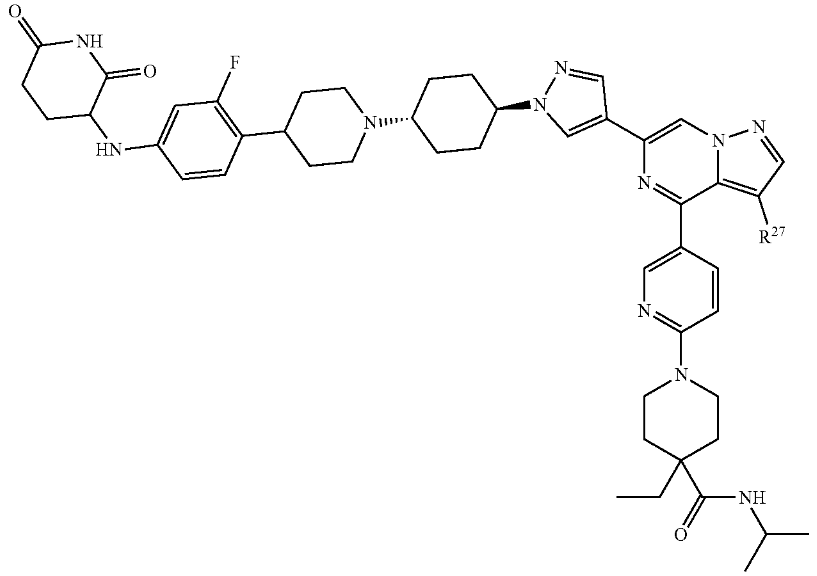

-continued
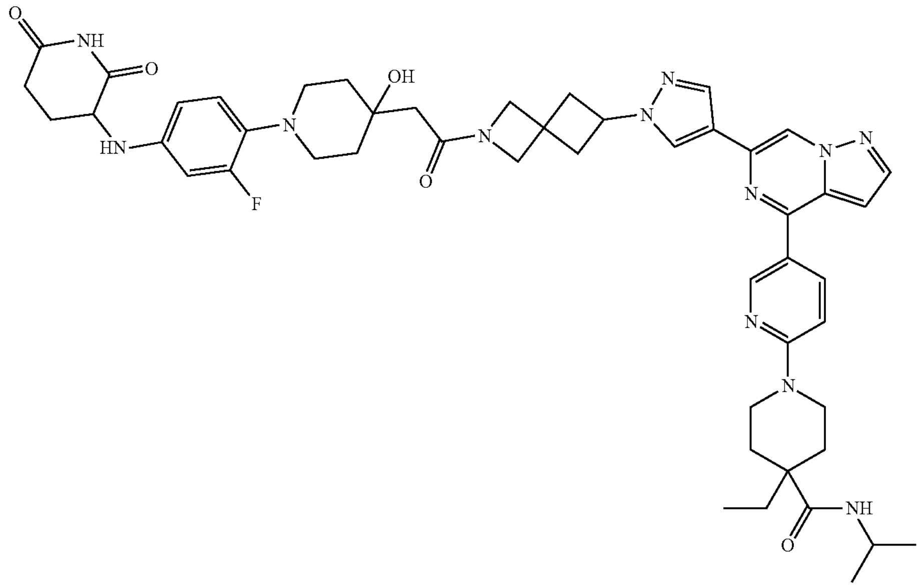
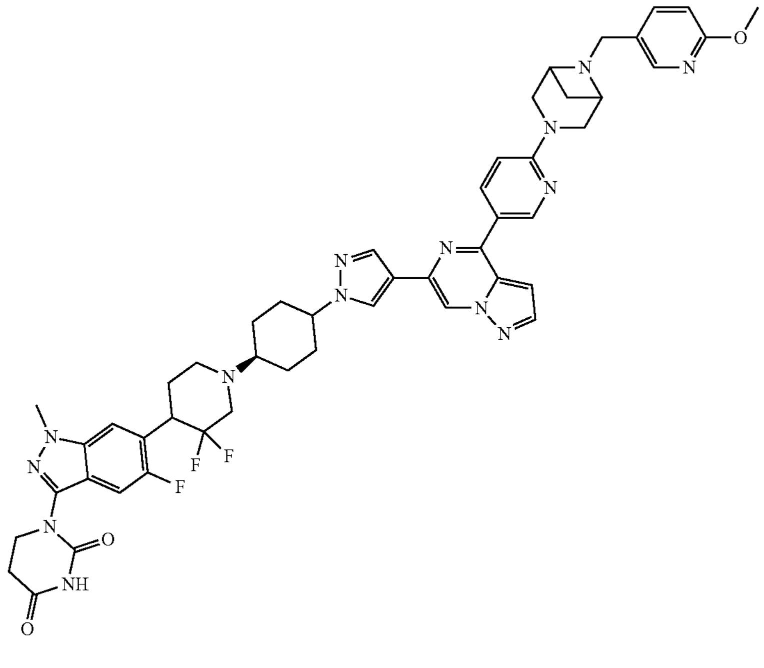

-continued
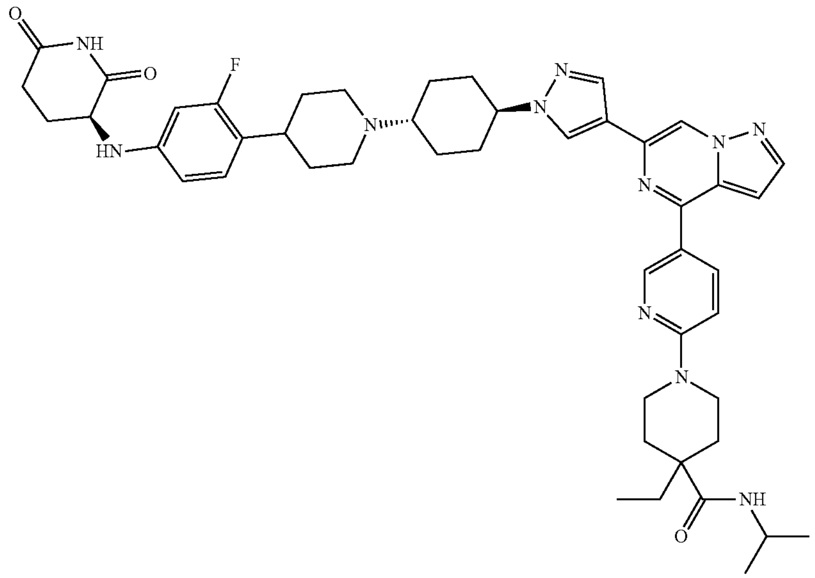
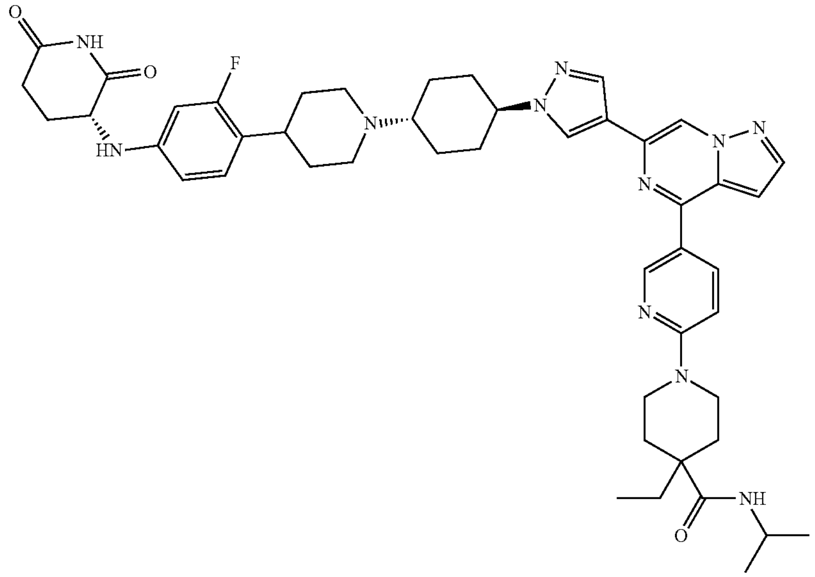
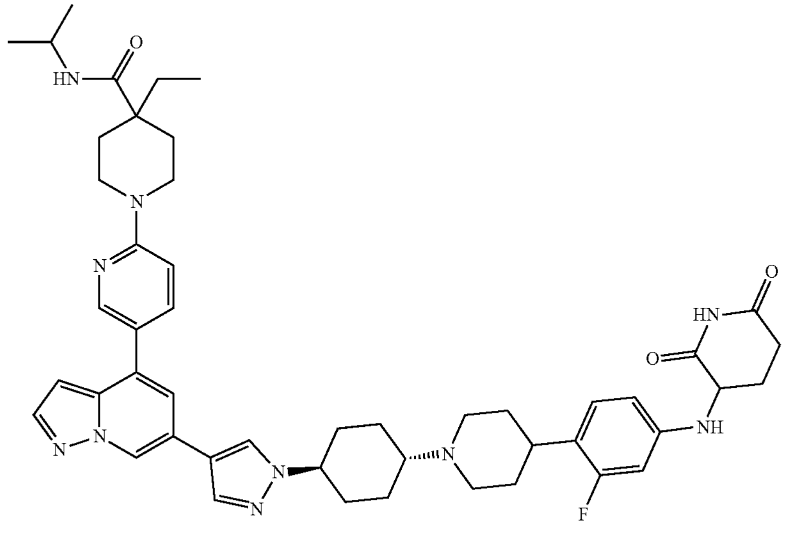

-continued

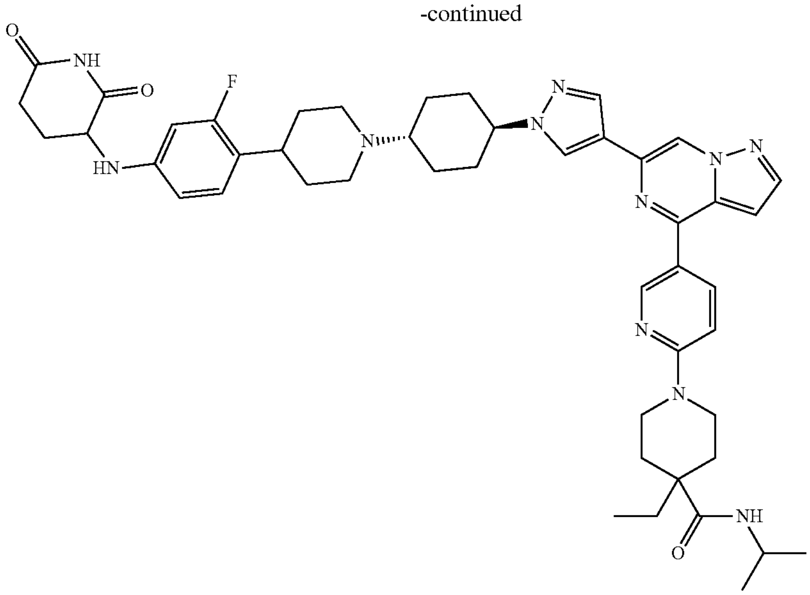

or a pharmaceutically acceptable salt thereof.

In certain embodiments $R^{27}$ is hydrogen.

In certain embodiments $R^{27}$ is halogen.

In certain embodiments $R^{27}$ is nitro.

IV. Linkers

A Linker is included in the compounds of Formula I, Formula II, Formula III, Formula IV, Formula V, Formula VI, or Formula VII. Linker is a chemically stable bivalent group that attaches an E3 Ligase binding portion to a Targeting Ligand. According to the invention, any desired linker, as described herein, can be used as long as the resulting compound has a stable shelf life for at least 2 months, 3 months, 6 months or 1 year as part of a pharmaceutically acceptable dosage form, and itself is pharmaceutically acceptable.

Linker as described herein can be used in either direction, i.e., either the left end is linked to the E3 Ligase Binding portion and the right end to the RET Targeting Ligand, or the left end is linked to the RET Targeting Ligand and the right end is linked to the E3 Ligase Binding portion.

In certain embodiments, the Linker has a chain of 2 to 14, 15, 16, 17, 18 or 20 or more carbon atoms of which one or more carbons can be replaced by a heteroatom such as O, N, S, or P.

In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units).

In certain embodiments the chain has at least 1, 2, 3, 4, 5, 6, 7, or 8 contiguous chains which can have branches which can be independently alkyl, aryl, heteroaryl, alkenyl, or alkynyl, aliphatic, heteroaliphatic, cycloalkyl or heterocycle substituents.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocycle, cycloalkyl, etc., as desired to achieve the appropriate drug properties.

In certain embodiments, Linker is selected from:

(LI)

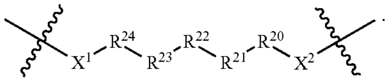

In one aspect, Linker is selected from the group consisting of a moiety of Formula LI, Formula LII, Formula LIII, Formula LIV, Formula LV, Formula LVI, Formula LVII Formula LVIII, Formula IX and Formula LX:

(LII)

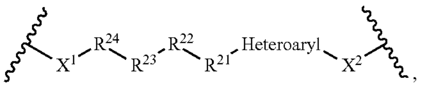

(LIII)

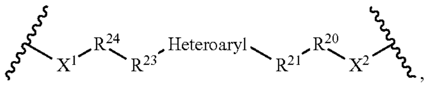

(LIV)

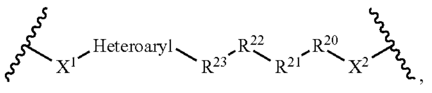

(LV)

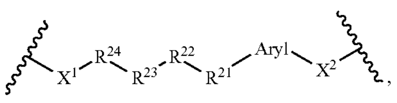

-continued (LVI)

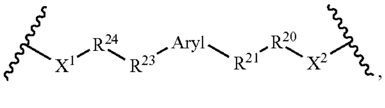, (LVII)

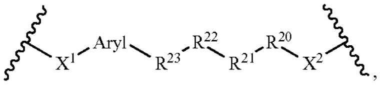, (LVIII)

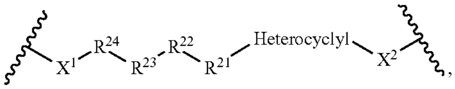, (LIX)

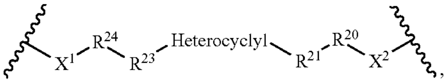, and (LX)

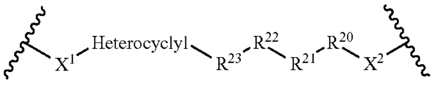;

wherein, $X^1$ and $X^2$ are independently at each occurrence selected from bond, heterocycle, $NR^2$, $C(R^2)_2$, O, C(O), and S;

$R^2$ is independently at each occurrence selected from the group consisting of hydrogen, alkyl, aliphatic, heteroaliphatic, heterocycle, aryl, heteroaryl, —C(O)H, —C(O)OH, —C(O)alkyl, —C(O)Oalkyl, —C(O)(aliphatic, aryl, heteroaliphatic or heteroaryl), —C(O)O (aliphatic, aryl, heteroaliphatic, or heteroaryl), alkene, and alkyne;

$R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —$SO_2$—, —S(O)—, —C(S)—, —C(O)$NR^2$—, —$NR^2$C(O)—, —O—, —S—, —$NR^2$—, —$C(R^{40}R^{40})$—, —P(O)($OR^{26}$)O—, —P(O)($OR^{26}$)—, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from $R^{40}$;

$R^{26}$ is independently at each occurrence selected from the group consisting of hydrogen, alkyl, arylalkyl, heteroarylalkyl, alkene, alkyne, aryl, heteroaryl, heterocycle, aliphatic and heteroaliphatic; and $R^{40}$ is independently at each occurrence selected from the group consisting of hydrogen, alkyl, alkene, alkyne, fluoro, bromo, chloro, hydroxyl, alkoxy, azide, amino, cyano, —NH(aliphatic, including alkyl), —N(aliphatic, including alkyl)$_2$, —$NHSO_2$(aliphatic, including alkyl), —N(aliphatic, including alkyl)$SO_2$alkyl, —$NHSO_2$(aryl, heteroaryl or heterocycle), —N(alkyl) $SO_2$(aryl, heteroaryl or heterocycle), —$NHSO_2$alkenyl, —N(alkyl)$SO_2$alkenyl, —$NHSO_2$alkynyl, —N(alkyl) $SO_2$alkynyl, haloalkyl, aliphatic, heteroaliphatic, aryl, heteroaryl, heterocycle, and cycloalkyl.

In certain embodiments, Linker selected from:

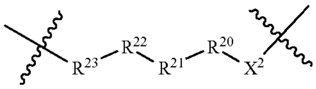.

In one aspect, Linker is selected from the group consisting of a moiety of Formula LDI, Formula LDII, Formula LDIII, Formula LDIV, Formula LDV, Formula LDVI, and Formula LDVII:

(LDI)

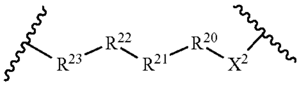, (LDII)

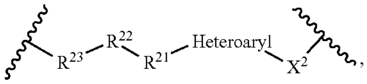, (LDIII)

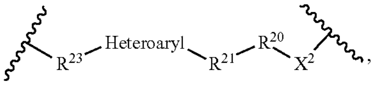, (LDIV)

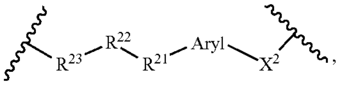, (LDV)

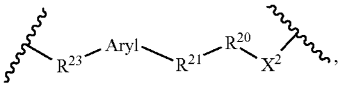, (LDVI)

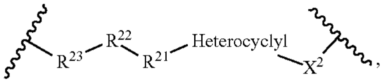, and (LDVII)

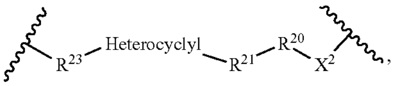, wherein all variables are described herein.

The following are non-limiting examples of Linkers that can be used in this invention. Based on this elaboration, those of skill in the art will understand how to use the full breadth of Linkers that will accomplish the goal of the invention.

Non-limiting examples of Linker include:

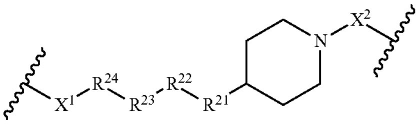

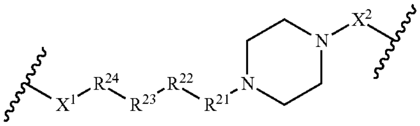

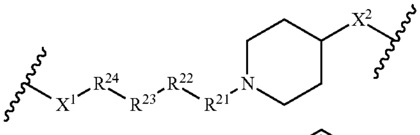

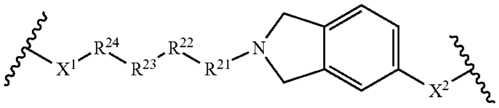

-continued
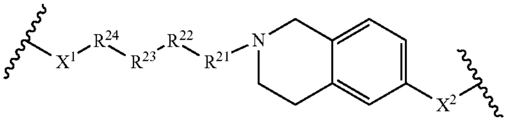
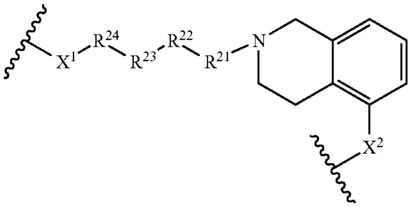
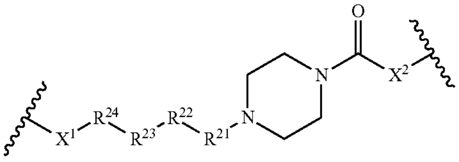
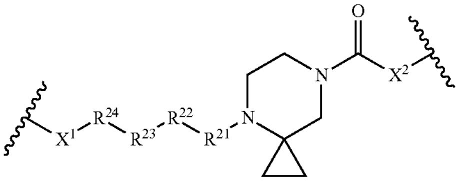
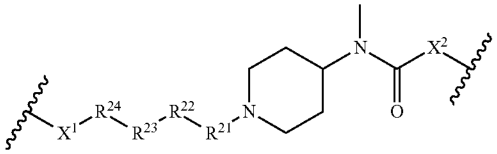
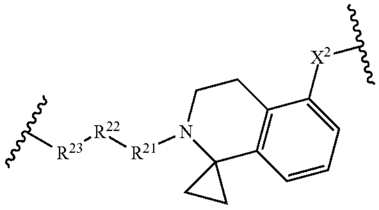
or
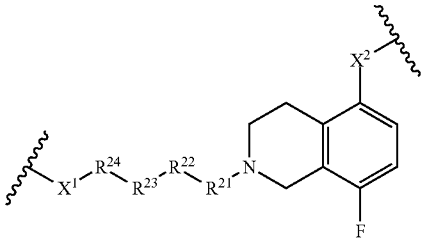
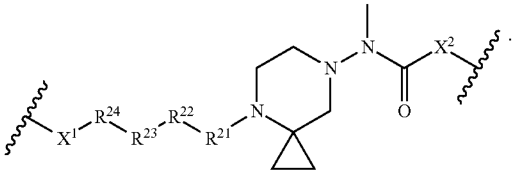
.
Non-limiting examples of Linker include:
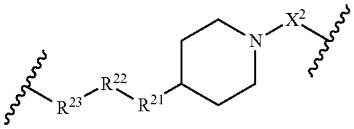
-continued
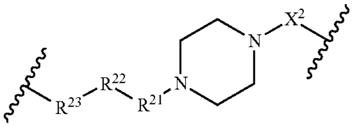
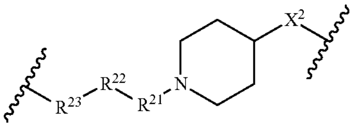
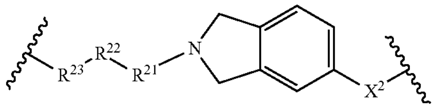
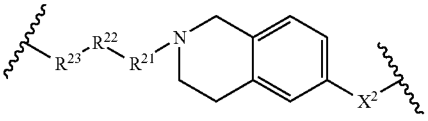
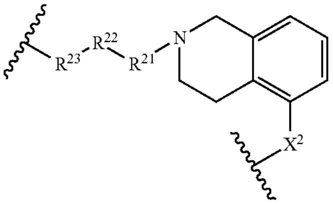
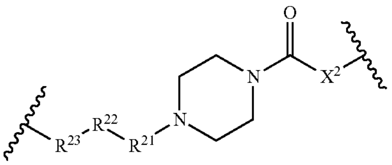
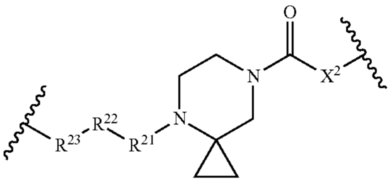
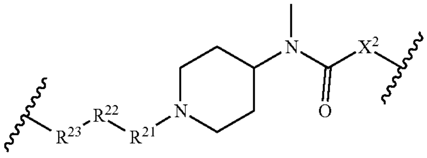
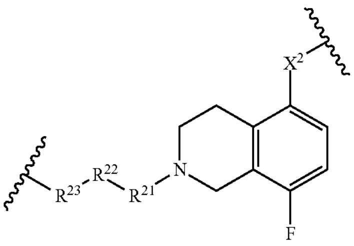
or
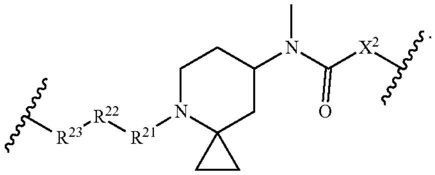
.
In one embodiment $X^2$ is attached to the RET Targeting Ligand. In another embodiment $X^1$ is attached to the RET Targeting Ligand.

Non-limiting examples of moieties of $R^{20}$, $R^{21}$, $R^{22}$, $R^{23}$, and $R^{24}$ include:
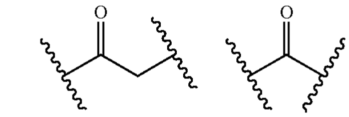
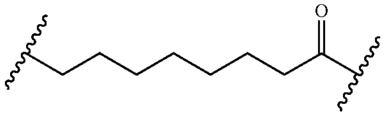
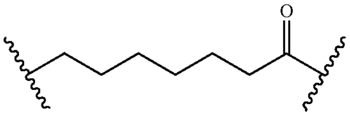
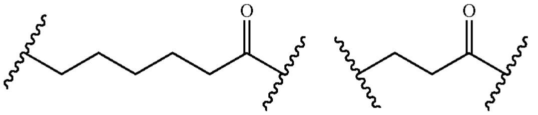
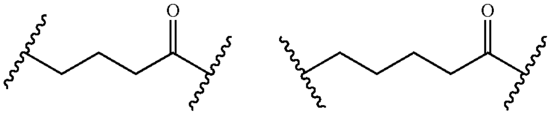
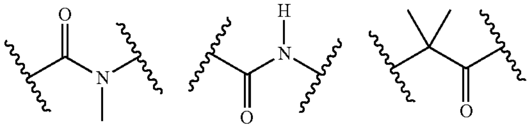
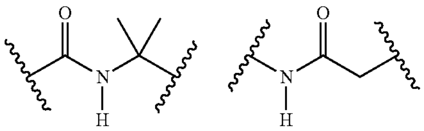
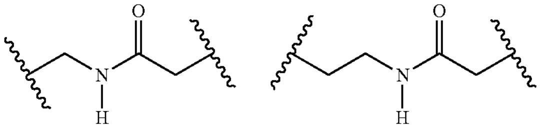
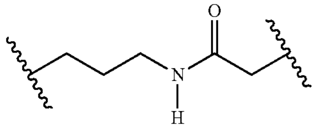
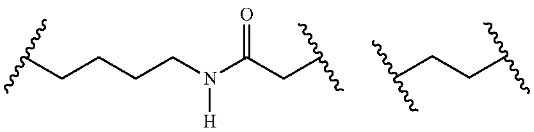
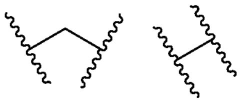
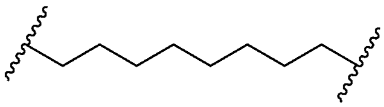
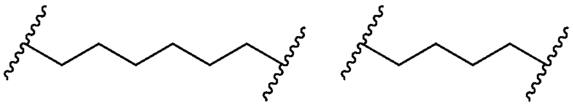
-continued
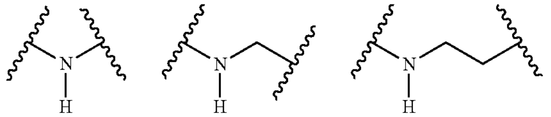
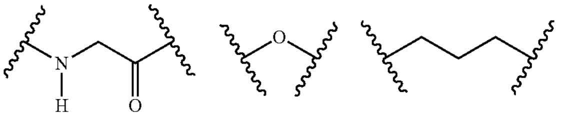
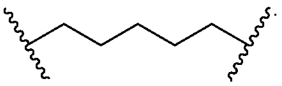
Additional non-limiting examples of moieties of $R^{20}$, $R^{21}$, $R^{22}$, $R^{23}$, and $R^{24}$ include:
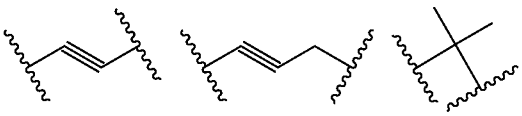
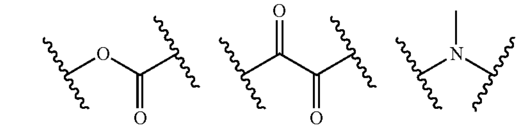
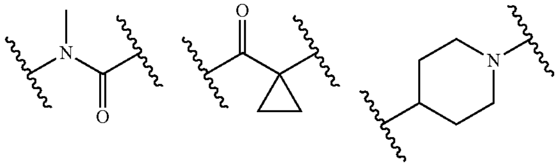
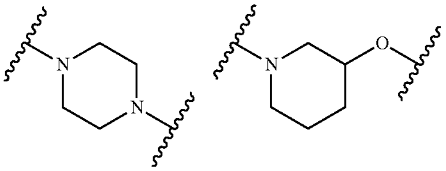
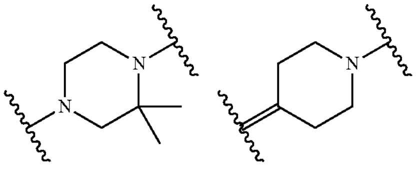
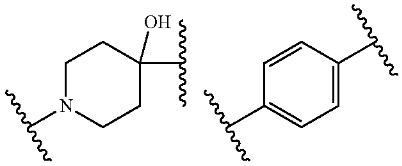
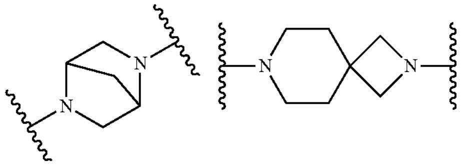
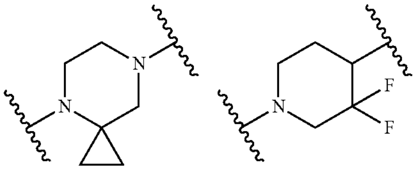

-continued

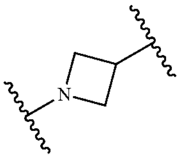
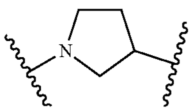
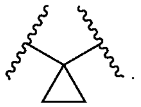

Additional non-limiting examples of moieties of $R^{20}$, $R^{21}$, $R^{22}$, $R^{23}$, and $R^{24}$ include:

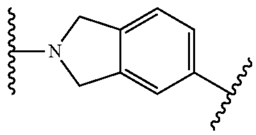
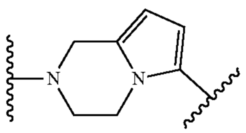
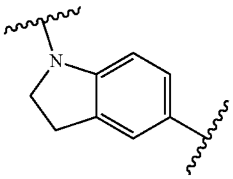
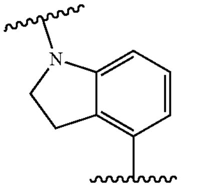
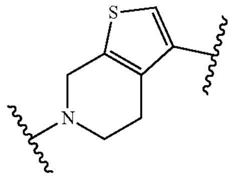
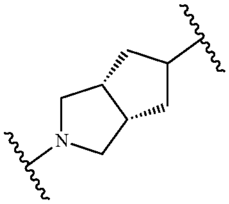
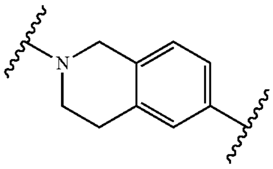
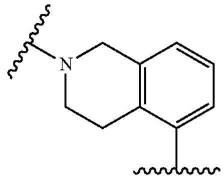
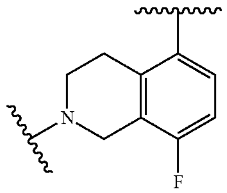
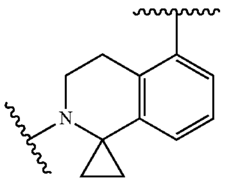
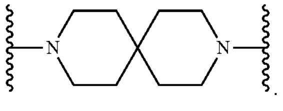

In additional embodiments, the Linker moiety is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms.

In certain embodiments, the Linker is flanked, substituted, or interspersed with an aryl, phenyl, benzyl, alkyl, alkylene, or heterocycle group.

In certain embodiments, the Linker may be asymmetric or symmetrical.

In certain embodiments, Linker can be a nonlinear chain, and can be, or include, aliphatic or aromatic or heteroaromatic cyclic moieties.

In any of the embodiments of the compounds described herein, the Linker group may be any suitable moiety as described herein.

In certain embodiments Linker is selected from the group consisting of

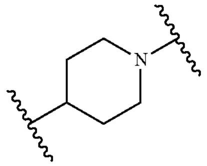
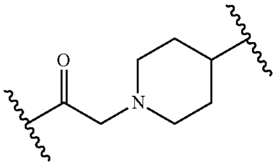
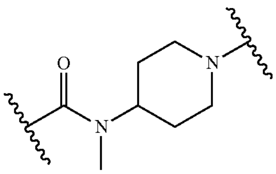
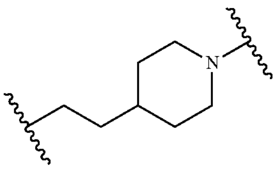
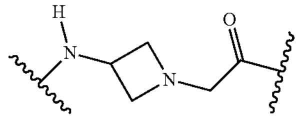
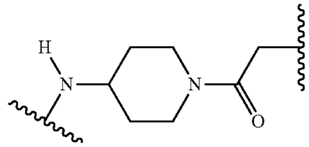
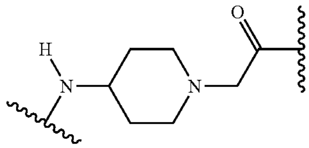
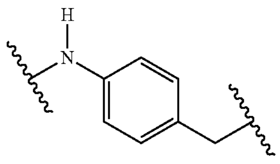
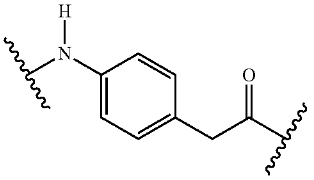
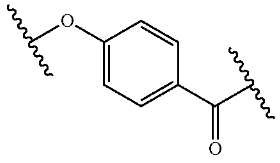

and

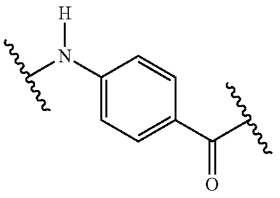

-continued
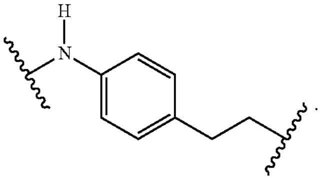
In certain embodiments, Linker is selected from the group consisting of:
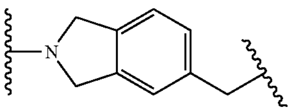
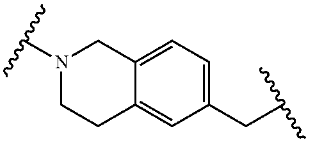
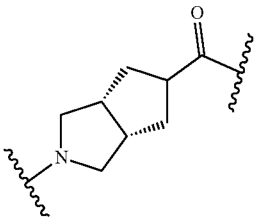
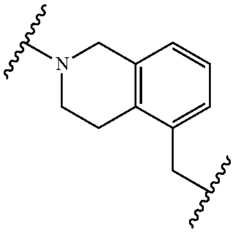
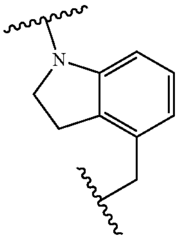
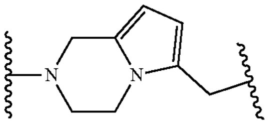
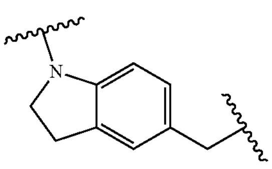
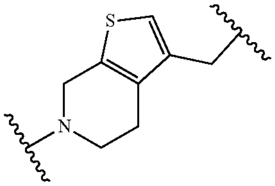
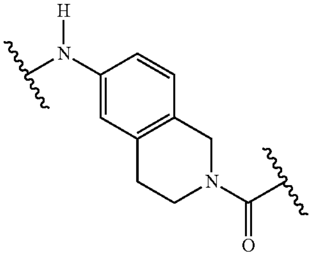
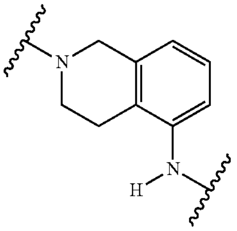
-continued
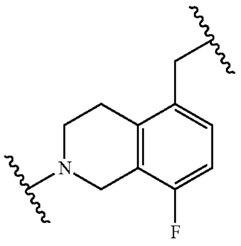
and
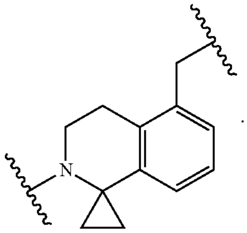
In certain embodiments, Linker is selected from the group consisting of:
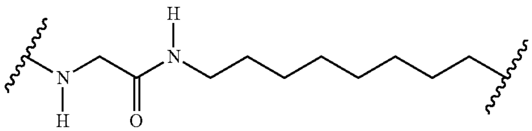
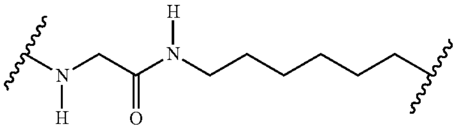
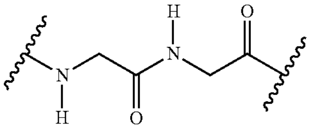
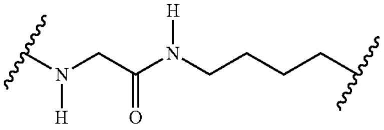
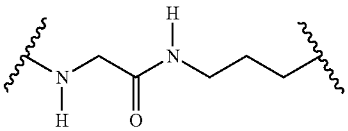
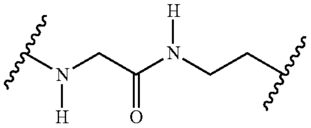
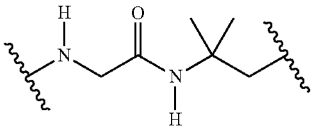
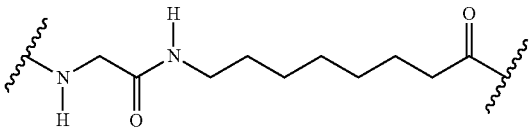
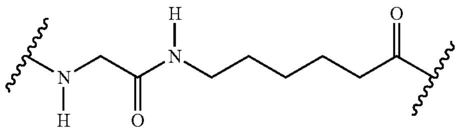
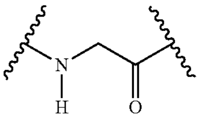

-continued
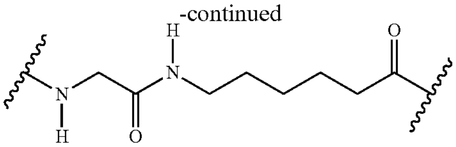
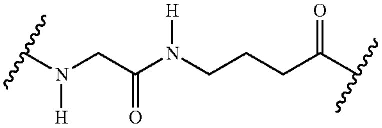
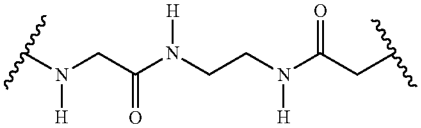
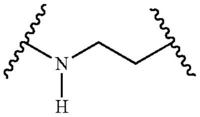
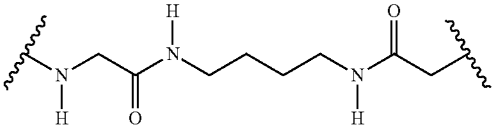
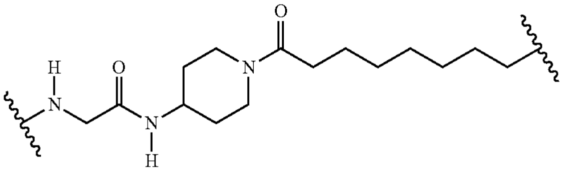
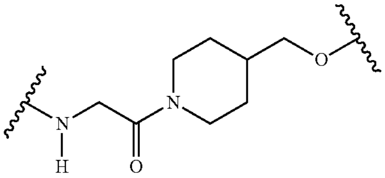
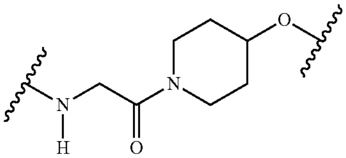
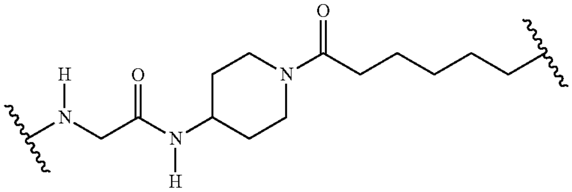
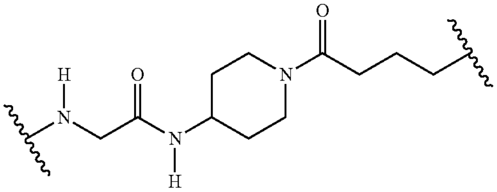
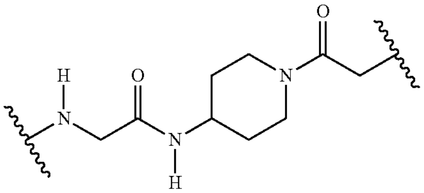
-continued
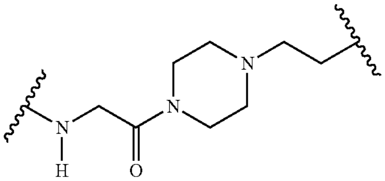
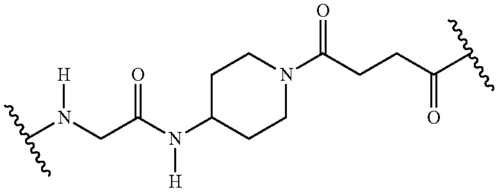
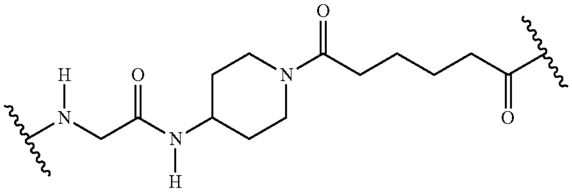
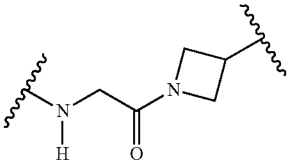
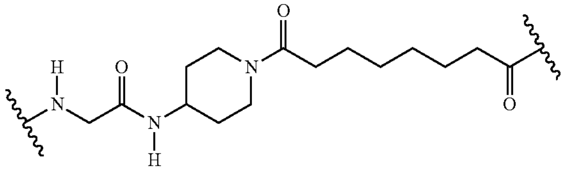
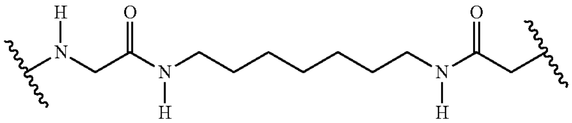
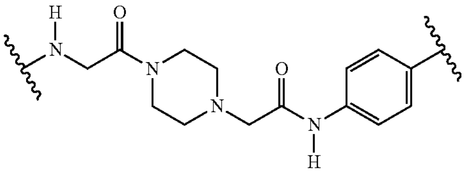
and
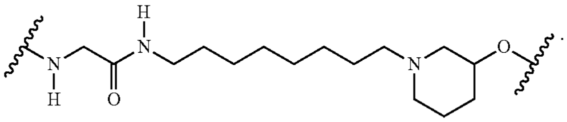
In certain embodiments, Linker is selected from the group consisting of:
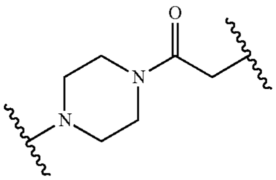
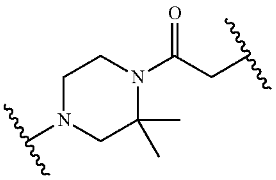

-continued
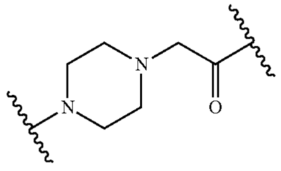
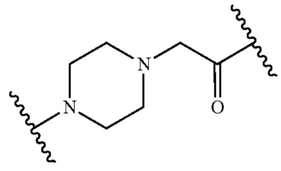
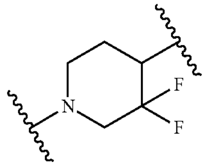
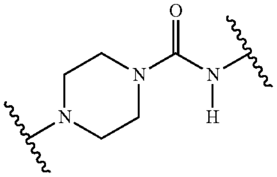
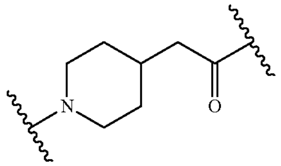
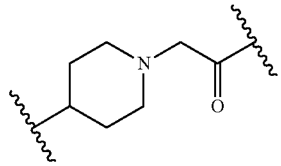
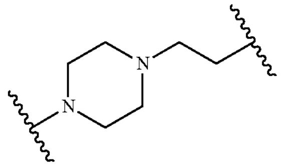
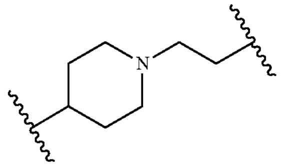
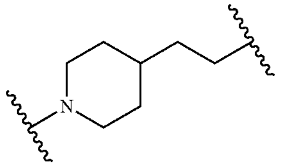
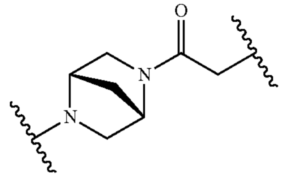
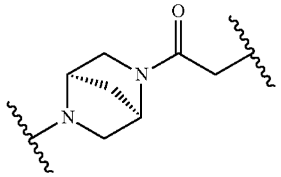
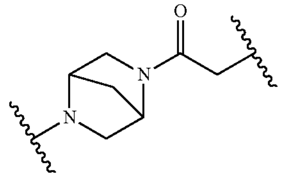
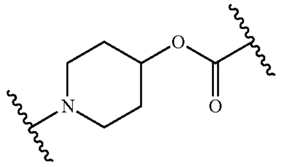
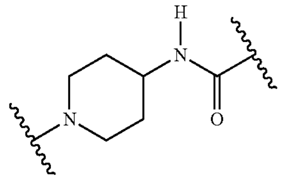
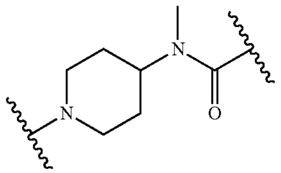
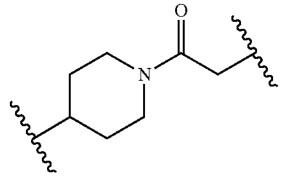
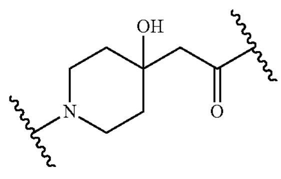
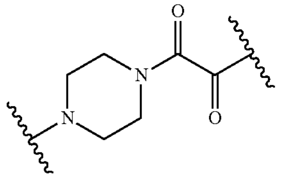
-continued
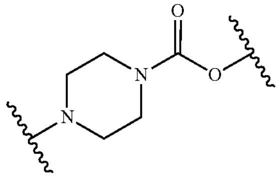
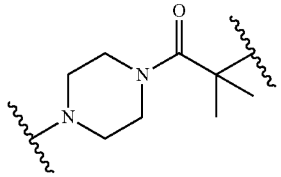
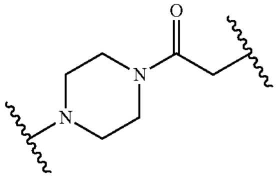
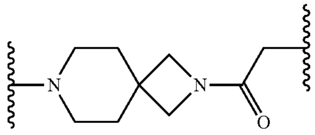
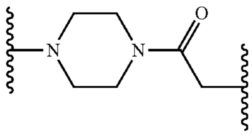
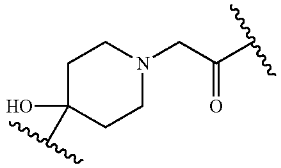
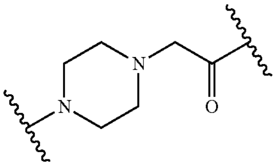
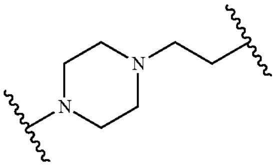
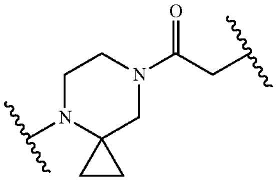
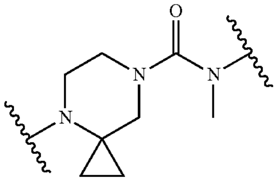
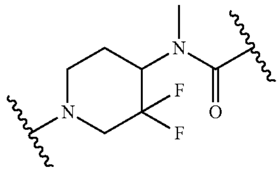
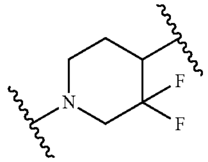 and
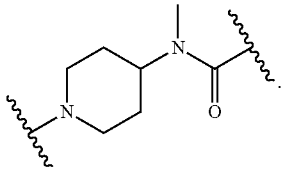.
In certain embodiments, Linker is selected from the group consisting of:
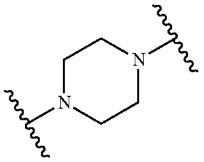

-continued
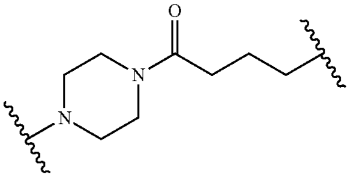
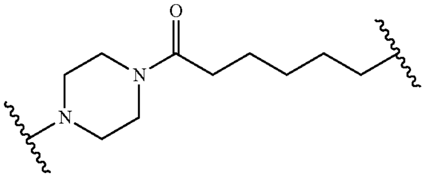
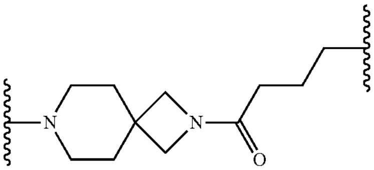
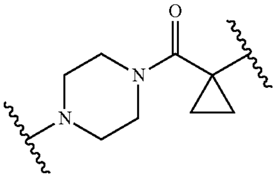
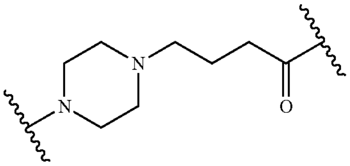
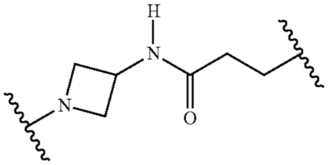
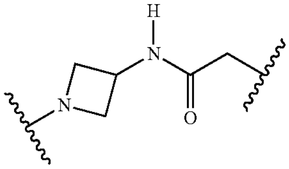
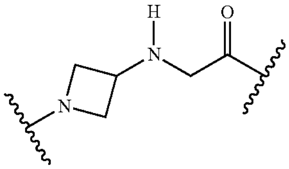
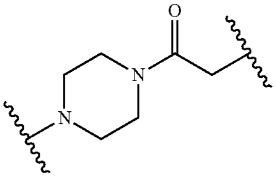
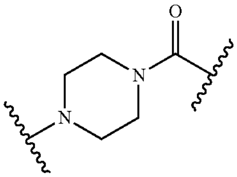
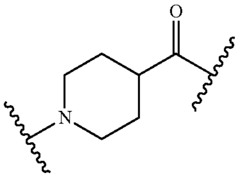
-continued
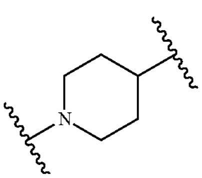
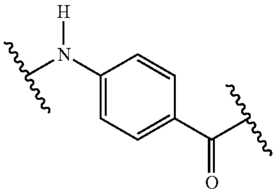
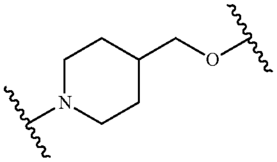
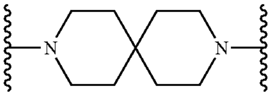
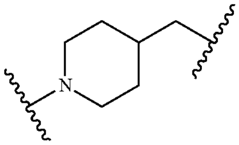
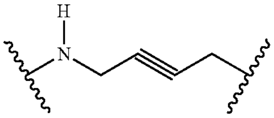
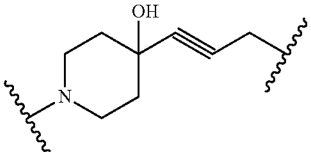
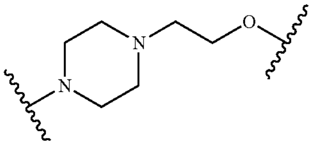
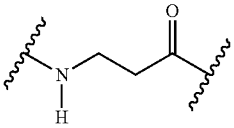
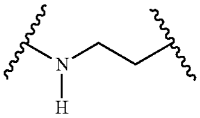
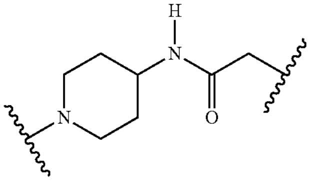
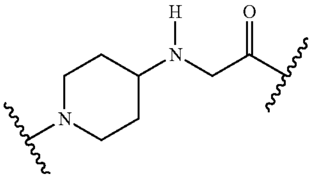
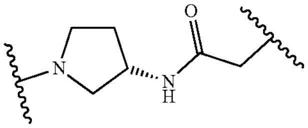
and
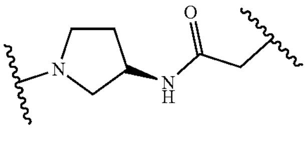

In certain embodiments Linker is selected from:
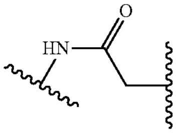
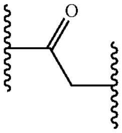
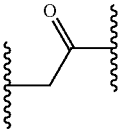
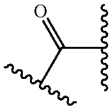
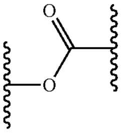
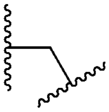
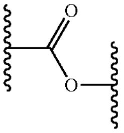
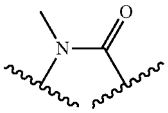
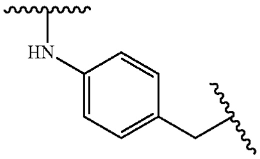
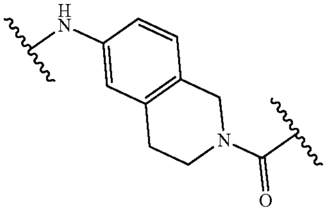
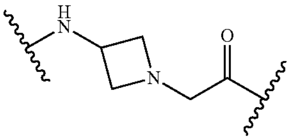
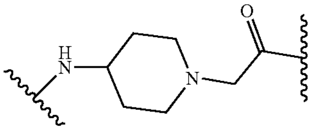
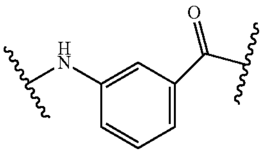
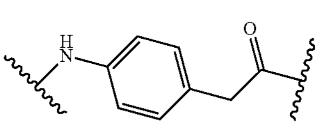
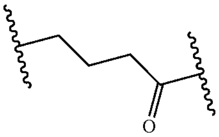
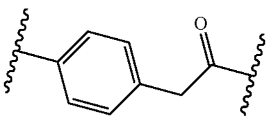
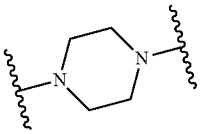
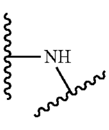
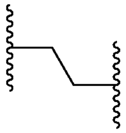
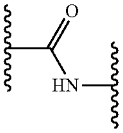
In certain embodiments, the Linker is selected from
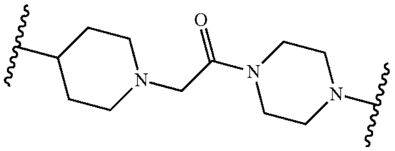
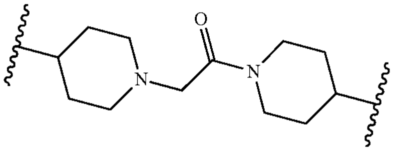
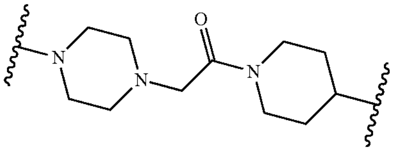
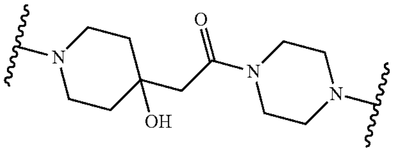
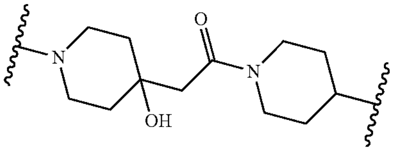
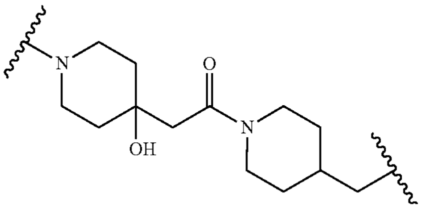
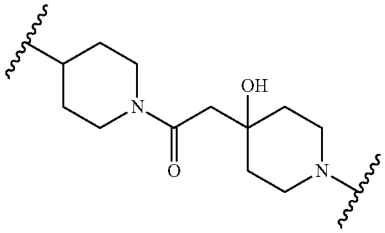
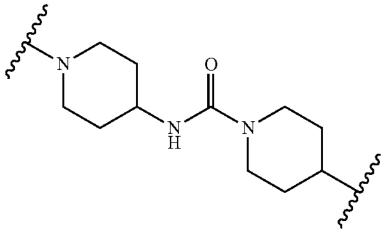
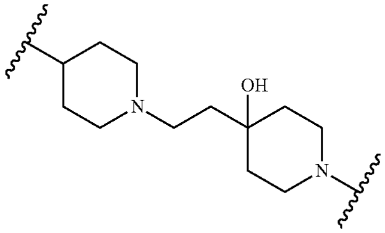

-continued
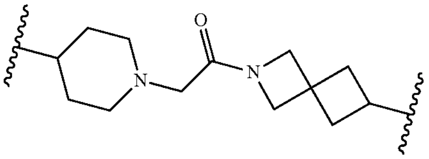
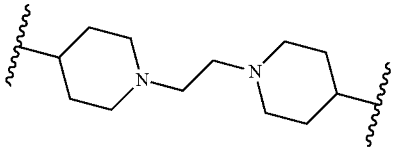
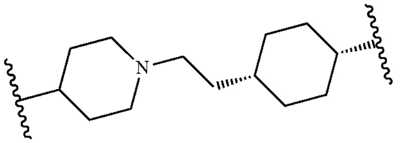
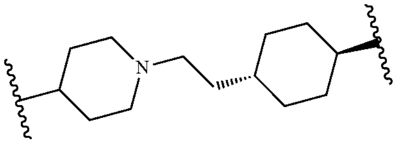
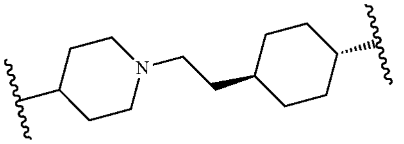
-continued
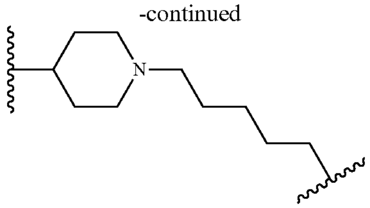
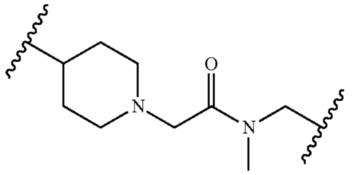
and
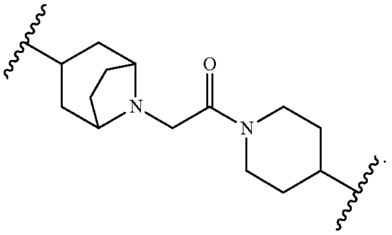
In certain embodiments the right bond of the Linker drawn above is attached to the RET Targeting Ligand. In certain embodiments the left bond of the Linker drawn above is attached to the RET Targeting Ligand.
In certain embodiments, the compound of the present invention is selected from:
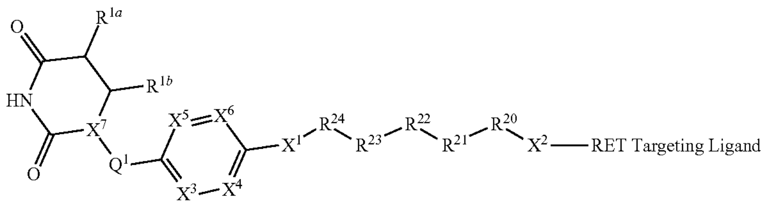
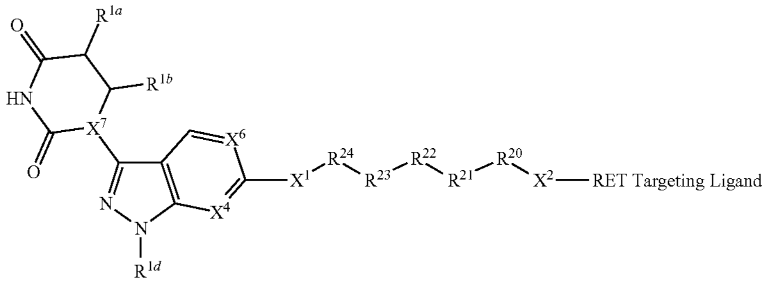
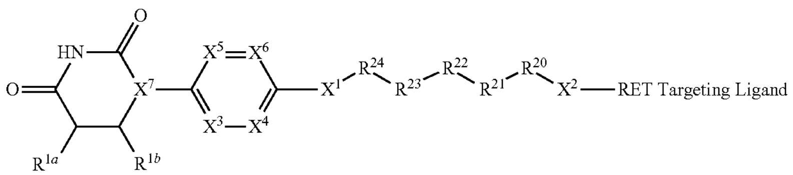

-continued
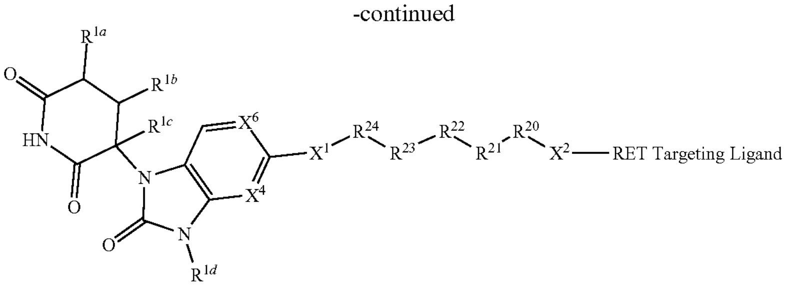
or a pharmaceutically acceptable salt thereof.
In certain embodiments, the compound of the present invention is selected from:
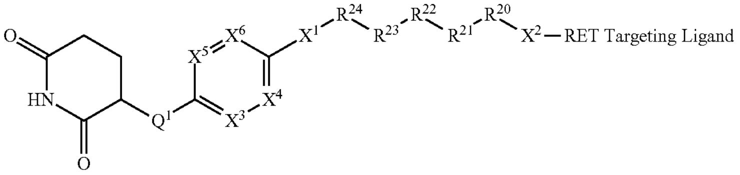
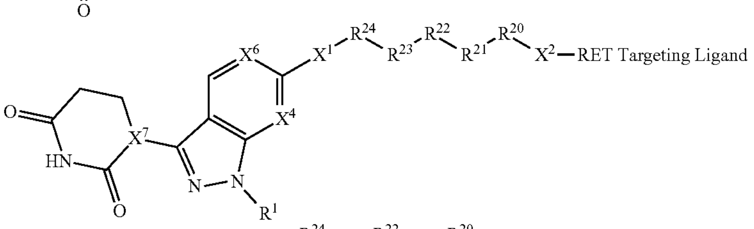
and
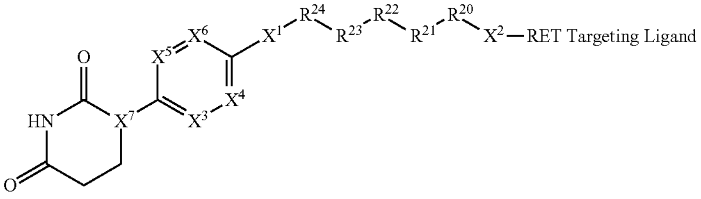
or a pharmaceutically acceptable salt thereof.
In certain embodiments, the compound of the present invention is selected from:
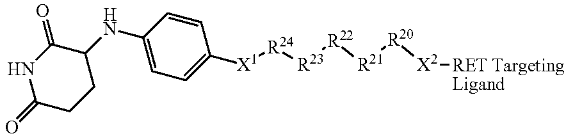
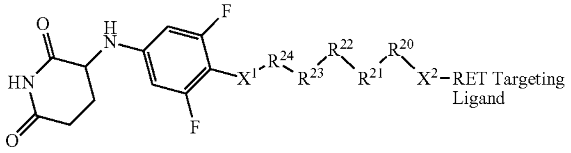
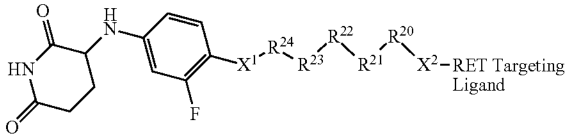
-continued
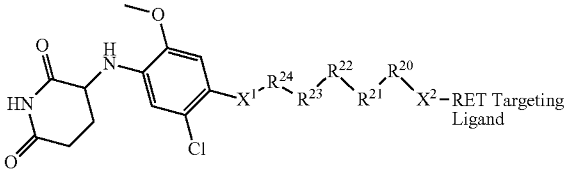
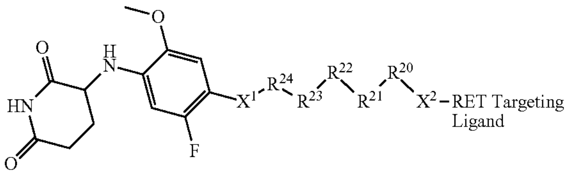
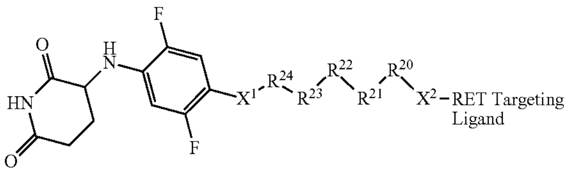

-continued

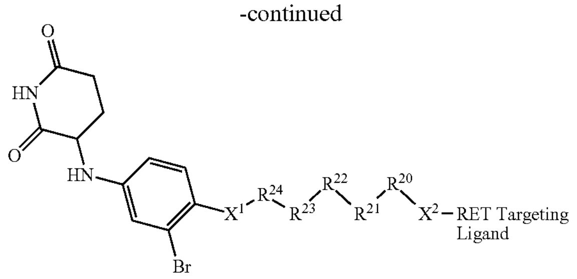

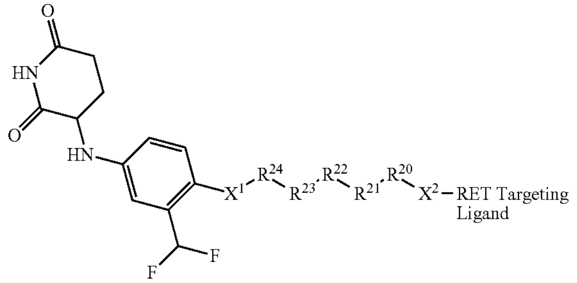

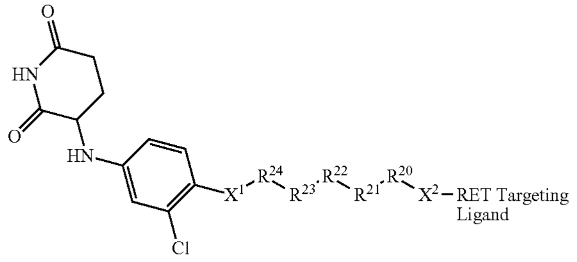

or a pharmaceutically acceptable salt thereof.

In certain embodiments, the compound of the present invention is selected from:

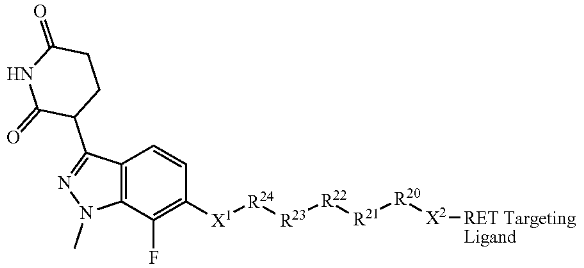

or a pharmaceutically acceptable salt thereof.

V. Methods of Treatment

A compound described herein can be used in an effective amount to treat a patient, typically a human, in need thereof, who have a disorder mediated by RET which can be a wild-type RET or mutant RET as described generally herein. In certain embodiments a compound of the present invention degrades an additional protein, for example an aurora kinase or VEGFR[2]. In certain embodiments a compound of the present invention degrades RET and aurora A kinase (AURKA).

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for treating or preventing cancer in a patient in need thereof; wherein there is a need of RET inhibition for the treatment or prevention of cancer.

In certain embodiments, the method comprises administering an effective amount of the active compound or its salt as described herein, optionally including a pharmaceutically acceptable excipient, carrier, or adjuvant (i.e., a pharmaceutically acceptable composition), or optionally in combination or alternation with another bioactive agent or combination of agents, to a patient in need thereof.

In certain embodiments, the present invention provides a method of treating any of the disorders described herein, in a patient in need thereof.

In other embodiments, the patient is administered an additional therapeutic agent. In other embodiments, the compound as described herein, and the additional therapeutic agent are administered simultaneously or sequentially.

In certain embodiments, the application provides a method of preventing any of the disorders described herein, in a patient in need thereof.

In certain embodiments, the patient is a human.

Another aspect of the present invention provides a method of treating or preventing a proliferative disease. The method comprises administering an effective amount of a pharmaceutical composition comprising a compound as described herein, or an enantiomer, diastereomer, or stereoisomer thereof, or pharmaceutically acceptable salt, hydrate, or solvate thereof and optionally a pharmaceutically acceptable carrier to a patient in need thereof.

In some embodiments, the disease is mediated by RET, for example, RET plays a role in the initiation or development of the disease.

In certain embodiments, the RET mediated disorder is a benign growth, metastasis, neoplasm, tumor, solid tumor, rhabdoid tumor, carcinoma, leukemia, cancer, abnormal cellular proliferation, an amyloid-based proteinopathy, a proteinopathy, fibrotic disorder, inflammation, arthritis, pulmonary disorders, or immune disorders.

In certain embodiments, the RET mediated disorder is a cancer that has metastasized, for example a cancer that has metastasized to the brain. In certain embodiments the RET mediated disorder is a cancer that has metastasized to the brain, lungs bone, liver, peritoneum, adrenal gland, skin, or muscle.

In certain embodiments a compound of the present invention penetrates the blood brain barrier and can be used for the treatment of a CNS involved cancer or a cancer that has metastasized to the brain.

In certain embodiments, the disease or disorder is cancer or a proliferation disease.

In certain embodiments, the RET mediated disorder is an abnormal cell proliferation, including, but not limited to, a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder.

In certain embodiments, the hematological cancer is acute myelogenous leukemia (AML), acute lymphoblastic leukemia (ALL), lymphoblastic T-cell leukemia, chronic myelogenous leukemia (CMIL), chronic lymphocytic leukemia (CLL), hairy-cell leukemia, chronic neutrophilic leukemia (CNL), acute lymphoblastic T-cell leukemia, acute monocytic leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukemia (MLL), erythroleukemia, malignant lymphoma, Hodgkins lymphoma, non-Hodgkins lymphoma, lymphoblastic T-cell lymphoma, Burkitt's lymphoma, follicular lymphoma, B cell acute lymphoblastic leukemia, diffuse large B cell lymphoma, Myc and B-Cell Leukemia (BCL)2 and/or BCL6 rearrangements/overexpression [double- and triple-hit lymphoma], myelodysplastic/myeloproliferative neoplasm, mantle cell lymphoma including bortezomib resistant mantle cell lymphoma.

Solid tumors that can be treated with the compounds described herein include, but are not limited to lung cancers, including small cell lung cancer (SCLC) and non-small cell lung cancer (NSCLC), breast cancers including inflammatory breast cancer, ER-positive breast cancer including tamoxifen resistant ER-positive breast cancer, and triple negative breast cancer, colon cancers, midline carcinomas, liver cancers, renal cancers, prostate cancers including castrate resistant prostate cancer (CRPC), brain cancers including gliomas, glioblastomas, neuroblastoma, and medulloblastoma including MYC-amplified medulloblastoma, colorectal cancers, Wilm's tumor, Ewing's sarcoma, rhabdomyosarcomas, ependymomas, head and neck cancers, melanomas, squamous cell carcinomas, ovarian cancers, pancreatic cancers including pancreatic ductal adenocarcinomas (PDAC) and pancreatic neuroendocrine tumors (PanNET), osteosarcomas, giant cell tumors of bone, thyroid cancers, bladder cancers, urothelial cancers, vulval cancers, cervical cancers, endometrial cancers, mesotheliomas, esophageal cancers, salivary gland cancers, gastric cancers, nasopharangeal cancers, buccal cancers, cancers of the mouth, GIST (gastrointestinal stromal tumors), NUT-midline carcinomas, testicular cancers, squamous cell carcinomas, hepatocellular carcinomas (HCC), MYCN driven solid tumors, and NUT midline carcinomas (NMC).

In further embodiments, the disease or disorder is sarcoma of the bones, muscles, tendons, cartilage, nerves, fat, or blood vessels.

In further embodiments, the disease or disorder is soft tissue sarcoma, bone sarcoma, or osteosarcoma.

In further embodiments, the disease or disorder is angiosarcoma, fibrosarcoma, liposarcoma, leiomyosarcoma, Karposi's sarcoma, osteosarcoma, gastrointestinal stromal tumor, synovial sarcoma, Pleomorphic sarcoma, chondrosarcoma, Ewing's sarcoma, reticulum cell sarcoma, meningiosarcoma, botryoid sarcoma, rhabdomyosarcoma, or embryonal rhabdomyosarcoma.

In further embodiments, the disease or disorder is multiple myeloma.

In other embodiments, the disease or disorder is inflammation, arthritis, rheumatoid arthritis, spondyiarthropathies, gouty arthritis, osteoarthritis, juvenile arthritis, and other arthritic conditions, neuroinflammation, allergy, pain, neuropathic pain, fever, pulmonary disorders, lung inflammation, adult respiratory distress chronic pulmonary inflammatory disease, and chronic obstructive pulmonary disease (COPD), liver disease and nephritis, gastrointestinal conditions, inflammatory bowel disease, Crohn's disease, gastritis, irritable bowel syndrome, ulcerative colitis, ulcerative diseases, gastric ulcers, autoimmune disease, graft vs. host reaction and allograft rejections, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, peripheral neuropathy, or B-Cell Lymphoma.

In other embodiments, the pharmaceutical composition comprising the compound as described herein and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, solid tumors, hematological cancers or solid cancers.

In some embodiments, said method is used to treat or prevent a condition selected from autoimmune diseases, inflammatory diseases, proliferative and hyperproliferative diseases, and immunologically-mediated diseases. In other embodiments, said condition is selected from a proliferative disorder.

In certain embodiments, the RET mediated disorder is an immune disorder, including but not limited to, autoimmune disorders such as Addison disease, Celiac disease, dermatomyositis, Graves disease, thyroiditis, multiple sclerosis, pernicious anemia, reactive arthritis, lupus, or type I diabetes.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers, such as oral, laryngeal, nasopharyngeal and esophageal, genitourinary cancers, such as prostate, bladder, renal, uterine, ovarian, testicular, lung cancer, such as small-cell and non-small cell, breast cancer, pancreatic cancer, melanoma and other skin cancers, stomach cancer, brain tumors, tumors related to Gorlin's syndrome, such as medulloblastoma or meningioma, and liver cancer.

Additional exemplary forms of cancer include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more compound as described herein, in the manufacture of a medicament for the treatment of cancer, including without limitation the various types of cancer disclosed herein.

In some embodiments, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compound as described herein is useful for treating hematopoietic disorders, in particular, acute-myelogenous leukemia (AML), chronic-myelogenous leukemia (CMIL), acute-promyelocytic leukemia, and acute lymphocytic leukemia (ALL).

In one embodiment, a compound or its corresponding pharmaceutically acceptable salt, or isotopic derivative, as described herein can be used in an effective amount to treat a host, for example a human, with a lymphoma or lymphocytic or myelocytic proliferation disorder or abnormality. For example, a compound as described herein can be administered to a host suffering from a Hodgkin's Lymphoma or a Non-Hodgkin's Lymphoma. For example, the host can be suffering from a Non-Hodgkin's Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, or isotopic derivative, as described herein can be used in an effective amount to treat a patient, for example a human, with a Hodgkin's lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin's Lymphoma; or Nodular Lymphocyte Predominant HL.

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

In certain embodiments a compound of the present invention is used to treat an abnormal cell proliferation such as a tumor or cancer that has a RET protein with a mutation, wherein the mutation is at one of the below listed amino acid sites. The mutation may, for example, be selected from one of the listed exemplary mutations, or may be a different mutation.

| Amino Acid Site | Exemplary Mutations |
|---|---|
| G810 | G810R, G810S, G810C, G810N |
| C634 | C634W, C634R |
| M918 | M918T |
| A883 | A883F |
| E762 | E762Q |
| G691 | G691S |
| L790 | L790F |
| R749 | R749T |
| R813 | R813Q |
| S891 | S891A |
| S904 | S904A, S904F |
| V778 | V778I |
| V804 | V804L, V804M, V804E |
| Y791 | Y791F |
| Y806 | Y806H |

In certain embodiments the RET protein has two mutations selected from the table above. In other embodiments the RET protein has three mutations selected from the table above. In other embodiments the RET protein has four or more mutations, which may optionally be selected from the table above.

In certain embodiments the tumor or cancer has a mutation in a RET protein that is a substantial or partial driver of tumor of cancer cell proliferation. In another embodiment the tumor or cancer has a RET altered protein that is not acting significantly as a driver of abnormal cell proliferation but can be used therapeutically to kill the tumor cell using a selected RET degrader as described herein.

In certain embodiments, a compound of the present invention is used to treat a tumor or cancer with a RET protein V804L mutation. In certain embodiments, a compound of the present invention is used to treat a tumor or cancer with a RET protein V804M mutation. In certain embodiments, a compound of the present invention is used to treat a tumor or cancer with a RET protein M918T mutation. In certain embodiments, a compound of the present invention is used to treat a tumor or cancer with a RET protein S891A mutation. In certain embodiments, a compound of the present invention is used to treat a tumor or cancer with a RET protein L790F mutation. In certain embodiments, a compound of the present invention is used treat a tumor or cancer with a RET protein E768D mutation. In certain embodiments, a compound of the present invention is used treat a tumor or cancer with a RET protein C618S mutation. In certain embodiments, a compound of the present invention is used treat a tumor or cancer with a RET protein C618R mutation. In certain embodiments, a compound of the present invention is used to treat a tumor or cancer with a RET protein 634 missense. In certain embodiments, a compound of the present invention is used to treat a tumor or cancer with a RET protein C634R mutation. In certain embodiments, a compound of the present invention is used to treat a tumor or cancer with a RET protein C634Y mutation. In certain embodiments, a compound of the present invention is used to treat a tumor or cancer with a RET protein C634G mutation.

In certain embodiments a compound of the present invention, or a pharmaceutically acceptable salt thereof, is used to treat an abnormal cell proliferation such as a tumor or cancer that has a RET protein with a G810R mutation.

In certain embodiments a compound of the present invention, or a pharmaceutically acceptable salt thereof, is used to treat an abnormal cell proliferation such as a tumor or cancer that has a RET protein with a G810S mutation.

In certain embodiments a compound of the present invention, or a pharmaceutically acceptable salt thereof, is used to treat an abnormal cell proliferation such as a tumor or cancer that has a RET protein with a G810C mutation.

In certain embodiments a compound of the present invention, or a pharmaceutically acceptable salt thereof, is used to treat an abnormal cell proliferation such as a tumor or cancer that has a RET protein with a C634W mutation.

In certain embodiments a compound of the present invention, or a pharmaceutically acceptable salt thereof, is used to treat an abnormal cell proliferation such as a tumor or cancer that has a RET protein with a M918T mutation.

In certain embodiments a compound of the present invention, or a pharmaceutically acceptable salt thereof, is used to treat an abnormal cell proliferation such as a tumor or cancer that has a RET protein with a V804L mutation.

In certain embodiments a compound of the present invention, or a pharmaceutically acceptable salt thereof, is used to treat an abnormal cell proliferation such as a tumor or cancer that has a RET protein with a V804M mutation.

In certain embodiments a compound of the present invention, or a pharmaceutically acceptable salt thereof, is used to treat an abnormal cell proliferation such as a tumor or cancer that has a RET protein fused to another protein, for example a fusion selected from CCDC6-RET, NCOA4-RET, KIF5B-RET, $PRKAR^1A$-RET, TRIM24-RET, TRIM33-RET, GOLGA5-RET, HOOK3-RET, KTN1-RET, ERC1-RET, MBD1-RET, TRIM27-RET, BRC-RET, $FGFR^{10}P$-RET, PCM1-RET, AKAP13-RET, FKBP15-RET, SPECCIL-RET, $TBL1XR^1$-RET, CUX1-RET, KIAA1468-RET, and KIAA1217-RET.

In certain embodiments a compound of the present invention, or a pharmaceutically acceptable salt thereof, is used to treat an abnormal cell proliferation such as a tumor or cancer that has a CCDC6-RET fusion.

In certain embodiments a compound of the present invention, or a pharmaceutically acceptable salt thereof, is used to treat an abnormal cell proliferation such as a tumor or cancer that has a NCOA4-RET fusion.

In certain embodiments a compound of the present invention, or a pharmaceutically acceptable salt thereof, is used to treat an abnormal cell proliferation such as a tumor or cancer that has a KIF5B-RET fusion.

In accordance with the foregoing, the present application further provides a method for preventing or treating any of the diseases or disorders described above in a patient in need of such treatment, which method comprises administering to said patient a therapeutically effective amount of a compound as described herein, or an enantiomer, diastereomer, or stereoisomer thereof, or pharmaceutically acceptable salt, hydrate, or solvate thereof. For any of the above uses, the required dosage will vary depending on the mode of administration, the particular condition to be treated and the effect desired.

VI. Combination Therapy

A compound of Formula I, Formula II, Formula III, Formula IV, Formula V, Formula VI, or Formula VII, or a pharmaceutically acceptable salt thereof can be used in an effective amount, either alone or in combination, to treat a patient such as a human with a disorder as described herein or a RET mediated disorder.

The disclosed compounds described herein can be used in an effective amount alone or in combination with another compound of the present invention or another bioactive agent or second therapeutic agent to treat a patient such as a human with a disorder, including but not limited to those described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a patient in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-Li/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In certain embodiments the checkpoint inhibitor is selected from nivolumab/OPDIVO®; pembrolizumab/KEYTRUDA®; and pidilizumab/CT-011, MPDL3280A/RG7446; MEDI4736; MSB0010718C; BMS 936559, a PDL2/lg fusion protein such as AMP 224 or an inhibitor of B7-H3 (e.g., MGA271), B7-H4, BTLA, HVEM, TIM3, GAL9, LAG 3, VISTA, KIR, 2B4, CD160, CGEN-15049, CHK 1, CHK2, A2aR, B-7 family ligands, or a combination thereof.

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including, but not limited to, a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors.

Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including, but not limited to a selective androgen receptor modulator, a selective androgen receptor degrader, a complete androgen receptor degrader, or another form of partial or complete androgen antagonist. In one embodiment, the prostate or testicular cancer is androgen-resistant.

Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include, but are not limited to, Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl] oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl) benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl) amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR$^{245409}$ (N-(4-(N-(3-((3,5-dimethoxyphenyl)amino)quinoxalin-2-yl)sulfamoyl) phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4] triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d] pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl] phenyl}propanenitrile) (dactolisib), XL-765 (N-(3-(N-(3-(3,5-dimethoxyphenylamino)quinoxalin-2-yl)sulfamoyl) phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422).

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-f{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, but are not limited to, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), $R^{09021}$ (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), $R^{112}$ (3,3'-((5-fluoropyrimidine-2,4-diyl)bis(azanediyl))diphenol), $R^{348}$ (3-Ethyl-4-methylpyridine), $R^{406}$ (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEAl 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), $R^{05126766}$ (3-[[3-Fluoro-2-(methylsulfamoylamino)-4-pyridyl]methyl]-4-methyl-7-pyrimidin-2-yloxychromen-2-one), WX-554, $R^{04987655}$/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino]phenoxy]-N-Methyl-2pyridinecarboxaMide 1—Oxide), PLX-4720, dabrafenib (GSK2118436), GDC-0879, RAF265, AZ 628, Sf590885, ZM336372, GW5074, TAK-632, CEP-32496, LY3009120, and GX818 (Encorafenib).

In one embodiment, the bioactive agent is an AKT inhibitor, including, but not limited to, MK-2206, GSK690693, Perifosine, (KRX-0401), GDC-0068, Triciribine, AZD5363, Honokiol, PF-04691502, and Miltefosine, a FLT-3 inhibitor, including, but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include, but are not limited to, rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4, 6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), $R^{05126766}$ (3-[[3-Fluoro-2-(methylsulfamoylamino)-4-pyridyl]methyl]-4-methyl-7-pyrimidin-2-yloxychromen-2-one), WX-554, $R^{04987655}$/CH4987655 (3,4-difluoro-2-((2-fluoro-4-iodophenyl)amino)-N-(2-hydroxyethoxy)-5-((3-oxo-1,2-oxazinan-2 yl)methyl) benzamide), or AZD8330 (2-((2-fluoro-4-iodophenyl) amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, aFLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, of atumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40—O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™).

Examples of additional suitable chemotherapeutic agents include, but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In some embodiments, the compound of the present invention is administered in combination with a chemotherapeutic agent (e.g., a cytotoxic agent or other chemical compound useful in the treatment of cancer). Examples of chemotherapeutic agents include alkylating agents, antimetabolites, folic acid analogs, pyrimidine analogs, purine analogs and related inhibitors, vinca alkaloids, epipodopyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Inti. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE®, cremophor-free, albumin-engineered nanoparticle formulation of paclitaxel (American Pharmaceutical Partners, Schaumberg, TL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-1 1); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the compound of the present invention. Suitable dosing regimens of combination chemotherapies are known in the ar. For example combination dosing regimes are described in Saltz et al., Proc. Am. Soc. Clin. Oncol. 18:233a (1999) and Douillard et al., Lancet 355(9209): 1041-1047 (2000).

Additional therapeutic agents that can be administered in combination with a Compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SVIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In some embodiments, the bioactive agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-l-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOURIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The combination therapy may include a therapeutic agent which is a non-drug treatment. For example, the compound could be administered in addition to radiation therapy, cryotherapy, hyperthermia, and/or surgical excision of tumor tissue.

In certain embodiments the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

In certain embodiments the second therapeutic agent is administered on a different dosage schedule than the compound of the present invention. For example the second therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In another embodiment the first therapeutic agent has a treatment holiday. For example the first therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In certain embodiments both the first and second therapeutic have a treatment holiday.

VII. Pharmaceutical Compositions

A compound of Formula I, Formula II, Formula III, Formula IV, Formula V, Formula VI, or Formula VII, or its pharmaceutically acceptable salt thereof, as described herein can be administered as the neat chemical, but is more typically administered as a pharmaceutical composition, that includes an effective amount for a patient, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.1, 1, 5, 10, 25, 50, 100, 200, 250, 300, 400, 500, 600, 700, or 750 mg of active compound, or its salt.

In certain embodiments the patient can be treated with low dosage therapy with a compound of the present invention. For example, the pharmaceutical composition can be in a dosage form that contains from about 0.1 μg to about 2000 μg, from about 10 μg to about 1000 μg, from about 100 μg to about 800 μg, or from about 200 μg to about 600 μg of the active compound. Examples are dosage forms with at least about 0.1, 1, 5, 10, 25, 50, 100, 200, 250, 300, 400, 500, 600, 700, or 750 μg of active compound, or its salt.

In certain embodiments the dose ranges from about 0.01-100 mg/kg of patient bodyweight, for example at least about 0.01 mg/kg, at least about 0.05 mg/kg, at least about 0.1 mg/kg, at least about 0.5 mg/kg, at least about 1 mg/kg, at least about 1.5 mg/kg, at least about 2 mg/kg, at least about 2.5 mg/kg, at least about 3 mg/kg, at least about 3.5 mg/kg, at least about 4 mg/kg, at least about 4.5 mg/kg, at least about 5 mg/kg, at least about 10 mg/kg, at least about 15 mg/kg, at least about 20 mg/kg, at least about 25 mg/kg, at least about 30 mg/kg, at least about 35 mg/kg, at least about 40 mg/kg, at least about 45 mg/kg, at least about 50 mg/kg, at least about 55 mg/kg, at least about 60 mg/kg, at least about 65 mg/kg, at least about 70 mg/kg, at least about 75 mg/kg, at least about 80 mg/kg, at least about 85 mg/kg, at least about 90 mg/kg, at least about 95 mg/kg, or at least about 100 mg/kg.

A pharmaceutically or therapeutically effective amount of the composition will be delivered to the patient. The precise effective amount will vary from patient to patient, and will depend upon the species, age, the subject's size and health, the nature and extent of the condition being treated, recommendations of the treating physician, and the therapeutics or combination of therapeutics selected for administration. The effective amount for a given situation can be determined by routine experimentation. For purposes of the disclosure, a therapeutic amount may for example be in the range of about 0.01 mg/kg to about 250 mg/kg body weight, more typically about 0.1 mg/kg to about 10 mg/kg, in at least one dose. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments the compound of the present invention is administered with a treatment holiday in between treatment cycles. For example, the compound may have a treatment holiday of 1 day, 2 days, 3 days, 4 days, 5 days, 6 days, 7 days, 8 days, 9 days, 10 days, 11 days, 12 days, 13 days, or 14 days per treatment cycle.

The pharmaceutical composition may also include a molar ratio of the active compound and an additional active agent. For example, the pharmaceutical composition may contain a molar ratio of about 0.5:1, about 1:1, about 2:1, about 3:1 or from about 1.5:1 to about 4:1 of an anti-inflammatory or immunosuppressing agent.

These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In certain embodiments the compound is administered as a pharmaceutically acceptable salt. Non-limiting examples of pharmaceutically acceptable salts include: acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Thus, the composition of the disclosure can be administered as a pharmaceutical formulation including one suitable for oral (including buccal and sub-lingual), rectal, nasal, topical, transdermal, pulmonary, vaginal or parenteral (including intramuscular, intra-arterial, intrathecal, subcutaneous and intravenous), injections, inhalation or spray, intra-aortal, intracranial, subdermal, intraperitioneal, subcutaneous, or by other means of administration containing conventional pharmaceutically acceptable carriers. A typical manner of administration is oral, topical or intravenous, using a convenient daily dosage regimen which can be adjusted according to the degree of affliction.

Depending on the intended mode of administration, the pharmaceutical compositions can be in the form of solid, semi-solid or liquid dosage forms, such as, for example, tablets, suppositories, pills, capsules, powders, liquids, syrup, suspensions, creams, ointments, lotions, paste, gel, spray, aerosol, foam, or oil, injection or infusion solution, a transdermal patch, a subcutaneous patch, an inhalation formulation, in a medical device, suppository, buccal, or sublingual formulation, parenteral formulation, or an ophthalmic solution, or the like, preferably in unit dosage form suitable for single administration of a precise dosage.

Some dosage forms, such as tablets and capsules, are subdivided into suitably sized unit doses containing appropriate quantities of the active components, e.g., an effective amount to achieve the desired purpose. The compositions will include an effective amount of the selected drug in combination with a pharmaceutically acceptable carrier and, in addition, can include other pharmaceutical agents, adjuvants, diluents, buffers, and the like.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to adjuvants, binders, buffering agents, coloring agents, diluents, disintegrants, excipients, emulsifiers, flavorants, gels, glidents, lubricants, preservatives, stabilizers, surfactants, solubilizer, tableting agents, wetting agents or solidifying material.

Some carriers may be listed in more than one class, for example vegetable oil may be used as a lubricant in some formulations and a diluent in others.

Exemplary pharmaceutically acceptable carriers include sugars, starches, celluloses, powdered tragacanth, malt, gelatin; talc, petroleum jelly, lanoline, polyethylene glycols, alcohols, transdermal enhancers and vegetable oils. Optional active agents may be included in a pharmaceutical composition, which do not substantially interfere with the activity of the compound of the present invention.

Some excipients include, but are not limited, to liquids such as water, saline, glycerol, polyethylene glycol, hyaluronic acid, ethanol, and the like. The compound can be provided, for example, in the form of a solid, a liquid, spray dried material, a microparticle, nanoparticle, controlled release system, etc., as desired according to the goal of the therapy. Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline, and the like.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment provided is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

The pharmaceutical compositions/combinations can be formulated for oral administration. For oral administration, the composition will generally take the form of a tablet, capsule, a softgel capsule or can be an aqueous or nonaqueous solution, suspension or syrup. Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

Parenteral formulations can be prepared in conventional forms, either as liquid solutions or suspensions, solid forms suitable for solubilization or suspension in liquid prior to injection, or as emulsions. Typically, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, typical methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be effected using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve.

Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

Formulations suitable for rectal administration are typically presented as unit dose suppositories. These may be prepared by admixing the active compound with one or more conventional solid carriers, for example, cocoa butter, and then shaping the resulting mixture.

In certain embodiments, the pharmaceutical composition is suitable for topical application to the skin using a mode of administration and defined above.

In certain embodiments, the pharmaceutical composition is suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound.

In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

VIII. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in one embodiment. A wide variety of chiral stationary phases are commercially available.

Synthesis

| Abbreviation | Definition |
|---|---|
| ACN or CAN | Acetonitrile |
| AcOH | Acetic acid |
| NaOAc | Sodium acetate |
| Boc | tert-butoxycarbonyl |
| CAN | Cerium Ammonium Nitrate |
| $CH_2Cl_2$ | Methylene dichloride/Dichloromethane |
| DCM | Methylene dichloride/Dichloromethane |
| dioxane | 1,4-dioxane |
| DIPEA | N,N-diisopropylethylamine |
| DMF | N,N-dimethylformamide |
| DMSO | Dimethylsulfoxide |
| dppf | diphenylphosphino ferrocene |
| ES+/ES | Electrospray positive ionization |
| ES− | Electrospray negative ionization |
| EtOAc | Ethyl Acetate |
| EtOH | Ethanol |
| Fe | Iron |
| GCMS | Gas Chromatography Mass Spectrometry |
| h | Hour |
| HATU | (1-[Bis(dimethylamino)methylene]-1H-1,2,3-triazolo[4,5-b]pyridinium 3-oxide hexafluorophosphate/Hexafluorophosphate Azabenzotriazole Tetramethyl Uronium |
| HCl | Hydrochloric acid/Hydrochloride |
| HPLC | High Performance Liquid Chromatography/High Pressure Liquid Chromatography |
| IBX | 2-Iodoxybenzoic acid |
| ISCO | Proprietary column purification unit |
| LCMS | Liquid Chromatography Mass Spectrometry |
| MeCN | Acetonitrile |
| MeOH | Methanol |
| MP-$CNBH_3$ | Macroporous polymer supported Cyanoborohydride |
| MQ-water | Milli Q water |
| MTBE | methyl tert-butyl ether |
| $NaHCO_3$ | Sodium bicarbonate |
| $NH_4Cl$ | Ammonium Chloride |
| NMR | nuclear magnetic resonance |
| OtBu | Tert-butoxy |
| Pd(dppf)$Cl_2$ | 1,1-Bis(diphenylphosphino)ferrocene-palladium(II)dichloride |
| Pet ether | Petroleum ether |
| r.t. | Room temperature |
| t-Bu | tert-Butyl |
| TBAF | tetrabutylammonium floride |
| TEA | triethyl amine |
| TFA | Trifluoroacetic acid/Trifluoroacetate |
| THF | tetrahydrofuran |
| TLC | Thin Layered Chromatography |
| UPLC | Ultra Performance Liquid Chromatography |

Synthesis of CRBN Binders

Example 1: Synthesis of 3-((4-(piperidin-4-yl)phenyl)amino)piperidine-2,6-dione

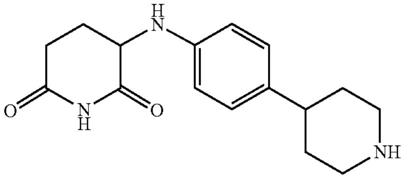 [SMILES: O=C1CCC(Nc2ccc(C3CCNCC3)cc2)C(=O)N1]

3-((4-(piperidin-4-yl)phenyl)amino)piperidine-2,6-dione HCl salt was prepared according to the method described on page 265 of WO2018237026A1.

Example 2: Synthesis of 3-((5-Fluoro-2-methoxy-4-(piperazin-1-yl)phenyl)amino)piperidine-2,6-dione Scheme 1

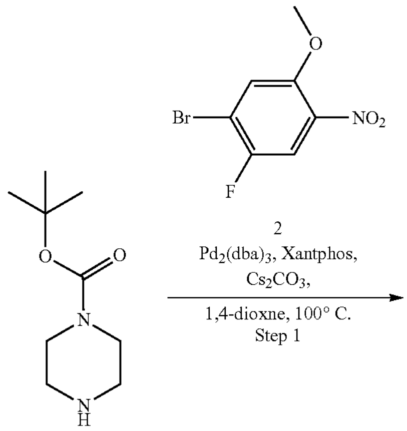

2

1

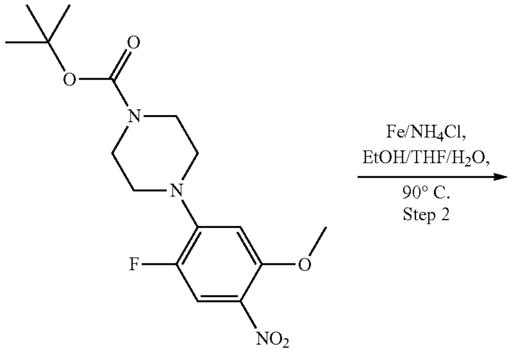

3

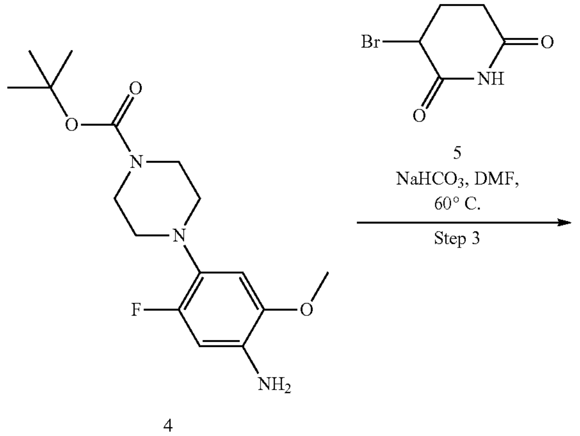

5

4

-continued

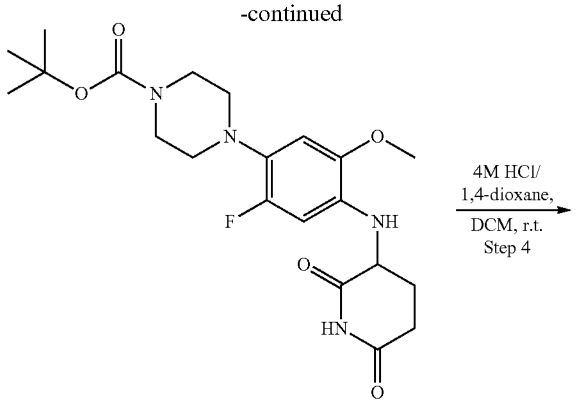

6

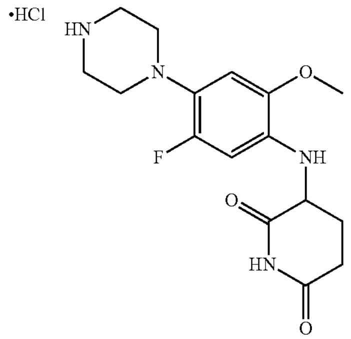

7

Step 1: Into a 250 mL sealed-tube containing a well-stirred solution of tert-butyl piperazine-1-carboxylate (1, 4.47 g, 24.00 mmol) and 1-bromo-2-fluoro-5-methoxy-4-nitro-benzene (2, 3 g, 12.00 mmol) in anhydrous 1,4-dioxane (60 mL) was added Cesium carbonate (7.82 g, 24.0 mmol) at ambient temperature under nitrogen atmosphere and the resulting mixture was degassed by bubbling nitrogen gas into the reaction mixture for 10 minutes. Subsequently, Xantphos (694.28 mg, 1.20 mmol) and $Pd_2(dba)_3$ (549.38 mg, 0.560 mmol) were added to the reaction mixture and the reaction mixture was heated to 100° C. for 16 h. The reaction mixture was cooled to ambient temperature and filtered through a pad of Celite, washing with DCM (100 mL). Combined filtrate was concentrated under reduced pressure to get a crude residue. The crude product was purified by flash silica-gel (230-400 mesh, 100 g) column with 0-40% EtOAc/pet ether to afford tert-butyl 4-(2-fluoro-5-methoxy-4-nitro-phenyl)piperazine-1-carboxylate (3, 3.2 g, 8.04 mmol, 67% yield) as a yellow gummy solid. LCMS ($ES^+$): 300.2 $[M-tBu+H]^+$ Step 2: Into a 250 mL single-necked round-bottomed flask containing a well-stirred suspension of tert-butyl 4-(2-fluoro-5-methoxy-4-nitro-phenyl)piperazine-1-carboxylate (3, 3.2 g, 9.00 mmol) in a mixture of EtOH (80 mL), water (40 mL) and THF (20 mL) were added Iron powder (3.52 g, 63.03 mmol) and Ammonium Chloride (2.41 g, 45.02 mmol) at ambient temperature under nitrogen atmosphere. The resulting suspension was heated to 90° C. for 2 h and the reaction mixture was cooled to ambient temperature. After completion, the reaction mixture was filtered through a pad of Celite, washing with EtOAc (100 mL). Combined filtrate was diluted with water (80 mL) and the product was extracted with EtOAc (2×100 mL). Organic phases were combined, dried (anhydrous $Na_2SO_4$), filtered and the filtrate was concentrated under reduced pressure to get a crude residue. The crude product was purified by flash silica-gel (230-400 mesh, 100 g) column with 0-40% EtOAc/pet ether to afford tert-butyl 4-(4-amino-2-fluoro-5-methoxy-phenyl) piperazine-1-carboxylate (4, 2.8 g, 8.61 mmol, 96% yield) as a yellow gummy solid. UPLC-MS ($ES^+$): 326.5 $[M+H]^+$ Step 3: Into a 250 mL sealed-tube containing a well-stirred solution of tert-butyl 4-(4-amino-2-fluoro-5-methoxy-phenyl)piperazine-1-carboxylate (4, 2.8 g, 8.61 mmol) and 3-bromopiperidine-2,6-dione (5, 2.48 g, 12.91 mmol) in anhydrous DMF (30 mL) was added Sodium bicarbonate (2.17 g, 25.82 mmol) at ambient temperature under nitrogen atmosphere. The reaction mixture was heated to 60° C. for 24 h and the reaction mixture was cooled to ambient temperature. The reaction mixture was quenched with water (80 mL) and the product was extracted with EtOAc (2×150 mL). Organic phases were combined, dried (anhydrous $Na_2SO_4$), filtered and the filtrate was concentrated under reduced pressure to get a crude residue. The crude product was purified by flash silica-gel (230-400 mesh, 100 g) column with 0-60% EtOAc/pet ether to afford tert-butyl 4-[4-[(2,6-dioxo-3-piperidyl)amino]-2-fluoro-5-methoxy-phenyl]piperazine-1-carboxylate (6, 3.1 g, 7.03 mmol, 82% yield) as a green solid. $^1H$ NMR (400 MHz, DMSO-$d_6$): δ10.85 (s, 1H), 6.63 (d, J=8 Hz, 1H), 6.56 (d, J=14.4 Hz, 1H), 5.13 (d, J=6.8 Hz, 1H), 4.30-4.24 (m, 1H), 3.79 (s, 3H), 3.45 (bs, 4H), 2.90-2.75 (m, 5H), 2.55 (m, 1H), 2.15 (m, 1H), 1.98-1.85 (m, 1H), 1.42 (s, 9H). LCMS ($ES^+$): 437.6 $[M+H]^+$ Step 4: Into a 50 mL single-necked round-bottomed flask containing a well-stirred solution of tert-butyl 4-[4-[(2,6-dioxo-3-piperidyl)amino]-2-fluoro-5-methoxy-phenyl]piperazine-1-carboxylate (6, 100 mg, 0.229 mmol) in anhydrous DCM (3 mL) was added 4M HCl in 1,4-dioxane (2 mL) at ambient temperature under nitrogen atmosphere. The resulting mixture was stirred for 1 h at ambient temperature. After completion of the starting material, excess solvent was removed under reduced pressure to get a crude mass. The crude product was washed with MTBE (10 mL) to get 3-(5-fluoro-2-methoxy-4-piperazin-1-yl-anilino)piperidine-2,6-dione hydrochloric acid salt (7, 70 mg, 0.075 mmol, 33% yield) as a light green solid. LCMS ($ES^+$): 337.1 $[M+H]^+$ Example 3: Synthesis of 3-((3,5-difluoro-4-(piperazin-1-yl)phenyl)amino)piperidine-2,6-dione

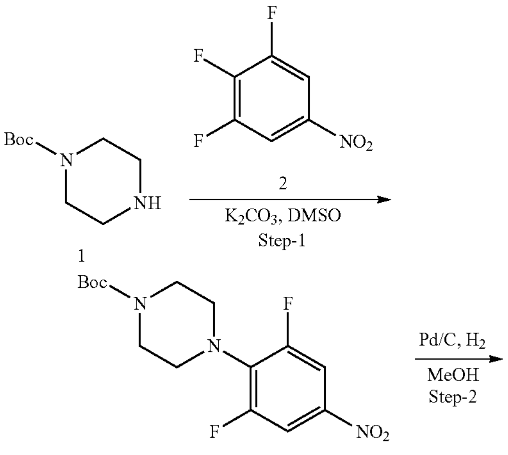

1

2

3

-continued

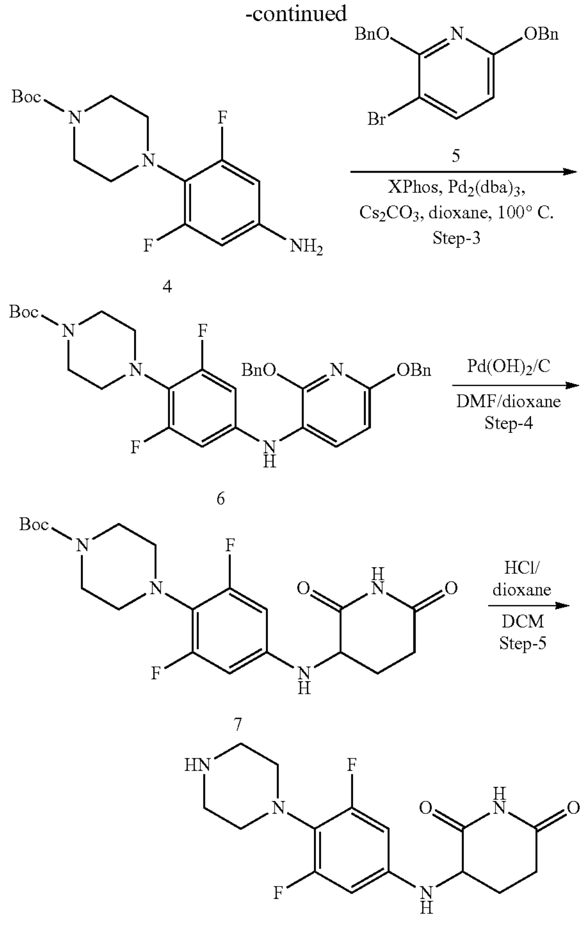

4

5

6

7

8

Step 1: To a solution of tert-butyl piperazine-1-carboxylate (1, 10 g, 53.69 mmol) and 1,2,3-trifluoro-5-nitrobenzene (2, 9.51 g, 53.69 mmol) in DMSO (100 mL) was added $K_2CO_3$ (14.84 g, 107.38 mmol), and the reaction mixture was stirred at 80° C. for 16 h. The reaction mixture was poured into water and a large quantity of yellow precipitate was formed. The yellow solid was filtered and concentrated under vacuum to give tert-butyl 4-(2,6-difluoro-4-nitrophenyl)piperazine-1-carboxylate (3, 17 g, 41.59 mmol, 78% yield) as a yellow solid. $^1H$ NMR (400 MHz, CHLOROFORM-d) δ=7.78 (d, J=9.6 Hz, 2H), 3.61-3.51 (m, 4H), 3.32 (br s, 4H), 1.49 (s, 9H)

Step 2: To a solution of tert-butyl 4-(2,6-difluoro-4-nitrophenyl)piperazine-1-carboxylate (3, 16.97 g, 49.43 mmol) in Methanol (1 L) was added Pd/C (1.70 g, 15.95 mmol). The reaction mixture was stirred under $H_2$ (15 Psi) atmosphere at 20° C. for 12 h. The reaction mixture was filtered and concentrated under vacuum to give tert-butyl 4-(4-amino-2,6-difluorophenyl)piperazine-1-carboxylate (4, 15.49 g, 48.45 mmol, 98% yield) as a white solid. LCMS ($ES^+$): 258.1 $[M+H]^+$ Step 3: To a solution of tert-butyl 4-(4-amino-2,6-difluoro-phenyl)piperazine-1-carboxylate (4, 6 g, 19.15 mmol) in dioxane (60 mL) were added 2,6-bis(benzyloxy)-3-bromopyridine (5, 8.51 g, 22.98 mmol), $Cs_2CO_3$ (12.48 g, 38.30 mmol), dicyclohexyl-[2-(2,4,6-triisopropylphen yl)phenyl] phosphane (913 mg, 1.92 mmol) and (1E,4E)-1,5-diphenylpental,4-dien-3-one; palladium (1.75 g, 1.91 mmol). The reaction mixture was stirred under $N_2$ atmosphere at 100° C.

for 16 h. The reaction mixture was extracted with ethyl acetate (300 mL). The organic layer was dried over $Na_2SO_4$, filtered and concentrated under vacuum. The residue was purified by column chromatography on silica gel (PE/EA=10/1) to give tert-butyl 4-[4-[(2,6-dibenzyloxy-3-pyridyl)amino]-2,6-difluoro-phenyl]piperazine-1-carboxylate (6, 7 g, 10.34 mmol, 54% yield) as a black oil. $^1H$ NMR (400 MHz, CHLOROFORM-d) δ=7.51-7.47 (m, 1H), 7.42 (s, 2H), 7.41-7.31 (m, 8H), 6.41-6.35 (m, 2H), 5.57-5.49 (m, 1H), 5.39 (s, 2H), 5.32 (s, 2H), 3.62-3.46 (m, 4H), 3.04 (d, J=4.4 Hz, 4H), 1.49 (s, 9H)

Step 4: To a solution of tert-butyl 4-[4-[(2,6-dibenzyloxy-3-pyridyl)amino]-2,6-difluoro-phenyl]piperazine-1-carboxylate (6, 4.5 g, 7.47 mmol) in dioxane (100 mL) was added $Pd(OH)_2/C$ (4.50 g, 32.03 mmol). The reaction mixture was stirred under $H_2$ (15 Psi) atmosphere at 35° C. for 16 h. The reaction mixture was filtered through a pad of Celite, washing with Ethyl acetate (200 mL). The filtrate was concentrated under vacuum. The residue was purified by column chromatography on silica gel (PE/EA=1/1) to give tert-butyl 4-[4-[(2,6-dioxo-3-piperidyl)amino]-2,6-difluoro-phenyl]piperazine-1-carboxylate (7, 2.38 g, 5.55 mmol, 74% yield) as a blue solid. $^1H$ NMR (400 MHz, CHLOROFORM-d) δ=8.21 (br s, 1H), 6.18 (d, J=10.8 Hz, 2H), 4.92-4.64 (m, 1H), 4.00 (dd, J=4.8, 12.8 Hz, 1H), 3.59-3.45 (m, 4H), 3.08-2.97 (m, 4H), 2.95-2.84 (m, 1H), 2.82-2.70 (m, 1H), 2.56-2.46 (m, 1H), 1.90 (dq, J=4.8, 13.2 Hz, 1H), 1.48 (s, 9H)

Step 5: To a solution of tert-butyl 4-[4-[(2,6-dioxo-3-piperidyl)amino]-2,6-difluoro-phenyl]piperazine-1-carboxylate (7, 2 g, 4.71 mmol) in DCM (20 mL) was added HCl/Dioxane (4 M, 40.00 mL). The reaction mixture stirred at 25° C. for 1 h. The reaction mixture was concentrated under vacuum to give 3-(3,5-difluoro-4-piperazin-1-yl-anilino) piperidine-2,6-dione hydrochloric acid salt (8, 1.76 g, 4.59 mmol, 97% yield) as a white solid. LCMS ($ES^+$): 325.2 $[M+H]^+$

Example 4: Synthesis of 3-[3-fluoro-4-(4-piperidyl)anilino]piperidine-2,6-dione

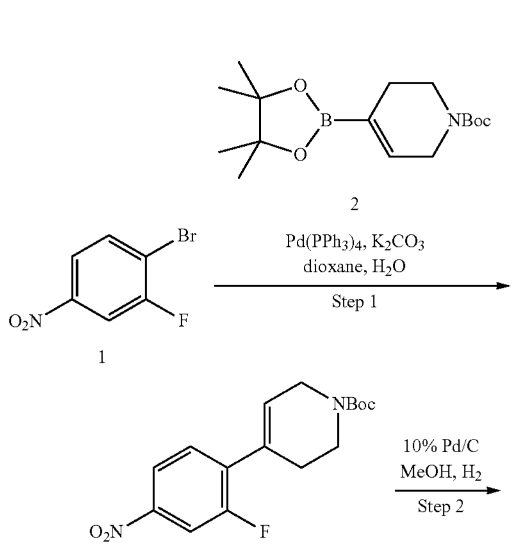

2

1

3

-continued

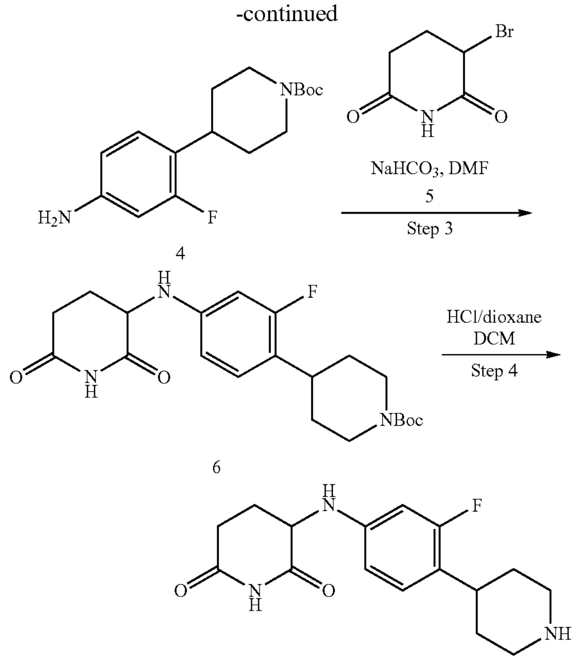

4

6

7

Step 1: A solution of 1-bromo-2-fluoro-4-nitro-benzene (1, 6 g, 27.27 mmol) and tert-butyl 4-(4,4,5,5-tetramethyl-1,3,2-dioxaborolan-2-yl)-3,6-dihydro-2H-pyridine-1-carboxylate (2, 8.43 g, 27.27 mmol) in dioxane (60 mL) and water (15 mL) in a round bottom flask was purged with argon gas for 10 minutes, followed by the addition of potassium carbonate, granular (11.31 g, 81.82 mmol). The solution was purged with argon gas for another 20 minutes before palladium;triphenylphosphane (1.58 g, 1.36 mmol) was added and the reaction was stirred at 90° C. for 16 hours. After completion of the reaction, the reaction mixture was filtered through celite bed and washed with ethyl acetate. The filtrate was concentrated under reduced pressure and the crude product was diluted with water and extracted with ethyl acetate (2×150 ml). The combined organic layer was concentrated in vacuo and purified by normal phase column chromatography (Davisil silica, 5% ethyl acetate in pet ether) to obtain tert-butyl 4-(2-fluoro-4-nitro-phenyl)-3,6-dihydro-2H-pyridine-1-carboxylate (3, 5.95 g, 18.27 mmol, 67% yield) as a light-yellow solid. LC-MS ($ES^+$): 267.15 $[M-tBu+H]^+$.

Step 2: To a stirred solution of tert-butyl 4-(2-fluoro-4-nitro-phenyl)-3,6-dihydro-2H-pyridine-1-carboxylate (3, 3 g, 9.31 mmol) in methanol (70 mL) was added palladium, 10% on carbon, type 487, dry (3 g, 28.19 mmol) at room temperature. The reaction mixture was stirred for 6 hours at this temperature under hydrogen atmosphere. After completion, the reaction mixture was filtered through celite and concentrated under reduced pressure to afford compound tert-butyl 4-(4-amino-2-fluoro-phenyl)piperidine-1-carboxylate (4, 2.5 g, 5.95 mmol, 64% yield) as purple solid, which was taken to the next step without purification. LC-MS ($ES^+$): 239.30 $[M-tBu+H]^+$.

Step 3: In a sealed tube, a solution of tert-butyl 4-(4-amino-2-fluoro-phenyl)piperidine-1-carboxylate (4, 2.5 g, 8.49 mmol) and 3-bromopiperidine-2,6-dione (5, 4.08 g, 21.23 mmol) in DMF (40 mL) was stirred for 10 minutes before sodium bicarbonate (3.57 g, 42.46 mmol) was added and the reaction was heated at 60° C. for 16 hours. After completion, the reaction mixture was filtered and concentrated in vacuo. The crude product was purified by column chromatography (Devisil silica, 0-30% ethyl acetate in pet ether) to furnish tert-butyl 4-[4-[(2,6-dioxo-3-piperidyl) amino]-2-fluoro-phenyl]piperidine-1-carboxylate (6, 1.8 g, 3.64 mmol, 43% yield) as a brown solid. LC-MS ($ES^-$): 404.3 $[M-H]^-$.

Step 4: To a solution of tert-butyl 4-(4-((2,6-dioxopiperidin-3-yl)amino)-2-fluorophenyl)piperidine-1-carboxylate (6, 100 mg, 246.63 mol) in DCM (1 mL) was added HCl/dioxane (2 mL). The mixture was stirred at 25° C. for 0.5 hour. After completion, the solvent was removed and the residue was dissolved in MeCN (30 mL), adjusted to pH=7 with $NaHCO_3$, and filtered. The filtrate was concentrated in vacuo to afford 3-[3-fluoro-4-(4-piperidyl)anilino]piperidine-2,6-dione (7, 75 mg, 233.34 mol, 95% yield) as a white solid, which was carried forward without further purification. LC-MS ($ES^+$): 306.2 $[M+H]^+$.

Example 5: Synthesis of 3-(5-(piperidin-4-yl)indolin-1-yl)piperidine-2,6-dione

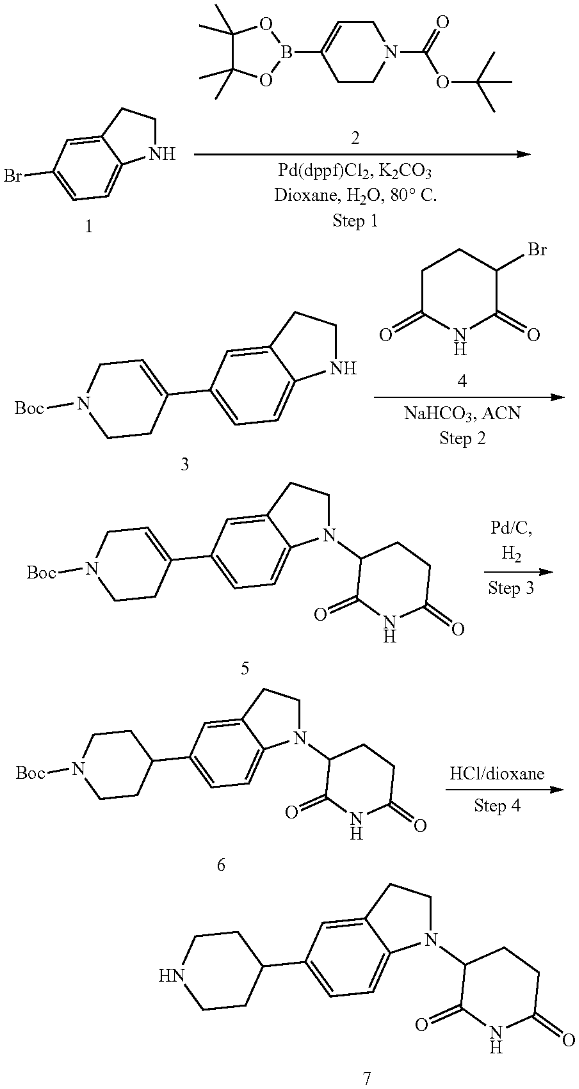

1

3

5

6

7

Step 1: A mixture of 5-bromoindoline (1, 3 g, 15.15 mmol), tert-butyl 4-(4,4,5,5-tetramethyl-1,3,2-dioxaborolan-2-yl)-5,6-dihydropyridine-1(2H)-carboxylate (2, 4.68 g, 15.15 mmol), tripotassium;phosphate (2 M, 15 mL) in dioxane (40 mL) was degassed and purged with $N_2$ 3 times, and then the mixture was stirred at 70° C. for 12 h under $N_2$ atmosphere. The reaction mixture was filtered and concentrated under reduced pressure. The residue was purified by column chromatography ($SiO_2$, Petroleum ether/Ethyl acetate=10/1 to 3/1). tert-butyl 4-(indolin-5-yl)-5,6-dihydropyridine-1(2H)-carboxylate (3, 3 g, 8.59 mmol, 58% yield) was obtained as a white solid. LCMS ($ES^+$): 301.1 $[M+H]^+$ Step 2: A solution of 3-bromopiperidine-2,6-dione (4, 2.30 g, 11.98 mmol), tert-butyl 4-(indolin-5-yl)-5,6-dihydropyridine-1(2H)-carboxylate (3, 3 g, 9.99 mmol) and sodium hydrogen carbonate (1.68 g, 19.97 mmol, 776.82 μL) in MeCN (10 mL). After addition, the solution was stirred at 90° C. for 12 hr. The reaction mixture was concentrated under reduced pressure. The residue was poured into water (40 mL), filtered and the filter cake was dried under reduced pressure. The filter cake was triturated with MTBE (40 mL) at 25° C. for 0.5 h, filtered and the filter cake was dried to afford tert-butyl 4-(1-(2,6-dioxopiperidin-3-yl)indolin-5-yl)-5,6-dihydropyridine-1(2H)-carboxylate (5, 3 g, 7.14 mmol, 72% yield) as blue solid. LCMS ($ES^+$): 412.0 $[M+H]^+$ Step 3: To a solution of tert-butyl 4-[1-(2,6-dioxo-3-piperidyl)indolin-5-yl]-3,6-dihydro-2H-pyridine-1-carboxylate (413 mg, 1.00 mmol) was added 10 wt. % Pd/C (121.89 mg, 100.37 μmol) under $N_2$ atmosphere. The suspension was degassed and purged with $H_2$ 3 times. The mixture was stirred under $H_2$ (15 Psi) at 30° C. for 2 hours. After completion, the reaction solution was filtered and the filtrate was concentrated in vacuum to give tert-butyl 4-[1-(2,6-dioxo-3-piperidyl)indolin-5-yl]piperidine-1-carboxylate (6, 415 mg, 903.25 μmol, 90% yield) as yellow solid, which was used without further purification. LCMS ($ES^+$): m/z 414.2 $[M+H]^+$.

Step 4: To a solution of tert-butyl 4-(1-(2,6-dioxopiperidin-3-yl)indolin-5-yl)piperidine-1-carboxylate (6, 1 g, 2.42 mmol) in DCM (10 mL) was added HCl/dioxane (4.0 M, 1.21 mmol, 8 mL). The reaction was stirred at 16° C. for 2 h. The reaction was concentrated under reduced pressure to get 3-(5-(piperidin-4-yl)indolin-1-yl)piperidine-2,6-dione (7, 840 mg, 2.35 mmol, 97% yield, HCl salt) as pink solid, which was used without further purification. LCMS ($ES^+$): 313.9 $[M+H]^+$.

Example 6: Synthesis of 3-(5-(piperazin-1-yl)indolin-1-yl)piperidine-2,6-dione

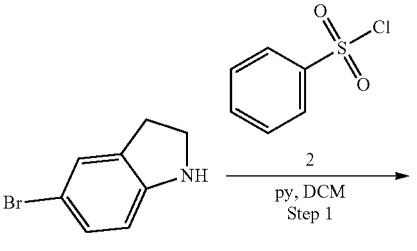

1

-continued

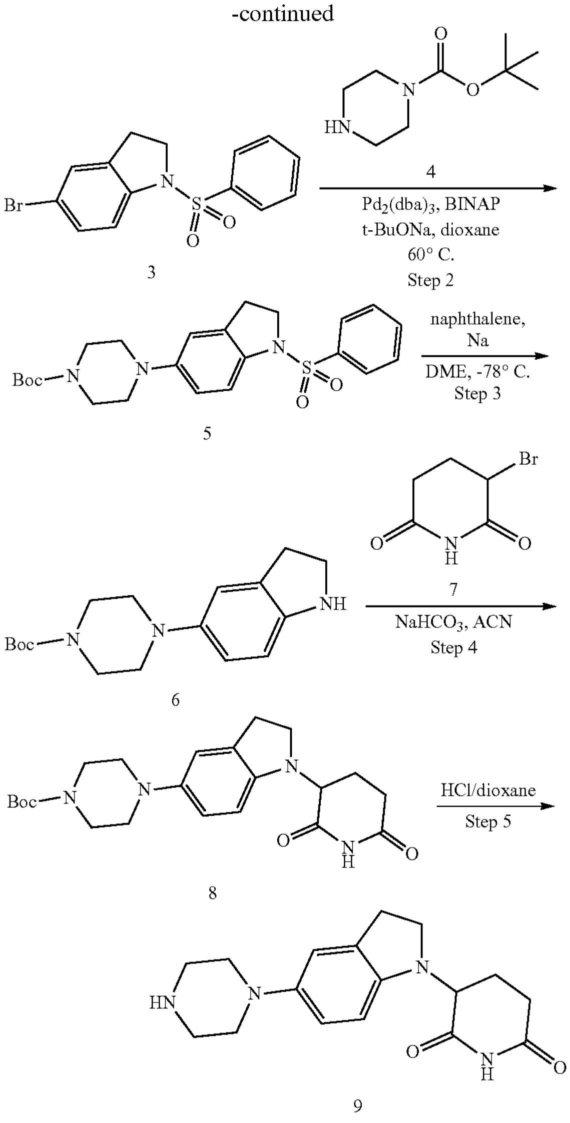

3

5

6

8

9

Step 1: To the mixture of 5-bromoindoline (1, 3 g, 15.15 mmol) and pyridine (4.79 g, 60.59 mmol, 4.90 mL) in DCM (30 mL) was added benzenesulfonyl chloride (2, 3.21 g, 18.18 mmol) at 0° C. Then the solution was stirred at 15° C. for 14 h. The reaction mixture was poured into sat. $NH_4Cl$ (50 mL) and extracted with DCM (20 mL×2). The combined organic layer was washed with brine (100 mL), dried over $Na_2SO_4$, filtered and the filtrate was concentrated. The residue was purified by column chromatography ($SiO_2$, Pet ether:EtOAc=10:1-2:1) to obtain 5-bromo-1-(phenylsulfonyl)indoline (3, 4.95 g, 14.64 mmol, 97% yield) as a white solid. LCMS ($ES^+$): 339.7 $[M+H]^+$ Step 2: To a solution of tert-butyl piperazine-1-carboxylate (4, 5.94 g, 31.87 mmol), 5-bromo-1-(phenylsulfonyl) indoline (3, 9.8 g, 28.98 mmol), (1E,4E)-1,5-diphenylpenta-1,4-dien-3-one;palladium (2.65 g, 2.90 mmol) and [1-(2-diphenylphosphanyl-1-naphthyl)-2-naphthyl]-diphenyl-phosphane (3.61 g, 5.80 mmol) in dioxane (100 mL) was added sodium; 2-methylpropan-2-olate (5.57 g, 57.95 mmol) under $N_2$ atmosphere. After addition, the solution was stirred at 100° C. for 12 h. The reaction mixture was diluted with DCM (100 mL) and filtered through a pad of Celite, washing with DCM (100 mL). The filtrate was washed with water (100 mL) and the organic layer was evaporated under reduced pressure to get crude. The residue was purified by column chromatography (SiO2, Pet ether: EtOAc=10:1-2:1) to obtain tert-butyl 4-(1-(phenylsulfonyl) indolin-5-yl)piperazine-1-carboxylate (5, 9.8 g, 22.09 mmol, 76% yield) as alight yellow solid. LCMS ($ES^+$): 444.1 $[M+H]^+$ Step 3: A solution of sodium naphthalenide in DME was prepared by adding sodium (3.05 g, 132.56 mmol) to a mixture of naphthalene (16.99 g, 132.56 mmol, 17.65 mL) in DME (100 mL), stirring at 15° C. for 2 h. To a solution of tert-butyl 4-(1-(phenylsulfonyl)indolin-5-yl)piperazine-1-carboxylate (5, 9.8 g, 22.09 mmol) in DME (300 mL) was added the above dark green sodium naphthalenide solution drop-wise at −78° C. until a light green color persisted. The reaction was stirred at −78° C. for 0.5 h. The reaction mixture of quenched with water (500 mL) and extracted with DCM (200 mL×3). The combined organic layer was washed with brine (500 mL), dried over $Na_2SO_4$, filtered and the filtrate was concentrated. The residue was purified by column chromatography ($SiO_2$, Pet ether:EtOAc=50:1-1:1) to obtain tert-butyl 4-(indolin-5-yl)piperazine-1-carboxylate (6, 4.2 g, 13.51 mmol, 61% yield) as a gray solid. LCMS ($ES^+$): 304.1 $[M+H]^+$ Step 4: The reaction mixture of tert-butyl 4-(indolin-5-yl)piperazine-1-carboxylate (6, 4.2 g, 13.84 mmol), 3-bromopiperidine-2,6-dione (7, 5.32 g, 27.69 mmol), sodium hydrogen carbonate (3.49 g, 41.53 mmol) and tetrabutylammonium iodide (511.32 mg, 1.38 mmol) in MeCN (20 mL) was stirred at 95° C. for 14 h. The mixture was poured into a mixture of water (100 mL) and MTBE (100 mL) and stirred for 1 h. The mixture was filtered and the filter cake was dried in vacuum. The residue was purified by column chromatography ($SiO_2$, DCM:EtOAc=100:1-2:1) to obtain tert-butyl 4-(1-(2,6-dioxopiperidin-3-yl)indolin-5-yl)piperazine-1-carboxylate (8, 4.7 g, 11.23 mmol, 81% yield) as a gray solid. LCMS ($ES^+$): 415.2 $[M+H]^+$ Step 5: The reaction mixture of tert-butyl 4-(1-(2,6-dioxopiperidin-3-yl)indolin-5-yl)piperazine-1-carboxylate (8, 1.5 g, 3.62 mmol) in HCl/dioxane (4 M, 15 mL) was stirred at 15° C. for 4 h. The mixture was concentrated under vacuum to obtain 3-(5-(piperazin-1-yl)indolin-1-yl)piperidine-2,6-dione (9, 1.2 g, 3.08 mmol, 85% yield, HCl salt) as a gray solid. LCMS ($ES^+$): 314.1 $[M+H]^+$. $^1H$ NMR (400 MHz, DMSO-$d_6$): δ=10.81 (s, 1H), 9.53-9.22 (m, 2H), 7.18-6.83 (m, 2H), 6.66-6.39 (m, 1H), 4.74-4.53 (m, 1H), 3.46-3.25 (m, 11H), 3.02-2.86 (m, 2H), 2.82-2.72 (m, 1H), 2.64-2.54 (m, 1H), 2.28-2.13 (m, 1H), 2.00-1.83 (m, 1H).

Example 7: Synthesis of 1-(7-fluoro-1-methyl-6-piperazin-1-yl-indazol-3-yl)hexahydropyrimidine-2,4-dione hydrochloride

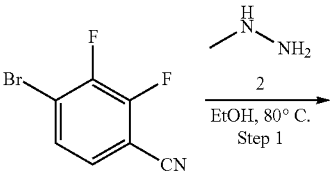

1

-continued

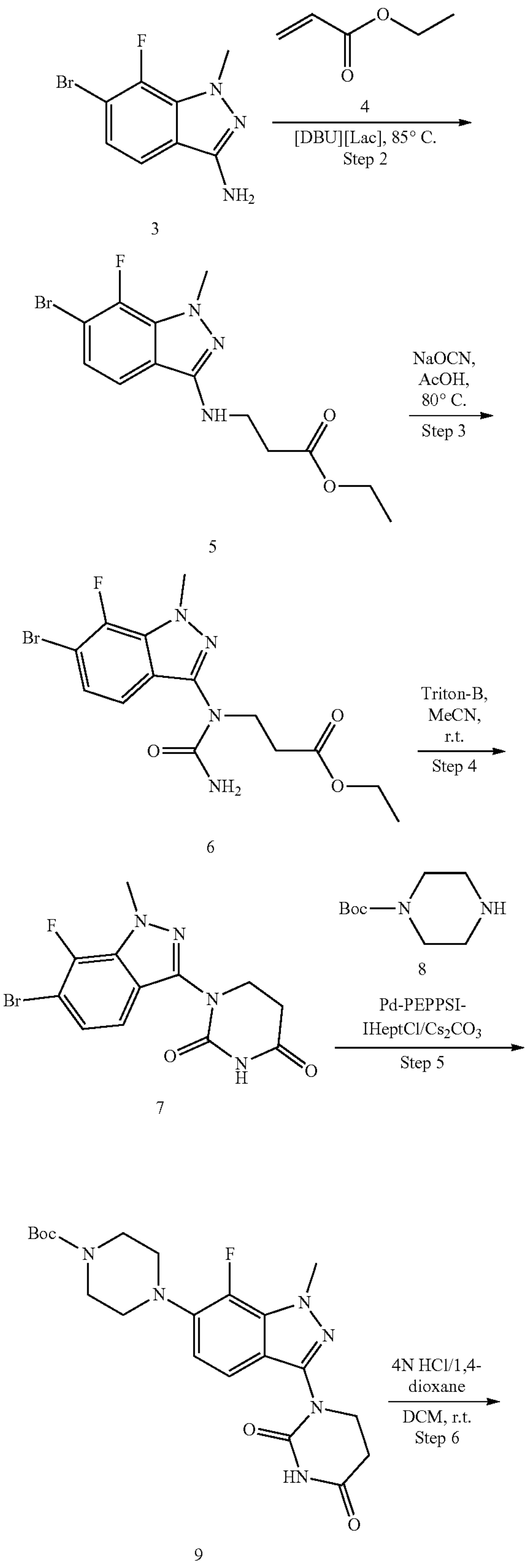

-continued

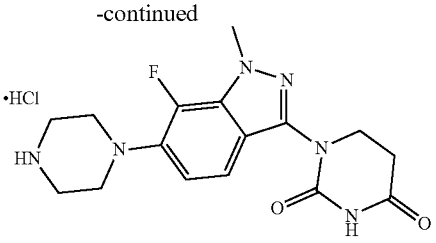

10

Step 1: Into a 250 mL sealed tube containing a well stirred solution of 4-bromo-2,3-difluoro-benzonitrile (1, 10 g, 45.87 mmol) in EtOH (100 mL) was added aqueous methylhydrazine (2, 12.43 g, 229.36 mmol, 85% purity) dropwise over a period of 10 minutes. The resulting mixture was stirred at 80° C. The reaction was complete after 12 h. The mixture was concentrated under reduced pressure to afford a crude solid. The crude solid was suspended in water (100 mL) and filtered to afford 6-bromo-7-fluoro-1-methyl-indazol-3-amine (3, 10.1 g, 39.64 mmol, 86% yield) as a light-yellow solid. UPLC-MS ($ES^+$): 244.2 $[M+H]^+$ Step 2: Into a 250 mL single-necked round-bottomed flask containing 1,8-Diazabicyclo[5.4.0]undec-7-ene (7.54 g, 49.54 mmol, 7.39 mL) was added Lactic acid (5.25 g, 49.54 mmol, 4.34 mL, 85% purity) at 0° C. and the resulting solution was stirred at ambient temperature for 20 h under nitrogen atmosphere. 6-Bromo-7-fluoro-1-methyl-indazol-3-amine (3, 10 g, 38.10 mmol) and ethyl prop-2-enoate (4, 26.70 g, 266.73 mmol, 28.90 mL) were added to the flask at ambient temperature. The resulting suspension was heated at 85° C. for 40 h. Ice-cold water (250 mL) was added to the mixture and aqueous phase was extracted with EtOAc (30×100 mL). Combined organic phase was washed successively with water (2×100 mL) and brine (100 mL), dried (anhydrous $Na_2SO_4$), and filtered. The filtrate was concentrated under reduced pressure to afford a crude residue, which was purified by flash silica-gel (230-400 mesh) column with 50-100% EtOAc/pet ether to afford ethyl 3-[(6-bromo-7-fluoro-1-methyl-indazol-3-yl)amino]propanoate (5, 6.9 g, 19.45 mmol, 51% yield) as a yellow solid. LC-MS ($ES^+$): 344.2 $[M+H]^+$ Step 3: Into a 250 mL sealed tube containing a well-stirred solution of ethyl 3-[(6-bromo-7-fluoro-1-methyl-indazol-3-yl)amino]propanoate (5, 6.0 g, 16.98 mmol) in glacial AcOH (75.10 mL) was added Sodium cyanate, 95% (2.21 g, 33.97 mmol) at ambient temperature. The resulting mixture was stirred at 80° C. for 40 h. The reaction was found complete after 40 h. The reaction mixture was cooled to ambient temperature and added carefully to ice-cold water (400 mL). The aqueous layer was extracted with EtOAc (3×150 mL). Combined organic phase was successively washed with saturated aqueous $NaHCO_3$ solution (500 mL) and brine (300 mL), dried (anhydrous $Na_2SO_4$) and filtered. The filtrate was concentrated under reduced pressure to afford a crude compound. The crude mass was purified by flash silica-gel (230-400 mesh) column with 50-100% EtOAc/pet ether to afford ethyl 3-[(6-bromo-7-fluoro-1-methyl-indazol-3-yl)-carbamoyl-amino]propanoate (6, 3.8 g, 9.32 mmol, 55% yield) as a pale-pink solid. UPLC-MS ($ES^+$): 387.1 $[M+H]^+$ Step 4: Into a 100 mL single-necked round-bottomed flask containing a well stirred solution of ethyl 3-[(6-bromo-7-fluoro-1-methyl-indazol-3-yl)-carbamoyl-amino]propanoate (6, 3.6 g, 8.83 mmol) in MECN (50 mL) was added Benzyl trimethyl ammonium hydroxide (1.11 g, 2.65 mmol, 40% purity) at ambient temperature. The resulting mixture was stirred at ambient temperature. The reaction was found complete after 2 h. The mixture was concentrated under reduced pressure to get a crude residue, which was suspended in water (50 mL) and filtered to afford 1-(6-bromo-7-fluoro-1-methyl-indazol-3-yl)hexahydropyrimidine-2,4-dione (7, 2.4 g, 6.96 mmol, 79% yield) as a white solid. LCMS ($ES^+$): 341.0 $[M+H]^+$ Step 5: Into a 250 mL sealed tube containing a well stirred solution of 1-(6-bromo-7-fluoro-1-methyl-indazol-3-yl) hexahydropyrimidine-2,4-dione (7, 1.2 g, 3.48 mmol) and tert-butyl piperazine-1-carboxylate (8, 1.30 g, 6.96 mmol) in 1,4-dioxane (75 mL) was added Cesium carbonate (2.84 g, 8.71 mmol) and the mixture was degassed by bubbling nitrogen gas for 5 minutes. Subsequently, Pd-PEPPSI-iHept-Cl (169.25 mg, 0.174 mmol) was added and the resulting mixture was stirred at 100° C. The reaction was complete after 16 h. The mixture was cooled to ambient temperature, filtered through a pad of Celite bed and Celite bed was washed with EtOAc (50 mL). The filtrate was concentrated under reduced pressure to afford a crude mass. The crude mass was purified by flash silica-gel (230-400 mesh) column with 50-100% EtOAc/pet ether to afford tert-butyl 4-[3-(2,4-dioxohexahydropyrimidin-1-yl)-7-fluoro-1-methyl-indazol-6-yl]piperazine-1-carboxylate (9, 1.15 g, 2.40 mmol, 69% yield) as a beige solid. LCMS ($ES^+$): 447.8 $[M+H]^+$ Step 6: Into a 100 mL single-necked round-bottomed flask containing a well stirred solution of tert-butyl 4-[3-(2,4-dioxohexahydropyrimidin-1-yl)-7-fluoro-1-methyl-indazol-6-yl]piperazine-1-carboxylate (9, 1.14 g, 2.37 mmol) in DCM (20 mL) was added 4M HCl in 1,4-dioxane (15 mL) at ambient temperature. The resulting mixture was stirred at ambient temperature for 2 h. Excess solvent was removed under reduced pressure to afford a crude mass. The crude mass was triturated with MTBE (40 mL) and solid thus obtained was filtered to afford 1-(7-fluoro-1-methyl-6-piperazin-1-yl-indazol-3-yl)hexahydropyrimidine-2,4-dione hydrochloric acid salt (10, 950 mg, 2.31 mmol, 97% yield) as a beige solid. $^1H$ NMR (400 MHz, DMSO-$d_6$). δ 10.60 (s, 1H), 9.16 (bs, 2H), 7.40 (d, J=8.8 Hz, 1H), 6.97 (t, J=8.8 Hz, 1H), 4.08 (s, 3H), 3.91 (t, J=6.8 Hz, 2H), 3.34-3.32 (m, 4H), 3.27 (m, 4H), 2.76 (t, J=6.8 Hz, 2H). LCMS ($ES^+$): 347.5 $[M+H]^+$ Example 8: Synthesis of tert-Butyl 4-[4-[(2,6-dioxo-3-piperidyl)amino]-2-fluoro-phenyl]piperazine-1-carboxylate (6), tert-butyl (S)-4-(4-((2,6-dioxopiperidin-3-yl)amino)-2-fluorophenyl)piperazine-1-carboxylate (7) and tert-butyl (R)-4-(4-((2,6-dioxopiperidin-3-yl)amino)-2-fluorophenyl) piperazine-1-carboxylate (8) (Configurations arbitrarily assigned)

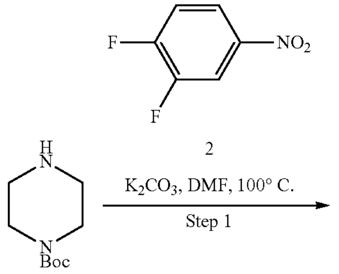

2

1

-continued

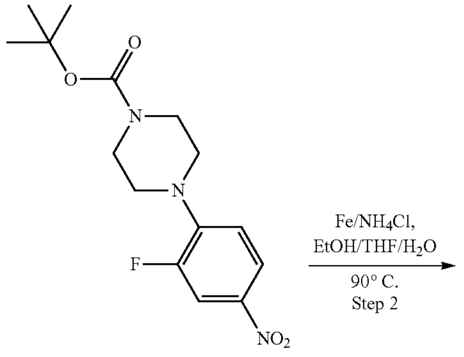

3

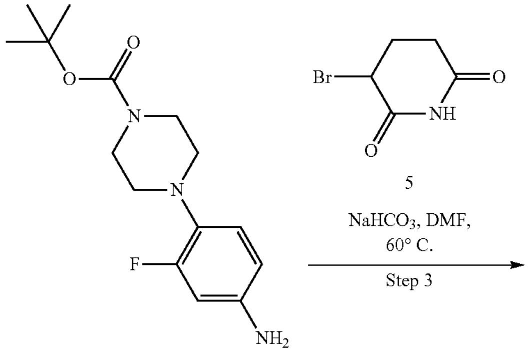

5

4

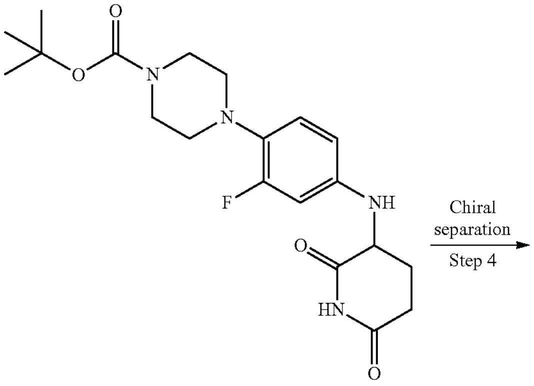

6

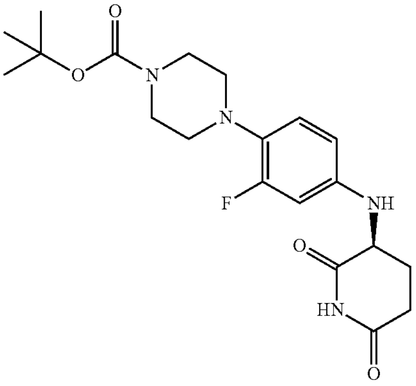

7

+

-continued

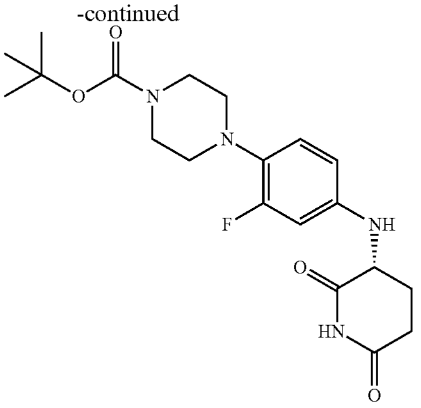

8

Step 1: Into a 250 mL sealed-tube containing a well-stirred solution of tert-butyl piperazine-1-carboxylate (1, 14.05 g, 75.43 mmol) and 1,2-difluoro-4-nitro-benzene (2, 10 g, 62.86 mmol, 6.94 mL) in anhydrous DMF (100 mL) was added potassium carbonate, anhydrous, 99% (13.03 g, 94.3 mmol) at ambient temperature under nitrogen atmosphere. The resulting mixture was stirred at 60° C. for 16 h. The mixture was cooled to ambient temperature and carefully added to ice-cold water (400 mL) and solid thus obtained was filtered to afford tert-butyl 4-(2-fluoro-4-nitro-phenyl)piperazine-1-carboxylate (3, 20.3 g, 57.7 mmol, 92% yield) as a yellow solid. UPLC-MS ($ES^+$): 270 $[M-tBu+H]^+$ Step 2: Into a 500 mL single-necked round-bottomed flask containing a well-stirred suspension of tert-butyl 4-(2-fluoro-4-nitro-phenyl)piperazine-1-carboxylate (3, 5 g, 15.37 mmol) in a mixture of THF (40 mL), EtOH (40 mL) and water (30 mL) were subsequently added Iron powder (4.29 g, 76.84 mmol) and ammonium chloride (4.11 g, 76.84 mmol) at ambient temperature under nitrogen atmosphere. The resulting suspension was heated to 85° C. for 2 h. The mixture was cooled to ambient temperature and filtered through a pad of Celite, washing with DCM (400 mL). The filtrate was concentrated under reduced pressure to get a crude residue. The crude residue was purified by flash silica-gel (230-400 mesh) column with 0-50% EtOAc/pet ether to afford tert-butyl 4-(4-amino-2-fluoro-phenyl)piperazine-1-carboxylate (4, 4.4 g, 14.6 mmol, 95% yield) as a light yellow solid. LCMS ($ES^+$): 296.2 $[M+H]^+$ Step 3: Into a 250 mL sealed-tube containing a well-stirred solution of tert-butyl 4-(4-amino-2-fluoro-phenyl) piperazine-1-carboxylate (4, 4.4 g, 14.9 mmol) and 3-bromopiperidine-2,6-dione (5, 4.29 g, 22.35 mmol) in anhydrous DMF (81.70 mL) was added sodium bicarbonate (3.7 g, 44.7 mmol) at ambient temperature under nitrogen atmosphere. The mixture was stirred at 60° C. for 16 h. The mixture was cooled to ambient temperature. An additional amount of 3-bromopiperidine-2,6-dione (5, 4.3 g, 22.3 mmol) and sodium bicarbonate (3.7 g, 44.7 mmol, 1.7 mL) were added to the mixture. The mixture was stirred at 60° C. for 24 h. The mixture was cooled to ambient temperature and carefully added to ice-cold water (100 mL). The aqueous layer was extracted with DCM (2×300 mL). The combined organic layer was washed with brine (300 mL) and dried (anhydrous $Na_2SO_4$), filtered, and concentrated under reduced pressure to get a crude residue. The crude was purified by flash silica-gel (230-400 mesh) column with 0-75% EtOAc/pet ether to afford tert-butyl 4-[4-[(2,6-dioxo-3-piperidyl)amino]-2-fluoro-phenyl]piperazine-1-carboxylate (6, 4.4 g, 10.5 mmol, 70% yield) as a light green solid. LCMS ($ES^+$): 407.2 $[M+H]^+$. $^1$H NMR (400 MHz, DMSO-$d_6$). δ 10.79 (s, 1H), 6.85 (t, J=9.6 Hz, 1H), 6.52 (dd, J=14.8, 2.4 Hz, 1H), 6.43 (dd, J=8.8, 2 Hz, 1H), 5.87 (d, J=7.6 Hz, 1H), 4.30-4.24 (m, 1H), 3.44 (m, 4H), 2.80 (m, 4H), 2.70 (m, 1H), 2.60 (m, 1H), 2.10 (m, 1H), 1.42 (s, 9H).

Step 4: tert-Butyl 4-[4-[(2,6-dioxo-3-piperidyl)amino]-2-fluoro-phenyl]piperazine-1-carboxylate (6, 200 mg, enantiomeric mixture) was separated by SFC (Instrument: PIC 175 Column: YMC Amylose SA (250×30) mm, 5 m; Mobile Phase: $CO_2$: {0.1% Isopropyl amine in IPA: Acetonitrile (1:1)} (50:50)%; Total flow: 100 g/minutes; Back pressure: 100 bar; Wave length: 254 nm; Cycle time: 5 minutes; About 0.210 mg of the mixture was dissolved in 2.0 mL of CAN/Isopropyl alcohol and injected 700 μL/injection: Fractions with RT=2.62 minutes were combined and concentrated at 30° C. under reduced pressure to afford the fast eluting enantiomer-tert-butyl (S)-4-(4-((2,6-dioxopiperidin-3-yl)amino)-2-fluorophenyl)piperazine-1-carboxylate (7, 90 mg, 98.8% chiral purity) as a light brown solid.

Whereas the fractions with RT=4.28 minutes were combined and concentrated at 30° C. under reduced pressure to afford the late eluting enantiomer-tert-butyl (R)-4-(4-((2,6-dioxopiperidin-3-yl)amino)-2-fluorophenyl)piperazine-1-carboxylate (8, 85 mg, 83% chiral purity) as a light brown solid.

Example 9: Synthesis of 3-[3-chloro-4-(4-piperidyl) anilino]piperidine-2,6-dione

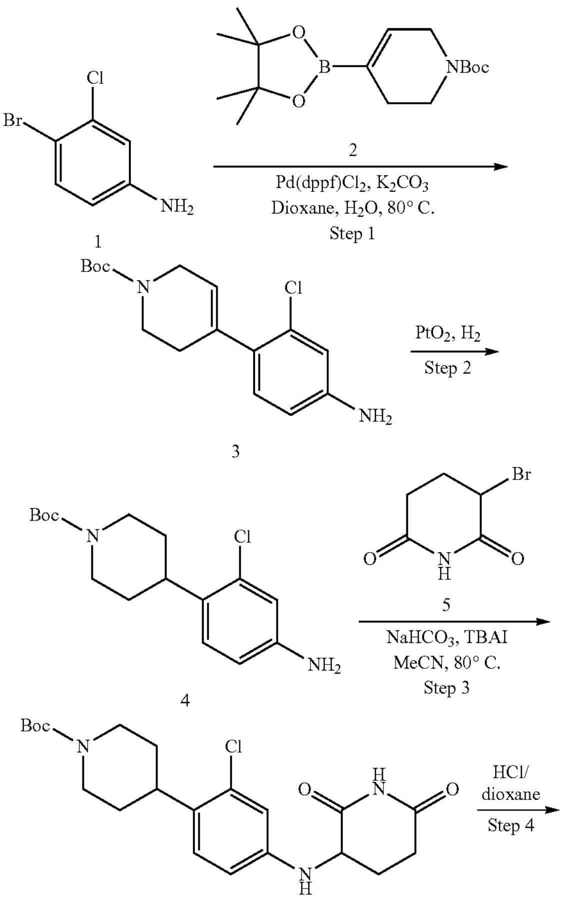

6

-continued

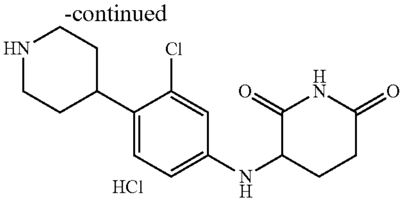

7

Step 1: To a solution of 4-bromo-3-chloro-aniline (1, 4.03 g, 19.52 mmol), tert-butyl 4-(4,4,5,5-tetramethyl-1,3,2-dioxaborolan-2-yl)-3,6-dihydro-2H-pyridine-1-carboxylate (2, 6.05 g, 19.55 mmol) in dioxane (80 mL) was added cyclopentyl(diphenyl)phosphane;dichloromethane;dichloropalladium;iron (800 mg, 979.63 μmol) in $N_2$ atmosphere, then the aqueous of tripotassium;phosphate (2 M, 20 mL) was added into the above solution. After that, the solution was stirred at 60° C. for 12 h. The reaction solution was quenched with water (200 mL) and the mixture extracted with EtOAc (200 mL×3). The combined organic layers were washed with brine (200 mL), dried over $Na_2SO_4$, and concentrated under vacuum. The residue was purified by flash silica gel chromatography ($SiO_2$, 20 g Silica Flash Column, Eluent of 0-30% EtOAc/Pet ether, 40 mL/min) to afford tert-butyl 4-(4-amino-2-chloro-phenyl)-3,6-dihydro-2H-pyridine-1-carboxylate (3, 3.18 g, 9.87 mmol, 51% yield) as yellow oil. LCMS ($ES^+$): 309.4 $[M+H]^+$ Step 2: To a solution of tert-butyl 4-(4-amino-2-chloro-phenyl)-3,6-dihydro-2H-pyridine-1-carboxylate (3, 2 g, 6.48 mmol) in EtOAc (10 mL) was added dioxoplatinum (607.84 mg, 2.68 mmol) under $N_2$ atmosphere. The suspension was degassed and purged with $H_2$ (3 times). The 10 mixture was stirred under $H_2$ (3.24 mmol) at 25° C. for 12 h. The reaction mixture was filtered, and the filtrate was concentrated in vacuum to afford tert-butyl 4-(4-amino-2-chlorophenyl)piperidine-1-carboxylate (4, 1 g, 3.22 mmol, 50% yield) as a pink solid, which was used without further purification. LCMS ($ES^+$): 255.1$[M+H-tBu]^+$ Step 3: To a solution of tert-butyl 4-(4-amino-2-chloro-phenyl)piperidine-1-carboxylate (4, 1.3 g, 4.18 mmol), 3-bromopiperidine-2,6-dione (5, 1 g, 5.21 mmol) in MeCN (20 mL) was added TBAI (155 mg, 419.64 μmol) and $NaHCO_3$ (1.05 g, 12.55 mmol, 488.00 μL). After addition, the solution was stirred at 90° C. for 12 h. The reaction solution was concentrated under vacuum. The residue was purified by flash silica gel chromatography ($SiO_2$, 10 g Flash Silica Column, Eluent of 0-40% EtOAc/Pet ether, 40 mL/min) to afford tert-butyl 4-(2-chloro-4-((2,6-dioxopiperidin-3-yl)amino)phenyl)piperidine-1-carboxylate (6, 500 mg, 1.17 mmol, 28% yield) as a blue solid. LCMS ($ES^+$): m/z 365.9 $[M+H]^+$. $^1H$ NMR (400 MHz, DMSO-d6) δ=10.78 (s, 1H), 7.03 (d, J=8.8 Hz, 1H), 6.70 (d, J=2.4 Hz, 1H), 6.60 (dd, J=2.4, 8.4 Hz, 1H), 4.33 (br dd, J=4.8, 11.6 Hz, 1H), 4.07 (br s, 1H), 2.98-2.87 (m, 1H), 2.84-2.65 (m, 3H), 2.62-2.54 (m, 2H), 2.43 (t, J=6.4 Hz, 3H), 1.86-1.77 (m, 2H), 1.66 (br d, J=12.4 Hz, 2H), 1.40 (s, 9H)

Step 4: To a solution of tert-butyl 4-(2-chloro-4-((2,6-dioxopiperidin-3-yl)amino)phenyl)piperidine-1-carboxylate (50 mg, 118.51 μmol) in DCM (0.5 mL) was added HCl in dioxane (4 M, 0.5 mL). The mixture was stirred at 20° C. for 0.5 h. After completion, the reaction mixture was concentrated under reduced pressure to remove solvent. The crude product 3-[3-chloro-4-(4-piperidyl)anilino]piperidine-2,6-dione (38 mg, 106.28 umol, 90% yield) was used in the next step without further purification. LCMS ($ES^+$): 322.1 $[M+H]^+$.

Example 10: Synthesis of 2-(1-(4-((2,6-dioxopiperidin-3-yl)amino)-2-fluorophenyl)-4-methoxypiperidin-4-yl)acetic acid

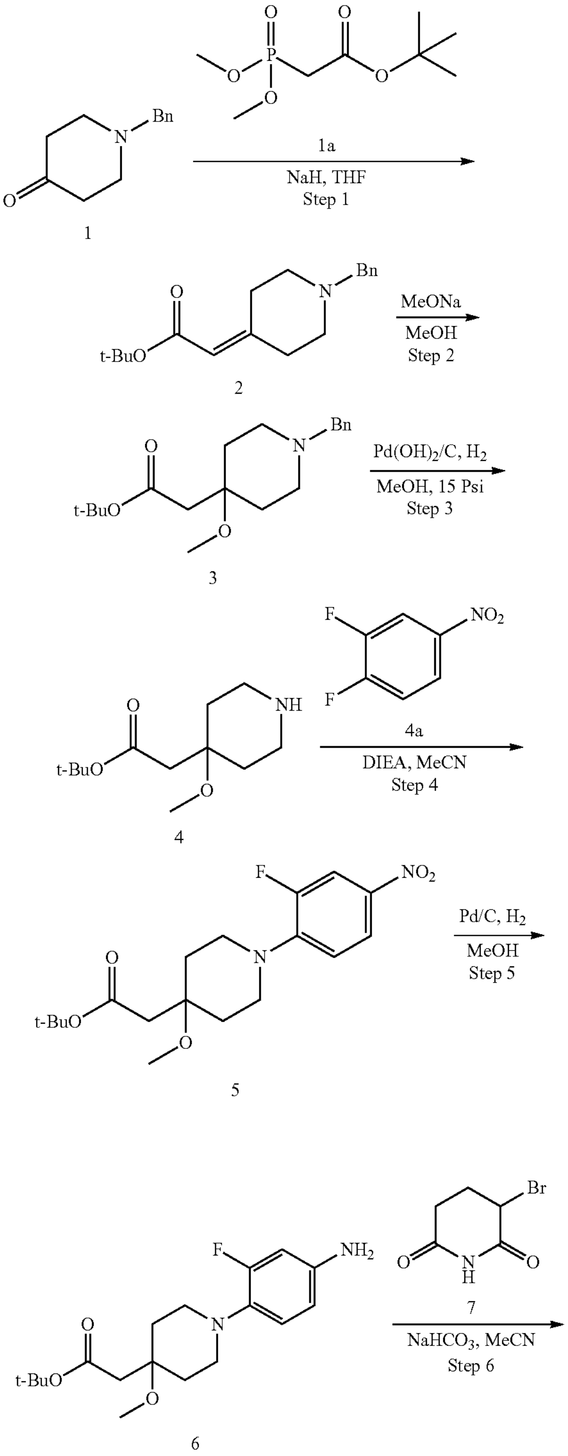

-continued

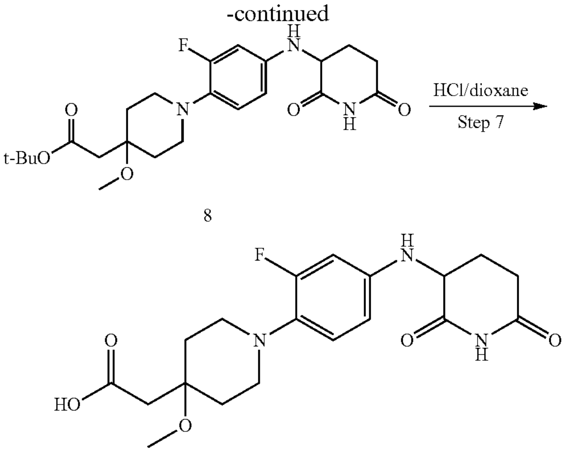

8

9

Step 1: To a solution of NaH (60% dispersion in mineral oil) (728.86 mg, 19.02 mmol) in THF (30 mL) was carefully added tert-butyl 2-(dimethoxyphosphoryl)acetate (1a, 5.33 g, 23.78 mmol, 385.94 μL) at −10° C. After the addition, the mixture was stirred at 0° C. for 30 min. Then a solution of 1-benzylpiperidin-4-one (1, 3 g, 15.85 mmol, 2.83 mL) in THF (10 mL) was added into the mixture drop wise so that the reaction temperature did not exceed 0° C. After the addition, the reaction was stirred at 20° C. for 12 hrs. The reaction mixture was added into $NH_4Cl$ (sat, 200 mL) and then diluted with EtOAc (300 mL) and extracted with EtOAc (100 mL×3). The combined organic layers were washed with brine (50 mL), dried with anhydrous $Na_2SO_4$, filtered, and concentrated under reduced pressure to give a residue. The crude product was purified by column chromatography ($SiO_2$, Pet ether:EtOAc=20:1-10:1-8:1) to get tert-butyl 2-(1-benzylpiperidin-4-ylidene)acetate (2, 4.1 g, 13.84 mmol, 87% yield) as white solid. LCMS ($ES^+$): 288.1 $[M+H]^+$ Step 2: To a solution of tert-butyl 2-(1-benzylpiperidin-4-ylidene)acetate (2, 500 mg, 1.74 mmol) in Methanol (3 mL) was carefully added sodium;methanolate (4 M, 1.74 mL) at −10° C., and the reaction was stirred at 20° C. for 12 hrs. The reaction was quenched by Py/HOAc (2 mL), and the reaction was added into water (20 mL), before extracting with EtOAc (10 mL×3). The combined organic layer was washed with brine (5 mL), dried over $Na_2SO_4$, filtered and concentrated. The crude product was purified by prep-TLC (Pet ether:EtOAc=2:1, Rf=0.3) to get tert-butyl 2-(1-benzyl-4-methoxypiperidin-4-yl)acetate (3, 150 mg, 469.58 μmol, 27% yield) as a yellow solid. LCMS ($ES^+$): 320.1 $[M+H]^+$ Step 3: To a solution of tert-butyl 2-(1-benzyl-4-methoxypiperidin-4-yl)acetate (3, 150 mg, 469.58 μmol) in MeOH (5 mL) was added 10 wt. % $Pd(OH)_2/C$ (50 mg, 494.39 μmol) under $N_2$. The suspension was degassed under vacuum and purged with $H_2$. The mixture was stirred under $H_2$ (15 PSI) at 20° C. for 12 hours. The reaction was filtered and filtrated was concentrated under vacuum to afford tert-butyl 2-(4-methoxypiperidin-4-yl)acetate (4, 80 mg, 348.87 μmol, 74% yield) as colorless oil which was used without further purification. LCMS ($ES^+$): 230.1 $[M+H]^+$ Step 4: To a solution of tert-butyl 2-(4-methoxypiperidin-4-yl)acetate (4, 500 mg, 2.18 mmol) and DIEA (10.90 mmol, 1.52 mL) in $CH_3CN$ (1 mL) was added 1,2-difluoro-4-nitrobenzene (4a, 520.32 mg, 3.27 mmol, 361.33 μL) at 25° C., and the mixture was stirred at 90° C. for 2 hrs. The reaction was concentrated under reduced pressure to get a residue. The yellow residue was purified by column chromatography ($SiO_2$, Pet ether:EtOAc=50:1-15:1-10:1) to get tert-butyl 2-(1-(2-fluoro-4-nitrophenyl)-4-methoxypiperidin-4-yl)acetate (5, 320 mg, 816.51 μmol, 37% yield) as light-yellow solid. LCMS ($ES^+$): 369.1 $[M+H]^+$ Step 5: To a solution of tert-butyl 2-(1-(2-fluoro-4-nitrophenyl)-4-methoxypiperidin-4-yl)acetate (5, 300 mg, 814.33 μmol) in MeOH (15 mL) was added 10 wt. % Pd/C (80 mg) under $N_2$. The suspension was degassed under vacuum and purged with $H_2$. The mixture was stirred under $H_2$ (15 PSI) at 20° C. for 12 hours. The reaction was filtered and concentrated under vacuum to afford tert-butyl 2-(1-(4-amino-2-fluorophenyl)-4-methoxypiperidin-4-yl)acetate (6, 270 mg, 797.83 μmol, 98% yield) as brown solid, which was used without purification. LCMS ($ES^+$): 339.0 $[M+H]^+$ Step 6: To a solution of tert-butyl 2-(1-(4-amino-2-fluorophenyl)-4-methoxypiperidin-4-yl)acetate (6, 270 mg, 797.83 μmol) and $NaHCO_3$ (335.12 mg, 3.99 mmol) in $CH_3CN$ (3 mL) was added 3-bromopiperidine-2,6-dione (7, 229.79 mg, 1.20 mmol) at 25° C., and the mixture was stirred at 90° C. for 12 hrs. The reaction was concentrated under reduced pressure to get a residue. The residue was washed by water (20 mL) and triturated with Pet ether: EtOAc=6:1 (100 mL) at 25° C. for 20 min. The mixture was filtered and the filtrated cake was dried to get tert-butyl 2-(1-(4-((2,6-dioxopiperidin-3-yl)amino)-2-fluorophenyl)-4-methoxypiperidin-4-yl)acetate (8, 300 mg, 667.39 μmol, 84% yield) as blue solid. LCMS ($ES^+$): 450.1 $[M+H]^+$ Step 7: To a solution of tert-butyl 2-(1-(4-((2,6-dioxopiperidin-3-yl)amino)-2-fluorophenyl)-4-methoxypiperidin-4-yl)acetate (8, 300 mg, 667.39 μmol) in DCM (2 mL) was added HCl (12 M, 0.5 mL), and the mixture was stirred at 25° C. for 2 hrs. The reaction was concentrated under reduced pressure to get 2-(1-(4-((2,6-dioxopiperidin-3-yl)amino)-2-fluorophenyl)-4-methoxypiperidin-4-yl)acetic acid (9, 240 mg, 558.31 μmol, 84% yield, HCl salt) as blue solid, which was used without further purification. LCMS ($ES^+$): 394.0 $[M+H]^+$.

Example 11: Synthesis of 2-(1-(2-chloro-4-((2,6-dioxopiperidin-3-yl)amino)-5-methoxyphenyl)-4-hydroxy piperidin-4-yl) acetic acid

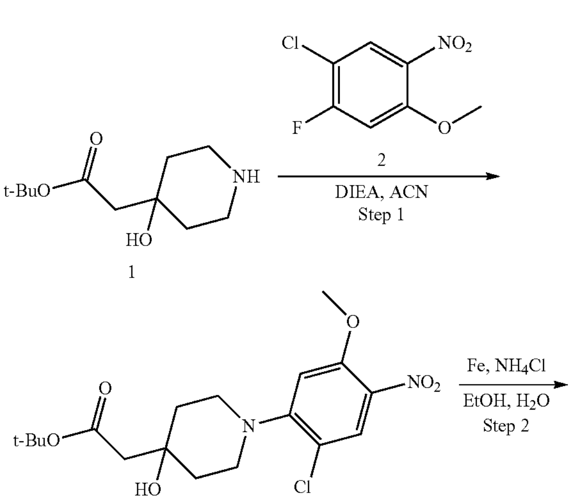

2

1

3

-continued

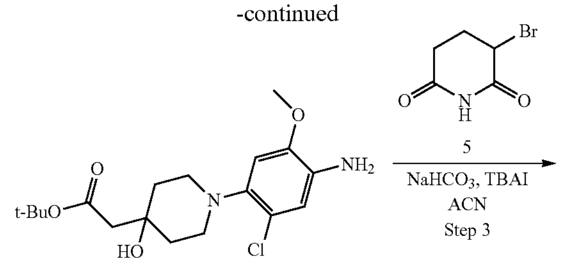

4

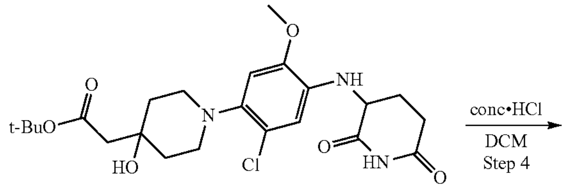

6

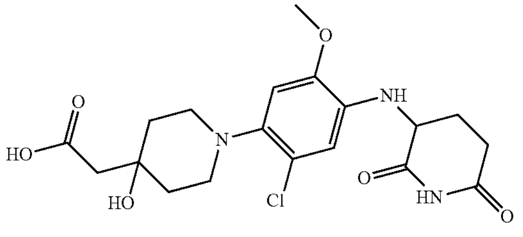

7

Step 1: To a solution of tert-butyl 2-(4-hydroxypiperidin-4-yl)acetate (1, 500 mg, 2.32 mmol) in MECN (5 mL) was added 1-chloro-2-fluoro-4-methoxy-5-nitrobenzene (2, 525.17 mg, 2.55 mmol) and N-ethyl-N-isopropyl-propan-2-amine (900.48 mg, 6.97 mmol, 1.21 mL). The mixture was stirred at 90° C. for 12 h. The residue was poured into water (10 mL), filtered and the filter cake was concentrated under reduced pressure. The filter cake was triturated with Pet ether (20 mL) at 25° C. for 0.5 h to afford tert-butyl 2-(1-(2-chloro-5-methoxy-4-nitrophenyl)-4-hydroxypiperidin-4-yl)acetate (3, 702 mg, 1.73 mmol, 75% yield) as yellow solid. LCMS ($ES^+$): 401.1 $[M+H]^+$ Step 2: To a solution of tert-butyl 2-(1-(2-chloro-5-methoxy-4-nitrophenyl)-4-hydroxypiperidin-4-yl)acetate (3, 700 mg, 1.75 mmol) in water (1.2 mL) and ethanol (5.5 mL) was added ammonia;hydrochloride (373.64 mg, 6.99 mmol) and Iron (390.08 mg, 6.99 mmol). The mixture was stirred at 70° C. for 12 h. The residue was diluted with water (10 mL) and extracted with EtOAc (10 mL×3). The combined organic layers were washed with brine (30 mL), dried over $Na_2SO_4$, filtered and concentrated under reduced pressure. The residue was purified by column chromatography (SiO2, Petroleum ether/Ethyl acetate=10/1 to 2/1) to afford tert-butyl 2-(1-(4-amino-2-chloro-5-methoxyphenyl)-4-hydroxypiperidin-4-yl)acetate (4, 633 mg, 1.67 mmol, 96% yield) as a white solid. LCMS ($ES^+$): 371.2 $[M+H]^+$ Step 3: To a solution of 3-bromopiperidine-2,6-dione (5, 621.27 mg, 3.24 mmol), tert-butyl 2-(1-(4-amino-2-chloro-5-methoxyphenyl)-4-hydroxypiperidin-4-yl)acetate (4, 600 mg, 1.62 mmol) in MECN (3 mL) was added $NaHCO_3$ (407.72 mg, 4.85 mmol, 188.76 μL) and TBAI (119.51 mg, mg, 323.56 μmol). The mixture was stirred at 90° C. for 12 h. The reaction mixture was concentrated under reduced pressure. The residue was poured to water (20 mL) and extracted with EtOAc (15 mL×3). The combined organic layer was washed with brine (50 mL×2), dried over $Na_2SO_4$, filtered and concentrated under reduced pressure to get a residue. The residue was purified by column chromatography ($SiO_2$, DCM:EtOAc=10:1-3:1) to afford tert-butyl 2-(1-(2-chloro-4-((2,6-dioxopiperidin-3-yl)amino)-5-methoxyphenyl)-4-hydroxypiperidin-4-yl)acetate (6, 600 mg, 1.12 mmol, 69% yield) as blue solid. LCMS ($ES^+$): 482.1 $[M+H]^+$ Step 4: To a solution of tert-butyl 2-(1-(2-chloro-4-((2,6-dioxopiperidin-3-yl)amino)-5-methoxyphenyl)-4-hydroxypiperidin-4-yl)acetate (6, 500 mg, 1.04 mmol) in DCM (4 mL) was added hydrochloric acid (12 M, 864.51 μL). The mixture was stirred at 25° C. for 2 h. The reaction was concentrated under reduced pressure to get 2-(1-(2-chloro-4-((2,6-dioxopiperidin-3-yl)amino)-5-methoxyphenyl)-4-hydroxy piperidin-4-yl) acetic acid (7, 470 mg, 813.28 μmol, 78% yield, HCl salt) as brown solid, which was used without purification. LCMS ($ES^+$): 426.1 $[M+H]^+$.

Example 12: Synthesis of 2-[1-[4-[(2,6-dioxo-3-piperidyl)amino]-2-fluoro-5-methoxy-phenyl]-4-hydroxy-4-piperidyl]acetic acid

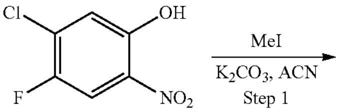

2A

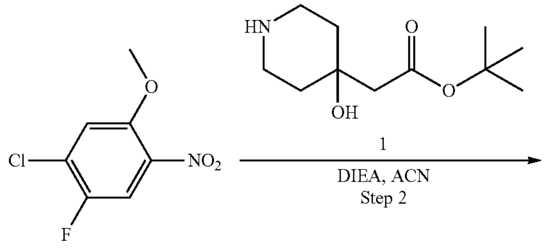

2

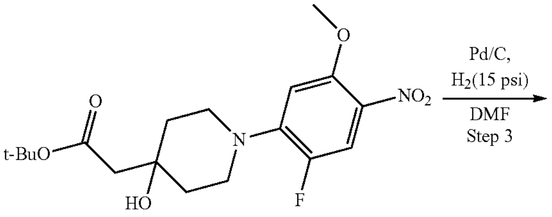

3

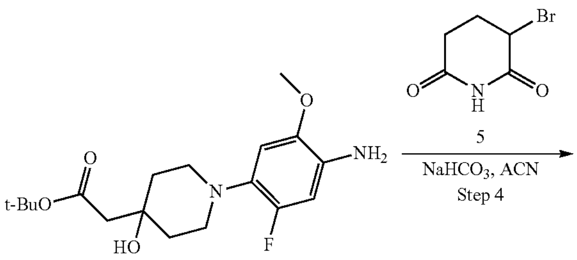

4

-continued

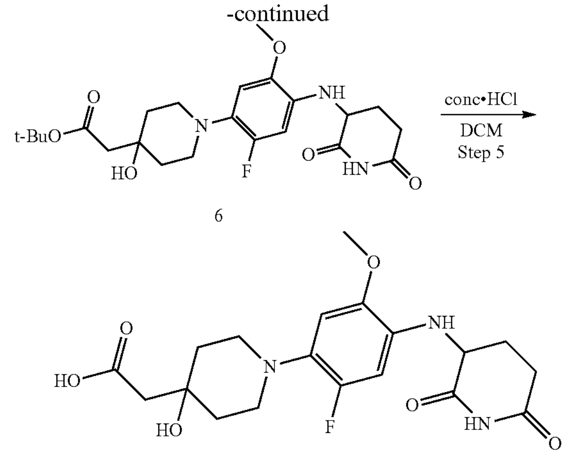

6

7

Step 1: To a solution of 5-chloro-4-fluoro-2-nitro-phenol (2A, 1 g, 5.22 mmol) and dipotassium;carbonate (1.80 g, 13.05 mmol) in MeCN (10 mL) was stirred at 25° C. for 0.5 h. A solution of iodomethane (3.71 g, 26.10 mmol, 1.63 mL) in MeCN (10 mL) was added. The mixture was stirred at 90° C. for 12 h. The reaction mixture was quenched by addition of $H_2O$ (2 mL) at 25° C., and concentrated under reduced pressure to remove MeCN. Then the mixture was diluted with $H_2O$ (10 mL) and extracted with EtOAc (5 mL×3). The combined organic layers were washed with brine (15 mL), dried over $Na_2SO_4$, filtered and concentrated under reduced pressure. The residue was purified by column chromatography ($SiO_2$, Petroleum ether/Ethyl acetate=10/1 to 5/1). 1-chloro-2-fluoro-5-methoxy-4-nitro-benzene (2, 1 g, 4.82 mmol, 92% yield) was obtained as a yellow solid. LCMS ($ES^+$): 206.0 $[M+H]^+$ Step 2: To a solution of tert-butyl 2-(4-hydroxy-4-piperidyl)acetate (1, 500 mg, 1.51 mmol) in MeCN (5 mL) was added 1-chloro-2-fluoro-5-methoxy-4-nitro-benzene (2, 341.36 mg, 1.66 mmol) and N-ethyl-N-isopropyl-propan-2-amine (585.30 mg, 4.53 mmol, 788.82 μL). The mixture was stirred at 90° C. for 4 h. The residue was diluted with water (10 mL) and extracted with EtOAc (10 mL×3). The combined organic layers were washed with brine (30 mL), dried over $Na_2SO_4$, filtered and concentrated under reduced pressure. The residue was purified by column chromatography ($SiO_2$, Petroleum ether/Ethyl acetate=10/1 to 4/1). tert-butyl 2-[1-(2-fluoro-5-methoxy-4-nitro-phenyl)-4-hydroxy-4-piperidyl]acetate (3, 510 mg, 1.27 mmol, 84% yield) was obtained as yellow solid. LCMS ($ES^+$): 385.1 $[M+H]^+$ Step 3: To a solution of tert-butyl 2-[1-(2-fluoro-5-methoxy-4-nitro-phenyl)-4-hydroxy-4-piperidyl]acetate (3, 490 mg, 1.27 mmol) in DMF (7 mL) was added 10 wt. % Pd/C (50 mg, 46.98 μmol) under $N_2$ atmosphere. The suspension was degassed and purged with $H_2$ (3 times). The mixture was stirred under $H_2$ (15 Psi) at 25° C. for 12 h. The reaction mixture was filtered and the filter liquor was concentrated under reduced pressure. The residue was triturated with MTBE (10 mL) at 25° C. for 0.5 min to afford tert-butyl 2-[1-(4-amino-2-fluoro-5-methoxy-phenyl)-4-hydroxy-4-piperidyl]acetate (4, 380 mg, 1.05 mmol, 82.43% yield) as yellow solid. LCMS ($ES^+$): 355.3 $[M+H]^+$ Step 4: To a solution of tert-butyl 2-[1-(4-amino-2-fluoro-5-methoxy-phenyl)-4-hydroxy-4-piperidyl]acetate (4, 370 mg, 1.04 mmol) and 3-bromopiperidine-2,6-dione (5, 240.54 mg, 1.25 mmol) in MeCN (2 mL) was added sodium hydrogen carbonate (263.10 mg, 3.13 mmol, 121.81 μL). The mixture was stirred at 90° C. for 12 h. The reaction mixture was concentrated under reduced pressure. The residue was poured into water (5 mL), filtered and the filter cake was concentrated under reduced pressure. The filter liquor was extracted with EtOAc (5 mL×3). The combined organic layers were washed with brine (20 mL), dried over $Na_2SO_4$, filtered and concentrated under reduced pressure to get a residue. The filter cake was triturated with EtOAc (10 mL) at 25° C. for 0.5 h. The residue was purified by column chromatography ($SiO_2$, DCM:EtOAc=10:1-3:1) to afford tert-butyl 2-[1-[4-[(2,6-dioxo-3-piperidyl)amino]-2-fluoro-5-methoxy-phenyl]-4-hydroxy-4-piperidyl]acetate (6, 266 mg, 570.84 μmol, 55% yield) as black solid. LCMS ($ES^+$): 466.2 $[M+H]^+$ Step 5: To a solution of tert-butyl 2-[1-[4-[(2,6-dioxo-3-piperidyl)amino]-2-fluoro-5-methoxy-phenyl]-4-hydroxy-4-piperidyl]acetate (6, 112 mg, 240.59 μmol) in DCM (1 mL) was added hydrochloric acid (12 M, 200.50 μL). The mixture was stirred at 25° C. for 1 h. The reaction was concentrated under reduced pressure to get 2-[1-[4-[(2,6-dioxo-3-piperidyl)amino]-2-fluoro-5-methoxy-phenyl]-4-hydroxy-4-piperidyl]acetic acid (7, 107 mg, 230.38 μmol, 96% yield, HCl salt) as white solid, which was used without further purification. LCMS ($ES^+$): 410.3 $[M+H]^+$

Example 13: Synthesis of 2-[1-[3-(2,4-dioxohexahydropyrimidin-1-yl)-1-methyl-indazol-6-yl]-4-hydroxy-4-piperidyl]acetic acid

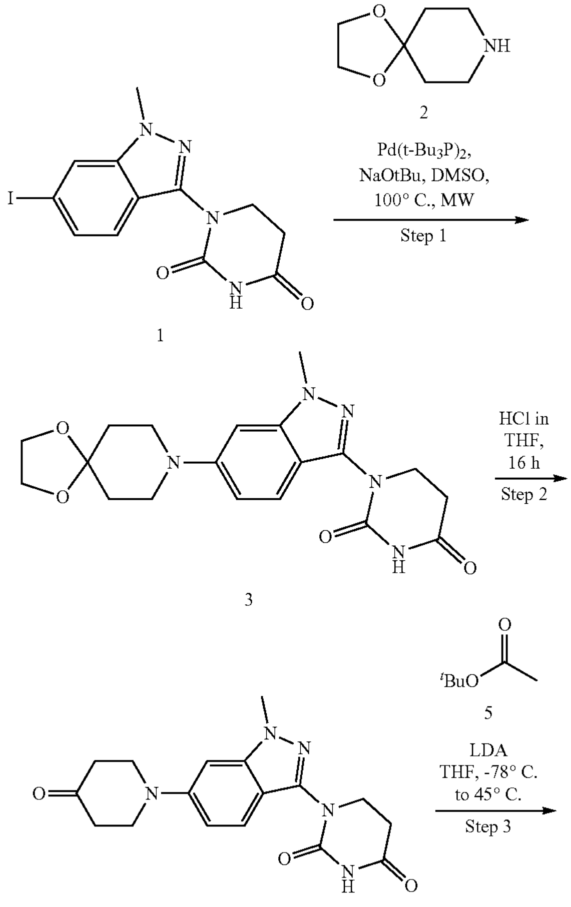

2

1

3

5

4

-continued

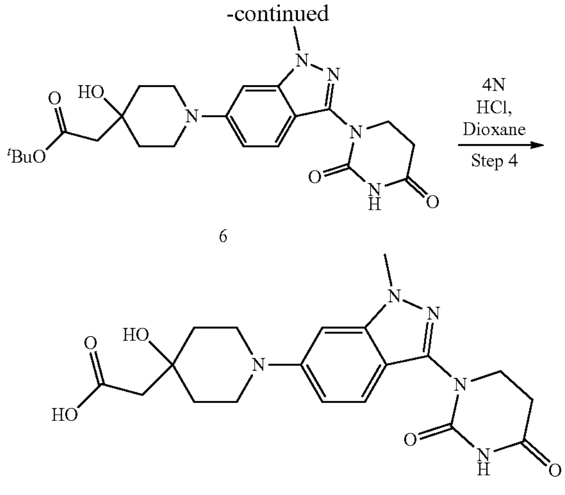

6

7

Step 1: To a solution of 1-(6-iodo-1-methyl-indazol-3-yl) hexahydropyrimidine-2,4-dione (1, 1.5 g, 4.05 mmol) in DMSO (15 mL) was added sodium tert-butoxide (467.33 mg, 4.86 mmol) and 1,4-dioxa-8-azaspiro[4.5]decane (2, 638.27 mg, 4.46 mmol, 569.88 μL) at room temperature under nitrogen. The reaction mixture was degassed with nitrogen for 5 min. Bis(tri-tert-butylphosphine)palladium(0) (414.20 mg, 810.49 μmol) was added, then the reaction mixture was stirred at 100° C. for 1 hour under microwave irradiation. The reaction mixture was diluted with water (50 mL), and the aqueous phase was extracted with ethyl acetate (2×50 mL). The combined organic layers were washed with brine solution (50 mL), and the organic layer was dried over sodium sulphate, filtered, and concentrated under reduced pressure. The crude residue thus obtained was purified by column chromatography on 60-120 silica gel using 3-4% of methanol in dichloromethane as eluent to afford 1-[6-(1,4-dioxa-8-azaspiro[4.5]decan-8-yl)-1-methyl-indazol-3-yl] hexahydropyrimidine-2,4-dione (3, 850 mg, 1.85 mmol, 46% yield) as pale brown semi-solid. LCMS (ESI+): 386.1 $[M+H]^+$.

Step 2: To a solution of 1-[6-(1,4-dioxa-8-azaspiro[4.5] decan-8-yl)-1-methyl-indazol-3-yl]hexahydropyrimidine-2, 4-dione (3, 850 mg, 2.21 mmol) in tetrahydrofuran (4 mL) was added hydrochloric acid (36% w/w aqueous solution, 6.40 g, 175.53 mmol, 8 mL) at room temperature under nitrogen. The reaction mixture was stirred at room temperature for 16 hours. Saturated aqueous sodium bicarbonate solution (50 mL) was added slowly to adjust the pH to 8.0, and the product was extracted using ethyl acetate (3×75 mL). The combined organic layers were dried over anhydrous sodium sulphate and concentrated under reduced pressure to yield crude product which was triturated with diethyl ether (15 mL) to afford 1-[1-methyl-6-(4-oxo-1-piperidyl)indazol-3-yl]hexahydropyrimidine-2,4-dione (4, 400 mg, 1.00 mmol, 45% yield) as brown solid. LCMS (ESI+): 342.1 $[M+H]^+$.

Step 3: To stirred solution of tert-butyl acetate (5, 503.61 mg, 4.34 mmol, 583.56 μL) in tetrahydrofuran (25 mL) was added (diisopropylamino)lithium (2 M solution, 2.17 mL) at −78° C. and stirred for 1 hour at the same temperature. The resultant solution was then added quickly using syringe to a solution of 1-[1-methyl-6-(4-oxo-1-piperidyl)indazol-3-yl] hexahydropyrimidine-2,4-dione (4, 370 mg, 1.08 mmol) in tetrahydrofuran (25 mL) at −78° C. The reaction mixture was slowly warmed to room temperature and stirred for 16 h at room temperature. The reaction was quenched using saturated aqueous ammonium chloride solution (50 mL), and the product was extracted using ethyl acetate (4×50 mL). The combined organic layers were dried over sodium sulphate and concentrated under reduced pressure get crude product which was purified by column chromatography on 60-120 silica gel using acetone and petroleum ether as eluents to afford tert-butyl 2-[1-[3-(2,4-dioxohexahydropyrimidin-1-yl)-1-methyl-indazol-6-yl]-4-hydroxy-4-piperidyl]acetate (6, 180 mg, 374.54 μmol, 35% yield) as pale brown solid. LCMS (ESI+): 458.0 $[M+H]^+$.

Step 4: To a stirred solution of tert-butyl 2-[1-[3-(2,4-dioxohexahydropyrimidin-1-yl)-1-methyl-indazol-6-yl]-4-hydroxy-4-piperidyl]acetate (6, 180 mg, 393.42 μmol) in 1,4-dioxane (0.2 mL) was added hydrogen chloride solution (4.0M in 1,4-dioxane, 4.00 g, 109.71 mmol, 5 mL) at 0-5° C. The reaction mixture was stirred at room temperature for 16 hours. The solvent was removed by concentrating the reaction mixture under reduced pressure to afford 2-[1-[3-(2,4-dioxohexahydropyrimidin-1-yl)-1-methyl-indazol-6-yl]-4-hydroxy-4-piperidyl]acetic acid (7, 145 mg, 307.63 μmol, 78% yield, hydrochloric acid salt) as pale yellow solid which was used in the next step without further purification. LCMS (ESI+): 402.2 $[M+H]^+$.

Example 14: Synthesis of 2-[3-[4-[(2,6-dioxo-3-piperidyl)amino]-2-fluoro-phenyl]-8-azabicyclo[3.2.1]octan-8-yl]acetic acid

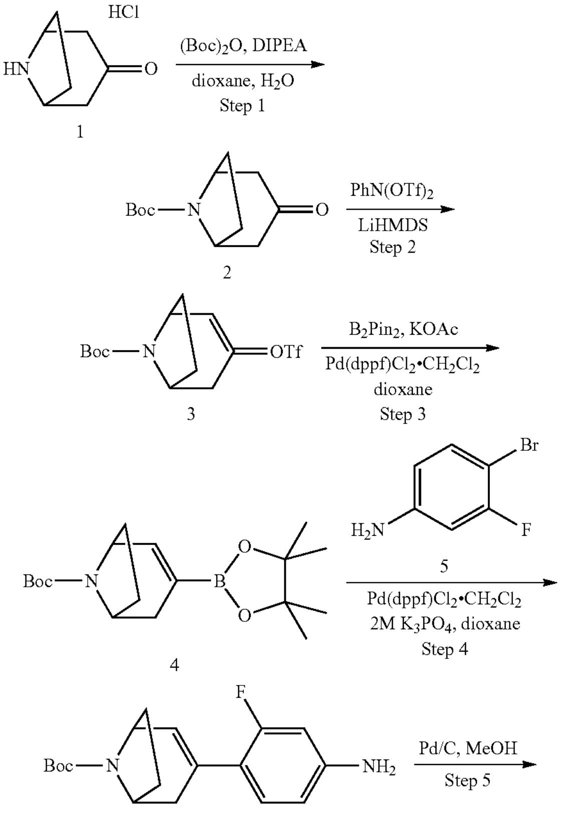

1

2

3

4

6

-continued

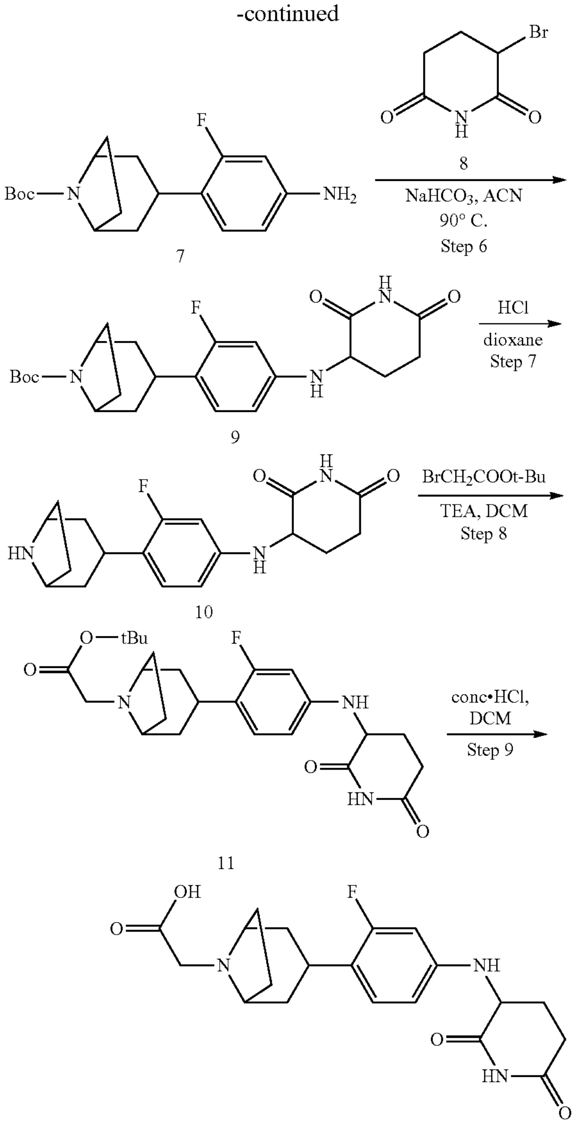

7

9

10

11

12

Step 1: To the reaction mixture of compound 1 (1, 1 g, 6.19 mmol, 021) and DIPEA (2.00 g, 15.47 mmol, 2.69 mL) in dioxane (20 mL) and Water (5 mL) was added tert-butoxycarbonyl tert-butyl carbonate (2.03 g, 9.28 mmol, 2.13 mL). The reaction mixture was stirred at 25° C. for 12 h. The reaction mixture was poured into sat. $NH_4Cl$ (20 mL) and extracted with EtOAc (10 mL×2). The combined organic layer was washed with brine (20 mL), dried over $Na_2SO_4$, filtered and the filtrate was concentrated. The residue was purified by column chromatography ($SiO_2$, Pet ether:EtOAc=50:1-10:1) to obtain tert-butyl 3-oxo-8-azabicyclo[3.2.1]octane-8-carboxylate (2, 1.3 g, 5.48 mmol, 89% yield) as a white solid. $^1H$ NMR (400 MHz, CDCl3-d): δ=4.64-4.33 (m, 2H), 2.80-2.54 (m, 2H), 2.38-2.28 (m, 2H), 2.15-2.03 (m, 2H), 1.72-1.61 (m, 2H), 1.50 (s, 9H).

Step 2: To a solution of tert-butyl 3-oxo-8-azabicyclo[3.2.1]octane-8-carboxylate (2, 1.3 g, 5.77 mmol) in THF (25 mL) was added lithium bis(trimethylsilyl)azanide (1 M, 6.92 mL) via dropwise addition under $N_2$ at −50° C. and the solution was warmed to −30° C. and stirred for 1 h. [N-(trifluoromethylsulfonyloxy)anilino] trifluoromethanesulfonate (2.70 g, 6.92 mmol) in THF (2 mL) was added at −30° C. via dropwise addition and the resulting mixture was warmed to 25° C. and stirred for another 4 h. The reaction mixture was poured into sat. $NH_4Cl$ (5 mL) and extracted with EtOAc (2 mL×3). The combined organic layer was washed with brine (5 mL), dried over $Na_2SO_4$, filtered and the filtrate was concentrated. The residue was purified by column chromatography ($SiO_2$, Pet ether:EtOAc=1:0-10:1) to obtain tert-butyl 3-(trifluoromethylsulfonyloxy)-8-azabicyclo[3.2.1]oct-3-ene-8-carboxylate (3, 1.4 g, 3.53 mmol, 61% yield) as a white solid. LCMS ($ES^+$): 301.9 $[M+H]^+$ Step 3: The solution of tert-butyl 3-(trifluoromethylsulfonyloxy)-8-azabicyclo[3.2.1]oct-3-ene-8-carboxylate (3, 1.4 g, 3.92 mmol) and 4,4,5,5-tetramethyl-2-(4,4,5,5-tetramethyl-1,3,2-dioxaborolan-2-yl)-1,3,2-dioxaborolane (1.99 g, 7.84 mmol) in dioxane (20 mL) was added cyclopentyl (diphenyl)phosphane;dichloromethane dichloropalladium iron (159.97 mg, 195.89 μmol) and potassium acetate (769.00 mg, 7.84 mmol). The reaction mixture was stirred at 90° C. for 12 h under $N_2$. The reaction mixture was diluted with EtOAc (50 mL) and filtered through a pad of Celite, washing with EtOAc (50 mL). The filtrate was washed with water (50 mL) and the organic layer was evaporated under reduced pressure to get crude. The residue was purified by column chromatography (SiO2, Pet ether:EtOAc=1:0-10:1) to obtain 3-(4,4,5,5-tetramethyl-1,3,2-dioxaborolan-2-yl)-8-azabicyclo[3.2.1]oct-3-ene-8-carboxylate (4, 1.2 g, 3.22 mmol, 82% yield) as a white solid. LCMS ($ES^+$): 280.0 $[M+H-tBu]^+$ Step 4: To a solution of 3-(4,4,5,5-tetramethyl-1,3,2-dioxaborolan-2-yl)-8-azabicyclo[3.2.1]oct-3-ene-8-carboxylate (4, 500 mg, 1.49 mmol), 4-bromo-3-fluoro-aniline (5, 283.39 mg, 1.49 mmol) and tripotassium;phosphate (2 M, 1.49 mL) in dioxane (7 mL) was added cyclopentyl (diphenyl) phosphane dichloromethane dichloropalladium iron (121.80 mg, 149.14 μmol) under $N_2$ atmosphere. After addition, the solution was stirred at 70° C. for 12 hr. The reaction solution was poured into water (30 mL). The aqueous solution was extracted with EtOAc (10 mL×2), the combined organic layer was washed with brine (20 mL×2), dried over $Na_2SO_4$ and concentrated in vacuum. The residue was purified by column chromatography ($SiO_2$, Pet ether: EtOAc=1:0-3:1) to obtain tert-butyl 3-(4-amino-2-fluoro-phenyl)-8-azabicyclo[3.2.1]oct-3-ene-8-carboxylate (6, 350 mg, 1.09 mmol, 73% yield) as a gray solid. LCMS ($ES^+$): 319.1 $[M+H]^+$ Step 5: To the mixture of tert-butyl 3-(4-amino-2-fluoro-phenyl)-8-azabicyclo[3.2.1]oct-3-ene-8-carboxylate (6, 350 mg, 1.10 mmol) in MeOH (5 mL) was added 10 wt. % Pd/C (50 mg, 1.10 mmol) under $N_2$. The suspension was degassed under vacuum and purged with $H_2$ (3 times). The reaction mixture kept stirred under $H_2$ (15 psi) at 25° C. for 14 h. The reaction mixture was filtered and the filtrate was concentrated to obtain tert-butyl 3-(4-amino-2-fluoro-phenyl)-8-azabicyclo[3.2.1]octane-8-carboxylate (7, 300 mg, 827.71 μmol, 75% yield) as a white solid. LCMS ($ES^+$): 321.1 $[M+H]^+$ Step 6: The mixture of tert-butyl 3-(4-amino-2-fluoro-phenyl)-8-azabicyclo[3.2.1]octane-8-carboxylate (7, 300 mg, 936.33 μmol), 3-bromopiperidine-2,6-dione (8, 269.68 mg, 1.40 mmol), tetrabutylammonium iodide (34.58 mg, 93.63 μmol) and sodium hydrogen carbonate (157.32 mg, 1.87 mmol, 72.83 μL) in MeCN (1 mL) was stirred at 90° C. for 14 h. The reaction mixture was poured into water (5 mL) and extracted with EtOAc (2 mL×3). The combined organic layer was washed with brine (5 mL), dried over $Na_2SO_4$, filtered and the filtrate was concentrated. The residue was purified by column chromatography (SiO2, Pet ether: EtOAc=10:1-1:1) to obtain 3-[4-[(2,6-dioxo-3-piperidyl) amino]-2-fluoro-phenyl]-8-azabicyclo[3.2.1]octane-8-carboxylate (9, 240 mg, 521.72 μmol, 56% yield) as a gray solid. LCMS ($ES^+$): 321.1 $[M+H]^+$.

Step 7: The mixture of 3-[4-[(2,6-dioxo-3-piperidyl) amino]-2-fluoro-phenyl]-8-azabicyclo[3.2.1]octane-8-carboxylate (9, 240 mg, 556.20 μmol) in HCl/dioxane (4 M, 3 mL) was stirred at 25° C. for 14 h. The reaction mixture was concentrated under vacuum to obtain 3-[4-(8-azabicyclo [3.2.1]octan-3-yl)-3-fluoro-anilino]piperidine-2,6-dione (10, 200 mg, 538.27 μmol, 97% yield, HCl salt) as a gray solid. LCMS ($ES^+$): 321.1 $[M+H]^+$.

Step 8: The mixture of 3-[4-(8-azabicyclo[3.2.1]octan-3-yl)-3-fluoro-anilino]piperidine-2,6-dione (390 mg, 1.06 mmol, 021), tert-butyl 2-bromoacetate (10, 206.80 mg, 1.06 mmol, 155.49 μL) and DIPEA (411.08 mg, 3.18 mmol, 554.02 μL) in MeCN (5 mL) was stirred at 25° C. for 14 h. The reaction mixture was concentrated under vacuum. The residue was purified by column chromatography (SiO2, Pet ether:EtOAc=10:1-1:1) to obtain tert-butyl 2-[3-[4-[(2,6-dioxo-3-piperidyl)amino]-2-fluoro-phenyl]-8-azabicyclo [3.2.1]octan-8-yl]acetate (11, 287 mg, 630.01 μmol, 59% yield) as a light yellow solid. LCMS ($ES^+$): 446.1 $[M+H]^+$ Step 9: To the mixture of tert-butyl 2-[3-[4-[(2,6-dioxo-3-piperidyl)amino]-2-fluoro-phenyl]-8-azabicyclo [3.2.1] octan-8-yl]acetate (11, 190 mg, 426.46 μmol) in DCM (2 mL) was added Chlorine (12 M, 355.39 μL). Then the mixture was stirred at 25° C. for 1 h. The reaction mixture was concentrated under vacuum, then azeotroped with toluene (5 mL×2) and then with toluene/THF (5 mL: 5 mL). The residue was diluted with EtOAc (10 mL), and the mixture was stirred at 25° C. for 12 h. The reaction was filtered and collected the filtered cake to obtain 2-[3-[4-[(2,6-dioxo-3-piperidyl)amino]-2-fluoro-phenyl]-8-azabicyclo[3.2.1]octan-8-yl]acetic acid (12, 166 mg, 350.80 μmol, 82% yield, HCl salt) as a gray solid. LCMS ($ES^+$): 390.0 $[M+H]^+$. $^1H$ NMR (400 MHz, $D_2O$-d6): δ=7.42-7.13 (m, 1H), 6.72-6.61 (m, 2H), 4.46-4.37 (m, 1H), 4.14-4.00 (m, 2H), 3.92-3.82 (m, 2H), 3.43-3.32 (m, 1H), 2.79-2.73 (m, 2H), 2.53 (br s, 2H), 2.34-2.25 (m, 2H), 2.22-2.11 (m, 3H), 2.03-1.93 (m, 3H).

Example 15: Synthesis of 2-[3-[4-[(2,6-dioxo-3-piperidyl)amino]-2-fluoro-phenyl]azetidin-1-yl]acetic acid

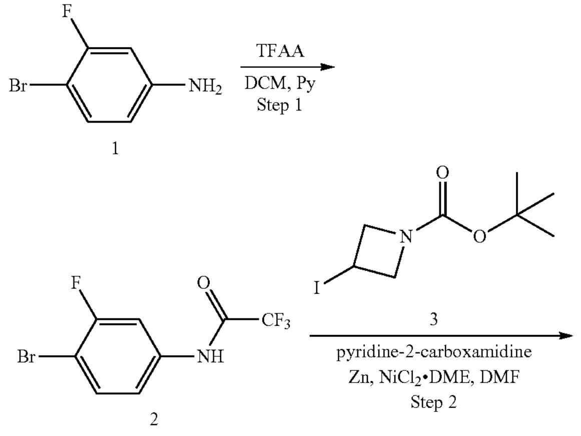

-continued

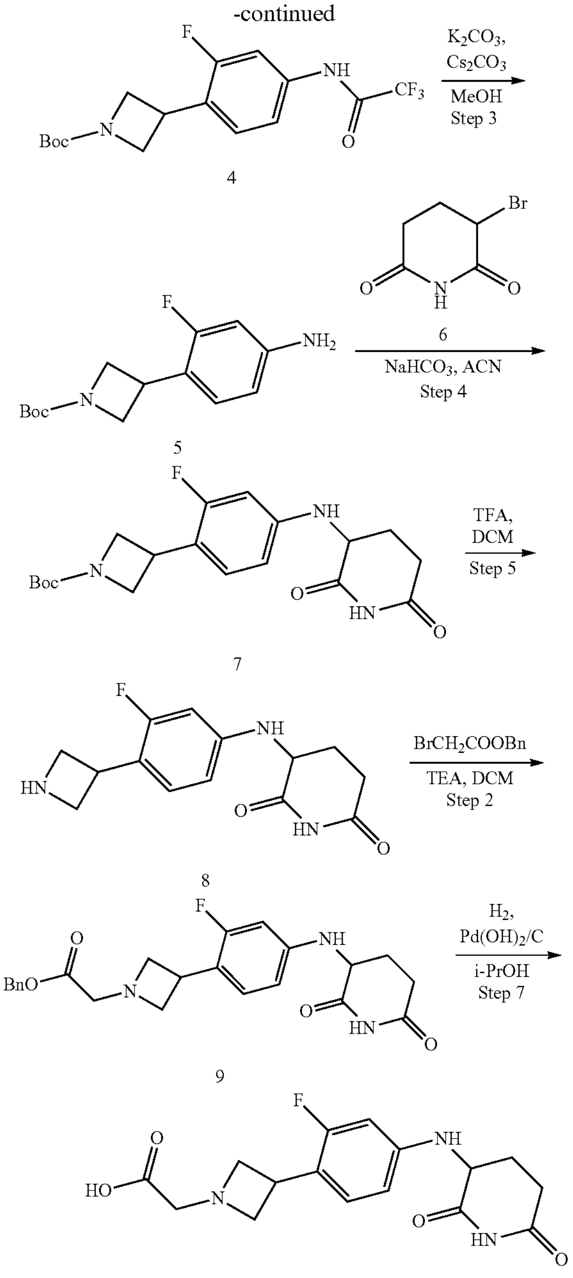

Step 1: To a solution of 4-bromo-3-fluoro-aniline (1, 5 g, 26.31 mmol), TEA (5.33 g, 52.63 mmol, 7.34 mL) in DCM (20 mL) was added (2,2,2-trifluoroacetyl) 2,2,2-trifluoroacetate (6.63 g, 31.58 mmol, 4.45 mL) at 10° C., then the mixture was stirred at 20° C. under $N_2$ for 12 h. The reaction mixture was poured into water (100 mL) and extracted with EtOAc (150 mL×3). The combined organic layer was washed with brine (50 mL), dried over $Na_2SO_4$, filtered and concentrated. The residue was purified by column chromatography ($SiO_2$, Pet ether:EtOAc=1:0-25:1-10:1) to get N-(4-bromo-3-fluoro-phenyl)-2,2,2-trifluoro-acetamide (2, 6.2 g, 20.81 mmol, 79% yield) as yellow solid. LCMS ($ES^+$): 288.0&286.0 $[M+H]^+$ Step 2: A solution of N-(4-bromo-3-fluoro-phenyl)-2,2,2-trifluoro-acetamide (2, 3 g, 10.49 mmol), tert-butyl 3-iodo-azetidine-1-carboxylate (3, 3.27 g, 11.54 mmol), Zinc (4 g, 61.17 mmol), Nickel(II) chloride ethylene glycol dimethyl ether (460.92 mg, 2.10 mmol) and pyridine-2-carboxamidine hydrochloride (330.61 mg, 2.10 mmol) in DMAC (30 mL) was stirred at 100° C. under $N_2$ for 4 h. The reaction was filtered and filtrated was poured into water (200 mL) and extracted with EtOAc (150 mL×5). The combined organic layer was washed with brine (150 mL), dried over $Na_2SO_4$, filtered and concentrated. The residue was purified by column chromatography (SiO2, Pet ether EtOAc=20:1-5:1-2:1) to get tert-butyl 3-[2-fluoro-4-[(2,2,2-trifluoroacetyl)amino]phenyl]azetidine-1-carboxylate (4, 2.2 g, 5.71 mmol, 54% yield) as yellow solid. LCMS ($ES^+$): 307.0 $[M+H-tBu]^+$ Step 3: A solution of tert-butyl 3-[2-fluoro-4-[(2,2,2-trifluoroacetyl)amino]phenyl]azetidine-1-carboxylate (4, 2 g, 5.52 mmol), $K_2CO_3$ (2.29 g, 16.56 mmol) and $Cs_2CO_3$ (1.80 g, 5.52 mmol) in MeOH (3 mL) was stirred at 60° C. under $N_2$ for 12 h. The reaction mixture was poured into water (100 mL) and extracted with EtOAc (150 mL×3). The combined organic layer was washed with brine (50 mL), dried over $Na_2SO_4$, filtered and concentrated. The residue was purified by column chromatography ($SiO_2$, Pet ether: EtOAc=1:0-3:1-2:1) to get tert-butyl 3-(4-amino-2-fluorophenyl)azetidine-1-carboxylate (5, 1.5 g, 5.18 mmol, 94% yield) as yellow solid. LCMS ($ES^+$): 201.1 $[M+H-tBu]^+$ Step 4: A solution of tert-butyl 3-(4-amino-2-fluoro-phenyl)azetidine-1-carboxylate (5, 1.5 g, 5.63 mmol), 3-bromopiperidine-2,6-dione (6, 1.62 g, 8.45 mmol) and $NaHCO_3$ (1.42 g, 16.90 mmol) in $CH_3CN$ (10 mL) was stirred at 90° C. under $N_2$ for 24 h. The reaction was filtered, and the solid was washed by water (20 mL) to get the crude product. The crude was purified by column chromatography ($SiO_2$, DCM: EtOAc=1:0-2:1-1:1) to get tert-butyl 3-(4-((2,6-dioxopiperidin-3-yl)amino)-2-fluorophenyl)azetidine-1-carboxylate (7, 860 mg, 2.28 mmol, 40% yield) as blue solid. LCMS ($ES^+$): 322.1 $[M+H-tBu]^+$ Step 5: A solution of tert-butyl 3-[4-[(2,6-dioxo-3-piperidyl)amino]-2-fluoro-phenyl]azetidine-1-carboxylate (7, 860 mg, 2.28 mmol) and TFA (55.81 mmol, 4.30 mL) in DCM (10 mL) was stirred at 20° C. under $N_2$ for 4 h. The reaction was concentrated under reduced pressure to get 3-[4-(azetidin-3-yl)-3-fluoro-anilino]piperidine-2,6-dione (8, 810 mg, 1.45 mmol, 64% yield, TFA salt) as blue solid, which was used without purification. LCMS ($ES^+$): 278.0 $[M+H]^+$ Step 6: To a solution of 3-[4-(azetidin-3-yl)-3-fluoro-anilino]piperidine-2,6-dione (8, 810 mg, 2.58 mmol, HCl salt) and TEA (12.91 mmol, 1.80 mL) in DCM (20 mL) was added benzyl 2-bromoacetate (768.79 mg, 3.36 mmol, 526.57 μL) at 20° C. before stirring under $N_2$ for 4 h. The reaction mixture was poured into water (100 mL) and extracted with EtOAc (150 mL×3). The combined organic layer was washed with brine (50 mL), dried over $Na_2SO_4$, filtered and concentrated The residue was purified by column chromatography ($SiO_2$, Pet ether:EtOAc=1:0-2:1-1:1) to get benzyl 2-[3-[4-[(2,6-dioxo-3-piperidyl)amino]-2-fluoro-phenyl]azetidin-1-yl]acetate (9, 420 mg, 908.21 μmol, 35% yield) as blue solid. LCMS ($ES^+$): 426.0 $[M+H]^+$ Step 7: To the solution of benzyl 2-[3-[4-[(2,6-dioxo-3-piperidyl)amino]-2-fluoro-phenyl]azetidin-1-yl]acetate (9, 50 mg, 117.52 μmol) in EtOH (10 mL) was added $Pd(OH)_2/C$ (12 mg, 117.52 μmol) under $N_2$. The suspension was degassed under vacuum and purged with $H_2$ (3 times). Then the mixture was stirred at 20° C. under $H_2$ for 4 h. The reaction was filtered and concentrated under vacuum to give 2-[3-[4-[(2,6-dioxo-3-piperidyl)amino]-2-fluoro-phenyl]azetidin-1-yl]acetic acid (10, 30 mg, 89.46 μmol, 76% yield) as blue solid, which was used without purification. LCMS ($ES^+$): 336.0 $[M+H]^+$. $^1H$ NMR (400 MHz, DMSO-$d_6$) δ=10.80 (s, 1H), 7.41-7.32 (m, 1H), 7.24-7.17 (m, 1H), 6.56-6.44 (m, 2H), 6.20 (d, J=8.0 Hz, 1H), 4.41-4.29 (m, 1H), 4.22-4.08 (m, 2H), 4.06-3.97 (m, 1H), 3.91-3.83 (m, 2H), 3.67 (br s, 2H), 2.83-2.65 (m, 2H), 2.12-2.05 (m, 1H), 1.94-1.83 (m, 1H)

Example 16: Synthesis of 2-(4'-((2,6-dioxopiperidin-3-yl)amino)-2'-fluoro-[1,1'-biphenyl]-4-yl)acetic acid

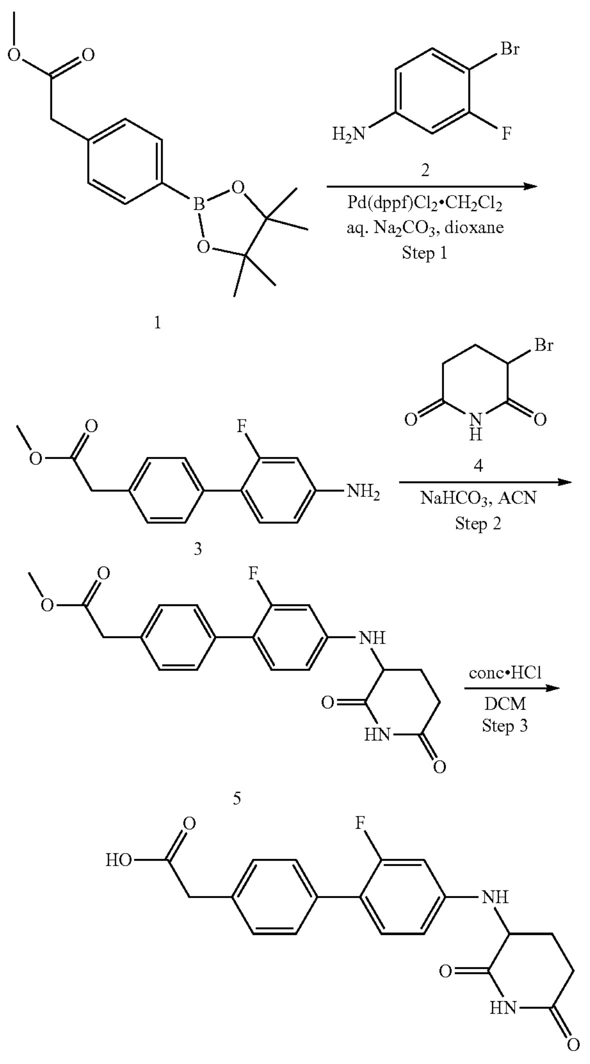

6

Step 1: To a solution of methyl 2-(4-(4,4,5,5-tetramethyl-1,3,2-dioxaborolan-2-yl)phenyl)acetate (1, 500 mg, 1.81 mmol), 4-bromo-3-fluoroaniline (2, 344.06 mg, 1.81 mmol) and $Pd(dppf)Cl_2$ (147.87 mg, 181.07 μmol) in dioxane (7 mL) was added KOAc (2 M, 1.81 mL) under $N_2$ atmosphere. After addition, the solution was stirred at 70° C. for 12 hr. The reaction solution was poured into water (30 mL). The aqueous solution was extracted with EtOAc (30 mL×3). The combined organic layer was washed with brine (50 mL×2), dried over $Na_2SO_4$, and concentrated in vacuum. The residue was purified by flash silica gel chromatography (20 g, Silica Flash Column, Eluent of 40%-50%, EtOAc/Pet ether, 30 mL/min) to afford methyl 2-(4'-amino-2'-fluoro-[1,1'-biphenyl]-4-yl)acetate (3, 426 mg, 1.48 mmol, 82% yield) as white solid. $^1$H NMR (400 MHz, CHLOROFORM-d) δ=7.42-7.35 (m, 2H), 7.27-7.21 (m, 2H), 7.13 (t, J=8.8 Hz, 1H), 6.43 (dd, J=2.4, 8.3 Hz, 1H), 6.38 (dd, J=2.4, 12.5 Hz, 1H), 3.63 (s, 3H), 3.58 (s, 2H)

Step 2: To a solution of methyl 2-(4'-amino-2'-fluoro-[1,1'-biphenyl]-4-yl)acetate (3, 500 mg, 1.93 mmol), 3-bromopiperidine-2,6-dione (4, 555.42 mg, 2.89 mmol) and TBAI (142.46 mg, 385.69 μmol) in MeCN (0.4 mL) was added $NaHCO_3$ (324.01 mg, 3.86 mmol). After addition, the solution was stirred at 90° C. for 12 hr. The reaction solution was poured into water (5 mL). The aqueous solution was extracted with EtOAc (5 mL×3), the combined organic layer was washed with brine (10 mL×2) dried over $Na_2SO_4$ and concentrated in vacuum. The residue was purified by flash silica gel chromatography (12 g Silica Flash Column, Eluent of 40%-50% EtOAc/Pet ether, 20 mL/min) to afford methyl 2-(4'-((2,6-dioxopiperidin-3-yl)amino)-2'-fluoro-[1,1'-biphenyl]-4-yl)acetate (5, 512 mg, 1.24 mmol, 65% yield) as white solid. LCMS ($ES^+$): 371.2 $[M+H]^+$ Step 3: To a solution of methyl 2-(4'-((2,6-dioxopiperidin-3-yl)amino)-2'-fluoro-[1,1'-biphenyl]-4-yl)acetate (5, 481 mg, 1.30 mmol) in DCM (2 mL) was added conc.HCl (12 M, 9.62 mL). After addition, the solution was stirred at 30° C. for 1 hr. The reaction solution was poured into water to give a suspension. Then the suspension was filtered, the filter cake was washed with water (2 mL) and concentrated in vacuum to afford 2-(4'-((2,6-dioxopiperidin-3-yl)amino)-2'-fluoro-[1,1'-biphenyl]-4-yl)acetic acid (6, 406 mg, 1.08 mmol, 83% yield) as white solid. $^1$H NMR (400 MHz, CHLOROFORM-d) δ=12.96-11.85 (m, 1H), 10.84 (s, 1H), 7.40 (br d, J=7.3 Hz, 2H), 7.33-7.19 (m, 3H), 6.66-6.54 (m, 2H), 6.35 (br d, J=1.8 Hz, 1H), 4.54-4.30 (m, 1H), 3.59 (s, 2H), 2.84-2.71 (m, 1H), 2.60 (br d, J=17.6 Hz, 1H), 2.20-2.07 (m, 1H), 2.00-1.83 (m, 1H).

Example 17: Synthesis of 2-[4-[1-(2,6-dioxo-3-piperidyl) indolin-5-yl]-1-piperidyl]acetic acid

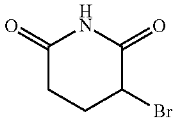
2
NaH, THF, 60° C.
Step 1

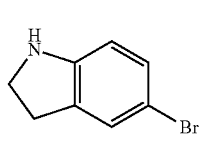
1

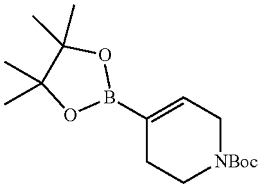
4

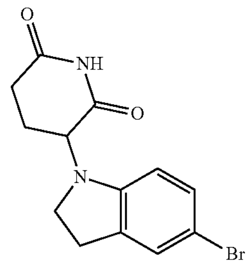
3

CsF, Pdcl2(dppf)•dcm,
DMF, 90° C., 16 h
Step 2

-continued

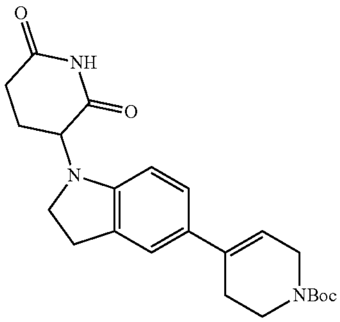
5

H2, Pd(OH)2,
1,4-dioxane, rt, 16 h
Step 3

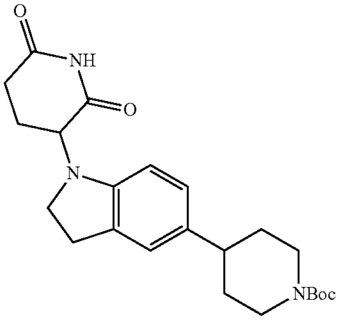
6

TFA, DCM,
rt, 2 h
Step 4

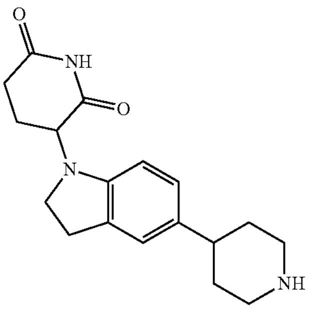
7

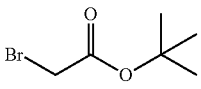
8

DIPEA, DMF, 0° C.,
20 min
Step 5

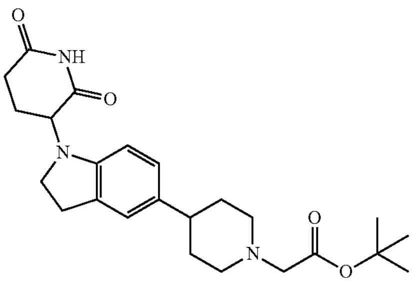
9

TFA, DCM,
rt, 2 h
Step 6

-continued

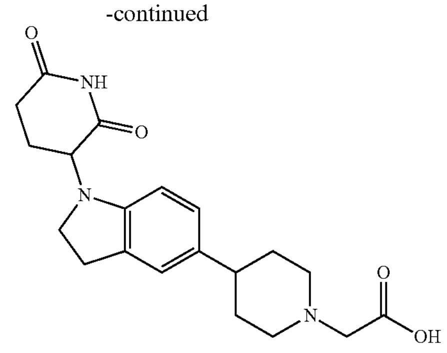

10

Step 1: A well-stirred solution of 5-bromoindoline (1, 1.0 g, 5.05 mmol) in anhydrous THF (100 mL) was treated with Sodium hydride (60% dispersion in mineral oil) (1.93 g, 50.49 mmol) at 0° C. under inert atmosphere. The reaction mixture was stirred for 1 h at rt. 3-bromopiperidine-2,6-dione (2, 3.03 g, 15.15 mmol) in THF (8 mL) was added to the reaction mixture and stirred for 16 h at 60° C. The reaction was quenched with $NH_4Cl$ solution (15 mL) at 0° C. and extracted with Ethyl Acetate (2×150 mL). Combined organic layer was concentrated and purified by column chromatography (230-400 silica gel) with 50-60% Ethyl Acetate in Pet ether to afford 3-(5-bromoindolin-1-yl)piperidine-2,6-dione (3, 550 mg, 1.60 mmol, 32% yield) as a pale yellow solid. LCMS ($ES^+$): 311.0 $[M+H]^+$ Step 2: Into a 25 mL pressure tube containing a well-stirred solution of 3-(5-bromoindolin-1-yl) piperidine-2,6-dione (3, 300 mg, 834.52 mol) and tert-butyl 4-(4,4,5,5-tetramethyl-1,3,2-dioxaborolan-2-yl)-3,6-dihydro-2H-pyridine-1-carboxylate (4, 516.08 mg, 1.67 mmol) in DMF (5 mL) was added cesium fluoride (316.92 mg, 2.09 mmol) and $Pd(dppf)Cl_2 \cdot CH_2Cl_2$ (204.45 mg, 250.36 mol). The reaction mixture was degassed by bubbling nitrogen gas for 10 min. The mixture was then stirred at 90° C. for 16 h. The reaction mixture was filtered through Celite and washed with ethyl acetate (150 mL), and the filtrate was washed with water (100 mL) followed by brine (100 mL). The organic layer was dried over $Na_2SO_4$, filtered and concentrated and purified by flash silica gel column chromatography (70% EtOAc in pet ether) to afford tert-butyl 4-[1-(2,6-dioxo-3-piperidyl) indolin-5-yl]-3,6-dihydro-2H-pyridine-1-carboxylate (5, 130 mg, 301.77 mol, 36% yield) as a brown solid. LCMS ($ES^+$): 412.3 $[M+H]^+$ Step 3: Into a 50 mL single neck round bottom flask containing a well-stirred solution of tert-butyl 4-[1-(2,6-dioxo-3-piperidyl)indolin-5-yl]-3,6-dihydro-2H-pyridine-1-carboxylate (5, 130 mg, 302.40 mol) in 1,4-dioxane (1.5 mL) was added 20 wt. % Palladium hydroxide on carbon (106.17 mg, 151.20 mol). The suspension was stirred at room temperature for 16 h under hydrogen atmosphere. The reaction mixture was filtered through Celite, washed with 1,4-dioxane (150 mL) and concentrated under reduced pressure to afford tert-butyl 4-[1-(2,6-dioxo-3-piperidyl) indolin-5-yl] piperidine-1-carboxylate (6, 120 mg, 275.69 mol, 91% yield) as a brown solid. LCMS ($ES^+$): 358.2 $[M-tBu+H]^+$ Step 4: Into a 50 mL single neck round bottom flask containing a well-stirred solution of tert-butyl 4-[1-(2,6-dioxo-3-piperidyl)indolin-5-yl]piperidine-1-carboxylate (6, 120 mg, 275.69 mol) in DCM (2 mL) was added TFA (5.51 mmol, 424.80 μL) and the reaction mixture was stirred at room temperature for 2 h. After completion, the reaction mixture was concentrated to dryness and washed with MTBE (25 mL) to afford 3-[5-(4-piperidyl)indolin-1-yl] piperidine-2,6-dione (7, 120 mg, 255.69 mol, 93% yield, TFA salt) as a brown solid. LCMS ($ES^+$): 314.2 $[M+H]^+$ Step 5: Into a 20 mL vial containing a well-stirred solution of 3-[5-(4-piperidyl) indolin-1-yl]piperidine-2,6-dione (7, 120 mg, 255.49 mol, TFA salt) in DMF (1 mL) was added DIPEA (165.10 mg, 1.28 mmol, 222.51 μL) and tert-butyl bromoacetate (8, 39.87 mg, 204.39 mol, 29.98 L) at 0° C. After 30 min, the reaction was quenched with cold water at 0° C. and extracted with ethyl acetate (2×100 mL). The combined organic layer was dried over anhydrous $Na_2SO_4$, filtered and concentrated under reduced pressure to afford tert-butyl 2-[4-[1-(2,6-dioxo-3-piperidyl) indolin-5-yl]-1-piperidyl]acetate (9, 90 mg, 178.93 mol, 70% yield) as a brown solid. LCMS ($ES^+$): 428.2 $[M+H]^+$ Step 6: Into a 25 mL single neck round bottom flask containing a well-stirred solution of tert-butyl 2-[4-[1-(2,6-dioxo-3-piperidyl)indolin-5-yl]-1-piperidyl]acetate (9, 90 mg, 178.93 mol) in DCM (1.5 mL) was added TFA (408.05 mg, 3.58 mmol, 275.71 μL) and the reaction mixture was stirred at ambient temperature for 3 h. The reaction mixture was concentrated to dryness and washed with MTBE (50 mL) and purified by reverse phase prep HPLC [Purification method: Column: XSelect C18 (150×19) mm 5 micron; Mobile phase A: 0.1% TFA in water; Mobile phase B: MeCN] to afford 2-[4-[1-(2,6-dioxo-3-piperidyl) indolin-5-yl]-1-piperidyl]acetic acid (10, 90 mg, 174.95 μmol, 98% yield, TFA salt) as a brown sticky solid. LCMS ($ES^+$): $372.2[M+H]^+$. $^1$HNMR (400 MHz, DMSO-d6): δ 10.81 (s, 1H), 6.91 (s, 1H), 6.82 (d, J=8.00 Hz, 1H), 6.41 (d, J=8.40 Hz, 1H), 4.60-4.57 (m, 1H), 3.40-3.26 (m, 6H), 3.17 (s, 2H), 2.94-2.79 (m, 2H), 2.79-2.69 (m, 1H), 2.21-2.17 (m, 1H), 1.93-1.82 (m, 1H), 1.81-1.71 (m, 4H).

Example 18: Synthesis of 1-[7-fluoro-1-methyl-6-(4-piperidyl)indazol-3-yl]hexahydropyrimidine-2,4-dione

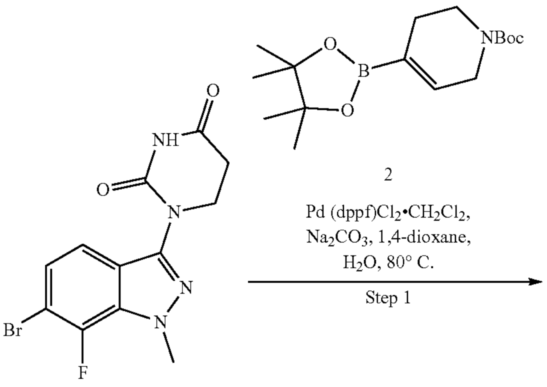

1

2

-continued

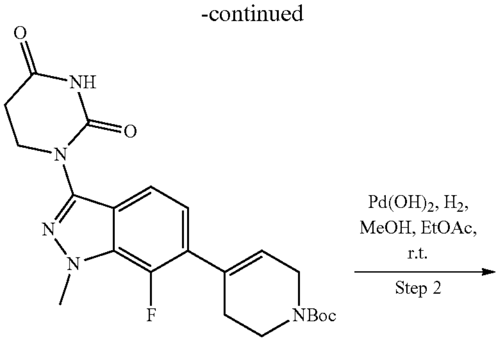

3

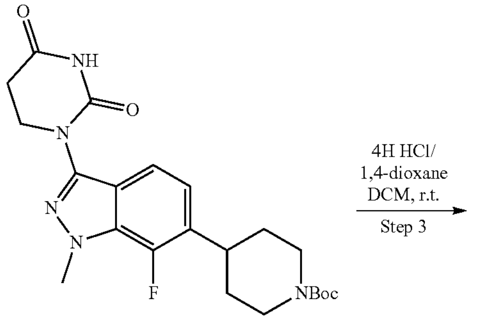

4

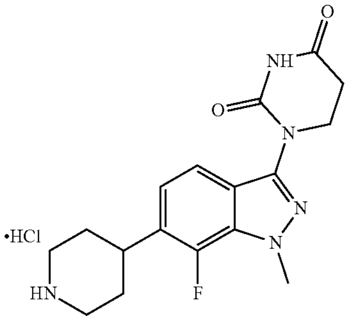

5

Step 1: Into a 25 mL sealed tube containing a well-stirred solution of 1-(6-bromo-7-fluoro-1-methyl-indazol-3-yl) hexahydropyrimidine-2,4-dione (1, 250 mg, 0.732 mmol) and tert-butyl 4-(4,4,5,5-tetramethyl-1,3,2-dioxaborolan-2-yl)-3,6-dihydro-2H-pyridine-1-carboxylate (2, 226.60 mg, 0.732 mmol) in 1,4-dioxane (5 mL) and water (1 mL) was added Sodium carbonate (233.02 mg, 2.20 mmol) and the mixture was degassed by bubbling nitrogen gas for 5 minutes. Subsequently, Pd(dppf)$Cl_2$·DCM (59.85 mg, 0.073 mmol) was added and the resulting mixture was stirred at 80° C. for 5 h. The mixture was filtered through a pad of Celite and the Celite bed was washed with EtOAc (15 mL). The filtrate was successively washed with water (10 mL) and brine (10 mL), dried (anhydrous $Na_2SO_4$), filtered and the filtrate was concentrated under reduced pressure to obtain tert-butyl 4-[3-(2,4-dioxohexahydropyrimidin-1-yl)-7-fluoro-1-methyl-indazol-6-yl]-3,6-dihydro-2H-pyridine-1-carboxylate (3, 300 mg, 0.514 mmol, 70% yield) as a light brown semi-solid. LCMS (ES$^+$): 444.6 [M+H]$^+$ Step 2: Into a 250 mL single-necked round-bottomed flask containing a well stirred solution of tert-butyl 4-[3-(2,4-dioxohexahydropyrimidin-1-yl)-7-fluoro-1-methyl-indazol-6-yl]-3,6-dihydro-2H-pyridine-1-carboxylate (3; 1.3 g, 2.58 mmol) in a mixture of EtOAc (75 mL) and MeOH (50 mL) was added Palladium hydroxide on carbon, 20 wt. % 50% water (700 mg) and the suspension was hydrogenated under a bladder pressure of hydrogen. The reaction stirred for 16 h. The reaction mixture was filtered through a pad of Celite, washing with EtOAc (100 mL) and MeOH (100 mL). Combined filtrate was concentrated under reduced pressure to afford tert-butyl 4-[3-(2,4-dioxohexahydropyrimidin-1-yl)-7-fluoro-1-methyl-indazol-6-yl]piperidine-1-carboxylate (4; 1.1 g, 2.43 mmol, 94% yield) as a light yellow solid. UPLC-MS (ES$^+$): 444.5 [M+H]$^+$ Step 3: Into a 10 mL single-necked round-bottomed flask containing a well stirred solution of tert-butyl 4-[3-(2,4-dioxohexahydropyrimidin-1-yl)-7-fluoro-1-methyl-indazol-6-yl]piperidine-1-carboxylate (4, 1.1 g, 2.43 mmol) in anhydrous DCM (20 mL) was added 4 M HCl in 1,4-dioxane (10 mL) dropwise at ambient temperature. The resulting mixture was stirred at ambient temperature for 3 h. Excess solvent was removed under reduced pressure to afford a crude residue. The crude mass was triturated with MTBE (25 mL) and the precipitate was filtered to obtain 1-[7-fluoro-1-methyl-6-(4-piperidyl)indazol-3-yl]hexahydropyrimidine-2,4-dione hydrochloride (5, 940 mg, 2.42 mmol, 99% yield) as an off-white solid. LCMS (ES$^+$): 346.5 [M+H]$^+$

Example 19: Synthesis of 1-[6-(3,3-difluoro-4-piperidyl)-5-fluoro-1-methyl-indazol-3-yl]hexahydropyrimidine-2,4-dione

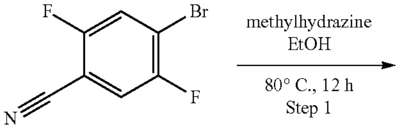

1

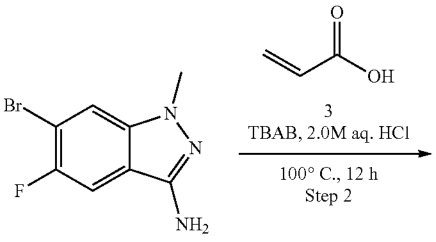

2

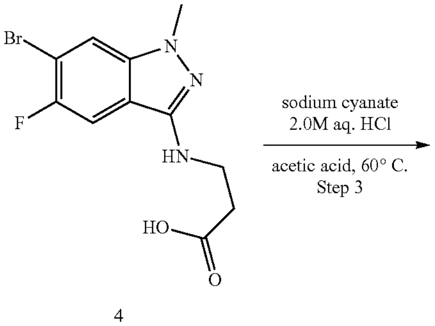

4

-continued

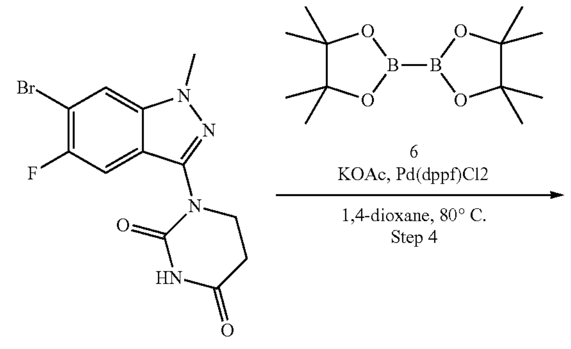

5

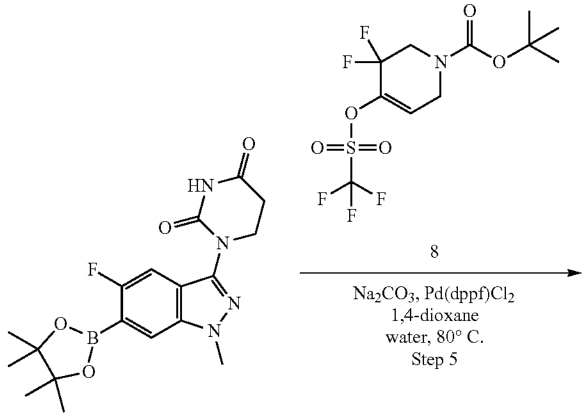

7

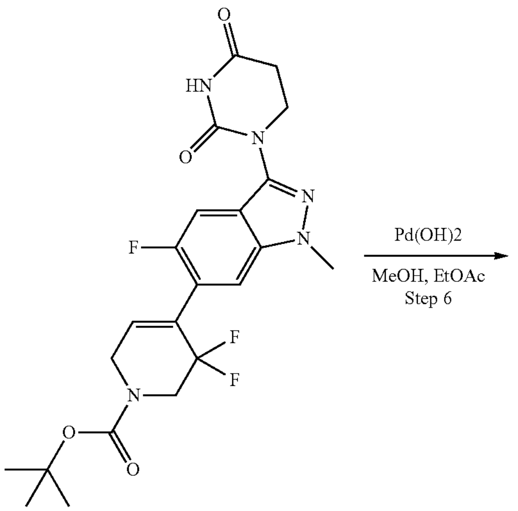

9

-continued

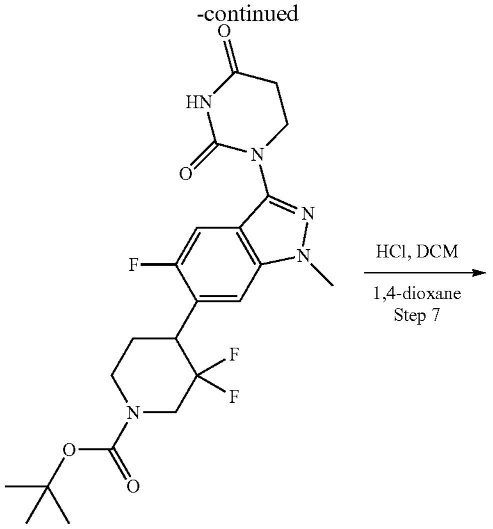

10

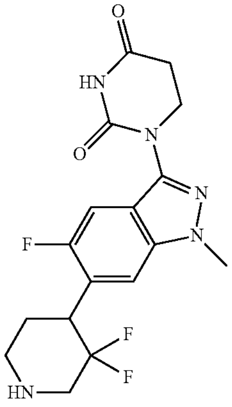

11

Step 1: To a solution of 4-bromo-2,5-difluoro-benzonitrile (1, 40 g, 183.49 mmol) in Ethanol (400 mL) was added methylhydrazine (40.42 g, 366.98 mmol, 40% purity). The mixture stirred at 80° C. for 12 h. After cooling, the reaction mixture was concentrated under reduced pressure. The residue was purified by column chromatography (SiO2, Petroleum ether/Ethyl acetate=20/1 to 1/1) to afford 6-bromo-5-fluoro-1-methyl-indazol-3-amine (2, 29 g, 118.82 mmol, 65% yield) as a white solid. $^1H$ NMR (400 MHz, DMSO-$d_6$) δ=7.82 (d, J=5.6 Hz, 1H), 7.63 (d, J=8.8 Hz, 1H), 5.52 (s, 2H), 3.72 (s, 3H).

Step 2: To a solution of 6-bromo-5-fluoro-1-methyl-indazol-3-amine (2, 22 g, 90.14 mmol) and acrylic acid (3, 9.74 g, 135.21 mmol, 9.28 mL) in 2 M aq. HCl (220 mL) was added tetrabutylammonium bromide (2.91 g, 9.01 mmol). The mixture was stirred at 100° C. for 12 h. The reaction mixture was made basic with saturated solution of $NaHCO_3$, to adjust pH=8. Then, the mixture was acidified with acetic acid, to adjust pH=5. A white precipitate formed, which was filtered and was washed with water (250 ml) to afford 3-[(6-bromo-5-fluoro-1-methyl-indazol-3-yl)amino]propanoic acid (4, 28 g, 88.57 mmol, 98% yield) as a white solid. LCMS ($ES^+$): 318.2 $[M+H]^+$ Step 3: To a solution of 3-[(6-bromo-5-fluoro-1-methyl-indazol-3-yl)amino]propanoic acid (4, 6 g, 18.98 mmol) in acetic acid (60 mL) was added Sodium cyanate (2.47 g, 37.96 mmol, 1.31 mL). The mixture was stirred at 60° C. for 14 h. Then, 2 M HCl in water (60 mL) was added, and the mixture was stirred at 60° C. for another 3 h. The reaction mixture was cooled to 20° C. A white solid precipitated, which was filtered and washed with water (100 ml) to afford 1-(6-bromo-5-fluoro-1-methyl-indazol-3-yl)hexahydropyrimidine-2,4-dione (5, 3.1 g, 9.09 mmol, 48% yield) as a white solid. $^1$H NMR (400 MHz, DMSO-$d_6$) δ=10.62 (s, 1H), 8.17 (d, J=5.6 Hz, 1H), 7.62 (d, J=9.2 Hz, 1H), 4.00 (s, 3H), 3.92 (t, J=6.8 Hz, 2H), 2.76 (t, J=6.8 Hz, 2H).

Step 4: Initially 1-(6-bromo-5-fluoro-1-methyl-indazol-3-yl)hexahydropyrimidine-2,4-dione (5, 826.39 mg, 2.42 mmol) and 4,4,5,5-tetramethyl-2-(4,4,5,5-tetramethyl-1,3,2-dioxaborolan-2-yl)-1,3,2-dioxaborolane (6, 676.67 mg, 2.66 mmol) were dissolved in 1,4-Dioxane (14.70 mL) along with potassium acetate (713.24 mg, 7.27 mmol) and [1,1'-Bis(diphenylphosphino)ferrocene]dichloropalladium(II), complex with dichloromethane (197.83 mg, 242.25 μmol). The mixture was heated to 90° C. for 16 h before being worked up using standard protocols to afford 1-[5-fluoro-1-methyl-6-(4,4,5,5-tetramethyl-1,3,2-dioxaborolan-2-yl)indazol-3-yl]hexahydropyrimidine-2,4-dione (7, 1.10 g, 2.40 mmol, 99% yield), which was carried forward without further purification. LCMS (ES$^+$): 389.5 [M+H]$^+$.

Step 5: To a solution of 1-[5-fluoro-1-methyl-6-(4,4,5,5-tetramethyl-1,3,2-dioxaborolan-2-yl)indazol-3-yl]hexahydropyrimidine-2,4-dione (7, 350 mg, 901.60 μmol) and tert-butyl 3,3-difluoro-4-(trifluoromethylsulfonyloxy)-2,6-dihydropyridine-1-carboxylate (8, 397.38 mg, 1.08 mmol) in dioxane (4.10 mL) and water (409.82 μL) was added cyclopentyl(diphenyl)phosphane;dichloropalladium;iron (65.97 mg, 90.16 μmol) and $Na_2CO_3$ (286.71 mg, 2.70 mmol). The mixture was stirred at 80° C. for 3 h under nitrogen atmosphere. Upon reaction completion, the mixture was quenched with water and extracted with EtOAc (×2) before being dried over sodium sulfate. The solution was concentrated, and the crude product was triturated with Ethyl acetate (30 ml) for 15 min to afford tert-butyl 4-[3-(2,4-dioxohexahydropyrimidin-1-yl)-5-fluoro-1-methyl-indazol-6-yl]-3,3-difluoro-2,6-dihydropyridine-1-carboxylate (9, 200 mg, 396.29 mol, 44% yield) as a yellow solid LCMS (ES$^+$): 444.2 [M+H]$^+$. $^1$H NMR (400 MHz, CDCl3) δ=7.74 (s, 1H), 7.40 (d, J=8.4 Hz, 1H), 7.03-6.96 (m, 1H), 5.97 (br, 1H), 4.19 (d, J=1.2 Hz, 3H), 4.15-4.08 (m, 4H), 3.67 (t, J=5.6 Hz, 2H), 2.91 (t, J=6.8 Hz, 2H), 2.57 (br, 2H), 1.53 (s, 9H).

Step 6: To a solution of tert-butyl 4-[3-(2,4-dioxohexahydropyrimidin-1-yl)-5-fluoro-1-methyl-indazol-6-yl]-3,3-difluoro-2,6-dihydropyridine-1-carboxylate (9, 180 mg, 375.43 mol) was added Palladium hydroxide on carbon, 20 wt. % 50% water (60 mg, 427.24 mol) under nitrogen. The suspension was degassed under vacuum. The mixture was stirred under pressure of 5 kgs at room temperature for 16 h. After completion, the reaction mixture was filtered through celite, washing with 10% MeOH in DCM (300 mL), and the filtrate was concentrated under reduced pressure to afford tert-butyl 4-[3-(2,4-dioxohexahydropyrimidin-1-yl)-5-fluoro-1-methyl-indazol-6-yl]-3,3-difluoro-piperidine-1-carboxylate (10, 170 mg, 340.62 mol, 91% yield) as off-white solid. LCMS (ES$^+$): 426.2 [M+H]$^+$.

Step 7: Into a 50 mL single neck round bottom flask containing a solution of tert-butyl 4-[3-(2,4-dioxohexahydropyrimidin-1-yl)-5-fluoro-1-methyl-indazol-6-yl]-3,3-difluoro-piperidine-1-carboxylate (10, 70 mg, 145.39 mol) in DCM (10 mL) was added Hydrogen chloride, 4 M in 1,4-dioxane, 99% (800.00 mg, 21.94 mmol, 1 mL) at 0° C., the resulting reaction mixture was stirred at room temperature for 1 hr. After completion, the reaction mixture was concentrated under vacuum and washed with diethyl ether to give product 1-[6-(3,3-difluoro-4-piperidyl)-5-fluoro-1-methyl-indazol-3-yl]hexahydropyrimidine-2,4-dione, hydrochloric acid salt (11, 60 mg, 119.77 mol, 82% yield) as off white solid. LCMS (ES$^+$): 382.2 [M+H]$^+$.

Example 20: Synthesis of 2-[1-[2-chloro-4-[(2,6-dioxo-3-piperidyl)amino]phenyl]-4-hydroxy-4-piperidyl]acetic acid

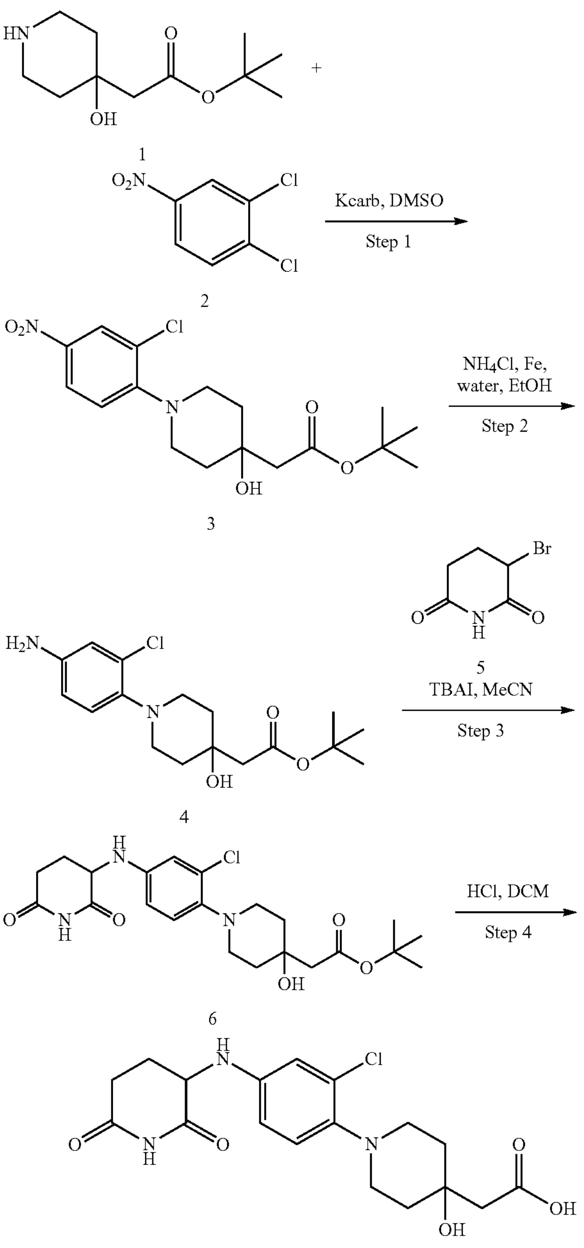

Step 1: To a solution of tert-butyl 2-(4-hydroxy-4-piperidyl)acetate (1, 6.17 g, 28.65 mmol) and 1,2-dichloro-4-nitro-benzene (2, 5 g, 26.04 mmol) in DMSO (50 mL) was added potassium carbonate (10.80 g, 78.13 mmol). The mixture was stirred at 110° C. for 1 hour. The reaction was cooled to 20° C. and poured into water (500 mL) and the mixture was extracted with EtOAc (200 mL×3). The combined organic phase was washed with brine (200×2 mL), dried with anhydrous sodium sulfate, filtered and concentrated in vacuo to afford tert-butyl 2-[1-(2-chloro-4-nitro-phenyl)-4-hydroxy-4-piperidyl]acetate (3, 9.4 g, 22.8 mmol, 88% yield). $^1$H NMR (400 MHz, DMSO-$d_6$) δ=8.20 (d, J=2.8 Hz, 1H), 8.12 (dd, J=2.8, 8.8 Hz, 1H), 7.28 (d, J=8.8 Hz, 1H), 4.65 (s, 1H), 3.29 (br d, J=12.0 Hz, 2H), 3.19-3.08 (m, 2H), 2.39 (s, 2H), 1.88-1.78 (m, 2H), 1.76-1.67 (m, 2H), 1.41 (s, 9H).

Step 2: A mixture of tert-butyl 2-[1-(2-chloro-4-nitro-phenyl)-4-hydroxy-4-piperidyl]acetate (3, 9.4 g, 25.35 mmol) in ethanol (190 mL) and water (38 mL) was added ammonium chloride (4.07 g, 76.05 mmol) and iron powder (4.25 g, 76.05 mmol). The reaction mixture was stirred at 90° C. for 16 hours. After completion, the reaction mixture was filtered to remove iron powder, and concentrated. It was then poured into water (400 mL) and the mixture was extracted with EtOAc (200 mL×3). The combined organic phase was washed with brine (200 mL×2), dried with anhydrous sodium sulfate, filtered, and concentrated in vacuo to give tert-butyl 2-[1-(4-amino-2-chloro-phenyl)-4-hydroxy-4-piperidyl]acetate (4, 8.64 g, 22.94 mmol, 90% yield). $^1$H NMR (400 MHz, DMSO-$d_6$) δ=6.88 (d, J=8.4 Hz, 1H), 6.61 (d, J=2.4 Hz, 1H), 6.47 (dd, J=2.4, 8.4 Hz, 1H), 4.96 (br s, 2H), 4.43 (s, 1H), 2.89-2.80 (m, 2H), 2.79-2.72 (m, 2H), 2.34 (s, 2H), 1.82-1.72 (m, 2H), 1.68-1.60 (m, 2H), 1.41 (s, 9H).

Step 3: To a stirred solution of tert-butyl 2-[1-(4-amino-2-chloro-phenyl)-4-hydroxy-4-piperidyl]acetate (4, 6.4 g, 18.78 mmol) in acetonitrile (100 mL) was added TBAI (13 g, 9.39 mmol) and $NaHCO_3$ (4.41 g, 56.33 mmol). After 5 minutes of stirring, 3-bromopiperidine-2,6-dione (5, 3.61 g, 18.78 mmol) was added at room temperature. After 10 minutes, the temperature of the reaction was raised to 90° C. and the reaction continued for 72 hours. The reaction mixture was concentrated under reduced pressure to remove solvent. The residue was diluted with water (400 mL) and extracted with EtOAc (150 mL×3). The combined organic layers were washed with brine (20 mL×2), dried over anhydrous sodium sulfate, filtered and concentrated under reduced pressure. The residue was purified by column chromatography (silica gel, petroleum ether/ethyl acetate=1:1) to give tert-butyl 2-[1-[2-chloro-4-[(2,6-dioxo-3-piperidyl)amino]phenyl]-4-hydroxy-4-piperidyl]acetatecarbamate (6, 4.0 g, 8.41 mmol, 45% yield) as a blue solid. $^1$H NMR (400 MHz, DMSO-$d_6$) δ=10.78 (s, 1H), 6.95 (d, J=8.8 Hz, 1H), 6.74 (d, J=2.4 Hz, 1H), 6.59 (dd, J=2.4, 8.8 Hz, 1H), 5.83 (d, J=8.0 Hz, 1H), 4.47 (s, 1H), 4.32-4.25 (m, 1H), 2.91-2.83 (m, 2H), 2.81-2.75 (m, 2H), 2.74-2.68 (m, 1H), 2.58 (t, J=4.0 Hz, 1H), 2.35 (s, 2H), 2.11-2.03 (m, 1H), 1.85 (dd, J=4.4, 12.0 Hz, 1H), 1.81-1.73 (m, 2H), 1.68-1.61 (m, 2H), 1.41 (s, 9H). LC-MS ($ES^+$): 452.2 $[M+H]^+$.

Step 4: Into a 25 mL single-neck round-bottom flask containing a well-stirred solution of tert-butyl 2-[1-[2-chloro-4-[(2,6-dioxo-3-piperidyl)amino]phenyl]-4-hydroxy-4-piperidyl]acetate (6, 150 mg, 331.90 μmol) in anhydrous DCM (2 mL) was added 4 M HCl in 1,4 dioxane (331.90 μmol, 3 mL) at ambient temperature under nitrogen atmosphere. The resulting mixture was stirred at rt for 16 hours. The reaction mixture was concentrated under reduced pressure to afford 2-[1-[2-chloro-4-[(2,6-dioxo-3-piperidyl)amino]phenyl]-4-hydroxy-4-piperidyl]acetic acid (7, 140 mg, 320.61 μmol, 97% yield, HCl salt) as an off-white solid. LC-MS ($ES^+$): 396.1 $[M+H]^+$.

Example 21: Synthesis of 2-[1-[4-[(2,6-dioxo-3-piperidyl)amino]-2-fluoro-phenyl]-4-hydroxy-4-piperidyl]acetic acid

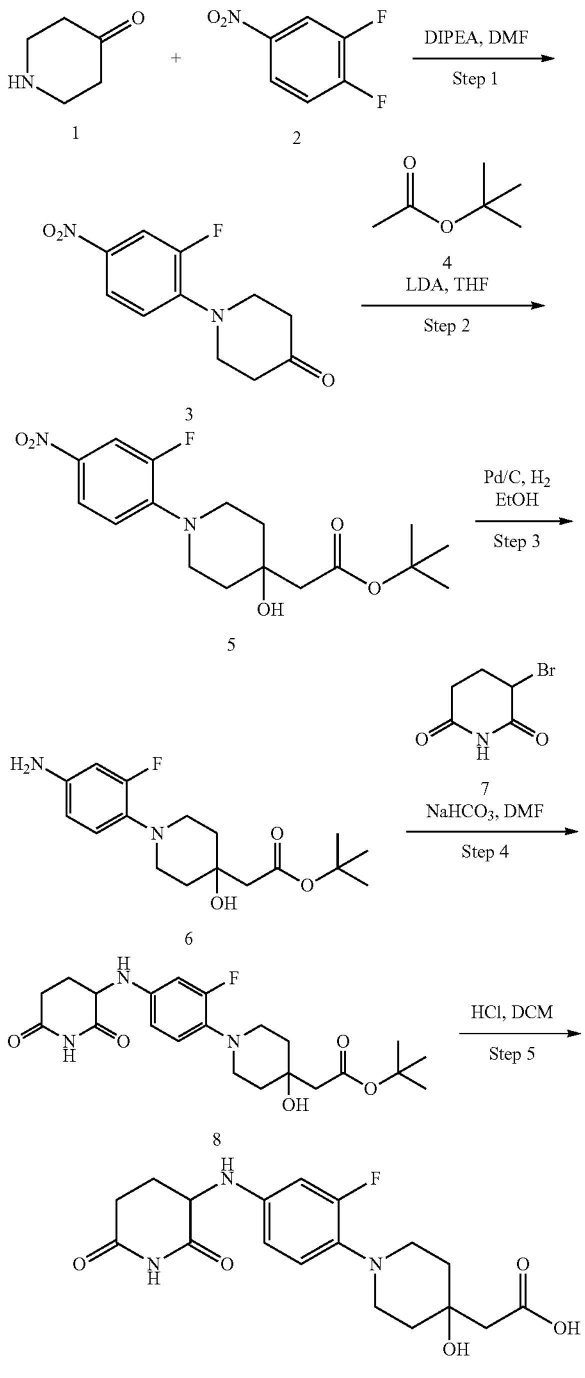

Step 1: To a stirred solution of piperidin-4-one HCl salt (1, 20 g, 147.50 mmol) and 1,2-difluoro-4-nitro-benzene (2, 26.99 g, 169.63 mmol, 18.74 mL) in DMSO (200 mL) was added N,N-diisopropylethylamine (147.50 mmol, 25.69 mL). The reaction was stirred at 80° C. for 16 hours. Ice cold water was added to the reaction mixture and the solid was filtered through Buchner funnel. and dried to obtain 1-(2- fluoro-4-nitro-phenyl)piperidin-4-one (3, 28 g, 115.66 mmol, 78% yield). LC-MS ($ES^-$): 237.1 $[M-H]^-$.

Step 2: To a stirred solution of tert-butyl acetate (4, 7.31 g, 62.97 mmol, 8.47 mL) in THF was added lithium diisopropylamide (13.49 g, 125.94 mmol) at −78'C. The mixture was allowed to stir for an hour, after which 1-(2-fluoro-4-nitro-phenyl)piperidin-4-one (3, 15 g, 62.97 mmol) was added and the reaction stirred for 2 hours. After completion, the reaction mixture was quenched with saturated ammonium chloride solution and the product was extracted with ethyl acetate (2×200 mL) and concentrated to provide the crude product. The crude product was purified using flash column chromatography (silica gel, 40% ethyl acetate in pet ether) to afford tert-butyl 2-[1-(2-fluoro-4-nitro-phenyl)-4-hydroxy-4-piperidyl]acetate (5, 17.6 g, 43.71 mmol, 69% yield) as a gummy brown liquid. LC-MS ($ES^+$): 355.2 $[M+H]^+$.

Step 3: To the stirred solution of tert-butyl 2-[1-(2-fluoro-4-nitro-phenyl)-4-hydroxy-4-piperidyl]acetate (5, 17.6 g, 49.67 mmol) in ethanol (200 mL) was added Palladium, 10% on carbon, type 487, dry (15 g, 140.95 mmol). The reaction was carried out under hydrogen atmosphere at room temperature for 5 hours. Upon completion, the reaction mixture was concentrated, and the crude product was purified using flash column chromatography (silica gel, 45% ethyl acetate in pet ether) to afford tert-butyl 2-[1-(4-amino-2-fluoro-phenyl)-4-hydroxy-4-piperidyl]acetate (6, 13 g, 38.99 mmol, 79% yield). LC-MS ($ES^+$): 325.2 $[M+H]^+$.

Step 4: To a stirred solution of tert-butyl 2-[1-(4-amino-2-fluoro-phenyl)-4-hydroxy-4-piperidyl]acetate (6, 13 g, 40.08 mmol) and 3-bromopiperidine-2,6-dione (7, 15.39 g, 80.15 mmol) in DMF (100 mL) was added sodium bicarbonate (6.73 g, 80.15 mmol). The reaction was carried out at 65° C. overnight. After completion of the reaction, the product was extracted with ethyl acetate and water. The extracted organic layer was dried over anhydrous sodium sulfate and concentrated to get the crude, which was purified using flash column chromatography (silica gel, 45% ethyl acetate in pet ether to give tert-butyl 2-[1-[4-[(2,6-dioxo-3-piperidyl)amino]-2-fluoro-phenyl]-4-hydroxy-4-piperidyl] acetate (8, 11.5 g, 65% yield). LC-MS ($ES^+$): 436.2 $[M+H]^+$.

Step 5: To the stirred solution of tert-butyl 2-[1-[4-[(2,6-dioxo-3-piperidyl)amino]-2-fluoro-phenyl]-4-hydroxy-4-piperidyl]acetate (8, 411 mg, 943.77 μmol) in DCM (10 mL) was added hydrogen chloride in 1,4-dioxane, 99% (4 M, 4.72 mL) dropwise at 0° C. The reaction mixture stirred at room temperature for 24 hours. After completion, the reaction mixture was evaporated to dryness. The product was redissolved in DCM, and MTBE was added to afford precipitation. The solid was isolated and dried to give 2-[1-[4-[(2,6-dioxo-3-piperidyl)amino]-2-fluoro-phenyl]-4-hydroxy-4-piperidyl]acetic acid (9, 365 mg, 789.96 μmol, 84% yield, HCl salt) as a gray solid. LC-MS ($ES^+$): 380.3 $[M+H]^+$.

Example 22: Synthesis of 2-(1-(2-(Difluoromethyl)-4-((2,6-dioxopiperidin-3-yl)amino)phenyl)-4-hydroxypiperidin-4-yl)acetic acid

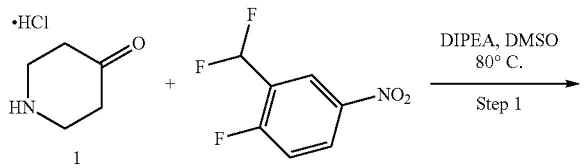

1 2

-continued

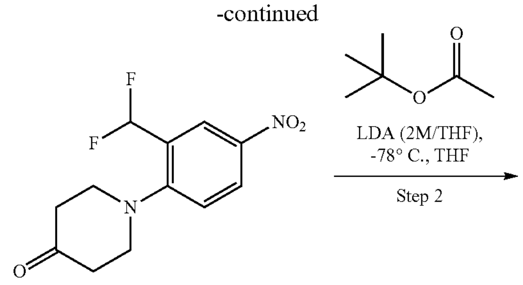

3

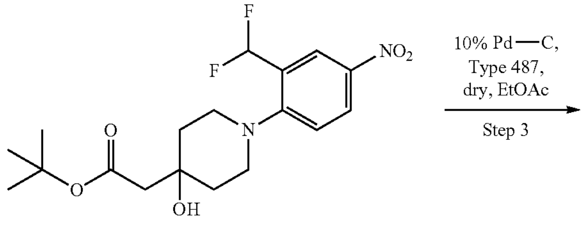

4

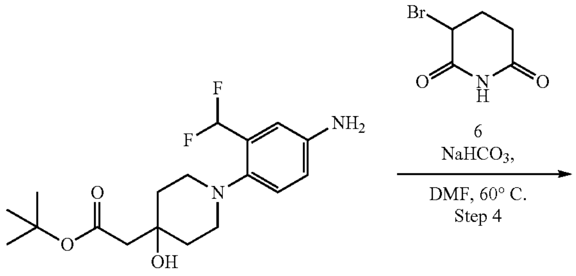

5

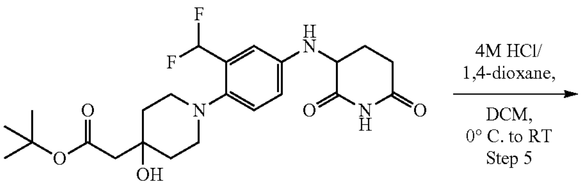

7

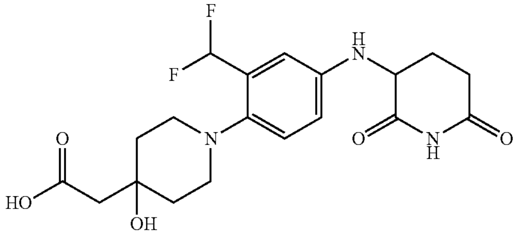

8

Step 1: Into a 250 mL sealed tube containing a well-stirred solution of piperidin-4-one hydrochloride (1, 3 g, 22.13 mmol) and 2-(difluoromethyl)-1-fluoro-4-nitro-benzene (2; 4.23 g, 22.13 mmol) in anhydrous DMSO (30 mL) were added N, N-Diisopropylethylamine (88.50 mmol, 15.41 mL) under nitrogen atmosphere. The resulting mixture was heated at 80° C. for 5 h. After completion, the reaction mixture was poured into ice-cold water and solid precipitated out, which was filtered and dried to get 1-(2-(difluoromethyl)-4-nitrophenyl)piperidin-4-one (3; 4.7 g, 16.32 mmol, 74% yield) as a yellow solid. LC-MS ($ES^-$): 269.0 $[M-H]^-$.

Step 2: Into a 100 mL single-necked round-bottomed flask containing a well-stirred solution of tert-butyl acetate (2.42 g, 20.87 mmol, 2.81 mL) in anhydrous THF (30 mL) under nitrogen atmosphere at −78° C. was added Lithium diisopropylamide solution 2M in THF (2.79 g, 26.09 mmol, 13 mL) dropwise over a period of 10 minutes. The resulting suspension was further stirred at −78° C. for 1 h. Then, solution of freshly prepared 1-(2-(difluoromethyl)-4-nitrophenyl)piperidin-4-one (3, 4.7 g, 17.39 mmol) in anhydrous THF (20 mL) was added dropwise to the reaction mixture while maintaining −78° C. and continued stirring for 3 h. After completion, the reaction mixture was brought to room temperature and excess reagent was quenched with saturated ammonium chloride solution. The organic layer was separated, and the aqueous layer was extracted with EtOAc (2×100 mL). The combined organic layer was washed with brine (100 mL) and concentrated under reduced pressure. The crude residue was purified by flash silica-gel (230-400 mesh) column with 0-40% EtOAc/pet ether get tert-butyl 2-(1-(2-(difluoromethyl)-4-nitrophenyl)-4-hydroxypiperidin-4-yl)acetate (4, 4.55 g, 11.26 mmol, 65% yield). LC-MS ($ES^+$): 387.2 $[M+H]^+$.

Step 3: Into a 250 mL single-necked round-bottomed flask containing a well-stirred solution of tert-butyl 2-[1-[2-(difluoromethyl)-4-nitro-phenyl]-4-hydroxy-4-piperidyl]acetate (4, 4.1 g, 10.61 mmol) in EtOAc (40 mL) was added Palladium, 10% on carbon, dry (1.58 g, 14.86 mmol) at ambient temperature under nitrogen atmosphere. The resulting suspension was stirred at ambient temperature under hydrogen atmosphere (bladder) for 6 h. After completion, the reaction mixture was filtered through a pad of Celite, washing with EtOAc (100 mL). The filtrate was concentrated under reduced pressure to yield tert-butyl 2-(1-(4-amino-2-(difluoromethyl)phenyl)-4-hydroxypiperidin-4-yl) acetate (5; 3.5 g, 9.40 mmol, 89% yield). LC-MS ($ES^+$): 357.2 $[M+H]^+$.

Step 4: Into a 100 mL sealed tube containing a well-stirred solution of tert-butyl 2-[1-[4-amino-2-(difluoromethyl)phenyl]-4-hydroxy-4-piperidyl]acetate (5, 3.4 g, 9.54 mmol) and 3-bromopiperidine-2,6-dione (6, 2.75 g, 14.31 mmol in anhydrous DMF (35 mL) under nitrogen atmosphere were added Sodium bicarbonate (1.60 g, 19.08 mmol) at room temperature. The resulting suspension was heated at 60° C. for 16 h. After completion, the reaction mixture was allowed to attain room temperature and water (30 mL) was added. The aqueous phase was extracted with EtOAc (2×100 mL). The organic phases were combined, dried (anhydrous $Na_2SO_4$), filtered and the filtrate was concentrated under reduced pressure to get a crude residue. The crude residue was purified by flash silica-gel (230-400 mesh; 100 g SNAP) column with 60% EtOAc/pet ether to afford tert-butyl 2-[1-[2-(difluoromethyl)-4-[(2,6-dioxo-3-piperidyl)amino]phenyl]-4-hydroxy-4-piperidyl]acetate (7, 3.3 g, 6.78 mmol, 71% yield). LC-MS ($ES^+$): 468.2 $[M+H]^+$.

Step 5: Into a 100 mL single-necked round-bottomed flask containing a well-stirred solution of tert-butyl 2-[1-[2-(difluoromethyl)-4-[(2,6-dioxo-3-piperidyl)amino]phenyl]-4-hydroxy-4-piperidyl]acetate (7, 3.2 g, 6.84 mmol) in anhydrous DCM (30 mL) was added 4M HCl (8.6 mL) at 0° C. under nitrogen atmosphere. The resulting mixture was stirred at ambient temperature for 8 h under nitrogen atmosphere. After completion of the reaction, excess solvent was removed from the reaction mixture to get a crude mass. The crude mass was triturated with $Et_2O$ (30 mL) to get 2-[1-[2-(difluoromethyl)-4-[(2,6-dioxo-3-piperidyl)amino]phenyl]-4-hydroxy-4-piperidyl]acetic acid hydrochloride (8; 3.11 g, 6.61 mmol, 97% yield, HCl salt) as an off-white solid. LC-MS ($ES^+$): 412.0 $[M+H]^+$.

Example 23: Synthesis of 2-(4-(4-((2,6-Dioxopiperidin-3-yl)amino)-2-fluorophenyl)piperidin-1-yl) acetic acid

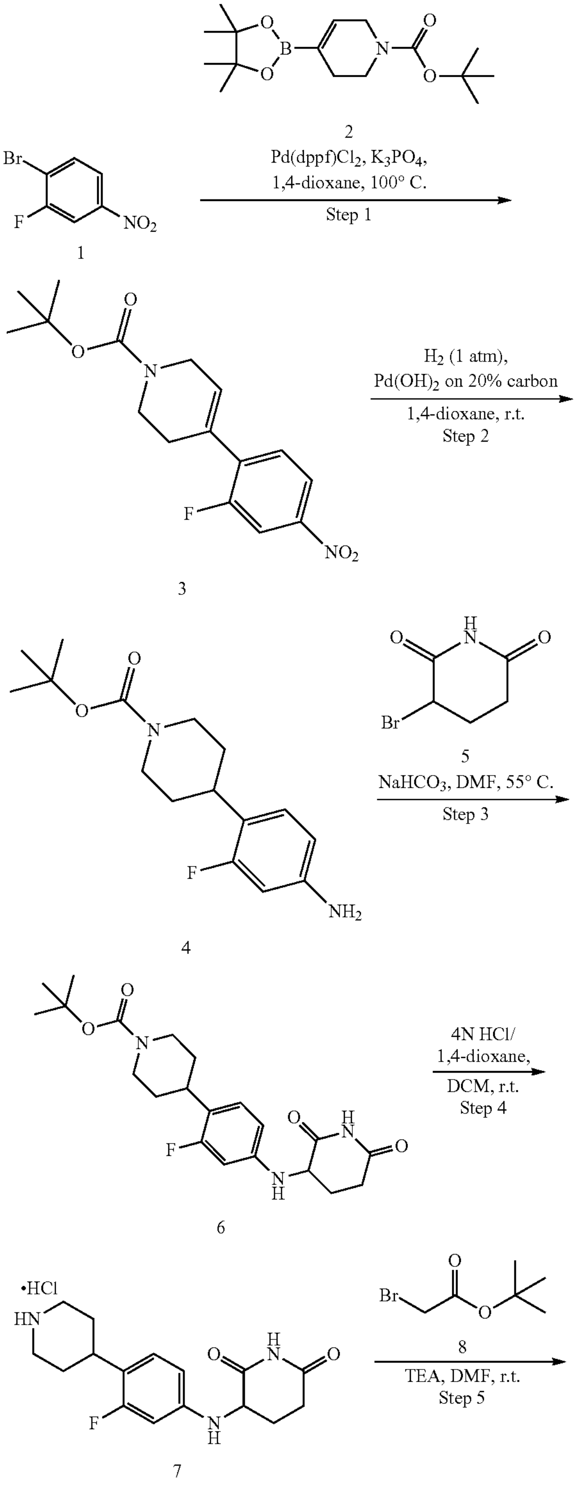

-continued

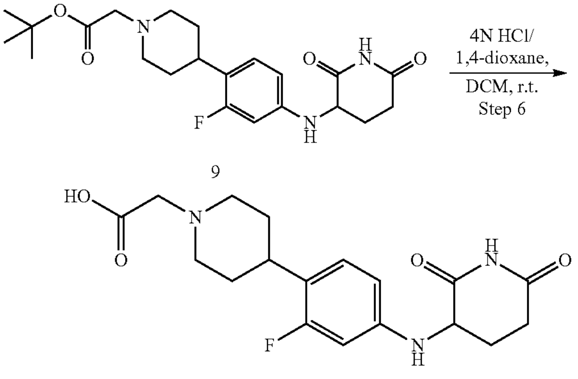

9

10

Step 1: Into a 250 mL sealed-tube containing a well stirred solution of tert-butyl 4-(4,4,5,5-tetramethyl-1,3,2-dioxaborolan-2-yl)-3,6-dihydro-2H-pyridine-1-carboxylate (2, 21.08 g, 68.18 mmol) and 1-bromo-2-fluoro-4-nitro-benzene (1; 10.0 g, 45.46 mmol) in 1,4-dioxane (100 mL) was added potassium phosphate tribasic anhydrous (28.95 g, 136.37 mmol) and the resulting mixture was purged with nitrogen for 15 minutes. Subsequently, 1,1'Bis(diphenylphosphino)ferrocene]dichloropalladium(II) complexed with dichloromethane (2.60 g, 3.18 mmol) was added and the reaction mixture was purged with nitrogen for 10 minutes. Later, the resulting mixture was heated with stirring at 100° C. for 5 h. After completion, the reaction mixture was diluted with water (200 mL) and extracted with EtOAc (2×100 mL). Combined organic phase was washed with brine (100 mL), dried (anhydrous $Na_2SO_4$), filtered and the filtrate was concentrated under reduced pressure to get the crude. The crude mass was purified by flash silica-gel (230-400 mesh, 100 g) column with a gradient of 0-100% EtOAc/pet ether while the desired product was eluting at 45-50% EtOAc/pet ether to afford tert-butyl 4-(2-fluoro-4-nitro-phenyl)-3,6-dihydro-2H-pyridine-1-carboxylate (3, 12.0 g, 35.96 mmol, 79% yield) as a pale yellow solid. LC-MS ($ES^-$): 321.1 $[M-H]^-$.

Step 2: Into a 500 mL single-necked round-bottomed flask containing a well stirred solution of tert-butyl 4-(2-fluoro-4-nitro-phenyl)-3,6-dihydro-2H-pyridine-1-carboxylate (3, 12.00 g, 37.23 mmol) in 1,4-dioxane (150 mL) was degassed by $N_2$ gas for 10 minutes, 20% palladiumhydroxide on dry basis (2.5 g, 37.23 mmol) was added at ambient temperature. Later, the reaction mixture was stirred at room temperature for 48 h under hydrogen atmosphere (Bladder). After completion, the reaction mixture was filtered through a pad of Celite, washing with EtOAc (200 mL). The filtrate was concentrated under reduced pressure to get crude tert-butyl 4-(4-amino-2-fluoro-phenyl)piperidine-1-carboxylate (4, 10.0 g, 23.10 mmol, 62% yield) as a yellow liquid. LC-MS ($ES^+$): 195.0 $[M\text{-}Boc+H]^+$.

Step 3: Into a 250 mL sealed-tube containing a well stirred solution of tert-butyl 4-(4-amino-2-fluoro-phenyl)piperidine-1-carboxylate (4, 10.0 g, 33.97 mmol) and 3-bromopiperidine-2,6-dione (5, 9.78 g, 50.96 mmol) in anhydrous DMF (130 mL) was added sodium bicarbonate (8.56 g, 101.91 mmol, 3.96 mL) at ambient temperature under nitrogen atmosphere. Later, the reaction contents were heated with stirring at 55° C. for 48 h. The reaction mixture was diluted with water (200 mL) and extracted with EtOAc (2×100 mL). The combined organic layers were washed with brine (100 mL), dried (anhydrous $Na_2SO_4$), filtered and concentrated under reduced pressure to get a crude mass. The crude was purified by flash silica-gel (230-400 mesh; 100 g SNAP) with a gradient of 0-100% EtOAc/pet ether to afford tert-butyl 4-[4-[(2,6-dioxo-3-piperidyl)amino]-2-fluoro-phenyl]piperidine-1-carboxylate (6, 7.0 g, 13.64 mmol, 40% yield) as pale blue-colored solid. LC-MS ($ES^-$): 404.1 $[M-H]^-$.

Step 4: Into a 250 mL single-necked round-bottomed flask containing a well-stirred solution of tert-butyl 4-[4-[(2,6-dioxo-3-piperidyl)amino]-2-fluoro-phenyl]piperidine-1-carboxylate (6; 7 g, 17.26 mmol) in anhydrous DCM (150 mL) was added dropwise 4.0 M HCl in 1,4-dioxane (17.26 mmol, 17.2 mL) at 0° C. under nitrogen atmosphere. The resulting reaction mixture was stirred at ambient temperature for 2 h. After completion, excess solvent was removed from the reaction mixture under reduced pressure to get a crude, which was co-distilled with DCM to get 3-[3-fluoro-4-(4-piperidyl)anilino]piperidine-2,6-dione·hydrochloride (7; 6 g, 14.92 mmol, 86% yield) as an ash-colored solid. LC-MS ($ES^+$): 306.0 $[M+H]^+$.

Step 5: Into a 250 mL single-necked round-bottomed flask containing a well stirred solution of 3-[3-fluoro-4-(4-piperidyl)anilino]piperidine-2,6-dione hydrochloride (7, 4 g, 13.10 mmol) and tert-butyl 2-bromoacetate (8, 2.81 g, 14.41 mmol, 2.11 mL) in anhydrous DMF (50 mL) was added TEA (39.30 mmol, 5.48 mL) at ambient temperature under nitrogen atmosphere. The reaction mixture was stirred at ambient temperature for 4 h. The reaction mixture was diluted with water (100 mL) and extracted with EtOAc (2×70 mL). The combined organic layers were washed with brine (100 mL), dried (anhydrous $Na_2SO_4$), filtered and the filtrate was concentrated under reduced pressure to get a crude mass. The crude was purified by flash silica-gel (230-400 mesh; 100 g SNAP) column with a gradient of 0-100% EtOAc/pet ether to afford tert-butyl 2-[4-[4-[(2,6-dioxo-3-piperidyl)amino]-2-fluoro-phenyl]-1-piperidyl]acetate (9, 4 g, 9.43 mmol, 72% yield) as a blue solid. LC-MS ($ES^+$): 420.3 $[M+H]^+$.

Step 6: Into a 250 mL single-necked round-bottomed flask containing a well-stirred solution of tert-butyl 2-[4-[4-[(2,6-dioxo-3-piperidyl)amino]-2-fluoro-phenyl]-1-piperidyl] acetate (9, 4.0 g, 9.54 mmol) in anhydrous DCM (40 mL) was added dropwise 4.0 M HCL in 1,4-dioxane (9.54 mmol, 20 mL) at 0° C. under nitrogen atmosphere. The resulting reaction mixture was stirred at ambient temperature for 2 h. After completion, the reaction was concentrated to get a crude mass. The crude mass was co-distilled with DCM and further triturated with $Et_2O$ to afford 2-[4-[4-[(2,6-dioxo-3-piperidyl)amino]-2-fluoro-phenyl]-1-piperidyl]acetic acid (10, 3.6 g, 8.30 mmol, 87% yield) as an off-white solid. LC-MS ($ES^+$): 364.1 $[M+H]^+$.

Example 24: Synthesis of tert-butyl 2-[4-[4-[(2,6-dioxo-3-piperidyl)amino]phenyl]-1-piperidyl]acetate

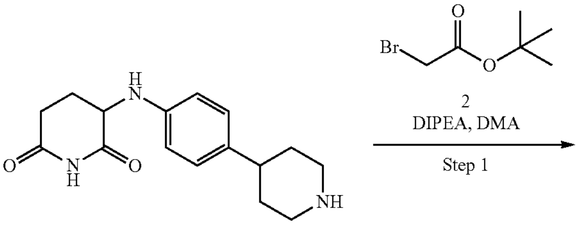

1

-continued

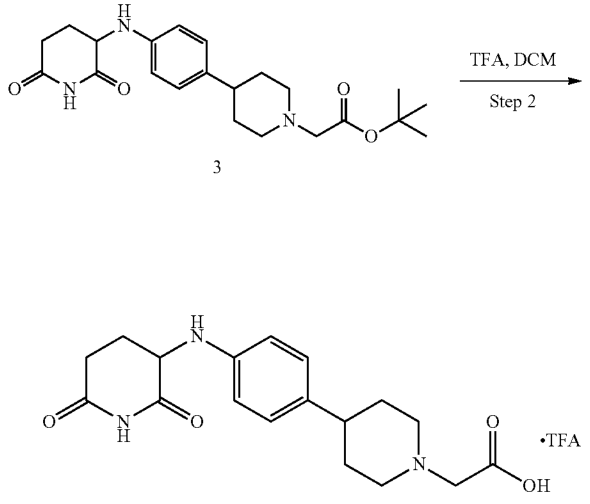

3

4

Step 1: 3-[4-(4-piperidyl)anilino]piperidine-2,6-dione hydrochloride (1, 1 g, 3.09 mmol) was dissolved in N,N-dimethylacetamide (15 mL) and N,N-diisopropylethylamine (1.60 g, 12.4 mmol, 2.15 mL) was added. The mixture was cooled to 0° C., and tert-butyl 2-bromoacetate (2, 663 mg, 3.40 mmol, 498 μL) was added. The mixture was stirred at 0° C. for 4 h. The reaction was diluted with ethyl acetate and washed with saturated sodium bicarbonate and brine. The organic layer was concentrated and purified by silica gel chromatography (0-10% Methanol in dichloromethane) to yield tert-butyl 2-[4-[4-[(2,6-dioxo-3-piperidyl)amino]phenyl]-1-piperidyl]acetate (3, 0.84 g, 2.09 mmol, 68% yield) as a white solid. LCMS (ESI+): 402.2 $[M+H]^+$ Step 2: tert-Butyl 2-[4-[4-[(2,6-dioxo-3-piperidyl)amino]phenyl]-1-piperidyl]acetate (3) was dissolved in dichloromethane (5 mL) and TFA (1.61 mL, 20.9 mmol) was added. The reaction mixture was heated at 40° C. for 4 h. The volatiles were evaporated under reduced pressure. The material was frozen to −78° C., submitted to high vacuum, and thawed to afford a dense solid. The solid was re-dissolved in methanol:dicloromethane (1:4), MTBE was added dropwise, until a precipitate formed. The suspension was submitted to sonication, and the solid was filtered under suction. The green solid was collected by filtration to afford 2-[4-[4-[(2,6-dioxo-3-piperidyl)amino]phenyl]-1-piperidyl]acetic acid, trifluoroacetic acid salt (4, 0.95 g, 2.07 mmol, 97% yield). LCMS (ESI+): 346.4 $[M+H]^+$.

Example 25: Synthesis of 2-[1-[2-bromo-4-[(2,6-dioxo-3-piperidyl)amino]phenyl]-4-hydroxy-4-piperidyl]acetic acid

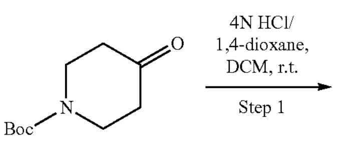

1

-continued

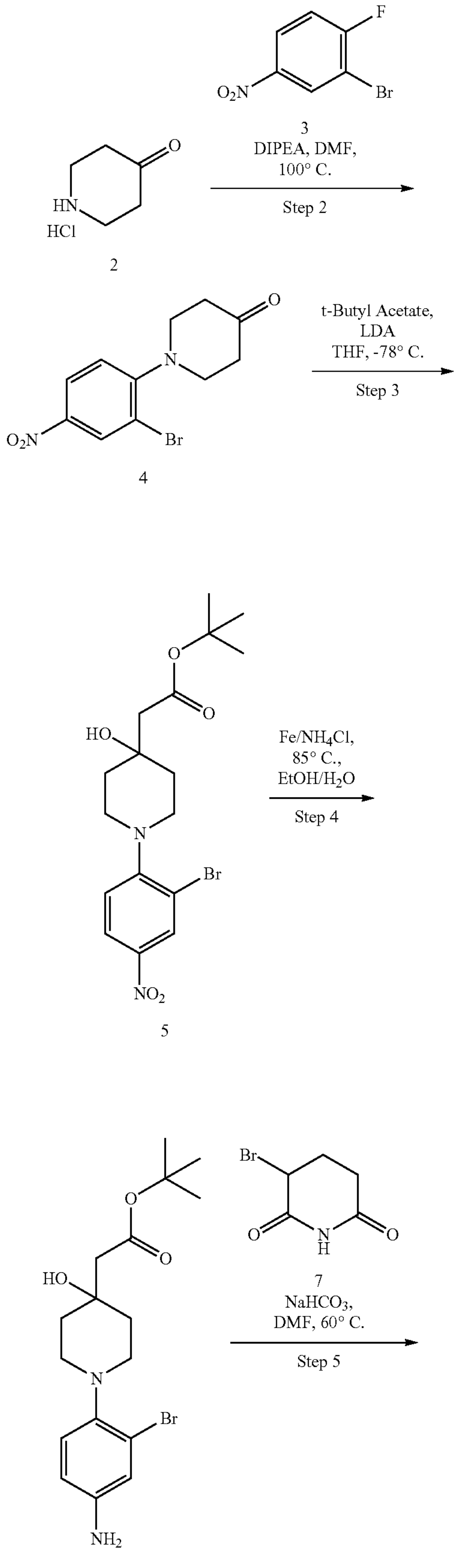

3

2

4

5

7

6

-continued

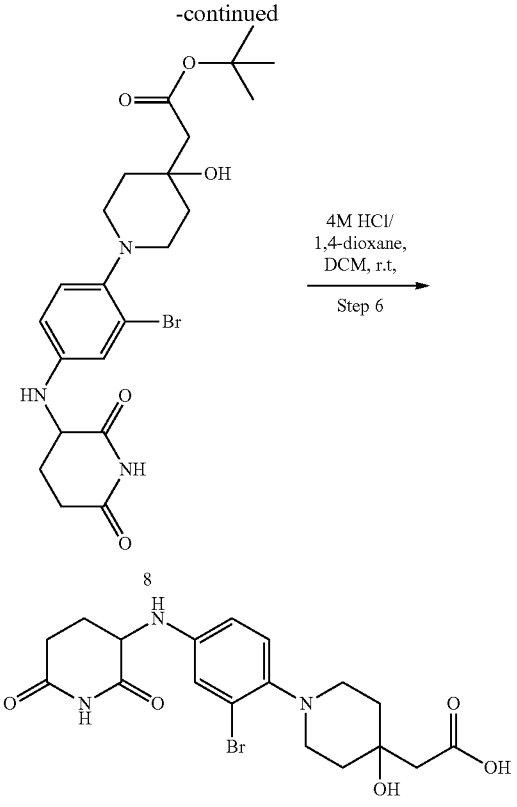

8

9

Step 1. Into a 100 mL single-necked round-bottomed flask containing a well-stirred solution of tert-butyl 4-oxopiperidine-1-carboxylate (1; 10 g, 50.19 mmol) in anhydrous DCM (30 mL) was added 4M HCl in 1,4-dioxane (37.64 mL) at ambient temperature under nitrogen atmosphere. The resulting reaction mixture was stirred at ambient temperature for 2 h. After completion, excess solvent was removed from the reaction mixture under reduced pressure to get a crude product. The crude mass was triturated with 10% DCM/pet ether to get piperidin-4-one hydrochloride (2; 6.2 g, 45.50 mmol, 91% yield) as a pale-yellow solid. $^1H$ NMR (400 MHz, DMSO-$d_6$). δ 9.76 (bs, 2H), 3.39 (t, J=6.4 Hz, 4H), 2.60 (t, J=6.4 Hz, 4H).

Step 2: Into a 100 mL sealed-tube containing a well-stirred solution of piperidin-4-one hydrochloride (2; 2.93 g, 29.55 mmol) and 2-bromo-1-fluoro-4-nitro-benzene (3; 5 g, 22.73 mmol) in anhydrous DMF (50 mL) was added DIPEA (68.18 mmol, 11.88 mL) at ambient temperature under nitrogen atmosphere. The resulting mixture was heated to 100° C. for 16 h. After cooling to rt, the reaction mixture was diluted with ice-water (150 mL), and resulting solution was stirred for 15 minutes at room temperature and a product was precipitated out. The solid crude product was filtered and purified by flash silica-gel (230-400 mesh; 100 g SNAP) column with 0-100% EtOAc/pet ether to get 1-(2-bromo-4-nitro-phenyl)piperidin-4-one (4; 4.4 g, 11.47 mmol, 51% yield) as a yellow solid. LCMS (ES+): 301.1 $[M+H]^+$.

Step 3: Into a 250 mL three-necked round-bottomed flask containing a well-stirred solution of tert-butyl acetate (932.00 mg, 8.02 mmol, 1.08 mL) in dry THF (20 mL) was added 2 M Lithium diisopropylamide in heptane (4.01 mL) in heptane at −78° C. under nitrogen atmosphere and the resulting reaction mixture was stirred at −78° C. for an hour under nitrogen atmosphere. 1-(2-bromo-4-nitro-phenyl)piperidin-4-one (4; 2 g, 6.69 mmol) in anhydrous THF (20 mL) was added at −78° C. under nitrogen atmosphere and the resulting reaction mixture was stirred at −78° C. for 2 h under nitrogen atmosphere. After completion, the reaction mixture was quenched with saturated solution of ammonium chloride (50 mL) and the product was extracted with EtOAc (2×150 mL). The organic phases were combined, dried (anhydrous $Na_2SO_4$), filtered and the filtrate was concentrated under reduced pressure to get a crude residue. The crude product was purified by flash silica-gel (230-400 mesh; 100 g SNAP) column with 0-60% EtOAc/pet ether to afford tert-butyl 2-[1-(2-bromo-4-nitro-phenyl)-4-hydroxy-4-piperidyl]acetate (5; 2.1 g, 4.12 mmol, 62% yield) as a yellow solid. LCMS (ES+): 415.0 $[M+H]^+$.

Step 4: Into a 250 mL single-necked round-bottomed flask containing a well-stirred suspension of tert-butyl 2-[1-(2-bromo-4-nitro-phenyl)-4-hydroxy-4-piperidyl]acetate (5; 2.1 g, 5.06 mmol) in 2:1 EtOH/$H_2O$ (60 mL) were added Iron powder (1.98 g, 35.40 mmol) and Ammonium Chloride (1.35 g, 25.28 mmol) at ambient temperature under nitrogen atmosphere. The resulting suspension was heated to 85° C. for 3 h and the reaction mixture was cooled to ambient temperature. After completion, the reaction mixture was filtered through a pad of Celite, washing with EtOAc (100 mL). The combined filtrate was diluted with water (80 mL) and the product was extracted with EtOAc (2×100 mL). The organic phases were combined, dried (anhydrous $Na_2SO_4$), filtered and the filtrate was concentrated under reduced pressure to get a crude residue. The crude product was purified by flash silica-gel (230-400 mesh; 100 g SNAP) column with 0-80% EtOAc/pet ether to afford tert-butyl 2-[1-(4-amino-2-bromo-phenyl)-4-hydroxy-4-piperidyl]acetate (6; 1.65 g, 4.19 mmol, 83% yield) as a brown gummy oil. LCMS (ES+): 385.2 $[M+H]^+$.

Step 5: Into a 250 mL sealed-tube containing a well-stirred solution of tert-butyl 2-[1-(4-amino-2-bromo-phenyl)-4-hydroxy-4-piperidyl]acetate (6; 1.65 g, 4.28 mmol) and 3-bromopiperidine-2,6-dione (7, 1.23 g, 6.42 mmol) in anhydrous DMF (15 mL) was added sodium bicarbonate (1.08 g, 12.85 mmol) at ambient temperature under nitrogen atmosphere. The reaction mixture was heated to 60° C. for 40 h and the reaction mixture was cooled to ambient temperature. The reaction mixture was quenched with water (80 mL) and the product was extracted with EtOAc (2×200 mL). The organic phases were combined, dried (anhydrous $Na_2SO_4$), filtered and the filtrate was concentrated under reduced pressure to get a crude residue. The crude product was purified by flash silica-gel (230-400 mesh; 100 g SNAP) column with 0-100% EtOAc/pet ether to afford tert-butyl 2-[1-[2-bromo-4-[(2,6-dioxo-3-piperidyl)amino]phenyl]-4-hydroxy-4-piperidyl]acetate (8; 1.4 g, 2.70 mmol, 63% yield) as a brown solid. LCMS (ES+): 496.2 $[M+H]^+$.

Step 6. Into a 100 mL single-necked round-bottomed flask containing a well-stirred solution of tert-butyl 2-[1-[2-bromo-4-[(2,6-dioxo-3-piperidyl)amino]phenyl]-4-hydroxy-4-piperidyl]acetate (8; 500 mg, 1.01 mmol) in anhydrous 1,4-dioxane (5 mL) was added 4M HCl in 1,4-dioxane (15 mL) at ambient temperature under nitrogen atmosphere. The resulting mixture was stirred at ambient temperature for 16 h. After completion, excess solvent was removed from the reaction mixture under reduced pressure to get a crude mass. The crude product was washed with MTBE (10 mL) to get 2-[1-[2-bromo-4-[(2,6-dioxo-3-piperidyl)amino]phenyl]-4-hydroxy-4-piperidyl]acetic acid hydrochloride (9; 450 mg, 0.891 mmol, 88% yield) as a yellow solid. LCMS (ES+): 440.2 $[M+H]^+$.

Example 26: Synthesis of 3-[3-fluoro-4-(4-oxo-1-piperidyl)anilino]piperidine-2,6-dione

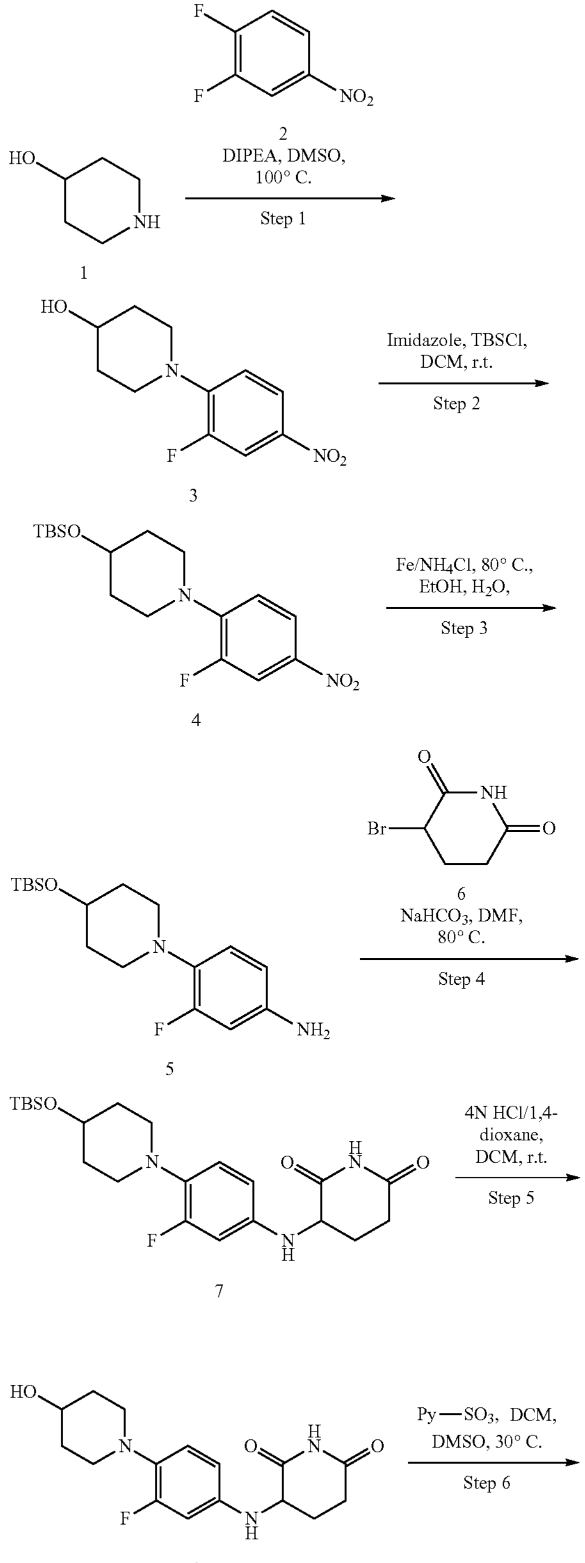

2

1

3

4

6

5

7

8

-continued

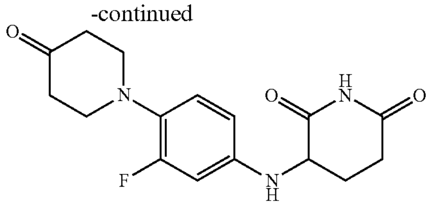

9

Step 1: Into a 100 mL sealed-tube containing a well-stirred solution of piperidin-4-ol (1; 2.38 g, 23.57 mmol) and 1,2-difluoro-4-nitro-benzene (2; 2.5 g, 15.71 mmol, 1.74 mL) in anhydrous DMF (25 mL) was added DIPEA (3.14 mmol, 0.547 mL) at ambient temperature under nitrogen atmosphere and the reaction mixture was heated to 80° C. for 16 h. The reaction mixture was then cooled to ambient temperature. The mixture was diluted with ice-water (100 mL) and the product was extracted with EtOAc (2×200 mL). The organic phases were combined, dried (anhydrous $Na_2SO_4$), filtered and concentrated under reduced pressure to get a crude residue. The crude residue was purified by flash silica-gel (230-400 mesh) column with 0-100% EtOAc/pet ether to afford 1-(2-fluoro-4-nitro-phenyl)piperidin-4-ol (3; 3.0 g, 12.5 mmol, 73% yield) as an off-white solid. LCMS (ES+): 241.1 $[M+H]^+$.

Step 2: Into a 25 mL single-necked round-bottomed flask containing a well-stirred solution of 1-(2-fluoro-4-nitro-phenyl)piperidin-4-ol (3; 250 mg, 1.04 mmol) in anhydrous DCM (2 mL) were added imidazole (127.52 mg, 1.87 mmol) and tert-Butyldimethylsilyl chloride (250.96 mg, 1.67 mmol, 0.309 mL) at ambient temperature under nitrogen atmosphere. The resulting mixture was stirred at ambient temperature for 12 h. After completion of the reaction, the reaction mixture was diluted with water (30 mL), the product was extracted with EtOAc (2×50 mL). The organic layer was dried (anhydrous $Na_2SO_4$), filtered and the filtrate was concentrated under reduced pressure to get a crude mass. The crude mass was purified by flash silica-gel (230-400 mesh) column with 0-100% EtOAc/pet ether to afford tert-butyl-[[1-(2-fluoro-4-nitro-phenyl)-4-piperidyl]oxy]-dimethyl-silane (4; 250 mg, 0.678 mmol, 65% yield) as an off-white solid. LCMS (ES+): $[M+H]^+$.

Step 3: Into a 25 mL single-necked round-bottomed flask containing a well-stirred suspension of tert-butyl-[[1-(2-fluoro-4-nitro-phenyl)-4-piperidyl]oxy]-dimethyl-silane (4; 250 mg, 0.705 mmol) in a mixture of EtOH (4 mL) and water (1 mL) were added Iron powder (196.92 mg, 3.53 mmol) and Ammonium chloride (377.24 mg, 7.05 mmol) at ambient temperature under nitrogen atmosphere. The resulting suspension was heated to 80° C. for 4 h. After completion, the reaction mixture was cooled to ambient temperature and filtered through a pad of Celite, washing with EtOAc (50 mL). The combined filtrate was diluted with water (30 mL) and the product was extracted with EtOAc (2×50 mL). The organic phases were combined, dried (anhydrous $Na_2SO_4$), filtered and the filtrate was concentrated under reduced pressure to get 4-[4-[tert-butyl(dimethyl)silyl]oxy-1-piperidyl]-3-fluoro-aniline (5; 200 mg, 0.537 mmol, 76% yield) as a green gummy oil. LCMS (ES+): 325.2 $[M+H]^+$.

Step 4. Into a 100 mL sealed-tube reactor containing a well-stirred solution of 4-[4-[tert-butyl(dimethyl)silyl]oxy-1-piperidyl]-3-fluoro-aniline (5; 900 mg, 2.77 mmol) in anhydrous DMF (10 mL) were added Sodium bicarbonate (1.16 g, 13.87 mmol) and 3-bromopiperidine-2,6-dione (6; 852.04 mg, 4.44 mmol) at room temperature under nitrogen atmosphere. The reaction mixture was heated at 80° C. for 48 h. After completion, the reaction mixture was cooled to room temperature, poured into water (100 mL), and extracted with EtOAc (2×100 mL). The organic phases were combined and washed with brine (100 mL). The combined organic phase was dried (anhydrous $Na_2SO_4$), filtered, and concentrated under reduced pressure to get a crude, which was purified by flash silica-gel (230-400 mesh) column with 0-100% EtOAc/pet ether to afford 3-[4-[4-[tert-butyl(dimethyl)silyl]oxy-1-piperidyl]-3-fluoro-anilino]piperidine-2,6-dione (7; 450 mg, 0.943 mmol. 34% yield) as a black gummy liquid. LCMS (ES+): 436.2 [M+H]$^+$.

Step 5: Into a 100 mL single-necked round-bottomed flask containing a well-stirred solution of 3-[4-[4-[tert-butyl(dimethyl)silyl]oxy-1-piperidyl]-3-fluoro-anilino]piperidine-2,6-dione (7; 350 mg, 0.803 mmol) in anhydrous DCM (0.75 mL) under nitrogen atmosphere were added dropwise 4M HCl in 1,4-dioxane (0.803 mmol, 1.0 mL) at 0° C. The reaction mixture was allowed to room temperature and stirred at ambient temperature for 2 h. After completion, the reaction mixture was concentrated under reduced pressure and co-distilled with DCM (2×25 mL) to afford 3-[3-fluoro-4-(4-hydroxy-1-piperidyl)anilino]piperidine-2,6-dione hydrochloride (8; 280 mg, 0.774 mmol 96% yield) as an off-white solid. LCMS (ES+): 322.2 [M+H]$^+$.

Step 6: Into a 50 mL single-necked round-bottomed containing a well-stirred solution of 3-[3-fluoro-4-(4-hydroxy-1-piperidyl)anilino]piperidine-2,6-dione hydrochloride (8; 335 mg, 1.04 mmol) in anhydrous DMSO (2.5 mL) were added DCM (7.5 mL), TEA (31.27 mmol, 4.36 mL) and pyridine sulfur trioxide (1.66 g, 10.42 mmol) under nitrogen atmosphere at 0° C. The resulting mixture was stirred at room temperature for 24 h. After completion, the mixture was poured into ice-water (50 mL) and extracted with EtOAc (2×50 mL). The organic phases were combined and washed with brine (25 mL). The combined organic phases were dried (anhydrous $Na_2SO_4$), filtered, and concentrated under reduced pressure to get a crude residue which was purified by flash silica-gel (230-400 mesh) column with 0-100% EtOAc/pet ether followed by 0-10% MeOH/DCM to afford 3-[3-fluoro-4-(4-oxo-1-piperidyl)anilino]piperidine-2,6-dione (9; 70 mg, 0.076 mmol, 7% yield) as a black thick liquid. LCMS (ES+): 319.8 [M+H]$^+$.

Example 27: Synthesis of 2-[2-[4-[(2,6-dioxo-3-piperidyl)amino]-2-fluoro-phenyl]-6-hydroxy-2-azaspiro[3.3]heptan-6-yl]acetic acid

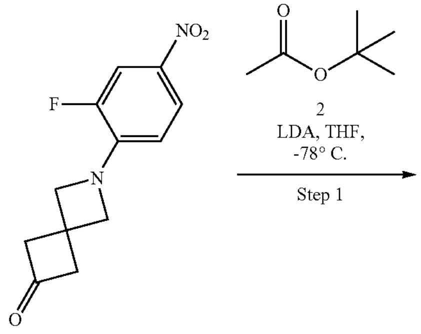

1

-continued

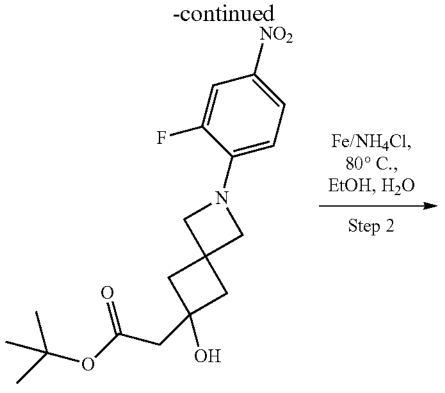

3

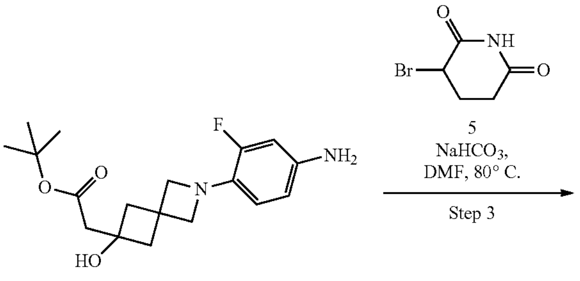

4

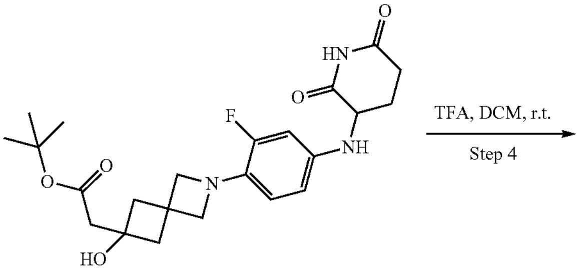

6

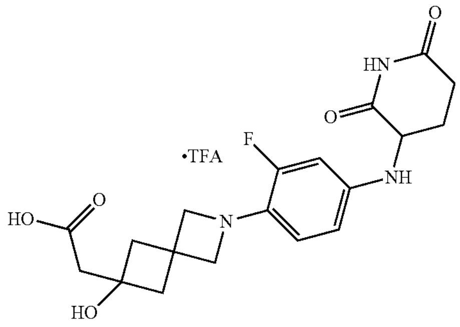

7

Step 1: Into a 25 mL two-necked round-bottomed flask containing a well-stirred solution of tert-butyl acetate (2; 46.42 mg, 0.399 mmol) in anhydrous THF (8 mL) was added dropwise a solution of (diisopropylamino)lithium (1.8M/THF) (64.22 mg, 0.599 mmol, 0.3 mL) under nitrogen atmosphere at −78° C. The resulting reaction mixture was stirred at −78° C. under nitrogen atmosphere for 45 minutes. Then, a prepared solution of 2-(2-fluoro-4-nitro-phenyl)-2-azaspiro[3.3]heptan-6-one (1; 100 mg, 0.399 mmol) in anhydrous THF (8 mL) was added dropwise to the reaction mixture at −78° C. under nitrogen atmosphere. After addition the reaction mixture was stirred at −78° C. under nitrogen atmosphere for 1 h. After completion, excess reagent was quenched with saturated ammonium chloride solution (4 mL) and the aqueous phase was extracted with EtOAc (3×50 mL). The combined organic phase was washed with brine (50 mL) and dried (anhydrous $Na_2SO_4$), filtered and concentrated under reduced pressure to afford a tert-butyl 2-(2-(2-fluoro-4-nitrophenyl)-6-hydroxy-2-azaspiro[3.3]heptan-6-yl) acetate (3; 80 mg, 0.15 mmol, 38% yield) as a brown thick gum. LCMS (ES+): 367.1 $[M+H]^+$.

Step 2: Into a 10 mL single-necked round-bottomed flask containing a well-stirred suspension of tert-butyl 2-[2-(2-fluoro-4-nitro-phenyl)-6-hydroxy-2-azaspiro[3.3]heptan-6-yl]acetate (3; 100 mg, 0.272 mmol) in a mixture of EtOH (2 mL) and water (1 mL) were added Iron powder (106.70 mg, 1.91 mmol) and Ammonium chloride (73.00 mg, 1.36 mmol) at ambient temperature under nitrogen atmosphere. The resulting suspension was heated to 85° C. for 3 h. After completion, the reaction mixture was cooled to ambient temperature and filtered through a pad of Celite, washing with EtOAc (20 mL). The combined filtrate was diluted with water (10 mL) and the product was extracted with EtOAc (2×20 mL). The organic phases were combined, dried (anhydrous $Na_2SO_4$), filtered and concentrated under reduced pressure to get tert-butyl 2-(2-(4-amino-2-fluorophenyl)-6-hydroxy-2-azaspiro[3.3]heptan-6-yl)acetate (4; 100 mg, 0.155 mmol, 57% yield) as a thick brown gummy solid. LCMS (ES+): 337.2 $[M+H]^+$.

Step 3: Into a 10 mL sealed-tube reactor containing a well-stirred solution of tert-butyl 2-[2-(4-amino-2-fluoro-phenyl)-6-hydroxy-2-azaspiro[3.3]heptan-6-yl]acetate (4; 80 mg, 0.237 mmol) and 3-bromopiperidine-2,6-dione (5; 54.79 mg, 0.285 mmol) in anhydrous DMF (2 mL) was added Sodium bicarbonate (59.93 mg, 0.713 mmol) at ambient temperature under nitrogen atmosphere. The resulting reaction mixture was stirred at 80° C. for 16 h. After completion, the reaction mixture was cooled to ambient temperature. The reaction mixture was diluted with ice-cold water (5 ml) and the product was extracted with EtOAc (3×10 ml) and washed with brine (10 mL). The organic phases were combined, dried (anhydrous $Na_2SO_4$), filtered and concentrated under reduced pressure to get a crude residue. The crude residue was purified by flash silica-gel (230-400 mesh) column with 0-100% EtOAc/pet ether to afford tert-butyl 2-[2-[4-[(2,6-dioxo-3-piperidyl)amino]-2-fluoro-phenyl]-6-hydroxy-2-azaspiro[3.3]heptan-6-yl]acetate (6; 40 mg, 0.067 mmol, 28% yield) as an ash-colored solid. LCMS (ES+): 448.2 $[M+H]^+$.

Step 4: Into a 25 mL single-necked round-bottomed flask containing a well-stirred solution of tert-butyl 2-[2-[4-[(2,6-dioxo-3-piperidyl)amino]-2-fluoro-phenyl]-6-hydroxy-2-azaspiro[3.3]heptan-6-yl]acetate (6; 50 mg, 0.111 mmol) in anhydrous DCM (4 mL) was added TFA (986.67 mg, 8.65 mmol) at ambient temperature under nitrogen atmosphere. The resulting reaction mixture stirred for 2 h. After completion, excess solvent was removed from the reaction mixture under reduced pressure to afford 2-[2-[4-[(2,6-dioxo-3-piperidyl)amino]-2-fluoro-phenyl]-6-hydroxy-2-azaspiro[3.3]heptan-6-yl]acetic acid trifluoroacetate (7; 50 mg, 0.0567 mmol, 51% yield) as a black gummy solid. LCMS (ES+): 392.2 $[M+H]^+$.

Example 28: Synthesis of 3-[3-fluoro-4-(4-oxo-1-piperidyl)anilino]piperidine-2,6-dione

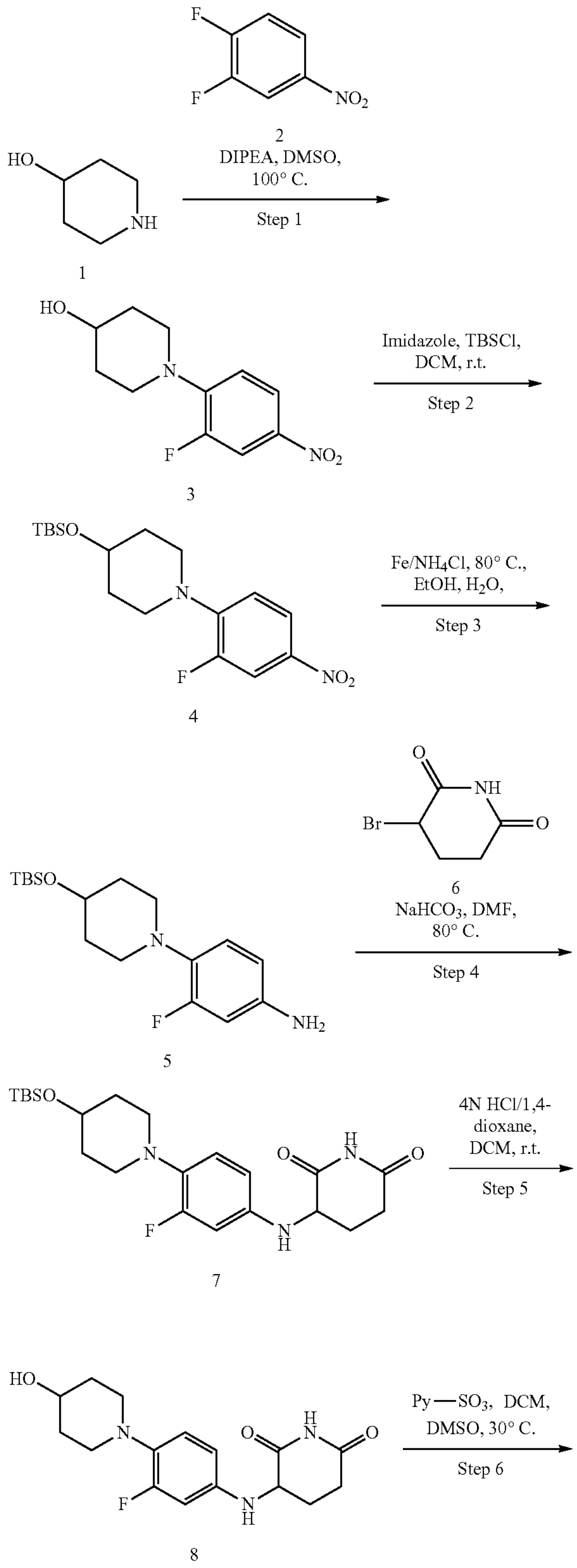

-continued

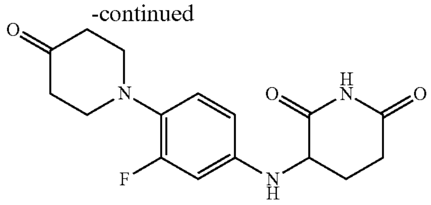

9

Step 1: Into a 100 mL sealed-tube containing a well-stirred solution of piperidin-4-ol (1; 2.38 g, 23.57 mmol) and 1,2-difluoro-4-nitro-benzene (2; 2.5 g, 15.71 mmol, 1.74 mL) in anhydrous DMF (25 mL) was added DIPEA (3.14 mmol, 0.547 mL) at ambient temperature under nitrogen atmosphere and the reaction mixture was heated to 80° C. for 16 h. The reaction mixture was then cooled to ambient temperature. The reaction mixture was diluted with ice-water (100 mL) and the product was extracted with EtOAc (2×200 mL). The organic phases were combined, dried (anhydrous $Na_2SO_4$), filtered and concentrated under reduced pressure to get a crude residue. The crude residue was purified by flash silica-gel (230-400 mesh) column with 0-100% EtOAc/pet ether to afford 1-(2-fluoro-4-nitro-phenyl)piperidin-4-ol (3, 3.0 g, 12.5 mmol, 73% yield) as an off-white solid. LCMS ($ES^+$): 241.1 $[M+H]^+$.

Step 2: Into a 25 mL single-necked round-bottomed flask containing a well-stirred solution of 1-(2-fluoro-4-nitro-phenyl)piperidin-4-ol (3, 250 mg, 1.04 mmol) in anhydrous DCM (2 mL) were added Imidazole (127.52 mg, 1.87 mmol) and tert-Butyldimethylsilyl chloride (250.96 mg, 1.67 mmol, 0.309 mL) at ambient temperature under nitrogen atmosphere. The resulting mixture was stirred at ambient temperature for 12 h. After completion, the reaction mixture was diluted with water (30 mL), the product was extracted with EtOAc (2×50 mL). The organic layer was dried (anhydrous $Na_2SO_4$), filtered and the filtrate was concentrated under reduced pressure to get a crude mass. The crude mass was purified by flash silica-gel (230-400 mesh) column with 0-100% EtOAc/pet ether to afford tert-butyl-[[1-(2-fluoro-4-nitro-phenyl)-4-piperidyl]oxy]-dimethyl-silane (4, 250 mg, 0.678 mmol, 65% yield) as an off-white solid. LCMS ($ES^+$): 355.2 $[M+H]^+$.

Step 3: Into a 25 mL single-necked round-bottomed flask containing a well-stirred suspension of tert-butyl-[[1-(2-fluoro-4-nitro-phenyl)-4-piperidyl]oxy]-dimethyl-silane (4, 250 mg, 0.705 mmol) in a mixture of EtOH (4 mL) and water (1 mL) were added Iron powder (196.92 mg, 3.53 mmol) and Ammonium chloride (377.24 mg, 7.05 mmol) at ambient temperature under nitrogen atmosphere. The resulting suspension was heated to 80° C. for 4 h. After completion, the reaction mixture was cooled to ambient temperature and filtered through a pad of Celite, washing with EtOAc (50 mL). The combined filtrate was diluted with water (30 mL) and the product was extracted with EtOAc (2×50 mL). The organic phases were combined, dried (anhydrous $Na_2SO_4$), filtered and concentrated under reduced pressure to get 4-[4-[tert-butyl(dimethyl)silyl]oxy-1-piperidyl]-3-fluoro-aniline (5, 200 mg, 0.537 mmol, 76% yield) as a green gummy oil. LCMS ($ES^+$): 325.2 $[M+H]^+$.

Step 4: Into a 100 mL sealed-tube reactor containing a well-stirred solution of 4-[4-[tert-butyl(dimethyl)silyl]oxy-1-piperidyl]-3-fluoro-aniline (5, 900 mg, 2.77 mmol) in anhydrous DMF (10 mL) were added Sodium bicarbonate (1.16 g, 13.87 mmol) and 3-bromopiperidine-2,6-dione (6, 852.04 mg, 4.44 mmol) at rt under nitrogen atmosphere. The reaction mixture was heated at 80° C. for 48 h. After completion, the reaction mixture was cooled to room temperature, poured into water (100 mL) and extracted with EtOAc (2×100 mL). The organic phases were combined and washed with brine (100 mL). The combined organic phase was dried (anhydrous $Na_2SO_4$), filtered and the filtrate was concentrated under reduced pressure to get a crude, which was purified by flash silica-gel (230-400 mesh) column with 0-100% EtOAc/pet ether to afford 3-[4-[4-[tert-butyl(dimethyl)silyl]oxy-1-piperidyl]-3-fluoro-anilino]piperidine-2,6-dione (7, 450 mg, 0.943 mmol, 34% yield) as a black gummy liquid. LCMS ($ES^+$): 436.2 $[M+H]^+$.

Step 5: Into a 100 mL single-necked round-bottomed flask containing a well-stirred solution of 3-[4-[4-[tert-butyl(dimethyl)silyl]oxy-1-piperidyl]-3-fluoro-anilino]piperidine-2,6-dione (7, 350 mg, 0.803 mmol) in anhydrous DCM (0.75 mL) under nitrogen atmosphere were added dropwise 4M HCl in 1,4-dioxane (0.803 mmol, 1.0 mL) at 0° C. The reaction mixture was allowed to room temperature and stirred at ambient temperature for 2 h. After completion, the reaction mixture was concentrated under reduced pressure and co-distilled with DCM (2×25 mL) to afford 3-[3-fluoro-4-(4-hydroxy-1-piperidyl)anilino]piperidine-2,6-dione hydrochloride (8, 280 mg, 0.774 mmol, 96% yield) as an off-white solid. LCMS ($ES^+$): 322.2 $[M+H]^+$.

Step 6: Into a 50 mL single-necked round-bottomed containing a well-stirred solution of 3-[3-fluoro-4-(4-hydroxy-1-piperidyl)anilino]piperidine-2,6-dione hydrochloride (8, 335 mg, 1.04 mmol) in anhydrous DMSO (2.5 mL) were added DCM (7.5 mL), TEA (3.16 g, 31.27 mmol, 4.36 mL) and pyridine,sulfur trioxide (1.66 g, 10.42 mmol) under nitrogen atmosphere at 0° C. The resulting mixture was stirred at room temperature for 24 h. After completion of the reaction, the mixture was poured into ice-water (50 mL) and extracted with EtOAc (2×50 mL). The organic phases were combined and washed with brine (25 mL). The combined organic phases were dried (anhydrous $Na_2SO_4$), filtered and the filtrate was concentrated under reduced pressure to get a crude residue which was purified by flash silica-gel (230-400 mesh) column with 0-100% EtOAc/pet ether followed by 0-10% MeOH/DCM to afford 3-[3-fluoro-4-(4-oxo-1-piperidyl)anilino]piperidine-2,6-dione (9, 70 mg, 0.076 mmol, 7% yield) as a black thick liquid. LCMS ($ES^+$): 319.8 $[M+H]^+$.

Example 29: Synthesis of 3-(4-(Piperidin-4-yl)phenyl)piperidine-2,6-dione hydrochloride salt

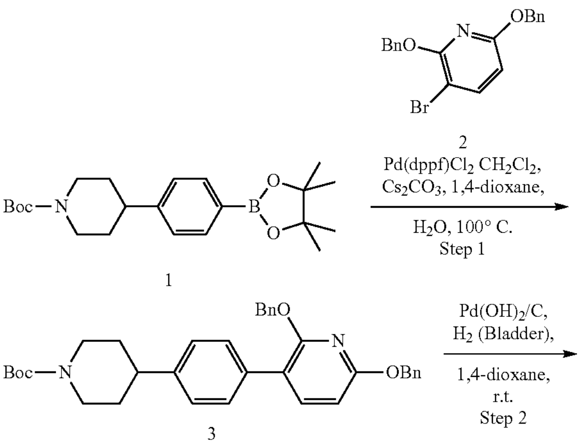

-continued

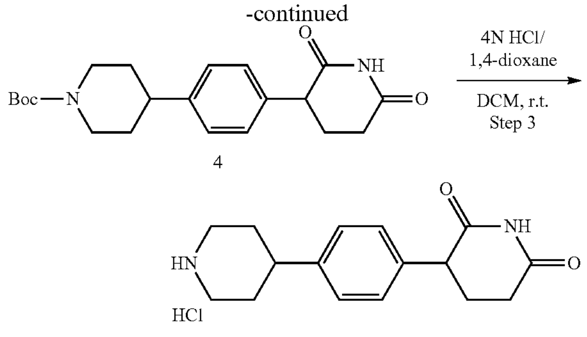

4

5

Step 1. Into a 100 ml sealed-tube reactor containing a well-stirred solution of tert-butyl 4-[4-(4,4,5,5-tetramethyl-1,3,2-dioxaborolan-2-yl)phenyl]piperidine-1-carboxylate (1; 400 mg, 1.03 mmol) and 2,6-dibenzyloxy-3-bromo-pyridine (2; 421 mg, 1.14 mmol) in 1,4-dioxane (6 mL) was added a solution of cesium carbonate (1.01 g, 3.10 mmol) in water (2 mL) at ambient temperature under nitrogen atmosphere and the resulting mixture was degassed by bubbling nitrogen gas into the reaction mixture for 10 minutes. Subsequently, 1,1'-Bis(diphenylphosphino)ferrocene-palladium(II)dichloride complexed with dichloromethane (84 mg, 0.103 mmol) was added to the reaction mixture and reaction mixture was heated to 100° C. for 3 h. After completion of the reaction as indicated by TLC, the reaction mixture was cooled to room temperature and poured into water (30 ml) and extracted with EtOAc (2×50 ml). Organic phases were combined and washed with brine (100 mL). Combined organic phases were dried (anhydrous $Na_2SO_4$), filtered and the filtrate was concentrated under reduced pressure to get a crude residue, which was purified by column chromatography (silica-gel (230-400 mesh) column, gradient 0%-60% EtOAc in pet ether) to afford tert-butyl 4-[4-(2,6-dibenzyloxy-3-pyridyl)phenyl]piperidine-1-carboxylate (3; 500 mg, 0.872 mmol) as a brown solid. Yield-85%; LC MS: ES+ (M+H) 551.2.

Step 2. Into a 100 mL single-necked round-bottomed flask containing a well-stirred suspension of tert-butyl 4-[4-(2,6-dibenzyloxy-3-pyridyl)phenyl]piperidine-1-carboxylate (3; 500 mg, 0.907 mmol) in 1,4-dioxane (20 mL) was added Palladium hydroxide on carbon, 20 wt. % with 50% water (383 mg, 2.72 mmol) at ambient temperature under hydrogen atmosphere (Bladder). The resulting suspension was stirred at ambient temperature under hydrogen atmosphere for 16 h. After complete consumption of the starting material as indicated by LCMS and TLC, the reaction mixture was filtered through a pad of Celite and the Celite bed was washed with EtOAc (15 mL). The combined filtrate was concentrated under reduced pressure to afford tert-butyl 4-[4-(2,6-dioxo-3-piperidyl)phenyl]piperidine-1-carboxylate (4; 320 mg, 0.827 mmol) as an off-white solid, which was carried forward without further purification. Yield-91%; LC MS: ES+ (M-Boc+H) 273.2

Step 3. Into a 100 mL single-necked round-bottomed flask containing a well-stirred solution of tert-butyl 4-[4-(2,6-dioxo-3-piperidyl)phenyl]piperidine-1-carboxylate (4; 320 mg, 0.859 mmol) in anhydrous DCM (2 mL) was added hydrogen chloride, 4 N in 1,4-dioxane (800 mg, 21.94 mmol, 1 mL) at ambient temperature under nitrogen atmosphere. The resulting mixture was stirred at ambient temperature for 2 h. After completion of reaction, the reaction mixture was concentrated under reduced pressure and washed with DCM followed by MTBE to afford 3-[4-(4-piperidyl)phenyl]piperidine-2,6-dione hydrochloric acid salt (5; 250 mg, 0.745 mmol) as an off-white solid, which was carried forward without further purification. Yield-86%; LC MS: ES+ (M+H) 273.2.

Example 30: Synthesis of 2-(4-(4-((2,6-Dioxopiperidin-3-yl)amino)phenyl)piperidin-1-yl)acetic acid

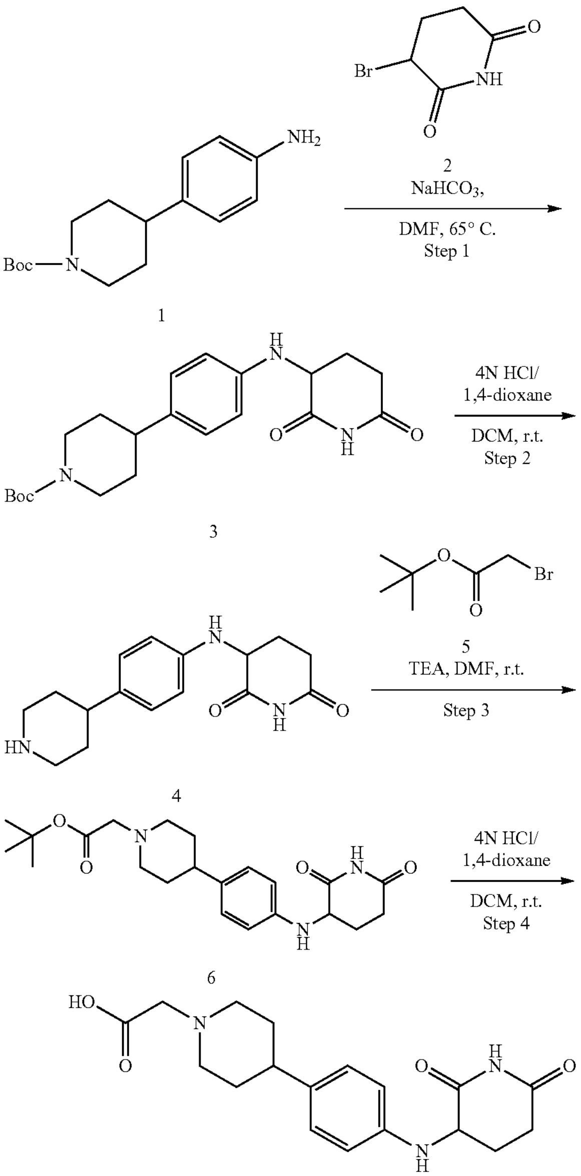

2

1

3

5

4

6

7

Step 1. Into a 100 mL sealed tube was taken tert-butyl 4-(4-aminophenyl)piperidine-1-carboxylate (1; 2 g, 7.24 mmol) and 3-bromopiperidine-2,6-dione (2; 2.08 g, 10.85 mmol) in anhydrous DMF (15 mL) at ambient temperature. To the resulting reaction mixture was added sodium bicarbonate (1.82 g, 21.71 mmol, 0.844 mL) at ambient temperature. The reaction mixture was stirred at 65° C. for 16 h. The progress of the reaction was monitored by LCMS and desired product mass was found in the reaction monitoring crude. Ice-water (30 mL) was added to the tube and the reaction mixture was stirred for 5 minutes. Desired product was precipitated out and the precipitate was filtered through buchner funnel and the solid thus obtained was dried under vacuum to afford tert-butyl 4-[4-[(2,6-dioxo-3-piperidyl) amino]phenyl]piperidine-1-carboxylate (3; 3.1 g, 6.81 mmol) as an off-white solid, which was carried forward without further purification. Yield-94%; LC MS: ES+ (M-Boc+H) 288.1.

Step 2. In a 100 mL single-necked round-bottomed flask was taken tert-butyl 4-[4-[(2,6-dioxo-3-piperidyl)amino] phenyl]piperidine-1-carboxylate (3; 3.1 g, 6.81 mmol) in dry DCM (10 mL) at ambient temperature. To the resulting mixture was added hydrogen chloride solution, 4 N in 1,4-dioxane (15 mL, 329.12 mmol) at 0° C. and then reaction mixture was stirred at ambient temperature for 2 h. Reaction was monitored by UPLC. After completion, solvent was removed under high vacuo to get a crude. The crude was triturated twice with $Et_2O$ (20 mL) to afford 3-[4-(4-piperidyl)anilino]piperidine-2,6-dione (4; 3.5 g, 8.75 mmol) as an off-white solid, which was carried forward without further purification. Yield-97%; LC MS: ES+ (M+H) 288.2.

Step 3. Into a 100 mL single-necked round-bottomed flask was taken 3-[4-(4-piperidyl)anilino]piperidine-2,6-dione (4; 3.1 g, 10.79 mmol) and tert-butyl 2-bromoacetate (5; 2.53 g, 12.95 mmol, 1.90 mL) in anhydrous DMF (15 mL) at ambient temperature under nitrogen atmosphere. To the resulting reaction mixture was added triethylamine, 99% (3.27 g, 32.36 mmol, 4.51 mL) at ambient temperature. The reaction mixture was stirred at ambient temperature for 16 h under $N_2$ atmosphere. The progress of the reaction was monitored by LCMS and found complete after 16 h. After completion, the reaction mixture was diluted with water (30 mL) and extracted with EtOAc (3×100 mL). The combined organic layers were washed with brine, dried (anhydrous $Na_2SO_4$), filtered and the filtrate was concentrated under reduced pressure to get a crude mass. The crude product was purified by column chromatography (silica-gel column (230-400 mesh, 100 g), gradient 0%-100% EtOAc in pet ether) to afford tert-butyl 2-[4-[4-[(2,6-dioxo-3-piperidyl) amino]phenyl]-1-piperidyl]acetate (6; 2.2 g, 4.78 mmol) as a pale green fluffy solid. Yield-45%; LC MS: ES+ (M+H) 402.1.

Step 4. In a 100 mL single-necked round-bottomed flask was taken tert-butyl 2-[4-[4-[(2,6-dioxo-3-piperidyl)amino] phenyl]-1-piperidyl]acetate (6; 1.2 g, 2.99 mmol) in dry DCM (10 mL) at ambient temperature under nitrogen atmosphere. To the resulting mixture was added hydrogen chloride solution 4 N in 1,4-dioxane (10 mL, 219.42 mmol) at 0° C. and then reaction mixture was stirred at ambient temperature for 16 h. After completion of the reaction as monitored by UPLC, solvent was removed under high vacuo and triturated twice with $Et_2O$ (2×10 mL) to afford 2-[4-[4-[(2,6-dioxo-3-piperidyl)amino]phenyl]-1-piperidyl]acetic acid hydrochloride (7; 1 g, 2.33 mmol) as an off-white solid, which was carried forward without further purification. Yield-78%; LC MS: ES+ (M+H) 346.0.

Example 31: Synthesis of 2-(4-(4-((2,6-Dioxopiperidin-3-yl)amino)-2-fluorophenyl)piperidin-1-yl) acetic acid

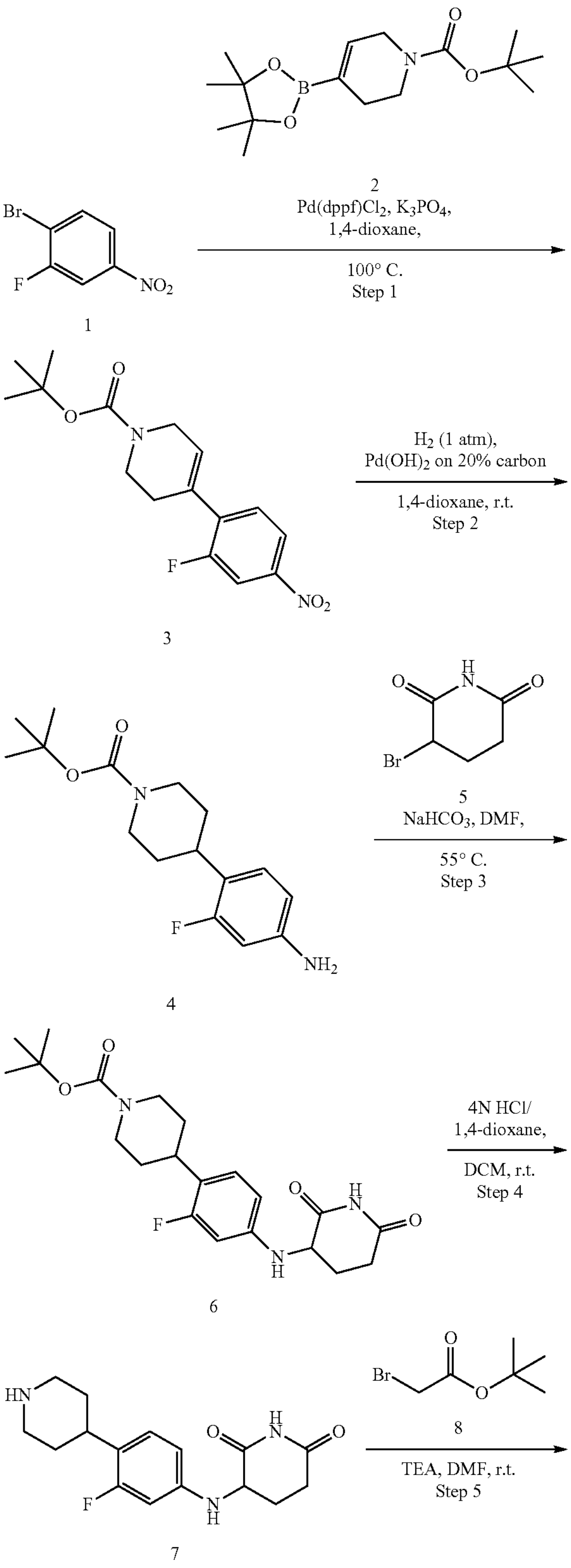

-continued

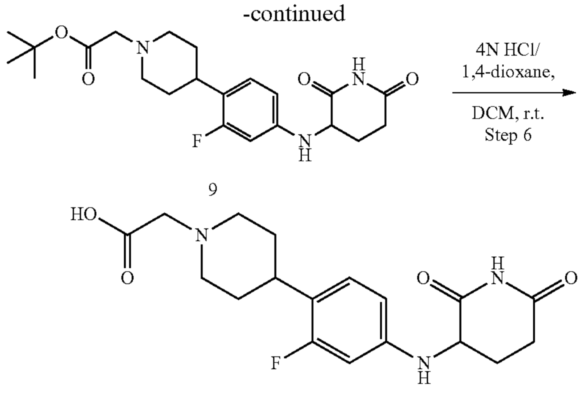

9

10

Step 1. Into a 250 mL sealed-tube containing a well stirred solution of tert-butyl 4-(4,4,5,5-tetramethyl-1,3,2-dioxaborolan-2-yl)-3,6-dihydro-2H-pyridine-1-carboxylate (2; 21.08 g, 68.18 mmol) and 1-bromo-2-fluoro-4-nitro-benzene (1; 10.0 g, 45.46 mmol) in 1,4-dioxane (100 mL) was added potassium phosphate tribasic anhydrous (28.95 g, 136.37 mmol) and the resulting mixture was purged with nitrogen for 15 minutes. Subsequently, 1,1'Bis(diphenylphosphino)ferrocene]dichloropalladium(II) complexed with dichloromethane (2.60 g, 3.18 mmol) was added to the reaction mixture and reaction mixture was purged with nitrogen for 10 minutes. Later, the reaction contents were heated with stirring at 100° C. for 5 h. The progress of the reaction was monitored by UPLC. After complete consumption of the starting material, the reaction mixture was diluted with water (200 mL) and extracted with EtOAc (2×100 mL). The combined organic layers were washed with brine (100 mL), dried (anhydrous $Na_2SO_4$), filtered, and the filtrate was concentrated under reduced pressure to get the crude. The crude mass was purified by column chromatography (silica-gel (230-400 mesh, 100 g), gradient of 0%-100% EtOAc in pet ether) to afford tert-butyl 4-(2-fluoro-4-nitro-phenyl)-3,6-dihydro-2H-pyridine-1-carboxylate (3; 12.0 g, 35.96 mmol) as a pale yellow-colored solid. Yield-79%; LC MS: ES+ (M+H) 321.1.

Step 2. A 500 mL single-necked round-bottomed flask containing a well stirred solution of tert-butyl 4-(2-fluoro-4-nitro-phenyl)-3,6-dihydro-2H-pyridine-1-carboxylate (3; 12.00 g, 37.23 mmol) in 1,4-dioxane (150 mL) was degassed by $N_2$ gas for 10 minutes, and 20% dry palladium hydroxide (2.5 g, 37.23 mmol) was added at ambient temperature. Later, the reaction mixture was stirred at room temperature for 48 h under hydrogen atmosphere (Bladder). After completion of the reaction as monitored by LCMS, reaction mixture was filtered through a pad of Celite and the Celite bed was washed with EtOAc (200 mL). The filterate was concentrated under reduced pressure to get crude mixture of tert-butyl 4-(4-amino-2-fluoro-phenyl)piperidine-1-carboxylate (4; 10.0 g, 23.10 mmol) as a yellow liquid, which was carried forward without further purification. Yield-62%; LC MS: ES+ (M-Boc+H) 195.0.

Step 3. Into a 250 mL sealed-tube containing a well stirred solution of tert-butyl 4-(4-amino-2-fluoro-phenyl)piperidine-1-carboxylate (4; 10.0 g, 33.97 mmol) and 3-bromopiperidine-2,6-dione (5; 9.78 g, 50.96 mmol) in anhydrous DMF (130 mL) was added sodium bicarbonate (8.56 g, 101.91 mmol, 3.96 mL) at ambient temperature under nitrogen atmosphere. Later, the reaction contents were heated with stirring at 55° C. for 48 h. The progress of the reaction was monitored by TLC, starting material (~20%) remained intact, the reaction mixture was diluted with water (200 mL) and extracted with EtOAc (2×100 mL). Combined organic layers were washed with brine (100 mL), dried (anhydrous $Na_2SO_4$), filtered and the filtrate was concentrated under reduced pressure to get a crude mass. The crude was purified by column chromatography (silica-gel (230-400 mesh; 100 g SNAP), gradient of 0%-100% EtOAc in pet ether) to afford tert-butyl 4-[4-[(2,6-dioxo-3-piperidyl)amino]-2-fluoro-phenyl]piperidine-1-carboxylate (6; 7.0 g, 13.64 mmol) as pale blue-colored solid. Yield-40%; LC MS: ES− (M−H) 404.1.

Step 4. Into a 250 mL single-necked round-bottomed flask containing a well-stirred solution of tert-butyl 4-[4-[(2,6-dioxo-3-piperidyl)amino]-2-fluoro-phenyl]piperidine-1-carboxylate (6; 7 g, 17.26 mmol) in anhydrous DCM (150 mL) was added dropwise 4 N HCl in 1,4-dioxane (17.26 mmol, 17.2 mL) at 0° C. under nitrogen atmosphere. The resulting reaction mixture was stirred at ambient temperature for 2 h. After completion of the reaction as monitored by LCMS, excess solvent was removed from the reaction mixture under reduced pressure to get a crude, which was co-distilled with DCM to get 3-[3-fluoro-4-(4-piperidyl)anilino]piperidine-2,6-dione hydrochloric acid salt (7; 6 g, 14.92 mmol) as an ash-coloured solid, which was carried forward without further purification. Yield-86%; LC MS: ES+ (M+H) 306.0.

Step 5. Into a 250 mL single-necked round-bottomed flask containing a well stirred solution of 3-[3-fluoro-4-(4-piperidyl)anilino]piperidine-2,6-dione hydrochloric acid salt (7; 4 g, 13.10 mmol) and tert-butyl 2-bromoacetate (8; 2.81 g, 14.41 mmol, 2.11 mL) in anhydrous DMF (50 mL) was added TEA (3.98 g, 39.30 mmol, 5.48 mL) at ambient temperature under nitrogen atmosphere. The reaction mixture was stirred at ambient temperature for 4 h. Later, completion of the reaction was indicated by LCMS. The reaction mixture was diluted with water (100 mL) and extracted with EtOAc (2×70 mL). Combined organic layers were washed with brine (100 mL), dried (anhydrous $Na_2SO_4$), filtered and the filtrate was concentrated under reduced pressure to get a crude mass. The crude was purified by column chromatography (silica-gel (230-400 mesh; 100 g SNAP), gradient of 0%-100% EtOAc in pet ether) to afford tert-butyl 2-[4-[4-[(2,6-dioxo-3-piperidyl)amino]-2-fluoro-phenyl]-1-piperidyl]acetate (9; 4 g, 9.43 mmol) as a blue solid. Yield-72%; LC MS: ES+ (M+H) 420.3.

Step 6. Into a 250 mL single-necked round-bottomed flask containing a well-stirred solution of tert-butyl 2-[4-[4-[(2,6-dioxo-3-piperidyl)amino]-2-fluoro-phenyl]-1-piperidyl]acetate (9; 4.0 g, 9.54 mmol) in anhydrous DCM (40 mL) was added dropwise 4 N HCl in 1,4-dioxane (9.54 mmol, 20 mL) at 0° C. under nitrogen atmosphere. The resulting reaction mixture was stirred at ambient temperature for 2 h. After completion of the reaction as monitored by LCMS, excess solvent was removed from the reaction mixture under reduced pressure to get a crude mass. The crude mass was co-distilled with DCM and further triturated with $Et_2O$ to afford 2-[4-[4-[(2,6-dioxo-3-piperidyl)amino]-2-fluoro-phenyl]-1-piperidyl]acetic acid hydrochloride (10; 3.6 g, 8.30 mmol) as an off-white solid. Yield-87%; LC MS: ES+ (M+H) 364.1.

Example 32: Synthesis of 2-(1-(4-((2,4-Dioxotetrahydropyrimidin-1(2H)-yl)methyl)phenyl)-4-hydroxypiperidin-4-yl)acetic acid hydrochloric acid salt

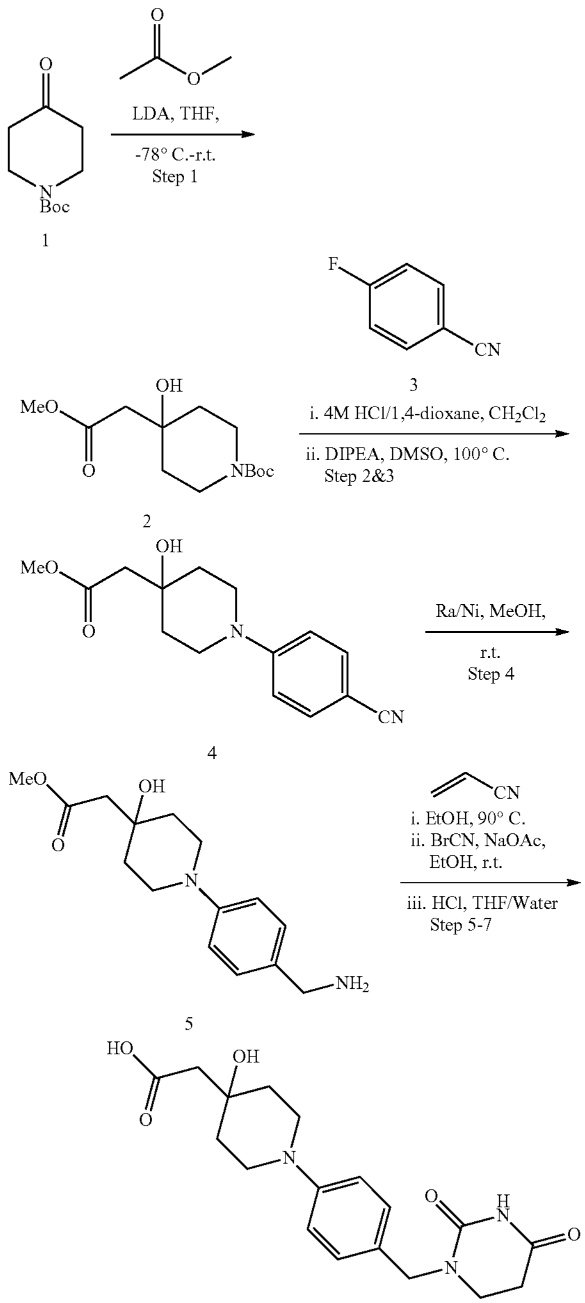

Step 1. Into a 500 mL three-necked round-bottomed flask containing a well-stirred solution of methyl acetate (4.46 g, 60.23 mmol, 4.78 mL; 99% grade) in anhydrous THF (50 mL) was added (diisopropylamino)lithium (10.75 g, 100.38 mmol) at −78° C. under a nitrogen atmosphere and the resulting mixture was stirred for 1 h. Subsequently, tert-butyl 4-oxopiperidine-1-carboxylate (1; 10 g, 50.19 mmol) in anhydrous THF (50 mL) was added dropwise at −78° C. and allowed to stir at ambient temperature for 2 h. The progress of the reaction was monitored by TLC. After completion of the reaction, the reaction mixture was treated with saturated $NH_4Cl$ solution (100 mL) and the aqueous phase was extracted with EtOAc (2×100 mL). The combined organic phases were washed with brine, dried (anhydrous $Na_2SO_4$), filtered and the filtrate was concentrated under reduced pressure to afford a crude residue which was purified by silica-gel (230-400 mesh) column chromatography with 3:7 EtOAc in pet ether to afford tert-butyl 4-hydroxy-4-(2-methoxy-2-oxo-ethyl)piperidine-1-carboxylate (2; 7 g, 24.84 mmol) as a yellow gummy liquid. Yield-49.5%; LC MS: ES+ (M-Boc+H) 174.0.

Step 2: Into a 250 mL single-necked round-bottomed flask containing a well-stirred solution of tert-butyl 4-hydroxy-4-(2-methoxy-2-oxo-ethyl)piperidine-1-carboxylate (2; 2.8 g, 10.24 mmol) in anhydrous $CH_2Cl_2$ (10 mL) was added 4 N HCl in 1,4-dioxane (10.24 mmol, 20 mL) at ambient temperature under a nitrogen atmosphere. The resulting mixture was stirred at ambient temperature for 2 h and found complete. Excess solvents were removed from the reaction mixture under reduced pressure to get a crude mass. The crude mass was triturated with $Et_2O$ (10 mL) to afford methyl 2-(4-hydroxy-4-piperidyl)acetate (Int.; 2 g, 9.52 mmol) as a yellow solid. Yield-93%; LC MS: ES+ (M+H) 174.0.

Step 3. Into a 100 mL sealed tube containing a mixture of 4-fluorobenzonitrile (3; 1.16 g, 9.54 mmol) and methyl 2-(4-hydroxy-4-piperidyl)acetate (Int. from step 2; 2 g, 9.54 mmol) in anhydrous DMSO (10 mL) was added DIPEA (1.23 g, 9.54 mmol, 1.66 mL) under a nitrogen atmosphere at ambient temperature. The resulting mixture was heated at 100° C. for 16 h. After completion of the reaction as indicated by TLC, the reaction mixture was cooled to room temperature, poured into water (50 mL) and extracted with EtOAc (2×75 mL). The combined organic phases were washed with brine, dried (anhydrous $Na_2SO_4$), filtered and the filtrate was concentrated under reduced pressure to afford a crude residue which was purified by silica-gel (230-400 mesh) column chromatography with 4:6 EtOAc in pet ether to afford methyl 2-[1-(4-cyanophenyl)-4-hydroxy-4-piperidyl]acetate (4; 1.9 g, 6.72 mmol) as a brown solid. Yield-70.4%; LC MS: ES+ (M+H) 275.1.

Step 4. Into a 50 mL single-necked round-bottomed flask containing a well-stirred solution of methyl 2-[1-(4-cyanophenyl)-4-hydroxy-4-piperidyl]acetate (4; 200 mg, 0.73 mmol) in MeOH (8 mL) was added Raney Nickel in $H_2O$ (200 mg, 2.33 mmol) at ambient temperature under a nitrogen atmosphere. The resulting suspension was stirred at ambient temperature under a hydrogen atmosphere (balloon) for 16 h. After complete consumption of the starting material as indicated by TLC, reaction mixture was filtered through a pad of Celite and the Celite bed was washed with MeOH (50 mL). The filtrate was concentrated under reduced pressure to afford methyl 2-[1-[4-(aminomethyl)phenyl]-4-hydroxy-4-piperidyl]acetate (5; 200 mg, 0.72 mmol) as an off-white solid, which was carried forward without further purification. Yield-70.4%; LC MS: ES+ (M+H) 278.9.

Step 5: A 25 mL sealed tube containing a mixture of methyl 2-[1-[4-(aminomethyl)phenyl]-4-hydroxy-4-piperidyl]acetate (5; 200 mg, 0.72 mmol) and acrylonitrile (45.75 mg, 0.86 mmol, 0.06 mL) in EtOH (5 mL) was heated at 90° C. for 3 h. After completion of the reaction as indicated by TLC, the reaction mixture was cooled to room temperature and the reaction mixture was concentrated under reduced pressure to afford a mixture of methyl 2-[1-[4-[(2-cyanoethylamino)methyl]phenyl]-4-hydroxy-4-piperidyl]acetate and ethyl 2-(1-(4-(((2-cyanoethyl)amino)methyl)phenyl)-4-hydroxypiperidin-4-yl)acetate (Int.; 200 mg, 0.29 mmol) as a colorless liquid. Yield-40.3%; LC MS: ES+ (M+H) 331.2 (Me ester), (M+H) 346.3 (Ethyl ester).

Step 6. Into a 50 mL two-necked round-bottomed flask containing a solution of methyl 2-[1-[4-[(2-cyanoethyl-amino)methyl]phenyl]-4-hydroxy-4-piperidyl]acetate (Int. from Step 5; 200 mg, 0.60 mmol) in EtOH (4 mL) were added cyanogen bromide (63.92 mg, 0.60 mmol, 31.64 μL) and anhydrous $Na_2CO_3$ (49.51 mg, 0.60 mmol) at ambient temperature under a nitrogen atmosphere.

The resulting mixture was stirred at ambient temperature for 16 h. After completion of the reaction as indicated by TLC, the reaction mixture was cooled to room temperature and poured into water (50 mL) and extracted with EtOAc (2×60 mL). The combined organic phases were washed with brine, dried (anhydrous $Na_2SO_4$), filtered and the filtrate was concentrated under reduced pressure to afford methyl 2-[1-[4-[[cyano(2-cyanoethyl)amino]methyl]phenyl]-4-hydroxy-4-piperidyl]acetate (Int.; 220 mg, 0.40 mmol) as a crude brown liquid. Yield-66.5%; LC MS: ES+(M+H) 357.2 (Me ester), (M+H) 371.1 (Ethyl ester). Note: Crude having both Ethyl and methyl ester were taken to the next step.

Step 7. Into a 25 mL sealed tube containing a mixture of methyl 2-[1-[4-[[cyano(2-cyanoethyl)amino]methyl]phenyl]-4-hydroxy-4-piperidyl]acetate and ethyl 2-(1-(4-((N-(2-cyanoethyl)cyanamido)methyl)phenyl)-4-hydroxypiperidin-4-yl)acetate (Int. from Step 6; 220 mg, 0.62 mmol) in THF (2 mL) was added HCl (617 mmol, 4 mL; 6N/$H_2O$) at ambient temperature and the resulting mixture was heated at 100° C. for 2 h. After completion of the reaction as indicated by TLC, the reaction mixture was cooled to room temperature and concentrated under reduced pressure to afford 2-[1-[4-[(2,4-dioxohexahydropyrimidin-1-yl)methyl]phenyl]-4-hydroxy-4-piperidyl]acetic acid hydrochloric acid salt (6; 250 mg, 0.52 mmol) as a brown gummy solid. Yield-85.2%; LC MS: ES− (M−H) 360.1.

Example 33: Synthesis of 2-(1-(4-((2,6-Dioxopiperidin-3-yl)amino)-2-fluorophenyl)-4-hydroxypiperidin-4-yl)acetic acid hydrochloric acid salt

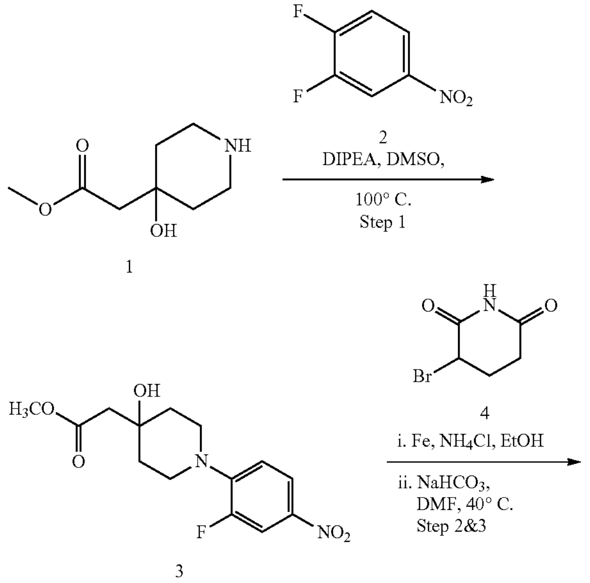

-continued

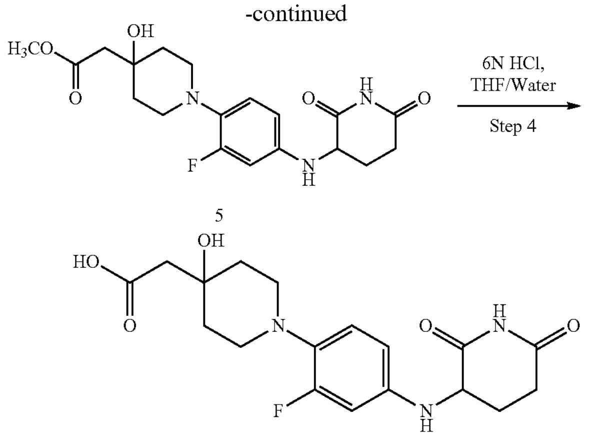

6

Step 1. Into a 100 mL sealed tube containing a mixture of methyl 2-(4-hydroxy-4-piperidyl)acetate (1; 1.5 g, 7.15 mmol) and 1,2-difluoro-4-nitro-benzene (2; 1.14 g, 7.15 mmol, 0.8 mL) in anhydrous DMSO (10 mL) was added DIPEA (924.60 mg, 7.15 mmol, 1.25 mL) at ambient temperature under a nitrogen atmosphere. The resulting mixture was heated at 100° C. for 16 h. After completion of the reaction as indicated by TLC, the reaction mixture was cooled to room temperature and poured into water (100 mL) and the aqueous phase was extracted with EtOAc (2×75 mL). The combined organic phases were washed with brine, dried (anhydrous $Na_2SO_4$), filtered and the filtrate was concentrated under reduced pressure to afford a crude residue which was purified by flash silica-gel (230-400 mesh) column chromatography with 2:3 EtOAc/pet ether to afford methyl 2-[1-(2-fluoro-4-nitro-phenyl)-4-hydroxy-4-piperidyl]acetate (3; 1.6 g, 4.20 mmol) as a brown-colored solid. Yield-58.7%; LC MS: ES+ (M+H) 313.1.

Step 2. Into a 50 mL two-necked round-bottomed flask containing a well-stirred solution of methyl 2-[1-(3-fluoro-4-nitro-phenyl)-4-hydroxy-4-piperidyl]acetate (3; 500 mg, 1.60 mmol) in water (2 mL) and EtOH (10 mL) were added Iron powder (447.06 mg, 8.01 mmol) and $NH_4Cl$ (171.29 mg, 3.20 mmol, 0.11 mL) at ambient temperature. The resulting mixture was heated to 90° C. and stirred for 2 h. After completion of the reaction as indicated by TLC, the reaction mixture was diluted with EtOAc (20 mL) and filtered through a pad of Celite. The filtrate was concentrated under reduced pressure to afford a crude residue. To the crude mass, water (50 mL) was added and the aqueous phase was extracted with EtOAc (2×75 mL), dried (anhydrous $Na_2SO_4$), filtered and the filtrate was concentrated under reduced pressure to afford methyl 2-[1-(4-amino-3-fluoro-phenyl)-4-hydroxy-4-piperidyl]acetate (Int.; 440 mg, 1.20 mmol) as a brown-colored solid. Yield-75%; LC MS: ES+ (M+H) 283.0.

Step 3. Into a 50 mL sealed tube containing a well-stirred solution of methyl 2-[1-(4-amino-3-fluoro-phenyl)-4-hydroxy-4-piperidyl]acetate (Int. from Step-2; 440 mg, 1.20 mmol) and 3-bromopiperidine-2,6-dione (4; 448.89 mg, 2.34 mmol) in anhydrous DMF (10 mL) was added $NaHCO_3$ (392.79 mg, 4.68 mmol, 181.85 μL) at ambient temperature under a nitrogen atmosphere. The resulting mixture was heated to 40° C. and stirred for 16 h. TLC indicated 20% of starting material still unreacted. Again, 1 eq of 3-bromopiperidine-2,6-dione (4; 448.89 mg, 2.34 mmol) was added to the reaction mixture and continued to stir for 16 h. After completion of the reaction as indicated by TLC, the reaction mixture was diluted with ice-water and the aqueous phase was extracted with EtOAc (2×75 mL). The combined organic phases were washed with brine, dried (anhydrous $Na_2SO_4$), filtered and the filtrate was concentrated under reduced pressure to afford a residue that was purified by flash silica-gel (230-400 mesh) column chromatography with 7:3 EtOAc/pet ether to get methyl 2-[1-[4-[(2,6-dioxo-3-piperidyl)amino]-2-fluoro-phenyl]-4-hydroxy-4-piperidyl]acetate (5; 380 mg, 0.74 mmol) as a brown gum. Yield-47.7%; LC MS: ES+(M+H) 394.2.

Step 4. Into a 25 mL single-necked round-bottomed flask containing a well-stirred solution of methyl 2-[1-[4-[(2,6-dioxo-3-piperidyl)amino]-3-fluoro-phenyl]-4-hydroxy-4-piperidyl]acetate (5; 60 mg, 0.15 mmol) in THF (2 mL) was added HCl (2 mL; 6N/water) and the resulting mixture was stirred at ambient temperature for 16 h. Excess solvents were removed from the reaction mixture under reduced pressure to get a crude mass. The crude mass was triturated with $Et_2O$ (10 mL) to afford 2-[1-[4-[(2,6-dioxo-3-piperidyl)amino]-3-fluoro-phenyl]-4-hydroxy-4-piperidyl]acetic acid hydrochloric acid salt (6; 50 mg, 0.09 mmol) as a brown solid. Yield-62.3%; LC MS: ES+ (M+H) 380.2.

Example 34: Synthesis of (R)- and (S)-2-[1-[2-chloro-4-[(2,6-dioxo-3-piperidyl)amino]phenyl]-4-hydroxy-4-piperidyl]acetic acid hydrochloric acid salt

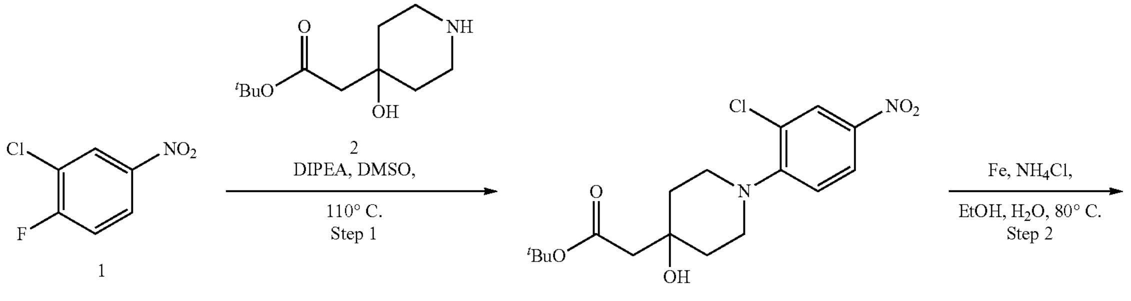

3

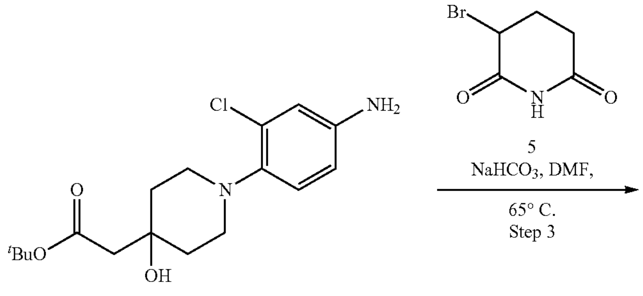

4

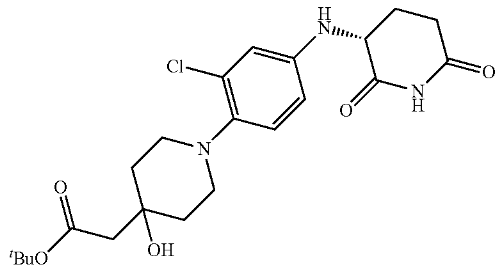

6a

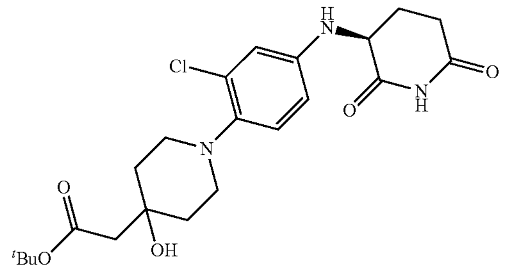

6b

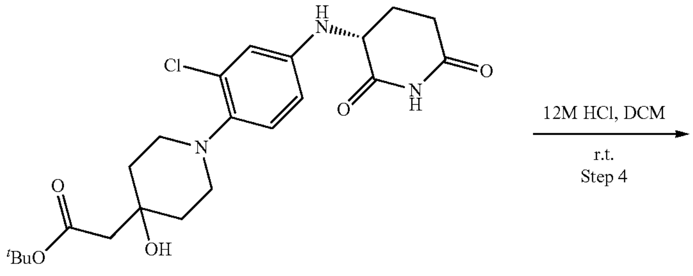

6a

-continued

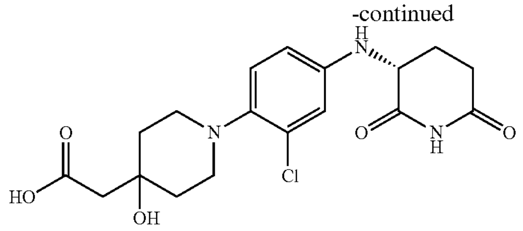

7a

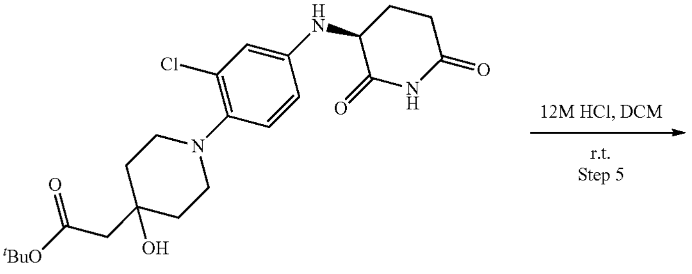

6b

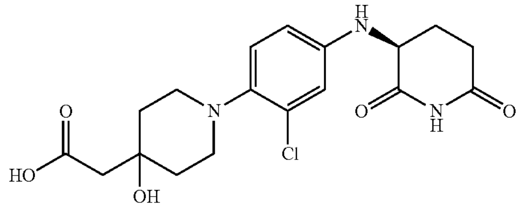

7b

Step 1. Into a 250 mL sealed tube containing a well-stirred solution of a mixture of 2-chloro-1-fluoro-4-nitro-benzene (1; 2 g, 11.39 mmol, 0.790 mL) and tert-butyl 2-(4-hydroxy-4-piperidyl)acetate (2; 2.7 g, 12.53 mmol) in anhydrous DMSO (20 mL) was added DIPEA (5.95 mL, 34.18 mmol) at ambient temperature. The resulting reaction mixture was stirred at 100° C. for 16 h. After completion of the reaction as indicated by LCMS, the reaction mixture was treated with ice-cold water (100 mL) and a solid precipitated out which was filtered. The filtered solid was dried under vacuum to afford tert-butyl 2-[1-(2-chloro-4-nitro-phenyl)-4-hydroxy-4-piperidyl]acetate (3; 3.3 g, 8.54 mmol) as a brown solid. Yield 75%; LC MS: ES+ (M+H) 371.2.

Step 2. Into a 250 mL three-necked round-bottomed flask containing a well-stirred solution of tert-butyl 2-[1-(2-chloro-4-nitro-phenyl)-4-hydroxy-4-piperidyl]acetate (3; 3.30 g, 8.90 mmol) in a mixture of EtOH (50 mL) and water (10 mL) were added ammonium chloride (952 mg, 17.80 mmol) and Iron powder (2.49 g, 44.50 mmol) at ambient temperature under nitrogen atmosphere. The resulting mixture was stirred at 90° C. for 2 h. After completion of the reaction as indicated by LCMS, the reaction mixture cooled to ambient temperature and was filtered through a pad of Celite which was washed with EtOAc (150 mL). The combined filtrate was concentrated under reduced pressure to afford a crude mass. Water (100 mL) was added to the crude mass and the aqueous layer was extracted with EtOAc (2×150 mL). Organic phases were combined, dried (anhydrous $Na_2SO_4$), filtered and the filtrate was concentrated under reduced pressure to afford crude residue. The crude material was purified by column chromatography (flash silica-gel (230-400 mesh) column, gradient of 0%-100% EtOAc in pet ether) to afford tert-butyl 2-[1-(4-amino-2-chloro-phenyl)-4-hydroxy-4-piperidyl]acetate (4; 2.9 g, 8.42 mmol) as a brown gummy liquid. Yield 95%; LC MS: ES+ (M+H) 341.2.

Step 3. Into a 250 mL three-necked round-bottomed flask containing a well-stirred solution of tert-butyl 2-(1-(4-amino-2-chlorophenyl)-4-hydroxypiperidin-4-yl)acetate (4; 2.9 g, 8.42 mmol) and 3-bromopiperidine-2,6-dione (5; 2.45 g, 12.76 mmol) in anhydrous DMF (30 mL) was added Sodium bicarbonate (2.14 g, 25.52 mmol) at ambient temperature under nitrogen atmosphere. The resulting reaction contents were stirred at 65° C. for 16 h. An additional 1.5 eq of 3-bromopiperidine-2,6-dione (2.45 g, 12.76 mmol) and 1.5 eq of Sodium bicarbonate (2.14 g, 25.52 mmol) were added and stirring was continued at 65° C. for 16 h. Water (100 mL) was added and aqueous layer was extracted with EtOAc (2×150 mL). Organic layers were combined, dried (anhydrous $Na_2SO_4$), filtered and the filtrate was concentrated under reduced pressure to afford crude residue which was purified by column chromatography (flash silica-gel (230-400 mesh) column, gradient of 0%-100% EtOAc in pet ether) to afford tert-butyl 2-[1-[2-chloro-4-[(2,6-dioxo-3-piperidyl)amino]phenyl]-4-hydroxy-4-piperidyl]acetate (a mixture of 6a and 6b; 3.6 g, 7.73 mmol) as a black gummy liquid. Yield 91%; LC MS: ES+ (M+H) 452.2.

SFC Conditions to Separate 6a & 6b (Chirality Arbitrarily Assigned):

| | | |
|---|---|---|
| Instrument | Waters 350 Preparative SFC system | |
| Column | Regis(s,s)Whelk-O1 column, 250 x 50 mm I.D., 10 um particle size; | |
| Mobile Phase | Phase A for Supercritical $CO_2$ | Phase B for EtOH |

-continued

| | |
|---|---|
| Isocratic elution | 40% Phase B, 60% Phase A |
| Flow rate | 200 g/min |
| cycle time | 6.5 min |
| Back Pressure | 100 bar to keep the CO2 in Supercritical flow |
| UV | 220 nm |

6a: $^1$H NMR (400 MHz, DMSO-$d_6$): δ 10.76 (s, 1H), 6.95 (d, 1H), 6.74 (d, 1H), 6.60-6.58 (m, 1H), 5.82 (d, 1H), 4.45 (s, 1H), 4.32-4.24 (m, 1H), 2.92-2.83 (m, 2H), 2.81-2.75 (m, 2H), 2.74-2.68 (m, 1H), 2.59 (t, 1H), 2.35 (s, 2H), 2.11-2.03 (m, 1H), 1.86-1.84 (m, 1H), 1.82-1.73 (m, 2H), 1.69-1.60 (m, 2H), 1.42 (s, 9H)

6b: $^1$H NMR (400 MHz, DMSO-$d_6$): δ 10.76 (s, 1H), 6.95 (d, 1H), 6.74 (d, 1H), 6.60-6.58 (m, 1H), 5.82 (d, 1H), 4.45 (s, 1H), 4.32-4.24 (m, 1H), 2.91-2.83 (m, 2H), 2.81-2.76 (m, 2H), 2.73-2.66 (m, 1H), 2.59 (t, 1H), 2.35 (s, 2H), 2.11-2.03 (m, 1H), 1.86-1.84 (m, 1H), 1.82-1.74 (m, 2H), 1.68-1.61 (m, 2H), 1.41 (s, 9H)

SFC Condition:

Column: (S,S) Whelk-O1 100×4.6 mm I.D., 3.5 μm

Mobile phase: Phase A for CO2, and Phase B for EtOH (0.05% DEA); Gradient elution: 40% EtOH (0.05% DEA) in CO2; Flow rate: 3 mL/min; Detector: PDA; Column Temp: 35C; Back Pressure: 100 Bar Step 4: To a solution of tert-butyl (R)-2-(1-(2-chloro-4-((2,6-dioxopiperidin-3-yl)amino)phenyl)-4-hydroxypiperidin-4-yl)acetate (6a; 700 mg, 1.55 mmol) in DCM (15 mL) was added conc. HCl (12 M, 1.29 mL) at 0° C. The mixture was stirred at 20° C. for 1 h. LCMS showed the starting material was consumed and the desired mass was given. The reaction mixture was concentrated in vacuum. The reaction mixture was concentrated, then azeotroped with toluene (2×50 mL) and then with toluene/THF (50 mL: 50 mL). The residue was diluted with EtOAc (100 mL), the mixture was stirred at 15° C. for 12 h, then filtered and collected the filtered cake. (R)-2-(1-(2-chloro-4-((2,6-dioxopiperidin-3-yl)amino)phenyl)-4-hydroxypiperidin-4-yl)acetic acid hydrochloric acid salt (7a; 517.08 mg, 956.90 umol) was obtained as a yellow solid, which was carried forward without further purification. Yield-61.78%. LC MS ES+ (M+H): 396.0

Step 5: To a solution of tert-butyl (S)-2-(1-(2-chloro-4-((2,6-dioxopiperidin-3-yl)amino)phenyl)-4-hydroxypiperidin-4-yl)acetate (6b; 700.00 mg, 1.55 mmol) in DCM (15 mL) was added conc.HCl (12 M, 1.29 mL) at 0° C. The mixture was stirred at 20° C. for 1 h. LCMS showed the starting material was consumed and the desired mass was given. The reaction mixture was concentrated in vacuum. The reaction mixture was concentrated, then azeotroped with toluene (2×50 mL) and then with toluene/THF (50 mL: 50 mL). The residue was diluted with EtOAc (100 mL), the mixture was stirred at 15° C. for 12 h, then filtered and collected the filtered cake. (S)-2-(1-(2-chloro-4-((2,6-dioxopiperidin-3-yl)amino)phenyl)-4-hydroxypiperidin-4-yl) acetic acid hydrochloric acid salt (7b; 481.68 mg, 891.39 umol) was obtained as a gray solid, which was carried forward without further purification. Yield-57.55%. LC MS ES+ (M+H): 396.0

Synthesis of Intermediates

Example 35: Synthesis of 4-ethyl-N-phenylpiperidine-4-carboxamide

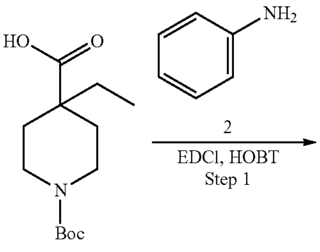

1

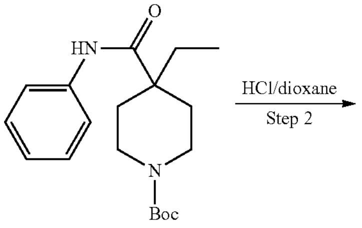

3

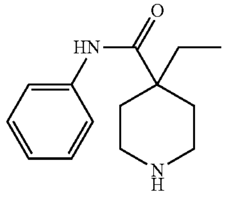

4

Step 1: To a solution of tert-butyl 4-ethyl-4-(phenylcarbamoyl)piperidine-1-carboxylate (1, 500 mg, 1.94 mmol, 576.70 μL), aniline (2, 235.24 mg, 2.53 mmol, 230.62 μL), EDCI (558.73 mg, 2.91 mmol) and HOBt (393.83 mg, 2.91 mmol) in DMF (5 mL) was added DIPEA (3.89 mmol, 676.89 μL). After addition, the solution was stirred at 30° C. for 12 hr. The reaction solution was poured into sat. $NH_4Cl$ (50 mL). The aqueous solution was extracted with EtOAc (50 mL×3), the combined organic layer was washed with brine (100 mL×2), dried over $Na_2SO_4$ and concentrated in vacuum. The residue was purified by flash silica gel chromatography (12 g Silica Flash Column, Eluent of 0-20% EA/PE 20 mL/min) to afford tert-butyl 4-ethyl-4-(phenylcarbamoyl)piperidine-1-carboxylate (3, 311 mg, 851.32 μmol, 44% yield) as white solid. LCMS (ES$^+$): 355.2 [M+Na]$^+$. $^1$H NMR (400 MHz, CHLOROFORM-d) δ=7.43 (d, J=7.6 Hz, 2H), 7.27 (t, J=8.0 Hz, 2H), 7.15 (br s, 1H), 7.10-7.03 (m, 1H), 3.73 (br dd, J=1.2, 3.6 Hz, 2H), 3.09 (br t, J=11.2 Hz, 2H), 2.01 (br d, J=13.2 Hz, 2H), 1.61-1.57 (m, 2H), 1.44 (m, 2H), 1.38 (s, 9H), 0.85 (t, J=7.6 Hz, 3H)

Step 2: To a solution of tert-butyl 4-ethyl-4-(phenylcarbamoyl)piperidine-1-carboxylate (3, 100 mg, 300.81 μmol) in DCM was added HCl/dioxane (4 M, 75.20 μL). After addition, the solution was stirred at 30° C. for 30 min. The reaction solution was concentrated in vacuum to afford 4-ethyl-N-phenylpiperidine-4-carboxamide (4, 80.85 mg, 285.76 μmol, 95% yield, HCl salt) as yellow solid.

Example 36: Synthesis of 4-ethyl-N-(4-fluorophenyl)piperidine-4-carboxamide

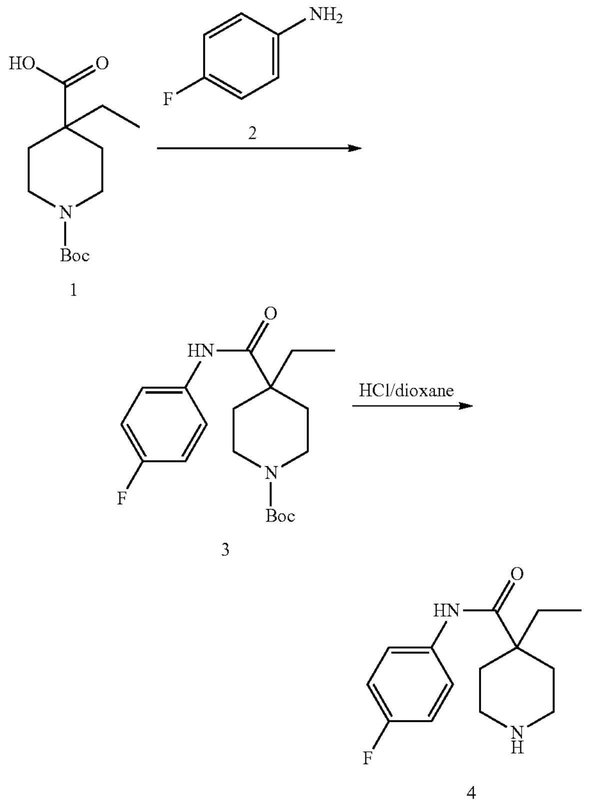

Step 1: To a solution of 1-(tert-butoxycarbonyl)-4-ethylpiperidine-4-carboxylic acid (1, 1 g, 3.89 mmol) in DCM (5 mL) was added thionyl chloride (536.31 mg, 4.51 mmol) and pyridine (768.48 mg, 9.72 mmol, 785.77 μL) at 25° C. The mixture was stirred at 25° C. for 0.5 h. N,N-diethylethanamine (1.18 g, 11.66 mmol, 1.62 mL) and 4-fluoroaniline (2, 464.00 mg, 4.18 mmol, 400.00 μL) was added to the mixture. The mixture was stirred at 25° C. for 12 h. The reaction mixture was quenched by addition of aq. $NaHCO_3$ (20 mL) at 10° C. and extracted with DCM (15 mL×3). The combined organic layers were washed with brine (50 mL×2), dried over $Na_2SO_4$, filtered and concentrated under reduced pressure. The residue was purified by column chromatography ($SiO_2$, Petroleum ether/Ethyl acetate=5/1 to 4/1) to afford tert-butyl 4-ethyl-4-((4-fluorophenyl)carbamoyl)piperidine-1-carboxylate (3, 650 mg, 1.67 mmol, 43% yield) as colorless oil. LCMS ($ES^+$): 295 $[M+H-tBu]^+$ Step 2: To a solution of tert-butyl 4-ethyl-4-((4-fluorophenyl)carbamoyl)piperidine-1-carboxylate (3, 600 mg, 1.71 mmol) in DCM (5 mL) was added HCl/dioxane (4 M, 4.28 mL). The mixture was stirred at 25° C. for 12 h. The reaction was concentrated under reduced pressure to get 4-ethyl-N-(4-fluorophenyl)piperidine-4-carboxamide (4, 490 mg, 1.55 mmol, 90.81% yield, HCl salt) as green solid, which was used without purification. LCMS ($ES^+$): m/z 251 $[M+H]^+$ Example 37: Synthesis of N-(tert-butyl)-4-ethylpiperidine-4-carboxamide hydrochloride

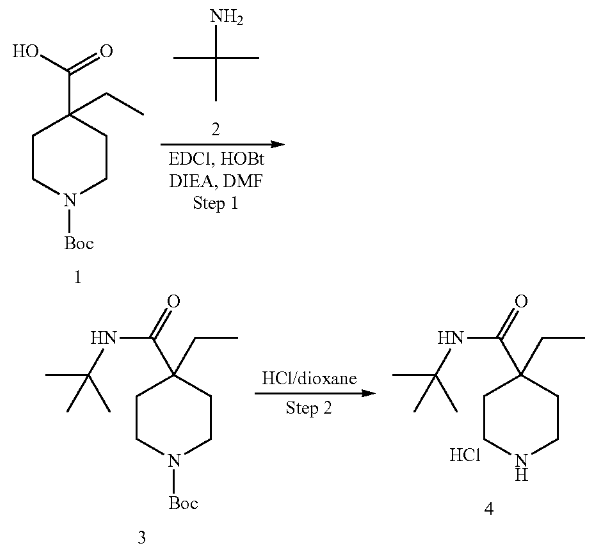

Step 1: To a solution of 1-(tert-butoxycarbonyl)-4-ethylpiperidine-4-carboxylic acid (1, 500 mg, 1.94 mmol, 576.70 μL), 2-methylpropan-2-amine (2, 170.53 mg, 2.33 mmol, 245.02 μL), EDCI (558.73 mg, 2.91 mmol) and HOBt (393.83 mg, 2.91 mmol) in DMF (5 mL) was added DIPEA (3.89 mmol, 676.89 μL). After addition, the solution was stirred at 30° C. for 12 hr. The reaction solution was poured into sat. $NH_4Cl$ (50 mL). The aqueous solution was extracted with EtOAc (50 mL×3), the combined organic layer was washed with brine (100 mL×2), dried over $Na_2SO_4$ and concentrated in vacuum. The residue was purified by flash silica gel chromatography (12 g Silica Flash Column, Eluent of 0-20% EtOAc/Pet ether 20 mL/min) to afford tert-butyl 4-(tert-butylcarbamoyl)-4-ethylpiperidine-1-carboxylate (3, 563 mg, 1.62 mmol, 84% yield) as white solid. $^1H$ NMR (400 MHz, CHLOROFORM-d) δ=3.68 (br d, J=1.6 Hz, 2H), 2.99 (br t, J=11.2 Hz, 2H), 2.00-1.68 (m, 2H), 1.46-1.39 (m, 2H), 1.38 (s, 9H), 1.28 (s, 9H), 0.77 (t, J=7.6 Hz, 3H)

Step 2: To a 250 mL single-necked round-bottomed flask containing a well-stirred solution of tert-butyl 4-(tert-butylcarbamoyl)-4-ethyl-piperidine-1-carboxylate (1.2 g, 3.84 mmol) in anhydrous DCM (15 mL) was added 4 M HCl in dioxane (700.15 mg, 19.20 mmol) at ambient temperature. The resulting mixture was stirred at ambient temperature under nitrogen atmosphere for 2 h. After completion of reaction as indicated by UPLC, excess solvents were removed from the reaction mixture under reduced pressure to get a crude mass which was triturated with methyl t-butyl ether (50 ml) and dried under vacuum to afford N-tert-butyl-4-ethyl-piperidine-4-carboxamide (0.95 g, 3.82 mmol, 99.39% yield, HCl salt) as a white solid. LCMS ($ES^+$): m/z 213.2 $[M+H]^+$. The product was used in the next step without further purification.

Example 38: Synthesis of N-Cyclobutyl-4-ethylpiperidine-4-carboxamide hydrochloride

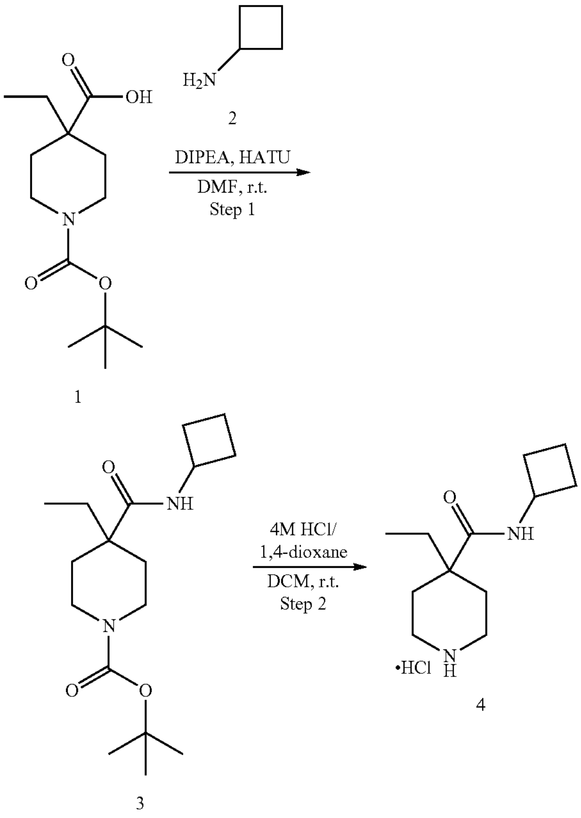

Step 1: Into a 250 mL single-necked round-bottomed flask containing a well-stirred solution of 1-tert-butoxycarbonyl-4-ethyl-piperidine-4-carboxylic acid (1, 5 g, 19.43 mmol) and cyclobutanamine (2, 2.76 g, 38.86 mmol, 3.32 mL) in anhydrous DMF (70 mL) was added DIPEA (97.15 mmol, 16.92 mL) at ambient temperature under nitrogen atmosphere and was stirred for 10 minutes. Subsequently, HATU (14.78 g, 38.86 mmol) was added to the reaction mixture and stirring was continued at ambient temperature for 4 h. After completion, the reaction mixture was diluted with ice-cold water (100 mL), extracted with EtOAc (3×100 mL) and washed with brine (70 mL). Organic phases were combined, dried (anhydrous $Na_2SO_4$), filtered and the filtrate was concentrated under reduced pressure to afford a crude residue. Crude residue was purified by flash silica-gel (60-120 mesh) column with 0-100% EtOAc/pet ether to afford tert-butyl N-[2-[4-[4-[(2,6-dioxo-3-piperidyl)amino]phenyl]-1-piperidyl]ethyl]carbamate (3, 490 mg, 1.13 mmol, 63% yield) as a thick brown gum. LCMS ($ES^+$): 211.2 $[M-Boc+H]^+$ Step 2: Into a 250 mL single-necked round-bottomed flask containing a well-stirred solution of tert-butyl 4-(cyclobutylcarbamoyl)-4-ethyl-piperidine-1-carboxylate (3, 6 g, 19.33 mmol) in anhydrous DCM (30 mL) was added 4M HCl in 1,4-dioxane (17.62 mL) under nitrogen atmosphere at 0° C. The resulting reaction mixture was stirred at ambient temperature under nitrogen atmosphere for 2 h. After completion, excess solvent was removed from the reaction mixture under reduced pressure. Crude thus obtained was co-distilled with DCM and triturated with methyl tert-butyl ether (3×50 mL) to afford N-cyclobutyl-4-ethyl-piperidine-4-carboxamide hydrochloride (4, 4.5 g, 17.94 mmol, 93% yield) as a thick gum. LCMS ($ES^+$): 211.2 $[M+H]^+$

Example 39: Synthesis of 2-(4-methylpiperidin-4-yl)pyrimidine

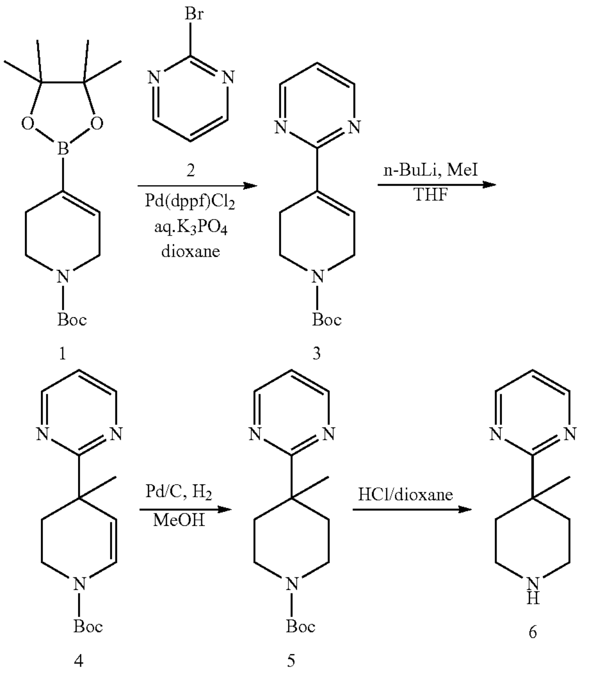

Step 1: To a solution of tert-butyl 4-(4,4,5,5-tetramethyl-1,3,2-dioxaborolan-2-yl)-5,6-dihydropyridine-1(2H)-carboxylate (1, 12.84 g, 41.51 mmol), 2-bromopyrimidine (2, 6 g, 37.74 mmol) and $Pd(dppf)Cl_2$ (1.54 g, 1.89 mmol) in dioxane (100 mL) was added $K_3PO_4$ (2 M, 37.74 mL) dropwise at 0° C. under $N_2$. After addition, the solution was stirred at 60° C. for 12 hr. The reaction solution was poured into water (400 mL). The aqueous solution was extracted with EtOAc (400 mL×3), the combined organic layer was washed with brine (1 L×3) dried over $Na_2SO_4$ and concentrated in vacuum. The residue was purified by flash silica gel chromatography (80 g Silica Flash Column, Eluent of 0-15% EtOAc/Pet ether 50 mL/min) to afford tert-butyl 4-(pyrimidin-2-yl)-5,6-dihydropyridine-1(2H)-carboxylate (3, 9.2 g, 34.50 mmol, 91% yield) as yellow solid. LCMS ($ES^+$): 206.2 $[M+H-tBu]^+$ Step 2: To a solution of tert-butyl 4-(pyrimidin-2-yl)-5,6-dihydropyridine-1(2H)-carboxylate (3, 1 g, 3.83 mmol) in THF (20 mL) was added n-BpLi (2 M, 2.87 mL) dropwise at −20° C. Then MeI (543.16 mg, 3.83 mmol, 238.23 μL) was added into above solution at −60° C. After addition, the solution was stirred at −60° C. for 2 hr. The reaction solution was poured into water (30 mL). The aqueous solution was extracted with EtOAc (30 mL×3). The combined organic layer was wash with brine (50 ml×3), dried over $Na_2SO_4$, filtered and concentrated in vacuum. The residue was purified by flash silica gel chromatography (12 g Silica Flash Column, Eluent of 0~15% EtOAc/Pet ether 20 mL/min) to afford tert-butyl 4-methyl-4-(pyrimidin-2-yl)-3,4-dihydropyridine-1(2H)-carboxylate (4, 343 mg, 1.20 mmol, 31% yield) as yellow solid. LCMS ($ES^+$): 276.2 $[M+H]^+$ Step 3: To a solution of tert-butyl 4-methyl-4-(pyrimidin-2-yl)-3,4-dihydropyridine-1(2H)-carboxylate (4, 1 g, 3.63 mmol) in Ethanol (4 mL) was added palladium on carbon (30 mg, 363.18 μmol, 10 purity) under $N_2$ atmosphere. The suspension was degassed and purged with $H_2$ (3 times). The mixture was stirred under $H_2$ (15 psi) at 80° C. for 50 min. The reaction mixture was filtered; the filtrate was concentrated in vacuum. The residue was purified by flash silica gel chromatography (12 g Silica Flash Column, Eluent of 0-15% EtOAc/Pet ether 20 mL/min) to afford tert-butyl 4-methyl-4-(pyrimidin-2-yl)piperidine-1-carboxylate (5, 770 mg, 2.69 mmol, 74% yield) as white solid. LCMS ($ES^+$): 222.1 $[M+H-tBu]^+$. $^1$HNMR (400 MHz, CHLOROFORM-d) δ=8.64 (d, J=4.8 Hz, 2H), 7.04 (t, J=4.8 Hz, 1H), 3.73-3.57 (m, 2H), 2.95 (ddd, J=2.8, 10.3, 13.3 Hz, 2H), 2.48-2.33 (m, 2H), 1.64-1.55 (m, 2H), 1.38 (s, 9H), 1.23 (s, 3H)

Step 4: A solution of tert-butyl 4-methyl-4-(pyrimidin-2-yl)piperidine-1-carboxylate (5, 100 mg, 360.54 μmol) in HCl/dioxane (219.65 μmol, 4 mL) was stirred at 30° C. for 1 hr. The reaction solution was concentrated in vacuum. 2-(4-methylpiperidin-4-yl)pyrimidine HCl salt (6, 77 mg, 360.31 μmol, 99% yield) was obtained as white solid.

Example 40: Synthesis of 2-(4-ethylpiperidin-4-yl)pyrimidine

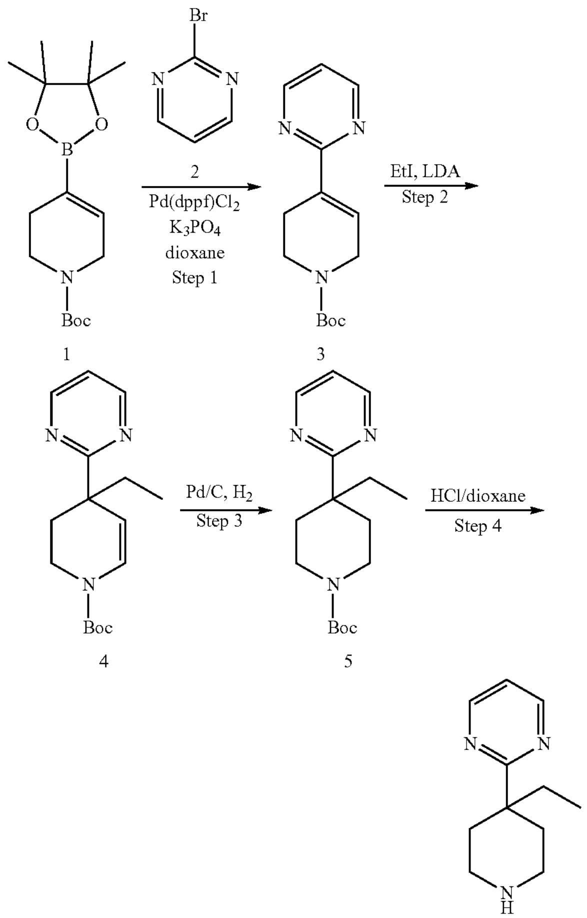

Step 1: To a solution of tert-butyl 4-(4,4,5,5-tetramethyl-1,3,2-dioxaborolan-2-yl)-5,6-dihydropyridine-1(2H)-carboxylate (1, 12.84 g, 41.51 mmol), 2-bromopyrimidine (2, 6 g, 37.74 mmol) and Pd(dppf)$Cl_2$ (1.54 g, 1.89 mmol) in dioxane (100 mL) was added $K_3PO_4$ (2 M, 37.74 mL) dropwise at 0° C. under $N_2$. After addition, the solution was stirred at 60° C. for 12 hr. The reaction solution was poured into water (400 mL). The aqueous solution was extracted with EtOAc (400 mL×3), the combined organic layer was washed with brine (1L×3) dried over $Na_2SO_4$ and concentrated in vacuum. The residue was purified by flash silica gel chromatography (80 g Silica Flash Column, Eluent of 0~15% EtOAc/Pet ether 50 mL/min) to afford tert-butyl 4-(pyrimidin-2-yl)-5,6-dihydropyridine-1(2H)-carboxylate (3, 9.2 g, 34.50 mmol, 91% yield) as yellow solid. LCMS ($ES^+$): m/z 206.2 $[M+H-tBu]^+$ Step 2: To a solution of tert-butyl 4-(pyrimidin-2-yl)-5,6-dihydropyridine-1(2H)-carboxylate (3, 9 g, 34.44 mmol) in THF (20 mL) was added LDA (2 M, 25.83 mL) dropwise at −20° C. Then iodoethane (6.45 g, 41.33 mmol, 3.32 mL) was added into above solution at −60° C. After addition, the solution was stirred at −60° C. for 2 hr. The reaction solution was poured into water (100 mL). The aqueous solution was extracted with EtOAc (100 mL×3), The combined organic layer was wash with brine (150 mL×3), dried over $Na_2SO_4$, filtered and concentrated in vacuum. The residue was purified by flash silica gel chromatography (120 g Silica Flash Column, Eluent of 0~15% EA/PE 50 mL/min) to afford tert-butyl 4-ethyl-4-(pyrimidin-2-yl)-3,4-dihydropyridine-1(2H)-carboxylate (4, 7.1 g, 22.08 mmol, 64% yield) as yellow solid. LCMS ($ES^+$): m/z 290.2 $[M+H]^+$ Step 3: To a solution of tert-butyl 4-ethyl-4-(pyrimidin-2-yl)-3,4-dihydropyridine-1(2H)-carboxylate (4, 0.5 g, 1.73 mmol) in Ethanol (1 mL) was added Pd/C (100 mg, 82.34 μmol, 0.1 purity) under $N_2$ atmosphere. After addition, the solution was stirred at 50° C. for 2 hr. The reaction solution was filtered; the filtrate was concentrated in vacuum. The residue was purified by flash silica gel chromatography (12 g Silica Flash Column, Eluent of 0~15% EtOAc/Pet ether 20 mL/min) to afford tert-butyl 4-ethyl-4-(pyrimidin-2-yl)piperidine-1-carboxylate (5, 338 mg, 1.15 mmol, 66% yield) as white solid. LCMS ($ES^+$): 236.1 $[M+H-tBu]^+$ $^1$H NMR (400 MHz, CHLOROFORM-d) δ=8.65 (d, J=4.8 Hz, 2H), 7.04 (t, J=4.8 Hz, 1H), 3.76 (br d, J=4.8 Hz, 2H), 2.76 (br t, J=11.6 Hz, 2H), 2.45 (br d, J=13.2 Hz, 2H), 1.64 (q, J=7.6 Hz, 2H), 1.56-1.48 (m, 2H), 1.37 (s, 9H), 0.51 (t, J=7.6 Hz, 3H)

Step 4: To a solution of tert-butyl 4-ethyl-4-pyrimidin-2-yl-piperidine-1-carboxylate (1.2 g, 4.12 mmol) in DCM (11 mL) was added HCl/dioxane (4 M, 11 mL). After addition, the solution was stirred at 20° C. for 30 min. After consumption of the reactant as confirmed by LCMS, the solution was concentrated under vacuum and the residue was used for next step directly without purification. The compound 2-(4-ethyl-4-piperidyl)pyrimidine (937.86 mg, 4.12 mmol, 100% yield, HCl salt) was obtained as a yellow solid. LCMS ($ES^+$): m/z 192.4 $[M+H]^+$

Example 41: Synthesis of N-(tert-Butyl)-4-ethylpiperidine-4-carboxamide hydrochloride

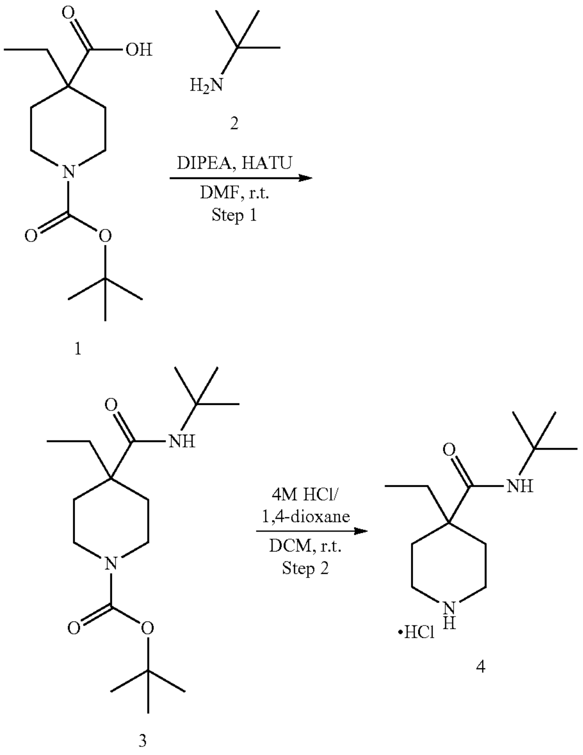

Step 1: Into a 100 mL single-necked round-bottomed flask containing a well-stirred solution of 1-tert-butoxycarbonyl-4-ethyl-piperidine-4-carboxylic acid (1, 1.0 g, 3.89 mmol) and 2-methylpropan-2-amine (2, 568.44 mg, 7.77 mmol, 0.816 mL) in anhydrous DMF (10 mL) were added DIPEA (9.72 mmol, 1.69 mL) and HATU (1.77 g, 4.66 mmol) at ambient temperature under nitrogen atmosphere. The resulting solution was stirred at ambient temperature for 3 h. The reaction mixture was diluted with EtOAc (100 mL) and washed successively with water (2×100 mL) and brine (2×100 mL). The organic layer was dried (anhydrous $Na_2SO_4$), filtered and the filtrate was evaporated to dryness under reduced pressure to obtain tert-butyl 4-(tert-butylcarbamoyl)-4-ethyl-piperidine-1-carboxylate (3, 1.2 g, 2.85 mmol, 73% yield) as an off-white solid. LCMS ($ES^+$): 213.4 $[M-Boc+H]^+$ Step 2: Into a 250 mL single-necked round-bottomed flask containing a well-stirred solution of tert-butyl 4-(tert-butylcarbamoyl)-4-ethyl-piperidine-1-carboxylate (3, 1.2 g, 3.84 mmol) in anhydrous DCM (15 mL) was added 4M HCl in 1,4-dioxane (700.15 mg, 19.20 mmol, 10 mL) at ambient temperature. The resulting mixture was stirred at ambient temperature under nitrogen atmosphere for 2 h. After completion, excess solvent was removed from the reaction mixture under reduced pressure to get a crude mass which was triturated with methyl tert-butyl ether (50 mL) and dried under vacuum afford N-tert-butyl-4-ethyl-piperidine-4-carboxamide hydrochloride (4, 0.95 g, 3.82 mmol, 99% yield) as a white solid. LCMS ($ES^+$): 213.2 $[M+H]^+$

Example 42: Synthesis of 2-[[4-(methoxymethyl)-4-piperidyl]methyl]pyridine. hydrochloride

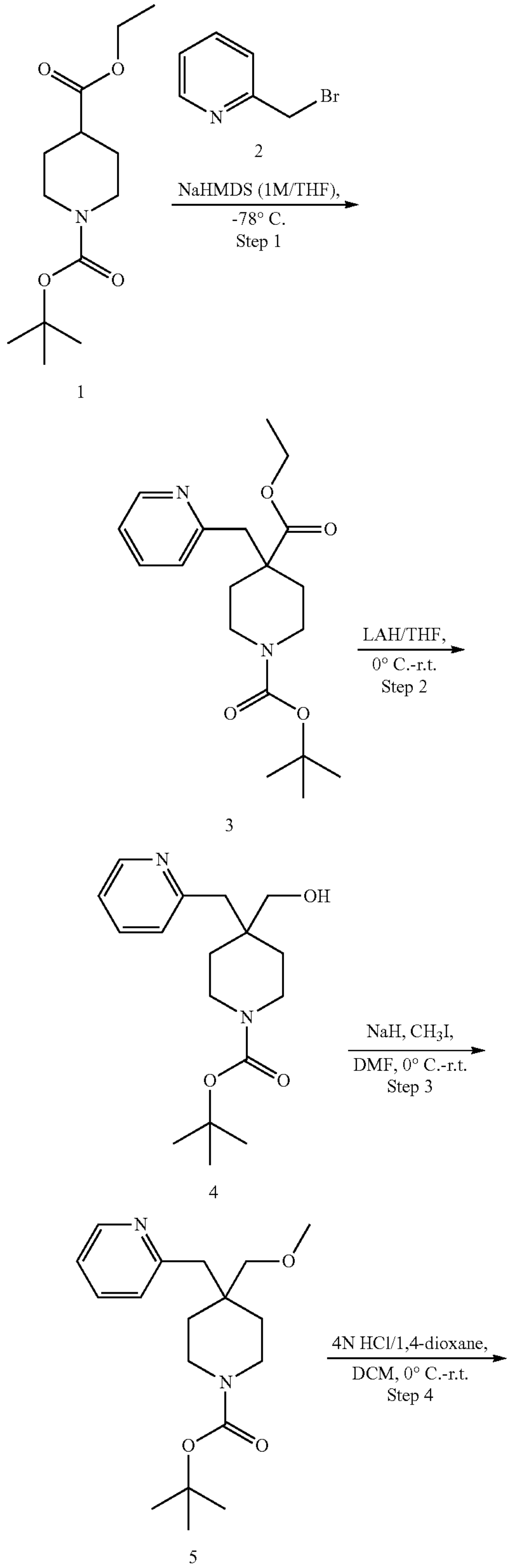

-continued

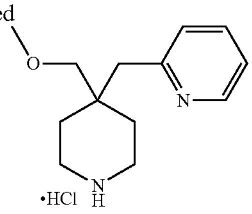

6

Step 1: Into a 250 mL three-necked round-bottomed flask containing a well-stirred solution of 1-(tert-butyl) 4-ethyl piperidine-1,4-dicarboxylate (1, 2 g, 7.77 mmol, 1.90 mL) in anhydrous THF (25 mL) was added dropwise Sodium bis(trimethylsilyl)amide, 98% (3.56 g, 19.43 mmol, 15 mL; 1M/THF) for 10 minutes at −78° C. under nitrogen atmosphere and the reaction mixture was stirred at −78° C. for 1 h and then to the reaction mixture was added solid 2-(bromomethyl)pyridine hydrobromide (2, 2.20 g, 8.70 mmol) at −78° C. The reaction mixture was gradually allowed to stir at ambient temperature for 16 h. The reaction mixture was diluted with DCM (30 mL) and washed with brine (50 mL) and ammonium chloride solution (50 mL), and extracted with DCM (2×50 mL). The combined organic phases were dried (anhydrous $Na_2SO_4$), filtered and concentrated under reduced pressure to get a crude residue, which was purified by flash silica-gel (230-400 mesh) column with 0-50% EtOAc/pet ether to afford 1-(tert-butyl) 4-ethyl 4-(pyridin-2-ylmethyl)piperidine-1,4-dicarboxylate (3, 1.6 g, 4.46 mmol, 57% yield) as a colorless liquid. LCMS ($ES^+$): m/z 349.2 $[M+H]^+$ Step 2: Into a 250 mL three-necked round-bottomed flask containing a well-stirred solution of 1-(tert-butyl) 4-ethyl 4-(pyridin-2-ylmethyl)piperidine-1,4-dicarboxylate (3, 1.66 g, 4.76 mmol) in anhydrous THF (100 mL) was added lithium aluminum hydride (161.61 mg, 4.26 mmol, 4.78 mL; 2M in THF) at 0° C. under nitrogen atmosphere and the reaction mixture was stirred at 0° C. for 1 h. After completion, the reaction mixture was cooled and quenched with saturated ammonium chloride (1 mL), and the reaction mixture was stirred for 10 minutes and then filtered through pad of Celite, washing with THF (2×20 mL). The combined filtrates were concentrated under reduced pressure to obtain tert-butyl 4-(hydroxymethyl)-4-(2-pyridylmethyl)piperidine-1-carboxylate (4, 1.3 g, 3.75 mmol, 79% yield) as a colorless liquid. LCMS ($ES^+$): m/z 307.1 $[M+H]^+$ Step 3: Into a 50 mL single-necked round-bottomed flask containing a well-stirred solution of tert-butyl 4-(hydroxymethyl)-4-(2-pyridylmethyl)piperidine-1-carboxylate (4, 200 mg, 0.652 mmol) in anhydrous DMF (5 mL) was added Sodium hydride (30.01 mg, 1.31 mmol; 60% dispersion in mineral oil) at 0° C. and after 30 minutes Iodomethane (185.30 mg, 1.31 mmol) was added at 0° C. The reaction mixture was stirred at ambient temperature for 12 h. After completion, the reaction mixture was cooled to 0° C. and quenched with saturated $NH_4Cl$ solution (10 mL) and extracted with EtOAc (2×50 mL). The organic phases were combined and washed with brine (50 mL), dried (anhydrous $Na_2SO_4$), filtered and concentrated to get a crude residue. The crude residue was purified by flash silica-gel (230-400 mesh) column with 0-100% EtOAc/pet ether to afford tert-butyl 4-(methoxymethyl)-4-(2-pyridylmethyl)piperidine-1-carboxylate (5, 94 mg, 0.282 mmol, 43% yield) as a colorless semi-solid. LCMS ($ES^+$): m/z 321.2 $[M+H]^+$ Step 4: Into a 25 mL single-necked round-bottomed flask containing a well-stirred solution of tert-butyl 4-(methoxymethyl)-4-(2-pyridylmethyl)piperidine-1-carboxylate (5, 90 mg, 0.280 mmol) in anhydrous DCM (3 mL) was added HCl (1.60 g, 43.88 mmol, 2 mL; 4N/1,4-dioxane) at 0° C. The resulting mixture was stirred at room temperature for 2 h. The reaction mixture was concentrated to get a crude mass, which was washed with MTBE (20 mL) to get the 2-[[4-(methoxymethyl)-4-piperidyl]methyl]pyridine. hydrochloride (6, 80 mg, 0.265 mmol, 95% yield) as an off-white solid. LCMS ($ES^+$): 221.2 $[M+H]^+$ Example 43: Synthesis of 2-(4-piperidyloxy)pyridine

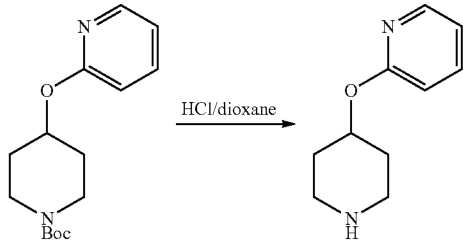

1 2

To a solution of tert-butyl 4-(2-pyridyloxy)piperidine-1-carboxylate (1, 170 mg, 610.75 μmol) in DCM (2 mL) was added HCl/dioxane (4 M, 152.69 μL). The mixture was stirred at 25° C. for 1 h. The reaction was concentrated under reduced pressure to get 2-(4-piperidyloxy)pyridine (2, 100 mg, 544.24 μmol, 89% yield) as yellow solid. LCMS ($ES^+$): 179.1 $[M+H]^+$ Example 44: Synthesis of 2-(4-ethyl-4-piperidyl)pyridine hydrochloride

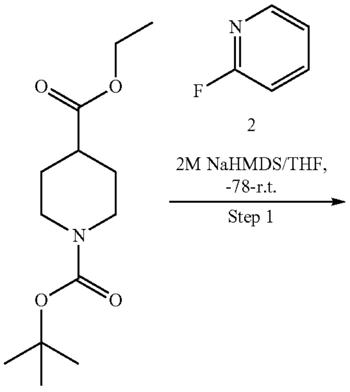

2

1

-continued

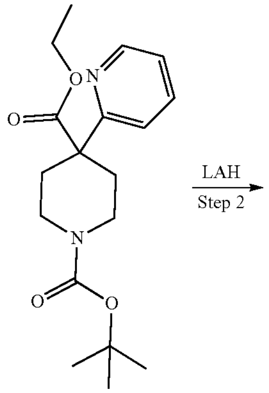

3

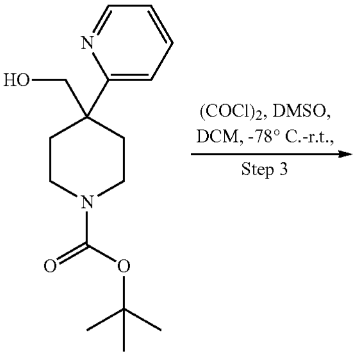

4

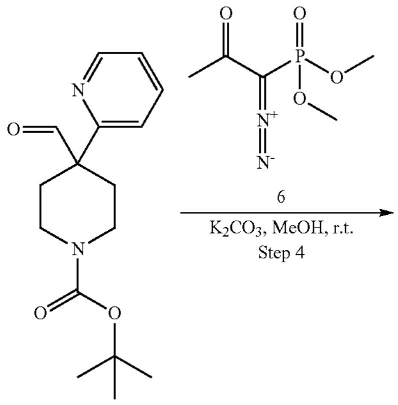

5

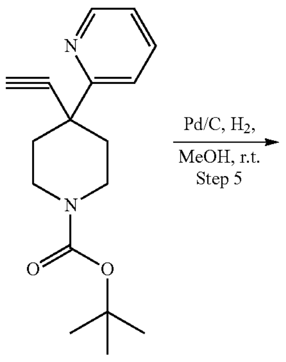

7

-continued

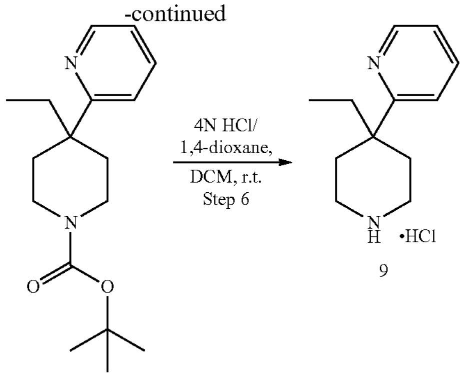

8

9

Step 1. Into a 250 mL three-necked round bottomed flask containing a well-stirred solution of 1-(tert-butyl) 4-ethyl piperidine-1,4-dicarboxylate (1, 3.0 g, 11.66 mmol, 2.86 mL) in anhydrous THF (30 mL) was added dropwise Sodium bis(trimethylsilyl)amide, 98% (12.82 mL; 2M/THF) at −78° C. under nitrogen atmosphere. After addition, stirring was continued for 45 minutes at the same temperature. Subsequently, 2-fluoropyridine (2, 1.70 g, 17.49 mmol, 1.50 mL) was added to the reaction mixture at −78° C. under nitrogen atmosphere. The resulting mixture was slowly allowed warm to room temperature and stirred at ambient temperature for 4 h under nitrogen atmosphere. Excess reagent was quenched with saturated ammonium chloride solution (60 mL) at 0° C. slowly and the aqueous layer was extracted with EtOAc (2×40 mL). The organic layer was washed with water followed by brine and dried (anhydrous $Na_2SO_4$), filtered and concentrated under reduced pressure to afford a crude mass. The crude residue was purified by flash silica-gel (230-400 mesh, 50 g) column with 0-100% EtOAc/pet ether to afford 1-(tert-butyl) 4-ethyl 4-(pyridin-2-yl)piperidine-1,4-dicarboxylate (3, 2.5 g, 7.34 mmol, 63% yield) as a colorless gum. LCMS ($ES^+$): 335.2 $[M+H]^+$.

Step 2. Into a 250 mL three-necked round bottomed flask containing a well stirred solution of 1-(tert-butyl) 4-ethyl 4-(pyridin-2-yl)piperidine-1,4-dicarboxylate (3, 2.5 g, 7.48 mmol) in anhydrous THF (30 mL) was added dropwise Lithium aluminium hydride (4.11 mL; 2M\THF) at 0° C. under nitrogen atmosphere. The resulting mixture was stirred at 0° C. for 2 h under nitrogen atmosphere. Excess reagent was quenched with saturated ammonium chloride solution (40 mL) at 0° C. slowly and the aqueous layer was extracted with EtOAc (2×70 mL). Combined organic phase was washed with water followed by brine and dried (anhydrous $Na_2SO_4$), filtered and concentrated under reduced pressure to afford tert-butyl 4-(hydroxymethyl)-4-(pyridin-2-yl)piperidine-1-carboxylate (4, 2.1 g, 7.01 mmol, 94% yield) as a colorless gum. LCMS ($ES^+$): 293.2 $[M+H]^+$.

Step 3. Into a 500 mL three-necked round-bottomed flask containing a well stirred solution of Oxalyl chloride (3.13 g, 24.63 mmol, 2.14 mL) in anhydrous DCM (20 mL) was added dropwise anhydrous DMSO (3.85 g, 49.25 mmol, 3.50 mL) at −78° C. under nitrogen atmosphere. After addition, the reaction mixture was stirred at −78° C. for 1 h under nitrogen atmosphere. Subsequently, tert-butyl 4-(hydroxymethyl)-4-(pyridin-2-yl)piperidine-1-carboxylate (4, 4.0 g, 13.68 mmol) in anhydrous DCM (40 mL) was added to the reaction mixture at −78° C. and resulting mixture was stirred at same temperature for 1 h under nitrogen atmosphere. To the reaction mixture was added dropwise TEA (95.77 mmol, 13.35 mL) at −78° C. and stirring was continued for 1 h under nitrogen atmosphere. Excess reagent was quenched with ice-water (100 mL) at −78° C. slowly and the aqueous layer was extracted with DCM (2×50 mL). Combined organic phase was washed with water followed by brine, dried (anhydrous $Na_2SO_4$), filtered and concentrated under reduced pressure to afford a crude mass. The crude mass was purified by flash silica-gel (230-400 mesh, 100 g) column with 0-100% EtOAc/pet ether to afford tert-butyl 4-formyl-4-(2-pyridyl)piperidine-1-carboxylate (5, 2.4 g, 8.27 mmol, 60% yield) as a colorless gum. $^1H$ NMR (300 MHz, DMSO-$d_6$). δ 9.61 (s, 1H), 8.59 (d, J=4.2 Hz, 1H), 7.84 (m, 1H), 7.49 (d, J=8.1 Hz, 1H), 7.34 (dd, J=6.9, 5.7 Hz, 1H), 3.58-3.52 (m, 2H), 3.19-3.15 (m, 2H), 2.33-2.21 (m, 2H), 2.10-2.00 (m, 2H), 1.40 (s, 9H)

Step 4. Into a 250 mL single-necked round bottomed flask containing a well stirred solution of tert-butyl 4-formyl-4-(2-pyridyl)piperidine-1-carboxylate (5, 2.4 g, 8.27 mmol) in MeOH (20 mL) was added Potassium carbonate, anhydrous, 99% (2.28 g, 16.53 mmol) and resulting mixture was stirred for 10 minutes. Subsequently, Dimethyl (1-diazo-2-oxopropyl)phosphonate (6, 1.91 g, 9.92 mmol) in MeOH (20 mL) was added to the reaction mixture at ambient temperature and the resulting suspension was stirred at ambient temperature for 2 h under nitrogen atmosphere. The reaction mixture was filtered through a pad of Celite pad, washing with MeOH (100 mL) and the filtrate was concentrated under reduced pressure to afford a crude mass. The crude mass was purified by flash silica-gel (230-400 mesh, 50 g) column with 0-100% EtOAc/pet ether to afford tert-butyl 4-ethynyl-4-(2-pyridyl)piperidine-1-carboxylate (7, 1.6 g, 5.35 mmol, 65% yield) as an off-white solid. LCMS ($ES^+$): 287.2 $[M+H]^+$.

Step 5. A well-stirred solution of tert-butyl 4-ethynyl-4-(2-pyridyl)piperidine-1-carboxylate (7, 1.6 g, 5.59 mmol) in anhydrous MeOH (25 mL) was purged with nitrogen into a 250 mL single-necked round-bottomed flask and then 5% Palladium on carbon dry basis (700 mg, 5.59 mmol) was added at ambient temperature under nitrogen atmosphere. The resulting suspension was stirred at ambient temperature under hydrogen atmosphere (bladder pressure) for 4 h. After completion, reaction mixture was filtered through a pad of Celite, washing with MeOH (100 mL). The filtrate was concentrated under reduced pressure to afford tert-butyl 4-ethyl-4-(2-pyridyl)piperidine-1-carboxylate (8, 1.4 g, 4.69 mmol, 84% yield) as a colorless viscous gum. LCMS ($ES^+$): 291.2 $[M+H]^+$.

Step 6. Into a 50 mL single-necked round-bottomed flask containing a well-stirred solution of tert-butyl 4-ethyl-4-(2-pyridyl)piperidine-1-carboxylate (8, 800 mg, 2.75 mmol) in anhydrous DCM (12 mL) was added dropwise 4M HCl in 1,4-dioxane (5 mL) at 0° C. under nitrogen atmosphere. The reaction mixture was allowed to stir at ambient temperature for 2 h. After completion, the reaction mixture was concentrated, co-distilled with DCM (2×3 mL) and triturated with diethyl ether to afford 2-(4-ethyl-4-piperidyl)pyridine hydrochloride (9, 630 mg, 2.74 mmol, 99% yield) as an off-white gum. LCMS ($ES^+$): 191.2 $[M+H]^+$.

Example 45: Synthesis of 2-methoxy-5-[(4-methoxy-4-piperidyl)methyl]pyridine

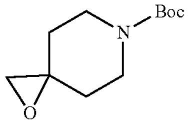

2

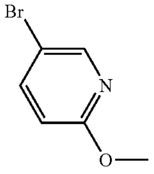

1

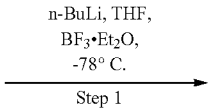

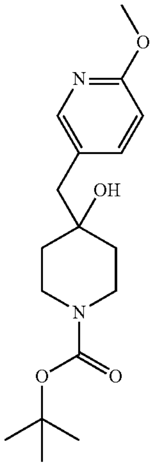

3

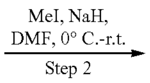

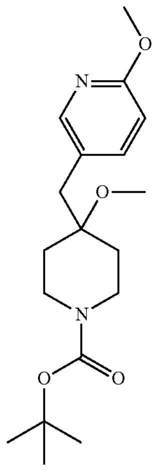

4

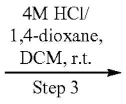

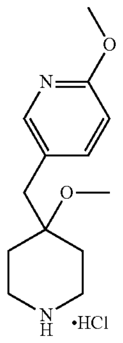

5

Step 1. Into a 100 mL three-necked round-bottomed flask containing a well-stirred solution of 5-bromo-2-methoxypyridine (1, 881.60 mg, 4.69 mmol, 0.608 mL) in anhydrous THF (20 mL) was added n-Butyllithium, 1.6 M in hexane (2.93 mL) dropwise at −78° C. under nitrogen atmosphere. After stirring at −78° C. for 1 h, a solution of tert-butyl 1-oxa-6-azaspiro[2.5]octane-6-carboxylate (2; 1 g, 4.69 mmol) in anhydrous THF (5 mL) was added dropwise to the reaction mixture, followed by Boron trifluoride diethyl etherate (665.49 mg, 4.69 mmol, 0.588 mL) at −78° C. The reaction mixture was stirred at −78° C. for 3 h and the reaction mixture was allowed to warm to ambient temperature and stirred at ambient temperature for 16 h. The reaction mixture was cooled to −30° C. and quenched with saturated ammonium chloride solution (20 mL). The resulting mixture was extracted with EtOAc (2×100 mL). The combined organic phase was washed with brine (80 mL), dried (anhydrous $Na_2SO_4$), filtered, and concentrated under reduced pressure. The crude residue was purified by flash silica-gel (230-400 mesh; 50 g SNAP) column with 0-60% EtOAc/pet ether to afford tert-butyl 4-hydroxy-4-[(6-methoxy-3-pyridyl)methyl]piperidine-1-carboxylate (3, 0.8 g, 2.39 mmol, 51% yield). LCMS ($ES^+$): 323.4 $[M+H]^+$.

Step 2. Into a 100 mL three-necked round-bottomed flask containing a well-stirred solution of tert-butyl 4-hydroxy-4-[(6-methoxy-3-pyridyl)methyl]piperidine-1-carboxylate (3, 700 mg, 2.17 mmol) in dry DMF (15 mL) was added sodium hydride (99.83 mg, 4.34 mmol; 60% dispersion in mineral oil) at 0° C. under nitrogen atmosphere for 30 minutes. Iodomethane (616.36 mg, 4.34 mmol, 0.270 mL) was added to the flask at 0° C. and the reaction mixture was allowed to stir at ambient temperature for 2 h. After completion, the reaction mixture was cooled to 0° C. and quenched with ice-water (60 mL). Aqueous phase was extracted with EtOAc (2×150 mL). Combined organic phase was washed with brine (50 mL), dried (anhydrous $Na_2SO_4$), filtered and concentrated under reduced pressure to get a crude residue. The crude residue was purified by flash silica-gel (230-400 mesh; 50 g SNAP) column with 0-100% EtOAc/pet ether to afford tert-butyl 4-methoxy-4-[(6-methoxy-3-pyridyl)methyl]piperidine-1-carboxylate (4, 715 mg, 2.08 mmol, 96% yield). LCMS ($ES^+$): 337.5 $[M+H]^+$.

Step 3. Into a 50 mL single-necked round-bottomed flask containing a well-stirred solution of tert-butyl 4-methoxy-4-[(6-methoxy-3-pyridyl)methyl]piperidine-1-carboxylate (4, 300 mg, 0.891 mmol) in anhydrous DCM (5 mL) was added 4M HCl in 1,4-dioxane (3 mL) at ambient temperature under nitrogen atmosphere. The resulting mixture was stirred for 1 h at ambient temperature. After completion, excess solvent was removed from the reaction mixture under reduced pressure to get a crude mass. The crude product was washed with MTBE (10 mL) to get 2-methoxy-5-[(4-methoxy-4-piperidyl)methyl]pyridine hydrochloride (5, 210 mg, 0.744 mmol, 83% yield) as an off-white solid. LCMS ($ES^+$): 237.1 $[M+H]^+$.

Example 46: Synthesis of 3-chloro-N-(4-ethyl-4-piperidyl)pyridine-2-carboxamide

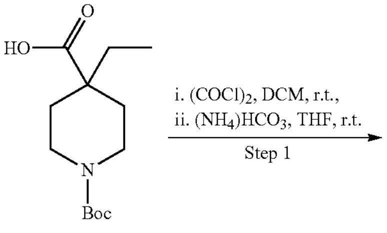

1

-continued

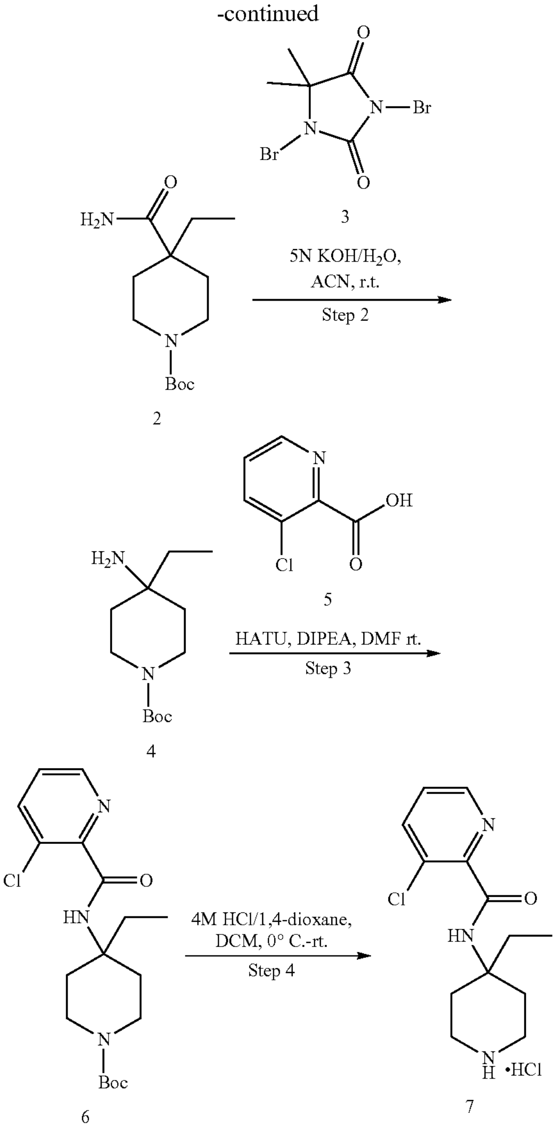

Step 1. Into a 50 mL single-necked round-bottomed flask containing a well-stirred solution of 1-tert-butoxycarbonyl-4-ethyl-piperidine-4-carboxylic acid (1; 2 g, 7.77 mmol; from Abintio Biosciences) in anhydrous DCM (30 mL) was added oxalyl dichloride (9.87 g, 77.72 mmol, 6.78 mL) dropwise at 0° C. under nitrogen atmosphere and the resulting mixture was stirred at ambient temperature. for 2 h. The mixture was concentrated under reduced pressure to obtain acid chloride as a crude. The crude acid chloride thus obtained was dissolved in anhydrous THF (20 mL) and was added dropwise to a stirred suspension of Ammonium bicarbonate (3.07 g, 38.86 mmol) in anhydrous THF (30 mL) at 0° C. The resulting mixture was stirred at ambient temperature for 16 h. The reaction mixture was filtered through a pad of Celite, washing with THF (50 mL). The combined filtrate was concentrated to get a crude mass, which was dissolved in DCM (50 mL) and washed successively with saturated sodium bicarbonate solution (30 mL) and brine (30 mL). The organic layer was dried (anhydrous $Na_2SO_4$), filtered and concentrated under reduced pressure to afford tert-butyl 4-carbamoyl-4-ethyl-piperidine-1-carboxylate (2; 730 mg, 2.80 mmol, 36% yield) as a light yellow gum. LCMS ($ES^+$): 201.3 $[M+H]^+$.

Step 2. Into a 50 mL single-necked round-bottomed flask containing a well-stirred solution of tert-butyl 4-carbamoyl-4-ethyl-piperidine-1-carboxylate (2; 725 mg, 2.83 mmol) in ACN (20 mL) was added a solution of KOH (834.25 mg, 14.87 mmol) in water (4 mL) and 1,3-dibromo-5,5-dimethyl-imidazolidine-2,4-dione (3; 404.33 mg, 1.41 mmol) at ambient temperature. The resulting mixture was stirred at ambient temperature for 20 h. The reaction mixture was concentrated under reduced pressure to get a crude residue. The residue was diluted with water (30 mL), cooled to 0° C. and the pH was adjusted to ~5 with 1 N aqueous HCl. The aqueous layer was washed with EtOAc (2x30 mL) and was basified to pH ~10 with 10% aqueous NaOH solution. The aqueous layer was extracted with EtOAc (2x30 mL). The combined organic layer was washed with brine (30 mL), dried (anhydrous $Na_2SO_4$), filtered and concentrated under reduced pressure to afford tert-butyl 4-amino-4-ethyl-piperidine-1-carboxylate (4; 300 mg, 1.31 mmol, 46% yield) as a colorless oil. LCMS ($ES^+$): 173.4 $[M-tBu+H]^+$.

Step 3. Into a 10 mL single-necked round-bottomed flask containing a well-stirred solution of 3-chloropyridine-2-carboxylic acid (5; 179.41 mg, 1.14 mmol) in anhydrous DMF (6 mL) were added DIPEA (735.83 mg, 5.69 mmol, 0.1 mL) and HATU (649.45 mg, 1.71 mmol). The resulting mixture was stirred at ambient temperature for 5 minutes. Subsequently, tert-butyl 4-amino-4-ethyl-piperidine-1-carboxylate (4; 260.0 mg, 1.14 mmol) was added and the reaction mixture was stirred at ambient temperature under nitrogen atmosphere for 12 h. The reaction mixture was slowly added to ice-cold water (25 mL) and solid thus obtained was filtered. The crude solid was purified by flash silica-gel (230-400 mesh) column with 10-100% EtOAc/pet ether to afford tert-butyl 4-[(3-chloropyridine-2-carbonyl)amino]-4-ethyl-piperidine-1-carboxylate (6; 370 mg, 0.966 mmol, 85% yield) as a yellow solid. LCMS ($ES^+$): 312.2 $[M-tBu+H]^+$.

Step 4. Into a 25 mL single-necked round-bottomed flask containing a well-stirred solution of tert-butyl 4-[(3-chloropyridine-2-carbonyl)amino]-4-ethyl-piperidine-1-carboxylate (6; 365 mg, 0.953 mmol) in anhydrous DCM (5 mL) was added 4M HCl in 1,4-dioxane (5 mL) dropwise at 25° C. under nitrogen atmosphere. The resulting mixture was stirred at ambient temperature under nitrogen atmosphere for 2 h. Excess solvent was removed under reduced pressure to afford a crude mass. The crude mass was triturated with MTBE (10 mL) and solid thus crashed out was filtered to afford 3-chloro-N-(4-ethyl-4-piperidyl)pyridine-2-carboxamide hydrochloride (7; 290 mg, 0.909 mmol, 95% yield) as an off-white solid. LCMS ($ES^+$): 268.1 $[M+H]^+$.

Example 47: Synthesis of 4-ethyl-N-tetrahydropyran-4-yl-piperidine-4-carboxamide hydrochloride

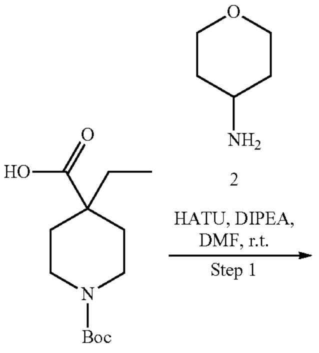

2

1

-continued

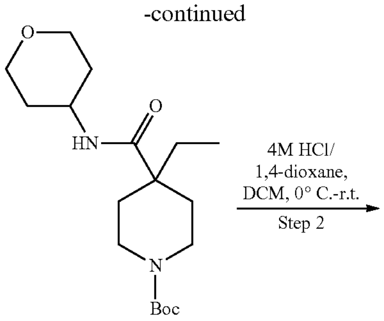

3

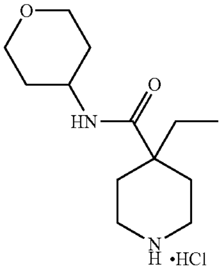

Step 1. Into a 250 mL single-necked round-bottomed flask containing a well-stirred solution of 1-tert-butoxycarbonyl-4-ethyl-piperidine-4-carboxylic acid (1; 3 g, 11.66 mmol) in anhydrous DMF (30 mL) were added DIPEA (7.53 g, 58.29 mmol, 10.15 mL) and HATU (6.65 g, 17.49 mmol) at ambient temperature under nitrogen atmosphere. The resulting mixture was stirred at ambient temperature for 5 minutes. Subsequently, tetrahydropyran-4-amine (2; 1.77 g, 17.49 mmol) was added and the mixture was stirred at ambient temperature under nitrogen atmosphere for 3 h. The reaction mixture was slowly added to ice-cold water (200 mL) and extracted with EtOAc (2×100 mL). Combined organic phase was washed with brine (10 mL) and dried (anhydrous $Na_2SO_4$), filtered and concentrated under reduced pressure to obtain a crude mass. The crude was purified by flash silica-gel (230-400 mesh) column with 0-100% EtOAc/pet ether to afford tert-butyl 4-ethyl-4-(tetrahydropyran-4-ylcarbamoyl)piperidine-1-carboxylate (3; 3.6 g, 10.04 mmol, 86% yield) as a colorless gummy liquid. LCMS ($ES^+$): 285.2 $[M-tBu+H]^+$.

Step 2. Into a 100 mL single-necked round-bottomed flask containing a well stirred solution of tert-butyl 4-ethyl-4-(tetrahydropyran-4-ylcarbamoyl)piperidine-1-carboxylate (3; 3.1 g, 9.11 mmol) in anhydrous DCM (20 mL) was added 4M HCl in 1,4-dioxane (30 mL) dropwise at ambient temperature under nitrogen atmosphere. The resulting mixture was stirred at ambient temperature for 2 h. Excess solvent was removed under reduced pressure to afford a crude residue. The crude mass was triturated with MTBE (25 mL) and solid thus precipitated out was filtered to obtain 4-ethyl-N-tetrahydropyran-4-yl-piperidine-4-carboxamide hydrochloride (4; 2.5 g, 8.79 mmol, 97% yield) as an off-white solid. LCMS ($ES^+$): 241.2 $[M+H]^+$.

Example 48: Synthesis of isoxazol-3-yl(piperazin-1-yl)methanone

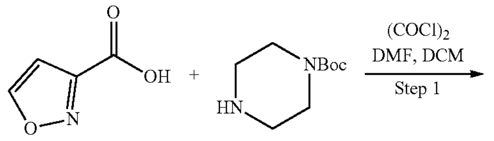

1 2

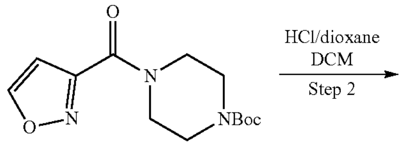

3

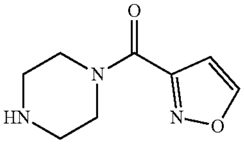

4

Step 1: To a solution of isoxazole-3-carboxylic acid (1, 500 mg, 4.42 mmol) in DCM (5 mL) was added DMF (32.32 mg, 442.20 μmol, 34.24 μL) under $N_2$ atmosphere and then adjusted the temperature to 0° C. Then oxalyl chloride (673.52 mg, 5.31 mmol, 461.31 μL) was added into above solution and stirred at 30° C. for 1 hr. The solution was concentrated in vacuo. The residue was dissolved in DCM (3 mL) and added into a solution of tert-butyl piperazine-1-carboxylate (2, 823.60 mg, 4.42 mmol) in DCM (5 mL). After addition, the solution was stirred at 30° C. for another 1 hr. After completion, the solution was concentrated under vacuum and the residue was purified by column chromatography ($SiO_2$,Pet ether:EtOAc=40:1 to 3:1) to afford tert-butyl 4-(isoxazole-3-carbonyl)piperazine-1-carboxylate (3, 970 mg, 3.41 mmol, 77% yield) as a white solid. LCMS ($ES^+$): m/z 281.1 $[M+H]^+$ Step 2: To a solution of tert-butyl 4-(isoxazole-3-carbonyl)piperazine-1-carboxylate (3, 100 mg, 355.48 μmol) in DCM (1 mL) was added HCl/dioxane (4 M, 277.78 μL). After addition, the solution was stirred at 30° C. for 30 min. After completion, the solution was concentrated under vacuum to afford isoxazol-3-yl(piperazin-1-yl)methanone (4, 77 mg, 353.78 μmol, 99% yield, HCl salt) as a white solid, which was used for next step directly without purification.

Example 49: Synthesis of 1-((1R,5S)-3-oxa-7,9-diazabicyclo[3.3.1]nonan-9-yl)-3,3-dimethylbutan-1-one

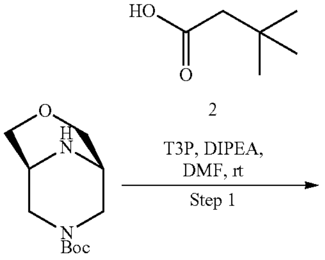

2

1

-continued

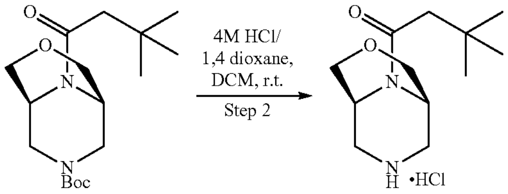

3 4

Step 1: Into a 25 mL single-necked round-bottomed flask containing a well-stirred solution of 3,3-dimethylbutanoic acid (2; 183.18 mg, 1.58 mmol) in anhydrous DMF (3 mL) were added DIPEA (849.19 mg, 6.57 mmol, 1.14 mL) and 1-Propanephosphonic anhydride 50% in EtOAc (1.25 g, 1.97 mmol, 50% purity) at ambient temperature under nitrogen atmosphere. The resulting mixture was stirred at ambient temperature for 5 minutes. Subsequently, tert-butyl (1R,5S)-3-oxa-7,9-diazabicyclo[3.3.1]nonane-7-carboxylate (1; 300 mg, 1.31 mmol) was added and the mixture was stirred at ambient temperature for 6 h. The reaction mixture was slowly added to ice-cold water (25 mL) and extracted with MTBE (3×15 mL). The combined organic phase was washed with brine (10 mL), dried (anhydrous $Na_2SO_4$), filtered and concentrated under reduced pressure. The crude solid was suspended in water (20 mL) and solid was filtered to obtain tert-butyl (1R,5S)-9-(3,3-dimethylbutanoyl)-3-oxa-7,9-diazabicyclo[3.3.1]nonane-7-carboxylate (3; 220 mg, 0.660 mmol, 50% yield) as an off-white solid. LCMS ($ES^+$): m/z 271.2 $[M-tBu+H]^+$.

Step 2. Into a 25 mL single-necked round-bottomed flask containing a well-stirred solution of tert-butyl (1R,5S)-9-(3,3-dimethylbutanoyl)-3-oxa-7,9-diazabicyclo[3.3.1]nonane-7-carboxylate (3; 100 mg, 0.300 mmol) in anhydrous DCM (2 mL) was added 4M HCl in 1,4-dioxane (3 mL) at 25° C. under nitrogen atmosphere. The resulting mixture was stirred at ambient temperature for 2 h. Excess solvent was removed under reduced pressure to afford 1-((1R,5S)-3-oxa-7,9-diazabicyclo[3.3.1]nonan-9-yl)-3,3-dimethylbutan-1-one hydrochloride (4; 73; 0 mg, 0.266 mmol, 89% yield) as an off-white solid. LCMS ($ES^+$): m/z 227.4 $[M+H]^+$.

Example 50: Synthesis of (1R,5S)-9-((4,4-difluorocyclohexyl)methyl)-3-oxa-7,9-diazabicyclo[3.3.1]nonane hydrochloride

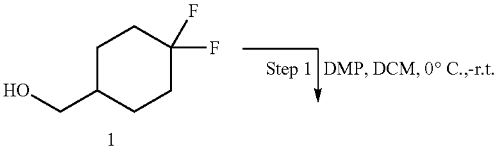

1

-continued

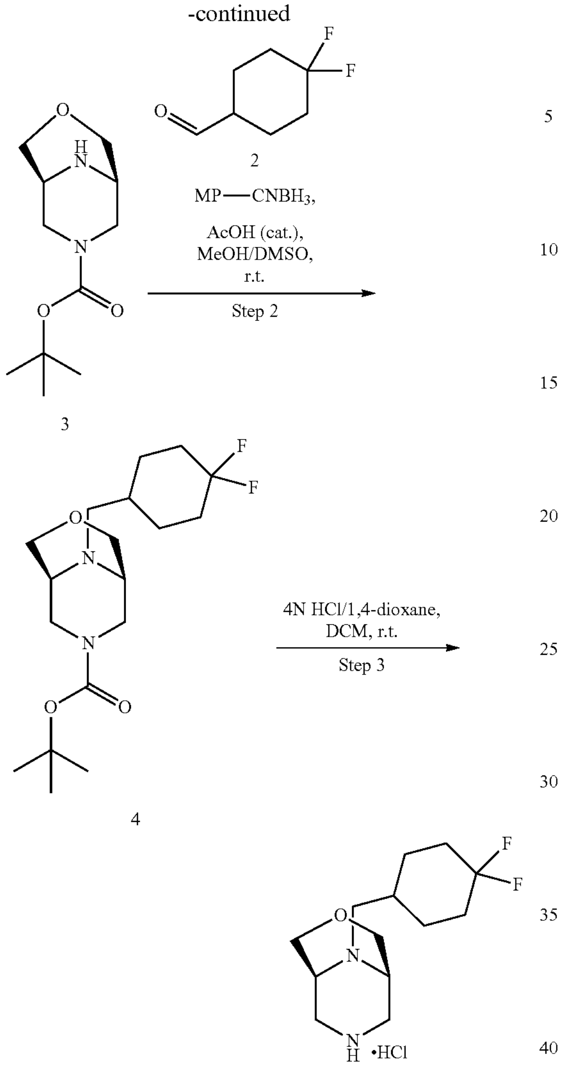

2

3

4

5

Step 1: Into a 100 mL single-necked round-bottomed flask containing a well-stirred solution of (4,4-difluorocyclohexyl)methanol (1, 1.5 g, 9.99 mmol) in anhydrous DCM (20 mL) was added Dess-Martin Periodinane (8.47 g, 19.98 mmol) at 0° C. under nitrogen atmosphere. After addition, the reaction mixture was stirred under nitrogen atmosphere at ambient temperature for 2 h. After completion, the reaction mixture was filtered through a pad of Celite, washing with DCM (50 mL). Combined organic phases were concentrated to obtain a crude. The crude mass was purified by flash silica-gel (100-200 mesh) column with 0-100% EtOAc/pet ether to afford 4,4-difluorocyclohexanecarbaldehyde (2, 0.9 g, 4.86 mmol, 48.6% yield) as a colorless liquid.

Step 2. Into a 50 mL single-necked round-bottomed flask containing a well-stirred solution of tert-butyl (1R,5S)-3-oxa-7,9-diazabicyclo[3.3.1]nonane-7-carboxylate (3, 300 mg, 1.31 mmol) and 4,4-difluorocyclohexanecarbaldehyde (2, 778.76 mg, 5.26 mmol) in MeOH (5 mL) was added Acetic acid (39.46 mg, 0.657 mmol, 0.037.61 mL) and the resulting mixture was stirred for 5 minutes at ambient temperature. MP-$CNBH_3$ (500 mg, 1.31 mmol) was added to the reaction mixture at ambient temperature and the reaction mixture was stirred for 2 h. The reaction mixture was filtered through the cotton plug and washed with MeOH (20 mL). The filtrate was concentrated under reduced pressure to obtain a crude mass. The crude mass was purified by flash silica-gel (100-200 mesh) column with 0-100% EtOAc/pet ether to afford tert-butyl (1R,5S)-9-((4,4-difluorocyclohexyl)methyl)-3-oxa-7,9-diazabicyclo[3.3.1] nonane-7-carboxylate (4, 330 mg, 0.915 mmol, 70% yield) as an off-white solid. UPLC-MS ($ES^+$): 361.2 $[M+H]^+$.

Step 3. Into a 50 mL single-necked round-bottomed flask containing a well-stirred solution of tert-butyl(1S,5R)-9-[(4, 4-difluorocyclohexyl)methyl]-3-oxa-7,9diazabicyclo[3.3.1] nonane-7-carboxylate (4, 440 mg, 1.22 mmol) in anhydrous DCM (5 mL) was added 4M HCl in 1,4-dioxane (1.53 mL) at 0° C. under nitrogen atmosphere. The resulting mixture was stirred at room temperature for 2 h. Excess solvent was removed from the reaction mixture under reduced pressure to get a crude mass. Reaction crude was washed with MTBE (20 mL) to afford (1R,5S)-9-((4,4-difluorocyclohexyl) methyl)-3-oxa-7,9-diazabicyclo[3.3.1]nonane hydrochloride (5, 360 mg, 1.21 mmol, 99% yield) as an off-white solid. LC-MS ($ES^+$): 261.2 $[M+H]^+$.

Example 51: Synthesis of (1S,5R)-9-[(5-fluoro-2-pyridyl)methyl]-3-oxa-7,9-diazabicyclo[3.3.1] nonane

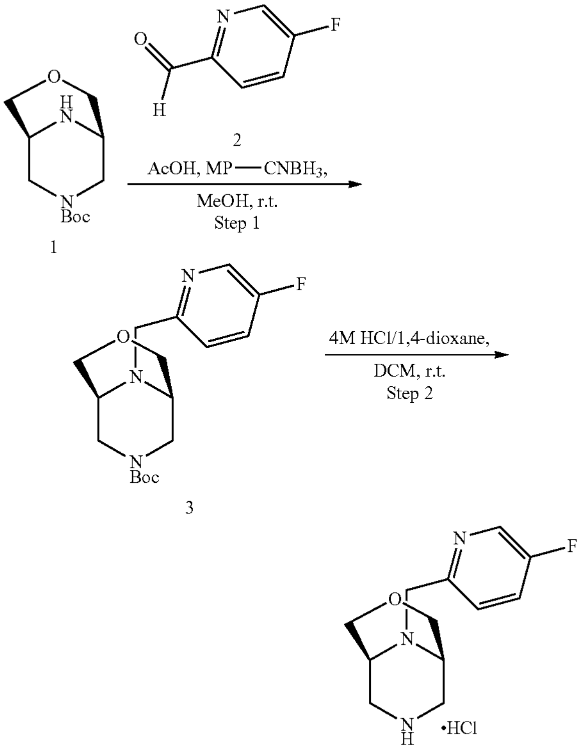

2

1

3

4

Step 1: Into a 100 mL single-necked round-bottomed flask containing a well-stirred solution of tert-butyl (1S,5R)-3-oxa-7,9-diazabicyclo[3.3.1]nonane-7-carboxylate (1, 800 mg, 3.50 mmol) and 5-fluoropyridine-2-carbaldehyde (2, 526.08 mg, 4.21 mmol) in anhydrous MeOH (8 mL) was added Acetic acid (210.44 mg, 3.50 mmol, 0.2 mL) and the resulting mixture was stirred for 10 minutes at ambient temperature. MP-$CNBH_3$ (1 g, 3.50 mmol) was added to the reaction mixture at ambient temperature and the reaction mixture was stirred for 5 h. After completion, the reaction mixture was filtered through a pad of Celite, washing with DCM (50 mL). Combined filtrate was concentrated under reduced pressure to get a crude residue. The crude product was purified by flash silica-gel (230-400 mesh; 50 g SNAP) column with 0-80% EtOAc/pet ether to afford tert-butyl (1S,5R)-9-[(5-fluoro-2-pyridyl)methyl]-3-oxa-7,9-diazabicyclo[3.3.1]nonane-7-carboxylate (3, 1.1 g, 3.19 mmol, 91% yield) as an off-white solid. UPLC-MS ($ES^+$): 338.4 $[M+H]^+$.

Step 2: Into a 50 mL single-necked round-bottomed flask containing a well-stirred solution of tert-butyl (1S,5R)-9-[(5-fluoro-2-pyridyl)methyl]-3-oxa-7,9-diazabicyclo[3.3.1]nonane-7-carboxylate (3, 300 mg, 0.889 mmol) in anhydrous DCM (5 mL) was added 4M HCl in 1,4-dioxane (5 mL) at ambient temperature under nitrogen atmosphere. The resulting mixture was stirred at ambient temperature for 5 h. Excess solvent was removed from the reaction mixture under reduced pressure to get a crude mass. The crude product was washed with MTBE (10 mL) to get (1S,5R)-9-[(5-fluoro-2-pyridyl)methyl]-3-oxa-7,9-diazabicyclo[3.3.1]nonane hydrochloride (4, 275 mg, 0.849 mmol, 96% yield) as an off-white solid. UPLC-MS ($ES^+$): 238.3 $[M+H]^+$.

Example 52: Synthesis of (1S,5R)-9-[(6-methoxy-3-pyridyl)methyl]-3-oxa-7,9-diazabicyclo[3.3.1]nonane (absolute configuration)

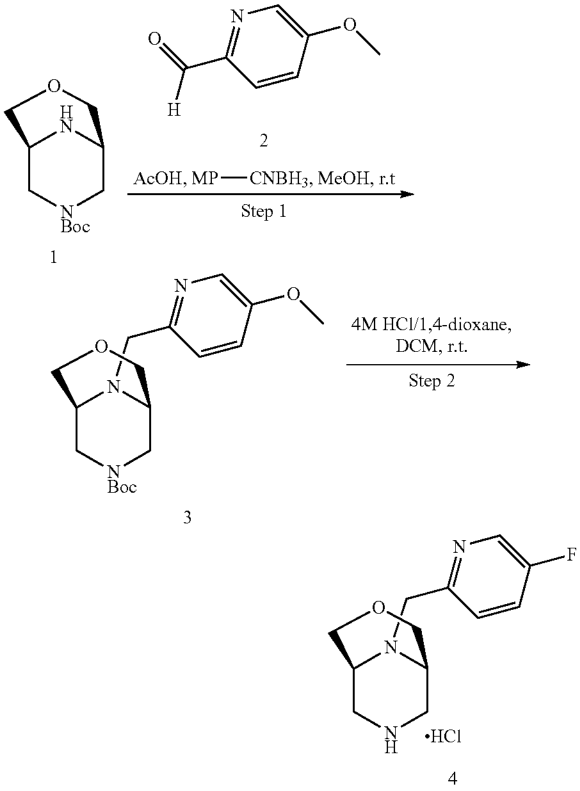

2
1
3
4

Step 1: Into a 250 mL single-necked round-bottomed flask containing a well-stirred solution of tert-butyl (1S,5R)-3-oxa-7,9-diazabicyclo [3.3.1]nonane-7-carboxylate (1; 2.0 g, 8.76 mmol) and 6-methoxypyridine-3-carbaldehyde (2; 1.44 g, 10.51 mmol) in anhydrous MeOH (20 mL) was added Acetic acid (1.5 mL, 26.23 mmol) at ambient temperature under nitrogen atmosphere. The resulting mixture was stirred at ambient temperature for 10 minutes. MP-$CNBH_3$ (2 g, 8.76 mmol) was added to the flask and stirred for 4 h. After completion, the reaction mixture was diluted with DCM (20 mL), filtered through a cotton-pad, and the filtrate was concentrated under reduced pressure to afford a crude mass. The crude mass was purified by flash silica-gel (230-400 mesh; 50 g) column with 0-100% EtOAc/pet ether to afford tert-butyl (1S,5R)-9-[(6-methoxy-3-pyridyl)methyl]-3-oxa-7,9-diazabicyclo[3.3.1]nonane-7-carboxylate (3; 2.1 g, 5.24 mmol, 60% yield) as a colorless liquid. UPLC-MS ($ES^+$): 350.5 $[M+H]^+$.

Step 2: Into a 250 mL single-necked round-bottomed flask containing a well-stirred solution of tert-butyl (1S,5R)-9-[(6-methoxy-3-pyridyl)methyl]-3-oxa-7,9-diazabicyclo[3.3.1]nonane-7-carboxylate (3; 2.1 g, 6.01 mmol) in anhydrous DCM (20 mL) was added dropwise 4N HCl in 1,4-dioxane, 99% (14.0 mL) at ambient temperature under nitrogen atmosphere. The resulting mixture was stirred at ambient temperature under nitrogen atmosphere for 2 h. After completion, excess solvent was removed from the reaction mixture under reduced pressure to get the crude. The crude mass was triturated with pet ether (2×30 mL) and the excess solvent was decanted. The solid was dried under vacuum to afford (1S,5R)-9-[(6-methoxy-3-pyridyl)methyl]-3-oxa-7,9-diazabicyclo[3.3.1]nonane hydrochloride (4; 1.8 g, 5.61 mmol, 93% yield) as an off-white solid. UPLC-MS ($ES^+$): 250.3 $[M+H]^+$.

Example 53: Synthesis of (1R,5S)-7-((6-methoxypyridin-3-yl)methyl)-3-oxa-7,9-diazabicyclo[3.3.1]nonane (absolute configuration)

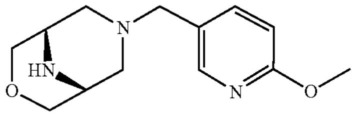 [SMILES: COc1ccc(CN2C[C@H]3COC[C@@H](C2)N3)cn1]

Procedure was similar to that of (1S,5R)-9-[(6-methoxy-3-pyridyl)methyl]-3-oxa-7,9-diazabicyclo[3.3.1]nonane hydrochloride. LCMS ($ES^+$): 250.1 $[M+H]^+$.

Example 54: Synthesis of 9-(tetrahydropyran-4-ylmethyl)-3-oxa-7,9-diazabicyclo[3.3.1]nonane

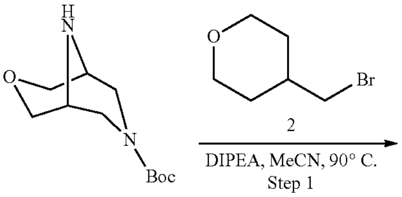

2
1

-continued

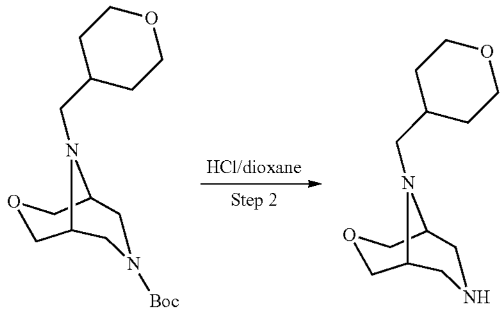

3 4

Step 1: To a solution of tert-butyl 3-oxa-7,9-diazabicyclo[3.3.1]nonane-7-carboxylate (1; 200 mg, 876.09 μmol) in MeCN (5 mL) were added 4-(bromomethyl)tetrahydropyran (2; 313.74 mg, 1.75 mmol) and DIPEA (2.63 mmol, 457.80 μL). The mixture was stirred at 90° C. for 16 h. The mixture was concentrated to give a residue. The residue was purified by Prep-HPLC (Waters Xbridge 150*25 mm*5 um; mobile phase: [water (10 mM $NH_4HCO_3$)-ACN]; B %: 31%-61%, 8 min) to give tert-butyl 9-(tetrahydropyran-4-ylmethyl)-3-oxa-7,9-diazabicyclo[3.3.1]nonane-7-carboxylate (3; 100 mg, 303.28 μmol, 35% yield) as a white solid. $^1$H NMR (400 MHz, CHLOROFORM-d) δ=3.96-3.67 (m, 8H), 3.38-3.17 (m, 4H), 2.58-2.32 (m, 4H), 1.67-1.46 (m, 4H), 1.40 (s, 9H), 1.27-1.11 (m, 2H)

Step 2: A solution of tert-butyl 9-(tetrahydropyran-4-ylmethyl)-3-oxa-7,9-diazabicyclo[3.3.1]nonane-7-carboxylate (3; 100 mg, 306.34 μmol) in HCl/dioxane (4 M, 5 mL) was stirred at 20° C. for 1 h. The mixture was concentrated to give 9-(tetrahydropyran-4-ylmethyl)-3-oxa-7,9-diazabicyclo[3.3.1]nonane (4; 80 mg, 304.44 μmol, 99% yield, HCl salt) as a white solid, it was used directly in the next step. LCMS ($ES^+$): 227.2 $[M+H]^+$

Example 55: Synthesis of (1R,5S)-9-[(4-fluorophenyl)methyl]-3-oxa-7,9-diazabicyclo[3.3.1]nonane (absolute configuration)

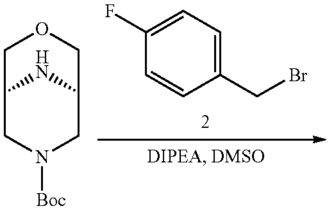

1

-continued

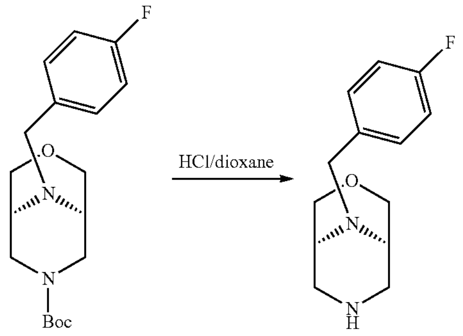

3 4

Step 1: To a solution of tert-butyl (1R,5S)-3-oxa-7,9-diazabicyclo[3.3.1]nonane-7-carboxylate (1, 50 mg, 219.02 μmol) and 1-(bromomethyl)-4-fluoro-benzene (2, 49.68 mg, 262.83 μmol, 32.68 μL) in DMSO (0.5 mL) was added DIPEA (438.04 μmol, 76.30 μL). The mixture was stirred at 20° C. for 12 h. The residue was poured into water (3 mL) and extracted with EtOAc (1 mL×3). The combined organic layers were washed with brine (3 mL), dried over $Na_2SO_4$, filtered and concentrated. The residue was purified by prep-TLC (SiO2, Pet ether:EtOAc=5:1) to afford tert-butyl (1R,5S)-9-[(4-fluorophenyl)methyl]-3-oxa-7,9-diazabicyclo[3.3.1]nonane-7-carboxylate (3, 70 mg, 183.12 μmol, 84% yield) as a light yellow solid. LCMS ($ES^+$): 337.0 $[M+H]^+$ Step 2: To a solution of tert-butyl (1R,5S)-9-[(4-fluorophenyl)methyl]-3-oxa-7,9-diazabicyclo[3.3.1]nonane-7-carboxylate (3, 70 mg, 208.09 μmol) in DCM (0.5 mL) was added HCl/dioxane (4 M, 0.5 mL). The mixture was stirred at 20° C. for 2 h. The reaction was concentrated under reduced pressure to get (1R,5S)-9-[(4-fluorophenyl)methyl]-3-oxa-7,9-diazabicyclo[3.3.1]nonane (4, 56 mg, 203.27 μmol, 98% yield, HCl salt) as white solid, which was used without further purification. LCMS ($ES^+$): 237.2 $[M+H]^+$

Example 56: Synthesis of spiro[5H-furo[3,4-b]pyridine-7,4'-piperidine]

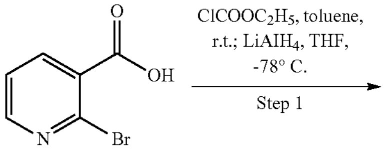

1

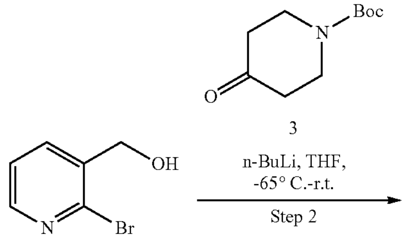

2

-continued

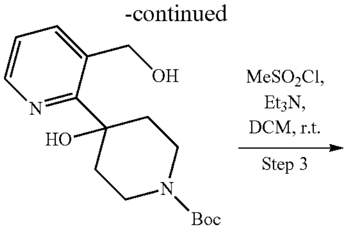

4

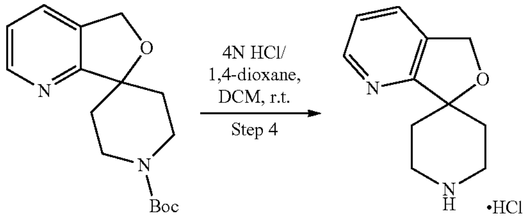

5 6

Step 1: Into a 1 L three-necked round-bottomed flask containing a well-stirred solution of 2-bromopyridine-3-carboxylic acid (1; 10 g, 49.50 mmol) and Triethylamine (54.45 mmol, 7.59 mL) in anhydrous toluene (500 mL) was added ethyl carbonochloridate (5.91 g, 54.45 mmol, 5.18 mL) at ambient temperature under nitrogen atmosphere and the reaction mixture was stirred for 1 h. The precipitated $Et_3N{\cdot}HCl$ was filtered off and the filtrate was concentrated under reduced pressure to dryness to get the mixed anhydride as a colorless oil. This material was immediately dissolved in THF (150 mL) and lithium aluminum hydride (29.70 mL; 2M/THF) was added at −78° C. dropwise. The resulting mixture was stirred at −78° C. for 1 h. After completion, the reaction mixture was cooled and quenched with saturated ammonium chloride (20 mL), stirring for 10 min. The reaction was then filtered through a pad of Celite, washing with THF (2×50 mL). The combined filtrate was concentrated under reduced pressure to get (2-bromo-3-pyridyl)methanol (2; 7.82 g, 40.63 mmol, 82% yield) as a white solid. LCMS ($ES^+$): 188.0 $[M+H]^+$.

Step 2: Into a 1 L three-necked round-bottomed flask containing a well-stirred solution of (2-bromo-3-pyridyl) methanol (2; 7.82 g, 41.59 mmol) in anhydrous THF (100 mL) was added dropwise butyllithium (34.94 mL; 2.5M/hexane) at −65° C. for 10 minutes and the resulting mixture was stirred at −78° C. for 2 h. To the reaction mixture was added tert-butyl 4-oxopiperidine-1-carboxylate (3; 9.12 g, 45.75 mmol) in THF (30 mL) at −65° C. under nitrogen atmosphere and the reaction mixture was gradually stirred at ambient temperature for 18 h. After completion, excess reagent was quenched with 10% citric acid in water (200 mL) and the compound was extracted with EtOAc (2×150 mL). Combined organic phases were washed with 10% aqueous $NaHCO_3$ (2×100 mL) and dried (anhydrous $Na_2SO_4$), filtered and concentrated under reduced pressure to get a crude residue. The crude was purified by flash silica-gel (230-400 mesh) column with 0-10% MeOH/DCM to afford tert-butyl 4-hydroxy-4-[3-(hydroxymethyl)-2-pyridyl]piperidine-1-carboxylate (4; 2.28 g, 7.31 mmol, 18% yield) as a brown semi solid. UPLC-MS ($ES^+$): 309.5 $[M+H]^+$.

Step 3: Into a 100 mL single-necked round-bottomed flask containing a well-stirred solution of tert-butyl 4-hydroxy-4-[3-(hydroxymethyl)-2-pyridyl]piperidine-1-carboxylate (4; 2.28 g, 7.39 mmol) in anhydrous DCM (20 mL) was added dropwise Triethylamine (15.55 mmol, 2.17 mL) at 0° C. for 10 minutes and then, to the reaction mixture was added methanesulfonyl chloride (931.32 mg, 8.13 mmol, 0.629 mL) at 0° C. under nitrogen atmosphere. The reaction mixture was gradually stirred at ambient temperature for 18 h. Then to the reaction mixture was added additional methanesulfonyl chloride (465.66 mg, 4.07 mmol, 0.314 mL) at ambient temperature and the reaction mixture was stirred for 5 h. Excess reagent was quenched with water (200 mL) and the compound was extracted with DCM (2×100 mL). Combined organic phases were dried (anhydrous $Na_2SO_4$), filtered and concentrated under reduced pressure to get a crude residue, which was purified by flash silica-gel (230-400 mesh) column with 0-100% EtOAc/pet ether to afford tert-butyl spiro[5H-furo[3,4-b]pyridine-7,4'-piperidine]-1'-carboxylate (5; 1.72 g, 4.87 mmol, 66% yield) as an yellow solid. UPLC-MS ($ES^+$): 291.2 $[M+H]^+$.

Step 4: Into a 100 mL single-necked round-bottomed flask containing a well-stirred solution of tert-butyl spiro[5H-furo[3,4-b]pyridine-7,4'-piperidine]-1'-carboxylate (5; 1.72 g, 5.92 mmol) in anhydrous DCM (15 mL) was added Trifluoroacetic acid (171.73 mmol, 13.23 mL) at 0° C. The resulting mixture was stirred at ambient temperature for 2 h. Excess solvent was removed under reduced pressure to get a crude mass. The reaction crude was washed with MTBE and n-hexane 1:1 (50 mL) to get spiro[5H-furo[3,4-b]pyridine-7,4'-piperidine]. trifluoroacetic acid (6; 2 g, 5.58 mmol, 94% yield) as a red gum. LCMS ($ES^+$): 191.1 $[M+H]^+$.

Example 57: Synthesis of 6-((6-methoxypyridin-3-yl)methyl)-3,6-diazabicyclo[3.1.1]heptane

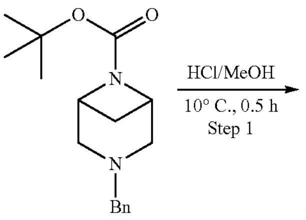

1

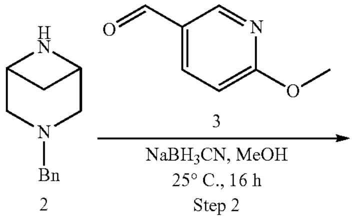

2

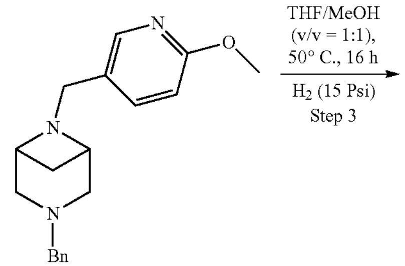

4

-continued

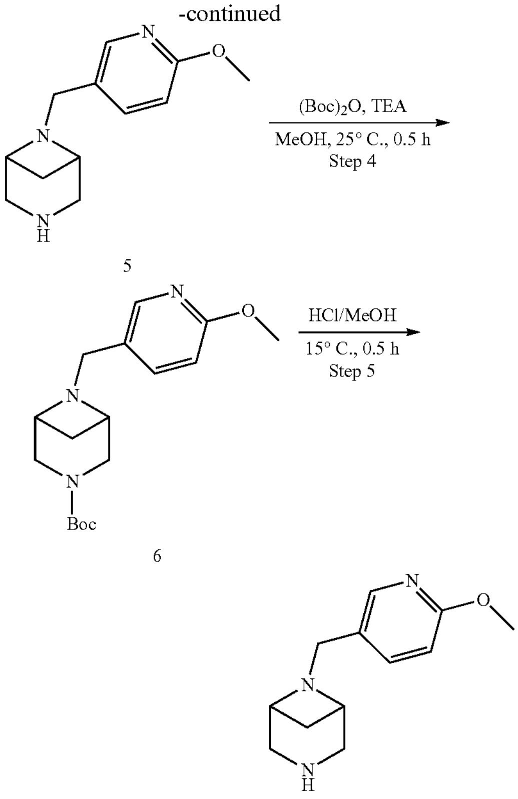

5

6

7

Step 1: A solution of tert-butyl 3-benzyl-3,6-diazabicyclo[3.1.1]heptane-6-carboxylate (1, 1 g, 3.47 mmol) in HCl/MeOH (5 mL, 4 mol/L) was stirred at 10° C. for 0.5 h. The reaction mixture was concentrated under reduced pressure, $K_2CO_3$ (500 mg) and DCM (10 ml) was added, it was filtered, the filtrate was concentrated in vacuum to afford 3-benzyl-3,6-diazabicyclo[3.1.1]heptane (2, 500 mg, 2.66 mmol, 77% yield) was obtained as a white solid, which was used without purification. $^1$H NMR (400 MHz, CHLOROFORM-d) δ=7.29-7.20 (m, 5H), 3.77-3.59 (m, 4H), 3.03 (br d, J=11.2 Hz, 2H), 2.73 (d, J=11.2 Hz, 2H), 2.53-2.46 (m, 1H), 1.95 (d, J=7.2 Hz, 1H)

Step 2: To a solution of 3-benzyl-3,6-diazabicyclo[3.1.1]heptane (2, 2 g, 10.62 mmol) in Methanol (20 mL) was added 6-methoxynicotinaldehyde (3, 1.46 g, 10.62 mmol) and acetic acid (1.06 mmol, 60.76 μL). The mixture was stirred at 25° C. for 0.5 h, before sodium cyanoboranuide (2.00 g, 31.87 mmol) was added. The reaction then stirred at 25° C. for 16 h. Saturated aq. $NH_4Cl$ (5 ml) was added into the mixture and it was concentrated in vacuum. The residue was purified by reversed phase flash. The pH of the pure fractions was adjusted to 8 by solid $NaHCO_3$. EtOAc (100 ml) was added, the organic layer was washed with brine (100 ml), dried over $Na_2SO_4$ and concentrated in vacuum to afford 3-benzyl-6-((6-methoxypyridin-3-yl)methyl)-3,6-diazabicyclo[3.1.1]heptane (4, 1.8 g, 4.65 mmol, 44% yield) was obtained as a yellow oil. $^1$H NMR (400 MHz, CHLOROFORM-d) δ=8.03 (d, J=1.6 Hz, 1H), 7.65-7.55 (m, 1H), 7.39-7.29 (m, 5H), 6.71 (d, J=8.8 Hz, 1H), 3.93 (s, 3H), 3.86 (s, 2H), 3.54 (br d, J=5.6 Hz, 2H), 3.47 (br s, 2H), 3.11 (br d, J=11.2 Hz, 2H), 2.86 (br d, J=11.2 Hz, 2H), 2.46 (m, 1H), 2.09-2.01 (m, 1H)

Step 3: To a solution of 3-benzyl-6-((6-methoxypyridin-3-yl)methyl)-3,6-diazabicyclo[3.1.1]heptane (4, 1700 mg, 5.49 mmol) in MeOH (15 mL) and THF (15 mL) was added Pd/C (2000 mg, 16.47 mmol), the mixture was charged with $H_2$ (3×) and stirred at 50° C. for 16 h under $H_2$ (15 psi). The reaction mixture was filtered and concentrated to afford 6-((6-methoxypyridin-3-yl)methyl)-3,6-diazabicyclo[3.1.1]heptane (5, 0.8 g, 904.66 μmol, 16% yield, HCl salt) as a yellow oil, which was used without purification. LCMS (ES$^+$): 220.1 [M+H]$^+$ Step 4: To a solution of 6-((6-methoxypyridin-3-yl)methyl)-3,6-diazabicyclo[3.1.1]heptane (5, 800 mg, 3.13 mmol, HCl salt) in Methanol (10 mL) was added TEA (9.38 mmol, 1.31 mL) and di-tert-butyl dicarbonate (1.02 g, 4.69 mmol, 1.08 mL). The mixture was stirred at 25° C. for 0.5 h. The reaction mixture was concentrated under reduced pressure. The residue was purified by reversed phase flash chromatography ($NH_4OH$) to afford tert-butyl 6-((6-methoxypyridin-3-yl)methyl)-3,6-diazabicyclo[3.1.1]heptane-3-carboxylate (6, 250 mg, 730.52 μmol, 23% yield) as a yellow oil. LCMS (ES$^+$): 320.1 [M+H]$^+$ Step 5: A solution of tert-butyl 6-((6-methoxypyridin-3-yl)methyl)-3,6-diazabicyclo[3.1.1]heptane-3-carboxylate (6, 250 mg, 782.72 μmol) in HCl/MeOH (1 mL) was stirred at 15° C. for 0.5 h. The reaction mixture was concentrated under reduced pressure to remove solvent. The residue was purified by reversed phase flash ($NH_4OH$ condition) to afford 6-((6-methoxypyridin-3-yl)methyl)-3,6-diazabicyclo[3.1.1]heptane (7, 200 mg, 735.42 μmol, 93.96% yield, HCl salt) as a yellow oil. LCMS (ES$^+$): 220.1 [M+H]$^+$.

Example 58: Synthesis of 1-(1,4-dioxaspiro[4.5]decan-8-yl)-4-(4,4,5,5-tetramethyl-1,3,2-dioxaborolan-2-yl)pyrazole

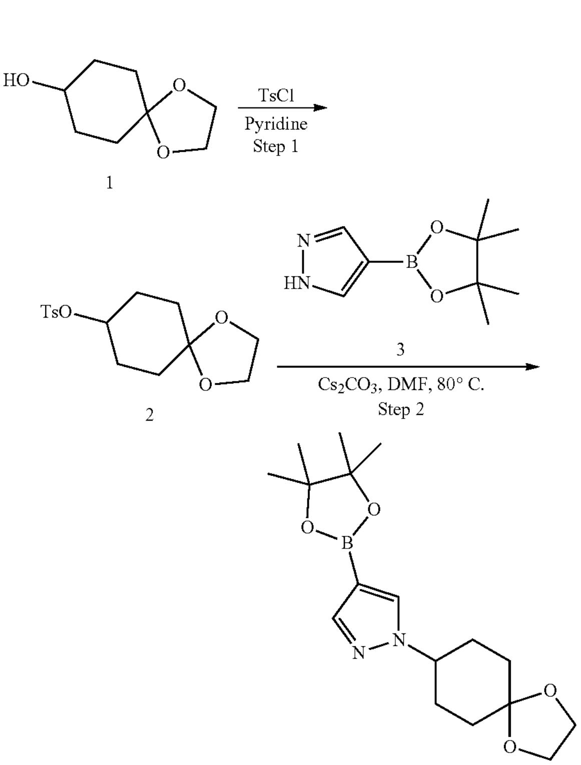

1

2

3

4

Step 1: To a solution of 1,4-dioxaspiro[4.5]decan-8-ol (50 g, 316.07 mmol) in pyridine (250 mL) was added 4-methylbenzenesulfonyl chloride (72.50 g, 380.28 mmol) in portions at 0° C. After addition, the mixture was stirred at 20° C. for 16 h. After consumption of the reactant as shown by TLC, the mixture was adjusted to pH=3 with 6M HCl (200 mL) followed by 12M HCl at 0° C. Then the mixture was poured into ice water (400 g ice in 1.6 L water). Large white precipitate was formed. The mixture was filtered, and the filter cake was washed with water (200 mL) and dried in vacuo. Compound 1,4-dioxaspiro[4.5]decan-8-yl 4-methylbenzenesulfonate (93.95 g, 285.72 mmol, 90.40% yield) was obtained as a white solid, which was used in the next step without further purification. $^1$H NMR (400 MHz, DMSO-$d_6$) δ=7.80 (d, J=8.4 Hz, 2H), 7.47 (d, J=8.0 Hz, 2H), 4.69-4.56 (m, 1H), 3.87-3.78 (m, 4H), 2.42 (s, 3H), 1.75-1.56 (m, 6H), 1.56-1.47 (m, 2H).

Step 2: To a solution of 1,4-dioxaspiro[4.5]decan-8-yl 4-methylbenzenesulfonate (2, 13 g, 41.62 mmol) and 4-(4,4,5,5-tetramethyl-1,3,2-dioxaborolan-2-yl)-1H-pyrazole (3, 8.08 g, 41.62 mmol) in DMF (100 mL) was added $Cs_2CO_3$ (27.12 g, 83.23 mmol). After addition, the solution was stirred at 80° C. for 12 hr. The reaction solution was poured into water (300 ml) to give a suspension. Then the suspension was filtered, the filter cake was washed with water (20 mL) and concentrated in vacuum. The residue was purified by flash silica gel chromatography (80 g Silica Flash Column, Eluent of 0-20% EtOAc/Pet ether 80 mL/min) to afford 1-(1,4-dioxaspiro[4.5]decan-8-yl)-4-(4,4,5,5-tetramethyl-1,3,2-dioxaborolan-2-yl)pyrazole (4, 4.4 g, 12.51 mmol, 30% yield) as white solid. LCMS ($ES^+$): 334.9 $[M+H]^+$. $^1$H NMR (400 MHz, CHLOROFORM-d) δ=7.70 (d, J=2.4 Hz, 2H), 4.16 (tt, J=4.4, 11.2 Hz, 1H), 3.91-3.87 (m, 4H), 2.12-1.95 (m, 4H), 1.84-1.76 (m, 2H), 1.69-1.60 (m, 2H), 1.24 (s, 12H)

Example 59: Synthesis of tert-butyl 4-(4-(4,4,5,5-tetramethyl-1,3,2-dioxaborolan-2-yl)phenyl)piperazine-1-carboxylate

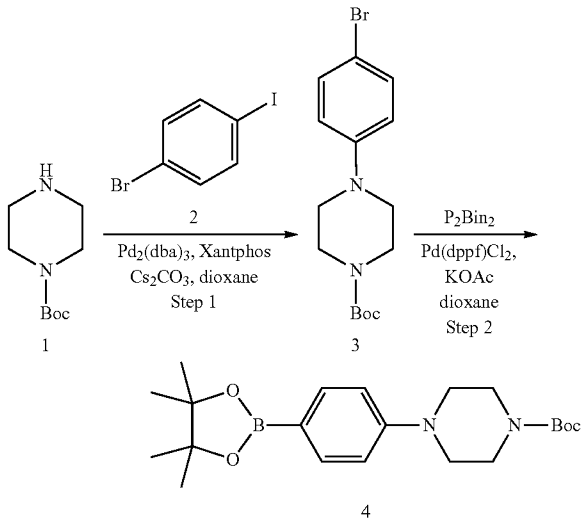

1 3 4

Step 1: To a solution of 1-bromo-4-iodobenzene (2, 3.5 g, 12.37 mmol, 1.71 mL), tert-butyl piperazine-1-carboxylate (1, 2.30 g, 12.37 mmol), Xantphos (1.43 g, 2.47 mmol) and $Cs_2CO_3$ (8.06 g, 24.74 mmol) in dioxane (50 mL) was added $Pd_2(dba)_3$ (1.13 g, 1.24 mmol) under $N_2$ atmosphere. After addition, the solution was stirred at 60° C. for 12 hr. The reaction solution was poured into sat. $NH_4Cl$ (200 mL). The aqueous solution was extracted with EtOAc (200 mL×3), the combined organic layer was washed with brine (500 mL×2) dried over $Na_2SO_4$ and concentrated in vacuum. The residue was purified by flash silica gel chromatography (20 g Silica Flash Column, Eluent of 0-20% EtOAc/Pet ether 30 mL/min) to afford tert-butyl 4-(4-bromophenyl)piperazine-1-carboxylate (3, 2.2 g, 5.80 mmol, 47% yield) as yellow solid. LCMS ($ES^+$): 343.1 $[M+H]^+$ Step 2: To a solution of tert-butyl 4-(4-bromophenyl)piperazine-1-carboxylate (3, 1 g, 2.93 mmol), $P_2Bin_2$ (1.12 g, 4.40 mmol) and KOAc (575.21 mg, 5.86 mmol) in dioxane (14 mL) was added $Pd(dppf)Cl_2$ (239.31 mg, 293.05 μmol). After addition, the solution was stirred at 70° C. for 12 hr. The reaction solution was poured into sat. $NH_4Cl$ (50 mL). The aqueous solution was extracted with EtOAc (50 mL×3), the combined organic layer was washed with brine (100 mL×2) dried over $Na_2SO_4$ and concentrated in vacuum. The residue was purified by flash silica gel chromatography (20 g Silica Flash Column, Eluent of 0-20% EtOAc/Pet ether, 30 mL/min) to afford Tert-butyl 4-(4-(4,4,5,5-tetramethyl-1,3,2-dioxaborolan-2-yl)phenyl)piperazine-1-carboxylate (4, 1 g, 2.45 mmol, 83% yield) as white solid. LCMS ($ES^+$): 389.3 $[M+H]^+$

Example 60: Synthesis of (1-(1-(tert-butoxycarbonyl)azetidin-3-yl)-1H-pyrazol-4-yl)boronic acid

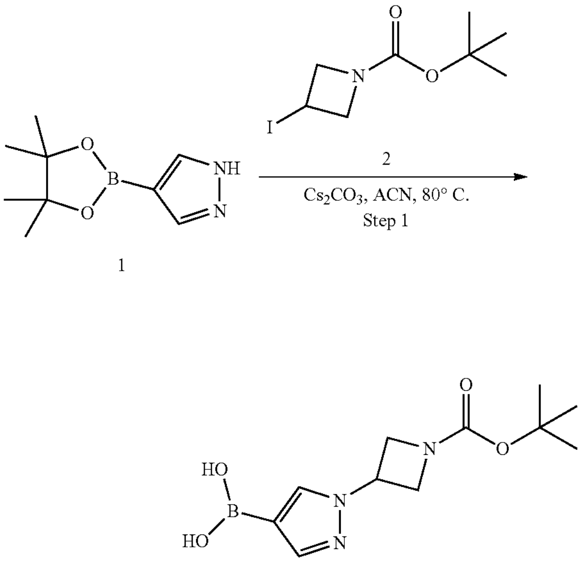

1 3

Step 1: Into a 50 mL sealed-tube containing a well-stirred solution of 4-(4,4,5,5-tetramethyl-1,3,2-dioxaborolan-2-yl)-1H-pyrazole (1; 400 mg, 2.06 mmol) and tert-butyl 3-iodoazetidine-1-carboxylate (2; 700.33 mg, 2.47 mmol) in anhydrous ACN (8 mL) were added Cesium carbonate (1.34 g, 4.12 mmol) at ambient temperature under nitrogen atmosphere and the resulting mixture was heated to 80° C. for 16 h. After completion, the reaction mixture was cooled to ambient temperature. The reaction mixture was concentrated to afford (1-(1-(tert-butoxycarbonyl)azetidin-3-yl)-1H-pyrazol-4-yl)boronic acid (3; 460 mg, 0.568 mmol), which was taken to the next step without further purification. LCMS ($ES^+$): 212.2 $[M-tBu+H]^+$.

Example 61: Synthesis of 4-ethyl-N-isopropyl-1-[4-(4,4,5,5-tetramethyl-1,3,2-dioxaborolan-2-yl)phenyl]piperidine-4-carboxamide

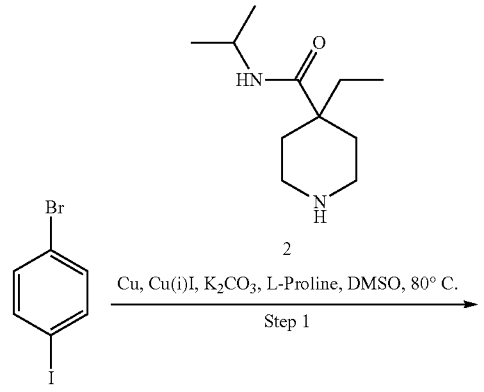

2

1

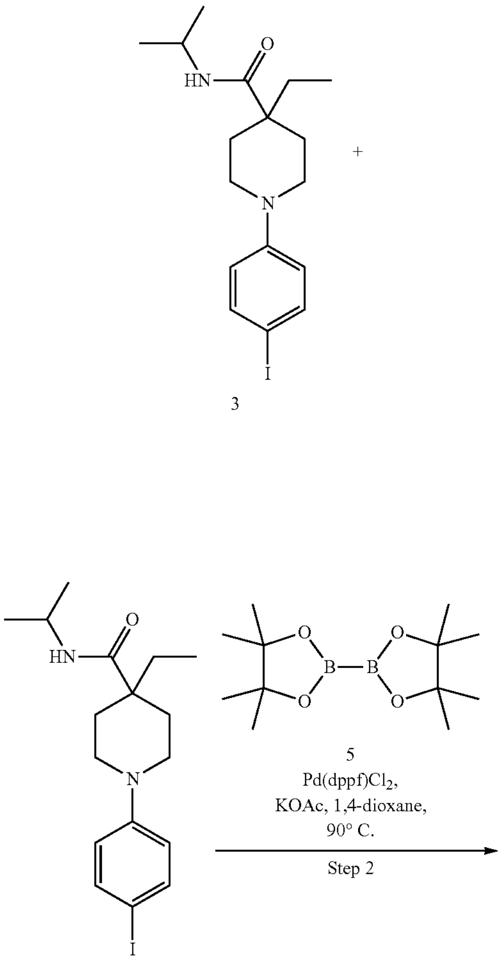

3

4

5

-continued

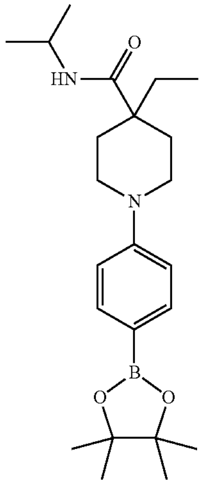

6

Step 1: Into a 50 mL sealed-tube containing a well-stirred solution of 4-ethyl-N-isopropyl-piperidine-4-carboxamide hydrochloride (2; 0.550 g, 2.34 mmol) in anhydrous DMSO (1.5 mL) were added 1-bromo-4-iodo-benzene (1; 795.33 mg, 2.81 mmol) and Potassium carbonate, anhydrous, 99% (647.57 mg, 4.69 mmol) and the mixture was degassed by bubbling nitrogen for 10 minutes. Subsequently, Copper metal powder (14.76 mg, 0.234 mmol), Copper (I) iodide (44.62 mg, 0.234 mmol) and L-Proline, 99% (53.94 mg, 0.468 mmol) were added. The resulting mixture was heated at 80° C. under closed condition for 16 h. The mixture was cooled to ambient temperature and quenched with water (5 mL). The aqueous layer was extracted with EtOAc (2×10 mL). The combined organic layer was washed with brine (10 mL) and dried (anhydrous $Na_2SO_4$), filtered and concentrated under reduced pressure to get a crude mass. The crude mass was purified by flash silica-gel (230-400 mesh) column with 0-75% EtOAc/pet ether to afford a mixture (1.7:1) of 1-(4-bromophenyl)-4-ethyl-N-isopropylpiperidine-4-carboxamide (3) and 4-ethyl-1-(4-iodophenyl)-N-isopropylpiperidine-4-carboxamide (4) (0.5 g), respectively as a pale-yellow solid. LCMS ($ES^+$): 353.2 $[M+H]^+$ Step 2: Into a 50 mL sealed-tube containing a well-stirred solution of a mixture (1.7:1) of 1-(4-bromophenyl)-4-ethyl-N-isopropyl-piperidine-4-carboxamide (3; 0.3 g, 0.849 mmol) and 4-ethyl-1-(4-iodophenyl)-N-isopropyl-piperidine-4-carboxamide (4; 0.2 g, 0.499 mmol) in anhydrous 1,4-dioxane (10 mL) were added Potassium acetate (166.67 mg, 1.70 mmol) and 4,4,5,5-tetramethyl-2-(4,4,5,5-tetramethyl-1,3,2-dioxaborolan-2-yl)-1,3,2-dioxaborolane (5, 237.19 mg, 0.934 mmol) at ambient temperature under nitrogen atmosphere and the resulting mixture was degassed by bubbling nitrogen gas for 5 minutes. Subsequently, Pd(dppf)$Cl_2$DCM (69.34 mg, 0.084 mmol) was added and the mixture was heated to 90° C. under closed condition for 16 h. The mixture was cooled to ambient temperature, filtered through a pad of Celite, washing with EtOAc (25 mL). The filtrate was concentrated under reduced pressure to get a crude mass. The crude was purified by flash silica-gel (230-400 mesh) column with 50-100% EtOAc/pet ether to afford 4-ethyl-N-isopropyl-1-[4-(4,4,5,5-tetramethyl-1,3,2-dioxaborolan-2-yl)phenyl]piperidine-4-carboxamide (6, 0.51 g, 0.416 mmol, 49% yield) as a brown liquid. LCMS ($ES^+$): 401.4 $[M+H]^+$

Example 62: Synthesis of 4-(2-fluoro-4-nitro-phenyl)-1-[4-[4-(4,4,5,5-tetramethyl-1,3,2-dioxaborolan-2-yl)pyrazol-1-yl]cyclohexyl]piperidine

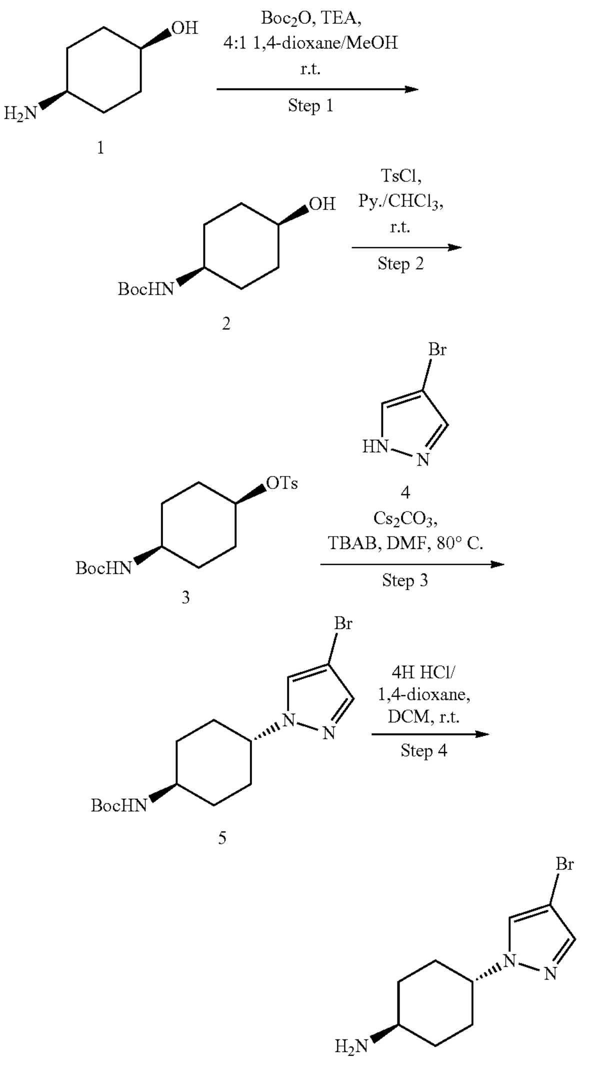

Step 1: Into a 2000 mL single-necked round-bottomed flask containing a well-stirred suspension of cis 4-aminocyclohexanol hydrochloride (1; 70 g, 461.64 mmol) in a mixture of anhydrous MeOH (125 mL) and 1,4-dioxane (500 mL) was added TEA (1150 mmol, 160.86 mL) followed by dropwise addition of di-tert-butyl dicarbonate (120.90 g, 553.97 mmol, 127.13 mL) at 0° C. under nitrogen atmosphere. After completion of the addition, the reaction mixture was stirred at ambient temperature for 6 h under nitrogen atmosphere. Excess solvent was concentrated under reduced pressure to afford a crude mass. The crude thus obtained was dissolved in EtOAc (600 mL) and washed with water followed by brine, dried (anhydrous $Na_2SO_4$) and concentrated under reduced pressure to afford tert-butyl N-(4-hydroxycyclohexyl)carbamate (2; 81 g, 376.24 mmol, 82% yield) as an off-white solid. GCMS ($ES^+$): 215.3 $[M]^+$.

Step 2: Into a 2000 mL single-necked round-bottomed flask containing a well-stirred suspension of tert-butyl N-(4-hydroxycyclohexyl)carbamate (2; 31 g, 143.99 mmol) in a mixture of anhydrous $CHCl_3$ (230 mL) and pyridine (97.80 g, 1240 mmol, 100 mL) was added para-toluenesulfonyl chloride (41.18 g, 215.99 mmol) at 0° C. under nitrogen atmosphere. The resulting suspension was stirred at ambient temperature for 16 h. After completion, the reaction mixture was poured into water (500 mL) and extracted by EtOAc (3×300 mL). Combined organic phases were dried (anhydrous $Na_2SO_4$), filtered and concentrated under reduced pressure to obtain a crude mass, which was purified by flash silica-gel (230-400 mesh) column with 0-100% EtOAc/pet ether to afford [4-(tert-butoxycarbonylamino)cyclohexyl] 4-methylbenzenesulfonate (3; 55 g, 119.83 mmol, 83% yield) as a white-colored solid. LCMS ($ES^+$): m/z 270.2 $[M\text{-}Boc+H]^+$.

Step 3: Into a 250 mL sealed-tube reactor containing a well-stirred solution of [4-(tert-butoxycarbonylamino)cyclohexyl] 4-methylbenzenesulfonate (3; 30 g, 81.20 mmol) and 4-bromo-1H-pyrazole (4; 13.13 g, 89.32 mmol) in anhydrous DMF (70 mL) was added Cesium carbonate (52.91 g, 162.39 mmol) followed by tetra butyl ammonium bromide (2.62 g, 8.12 mmol) at ambient temperature. The resulting reaction mixture was stirred at 80° C. for 10 h. After completion, the reaction mixture was allowed to attain room temperature and ice-cold water (150 mL) was added. The resulting solid was filtered and washed with pet ether (200 mL) to afford tert-butyl N-[4-(4-bromopyrazol-1-yl)cyclohexyl]carbamate (5; 13.5 g, 38.75 mmol, 48% yield) as an off-white solid. LCMS ($ES^+$): 288.0 $[M\text{-}tBu+H]^+$.

Step 4: Into a 500 mL single-necked round-bottomed flask containing a well-stirred solution of tert-butyl N-[4-(4-bromopyrazol-1-yl)cyclohexyl]carbamate (5; 13 g, 37.76 mmol) in anhydrous DCM (130 mL) was added hydrogen chloride (32.0 g, 877.65 mmol, 40 mL; 4M/1,4-dioxane) under nitrogen atmosphere at 0° C. The resulting reaction mixture was stirred at ambient temperature under nitrogen atmosphere for 2 h. After completion, excess solvent was removed from the reaction mixture under reduced pressure and crude thus obtained was co-distilled with DCM, triturated with methyl tert-butyl ether (3×60 mL) to afford 4-(4-bromopyrazol-1-yl)cyclohexanamine hydrochloride (6; 10.5 g, 36.78 mmol, 97% yield) as an off-white solid. LCMS ($ES^+$): 244.2 $[M+H]^+$.

Example 63: Synthesis of 4-(2-fluoro-4-nitro-phenyl)-1-[4-[4-(4,4,5,5-tetramethyl-1,3,2-dioxaborolan-2-yl)pyrazol-1-yl]cyclohexyl]piperidine

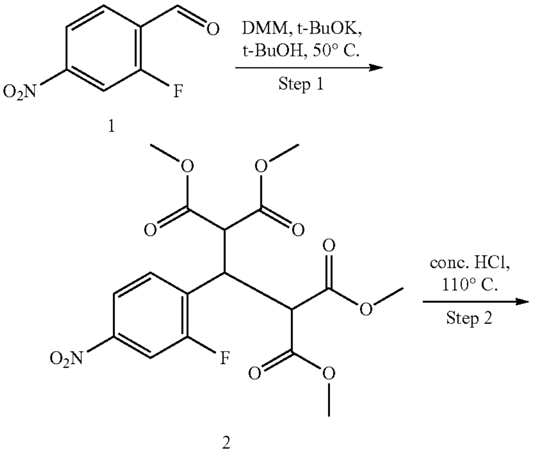

-continued

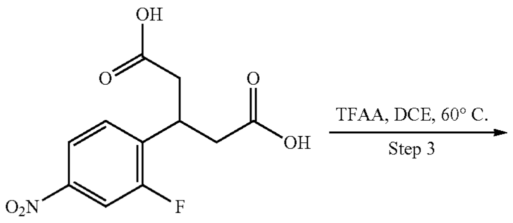

3

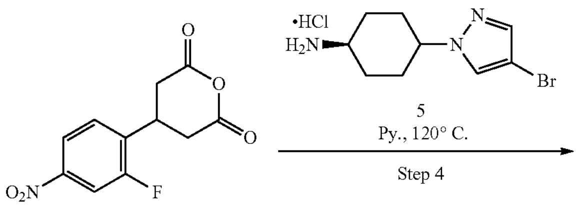

4

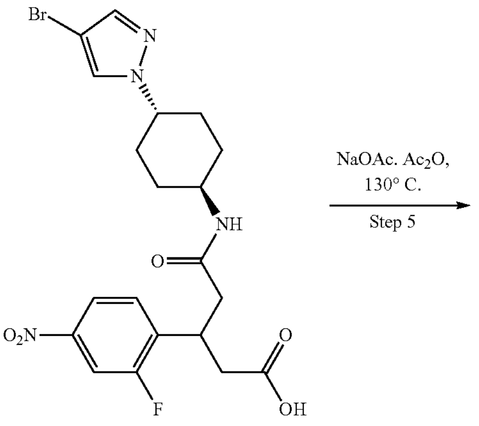

6

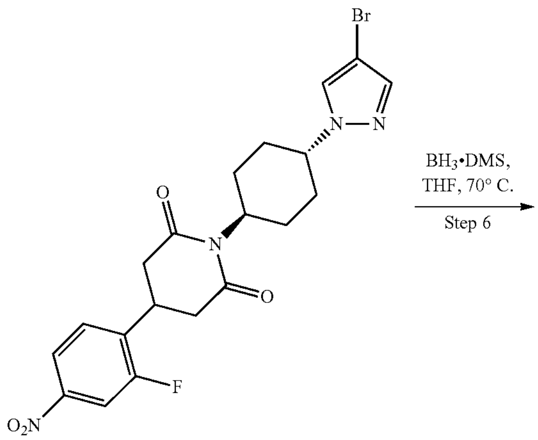

7

-continued

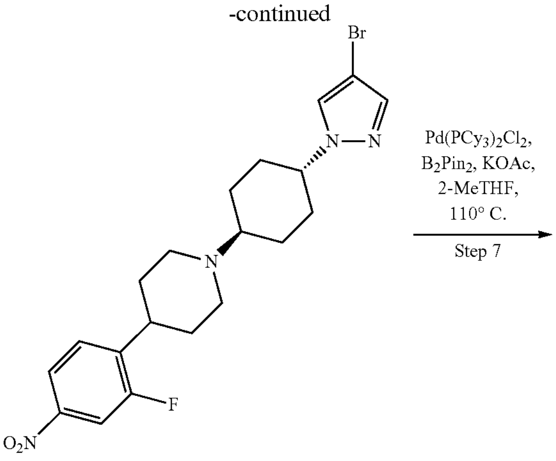

8

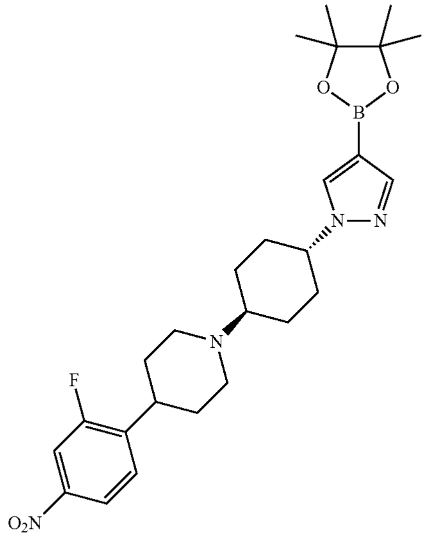

9

Step 1: Into a 1000 mL single-necked round-bottomed flask containing a well-stirred solution of 2-fluoro-4-nitro-benzaldehyde (1, 25 g, 147.83 mmol) and dimethyl malonate (39.06 g, 295.67 mmol, 33.67 mL) in anhydrous tert-BuOH (250 mL) was added Potassium tert-butoxide (33.18 g, 295.67 mmol) at ambient temperature under nitrogen atmosphere. The reaction mixture was stirred at 50° C. for 2 h. After completion, the reaction mixture was quenched with cold 1N HCl in water (300 mL) and extracted with EtOAc (3×200 mL). The organic phases were combined and dried (anhydrous $Na_2SO_4$), filtered and the filtrate was concentrated under reduced pressure to get tetramethyl 2-(2-fluoro-4-nitro-phenyl)propane-1,1,3,3-tetracarboxylate (2, 37 g, 65.12 mmol, 44% yield) as a pale crude brown gum. LCMS (ES$^+$): m/z 416.5 [M+H]$^+$.

Step 2: Into a 500 mL single-necked round-bottomed flask containing a well-stirred solution of tetramethyl 2-(2-fluoro-4-nitro-phenyl)propane-1,1,3,3-tetracarboxylate (2, 37 g, 89.09 mmol) in hydrochloric acid (120.0 g, 3290 mmol, 150 mL; 36% w/w aqueous solution) under nitrogen atmosphere was stirred at 110° C. for 6 h. After completion, the reaction mixture was allowed to attain ambient temperature, quenched with cold water (500 mL) and extracted with EtOAc (3×100 mL). The organic phases were combined and dried (anhydrous $Na_2SO_4$), filtered and concentrated under reduced pressure to get a crude residue. The crude product was triturated with 20% DCM/pet ether to get 3-(2-fluoro-4-nitro-phenyl)pentanedioic acid (3; 20 g, 68.51 mmol, 77% yield) as a pale brown solid. LCMS ($ES^-$): 270.0 $[M-H]^-$.

Step 3: Into a 100 mL single-necked round-bottomed flask containing a well-stirred solution of 3-(2-fluoro-4-nitro-phenyl)pentanedioic acid (3, 8 g, 29.50 mmol) in anhydrous DCE (30 mL) was added Trifluoroacetic anhydride (59.6 g, 283.77 mmol, 40.0 mL) slowly at 0° C. under nitrogen atmosphere. The resulting reaction mixture was stirred at 70° C. under nitrogen atmosphere for 16 h. After completion, the reaction mixture was concentrated under reduced pressure to afford 4-(2-fluoro-4-nitro-phenyl)tetrahydropyran-2,6-dione (4, 7 g, 16.77 mmol, 57% yield) as a brown solid. LCMS ($ES^-$): m/z 252.2 $[M-H]^-$.

Step 4: Into a 250 mL single-necked round-bottomed flask containing a well-stirred solution of 4-(2-fluoro-4-nitro-phenyl)tetrahydropyran-2,6-dione (4, 5.5 g, 15.21 mmol) in anhydrous pyridine (62.76 g, 793.36 mmol, 64.17 mL) was added 4-(4-bromopyrazol-1-yl)cyclohexanamine hydrochloride (5, 4.27 g, 15.21 mmol) under nitrogen atmosphere. The resulting mixture was stirred at 120° C. under nitrogen atmosphere for 8 h. After completion, the reaction mixture was concentrated under reduced pressure and the crude mass thus obtained was triturated with pet ether (3×70 mL) to obtain 5-[[4-(4-bromopyrazol-1-yl)cyclohexyl]amino]-3-(2-fluoro-4-nitro-phenyl)-5-oxo-pentanoic acid (6, 8 g, 4.25 mmol, 28% yield) as a brown gum which was used without further purification. LCMS ($ES^+$): 497.2 $[M+H]^+$.

Step 5: Into a 25 mL single-necked round-bottomed flask containing a well-stirred solution of 5-[[4-(4-bromopyrazol-1-yl)cyclohexyl]amino]-3-(2-fluoro-4-nitro-phenyl)-5-oxo-pentanoic acid (6, 8 g, 16.09 mmol) in anhydrous Acetic anhydride (72.0 g, 705.26 mmol, 66.67 mL) was added anhydrous Sodium acetate (2.64 g, 32.17 mmol, 1.72 mL) under nitrogen atmosphere. The resulting mixture was stirred at 130° C. under nitrogen atmosphere for 5 h. After completion, the reaction mixture was concentrated under reduced pressure. The crude mass thus obtained was dissolved into water (100 mL) and aqueous phase was extracted with EtOAc (3×100 mL). Combined organic phases were dried (anhydrous $Na_2SO_4$), filtered and the filtrate was concentrated under reduced pressure to afford a crude mass. The crude residue was purified by flash silica-gel (230-400 mesh) column with 0-100% EtOAc/pet ether, and isolated product was further triturated with 10% DCM/pet ether to afford 1-[4-(4-bromopyrazol-1-yl)cyclohexyl]-4-(2-fluoro-4-nitro-phenyl)piperidine-2,6-dione (7, 2.23 g, 4.28 mmol, 27% yield) as a light brown solid. LCMS ($ES^+$): 479.5 $[M+H]^+$.

Step 6: Into a 250 mL three-necked round-bottomed flask containing a well-stirred solution of 1-[4-(4-bromopyrazol-1-yl)cyclohexyl]-4-(2-fluoro-4-nitro-phenyl)piperidine-2,6-dione (7, 2.2 g, 4.59 mmol) in anhydrous THF (20 mL) was slowly added Borane dimethyl sulfide complex (18 mL; 1M/THF) at 0° C. under nitrogen atmosphere. The resulting mixture was stirred at 70° C. under nitrogen atmosphere for 6 h. After completion, the reaction mixture was quenched with aqueous saturated $NH_4Cl$ solution (50 mL) and aqueous phase was extracted with EtOAc (3×70 mL). Combined organic phases were washed with brine (50 mL) and dried (anhydrous $Na_2SO_4$), filtered and concentrated under reduced pressure. This crude residue was taken into 2M HCl/water (20 mL) and heated to 110° C. for 4 h. The reaction mixture was cooled to 10° C. and pH of the solution was adjusted to 12 with 50% sodium hydroxide solution, during this time brownish solid precipitated out. The solid was filtered and washed with pet ether (100 mL) to afford 1-[4-(4-bromopyrazol-1-yl)cyclohexyl]-4-(2-fluoro-4-nitro-phenyl)piperidine (8, 1.2 g, 1.91 mmol, 42% yield) as a brown solid. LCMS ($ES^+$): m/z 451.5 $[M+H]^+$.

Step 7: A well-stirred solution of 1-[4-(4-bromopyrazol-1-yl)cyclohexyl]-4-(2-fluoro-4-nitro-phenyl)piperidine (8, 1 g, 2.2 mmol) and 4,4,5,5-tetramethyl-2-(4,4,5,5-tetramethyl-1,3,2-dioxaborolan-2-yl)-1,3,2-dioxaborolane (1.01 g, 3.99 mmol) in anhydrous 2-Methyltetrahydrofuran (60 mL) taken into a 250 mL sealed tube was degassed by bubbling nitrogen gas into the reaction mixture for 5 minutes. Subsequently, potassium acetate (652.34 mg, 6.65 mmol, 0.415 mL) and Dichlorobis(tricyclohexylphosphine)palladium(II) (327.11 mg, 0.443 mmol) were added to the reaction mixture. The reaction mixture was stirred at 90° C. for 16 h. After completion, the reaction mixture was filtered through a pad of Celite and filtrate was concentrated under reduced pressure to get 4-(2-fluoro-4-nitro-phenyl)-1-[4-[4-(4,4,5,5-tetramethyl-1,3,2-dioxaborolan-2-yl)pyrazol-1-yl]cyclohexyl]piperidine (9, 2.7 g, 2.06 mmol, 93% yield) a yellow-colored gum. UPLC-MS ($ES^+$): 499.8 $[M+H]^+$.

Example 64: Synthesis of tert-butyl-diphenyl-[[4-[4-(4,4,5,5-tetramethyl-1,3,2-dioxaborolan-2-yl)pyrazol-1-yl]cyclohexyl]methoxy]silane

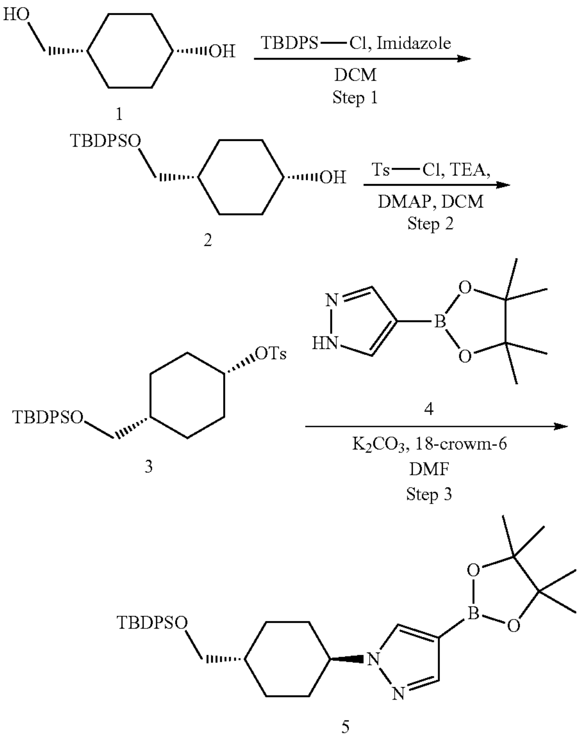

5

Step 1: To a solution of tert-butyl-chloro-diphenyl-silane (12.67 g, 46.09 mmol, 11.84 mL) and Imidazole (6.28 g, 92.18 mmol) in DMF (300 mL) was added 4-(hydroxymethyl)cyclohexanol (1, 10 g, 76.81 mmol). The mixture was stirred at 20° C. for 1 h under $N_2$. The reaction mixture was poured into water (600 ml), extracted with Ethyl acetate (200 mL×2). The combined organic layers were washed with brine (300 mL×2), dried over $Na_2SO_4$, filtered and concentrated. The residue was purified by flash silica gel chromatography (ISCO®; 80 g SepaFlash® Silica Flash Column, Eluent of 0-10% Ethylacetate/Petroleum ethergradient @ 80 mL/min) to afford 4-[[tert-butyl(diphenyl)silyl]oxymethyl]cyclohexanol (2, 13 g, 35.27 mmol, 46% yield) as colorless oil. $^1$H NMR (400 MHz, DMSO-d6) δ=7.61-7.59 (m, 4H), 7.45-7.42 (m, 6H), 4.22 (d, 1H), 3.75 (s, 1H), 3.46 (d, 2H), 1.55-1.53 (m, 3H), 1.43-1.38 (m, 6H), 0.99 (s, 9H).

Step 2: To a solution of 4-[[tert-butyl(diphenyl)silyl]oxymethyl]cyclohexanol (2, 1 g, 2.71 mmol), 4-(dimethylamino)pyridine (16.57 mg, 135.65 μmol) and pyridine (19.05 mmol, 1.54 mL) in DCM (10 mL) was added 4-methylbenzene-1-sulfonyl chloride (672.43 mg, 3.53 mmol) at 0° C., then the mixture was warmed to 20° C. and stirred for 5 h. The reaction mixture was concentrated and the residue was purified by flash silica gel chromatography (ISCO®; 12 g SepaFlash® Silica Flash Column, Eluent of 0-15% Ethylacetate/Petroleum ethergradient @ 40 mL/min) to afford [4-[[tert-butyl(diphenyl)silyl]oxymethyl]cyclohexyl] 4-methylbenzenesulfonate (3, 0.5 g, 956.44 μmol, 35% yield) as colorless oil. $^1$H NMR (400 MHz, DMSO-d6) δ=7.78-7.59 (d, 2H), 7.58-7.57 (d, 4H), 7.46-7.40 (m, 8H), 4.70 (s, 1H), 3.47-3.45 (m, 2H), 2.41 (s, 3H), 1.69-1.66 (m, 2H), 1.52-1.45 (m, 5H), 1.29-1.23 (m, 2H), 0.98 (s, 9H).

Step 3: To a solution of [4-[[tert-butyl(diphenyl)silyl]oxymethyl]cyclohexyl] 4-methylbenzenesulfonate (3, 3 g, 5.74 mmol) and 4-(4,4,5,5-tetramethyl-1,3,2-dioxaborolan-2-yl)-1H-pyrazole (4, 1.11 g, 5.74 mmol) in DMF (40 mL) was added Cesium carbonate (5.61 g, 17.22 mmol). The mixture was stirred at 100° C. for 10 h. The reaction mixture was diluted with $H_2O$ (200 mL) and extracted with EtOAc (100 mL×2). The combined organic layers were washed with brine (200 mL×2), dried over $Na_2SO_4$, filtered, and concentrated under reduced pressure. The residue was purified by flash silica gel chromatography (ISCO®; 80 g SepaFlash® Silica Flash Column, Eluent of 0-15% Ethylacetate/Petroleum ether gradient @ 60 mL/min) to afford tert-butyl-diphenyl-[[4-[4-(4,4,5,5-tetramethyl-1,3,2-dioxaborolan-2-yl)pyrazol-1-yl]cyclohexyl]methoxy]silane (5, 230 mg, 422.32 μmol, 7% yield) as colorless oil. LCMS (ES$^+$): 545.5 [M+H]$^+$.

Example 65: Synthesis of 3',3'-difluoro-1'-(2-fluoro-4-nitrophenyl)-4-(4-(4,4,5,5-tetramethyl-1,3,2-dioxaborolan-2-yl)-1H-pyrazol-1-yl)-1,4'-bipiperidine

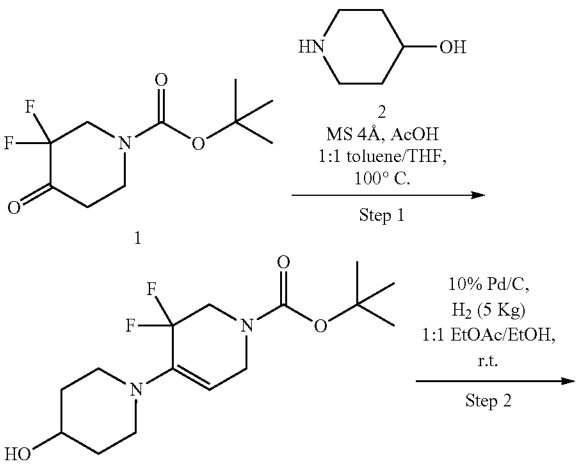

1
3

-continued

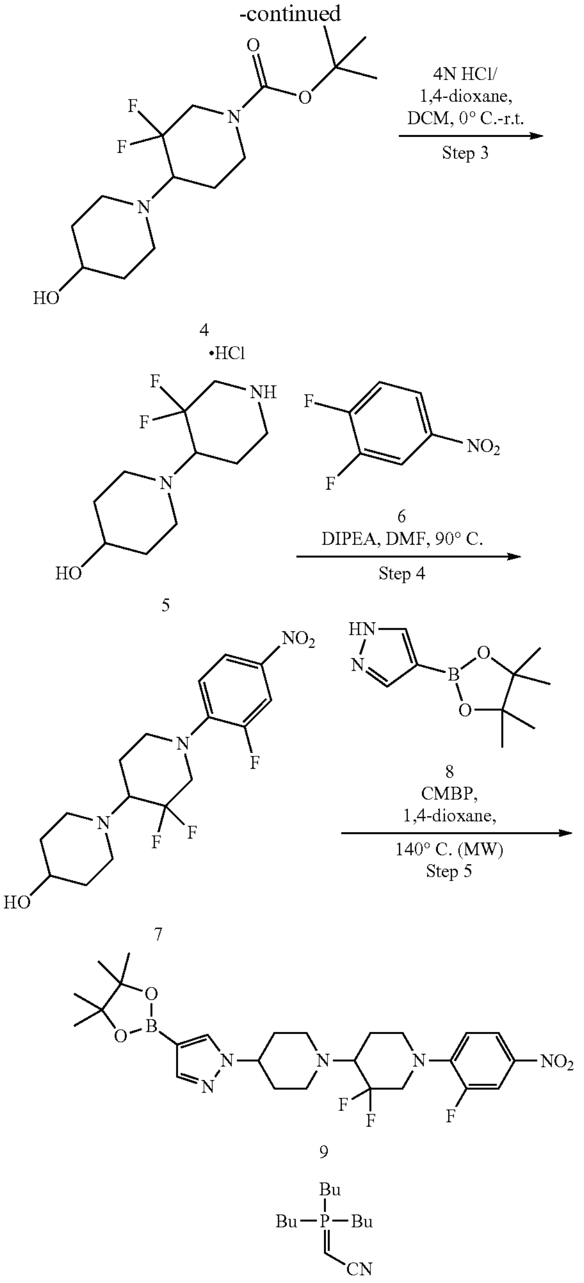

4
5
7
9
CMBP

Step 1: Into a 250 mL two-necked round-bottomed flask containing a well-stirred solution of tert-butyl 3,3-difluoro-4-oxo-piperidine-1-carboxylate (1; 10.0 g, 42.51 mmol; Source: CombiBlocks) and piperidin-4-ol (2; 5.16 g, 51.01 mmol) in 1:1 Toluene/THF (200 mL) was added 4 Å molecular sieve. The reaction mixture adjusted to pH=5 with Acetic acid (2.55 g, 42.51 mmol, 2.43 mL) and then the resulting mixture was heated at 100° C. for 16 h. After completion, the reaction mixture was filtered through a pad of Celite pad, washing with THF (250 mL). The filtrate was concentrated under reduced pressure to obtain tert-butyl 3,3-difluoro-4-(4-hydroxypiperidin-1-yl)-3,6-dihydropyridine-1(2H)-carboxylate (3; 11.2 g crude; taken to the next step) as a pale brown gum. LCMS (ES$^+$): 319.2 [M+H]$^+$.

Step 2: Into a 1.0 L autoclave containing a well-stirred suspension of tert-butyl 3,3-difluoro-4-(4-hydroxypiperidin- 1-yl)-3,6-dihydropyridine-1(2H)-carboxylate (3; 11.2 g, 35.18 mmol; crude) in 1:1 EtOAc/EtOH (300 mL) was added Palladium, 10% on carbon, Type 487, dry (10.0 g, 93.97 mmol) at ambient temperature under nitrogen atmosphere. The resulting suspension was stirred at ambient temperature under hydrogen atmosphere (5.0 Kg pressure) for 24 h. After completion, reaction mixture was filtered through a pad of Celite and washed with 1:1 EtOAc/EtOH (200 mL). The combined filtrate was concentrated under reduced pressure to get a crude residue. The crude product was purified by flash silica-gel (230-400 mesh) column with 10-100% EtOAc/pet ether to afford tert-butyl 3',3'-difluoro-4-hydroxy-[1,4'-bipiperidine]-1'-carboxylate (4; 1.6 g, 4.99 mmol, 14% yield) as a pale-yellow solid. LCMS ($ES^+$): 321.2 $[M+H]^+$.

Step 3. Into a 100 mL single-necked round-bottomed flask containing a well-stirred solution of tert-butyl 3',3'-difluoro-4-hydroxy-[1,4'-bipiperidine]-1'-carboxylate (4; 1.6 g, 4.99 mmol) in DCM (20 mL) was added 4M HCl in 1,4-dioxane (28.44 mL, 624.12 mmol) at 0° C. The resulting mixture was stirred at ambient temperature under nitrogen atmosphere for 2 h. Excess solvent was removed from the reaction mixture under reduced pressure to get a crude mass. The crude mass was triturated with MTBE (2×50 mL) to get 3',3'-difluoro-[1,4'-bipiperidin]-4-ol hydrochloride (5; 1.2 g, 4.42 mmol, 89% yield) as a white solid. LCMS ($ES^+$): m/z 221.1 $[M+H]^+$.

Step 4. Into 50 mL single-necked round-bottomed flask containing a well-stirred solution of 3',3'-difluoro-[1,4'-bipiperidin]-4-ol hydrochloride (5; 1.2 g, 4.67 mmol) and 1,2-difluoro-4-nitro-benzene (6; 966.74 mg, 6.08 mmol; Source: Spectrochem) in anhydrous DMSO (5 mL) was added N,N-Diisopropylethylamine (3.62 g, 28.05 mmol, 4.89 mL) at room temperature and the resulting mixture was heated at 100° C. for 16 h. The reaction mixture was allowed to attain room temperature and poured into ice-water (25 mL) and aqueous phase was extracted with EtOAc (2×100 mL). Combined organic layer was washed with brine (50 mL), dried (anhydrous $Na_2SO_4$), filtered and concentrated under reduced pressure to get a crude residue. The crude mass was purified by silica-gel (230-400 mesh) with 0-100% EtOAc/pet ether to afford 3',3'-difluoro-1'-(2-fluoro-4-nitrophenyl)-[1,4'-bipiperidin]-4-ol (7; 1.1 g, 2.96 mmol, 63% yield) as a yellow solid. LCMS ($ES^+$): 360.2 $[M+H]^+$.

Step 5. Into a 20 mL microwave tube, a well-stirred solution of 3',3'-difluoro-1'-(2-fluoro-4-nitrophenyl)-[1,4'-bipiperidin]-4-ol (7; 750 mg, 2.09 mmol) and 4-(4,4,5,5-tetramethyl-1,3,2-dioxaborolan-2-yl)-1H-pyrazole (8; 404.99 mg, 2.09 mmol) in anhydrous 1,4-dioxane (10 mL) was degassed by bubbling nitrogen gas into the reaction mixture for 10 minutes. Subsequently, 2-(tributyl-k-phosphaneylidene)acetonitrile, CMBP (1.01 g, 4.17 mmol) was added to the reaction mixture under nitrogen gas. The solution was heated to 140° C. for 2 h in the microwave reactor and allowed to attain room temperature. The reaction mixture was diluted with EtOAc (10 mL) and water (50 mL). The aqueous layer was extracted with EtOAc (2×100 mL). Combined organic layer was washed with brine (15 mL), dried (anhydrous $Na_2SO_4$), filtered and the filtrate was concentrated under reduced pressure to get a crude mass. The crude mass was purified by flash silica-gel (230-400 mesh) with 1:24 EtOAc/hexanes to provide 3',3'-difluoro-1'-(2-fluoro-4-nitrophenyl)-4-(4-(4,4,5,5-tetramethyl-1,3,2-dioxaborolan-2-yl)-1H-pyrazol-1-yl)-1,4'-bipiperidine (9; 460 mg, 0.67 mmol, 32% yield) as a colorless oil. LCMS ($ES^+$): 536.2 $[M+H]^+$.

Example 66: Synthesis of 1-((1-fluoro-3-(4-(4,4,5,5-tetramethyl-1,3,2-dioxaborolan-2-yl)-1H-pyrazol-1-yl)cyclobutyl)methyl)-4-(2-fluoro-4-nitrophenyl)piperazine

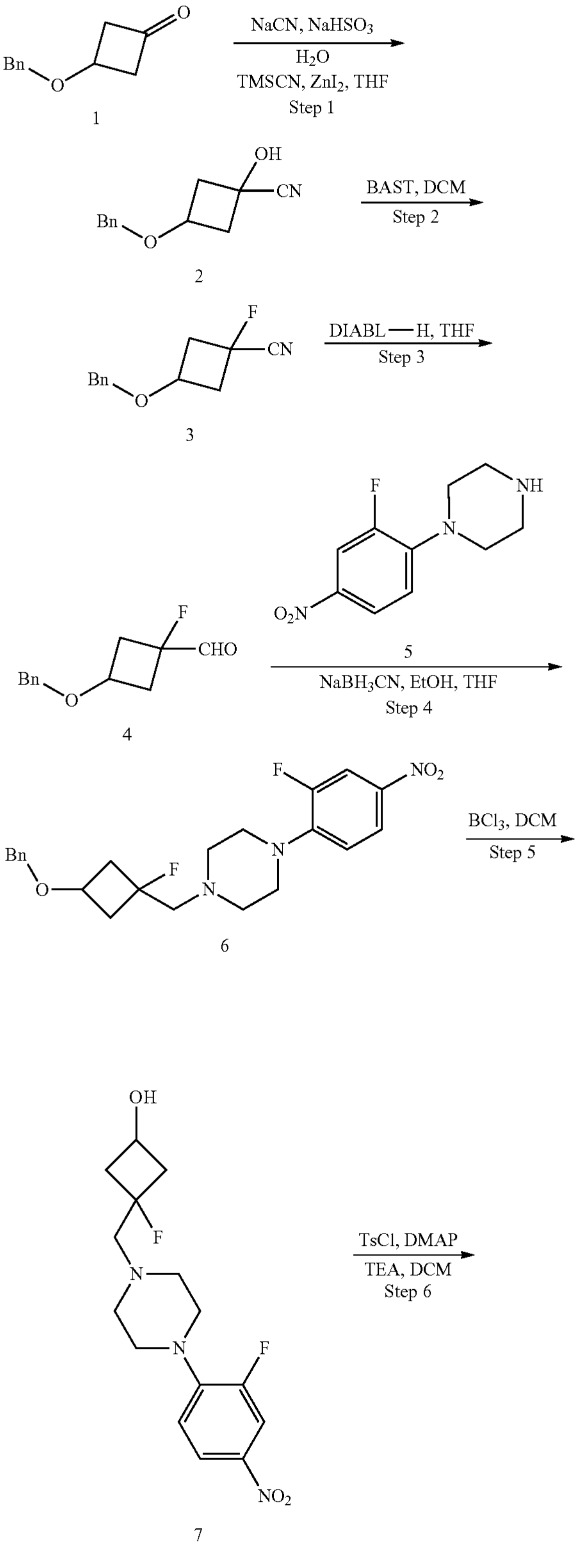

1

2

3

4

5

6

7

-continued

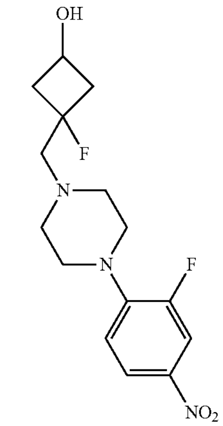

8

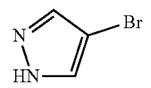

9

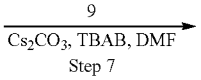

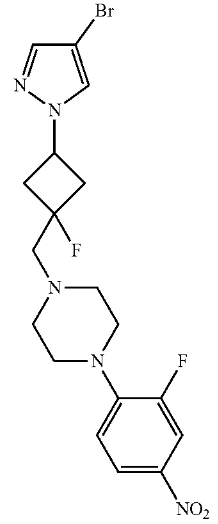

10

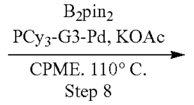

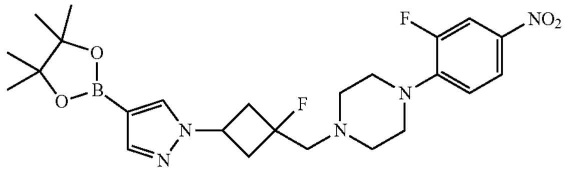

11

Step 1: To solution of 3-(benzyloxy)cyclobutanone (1, 10 g, 56.75 mmol) and cyanosodium (3.5 g, 71.42 mmol) in $H_2O$ (400 mL) was added $NaHSO_3/H_2O$ (1 M, 85.13 mL) at 0° C. After addition, the resulting mixture was stirred at 25° C. for 2 hrs. The reaction mixture was extracted with EtOAc (100 mL×3). The combined organic layer was washed with brine (30 mL), dried over $Na_2SO_4$, filtered and concentrated. The yellow residue was purified by column chromatography ($SiO_2$, Pet ether:EtOAc=1:0-10:1-5:1) to get 3-(benzyloxy)-1-hydroxycyclobutanecarbonitrile (2, 7.2 g, 35.43 mmol, 62% yield) as colorless oil. $^1$H NMR (400 MHz, CHLOROFORM-d) δ=7.48-7.31 (m, 5H), 4.52-4.44 (m, 2H), 4.35 (quin, J=6.8 Hz, 0.3H), 4.01 (quin, J=6.8 Hz, 0.6H), 3.27 (s, 0.6H), 3.12 (s, 0.3H), 3.09-2.98 (m, 1.5H), 2.71-2.56 (m, 1.5H), 2.45-2.32 (m, 1.5H)

Step 2: To solution of 3-benzyloxy-1-hydroxy-cyclobutanecarbonitrile (2, 7 g, 34.44 mmol) in DCM (100 mL) was added 2-methoxy-N-(2-methoxyethyl)-N-(trifluoro-`$1^{4}`-sulfanyl)ethanamine (15.24 g, 68.89 mmol) (BAST) at 0° C. After addition, the resulting mixture was stirred at 0° C. for 12 hrs. The reaction mixture was poured into sat.$NaHCO_3$ (400 mL) and extracted with EtOAc (150 mL×4). The combined organic layer was washed with brine (50 mL), dried over $Na_2SO_4$, filtered and concentrated. The yellow residue was purified by column chromatography ($SiO_2$, Pet ether:EtOAc=1:0-25:1-10:1) to get 3-benzyloxy-1-fluoro-cyclobutanecarbonitrile (3, 3.6 g, 17.54 mmol, 51% yield) as white solid. $^1$H NMR (400 MHz, CHLOROFORM-d) δ=7.39-7.31 (m, 5H), 4.48 (s, 2H), 4.43-4.33 (m, 1H), 2.93-2.80 (m, 2H), 2.80-2.65 (m, 2H)

Step 3: To solution of 3-benzyloxy-1-fluoro-cyclobutanecarbonitrile (3, 3.6 g, 17.54 mmol) in THF (100 mL) was added Diisobutylaluminum hydride, 1M solution in toluene (1 M, 35.08 mL) (DIBAL-H) at −70° C. After addition, the resulting mixture was stirred at −70° C. for 1 hr. The reaction mixture was poured $NH_4Cl$ (aq. sat. 300 mL) and extracted with EtOAc (150 mL×3). The combined organic layer was washed with brine (150 mL), dried over $Na_2SO_4$, filtered and concentrated. The yellow residue was purified by column chromatography ($SiO_2$, Pet ether: EtOAc=1:0-3:1-1:1) to get 3-benzyloxy-1-fluoro-cyclobutanecarbaldehyde (4, 2.7 g, 12.97 mmol, 74% yield) as white solid. $^1$H NMR (400 MHz, CHLOROFORM-d) δ=9.84 (s, 1H), 7.39-7.31 (m, 5H), 4.46-4.42 (m, 2H), 4.17-4.09 (m, 1H), 2.62-2.52 (m, 2H), 2.34-2.22 (m, 2H)

Step 4: To solution of 1-(2-fluoro-4-nitro-phenyl)piperazine (5, 2.92 g, 11.16 mmol, 021) in EtOH (100 mL) was added N,N-diethylethanamine (2.62 g, 25.93 mmol, 3.61 mL) at 25° C., then 3-benzyloxy-1-fluoro-cyclobutanecarbaldehyde (4, 2.7 g, 12.97 mmol) and acetic acid (2.34 g, 38.90 mmol, 2.22 mL) was added into the mixture and stirred at 25° C. for 10 min. $NaBH_3CN$ (4.07 g, 64.83 mmol) was added and the mixture was stirred at 25° C. for 12 hrs. The reaction mixture was poured into water (200 mL) and extracted with EtOAc (150 mL×3). The combined organic layer was washed with brine (50 mL), dried over $Na_2SO_4$, filtered and concentrated. The yellow residue was purified by column chromatography ($SiO_2$, Pet ether:EtOAc=1:0-10:1-5:1) to get 1-((3-(benzyloxy)-1-fluorocyclobutyl)methyl)-4-(2-fluoro-4-nitrophenyl)piperazine (6, 2.7 g, 6.47 mmol, 50% yield) as white solid. LCMS ($ES^+$): 418.1 $[M+H]^+$ Step 5: To solution of 1-[(3-benzyloxy-1-fluoro-cyclobutyl)methyl]-4-(2-fluoro-4-nitro-phenyl)piperazine (6, 2.7 g, 6.47 mmol) and in DCM (20 mL) was added $BCl_3$ (7.58 g, 64.68 mmol) at 0° C. After addition, the resulting mixture was stirred at 0° C. for 12 hrs. The reaction mixture was poured into $NaHCO_3$ (aq. sat. 300 mL) and extracted with EtOAc (150 mL×3). The combined organic layer was washed with brine (50 mL), dried over $Na_2SO_4$, filtered and concentrated. The residue was purified by column chromatography ($SiO_2$, Pet ether:EtOAc=1:0-2:1-1:1) to get 3-fluoro-3-[[4-(2-fluoro-4-nitro-phenyl)piperazin-1-yl] methyl]cyclobutanol (7, 1.5 g, 4.58 mmol, 71% yield) as yellow solid. LCMS ($ES^+$): 327.9 $[M+H]^+$ Step 6: To solution of 3-fluoro-3-[[4-(2-fluoro-4-nitro-phenyl)piperazin-1-yl]methyl]cyclobutanol (7, 1.5 g, 4.58 mmol), TEA (1.92 mL, 13.75 mmol) and DMAP (167.96 mg, 1.37 mmol) in DCM (2 mL) was added 4-methylbenzenesulfonyl chloride (1.05 g, 5.50 mmol) at 0° C. After addition, the resulting mixture was stirred at 20° C. for 12 hrs. The reaction was added into DCM (100 mL), filtered, and concentrated to get a residue. The crude was purified by column chromatography ($SiO_2$, Pet ether:EtOAc=1:0-10:1-5:1) to get [3-fluoro-3-[[4-(2-fluoro-4-nitro-phenyl)piperazin-1-yl]methyl]cyclobutyl] 4-methylbenzenesulfonate (8, 1.5 g, 2.68 mmol, 58% yield) as yellow solid. LCMS ($ES^+$): 481.9, $[M+H]^+$ Step 7: To a solution of 3-fluoro-3-((4-(2-fluoro-4-nitrophenyl)piperazin-1-yl)methyl)cyclobutyl 4-methylbenzenesulfonate (8, 1.5 g, 3.12 mmol), 4-bromo-1H-pyrazole (9, 595.20 mg, 4.05 mmol) and tetrabutylammonium bromide (200.85 mg, 623.04 μmol) in DMF (20 mL) was added dicesium carbonate (2.03 g, 6.23 mmol) under $N_2$ at 25° C. The mixture was stirred at 90° C. for 4 hours. The reaction mixture was quenched by water (200) mL at 10° C., and then diluted with solvent EtOAc (50 mL) and extracted with EtOAc (100 mL×3). The combined organic layers were washed with brine (50 mL), dried with anhydrous $Na_2SO_4$, filtered, and concentrated under reduced pressure to give a residue. The crude product was purified by prep-TLC ($SiO_2$, DCM:EtOAc=4:1, Rf=0.6) to get 1-[[3-(4-bromopyrazol-1-yl)-1-fluoro-cyclobutyl]methyl]-4-(2-fluoro-4-nitro-phenyl) piperazine (10, 1.1 g, 1.95 mmol, 63% yield) as colorless oil. LCMS (ESI): 356.0 & 458.0 $[M+H]^+$ Step 8: To a solution of 1-[[3-(4-bromopyrazol-1-yl)-1-fluoro-cyclobutyl]methyl]-4-(2-fluoro-4-nitro-phenyl)piperazine (10, 1.1 g, 2.41 mmol), 4,4,5,5-tetramethyl-2-(4,4,5,5-tetramethyl-1,3,2-dioxaborolan-2-yl)-1,3,2-dioxaborolane (1.84 g, 7.23 mmol), and PCy3-G3-Pd (400 mg) in CPME (20 mL) was added potassium acetate (1.18 g, 12.05 mmol, 10.19 mL) at 20° C. under $N_2$. The mixture was stirred at 100° C. for 1 hour under $N_2$. The mixture was added into water (100 mL), and EtOAc (200 mL) was added. The reaction mixture was filtered, washed with brine (5 mL), dried (anhydrous $Na_2SO_4$), filtered and concentrated. The product was purified by column chromatography ($SiO_2$, Pet ether:EtOAc=10:0-2:1-1:1) to get 1-((1-fluoro-3-(4-(4,4,5,5-tetramethyl-1,3,2-dioxaborolan-2-yl)-1H-pyrazol-1-yl) cyclobutyl)methyl)-4-(2-fluoro-4-nitrophenyl)piperazine (11, 810 mg, 1.13 mmol, 47% yield) as a yellow solid. LCMS ($ES^+$): 504.2 $[M+H]^+$

Example 67: Synthesis of tert-butyl 7-[4-(4,4,5,5-tetramethyl-1,3,2-dioxaborolan-2-yl)pyrazol-1-yl]-2-azaspiro[3.5]nonane-2-carboxylate

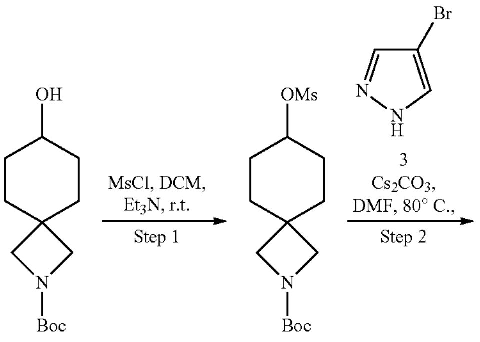

1 2

-continued

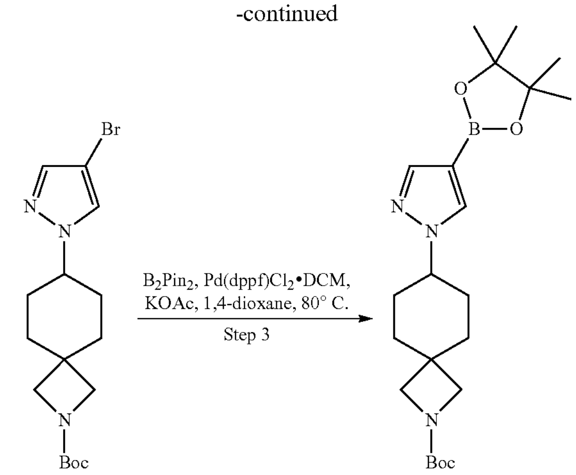

4 5

Step 1: Into a 100 mL single-necked round-bottomed flask containing a well-stirred solution of tert-butyl 7-hydroxy-2-azaspiro[3.5]nonane-2-carboxylate (1; 500 mg, 2.07 mmol) in anhydrous DCM (15 mL) were added Triethylamine, 99% (628.96 mg, 6.22 mmol, 0.866 mL) and methanesulfonyl chloride (356.00 mg, 3.11 mmol, 0.240 mL) at 0° C. under nitrogen atmosphere. The reaction mixture was stirred at ambient temperature for 3 h. After completion, the reaction mixture was cooled to 0° C. and diluted with saturated $NH_4Cl$ solution (20 mL) and extracted with DCM (3×25 mL). Organic layer was combined and washed with brine (25 mL). Combined organic phases was dried (anhydrous $Na_2SO_4$), filtered and concentrated under reduced pressure to get tert-butyl 7-methylsulfonyloxy-2-azaspiro[3.5] nonane-2-carboxylate (2; 660 mg, 1.86 mmol, 90% yield) as an off white solid. $^1H$ NMR (300 MHz, $CDCl_3$). δ 4.74-4.73 (m, 1H), 3.64-3.62 (d, J=9.2 Hz, 4H), 3.03 (s, 3H), 1.98-1.90 (m, 4H), 1.81-1.76 (m, 2H), 1.64-1.61 (m, 2H), 1.53-1.40 (m, 9H).

Step 2: Into a 50 mL sealed glass tube reactor containing a well-stirred solution of tert-butyl 7-methylsulfonyloxy-2-azaspiro[3.5]nonane-2-carboxylate (3; 660 mg, 2.07 mmol) and 4-bromo-1H-pyrazole (303.69 mg, 2.07 mmol) in anhydrous DMF (15 mL) was added Cesium carbonate (875.20 mg, 2.69 mmol) at ambient temperature under nitrogen atmosphere and the reaction mixture was heated at 80° C. for 16 h. After completion, the reaction mixture was filtered through a pad of Celite, washing with EtOAc (2×50 mL). The combined filtrate was concentrated under reduced pressure to obtain a crude residue. The crude was purified by flash neutral alumina column with 0-70% EtOAc/pet ether to afford tert-butyl 7-(4-bromopyrazol-1-yl)-2-azaspiro[3.5] nonane-2-carboxylate (4; 332 mg, 0.837 mmol, 41% yield) as a white solid. LCMS ($ES^+$): 370 $[M+H]^+$.

Step 3: A well-stirred solution of tert-butyl 7-(4-bromopyrazol-1-yl)-2-azaspiro[3.5]nonane-2-carboxylate (4; 332 mg, 0.896 mmol) and 4,4,5,5-tetramethyl-2-(4,4,5,5-tetramethyl-1,3,2-dioxaborolan-2-yl)-1,3,2-dioxaborolane (295.99 mg, 1.17 mmol) in 1,4-dioxane (10 mL) taken in a 50 mL sealed glass tube reactor was degassed for 5 minutes by bubbling the mixture with nitrogen. Subsequently, Pd(dppf) $Cl_2$·DCM (73.22 mg, 0.089 mmol) and Potassium acetate (263.99 mg, 2.69 mmol) were added, and the mixture was heated at 80° C. for 16 h. After completion, the reaction mixture was cooled and filtered through a pad of Celite. The filtrate was concentrated under reduced pressure. The crude residue was triturated with pet ether (4×25 mL) and solvent was concentrated under reduced pressure to afford tert-butyl 7-[4-(4,4,5,5-tetramethyl-1,3,2-dioxaborolan-2-yl)pyrazol-1-yl]-2-azaspiro[3.5]nonane-2-carboxylate (5; 500 mg, 0.796 mmol, 89% yield) as a dark semi-solid. LCMS ($ES^+$): 418.3 $[M+H]^+$.

Example 68: Synthesis of tert-butyl 6-[4-(4,4,5,5-tetramethyl-1,3,2-dioxaborolan-2-yl)pyrazol-1-yl]-2-azaspiro[3.3]heptane-2-carboxylate

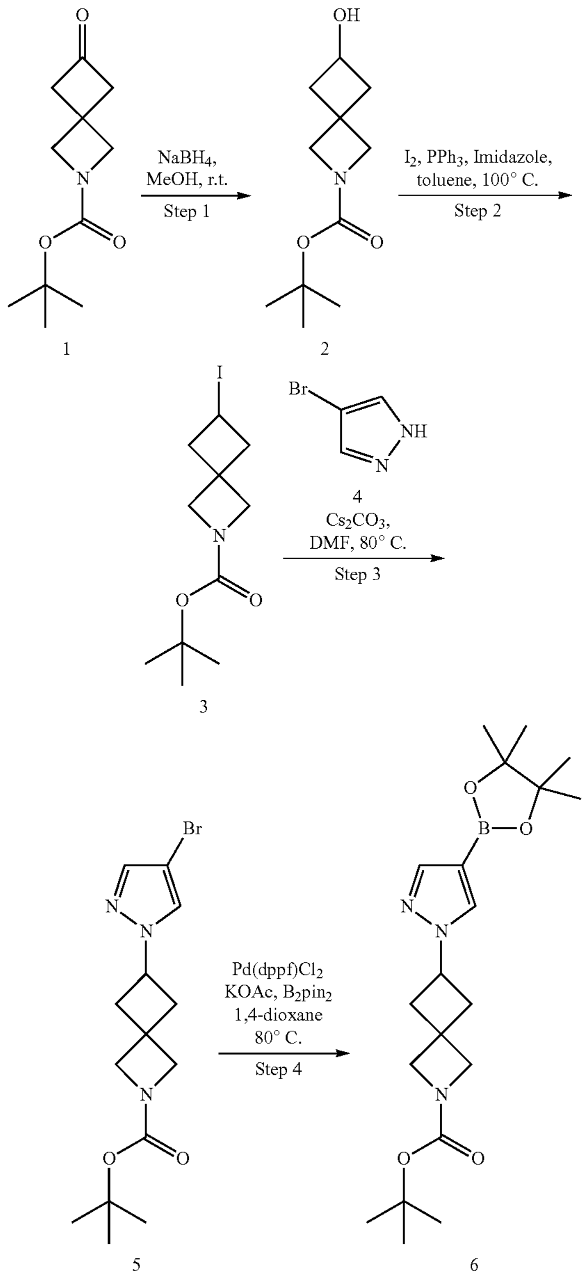 [SMILES: CC(C)(C)OC(=O)N1CC2(CC(=O)C2)C1 ; CC(C)(C)OC(=O)N1CC2(CC(O)C2)C1 ; CC(C)(C)OC(=O)N1CC2(CC(I)C2)C1 ; Brc1cn[nH]c1 ; CC(C)(C)OC(=O)N1CC2(CC(n3cc(Br)cn3)C2)C1 ; CC(C)(C)OC(=O)N1CC2(CC(n3cc(B4OC(C)(C)C(C)(C)O4)cn3)C2)C1]

1
2
4
3
5
6

Step 1: Into a 500 mL three-necked round-bottomed flask containing a well-stirred solution of tert-butyl 6-oxo-2-azaspiro[3.3]heptane-2-carboxylate (1, 5.0 g, 23.67 mmol) in MeOH (100 mL) were added Sodium borohydride (1.79 g, 47.34 mmol, 1.67 mL) at 0° C. under nitrogen atmosphere. The reaction mixture was allowed to room temperature for 3 h under nitrogen atmosphere. After completion, the reaction mixture was diluted with ice-cold water and concentrated under reduced pressure to give a crude residue. The crude residue was diluted with cold saturated sodium bicarbonate (100 mL) and extracted with DCM (2×250 mL). Combined organic phase was dried (anhydrous $Na_2SO_4$), filtered, and the filtrate was concentrated under reduced pressure to get tert-butyl 6-hydroxy-2-azaspiro[3.3]heptane-2-carboxylate (2, 5.0 g, 22.27 mmol, 94% yield) as an off-white solid. $^1$H NMR (400 MHz, DMSO-$d_6$). δ5.01 (d, J=8.4 Hz, 1H), 3.91 (m, 1H), 3.75 (d, J=20.8 Hz, 4H), 2.38 (m, 2H), 1.91 (m, 2H), 1.30 (s, 9H).

Step 2: Into a 250 mL single-necked round-bottomed flask containing a well-stirred suspension of tert-butyl 6-hydroxy-2-azaspiro[3.3]heptane-2-carboxylate (2, 5.0 g, 23.44 mmol) in Toluene (100 mL) were added Triphenylphosphine (12.30 g, 46.89 mmol) and Imidazole (4.79 g, 70.33 mmol). The reaction mixture was refluxed at 100° C. for 1 h. After completion, the reaction mixture was allowed to cool at ambient temperature and washed successively with water (100 mL) and brine (100 mL). Organic phase was dried (anhydrous $Na_2SO_4$), filtered and concentrated under reduced pressure to get a crude residue. The crude was purified by flash silica-gel (230-400 mesh) column with 0-100% EtOAc/pet ether to afford tert-butyl 6-iodo-2-azaspiro[3.3]heptane-2-carboxylate (3, 5.0 g, 13.92 mmol, 59% yield) as an off-white solid. $^1$H NMR (400 MHz, DMSO-$d_6$). δ4.43 (quin, 1H), 3.86 (s, 4H), 2.93 (m, 2H), 2.90 (m, 2H), 1.32 (s, 9H).

Step 3: Into a 100 mL sealed-tube containing a well-stirred solution of tert-butyl 6-iodo-2-azaspiro[3.3]heptane-2-carboxylate (3; 3.0 g, 9.28 mmol) and 4-bromo-1H-pyrazole (4, 1.36 g, 9.28 mmol) in anhydrous DMF (15 mL) was added Cesium carbonate (9.07 g, 27.85 mmol) at ambient temperature under nitrogen atmosphere and the reaction mixture was heated to 80° C. for 16 h. The reaction mixture was then cooled to ambient temperature. The reaction mixture was diluted with ice-water (100 mL), and the product was extracted with EtOAc (2×200 mL). Organic phases were combined, dried (anhydrous $Na_2SO_4$), filtered and the filtrate was concentrated under reduced pressure to get a crude residue, which was purified by flash silica-gel (230-400 mesh) column with 0-100% EtOAc/pet ether to afford tert-butyl 6-(4-bromopyrazol-1-yl)-2-azaspiro[3.3]heptane-2-carboxylate (5, 2.5 g, 7.31 mmol, 79% yield) as an off-white solid. LCMS ($ES^+$): 342.1 $[M+H]^+$.

Step 4: Into a 100 mL sealed tube containing a well-stirred solution of mixture of tert-butyl 6-(4-bromopyrazol-1-yl)-2-azaspiro[3.3]heptane-2-carboxylate (5; 1.5 g, 4.38 mmol) and 4,4,5,5-tetramethyl-2-(4,4,5,5-tetramethyl-1,3,2-dioxaborolan-2-yl)-1,3,2-dioxaborolane (1.34 g, 5.26 mmol) in 1,4-dioxane (15 mL) was added Potassium acetate (1.29 g, 13.15 mmol, 0.821 mL) and the mixture was purged by bubbling nitrogen gas for 15 minutes. Subsequently, added cyclopentyl(diphenylphosphane;dichloromethane;dichloropalladium;iron (357.93 mg, 0.438 mmol) and the mixture was purged by bubbling nitrogen gas for 10 minutes. The resulting solution was heated with stirring at 80° C. for 16 h. After completion of starting material, the reaction mixture was diluted with EtOAc (100 mL). The reaction mixture was filtered through a pad of Celite, washing with EtOAc. Combined filtrate was concentrated under reduced pressure to get a crude residue. The crude residue was purified by flash silica-gel column (230-400 mesh) with 0-100% EtOAc/pet ether to afford tert-butyl 6-[4-(4,4,5,5-tetramethyl-1,3,2-dioxaborolan-2-yl)pyrazol-1-yl]-2-azaspiro[3.3]

heptane-2-carboxylate (6, 1.2 g, 2.47 mmol, 56% yield) as a colorless liquid. LCMS ($ES^+$): 390.3 $[M+H]^+$.

Example 69: Synthesis of 2-((1r,4r)-4-(4-(4,4,5,5-tetramethyl-1,3,2-dioxaborolan-2-yl)-1H-pyrazol-1-yl)cyclohexyl)ethan-1-ol

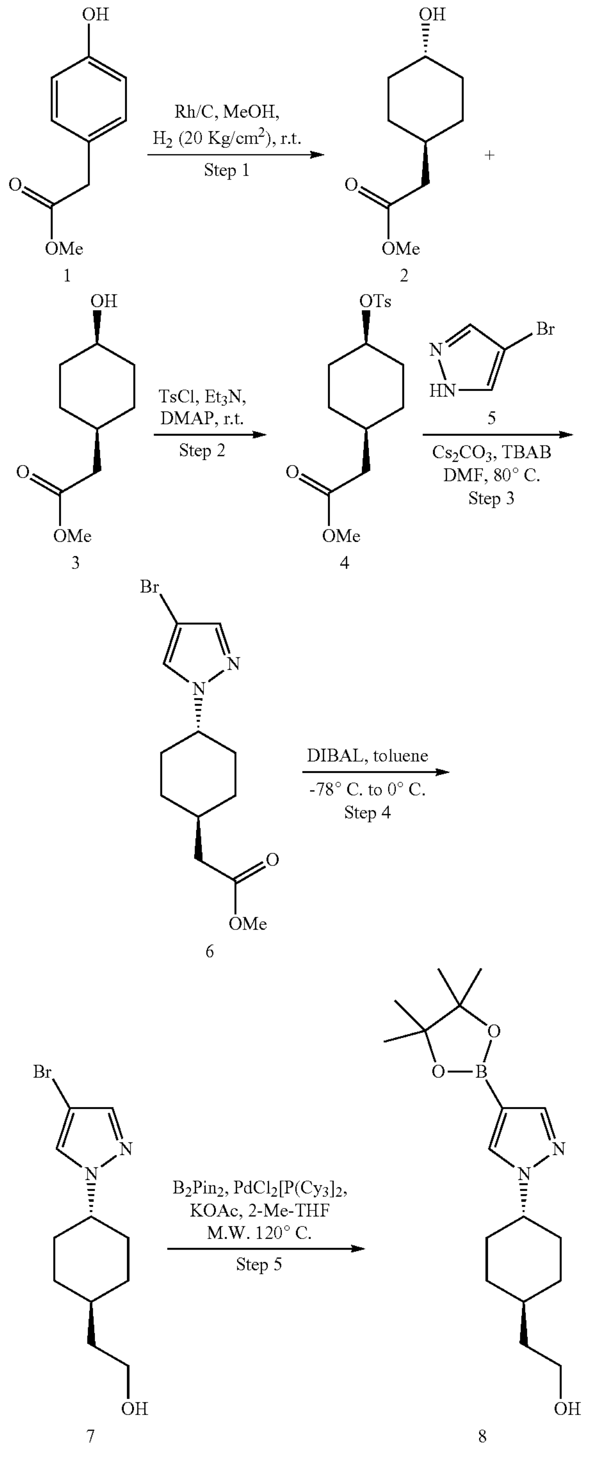

Step 1: Into a 1000 mL autoclave were added methyl 2-(4-hydroxyphenyl)acetate (1; 15 g, 90.27 mmol) in anhydrous MeOH (300 mL) and purged with nitrogen. Later to the autoclave, 5% Rhodium on carbon (2 g) was added in portions and the flask was filled with hydrogen gas with 20 kg/cm$^2$ pressure and stirred at ambient temperature for 48 h under hydrogen atmosphere. After completion, the reaction mixture was purged with nitrogen and the catalyst was removed by filtration through a pad of Celite, washing with MeOH (200 mL). The filtrate was concentrated under reduced pressure to afford crude (16 g) which was purified by silica-gel (230-400 mesh) column with 0-100% EtOAc/pet ether to get a mixture of cis/trans isomers. Diastereomers were separated by preparative SFC following method: Lux A1 column; Mobile phase: 0.1% Isopropyl amine in IPA: MeOH (1:1); Fractions with RT=2.44 minutes were combined and concentrated under reduced pressure to afford methyl 2-((1r,4r)-4-hydroxycyclohexyl)acetate (2, trans isomer; 2 g, 11.52 mmol, 13% yield) as a pale-yellow liquid. $^1H$ NMR (400 MHz, $CDCl_3$). δ 3.67 (s, 3H), 3.57-3.52 (m, 2H), 2.20 (d, J=6.8 Hz, 2H), 1.99-1.95 (m, 1H), 1.80-1.72 (m, 4H), 1.34-1.24 (m, 2H) and 1.09-1.03 (m, 2H).

Whereas fractions with RT=2.82 minutes were combined and concentrated under reduced pressure to afford methyl 2-((1s,4s)-4-hydroxycyclohexyl)acetate (3, cis-isomer; 3.8 g, 21.03 mmol, 23% yield) as a pale-yellow liquid. $^1H$ NMR (400 MHz, $CDCl_3$). δ. 3.96-3.92 (m, 1H), 3.64 (s, 3H), 2.23 (d, J=6.8 Hz, 2H), 1.88-1.81 (m, 1H), 1.69-1.65 (m, 2H) and 1.59-1.36 (m, 6H).

Step 2: Into a 250 mL single-necked round-bottomed flask containing a well-stirred solution of methyl 2-((1s,4s)-4-hydroxycyclohexyl)acetate (3, 3 g, 17.42 mmol) in anhydrous $CH_2Cl_2$ (40 mL) were added $Et_3N$ (5.29 g, 52.26 mmol, 7.28 mL), DMAP (212.81 mg, 1.74 mmol) and 4-methylbenzenesulfonyl chloride (4.98 g, 26.13 mmol) in portions at 0° C. under nitrogen atmosphere. Contents of the reaction mixture was stirred at ambient temperature. After 48 h, to the reaction mixture was added 10% aq. $NaHCO_3$ solution and desired product was extracted with $CH_2Cl_2$ (2×100 mL). Combined organic phases were washed with brine (25 mL), dried (anhydrous $Na_2SO_4$), filtered and the filtrate was concentrated under reduced pressure to afford a crude residue. The crude mixture was purified by flash silica-gel (230-400 mesh) column with a gradient of 0-100% EtOAc/pet ether to get methyl 2-((1s,4s)-4-(tosyloxy)cyclohexyl)acetate (4, 3.6 g, 10.92 mmol, 63% yield) as a yellow gum. LCMS ($ES^+$): 311.0 $[M+H]^+$ Step 3: Into a 250 mL sealed-tube reactor containing a well-stirred solution of methyl 2-((1s,4s)-4-(tosyloxy)cyclohexyl)acetate (4, 3.58 g, 10.95 mmol) and 4-bromo-1H-pyrazole (5, 1.15 g, 7.82 mmol) in anhydrous DMF (70 mL) were added $Cs_2CO_3$ (5.10 g, 15.65 mmol) followed by tetrabutylammonium bromide (TBAB; 252.24 mg, 0.782 mmol) at ambient temperature under nitrogen atmosphere. Resulting mixture was stirred at 80° C. for 16 h. After completion, 100 mL of ice-cooled water was added to the reaction mixture. A precipitate formed, which was filtered and dried to get methyl 2-((1r,4r)-4-(4-bromo-1H-pyrazol-1-yl)cyclohexyl)acetate (6; 1 g, 3.29 mmol, 42% yield) as an off-white solid. LCMS ($ES^+$): 300.8 $[M+H]^+$ Step 4: Into a 100 mL single-necked round-bottomed flask containing a well-stirred solution of methyl 2-((1r,4r)-4-(4-bromo-1H-pyrazol-1-yl)cyclohexyl)acetate (6, 1 g, 3.32 mmol) in anhydrous toluene (20 mL) was added diisobutylaluminum hydride (1.42 g, 9.96 mmol, 1.78 mL; 1M/toluene) at −78° C. under nitrogen atmosphere. After complete addition, the reaction mixture was stirred under nitrogen atmosphere at ambient temperature. After completion, saturated $NH_4Cl$ solution was added to the reaction mixture dropwise at 0° C. EtOAc (50 mL) was added to the reaction mixture. The reaction mixture was filtered through Buchner funnel. The combined filtrate was washed with brine (50 mL), dried (anhydrous $Na_2SO_4$), filtered and the filtrate was concentrated under reduced pressure to get 2-((1r,4r)-4-(4-bromo-1H-pyrazol-1-yl)cyclohexyl)ethan-1-ol (7; 850 mg, 3.08 mmol, 93% yield) as an off-white solid. LCMS ($ES^+$): 275.0 $[M+H]^+$ Step 5: Into a 20 mL microwave vial, a well-stirred solution of 2-((1r,4r)-4-(4-bromo-1H-pyrazol-1-yl)cyclohexyl)ethan-1-ol (7, 750 mg, 2.75 mmol; performed in 3×250 mg batches—each in 20 mL microwave glass vial) and 4,4,5,5-tetramethyl-2-(4,4,5,5-tetramethyl-1,3,2-dioxaborolan-2-yl)-1,3,2-dioxaborolane (1.05 g, 4.12 mmol) in anhydrous 2-methyltetrahydrofuran (9 mL) was stirred at ambient temperature under nitrogen atmosphere for 15 minutes. The resulting mixture was degassed by bubbling nitrogen gas into the reaction mixture for 10 minutes. Subsequently, KOAc (808.35 mg, 8.24 mmol) and dichloropalladium;tricyclohexylphosphane (202.67 mg, 0.274 mmol) were added to the vial. The reaction mixture stirred at 120° C. (microwave) for 1 h. After completion, the reaction mixture was filtered through a pad of Celite. Filtrate was concentrated under reduced pressure to get a crude mass, which was purified by flash silica-gel (230-400 mesh) column with a gradient of 0-100% EtOAc/pet ether followed by 0-20% MeOH/DCM as eluents to get 2-((1r,4r)-4-(4-(4,4,5,5-tetramethyl-1,3,2-dioxaborolan-2-yl)-1H-pyrazol-1-yl)cyclohexyl)ethan-1-ol (5; 680 mg, 2.08 mmol, 76% yield) as a black-colored gum. LCMS ($ES^+$): 321.0 $[M+H]^+$. $^1H$ NMR (400 MHz, DMSO-$d_6$). δ 7.93 (s, 1H), 7.56 (s, 1H), 4.36 (t, J=4.8 Hz, 1H), 4.15-4.09 (m, 1H), 3.47-3.43 (m, 2H), 1.98 (d, J=8.8 Hz, 2H), 1.82 (d, J=12 Hz, 2H), 1.76-1.69 (m, 2H), 1.28-1.35 (m, 3H), 1.25 (s, 12H), 1.09-1.07 (m, 2H).

Example 70a: Synthesis of 1-(5-(3-Cyano-6-(1-(piperidin-4-yl)-1H-pyrazol-4-yl)pyrazolo[1,5-a]pyridin-4-yl)pyridin-2-yl)-N-isopropyl-4-methylpiperidine-4-carboxamide hydrochloric acid

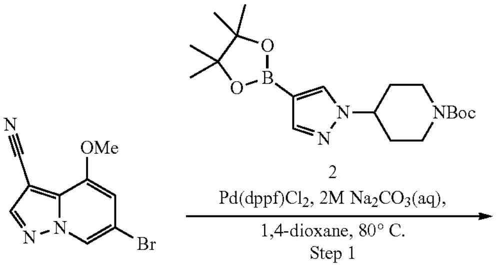

1 2

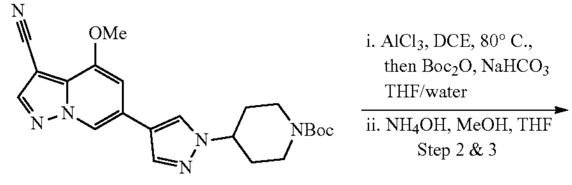

3

-continued

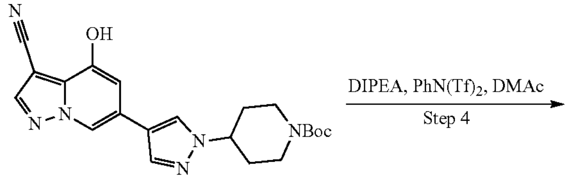

4

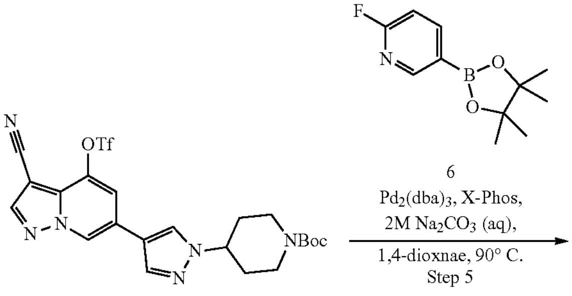

6 5

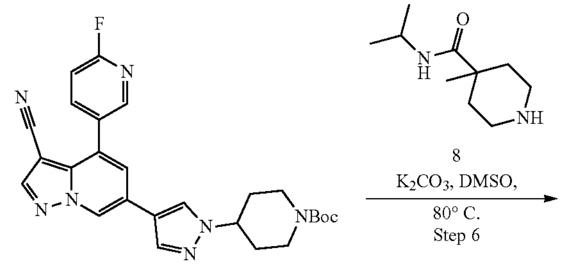

8 7

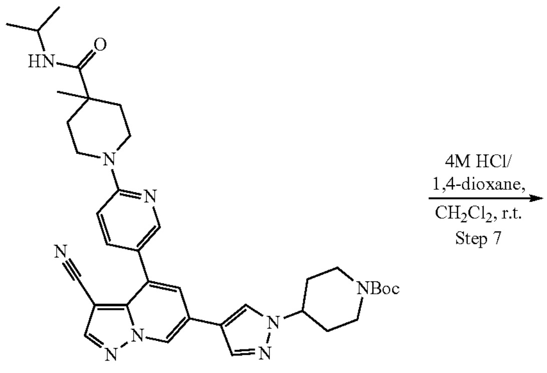

9

-continued

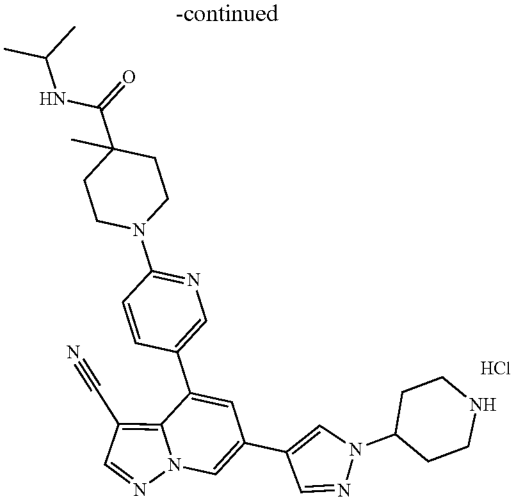

10

Step 1. Into a 50 mL sealed-tube reactor containing a well-stirred solution of 6-bromo-4-methoxy-pyrazolo[1,5-a] pyridine-3-carbonitrile (1; 600 mg, 2.38 mmol) and tert-butyl 4-[4-(4,4,5,5-tetramethyl-1,3,2-dioxaborolan-2-yl) pyrazol-1-yl]piperidine-1-carboxylate (2; 987.87 mg, 2.62 mmol) in anhydrous 1,4-dioxane (10 mL) was added aqueous $Na_2CO_3$ (3.57 mL; 2M) at ambient temperature and the resulting mixture was degassed by bubbling nitrogen gas into the reaction mixture for 10 minutes. Subsequently, $Pd(dppf)Cl_2·CH_2Cl_2$ complex (194.39 mg, 238.03 mmol) was added to the reaction mixture and reaction mixture was heated to 90° C. for 2 h. After completion of the reaction as indicated by TLC, the reaction mixture was cooled to room temperature and poured into water (50 mL) and extracted with EtOAc (2×150 mL). Organic phases were combined and washed with brine (100 mL). Combined organic phases were dried (anhydrous $Na_2SO_4$), filtered and the filtrate was concentrated under reduced pressure to get a crude residue, which was purified by silica-gel (230-400 mesh) column with 80% EtOAc in pet ether to yield tert-butyl 4-(4-(3-cyano-4-methoxypyrazolo[1,5-a]pyridin-6-yl)-1H-pyrazol-1-yl)piperidine-1-carboxylate (3; 630 mg, 1.35 mmol) as a yellow solid. Yield-56.8%; LC MS: ES+(M-tBu+H) 367.2.

Step 2. An oven-dried 250 mL single-necked round-bottomed flask was charged with a solution of tert-butyl 4-[4-(3-cyano-4-methoxy-pyrazolo[1,5-a]pyridin-6-yl) pyrazol-1-yl]piperidine-1-carboxylate (3; 620 mg, 1.47 mmol) in anhydrous DCE (15 mL) at room temperature under a nitrogen atmosphere. After cooling the flask to 0° C., aluminium chloride (587.04 mg, 4.40 mmol) was added. The reaction mixture was allowed to attain room temperature and then heated to 80° C. for 3 h. The reaction mixture was cooled to 0° C. and the reaction mixture was quenched with water (10 mL) and THF (7 mL). Sodium bicarbonate (616.41 mg, 7.34 mmol) was added at 0° C. Di-tert-butyl dicarbonate (960.85 mg, 4.40 mmol, 1.01 mL) was added to the reaction mixture at 0° C. The reaction mixture was warmed to room temperature and stirred for 5 h at ambient temperature. After completion of the reaction as indicated by TLC, the reaction mixture was acidified with a saturated solution of $KHSO_4$ up to pH~6. The product was extracted with EtOAc (2×50 mL). The combined organic phases were dried (anhydrous $Na_2SO_4$), filtered and the filtrate was concentrated under reduced pressure to get a crude residue, which was triturated with pet ether to give tert-butyl 4-(4-

(4-((tert-butoxycarbonyl)oxy)-3-cyanopyrazolo[1,5-a]pyridin-6-yl)-1H-pyrazol-1-yl)piperidine-1-carboxylate (Int.; 590 mg, 1.10 mmol). Yield-75%; LC MS: ES+ (M+H) 509.2.

Step 3. Into a 50 mL single-necked round-bottomed flask containing a well-stirred solution of tert-butyl 4-[4-(4-tert-butoxycarbonyloxy-3-cyano-pyrazolo[1,5-a]pyridin-6-yl) pyrazol-1-yl]piperidine-1-carboxylate (Int. from step-2; 590 mg, 1.16 mmol) in THF (10 mL) was added aq. $NH_4OH$ (9.00 g, 256.81 mmol, 10 mL; 28% $NH_3$) at ambient temperature. The reaction mixture was stirred for 1 h at ambient temperature. The reaction mixture was acidified with saturated aq. potassium hydrogen sulfate to a pH-6. The product was extracted with EtOAc (2×100 mL) and the combined organic layers were dried (anhydrous $Na_2SO_4$), filtered and the filtrate was concentrated under reduced pressure to yield tert-butyl 4-[4-(3-cyano-4-hydroxy-pyrazolo[1,5-a]pyridin-6-yl)pyrazol-1-yl]piperidine-1-carboxylate (4; 550 mg, 0.41 mmol) as a brown gum. Yield-35.3%; LC MS: ES− (M−H) 407.2.

Step 4. Into a 50 mL single-necked round-bottomed flask containing a well-stirred solution of tert-butyl 4-[4-(3-cyano-4-hydroxy-pyrazolo[1,5-a]pyridin-6-yl)pyrazol-1-yl] piperidine-1-carboxylate (4; 550 mg, 1.35 mmol) and N,N-bis(trifluoromethylsulfonyl)aniline (577.26 mg, 1.62 mmol) in N,N-dimethylacetamide (10 mL) was added DIPEA (348.06 mg, 2.69 mmol, 469.09 µL) at ambient temperature. The reaction mixture was stirred for 2 h at ambient temperature. The progress of the reaction was monitored by UPLC. After completion of the reaction, the reaction mixture was quenched with water (40 mL). The reaction mixture was extracted with EtOAc (2×80 mL). The organic phases were combined and washed with brine (50 mL), dried (anhydrous $Na_2SO_4$), filtered and the filtrate was concentrated under reduced pressure to get a crude residue, which was purified by silica-gel (230-400 mesh) column chromatography with 70% EtOAc in Pet ether to yield tert-butyl 4-[4-[3-cyano-4-(trifluoromethylsulfonyloxy)pyrazolo[1,5-a]pyridin-6-yl]pyrazol-1-yl]piperidine-1-carboxylate (5; 530 mg, 0.91 mmol) as a yellow solid. Yield-67.6%; LC MS: ES+ (M-tBu+H) 485.0.

Step 5. Into a 50 mL sealed-tube reactor containing a well-stirred solution of tert-butyl 4-[4-[3-cyano-4-(trifluoromethylsulfonyloxy)pyrazolo[1,5-a]pyridin-6-yl]pyrazol-1-yl]piperidine-1-carboxylate (5; 220 mg, 0.41 mmol) and (6-fluoro-3-pyridyl)boronic acid pinacol ester (6; 86.03 mg, 0.61 mmol) in 1,4-dioxane (5 mL) was added aqueous $Na_2CO_3$ (3.57 mL; 2M) solution at ambient temperature and the resulting mixture was degassed by bubbling nitrogen into the reaction mixture for 10 minutes. Subsequently, $Pd(dppf)C12-CH_2Cl_2$ complex (33.24 mg, 0.04 mmol) was added to the reaction mixture and reaction mixture was heated to 90° C. for 2 h. After completion of the reaction as indicated by TLC, the reaction mixture was cooled to room temperature and poured into water (50 mL) and extracted with EtOAc (2×150 mL). The organic phases were combined and washed with brine (100 mL). Combined organic phases were dried (anhydrous $Na_2SO_4$), filtered and the filtrate was concentrated under reduced pressure to get a crude residue, which was purified by column chromatography on a silica-gel (230-400 mesh) column with 3:2 EtOAc in pet ether to yield tert-butyl 4-[4-[3-cyano-4-(6-fluoro-3-pyridyl)pyrazolo[1,5-a]pyridin-6-yl]pyrazol-1-yl]piperidine-1-carboxylate (7; 130 mg, 0.21 mmol) as pale yellow solid. Yield-51.5%; LC MS: ES+ (M-tBu+H) 432.1.

Step 6. An oven dried sealed-tube reactor with a solution of tert-butyl 4-[4-[3-cyano-4-(6-fluoro-3-pyridyl)pyrazolo

[1,5-a]pyridin-6-yl]pyrazol-1-yl]piperidine-1-carboxylate (7; 50 mg, 0.102 mmol) and N-isopropyl-4-methylpiperidine-4-carboxamide (8; 28.35 mg, 0.153 mmol) in anhydrous DMSO was added $K_2CO_3$ (42.52 mg, 0.308 mmol) at ambient temperature. The reaction mixture was heated to 80° C. and stirred for 16 h. After completion of the reaction as indicated by UPLC, the reaction mixture was cooled to room temperature. The reaction mixture was quenched with cold water (10 mL) and a solid precipitate formed and was collected by filtration. The filtered solid was dried under vacuum to give tert-butyl 4-[4-[3-cyano-4-[6-[4-(isopropylcarbamoyl)-4-methyl-1-piperidyl]-3-pyridyl]pyrazolo[1,5-a]pyridin-6-yl]pyrazol-1-yl]piperidine-1-carboxylate (9; 55 mg, 0.083 mmol) as a yellow solid. Yield-80.6%; LC MS: ES+ (M+H) 652.5.

Step 7. Into a 25 mL single-necked round-bottomed flask containing a well-stirred solution of tert-butyl 4-[4-[3-cyano-4-[6-[4-(isopropylcarbamoyl)-4-methyl-1-piperidyl]-3-pyridyl]pyrazolo[1,5-a]pyridin-6-yl]pyrazol-1-yl]piperidine-1-carboxylate (9; 55 mg, 0.084 mmol) in anhydrous $CH_2Cl_2$ (5 mL) was added HCl (0.038 mL, 0.843 mmol; 4 N in 1,4-dioxane) at ambient temperature. The reaction mixture was stirred for 2 h and found complete. Excess solvents were removed from the reaction mixture under reduced pressure to get a crude mass. Crude product was washed with pet ether to give 1-[5-[3-cyano-6-[1-(4-piperidyl)pyrazol-4-yl]pyrazolo[1,5-a]pyridin-4-yl]-2-pyridyl]-N-isopropyl-4-methyl-piperidine-4-carboxamide hydrochloric acid salt (10; 40 mg, 0.064 mmol) as a pale brown solid. Yield-76.8%; LC MS: ES+ (M+H) 552.3.

Example 70b: Synthesis of Additional RET Inhibitors

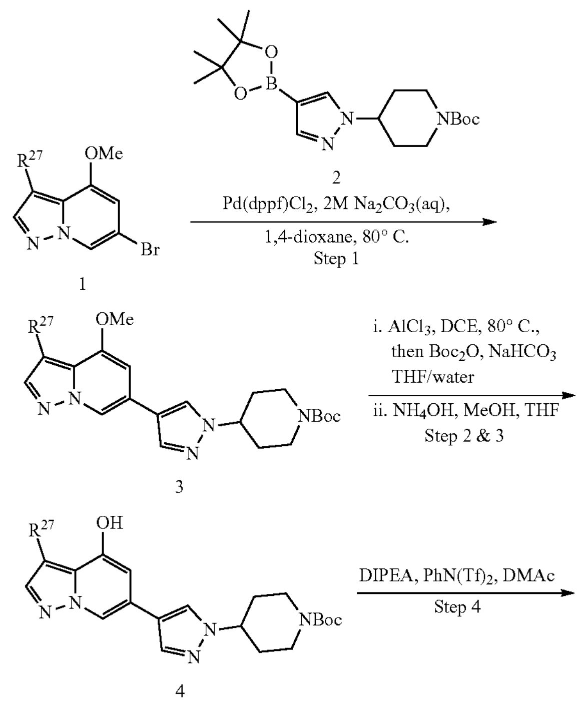

-continued

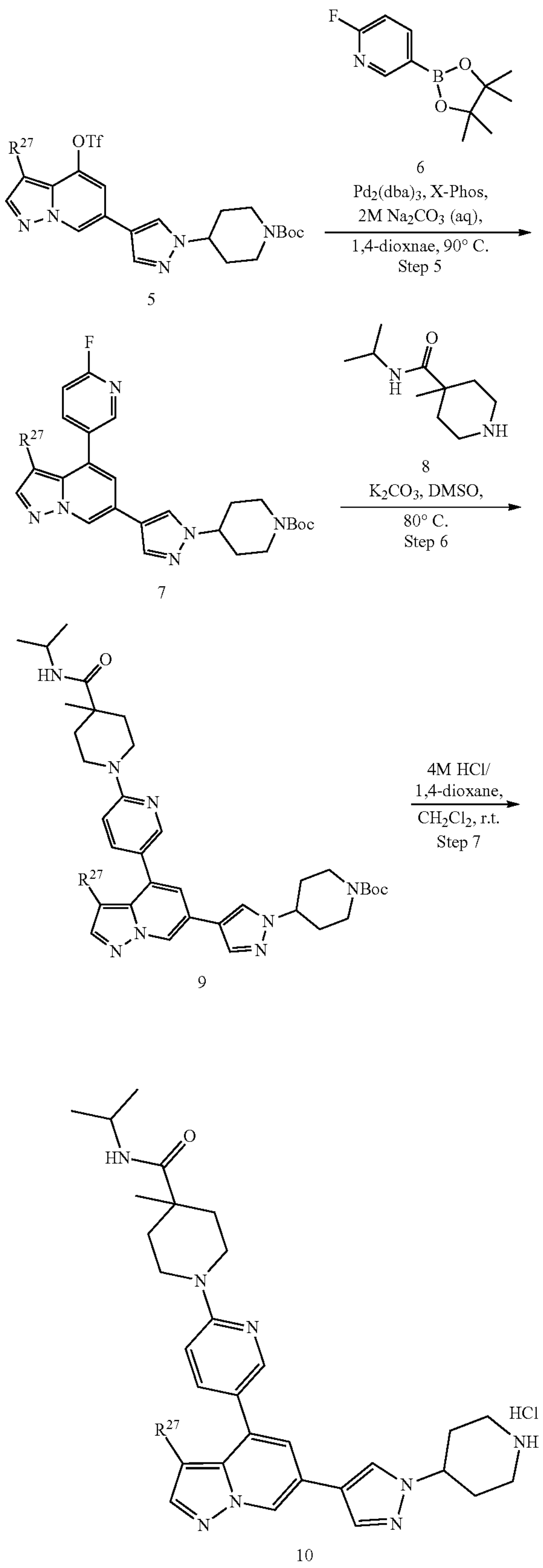

Synthesis of Representative Compounds

Example 71: Synthesis of 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-[(1R)-1-(2-pyridyl)ethyl]piperazin-1-yl]-3-pyridyl]pyrazolo[1,5-a]pyrazine-3-carbonitrile (Compound 1)

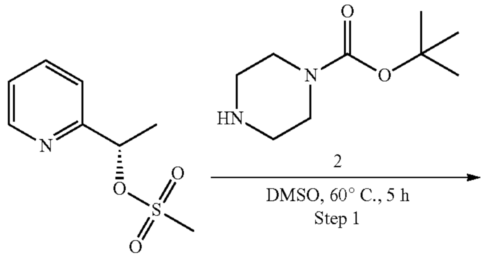

1

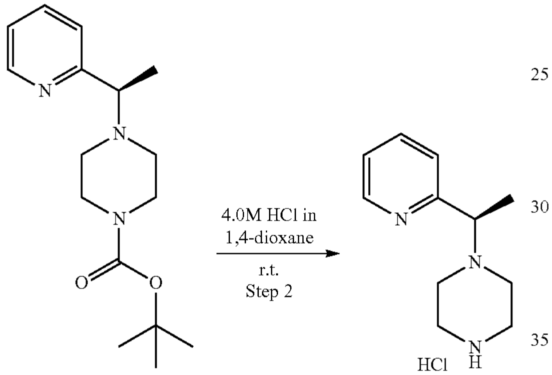

3

4

Step 1. To a solution of [(1S)-1-(2-pyridyl)ethyl] methanesulfonate (1; 2.7 g, 13.42 mmol) in DMSO (15 mL) was added tert-butyl piperazine-1-carboxylate (2; 10.00 g, 53.67 mmol) at 25° C. The resulting mixture stirred at 60° C. for 5 hr. The reaction mixture was quenched by addition of $H_2O$ (30 mL) and was extracted with ethyl acetate (3x30 mL). The combined organic layers were washed with brine (20 mL), dried (anhydrous $Na_2SO_4$), filtered and concentrated under reduced pressure to give a residue. The residue was purified by column chromatography (silica, gradient of 10% to 100% EtOAc in pet ether) to afford tert-butyl 4-[(1R)-1-(2-pyridyl)ethyl]piperazine-1-carboxylate (3; 1.4 g, 4.61 mmol) as a colorless oil. Yield-34.4%; LC MS: ES+ (M+H) 292.0

Step 2. tert-butyl 4-[(1R)-1-(2-pyridyl)ethyl]piperazine-1-carboxylate (3; 1.4 g, 4.80 mmol) was added into a solution of 4 NHCl in 1,4-dioxane (13 mL) and the mixture stirred at 25° C. for 1 hr. The mixture was concentrated under reduced pressure to give a residue. The residue was triturated with methyl tert-butyl ether (12 mL), then filtered to afford 1-[(1R)-1-(2-pyridyl)ethyl]piperazine hydrochloric acid salt (4; 1.1 g, 3.26 mmol) as a white solid. Yield-67.9%; LC MS: ES+ (M+H) 192.0

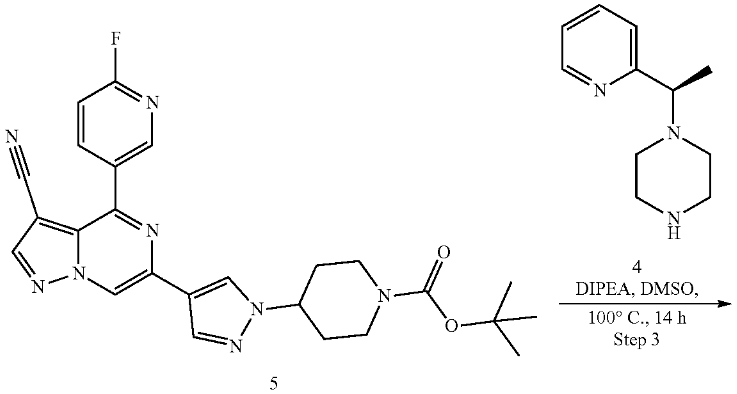

5

-continued
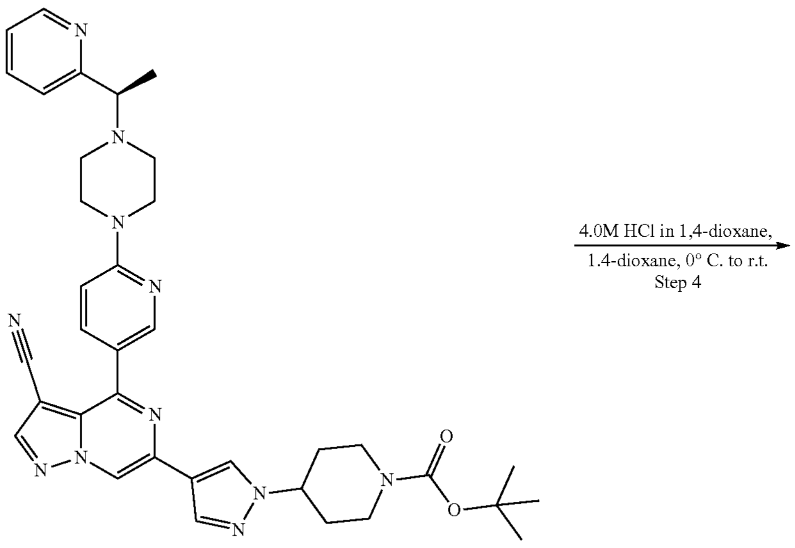
6
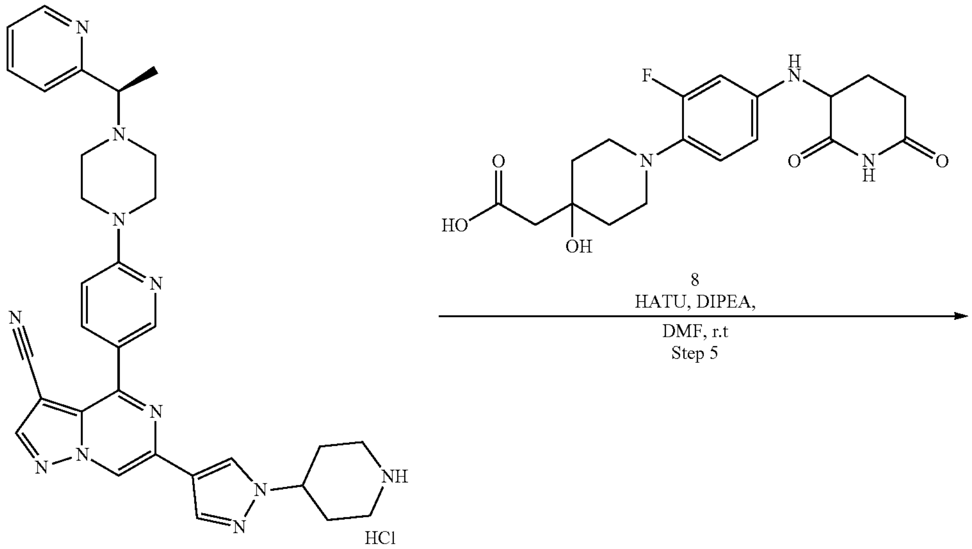
7

-continued

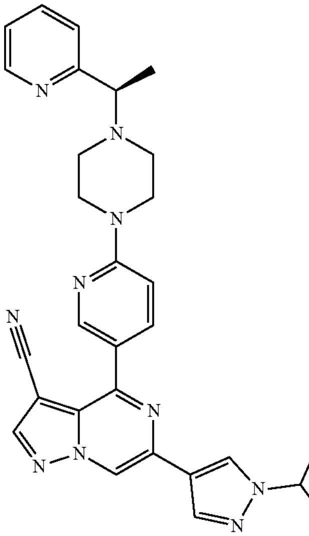

7

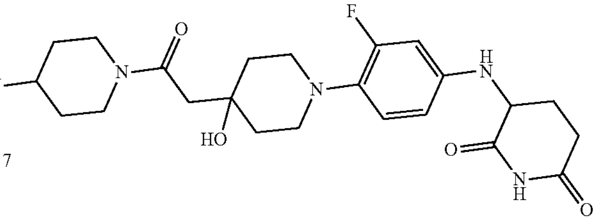

Compound 1

Step 3. To a solution of 1-[(1R)-1-(2-pyridyl)ethyl]piperazine hydrochloric acid salt (4; 61.54 mg, 204.70 umol) and DIPEA (614.11 umol, 106.97 uL) in DMSO (2 mL) was added tert-butyl 4-[4-[3-cyano-4-(6-fluoro-3-pyridyl)pyrazolo[1,5-a]pyrazin-6-yl]pyrazol-1-yl]piperidine-1-carboxylate (5; 100 mg, 204.70 umol) at 10° C. After addition, the mixture was heated to 100° C. for 14 hr. Then the mixture was poured into $H_2O$ (10 mL) and extracted with EtOAc (4×10 mL). The combined organic layers were washed with brine (10 mL), dried (anhydrous $Na_2SO_4$), and concentrated in vacuum to give a residue. The residue was tritiated with pet ether/EtOAc (20:1, 15 mL) to afford tert-butyl 4-[4-[3-cyano-4-[6-[4-[(1R)-1-(2-pyridyl)ethyl]piperazin-1-yl]-3-pyridyl]pyrazolo[1,5-a]pyrazin-6-yl]pyrazol-1-yl]piperidine-1-carboxylate (6; 100 mg, 137.92 umol) as a yellow solid. Yield-67.4%; LC MS: ES+ (M+H) 660.1

Step 4. To a solution of tert-butyl 4-[4-[3-cyano-4-[6-[4-[(1R)-1-(2-pyridyl)ethyl]piperazin-1-yl]-3-pyridyl]pyrazolo[1,5-a]pyrazin-6-yl]pyrazol-1-yl]piperidine-1-carboxylate (6; 100 mg, 151.57 umol) in 1,4-dioxane (0.5 mL) was added 4.0 M HCl in 1,4-dioxane (378.91 uL) dropwise at 0° C. After addition, the mixture was kept at 20° C. for 14 hrs. Then the mixture was concentrated in vacuum to afford 6-[1-(4-piperidyl)pyrazol-4-yl]-4-[6-[4-[(1R)-1-(2-pyridyl)ethyl]piperazin-1-yl]-3-pyridyl]pyrazolo[1,5-a]pyrazine-3-carbonitrile hydrochloric acid salt (7; 82 mg, 123.80 umol) as a white solid. Yield-81.7%; LC MS: ES+ (M+H) 560.2

Step 5. To a solution of 6-[1-(4-piperidyl)pyrazol-4-yl]-4-[6-[4-[(1R)-1-(2-pyridyl)ethyl]piperazin-1-yl]-3-pyridyl]pyrazolo[1,5-a]pyrazine-3-carbonitrile hydrochloric acid salt (7; 46.94 mg, 83.87 umol), HATU (47.84 mg, 125.81 umol), and 2-(1-(4-((2,6-dioxopiperidin-3-yl)amino)-2-fluorophenyl)-4-hydroxypiperidin-4-yl)acetic acid (8; 31.82 mg, 83.87 umol) in DMF (2 mL) was added DIPEA (251.63 umol, 35.07 uL) at 10° C. After addition, the solution was stirred at 20° C. for 6 hr. The reaction mixture was quenched by addition of water (20 mL), and then diluted with EtOAc (10 mL) The mixture was extracted with EtOAc (3×10 mL). The combined organic layers were washed with brine (15 mL), dried (anhydrous $Na_2SO_4$), filtered and concentrated under reduced pressure to give a residue. The crude product was purified by prep-HPLC to afford the product (HCl salt, 63 mg). A solution of $NaHCO_3$ (sat, 0.3 mL) was added into a solution of the product (HCl salt, 63 mg) in DCM (2 mL) and CH3CN (1 mL), then the mixture was purified by prep-TLC (DCM:MeOH:EtOH=100:10:1, SiO2, Rf=0.36, plate 1) to afford the product 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-[(1R)-1-(2-pyridyl)ethyl]piperazin-1-yl]-3-pyridyl]pyrazolo[1,5-a]pyrazine-3-carbonitrile (Compound 1; 16.33 mg, 17.55 umol) as a yellow solid. Yield-20.9%; $^1H$ NMR (400 MHz, DMSO-$d_6$) δ 10.78 (s, 1H), 9.30 (s, 1H), 8.83 (s, 1H), 8.67 (d, J=2.4 Hz, 1H), 8.56-8.45 (m, 2H), 8.20-8.15 (m, 1H), 8.10-8.02 (m, 1H), 7.83-7.72 (m, 1H), 7.48 (d, J=7.8 Hz, 1H), 7.31-7.23 (m, 1H), 6.97 (d, J=9.2 Hz, 1H), 6.90-6.81 (m, 1H), 6.50 (dd, J=2.4, 14.8 Hz, 1H), 6.36 (d, J=2.8 Hz, 1H), 5.78 (d, J=7.6 Hz, 1H), 4.90 (s, 1H), 4.62-4.47 (m, 2H), 4.30-4.14 (m, 2H), 3.75-3.59 (m, 5H), 3.27-3.20 (m, 1H), 2.96-2.69 (m, 6H), 2.63-2.57 (m, 4H), 2.47-2.43 (m, 1H), 2.18-2.02 (m, 3H), 2.02-1.63 (m, 7H), 1.38 (d, J=6.8 Hz, 3H). LC MS: ES+ (M/2+H) 461.4

Example 72: Synthesis of 1-(5-(3-Cyano-6-(1-(1-(2-(4-(4-((2,6-dioxopiperidin-3-yl)amino)-2-fluorophenyl)piperidin-1-yl)acetyl)piperidin-4-yl)-1H-pyrazol-4-yl)pyrazolo[1,5-a]pyridin-4-yl)pyridin-2-yl)-N-isopropyl-4-methylpiperidine-4-carboxamide (Compound 2)

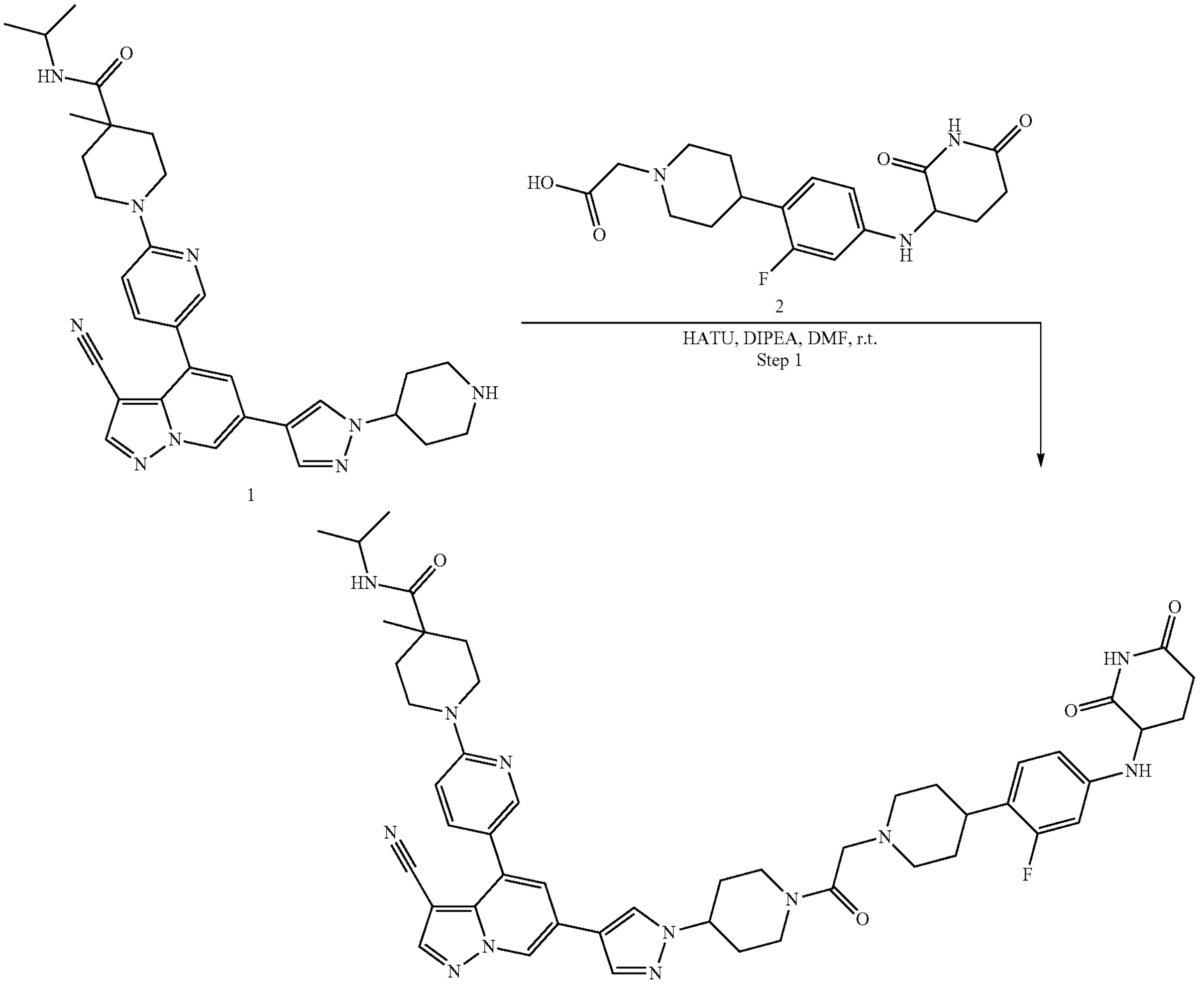

Compound 2

Step 1. Into a 25 mL single-necked round-bottomed flask containing a solution of 1-[5-[3-cyano-6-[1-(4-piperidyl) pyrazol-4-yl]pyrazolo[1,5-a]pyridin-4-yl]-2-pyridyl]-N-isopropyl-4-methyl-piperidine-4-carboxamide hydrochloride salt (1; 41.75 mg, 0.075 mmol) and 2-[4-[4-[(2,6-dioxo-3-piperidyl)amino]-2-fluoro-phenyl]-1-piperidyl] acetic acid (2; 25 mg, 0.069 mmol) in anhydrous DMF (3 mL) was added DIPEA (0.036 mL, 0.206 mmol) at ambient temperature under nitrogen atmosphere and the resulting mixture was stirred for 15 minutes. Subsequently, HATU (39.24 mg, 0.103 mmol) was added to the flask and the reaction mixture was stirred for another 2 h at ambient temperature. The progress of the reaction was monitored by UPLC. After completion of the reaction, the reaction mixture was treated with water (1 mL) and solid precipitated out was filtered. The filtered solid was dried under vacuum to get a crude mixture, which was purified by prep HPLC purification following method: (Column: SUNFIRE OBD C18 (100×30) MM 5 micron), Mobile phase: A: 0.1% Ammonium acetate in water, B: Acetonitrile) to yield 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a] pyridin-4-yl]-2-pyridyl]-N-isopropyl-4-methyl-piperidine-4-carboxamide (Compound 2; 15.4 mg, 0.016 mmol) as a white solid. Yield-24%. $^1$H NMR (400 MHz, DMSO-$d_6$) δ 10.76 (s, 1H), 9.24 (d, J=1.2 Hz, 1H), 8.64 (s, 1H), 8.56 (s, 1H), 8.37 (d, J=2.8 Hz, 1H), 8.17 (s, 1H), 7.82-7.77 (m, 2H), 7.34 (d, J=8.0 Hz, 1H), 6.96 (d, J=8.4 Hz, 2H), 6.46 (s, 1H), 6.43 (d, J=4.4 Hz, 1H), 5.98 (d, J=7.6 Hz, 1H), 4.47-4.45 (m, 2H), 4.28-4.20 (m, 2H), 3.97-3.90 (m, 3H), 3.27-3.24 (m, 4H), 2.96 (brs, 2H), 2.88-2.80 (m, 2H), 2.59 (d, J=4.0 Hz, 2H), 2.11-2.08 (m, 7H), 1.92-1.84 (m, 4H), 1.68 (s, 4H), 1.42-1.36 (m, 2H), 1.14 (s, 3H), 1.08 (d, J=6.8 Hz, 6H). LC MS: ES+ (M+H) 897.2.

Example 73: Synthesis of 1-(5-(3-Cyano-6-(1-(1-(2-(4-(4-((2,6-dioxopiperidin-3-yl)amino)-2-fluorophenyl)piperidin-1-yl)acetyl)piperidin-4-yl)-1H-pyrazol-4-yl)pyrazolo[1,5-a]pyridin-4-yl)pyridin-2-yl)-4-ethyl-N-isopropylpiperidine-4-carboxamide (Compound 3)
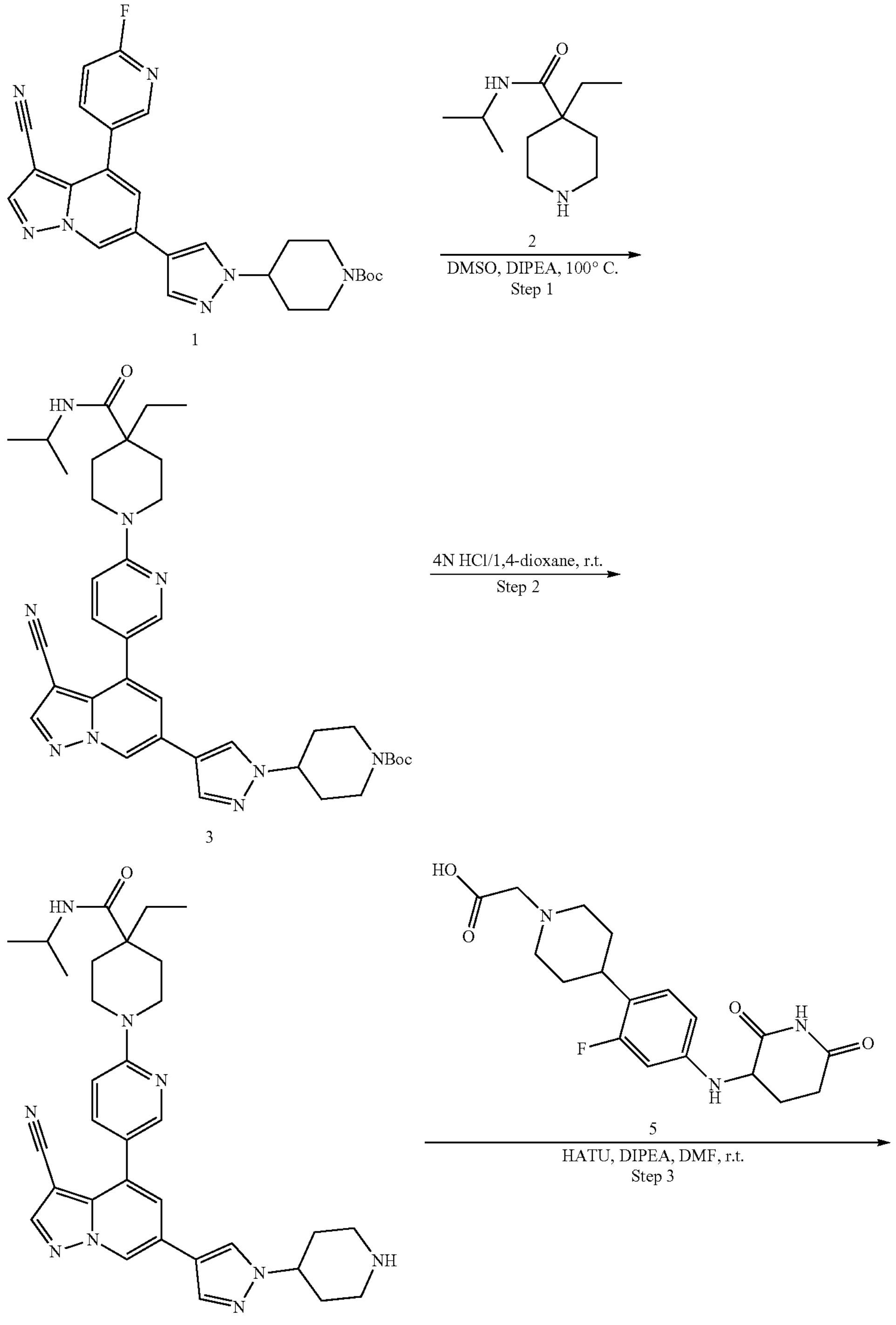
1
2
3
4
5

-continued

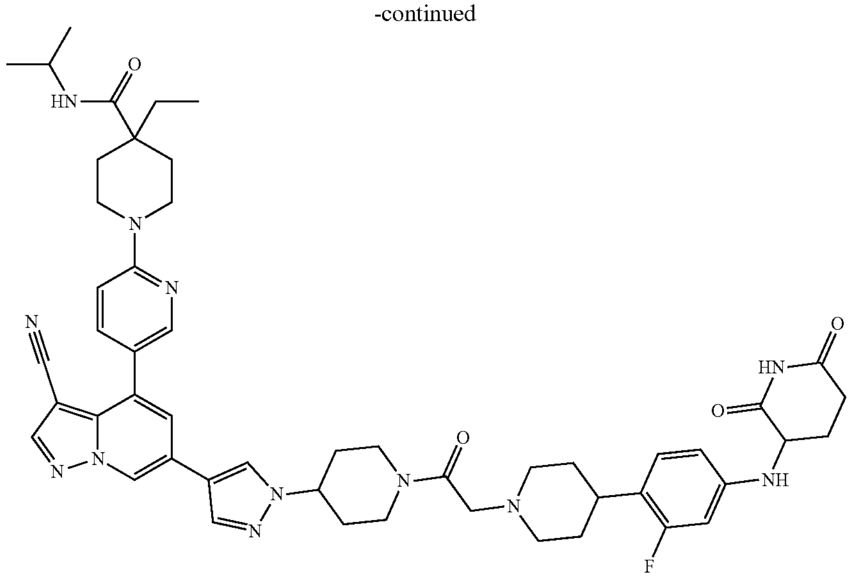

Compound 3

Step 1. Into a 25 mL sealed-tube reactor containing a well-stirred solution of tert-butyl 4-[4-[3-cyano-4-(6-fluoro-3-pyridyl)pyrazolo[1,5-a]pyridin-6-yl]pyrazol-1-yl]piperidine-1-carboxylate (1; 120 mg, 0.246 mmol) and 4-ethyl-N-isopropyl-piperidine-4-carboxamide (2; 58.57 mg, 0.295 mmol) in anhydrous DMSO (3 mL) was added DIPEA (0.64 mL, 0.369 mmol) at ambient temperature. The reaction mixture was heated to 100° C. for 16 h. After completion of the reaction as indicated by UPLC, the reaction mixture was cooled to room temperature and poured into water (10 mL) and precipitate was filtered. The solid product was dried to yield tert-butyl 4-[4-[3-cyano-4-[6-[4-ethyl-4-(isopropylcarbamoyl)-1-piperidyl]-3-pyridyl]pyrazolo[1,5-a]pyridin-6-yl]pyrazol-1-yl]piperidine-1-carboxylate (3; 130 mg, 0.169 mmol) as a yellow solid. Yield-68.7%; LC MS: ES+ (M+H) 666.3.

Step 2. Into a 25 mL single-necked round-bottomed flask containing a well-stirred solution of tert-butyl 4-[4-[3-cyano-4-[6-[4-ethyl-4-(isopropylcarbamoyl)-1-piperidyl]-3-pyridyl]pyrazolo[1,5-a]pyridin-6-yl]pyrazol-1-yl]piperidine-1-carboxylate (3; 130 mg, 0.195 mmol) in anhydrous $CH_2Cl_2$ (5 mL) was added HCl (8 mL; 4 M in 1,4-dioxane) at ambient temperature. The resulting mixture was stirred at ambient temperature for 2 h. Excess solvents were removed from the reaction mixture under reduced pressure to get a crude mass. The crude mass was triturated with $Et_2O$ (10 mL) to yield 1-[5-[3-cyano-6-[1-(4-piperidyl)pyrazol-4-yl]pyrazolo[1,5-a]pyridin-4-yl]-2-pyridyl]-4-ethyl-N-isopropyl-piperidine-4-carboxamide hydrochloric acid salt (4; 120 mg, 0.170 mmol) as a yellow solid. Yield-87%; LC MS: ES+ (M+H) 566.3.

Step 3. Into a 50 mL single-necked round-bottomed flask containing a well-stirred solution of 1-[5-[3-cyano-6-[1-(4-piperidyl)pyrazol-4-yl]pyrazolo[1,5-a]pyridin-4-yl]-2-pyridyl]-4-ethyl-N-isopropyl-piperidine-4-carboxamide hydrochloric acid salt (4; 120.48 mg, 0.200 mmol) and 2-[4-[4-[(2,6-dioxo-3-piperidyl)amino]-2-fluoro-phenyl]-1-piperidyl]acetic acid (5; 80 mg, 0.200 mmol) in anhydrous DMF (3 mL) were added DIPEA (0.174 mL, 1 mmol) and HATU (91.29 mg, 0.240 mmol) at ambient temperature under nitrogen atmosphere. The reaction mixture was stirred at ambient temperature for 3 h. The progress of the reaction was monitored by UPLC. After completion of the reaction, the reaction mixture was treated with water (10 mL) and the precipitate was filtered and dried under vacuum. The crude solid was purified by reverse phase column chromatography using ISCO C18 (30 g), Mobile phase: A: 0.1% Formic acid in MQ-water; B: Acetonitrile to yield 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-4-ethyl-N-isopropyl-piperidine-4-carboxamide formic acid salt (Compound 3; 47.33 mg, 0.047 mmol) as an off-white solid. Yield-23.7%. $^1H$ NMR (400 MHz, DMSO-$d_6$). δ 10.79 (s, 1H), 9.25 (d, J=1.6 Hz, 1H), 8.65 (s, 1H), 8.57 (s, 1H), 8.36 (d, J=2.8 Hz, 1H), 8.18 (s, 1H), 7.82 (d, J=1.2 Hz, 1H), 7.78 (dd, J=8.8, 2.4 Hz, 1H), 7.39 (d, J=8.0 Hz, 1H), 6.96 (d, J=8.8 Hz, 2H), 6.45 (s, 1H), 6.42 (d, J=2.8 Hz, 1H), 5.99 (d, J=8.0 Hz, 1H), 4.52-4.45 (m, 2H), 4.31-4.22 (m, 2H), 4.08 (d, J=9.2 Hz, 2H), 4.01-3.99 (m, 1H), 3.28-3.25 (m, 2H), 3.16-3.04 (m, 3H), 2.92 (brs, 2H), 2.82-2.67 (m, 2H), 2.60-2.58 (m, 2H), 2.17-2.05 (m, 7H), 1.87-1.83 (m, 3H), 1.66 (brs, 4H), 1.49 (q, J=7.2 Hz, 2H), 1.38-1.32 (m, 2H), 1.09 (d, J=6.4 Hz, 6H) and 0.75 (t, J=7.2 Hz, 3H); LC MS: ES+ (M+H) 912.4.

Example 74: Synthesis of 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyridin-4-yl]-2-pyridyl]-4-ethyl-N-isopropyl-piperidine-4-carboxamide (Compound 4)

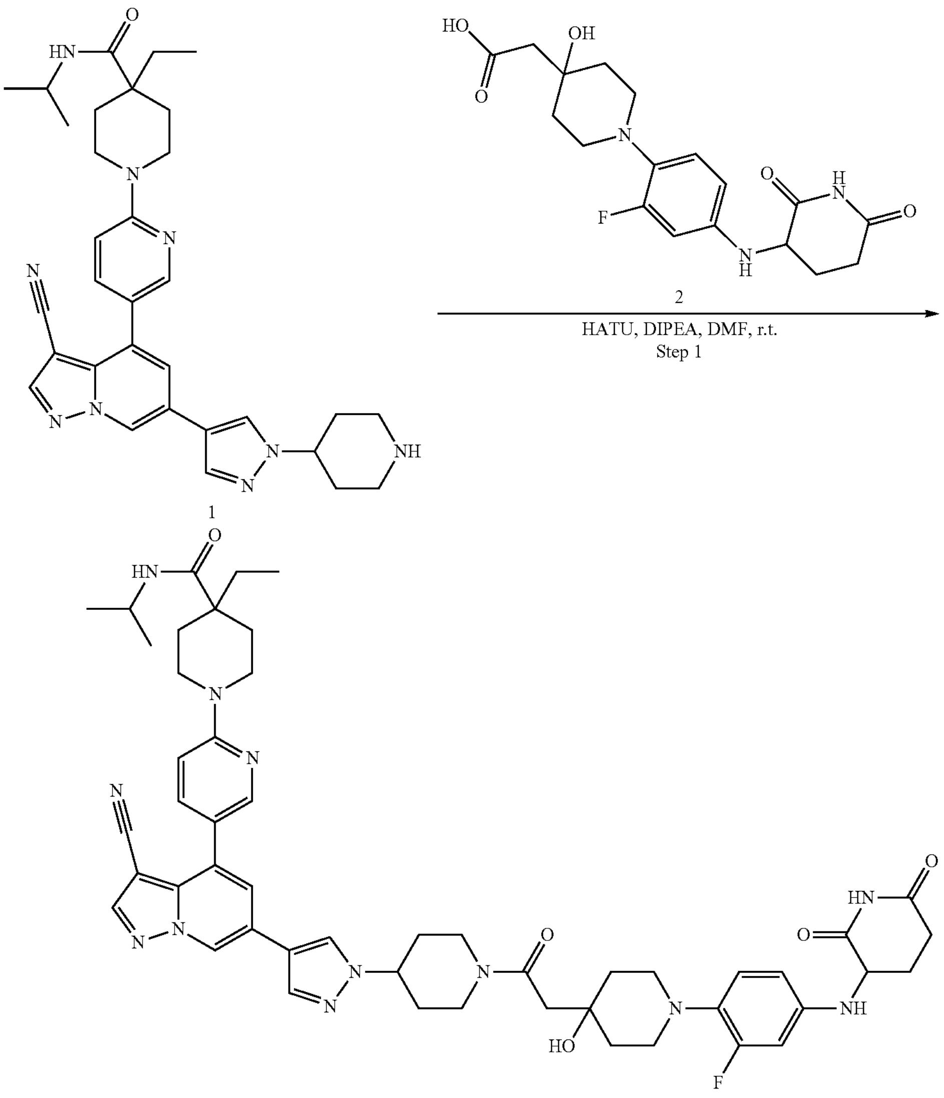

Compound 4

Step 1. Into a 50 mL single-necked round-bottomed flask containing a well-stirred solution of 1-[5-[3-cyano-6-[1-(4-piperidyl)pyrazol-4-yl]pyrazolo[1,5-a]pyridin-4-yl]-2-pyridyl]-4-ethyl-N-isopropyl-piperidine-4-carboxamide hydrochloride salt (1; 79.36 mg, 0.132 mmol) and 2-[1-[4-[(2,6-dioxo-3-piperidyl)amino]-2-fluoro-phenyl]-4-hydroxy-4-piperidyl]acetic acid (2; 50 mg, 0.132 mmol) in anhydrous DMF (3 mL) were added DIPEA (0.114 mL, 0.66 mmol) and HATU (60.13 mg, 0.16 mmol) at ambient temperature under nitrogen atmosphere. The resulting mixture was stirred at ambient temperature for 3 h and the progress of the reaction was monitored by LCMS. After completion of the reaction, the reaction mixture was treated with water (20 mL) and the precipitate was filtered and dried under vacuum. The crude product was purified by prep HPLC (method: XSELECT C18 (30×150), 5 MIC; Mobile Phase A: 0.1% $NH_4OAc$ in milli-Q water; Mobile phase B: Acetonitrile) to afford 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyridin-4-yl]-2-pyridyl]-4-ethyl-N-isopropyl-piperidine-4-carboxamide (Compound 4; 21 mg, 0.023 mmol) as an off-white solid. Yield-17.2%. $^1H$ NMR (400 MHz, DMSO-$d_6$) δ 10.78 (s, 1H), 9.25 (d, J=1.6 Hz, 1H), 8.65 (s, 1H), 8.58 (s, 1H), 8.37 (d, J=2.4 Hz, 1H), 8.18 (s, 1H), 7.83 (d, J=1.2 Hz, 1H), 7.79 (dd, J=8.8, 2.4 Hz, 1H), 7.39 (d, J=8.0 Hz, 1H), 6.96 (d, J=9.2 Hz, 1H), 6.86 (t, J=8.8 Hz, 1H), 6.50 (dd, J=14.8, 2.4 Hz, 1H), 6.42 (d, J=8.8, 2.4 Hz, 1H), 5.78 (d, J=7.6 Hz, 1H), 4.89 (s, 1H), 4.59-4.46 (m, 2H), 4.28-4.14 (m, 2H), 4.08 (d, J=13.6 Hz, 2H), 4.02-3.98 (m, 1H), 3.29-3.22 (m, 1H), 3.07 (t, J=11.2 Hz, 2H), 2.91-2.67 (m, 6H), 2.59-2.55 (m, 3H), 2.17-2.10 (m, 5H), 1.87-1.77 (m, 5H), 1.67-1.65 (m, 2H), 1.51-1.49 (m, 2H), 1.36-1.34 (m, 2H), 1.09 (d, J=6.4 Hz, 6H) and 0.75 (t, J=7.2 Hz, 3H). LC MS: ES+ (M+H) 927.2.
Example 75: Synthesis of 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[4-[2-(5-fluoro-2-pyridyl)acetyl]piperazin-1-yl]-3-pyridyl]pyrazolo[1,5-a]pyridine-3-carbonitrile (Compound 5)
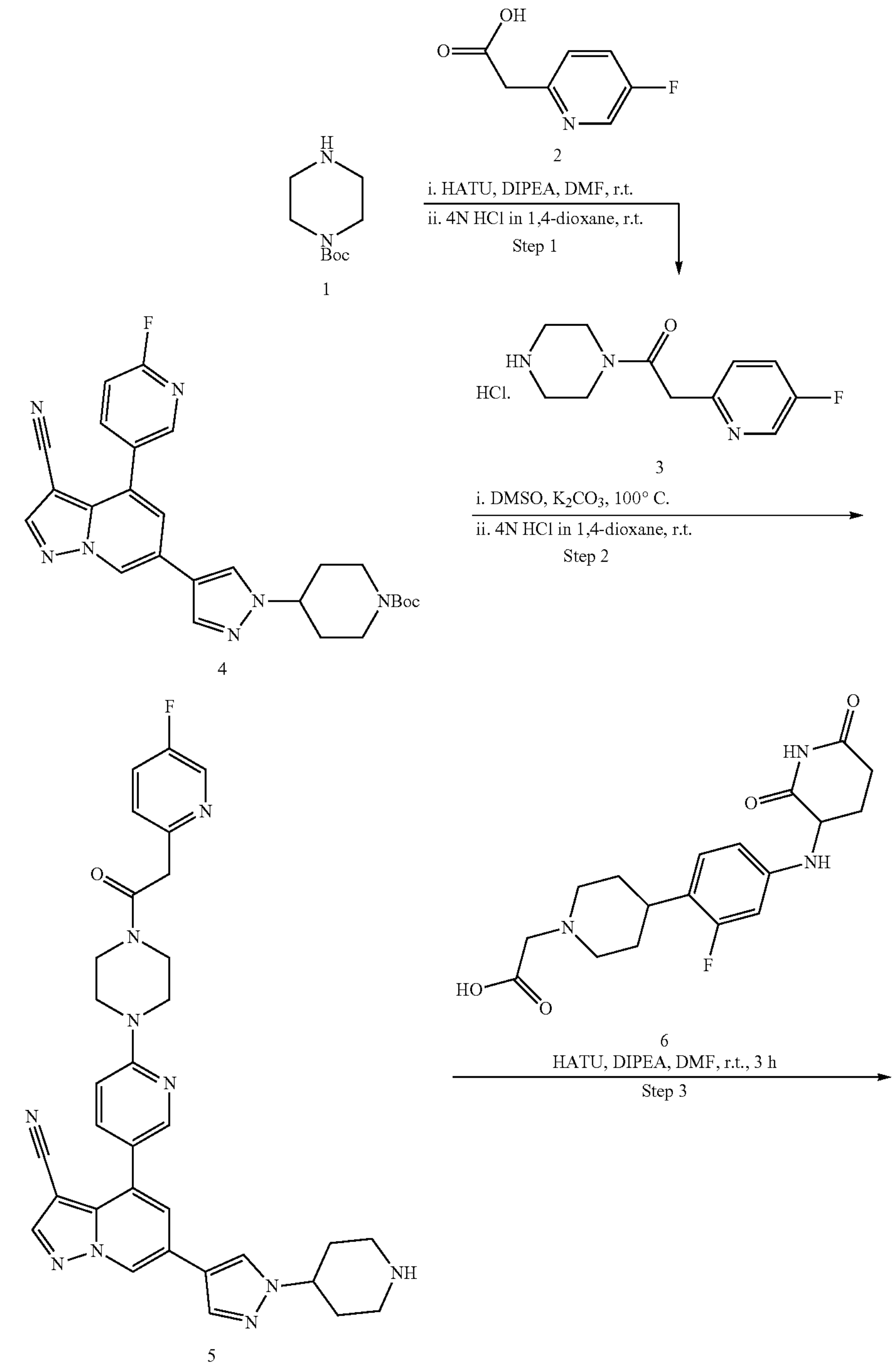 [SMILES: O=C(O)Cc1ccc(F)cn1 ; CC(C)(C)OC(=O)N1CCNCC1 ; CC(C)(C)OC(=O)N1CCC(n2cc(-c3cc(-c4ccc(F)nc4)c4c(C#N)cnn4c3)cn2)CC1 ; O=C(Cc1ccc(F)cn1)N1CCNCC1 ; N#Cc1cnn2cc(-c3cnn(C4CCNCC4)c3)cc(-c3ccc(N4CCN(C(=O)Cc5ccc(F)cn5)CC4)nc3)c12 ; O=C(O)CN1CCC(c2ccc(NC3CCC(=O)NC3=O)cc2F)CC1]

-continued

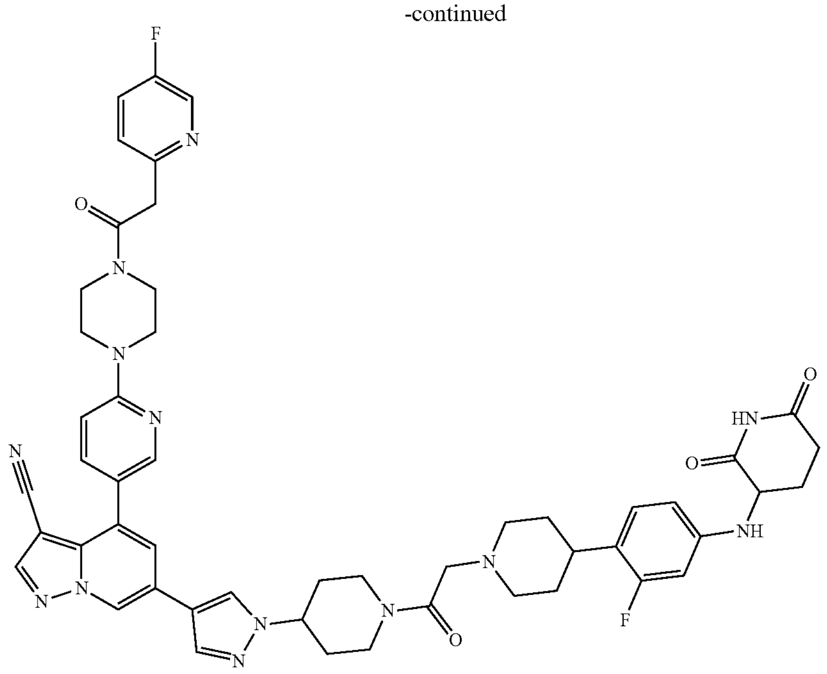

Compound 5

Step 1i. To a well-stirred solution of a mixture of tert-butyl piperazine-1-carboxylate (1; 546.29 mg, 2.93 mmol)) and 2-(5-fluoro-2-pyridyl)acetic acid (2; 350 mg, 2.26 mmol) in anhydrous DMF (5 mL) in a 25 mL single-necked round-bottomed flask was added DIPEA (1.18 mL, 6.77 mmol) and the resulting solution was stirred for 15 minutes at ambient temperature under nitrogen atmosphere. HATU (1.29 g, 3.38 mmol) was added to the reaction mixture and stirring was continued at ambient temperature for 3 h. The progress of the reaction was monitored by UPLC. After completion of the reaction, the reaction mixture was quenched with water (10 mL) and extracted with $CH_2Cl_2$ (2×50 mL). The combined organic layers were dried over anhydrous $Na_2SO_4$, filtered and concentrated under reduced pressure to obtain a crude residue. The crude product was purified by silica-gel (230-400 mesh) column with 60% EtOAc/pet ether to afford tert-butyl 4-[2-(5-fluoro-2-pyridyl)acetyl]piperazine-1-carboxylate (Int; 510 mg, 1.18 mmol) as a sticky oil. Yield-52.4%; LC MS: ES+ (M+H) 324.1.

Step 1ii. Into a 25 mL single-necked round-bottomed flask containing a well-stirred solution of tert-butyl 4-[2-(5-fluoro-2-pyridyl)acetyl]piperazine-1-carboxylate (Int from Step 1i; 510 mg, 1.58 mmol) in anhydrous $CH_2Cl_2$ (5 mL) was added HCl (0.7 mL; 4M in 1,4-dioxane) at ambient temperature under nitrogen atmosphere. The reaction mixture was stirred for 3 h at ambient temperature. Excess solvents were removed from the reaction mixture under reduced pressure to obtain a crude material. The crude material was triturated with $Et_2O$ (10 mL) to yield 2-(5-fluoro-2-pyridyl)-1-piperazin-1-yl-ethanone hydrochloride salt (3; 390 mg, 1.43 mmol) as a pale brown solid. Yield-90.4%; LC MS: ES+ (M+H) 224.1.

Step 2i. Into a 10 mL sealed tube containing a well-stirred solution of a mixture of 2-(5-fluoro-2-pyridyl)-1-piperazin-1-yl-ethanone hydrochloride salt (3; 51.14 mg, 0.197 mmol) and tert-butyl 4-[4-[3-cyano-4-(6-fluoro-3-pyridyl)pyrazolo[1,5-a]pyridin-6-yl]pyrazol-1-yl]piperidine-1-carboxylate (4; 80 mg, 0.164 mmol) in anhydrous DMSO (2 mL) was added anhydrous $K_2CO_3$ (113.40 mg, 0.820 mmol). The reaction mixture was heated to 100° C. for 24 h. After completion of the reaction, the reaction mixture was cooled to room temperature and poured into water (10 mL). The resulting precipitate was filtered and dried to afford tert-butyl 4-[4-[3-cyano-4-[6-[4-[2-(5-fluoro-2-pyridyl)acetyl]piperazin-1-yl]-3-pyridyl]pyrazolo[1,5-a]pyridin-6-yl]pyrazol-1-yl]piperidine-1-carboxylate (Int; 75 mg, 0.086 mmol) as a yellow solid. Yield-52.8%; LC MS: ES+ (M+H) 691.3.

Step 2ii. Into a 25 mL single-necked round-bottomed flask containing a well-stirred solution of tert-butyl 4-[4-[3-cyano-4-[6-[4-[2-(5-fluoro-2-pyridyl)acetyl]piperazin-1-yl]-3-pyridyl]pyrazolo[1,5-a]pyridin-6-yl]pyrazol-1-yl]piperidine-1-carboxylate (Int from Step 2i; 75 mg, 0.108 mmol) in anhydrous $CH_2Cl_2$ (2 mL) was added HCl (4 mL; 4M in 1,4-dioxane) at ambient temperature under nitrogen atmosphere. The reaction mixture was stirred for 3 h at ambient temperature. Excess solvent was removed from the reaction mixture under reduced pressure. The crude material was triturated with $Et_2O$ (10 mL) to afford 4-[6-[4-[2-(5-fluoro-2-pyridyl)acetyl]piperazin-1-yl]-3-pyridyl]-6-[1-(4-piperidyl)pyrazol-4-yl]pyrazolo[1,5-a]pyridine-3-carbonitrile hydrochloride salt (5; 70 mg, 0.084.26 mmol) as a yellow solid. Yield-77.6%; LC MS: ES+591.2.

Step 3. To a well-stirred mixture of 4-[6-[4-[2-(5-fluoro-2-pyridyl)acetyl]piperazin-1-yl]-3-pyridyl]-6-[1-(4-piperidyl)pyrazol-4-yl]pyrazolo[1,5-a]pyridine-3-carbonitrile hydrochloride salt (5; 43.13 mg, 0.069 mmol) and 2-[4-[4-[(2,6-dioxo-3-piperidyl)amino]-2-fluoro-phenyl]-1-piperidyl]acetic acid (6; 25 mg, 0.062 mmol) in anhydrous DMF (2 mL) was added DIPEA (0.054 mL, 0.003 mmol) and the resulting solution was stirred for 15 minutes at ambient temperature under nitrogen atmosphere. HATU (28.53 mg, 0.075 mmol) was added to the reaction mixture and stirring was continued at ambient temperature for 2 h.

The progress of the reaction was monitored by UPLC. After completion of the reaction, the reaction mixture was treated with water (1 mL). The precipitate was filtered and dried under vacuum. The material was purified by reverse phase column chromatography using ISCO C-18 CombiFlash column (Mobile phase: A: 0.1% FA in water, B: Acetonitrile) to yield 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[4-[2-(5-fluoro-2-pyridyl)acetyl]piperazin-1-yl]-3-pyridyl]pyrazolo[1,5-a]pyridine-3-carbonitrile formic acid salt (Compound 5; 2.4 mg, 0.002 mmol) as a white solid. Yield-3.7%. $^1$H NMR (400 MHz, DMSO-$d_6$) δ 10.80 (s, 1H), 9.27 (s, 1H), 8.66 (s, 1H), 8.56 (s, 1H), 8.49 (d, J=2.8 Hz, 1H), 8.41 (d, J=1.6 Hz, 1H), 8.18 (s, 1H), 7.87-7.83 (m, 2H), 7.69-7.67 (m, 1H), 7.42-7.39 (m, 1H), 7.02-6.96 (m, 2H), 6.46-6.43 (m, 2H), 6.04 (d, J=7.6 Hz, 1H), 5.76 (s, 1H), 4.49-4.44 (m, 2H), 4.28-4.27 (m, 1H), 4.08 (brs, 1H), 3.98 (s, 2H), 3.68 (s, 3H), 3.62 (s, 6H), 3.13 (brs, 2H), 2.88-2.86 (m, 1H), 2.76-2.68 (m, 2H), 2.59 (s, 1H), 2.17-2.05 (m, 4H) and 1.95-1.74 (m, 7H); LC MS: ES+(M+H) 936.3.

Example 76: Synthesis of 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-N-isopropyl-4-methoxy-piperidine-4-carboxamide (Compound 6)

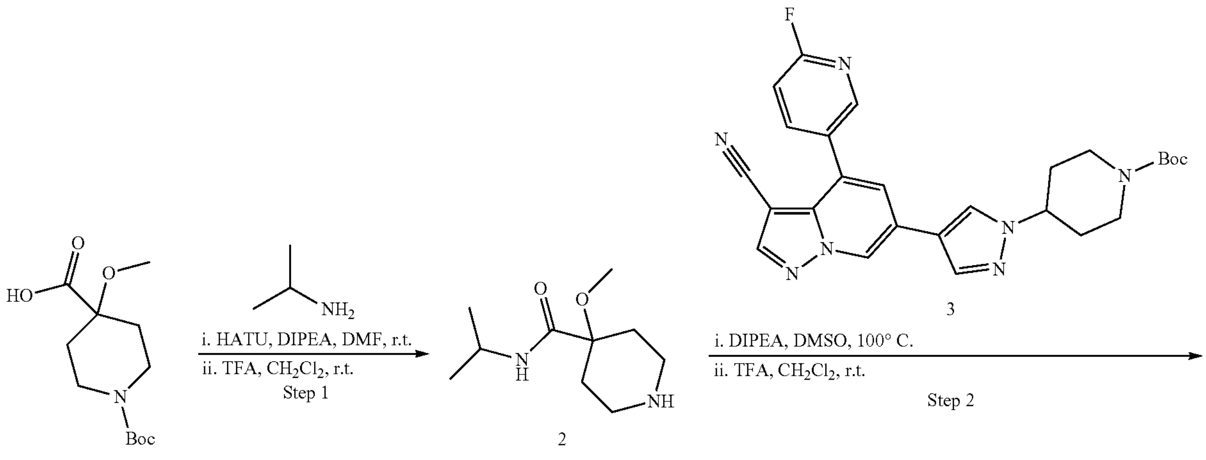

1 2 3

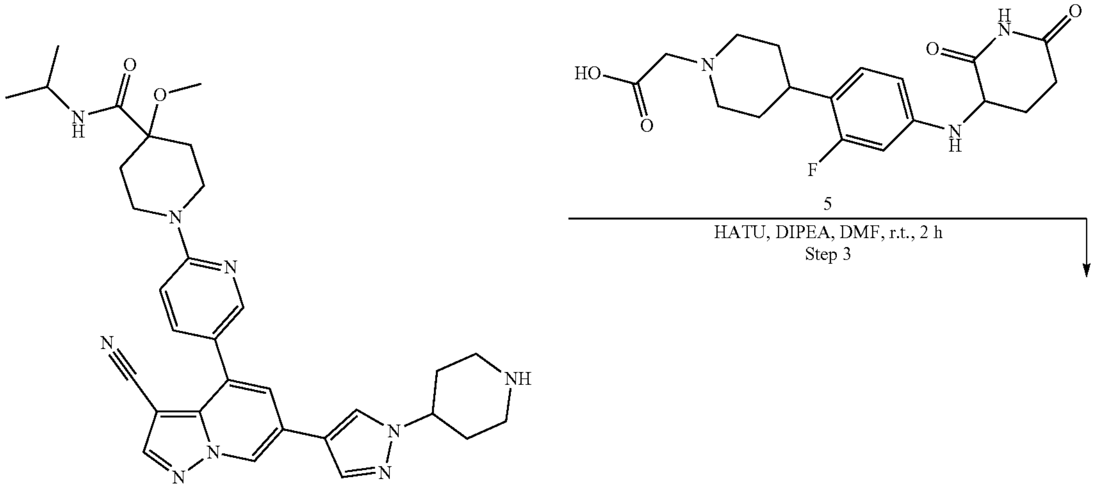

4 5

-continued

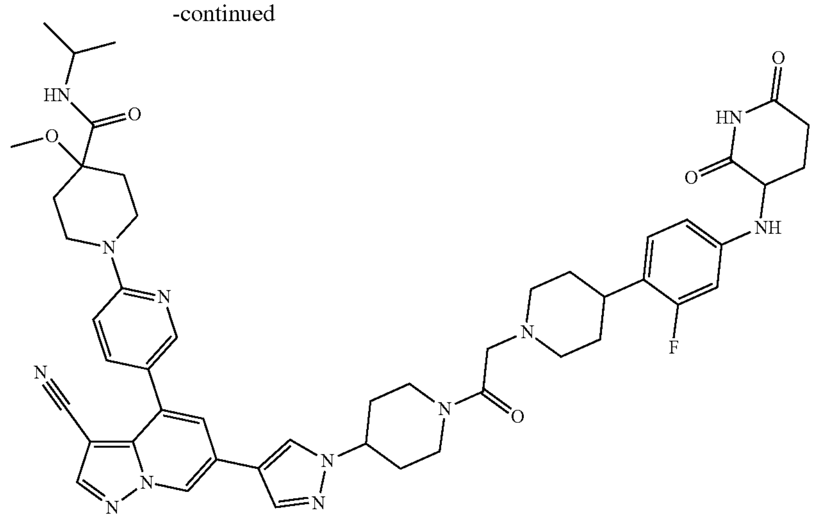

Compound 6

Step 1i. Into a 10 mL single-necked round-bottomed flask containing a well-stirred solution of 1-tert-butoxycarbonyl-4-methoxy-piperidine-4-carboxylic acid (1; 50 mg, 0.193 mmol) and propan-2-amine (12.54 mg, 0.212 mmol, 0.018 mL) in anhydrous DMF (0.5 mL) was added DIPEA (0.1 mL, 0.578 mmol) and the resulting solution was stirred for 15 minutes at ambient temperature under nitrogen atmosphere. HATU (109.98 mg, 0.289 mmol) was added to the reaction mixture and stirring was continued at ambient temperature for 2 h. The progress of the reaction was monitored by TLC. The reaction mixture was treated with water and extracted with EtOAc (2×20 mL). The combined organics were washed with brine (100 mL), dried (anhydrous $Na_2SO_4$), filtered and concentrated under reduced pressure to obtain crude tert-butyl 4-(isopropylcarbamoyl)-4-methoxy-piperidine-1-carboxylate (Int; 65 mg, 0.186 mmol) as colourless liquid. Yield-96.5%; LC MS: ES+ (M-Boc+H) 201.1.

Step 1ii. Into another 25 mL single-necked round-bottom flask containing a well stirred solution of tert-butyl 4-(isopropylcarbamoyl)-4-methoxy-piperidine-1-carboxylate (Int from Step 1i; 250 mg, 0.832 mmol) in anhydrous $CH_2Cl_2$ (3 mL) was added TFA (2.37 g, 20.81 mmol, 1.60 mL) at 0° C. under nitrogen atmosphere. The reaction mixture was stirred at ambient temperature for 2 h. The progress of the reaction was monitored by UPLC. The reaction mixture was concentrated under reduced pressure (co-distilled with $CH_2Cl_2$) to afford a crude residue, which was triturated with $Et_2O$ (2×) to afford N-isopropyl-4-methoxy-piperidine-4-carboxamide trifluoroacetic acid salt (2; 220 mg, 0.573 mmol) as a brown-coloured liquid. Yield-69%; LC MS: ES+ (M+H) 201.1.

Step 1ii. Into a 10 mL sealed tube containing a well-stirred solution of tert-butyl 4-[4-[3-cyano-4-(6-fluoro-3-pyridyl) pyrazolo[1,5-a]pyridin-6-yl]pyrazol-1-yl]piperidine-1-carboxylate (3; 110 mg, 225.63 mmol) and N-isopropyl-4-methoxy-piperidine-4-carboxamide trifluoroacetic acid salt (2; 45.19 mg, 0.143 mmol) in anhydrous DMSO (1.2 mL) was added DIPEA (145.80 mg, 1.13 mmol, 0.196 mL) at ambient temperature. The resulting reaction mixture was stirred at 100° C. for 16 h. The progress of the reaction was monitored by UPLC. The reaction mixture was treated with water and the precipitate filtered. The solid was dried under vacuum to afford tert-butyl 4-[4-[3-cyano-4-[6-[4-(isopropylcarbamoyl)-4-methoxy-1-piperidyl]-3-pyridyl]pyrazolo [1,5-a]pyridin-6-yl]pyrazol-1-yl]piperidine-1-carboxylate (Int; 130 mg, 0.116 mmol) as a brown-coloured solid. Yield-51%; LC MS: ES+ (M+H) 668.4.

Step 2i. Into a 25 mL single-necked round-bottomed flask containing a well-stirred solution of tert-butyl 4-[4-[3-cyano-4-[6-[4-(isopropylcarbamoyl)-4-methoxy-1-piperidyl]-3-pyridyl]pyrazolo[1,5-a]pyridin-6-yl]pyrazol-1-yl] piperidine-1-carboxylate (Int from Step 2i; 130 mg, 0.194 mmol) in anhydrous $CH_2Cl_2$ (2 mL) was added TFA (554.92 mg, 4.87 mmol, 0.374 mL) at 0° C. under nitrogen atmosphere. After addition, the reaction mixture was stirred at ambient temperature for 2 h. The progress of the reaction was monitored by UPLC. The reaction mixture was concentrated under reduced pressure (co-distilled with $CH_2Cl_2$) to afford a crude residue, which was triturated with $Et_2O$ (twice) to yield 1-[5-[3-cyano-6-[1-(4-piperidyl)pyrazol-4-yl]pyrazolo[1,5-a]pyridin-4-yl]-2-pyridyl]-N-isopropyl-4-methoxy-piperidine-4-carboxamide trifluoroacetic acid salt (4; 140 mg, 0.113 mmol) as a brown-coloured liquid. Yield-58%; LC MS: ES+ (M+H) 567.9.

Step 3. To a well-stirred solution of 1-[5-[3-cyano-6-[1-(4-piperidyl)pyrazol-4-yl]pyrazolo[1,5-a]pyridin-4-yl]-2-pyridyl]-N-isopropyl-4-methoxy-piperidine-4-carboxamide trifluoroacetic acid salt (4; 140 mg, 0.205 mmol) and 2-[4-[4-[(2,6-dioxo-3-piperidyl)amino]-2-fluoro-phenyl]-1-piperidyl]acetic acid (5; 82.11 mg, 0.205 mmol) in anhydrous DMF (1.5 mL) was added DIPEA (0.178 mL, 1.03 mmol). The resulting solution was stirred for 15 minutes at ambient temperature under nitrogen atmosphere. HATU (117.13 mg, 0.308 mmol) was added to the reaction mixture and stirring was continued at ambient temperature for 2 h. The progress of the reaction was monitored by UPLC. After completion of the reaction, the reaction mixture was treated with water (2 mL). The precipitate was filtered and dried under vacuum. The crude residue was purified by reverse phase column chromatography (30 g Biotage C-18 column (Mobile phase: A: 0.1 M $NH_4OAc$ in water, B: Acetonitrile)) to afford 1-[5-[3-cyano-6-[1-[1-[2-[4-[4-[(2,6-dioxo-3-piperidyl) amino]-2-fluoro-phenyl]-1-piperidyl]acetyl]-4-piperidyl] pyrazol-4-yl]pyrazolo[1,5-a]pyridin-4-yl]-2-pyridyl]-N-isopropyl-4-methoxy-piperidine-4-carboxamide (Compound 6;

61.75 mg, 0.065 mmol) as an off-white solid. Yield-32%. $^1$H NMR (400 MHz, DMSO-$d_6$) δ 10.79 (s, 1H), 9.26 (d, J=1.6 Hz, 1H), 8.65 (s, 1H), 8.58 (s, 1H), 8.39 (d, J=2.4 Hz, 1H), 8.18 (s, 1H), 7.85 (d, J=1.2 Hz, 1H), 7.82 (dd, J=8.8, 2.4 Hz, 1H), 7.72 (d, J=8.0 Hz, 1H), 7.01 (d, J=8.8 Hz, 1H), 6.97 (t, J=8.8 Hz, 1H), 6.45 (s, 1H), 6.42-6.41 (m, 1H), 5.99 (d, J=8.0 Hz, 1H), 4.51-4.45 (m, 2H), 4.29-4.12 (m, 4H), 3.93-3.91 (m, 1H), 3.29-3.25 (m, 4H), 3.13-3.17 (m, 4H), 2.93 (brs, 2H), 2.81-2.68 (m, 2H), 2.13-2.05 (m, 6H), 1.91-1.76 (m, 8H), 1.66 (brs, 4H), 1.08 (d, J=6.8 Hz, 6H); LC MS: ES+ (M+H) 913.4.

Example 77: Synthesis of 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-4-ethyl-N-[(1R)-2,2,2-trifluoro-1-methyl-ethyl]piperidine-4-carboxamide (Compound 7)

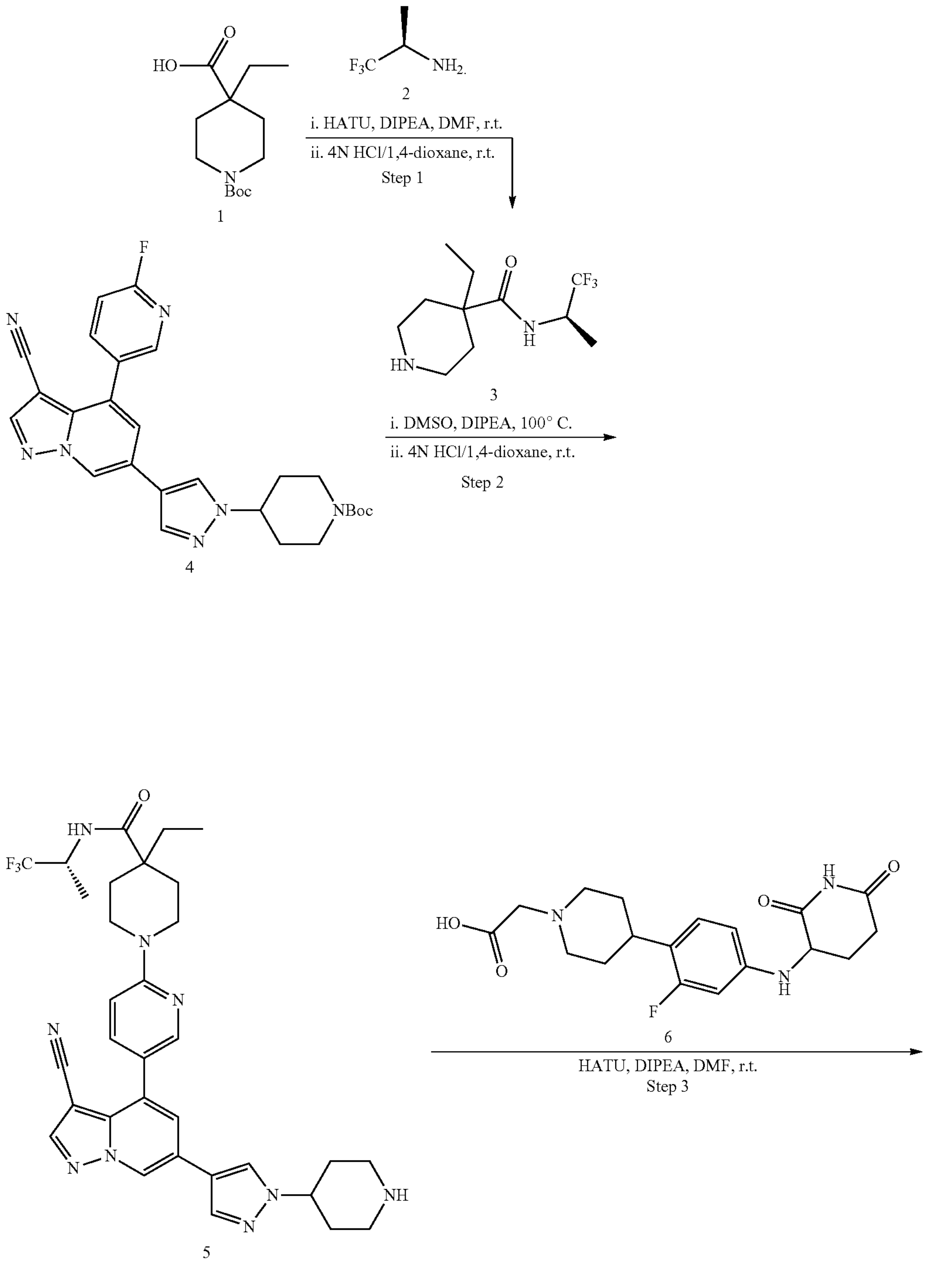

-continued

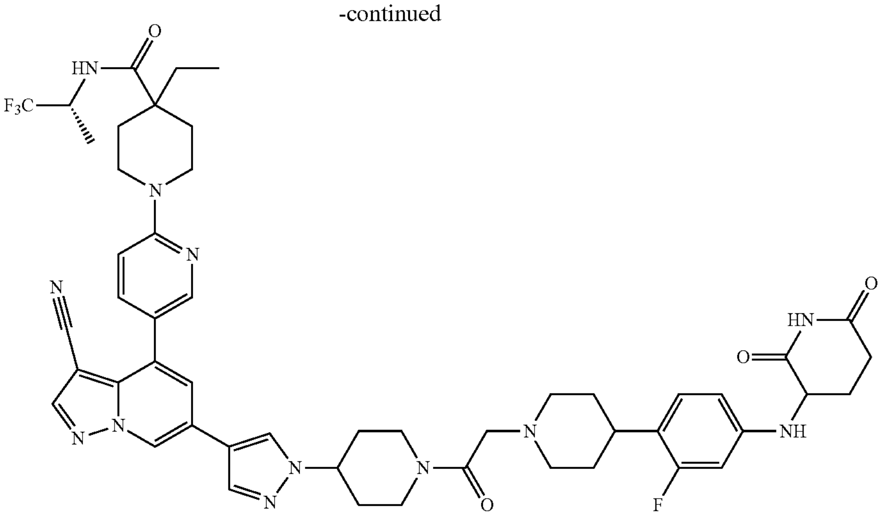

Compound 7

Step 1i. Into a well-stirred solution of 1-tert-butoxycarbonyl-4-ethyl-piperidine-4-carboxylic acid (1; 300 mg, 1.17 mmol) and (2R)-1,1,1-trifluoropropan-2-amine (2; 209.21 mg, 1.40 mmol) in anhydrous DMF (1.5 mL) was added DIPEA (1.02 mL, 5.83 mmol), and the resulting solution was stirred for 15 minutes at ambient temperature under nitrogen atmosphere. HATU (576.27 mg, 1.52 mmol) was added to the reaction mixture and stirring was continued at ambient temperature for 2 h. The progress of the reaction was monitored by LCMS. The reaction mixture was treated with water (10 mL) and extracted with EtOAc (2×30 mL). Organic layers were dried (anhydrous $Na_2SO_4$), filtered and concentrated under reduced pressure. The crude residue was purified by flash silica-gel (230-400 mesh) column with 0-100% EtOAc/pet ether to afford tert-butyl 4-ethyl-4-[[(1R)-2,2,2-trifluoro-1-methyl-ethyl]carbamoyl]piperidine-1-carboxylate (Int; 400 mg, 0.852 mmol) as a colourless semi-solid. Yield-73.1%; LC MS: ES+ (M-tBu+H) 253.0.

Step 1ii. Into a 50 mL single-necked round-bottomed flask containing a well-stirred solution of tert-butyl 4-ethyl-4-[[(1R)-2,2,2-trifluoro-1-methyl-ethyl]carbamoyl]piperidine-1-carboxylate (Int from Step 1i; 400 mg, 1.14 mmol) in anhydrous $CH_2Cl_2$ (5 mL) was added HCl (3 mL; 4M in 1,4-dioxane) dropwise at 0° C. under nitrogen atmosphere. The resulting mixture was stirred at ambient temperature for 2 h. The progress of the reaction was monitored by LCMS. Excess solvents were removed from the reaction mixture under reduced pressure to afford a residue, which was co-distilled with $CH_2Cl_2$ to afford 4-ethyl-N-[(1R)-2,2,2-trifluoro-1-methyl-ethyl]piperidine-4-carboxamide hydrochloride salt (3; 300 mg, 0.391 mmol) as a yellow-coloured semi-solid. Yield-34.5%; LC MS: ES+ (M+H) 253.0.

Step 2i. Into a 50 mL sealed tube containing a well-stirred solution of tert-butyl 4-[4-[3-cyano-4-(6-fluoro-3-pyridyl)pyrazolo[1,5-a]pyridin-6-yl]pyrazol-1-yl]piperidine-1-carboxylate (4; 300 mg, 0.615 mmol) and 4-ethyl-N-[(1R)-2,2,2-trifluoro-1-methyl-ethyl]piperidine-4-carboxamide hydrochloride salt (3; 310.48 mg, 1.23 mmol) in anhydrous DMSO (5 mL) was added DIPEA (0.107 mL, 0.615 mmol) at ambient temperature. The reaction mixture was stirred at 100° C. for 16 h. After completion of the reaction as indicated by LCMS, the reaction mixture was allowed to cool to room temperature and treated with ice-water (3 mL). The resulting mixture was stirred for 15 minutes at room temperature, during which time a precipitate formed. The solid was filtered and washed with water before drying under vacuum. The material was purified by flash silica-gel (230-400 mesh) column with 0-100% EtOAc/pet ether to afford tert-butyl 4-[4-[3-cyano-4-[6-[4-ethyl-4-[[(1R)-2,2,2-trifluoro-1-methyl-ethyl]carbamoyl]-1-piperidyl]-3-pyridyl]pyrazolo[1,5-a]pyridin-6-yl]pyrazol-1-yl]piperidine-1-carboxylate (Int; 140 mg, 0.169 mmol) as a yellow-coloured solid. Yield-27.6%; LC MS: ES+ (M+H) 720.3.

Step 2ii. Into a 50 mL single-necked round-bottomed flask containing a well-stirred solution of tert-butyl 4-[4-[3-cyano-4-[6-[4-ethyl-4-[[(1R)-2,2,2-trifluoro-1-methyl-ethyl]carbamoyl]-1-piperidyl]-3-pyridyl]pyrazolo[1,5-a]pyridin-6-yl]pyrazol-1-yl]piperidine-1-carboxylate (Int from Step 2i; 140 mg, 0.194 mmol) in anhydrous $CH_2Cl_2$ (1.5 mL) was added HCl (1.5 mL; 4M in 1,4-dioxane) dropwise at 0° C. under nitrogen atmosphere. The resulting mixture was stirred at ambient temperature for 2 h. The progress of the reaction monitored by LCMS. Excess solvents were removed under reduced pressure to obtain a crude residue, which was co-distilled with $CH_2Cl_2$ to afford 1-[5-[3-cyano-6-[1-(4-piperidyl)pyrazol-4-yl]pyrazolo[1,5-a]pyridin-4-yl]-2-pyridyl]-4-ethyl-N-[(1R)-2,2,2-trifluoro-1-methyl-ethyl]piperidine-4-carboxamide hydrochloride salt (5; 110 mg, 0.150 mmol) as a brown-colored solid. Yield-77.4%; LC MS: ES+ (M+H) 620.3.

Step 3: Into an 8 mL vial containing a well-stirred solution of 1-[5-[3-cyano-6-[1-(4-piperidyl)pyrazol-4-yl]pyrazolo[1,5-a]pyridin-4-yl]-2-pyridyl]-4-ethyl-N-[(1R)-2,2,2-trifluoro-1-methyl-ethyl]piperidine-4-carboxamide hydrochloride salt (5; 110 mg, 0.167 mmol) and 2-[4-[4-[(2,6-dioxo-3-piperidyl)amino]-2-fluoro-phenyl]-1-piperidyl]acetic acid (6; 60.92 mg, 0.152 mmol) in anhydrous DMF (1.5 mL) was added DIPEA (0.146 mL, 0.838 mmol) at ambient temperature. HATU (82.87 mg, 0.217 mmol) was added to the reaction mixture and stirring was continued at ambient temperature for 3 h. The progress of the reaction was monitored by UPLC. The reaction mixture was treated with water (1 mL) and the precipitate filtered, washed with water and dried under vacuum. The crude material was purified by prep-HPLC (column: Waters XBridge C-18.5 um, 19×150 mm; Mobile phase: 0.1% Formic acid in water/ACN) to afford 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-4-ethyl-N-[(1R)-2,2,2-trifluoro-1-methyl-ethyl] piperidine-4-carboxamide formic acid salt (Compound 7; 39.44 mg, 0.038 mmol) as an off-white solid. Yield-23.1%; $^{1}$H NMR (400 MHz, DMSO-$d_6$). δ 10.79 (s, 1H), 9.25 (d, J=1.6 Hz, 1H), 8.65 (s, 1H), 8.57 (s, 1H), 8.37 (d, J=2.8 Hz, 2H), 8.18 (s, 1H), 8.09 (d, J=8.8 Hz, 1H), 7.83 (d, J=1.2 Hz, 1H), 7.79 (dd, J=8.8, 2.4 Hz, 1H), 6.98-6.95 (m, 2H), 6.44-6.41 (m, 2H), 6.00 (d, J=8.0 Hz, 1H), 4.79-4.69 (m, 1H), 4.47-4.43 (m, 2H), 4.29-4.21 (m, 2H), 4.12 (d, J=13.6 Hz, 2H), 3.29-3.23 (m, 4H), 3.15-3.12 (m, 1H), 3.03 (t, J=11.2 Hz, 2H), 2.92 (brs, 1H), 2.85-2.73 (m, 1H), 2.71-2.65 (m, 1H), 2.57-2.52 (m, 2H), 2.20 (d, J=15.2 Hz, 2H), 2.11-2.08 (m, 5H), 1.89-1.83 (m, 3H), 1.66 (brs, 4H), 1.58-1.55 (m, 2H), 1.39 (t, J=12.0 Hz, 2H), 1.29 (d, J=7.2 Hz, 3H) and 0.75 (t, J=7.2 Hz, 3H); LC MS: ES+ (M+H) 965.05.

Example 78: Synthesis of 1-(5-(3-Cyano-6-(1-(1-(2-(4-(4-((2,6-dioxopiperidin-3-yl)amino)-2-fluorophenyl)piperidin-1-yl)acetyl)piperidin-4-yl)-1H-pyrazol-4-yl)pyrazolo[1,5-a]pyridin-4-yl)pyridin-2-yl)-N-cyclobutyl-4-ethylpiperidine-4-carboxamide (Compound 8)

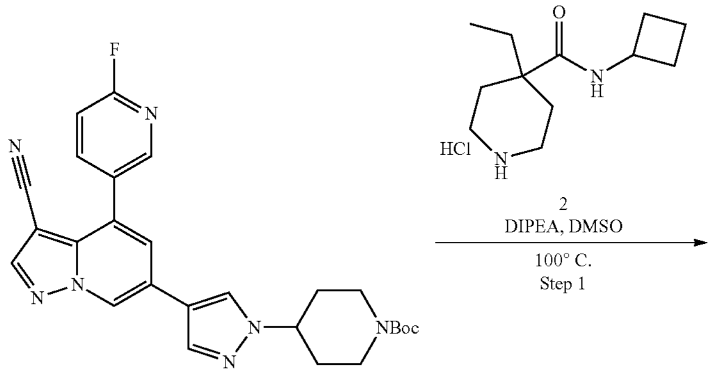

1
2

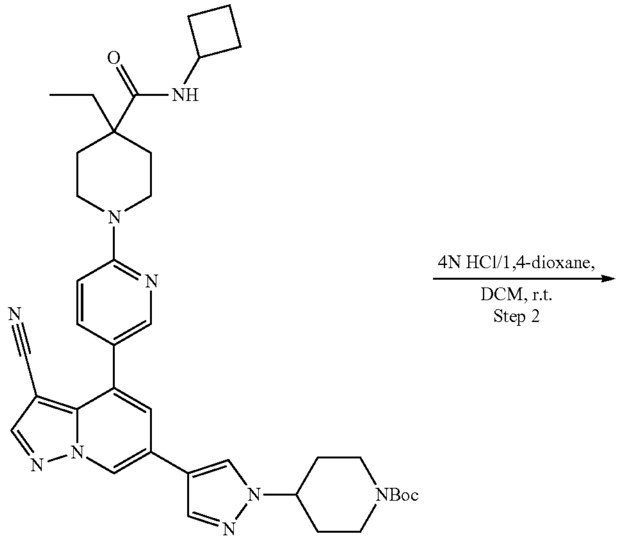

3

-continued

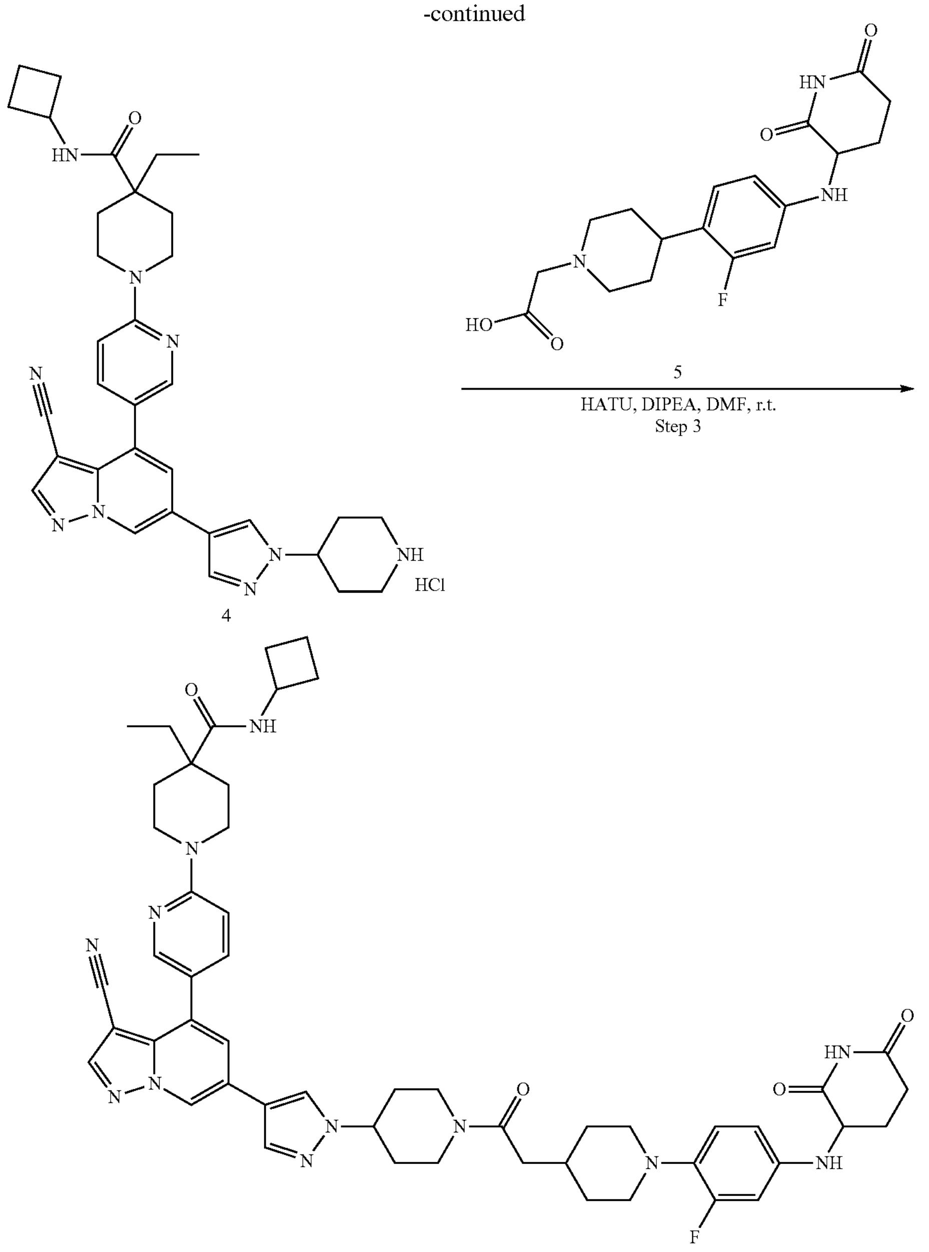

Compound 8

Step 1. Into a 25 mL sealed tube containing a well-stirred solution of a mixture of tert-butyl 4-[4-[3-cyano-4-(6-fluoro-3-pyridyl)pyrazolo[1,5-a]pyridin-6-yl]pyrazol-1-yl] piperidine-1-carboxylate (1; 150 mg, 0.307 mmol) and N-cyclobutyl-4-ethyl-piperidine-4-carboxamide hydrochloride salt (2; 162 mg, 0.652 mmol) in anhydrous DMSO (5 mL) was added DIPEA (0.26 mL, 1.54 mmol) at ambient temperature. The reaction mixture was stirred at 100° C. for 16 h. After completion of the reaction as indicated by UPLC, the reaction mixture was allowed to attain room temperature and treated with ice-water (15 mL). The resulting solution was stirred for 15 minutes at room temperature, during which time the product precipitated out. The solid product was filtered and washed with $Et_2O$. The filtered solid was dried under vacuum for 5 h to afford tert-butyl 4-[4-[3-cyano-4-[6-[4-(cyclobutylcarbamoyl)-4-ethyl-1-piperidyl]-3-pyridyl]pyrazolo[1,5-a]pyridin-6-yl]pyrazol-1-yl]piperidine-1-carboxylate (3; 190 mg, 0.266 mmol) as a brown solid. Yield 86%; LC MS: ES+ (M+H) 678.4.

Step 2. Into a 25 mL single-necked round-bottomed flask containing a well-stirred solution of tert-butyl 4-[4-[3-mcyano-4-[6-[4-(cyclobutylcarbamoyl)-4-ethyl-1-piperidyl]-3-pyridyl]pyrazolo[1,5-a]pyridin-6-yl]pyrazol-1-yl] piperidine-1-carboxylate (3; 190 mg, 0.280 mmol) in DCM (2 mL) was added 4 N HCl in 1,4-dioxane (2 mL, 0.280 mmol) under nitrogen atmosphere at room temperature, and the resulting mixture was stirred at room temperature for 2 h. The reaction mixture was concentrated under reduced pressure to afford 1-[5-[3-cyano-6-[1-(4-piperidyl)pyrazol-4-yl]pyrazolo[1,5-a]pyridin-4-yl]-2-pyridyl]-N-cyclobutyl-4-ethyl-piperidine-4-carboxamide hydrochloride salt (4; 160 mg, 0.145 mmol) as a crude brown solid which was used without further purification. Yield 52%; LC MS: ES+ (M+H) 578.1.

Step 3. Into a 25 mL single-necked round-bottomed flask containing a well-stirred solution of 1-[5-[3-cyano-6-[1-(4-piperidyl)pyrazol-4-yl]pyrazolo[1,5-a]pyridin-4-yl]-2-pyridyl]-N-cyclobutyl-4-ethyl-piperidine-4-carboxamide hydrochloride salt (4; 80 mg, 0.130 mmol) and 2-[4-[4-[(2,6-dioxo-3-piperidyl)amino]-2-fluoro-phenyl]-1-piperidyl] acetic acid (5; 52.07 mg, 0.130 mmol) in anhydrous DMF (3 mL) were added DIPEA (60 μL, 0.390 mmol) and HATU (74 mg, 0.195 mmol) at ambient temperature under nitrogen atmosphere. The contents were stirred at ambient temperature for 2 h. After completion of the reaction as indicated by UPLC, water (20 mL) was added and stirred for 10 minutes, the resulting solid was filtered and dried to afford a crude solid which was purified by reverse phase HPLC using the method: Column: Zorbax (250×21.2 mm), 7 mm; Mobile phase: A: 0.1% Ammonium acetate in MQ-water; B: Acetonitrile; Flow rate: 15 mL/minutes; to afford 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-N-cyclobutyl-4-ethyl-piperidine-4-carboxamide (Compound 8; 28 mg, 0.029 mmol) as a yellow solid. Yield 22%; $^1H$ NMR (400 MHz, DMSO-$d_6$) δ 10.80 (bs, 1H), 9.25 (s, 1H), 8.65 (s, 1H), 8.57-8.54 (m, 1H), 8.36 (d, J=2.4 Hz, 1H), 8.18 (s, 1H), 7.82 (m, 3H), 6.99 (m, 2H), 6.44 (m, 2H), 6.00 (d, J=8 Hz, 1H), 4.42 (m, 2H), 4.27 (m, 3H), 4.15 (m, 2H), 3.28-3.10 (m, 4H), 2.90 (m, 2H), 2.85-2.75 (m, 2H), 2.55 (m, 3H), 2.15 (m, 5H), 1.99-1.78 (m, 5H), 1.65 (m, 10H), 1.49 (m, 2H), 1.35 (m, 2H), 0.73 (t, J=7.6 Hz, 3H). LC MS: ES+ (M+H) 923.5.

Example 79: Synthesis of 1-[5-[3-cyano-6-[1-[1-[2-[3-[4-[(2,6-dioxo-3-piperidyl)amino]phenyl]-8-azabicyclo[3.2.1]octan-8-yl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 9)

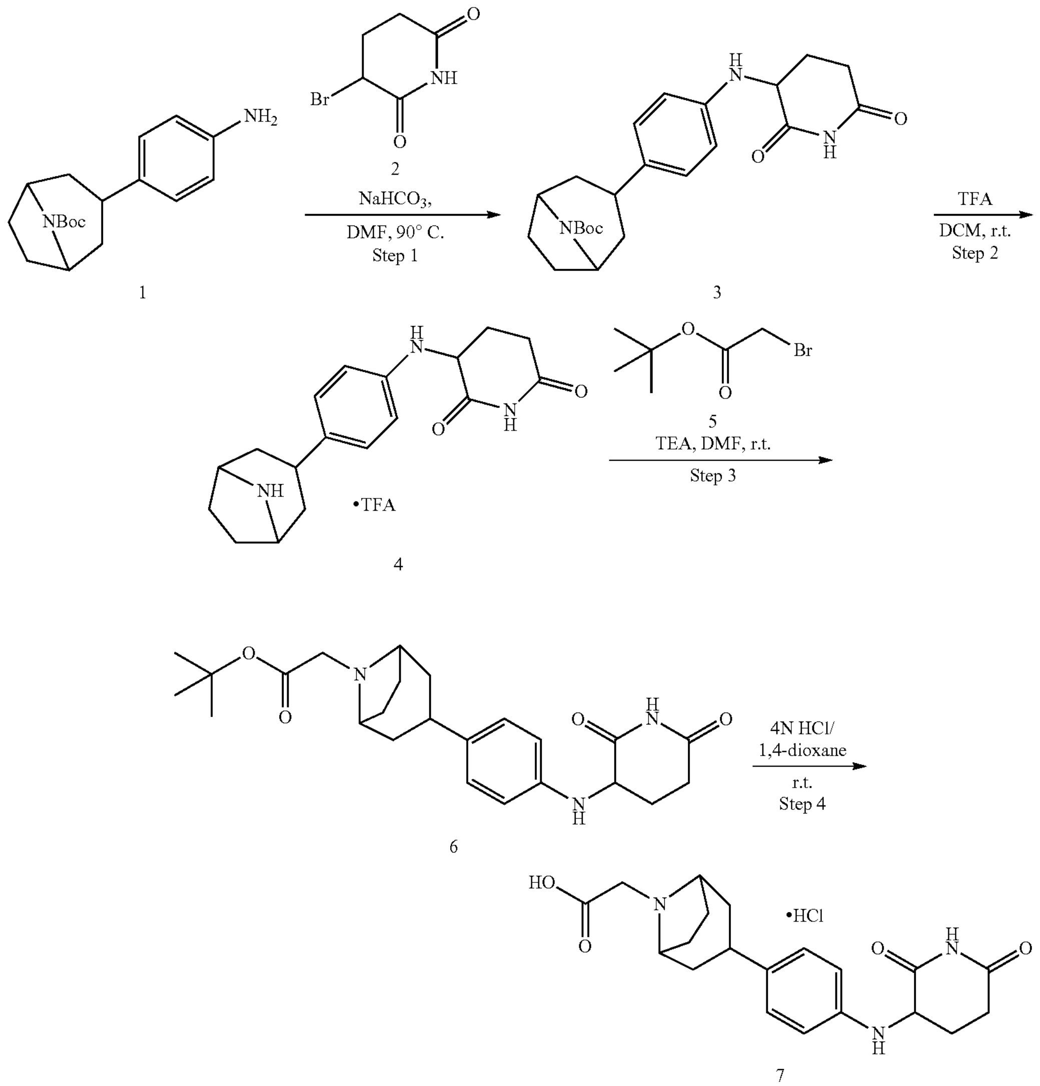

7

-continued

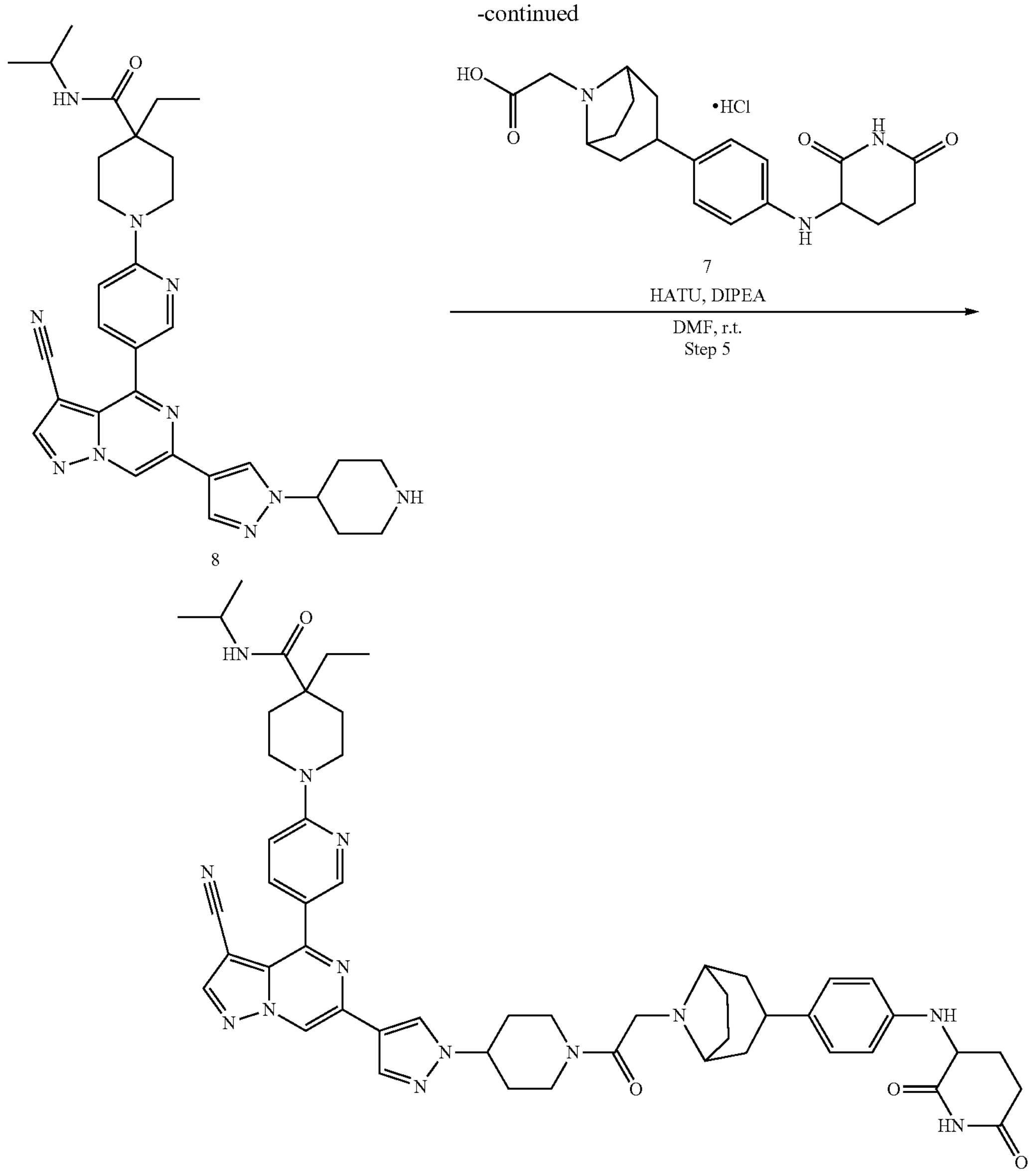

8

Compound 9

Step 1. To a solution of tert-butyl 3-(4-aminophenyl)-8-azabicyclo[3.2.1]octane-8-carboxylate (1; 1.2 g, 3.97 mmol) in DMF (25 mL) was added sodium bicarbonate (833 mg, 9.92 mmol, 386 μL) followed by 3-bromopiperidine-2,6-dione (2; 1.22 g, 6.35 mmol) and heated to 90° C. for 16 h in a sealed tube. Crude LCMS showed formation of product with some starting material. At room temperature, additional sodium bicarbonate (833 mg, 9.92 mmol, 386 μL) and 3-bromopiperidine-2,6-dione (2; 1.22 g, 6.35 mmol) were added and again heated to 90° C. for 16 h. The reaction was quenched with water at room temperature and extracted with EtOAc. The combined organics were washed with water and dried over $Na_2SO_4$. The crude residue was purified by Combiflash with amine-silica with eluting solvent 30-80% EtOAc in hexane to afford tert-butyl 3-[4-[(2,6-dioxo-3-piperidyl)amino]phenyl]-8-azabicyclo[3.2.1]octane-8-carboxylate (3; 710 mg, 1.72 mmol) as a solid. Yield-43%. LC MS ES+[M+H]+ 414.3.

Step 2. To a stirred solution of tert-butyl 3-[4-[(2,6-dioxo-3-piperidyl)amino]phenyl]-8-azabicyclo[3.2.1]octane-8-carboxylate (3; 300 mg, 0.723 mmol) dissolved in DCM (3 mL) was added 2,2,2-trifluoroacetic acid (827 mg, 7.25 mmol, 559 μL) at 0° C. and stirred for 4 h at room temperature. After completion of the reaction, it was concentrated by a rotary evaporator to afford the crude product. The crude product was stirred with ether for 3 h and then ether was decanted to afford 3-[4-(8-azabicyclo[3.2.1]octan-3-yl)anilino]piperidine-2,6-dione trifluoroacetic acid salt (4; 300 mg, 456 μmol) as an off white solid. Yield-63%. LC MS: ES+ (M+H) 314.4.

Step 3. To a stirred solution of 3-[4-(8-azabicyclo[3.2.1]octan-3-yl)anilino]piperidine-2,6-dione trifluoroacetic acid salt (4; 200 mg, 456 μmol) in DMF (3.0 mL) was added Triethylamine (323 mg, 3.19 mmol, 445 μL) and tert-butyl 2-bromoacetate (5; 124 mg, 638 μmol, 94 μL) at room temperature and the resulting reaction mixture was stirred for 16 h and monitored by TLC/LCMS. Upon reaction completion the mixture was quenched with water and diluted with ethyl acetate. The layers were extracted with ethyl acetate (3×), after which the organic layers were washed with LiCl (5% aq solution) (2×), brine and dried over $Na_2SO_4$ before being filtered and concentrated to a crude residue which was purified via Isco flash column chromatography Hex:EA up to 1:1) to afford the product tert-butyl 2-[3-[4-[(2,6-dioxo-3-piperidyl)amino]phenyl]-8-azabicyclo[3.2.1]octan-8-yl]acetate (6; 98 mg, 218 μmol) as a solid. Yield-46%. LC MS: ES+(M+H) 428.4.

Step 4. tert-butyl 2-[3-[4-[(2,6-dioxo-3-piperidyl)amino]phenyl]-8-azabicyclo[3.2.1]octan-8-yl]acetate (6; 98 mg, 218 μmol) was suspended in Hydrogen chloride, 4N in 1,4-dioxane (66 mg, 1.81 mmol, 82 μL) and stirred for 2 h at room temperature. LCMS check after 2 h revealed the reaction was complete. The mixture was then concentrated to dryness and resuspended in hexanes followed by concentration under reduced pressure to afford 2-[3-[4-[(2,6-dioxo-3-piperidyl)amino]phenyl]-8-azabicyclo[3.2.1]octan-8-yl]acetic acid hydrochloric acid salt (7; 67 mg, 156 μmol). Yield-86%. LC MS: ES+ (M+H) 372.3.

Step 5. Into a 4 mL vial containing a well-stirred solution of 2-[3-[4-[(2,6-dioxo-3-piperidyl)amino]phenyl]-8-azabicyclo[3.2.1]octan-8-yl]acetic acid hydrochloride salt (7; 30 mg, 81 μmol) and 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide hydrochloride salt (8; 46 mg, 81 μmol) in anhydrous DMF (2 mL) were added DIPEA (31 mg, 242 μmol, 42 μL) and HATU (37 mg, 97 μmol) at ambient temperature under nitrogen atmosphere. The contents were stirred at ambient temperature for 2 h and the progress of the reaction was monitored by LCMS. After completion of the reaction, the reaction mixture was immediately purified via Isco reverse phase flash column chromatography (0.1% FA in MeCN/Water) to afford the product 1-[5-[3-cyano-6-[1-[1-[2-[3-[4-[(2,6-dioxo-3-piperidyl)amino]phenyl]-8-azabicyclo[3.2.1]octan-8-yl]acetyl]-4-piperidyl]pyrazol-4-yl]pyrazolo[1,5-a]pyrazin-4-yl]-2-pyridyl]-4-ethyl-N-isopropyl-piperidine-4-carboxamide formic acid salt (Compound 9; 16.6 mg, 16.4 μmol) as a solid. Yield-20%; $^1$H NMR (400 MHz, DMSO-$d_6$) δ 10.75 (d, J=3.9 Hz, 1H), 9.28 (d, J=2.6 Hz, 1H), 8.82 (s, 1H), 8.66 (d, J=2.5 Hz, 1H), 8.49 (d, J=1.6 Hz, 1H), 8.22 (s, 1H), 8.18 (d, J=3.6 Hz, 1H), 8.02 (dt, J=8.9, 2.3 Hz, 1H), 7.40 (d, J=8.0 Hz, 1H), 7.05-6.87 (m, 3H), 6.70-6.45 (m, 2H), 5.58 (dd, J=7.5, 4.9 Hz, 1H), 4.62-3.85 (m, 6H), 3.38 (d, J=13.6 Hz, 2H), 3.24 (d, J=11.6 Hz, 4H), 3.10 (t, J=11.5 Hz, 3H), 2.98-2.54 (m, 4H), 2.34-1.62 (m, 10H), 1.61-1.17 (m, 8H), 1.09 (d, J=6.6 Hz, 6H), 0.75 (t, J=7.4 Hz, 3H). LC MS: ES+ (M+H) 920.8.

Example 80: Synthesis of (S)-1-(5-(6-(1-(1-(2-(1-(2-chloro-4-((2,6-dioxopiperidin-3-yl)amino)phenyl)-4-hydroxypiperidin-4-yl)acetyl)piperidin-4-yl)-1H-pyrazol-4-yl)-3-cyanopyrazolo[1,5-a]pyrazin-4-yl)pyridin-2-yl)-4-ethyl-N-isopropylpiperidine-4-carboxamide (Compound 10)

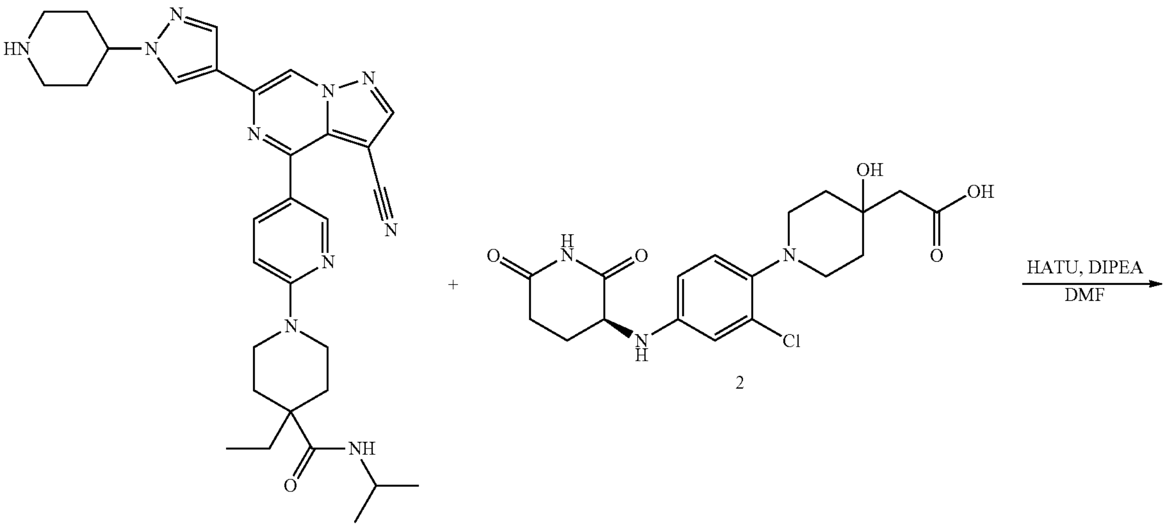

1

2

-continued

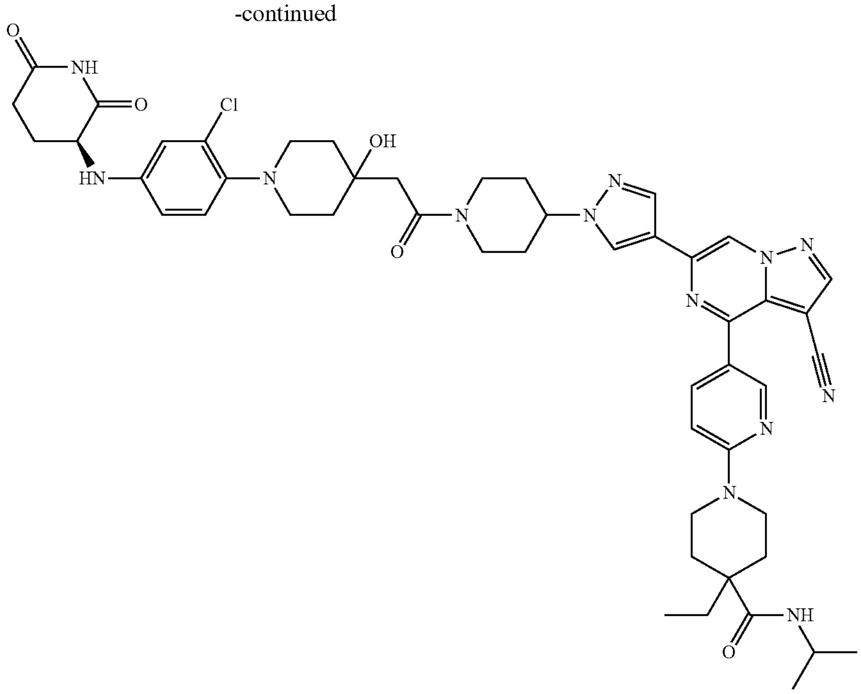

Compound 10

Step 1. To a solution of 1-(5-(3-cyano-6-(1-(piperidin-4-yl)-1H-pyrazol-4-yl)pyrazolo[1,5-a]pyrazin-4-yl)pyridin-2-yl)-4-ethyl-N-isopropylpiperidine-4-carboxamide hydrochloric acid salt (1, 100 mg, 166 μmol) and 2-[1-[2-chloro-4-[[(3S)-2,6-dioxo-3-piperidyl]amino]phenyl]-4-hydroxy-4-piperidyl]acetic acid (2, 65.63 mg, 166 μmol) in DMF (0.7 mL) were added HATU (64 mg, 166 μmol) and N-ethyl-N-isopropyl-propan-2-amine (64 mg, 497 μmol, 86 μL). The mixture was stirred at 20° C. for 16 h. The reaction mixture was diluted with water (3 mL) and extracted with DCM (4×3 mL). The combined organic layers were washed with brine, dried over $Na_2SO_4$, filtered and concentrated under reduced pressure. The residue was purified by prep-TLC (SiO2, DCM: MeOH=12:1), the eluant concentrated and EtOAc (2 mL) was added to the residue followed by petroleum ether (20 mL). The precipitate was collected to give 1-[5-[6-[1-[1-[2-[1-[2-chloro-4-[[(3S)-2,6-dioxo-3-piperidyl]amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-isopropyl-piperidine-4-carboxamide (Compound 10; 26.36 mg, 27.82 μmol) as a yellow solid. Yield-16.8%; $^1$H NMR (400 MHz, DMSO-$d_6$) δ=10.78 (s, 1H), 9.28 (s, 1H), 8.83 (s, 1H), 8.68 (d, J=2.4 Hz, 1H), 8.50 (s, 1H), 8.18 (s, 1H), 8.05 (dd, J=2.4, 8.8 Hz, 1H), 7.41 (d, J=7.6 Hz, 1H), 6.99 (t, J=9.2 Hz, 2H), 6.75 (d, J=2.4 Hz, 1H), 6.60 (dd, J=8.8, 2.8 Hz, 1H), 5.83 (d, J=7.6 Hz, 1H), 4.93 (s, 1H), 4.63-4.45 (m, 2H), 4.33-4.24 (m, 1H), 4.23-4.11 (m, 3H), 4.06-3.97 (m, 1H), 3.27-3.18 (m, 1H), 3.16-3.03 (m, 2H), 2.95-2.72 (m, 5H), 2.62-2.57 (m, 3H), 2.19-2.09 (m, 4H), 1.97-1.66 (m, 7H), 1.54-1.47 (m, 2H), 1.39-1.31 (m, 2H), 1.27-1.16 (m, 2H), 1.09 (d, J=6.4 Hz, 6H), 0.75 (t, J=7.2 Hz, 3H); LC MS: ES+ (M+H) 944.5.

Example 81: Synthesis of (R)-1-(5-(6-(1-(1-(2-(1-(2-chloro-4-((2,6-dioxopiperidin-3-yl)amino)phenyl)-4-hydroxypiperidin-4-yl)acetyl)piperidin-4-yl)-1H-pyrazol-4-yl)-3-cyanopyrazolo[1,5-a]pyrazin-4-yl)pyridin-2-yl)-4-ethyl-N-isopropylpiperidine-4-carboxamide (Compound 11)

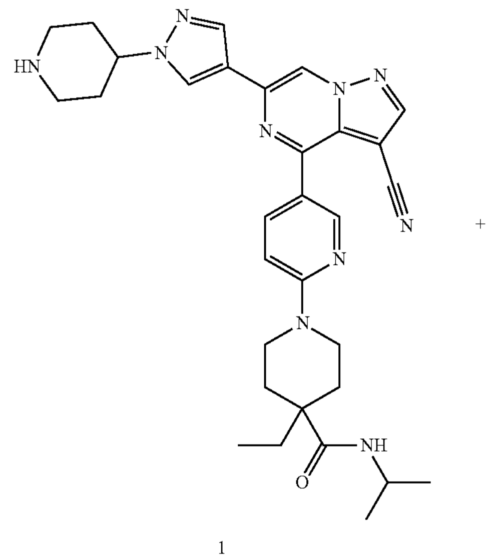

1

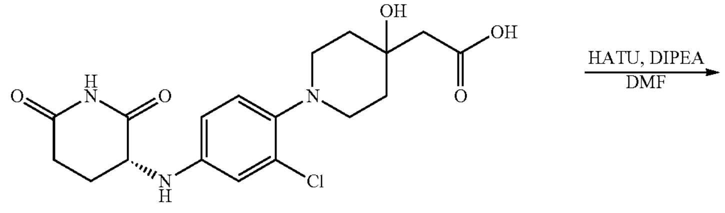

2

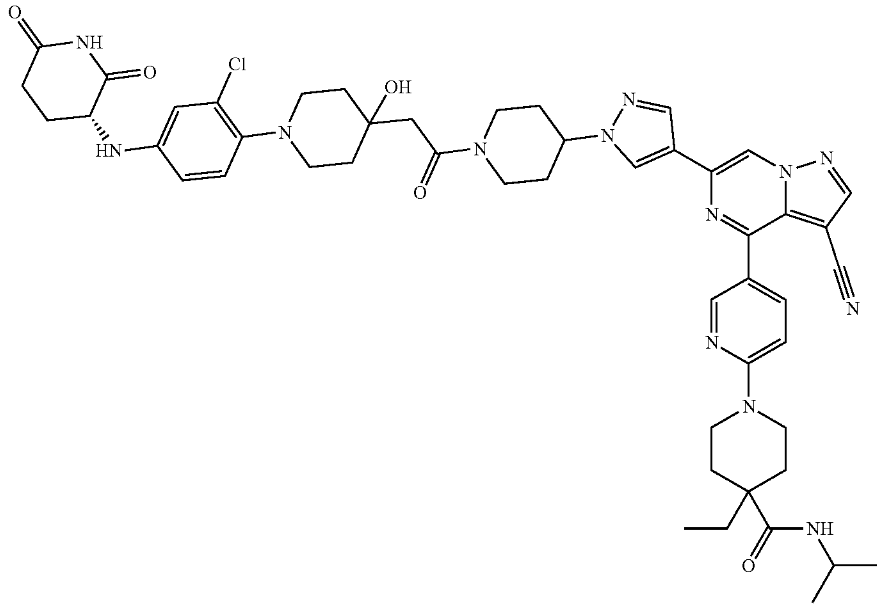

Compound 11

Step 1. To a solution of 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide hydrochloric acid salt (1, 100 mg, 166 μmol) and (R)-2-(1-(2-chloro-4-((2,6-dioxopiperidin-3-yl)amino)phenyl)-4-hydroxypiperidin-4-yl)acetic acid (2, 65.63 mg, 166 μmol) in DMF (1 mL) were added HATU (64 mg, 166 μmol) and N-ethyl-N-isopropyl-propan-2-amine (64 mg, 497 μmol, 86 μL). The mixture was stirred at 20° C. for 16 h. The reaction mixture was diluted with water (3 mL) and extracted with DCM (4×3 mL). The combined organic layers were washed with brine, dried over $Na_2SO_4$, filtered and concentrated under reduced pressure. The residue was purified by prep-TLC (SiO2, DCM: MeOH=12:1), the eluant concentrated and EtOAc (2 mL) was added to the residue followed by petroleum ether (20 mL). The precipitate was collected to give 1-[5-[6-[1-[1-[2-[1-[2-chloro-4-[[(3R)-2,6-dioxo-3-piperidyl]amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-isopropyl-piperidine-4-carboxamide (Compound 11; 12.89 mg, 13.58 μmol) as a yellow solid. Yield-8.2%; $^1H$ NMR (400 MHz, DMSO-$d_6$) δ=10.77 (s, 1H), 9.28 (s, 1H), 8.82 (s, 1H), 8.66 (d, J=2.8 Hz, 1H), 8.49 (s, 1H), 8.17 (s, 1H), 8.04 (dd, J=2.4, 8.8 Hz, 1H), 7.41 (d, J=8.0 Hz, 1H), 6.98 (t, 2H), 6.75 (d, J=2.8 Hz, 1H), 6.60 (dd, J=2.4, 8.8 Hz, 1H), 5.82 (d, J=8.0 Hz, 1H), 4.93 (s, 1H), 4.61-4.48 (m, 2H), 4.33-4.24 (m, 1H), 4.23-4.11 (m, 3H), 4.06-3.96 (m, 1H), 3.24 (br d, J=4.0 Hz, 1H), 3.14-3.06 (m, 2H), 2.93-2.77 (m, 5H), 2.59 (br s, 3H), 2.19-2.07 (m, 4H), 2.00-1.65 (m, 7H), 1.53-1.46 (m, 2H), 1.39-1.30 (m, 2H), 1.28-1.19 (m, 2H), 1.08 (d, J=6.4 Hz, 6H), 0.74 (t, J=7.6 Hz, 3H). LC MS: ES+ (M+H) 944.5.

Example 82: Synthesis of 6-(1-(1-(2-(4-(4-((2,6-Dioxopiperidin-3-yl)amino)-2-fluorophenyl)piperidin-1-yl)ethyl)piperidin-4-yl)-1H-pyrazol-4-yl)-4-(6-(4-(pyridin-2-ylmethyl)piperazin-1-yl)pyridin-3-yl)pyrazolo[1,5-a]pyridine-3-carbonitrile (Compound 12)

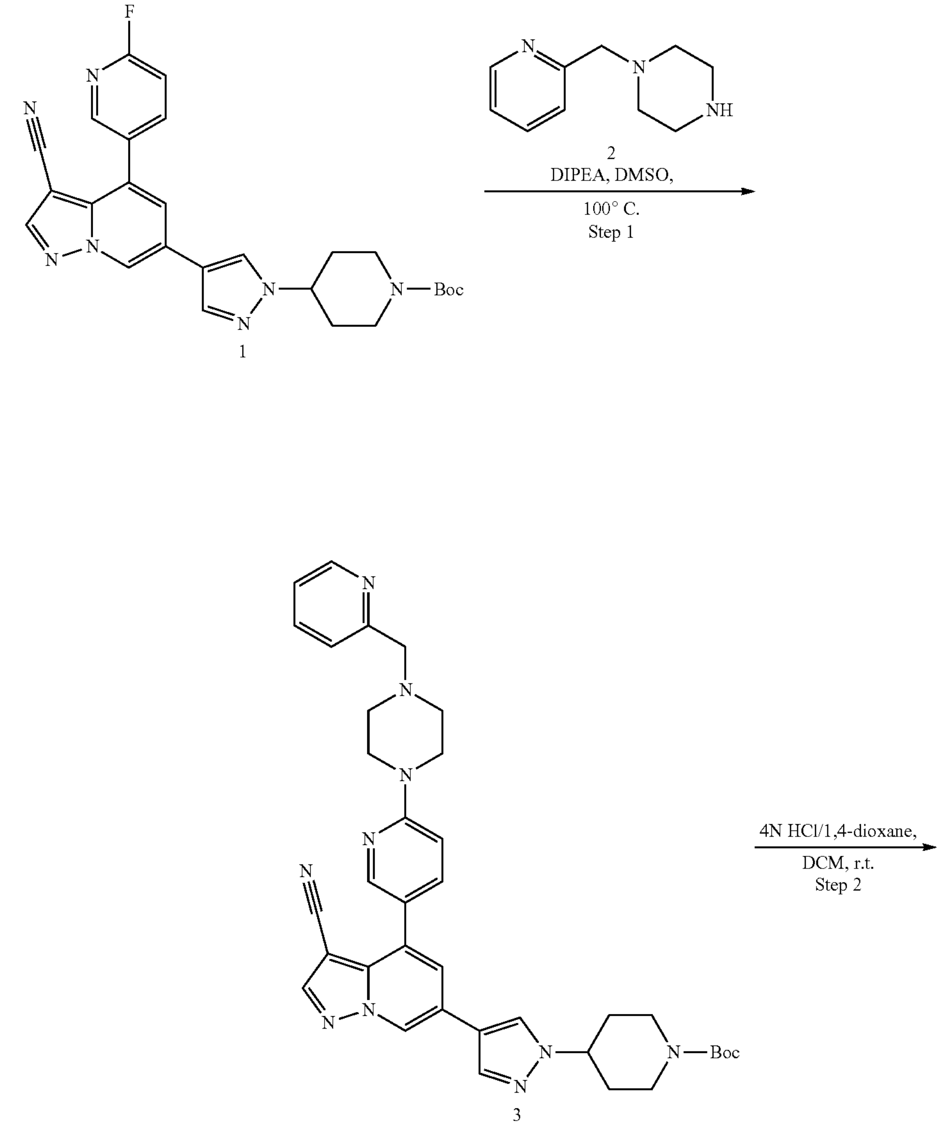

1

2

3

-continued
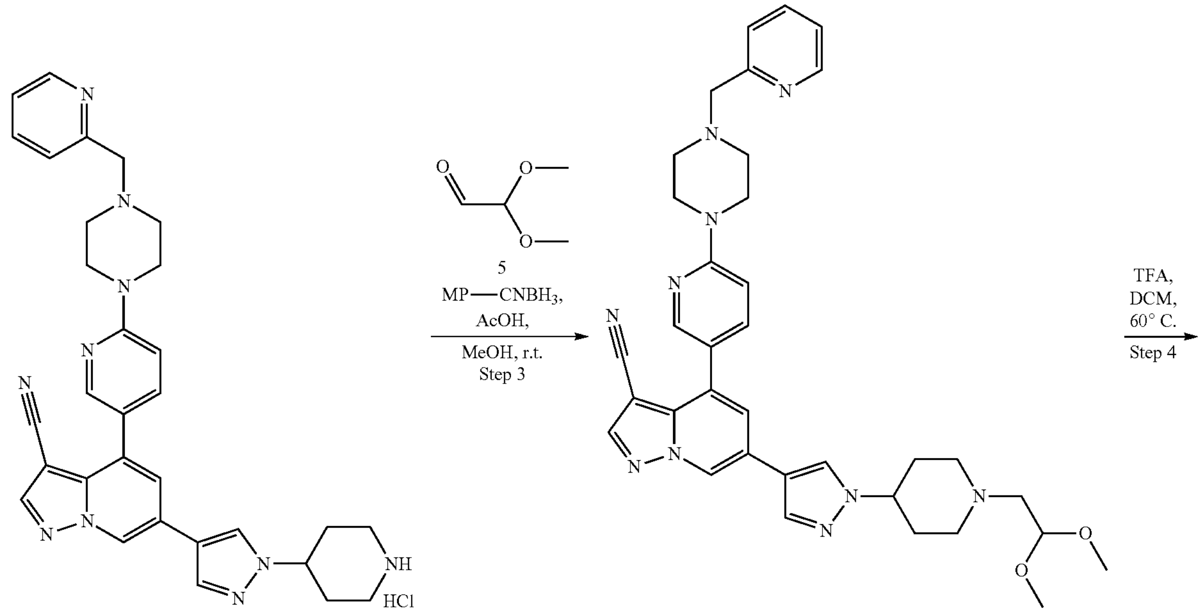
4 6
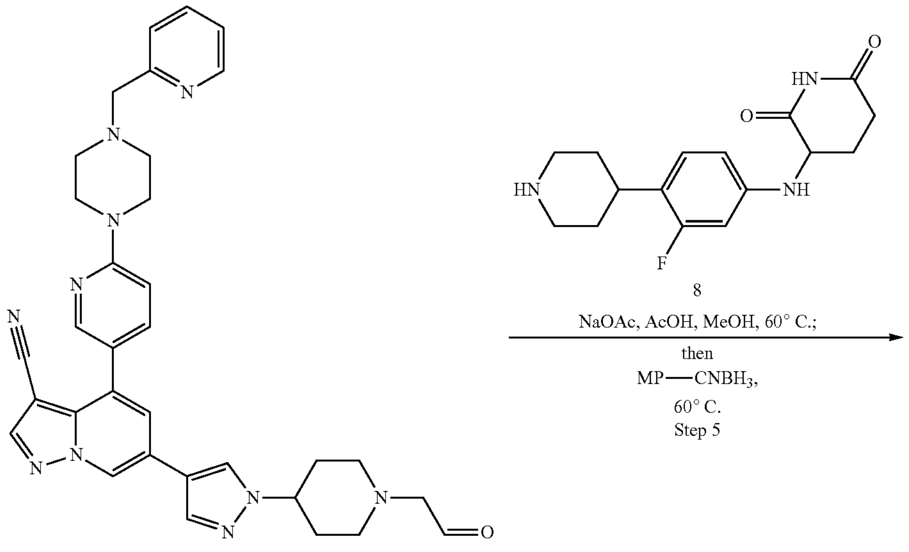
7

-continued

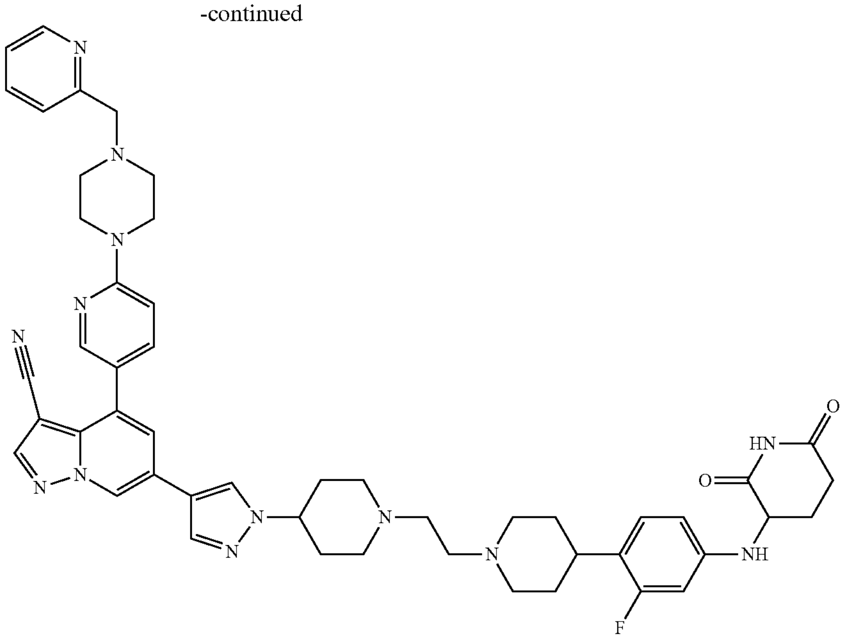

Compound 12

Step 1. Into a 100 mL sealed tube containing a well-stirred solution of tert-butyl 4-[4-[3-cyano-4-(6-fluoro-3-pyridyl) pyrazolo[1,5-a]pyridin-6-yl]pyrazol-1-yl]piperidine-1-carboxylate (1; 500 mg, 1.03 mmol) and 1-(2-pyridylmethyl) piperazine (2; 199.96 mg, 1.13 mmol) in anhydrous DMSO (5 mL) was added DIPEA (0.6 mL, 3.44 mmol) under nitrogen atmosphere. The resulting reaction mixture was heated to 100° C. for 16 h. The progress of the reaction was monitored by LCMS. The reaction mixture was added to conical flask (250 mL) containing water (100 mL) and extracted with EtOAc (2×50 mL). The combined organic layers were washed with brine (30 mL), dried (anhydrous $Na_2SO_4$) and concentrated under reduced pressure to get a crude, which was was purified by column chromatography (flash silica-gel (230-400 mesh) column, gradient of 0%-20% MeOH in DCM) to afford tert-butyl 4-[4-[3-cyano-4-[6-[4-(2-pyridylmethyl)piperazin-1-yl]-3-pyridyl]pyrazolo[1,5-a]pyridin-6-yl]pyrazol-1-yl]piperidine-1-carboxylate (3; 450 mg, 697.93 μmol) as a brown solid. Yield-59%; LCMS: ES+ (M+H) 645.3.

Step 2. Into a 250 mL single-necked round-bottomed flask containing a well-stirred solution of tert-butyl 4-[4-[3-cyano-4-[6-[4-(2-pyridylmethyl)piperazin-1-yl]-3-pyridyl] pyrazolo[1,5-a]pyridin-6-yl]pyrazol-1-yl]piperidine-1-carboxylate (3; 450 mg, 697.93 μmol) in anhydrous DCM (3 mL) was added Hydrogen chloride, 4 M in 1,4-dioxane, 99% (0.87 mL, 3.49 mmol) at ambient temperature under nitrogen atmosphere. The resulting mixture was stirred at ambient temperature for 2 h. Reaction was found complete by LCMS. Excess solvents were removed under reduced pressure, crude thus obtained was successively washed with DCM (20 mL) and pet ether (20 mL) and dried to get 6-[1-(4-piperidyl)pyrazol-4-yl]-4-[6-[4-(2-pyridylmethyl) piperazin-1-yl]-3-pyridyl]pyrazolo[1,5-a]pyridine-3-carbonitrile hydrochloric acid salt (4; 420 mg, 639.64 μmol) as a brown solid, which was carried forward without further purification. Yield-92%; LCMS: ES+ (M+H) 545.3.

Step 3. Into a 100 mL sealed tube flask containing a well stirred solution of 6-[1-(4-piperidyl)pyrazol-4-yl]-4-[6-[4-(2-pyridylmethyl)piperazin-1-yl]-3-pyridyl]pyrazolo[1,5-a] pyridine-3-carbonitrile hydrochloric acid salt (4; 200 mg, 304.59 μmol) and 2,2-dimethoxyacetaldehyde (5; 136.37 mg, 1.31 mmol; 60% in aq. solution) in MeOH (1 mL) was added MP-$CNBH_3$ (400 mg, 1.31 mmol) and catalytic acetic acid at ambient temperature and the reaction mixture was stirred for 6 h at ambient temperature. The progress of the reaction was monitored by LCMS. After consumption of starting material, the reaction mixture was filtered and washed with MeOH and concentrated under reduced pressure to afford crude, which was purified by column chromatography (flash silica-gel (230-400 mesh) column, gradient of 0%-20% MeOH in DCM) to afford 6-(1-(1-(2,2-dimethoxyethyl)piperidin-4-yl)-1H-pyrazol-4-yl)-4-(6-(4-(pyridin-2-ylmethyl)piperazin-1-yl)pyridin-3-yl)pyrazolo [1,5-a]pyridine-3-carbonitrile (6; 100 mg, 158.04 μmol) as an off-white solid. Yield-18%; LCMS: ES+ (M+H) 633.3

Step 4. Into a 50 mL sealed tube flask containing a well stirred solution of 6-[1-[1-(2,2-dimethoxyethyl)-4-piperidyl]pyrazol-4-yl]-4-[6-[4-(2-pyridylmethyl)piperazin-1-yl]-3-pyridyl]pyrazolo[1,5-a]pyridine-3-carbonitrile (6; 120 mg, 189.65 μmol) in anhydrous DCM (1 mL) was added TFA (2.22 g, 19.47 mmol, 1.50 mL) at ambient temperature and the reaction mixture was heated for 6 h at 60° C. The progress of the reaction was monitored by LCMS. After completion of starting material, the reaction mixture was added to conical flask (100 mL) containing water (50 mL) and extracted with EtOAc (2×50 mL). The combined organic layers were washed with brine, dried (anhydrous $Na_2SO_4$), filtered and the filtrate was concentrated under reduced pressure to afford 6-[1-[1-(2-oxoethyl)-4-piperidyl] pyrazol-4-yl]-4-[6-[4-(2-pyridylmethyl)piperazin-1-yl]-3-pyridyl]pyrazolo[1,5-a]pyridine-3-carbonitrile (7; 110 mg, 41.60 μmol) Yield-22%; LCMS: ES+ (M+H) 587.3.

Step 5. Into a 50 mL sealed tube flask containing a well stirred solution of 6-[1-[1-(2-oxoethyl)-4-piperidyl]pyrazol-4-yl]-4-[6-[4-(2-pyridylmethyl)piperazin-1-yl]-3-pyridyl] pyrazolo[1,5-a]pyridine-3-carbonitrile (7; 110 mg, 156.98 μmol) and 3-[3-fluoro-4-(4-piperidyl)anilino]piperidine-2, 6-dione hydrochloric acid salt (8; 47.93 mg, 156.98 μmol) in MeOH (2 mL) was added Sodium acetate, anhydrous (12.88 mg, 156.98 μmol) and catalytic amount of AcOH (942.69 mg, 15.70 mmol) at ambient temperature. The reaction mixture was heated to 60° C. for 16 h and cooled to RT. MP-$CNBH_3$ (220 mg, 313.97 μmol) was added and the mixture was heated to 60° C. for 2 h. The progress of the reaction was monitored by LCMS. The reaction mixture was filtered, washed with MeOH and concentrated under reduced pressure to afford crude, which was purified by Prep-HPLC (column XBRIDGE C8 (19×150)MM, 5MIC. Mobile phase: 10 mm ammonium acetate: ACN) to afford 6-[1-[1-[2-[4-[4-[(2,6-dioxo-3-piperidyl)amino]-2-fluoro-phenyl]-1-piperidyl]ethyl]-4-piperidyl]pyrazol-4-yl]-4-[6-[4-(2-pyridylmethyl)piperazin-1-yl]-3-pyridyl]pyrazolo[1,5-a]pyridine-3-carbonitrile (Compound 12; 5 mg, 5.59 μmol) as an off-white solid. Yield-4%; $^1$H NMR (400 MHz, DMSO-$d_6$). δ 10.80 (s, 1H), 9.25 (d, J=1.6 Hz, 1H), 8.66 (s, 1H), 8.58 (s, 1H), 8.53-8.51 (m, 1H), 8.39 (d, J=2.4 Hz, 1H), 8.16 (s, 1H), 7.85-7.78 (m, 3H), 7.51 (d, J=7.6 Hz, 1H), 7.31-7.28 (m, 1H), 6.99 (m, 2H), 6.46 (m, 2H), 5.98 (d, J=59.2 Hz, 1H), 4.31-4.25 (m, 1H), 4.20-4.10 (m, 1H), 3.68-3.62 (m, 6H), 2.99-2.97 (m, 4H), 2.74-2.71 (m, 1H), 2.61-2.51 (m, 7H), 2.17-1.84 (m, 12H), 1.69-1.63 (m, 5H). LCMS: ES+ (M+H) 877.4.

Example 83: Synthesis of 6-(1-(1-(2-(4-(3-(2,4-dioxotetrahydropyrimidin-1(2H)-yl)-1-methyl-1H-indazol-6-yl)piperidin-1-yl)acetyl)piperidin-4-yl)-1H-pyrazol-4-yl)-4-(6-(4-(pyridin-2-ylmethyl)piperazin-1-yl)pyridin-3-yl)pyrazolo[1,5-a]pyridine-3-carbonitrile (Compound 13)

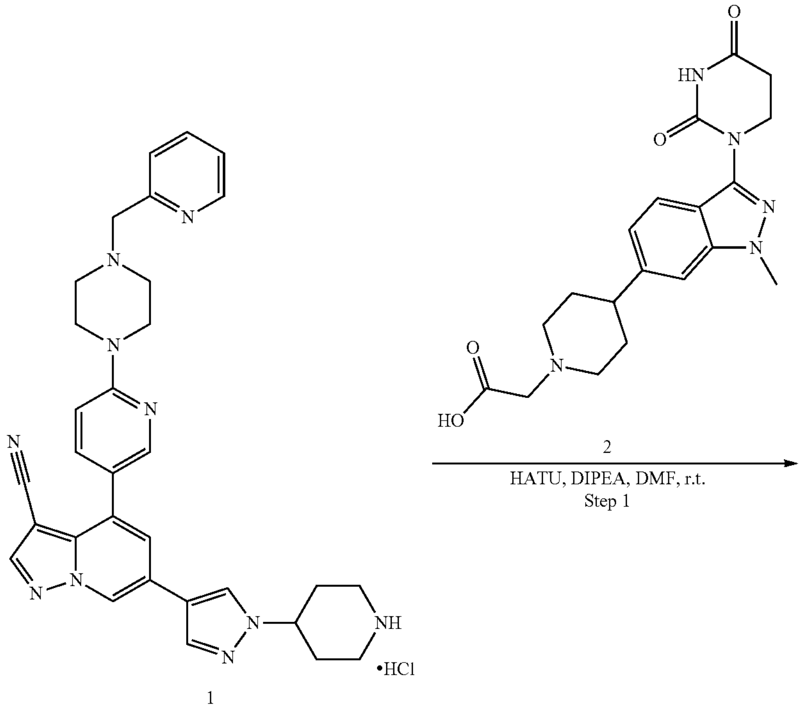

1

2

-continued

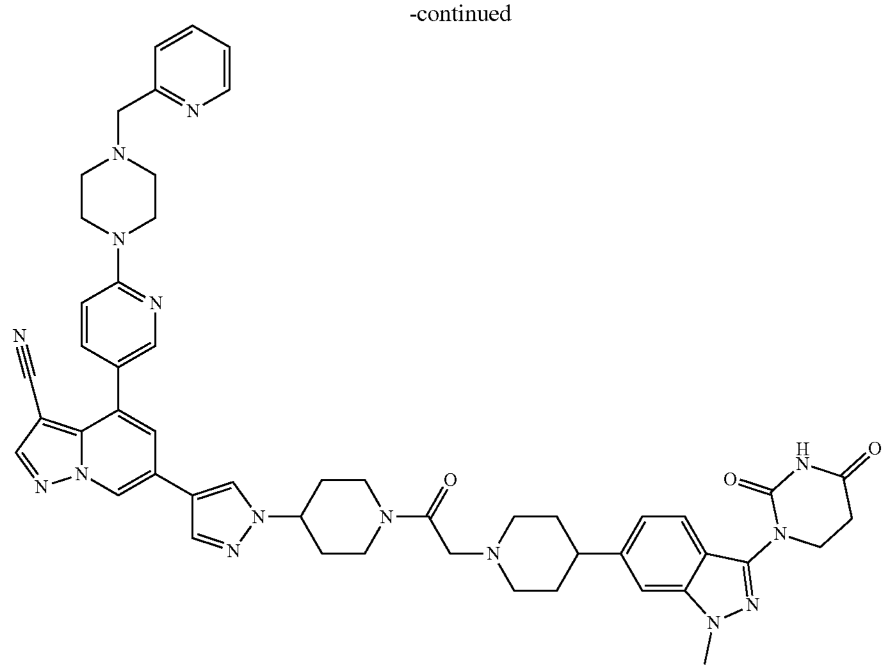

Compound 13

Step 1. Into a 50 mL single-necked round-bottomed flask containing a well-stirred solution of 6-[1-(4-piperidyl)pyrazol-4-yl]-4-[6-[4-(2-pyridylmethyl)piperazin-1-yl]-3-pyridyl]pyrazolo[1,5-a]pyridine-3-carbonitrile·hydrochloride (1; 49.46 mg, 90.81 μmol) in anhydrous DMF (1 mL) was added 2-[4-[3-(2,4-dioxohexahydropyrimidin-1-yl)-1-methyl-indazol-6-yl]-1-piperidyl] acetic acid (2; 35 mg, 90.81 μmol) followed by DIPEA (58.68 mg, 454.05 μmol) and HATU (51.79 mg, 136.22 μmol) at ambient temperature and the reaction contents were stirred at ambient temperature for 2 h. After completion of the reaction as indicated by LCMS, the reaction mixture was poured to a conical flask (100 mL) containing ice-cold water (50 mL) and stirred for 10 minutes, the resulting solid was filtered and dried to afford a crude solid which was purified by Prep-HPLC (XBRIDGE C8 (19×150)MM, 5MIC. Mobile phase: 10 mm AMMONIUM ACETATE: ACN) to afford 6-[1-[1-[2-[4-[3-(2,4-dioxohexahydropyrimidin-1-yl)-1-methyl-indazol-6-yl]-1-piperidyl]acetyl]-4-piperidyl] pyrazol-4-yl]-4-[6-[4-(2-pyridylmethyl)piperazin-1-yl]-3-pyridyl]pyrazolo[1,5-a]pyridine-3-carbonitrile (Compound 13; 12 mg, 13.04 μmol) as an off-white solid. Yield-14%; $^{1}H$ NMR (400 MHz, DMSO-$d_6$). δ 10.54 (s, 1H), 9.26 (d, J=1.2 Hz, 1H), 8.66 (s, 1H), 8.56 (m, 1H), 8.52 (m, 1H), 8.38 (d, J=2.8 Hz, 1H), 8.18 (s, 1H), 7.84-7.78 (m, 3H), 7.56-7.50 (m, 2H), 7.43 (m, 1H), 7.31-7.28 (m, 1H), 7.04 (d, J=1.2 Hz, 1H), 7.02 (d, J=0.8 Hz, 1H), 4.48 (m, 2H), 4.25 (m, 1H), 3.95 (s, 3H), 3.90 (t, J=6.8 Hz, 2H), 3.68 (s, 2H), 3.63 (t, J=5.2 Hz, 4H), 3.25 (m, 2H), 3.00 (m, 2H), 2.76-2.73 (m, 3H), 2.60-2.55 (m, 4H), 2.18 (t, J=10.4 Hz, 4H), 1.92 (m, 2H), 1.84-1.78 (m, 6H). LCMS: ES+ (M+H) 913.4.

Example 84: Synthesis of 1-(5-(6-(1-(1-(2-(1-(2-Chloro-4-((2,6-dioxopiperidin-3-yl)amino)phenyl)-4-hydroxypiperidin-4-yl)acetyl)piperidin-4-yl)-1H-pyrazol-4-yl)-3-cyanopyrazolo[1,5-a]pyrazin-4-yl)pyridin-2-yl)-4-ethyl-N-isopropylpiperidine-4-carboxamide (Compound 14)

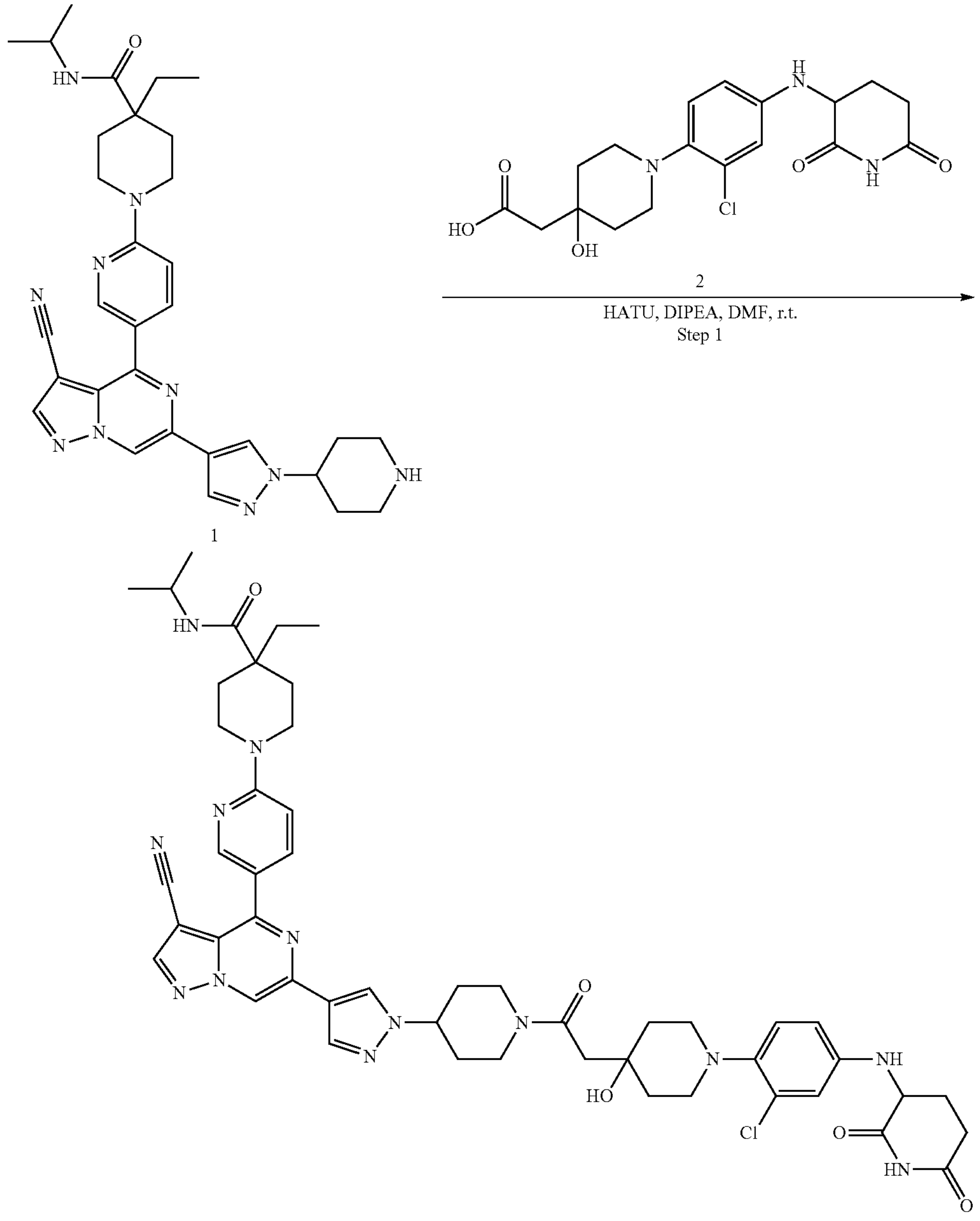

Compound 14

Step 1. Into a 100 mL single-necked round-bottomed flask containing a well-stirred solution of 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide (1; 1 g, 1.66 mmol) and 2-[1-[2-chloro-4-[(2,6-dioxo-3-piperidyl)amino]phenyl]-4-hydroxy-4-piperidyl]acetic acid (2; 788 mg, 1.82 mmol) in anhydrous DMF (15 mL) were added DIPEA (1.44 mL, 8.29 mmol) and HATU (946 mg, 2.49 mmol) at ambient temperature under nitrogen atmosphere. The contents were stirred at ambient temperature for 2 h. After completion of the reaction as indicated by LCMS, the reaction mixture was treated with water (100 mL) and solid precipitated out was filtered. The filtered solid was dried under vacuum to afford a crude residue. The crude material was purified by column chromatography (flash silica-gel (230-400 mesh) column, gradient of 0%-10% EtOAc in MeOH) to afford 1-[5-[6-[1-[1-[2-[1-[2-chloro-4-[(2,6-dioxo-3-piperidyl)amino]phenyl]-4-hydroxy-4-piperidyl]

acetyl]-4-piperidyl]pyrazol-4-yl]-3-cyano-pyrazolo[1,5-a]pyrazin-4-yl]-2-pyridyl]-4-ethyl-N-isopropyl-piperidine-4-carboxamide (Compound 14; 700 mg, 0.730 mmol) as a yellow solid. Yield 44%. $^1$H NMR (400 MHz, DMSO-$d_6$). δ 10.75 (s, 1H), 9.30 (s, 1H), 8.83 (s, 1H), 8.67 (d, J=2.4 Hz, 1H), 8.50 (s, 1H), 8.18 (s, 1H), 8.05 (dd, J=11.2, 2.4 Hz, 1H), 7.42 (d, J=8 Hz, 1H), 7.01 (m, 2H), 6.76 (s, 1H), 6.61 (m, 1H), 5.80 (bs, 1H), 4.90 (bs, 1H), 4.60 (m, 2H), 4.30 (m, 1H), 4.20 (m, 3H), 4.00 (m, 1H), 3.20 (m, 1H), 3.11 (m, 2H), 2.90 (m, 8H), 2.70 (m, 4H), 2.25 (m, 5H), 1.80 (m, 3H), 1.51 (m, 2H), 1.48 (m, 3H), 1.09 (d, J=8 Hz, 6H), 0.75 (t, J=7.2 Hz, 3H). LC MS: ES+(M+H) 944.0.

Example 85: Synthesis of 6-[1-[1-[2-[4-[4-[(2,6-dioxo-3-piperidyl)amino]phenyl]-1-piperidyl]acetyl]-4-piperidyl]pyrazol-4-yl]-4-[6-[4-[2-(5-fluoro-2-pyridyl)acetyl]piperazin-1-yl]-3-pyridyl]pyrazolo[1,5-a]pyridine-3-carbonitrile formic acid salt (Compound 15)

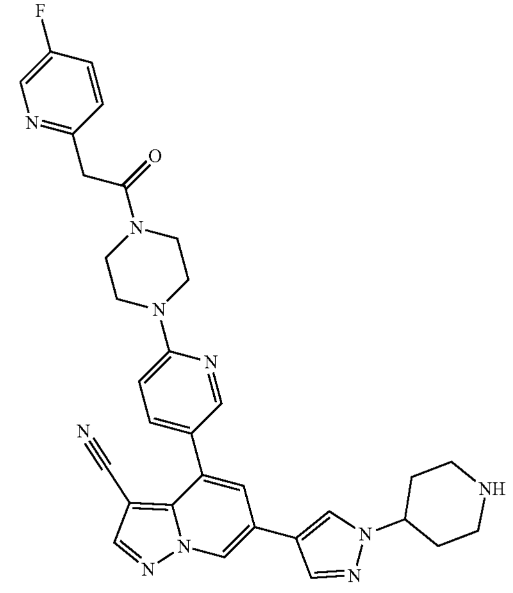

1

+

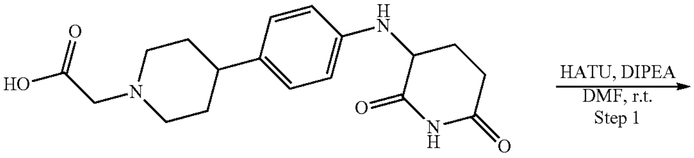

2

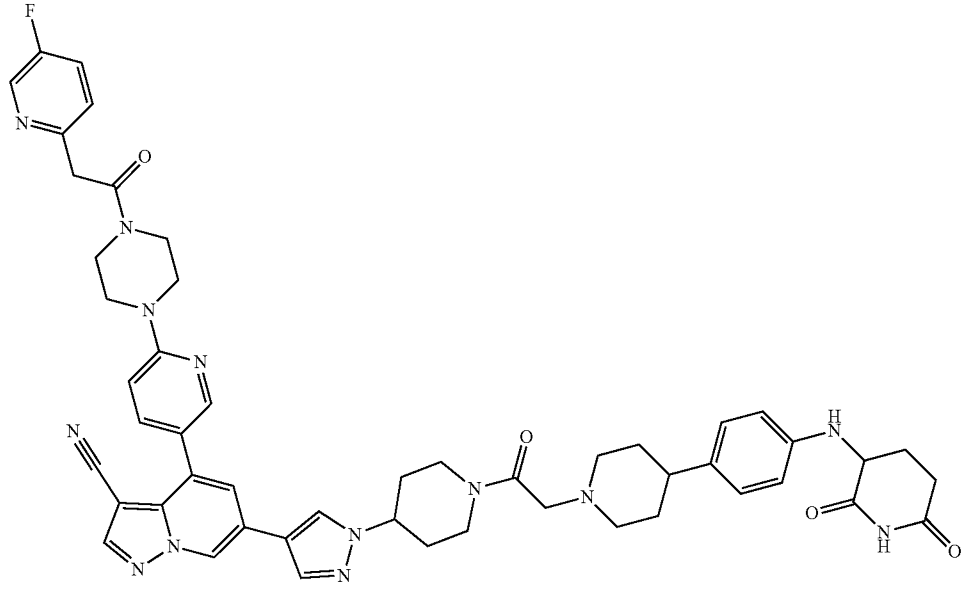

Compound 15

Step 1. Into a 25 mL single-necked round-bottomed flask containing a well-stirred solution of 4-[6-[4-[2-(5-fluoro-2-pyridyl)acetyl]piperazin-1-yl]-3-pyridyl]-6-[1-(4-piperidyl)pyrazol-4-yl]pyrazolo[1,5-a]pyridine-3-carbonitrile hydrochloric acid salt (1, 30 mg, 47.84 μmol) and 2-[4-[4-[(2,6-dioxo-3-piperidyl)amino]phenyl]-1-piperidyl]acetic acid hydrochloric acid salt (2, 18.27 mg, 47.84 μmol) in anhydrous DMF (0.5 mL) were added DIPEA (143.51 μmol, 25.00 μL) and HATU (27.28 mg, 71.76 μmol) under nitrogen atmosphere at room temperature. The resulting mixture was stirred at room temperature for 3 h. The reaction mixture was concentrated under reduced pressure and purified by reverse phase isco column (Mobile phase: A: 0.1% Formic Acid in water B: ACN) to afford 6-[1-[1-[2-[4-[4-[(2,6-dioxo-3-piperidyl)amino]phenyl]-1-piperidyl]acetyl]-4-piperidyl]pyrazol-4-yl]-4-[6-[4-[2-(5-fluoro-2-pyridyl)acetyl]piperazin-1-yl]-3-pyridyl]pyrazolo[1,5-a]pyridine-3-carbonitrile formic acid salt (Compound 15; 10 mg, 10.01 μmol, 20.92% yield) as a white solid. Yield-20.9%; LC MS: ES+ (M+H) 919.3.

Example 86: Synthesis of 4-(6-fluoro-3-pyridyl)-6-[1-[trans-4-(2-hydroxyethyl)cyclohexyl]pyrazol-4-yl]pyrazolo[1,5-a]pyridine-3-carbonitrile

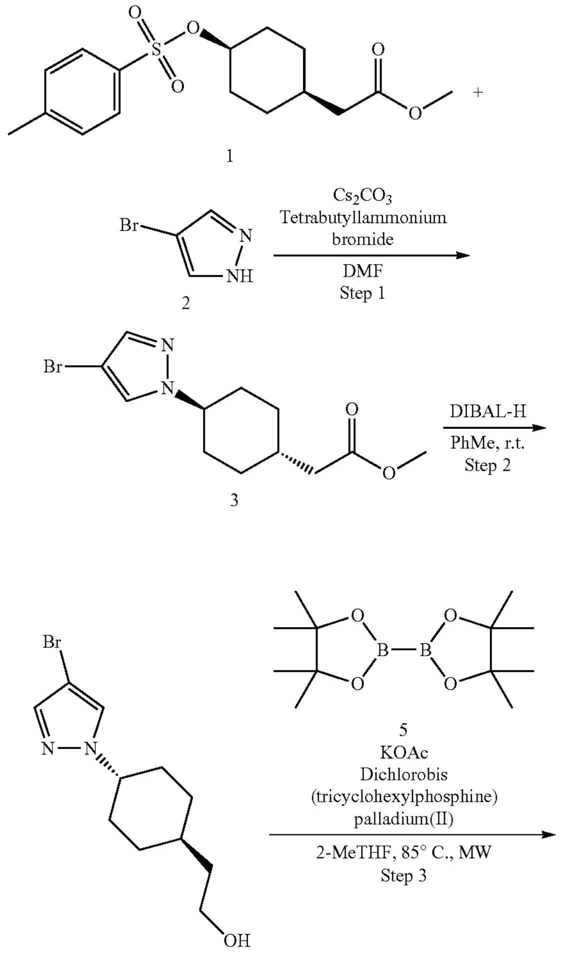

1
2
3
4
5

-continued

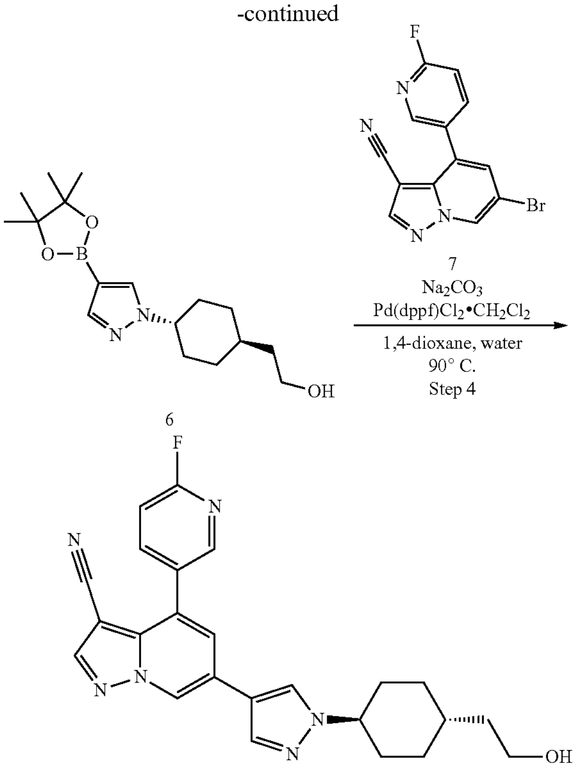

6
7
8

Step 1. Into a 250 mL sealed-tube reactor containing a well-stirred solution of mixture of methyl 2-[4-(p-tolylsulfonyloxy)cyclohexyl]acetate (1, 15.55 g, 47.63 mmol) in anhydrous DMF (100 mL) were added 4-bromo-1H-pyrazole (2, 5 g, 34.02 mmol) and cesium carbonate (27.71 g, 85.05 mmol), followed by tetrabutylammonium bromide (1.10 g, 3.40 mmol) at ambient temperature. Contents of the reaction were stirred at 80° C. for 16 h. After 16 h, the reaction mixture was cooled to room temperature and 100 mL of ice cooled water was added to the reaction mixture, and extracted with EtOAc (2×50 mL). The organic phases were combined, dried (anhydrous $Na_2SO_4$), filtered and concentrated under reduced pressure. The crude residue was purified by column chromatography (50 g, silica-gel column) with 0-40% EtOAc/pet ether to afford trans-methyl 2-[4-(4-bromopyrazol-1-yl)cyclohexyl]acetate (3, 670 mg, 1.51 mmol, 68% purity) as a white solid. Yield-4.5%; LC MS: ES+ (M+H) 303.2.

Step 2. Into a 250 mL two-necked round-bottomed flask containing a well-stirred solution of trans-methyl 2-[4-(4-bromopyrazol-1-yl)cyclohexyl]acetate (3, 1.8 g, 5.98 mmol) in anhydrous toluene (50 mL) was added Diisobutylaluminum hydride (1M solution in toluene) (17.93 mmol, 18 mL) at −78° C. in 15 minutes. After complete addition, reaction mixture was stirred under nitrogen atmosphere at ambient temperature. Progress of the reaction was monitored by TLC. After completion, saturated $NH_4Cl$ solution was added to the reaction mixture dropwise at 0° C. EtOAc (50 mL) was added to the reaction mixture and the mixture filtered through a Buchner funnel. The filtrate was washed with brine (50 mL), dried over $Na_2SO_4$, filtered and the filtrate was concentrated under reduced pressure to afford trans-2-[4-(4-bromopyrazol-1-yl)cyclohexyl]ethanol (4, 1.65 g, 5.80 mmol) as an off-white solid. Yield-97%; LC MS: ES+(M+H) 273.2.

Step 3. Into a 20 mL microwave vial containing a well-stirred solution of trans-2-[4-(4-bromopyrazol-1-yl)cyclohexyl]ethanol (3, 200 mg, 732.15 μmol) and 4,4,5,5-tetramethyl-2-(4,4,5,5-tetramethyl-1,3,2-dioxaborolan-2-yl)-1,3,2-dioxaborolane (5, 278.88 mg, 1.10 mmol) in anhydrous 2-methyltetrahydrofuran (10 mL) was stirred at ambient temperature under nitrogen atmosphere. The resulting mixture was degassed by bubbling nitrogen gas into the reaction mixture for 10 minutes. Subsequently, potassium acetate (215.56 mg, 2.20 mmol) followed by dichloropalladium tricyclohexylphosphane (54 mg, 73.21 μmol) was added to the reaction mixture. The reaction mixture was stirred at 85° C. under microwave irradiation for 1.5 h. After completion, the reaction mixture was filtered through celite. Filtrate was concentrated to afford 2-[(trans)-4-[4-(4,4,5,5-tetramethyl-1,3,2-dioxaborolan-2-yl)pyrazol-1-yl]cyclohexyl]ethanol (6, 240 mg, 580.08 μmol) as a yellow colored solid. Yield-79%; LC MS: ES+ (M+H) 321.2.

Step 4. In a 100 mL sealed-tube reactor containing a well-stirred solution of mixture of 6-bromo-4-(6-fluoro-3-pyridyl)pyrazolo[1,5-a]pyridine-3-carbonitrile (7, 670 mg, 2.11 mmol) and 2-[(trans)-4-[4-(4,4,5,5-tetramethyl-1,3,2-dioxaborolan-2-yl)pyrazol-1-yl]cyclohexyl]ethanol (6, 879.56 mg, 2.75 mmol) in 1,4-dioxane (12 mL) and water (4 mL) was added sodium carbonate (223.93 mg, 2.11 mmol) at ambient temperature under nitrogen atmosphere and the resulting mixture was degassed by bubbling nitrogen gas into the reaction mixture for 10 minutes. Subsequently, $Pd(dppf)Cl_2$ $CH_2Cl_2$ (172.40 mg, 211.12 μmol) was added to the reaction mixture and reaction mixture was heated to 90° C. for 16 h. After 2 h, the reaction mixture was allowed to cool to room temperature. The reaction mixture was filtered through celite and washed with ethyl acetate to afford crude product, which was purified by flash silica-gel (230-400 mesh) column with 0-100% EtOAc/pet ether to afford 4-(6-fluoro-3-pyridyl)-6-[1-[trans-4-(2-hydroxyethyl)cyclohexyl]pyrazol-4-yl]pyrazolo[1,5-a]pyridine-3-carbonitrile (8, 790 mg, 1.56 mmol) as a brown solid. Yield-74%; LC MS: ES+ (M+H) 431.2.

Example 87: Synthesis of tert-Butyl 4-(4-(3-cyano-4-(6-fluoropyridin-3-yl)pyrazolo[1,5-a]pyridin-6-yl)phenyl)piperazine-1-carboxylate

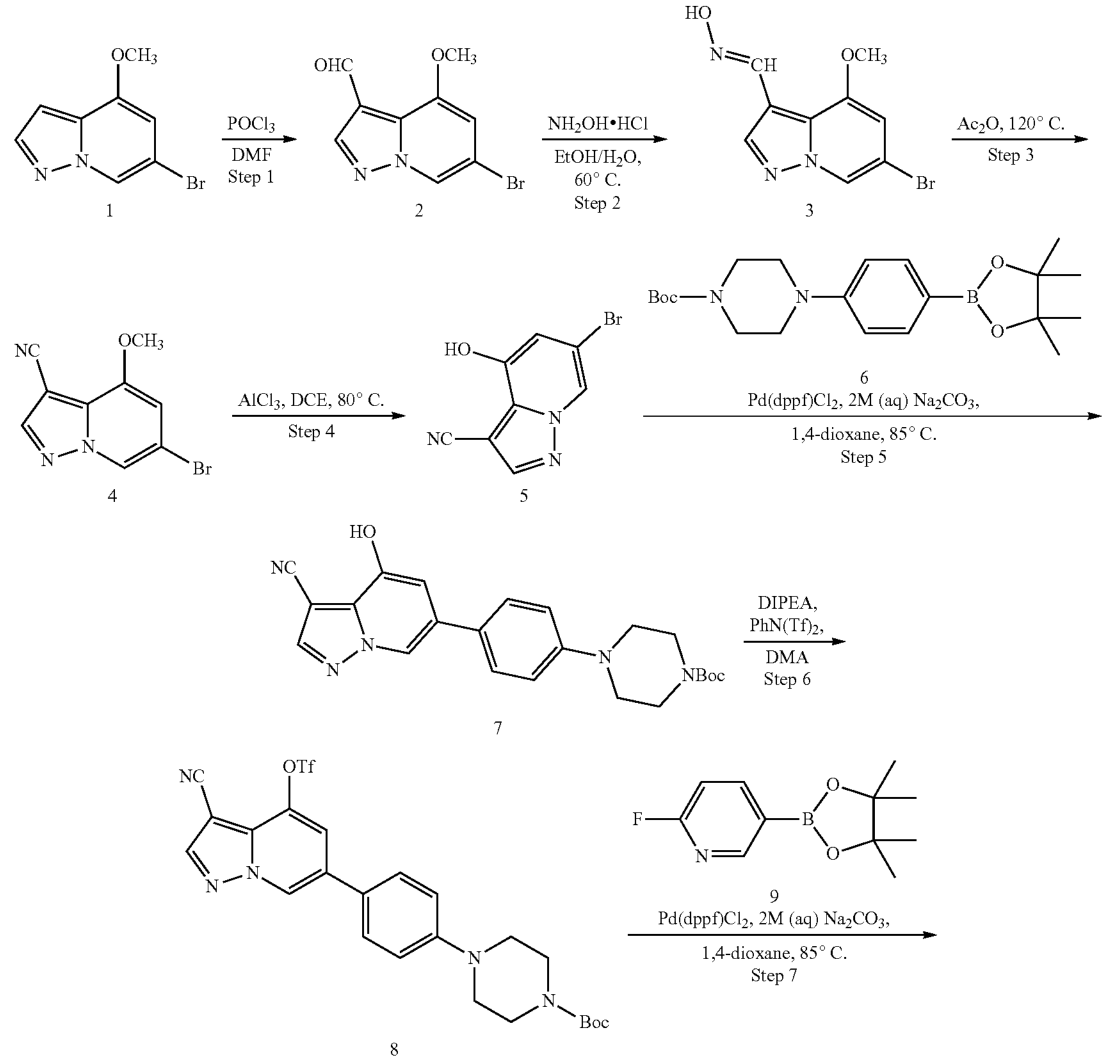

-continued

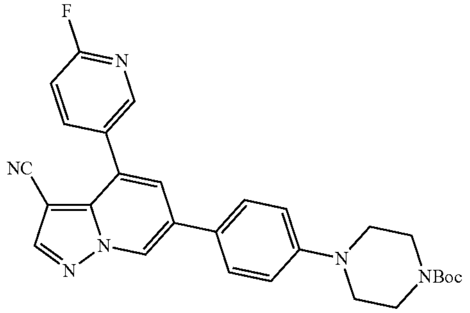

10

Step 1. An oven dried 2 L three-necked round-bottomed flask was charged with a solution of 6-bromo-4-methoxy-pyrazolo[1,5-a]pyridine (1; 1 g, 4.4 mmol) in anhydrous DMF (100 mL) and the resulting solution was cooled to 0° C., phosphorus oxychloride (2.03 g, 13.21 mmol) was added to the flask at room temperature under a nitrogen atmosphere. The reaction mixture was stirred at ambient temperature for 4 h. After completion of the reaction as indicated by TLC, the reaction mixture was quenched with cold water. pH of the solution was adjusted to 8 by adding 10% NaOH solution. The desired product precipitated out and was collected by filtration. The collected solid on the filter was washed with pet ether to afford 6-bromo-4-methoxy-pyrazolo[1,5-a] pyridine-3-carbaldehyde (2; 1.1 g, 4.23 mmol) as an off-white coloured solid, which was carried forward without further purification. Yield-95.9%; LC MS: ES+ (M+H) 256.8.

Step 2. An oven dried 2 L three-necked round-bottomed flask was charged with a solution of 6-bromo-4-methoxy-pyrazolo[1,5-a]pyridine-3-carbaldehyde (2; 27.5 g, 107.81 mmol) in EtOH (750 mL) and to the flask was added hydroxylamine hydrochloride (29.97 g, 431.26 mmol, 17.94 mL) and water (350 mL) at ambient temperature. The reaction mixture was heated to 60° C. for 16 h. Progress of the reaction was monitored by TLC and found complete after 16 h. Excess solvent was removed under reduced pressure to get a crude which was dissolved in water and the pH of the solution was adjusted with aqueous saturated sodium bicarbonate solution to pH=7. The desired product was precipitated out and filtered. The collected solid was washed with water followed by pet ether and dried under vacuum to get (3E)-6-bromo-4-methoxy-pyrazolo[1,5-a] pyridine-3-carbaldehyde oxime (3; 28.5 g, 95.92 mmol) as a white solid, which was carried forward without further purification. Yield-89%; LC MS: ES+ (M+H) 270.0.

Step 3. An oven dried 2 L three-necked round-bottomed flask was charged with a solution of (3E)-6-bromo-4-methoxy-pyrazolo[1,5-a]pyridine-3-carbaldehyde oxime (3; 42 g, 155.51 mmol) in acetic anhydride (440 mL) and the resulting solution was stirred at 120° C. for 16 h. Progress of the reaction was monitored by TLC and found complete. Excess acetic anhydride was removed under reduced pressure and the crude thus obtained was washed with 20% $Et_2O$/pet ether to give 6-bromo-4-methoxy-pyrazolo[1,5-a] pyridine-3-carbonitrile (4; 30 g, 111.87 mmol) as a pale brown solid, which was carried forward without further purification. Yield-72%.

Step 4. Into a 1 L three-necked round-bottomed flask fitted with mechanical stirrer containing a well stirred solution of 6-bromo-4-methoxy-pyrazolo[1,5-a] pyridine-3-carbonitrile (4; 25 g, 99.18 mmol) in 1,2-dichloroethane (400 mL) was added in portions anhydrous Aluminium chloride (52.90 g, 396.72 mmol, 21.68 mL) at room temperature. After completion of the addition, resulting reaction mixture was stirred at 80° C. for 4 h. The progress of the reaction was monitored by UPLC. After completion of the reaction, THF (200 mL) was slowly added to the reaction mixture at 0° C. and was stirred for 30 minutes. Later, a solution of sodium sulfate decahydrate (60 g) in water was added at room temperature and the content was stirred at room temperature for 12 h. The reaction mixture was filtered through a pad of Celite and the Celite bed was washed with THF (2×200 mL). Combined filtrate was concentrated under reduced pressure to afford a brown-coloured solid. To the brown solid was added EtOAc (500 mL) and the suspension was stirred for 1 h, the organic layer was decanted and concentrated under reduced pressure to afford 6-bromo-4-hydroxy-pyrazolo[1,5-a]pyridine-3-carbonitrile (5; 20 g, 73.10 mmol) as a brown-coloured solid, which was carried forward without further purification. Yield-73%; LC MS: ES+ (M+H) 236.0.

Step 5. An oven dried 250 mL sealed-tube was charged with a solution of 6-bromo-4-hydroxy-pyrazolo[1,5-a]pyridine-3-carbonitrile (5; 7 g, 29.41 mmol) and tert-butyl 4-[4-(4,4,5,5-tetramethyl-1,3,2-dioxaborolan-2-yl)phenyl] piperazine-1-carboxylate (6; 12.56 g, 32.35 mmol) in a mixture of water (15 mL) and 1,4-dioxane (70 mL) and to the tube were added [1,1'-Bis(diphenylphosphino)ferrocene] dichloropalladium(II) complexed with dichloromethane (2.40 g, 2.94 mmol) and sodium carbonate (9.35 g, 88.22 mmol) at ambient temperature. The reaction mixture was stirred for 2 h at 85° C. under closed condition. Reaction progress was monitored by TLC and UPLC and found that starting material was consumed. The reaction mixture was quenched with water (100 mL). The product was extracted with EtOAc (2×300 mL) and combined organic layer was dried (anhydrous $Na_2SO_4$), filtered and the filtrate was concentrated under reduced pressure to afford crude. The crude product was washed with pet ether to afford tert-butyl 4-[4-(3-cyano-4-hydroxy-pyrazolo[1,5-a]pyridin-6-yl)phenyl]piperazine-1-carboxylate (7; 7.0 g, 12.52 mmol) as a brown-coloured solid, which was carried forward without further purification. Yield-30%; LC MS: ES− (M−H) 418.0.

Step 6. An oven dried 1 L single-necked round-bottomed flask was charged with a solution of tert-butyl 4-[4-(3-cyano-4-hydroxy-pyrazolo[1,5-a]pyridin-6-yl)phenyl]piperazine-1-carboxylate (7; 20 g, 47.68 mmol) in anhydrous DMA (200 mL) and cooled to 0° C. under nitrogen atmosphere, DIPEA (18.49 g, 143.04 mmol, 24.91 mL) and N-Phenyl-bis(trifluoromethanesulfonimide) (20.44 g, 57.21 mmol) were added to the flask at ambient temperature. The reaction mixture was stirred for 3 h at ambient temperature and the reaction mixture was quenched with water (300 mL). The product was extracted with EtOAc (2×300 mL) and combined organic layer was dried (anhydrous $Na_2SO_4$), filtered and the filtrate was concentrated under reduced pressure to get a crude. The crude mixture was purified by column chromatography (silica-gel flash column (230-400 mesh), gradient 0%-100% EtOAc in pet ether) to yield tert-butyl 4-[4-[3-cyano-4-(trifluoromethylsulfonyloxy) pyrazolo[1,5-a]pyridin-6-yl]phenyl]piperazine-1-carboxylate (8; 13 g, 21.92 mmol) as a pale yellow solid. Yield-46%; LC MS: ES+ (M-tBu+H) 496.0.

Step 7. An oven dried 250 mL pressure tube was charged with a solution of tert-butyl 4-[4-[3-cyano-4-(trifluoromethylsulfonyloxy) pyrazolo[1,5-a]pyridin-6-yl]phenyl]piperazine-1-carboxylate (8; 2 g, 3.63 mmol) and 2-fluoro-5-(4,4,5,5-tetramethyl-1,3,2-dioxaborolan-2-yl)pyridine (1.05 g, 4.71 mmol) in a mixture of 1,4-dioxane (15 mL) and water (5 mL) at ambient temperature. Sodium carbonate (1.15 g, 10.88 mmol) was added to the tube at room temperature, the resulting reaction mixture was purged with nitrogen for 5 minutes, and [1,1'-Bis(diphenylphosphino)ferrocene] dichloropalladium(II) complexed with dichloromethane (2.96 g, 3.63 mmol) was added. The reaction mixture was stirred for 2 h at 85° C. under closed condition, the pressure tube was allowed to attain room temperature and excess reagent was quenched with water (40 mL). The product was extracted with EtOAc (2×200 mL) and the combined organic layer was dried (anhydrous $Na_2SO_4$), filtered and the filtrate was concentrated under reduced pressure to get a crude. The crude mixture was purified by column chromatography (silica-gel flash column (230-400 mesh), gradient 0%-100% EtOAc in pet ether) to yield tert-butyl 4-[4-[3-cyano-4-(6-fluoro-3-pyridyl) pyrazolo[1,5-a]pyridin-6-yl] phenyl]piperazine-1-carboxylate (10; 1.6 g, 2.79 mmol) as yellow solid. Yield-77%; LC MS: ES+ (M+H) 498.9.

Example 88: Synthesis of 6-[4-[4-[2-[4-[4-[(2,6-dioxo-3-piperidyl)amino]-2-fluoro-phenyl]-1-piperidyl]acetyl]piperazin-1-yl]phenyl]-4-[6-[4-[2-(5-fluoro-2-pyridyl)acetyl]piperazin-1-yl]-3-pyridyl] pyrazolo[1,5-a]pyridine-3-carbonitrile (Compound 16)

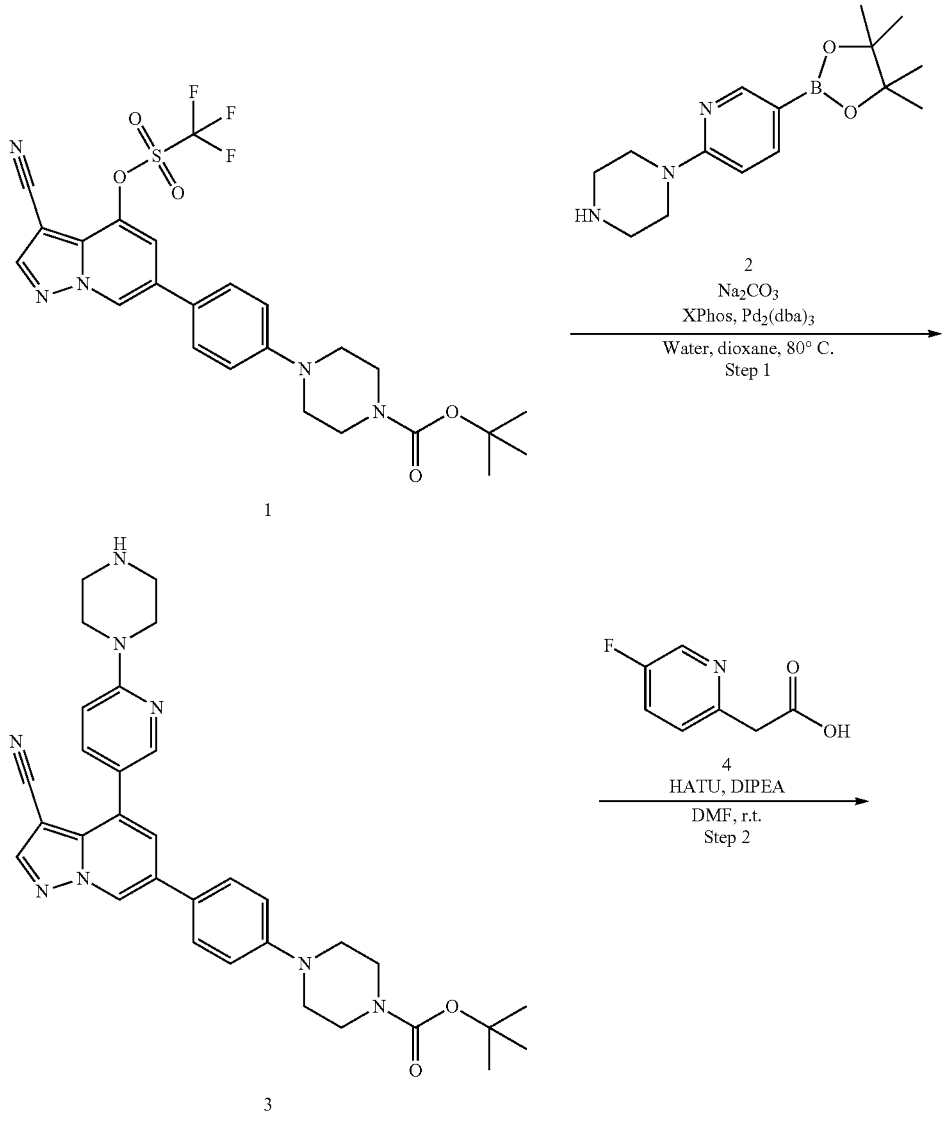

-continued
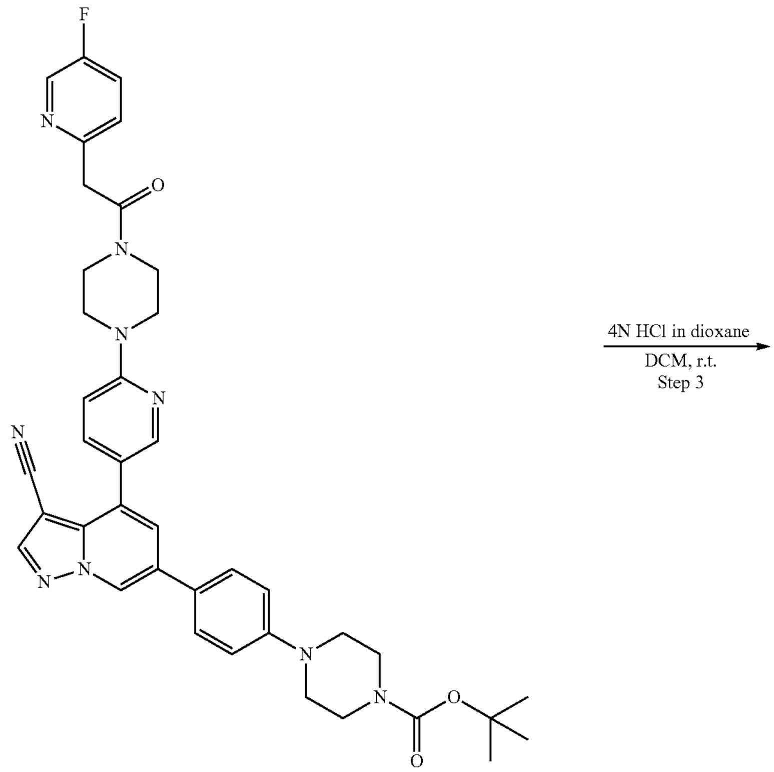
5
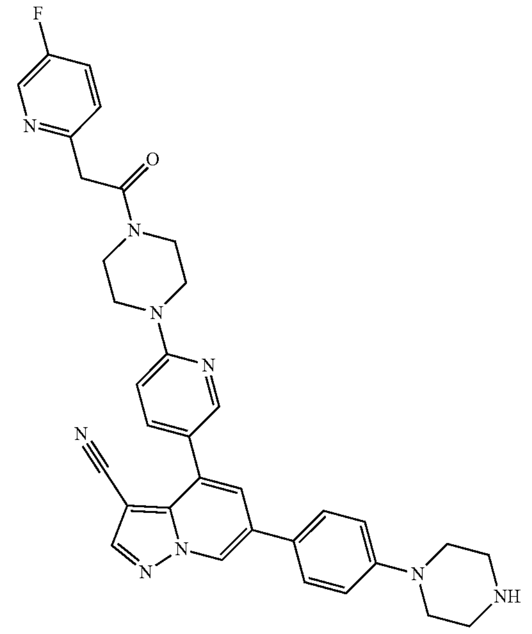
+
6
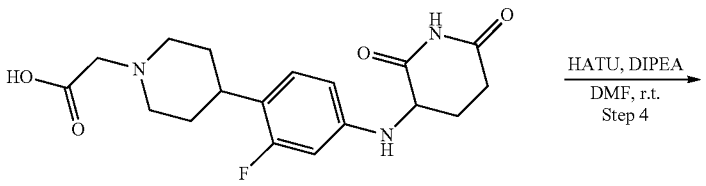
7

-continued

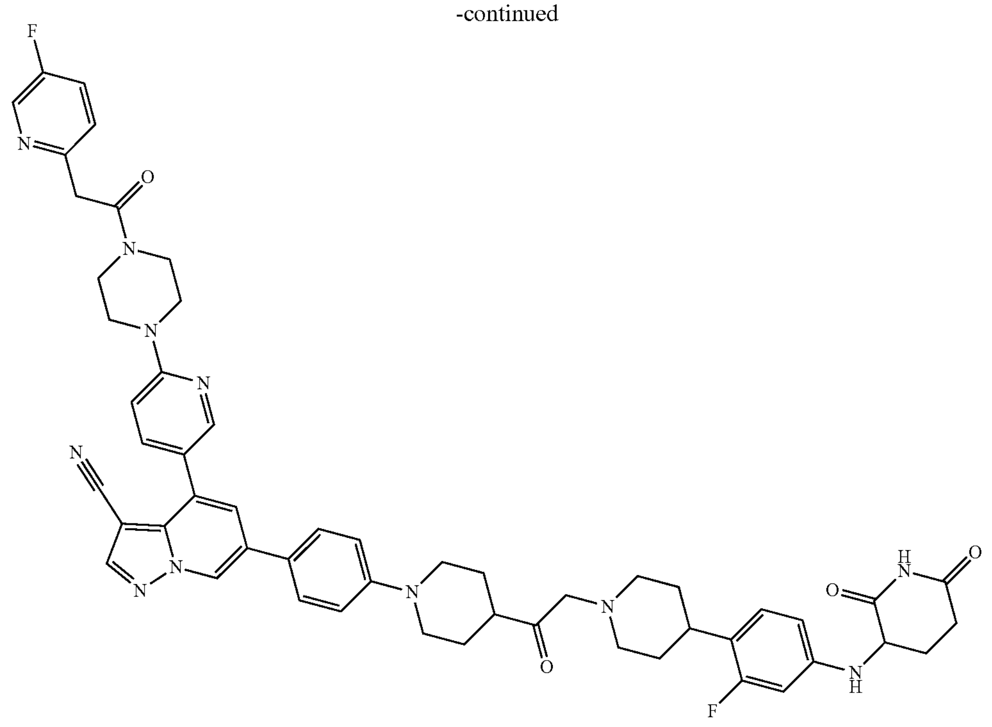

Compound 16

Step 1. Into a 100 mL sealed tube containing a mixture of tert-butyl 4-[4-[3-cyano-4-(trifluoromethylsulfonyloxy) pyrazolo[1,5-a]pyridin-6-yl]phenyl]piperazine-1-carboxylate (1, 1.00 g, 1.81 mmol) and 1-[5-(4,4,5,5-tetramethyl-1,3,2-dioxaborolan-2-yl)-2-pyridyl]piperazine (2, 629.18 mg, 2.18 mmol) in water (2 mL) and dioxane (10 mL) was added sodium carbonate (576.52 mg, 5.44 mmol). Argon gas was bubbled through the reaction mixture for 10 minutes. Then tris(dibenzylideneacetone)dipalladium(0) (166.03 mg, 181.31 μmol) and XPhos (476.72 g, 362.62 μmol) were added and the resulting suspension was purged with argon gas for an additional 10 minutes. The mixture was stirred at 80° C. for 2 h. The reaction mixture was passed through a pad of Celite, and the filtrate was concentrated under reduced pressure. The crude material was purified by neutral alumina with 1:9 MeOH/DCM to afford tert-butyl 4-[4-[3-cyano-4-(6-piperazin-1-yl-3-pyridyl)pyrazolo[1,5-a]pyridin-6-yl]phenyl]piperazine-1-carboxylate (3, 500 mg, 734.93 μmol) as a brown solid. Yield-40.53%; LC MS: ES+ (M+H) 565.3.

Step 2. Into a 50 mL single-necked round-bottomed flask containing a well-stirred solution of tert-butyl 4-[4-[3-cyano-4-(6-piperazin-1-yl-3-pyridyl)pyrazolo[1,5-a]pyridin-6-yl]phenyl]piperazine-1-carboxylate (3, 500 mg, 885.46 μmol) and 2-(5-fluoro-2-pyridyl)acetic acid (4, 151.09 mg, 974.00 μmol) in DMF (10 mL) were added HATU (336.68 mg, 885.46 μmol) and DIPEA (114.44 mg, 885.46 μmol, 154.23 μL) under nitrogen atmosphere at room temperature, the resulting mixture was stirred at room temperature for 2 h. Ice cold water (40 mL) was added and stirred for 10 minutes, the resulting solid was filtered and dried to afford tert-butyl 4-[4-[3-cyano-4-[6-[4-[2-(5-fluoro-2-pyridyl)acetyl]piperazin-1-yl]-3-pyridyl]pyrazolo[1,5-a]pyridin-6-yl]phenyl]piperazine-1-carboxylate (5, 610 mg, 704.06 μmol) as a brown solid. Yield-79.5%; LC MS: ES+ (M+H) 702.3.

Step 3. Into a 50 mL single neck round-bottomed flask containing a well-stirred solution of tert-butyl 4-[4-[3-cyano-4-[6-[4-[2-(5-fluoro-2-pyridyl)acetyl]piperazin-1-yl]-3-pyridyl]pyrazolo[1,5-a]pyridin-6-yl]phenyl]piperazine-1-carboxylate (5, 600 mg, 854.96 μmol) in DCM (5 mL) was added 4 N HCl in dioxane (8 mL) under nitrogen atmosphere at room temperature. The resulting mixture was stirred at room temperature for 2 h. The reaction mixture was concentrated under reduced pressure to afford 4-[6-[4-[2-(5-fluoro-2-pyridyl)acetyl]piperazin-1-yl]-3-pyridyl]-6-(4-piperazin-1-ylphenyl)pyrazolo[1,5-a]pyridine-3-carbonitrile hydrochloride salt (6, 610 mg, 812.52 μmol) as a brown solid. Yield-95.0%; LC MS: ES+ (M+H) 602.3.

Step 4. Into a 25 mL single-necked round-bottomed flask containing a well-stirred solution of 4-[6-[4-[2-(5-fluoro-2-pyridyl)acetyl]piperazin-1-yl]-3-pyridyl]-6-(4-piperazin-1-ylphenyl)pyrazolo[1,5-a]pyridine-3-carbonitrile hydrochloric acid salt (6, 30 mg, 47.01 μmol) and 2-[4-[4-[(2,6-dioxo-3-piperidyl)amino]-2-fluoro-phenyl]-1-piperidyl]acetic acid hydrochloric acid salt (7,18.79 mg, 47.00 μmol) in anhydrous DMF (0.5 mL) were added DIPEA (6.08 mg, 47.01 μmol, 8.19 μL) and HATU (17.88 mg, 47.01 μmol) under nitrogen atmosphere at room temperature, the resulting mixture was stirred at room temperature for 3 h. The reaction mixture was concentrated under reduced pressure and purified by reverse phase column chromatography (isco column, Mobile phase: A: 0.1% Formic Acid in water B: ACN) to afford 6-[4-[4-[2-[4-[4-[(2,6-dioxo-3-piperidyl)amino]-2-fluoro-phenyl]-1-piperidyl]acetyl]piperazin-1-yl]phenyl]-4-[6-[4-[2-(5-fluoro-2-pyridyl)acetyl]piperazin-1-yl]-3-pyridyl]pyrazolo[1,5-a]pyridine-3-carbonitrile formic acid salt (Compound 16, 12 mg, 12.01 μmol) as a white solid. Yield-22.5%; LC MS: ES+(M+H) 947.8.

Example 89: Synthesis of 4-(6-(3-Azabicyclo[3.1.0]hexan-3-yl)pyridin-3-yl)-6-(4-(4-(2-(4-(4-((2,6-dioxopiperidin-3-yl)amino)phenyl)piperidin-1-yl)acetyl)piperazin-1-yl)phenyl)pyrazolo[1,5-a]pyridine-3-carbonitrile (Compound 17)
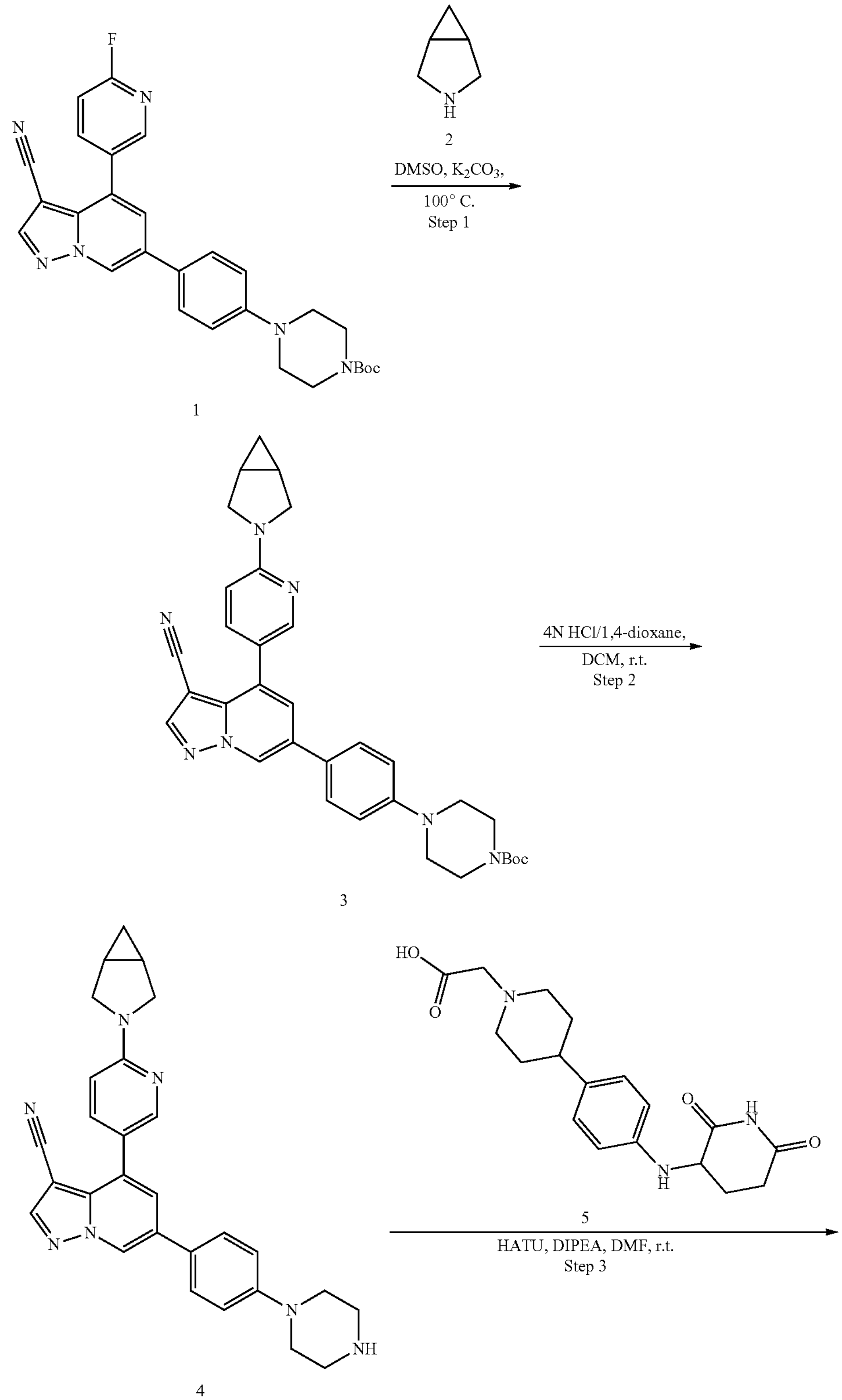
1
2
3
4
5

-continued

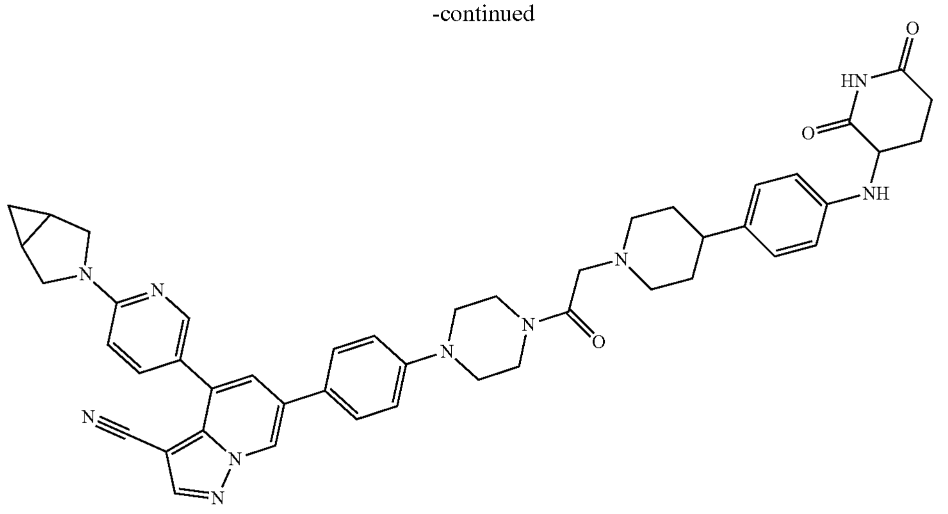

Compound 17

Step 1. Into a 10 mL sealed tube containing a well-stirred solution of a mixture of tert-butyl 4-[4-[3-cyano-4-(6-fluoro-3-pyridyl)pyrazolo[1,5-a]pyridin-6-yl]phenyl]piperazine-1-carboxylate (1; 70 mg, 0.140 mmol) and 3-azabicyclo[3.1.0]hexane (2; 20.15 mg, 0.168 mmol) in anhydrous DMSO (2 mL) was added anhydrous $K_2CO_3$ (97.03 mg, 0.702 mmol) at ambient temperature. The reaction mixture was heated to 100° C. for 6 h. After completion of the reaction as indicated by UPLC, the reaction mixture was cooled to room temperature and poured into water (10 mL) and solid precipitated out was filtered. The solid product was dried to yield tert-butyl 4-[4-[4-[6-(3-azabicyclo[3.1.0]hexan-3-yl)-3-pyridyl]-3-cyano-pyrazolo[1,5-a]pyridin-6-yl]phenyl]piperazine-1-carboxylate (3; 65 mg, 0.111 mmol) as yellow solid, which was carried forward without further purification. Yield-79%; LC MS: ES+ (M+H) 562.3.

Step 2. Into a 50 mL single-necked round-bottomed flask containing a well-stirred solution of tert-butyl 4-[4-[4-[6-(3-azabicyclo[3.1.0]hexan-3-yl)-3-pyridyl]-3-cyano-pyrazolo[1,5-a]pyridin-6-yl]phenyl]piperazine-1-carboxylate (3; 65 mg, 0.115 mmol) in anhydrous $CH_2Cl_2$ (3 mL) was added HCl (5 mL; 4M/1,4-dioxane) at ambient temperature under nitrogen atmosphere. The reaction mixture was stirred for 2 h at ambient temperature and found complete. Excess solvents were removed from the reaction mixture under reduced pressure to get a crude mass. The crude mass was triturated with $Et_2O$ (10 mL) to get 4-[6-(3-azabicyclo[3.1.0]hexan-3-yl)-3-pyridyl]-6-(4-piperazin-1-ylphenyl)pyrazolo[1,5-a]pyridine-3-carbonitrile hydrochloric acid salt (4; 50 mg, 0.097 mmol) as a yellow solid, which was carried forward without further purification. Yield-84%; LC MS: ES+ (M+H) 462.2.

Step 3. To a well-stirred mixture of 4-[6-(3-azabicyclo[3.1.0]hexan-3-yl)-3-pyridyl]-6-(4-piperazin-1-ylphenyl)pyrazolo[1,5-a]pyridine-3-carbonitrile hydrochloric acid salt (4; 33.24 mg, 0.072 mmol) and 2-[4-[4-[(2,6-dioxo-3-piperidyl)amino]phenyl]-1-piperidyl]acetic acid hydrochloric acid salt (5; 25 mg, 0.065 mmol) in anhydrous DMF (3 mL) in a 25-mL single-necked round-bottomed flask was added DIPEA (42.31 mg, 0.327 mmol, 0.057 mL) and the resulting solution was stirred for 15 minutes at ambient temperature under nitrogen atmosphere. HATU (29.87 mg, 0.078 mmol) was added to the reaction mixture and stirring was continued at ambient temperature for 3 h. The progress of the reaction was monitored by UPLC. After completion of the reaction, the reaction mixture was treated with water (1 mL) and solid precipitated out was filtered. The filtered solid was dried under vacuum to get crude mixture, which was purified by reverse phase column chromatography (30 g Biotage C-18 column, Mobile phase: A: 0.1% Formic acid in water, B: Acetonitrile) to yield 4-[6-(3-azabicyclo[3.1.0]hexan-3-yl)-3-pyridyl]-6-[4-[4-[2-[4-[4-[(2,6-dioxo-3-piperidyl)amino]phenyl]-1-piperidyl]acetyl]piperazin-1-yl]phenyl]pyrazolo[1,5-a]pyridine-3-carbonitrile formic acid salt (Compound 17; 4.51 mg, 0.005 mmol) as white solid. Yield-8%. $^1$H NMR (400 MHz, DMSO-$d_6$): δ 10.78 (s, 1H), 9.17 (d, J=1.6 Hz, 1H), 8.68 (s, 1H), 8.37 (d, J=2.4 Hz, 1H), 7.82-7.74 (m, 4H), 7.10 (d, J=8.8 Hz, 2H), 6.97 (d, J=8.0 Hz, 2H), 6.64-6.58 (m, 3H), 5.70 (d, J=7.2 Hz, 1H), 4.27-4.25 (m, 1H), 3.74-3.66 (m, 6H), 3.47-3.42 (m, 8H), 3.25 (m, 4H), 2.74-2.68 (m, 1H), 2.58-2.56 (m, 1H), 2.11-2.08 (m, 1H), 1.88-1.72 (m, 7H), 0.79-0.77 (m, 1H), 0.21 (q, J=4.0 Hz, 1H), 0.07 (s, 1H). LC MS: ES+ (M+H) 790.0.

Example 90: Synthesis of 6-(4-(4-(2-(4-(4-((2,6-Dioxopiperidin-3-yl)amino)phenyl)piperidin-1-yl)acetyl)piperazin-1-yl)phenyl)-4-(6-(4-(2-(pyridin-2-yl)ethyl)piperazin-1-yl)pyridin-3-yl)pyrazolo[1,5-a]pyridine-3-carbonitrile (Compound 18)
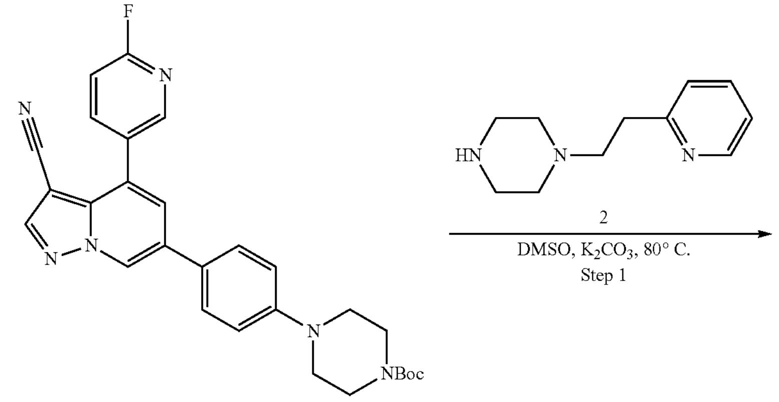
1
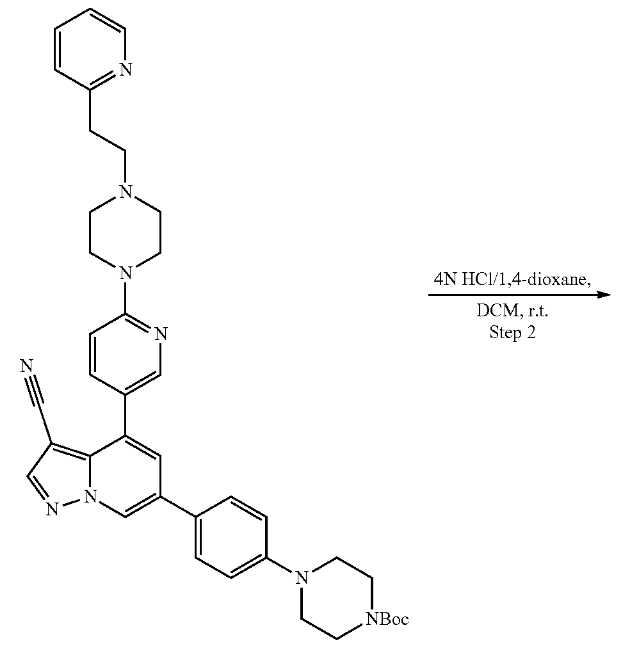
3

-continued

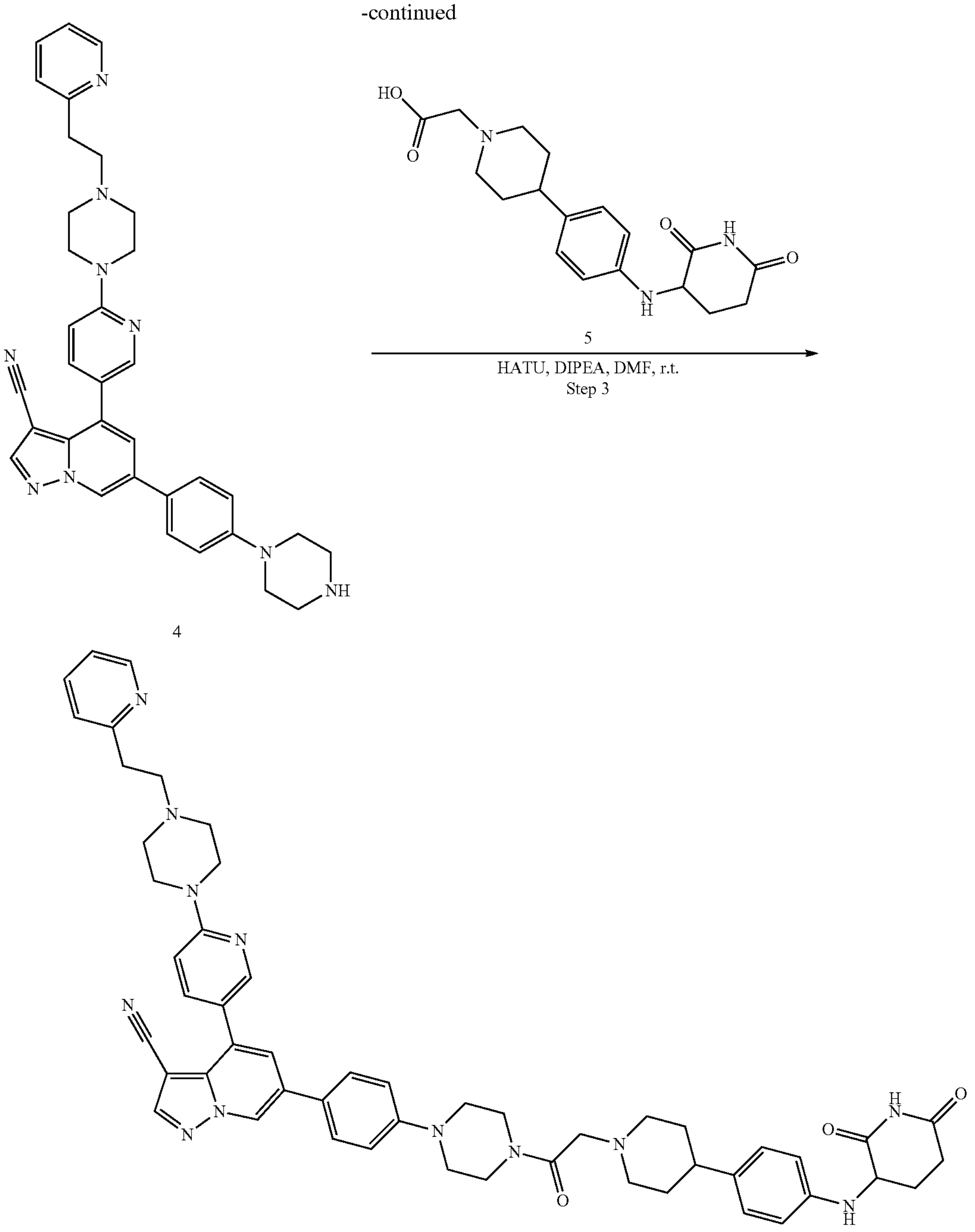

4

5

Compound 18

Step 1. Into a 25 mL sealed tube containing a well-stirred solution of a mixture of tert-butyl 4-[4-[3-cyano-4-(6-fluoro-3-pyridyl)pyrazolo[1,5-a]pyridin-6-yl]phenyl]piperazine-1-carboxylate (1; 100 mg, 0.2 mmol) and 1-[2-(2-pyridyl)ethyl]piperazine (2; 42.20 mg, 0.220 mmol) in anhydrous DMSO (2 mL) was added $K_2CO_3$ (138.61 mg, 1.00 mmol) at ambient temperature. The reaction mixture was heated to 80° C. for 24 h. After completion of the reaction as indicated by UPLC, the reaction mixture was cooled to room temperature and poured into water (10 mL) and solid precipitated out was filtered. The solid product was dried to yield tert-butyl 4-[4-[3-cyano-4-[6-[4-[2-(2-pyridyl)ethyl]piperazin-1-yl]-3-pyridyl]pyrazolo[1,5-a]pyridin-6-yl]phenyl]piperazine-1-carboxylate (3; 120 mg, 0.159 mmol) as a yellow solid, which was carried forward without further purification. Yield-79%; LC MS: ES+ (M+H) 670.5.

Step 2. Into a 25 mL single-necked round-bottomed flask containing a well-stirred solution of tert-butyl 4-[4-[3-cyano-4-[6-[4-[2-(2-pyridyl)ethyl]piperazin-1-yl]-3-pyridyl]pyrazolo[1,5-a]pyridin-6-yl]phenyl]piperazine-1-carboxylate (3; 120 mg, 0.179 mmol) in anhydrous $CH_2Cl_2$ (2 mL) was added 4M HCl in 1,4-dioxane solution (5 mL) at ambient temperature. The reaction mixture was stirred for 1 h at ambient temperature and found complete. Excess solvents were removed from the reaction mixture under reduced pressure to get a crude mass. The crude mass was triturated with $Et_2O$ (10 mL) to yield 6-(4-piperazin-1-ylphenyl)-4-[6-[4-[2-(2-pyridyl)ethyl]piperazin-1-yl]-3-pyridyl]pyrazolo[1,5-a]pyridine-3-carbonitrile hydrochloric acid salt (4; 90 mg, 0.132 mmol) as a yellow solid, which was carried forward without further purification. Yield-74%; LC MS: ES+ (M+H) 570.2.

Step 3. Into a 25 mL single-necked round-bottomed flask containing a well-stirred solution of 6-(4-piperazin-1-ylphenyl)-4-[6-[4-[2-(2-pyridyl)ethyl]piperazin-1-yl]-3-pyridyl]pyrazolo[1,5-a]pyridine-3-carbonitrile hydrochloric acid salt (4; 49.23 mg, 0.086 mmol) and 2-[4-[4-[(2,6-dioxo-3-piperidyl)amino]phenyl]-1-piperidyl]acetic acid hydrochloric acid salt (5; 30 mg, 0.078 mmol) in anhydrous DMF (5 mL) were added DIPEA (50.77 mg, 0.392 mmol, 0.068 mL) and HATU (35.85 mg, 0.094 mmol) at ambient temperature. The reaction mixture was stirred for 5 h at ambient temperature. The progress of the reaction was monitored by UPLC. After completion of the reaction, the reaction mixture was treated with water (1 mL) and solid precipitated out was filtered. The filtered solid was dried under vacuum to get crude mixture, which was purified by preparative reverse phase column chromatography (Column: X-Bridge C18 [(150×19 mm), Sum], Mobile phase: A: 0.1% TFA in water, B: Acetonitrile) to yield 6-[4-[4-[2-[4-[4-[(2,6-dioxo-3-piperidyl)amino]phenyl]-1-piperidyl]acetyl]piperazin-1-yl]phenyl]-4-[6-[4-[2-(2-pyridyl)ethyl]piperazin-1-yl]-3-pyridyl]pyrazolo[1,5-a]pyridine-3-carbonitrile trifluoroacetic acid salt (Compound 18; 26 mg, 0.025 mmol) as a green solid. Yield-32%. $^1H$ NMR (400 MHz, DMSO-$d_6$) δ 10.79 (s, 1H), 9.56-9.52 (m, 1H), 9.24 (s, 1H), 8.71 (d, J=2.8 Hz, 1H), 8.58-8.57 (m, 1H), 8.51 (d, J=2.4 Hz, 1H), 7.99-7.98 (m, 1H), 7.87-7.60 (m, 4H), 7.44-7.24 (m, 2H), 7.16-7.04 (m, 3H), 6.97 (d, J=8.8 Hz, 2H), 6.65 (d, J=8.4 Hz, 2H), 4.48-4.28 (m, 4H), 3.92 (brs, 4H), 3.71-3.26 (m, 18H), 3.09 (d, J=8.8 Hz, 2H), 2.74-2.67 (m, 2H), 2.10-1.86 (m, 6H). LC MS: ES+(M+H) 898.4.

Example 91: Synthesis of 4-(6-((1R,5S)-8—Oxa-3-azabicyclo[3.2.1]octan-3-yl)pyridin-3-yl)-6-(4-(4-(2-(4-(4-((2,6-dioxopiperidin-3-yl)amino)phenyl)piperidin-1-yl)acetyl)piperazin-1-yl)phenyl)pyrazolo[1,5-a]pyridine-3-carbonitrile (Compound 19)

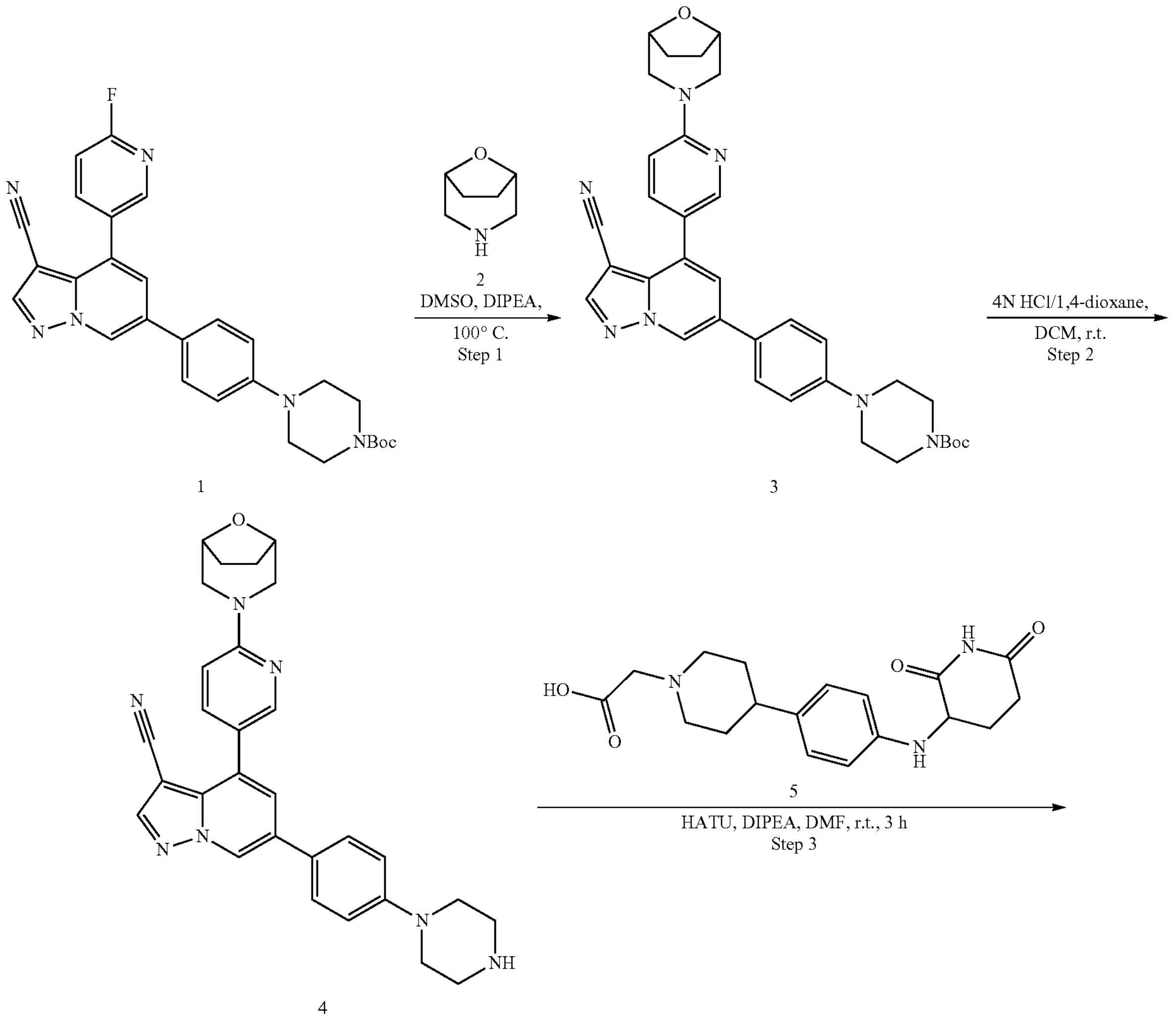

-continued

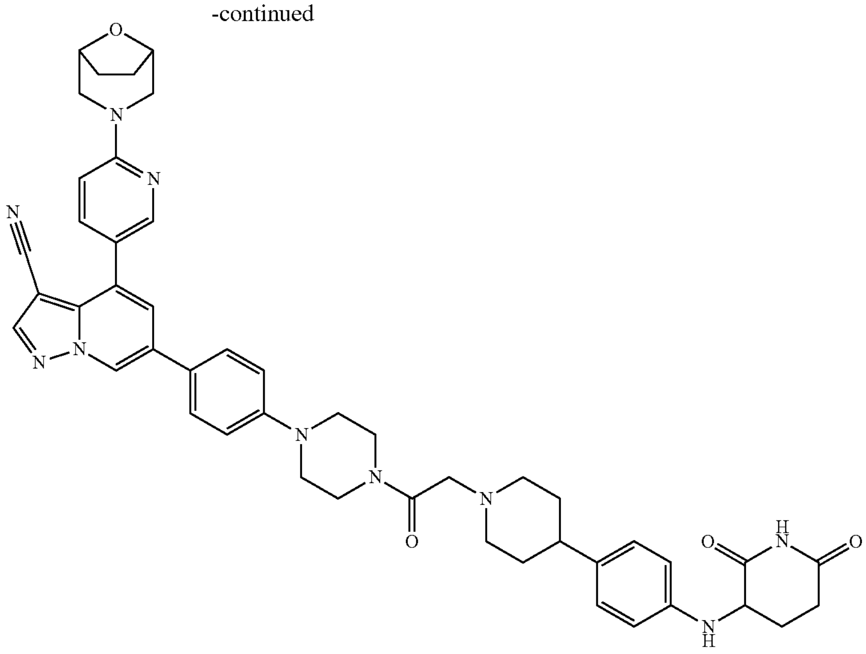

Compound 19

Step 1. Into a 50 mL sealed-tube reactor containing a well-stirred solution of tert-butyl 4-[4-[3-cyano-4-(6-fluoro-3-pyridyl)pyrazolo[1,5-a]pyridin-6-yl]phenyl]piperazine-1-carboxylate (1; 70 mg, 0.140 mmol) and 8-oxa-3-azabicyclo [3.2.1]octane (2; 25.21 mg, 0.168 mmol) in anhydrous DMSO (2 mL) was added DIPEA (97.03 mg, 0.702 mmol, 0.042 mL) at ambient temperature. The reaction mixture was heated to 100° C. for 30 h. After completion of the reaction as indicated by UPLC, the reaction mixture was cooled to room temperature and poured into water (10 mL) and the solid precipitated out was filtered. The solid product was dried to yield tert-butyl 4-[4-[3-cyano-4-[6-(8-oxa-3-azabicyclo[3.2.1]octan-3-yl)-3-pyridyl]pyrazolo[1,5-a]pyridin-6-yl]phenyl]piperazine-1-carboxylate (3; 60 mg, 0.087 mmol) as a yellow solid, which was carried forward without further purification. Yield-62%; LC MS: ES+ (M+H) 592.9.

Step 2. Into a 25 mL single-necked round-bottomed flask containing a well-stirred solution of tert-butyl 4-[4-[3-cyano-4-[6-(8-oxa-3-azabicyclo[3.2.1]octan-3-yl)-3-pyridyl]pyrazolo[1,5-a]pyridin-6-yl]phenyl]piperazine-1-carboxylate (3; 60 mg, 0.101 mmol) in anhydrous $CH_2Cl_2$ (3 mL) was added HCl (3 mL; 4 N/1,4-dioxane) was added at ambient temperature. The reaction mixture was stirred for 1 h at ambient temperature and before the reaction was complete. Excess solvents were removed from the reaction mixture under reduced pressure to get a crude mass. The crude mass was triturated with $Et_2O$ (10 mL) to yield 4-[6-(8-oxa-3-azabicyclo[3.2.1]octan-3-yl)-3-pyridyl]-6-(4-piperazin-1-ylphenyl)pyrazolo[1,5-a]pyridine-3-carbonitrile hydrochloric acid salt (4; 48 mg, 0.080 mmol) as a yellow solid, which was carried forward without further purification. Yield-80%; LC MS: ES+ (M+H) 491.9.

Step 3. Into a 25 mL single-necked round-bottomed flask containing a well-stirred solution of 4-[6-(8-oxa-3-azabicyclo[3.2.1]octan-3-yl)-3-pyridyl]-6-(4-piperazin-1 ylphenyl) pyrazolo[1,5-a]pyridine-3-carbonitrile hydrochloric acid salt (4; 35.40 mg, 0.072 mmol) and 2-[4-[4-[(2,6-dioxo-3-piperidyl)amino]phenyl]-1-piperidyl]acetic acid hydrochloric acid salt (5; 25 mg, 0.065 mmol) in anhydrous DMF (2 mL) was added DIPEA (42.31 mg, 0.327 mmol, 0.057 mL) and the resulting solution was stirred for 15 minutes at ambient temperature under nitrogen atmosphere. HATU (29.87 mg, 0.078 mmol) was then added to the reaction mixture and stirring was continued at ambient temperature for 3 h. The progress of the reaction was monitored by UPLC. After completion of the reaction, the reaction mixture was treated with water (1 mL) and solid precipitated out was filtered. The filtered solid was dried under vacuum to get crude mixture, which was purified by reverse phase column chromatography (30 g Biotage C18 column, Mobile phase: A: 0.1% Formic acid in water and B: Acetonitrile) to yield 6-[4-[4-[2-[4-[4-[(2,6-dioxo-3-piperidyl)amino]phenyl]-1-piperidyl]acetyl]piperazin-1-yl]phenyl]-4-[6-(8-oxa-3-azabicyclo[3.2.1]octan-3-yl)-3-pyridyl]pyrazolo[1,5-a]pyridine-3-carbonitrile formic acid salt (Compound 19; 4.92 mg, 0.005 mmol) as a grey solid. Yield-8%. $^1H$ NMR (400 MHz, DMSO-$d_6$). δ 10.79 (s, 1H), 9.50 (brs, 1H), 9.21 (d, J=1.2 Hz, 1H), 8.70 (s, 1H), 8.43 (d, J=2.4 Hz, 1H), 7.89 (dd, J=8.8, 2.4 Hz, 1H), 7.83 (s, 1H), 7.80 (s, 2H), 7.12-7.07 (m, 2H), 6.99-6.97 (m, 2H), 6.91 (d, J=8.8 Hz, 1H), 6.65 (d, J=8.4 Hz, 2H), 4.48 (s, 2H), 4.38 (d, J=2.4 Hz, 1H), 4.31-4.27 (m, 1H), 3.95 (d, J=12.0 Hz, 3H), 3.71 (s, 3H), 3.58-3.56 (m, 5H), 3.31-3.29 (m, 4H), 3.25-3.03 (m, 5H), 2.74-2.69 (m, 1H), 2.13-2.08 (m, 1H), 1.99-1.83 (m, 6H), 1.81-1.76 (m, 2H). LC MS: ES+ (M+H) 819.3.

Example 92: Synthesis of 6-(4-(4-(2-(4-(4-((2,6-Dioxopiperidin-3-yl)amino)phenyl)piperidin-1-yl)acetyl)piperazin-1-yl)phenyl)-4-(6-(4-(phenylamino)piperidin-1-yl)pyridin-3-yl)pyrazolo[1,5-a]pyridine-3-carbonitrile formic acid salt (Compound 20)
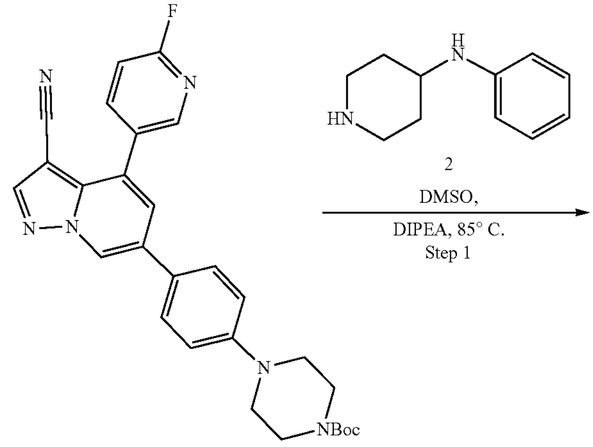
1
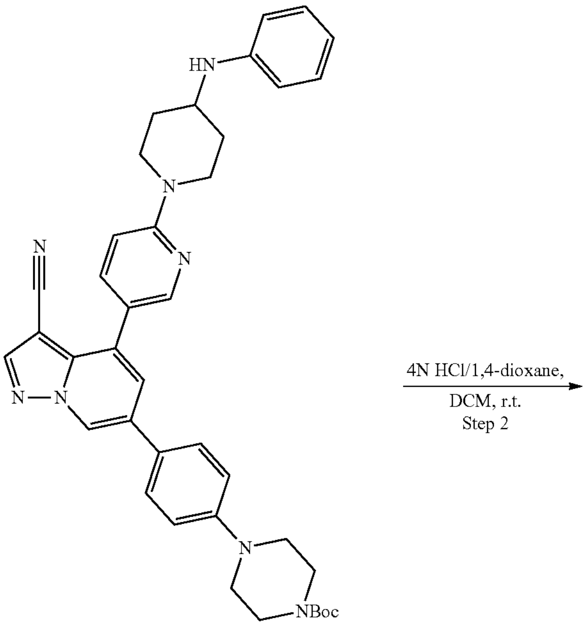
3

-continued

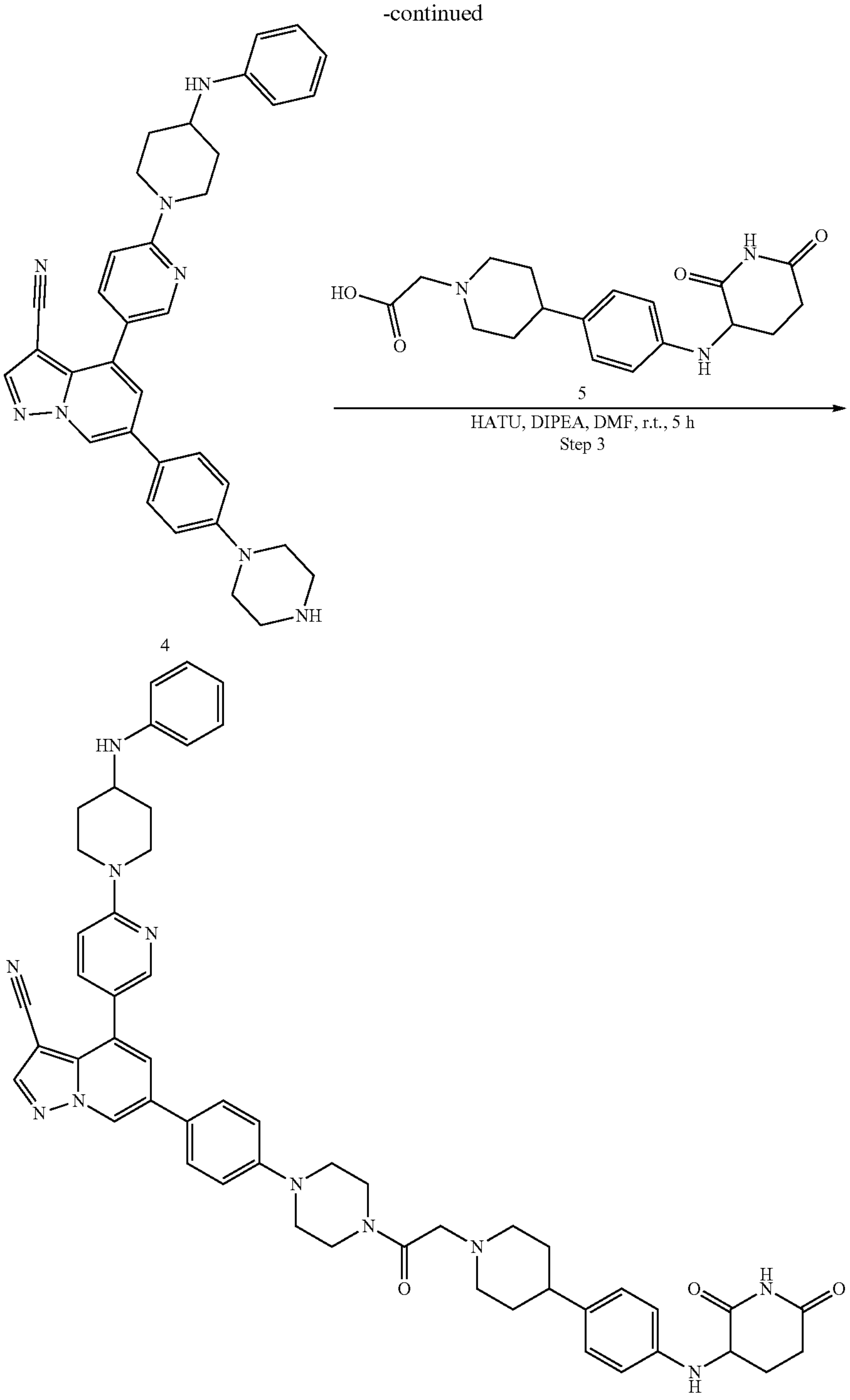

4

Compound 20

Step 1. Into a 50 mL sealed-tube reactor containing a well-stirred solution of tert-butyl 4-[4-[3-cyano-4-(6-fluoro-3-pyridyl)pyrazolo[1,5-a]pyridin-6-yl]phenyl]piperazine-1-carboxylate (1; 50 mg, 0.1 mmol) and N-phenylpiperidin-4-amine (2; 19.44 mg, 0.110 mmol) in anhydrous DMSO (1 mL) was added DIPEA (19.44 mg, 0.150 mmol, 0.026.20 mL) at ambient temperature. The reaction mixture was heated to 85° C. for 16 h. After completion of the reaction as indicated by UPLC, the reaction mixture was cooled to room temperature and poured into water (10 mL) and solid precipitated out was filtered. The solid product was dried to yield tert-butyl 4-[4-[4-[6-(4-anilino-1-piperidyl)-3-pyridyl]-3-cyano-pyrazolo[1,5-a]pyridin-6-yl]phenyl]piperazine-1-carboxylate (3; 55 mg, 0.076 mmol) as a yellow solid, which was carried forward without further purification. Yield-75.8%. LC MS: ES+ (M+H) 655.3.

Step 2. Into a 25 mL single-necked round-bottomed flask containing a well-stirred solution of tert-butyl 4-[4-[4-[6-(4- anilino-1-piperidyl)-3-pyridyl]-3-cyano-pyrazolo[1,5-a]pyridin-6-yl]phenyl]piperazine-1-carboxylate (3; 55 mg, 0.084 mmol) in anhydrous $CH_2Cl_2$ (2 mL) was added 4 N HCl in 1,4-dioxane solution (5 mL) at ambient temperature. The reaction mixture was stirred at ambient temperature for 1 h and found complete. Excess solvents were removed from the reaction mixture under reduced pressure to get a crude mass. The crude mass was triturated with $Et_2O$ (10 mL) to get 4-[6-(4-anilino-1-piperidyl)-3-pyridyl]-6-(4-piperazin-1-ylphenyl)pyrazolo[1,5-a]pyridine-3-carbonitrile (4; 45 mg, 0.070 mmol) as a yellow solid, which was carried forward without further purification. Yield-83.8%; LC MS: ES+ (M+H) 555.3.

Step 3. Into a 25 mL single-necked round-bottomed flask containing a well-stirred solution of 4-[6-(4-anilino-1-piperidyl)-3-pyridyl]-6-(4-piperazin-1-ylphenyl)pyrazolo[1,5-a]pyridine-3-carbonitrile (4; 39.95 mg, 0.072 mmol) and 2-[4-[4-[(2,6-dioxo-3-piperidyl)amino]phenyl]-1-piperidyl]acetic acid hydrochloric acid salt (5; 25 mg, 0.065 mmol) in anhydrous DMF (3 mL) were added DIPEA (42.31 mg, 0.327 mmol, 0.057 mL) and HATU (29.87 mg, 0.078 mmol) at ambient temperature under nitrogen atmosphere. The reaction mixture was stirred for 5 h at ambient temperature. The progress of the reaction was monitored by UPLC. After completion of the reaction, the reaction mixture was treated with water (1 mL) and solid precipitated out was filtered. The filtered solid was dried under vacuum to get crude mixture, which was purified by preparative reverse phase column chromatography (Column: X-Bridge C18 [(150×19 mm), 5 um], Mobile phase: A: 0.1% formic acid in water, B: acetonitrile) to yield 4-[6-(4-anilino-1-piperidyl)-3-pyridyl]-6-[4-[4-[2-[4-[4-[(2,6-dioxo-3-piperidyl)amino]phenyl]-1-piperidyl]acetyl]piperazin-1-yl]phenyl]pyrazolo[1,5-a]pyridine-3-carbonitrile formic acid salt (Compound 20; 2.40 mg, 0.0025 mmol) as a white solid. Yield-3.8%. $^1H$ NMR (400 MHz, DMSO-$d_6$): δ 10.77 (s, 1H), 9.18 (d, J=1.6 Hz, 1H), 8.68 (s, 1H), 8.43 (d, J=2.4 Hz, 1H), 7.87-7.78 (m, 4H), 7.11-6.94 (m, 7H), 6.64-6.49 (m, 5H), 5.65 (d, J=7.2 Hz, 1H), 5.51 (d, J=7.6 Hz, 1H), 4.35 (d, J=12.8 Hz, 2H), 4.27-4.13 (m, 1H), 3.76 (s, 3H), 3.62-3.59 (m, 2H), 3.21 (s, 5H), 3.17-3.11 (m, 1H), 2.92 (d, J=10.8 Hz, 3H), 2.73-2.67 (m, 2H), 2.11-1.99 (m, 6H), 1.88-1.84 (m, 1H), 1.69 (d, J=10.8 Hz, 2H), 1.58-1.55 (m, 2H), 1.39-1.37 (m, 2H). LC MS: ES+ (M+H) 882.5.

Example 93: Synthesis of 6-(4-(4-(2-(4-(4-((2,6-Dioxopiperidin-3-yl)amino)phenyl)piperidin-1-yl)acetyl)piperazin-1-yl)phenyl)-4-(6-(1-(hydroxymethyl)cyclohexyl)pyridin-3-yl)pyrazolo[1,5-a]pyridine-3-carbonitrile formic acid salt (Compound 21)

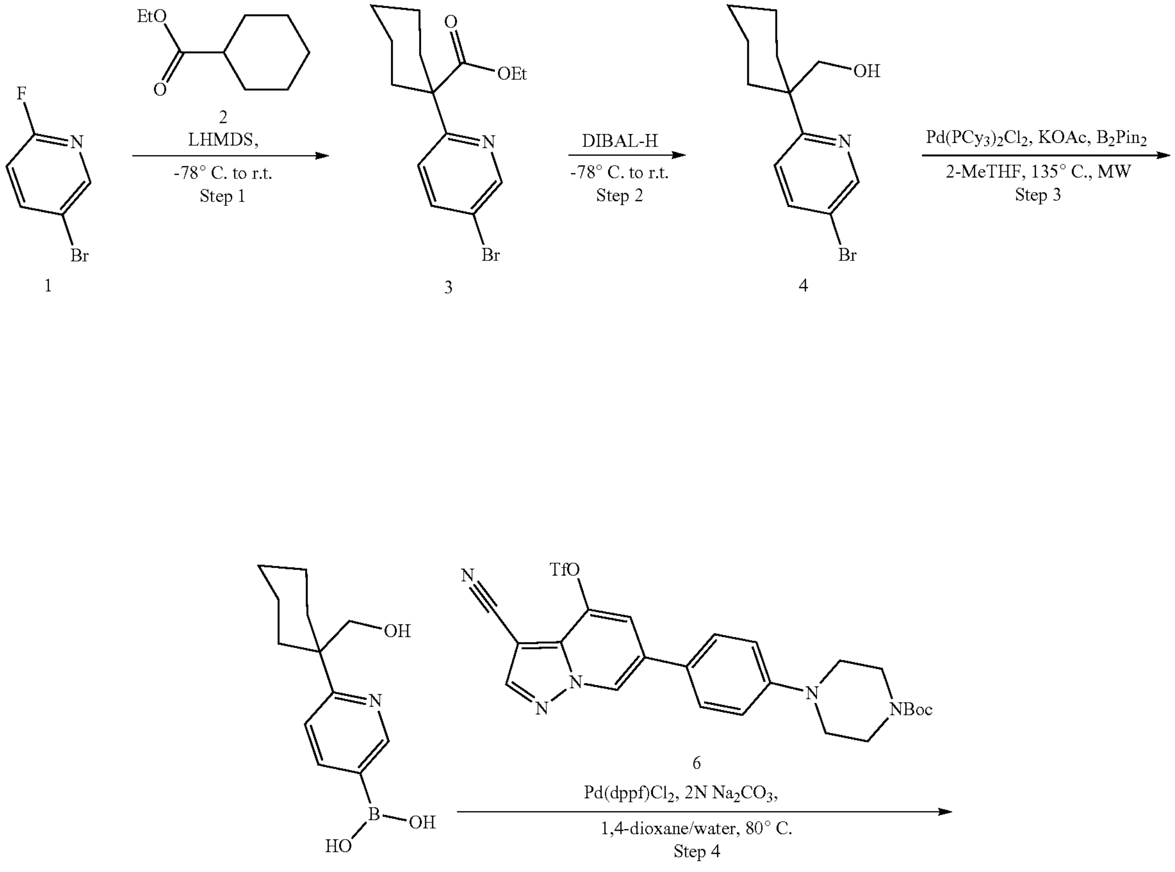

1 3 4 5

-continued
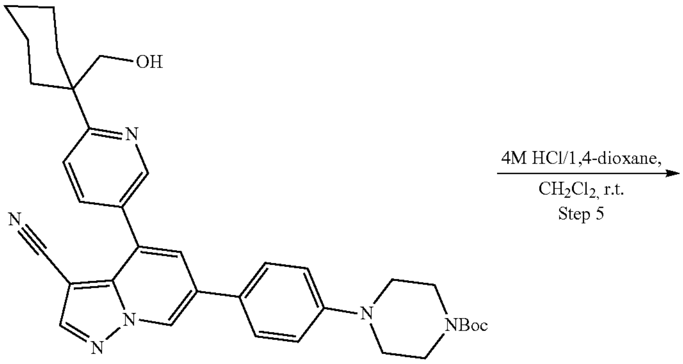
7
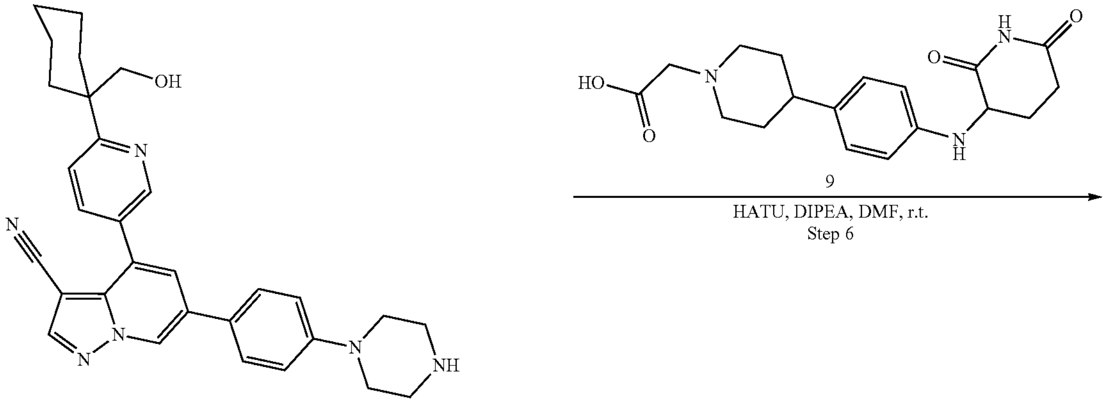
8
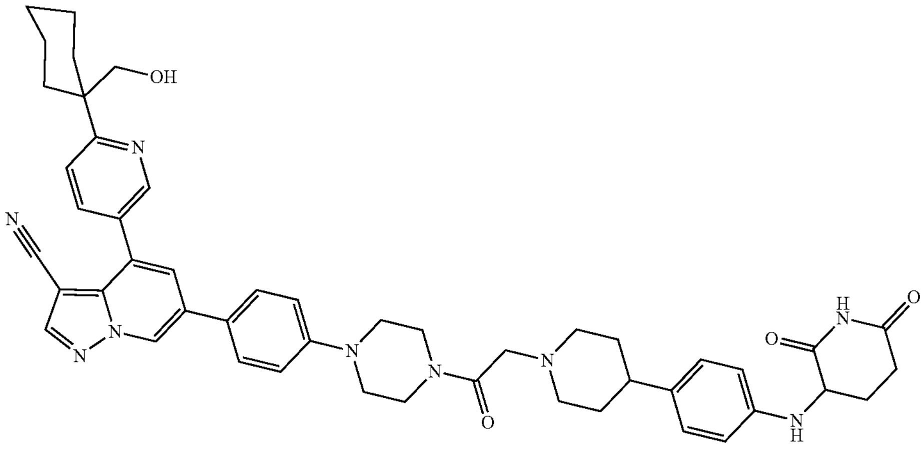
Compound 21

Step 1. Into a 250 mL two-necked round-bottomed flask containing a well-stirred solution of ethyl cyclohexanecarboxylate (2; 2 g, 12.80 mmol) in anhydrous THF (6 mL) was added 1M LHMDS in THF (2.57 g, 15.36 mmol) at −78° C. under nitrogen atmosphere. The resulting mixture was stirred at −78° C. for 1 h. Then, 5-bromo-2-fluoro-pyridine (1; 2.25 g, 12.80 mmol, 1.32 mL) in anhydrous THF (8 mL) was added dropwise to the reaction mixture and the resulting solution was allowed to stir at ambient temperature. After completion of the reaction as indicated by TLC, $NH_4Cl$ solution (100 mL) was added to the flask and aqueous phase was extracted twice with EtOAc (2×100 mL). Combined organic phases were washed with brine, dried (anhydrous $Na_2SO_4$), filtered and the filtrate was concentrated under reduced pressure to afford a residue that was purified by column chromatography (flash silica-gel (230-400 mesh) column, using 10% EtOAc in petroleum ether) to afford ethyl 1-(5-bromo-2-pyridyl)cyclohexanecarboxylate (3; 2.8 g, 7.26 mmol) as a colorless liquid. Yield-56.7%; LC MS: ES+ (M+H) 312.0.

Step 2. Into a 50 mL two-necked round-bottomed flask containing a well-stirred solution of ethyl 1-(5-bromo-2-pyridyl)cyclohexanecarboxylate (3; 500 mg, 1.60 mmol) in anhydrous toluene (5 mL) was added DIBAL-H (4 mL, 1.8 mmol; 1.2M toluene) at −78° C. under nitrogen atmosphere and the resulting mixture was allowed to stir at ambient temperature. After completion of the reaction as indicated by TLC, $NH_4Cl$ solution (50 mL) was added to the flask and aqueous phase was extracted with EtOAc (2×50 mL). Combined organic phases were washed with brine, dried (anhydrous $Na_2SO_4$), filtered and the filtrate was concentrated under reduced pressure to afford [1-(5-bromo-2-pyridyl) cyclohexyl]methanol (4; 400 mg, 1.11 mmol) as a colorless liquid, which was carried forward without further purification. Yield-69.3%; LC MS: ES+ (M+H) 272.0.

Step 3. Into a 20 mL microwave vial containing a mixture of [1-(5-bromo-2-pyridyl)cyclohexyl]methanol (4; 375 mg, 1.39 mmol) and 4,4,5,5-tetramethyl-2-(4,4,5,5-tetramethyl-1,3,2-dioxaborolan-2-yl)-1,3,2-dioxaborolane (422.97 mg, 1.67 mmol) in anhydrous 2-Methyl THF (8 mL) was added KOAc (408.68 mg, 4.16 mmol, 0.260 mL) at ambient temperature. The resulting mixture was degassed by bubbling nitrogen gas into the reaction mixture for 10 minutes. Subsequently, trans-dichlorobis(tricyclohexyl)phosphine Palladium (51.23 mg, 0.069 mmol) was added to the tube and again the resulting suspension was purged with nitrogen gas for additional 10 minutes. The contents were stirred at 135° C. under microwave for 1 h. After completion of the reaction as indicated by TLC, the reaction mixture was passed through a pad of Celite, the Celite bed was washed with EtOAc (50 mL) and the combined filtrates were concentrated under reduced pressure to get [6-[1-(hydroxymethyl)cyclohexyl]-3-pyridyl]boronic acid (5; 440 mg, 1.37 mmol) as a brown liquid. Yield-98.4%; LC MS: ES+ (M+H) 236.2

Step 4. Into a 25 mL sealed tube containing a mixture of tert-butyl 4-[4-[3-cyano-4-(trifluoromethylsulfonyloxy) pyrazolo[1,5-a]pyridin-6-yl]phenyl]piperazine-1-carboxylate (6; 130 mg, 0.235 mmol) and [6-[1-(hydroxymethyl) cyclohexyl]-3-pyridyl]boronic acid (5; 83.12 mg, 0.353 mmol) in a mixture of water (1 mL) and 1,4-dioxane (4 mL) was added $Na_2CO_3$ (74.95 mg, 0.707 mmol, 0.029 mL). The resulting mixture was degassed by bubbling nitrogen gas into the reaction mixture for 10 minutes. Subsequently, $Pd(dppf)\cdot Cl_2\cdot CH_2Cl_2$ (20.39 mg, 0.023 mmol) was added and again the resulting suspension was purged with nitrogen gas for additional 10 minutes. The contents were stirred at 80° C. under closed condition for 2 h. After completion of the reaction as indicated by TLC, the reaction mixture was passed through a pad of Celite, the Celite bed was washed with EtOAc (50 mL) and the combined filtrates were concentrated under reduced pressure to get crude residue which was purified by flash silica-gel (230-400 mesh) column with 5:5 EtOAc/petroleum ether to render tert-butyl 4-[4-[3-cyano-4-[6-[1-(hydroxymethyl)cyclohexyl]-3-pyridyl]pyrazolo[1,5-a]pyridin-6-yl]phenyl]piperazine-1-carboxylate (7; 90 mg, 0.135 mmol) as a brown solid. Yield-57.3%; LC MS: ES+ (M+H) 593.3.

Step 5. Into a 25 mL single-necked round-bottomed flask containing a well-stirred solution of tert-butyl 4-[4-[3-cyano-4-[6-[1-(hydroxymethyl)cyclohexyl]-3-pyridyl]pyrazolo[1,5-a]pyridin-6-yl]phenyl]piperazine-1-carboxylate (7; 90 mg, 0.151 mmol) in anhydrous $CH_2Cl_2$ (1 mL) was added 4 N HCl in 1,4-dioxane (2 mL, 0.151 mmol) at ambient temperature under nitrogen atmosphere. The reaction mixture was stirred at ambient temperature for 2 h. Excess solvents were removed from the reaction mixture under reduced pressure to get a crude mass. The crude mass was triturated with $Et_2O$ (10 mL) to yield 4-[6-[1-(hydroxymethyl)cyclohexyl]-3-pyridyl]-6-(4-piperazin-1-ylphenyl) pyrazolo[1,5-a]pyridine-3-carbonitrile (8; 90 mg, 0.148 mmol) as a brown solid, which was carried forward without further purification. Yield-97.5%; LC MS: ES+ (M+H) 493.3.

Step 6. Into a 25 mL single-necked round-bottomed flask containing a well-stirred solution of 4-[6-[1-(hydroxymethyl)cyclohexyl]-3-pyridyl]-6-(4-piperazin-1-ylphenyl) pyrazolo[1,5-a]pyridine-3-carbonitrile (8; 35 mg, 0.071 mmol) and 2-[4-[4-[(2,6-dioxo-3-piperidyl)amino]phenyl]-1-piperidyl]acetic acid (9; 26.99 mg, 0.078 mmol) in anhydrous DMF (2 mL) were added DIPEA (27.55 mg, 0.213 mmol, 0.037 mL) and HATU (40.52 mg, 0.106 mmol) at ambient temperature under nitrogen atmosphere. The resulting mixture was stirred at ambient temperature for 2 h. The progress of the reaction was monitored by UPLC. After completion of the reaction, the reaction mixture was treated with water (10 mL) and solid precipitated out was filtered and dried under vacuum. The crude solid was purified by reverse-phase column chromatography (ISCO column, Mobile solvent A: 0.1% HCOOH in water and solvent B: acetonitrile) to afford 6-[4-[4-[2-[4-[4-[(2,6-dioxo-3-piperidyl)amino]phenyl]-1-piperidyl]acetyl]piperazin-1-yl] phenyl]-4-[6-[1-(hydroxymethyl)cyclohexyl]-3-pyridyl] pyrazolo[1,5-a]pyridine-3-carbonitrile formic acid salt (Compound 21; 15 mg, 0.017 mmol) as an off-white solid. Yield-24.3%. $^1H$ NMR (400 MHz, DMSO-$d_6$). δ 10.76 (s, 1H), 9.28 (d, J=1.6 Hz, 1H), 8.85 (d, J=1.6 Hz, 1H), 8.70 (s, 1H), 8.33 (s, 1H), 8.03 (dd, J=8.0, 2.0 Hz, 1H), 7.94 (d, J=1.2 Hz, 1H), 7.83 (d, J=8.8 Hz, 2H), 7.57 (d, J=8.4 Hz, 1H), 7.10 (d, J=8.8 Hz, 2H), 6.95 (d, J=8.4 Hz, 2H), 6.60 (d, J=8.8 Hz, 2H), 5.65 (d, J=7.2 Hz, 1H), 4.55 (s, 1H), 4.27-4.24 (m, 1H), 3.77 (s, 2H), 3.63 (s, 2H), 3.44-3.37 (m, 4H), 3.25-3.18 (m, 4H), 2.93 (d, J=10.4 Hz, 2H), 2.73-2.67 (m, 1H), 2.61-2.59 (m, 2H), 2.34-2.30 (m, 3H), 2.09 (t, J=10.0 Hz, 3H), 1.89-1.81 (m, 1H), 1.72-1.69 (m, 2H), 1.58-1.53 (m, 6H), 1.29-1.22 (m, 2H). LC MS: ES+ (M+H) 819.8.

Example 94: Synthesis of tert-butyl 4-[4-[4-[6-(6-benzyl-3,6-diazabicyclo[3.1.1]heptan-3-yl)-3-pyridyl]-3-cyano-pyrazolo[1,5-a]pyridin-6-yl]phenyl]piperazine-1-carboxylate
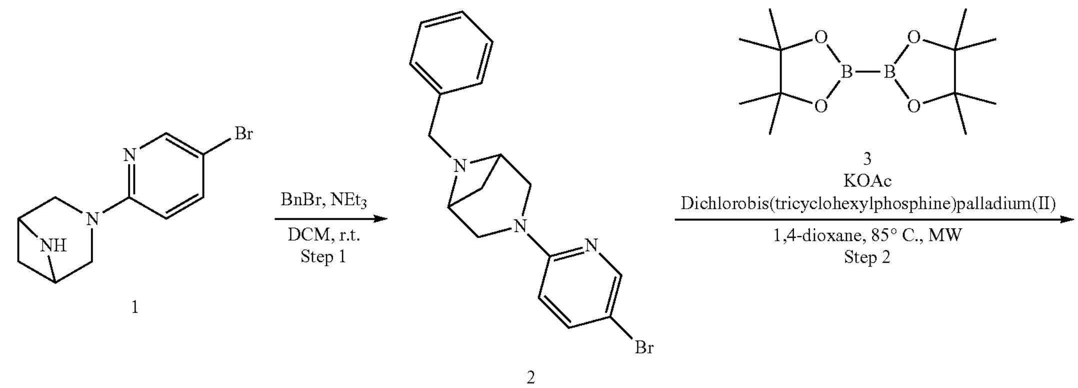
1
2
3
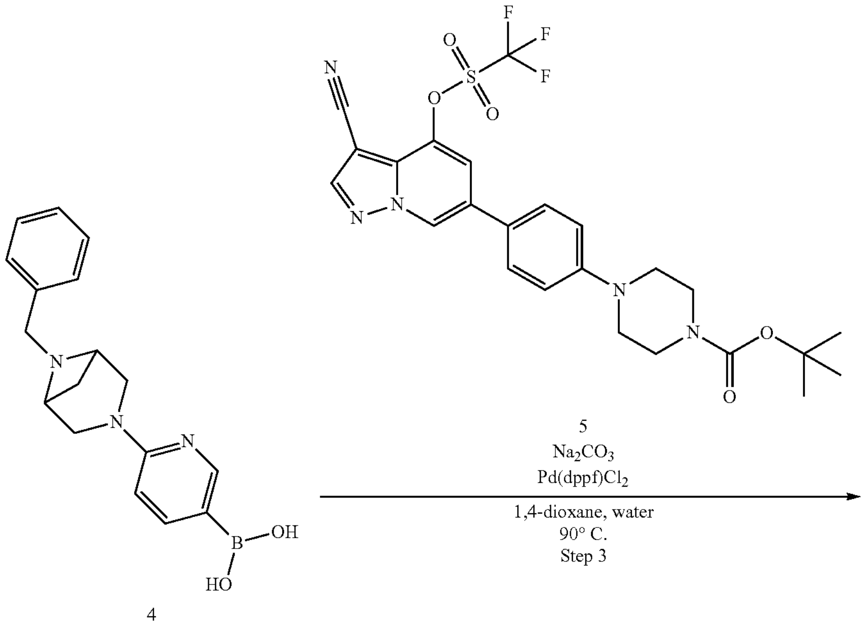
4
5

-continued

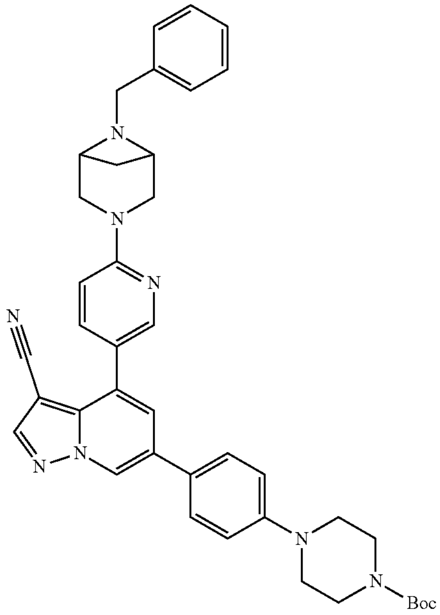

6

Step 1. An oven dried 50 mL single necked round bottom flask was charged with a solution of 3-(5-bromo-2-pyridyl)-3,6-diazabicyclo[3.1.1]heptane hydrochloric acid salt (1, 300 mg, 1.03 mmol) in DCM (10 mL), triethylamine (104.47 mg, 1.03 mmol, 143.90 µL) was added. The reaction mixture was cooled to 0° C. Benzylbromide (176.57 mg, 1.03 mmol, 122.62 µL) was added. The reaction was stirred for 3 h at room temperature. The reaction mixture was quenched with water (30 mL). The product was extracted with DCM (2×50 mL) and the combined organic layer was dried over anhydrous sodium sulfate, filtered and concentrated under reduced pressure. The crude mixture was purified by column chromatography on silica (50% Ethyl acetate/Petroleum ether) to afford 6-benzyl-3-(5-bromo-2-pyridyl)-3,6-diazabicyclo[3.1.1]heptane (2, 270 mg, 752.95 µmol) as brown solid. Yield-73%; LC MS: ES+(M+H) 344.

Step 2. An oven dried pressure tube was charged with a solution of 6-benzyl-3-(5-bromo-2-pyridyl)-3,6-diazabicyclo[3.1.1]heptane (2, 270 mg, 784.32 µmol) and Bis(pinacolato)diboron (3, 298.75 mg, 1.18 mmol) in Dioxane (7 mL) and potassium acetate (230.92 mg, 2.35 mmol, 147.09 pL) was added and stirred for 10 minutes. [1,1'-Bis(diphenylphosphino)ferrocene]dichloropalladium(II) (64.05 mg, 78.43 µmol) was added at room temperature. The reaction mixture was stirred for 3 h at 85° C. The reaction was quenched with water (15 mL). The product was extracted with ethyl acetate (2×50 mL) and the combined organic layer was dried over anhydrous sodium sulfate, filtered and concentrated under reduced pressure to afford [6-(6-benzyl-3,6-diazabicyclo[3.1.1]heptan-3-yl)-3-pyridyl]boronic acid (4, 290 mg, 215.74 µmol) as a brown oil, which was used in the next step without further purification. Yield-28%; LC MS: ES+ (M+H) 310.

Step 3. An oven dried pressure tube was charged with a solution of [6-(6-benzyl-3,6-diazabicyclo[3.1.1]heptan-3-yl)-3-pyridyl]boronic acid (4, 290 mg, 938 µmol) in 1,4-dioxane (6 mL) and tert-butyl 4-[4-[3-cyano-4-(trifluoromethylsulfonyloxy)pyrazolo[1,5-a]pyridin-6-yl]phenyl]piperazine-1-carboxylate (5, 362.14 mg, 656.6 µmol) and 2M aqueous solution of sodium carbonate were added. The reaction mixture was purged with nitrogen for 5 minutes, and [1,1'-Bis(diphenylphosphino)ferrocene]dichloropalladium(II) (76.60 mg, 93.80 µmol) was added. The reaction mixture was heated to 90° C. for 2 h. The reaction mixture was filtered through celite and the filtrate was concentrated under reduced pressure. The crude mixture was purified by column chromatography on silica gel (80% Ethyl acetate/petroleum ether) to afford tert-butyl 4-[4-[4-[6-(6-benzyl-3,6-diazabicyclo[3.1.1]heptan-3-yl)-3-pyridyl]-3-cyano-pyrazolo[1,5-a]pyridin-6-yl]phenyl]piperazine-1-carboxylate (6, 220 mg, 240.85 µmol, 25.68% yield) as brown solid. Yield-26%; LC MS: ES+ (M+H) 668.

Example 95: Synthesis of 4-(6-(6-Benzyl-3,6-diazabicyclo[3.1.1]heptan-3-yl)pyridin-3-yl)-6-(4-(4-(2-(4-(4-((2,6-dioxopiperidin-3-yl)amino)phenyl)piperidin-1-yl)acetyl)piperazin-1-yl)phenyl)pyrazolo[1,5-a]pyridine-3-carbonitrile (Compound 22)
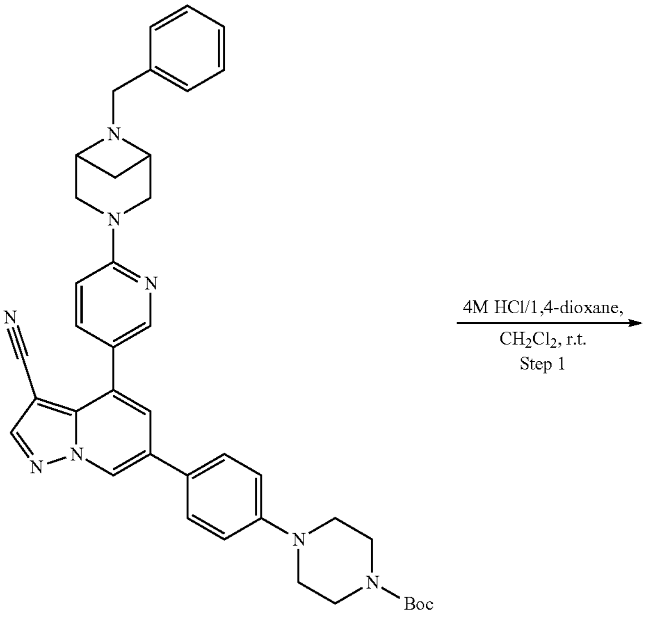
1
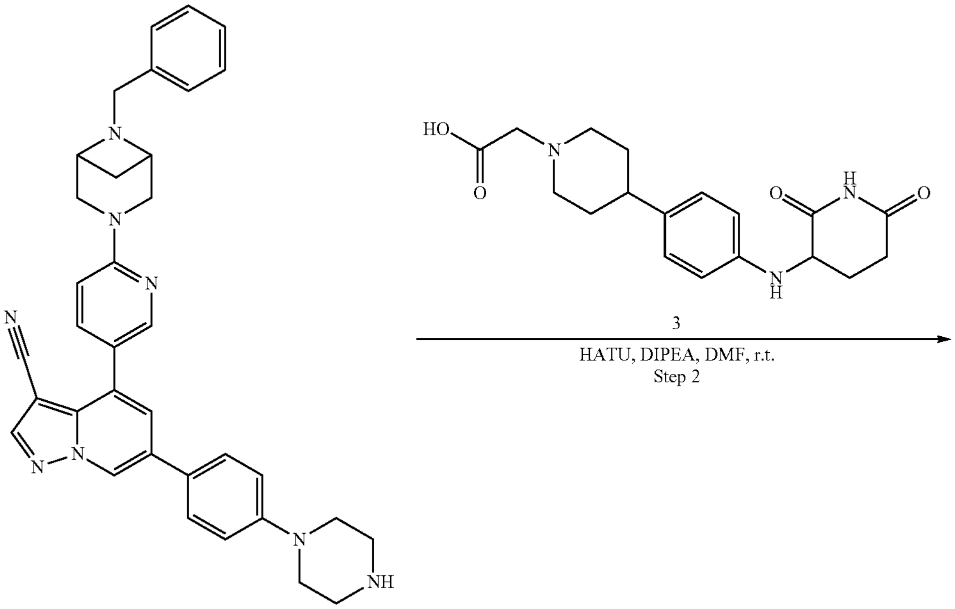
3
2

-continued

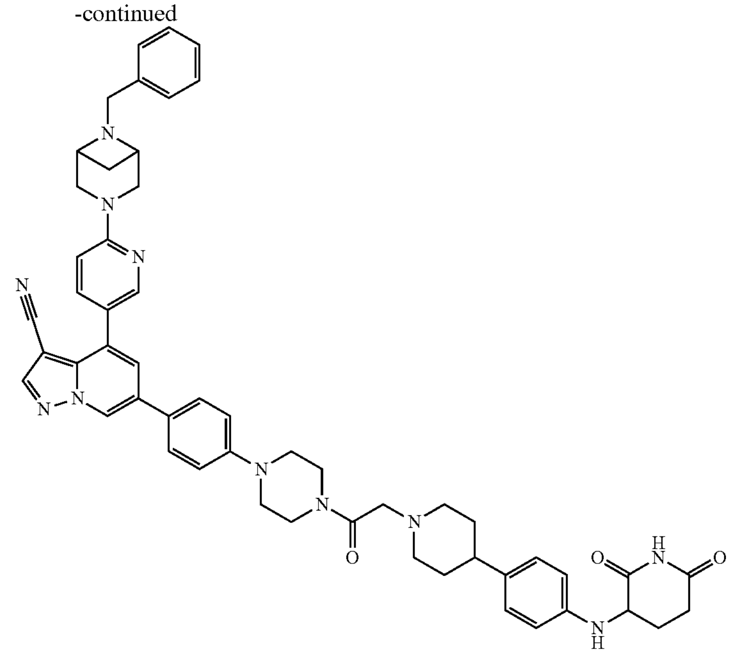

Compound 22

Step 1. Into a 25 mL single-necked round-bottomed flask containing a well-stirred solution of tert-butyl 4-[4-[4-[6-(6-benzyl-3,6-diazabicyclo[3.1.1]heptan-3-yl)-3-pyridyl]-3-cyano-pyrazolo[1,5-a]pyridin-6-yl]phenyl]piperazine-1-carboxylate (1; 220 mg, 0.329 mmol) in anhydrous CH2C12 (5 mL) was added HCl (2 mL; 4 N 1,4-dioxane) at ambient temperature. The resulting mixture was stirred at ambient temperature for 2 h and found complete. Excess solvents were removed from the reaction mixture under reduced pressure to get a crude mass which was co-distilled with $CH_2Cl_2$ to get 4-[6-(6-benzyl-3,6-diazabicyclo[3.1.1]heptan-3-yl)-3-pyridyl]-6-(4-piperazin-1-ylphenyl)pyrazolo[1,5-a]pyridine-3-carbonitrile hydrochloric acid salt (2; 175 mg, 0.229 mmol) as a brown solid, which was carried forward without further purification. Yield-69.6%; LC MS: ES+ (M+H) 567.0.

Step 2. To a well-stirred mixture of 4-[6-(6-benzyl-3,6-diazabicyclo[3.1.1]heptan-3-yl)-3-pyridyl]-6-(4-piperazin-1-ylphenyl)pyrazolo[1,5-a]pyridine-3-carbonitrile hydrochloric acid salt (2; 59.07 mg, 0.104 mmol) and 2-[4-[4-[(2,6-dioxo-3-piperidyl)amino]phenyl]-1-piperidyl]acetic acid hydrochloric acid salt (3; 30 mg, 0.086 mmol) in anhydrous DMF (3 mL) taken in 25-mL single-necked round-bottomed flask was added DIPEA (33.68 mg, 0.260 mmol, 0.045 mL) and the resulting solution was stirred for 15 minutes at ambient temperature under nitrogen atmosphere. HATU (49.54 mg, 0.130 mmol) was added to the reaction mixture and stirring was continued at ambient temperature for 2 h. The progress of the reaction was monitored by UPLC. After completion, the reaction mixture was treated with water (1 mL) and solid precipitated out was filtered through a filter paper. Solid on the filter was washed with water and filtered solid was dried under vacuum for 3 h to afford crude mass. The crude mixture was purified by preparative reverse phase column chromatography (Column: SUNFIRE C18, Mobile phase: A: 0.1% formic acid in water, B: acetonitrile) to yield 4-[6-(6-benzyl-3,6-diazabicyclo[3.1.1]heptan-3-yl)-3-pyridyl]-6-[4-[4-[2-[4-[4-[(2,6-dioxo-3-piperidyl)amino]phenyl]-1-piperidyl]acetyl]piperazin-1-yl]phenyl]pyrazolo[1,5-a]pyridine-3-carbonitrile formic acid salt (Compound 22; 7.55 mg, 0.007 mmol) as a brown-coloured solid. Yield-8.6%. $^1$H NMR (400 MHz, DMSO-$d_6$). δ 10.70 (s, 1H), 9.13 (d, J=1.2 Hz, 1H), 8.63 (s, 1H), 8.43 (d, J=2.4 Hz, 1H), 8.19 (s, 2H), 7.86 (dd, J=8.8, 2.4 Hz, 1H), 7.74-7.72 (m, 3H), 7.29-7.14 (m, 5H), 7.04 (d, J=8.8 Hz, 2H), 6.88 (d, J=8.4 Hz, 2H), 6.75 (d, J=8.8 Hz, 1H), 6.53 (d, J=8.8 Hz, 2H), 5.58 (d, J=7.2 Hz, 1H), 4.21-4.15 (m, 1H), 6.69-6.63 (m, 6H), 3.55-3.48 (m, 6H), 3.28-3.14 (m, 6H), 2.85 (d, J=10.8 Hz, 3H), 2.66-2.63 (m, 1H), 2.05-1.99 (m, 3H), 1.80-1.75 (m, 1H), 1.64-1.62 (m, 2H), 1.55-1.49 (m, 3H). LC MS: ES+(M+H) 895.4.

Example 96: Synthesis of N-(1-(5-(3-Cyano-6-(4-(4-(2-(4-(4-((2,6-dioxopiperidin-3-yl)amino)-2-fluorophenyl)piperidin-1-yl)acetyl)piperazin-1-yl)phenyl)pyrazolo[1,5-a]pyridin-4-yl)pyridin-2-yl)-4-methylpiperidin-4-yl)-2-phenylacetamide) (Compound 23)
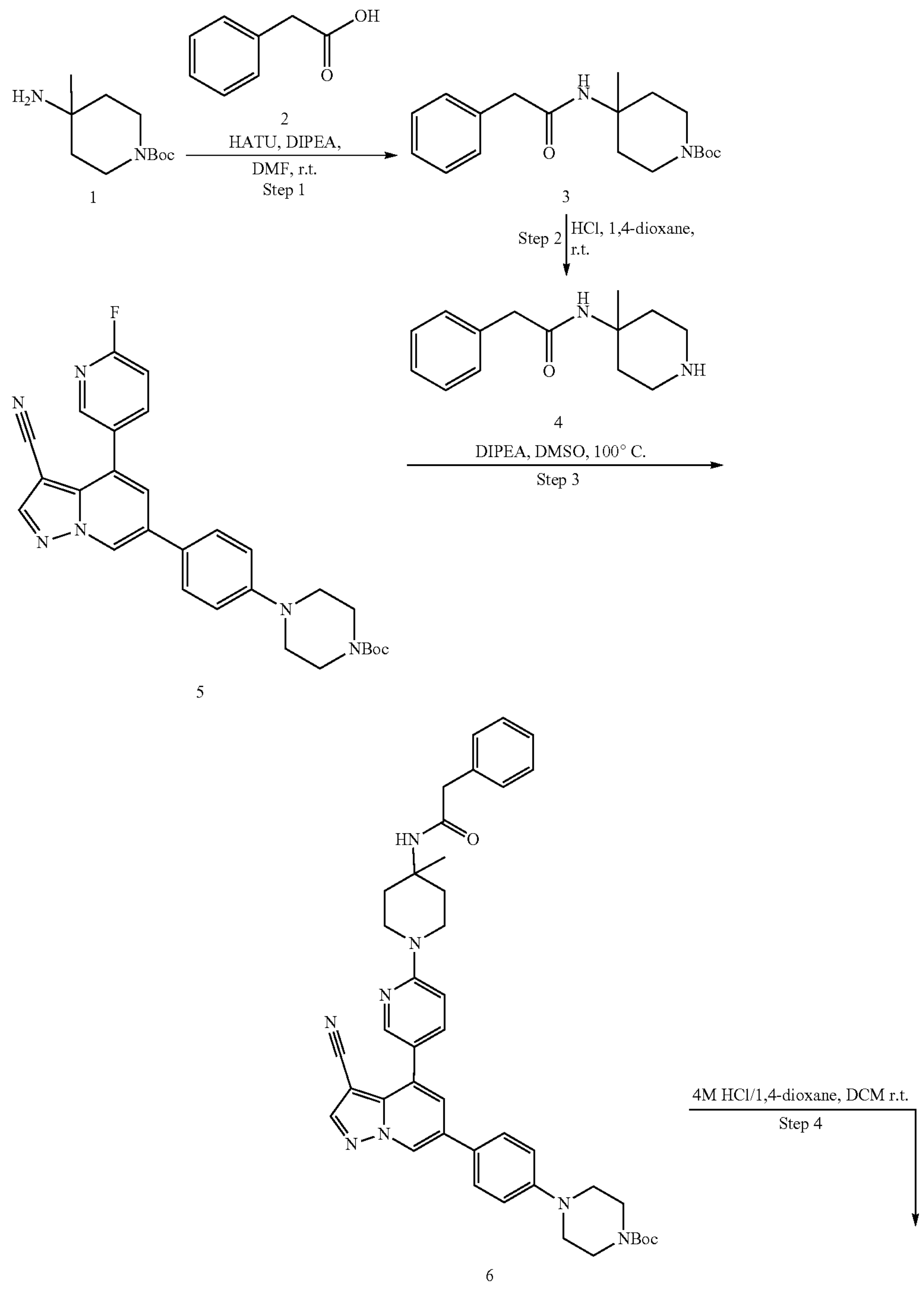

-continued

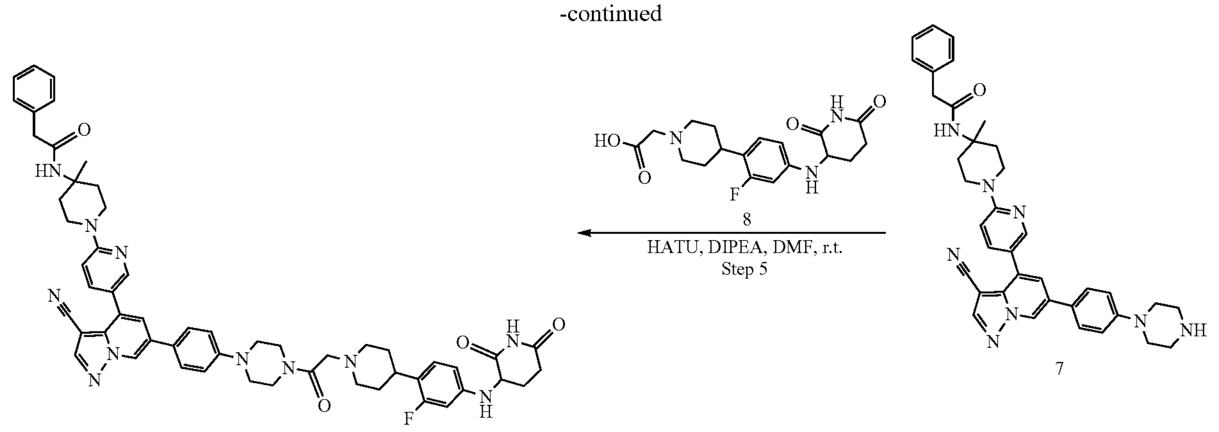

8

7

Compound 23

Step 1. Into a 50 mL single-necked round-bottomed flask containing a well-stirred solution of 2-phenylacetic acid (2; 350 mg, 2.57 mmol, 0.318 mL) and tert-butyl 4-amino-4-methyl-piperidine-1-carboxylate (1; 716.19 mg, 3.34 mmol)) in anhydrous DMF (6 mL) was added DIPEA (996.75 mg, 7.71 mmol, 1.34 mL) and the resulting solution was stirred for 15 minutes at ambient temperature under nitrogen atmosphere. HATU (1.27 g, 3.34 mmol) was added to the reaction mixture and stirring was continued at ambient temperature for 2 h. The progress of the reaction was monitored by UPLC. After completion, the reaction mixture was quenched with cold water and solid precipitated out was filtered. The crude solid was purified by column chromatography (flash silica-gel (230-400 mesh), gradient of 20%-100% EtOAc in petroleum ether) to afford tert-butyl 4-methyl-4-[(2-phenylacetyl)amino]piperidine-1-carboxylate (3; 460 mg, 1.37 mmol) as a pale yellow solid. Yield-53.3%; LC MS: ES+ (M+H) 277.0.

Step 2. Into a 50 mL single-necked round-bottomed flask containing a well-stirred solution of tert-butyl 4-methyl-4-[(2-phenylacetyl)amino]piperidine-1-carboxylate (3; 160 mg, 0.481 mmol) in anhydrous $CH_2Cl_2$ (5 mL) was added HCl (0.219 mL; 4 N 1,4-dioxane) at ambient temperature under nitrogen atmosphere. The resulting mixture was stirred at ambient temperature for 2 h and found complete. Excess solvents were removed from the reaction mixture under reduced pressure to get a crude mass. Crude product was washed with petroleum ether to give N-(4-methyl-4-piperidyl)-2-phenyl-acetamide (4; 104 mg, 0.377 mmol) as a pale brown solid, which was carried forward without further purification. Yield-78.5%; LC MS: ES+ (M+H) 133.2.

Step 3: Into a 25 mL sealed-tube reactor containing a well-stirred solution of tert-butyl 4-[4-[3-cyano-4-(6-fluoro-3-pyridyl)pyrazolo[1,5-a]pyridin-6-yl]phenyl]piperazine-1-carboxylate (5; 100 mg, 0.2 mmol) and N-(4-methyl-4-piperidyl)-2-phenyl-acetamide (4; 55.92 mg, 0.240 mmol) in anhydrous DMSO (3 mL) was added DIPEA (77.77 mg, 0.601 mmol, 0.104 mL) at ambient temperature. The reaction mixture was stirred at 100° C. for 16 h. After completion of the reaction as indicated by TLC, the reaction mixture was cooled to room temperature. The reaction mixture was quenched with cold water (10 mL) and solid precipitated out was filtered through a filter paper. The crude solid was purified by column chromatography (flash silica gel (230-400 mesh), gradient of 0%-50% EtOAc in petroleum ether) to give a tert-butyl 4-[4-[3-cyano-4-[6-[4-methyl-4-[(2-phenylacetyl)amino]-1-piperidyl]-3-pyridyl]pyrazolo[1,5-a]pyridin-6-yl]phenyl]piperazine-1-carboxylate (6; 45 mg, 0.054 mmol). Yield-17.1%; LC MS: ES+ (M+H) 711.3.

Step 4. Into a 50 mL single-necked round-bottomed flask containing a well-stirred solution of tert-butyl 4-[4-[3-cyano-4-[6-[4-methyl-4-[(2-phenylacetyl)amino]-1-piperidyl]-3-pyridyl]pyrazolo[1,5-a]pyridin-6-yl]phenyl]piperazine-1-carboxylate (6; 135 mg, 0.189 mmol) in anhydrous $CH_2Cl_2$ (5 mL) was added HCl (0.086 mL; 4 N 1,4-dioxane) at 0° C. under nitrogen atmosphere. The resulting mixture was stirred at ambient temperature for 2 h and found complete. Excess solvents were removed from the reaction mixture under reduced pressure to get a crude mass. Crude product was washed with petroleum ether to gave N-[1-[5-[3-cyano-6-(4-piperazin-1-ylphenyl)pyrazolo[1,5-a]pyridin-4-yl]-2-pyridyl]-4-methyl-4-piperidyl]-2-phenyl-acetamide (7; 125 mg, 0.148 mmol) as a pale brown solid. Yield-78.3%; LC MS: ES+ (M+H) 611.3.

Step 5. Into a 50 mL single-necked round-bottomed flask containing a well-stirred solution of 2-[4-[4-[(2,6-dioxo-3-piperidyl)amino]-2-fluoro-phenyl]-1-piperidyl]acetic acid hydrochloric acid (8; 75 mg, 0.206 mmol) and N-[1-[5-[3-cyano-6-(4-piperazin-1-ylphenyl)pyrazolo[1,5-a]pyridin-4-yl]-2-pyridyl]-4-methyl-4-piperidyl]-2-phenyl-acetamide (7; 138.66 mg, 0.227 mmol) in anhydrous DMF (3 mL) was added DIPEA (80.02 mg, 0.619 mmol, 0.107 mL) and the resulting solution was stirred for 15 minutes at ambient temperature under nitrogen atmosphere. HATU (102.02 mg, 0.268 mmol) was added to the reaction mixture and stirring was continued at ambient temperature for 2 h. The progress of the reaction was monitored by UPLC. After completion, the reaction mixture was treated with water (1 mL) and solid precipitated out was filtered. The filtered solid was dried under vacuum to get crude mixture. The crude mixture was purified by reverse phase column chromatography (Column: SUNFIRE OBD C18 (100×30)MM 5 m, Mobile phase: A: 0.1% $NH_4OAc$ in water, B: acetonitrile) to yield N-[1-[5-[3-cyano-6-[4-[4-[2-[4-[4-[(2,6-dioxo-3-piperidyl)amino]-2-fluoro-phenyl]-1-piperidyl]acetyl]piperazin-1-yl]phenyl]pyrazolo[1,5-a]pyridin-4-yl]-2-pyridyl]-4-methyl-4-piperidyl]-2-phenyl-acetamide (Compound 23; 24.5 mg, 0.024 mmol) as a pale white solid. Yield-11.9%. $^1H$ NMR (400 MHz, DMSO-$d_6$). δ 10.78 (s, 1H), 9.19 (d, J=1.2 Hz, 1H), 8.68 (s, 1H), 8.42 (d, J=2.8 Hz, 1H), 7.85-7.73 (m, 5H), 7.31-7.28 (m, 4H), 7.24-7.19 (m, 1H), 7.10 (d, J=9.2 Hz, 2H), 6.98 (d, J=8.8 Hz, 2H), 6.46-6.42 (m, 2H), 6.00 (d, J=7.6 Hz, 1H), 4.32-4.28 (m, 1H), 3.99 (d, J=13.6 Hz, 2H), 3.76 (s, 2H), 3.63 (s, 2H), 3.45 (s, 2H), 3.22-3.18 (m, 6H), 2.94 (d, J=9.6 Hz, 2H), 2.73-2.67 (m, 1H), 2.60-2.56 (m, 2H), 2.19-2.06 (m, 6H), 1.90-1.84 (m, 2H), 1.65 (s, 4H), 1.49 (t, J=10.0 Hz, 2H), 1.32 (s, 3H). LC MS: ES+ (M+H) 957.3.

Example 97: Synthesis of 6-(4-(4-(2-(4-(4-((2,6-Dioxopiperidin-3-yl)amino)phenyl)piperidin-1-yl)acetyl)piperazin-1-yl)phenyl)-4-(6-morpholinopyridin-3-yl)pyrazolo[1,5-a]pyridine-3-carbonitrile (Compound 24)
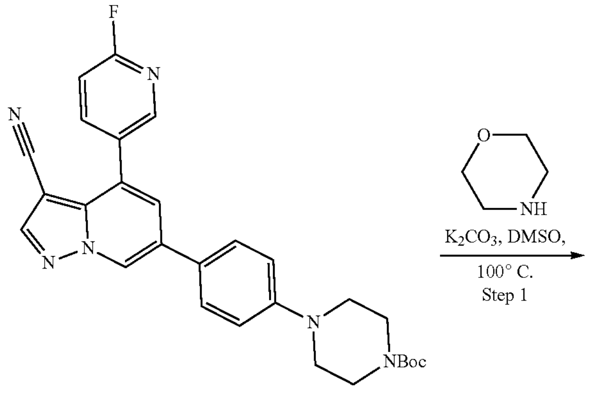
1
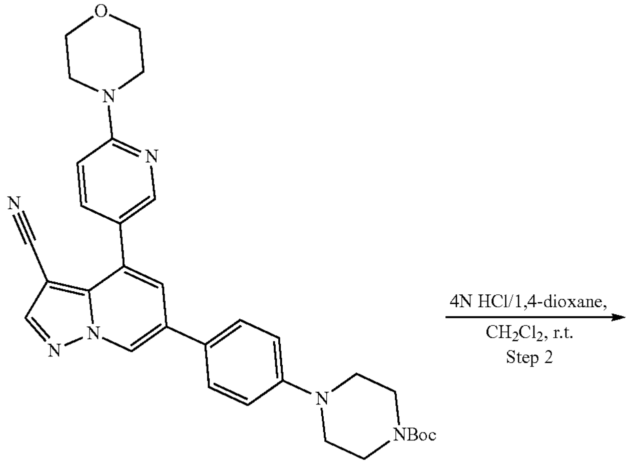
2
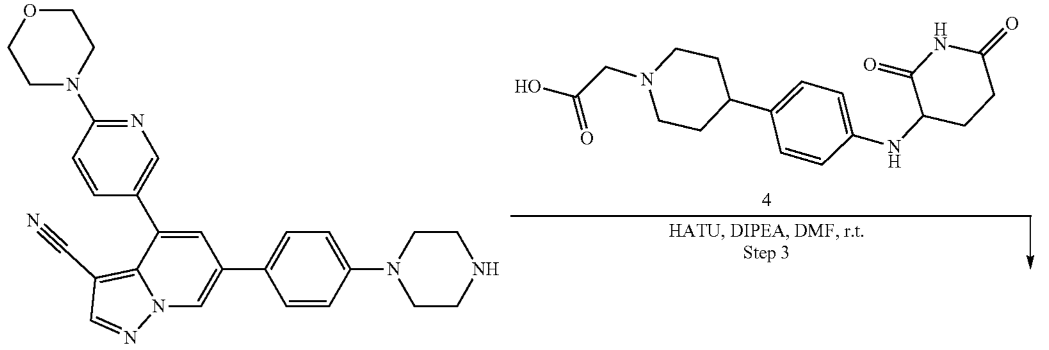
4
3

-continued

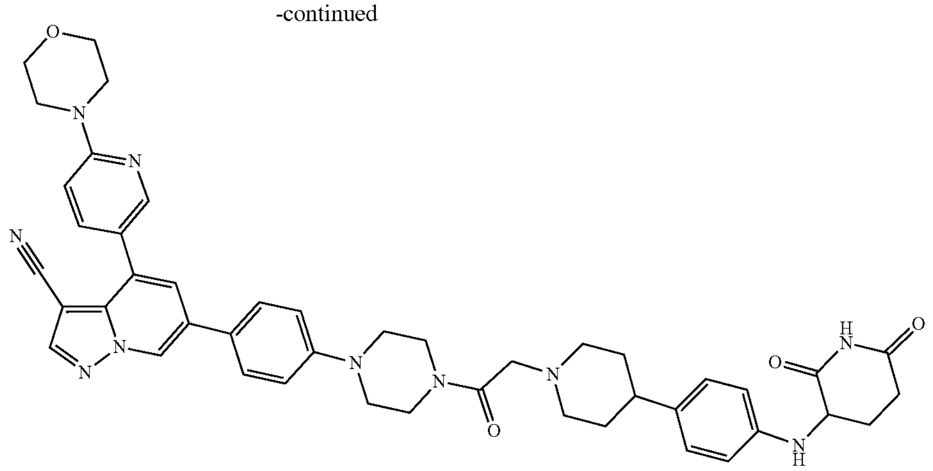

Compound 24

Step 1. Into a 10 mL sealed-tube reactor containing a well-stirred solution of tert-butyl 4-[4-[3-cyano-4-(6-fluoro-3-pyridyl)pyrazolo[1,5-a]pyridin-6-yl]phenyl]piperazine-1-carboxylate (1; 120 mg, 0.194 mmol) and morpholine (20.38 mg, 0.233 mmol, 0.020 mL) in anhydrous DMSO (2 mL) was added anhydrous $K_2CO_3$ (134.73 mg, 0.974 mmol, 0.059 mL) at ambient temperature. The reaction mixture was stirred at 100° C. for 16 h. The progress of the reaction was monitored by LCMS. After completion, the reaction mixture was added into ice-water (6 mL). A solid precipitated out and was filtered. The filtered solid was dried well under vacuum to afford tert-butyl-4-[4-[3-cyano-4-(6-morpholino-3-pyridyl)pyrazolo[1,5-a]pyridin-6-yl]phenyl]piperazine-1-carboxylate (2; 100 mg, 0.168 mmol) as a yellow solid, which was carried forward without further purification. Yield-86.3%; LC MS: ES+ (M+H) 566.3.

Step 2. Into a 25 mL single-necked round-bottomed flask containing a well-stirred solution of tert-butyl-4-[4-[3-cyano-4-(6-morpholino-3-pyridyl)pyrazolo[1,5-a]pyridin-6-yl]phenyl]piperazine-1-carboxylate (2; 100 mg, 0.176 mmol) in anhydrous $CH_2Cl_2$ (3 mL) was added HCl (3 mL, 4 N 1,4-dioxane) at 0° C. The resulting mixture was stirred at ambient temperature for 2 h. The progress of the reaction was monitored by LCMS. After completion, excess solvents were removed from the reaction mixture under reduced pressure to get a crude mass which was triturated with $Et_2O$ (2×5 mL) to give 4-(6-morpholino-3-pyridyl)-6-(4-piperazin-1-ylphenyl)pyrazolo[1,5-a]pyridine-3-carbonitrile (3; 80 mg, 0.135 mmol) as an off-white solid, which was carried forward without further purification. Yield-77%; LC MS: ES+ (M+H) 466.2.

Step 3. Into a 25 mL single-necked round-bottomed flask containing a well-stirred solution of 4-(6-morpholino-3-pyridyl)-6-(4-piperazin-1-ylphenyl)pyrazolo[1,5-a]pyridine-3-carbonitrile (3; 101.23 mg, 0.201 mmol) and 2-[4-[4-[(2,6-dioxo-3-piperidyl)amino]phenyl]-1-piperidyl] acetic acid (4; 70 mg, 0.183 mmol) in anhydrous DMF (1 mL) were added DIPEA (118.46 mg, 0.916 mmol, 0.159 mL) and HATU (83.64 mg, 0.219 mmol) at 0° C. under nitrogen atmosphere. The reaction mixture was stirred at ambient temperature for 2 h. The progress of the reaction was monitored by LCMS. After completion, the reaction mixture was treated with water (5 mL) and extracted with EtOAc (3×5 mL). The combined organic phases were washed with brine (5 mL), dried (anhydrous $Na_2SO_4$), filtered, and the filtrate was concentrated in vacuo to get crude mixture. The resulting crude mixture was purified by Biotage (30 g) reverse phase purification (0.1M HCOOH/water) to afford 6-[4-[4-[2-[4-[4-[(2,6-dioxo-3-piperidyl)amino]phenyl]-1-piperidyl]acetyl]piperazin-1-yl]phenyl]-4-(6-morpholino-3-pyridyl)pyrazolo[1,5-a]pyridine-3-carbonitrile formic acid salt (Compound 24; 13.51 mg, 0.016 mmol) as an off-white solid. Yield-9.0%. $^1$H NMR (400 MHz, DMSO-$d_6$). δ 10.77 (s, 1H), 9.19 (s, 1H), 8.68 (s, 1H), 8.45 (d, J=2.0 Hz, 1H), 8.89 (dd, J=8.8, 2.0 Hz, 1H), 7.79-7.78 (m, 3H), 7.09 (d, J=8.4 Hz, 2H), 6.99-6.94 (m, 3H), 6.59 (d, J=8.4 Hz, 2H), 5.65 (d, J=7.2 Hz, 1H), 4.28-4.22 (m, 1H), 3.75-3.73 (m, 7H), 3.65-3.62 (m, 7H), 3.22 (s, 4H), 2.94-2.92 (m, 2H), 2.73-2.68 (m, 1H), 2.57-2.55 (m, 1H), 2.30-2.27 (m, 1H), 2.13-2.08 (m, 3H), 1.88-1.83 (m, 1H), 1.71-1.69 (m, 2H), 1.61-1.53 (m, 2H). LC MS: ES+(M+H) 793.3.

Example 98: Synthesis of N-(tert-butyl)-1-(5-(3-cyano-6-(4-(4-(2-(4-(4-((2,6-dioxopiperidin-3-yl)amino)-2-fluorophenyl)piperidin-1-yl)acetyl)piperazin-1-yl)phenyl)pyrazolo[1,5-a]pyridin-4-yl)pyridin-2-yl)-4-methylpiperidine-4-carboxamide (Compound 25)
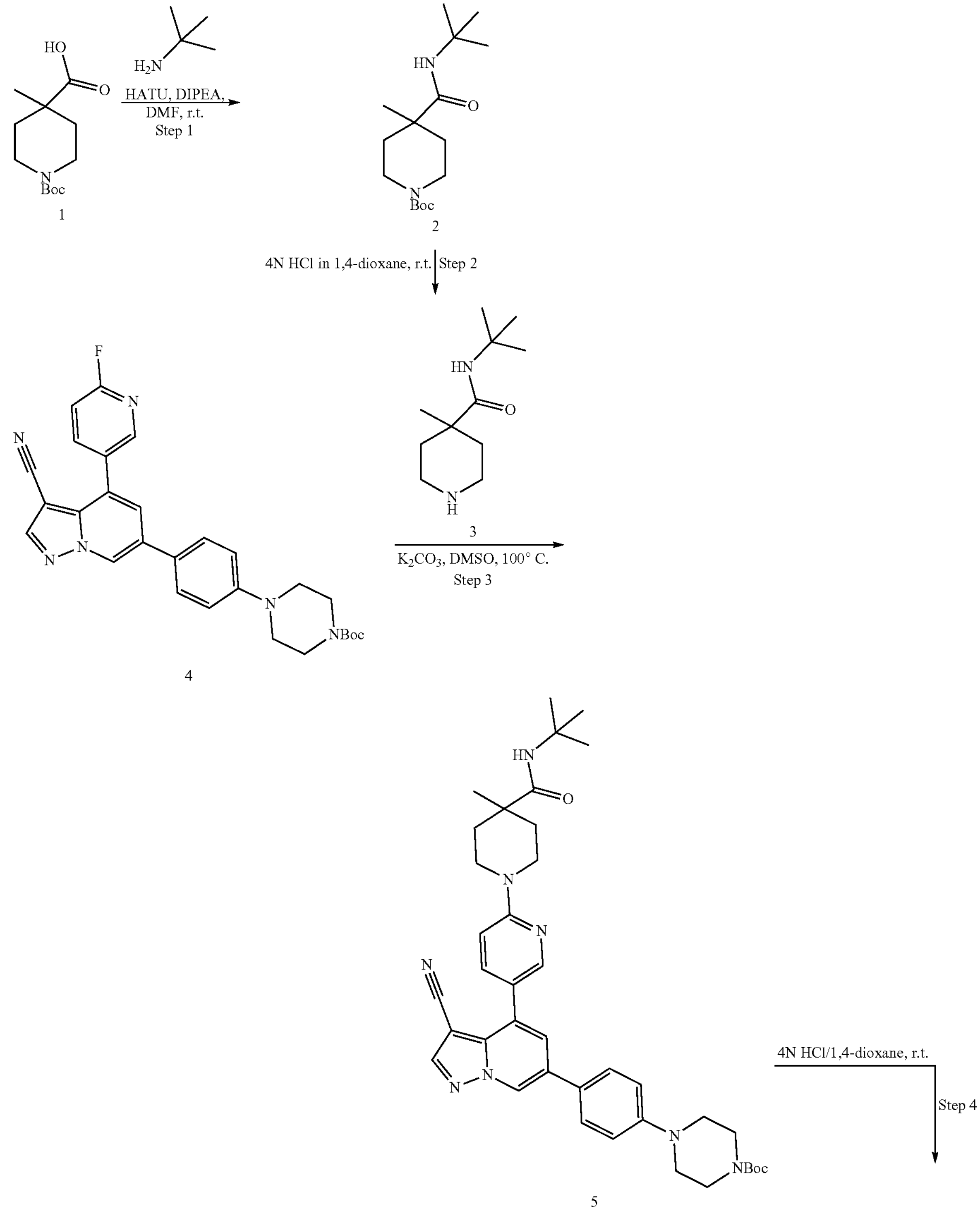

-continued

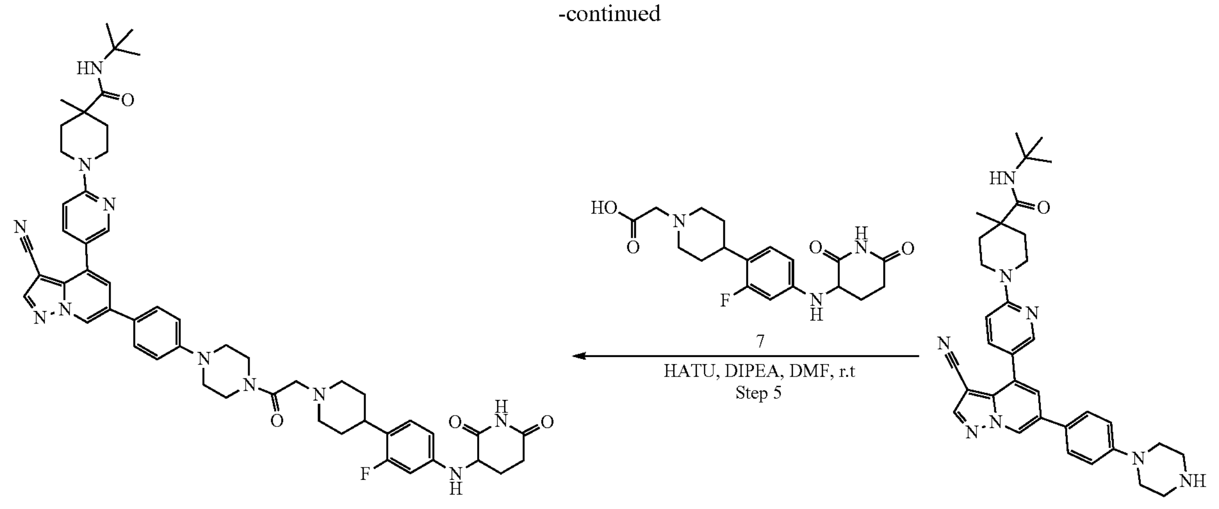

Compound 25

6

Step 1. Into a 50 mL single-necked round-bottomed flask containing a well-stirred solution of 1-tert-butoxycarbonyl-4-methyl-piperidine-4-carboxylic acid (1; 500 mg, 2.06 mmol;) and 2-methylpropan-2-amine (225.45 mg, 3.08 mmol, 0.323 mL) in anhydrous DMF (5 mL) were added DIPEA (1.33 g, 10.28 mmol, 1.79 mL) followed by HATU (1.17 g, 3.08 mmol) at 0° C. under nitrogen atmosphere. The resulting reaction mixture was stirred for 2 h at ambient temperature. The progress of the reaction was monitored by LCMS. After completion, the reaction mixture was diluted with water (75 mL) and extracted with EtOAc (3×75 mL). The combined organic layers were washed with brine (25 mL), dried (anhydrous $Na_2SO_4$), filtered, and the filtrate was concentrated under reduced pressure to get a crude residue. The resulting crude was purified by column chromatography (flash silica-gel (230-400 mesh), gradient of 40%-70% EtOAc in petroleum ether) to afford tert-butyl 4-(tert-butylcarbamoyl)-4-methyl-piperidine-1-carboxylate (2; 570 mg, 1.91 mmol) as an off-white semisolid. Yield-93%; LC MS: ES+ (M+H-$CO_2$tBu) 199.1.

Step 2. Into a 50 mL single-necked round-bottomed flask containing a well-stirred solution of tert-butyl 4-(tert-butylcarbamoyl)-4-methyl-piperidine-1-carboxylate (2; 570 mg, 1.91 mmol) in anhydrous $CH_2Cl_2$ (5 mL) was added HCl (5 mL; 4 N/1,4-dioxane) at 0° C., and then reaction mixture was stirred at ambient temperature for 2 h. The progress of the reaction was monitored by LCMS. After completion, excess solvent was removed under high vacuo and the mixture was triturated twice with $Et_2O$ (2×10 mL) to afford N-tert-butyl-4-methyl-piperidine-4-carboxamide (3; 460 mg, 1.65 mmol) as an off-white fluffy solid, which was carried forward without purification. Yield-86.4%; LC MS: ES+ (M+H) 199.1.

Step 3. Into a 10 mL sealed-tube reactor containing a well-stirred solution of tert-butyl 4-[4-[3-cyano-4-(6-fluoro-3-pyridyl)pyrazolo[1,5-a]pyridin-6-yl]phenyl]piperazine-1-carboxylate (4; 80 mg, 0.134 mmol) and N-tert-butyl-4-methyl-piperidine-4-carboxamide (3; 37.97 mg, 0.161 mmol) in anhydrous DMSO (2 mL) was added anhydrous $K_2CO_3$ (93.14 mg, 0.673 mmol, 0.040 mL) at ambient temperature. The reaction mixture was stirred at 100° C. for 16 h. The progress of the reaction was monitored by LCMS. After completion, the reaction mixture was added ice-water (6 mL) and solid precipitated out was filtered. The filtered solid was dried well under vacuum to afford tert-butyl 4-[4-[4-[6-[4-(tert-butylcarbamoyl)-4-methyl-1-piperidyl]-3-pyridyl]-3-cyano-pyrazolo[1,5-a]pyridin-6-yl]phenyl]piperazine-1-carboxylate (5; 80 mg, 0.077 mmol) as a brown solid, which was carried forward without further purification. Yield-57%; LC MS: ES+(M+H) 677.3.

Step 4. Into a 50 mL single-necked round-bottomed flask containing a well-stirred solution of tert-butyl 4-[4-[4-[6-[4-(tert-butylcarbamoyl)-4-methyl-1-piperidyl]-3-pyridyl]-3-cyano-pyrazolo[1,5-a]pyridin-6-yl]phenyl]piperazine-1-carboxylate (5; 70 mg, 0.103 mmol) in anhydrous $CH_2Cl_2$ (3 mL) was added HCl (3 mL; 4 N/1,4-dioxane) at 0° C. and then reaction mixture was stirred at ambient temperature for 2 h. The progress of reaction was monitored by LCMS. After completion, excess solvents were removed under high vacuo to get a crude residue which was triturated twice with $Et_2O$ to afford N-tert-butyl-1-[5-[3-cyano-6-(4-piperazin-1-ylphenyl)pyrazolo[1,5-a]pyridin-4-yl]-2-pyridyl]-4-methyl-piperidine-4-carboxamide hydrochloric acid salt (6; 70 mg, 0.055 mmol) as a brown-coloured solid, which was carried forward without further purification. Yield-53%; LC MS: ES+ (M+H) 577.0.

Step 5. To a well-stirred solution of a mixture of 2-[4-[4-[(2,6-dioxo-3-piperidyl)amino]-2-fluoro-phenyl]-1-piperidyl]acetic acid (7; 35 mg, 0.087 mmol) and N-tert-butyl-1-[5-[3-cyano-6-(4-piperazin-1-ylphenyl)pyrazolo[1,5-a]pyridin-4-yl]-2-pyridyl]-4-methyl-piperidine-4-carboxamide hydrochloric acid salt (6; 53.68 mg, 0.087 mmol) in anhydrous DMF (1 mL) taken in 25-mL single-necked round-bottomed flask were added DIPEA (118.46 mg, 0.916 mmol, 0.159 mL) and HATU (83.64 mg, 0.219 mmol) at 0° C. The reaction mixture was stirred at ambient temperature for 2 h. The progress of the reaction was monitored by LCMS. After completion, the reaction mixture was treated with water (5 mL) and extracted with EtOAc (3×5 mL). The combined organic phases were washed with brine (5 mL), dried (anhydrous $Na_2SO_4$), filtered and the filtrate was concentrated in vacuo to get crude mixture. The resulting crude mixture was purified by column chromatography (Biotage (30 g) reverse phase purification, 0.1 M HCOOH in water) to afford N-tert-butyl-1-[5-[3-cyano-6-[4-[4-[2-[4-[4-[(2,6-dioxo-3-piperidyl)amino]-2-fluoro-phenyl]-1-piperidyl]acetyl]piperazin-1-yl]phenyl]pyrazolo[1,5-a]pyridin-4-yl]-2-pyridyl]-4-methyl-piperidine-4- carboxamide (Compound 25; 4.52 mg, 0.004 mmol) as an off-white solid. Yield-5.1%. $^1$H NMR (400 MHz, DMSO-$d_6$). δ 10.79 (s, 1H), 9.18 (d, J=1.6 Hz, 1H), 8.68 (s, 1H), 8.41 (d, J=2.4 Hz, 1H), 7.84-7.79 (m, 4H), 7.10 (d, J=9.2 Hz, 2H), 6.99-6.96 (m, 2H), 6.82 (s, 1H), 6.48-6.43 (m, 2H), 6.04 (d, J=8.0 Hz, 1H), 4.32-428 (m, 1H), 3.93-3.89 (m, 2H), 3.69-3.65 (m, 4H), 3.27-3.22 (m, 12H), 2.73-2.67 (m, 2H), 2.10-2.07 (m, 3H), 1.88-1.74 (m, 6H), 1.42-1.36 (m, 2H), 1.29 (s, 9H), 1.15 (s, 3H). LC MS: ES+ (M+H) 922.9.
Example 99: Synthesis of 6-[4-[4-[2-[1-[4-[(2,6-Dioxo-3-piperidyl)amino]-2-fluoro-phenyl]-4-hydroxy-4-piperidyl]acetyl]piperazin-1-yl]phenyl]-4-[6-[4-[2-(5-fluoro-2-pyridyl)acetyl]piperazin-1-yl]-3-pyridyl]pyrazolo[1,5-a]pyridine-3-carbonitrile (Compound 26)
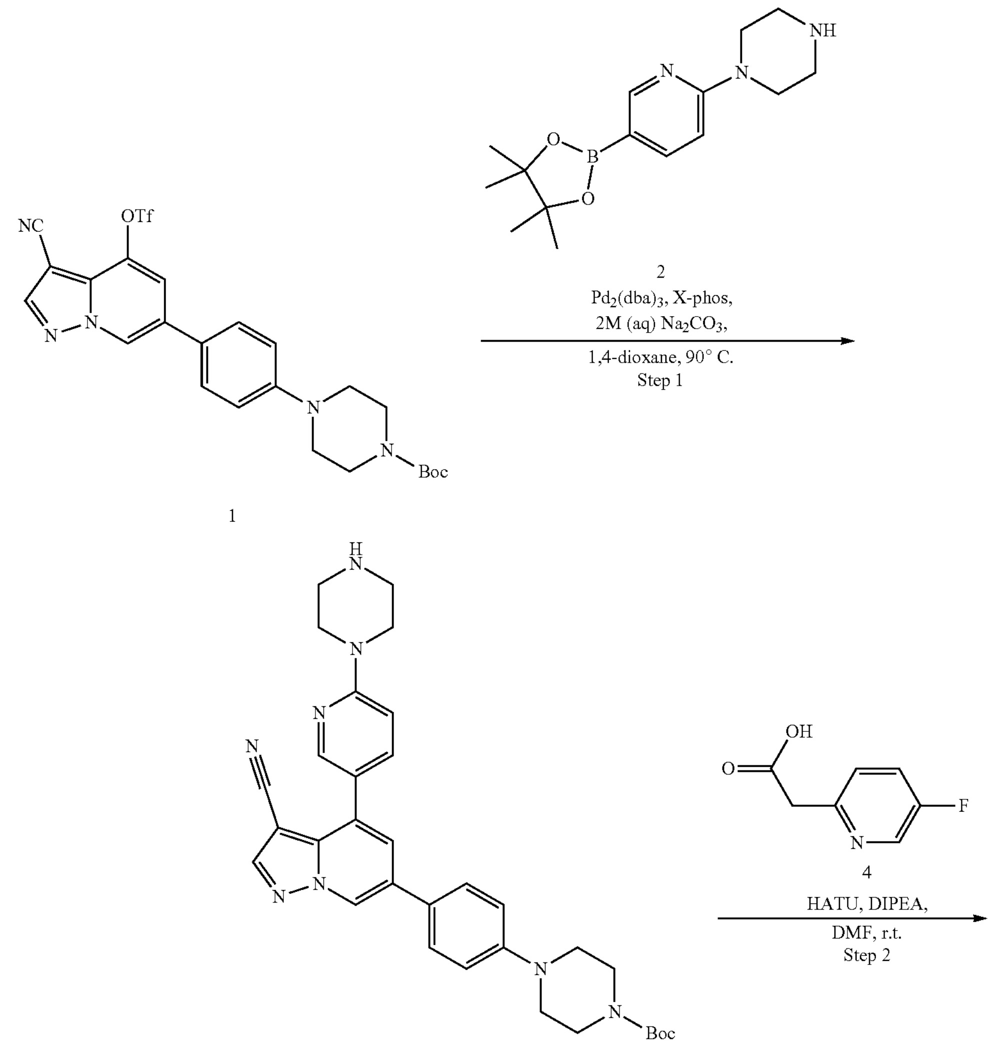
2
1
4
3

-continued
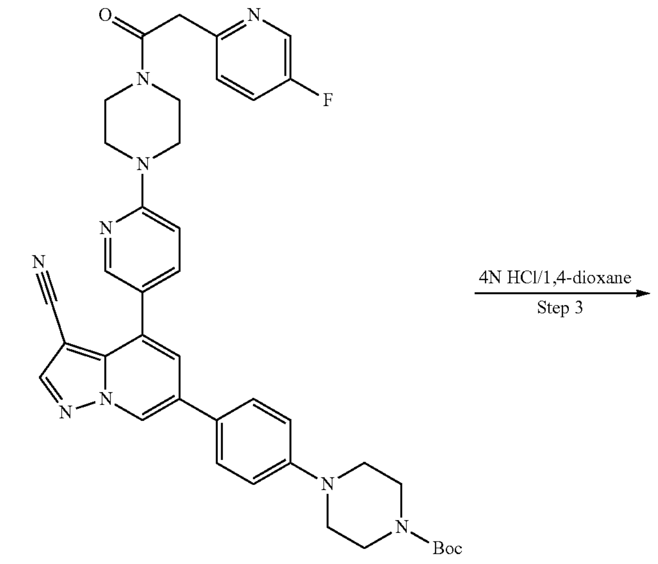
5
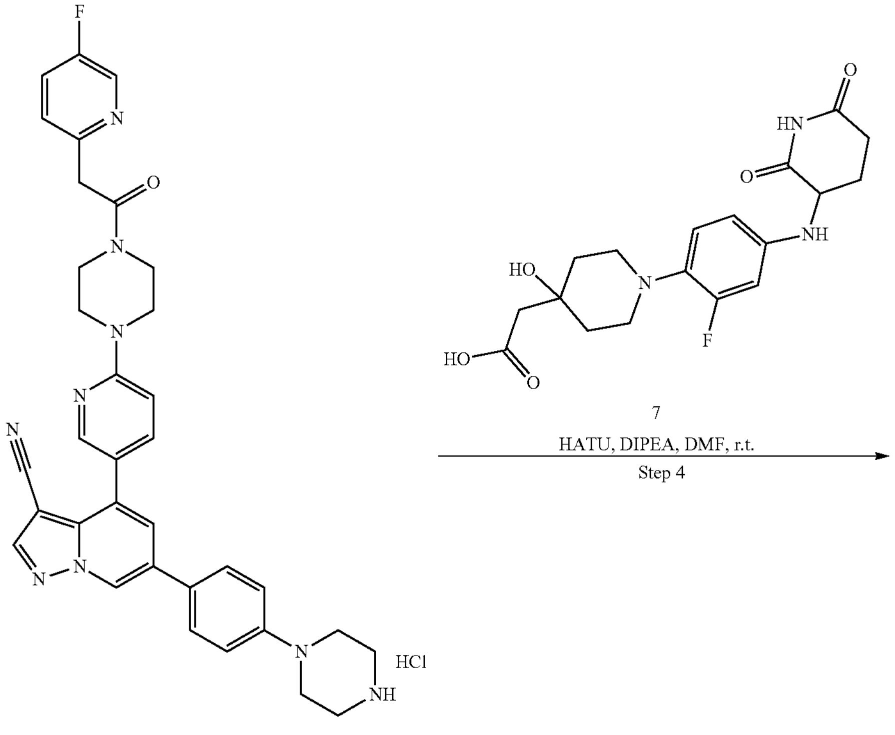
6

-continued

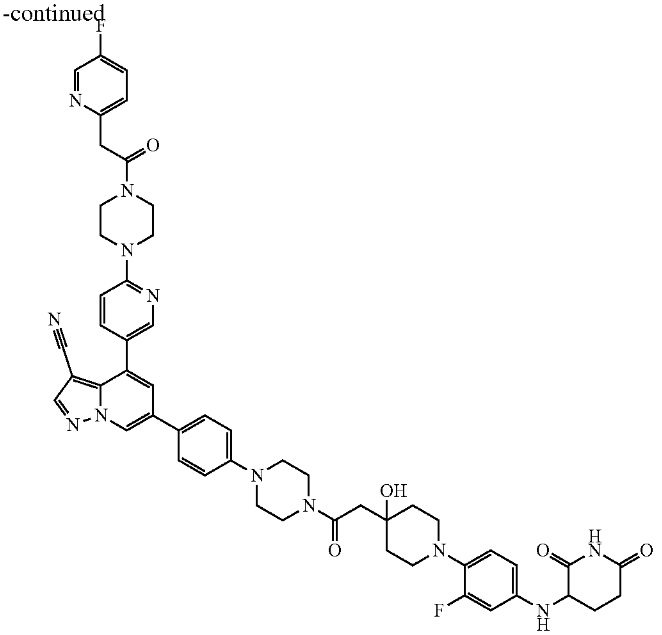

Compound 26

Step 1. Into a 100 mL sealed tube containing a mixture of tert-butyl 4-[4-[3-cyano-4-(trifluoromethylsulfonyloxy) pyrazolo[1,5-a]pyridin-6-yl]phenyl]piperazine-1-carboxylate (1; 1 g, 1.81 mmol) and 1-[5-(4,4,5,5-tetramethyl-1,3,2-dioxaborolan-2-yl)-2-pyridyl]piperazine (2; 629 mg, 2.18 mmol) in a mixture of water (2 mL) and 1,4-dioxane (10 mL) was added Sodium carbonate (577 mg, 5.44 mmol) and argon gas was bubbled through reaction mixture for 10 minutes. Later to the tube, $Pd_2(dba)_3$ (166 mg, 0.181 mmol) and X-Phos (477 mg, 0.362 mmol) were added and again the resulting suspension was purged with argon gas for additional 10 minutes. The resulting mixture was stirred at 80° C. under sealed conditions for 2 h. Progress of the reaction was monitored by LCMS and found to be complete after 2 h. The reaction mixture was passed through a pad of Celite, and the filtrate was concentrated under reduced pressure to get the crude mass. The crude material was purified by neutral alumina with 1:9 MeOH/DCM to generate tert-butyl 4-[4-[3-cyano-4-(6-piperazin-1-yl-3-pyridyl)pyrazolo[1,5-a]pyridin-6-yl]phenyl]piperazine-1-carboxylate (3; 500 mg, 0.734 mmol) as a brown solid. Yield 41%; LC MS: ES+ (M+H) 565.3.

Step 2. Into a 50 mL single-necked round-bottomed flask containing a well-stirred solution of tert-butyl 4-[4-[3-cyano-4-(6-piperazin-1-yl-3-pyridyl)pyrazolo[1,5-a]pyridin-6-yl]phenyl]piperazine-1-carboxylate (3; 500 mg, 0.885 mmol) and 2-(5-fluoro-2-pyridyl)acetic acid (4; 151 mg, 0.974 mmol) in anhydrous DMF (10 mL) were added HATU (337 mg, 0.885 mmol) and DIPEA (0.154 mL, 0.885 mmol) at room temperature under nitrogen atmosphere. The resulting mixture was stirred at room temperature for 2 h. Ice-cold water (40 mL) was added and stirred for 10 minutes, the resulting solid was filtered and dried to afford tert-butyl 4-[4-[3-cyano-4-[6-[4-[2-(5-fluoro-2-pyridyl)acetyl]piperazin-1-yl]-3-pyridyl]pyrazolo[1,5-a]pyridin-6-yl]phenyl]piperazine-1-carboxylate (5; 610 mg, 0.704 mmol) as a brown solid. Yield 79%; LC MS: ES+ (M+H) 702.3.

Step 3. Into a 50 mL single-necked round-bottomed flask containing a well-stirred solution of tert-butyl 4-[4-[3-cyano-4-[6-[4-[2-(5-fluoro-2-pyridyl)acetyl]piperazin-1-yl]-3-pyridyl]pyrazolo[1,5-a]pyridin-6-yl]phenyl]piperazine-1-carboxylate (5; 600 mg, 0.854 mmol) in anhydrous DCM (5 mL) was added 4 N HCl in 1,4-dioxane (8 mL, 0.854 mmol) at ambient temperature under nitrogen atmosphere. The resulting mixture was stirred at ambient temperature for 2 h. The reaction mixture was concentrated under reduced pressure to afford 4-[6-[4-[2-(5-fluoro-2-pyridyl)acetyl]piperazin-1-yl]-3-pyridyl]-6-(4-piperazin-1-ylphenyl)pyrazolo[1,5-a]pyridine-3-carbonitrile hydrochloride salt (6; 610 mg, 0.812 mmol,) as a brown solid. Yield 95%; LC MS: ES+ (M+H) 602.3.

Step 4. Into a 25 mL single-necked round-bottomed flask containing a well-stirred solution of 4-[6-[4-[2-(5-fluoro-2-pyridyl)acetyl]piperazin-1-yl]-3-pyridyl]-6-(4-piperazin-1-ylphenyl)pyrazolo[1,5-a]pyridine-3-carbonitrile hydrochloride salt (6; 100 mg, 0.156 mmol, 021) and 2-[1-[4-[(2,6-dioxo-3-piperidyl)amino]-2-fluoro-phenyl]-4-hydroxy-4-piperidyl]acetic acid (7; 78 mg, 0.188 mmol) in anhydrous DMF (3 mL) were added DIPEA (80 μL, 0.47 mmol) and HATU (89 mg, 0.235 mmol) at ambient temperature under nitrogen atmosphere, the resulting mixture was stirred at ambient temperature for 2 h. Ice-cold water (25 mL) was added and stirred for 10 minutes, the resulting solid was filtered and dried to afford a crude solid. The crude was purified by reverse phase HPLC using the method: Column: X Bridge (150×19 mm), 5 pm; Mobile phase: A: 0.1% Ammonium acetate in MQ-water; B: Acetonitrile; Flow rate: 15 mL/minutes; RT=2.95 minutes to get 6-[4-[4-[2-[1-[4-[(2,6-dioxo-3-piperidyl)amino]-2-fluoro-phenyl]-4-hydroxy-4-piperidyl]acetyl]piperazin-1-yl]phenyl]-4-[6-[4-[2-(5-fluoro-2-pyridyl)acetyl]piperazin-1-yl]-3-pyridyl]pyrazolo[1,5-a]pyridine-3-carbonitrile (Compound 26; 10 mg, 0.01 mmol) as an off-white solid. Yield 6%; $^1H$ NMR (400 MHz, DMSO-$d_6$). δ 10.80 (s, 1H), 9.20 (s, 1H), 8.69 (s, 1H), 8.49 (m, 1H), 7.90 (m, 1H), 7.80 (m, 3H), 7.69 (m, 1H), 7.41 (dd, J=8.4, 4.4 Hz, 1H), 7.09 (m, 2H), 7.02 (m, 1H), 6.86 (t, J=9.2 Hz, 1H), 6.50 (m, 1H), 6.45 (m, 1H), 5.78 (m, 1H), 4.86 (s, 1H), 4.35 (m, 1H), 3.98 (s, 2H), 3.80-3.63 (m, 13H), 3.24 (s, 3H), 2.87 (m, 4H), 2.75 (m, 1H), 2.68 (s, 3H), 2.11 (m, 1H), 1.87-1.66 (m, 6H). LC MS: ES+ (M+H) 963.3.

Example 100: Synthesis of 4-(6-(4-acetylpiperazin-1-yl)pyridin-3-yl)-6-(4-(4-(2-(4-(4-((2,6-dioxopiperidin-3-yl)amino)phenyl)piperidin-1-yl)acetyl)piperazin-1-yl)phenyl)pyrazolo[1,5-a]pyrazine-3-carbonitrile (Compound 27)
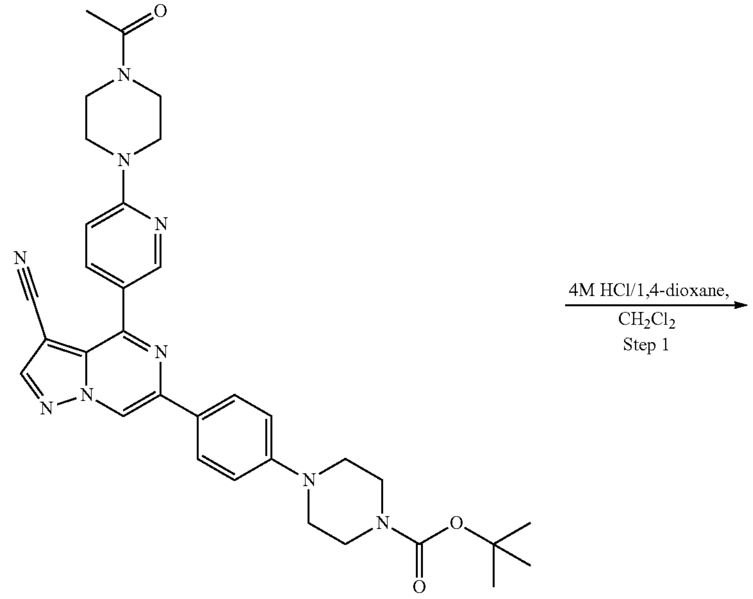
1
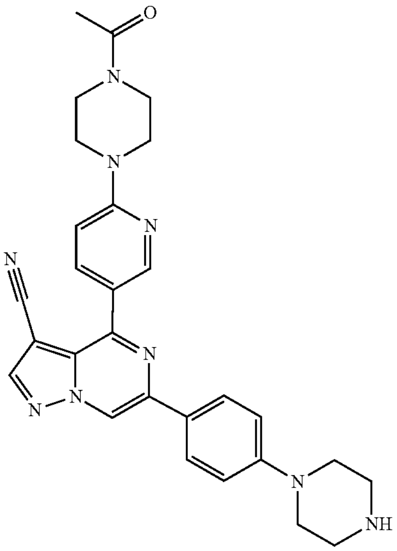
2
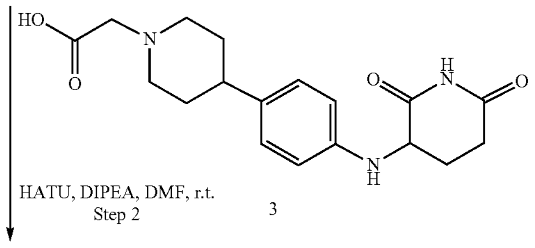
3

-continued

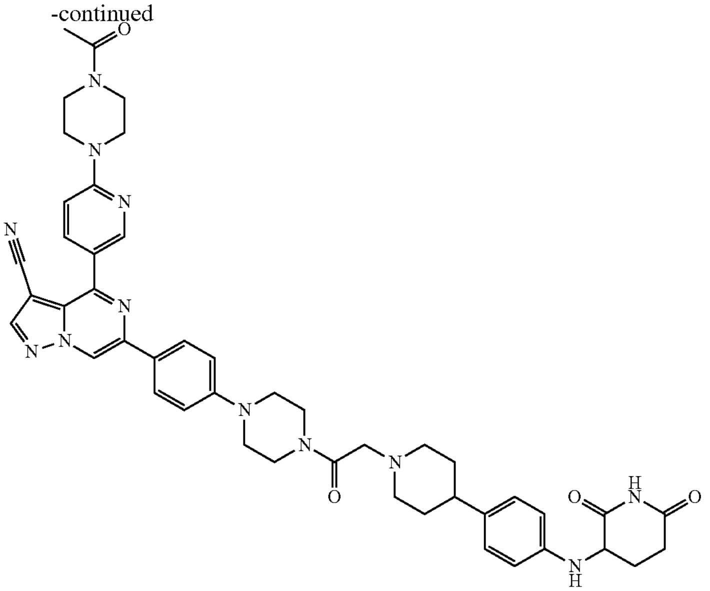

Compound 27

Step 1. Into a 50 mL single-necked round-bottomed flask containing a well-stirred solution of tert-butyl 4-[4-[4-[6-(4-acetylpiperazin-1-yl)-3-pyridyl]-3-cyano-pyrazolo[1,5-a]pyrazin-6-yl]phenyl]piperazine-1-carboxylate (1; 75 mg, 0.123 mmol) in anhydrous $CH_2Cl_2$ (2 mL) was added HCl (0.12 mmol, 2 mL; 4 M in 1,4-dioxane) at ambient temperature under nitrogen atmosphere. The resulting mixture was stirred at ambient temperature for 6 h. Excess solvents were removed from the reaction mixture under reduced pressure to get a crude mass. The crude mass was triturated with $Et_2O$ (5 mL) to afford 4-[6-(4-acetylpiperazin-1-yl)-3-pyridyl]-6-(4-piperazin-1-ylphenyl)pyrazolo[1,5-a]pyrazine-3-carbonitrile hydrochloric acid salt (2; 65 mg, 0.115 mmol) as a yellow solid. Yield-93%; LC MS: ES+ (M+H) 508.3.

Step 2. Into a 25 mL single-necked round-bottomed flask containing a well-stirred solution of 2-[4-[4-[(2,6-dioxo-3-piperidyl)amino]phenyl]-1-piperidyl]acetic acid hydrochloric acid salt (3; 57.90 mg, 0.152 mmol) and 4-[6-(4-acetylpiperazin-1-yl)-3-pyridyl]-6-(4-piperazin-1-ylphenyl)pyrazolo[1,5-a]pyrazine-3-carbonitrile hydrochloric acid salt (2; 75 mg, 0.138 mmol) in anhydrous DMF (4 mL) were added DIPEA (89.08 mg, 0.69 mmol, 0.12 mL) and HATU (62.90 mg, 0.165 mmol) at ambient temperature under nitrogen atmosphere. The resulting mixture was stirred at ambient temperature for 3 h. The progress of the reaction was monitored by LCMS. After completion of the reaction, the reaction mixture was treated with water (4 mL) and precipitated solid was filtered and dried under vacuum to get crude residue. The crude residue was purified by prep HPLC following a method: Column: X-Select C18 (150×19) mm, 5 micron; Mobile Phase A: 0.1% Ammonium acetate in milli-Q water; Mobile phase B: Acetonitrile; Flow rate: 15 mL/min; to yield 4-[6-(4-acetylpiperazin-1-yl)-3-pyridyl]-6-[4-[4-[2-[4-[4-[(2,6-dioxo-3-piperidyl)amino]phenyl]-1-piperidyl]acetyl]piperazin-1-yl]phenyl]pyrazolo[1,5-a]pyrazine-3-carbonitrile (Compound 27; 24 mg, 0.028 mmol) as a yellow solid. Yield-20%. $^1H$ NMR (400 MHz, DMSO-$d_6$). δ 10.77 (s, 1H), 9.44 (s, 1H), 8.86 (s, 1H), 8.73 (d, J=2.4 Hz, 1H), 8.15-8.10 (m, 3H), 7.12 (d, J=9.2 Hz, 2H), 7.06 (d, J=9.2 Hz, 1H), 6.96 (d, J=8.4 Hz, 2H), 6.61 (d, J=8.8 Hz, 2H), 5.65 (d, J=7.2 Hz, 1H), 4.27-4.24 (m, 1H), 3.77-3.74 (m, 4H), 3.68-3.66 (m, 2H), 3.62-3.59 (m, 6H), 3.28-3.22 (m, 4H), 2.94 (d, J=7.6 Hz, 2H), 2.66-2.63 (m, 2H), 2.55-2.53 (m, 3H), 2.34-2.33 (m, 2H), 2.12-2.08 (m, 4H), 1.86-1.83 (m, 1H), 1.72-1.69 (m, 2H), 1.59-1.57 (m, 2H). LC MS: ES+ (M+H) 835.3.

Example 101: Synthesis of 6-(4-(4-(2-(4-(4-((2,6-Dioxopiperidin-3-yl)amino)-2-fluorophenyl)piperidin-1-yl)acetyl)piperazin-1-yl)phenyl)-4-(6-(4-(pyridin-2-ylmethyl)piperazin-1-yl)pyridin-3-yl)pyrazolo[1,5-a]pyridine-3-carbonitrile (Compound 28)

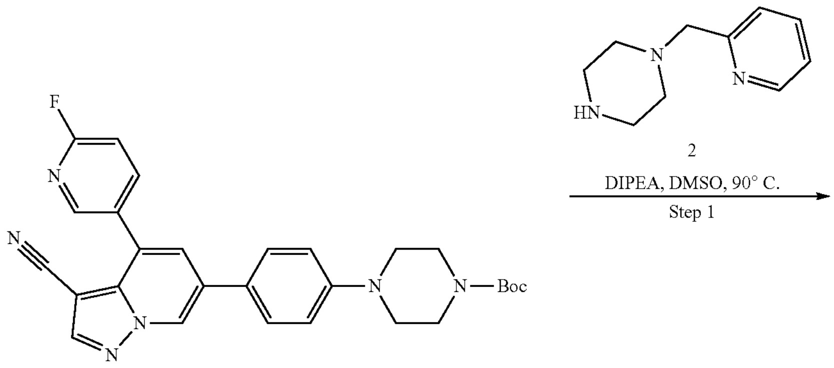

1

-continued

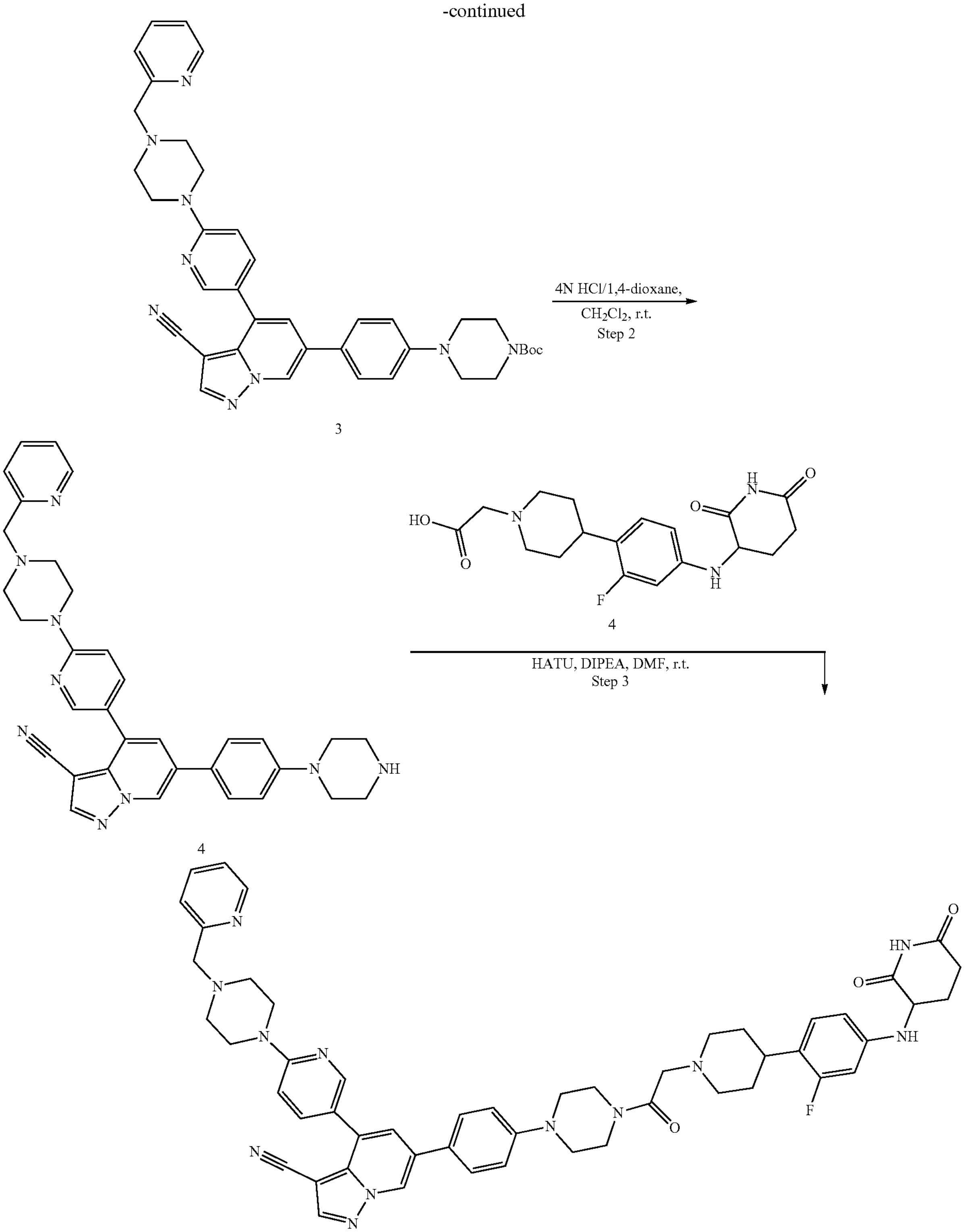

3

4

4

Compound 28

Step 1. Into a 10 mL sealed tube containing a well-stirred solution of a mixture of tert-butyl 4-[4-[3-cyano-4-(6-fluoro-3-pyridyl)pyrazolo[1,5-a]pyridin-6-yl]phenyl]piperazine-1-carboxylate (1; 150 mg, 0.300 mmol) and 1-(2-pyridylmethyl)piperazine (2; 53.33 mg, 0.3 mmol) in anhydrous DMSO (4.0 mL) was added DIPEA (155.54 mg, 1.20 mmol, 0.209 mL) at ambient temperature. The reaction mixture was stirred at 90° C. for 16 h. After completion of the reaction as indicated by UPLC, the reaction mixture was cooled to room temperature and treated with ice-water (20 mL). The resulting solution was stirred for 15 minutes at room temperature, during which time the desired product precipitated out. The solid product was filtered through filter paper, was washed with $Et_2O$, and dried under vacuum for 1 h to afford tert-butyl 4-[4-[3-cyano-4-[6-[4-(2-pyridylmethyl)piperazin-1-yl]-3-pyridyl]pyrazolo[1,5-a]pyridin-6-yl]phenyl]piperazine-1-carboxylate (3; 116 mg, 0.169 mmol) as a brown-coloured solid. Yield-56%; LC MS: ES+ (M+H) 656.3.

Step 2. Into a 25 mL single-necked round-bottomed flask containing a well stirred solution of tert-butyl 4-[4-[3-cyano-4-[6-[4-(2-pyridylmethyl)piperazin-1-yl]-3-pyridyl]pyrazolo[1,5-a]pyridin-6-yl]phenyl]piperazine-1-carboxylate (3; 116 mg, 0.176 mmol) in anhydrous $CH_2Cl_2$ (2.0 mL) was added HCl (2 mL, 4M/1,4-dioxane) at 0° C. After addition, the resulting solution was stirred at ambient temperature for 2 h. The progress of the reaction was monitored by UPLC. After completion of starting material, the reaction mixture was concentrated under reduced pressure (and co-distilled with $CH_2Cl_2$) to afford crude mixture, which was triturated with $Et_2O$ to get 6-(4-piperazin-1-ylphenyl)-4-[6-[4-(2-pyridylmethyl)piperazin-1-yl]-3-pyridyl]pyrazolo[1,5-a]pyridine-3-carbonitrile (4; 101 mg, 0.139 mmol) as a brown semi-solid. Yield-79%; LC MS: ES+ (M+H) 556.3.

Step 3. To a well-stirred solution of a mixture of 6-(4-piperazin-1-ylphenyl)-4-[6-[4-(2-pyridylmethyl)piperazin-1-yl]-3-pyridyl]pyrazolo[1,5-a]pyridine-3-carbonitrile (4; 100 mg, 0.168 mmol) and 2-[4-[4-[(2,6-dioxo-3-piperidyl)amino]-2-fluoro-phenyl]-1-piperidyl]acetic acid (5; 67.53 mg, 0.168 mmol) in anhydrous DMF (2.0 mL) was added DIPEA (87.30 mg, 0.675 mmol, 0.117 mL), and the resulting solution was stirred for 15 minutes at ambient temperature under nitrogen atmosphere. HATU (83.48 mg, 0.219 mmol) was added to the reaction mixture, and stirring was continued at ambient temperature for 2 h. The progress of the reaction was monitored by UPLC. After completion of the reaction, the reaction mixture was treated with water (10 mL), and precipitated solid was collected by filtration. The filtered solid was dried under vacuum and purified by prep HPLC purification method: (Mobile phase A: 10 mM $NH_4OAc$ in water, B: acetonitrile) to provide 6-[4-[4-[2-[4-[4-[(2,6-dioxo-3-piperidyl)amino]-2-fluoro-phenyl]-1-piperidyl]acetyl]piperazin-1-yl]phenyl]-4-[6-[4-(2-pyridylmethyl)piperazin-1-yl]-3-pyridyl]pyrazolo[1,5-a]pyridine-3-carbonitrile (Compound 28; 42 mg, 0.046 mmol) as an off-white solid. Yield-27%. $^1H$ NMR (400 MHz, DMSO-$d_6$). δ 10.80 (s, 1H), 9.19 (d, J=1.2 Hz, 1H), 8.68 (s, 1H), 8.54-8.51 (m, 1H), 8.43 (d, J=2.8 Hz, 1H), 7.87 (dd, J=8.8, 2.4 Hz, 1H), 7.82-7.78 (s, 4H), 7.51 (d, J=6.8 Hz, 1H), 7.31-7.27 (m, 1H), 7.09 (d, J=8.8 Hz, 2H), 6.97 (d, J=8.8 Hz, 2H), 6.47-6.42 (m, 2H), 6.00 (d, J=7.6 Hz, 1H), 4.31-4.28 (m, 1H), 3.76 (brs, 2H), 3.68-3.62 (m, 8H), 3.35-3.32 (m, 4H), 3.22 (s, 4H), 2.93 (d, J=10.8 Hz, 2H), 2.77-2.69 (m, 1H), 2.68-2.53 (m, 4H), 2.11-2.06 (m, 3H), 1.88-1.84 (m, 1H), 1.65-1.63 (m, 4H). LC MS: ES+ (M+H) 901.4.

Example 102: Synthesis of 1-(5-(3-Cyano-6-(4-(piperazin-1-yl)phenyl)pyrazolo[1,5-a]pyridin-4-yl)pyridin-2-yl)-4-ethyl-N-isopropylpiperidine-4-carboxamide hydrochloride salt and 1-(5-(3-cyano-6-(4-(piperazin-1-yl)phenyl)pyrazolo[1,5-a]pyridin-4-yl)pyridin-2-yl)-N-isopropyl-4-methylpiperidine-4-carboxamide hydrochloric acid salt

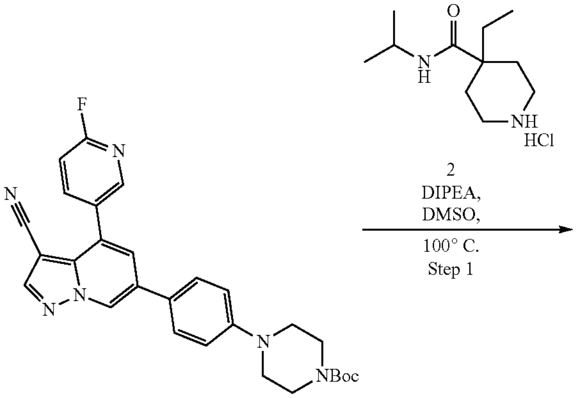

1

2

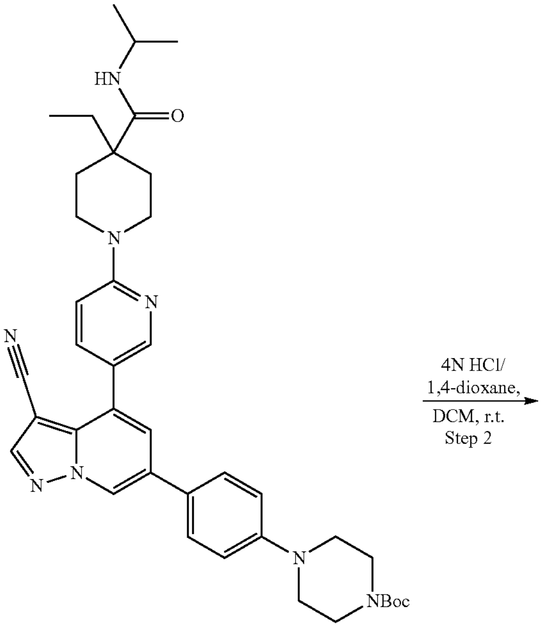

3

-continued

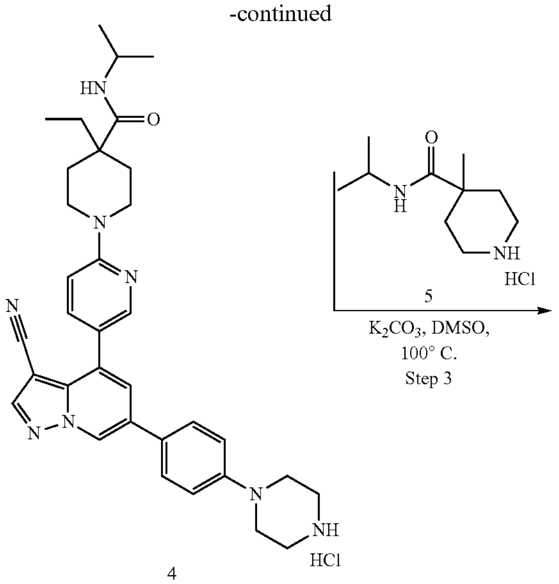

4

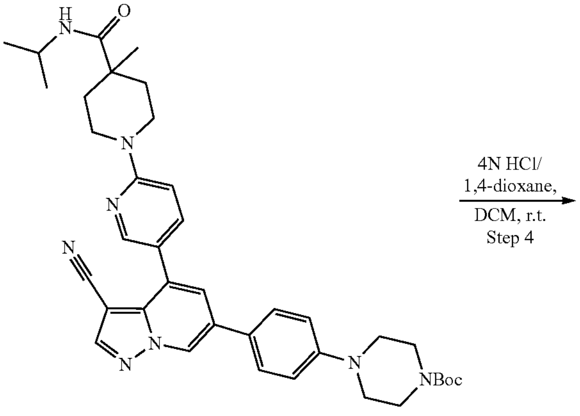

6

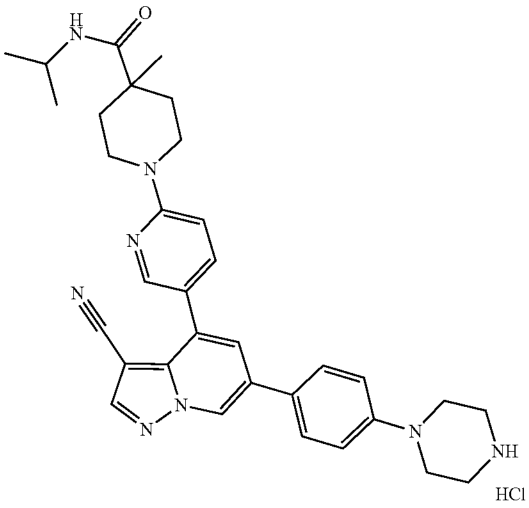

7

Step 1. Into a 50 mL sealed-tube containing a well-stirred solution of 4-ethyl-N-isopropyl-piperidine-4-carboxamide hydrochloride (2; 395.55 mg, 1.68 mmol) and tert-butyl 4-[4-[3-cyano-4-(6-fluoro-3-pyridyl) pyrazolo[1,5-a]pyridin-6-yl]phenyl]piperazine-1-carboxylate (1; 700 mg, 1.40 mmol) in anhydrous DMSO (8 mL) was added DIPEA (544.40 mg, 4.21 mmol, 0.733 mmol) at ambient temperature under nitrogen atmosphere. The resulting reaction mixture was heated to 100° C. for 16 h. After completion of the reaction as monitored by LCMS, the reaction mixture was cooled to ambient temperature. The reaction mixture was quenched with ice-water (15 mL), and the resulting solution was stirred for 15 minutes at room temperature, during which time the desired product precipitated out. The solid crude product was collected by filtration through filter paper. The solid was dried under vacuum to afford tert-butyl 4-[4-[3-cyano-4-[6-[4-ethyl-4-(isopropylcarbamoyl)-1-piperidyl]-3-pyridyl] pyrazolo[1,5-a]pyridin-6-yl]phenyl]piperazine-1-carboxylate (3; 710 mg, 0.961 mmol) as a brown solid, which was carried forward without further purification. Yield-68%; LC MS: ES+ (M+H) 677.4.

Step 2. Into a 50 mL single-necked round-bottomed flask containing a well-stirred solution of tert-butyl 4-[4-[3-cyano-4-[6-[4-ethyl-4-(isopropylcarbamoyl)-1-piperidyl]-3-pyridyl] pyrazolo[1,5-a]pyridin-6-yl]phenyl]piperazine-1-carboxylate (3; 710 mg, 1.05 mmol) in anhydrous dichloromethane (7 mL) was added hydrogen chloride solution 4.0 M in 1,4-dioxane (1.15 g, 31.47 mmol, 10.49 mL) at ambient temperature under nitrogen atmosphere. The resulting mixture was stirred at ambient temperature for 2 h. After completion of the reaction as monitored by UPLC, excess solvents were removed from the reaction mixture under reduced pressure to provide a crude residue. The crude residue was triturated with petroleum ether (50 ml) to yield 1-[5-[3-cyano-6-(4-piperazin-1-ylphenyl) pyrazolo[1,5-a]pyridin-4-yl]-2-pyridyl]-4-ethyl-N-isopropyl-piperidine-4-carboxamide hydrochloric acid salt (4; 630 mg, 0.863 mmol) as a pale yellow solid, which was carried forward without further purification. Yield-82%; LC MS: ES+ (M+H) 577.4.

Step 3. Into a 50 mL sealed tube containing a mixture of N-isopropyl-4-methyl-piperidine-4-carboxamide (5; 166.33 mg, 902.62 umol) and tert-butyl 4-[4-[3-cyano-4-(6-fluoro-3-pyridyl) pyrazolo[1,5-a]pyridin-6-yl]phenyl]piperazine-1-carboxylate (1; 300 mg, 0.601 mmol) in anhydrous DMSO (8 mL) was added anhydrous potassium carbonate (249.50 mg, 1.81 mmol, 0.108 mL) at ambient temperature under nitrogen atmosphere. The resulting mixture was heated at 100° C. for 16 h. Ice water (25 mL) was added, the reaction mixture was stirred for 10 minutes, and the resulting solid was filtered and dried to afford tert-butyl 4-[4-[3-cyano-4-[6-[4-(isopropylcarbamoyl)-4-methyl-1-piperidyl]-3-pyridyl] pyrazolo[1,5-a]pyridin-6-yl]phenyl]piperazine-1-carboxylate (6; 320 mg, 0.386 mmol) as a brown solid, which was carried forward without further purification. Yield-64%; LC MS: ES+ (M+H) 663.3.

Step 4. Into a 50 mL single-necked round-bottomed flask containing a well-stirred solution of tert-butyl 4-[4-[3-cyano-4-[6-[4-(isopropylcarbamoyl)-4-methyl-1-piperidyl]-3-pyridyl]pyrazolo[1,5-a]pyridin-6-yl]phenyl]piperazine-1-carboxylate (6; 320 mg, 0.482 mmol) in anhydrous dichloromethane (2 mL) was added 4 N hydrochloric acid in 1,4-dioxane (482.78 umol, 5 mL) at room temperature under nitrogen atmosphere and the resulting mixture was stirred at room temperature for 2 h. The reaction mixture was concentrated under reduced pressure to afford 1-[5-[3-cyano-6-(4-piperazin-1-ylphenyl)pyrazolo[1,5-a]pyridin-4-yl]-2-pyridyl]-N-isopropyl-4-methyl-piperidine-4-carboxamide hydrochloric acid salt (7; 280 mg, 0.444 mmol) as a brown solid, which was carried forward without further purification. Yield-92%; LC MS: ES+ (M+H) 563.3.

Example 103: Synthesis of 4-Ethyl-N-isopropylpiperidine-4-carboxamide hydrochloric acid salt

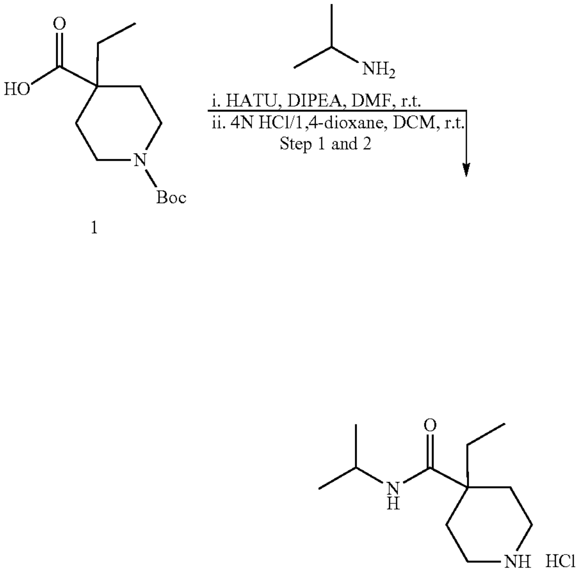

1

2

Step 1. Into a 50 mL single-necked round-bottomed flask containing a well-stirred solution of 1-tert-butoxycarbonyl-4-ethyl-piperidine-4-carboxylic acid (1; 1 g, 3.89 mmol) and propan-2-amine (229.71 mg, 3.89 mmol, 0.332 mL) in anhydrous DMF (10 mL) were added DIPEA (1.51 g, 11.66 mmol, 2.03 mL) and HATU (1.77 g, 4.66 mmol) at ambient temperature under nitrogen atmosphere. The reaction mixture was stirred at ambient temperature for 3 h. After completion of the reaction as indicated by LCMS, the reaction mixture was quenched with ice-cold water (50 mL) and extracted with EtOAc (2×100 mL). The organic phases were combined and dried (anhydrous $Na_2SO_4$), filtered, and the filtrate concentrated under reduced pressure to furnish crude residue. The crude product was purified by column chromatography (silica-gel (230-400 mesh), gradient of 0%-100% EtOAc in petroleum ether) to afford tert-butyl 4-ethyl-4-(isopropylcarbamoyl)piperidine-1-carboxylate (1 g, 3.32 mmol) as a pale yellow gum. Yield-85.4%; LC MS: ES+ (M-Boc+H) 199.1.

Step 2. Into another 50 mL single-necked round-bottomed flask containing a well-stirred solution of tert-butyl 4-ethyl-4-(isopropylcarbamoyl)piperidine-1-carboxylate (1 g, 3.32 mmol) in anhydrous $CH_2Cl_2$ (10 mL) was added 4.0 M hydrochloric acid in 1,4-dioxane (10 mL) at ambient temperature under nitrogen atmosphere. The resulting reaction mixture was stirred at ambient temperature for 2 h. After completion of the reaction as monitored by UPLC, excess solvent was removed from the reaction mixture under reduced pressure to provide a crude residue. The crude residue as triturated with petroleum ether (50 mL) to furnish 4-ethyl-N-isopropyl-piperidine-4-carboxamide hydrochloric acid salt (2; 750 mg, 3.16 mmol) as an off-white solid, which was carried forward without further purification. Yield-94.4%; LC MS: ES+ (M+H) 199.1.

Example 104: Synthesis of N-Isopropyl-4-methylpiperidine-4-carboxamide hydrochloric acid salt

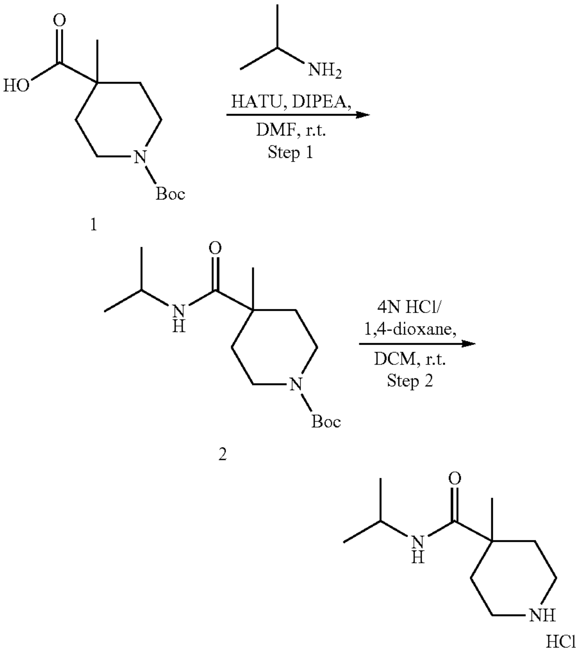

1

2

3

Step 1. Into a 250 mL single-necked round-bottomed flask containing a well-stirred solution of 1-tert-butoxycarbonyl-4-methyl-piperidine-4-carboxylic acid (1; 5 g, 20.55 mmol) and propan-2-amine (1.82 g, 30.83 mmol; 2.64 mL) in anhydrous DMF (70 mL) were added DIPEA (7.97 g, 61.65 mmol, 10.74 mL) and HATU (11.72 g, 30.83 mmol) at ambient temperature under nitrogen atmosphere. The reaction mixture was stirred at ambient temperature for 3 h. After completion of the reaction as indicated by LCMS, the reaction mixture was quenched with cold water (150 mL) and extracted with EtOAc (2×200 mL). The organic phases were combined and dried (anhydrous $Na_2SO_4$), filtered, and the filtrate concentrated under reduced pressure to provide a crude residue. The crude product was purified by column chromatography (silica-gel (230-400 mesh), gradient of 0%-100% EtOAc in pet ether) to afford tert-butyl 4-(isopropyl carbamoyl)-4-methyl-piperidine-1-carboxylate (2; 4.7 g, 16.51 mmol) as a pale yellow gum. Yield-80%; LC MS: ES+ (M-Boc+H) 185.3.

Step 2. Into a 100 mL single-necked round-bottomed flask containing a well-stirred solution of tert-butyl 4-(isopropyl carbamoyl)-4-methyl-piperidine-1-carboxylate (2; 4.7 g, 16.51 mmol) in anhydrous dichloromethane (20 mL) was added 4.0 M HCl in 1,4-dioxane (20.66 mL) at ambient temperature under nitrogen atmosphere. The resulting reaction mixture was stirred at ambient temperature for 2 h. After completion of the reaction as monitored by UPLC, excess solvent was removed from the reaction mixture under reduced pressure to provide a crude residue. The crude residue was titrated with 10% dichloromethane in petroleum ether to get N-isopropyl-4-methyl-piperidine-4-carboxamide hydrochloric acid salt (3; 3.1 g, 13.95 mmol) as a yellow solid. Yield-84%; LC MS: ES+ (M+H) 185.3.

Example 105: Synthesis of 1-(5-(3-Cyano-6-(4-(4-(2-(4-(4-(2,6-dioxopiperidin-3-yl)phenyl)piperidin-1-yl)acetyl)piperazin-1-yl)phenyl)pyrazolo[1,5-a]pyridin-4-yl)pyridin-2-yl)-4-ethyl-N-isopropylpiperidine-4-carboxamide (Compound 29)
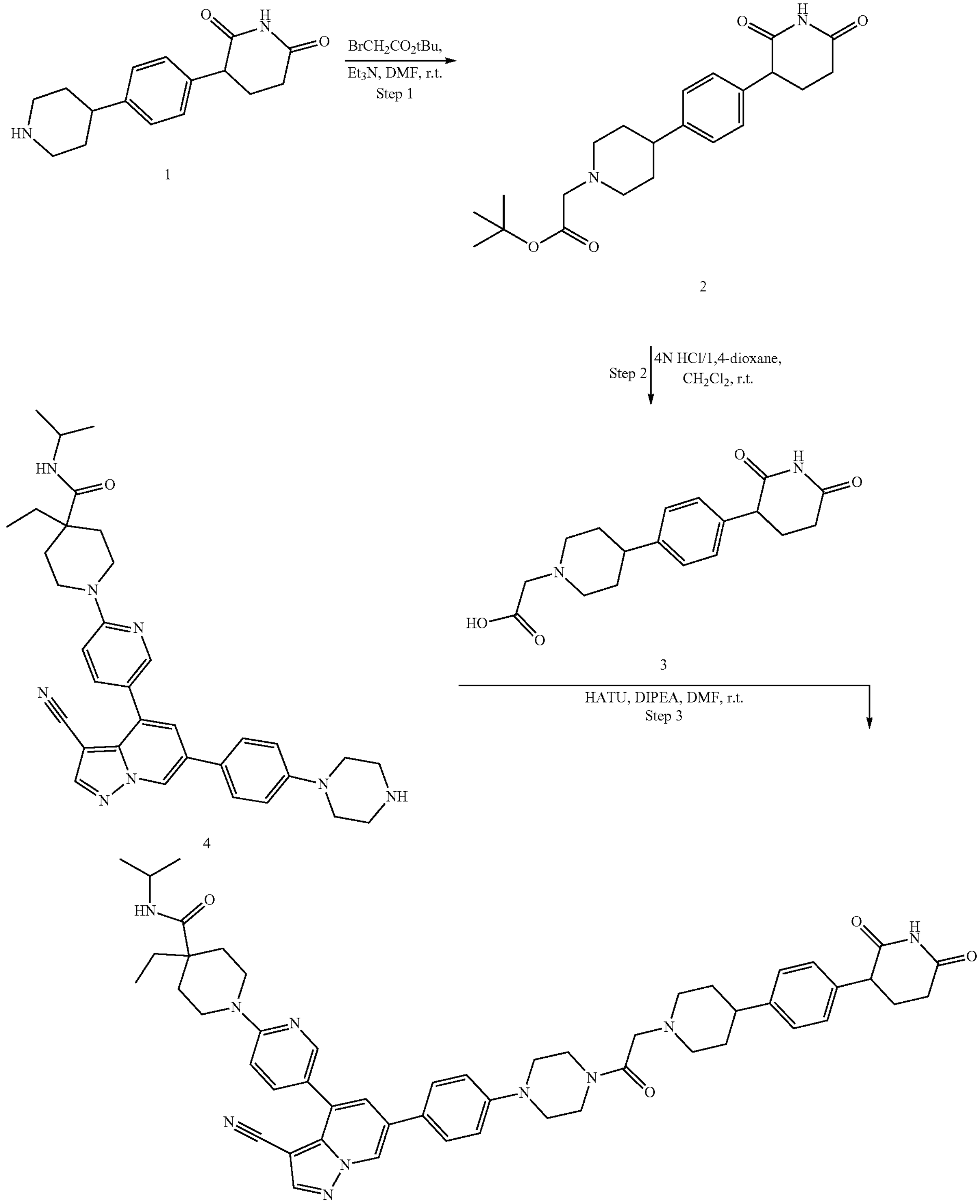
Compound 29

Step 1. Into a 50 mL single-necked round-bottomed flask containing a well stirred solution of 3-[4-(4-piperidyl)phenyl]piperidine-2,6-dione (1; 60 mg, 0.220 mmol) and tert-butyl bromo acetate (51.57 mg, 0.264 mmol) in anhydrous DMF (3 mL) was added $Et_3N$ (66.88 mg, 0.660 mmol, 0.092 mL) at ambient temperature under nitrogen atmosphere. The resulting reaction mixture was stirred at ambient temperature under nitrogen atmosphere for 16 h. After the reaction proceeded to completion (monitored by TLC), the reaction mixture was quenched with ice-cold water. The combined layers were extracted with EtOAc (2×60 mL). The combined organic layers were dried (anhydrous $Na_2SO_4$), filtered and the filtrate was concentrated under reduced pressure to provide a crude mixture. The crude mixture was washed with petroleum ether to afford tert-butyl 2-[4-[4-(2,6-dioxo-3-piperidyl)phenyl]-1-piperidyl]acetate (2; 50 mg, 0.087 mmol) as a white solid. Yield-40%; LC MS: ES+ (M+H) 387.0.

Step 2. Into a 25 mL single-necked round-bottomed flask containing a well stirred solution of tert-butyl 2-[4-[4-(2,6-dioxo-3-piperidyl)phenyl]-1-piperidyl]acetate (2; 40 mg, 0.103 mmol) in anhydrous $CH_2Cl_2$ (5 mL) was added HCl (56.60 mg, 1.55 mmol; 4M/1,4-dioxane) at ambient temperature under nitrogen atmosphere. The resulting reaction mixture was stirred at ambient temperature for 16 h. After the reaction proceeded to completion (monitored by TLC), the reaction mixture was concentrated under reduced pressure to get the crude mixture. The crude mixture was washed with petroleum ether to afford 2-[4-[4-(2,6-dioxo-3-piperidyl)phenyl]-1-piperidyl]acetic acid (3; 40 mg, 0.103 mmol) as a white solid. Yield-99%; LC MS: ES+ (M+H) 331.0.

Step 3. Into a 25 mL single-necked round-bottomed flask containing a well-stirred solution of 1-[5-[3-cyano-6-(4-piperazin-1-ylphenyl)pyrazolo[1,5-a]pyridin-4-yl]-2-pyridyl]-4-ethyl-N-isopropyl-piperidine-4-carboxamide (4; 50 mg, 0.086 mmol) and 2-[4-[4-(2,6-dioxo-3-piperidyl)phenyl]-1-piperidyl]acetic acid (3; 25.78 mg, 0.078 mmol) in anhydrous DMF (3 mL) were added N,N-diisopropylethylamine (44.82 mg, 0.346 mmol, 0.060 mL) and HATU (49.45 mg, 0.130 mmol) at ambient temperature under nitrogen atmosphere. The contents were stirred at ambient temperature for 2 h. The progress of the reaction was monitored by LCMS. After completion of the reaction, excess solvents were removed from the reaction mixture under reduced pressure to provide a crude product. The crude product was purified by prep HPLC purification using the following method: X-SELECT C18 (30×150) mm, 5 mic; Mobile Phase A: 10 mM $NH_4OAc$; Mobile phase B: Acetonitrile to yield 1-[5-[3-cyano-6-[4-[4-[2-[4-[4-(2,6-dioxo-3-piperidyl)phenyl]-1-piperidyl]acetyl]piperazin-1-yl]phenyl]pyrazolo[1,5-a]pyridin-4-yl]-2-pyridyl]-4-ethyl-N-isopropyl-piperidine-4-carboxamide (Compound 29; 24 mg, 0.026 mmol) as an off-white solid. Yield-30%. $^1H$ NMR (400 MHz, DMSO-$d_6$). δ 10.82 (s, 1H), 9.19 (d, J=1.2 Hz, 1H), 8.68 (s, 1H), 8.41 (d, J=2.4 Hz, 1H), 7.84-7.78 (m, 4H), 7.40 (d, J=7.6 Hz, 1H), 7.21 (d, J=8.4 Hz, 2H), 7.14-7.09 (m, 4H), 6.96 (d, J=8.8 Hz, 1H), 4.09 (d, J=14.0 Hz, 2H), 4.01-3.98 (m, 1H), 3.81-3.77 (m, 3H), 3.63 (brs, 2H), 3.35 (m, 4H), 3.23 (s, 4H), 3.06 (t, J=11.2 Hz, 2H), 2.95 (d, J=10.4 Hz, 2H), 2.61 (s, 1H), 2.17-2.08 (m, 5H), 2.04-1.98 (m, 1H), 1.78-1.75 (m, 2H), 1.69-1.63 (m, 2H), 1.51 (q, J=7.6 Hz, 2H), 1.38-1.33 (m, 2H), 1.09 (d, J=6.4 Hz, 6H), 0.75 (t, J=7.2 Hz, 3H). LC MS: ES+ (M+H) 889.4.

Example 106: Synthesis of 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide

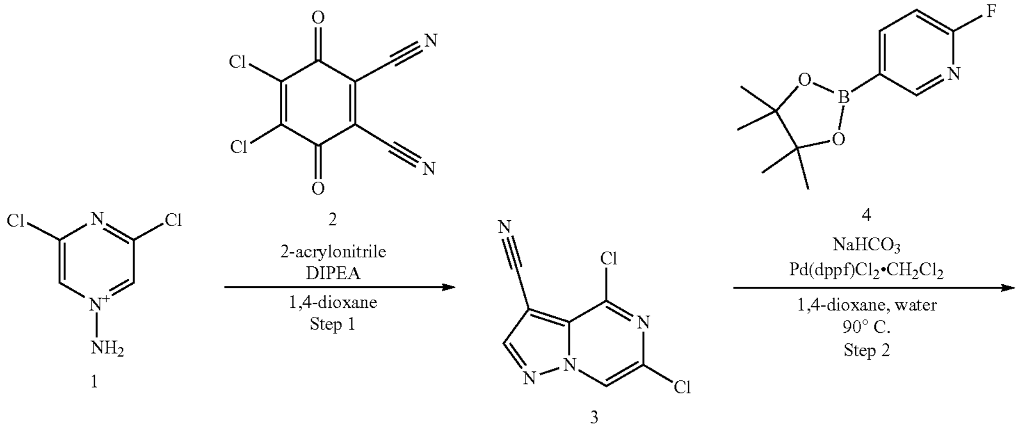

-continued
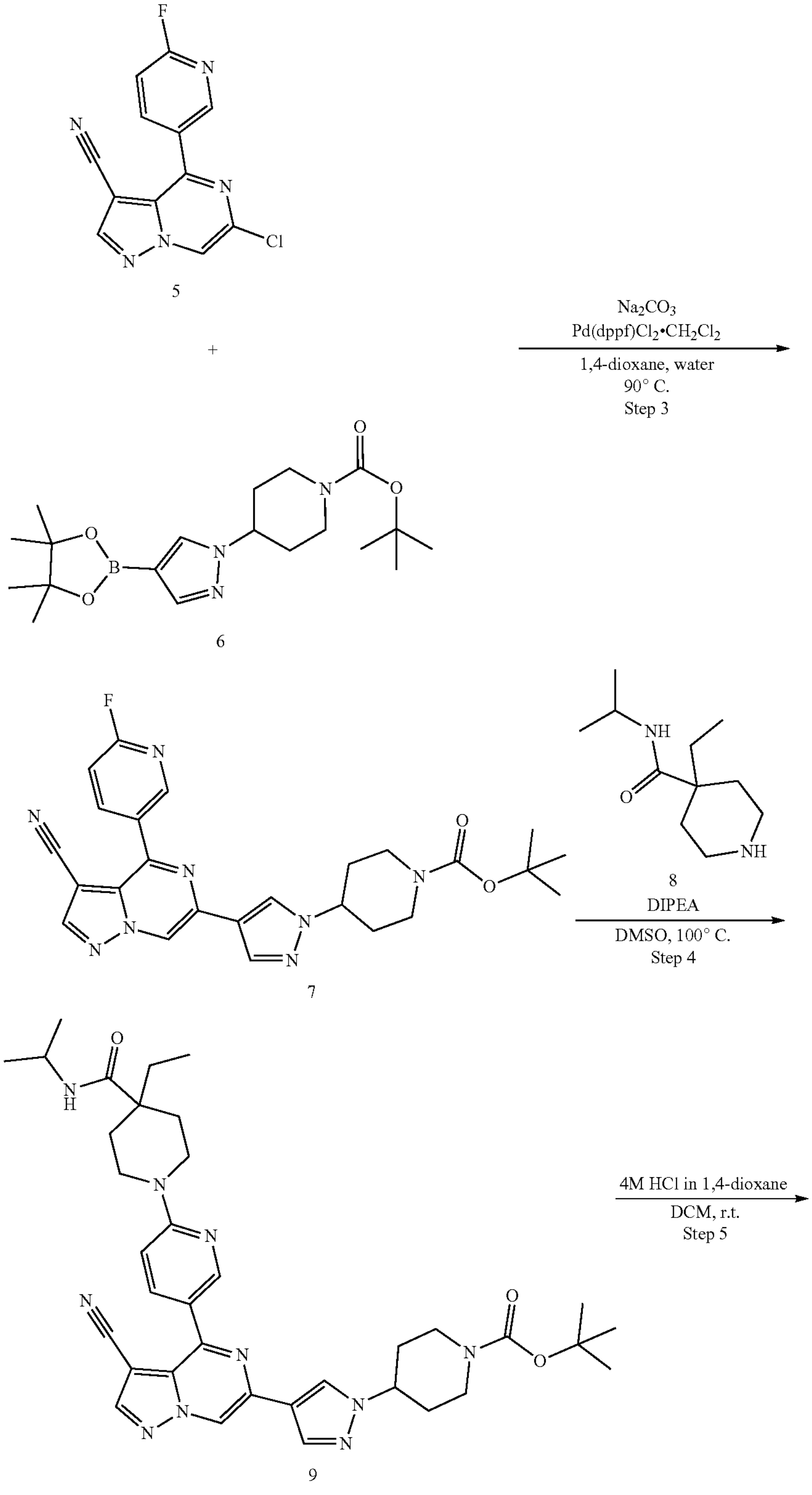

-continued

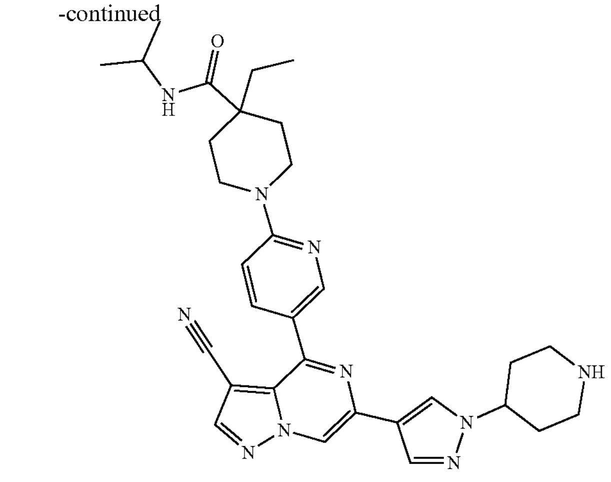

10

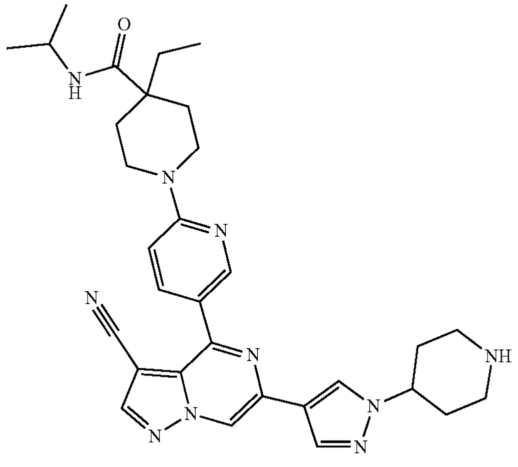

10

Step 1. Into a 100 mL single neck round bottom flask, containing a well stirred solution of 3,5-dichloropyrazin-1-ium-1-amine (2.0 g, 5.48 mmol, 191) in 1,4-dioxane (20 mL), was added 2-chloroacrylonitrile (958.35 mg, 10.95 mmol) and DIPEA (1.77 g, 13.69 mmol, 2.38 mL) room temperature. After stirring for 2 h, 2,3-dichloro-5,6-dicyano-1,4-benzoquinone (2.49 g, 10.95 mmol) was added portion-wise at 0° C. The resultant reaction mixture was stirred at room temperature for 12 h. The progress of the reaction was monitored by TLC. After consumption of starting material, the reaction mixture was quenched with brine (50 mL) and extracted with ethyl acetate (3×100 mL), dried over anhydrous sodium sulphate, filtered and concentrated under reduced pressure. The crude residue was purified by column chromatography (silica gel eluted with 10-20% ethyl acetate in petroleum ether) to furnish 4,6-dichloropyrazolo[1,5-a]pyrazine-3-carbonitrile as brown solid. Yield-54%; GCMS: (M+H) 212.0.

Step 2. Into a 250 mL sealed-tube containing a well stirred solution of 2-fluoro-5-(4,4,5,5-tetramethyl-1,3,2-dioxaborolan-2-yl)pyridine (11.52 g, 51.64 mmol) and 4,6-dichloropyrazolo[1,5-a]pyrazine-3-carbonitrile (10.0 g, 46.94 mmol) in anhydrous 1,4-dioxane (200 mL) was added sodium bicarbonate (15.77 g, 187.77 mmol) and water (50 mL), and the resulting reaction mixture was purged with nitrogen for 10 minutes. Pd(dppf)$Cl_2$*$CH_2Cl_2$ (1.92 g, 2.35 mmol) was added, and the resultant mixture was purged with nitrogen for 10 minutes. The reaction mixture was heated with stirring at 100° C. for 2 h. The progress of the reaction was monitored by TLC (30% EtOAc/Pet ether). After consumption of the starting material, the reaction mixture was diluted with EtOAc and water. The reaction mixture was filtered through a pad of Celite, and the celite bed was washed with EtOAc. The phases of the filtrate were separated, and the organic layer was dried over anhydrous sodium sulfate and concentrated under reduced pressure to provide the crude residue. The crude residue was purified by silica-gel column chromatography (230-400 mesh, 100 g) using a gradient of 0-100% EtOAc/petroleum ether to afford 6-chloro-4-(6-fluoro-3-pyridyl)pyrazolo[1,5-a]pyrazine-3-carbonitrile as a brown solid. Yield-59%; LCMS: ES+ (M+H) 274.0.

Step 3. Into a 10 mL sealed-tube containing a well-stirred solution of 6-chloro-4-(6-fluoro-3-pyridyl)pyrazolo[1,5-a]pyrazine-3-carbonitrile (40 mg, 146.17 umol) and tert-butyl 4-[4-(4,4,5,5-tetramethyl-1,3,2-dioxaborolan-2-yl)pyrazol-1-yl]piperidine-1-carboxylate (66.18 mg, 175.41 umol, 000) in anhydrous 1,4-dioxane (2 mL) was added sodium carbonate (46.48 mg, 438.51 umol, 18.37 uL) in water (0.5 mL) at ambient temperature under nitrogen atmosphere, and the resulting mixture was degassed with nitrogen gas for 10 minutes. Subsequently, Pd(dppf)$Cl_2$*$CH_2Cl_2$ (11.94 mg, 14.62 umol) was added to the reaction mixture, and reaction mixture was heated to 90° C. for 3 h. After completion of the reaction as indicated by TLC, the reaction mixture was cooled to room temperature, poured into water (10 mL), and extracted with EtOAc (2×20 mL). The combined organic phases were washed with brine (10 mL), dried (anhydrous $Na_2SO_4$), and filtered. The filtrate was concentrated under reduced pressure to provide a crude residue which was purified by silicagel (230-400 mesh) column chromatography using a gradient of 0-100% EtOAc/petroleum ether to afford tert-butyl 4-[4-[3-cyano-4-(6-fluoro-3-pyridyl)pyrazolo[1,5-a]pyrazin-6-yl]pyrazol-1-yl]piperidine-1-carboxylate as an off-white solid. Yield-70%; LCMS: (M+H-$CO_2$tBu) 389.2.

Step 4. Into a 100 mL sealed tube containing a well-stirred solution of a mixture of tert-butyl 4-[4-[3-cyano-4-(6-fluoro-3-pyridyl)pyrazolo[1,5-a]pyrazin-6-yl]pyrazol-1-yl]piperidine-1-carboxylate (1.0 g, 2.05 mmol), 4-ethyl-N-isopropyl-piperidine-4-carboxamide (720.85 mg, 3.07 mmol, 021) in anhydrous DMSO (15 mL) was added DIPEA (1.32 g, 10.24 mmol, 1.78 mL) at ambient temperature. The reaction mixture was stirred at 100° C. for 16 h. After completion of the reaction as indicated by UPLC, the reaction mixture was warmed to room temperature and treated with ice-water (50 mL). The resulting mixture was stirred for 15 minutes at room temperature, during which time the desired product precipitated out. The solid product was collected by filtration over filter paper, and the solid was washed with water and dried under vacuum for 5 h to afford crude tert-butyl 4-[4-[3-cyano-4-[6-[4-ethyl-4-(isopropylcarbamoyl)-1-piperidyl]-3-pyridyl]pyrazolo[1,5-a]pyrazin-6-yl]pyrazol-1-yl]piperidine-1-carboxylate as a faint brown solid. Yield-80%; LCMS: ES+ (M+H) 667.4.

Step 5. Into a 250 mL single-necked round-bottomed flask containing a well-stirred solution of tert-butyl 4-[4-[3-cyano-4-[6-[4-ethyl-4-(isopropylcarbamoyl)-1-piperidyl]-3-pyridyl]pyrazolo[1,5-a]pyrazin-6-yl]pyrazol-1-yl]piperidine-1-carboxylate (5.6 g, 8.40 mmol) in anhydrous DCM (50 mL) under nitrogen atmosphere was added dropwise HCl in dioxane (4 M, 40 mL) at 0° C. The reaction mixture was warmed to room temperature and stirred at ambient temperature for 2 h. After completion of the reaction as indicated by UPLC, the reaction mixture was concentrated under reduced pressure and co-distilled with DCM (2×10 mL) to afford 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide as a yellow solid. Yield-95%; LCMS: ES+ (M+H) 567.2.

Example 107: Synthesis of 1-(5-(3-Cyano-6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)pyrazolo[1,5-a]pyrazin-4-yl)pyridin-2-yl)-4-ethyl-N-isopropylpiperidine-4-carboxamide (Compound 30)

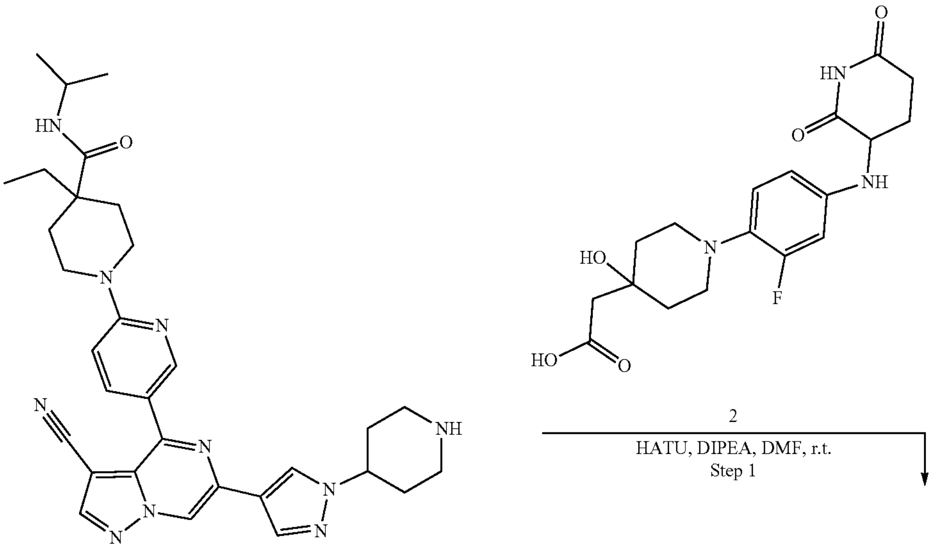

1

-continued

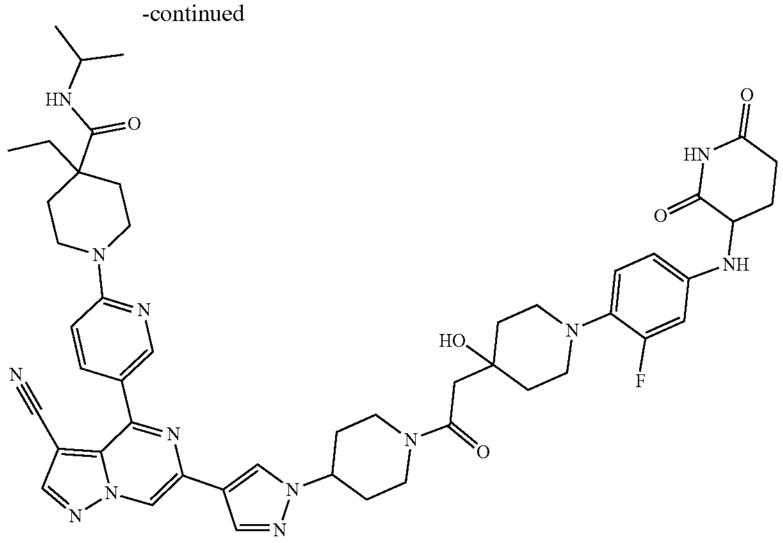

Compound 30

Step 1. Into a 25 mL single-necked round-bottomed flask containing a well-stirred solution of 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide (1; 72.52 mg, 0.120 mmol) and 2-[1-[4-[(2,6-dioxo-3-piperidyl)amino]-2-fluoro-phenyl]-4-hydroxy-4-piperidyl]acetic acid (2; 50 mg, 0.120 mmol) in anhydrous DMF (1.5 mL) was added DIPEA (155.40 mg, 1.20 mmol, 0.209 mL). The resultant solution was stirred for 10 minutes at ambient temperature under nitrogen atmosphere. HATU (59.43 mg, 0.156 mmol) was added to the reaction mixture, and stirring was continued at ambient temperature for 2 h. The progress of the reaction was monitored by UPLC. After completion of the reaction, the reaction mixture was treated with ice-cold water (6 mL). The resultant mixture was stirred for 15 minutes at room temperature, during which time the desired product precipitated. The solid product was collected by filtration and dried under vacuum to a get crude mixture which was purified by prep HPLC purification using the following method: Column: X-Select C18 (19×150) MM 5 MICRONS; Mobile phase: (0.1% ammonium acetate in water/ACN). The prep fractions were lyophilized to afford 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 30; 23.16 mg, 0.24 mmol) as a yellow-coloured solid. Yield-20%. $^1$H NMR (400 MHz, DMSO-$d_6$). δ 10.79 (s, 1H), 9.29 (s, 1H), 8.83 (s, 1H), 8.68 (d, J=2.4 Hz, 1H), 8.50 (s, 1H), 8.18 (s, 1H), 8.05 (dd, J=9.2, 2.4 Hz, 1H), 7.42 (d, J=7.6 Hz, 1H), 7.00 (d, J=9.2 Hz, 1H), 6.86 (t, J=9.2 Hz, 1H), 6.50 (dd, J=14.8, 2.4 Hz, 1H), 6.42 (dd, J=10.8, 2.0 Hz, 1H), 5.78 (d, J=8.0 Hz, 1H), 4.90 (s, 1H), 4.60-4.99 (m, 2H), 4.29-4.15 (m, 4H), 4.05-3.97 (m, 1H), 3.19-3.07 (m, 3H), 2.92-2.68 (m, 6H), 2.60-2.55 (m, 4H), 2.19-2.08 (m, 5H), 2.11-1.65 (m, 6H), 1.52-1.48 (m, 2H), 1.38-1.32 (m, 2H), 1.09 (d, J=6.4 Hz, 6H), 0.75 (t, J=7.6 Hz, 3H). LC MS: ES+ (M+H) 928.2.

Example 108: Synthesis of 1-(5-(3-Cyano-6-(1-(1-(2-(4-(4-((2,6-dioxopiperidin-3-yl)amino)phenyl)piperidin-1-yl)acetyl)piperidin-4-yl)-1H-pyrazol-4-yl)pyrazolo[1,5-a]pyrazin-4-yl)pyridin-2-yl)-4-ethyl-N-isopropylpiperidine-4-carboxamide (Compound 31)

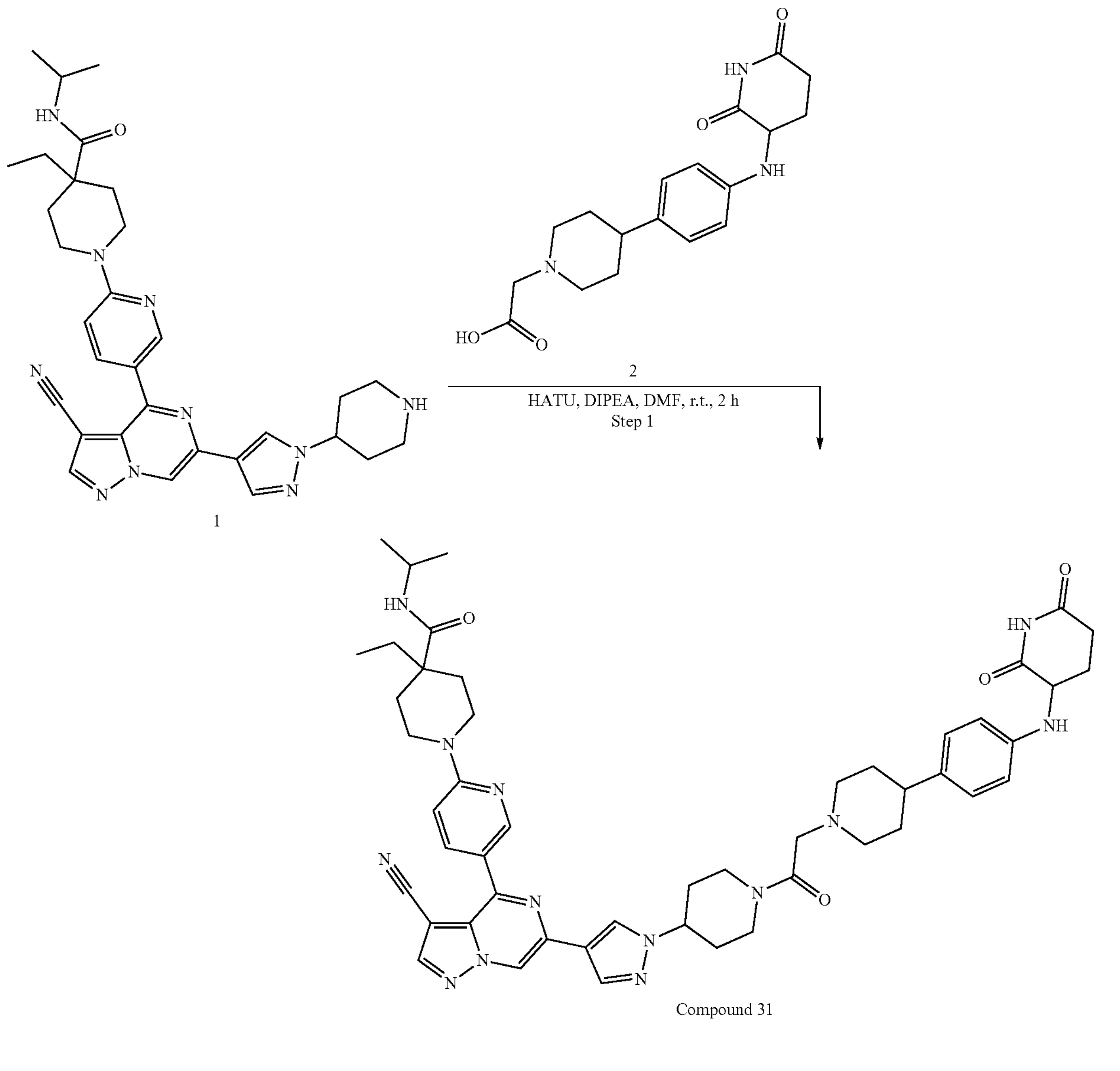 [SMILES: CCC1(C(=O)NC(C)C)CCN(c2ccc(-c3nc(-c4cnn(C5CCNCC5)c4)cn4ncc(C#N)c34)cn2)CC1 ; O=C(O)CN1CCC(c2ccc(NC3CCC(=O)NC3=O)cc2)CC1 ; CCC1(C(=O)NC(C)C)CCN(c2ccc(-c3nc(-c4cnn(C5CCN(C(=O)CN6CCC(c7ccc(NC8CCC(=O)NC8=O)cc7)CC6)CC5)c4)cn4ncc(C#N)c34)cn2)CC1]

Step 1. Into a 25 mL single-necked round-bottomed flask containing a well-stirred solution of 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide (1; 70 mg, 0.116 mmol) and 2-[4-[4-[(2,6-dioxo-3-piperidyl)amino]phenyl]-1-piperidyl]acetic acid (2; 44.09 mg, 0.115 mmol) in anhydrous DMF (2 mL) was added DIPEA (149.99 mg, 1.16 mmol, 0.202 mL), and the resulting solution was stirred for 10 minutes at ambient temperature under nitrogen atmosphere. HATU (52.95 mg, 0.139 mmol) was added to the reaction mixture and stirring was continued at ambient temperature for 2 h. The progress of the reaction was monitored by UPLC. After completion of the reaction, the reaction mixture was treated with ice-water (6 mL), and the desired product precipitated out. The solid was collected by filtration and dried under vacuum to get a crude mixture, which was purified by prep HPLC following a method: Column: XBRIDGE C8 (19×150) mm, 5 micron; Mobile phase: (0.1% $NH_4OAc$ in water/acetonitrile) to get desired prep-fraction. Combined prep-fraction was lyophilized to afford 1-[5-[3-cyano-6-[1-[1-[2-[4-[4-[(2,6-dioxo-3-piperidyl)amino]phenyl]-1-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 31; 17.97 mg, 0.019 mmol) as a yellow-coloured solid. Yield-17%. $^1H$ NMR (400 MHz, DMSO-$d_6$). δ 10.78 (s, 1H), 9.29 (s, 1H), 8.83 (s, 1H), 8.67 (d, J=2.4 Hz, 1H), 8.49 (s, 1H), 8.18 (s, 1H), 8.04 (dd, J=8.8, 2.4 Hz, 1H), 7.42 (d, J=8.0 Hz, 1H), 6.99-6.94 (m, 3H), 6.59 (d, J=8.0 Hz, 2H), 5.66 (s, 1H), 4.55-4.45 (m, 2H), 4.26-4.24 (m, 2H), 4.15 (d, J=14.0 Hz, 2H), 4.02-4.00 (m, 1H), 3.30 (m, 6H), 3.10 (t, J=10.8 Hz, 3H), 2.94 (brs, 3H), 2.19-2.08 (m, 6H), 2.05-1.97 (m, 1H), 1.91-1.83 (m, 2H), 1.77-1.73 (m, 2H), 1.65-1.56 (m, 2H), 1.49 (q, J=7.2 Hz, 2H), 1.34 (t, J=10.0 Hz, 2H), 1.09 (d, J=6.4 Hz, 6H), 0.75 (t, J=7.2 Hz, 3H). LC MS: ES+ (M+H) 895.3.
Example 109: Synthesis of 1-(5-(3-Cyano-6-(4-(4-(2-(1-(4-((2,6-dioxopiperidin-3-yl)amino)-2-fluorophenyl)-4-hydroxypiperidin-4-yl)acetyl)piperazin-1-yl)phenyl)pyrazolo[1,5-a]pyridin-4-yl)pyridin-2-yl)-N-isopropyl-4-methylpiperidine-4-carboxamide formic acid salt (Compound 32)
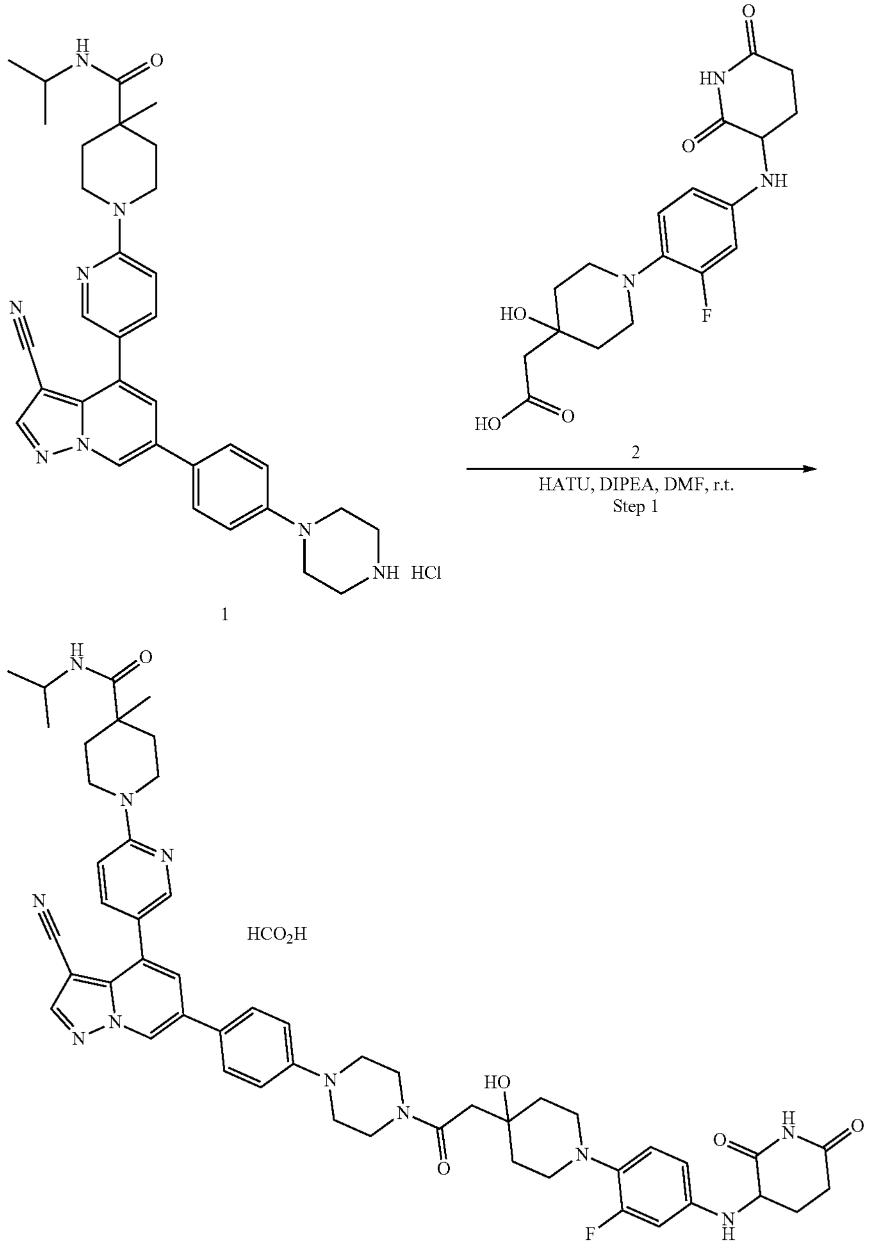
1
2
Compound 32

Step 1. Into a 25 mL single-necked round-bottomed flask containing a well-stirred solution of 2-[1-[4-[(2,6-dioxo-3-piperidyl)amino]-2-fluoro-phenyl]-4-hydroxy-4-piperidyl] acetic acid hydrochloride salt (2; 33 mg, 0.08 mmol) and 1-[5-[3-cyano-6-(4-piperazin-1-ylphenyl)pyrazolo[1,5-a] pyridin-4-yl]-2-pyridyl]-N-isopropyl-4-methyl-piperidine-4-carboxamide hydrochloride (1; 40 mg, 0.066 mmol, 021) in anhydrous DMF (3 mL) were added DIPEA (26 mg, 0.200 mmol, 34 μL) and HATU (38 mg, 0.1 mmol) under nitrogen atmosphere at room temperature, and the resulting mixture was stirred at room temperature for 2 h. Ice-cold water (25 mL) was added, stirring was continued for 10 minutes, and the resulting precipitated solid was filtered and dried to afford a crude solid which was purified by prep-HPLC column X-select C18 (150×19) mm, 5 microns. Mobile phase. 0.1% HCOOH in water and ACN to afford 1-[5-[3-cyano-6-[4-[4-[2-[1-[4-[(2,6-dioxo-3-piperidyl)amino]-2-fluoro-phenyl]-4-hydroxy-4-piperidyl]acetyl]piperazin-1-yl]phenyl]pyrazolo[1,5-a]pyridin-4-yl]-2-pyridyl]-N-isopropyl-4-methyl-piperidine-4-carboxamide formic acid salt (Compound 32; 9 mg, 0.09 mmol) as an off-white solid. Yield 14%. $^1$H NMR (400 MHz, DMSO-$d_6$). δ 10.79 (s, 1H), 9.19 (d, J=1.20 Hz, 1H), 8.68 (s, 1H), 8.41 (m, 1H), 7.82 (m, 5H), 7.38 (m, 1H), 7.09 (m, 3H), 6.98 (m, 2H), 6.53-6.42 (m, 2H), 5.83-5.74 (m, 1H), 4.88 (s, 1H), 4.27 (m, 1H), 3.98-3.91 (m, 4H), 3.70 (m, 6H), 3.35 (m, 5H), 2.95 (m, 4H), 2.11 (m, 5H), 1.89-1.65 (m, 4H), 1.45 (m, 2H), 1.13 (s, 3H), 1.08 (d, J=6.8 Hz, 6H). LC MS: ES+ (M+H) 925.3.

Example 110: Synthesis of 1-[5-[3-cyano-6-[4-[4-[2-[1-[4-[(2,4-dioxohexahydropyrimidin-1-yl)methyl]phenyl]-4-hydroxy-4-piperidyl]acetyl]piperazin-1-yl]phenyl]pyrazolo[1,5-a]pyridin-4-yl]-2-pyridyl]-N-isopropyl-4-methyl-piperidine-4-carboxamide formic acid salt (Compound 33)

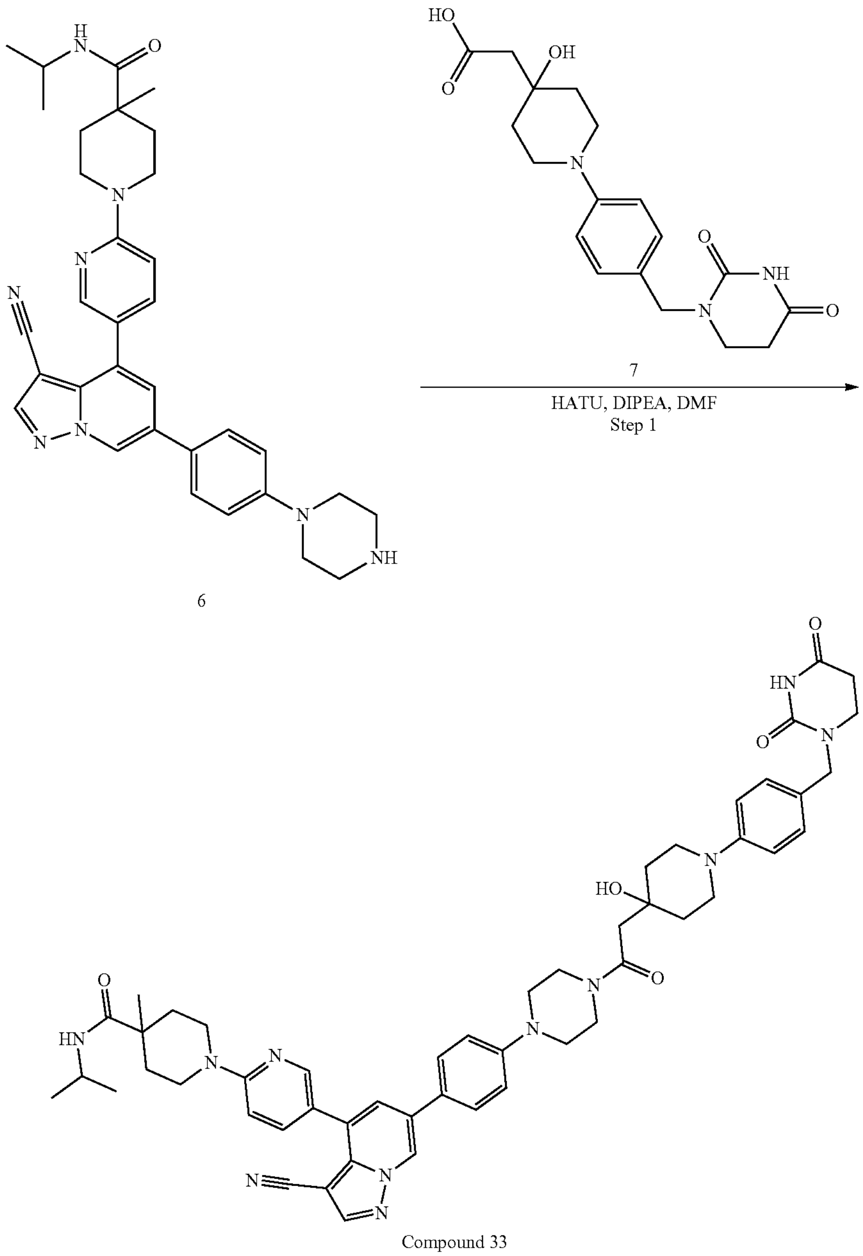

6

7

Compound 33

Step 1. Into a 25 mL single-necked round-bottomed flask containing a well-stirred solution of 1-[5-[3-cyano-6-(4-piperazin-1-ylphenyl)pyrazolo[1,5-a]pyridin-4-yl]-2-pyridyl]-N-isopropyl-4-methyl-piperidine-4-carboxamide (6; 40 mg, 0.066 mmol) and 2-[1-[4-[(2,4-dioxohexahydro-pyrimidin-1-yl)methyl]phenyl]-4-hydroxy-4-piperidyl]acetic acid (7; 31.87 mg, 0.080 mmol) in anhydrous DMF (3 mL) were added DIPEA (25.88 mg, 0.2 mmol, 0.035 mL) and HATU (38.08 mg, 0.1 mmol) at ambient temperature under nitrogen atmosphere. The contents were stirred at ambient temperature for 3 h. The progress of the reaction was monitored by LCMS. After completion of the reaction, the reaction mixture was treated with water (4 mL) and solid product was precipitated out. The solid was filtered and dried under vacuum to get crude residue. The crude residue was purified by reverse phase ISCO column using Mobile phase A: 0.1% HCOOH in water and B: Acetonitrile to afford 1-[5-[3-cyano-6-[4-[4-[2-[1-[4-[(2,4-dioxohexahydropyrimidin-1-yl)methyl]phenyl]-4-hydroxy-4-piperidyl]acetyl]piperazin-1-yl]phenyl]pyrazolo[1,5-a]pyridin-4-yl]-2-pyridyl]-N-isopropyl-4-methyl-piperidine-4-carboxamide formic acid salt (Compound 33; 8 mg, 0.008 mmol) as an off-white solid. Yield-12%. $^{1}H$ NMR (400 MHz, DMSO-$d_6$). δ 10.15 (s, 1H), 9.18 (d, J=1.2 Hz, 1H), 8.68 (s, 1H), 8.41 (d, J=2.8 Hz, 1H), 7.84-7.78 (m, 4H), 7.37 (d, J=8.0 Hz, 1H), 7.13-7.07 (m, 4H), 6.97 (d, J=8.8 Hz, 1H), 6.91 (d, J=8.8 Hz, 2H), 4.91 (s, 1H), 4.39 (s, 2H), 3.96-3.91 (m, 3H), 3.72-3.67 (m, 4H), 3.27-3.22 (m, 7H), 3.07 (t, J=9.2 Hz, 3H), 2.57 (s, 3H), 2.09 (d, J=14.4 Hz, 1H), 1.72-1.68 (m, 5H), 1.42-1.39 (m, 2H), 1.13 (s, 3H), 1.08 (d, J=6.4 Hz, 6H). LC MS: ES+ (M+H) 906.5.

Example 111: Synthesis of 1-(5-(3-Cyano-6-(1-((1r,4r)-4-(2-(4-(4-((2,6-dioxopiperidin-3-yl)amino)-2-fluorophenyl)piperidin-1-yl)ethyl)cyclohexyl)-1H-pyrazol-4-yl)pyrazolo[1,5-a]pyridin-4-yl)pyridin-2-yl)-N-isopropyl-4-methylpiperidine-4-carboxamide formic acid salt (Compound 34)

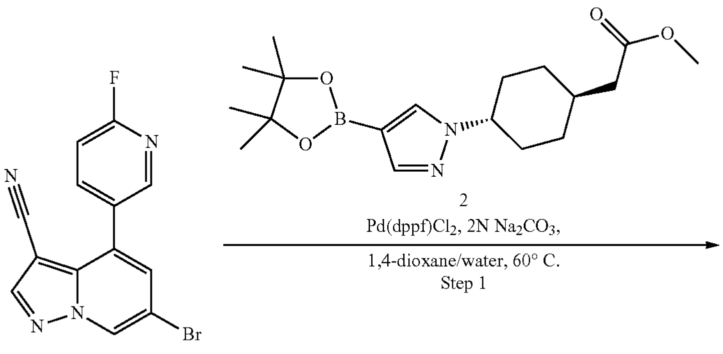

1 2

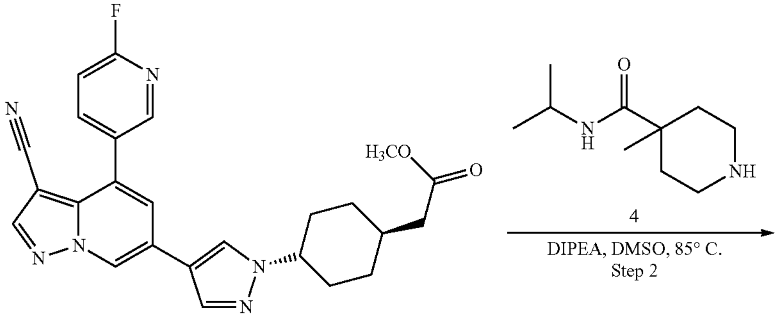

3 4

-continued
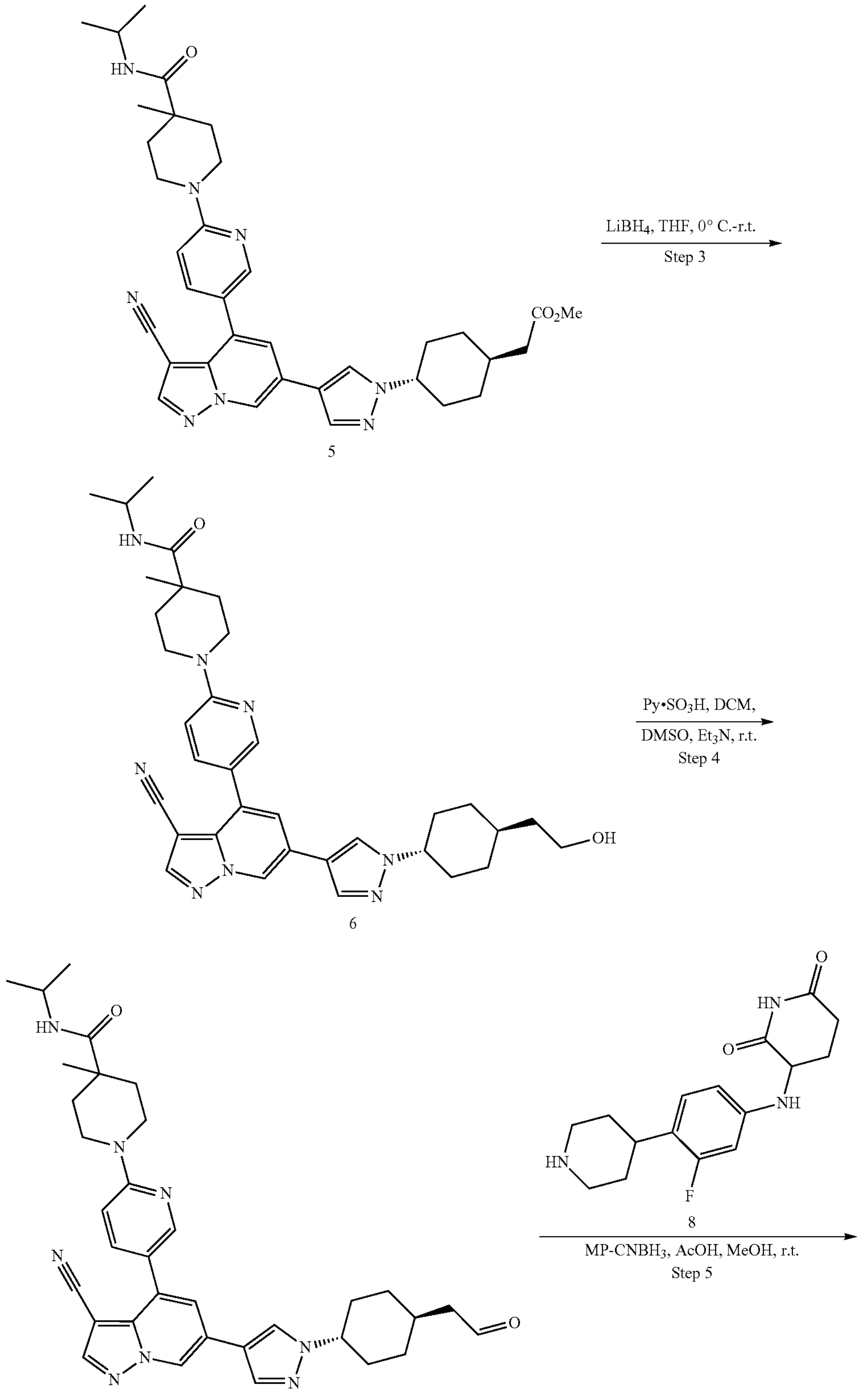

-continued

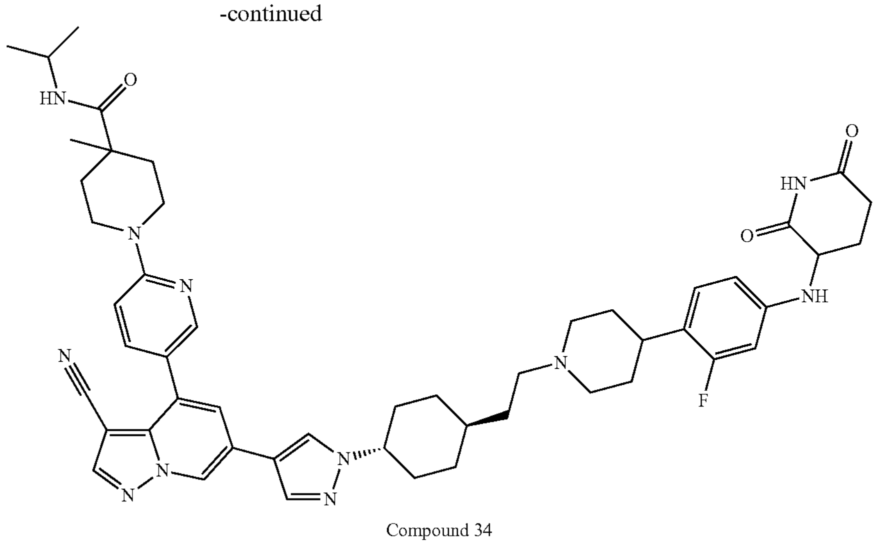

Compound 34

Step 1. Into a 25 mL sealed-tube containing a well stirred solution of 6-bromo-4-(6-fluoro-3-pyridyl)pyrazolo[1,5-a] pyridine-3-carbonitrile (1; 400 mg, 1.26 mmol) and methyl 2-((1r,4r)-4-(4-(4,4,5,5-tetramethyl-1,3,2-dioxaborolan-2-yl)-1H-pyrazol-1-yl)cyclohexyl)acetate (2; 483.19 mg, 1.39 mmol) in anhydrous 1,4-dioxane (8 mL) was added sodium carbonate (401.07 mg, 3.78 mmol, 0.158 mL) and water (2 mL). The mixture was purged with nitrogen for 5 minutes. Subsequently, Pd(dppf)$Cl_2$·$CH_2Cl_2$ (102.95 mg, 0.126 mmol) was added to the sealed tube, and the reaction mixture was purged with nitrogen for 5 minutes. The resultant reaction mixture was heated with stirring at 60° C. for 4 h. The progress of the reaction was monitored by UPLC. After consumption of starting material as monitored by UPLC, the reaction mixture was diluted with EtOAc (20 mL), filtered through a pad of Celite, and the Celite bed washed with EtOAc. The combined filtrate was concentrated under reduced pressure to afford a crude residue. The crude was purified by flash silica-gel (230-400 mesh; 10 g) column with a gradient of 0-100% EtOAc/pet ether while the desired product was eluting at 30-40% to afford methyl 2-((1r,4r)-4-(4-(3-cyano-4-(6-fluoropyridin-3-yl)pyrazolo[1,5-a]pyridin-6-yl)-1H-pyrazol-1-yl)cyclohexyl)acetate (3; 330 mg, 0.536 mmol) as a brown solid. Yield-42%; LC MS: ES+ (M+H) 459.2.

Step 2. Into a 25 mL sealed-tube reactor containing a well-stirred solution of methyl 2-((1r,4r)-4-(4-(3-cyano-4-(6-fluoropyridin-3-yl)pyrazolo[1,5-a]pyridin-6-yl)-1H-pyrazol-1-yl)cyclohexyl)acetate (3; 280 mg, 0.610 mmol) and N-isopropyl-4-methyl-piperidine-4-carboxamide (4; 168.81 mg, 0.764 mmol, 021) in anhydrous DMSO (4.0 mL) was added DIPEA (789.27 mg, 6.11 mmol, 1.06 mL), and the resultant reaction mixture was heated at 85° C. for 48 h. The progress of the reaction was monitored by UPLC. After consumption of starting material, ice-water (20 mL) was added to the reaction mixture, and the aqueous mixture was extracted with EtOAc (60 mL). The combined organic layers were washed with brine, dried (anhydrous $Na_2SO_4$), filtered, and the filtrate concentrated under reduced pressure to afford the crude mass. The crude mass was purified by flash silica-gel (230-400 mesh) with 0-100% EtOAc/pet ether while the desired product eluting at 75-85% of the mobile phase to afford methyl 2-((1r,4r)-4-(4-(3-cyano-4-(6-(4-(isopropylcarbamoyl)-4-methylpiperidin-1-yl)pyridin-3-yl) pyrazolo[1,5-a]pyridin-6-yl)-1H-pyrazol-1-yl)cyclohexyl) acetate (5; 190 mg, 0.278 mmol) as an off-white solid. Yield-45.5%; LC MS: ES+623.3.

Step 3. To a well-stirred solution of a mixture of methyl 2-((1r,4r)-4-(4-(3-cyano-4-(6-(4-(isopropylcarbamoyl)-4-methylpiperidin-1-yl)pyridin-3-yl)pyrazolo[1,5-a]pyridin-6-yl)-1H-pyrazol-1-yl)cyclohexyl)acetate (5; 190 mg, 0.305 mmol) in anhydrous THF (6.0 mL) taken in 25-mL single-necked round-bottomed flask was added dropwise $LiBH_4$ in THF (2.0 M, 0.305 mL) at 0° C. under nitrogen atmosphere and stirring was continued at 0° C. for 2 h. The reaction mixture was stirred at ambient temperature for 16 h. The progress of the reaction was monitored by LCMS & TLC, starting material was consumed completely. The reaction mixture was quenched with saturated $NH_4Cl$ solution (20 mL) at 0° C. and diluted with EtOAc (50 mL) and stirred for 10 minutes. The organic layer was collected, dried (anhydrous $Na_2SO_4$), filtered, and concentrated under reduced pressure to afford the crude mass. The crude mass was purified by flash silica-gel (230-400 mesh) column with 0-100% EtOAc/pet ether while the desired product eluting at 80-100% EtOAc/pet ether to afford 1-(5-(3-cyano-6-(1-((1r,4r)-4-(2-hydroxyethyl)cyclohexyl)-1H-pyrazol-4-yl)pyrazolo[1,5-a]pyridin-4-yl)pyridin-2-yl)-N-isopropyl-4-methylpiperidine-4-carboxamide (6; 140 mg, 0.124 mmol) as an off-white solid. Yield-41%; LC MS: ES+ (M+H) 595.3.

Step 4. Into a 20 mL vial containing a well-stirred solution of 1-(5-(3-cyano-6-(1-((1r,4r)-4-(2-hydroxyethyl)cyclohexyl)-1H-pyrazol-4-yl)pyrazolo[1,5-a]pyridin-4-yl)pyridin-2-yl)-N-isopropyl-4-methylpiperidine-4-carboxamide (6; 140 mg, 0.235 mmol) in anhydrous $CH_2Cl_2$ (3.0 mL) and DMSO (1.0 mL) was added $Et_3N$ (726.00 mg, 7.17 mmol, 1.0 mL) and the resulting mixture was stirred for 5 minutes. Then, pyridine;sulfur trioxide (149.86 mg, 0.941 mmol) was added and stirring was continued at ambient temperature for 16 h. The progress of the reaction was monitored by UPLC, unreacted starting material and product mass were observed. Again, pyridine;sulfur trioxide (149.86 mg, 0.941 mmol) was added to the reaction mixture and stirring was continued at ambient temperature for 32 h. The reaction mixture was diluted with EtOAc (100 mL) and washed successively with $H_2O$ (2×50 mL) and brine (2×50 mL). The separated organic layer was dried (anhydrous $Na_2SO_4$), filtered and the filtrate was evaporated to dryness under reduced pressure to obtain 1-(5-(3-cyano-6-(1-((1r,4r)-4-(2-oxoethyl)cyclohexyl)-1H-pyrazol-4-yl)pyrazolo[1,5-a]pyridin-4-yl)pyridin-2-yl)-N-isopropyl-4-methylpiperidine-4-carboxamide (7; 120 mg, 0.098 mmol) as an off-white solid (crude). Yield-42%; LC MS: ES+(M+H) 593.3.

Step 5. Into a 8 mL vial containing a well-stirred solution of 1-(5-(3-cyano-6-(1-((1r,4r)-4-(2-oxoethyl)cyclohexyl)-1H-pyrazol-4-yl)pyrazolo[1,5-a]pyridin-4-yl)pyridin-2-yl)-N-isopropyl-4-methylpiperidine-4-carboxamide (7; 120 mg, 0.202 mmol) and 3-[3-fluoro-4-(4-piperidyl)anilino]piperidine-2,6-dione (8; 61.82 mg, 0.202 mmol) in anhydrous MeOH (2.0 mL) were added AcOH (52.50 mg, 0.874 mmol, 0.05 mL) followed by MP-CNBH$_3$ (240 mg, 0.202 mmol) and stirring was continued at ambient temperature for 4 h. The progress of the reaction was monitored by UPLC. After completion of starting material, the reaction mixture was filtered and concentrated under reduced pressure to afford crude product. The crude mass was purified by prep-HPLC column: X-BRIDGE C8 (150×19)MM 5 MICRONS; Mobile phase: 0.1% HCO$_2$H in milli Q water/Acetonitrile and the prep fractions were lyophilized to afford 1-[5-[3-cyano-6-[1-[4-[2-[4-[4-[(2,6-dioxo-3-piperidyl)amino]-2-fluoro-phenyl]-1-piperidyl]ethyl]cyclohexyl]pyrazol-4-yl]pyrazolo[1,5-a]pyridin-4-yl]-2-pyridyl]-N-isopropyl-4-methyl-piperidine-4-carboxamide formic acid salt (Compound 34; 24.17 mg, 0.025 mmol) as an off-white solid. Yield-13%. $^1$H NMR (400 MHz, DMSO-d$_6$). δ 10.79 (s, 1H), 9.23 (d, J=2.8 Hz, 1H), 8.64 (s, 1H), 8.53 (s, 1H), 8.37 (d, J=2.8 Hz, 1H), 8.13 (s, 1H), 7.82-7.78 (m, 2H), 7.36 (d, J=7.6 Hz, 1H), 7.02-6.96 (m, 2H), 6.47-6.42 (m, 2H), 6.00 (d, J=8.0 Hz, 1H), 4.34-4.29 (m, 1H), 4.15-4.09 (m, 1H), 3.97-3.92 (m, 3H), 2.98 (d, J=10.8 Hz, 2H), 2.34-2.33 (m, 2H), 2.11-2.09 (m, 6H), 2.00-1.97 (m, 2H), 1.90-1.88 (m, 3H), 1.75-1.72 (m, 2H), 1.65-1.63 (m, 4H), 1.41-1.36 (m, 5H), 1.24 (s, 3H), 1.14 (s, 6H), 1.08 (d, J=6.8 Hz, 6H). LC MS: ES+ (M+H) 882.2.

Example 112: Synthesis of 1-(5-(3-Cyano-6-(4-(4-(2-(4-(4-((2,6-dioxopiperidin-3-yl)amino)phenyl)piperidin-1-yl)acetyl)piperazin-1-yl)phenyl)pyrazolo[1,5-a]pyridin-4-yl)pyridin-2-yl)-N-isopropyl-4-methylpiperidine-4-carboxamide (Compound 35)

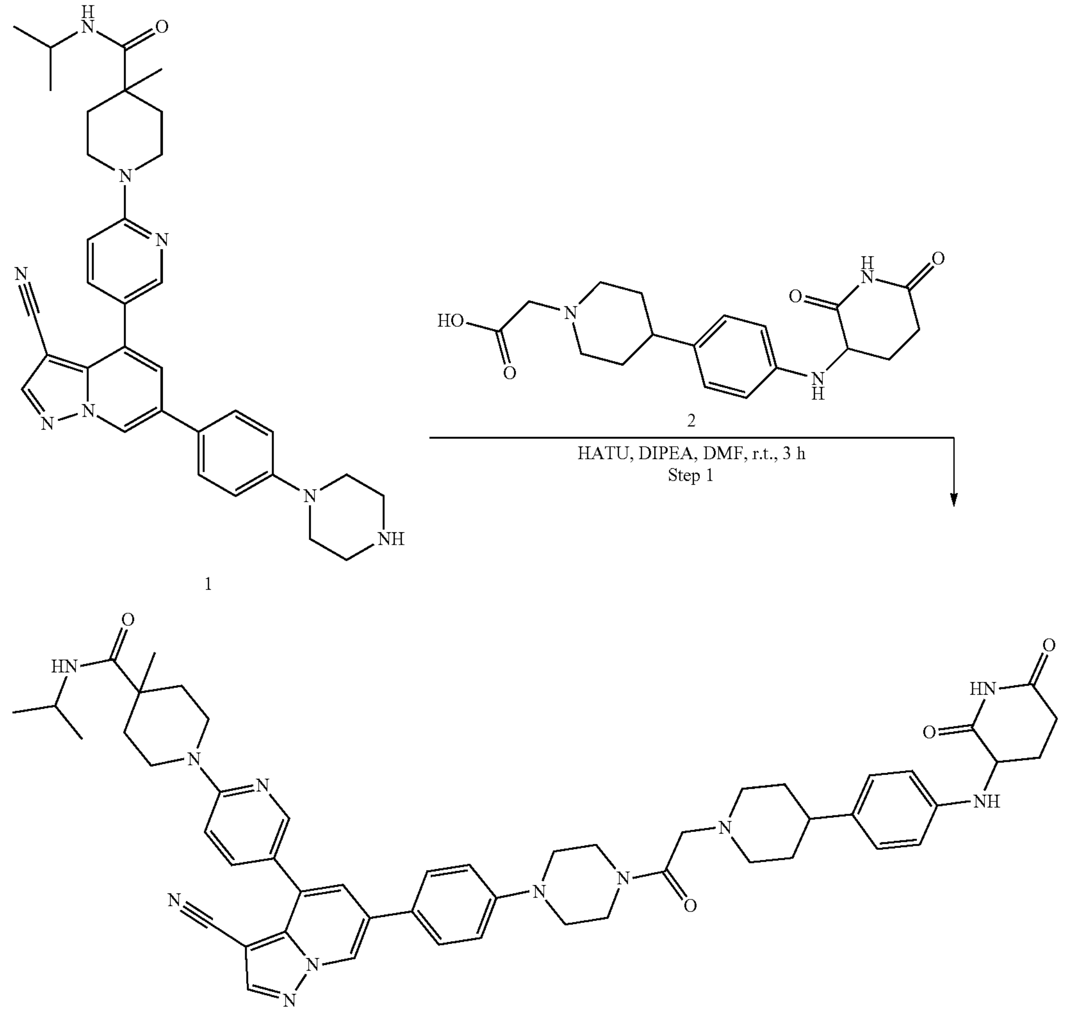

Compound 35

Step 1. Into a 25 mL single-necked round-bottomed flask containing a well-stirred solution of 1-[5-[3-cyano-6-(4-piperazin-1-ylphenyl)pyrazolo[1,5-a]pyridin-4-yl]-2-pyridyl]-N-isopropyl-4-methyl-piperidine-4-carboxamide (1; 48.63 mg, 0.086 mmol) and 2-[4-[4-[(2,6-dioxo-3-piperidyl)amino]phenyl]-1-piperidyl]acetic acid (2; 30 mg, 0.078 mmol) in anhydrous DMF (5 mL) were added DIPEA (50.77 mg, 0.392 mmol, 0.068 mL) and HATU (35.85 mg, 0.094 mmol) at ambient temperature under nitrogen atmosphere. The progress of the reaction was monitored by UPLC. After completion of the reaction, the reaction mixture was treated with water (1 mL) and solid precipitated out was filtered. The filtered solid was dried under vacuum to get crude mixture, which was purified by reverse phase column chromatography using ISCO C-18 CombiFlash column (Mobile phase: A: 0.1% FA in water, B: Acetonitrile) to yield 1-[5-[3-cyano-6-[4-[4-[2-[4-[4-[(2,6-dioxo-3-piperidyl)amino]phenyl]-1-piperidyl]acetyl]piperazin-1-yl]phenyl]pyrazolo[1,5-a]pyridin-4-yl]-2-pyridyl]-N-isopropyl-4-methyl-piperidine-4-carboxamide (Compound 35; 11.10 mg, 0.011 mmol) as a white solid. LCMS (MW: 890.08, observed [M−H]: 888.8). Yield-14%. $^1$H NMR (400 MHz, DMSO-$d_6$). δ 10.79 (s, 1H), 9.21 (brs, 1H), 9.20 (d, J=1.2 Hz, 1H), 8.69 (s, 1H), 8.41 (d, J=2.4 Hz, 1H), 7.85-7.79 (m, 4H), 7.38 (d, J=8.0 Hz, 1H), 7.12-7.06 (m, 2H), 6.97 (d, J=8.4 Hz, 2H), 6.65 (d, J=8.4 Hz, 2H), 5.78 (d, J=6.0 Hz, 1H), 4.45-4.28 (m, 3H), 3.98-3.91 (m, 3H), 3.71 (s, 2H), 3.63-3.55 (m, 4H), 3.30-3.24 (m, 7H), 3.09 (d, J=7.2 Hz, 2H), 2.11-2.08 (m, 4H), 1.98-1.85 (m, 6H), 1.39 (t, J=9.6 Hz, 2H), 1.13 (s, 3H), 1.08 (d, J=6.4 Hz, 6H); LC MS. ES−(M-1) 888.8.

Example 113: Synthesis of 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-(4-pyrimidin-2-yl-1-piperidyl)-3-pyridyl]pyrazolo[1,5-a]pyrazine-3-carbonitrile formic acid salt (Compound 36)

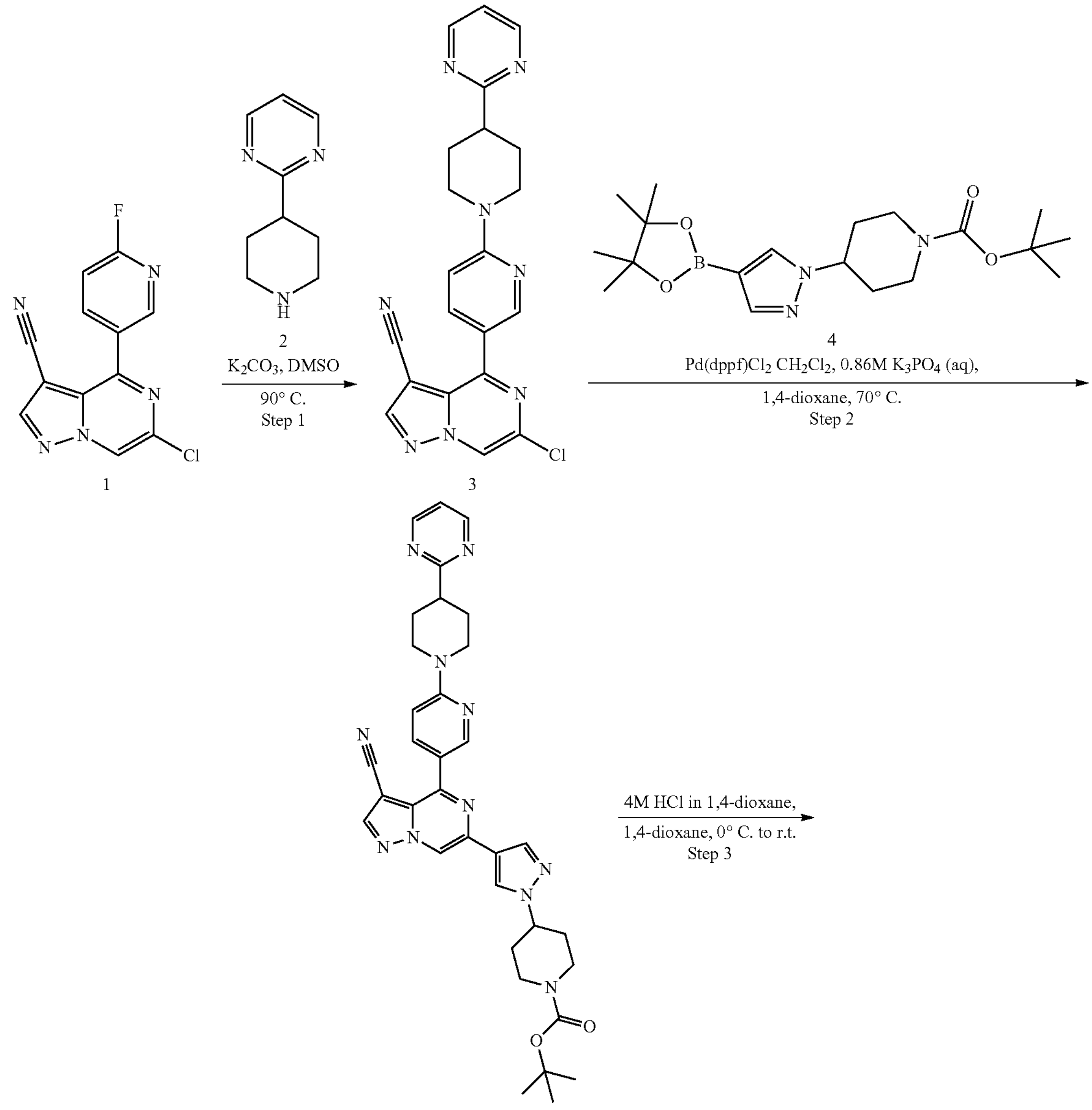

5

-continued

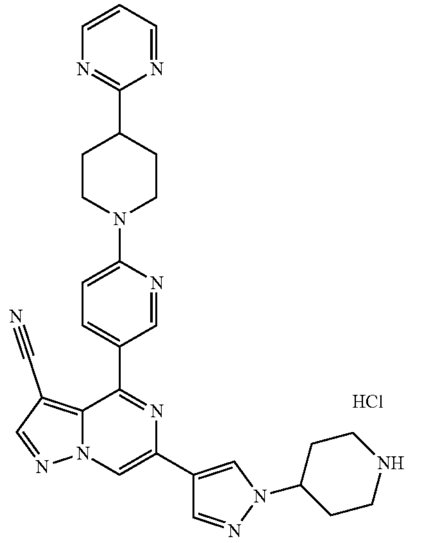

6

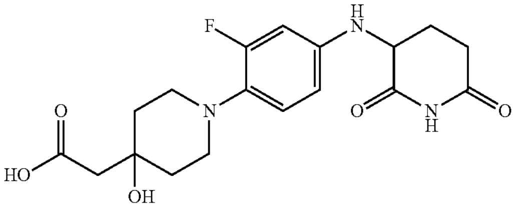

7

HATU, DIPEA,

DMF, r.t.

Step 4

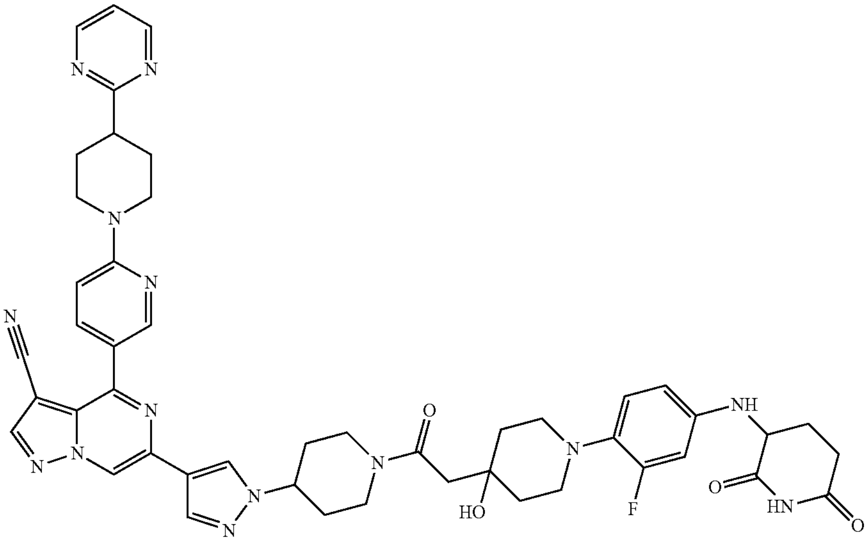

Compound 36

Step 1. A solution of 6-chloro-4-(6-fluoro-3-pyridyl)pyrazolo[1,5-a]pyrazine-3-carbonitrile (1; 390 mg, 1.43 mmol), 2-(4-piperidyl)pyrimidine (2; 255.88 mg, 1.57 mmol) and Potassium carbonate, anhydrous, 99% (984.86 mg, 7.13 mmol, 430.07 uL) in DMSO (4.5 mL) was stirred at 90° C. for 1 hr. After cooling, 10 mL of water was added into the reaction mixture and was extracted with DCM (4×8 mL). The combined organic layers were washed with brine (8 mL), dried (anhydrous $Na_2SO_4$), filtered and concentrated under reduced pressure to afford 6-chloro-4-[6-(4-pyrimidin-2-yl-1-piperidyl)-3-pyridyl]pyrazolo[1,5-a]pyrazine-3-carbonitrile (3; 45 mg, 90.24 umol) as a yellow solid, which was carried forward without further purification. Yield-6%; LC MS: ES+ (M+H) 417.0

Step 2. To a solution of 6-chloro-4-[6-(4-pyrimidin-2-yl-1-piperidyl)-3-pyridyl]pyrazolo[1,5-a]pyrazine-3-carbonitrile (3; 45 mg, 107.95 umol), tert-butyl 4-[4-(4,4,5,5-tetramethyl-1,3,2-dioxaborolan-2-yl)pyrazol-1-yl]piperidine-1-carboxylate (4; 40.73 mg, 107.95 umol), cyclopentyl (diphenyl)phosphane;dichloromethane;dichloropalladium; iron (17.63 mg, 21.59 umol) in 1,4-dioxane (1 mL) was added a solution of tripotassium;phosphate (45.83 mg, 215.90 umol) in Water (0.25 mL) under $N_2$ atmosphere and the mixture was stirred at 70° C. for 8 hr under $N_2$ atmosphere. The mixture was diluted with $H_2O$ (3 mL) and extracted with ethyl acetate (4×3 mL). The combined organic layers were washed with brine (3 mL), dried (anhydrous $Na_2SO_4$), filtered and concentrated under reduced pressure to give a residue. The crude material was purified by prep-TLC ($SiO_2$, using pet ether and EtOAc) to afford tert-butyl 4-[4-[3-cyano-4-[6-(4-pyrimidin-2-yl-1-piperidyl)-3-pyridyl]pyrazolo[1,5-a]pyrazin-6-yl]pyrazol-1-yl]piperidine-1-carboxylate (5; 25 mg, 36.41 umol, 33.73% yield) as a light yellow solid. Yield-34%; LC MS: ES+ (M+H) 632.2

Step 3. A mixture of tert-butyl 4-[4-[3-cyano-4-[6-(4-pyrimidin-2-yl-1-piperidyl)-3-pyridyl]pyrazolo[1,5-a]pyrazin-6-yl]pyrazol-1-yl]piperidine-1-carboxylate (5; 70 mg, 110.81 umol) in 1,4-dioxane (1 mL) was added 4.0 M HCl in 1,4-dioxane (277.02 uL) at 0° C. and the mixture was stirred at 25° C. for 5 hr. The mixture was concentrated under reduced pressure to afford 6-[1-(4-piperidyl)pyrazol-4-yl]-4-[6-(4-pyrimidin-2-yl-1-piperidyl)-3-pyridyl]pyrazolo[1,5-a]pyrazine-3-carbonitrile hydrochloric acid salt (6; 80 mg, 125.76 umol) as a yellow solid, which was carried forward without further purification. Yield-99%; LC MS: ES+ (M+H) 532.1

Step 4. A mixture of 6-[1-(4-piperidyl)pyrazol-4-yl]-4-[6-(4-pyrimidin-2-yl-1-piperidyl)-3-pyridyl]pyrazolo[1,5-a]pyrazine-3-carbonitrile hydrochloric acid salt (6; 60 mg, 94.00 umol), 2-[1-[4-[(2,6-dioxo-3-piperidyl)amino]-2-fluoro-phenyl]-4-hydroxy-4-piperidyl]acetic acid hydrochloride (7; 35.66 mg, 85.76 umol), HATU (71.48 mg, 188.00 umol), and N-ethyl-N-isopropyl-propan-2-amine (97.19 mg, 752.01 umol, 130.99 uL) in DMF (0.6 mL) was stirred at 25° C. for 30 min. Water (50 mL) was added into the mixture and extracted with ethyl acetate (6x5 mL). The combined organic layers were washed with brine (5 mL), dried (anhydrous $Na_2SO_4$), filtered and concentrated under reduced pressure to give the crude. The crude was purified by by Prep-HPLC (Shim-pack C18 150*25*10 um, water (0.225% formic acid)-acetonitrile, 19%-39%, 2 ml/min 10 min) to afford 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-(4-pyrimidin-2-yl-1-piperidyl)-3-pyridyl]pyrazolo[1,5-a]pyrazine-3-carbonitrile formic acid salt (Compound 36; 12.82 mg, 13.50 umol) as a white solid. Yield-14%; $^1H$ NMR (400 MHz, DMSO-$d_6$): δ=10.84-10.69 (m, 1H), 9.29 (s, 1H), 8.82 (s, 1H), 8.75 (d, J=4.9 Hz, 2H), 8.70 (d, J=2.4 Hz, 1H), 8.50 (s, 1H), 8.39 (s, 1H), 8.18 (s, 1H), 8.08 (m, 1H), 7.39-7.30 (m, 1H), 7.06 (d, J=8.8 Hz, 1H), 6.85 (t, J=9.2 Hz, 1H), 6.49 (m, 1H), 6.41 (m, 1H), 5.76 (d, J=7.6 Hz, 1H), 4.90 (s, 1H), 4.56 (d, J=12.6 Hz, 4H), 4.30-4.13 (m, 2H), 3.21-3.12 (m, 4H), 2.95-2.69 (m, 7H), 2.57 (s, 2H), 2.16-2.00 (m, 6H), 1.90-1.62 (m, 9H). LC MS: ES+ (M/2+H) 447.4

Example 114: Synthesis of 1-(5-(3-Cyano-6-(2-(4-(2-(4-(4-((2,6-dioxopiperidin-3-yl)amino)-2-fluorophenyl)piperidin-1-yl)acetyl)piperazin-1-yl)pyrimidin-5-yl)pyrazolo[1,5-a]pyridin-4-yl)pyridin-2-yl)-4-ethyl-N-isopropylpiperidine-4-carboxamide (Compound 37)

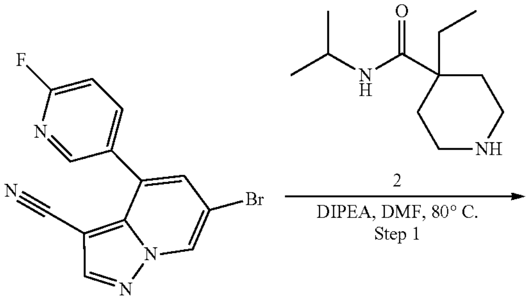

1

2

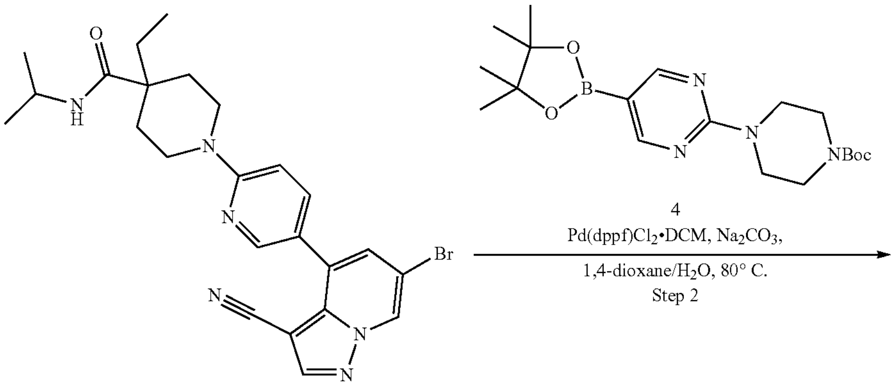

3

4

-continued

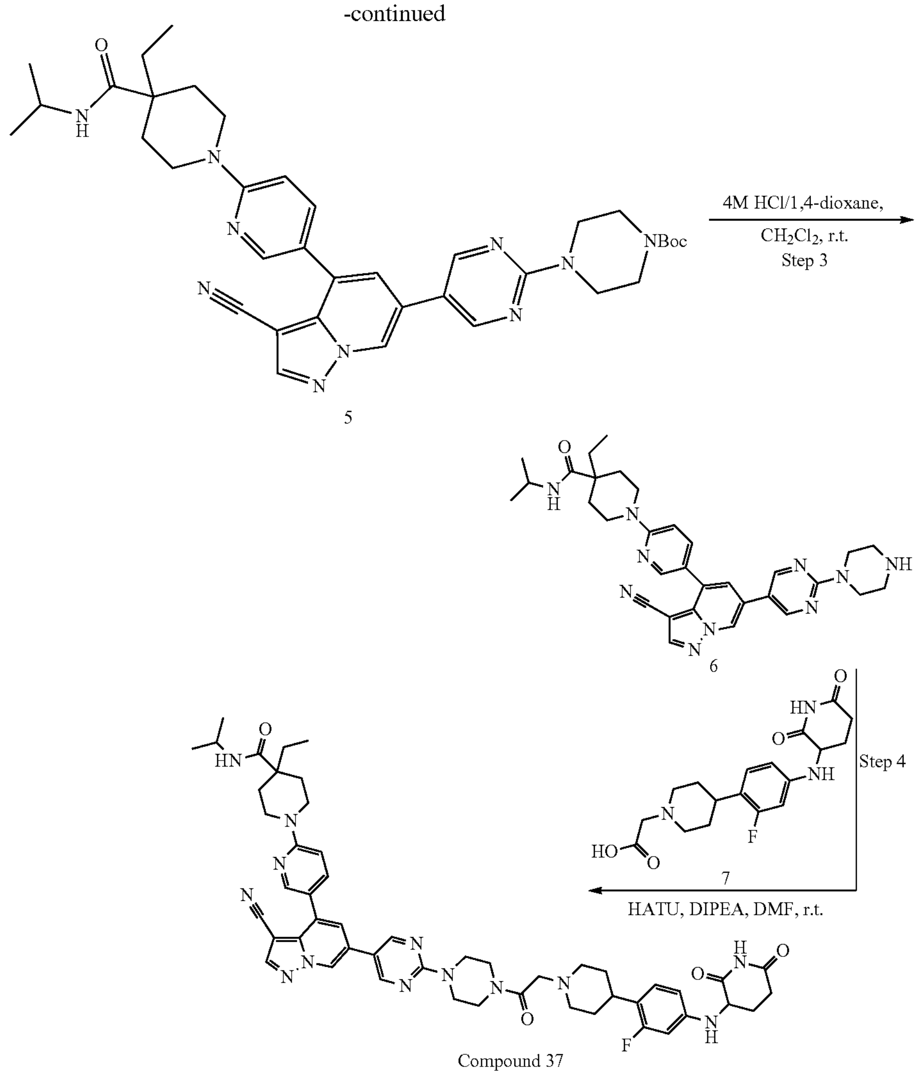

5

6

7

Compound 37

Step 1. Into a 25 mL sealed tube containing a well-stirred solution of a mixture of 6-bromo-4-(6-fluoro-3-pyridyl) pyrazolo[1,5-a]pyridine-3-carbonitrile (1; 500 mg, 1.58 mmol) and 4-ethyl-N-isopropyl-piperidine-4-carboxamide (2; 312.67 mg, 1.33 mmol) in anhydrous DMF (8 mL) was added DIPEA (1.02 g, 7.88 mmol, 1.37 mL) at ambient temperature under nitrogen atmosphere. The reaction mixture was stirred at 80° C. for 16 h. After complete consumption of the starting material as indicated by TLC, water (20 mL) was added and resulting mixture was stirred for 10 minutes. The resulting solid was filtered and dried to afford a crude residue. The crude was purified by flash silica-gel (230-400 mesh) column chromatography with 0-100% EtOAc/petroleum ether to afford 1-[5-(6-bromo-3-cyano-pyrazolo[1,5-a]pyridin-4-yl)-2-pyridyl]-4-ethyl-N-isopropyl-piperidine-4-carboxamide (3; 400 mg, 0.690 mmol) as a brown solid. Yield-44%; LC MS: ES+ (M+H) 495.1.

Step 2. Into a 25 mL sealed-tube reactor containing a well-stirred solution of 1-[5-(6-bromo-3-cyano-pyrazolo[1,5-a]pyridin-4-yl)-2-pyridyl]-4-ethyl-N-isopropyl-piperidine-4-carboxamide (3; 400 mg, 0.807 mmol) and tert-butyl 4-[5-(4,4,5,5-tetramethyl-1,3,2-dioxaborolan-2-yl)pyrimidin-2-yl]piperazine-1-carboxylate (4; 378.14 mg, 0.968 mmol) in anhydrous 1,4-dioxane (8 mL) was added sodium carbonate (256.73 mg, 2.42 mmol) in water (2 mL) at ambient temperature under nitrogen atmosphere and the resulting mixture was degassed by bubbling nitrogen gas into the reaction mixture for 10 minutes. Subsequently, $Pd(dppf)Cl_2 \cdot CH_2Cl_2$ (65.94 mg, 0.080 mmol) was added to the reaction mixture and reaction mixture was heated to 80° C. for 4 h. After completion of the reaction as indicated by TLC, the reaction mixture was cooled to room temperature. The reaction mixture was concentrated under reduced pressure to get a crude residue, which was purified by neutral alumina column with 0-100% EtOAc/petroleum ether to afford tert-butyl 4-[5-[3-cyano-4-[6-[4-ethyl-4-(isopropylcarbamoyl)-1-piperidyl]-3-pyridyl]pyrazolo[1,5-a]pyridin-6-yl]pyrimidin-2-yl]piperazine-1-carboxylate (5; 310 mg, 0.354 mmol) as a brown solid. Yield-44%; LC MS: ES+ (M+H) 679.3.

Step 3. Into a 50 mL single-necked round-bottomed flask containing a well-stirred solution of tert-butyl 4-[5-[3-cyano-4-[6-[4-ethyl-4-(isopropylcarbamoyl)-1-piperidyl]-3-pyridyl]pyrazolo[1,5-a]pyridin-6-yl]pyrimidin-2-yl]piperazine-1-carboxylate (5; 310 mg, 0.457 mmol) in anhydrous $CH_2Cl_2$ (5 mL) was added HCl (5 mL; 4 M in 1,4-dioxane) at ambient temperature. The resulting mixture was stirred at room temperature for 2 h and monitored by TLC. Excess solvents were removed from the reaction mixture under reduced pressure to get a crude residue. Reaction crude was washed with MTBE (10 mL) to get the 1-[5-[3-cyano-6-(2-piperazin-1-ylpyrimidin-5-yl)pyrazolo[1,5-a]pyridin-4-yl]-2-pyridyl]-4-ethyl-N-isopropyl-piperidine-4-carboxamide hydrochloric acid salt (6; 300 mg, 0.326 mmol) as a light brown solid. Yield-71.3%; LC MS: ES+(M+H) 579.3.

Step 4. Into a 25 mL single-necked round-bottomed flask containing a well-stirred solution of 1-[5-[3-cyano-6-(2-piperazin-1-ylpyrimidin-5-yl)pyrazolo[1,5-a]pyridin-4-yl]-2-pyridyl]-4-ethyl-N-isopropyl-piperidine-4-carboxamide hydrochloric acid salt (6; 100 mg, 0.16 mmol) and 2-[4-[4-[(2,6-dioxo-3-piperidyl)amino]-2-fluoro-phenyl]-1-piperidyl]acetic acid (7; 71.50 mg, 0.179 mmol) in anhydrous DMF (2 mL) were added DIPEA (0.085 mL, 0.487 mmol) and HATU (74.17 mg, 0.195 mmol) at ambient temperature under nitrogen atmosphere. The contents were stirred at ambient temperature for 3 h. The progress of the reaction was monitored by LCMS. After completion of the reaction, the reaction mixture was treated with water (4 mL) and solid product precipitated out. The solid was filtered, dried under vacuum to get crude residue. The crude residue was purified by prep HPLC following a method: Column: X-Select C18 (150×19) mm, 5 micron; Mobile Phase A: 0.1% Ammonium acetate in milli-Q water; Mobile phase B: Acetonitrile; Flow rate: 15 mL/min; RT=12.4 min. to yield 1-[5-[3-cyano-6-[2-[4-[2-[4-[4-[(2,6-dioxo-3-piperidyl)amino]-2-fluoro-phenyl]-1-piperidyl]acetyl]piperazin-1-yl]pyrimidin-5-yl]pyrazolo[1,5-a]pyridin-4-yl]-2-pyridyl]-4-ethyl-N-isopropyl-piperidine-4-carboxamide (Compound 37; 38 mg, 0.040 mmol) as an off-white solid. Yield-25%. $^{1}$H NMR (400 MHz, DMSO-$d_6$). δ 10.77 (s, 1H), 9.32 (d, J=1.6 Hz, 1H), 8.94 (s, 2H), 8.71 (s, 1H), 8.41 (d, J=2.4 Hz, 1H), 7.85-7.81 (m, 2H), 7.38 (d, J=7.6 Hz, 1H), 7.02-6.95 (m, 2H), 6.47-6.42 (m, 2H), 5.99 (d, J=7.6 Hz, 1H), 4.32-4.28 (m, 1H), 4.09-3.99 (m, 3H), 3.85 (d, J=28.8 Hz, 4H), 3.71 (s, 2H), 3.58 (s, 2H), 3.22 (s, 2H), 3.08 (t, J=11.2 Hz, 2H), 2.85 (d, J=11.2 Hz, 2H), 2.74-2.68 (m, 1H), 2.60-2.58 (m, 1H), 2.18-2.08 (m, 6H), 1.91-1.79 (m, 1H), 1.66 (brs, 4H), 1.51-1.49 (m, 2H), 1.38-1.36 (m, 2H), 1.09 (d, J=6.4 Hz, 6H), 0.76 (t, J=7.6 Hz, 3H). LC MS: ES+ (M+H) 924.5.

Example 115: Synthesis of 6-chloro-4-(4-piperazin-1-ylphenyl)pyrazolo[1,5-a]pyrazine-3-carbonitrile

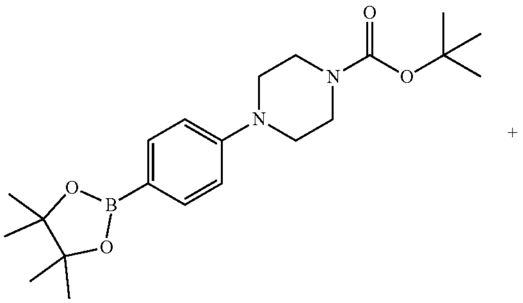

1

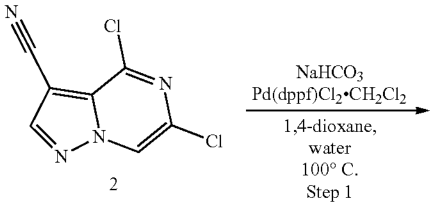

2

-continued

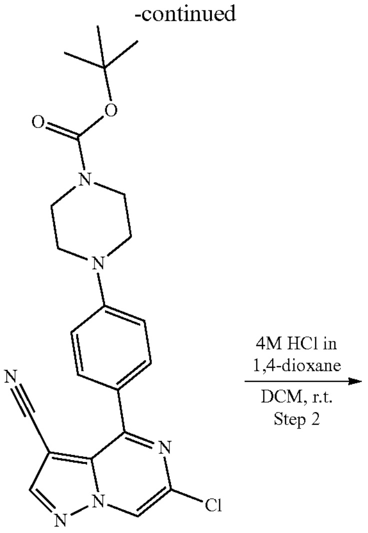

3

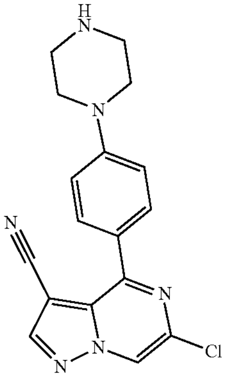

4

Step 1. Into a 50 mL single neck round bottom flask was charged with tert-butyl 4-[4-(4,4,5,5-tetramethyl-1,3,2-dioxaborolan-2-yl)phenyl]piperazine-1-carboxylate (348.18 mg, 896.66 umol) and 4,6-dichloropyrazolo[1,5-a]pyrazine-3-carbonitrile (200 mg, 938.86 umol) in Water (1 mL) and 1,4-dioxane (5 mL) was added Sodium bicarbonate (296.75 mg, 3.53 mmol, 137.38 uL). Then nitrogen gas was purged through reaction mixture for 10 minutes, Later was added 1,1'-Bis(diphenylphosphino)ferrocene-palladium(II)dichloride dichloromethane complex (36.95 mg, 45.29 umol) and again the resulting suspension was purged with nitrogen gas for additional 10 minutes. The reaction mixture was heated at 100° C. under nitrogen atmospheric pressure for 2 hr. Progress of reaction was monitored by TLC and LCMS. The reaction mixture was passed through a pad of Celite, and the filtrate was concentrated under reduced pressure to get crude residue which was purified by silica-gel (230-400 mesh) with 30% EtOAc/Pet ether to get tert-butyl 4-[4-(6-chloro-3-cyano-pyrazolo[1,5-a]pyrazin-4-yl)phenyl]piperazine-1-carboxylate as a brown solid. Yield-91%; LCMS: ES+ (M+H) 439.1, 440.0 (chlorine pattern).

Step 2. To a solution of tert-butyl 4-[4-(6-chloro-3-cyano-pyrazolo[1,5-a]pyrazin-4-yl)phenyl]piperazine-1-carboxylate (2.3 g, 5.24 mmol) in 1,4-dioxane (8 mL) was added Hydrogen chloride, 4M in 1,4-dioxane, 99% (4 M, 6.27 mL) at 0° C. and stirred at room temperature for 6 h. The progress of the reaction was monitored by LCMS/TLC. The reaction mixture was concentrated under reduced pressure to get crude which was triturated with pet ether to afford 6-chloro-4-(4-piperazin-1-ylphenyl)pyrazolo[1,5-a]pyrazine-3-carbonitrile hydrochloric acid salt as a light brown solid. Yield-97%; LCMS: ES+ (M+H) 339.0.

Example 116: Synthesis of 6-(1-(1-(2-(4-(4-((2,6-Dioxopiperidin-3-yl)oxy)-2-fluorophenyl)piperidin-1-yl)acetyl)piperidin-4-yl)-1H-pyrazol-4-yl)-4-(4-(4-((4-fluoropyridin-2-yl)methyl)piperazin-1-yl)phenyl)pyrazolo[1,5-a]pyrazine-3-carbonitrile (Compound 38)
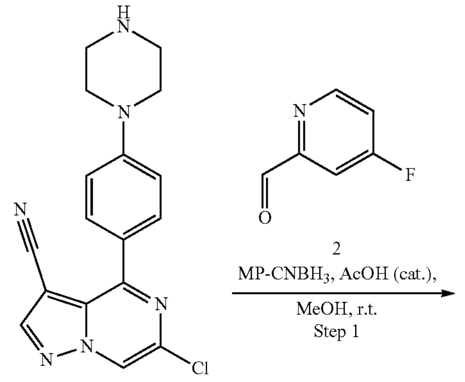
1
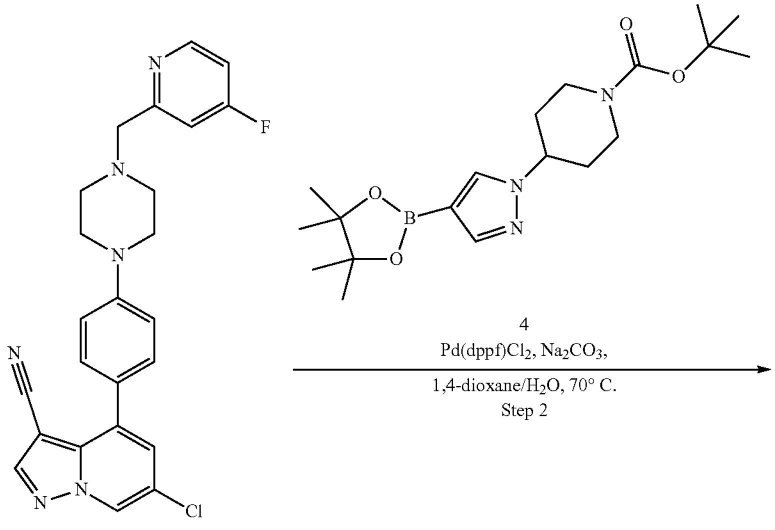
3

-continued
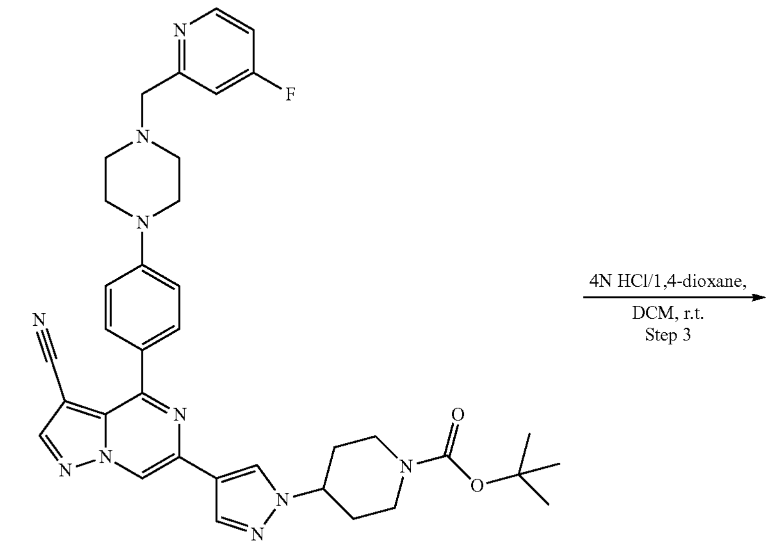
5
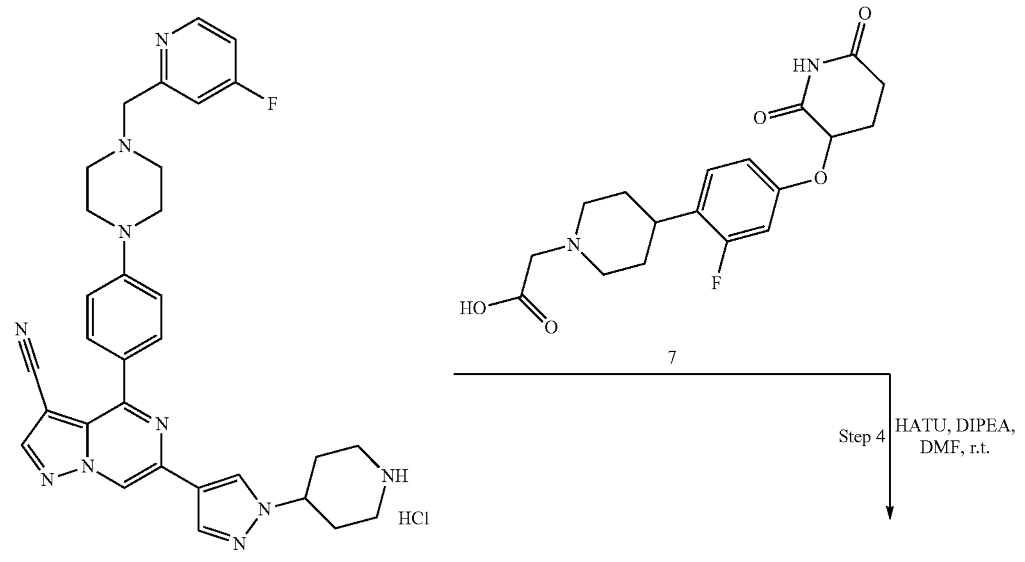
7
6

-continued

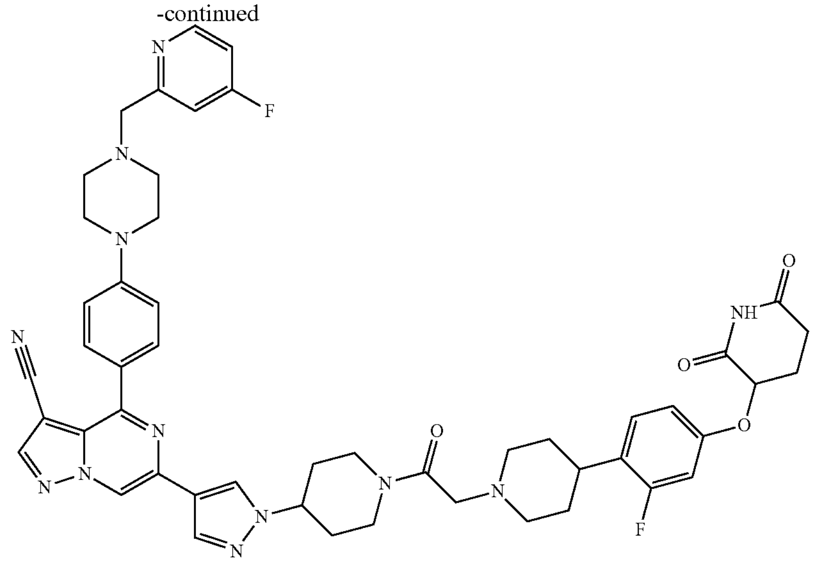

Compound 38

Step 1. Into a 50 mL single-necked round-bottomed flask containing a well-stirred solution of 6-chloro-4-(4-piperazin-1-ylphenyl)pyrazolo[1,5-a]pyrazine-3-carbonitrile hydrochloride salt (1; 675 mg, 1.80 mmol) and 4-fluoropyridine-2-carbaldehyde (2; 225 mg, 1.80 mmol) in anhydrous MeOH (12 mL) were added acetic acid (11 mg, 0.179 mmol, 0.01 mL) and MP-$CNBH_3$ (1.5 g, 1.80 mmol) at ambient temperature. The resulting mixture was stirred at ambient temperature for 16 h. The reaction mixture was filtered through sintered funnel and the filtrate was concentrated under reduced pressure to get a crude which was purified by flash silica-gel (230-400 mesh) column with 0-100% EtOAc/pet ether with the desired compound eluting at 80-100% EtOAc to afford 6-chloro-4-[4-[4-[(4-fluoro-2-pyridyl)methyl]piperazin-1-yl]phenyl]pyrazolo[1,5-a]pyrazine-3-carbonitrile (3; 200 mg, 0.330 mmol) as a yellow gummy liquid. Yield 18%; LC MS: ES+ (M+H) 448.1.

Step 2. Into a 10 mL sealed-tube reactor containing a well-stirred solution of 6-chloro-4-[4-[4-[(4-fluoro-2-pyridyl)methyl]piperazin-1-yl]phenyl]pyrazolo[1,5-a]pyrazine-3-carbonitrile (3; 100 mg, 0.223 mmol) and tert-butyl 4-[4-(4,4,5,5-tetramethyl-1,3,2-dioxaborolan-2-yl)pyrazol-1-yl]piperidine-1-carboxylate (4; 101 mg, 0.267 mmol) in a mixture of water (1 mL) and 1,4-dioxane (3 mL) was added Sodium carbonate (71 mg, 0.669 mmol) at ambient temperature under nitrogen atmosphere and the resulting mixture was degassed by bubbling nitrogen gas into the reaction mixture for 10 minutes. Subsequently, Pd(dppf)$Cl_2$·DCM complex (18 mg, 0.0223 mmol) was added to the reaction mixture and reaction mixture was stirred at 90° C. for 16 h. After completion of the reaction as indicated by TLC, the reaction mixture was cooled to room temperature and poured into water (50 mL) and extracted with EtOAc (2×50 mL). Organic phases were combined and washed with brine (100 mL). Combined organic phases were dried (anhydrous $Na_2SO_4$), filtered and the filtrate was concentrated under reduced pressure to get a crude residue, which was purified by flash silica-gel (230-400 mesh) column with 0-100% EtOAc/pet ether with the desired compound eluting at 80-100% EtOAc to afford tert-butyl 4-[4-[3-cyano-4-[4-[4-[(4-fluoro-2-pyridyl)methyl]piperazin-1-yl]phenyl]pyrazolo[1,5-a]pyrazin-6-yl]pyrazol-1-yl]piperidine-1-carboxylate (5; 90 mg, 0.107 mmol) as a yellow gummy liquid. Yield 48%; LC MS: ES+ (M+H) 663.3.

Step 3. Into a 25 mL single-necked round-bottomed flask containing a well-stirred solution of tert-butyl 4-[4-[3-cyano-4-[4-[4-[(4-fluoro-2-pyridyl)methyl]piperazin-1-yl]phenyl]pyrazolo[1,5-a]pyrazin-6-yl]pyrazol-1-yl]piperidine-1-carboxylate (5; 90 mg, 0.135 mmol) in anhydrous DCM (2 mL) was added 4 N HCl in 1,4-dioxane (3 mL, 0.135 mmol) at ambient temperature under nitrogen atmosphere. The resulting mixture was stirred at room temperature for 2 h. The reaction mixture was concentrated under reduced pressure to afford 4-[4-[4-[(4-fluoro-2-pyridyl)methyl]piperazin-1-yl]phenyl]-6-[1-(4-piperidyl)pyrazol-4-yl]pyrazolo[1,5-a]pyrazine-3-carbonitrile hydrochloride salt (6; 70 mg, 0.088 mmol) as an orange solid. Yield 65%; LC MS: ES+ (M+H) 563.3.

Step 4. Into a 25 mL single-necked round-bottomed flask containing a well-stirred solution of 4-[4-[4-[(4-fluoro-2-pyridyl)methyl]piperazin-1-yl]phenyl]-6-[1-(4-piperidyl)pyrazol-4-yl]pyrazolo[1,5-a]pyrazine-3-carbonitrile hydrochloride salt (6; 70 mg, 0.116 mmol) and 2-[4-[4-[(2,6-dioxo-3-piperidyl)oxy]-2-fluoro-phenyl]-1-piperidyl]acetic acid (7; 43 mg, 0.106 mmol) in anhydrous DMF (3 mL) were added DIPEA (60 μL, 0.35 mmol) and HATU (67 mg, 0.175 mmol) at ambient temperature under nitrogen atmosphere. The reaction contents were stirred at ambient temperature for 2 h. After completion of the reaction as indicated by UPLC, water (20 mL) was added and stirred for 10 minutes, the resulting solid was filtered and dried to afford a solid crude which was purified by reverse phase HPLC using the method: Column: X Select (150×19 mm), 10 mm; Mobile phase: A: 0.1% $HCO_2H$ MQ-water; B: Acetonitrile; Flow rate: 15 mL/minutes to get 6-[1-[1-[2-[4-[4-[(2,6-dioxo-3-piperidyl)oxy]-2-fluoro-phenyl]-1-piperidyl]acetyl]-4-piperidyl]pyrazol-4-yl]-4-[4-[4-[(4-fluoro-2-pyridyl)methyl]piperazin-1-yl]phenyl]pyrazolo[1,5-a]pyrazine-3-carbonitrile formic acid salt (Compound 38; 19 mg, 0.019 mmol) as a yellow solid. Yield 16%. $^1H$ NMR (400 MHz, DMSO-$d_6$). δ 10.95 (s, 1H), 9.28 (s, 1H), 8.82 (s, 1H), 8.55-8.58 (m, 1H), 8.47 (s, 1H), 8.18 (s, 1H), 7.80 (d, J=8.8 Hz, 2H), 7.38 (m, 1H), 7.27-7.23 (m, 2H), 7.15 (m, 1H), 6.86 (m, 1H), 6.79 (m, 1H), 5.22 (m, 1H), 4.45 (m, 2H), 4.3 (m, 1H), 3.72 (s, 2H), 3.45 (m, 2H), 3.17 (m, 3H), 2.95 (bs, 3H), 2.8 (m, 1H), 2.69-2.62 (m, 8H), 2.15 (m, 8H), 1.8 (m, 1H), 1.60 (m, 4H). LCMS: ES+ (M+H) 907.4.

Example 117: Synthesis of 1-(5-(3-Cyano-6-(4-(4-(2-(4-(4-((2,6-dioxopiperidin-3-yl)amino)-2-fluoro-phenyl)piperidin-1-yl)ethyl)-4-hydroxypiperidin-1-yl)phenyl)pyrazolo[1,5-a]pyridin-4-yl)pyridin-2-yl)-4-ethyl-N-isopropylpiperidine-4-carboxamide (Compound 39)

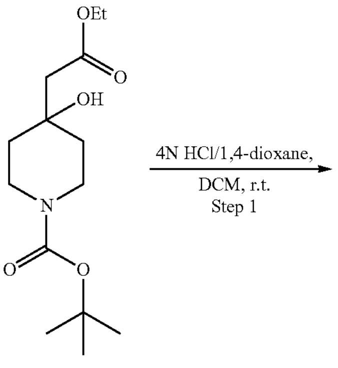

1

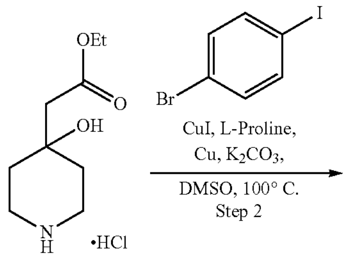

2

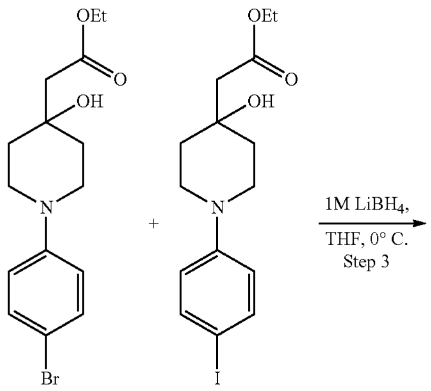

3 3′

-continued

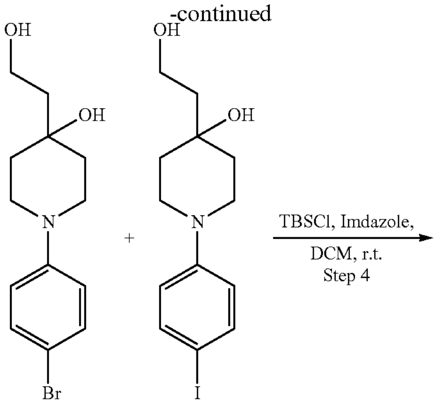

4 4′

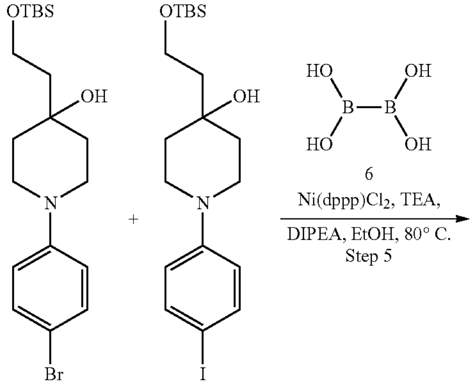

5 5′

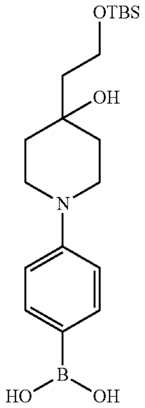

7

Step 1. Into a 100 mL single-necked round-bottomed flask containing a well-stirred solution of tert-butyl 4-(2-ethoxy-2-oxo-ethyl)-4-hydroxy-piperidine-1-carboxylate (1; 3 g, 10.44 mmol) in anhydrous DCM (30 mL) was added Hydrogen chloride, 4M in 1,4-dioxane (4.76 mL, 104.40 mmol) at ambient temperature under nitrogen atmosphere. The resulting mixture was stirred at room temperature for 2 h. After completion of reaction, the reaction mixture was concentrated under reduced pressure to get a crude, which was dissolved in DCM (25 mL) and pet ether (25 mL) and concentrated for several times to get ethyl 2-(4-hydroxy-4-piperidyl)acetate hydrochloric acid salt (2; 2.6 g, 9.94 mmol) as a brown solid. Yield-96%; LCMS: ES+ (M+H) 188.2.

Step 2. Into a 250 mL sealed tube containing a well-stirred solution of a mixture of 1-bromo-4-iodo-benzene (4.32 g, 15.27 mmol) in DMSO (30 mL) were added ethyl 2-(4-hydroxy-4-piperidyl)acetate (2.6 g, 13.89 mmol) and Potassium carbonate-granular (3.84 g, 27.77 mmol, 1.68 mL) and the mixture was degassed with nitrogen gas for 20 minutes. Then, L-Proline, 99% purity (319.74 mg, 2.78 mmol) followed by Copper powder (88.25 mg, 1.39 mmol) and Copper(I)iodide (264.46 mg, 1.39 mmol) were added to the reaction mixture and the suspension was heated at 100° C. for 16 h. The progress of the reaction mixture was monitored by TLC. Then the reaction mixture was added to conical flask (250 mL) containing water (200 mL) and extracted with DCM (2×100 mL). Combined organic layers were washed with brine (25 mL), dried (anhydrous $Na_2SO_4$), filtered and the filtrate was concentrated under reduced pressure to get crude which was purified by silica-gel column (230-400 mesh) with 30-40% EtOAc/pet ether to yield 3:1 of ethyl 2-[1-(4-bromophenyl)-4-hydroxy-4-piperidyl]acetate and ethyl 2-(4-hydroxy-1-(4-iodophenyl)piperidin-4-yl)acetate (3&3'; 2.4 g) as an brown solid. Yield-36%; LCMS: ES+(M+H) 342.0, 344.0 (Bromo-) and ES+ (M+H) 390.0 (Iodo-).

Step 3. Into a 250 mL three-necked round-bottomed flask containing a well-stirred solution of a mixture of ethyl 2-[1-(4-bromophenyl)-4-hydroxy-4-piperidyl]acetate and ethyl 2-(4-hydroxy-1-(4-iodophenyl)piperidin-4-yl)acetate (3&3'; 2.3 g, 6.72 mmol) in anhydrous THF (25 mL) was added dropwise 1M $LiBH_4$ solution in THF (4 mL, 8.06 mmol) at 0° C. under nitrogen atmosphere and the resulting reaction was stirred at 0° C. for 2 h. The progress of the reaction was monitored by LCMS & TLC, starting material was consumed. The reaction mixture was quenched with saturated ammonium chloride solution (100 mL) at 0° C., diluted with EtOAc (100 mL) and stirred for 10 minutes. The layers were separated and the organic layer was dried (anhydrous $Na_2SO_4$), filtered and the filtrate was concentrated under reduced pressure to afford 3:1 1-(4-bromophenyl)-4-(2-hydroxyethyl)piperidin-4-ol and 4-(2-hydroxyethyl)-1-(4-iodophenyl)piperidin-4-ol (4&4'; 2 g) as a colourless gum. Yield-75%; LCMS: ES+ (M+H) 300.0, 302.0 (Bromo-) and ES+ (M+H) 348.0 (Iodo-).

Step 4. Into a 100 mL three-necked round-bottomed flask charged with 3:1 1-(4-bromophenyl)-4-(2-hydroxyethyl)piperidin-4-ol and 4-(2-hydroxyethyl)-1-(4-iodophenyl)piperidin-4-ol (4&4'; 1.9 g, 6.33 mmol) in anhydrous DCM (20 mL) was added Imidazole, 99% (1.72 g, 25.32 mmol) at ambient temperature under nitrogen atmosphere. The resulting mixture was stirred at 0° C. and tert-butyl-chloro-dimethyl-silane (2.38 g, 15.82 mmol, 2.94 mL) was added and the resulting mixture was stirred for 12 h at 25° C. Progress of the reaction was monitored by TLC. After completion of the reaction as indicated by TLC, the reaction mixture was poured into water (100 mL) and extracted with EtOAc (2×100 mL). Organic phases were combined and washed with brine (100 mL). Combined organic phases were dried (anhydrous $Na_2SO_4$), filtered and the filtrate was concentrated under reduced pressure to get a crude, which was purified by flash silica-gel (230-400 mesh) column with 0-100% EtOAc/pet ether while desired compound eluting at 20-30% to afford 3:1 1-(4-bromophenyl)-4-[2-[tert-butyl(dimethyl)silyl]oxyethyl]piperidin-4-ol and 4-(2-((tert-butyldimethylsilyl)oxy)ethyl)-1-(4-iodophenyl)piperidin-4-ol (5&5'; 1.4 g) as an off-white solid. Yield-40%; LCMS: ES+ (M+H) 414.2, 416.2 (Bromo-) and ES+ (M+H) 462.2 (Iodo-).

Step 5. Into a 250 mL sealed-tube reactor containing a well-stirred solution of 3:1 1-(4-bromophenyl)-4-[2-[tert-butyl(dimethyl)silyl]oxyethyl]piperidin-4-ol and 4-(2-((tert-butyldimethylsilyl)oxy)ethyl)-1-(4-iodophenyl)piperidin-4-ol (5&5'; 1.4 g, 3.38 mmol) and hypoboric acid (6; 454.26 mg, 5.07 mmol) in EtOH (15 mL) was added DIPEA (1.77 mL, 10.13 mmol) at ambient temperature under nitrogen atmosphere and the resulting mixture was degassed by bubbling nitrogen gas into the reaction mixture for 10 minutes. Subsequently, Triphenylphosphine (88.60 mg, 0.337 mmol) and 1,3-Bis(diphenylphosphino)propane nickel (II) chloride (18.31 mg, 0.033 mmol) were added to the reaction mixture and reaction mixture was heated to 80° C. for 16 h. After completion of the reaction as indicated by TLC, the reaction mixture was cooled to ambient temperature, concentrated and poured into water (100 mL) and extracted with EtOAc (2×100 mL). Organic phases were combined and washed with brine (100 mL). Combined organic phases were dried (anhydrous $Na_2SO_4$), filtered and the filtrate was concentrated under reduced pressure to get [4-[4-[2-[tert-butyl(dimethyl)silyl]oxyethyl]-4-hydroxy-1-piperidyl]phenyl]boronic acid (7; 1.45 g, 1.43 mmol) as a brown-coloured crude solid. Yield-42%; LCMS: ES+ (M+H) 380.2.

Example 118: Synthesis of 1-[5-(6-bromo-3-cyano-pyrazolo[1,5-a]pyridin-4-yl)-2-pyridyl]-4-ethyl-N-isopropyl-piperidine-4-carboxamide

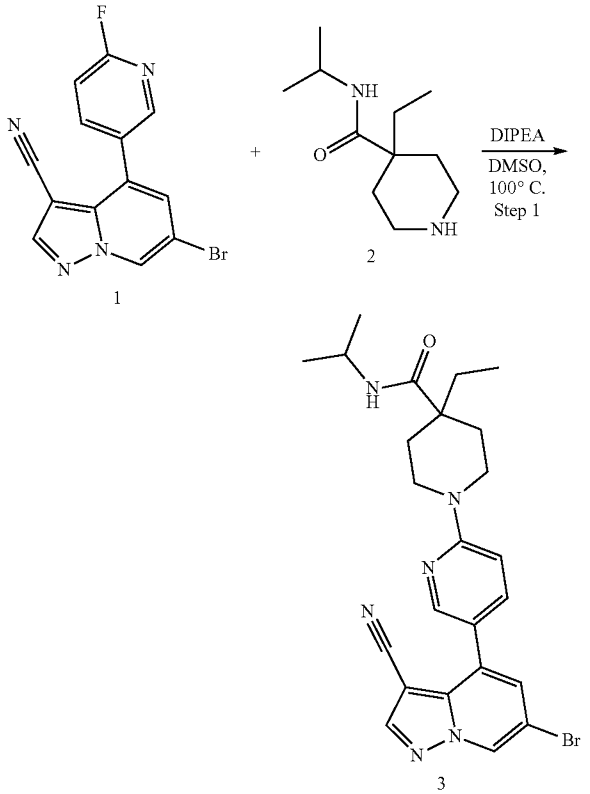

1 2 3

Step 1. Into a 100 mL sealed-tube reactor containing a well-stirred solution of a mixture of 6-bromo-4-(6-fluoro-3-pyridyl)pyrazolo[1,5-a]pyridine-3-carbonitrile (1, 1.5 g, 4.73 mmol) and 4-ethyl-N-isopropyl-piperidine-4-carboxamide hydrochloride salt (2, 1.44 g, 6.15 mmol) in anhydrous DMSO (15 mL) was added DIPEA (1.83 g, 14.19 mmol, 2.47 mL) at ambient temperature under nitrogen atmosphere. The resulting reaction mixture was stirred at 100° C. for 24 h. Upon completion, the reaction mixture was cooled to ambient temperature and poured into ice cold water (70 mL) and the resulting solid was filtered, washed with pet ether and dried to afford a crude residue. The crude residue was purified by Silica-gel (60-120 mesh) column eluting with 0-100% EtOAc/pet ether to afford 1-[5-(6-bromo-3-cyano-pyrazolo[1,5-a]pyridin-4-yl)-2-pyridyl]-4-ethyl-N-isopropyl-piperidine-4-carboxamide (3, 1.6 g, 3.12 mmol) as pale yellow solid. Yield-66%; LC MS: ES+ (M+H) 495.2.

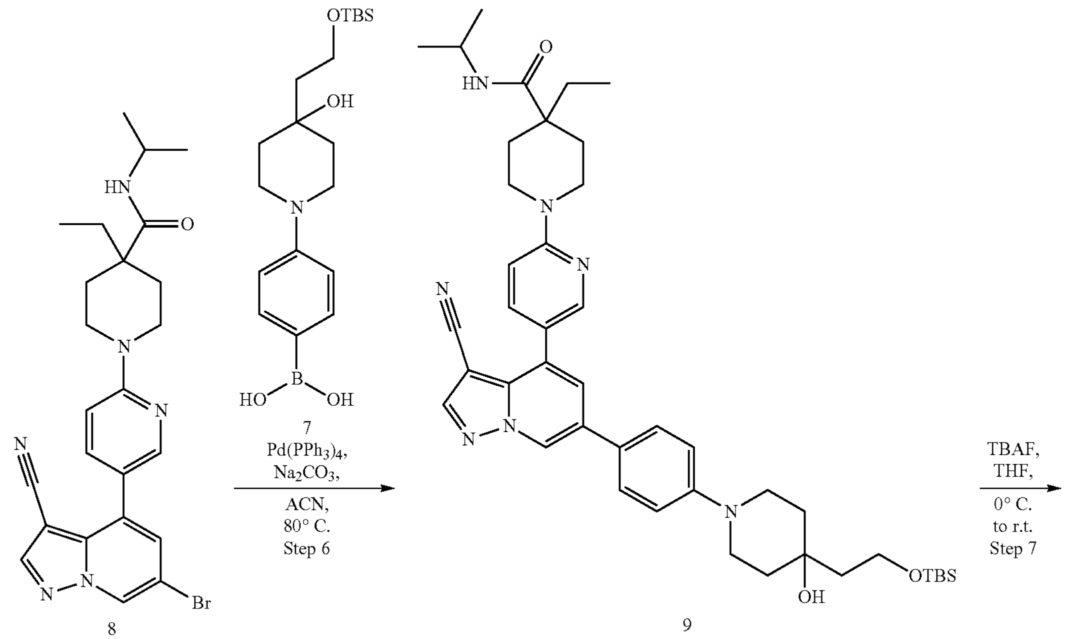

8

9

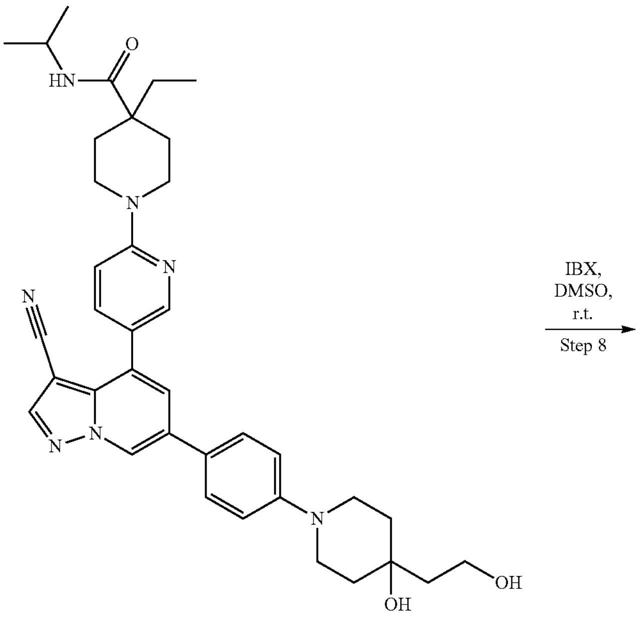

10

-continued

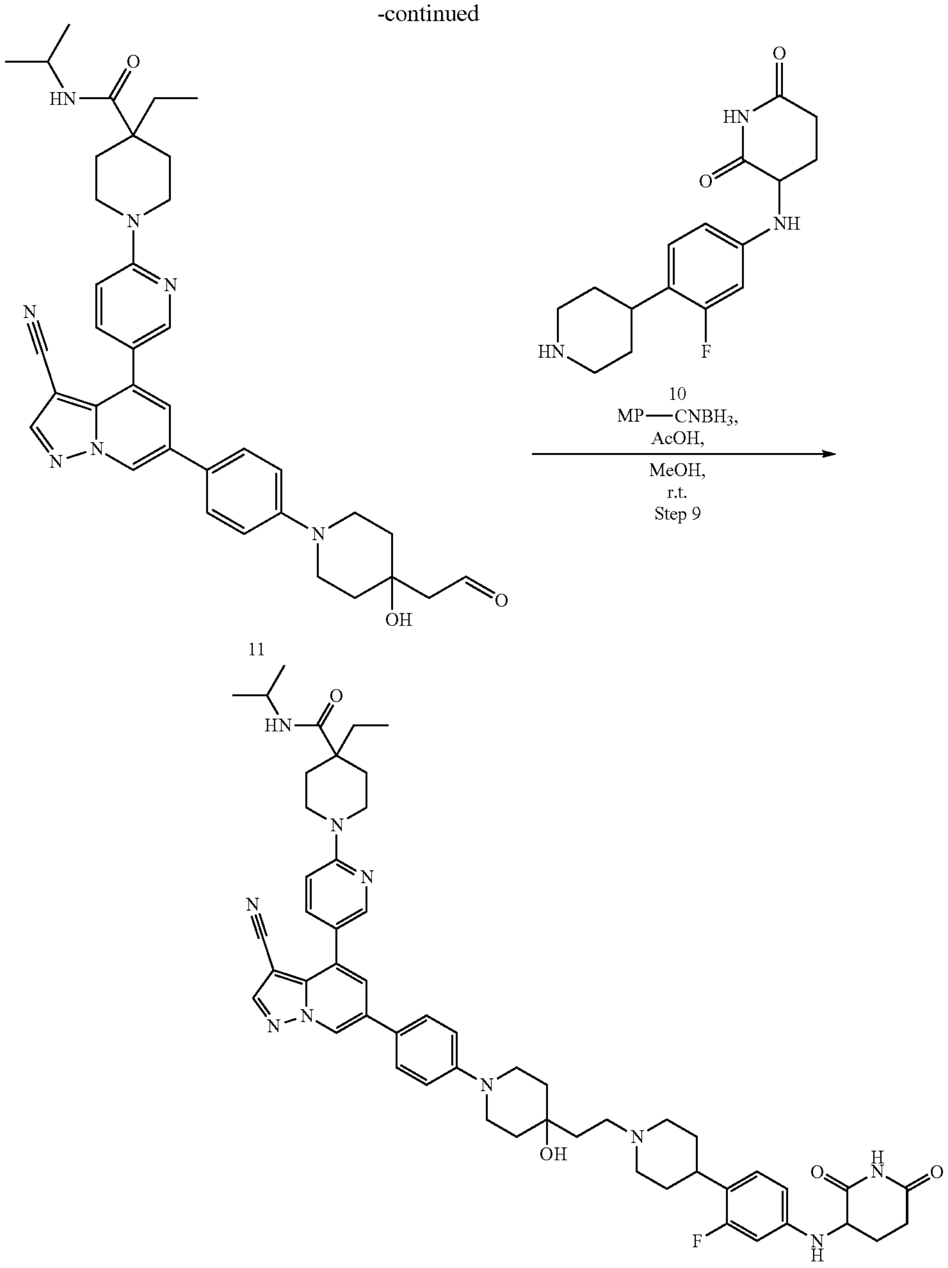

11

Compound 39

Step 6. Into a 250 mL sealed-tube reactor containing a well-stirred solution of 1-[5-(6-bromo-3-cyano-pyrazolo[1,5-a]pyridin-4-yl)-2-pyridyl]-4-ethyl-N-isopropyl-piperidine-4-carboxamide (8; 1.51 g, 3.06 mmol) and [4-[4-[2-[tert-butyl(dimethyl)silyl]oxyethyl]-4-hydroxy-1-piperidyl]phenyl]boronic acid (7; 1.45 g, 3.82 mmol) in 1,4-dioxane (15 mL) was added solution of Sodium carbonate (1.22 g, 11.47 mmol, 0.480 mL) in water (3 mL) at ambient temperature under nitrogen atmosphere and the resulting mixture was degassed by bubbling nitrogen gas into the reaction mixture for 10 minutes. Subsequently, cyclopentyl(diphenyl)phosphane;dichloromethane;dichloropalladium;iron (312.13 mg, 0.382 mmol) was added to the reaction mixture and reaction mixture was heated to 80° C. for 16 h with stirring. After completion of the reaction as indicated by TLC, the reaction mixture was cooled to room temperature and poured into water (200 mL) and extracted with EtOAc (2×200 mL). Organic phases were combined and washed with brine (100 mL). Combined organic phases were dried (anhydrous $Na_2SO_4$), filtered and the filtrate was concentrated under reduced pressure to get a crude residue, which was purified by flash silica-gel (230-400 mesh) column with 0-100% EtOAc/pet ether while desired compound eluting at 75-85% to afford 1-[5-[6-[4-[4-[2-[tert-butyl(dimethyl)silyl]oxyethyl]-4-hydroxy-1-piperidyl]phenyl]-3-cyano-pyrazolo[1,5-a]pyridin-4-yl]-2-pyridyl]-4-ethyl-N-isopropyl-piperidine-4-carboxamide (9; 700 mg, 0.623 mmol) as a brown solid. Yield-16%; LCMS: ES+ (M+H) 750.4.

Step 7. Into a 50 mL single-necked round-bottomed flask containing a well-stirred solution of 1-[5-[6-[4-[4-[2-[tert-butyl(dimethyl)silyl]oxyethyl]-4-hydroxy-1-piperidyl]phenyl]-3-cyano-pyrazolo[1,5-a]pyridin-4-yl]-2-pyridyl]-4-ethyl-N-isopropyl-piperidine-4-carboxamide (9; 600 mg, 0.799 mmol) in anhydrous THE (10 mL) was added Tetrabutylammonium fluoride solution (418.31 mg, 1.60 mmol, 1.5 mL; 1M/THF) at 0° C. The resulting mixture was stirred at ambient temperature for 2 h. After completion of the reaction by TLC, the reaction mixture was poured into water (50 mL) and extracted with EtOAc (2×50 mL). Organic phases were combined and washed with brine (50 mL). Combined organic phases were dried (anhydrous $Na_2SO_4$), filtered and the filtrate was concentrated under reduced pressure to get a crude residue, which was purified by flash silica-gel (230-400 mesh) column with respective solvent system; first with 0-100% EtOAc/pet ether followed by 0-20% MeOH/DCM while desired compound eluting at 5-10% to afford 1-[5-[3-cyano-6-[4-[4-hydroxy-4-(2-hydroxyethyl)-1-piperidyl]phenyl]pyrazolo[1,5-a]pyridin-4-yl]-2-pyridyl]-4-ethyl-N-isopropyl-piperidine-4-carboxamide (10; 300 mg, 0.443 mmol) as a brown solid. Yield-55%; LCMS: ES+ (M+H) 636.4.

Step 8. Into a 8 mL vial containing a well-stirred solution of 1-[5-[3-cyano-6-[4-[4-hydroxy-4-(2-hydroxyethyl)-1-piperidyl]phenyl]pyrazolo[1,5-a]pyridin-4-yl]-2-pyridyl]-4-ethyl-N-isopropyl-piperidine-4-carboxamide (10; 200 mg, 0.314 mmol) in anhydrous DMSO (5 mL) was added 2-iodoxybenzoic acid (176.17 mg, 0.629 mmol) at ambient temperature under nitrogen atmosphere and the resulting mixture was stirred at ambient temperature for 16 h. After completion of the reaction as indicated by LCMS, reaction mixture was poured into water (10 mL) and extracted with EtOAc (2×30 mL). Combined organic phases were dried (anhydrous $Na_2SO_4$), filtered and the filtrate was concentrated under reduced pressure to get 1-[5-[3-cyano-6-[4-[4-hydroxy-4-(2-oxoethyl)-1-piperidyl]phenyl]pyrazolo[1,5-a]pyridin-4-yl]-2-pyridyl]-4-ethyl-N-isopropyl-piperidine-4-carboxamide (11; 400 mg, 0.126 mmol) as a brown gum. Yield-40%; LCMS: ES+(M+H) 634.4.

Step 9. Into a 10 mL single-necked round-bottomed flask containing a well stirred solution of 1-[5-[3-cyano-6-[4-[4-hydroxy-4-(2-oxoethyl)-1-piperidyl]phenyl]pyrazolo[1,5-a]pyridin-4-yl]-2-pyridyl]-4-ethyl-N-isopropyl-piperidine-4-carboxamide (11; 400 mg, 0.631 mmol) and 3-[3-fluoro-4-(4-piperidyl)anilino]piperidine-2,6-dione (10; 192.71 mg, 0.631 mmol) in MeOH (1 mL) was added $MPCNBH_3$ (400 mg, 1.26 mmol) and catalytic amount of AcOH (94.75 mg, 1.58 mmol, 0.090 mL) at ambient temperature and the reaction mixture was stirred at ambient temperature for 16 h. The progress of the reaction was monitored by LCMS, reaction mixture was filtered and the solid was washed with DCM and combined filtrates were concentrated under reduced pressure to afford a crude gum which was purified by Prep-HPLC column following the method: X Select C18 (150×30)mm, 5 microns; Mobile phase: 10 mm ammonium acetate:acetonitrile to afford 1-[5-[3-cyano-6-[4-[4-[2-[4-[4-[(2,6-dioxo-3-piperidyl)amino]-2-fluoro-phenyl]-1-piperidyl]ethyl]-4-hydroxy-1-piperidyl]phenyl]pyrazolo[1,5-a]pyridin-4-yl]-2-pyridyl]-4-ethyl-N-isopropyl-piperidine-4-carboxamide (Compound 39; 17 mg, 0.018 mmol) as an off-white solid. Yield-3%; $^1H$ NMR (400 MHz, DMSO-$d_6$). δ 10.79 (s, 1H), 9.15 (d, J=1.6 Hz, 1H), 8.67 (s, 1H), 8.40 (d, J=2.4 Hz, 1H), 7.84-7.73 (m, 4H), 7.39 (d, J=8 Hz, 1H), 7.06-6.95 (m, 4H), 6.46-6.42 (m, 2H), 6.02 (s, 1H), 4.30 (m, 1H), 4.07-4.00 (m, 3H), 3.51 (m, 2H), 3.19 (m, 2H), 3.17-3.02 (m, 4H), 2.74-2.67 (m, 1H), 2.59 (m, 1H), 2.55-2.50 (m, 2H), 2.50 (m, 1H), 2.18-2.15 (m, 3H), 1.97 (t, J=11.2 Hz, 2H), 1.83 (m, 2H), 1.66-1.47 (m, 12H), 1.36 (t, J=10.4 Hz, 2H), 1.09 (d, J=6.4 Hz, 6H), 0.76 (t, J=7.2 Hz, 3H). LCMS: ES+ (M−H) 922.5.

Example 119: Synthesis of 1-(5-(3-Cyano-6-(1-((trans)-4-(2-(4-(4-((2,6-dioxopiperidin-3-yl)amino)-2-fluorophenyl)piperidin-1-yl)ethyl)cyclohexyl)-1H-pyrazol-4-yl)pyrazolo[1,5-a]pyridin-4-yl)pyridin-2-yl)-4-ethyl-N-(tetrahydro-2H-pyran-4-yl)piperidine-4-carboxamide (Compound 40)

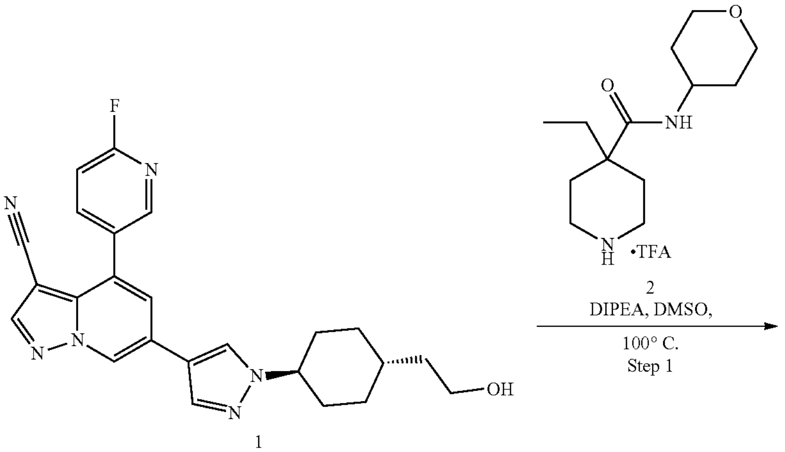

1

-continued
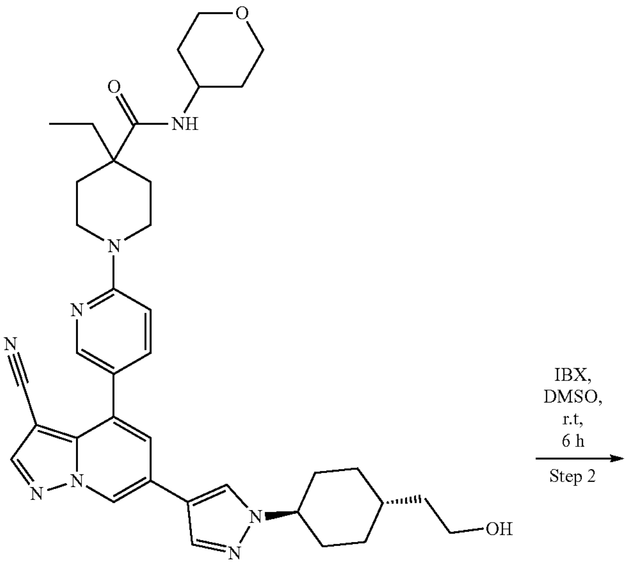
3
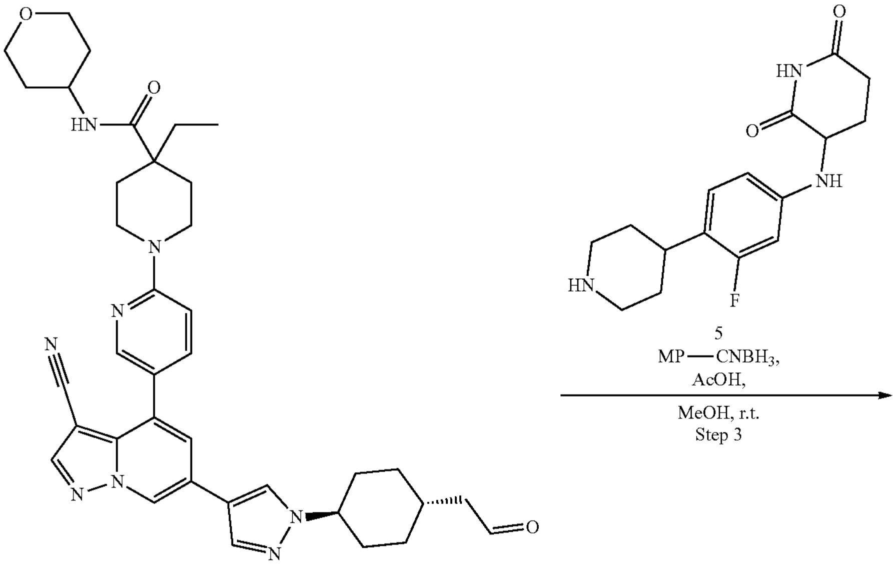
4

-continued

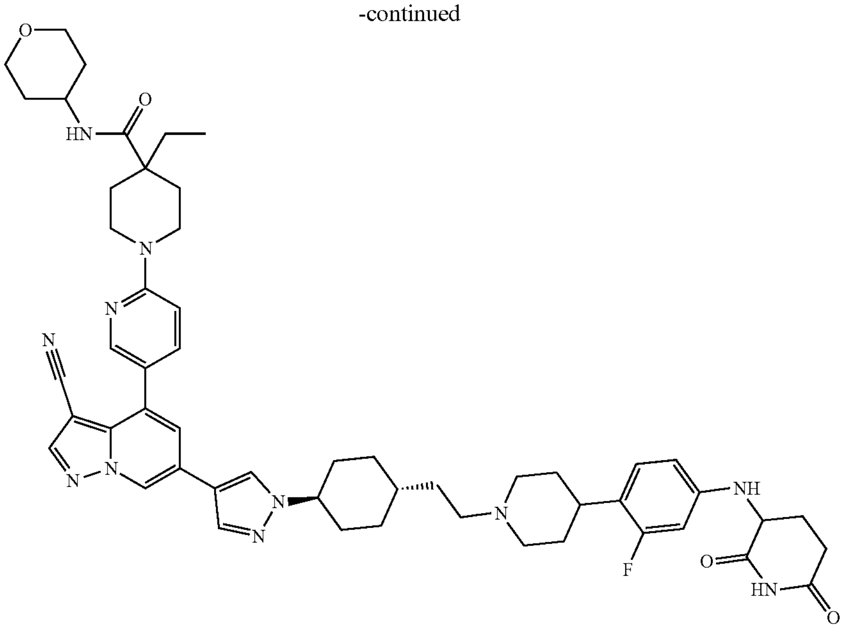

Compound 40

Step 1. Into a 25 mL sealed tube containing a well-stirred solution of a mixture of 4-(6-fluoropyridin-3-yl)-6-(1-((trans)-4-(2-hydroxyethyl)cyclohexyl)-1H-pyrazol-4-yl) pyrazolo[1,5-a]pyridine-3-carbonitrile (1; 130 mg, 0.301 mmol) and 4-ethyl-N-tetrahydropyran-4-yl-piperidine-4-carboxamide·trifluoroacetate (2; 214 mg, 0.603 mmol) in anhydrous DMSO (3 mL) was added DIPEA (0.263 mL, 1.51 mmol) at ambient temperature. The resulting content was stirred at 100° C. for 32 h. After completion of the reaction as indicated by LCMS, ice-cold water (20 mL) was added and stirred at room temperature for 10 minutes, the resulting solid was filtered and dried to afford a crude solid, which was purified by column chromatography (flash silica-gel (230-400 mesh) column, gradient of 0%-20% MeOH in DCM) to afford 1-(5-(3-cyano-6-(1-((trans)-4-(2-hydroxyethyl)cyclohexyl)-1H-pyrazol-4-yl)pyrazolo[1,5-a]pyridin-4-yl)pyridin-2-yl)-4-ethyl-N-(tetrahydro-2H-pyran-4-yl)piperidine-4-carboxamide (3; 90 mg, 0.099 mmol) as a brown solid. Yield 33%; LC MS: ES+ (M+H) 651.4

Step 2. Into a 20 mL vial containing a well-stirred solution of 1-(5-(3-cyano-6-(1-((trans)-4-(2-hydroxyethyl)cyclohexyl)-1H-pyrazol-4-yl)pyrazolo[1,5-a]pyridin-4-yl)pyridin-2-yl)-4-ethyl-N-(tetrahydro-2H-pyran-4-yl)piperidine-4-carboxamide (3; 80 mg, 0.122 mmol) in DMSO (3 mL) was added 2-iodoxybenzoic acid (69 mg, 0.245 mmol) at ambient temperature, the resulting mixture was stirred at ambient temperature for 6 h. After completion of the reaction as indicated by TLC, water (50 mL) was added to the reaction mixture and reaction mixture was extracted with EtOAc (2×50 mL). Organic phases were combined and washed with brine (50 mL). Combined organic phases were dried (anhydrous $Na_2SO_4$), filtered and the filtrate was concentrated under reduced pressure to afford 1-(5-(3-cyano-6-(1-((trans)-4-(2-oxoethyl)cyclohexyl)-1H-pyrazol-4-yl)pyrazolo[1,5-a]pyridin-4-yl)pyridin-2-yl)-4-ethyl-N-(tetrahydro-2H-pyran-4-yl)piperidine-4-carboxamide (4; 100 mg, 0.107 mmol) as a brown gummy liquid, which was used without further purification. Yield 70%; LC MS: ES+ (M+H) 649.3.

Step 3. Into a 20 mL vial containing a well-stirred solution of 1-(5-(3-cyano-6-(1-((trans)-4-(2-oxoethyl)cyclohexyl)-1H-pyrazol-4-yl)pyrazolo[1,5-a]pyridin-4-yl)pyridin-2-yl)-4-ethyl-N-(tetrahydro-2H-pyran-4-yl)piperidine-4-carboxamide (4; 100 mg, 0.154 mmol) and 3-[3-fluoro-4-(4-piperidyl)anilino]piperidine-2,6-dione (47 mg, 0.154 mmol) in anhydrous MeOH (4 mL) were added acetic acid (8 μL, 0.154 mmol) and MP-$CNBH_3$ (200 mg, 0.154 mmol) at ambient temperature. The resulting mixture was stirred at ambient temperature for 2 h. After completion of the reaction (LCMS), reaction mixture was filtered through sintered funnel and the filtrate was concentrated under reduced pressure to get a crude mass which was purified by column chromatography (reverse phase purification (ISCO column) with the mobile phase: Mobile Phase A: 0.1% Ammonium acetate in water; Mobile phase B: Acetonitrile; Flow rate: 15 mL/min) to afford 30 mg of crude which was then purified by HPLC (Column: X-select (150×19)mm, 5 microns; Mobile phase: A: 0.1% Ammonium acetate in MQ-water; B: Acetonitrile; Flow rate: 15 mL/minutes; RT=11.69 min) to afford 1-[5-[3-cyano-6-[1-[4-[2-[4-[4-[(2,6-dioxo-3-piperidyl)amino]-2-fluoro-phenyl]-1-piperidyl]ethyl]cyclohexyl]pyrazol-4-yl]pyrazolo[1,5-a]pyridin-4-yl]-2-pyridyl]-4-ethyl-N-tetrahydropyran-4-yl-piperidine-4-carboxamide (Compound 40; 12 mg, 0.0121 mmol) as an off-white solid. Yield 8%. LC MS: ES+ (M+H) 938.4.

Example 120: Synthesis of 1-(5-(3-cyano-6-(1-((1r, 4r)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 87 and Compound 88)
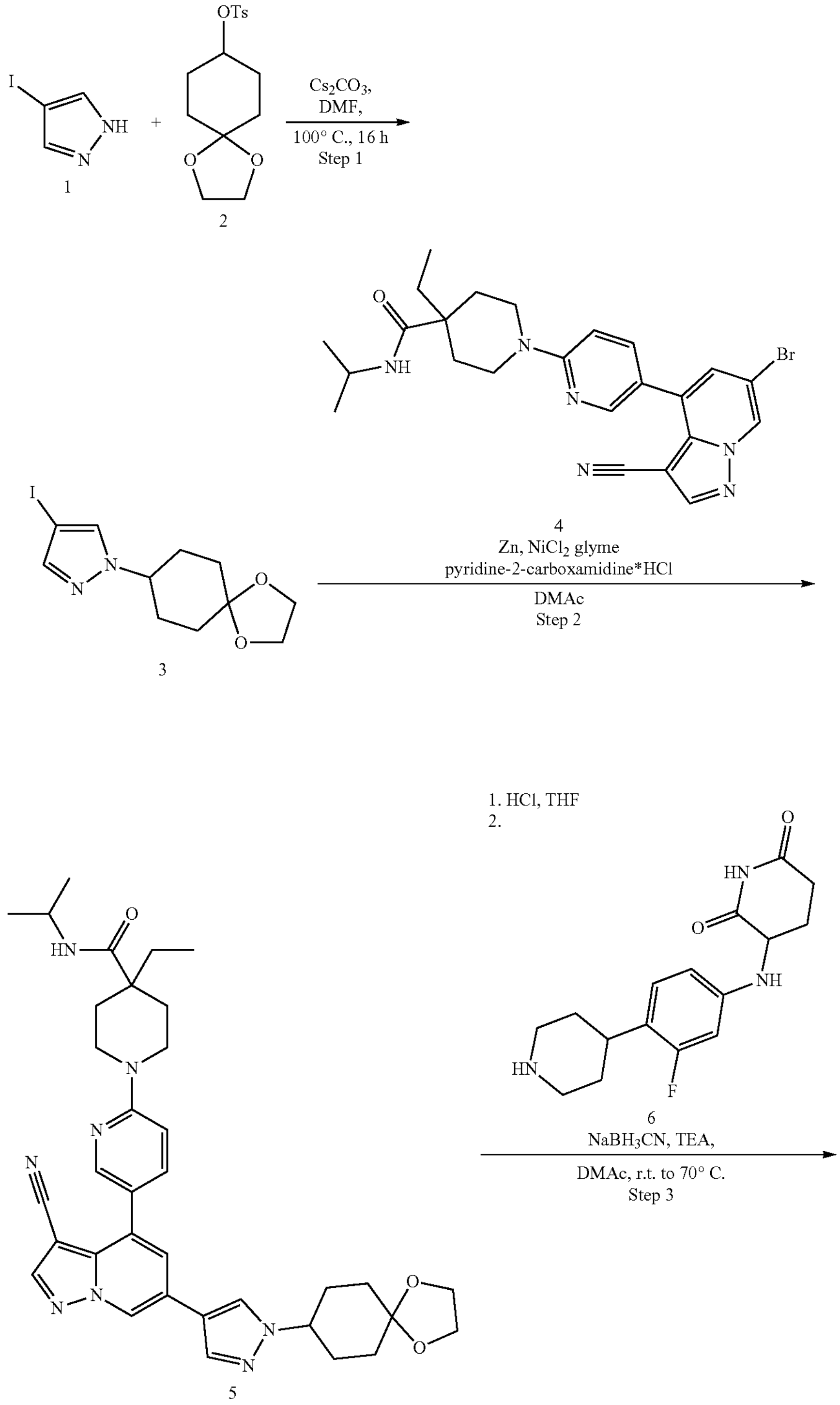

-continued

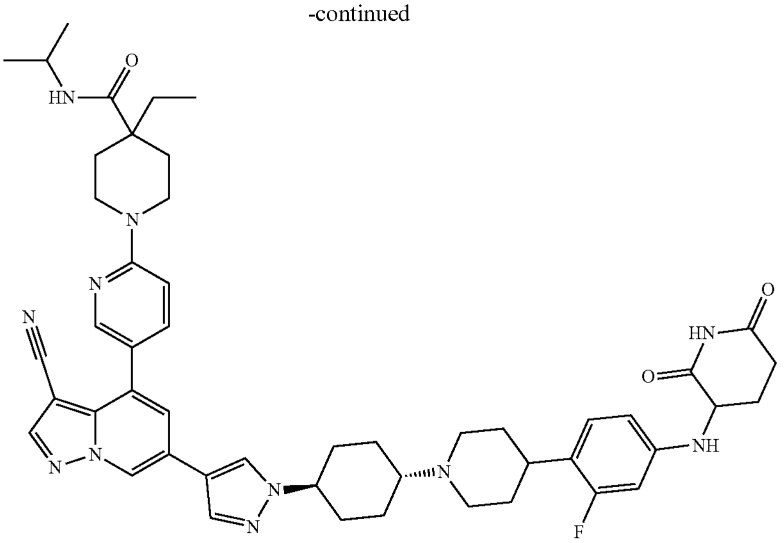

Compound 87

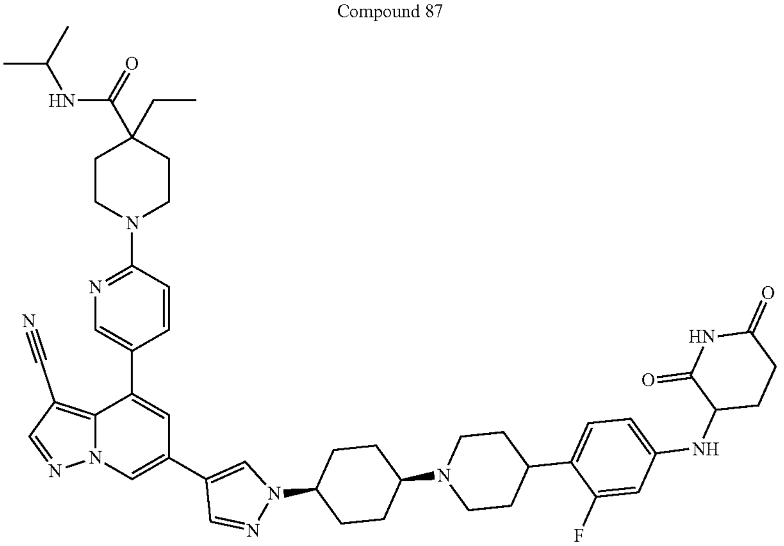

Compound 88

Step 1. Initially a solution of 4-iodo-1H-pyrazole (1; 6 g, 30.93 mmol) and 1,4-dioxaspiro[4.5]decan-8-yl 4-methylbenzenesulfonate (2; 10.63 g, 34.03 mmol) in DMF (100 mL) had cesium carbonate (20.16 g, 61.86 mmol) added in one portion. After the addition, the mixture was stirred at 100° C. for 16 h. Upon reaction completion the mixture was poured into $H_2O$ (500 mL) after which a white precipitate formed which was filtered off and washed with $H_2O$ (50 mL×3) before being dried under vacuum to afford 1-(1,4-dioxaspiro[4.5]decan-8-yl)-4-iodo-pyrazole (3; 7 g, 18.85 mmol) which was used without further purification. Yield 61%; LC MS: ES+ (M+H) 335.1

Step 2. To a mixture of 1-(1,4-dioxaspiro[4.5]decan-8-yl)-4-iodo-pyrazole (3; 1.4 g, 4.19 mmol), 1-[5-(6-bromo-3-cyano-pyrazolo[1,5-a]pyridin-4-yl)-2-pyridyl]-4-ethyl-N-isopropyl-piperidine-4-carboxamide (4; 2.08 g, 4.19 mmol, 489.49 μL), zinc (575 mg, 8.80 mmol, 80.58 μL) and pyridine-2-carboxamidine hydrochloride (132 mg, 837.94 μmol) in DMAc (30 mL) was added Nickel (II) chloride ethylene glycol dimethyl ether (184 mg, 837.94 μmol) in portions under $N_2$. After addition, the mixture was warmed to 70° C. for 16 h under $N_2$. Upon reaction completion the mixture was poured into $H_2O$ (250 mL) dropwise to which a precipitate formed which was filtered off and the filter cake then washed with $H_2O$ (30 mL×3) to afford 1-[5-[3-cyano-6-[1-(1,4-dioxaspiro[4.5]decan-8-yl)pyrazol-4-yl]pyrazolo[1,5-a]pyridin-4-yl]-2-pyridyl]-4-ethyl-N-isopropyl-piperidine-4-carboxamide (5; 2 g, 2.99 mmol) which was used without further purification. Yield 71%; LC MS: ES+ (M+H) 623.0.

Step 3.

Part i:

Initially 1-[5-[3-cyano-6-[1-(1,4-dioxaspiro[4.5]decan-8-yl)pyrazol-4-yl]pyrazolo[1,5-a]pyridin-4-yl]-2-pyridyl]-4-ethyl-N-isopropyl-piperidine-4-carboxamide (5; 2.2 g, 3.53 mmol) was dissolved in THF (20 mL) before concentrated HCl (12 M, 21.15 mL) was added dropwise. After addition, the solution was stirred at 20° C. for 12 hr. Upon reaction completion the mixture was neutralized by pouring into a $NaHCO_3$ aqueous solution to which a precipitate then formed. The precipitate was then filtered off and washed with $H_2O$ before being extensively dried under vacuum to afford 1-[5-[3-cyano-6-[1-(4-oxocyclohexyl)pyrazol-4-yl]pyrazolo[1,5-a]pyridin-4-yl]-2-pyridyl]-4-ethyl-N-isopropyl-piperidine-4-carboxamide (2.0 g, 3.46 mmol) as a yellow solid. Yield 98%; LC MS: ES+ (M+H) 579.4.

Part ii: To a suspension of 1-[5-[1-cyano-6-[1-(4-oxocyclohexyl)pyrazol-4-yl]indolizin-8-yl]-2-pyridyl]-4-ethyl-N-isopropyl-piperidine-4-carboxamide (1.56 g, 1.62 mmol) and 3-[3-fluoro-4-(4-piperidyl)anilino]piperidine-2,6-dione hydrochloride (6; 609 mg, 1.78 mmol) in DMAc (16 mL) was added triethylamine (8.10 mmol, 1.13 mL) dropwise. After addition, the mixture was kept at 23° C. for 14 hrs. Subsequently, sodium cyanoborohydride (1.02 g, 16.20 mmol) was then added to the mixture at 0° C. and stirring was continued at 70° C. for 16 h. Upon reaction completion the reaction was quenched by the addition of $H_2O$ (200 mL) after which a white precipitate formed. Then the suspension was filtered, and the filtered cake was washed with $H_2O$ (30 mL×3). The filtered cake was dried under vacuum to give a crude product which was purified via Prep-TLC (DCM/MeOH=12:1) and Prep-HPLC (column: Waters Xbridge 150*25 mm*5 μm; mobile phase: [water (10 mM $NH_4HCO_3$)-ACN]; B %: 43%-73%, 9 min) after which two peaks were obtained.

trans isomer: 1-(5-(3-cyano-6-(1-((1r, 4r)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 87; 55 mg, 61.74 μmol) was obtained as a white solid. Yield 4%; $^1$H NMR (400 MHz, DMSO-d) δ 10.89-10.71 (m, 1H), 9.23 (d, 1H), 8.64 (s, 1H), 8.52 (s, 1H), 8.36 (d, 1H), 8.13 (s, 1H), 7.85-7.74 (m, 2H), 7.45-7.36 (m, 1H), 7.03-6.90 (m, 2H), 6.49-6.38 (m, 2H), 6.04-5.95 (m, 1H), 4.35-4.25 (m, 1H), 4.18-3.94 (m, 4H), 3.11-2.99 (m, 2H), 2.98-2.88 (m, 2H), 2.79-2.69 (m, 1H), 2.63-2.53 (m, 2H), 2.45-2.37 (m, 1H), 2.36-2.25 (m, 2H), 2.21-2.03 (m, 5H), 1.96-1.45 (m, 13H), 1.40-1.28 (m, 2H), 1.12-1.04 (m, 6H), 0.79-0.70 (m, 3H). LC MS: ES+ (M+H) 869.8 cis isomer: 1-(5-(3-cyano-6-(1-((1s, 4s)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 88; 60 mg, 67.98 μmol). Yield 4%; $^1$H NMR (400 MHz, DMSO-d) δ 10.79 (s, 1H), 9.28 (d, 1H), 8.64 (s, 1H), 8.57 (s, 1H), 8.37 (d, 1H), 8.17 (s, 1H), 7.90-7.83 (m, 1H), 7.82-7.73 (m, 1H), 7.44-7.35 (m, 1H), 7.01-6.91 (m, 2H), 6.47-6.36 (m, 2H), 5.99 (d, 1H), 4.35-4.21 (m, 2H), 4.13-3.93 (m, 3H), 3.11-2.97 (m, 4H), 2.79-2.65 (m, 1H), 2.62-2.53 (m, 2H), 2.36-2.22 (m, 3H), 2.19-2.10 (m, 2H), 2.10-1.96 (m, 3H), 1.91-1.72 (m, 5H), 1.70-1.53 (m, 6H), 1.48 (q, 2H), 1.39-1.28 (m, 2H), 1.12-1.03 (m, 6H), 0.78-0.68 (m, 3H). LC MS: ES+ (M+H) 870.3.

Example 121: Synthesis of tert-butyl 4-[4-[3-cyano-4-(6-fluoro-3-pyridyl)pyrazolo[1,5-a]pyrazin-6-yl]pyrazol-1-yl]piperidine-1-carboxylate

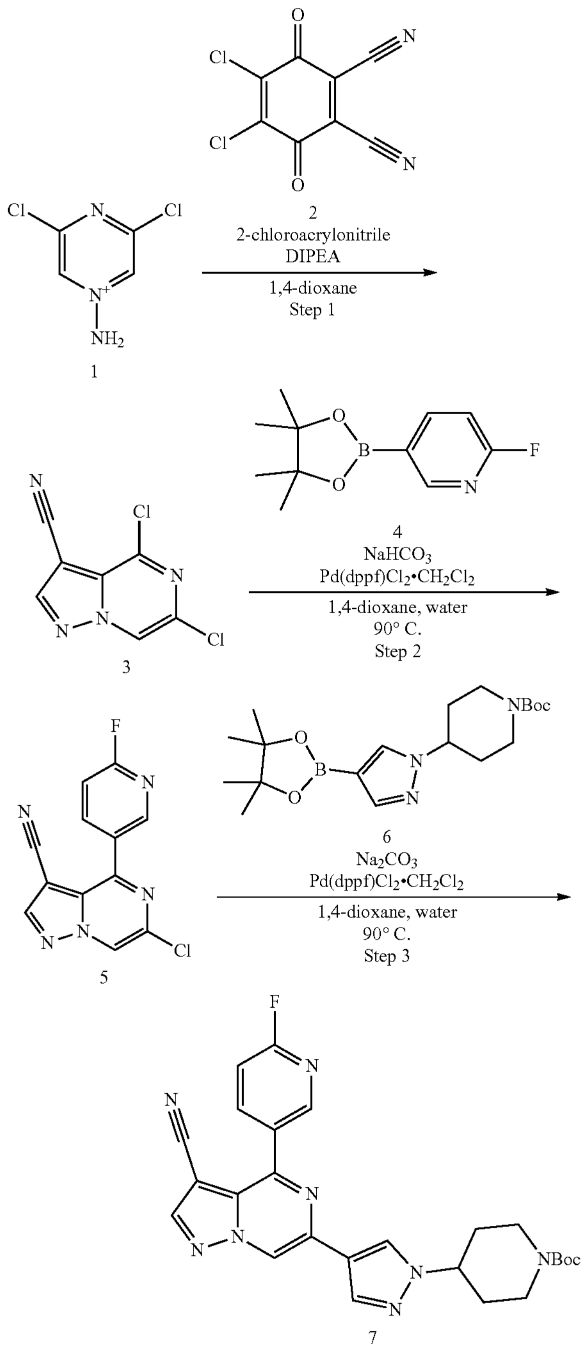

Step 1: Into a 100 mL single neck round bottom flask, containing a well stirred solution of 3,5-dichloropyrazin-1-ium-1-amine (1, 2.0 g, 5.48 mmol, 2,4,6-trimethylbenzenesulfonic acid salt) in 1,4-dioxane (20 mL), was added 2-chloroacrylonitrile (958.35 mg, 10.95 mmol) and DIPEA (1.77 g, 13.69 mmol, 2.38 mL) room temperature. After stirring for 2 h, 2,3-dichloro-5,6-dicyano-1,4-benzoquinone (2, 2.49 g, 10.95 mmol) was added portionwise at 0° C. The resultant reaction mixture was stirred at room temperature for 12 h. The progress of the reaction was monitored by TLC. After consumption of starting material, the reaction mixture was quenched with brine (50 mL) and extracted with ethyl acetate (3×100 mL), dried over anhydrous sodium sulphate, filtered and concentrated under reduced pressure. The crude residue was purified by column chromatography (silica gel eluted with 10-20% ethyl acetate in petroleum ether) to furnish 4,6-dichloropyrazolo[1,5-a]pyrazine-3-carbonitrile (3, 54% yield) as brown solid. GCMS ($ES^+$): m/z 212.0 $[M+H]^+$.

Step 2: Into a 250 mL sealed-tube containing a well stirred solution of 2-fluoro-5-(4,4,5,5-tetramethyl-1,3,2-dioxaborolan-2-yl)pyridine (4, 11.52 g, 51.64 mmol) and 4,6-dichloropyrazolo[1,5-a]pyrazine-3-carbonitrile (3, 10.0 g, 46.94 mmol) in anhydrous 1,4-dioxane (200 mL) was added sodium bicarbonate (15.77 g, 187.77 mmol) and water (50 mL), and the resulting reaction mixture was purged with nitrogen for 10 minutes. $Pd(dppf)Cl_2*CH_2Cl_2$ (1.92 g, 2.35 mmol) was added, and the resultant mixture was purged with nitrogen for 10 minutes. The reaction mixture was heated with stirring at 100° C. for 2 h. The progress of the reaction was monitored by TLC (30% EtOAc/Pet ether). After consumption of the starting material, the reaction mixture was diluted with EtOAc and water. The reaction mixture was filtered through a pad of Celite, and the celite bed was washed with EtOAc. The phases of the filtrate were separated, and the organic layer was dried over anhydrous sodium sulfate and concentrated under reduced pressure to provide the crude residue. The crude residue was purified by silica-gel column chromatography (230-400 mesh, 100 g) using a gradient of 0-100% EtOAc/petroleum ether to afford 6-chloro-4-(6-fluoro-3-pyridyl)pyrazolo[1,5-a]pyrazine-3-carbonitrile (5, 59% yield) as a brown solid. LCMS ($ES^+$): m/z 274.0 $[M+H]^+$.

Step 3: Into a 10 mL sealed-tube containing a well-stirred solution of 6-chloro-4-(6-fluoro-3-pyridyl)pyrazolo[1,5-a]pyrazine-3-carbonitrile (5, 40 mg, 146.17 μmol) and tert-butyl 4-[4-(4,4,5,5-tetramethyl-1,3,2-dioxaborolan-2-yl)pyrazol-1-yl]piperidine-1-carboxylate (6, 66.18 mg, 175.41 μmol) in anhydrous 1,4-dioxane (2 mL) was added sodium carbonate (46.48 mg, 438.51 μmol) in water (0.5 mL) at ambient temperature under nitrogen atmosphere, and the resulting mixture was degassed with nitrogen gas for 10 minutes. Subsequently, $Pd(dppf)Cl_2*CH_2Cl_2$ (11.94 mg, 14.62 μmol) was added to the reaction mixture, and reaction mixture was heated to 90° C. for 3 h. After completion of the reaction as indicated by TLC, the reaction mixture was cooled to room temperature, poured into water (10 mL), and extracted with EtOAc (2×20 mL). The combined organic phases were washed with brine (10 mL), dried (anhydrous $Na_2SO_4$), and filtered. The filtrate was concentrated under reduced pressure to provide a crude residue which was purified by silicagel (230-400 mesh) column chromatography using a gradient of 0-100% EtOAc/petroleum ether to afford tert-butyl 4-[4-[3-cyano-4-(6-fluoro-3-pyridyl)pyrazolo[1,5-a]pyrazin-6-yl]pyrazol-1-yl]piperidine-1-carboxylate (7, 70% yield) as an off-white solid. LCMS ($ES^+$): m/z 389.2 $[M+H-CO_2tBu]^+$.

Example 122: Synthesis of 1-[5-[3-cyano-6-[1-[1-[2-[4-[4-[(2,6-dioxo-3-piperidyl)amino]-2-fluoro-phenyl]phenyl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 89)

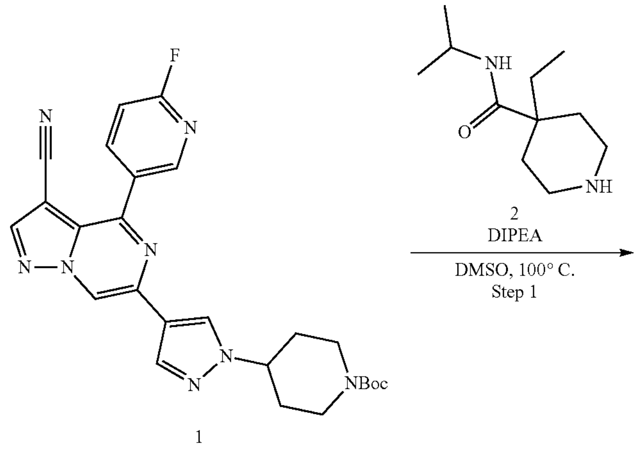

1

-continued
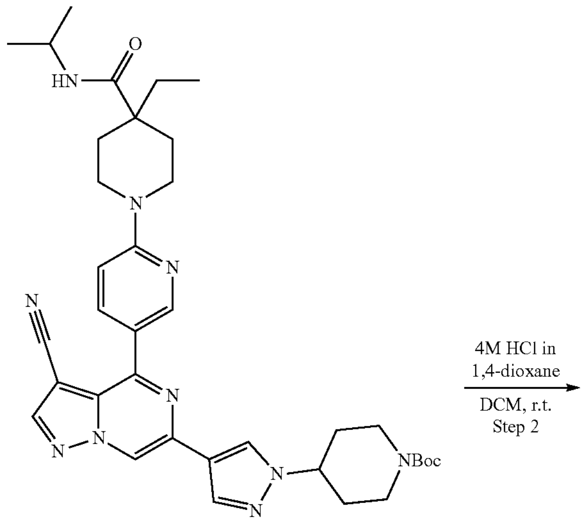
3
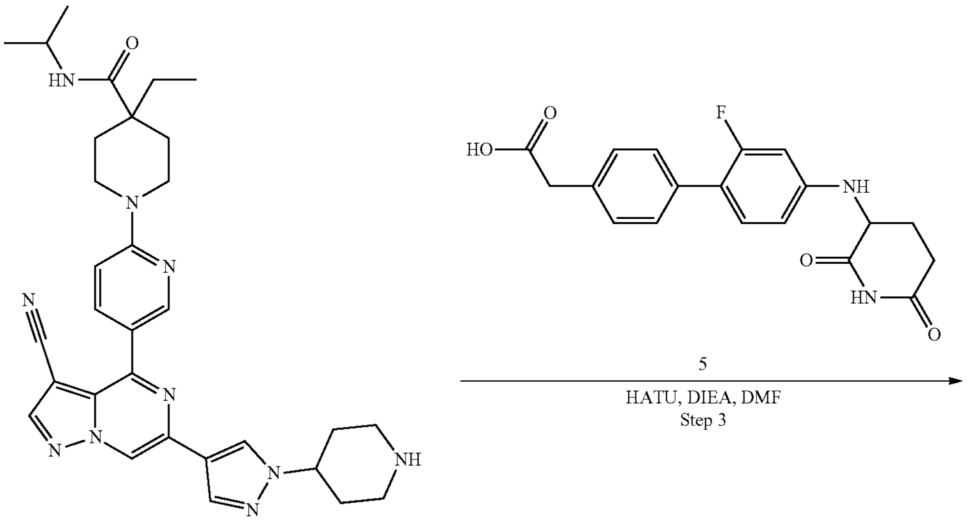
4

-continued

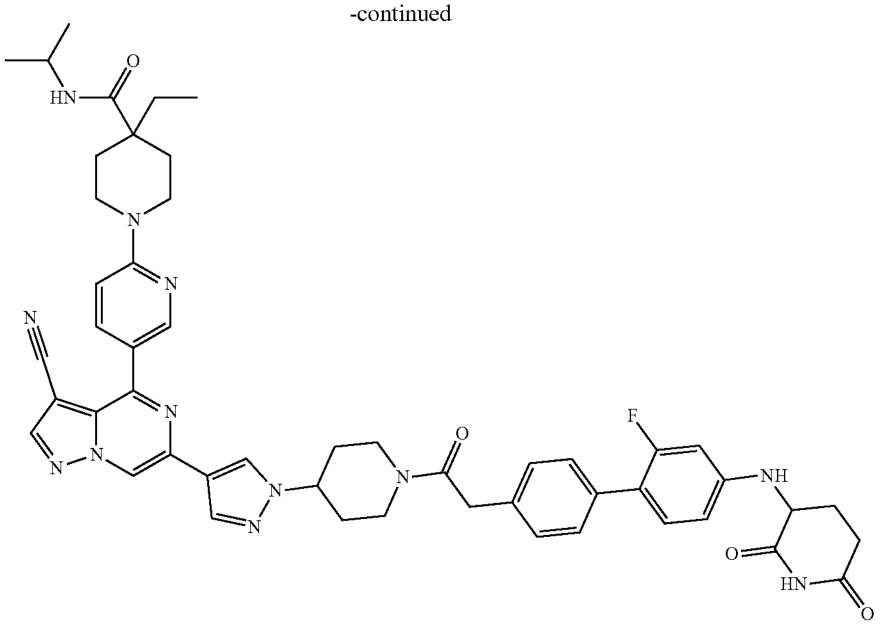

Compound 89

Step 1: Into a 100 mL sealed tube containing a well-stirred solution of a mixture of tert-butyl 4-[4-[3-cyano-4-(6-fluoro-3-pyridyl)pyrazolo[1,5-a]pyrazin-6-yl]pyrazol-1-yl]piperidine-1-carboxylate (1, 1.0 g, 2.05 mmol), 4-ethyl-N-isopropyl-piperidine-4-carboxamide (2, 720.85 mg, 3.07 mmol, HCl salt) in anhydrous DMSO (15 mL) was added DIPEA (1.32 g, 10.24 mmol, 1.78 mL) at ambient temperature. The reaction mixture was stirred at 100° C. for 16 h. After completion of the reaction as indicated by UPLC, the reaction mixture was warmed to room temperature and treated with ice-water (50 mL). The resulting mixture was stirred for 15 minutes at room temperature, during which time the desired product precipitated out. The solid product was collected by filtration over filter paper, and the solid was washed with water and dried under vacuum for 5 h to afford crude tert-butyl 4-[4-[3-cyano-4-[6-[4-ethyl-4-(isopropylcarbamoyl)-1-piperidyl]-3-pyridyl]pyrazolo[1,5-a]pyrazin-6-yl]pyrazol-1-yl]piperidine-1-carboxylate (3, 80% yield) as a faint brown solid. LCMS ($ES^+$): m/z 667.4 $[M+H]^+$.

Step 2: Into a 250 mL single-necked round-bottomed flask containing a well-stirred solution of tert-butyl 4-[4-[3-cyano-4-[6-[4-ethyl-4-(isopropylcarbamoyl)-1-piperidyl]-3-pyridyl]pyrazolo[1,5-a]pyrazin-6-yl]pyrazol-1-yl]piperidine-1-carboxylate (3, 5.6 g, 8.40 mmol) in anhydrous DCM (50 mL) under nitrogen atmosphere was added dropwise HCl in dioxane (4 M, 40 mL) at 0° C. The reaction mixture was warmed to room temperature and stirred at ambient temperature for 2 h. After completion of the reaction as indicated by UPLC, the reaction mixture was concentrated under reduced pressure and co-distilled with DCM (2×10 mL) to afford 1-[5-[3-cyano-6-[1-(4-piperidyl)pyrazol-4-yl]pyrazolo[1,5-a]pyrazin-4-yl]-2-pyridyl]-4-ethyl-N-isopropyl-piperidine-4-carboxamide (4, 95% yield) as a yellow solid. LCMS ($ES^+$): m/z 567.2 $[M+H]^+$.

Step 3: To a solution of 1-(5-(3-cyano-6-(1-(piperidin-4-yl)-1H-pyrazol-4-yl)pyrazolo[1,5-a]pyrazin-4-yl)pyridin-2-yl)-4-ethyl-N-isopropylpiperidine-4-carboxamide (4, 90 mg, 149.21 μmol, HCl salt), 2-(4'-((2,6-dioxopiperidin-3-yl)amino)-2'-fluoro-[1,1'-biphenyl]-4-yl)acetic acid (5, 53.17 mg, 149.21 μmol) and DIPEA (57.85 mg, 447.64 μmol, 77.97 μL) in DMF (0.6 mL) was added HATU (85.10 mg, 223.82 μmol). After addition, the solution was stirred at 30° C. for 2 hr. The reaction solution was acidified to pH=7 with formic acid and concentrated in vacuum. The residue was purified by Prep-HPLC (Shim-pack C18 150*25*10 um, water (0.225% FA)-ACN, 44%-64%, 25 ml/min, 10 min) to afford 1-(5-(3-cyano-6-(1-(1-(2-(4'-((2,6-dioxopiperidin-3-yl)amino)-2'-fluoro-[1,1'-biphenyl]-4-yl)acetyl)piperidin-4-yl)-1H-pyrazol-4-yl)pyrazolo[1,5-a]pyrazin-4-yl)pyridin-2-yl)-4-ethyl-N-isopropylpiperidine-4-carboxamide (Compound 89, 87.26 mg, 88.72 μmol, 59% yield, formic acid salt) as yellow solid. LCMS ($ES^+$): m/z 905.5 $[M+H]^+$. $^1H$ NMR (400 MHz, DMSO-$d_6$) δ=10.83 (s, 1H), 9.27 (s, 1H), 8.82 (s, 1H), 8.67 (d, J=2.4 Hz, 1H), 8.48 (s, 1H), 8.16 (s, 1H), 8.04 (dd, J=2.4, 9.2 Hz, 1H), 7.41 (br d, J=8.0 Hz, 3H), 7.29 (d, J=8.0 Hz, 2H), 7.27-7.21 (m, 1H), 6.99 (d, J=9.2 Hz, 1H), 6.64-6.54 (m, 2H), 6.32 (d, J=8.0 Hz, 1H), 4.56-4.46 (m, 2H), 4.45-4.37 (m, 1H), 4.19-4.09 (m, 3H), 4.01 (qd, J=6.8, 14.0 Hz, 1H), 3.89-3.67 (m, 3H), 3.29-3.16 (m, 2H), 3.11 (br t, J=11.2 Hz, 2H), 2.86-2.71 (m, 2H), 2.65-2.56 (m, 1H), 2.24-2.05 (m, 5H), 1.99-1.77 (m, 3H), 1.50 (q, J=7.2 Hz, 2H), 1.41-1.30 (m, 2H), 1.09 (d, J=6.8 Hz, 6H), 0.75 (t, J=7.6 Hz, 3H)

Example 123: 1-[5-[6-[1-[1-[2-[1-[2-chloro-4-[(2,6-dioxo-3-piperidyl)amino]-5-methoxy-phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-isopropyl-piperidine-4-carboxamide (Compound 90)

Compound 90 was Prepared Following the Synthesis of Compound 89

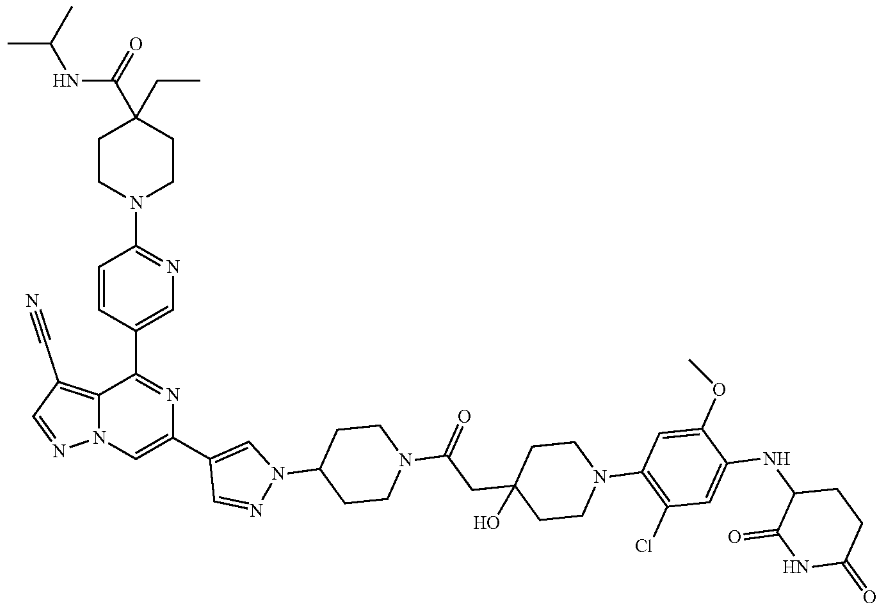

LCMS ($ES^+$): m/z 974.4 $[M+H]^+$ $^1H$ NMR (400 MHz, DMSO-$d_6$) δ=10.83 (br d, J=1.2 Hz, 1H), 9.29 (s, 1H), 8.82 (s, 1H), 8.67 (d, J=2.8 Hz, 1H), 8.49 (s, 1H), 8.17 (s, 1H), 8.04 (dd, J=2.8, 8.8 Hz, 1H), 7.40 (d, J=8.0 Hz, 1H), 6.99 (d, J=9.2 Hz, 1H), 6.76-6.64 (m, 2H), 5.10 (d, J=6.8 Hz, 1H), 4.95 (s, 1H), 4.60-4.49 (m, 2H), 4.35-4.27 (m, 1H), 4.22-4.11 (m, 3H), 4.05-3.96 (m, 1H), 3.82 (s, 3H), 3.14-3.07 (m, 2H), 3.01-2.91 (m, 2H), 2.88-2.76 (m, 4H), 2.62-2.58 (m, 2H), 2.20-2.07 (m, 6H), 2.01-1.90 (m, 2H), 1.85-1.66 (m, 6H), 1.49 (q, J=7.2 Hz, 2H), 1.38-1.30 (m, 2H), 1.09 (s, 3H), 1.08 (s, 3H), 0.74 (t, J=7.6 Hz, 3H).

Example 124: 1-[5-[3-cyano-6-[1-[1-[2-[1-[4-[(2,6-dioxo-3-piperidyl)amino]-2-fluoro-5-methoxy-phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 91)

Compound 91 was Prepared Following the Synthesis of Compound 89

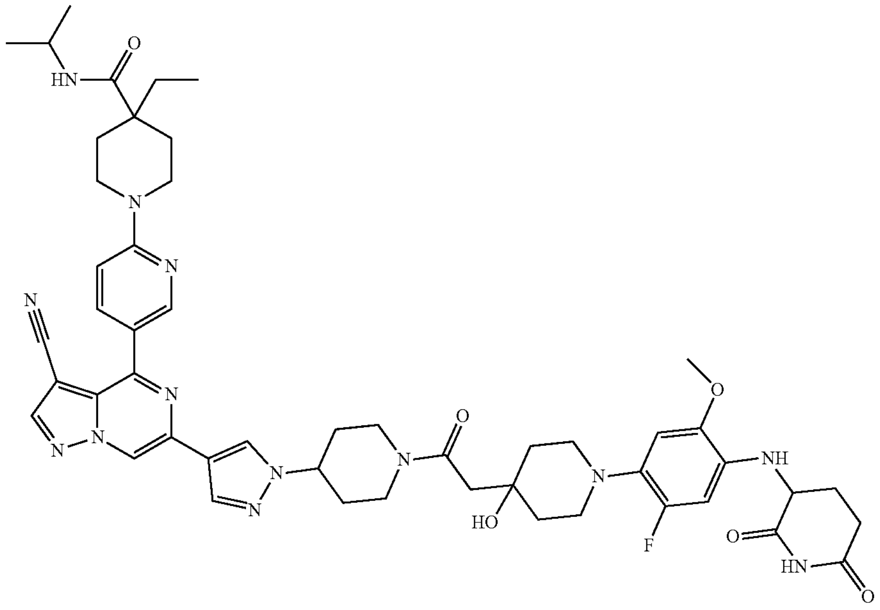 [SMILES: CCC1(C(=O)NC(C)C)CCN(c2ccc(-c3nc(-c4cnn(C5CCN(C(=O)CC6(O)CCN(c7cc(OC)c(NC8CCC(=O)NC8=O)cc7F)CC6)CC5)c4)cn4ncc(C#N)c34)cn2)CC1]

LCMS ($ES^+$): m/z 958.6 $[M+H]^+$ $^1$H NMR (400 MHz, DMSO-$d_6$) δ=10.84 (s, 1H), 9.28 (s, 1H), 8.82 (s, 1H), 8.66 (d, J=2.4 Hz, 1H), 8.49 (s, 1H), 8.17 (s, 1H), 8.04 (dd, J=2.4, 9.2 Hz, 1H), 7.40 (d, J=8.4 Hz, 1H), 6.99 (d, J=8.8 Hz, 1H), 6.62 (d, J=8.4 Hz, 1H), 6.53 (d, J=14.0 Hz, 1H), 5.06 (d, J=6.8 Hz, 1H), 4.91 (s, 1H), 4.61-4.48 (m, 2H), 4.28-4.10 (m, 4H), 4.06-3.95 (m, 1H), 3.78 (s, 3H), 3.13-3.08 (m, 2H), 3.00-2.94 (m, 2H), 2.92-2.86 (m, 2H), 2.82-2.73 (m, 2H), 2.60-2.54 (m, 2H), 2.21-2.05 (m, 6H), 1.98-1.87 (m, 2H), 1.86-1.63 (m, 6H), 1.53-1.46 (m, 2H), 1.38-1.30 (m, 2H), 1.11-1.06 (m, 6H), 0.74 (t, J=7.3 Hz, 3H).

Example 125: 1-[5-[3-cyano-6-[1-[1-[2-[1-[4-[(2,6-dioxo-3-piperidyl)amino]-2-fluoro-phenyl]-4-methoxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 92)

Compound 92 was Prepared Following the Synthesis of Compound 89

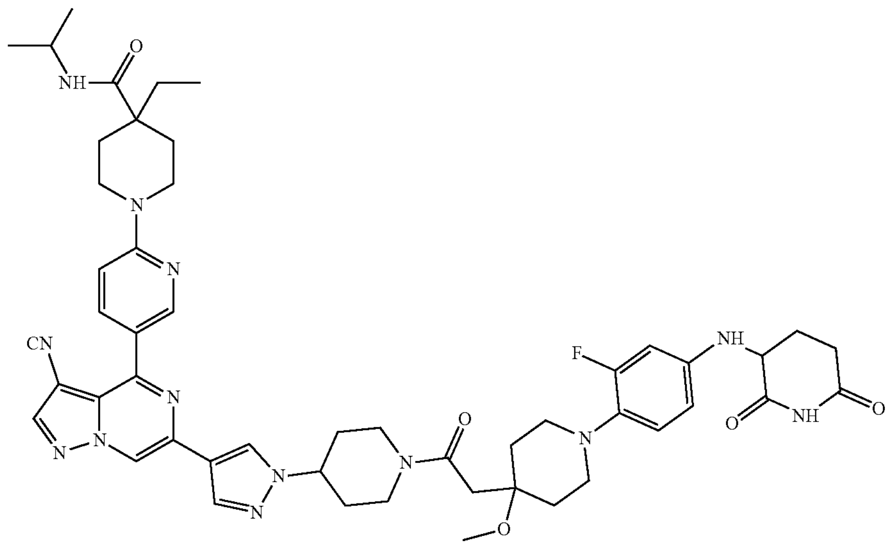

LCMS ($ES^+$): m/z 942.5 $[M+H]^+$ $^1$H NMR (400 MHz, DMSO-$d_6$) δ=10.79 (s, 1H), 9.29 (s, 1H), 8.83 (s, 1H), 8.67 (s, 1H), 8.50 (s, 1H), 8.17 (s, 1H), 8.05 (d, J=8.0 Hz, 1H), 7.43 (d, J=7.2 Hz, 1H), 7.00 (d, J=8.8 Hz, 1H), 6.91-6.75 (m, 1H), 6.56-6.36 (m, 2H), 5.79 (d, J=7.2 Hz, 1H), 4.67-4.44 (m, 2H), 4.30-4.13 (m, 4H), 4.07-3.97 (m, 1H), 3.20 (s, 3H), 3.14-3.08 (m, 2H), 2.90-2.67 (m, 8H), 2.20-2.05 (m, 5H), 1.96-1.79 (m, 7H), 1.54-1.46 (m, 2H), 1.41-1.30 (m, 2H), 1.29-1.17 (m, 2H), 1.09 (br d, J=6.4 Hz, 6H), 0.75 (t, J=7.2 Hz, 3H)

Example 126: 1-[5-[3-cyano-6-[1-[1-[2-[4-[1-(2,6-dioxo-3-piperidyl) indolin-5-yl]-1-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 93)

Compound 93 was Prepared Following the Synthesis of Compound 89

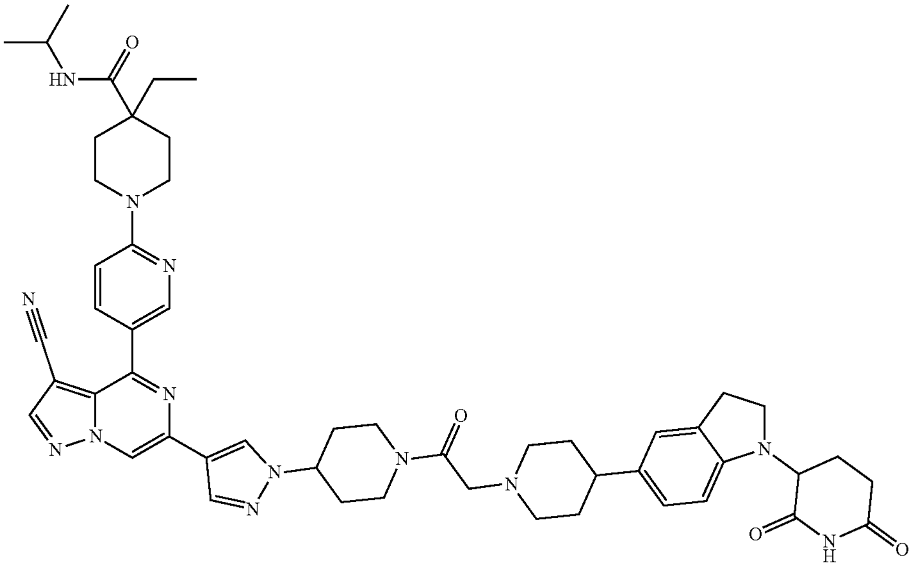 [SMILES: CCC1(C(=O)NC(C)C)CCN(c2ccc(-c3nc(-c4cnn(C5CCN(C(=O)CN6CCC(c7ccc8c(c7)CCN8C7CCC(=O)NC7=O)CC6)CC5)c4)cn4ncc(C#N)c34)cn2)CC1]

LCMS (ES+): m/z 920.6 [M+H]+

$^1$H NMR (400 MHz, DMSO-$d_6$) δ=9.29 (s, 1H), 8.83 (s, 1H), 8.67 (d, J=2.0 Hz, 1H), 8.51 (br s, 1H), 8.50 (s, 1H), 8.18 (s, 1H), 8.07-7.99 (m, 1H), 7.45-7.39 (m, 1H), 7.47-7.27 (m, 1H), 7.06-6.95 (m, 1H), 7.00-6.94 (m, 1H), 6.89 (s, 1H), 6.84-6.76 (m, 1H), 6.42-6.33 (m, 1H), 4.59-4.52 (m, 1H), 4.52-4.44 (m, 1H), 4.33-4.21 (m, 1H), 4.19-4.09 (m, 2H), 4.01 (dd, J=6.8, 14.4 Hz, 1H), 3.41-3.39 (m, 2H), 3.30-3.28 (m, 1H), 3.28-3.15 (m, 5H), 3.15-3.07 (m, 3H), 3.05-2.70 (m, 7H), 2.22-1.95 (m, 9H), 1.94-1.67 (m, 5H), 1.63-1.55 (m, 1H), 1.50 (q, J=7.2 Hz, 2H), 1.39-1.30 (m, 2H), 1.09 (d, J=6.8 Hz, 6H), 0.75 (t, J=7.2 Hz, 3H)

Example 127: 1-[5-[3-cyano-6-[1-[1-[2-[3-[4-[(2,6-dioxo-3-piperidyl)amino]-2-fluoro-phenyl]-8-azabicyclo[3.2.1]octan-8-yl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 94)

Compound 94 was Prepared Following the Synthesis of Compound 89

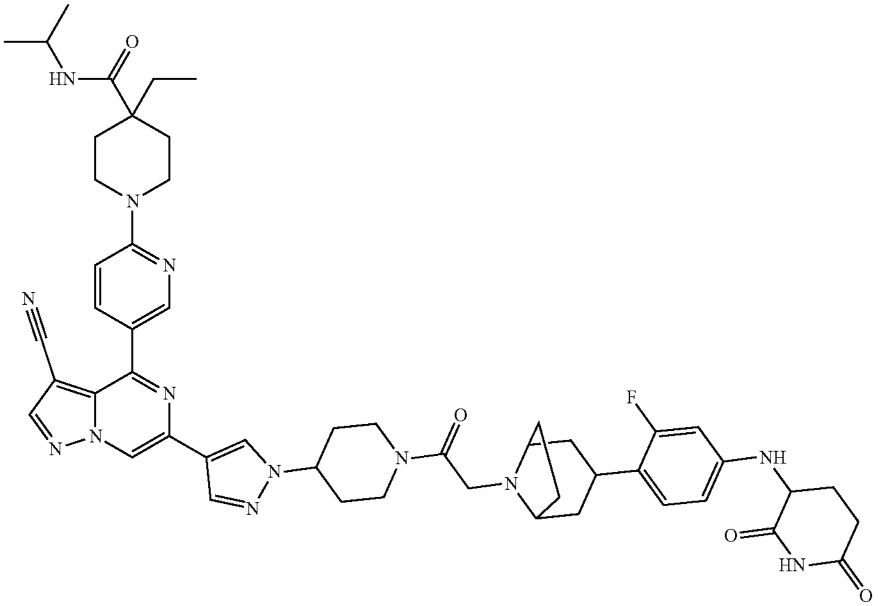 [SMILES: CCC1(C(=O)NC(C)C)CCN(c2ccc(-c3nc(-c4cnn(C5CCN(C(=O)CN6C7CCC6CC(c6ccc(NC8CCC(=O)NC8=O)cc6F)C7)CC5)c4)cn4ncc(C#N)c34)cn2)CC1]

LCMS ($ES^+$): m/z 938.5 $[M+H]^+$ $^1H$ NMR (400 MHz, DMSO-$d_6$): δ=10.76 (s, 1H), 9.33-9.21 (m, 1H), 8.81 (s, 1H), 8.65 (s, 1H), 8.47 (s, 1H), 8.21-8.13 (m, 1H), 8.06-7.98 (m, 1H), 7.45-7.36 (m, 1H), 7.11-6.89 (m, 2H), 6.53-6.30 (m, 2H), 6.11-5.87 (m, 1H), 4.64-4.37 (m, 3H), 4.33-4.08 (m, 3H), 4.04-3.96 (m, 1H), 3.28-3.20 (m, 4H), 3.16-3.04 (m, 4H), 2.91-2.69 (m, 2H), 2.64-2.53 (m, 4H), 2.22-1.97 (m, 9H), 1.86-1.78 (m, 2H), 1.54-1.44 (m, 3H), 1.37-1.30 (m, 2H), 1.08 (d, J=6.4 Hz, 6H), 0.74 (t, J=7.2 Hz, 3H).

Example 128: 1-[5-[6-[1-[1-[2-[1-[2-bromo-4-[(2,6-dioxo-3-piperidyl)amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-isopropyl-piperidine-4-carboxamide (Compound 95)

Compound 95 was Prepared Following the Synthesis of Compound 89

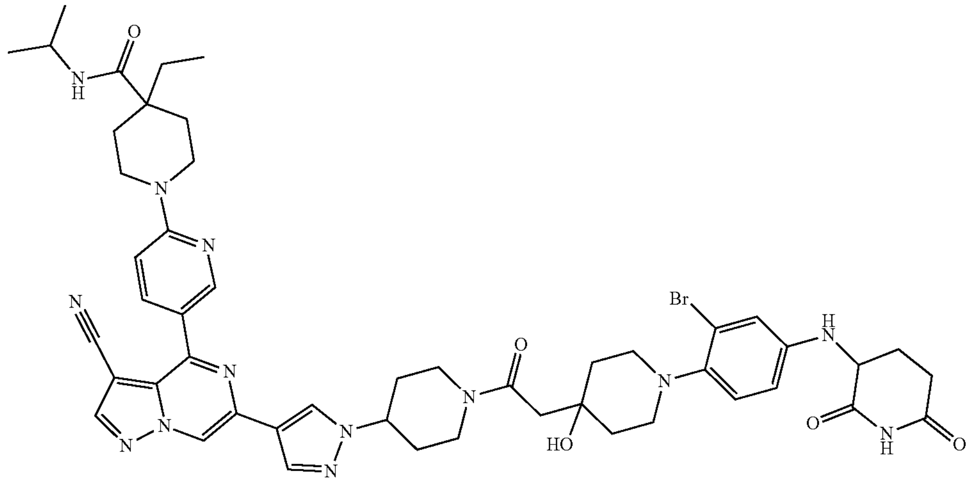 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7Br)CC6)CC5)c4)cn4ncc(C#N)c34)cn2)CC1]

LCMS ($ES^+$): m/z 988.2 $[M+H]^+$ $^1H$ NMR (400 MHz, DMSO-$d_6$). δ 10.77 (s, 1H), 9.29 (s, 1H), 8.83 (s, 1H), 8.68 (d, J=2.8 Hz, 1H), 8.50 (s, 1H), 8.18 (s, 1H), 8.05 (dd, J=9.2, 2.4 Hz, 1H), 7.41 (d, J=8 Hz, 1H), 6.99 (dd, J=8.8, 5.2 Hz, 2H), 6.94 (d, J=2.8 Hz, 1H), 6.65 (d, J=2.8 Hz, 1H), 5.85 (d, J=8 Hz, 1H), 4.95 (s, 1H), 4.63-4.45 (m, 2H), 4.41-4.31 (m, 1H), 4.25-4.12 (m, 3H), 4.06-3.97 (m, 1H), 3.32-3.20 (m, 1H), 3.18-3.05 (m, 2H), 2.94-2.85 (m, 2H), 2.82-2.72 (m, 3H), 2.62-2.55 (m, 2H), 2.21-2.05 (m, 6H), 2.01-1.65 (m, 8H), 1.55-1.45 (m, 2H), 1.40-1.30 (m, 2H), 1.09 (d, J=6.4 Hz, 6H) and 0.76 (t, J=7.6 Hz, 3H).

Example 129: 1-[5-[3-cyano-6-[1-[1-[2-[1-[2-(difluoromethyl)-4-[(2,6-dioxo-3-piperidyl)amino]phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 96)

Compound 96 was Prepared Following the Synthesis of Compound 89

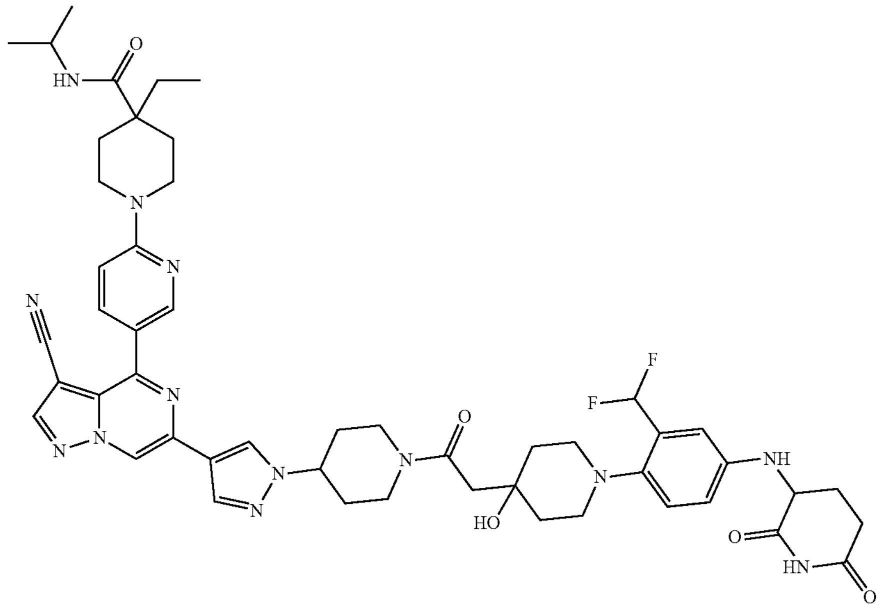 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7C(F)F)CC6)CC5)c4)cn4ncc(C#N)c34)cn2)CC1]

LCMS ($ES^+$): m/z 960.0 $[M+H]^+$.

$^1$H-NMR (400 MHz, DMSO-$d_6$): δ 10.76 (s, 1H), 9.30 (s, 1H), 8.83 (s, 1H), 8.67 (d, J=2.8 Hz, 1H), 8.50 (s, 1H), 8.18 (s, 1H), 8.05 (dd, J=8.8, 2.4 Hz, 1H), 7.43 (d, J=8 Hz, 1H), 7.24-6.96 (m, 3H), 6.82 (t, J=8.8 Hz, 2H), 5.99 (d, J=8 Hz, 1H), 4.95 (s, 1H), 4.63-4.50 (m, 2H), 4.41-4.31 (m, 1H), 4.25-4.12 (m, 3H), 4.06-3.97 (m, 1H), 3.32-3.20 (m, 1H), 3.18-3.05 (m, 2H), 3.11 (t, J=10.8 Hz, 2H), 2.97 (t, J=9.2 Hz, 2H), 2.82-2.70 (m, 2H), 2.62-2.55 (m, 3H), 2.21-2.05 (m, 5H), 2.01-1.72 (m, 5H), 1.71-1.65 (m, 2H), 1.55-1.45 (m, 2H), 1.40-1.30 (m, 2H), 1.09 (d, J=6.8 Hz, 6H) and 0.75 (t, J=7.6 Hz, 3H).

Example 130: 1-[5-[3-cyano-6-[1-[1-[2-[2-[4-[(2,6-dioxo-3-piperidyl)amino]-2-fluoro-phenyl]-6-hydroxy-2-azaspiro[3.3]heptan-6-yl]acetyl]-4-piperidyl]pyrazol-4-yl]pyrazolo[1,5-a]pyrazin-4-yl]-2-pyridyl]-4-ethyl-N-isopropyl-piperidine-4-carboxamide (Compound 97)

Compound 97 was Prepared Following the Synthesis of Compound 89

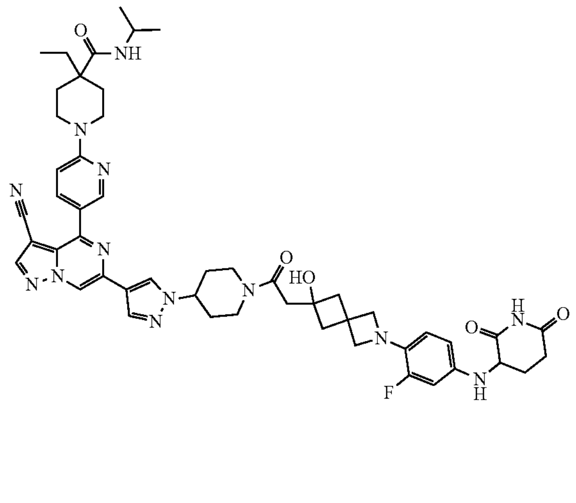 [SMILES: CCC1(C(=O)NC(C)C)CCN(c2ccc(-c3nc(-c4cnn(C5CCN(C(=O)CC6(O)CC7(CN(c8ccc(NC9CCC(=O)NC9=O)cc8F)C7)C6)CC5)c4)cn4ncc(C#N)c34)cn2)CC1]

LCMS ($ES^+$): m/z 940.4 $[M+H]^+$.

$^1H$ NMR (400 MHz, DMSO-$d_6$). δ 10.75 (s, 1H), 9.29 (s, 1H), 8.83 (s, 1H), 8.68 (d, J=2.8 Hz, 1H), 8.49 (s, 1H), 8.18 (s, 1H), 8.05 (dd, J=9, 2.8 Hz, 1H), 7.40 (d, J=8 Hz, 1H), 7.00 (d, J=9.2 Hz, 1H), 6.50-6.39 (m, 3H), 5.53 (d, J=7.6 Hz, 1H), 5.13 (s, 1H), 4.50 (m, 2H), 4.15 (m, 4H), 4.00 (m, 1H), 3.72 (d, J=9.2 Hz, 4H), 3.29-3.12 (m, 4H), 2.69-2.67 (m, 1H), 2.59 (bs, 2H), 2.21-2.16 (m, 8H), 2.11-1.76 (m, 5H), 1.51 (m, 2H), 1.36 (m, 2H), 1.10 (d, J=6.4 Hz, 6H) and 0.76 (t, J=7.6 Hz, 3H).

Example 131: 1-[5-[6-[1-[1-[2-[1-[2-chloro-4-[(2,6-dioxo-3-piperidyl)amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-phenyl-piperidine-4-carboxamide (Compound 98)

Compound 98 was Prepared Following the Synthesis of Compound 89

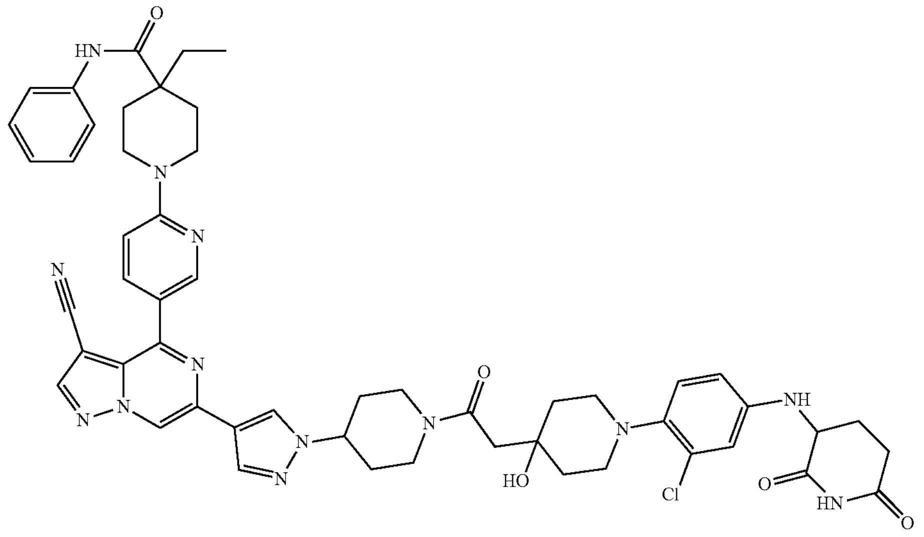

LCMS ($ES^+$): m/z 978.4 $[M+H]^+$.

$^1H$ NMR (400 MHz, DMSO-$d_6$) δ=10.78 (s, 1H), 9.41 (s, 1H), 9.29 (s, 1H), 8.83 (s, 1H), 8.69 (d, J=2.4 Hz, 1H), 8.50 (s, 1H), 8.18 (s, 1H), 8.15 (s, 1H), 8.06 (dd, J=2.4, 9.2 Hz, 1H), 7.65 (d, J=7.6 Hz, 2H), 7.31 (t, J=8.0 Hz, 2H), 7.11-6.95 (m, 3H), 6.75 (d, J=2.4 Hz, 1H), 6.60 (dd, J=2.4, 8.8 Hz, 1H), 5.83 (d, J=7.6 Hz, 1H), 4.94 (s, 1H), 4.65-4.48 (m, 2H), 4.34-4.25 (m, 1H), 4.19 (br d, J=13.2 Hz, 3H), 3.30-3.19 (m, 4H), 2.95-2.87 (m, 2H), 2.86-2.64 (m, 5H), 2.59 (s, 3H), 2.34-2.27 (m, 2H), 2.16-2.04 (m, 3H), 2.01-1.90 (m, 1H), 1.89-1.79 (m, 2H), 1.78-1.63 (m, 6H), 1.59-1.45 (m, 2H), 0.81 (t, J=7.2 Hz, 3H)

Example 132: 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-phenyl-piperidine-4-carboxamide (Compound 99)

Compound 99 was Prepared Following the Synthesis of Compound 89

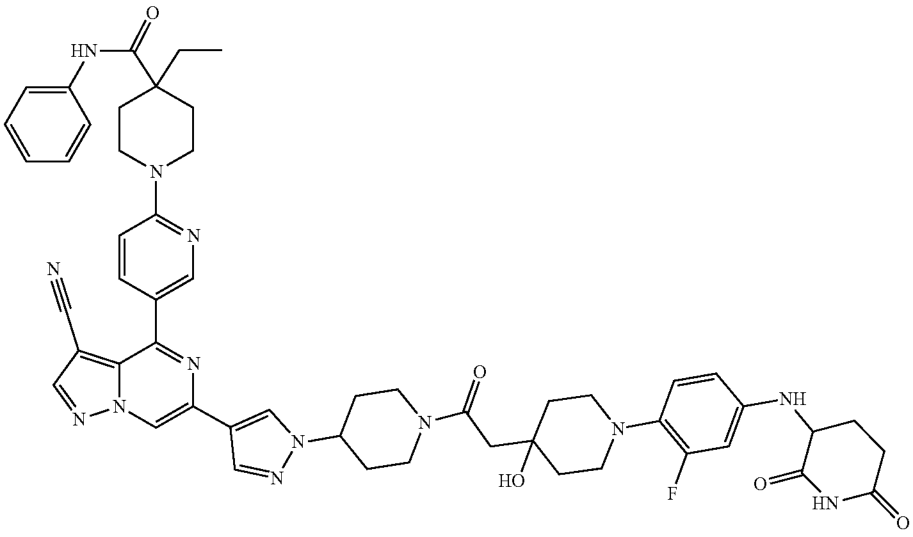 [SMILES: CCC1(C(=O)Nc2ccccc2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1]

LCMS ($ES^+$): m/z 962.4 $[M+H]^+$.

$^1$H NMR (400 MHz, DMSO-$d_6$) δ=10.78 (s, 1H), 9.41 (s, 1H), 9.29 (s, 1H), 8.83 (s, 1H), 8.69 (d, J=2.4 Hz, 1H), 8.50 (s, 1H), 8.41 (s, 1H), 8.18 (s, 1H), 8.10-8.03 (m, 1H), 7.65 (d, J=7.6 Hz, 2H), 7.31 (t, J=8.0 Hz, 2H), 7.12-6.99 (m, 2H), 6.86 (t, J=9.2 Hz, 1H), 6.50 (dd, J=2.4, 15.2 Hz, 1H), 6.42 (dd, J=2.4, 8.8 Hz, 1H), 5.78 (d, J=8.0 Hz, 1H), 4.91 (s, 1H), 4.64-4.45 (m, 2H), 4.31-4.14 (m, 4H), 3.28-3.20 (m, 5H), 2.97-2.81 (m, 5H), 2.81-2.66 (m, 3H), 2.63-2.56 (m, 3H), 2.37-2.26 (m, 3H), 2.15-2.05 (m, 3H), 2.02-1.92 (m, 1H), 1.92-1.77 (m, 3H), 1.77-1.65 (m, 6H), 1.57-1.46 (m, 2H), 0.81 (t, J=7.6 Hz, 3H)

Example 133: 1-[5-[6-[1-[1-[2-[1-[2-chloro-4-[(2,6-dioxo-3-piperidyl)amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-(4-fluorophenyl)piperidine-4-carboxamide (Compound 100)

Compound 100 was Prepared Following the Synthesis of Compound 89

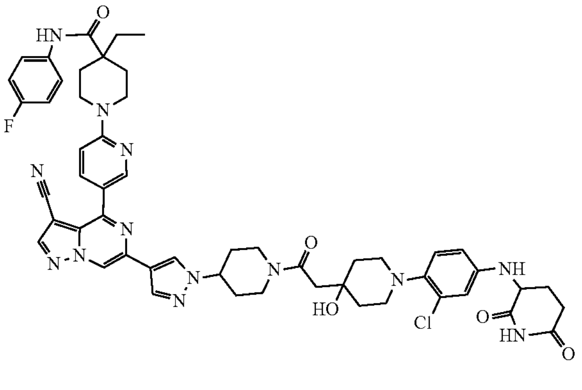 [SMILES: CCC1(C(=O)Nc2ccc(F)cc2)CCN(c2ccc(-c3nc(-c4cnn(C5CCN(C(=O)CC6(O)CCN(c7ccc(NC8CCC(=O)NC8=O)cc7Cl)CC6)CC5)c4)cn4ncc(C#N)c34)cn2)CC1]

LCMS ($ES^+$): m/z 996.5 $[M+H]^+$.

$^1$H NMR (400 MHz, DMSO-$d_6$) δ=10.76 (s, 1H), 9.47 (s, 1H), 9.26 (s, 1H), 8.80 (s, 1H), 8.67 (d, J=2.4 Hz, 1H), 8.48 (s, 1H), 8.16 (s, 1H), 8.13 (s, 1H), 8.05 (dd, J=2.4, 8.8 Hz, 1H), 7.68-7.59 (m, 2H), 7.14 (t, J=8.8 Hz, 2H), 7.00 (dd, J=8.8, 13.2 Hz, 2H), 6.75 (d, J=2.4 Hz, 1H), 6.60 (dd, J=2.4, 8.8 Hz, 1H), 4.61-4.47 (m, 2H), 4.28 (br dd, J=4.8, 11.6 Hz, 1H), 4.23-4.11 (m, 3H), 3.27-3.19 (m, 4H), 2.94-2.87 (m, 2H), 2.86-2.65 (m, 5H), 2.60-2.54 (m, 3H), 2.34-2.24 (m, 2H), 2.13-2.05 (m, 3H), 1.96-1.65 (m, 9H), 1.55-1.44 (m, 2H), 0.80 (t, J=7.2 Hz, 3H).

Example 134: 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-(4-fluorophenyl)piperidine-4-carboxamide (Compound 101)

Compound 101 was Prepared Following the Synthesis of Compound 89

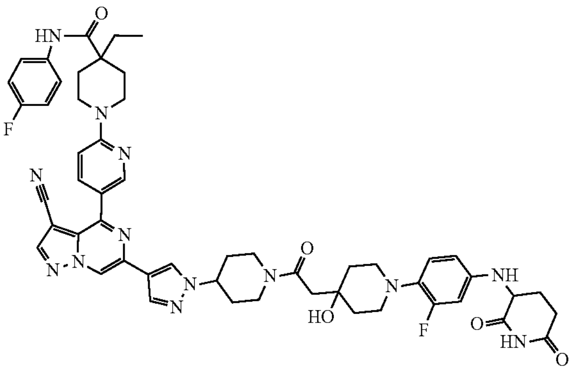 [SMILES: CCC1(C(=O)Nc2ccc(F)cc2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1]

LCMS ($ES^+$): m/z 491.0 $[M/2+H]^+$ $^1$H NMR (400 MHz, DMSO-$d_6$) δ=10.76 (s, 1H), 9.47 (s, 1H), 9.26 (s, 1H), 8.80 (s, 1H), 8.67 (d, J=2.4 Hz, 1H), 8.48 (s, 1H), 8.16 (s, 1H), 8.13 (s, 1H), 8.05 (dd, J=2.4, 8.8 Hz, 1H), 7.68-7.60 (m, 2H), 7.14 (t, J=8.8 Hz, 2H), 7.01 (d, J=9.2 Hz, 1H), 6.85 (t, J=9.2 Hz, 1H), 6.54-6.38 (m, 2H), 5.75 (d, J=7.6 Hz, 1H), 4.91 (s, 1H), 4.61-4.47 (m, 2H), 4.28-4.12 (m, 2H), 3.28-3.19 (m, 4H), 2.94-2.82 (m, 4H), 2.80-2.65 (m, 2H), 2.63-2.52 (m, 4H), 2.34-2.24 (m, 2H), 2.12-2.07 (m, 2H), 1.98-1.65 (m, 9H), 1.56-1.44 (m, 2H), 0.84-0.75 (m, 3H).

Example 135: N-tert-butyl-1-[5-[6-[1-[1-[2-[1-[2-chloro-4-[(2,6-dioxo-3-piperidyl)amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-piperidine-4-carboxamide (Compound 102)

Compound 102 was Prepared Following the Synthesis of Compound 89

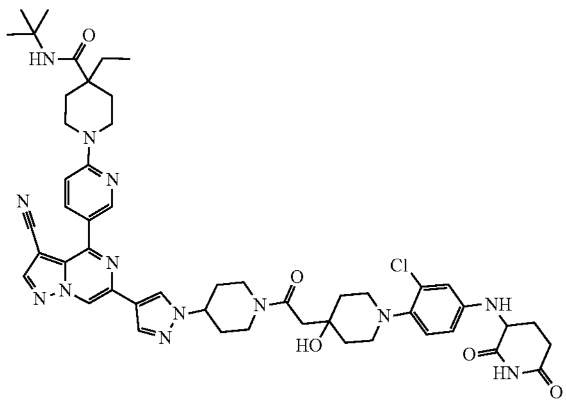

LCMS ($ES^+$): m/z 958.4 $[M+H]^+$.

1H NMR (400 MHz, DMSO-$d_6$) δ=10.77 (s, 1H), 9.29 (s, 1H), 8.82 (s, 1H), 8.67 (d, J=2.4 Hz, 1H), 8.49 (s, 1H), 8.18 (s, 1H), 8.14 (s, 1H), 8.05 (dd, J=2.4, 8.8 Hz, 1H), 7.08-6.92 (m, 2H), 6.86 (s, 1H), 6.76 (d, J=2.4 Hz, 1H), 6.61 (dd, J=2.4, 8.8 Hz, 1H), 6.15-5.62 (m, 1H), 4.96-4.73 (m, 1H), 5.20-4.69 (m, 1H), 4.66-4.45 (m, 2H), 4.35-4.25 (m, 1H), 4.24-4.08 (m, 3H), 3.27-3.20 (m, 2H), 3.19-3.09 (m, 3H), 2.98-2.87 (m, 2H), 2.87-2.78 (m, 3H), 2.77-2.64 (m, 2H), 2.20-2.05 (m, 5H), 2.01-1.90 (m, 1H), 1.86 (br dd, J=4.0, 12.4 Hz, 1H), 1.83-1.63 (m, 5H), 1.53 (q, J=7.2 Hz, 2H), 1.40-1.32 (m, 2H), 1.30 (s, 9H), 0.77 (t, J=7.2 Hz, 3H)

Example 136: N-tert-butyl-1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazin-4-yl]-2-pyridyl]-4-ethyl-piperidine-4-carboxamide (Compound 103)

Compound 103 was Prepared Following the Synthesis of Compound 89

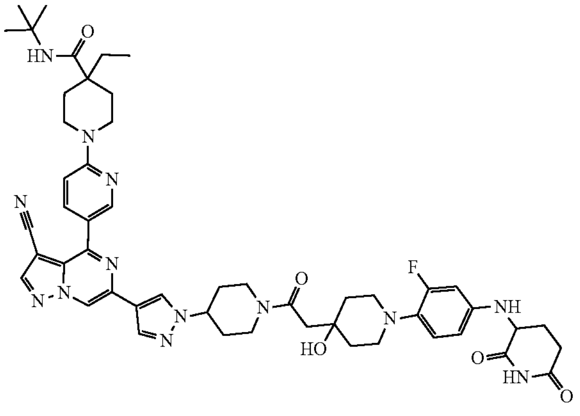 [SMILES: CCC1(C(=O)NC(C)(C)C)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1]

LCMS ($ES^+$): m/z 942.4 $[M+H]^+$.

$^1$H NMR (400 MHz, DMSO-$d_6$) δ=10.77 (s, 1H), 9.28 (s, 1H), 8.82 (s, 1H), 8.67 (d, J=2.4 Hz, 1H), 8.50 (s, 1H), 8.18 (s, 1H), 8.14 (s, 1H), 8.05 (dd, J=2.4, 9.2 Hz, 1H), 7.00 (d, J=9.2 Hz, 1H), 6.91-6.83 (m, 2H), 6.55-6.47 (m, 1H), 6.45-6.39 (m, 1H), 5.80-5.73 (m, 1H), 4.91 (s, 1H), 4.62-4.48 (m, 2H), 4.27-4.10 (m, 4H), 3.29-3.19 (m, 5H), 3.18-3.10 (m, 4H), 2.96-2.82 (m, 5H), 2.81-2.70 (m, 3H), 2.62-2.57 (m, 5H), 2.21-2.06 (m, 6H), 2.02-1.88 (m, 2H), 1.88-1.71 (m, 5H), 1.71-1.64 (m, 2H), 1.53 (q, J=7.2 Hz, 2H), 1.39-1.33 (m, 2H), 1.30 (s, 9H), 0.77 (t, J=7.6 Hz, 3H)

Example 137: 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-(4-methyl-4-pyrimidin-2-yl-1-piperidyl)-3-pyridyl]pyrazolo[1,5-a]pyrazine-3-carbonitrile (Compound 104)

Compound 104 was Prepared Following the Synthesis of Compound 89

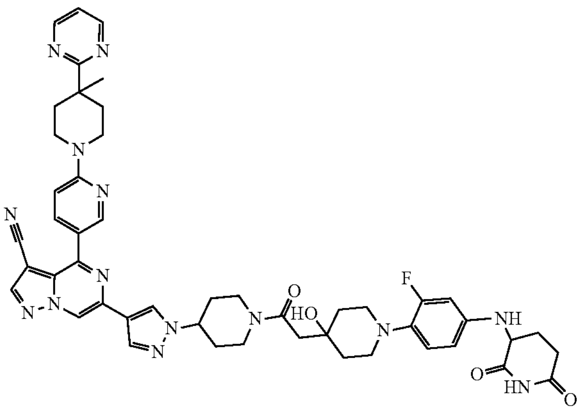 [SMILES: CC1(c2ncccn2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1]

LCMS ($ES^+$): m/z 907.4 $[M+H]^+$.

$^1$H NMR (400 MHz, DMSO-$d_6$) δ=10.80 (s, 1H), 9.29 (s, 1H), 8.85 (s, 1H), 8.83 (d, J=2.8 Hz, 2H), 8.68 (d, J=2.4 Hz, 1H), 8.50 (s, 1H), 8.18 (s, 1H), 8.14 (s, 1H), 8.06 (dd, J=2.4, 8.8 Hz, 1H), 7.37 (t, J=4.8 Hz, 1H), 7.16-6.74 (m, 2H), 6.63-6.43 (m, 2H), 4.64-4.46 (m, 2H), 4.38-4.23 (m, 1H), 4.22-4.13 (m, 1H), 4.13-4.02 (m, 2H), 3.28-3.20 (m, 5H), 3.09-2.87 (m, 3H), 2.87-2.69 (m, 3H), 2.61 (br s, 2H), 2.19-2.04 (m, 4H), 2.03-1.67 (m, 10H), 1.31 (s, 3H)

Example 138: 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-(4-ethyl-4-pyrimidin-2-yl-1-piperidyl)-3-pyridyl]pyrazolo[1,5-a]pyrazine-3-carbonitrile (Compound 105)

Compound 105 was Prepared Following the Synthesis of Compound 89

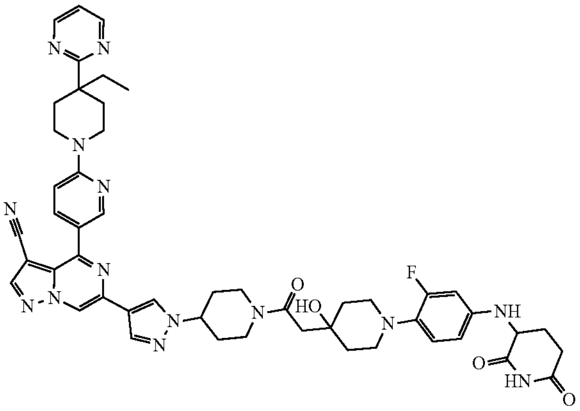 [SMILES: CCC1(c2ncccn2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1]

LCMS ($ES^+$): m/z 921.5 $[M+H]^+$.

1H NMR (400 MHz, DMSO-$d_6$) δ=10.80 (br s, 1H), 9.29 (s, 1H), 8.91-8.77 (m, 3H), 8.67 (d, J=2.4 Hz, 1H), 8.50 (s, 1H), 8.18 (s, 1H), 8.14 (s, 1H), 8.05 (dd, J=2.4, 8.8 Hz, 1H), 7.38 (t, J=4.8 Hz, 1H), 7.14-6.69 (m, 2H), 6.64-6.36 (m, 2H), 4.66-4.45 (m, 2H), 4.37-4.10 (m, 4H), 3.28-3.18 (m, 2H), 3.11-2.98 (m, 3H), 2.97-2.85 (m, 2H), 2.84-2.68 (m, 3H), 2.60 (br d, J=4.0 Hz, 6H), 2.16-2.06 (m, 3H), 2.03-1.89 (m, 1H), 1.89-1.75 (m, 4H), 1.75-1.63 (m, 6H), 0.54 (t, J=7.2 Hz, 3H).

Example 139: 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-(pyridine-3-carbonyl)piperazin-1-yl]-3-pyridyl]pyrazolo[1,5-a]pyrazine-3-carbonitrile (Compound 106)

Compound 106 was Prepared Following the Synthesis of Compound 89

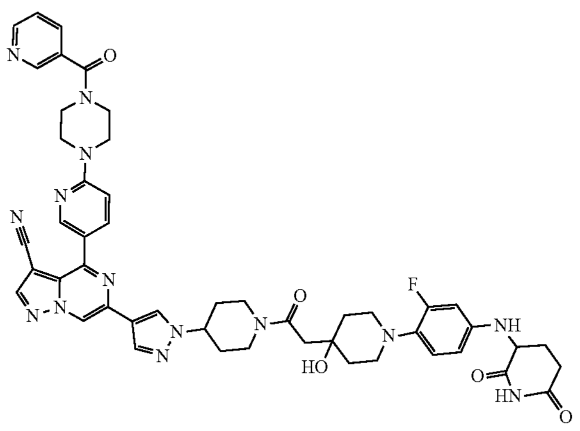 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCN(C(=O)c5cccnc5)CC4)nc3)c12]

LCMS ($ES^+$): m/z 461.6 $[M/2+H]^+$.

$^1H$ NMR (400 MHz, DMSO-$d_6$) δ=10.78 (s, 1H), 9.35-9.29 (m, 1H), 8.84 (s, 1H), 8.73-8.67 (m, 3H), 8.51 (s, 1H), 8.19 (s, 1H), 8.15-8.10 (m, 1H), 7.95-7.90 (m, 1H), 7.56-7.48 (m, 1H), 7.05 (d, J=8.8 Hz, 1H), 6.91-6.82 (m, 1H), 6.55-6.38 (m, 2H), 5.82-5.75 (m, 1H), 4.93-4.87 (m, 1H), 4.64-4.47 (m, 2H), 4.31-4.12 (m, 2H), 3.90-3.68 (m, 6H), 3.53-3.48 (m, 1H), 3.27-3.19 (m, 1H), 2.98-2.71 (m, 7H), 2.59-2.57 (m, 2H), 2.16-2.05 (m, 3H), 2.01-1.62 (m, 8H)

Example 140: 4-[6-[4-(cyclohexanecarbonyl)piperazin-1-yl]-3-pyridyl]-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazine-3-carbonitrile (Compound 107)

Compound 107 was Prepared Following the Synthesis of Compound 89

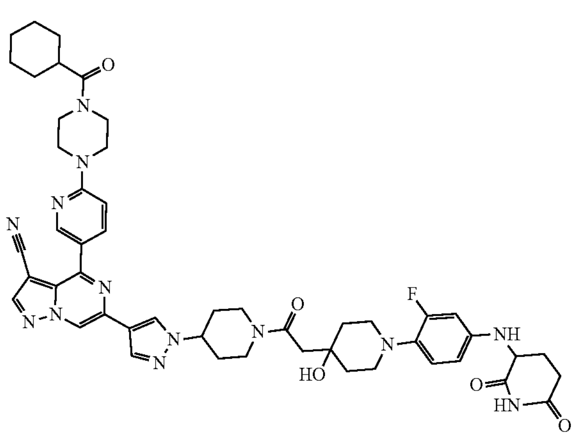 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCN(C(=O)C5CCCCC5)CC4)nc3)c12]

LCMS ($ES^+$): m/z 926.3 $[M+H]^+$. $^1H$ NMR (400 MHz, DMSO-$d_6$) δ=10.77 (s, 1H), 9.31 (s, 1H), 8.83 (s, 1H), 8.70 (d, J=2.4 Hz, 1H), 8.50 (s, 1H), 8.32 (s, 1H), 8.18 (s, 1H), 8.11 (m, 1H), 7.03 (d, J=9.2 Hz, 1H), 6.85 (m, 1H), 6.49 (m, 1H), 6.41 (m, 1H), 5.77 (d, J=7.6 Hz, 1H), 4.90 (s, 1H), 4.63-4.46 (m, 2H), 4.32-4.11 (m, 2H), 3.74-3.57 (m, 8H), 3.28-3.13 (m, 3H), 2.94-2.81 (m, 4H), 2.81-2.60 (m, 4H), 2.59-2.53 (m, 3H), 2.16-2.05 (m, 3H), 2.02-1.91 (m, 1H), 1.91-1.60 (m, 12H), 1.42-1.25 (m, 4H), 1.24-1.12 (m, 1H)

Example 141: 4-[6-(4-benzyl-1,4-diazepan-1-yl)-3-pyridyl]-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazine-3-carbonitrile (Compound 108)

Compound 108 was Prepared Following the Synthesis of Compound 89

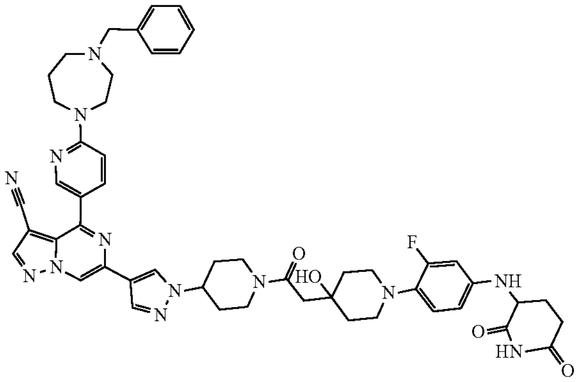 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCCN(Cc5ccccc5)CC4)nc3)c12]

LCMS ($ES^+$): m/z 920.4 $[M+H]^+$.

$^1H$ NMR (400 MHz, DMSO-$d_6$) δ=10.81-10.73 (m, 1H), 9.33-9.23 (m, 1H), 8.85-8.78 (m, 1H), 8.67 (d, J=2.0 Hz, 1H), 8.54-8.45 (m, 1H), 8.18 (s, 1H), 8.18 (s, 1H), 8.05 (m, 1H), 7.35-7.27 (m, 4H), 7.26-7.19 (m, 1H), 6.89-6.78 (m, 2H), 6.49 (m, 1H), 6.44-6.36 (m, 1H), 5.77 (d, J=7.6 Hz, 1H), 4.98-4.85 (m, 1H), 4.64-4.44 (m, 1H), 4.32-4.10 (m, 2H), 3.90-3.69 (m, 4H), 3.62 (s, 2H), 2.96-2.81 (m, 5H), 2.80-2.70 (m, 4H), 2.60-2.55 (m, 5H), 2.15-2.04 (m, 3H), 2.02-1.60 (m, 10H)

Example 142: 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-(2-pyridyloxy)-1-piperidyl]-3-pyridyl]pyrazolo[1,5-a]pyrazine-3-carbonitrile (Compound 109)

Compound 109 was Prepared Following the Synthesis of Compound 89

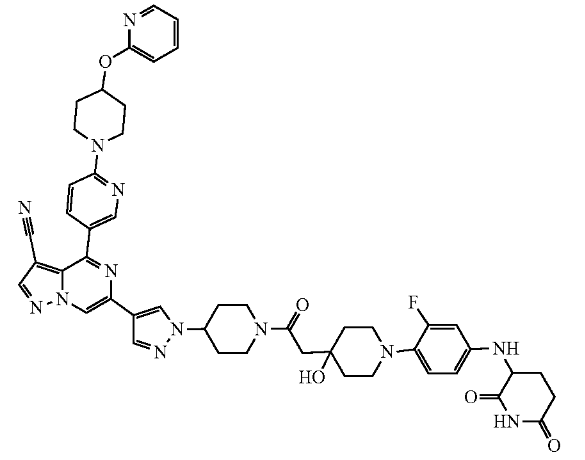 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC(Oc5ccccn5)CC4)nc3)c12]

LCMS ($ES^+$): m/z 908.5 $[M+H]^+$.

$^1H$ NMR (400 MHz, DMSO-$d_6$) δ=10.77 (s, 1H), 9.29 (s, 1H), 8.83 (s, 1H), 8.70 (d, J=2.4 Hz, 1H), 8.50 (s, 1H), 8.20-8.15 (m, 2H), 8.08 (dd, J=2.4, 8.8 Hz, 1H), 7.74-7.67 (m, 1H), 7.07 (d, J=8.8 Hz, 1H), 6.97 (dd, J=5.2, 6.4 Hz, 1H), 6.90-6.83 (m, 1H), 6.83-6.78 (m, 1H), 6.50 (br d, J=15.0 Hz, 1H), 6.41 (br d, J=7.6 Hz, 1H), 5.86-5.66 (m, 1H), 5.40-5.24 (m, 1H), 4.90 (br d, J=2.0 Hz, 1H), 4.62-4.45 (m, 2H), 4.29-4.21 (m, 1H), 4.21-4.13 (m, 3H), 3.55-3.44 (m, 2H), 3.27-3.19 (m, 2H), 2.95-2.82 (m, 4H), 2.81-2.68 (m, 2H), 2.58 (br s, 2H), 2.09 (br dd, J=4.4, 8.0 Hz, 5H), 2.00-1.92 (m, 1H), 1.88-1.79 (m, 2H), 1.78-1.64 (m, 6H)

Example 143: 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[4-ethyl-4-(2-pyridyl)-1-piperidyl]-3-pyridyl]pyrazolo[1,5-a]pyrazine-3-carbonitrile (Compound 110)

Compound 110 was Prepared Following the Synthesis of Compound 89

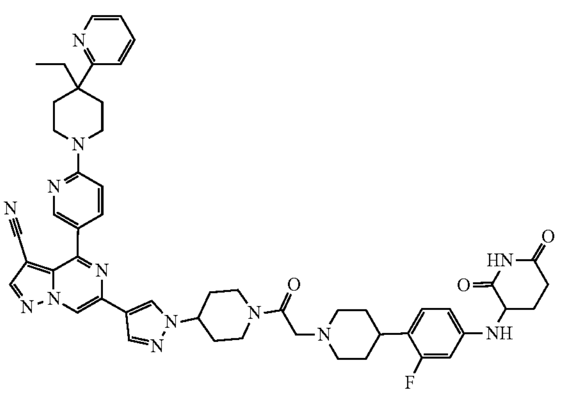 [SMILES: CCC1(c2ccccn2)CCN(c2ccc(-c3nc(-c4cnn(C5CCN(C(=O)CN6CCC(c7ccc(NC8CCC(=O)NC8=O)cc7F)CC6)CC5)c4)cn4ncc(C#N)c34)cn2)CC1]

LCMS ($ES^+$): m/z 904.4 $[M+H]^+$.

$^1H$ NMR (400 MHz, DMSO-$d_6$). δ 10.79 (s, 1H), 9.29 (s, 1H), 9.83 (s, 1H), 8.67 (d, J=2.4 Hz, 1H), 8.61 (dd, J=4.8, 1.2 Hz, 1H), 8.49 (s, 1H), 8.18 (s, 1H), 8.04 (dd, J=9, 2.4 Hz, 1H), 7.82-7.77 (m, 1H), 7.51 (d, J=8 Hz, 1H), 7.24 (dd, J=7.2, 5.6 Hz, 1H), 6.99-6.95 (m, 2H), 6.45-6.42 (m, 2H), 6.00 (d, J=7.6 Hz, 1H), 4.53-4.45 (m, 2H), 4.30-4.23 (m, 2H), 4.10-4.07 (m, 2H), 3.25 (m, 1H), 3.15 (m, 4H), 2.94 (m, 2H), 2.82-2.74 (m, 2H), 2.58 (m, 2H), 2.42 (m, 2H), 2.11-2.05 (m, 5H), 2.00 (m, 1H), 1.80 (m, 2H), 1.65 (m, 8H) and 0.54 (t, J=7.2 Hz, 3H).

Example 144: 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyrazin-4-yl]-2-pyridyl]-4-ethyl-N-tetrahydropyran-4-yl-piperidine-4-carboxamide (Compound 111)

Compound 111 was Prepared Following the Synthesis of Compound 89

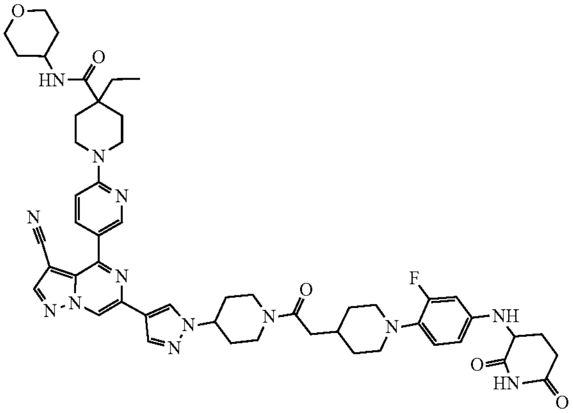 [SMILES: CCC1(C(=O)NC2CCOCC2)CCN(c2ccc(-c3nc(-c4cnn(C5CCN(C(=O)CC6CCN(c7ccc(NC8CCC(=O)NC8=O)cc7F)CC6)CC5)c4)cn4ncc(C#N)c34)cn2)CC1]

LCMS ($ES^+$): m/z 954.2 $[M+H]^+$.

$^1H$ NMR (400 MHz, DMSO-$d_6$). δ 10.79 (s, 1H), 9.29 (s, 1H), 8.83 (s, 1H), 8.67 (d, J=2.4 Hz, 1H), 8.50 (s, 1H), 8.18 (s, 1H), 8.04 (d, J=9.2 Hz, 1H), 7.51 (d, J=7.6 Hz, 1H), 6.98 (m, 2H), 6.43 (m, 2H), 5.99 (d, J=7.6 Hz, 1H), 4.53 (m, 2H), 4.29-4.14 (m, 5H), 3.90-3.84 (m, 4H), 3.20 (m, 5H), 2.94 (m, 2H), 2.80-2.76 (m, 3H), 2.15 (m, 6H), 1.85 (m, 5H), 1.67-1.65 (m, 6H), 1.53-1.51 (m, 4H), 1.37 (t, J=10.4 Hz, 2H) and 0.76 (t, J=7.2 Hz, 3H).

Example 145: 4-[6-[4-(cyclobutanecarbonyl)piperazin-1-yl]-3-pyridyl]-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazine-3-carbonitrile (Compound 112)

Compound 112 was Prepared Following the Synthesis of Compound 89

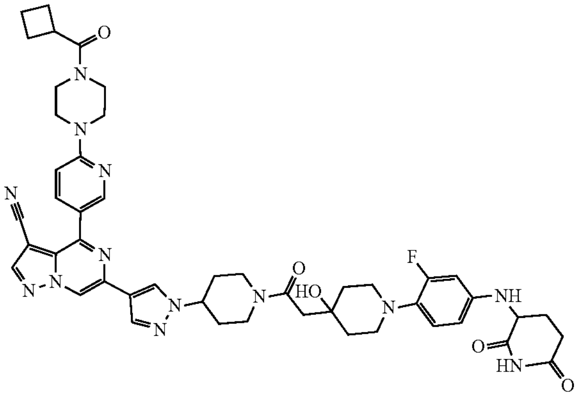 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCN(C(=O)C5CCC5)CC4)nc3)c12]

LCMS ($ES^+$): m/z 898.5 $[M+H]^+$.

$^1H$ NMR (400 MHz, DMSO-$d_6$) δ=10.77 (s, 1H), 9.30 (s, 1H), 8.83 (s, 1H), 8.70 (d, J=2.4 Hz, 1H), 8.49 (s, 1H), 8.19-8.18 (m, 1H), 8.18-8.17 (m, 1H), 8.10 (dd, J=2.4, 9.2 Hz, 1H), 7.03 (d, J=9.2 Hz, 1H), 6.86 (br s, 1H), 6.55-6.37 (m, 2H), 5.77 (br d, J=7.6 Hz, 1H), 4.90 (br d, J=2.4 Hz, 1H), 4.62-4.46 (m, 2H), 4.31-4.12 (m, 2H), 3.70-3.63 (m, 4H), 3.62-3.56 (m, 2H), 3.50-3.45 (m, 2H), 3.44-3.39 (m, 1H), 3.28-3.18 (m, 1H), 2.96-2.81 (m, 4H), 2.80-2.65 (m, 2H), 2.61-2.56 (m, 3H), 2.25-2.16 (m, 2H), 2.16-2.06 (m, 5H), 1.98-1.88 (m, 2H), 1.87-1.64 (m, 7H)

Example 146: 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (Compound 113)

Compound 113 was Prepared Following the Synthesis of Compound 89

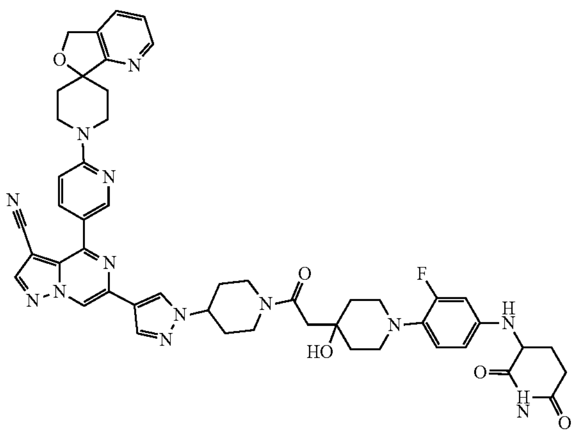 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC5(CC4)OCc4cccnc45)nc3)c12]

LCMS ($ES^+$): m/z 460.9 $[M/2+H]^+$.

$^1H$ NMR (400 MHz, DMSO-$d_6$): δ=10.82-10.68 (m, 1H), 9.30 (s, 1H), 8.84 (s, 1H), 8.72 (d, 1H), 8.51 (s, 1H), 8.42 (d, 1H), 8.19 (s, 1H), 8.10 (d, 1H), 7.78 (d, 1H), 7.30 (d, 1H), 7.11 (d, 1H), 6.85 (t, 1H), 6.49 (d, 1H), 6.41 (d, 1H), 5.76 (d, 1H), 5.10 (s, 2H), 4.89 (s, 1H), 4.61-4.43 (m, 4H), 4.30-4.12 (m, 2H), 3.48-3.40 (m, 3H), 2.93-2.81 (m, 4H), 2.80-2.70 (m, 2H), 2.57 (s, 3H), 2.17-2.05 (m, 3H), 1.99-1.90 (m, 3H), 1.88-1.80 (m, 2H), 1.77-1.63 (m, 6H)

Example 147: 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-(methoxymethyl)-4-(2-pyridylmethyl)-1-piperidyl]-3-pyridyl]pyrazolo[1,5-a]pyrazine-3-carbonitrile (Compound 114)

Compound 114 was Prepared Following the Synthesis of Compound 89

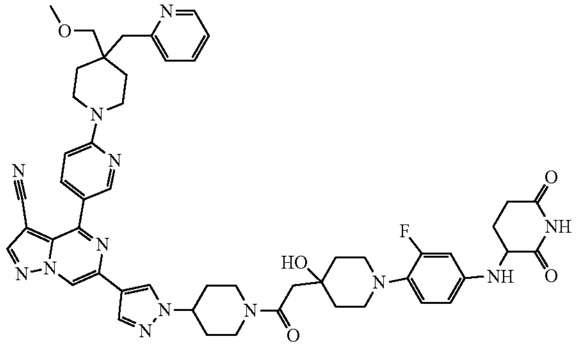 [SMILES: COCC1(Cc2ccccn2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1]

LCMS ($ES^+$): m/z 950.4 $[M+H]^+$.

$^1H$ NMR (400 MHz, DMSO-$d_6$). δ 10.79 (s, 1H), 9.30 (s, 1H), 8.84 (s, 1H), 8.68 (d, J=2 Hz, 1H), 8.53-8.51 (m, 2H), 8.19 (s, 1H), 8.06 (dd, J=9.2, 2.4 Hz, 1H), 7.74-7.70 (m, 1H), 7.25-7.22 (m, 2H), 7.00 (d, J=8.8 Hz, 1H), 6.86 (t, J=9.2 Hz, 1H), 6.50 (d, J=15.2 Hz, 1H), 6.42 (d, J=8.8 Hz, 1H), 5.79 (d, J=8 Hz, 1H), 4.91 (s, 1H), 4.59-4.53 (m, 2H), 4.26-4.10 (m, 2H), 3.84-3.81 (m, 2H), 3.75-3.72 (m, 2H), 3.27 (m, 3H), 3.15 (m, 4H), 2.91 (m, 4H), 2.70 (m, 1H), 2.56 (s, 2H), 2.10-2.08 (m, 5H), 1.95 (m, 1H), 1.90-1.80 (m, 2H), 1.79-1.70 (m, 2H), 1.65 (m, 2H), 1.55-1.52 (m, 5H).

Example 148: 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-(4-methylpyrimidin-2-yl)-1-piperidyl]-3-pyridyl]pyrazolo[1,5-a]pyrazine-3-carbonitrile (Compound 115)

Compound 115 was Prepared Following the Synthesis of Compound 89

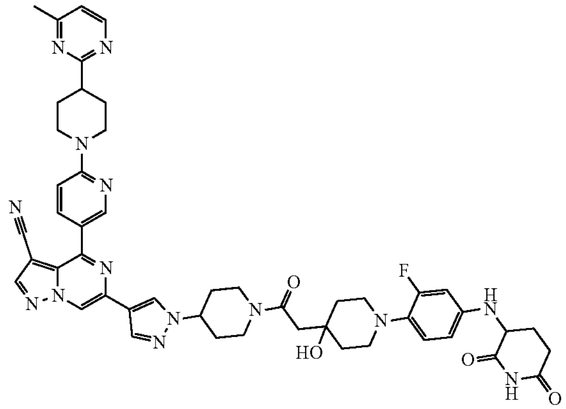 [SMILES: Cc1ccnc(C2CCN(c3ccc(-c4nc(-c5cnn(C6CCN(C(=O)CC7(O)CCN(c8ccc(NC9CCC(=O)NC9=O)cc8F)CC7)CC6)c5)cn5ncc(C#N)c45)cn3)CC2)n1]

LCMS (ES$^+$): m/z 907.5 [M+H]$^+$

1H NMR (400 MHz, DMSO-$d_6$) δ=10.79 (s, 1H), 9.28 (s, 1H), 8.82 (s, 1H), 8.70 (d, J=2.4 Hz, 1H), 8.58 (d, J=5.2 Hz, 1H), 8.50 (s, 1H), 8.18 (s, 1H), 8.14 (s, 1H), 8.08 (dd, J=2.4, 8.8 Hz, 1H), 7.21 (d, J=5.2 Hz, 1H), 7.06 (br d, J=9.2 Hz, 1H), 7.01-6.83 (m, 1H), 6.57-6.40 (m, 2H), 5.14-4.85 (m, 1H), 4.57 (br d, J=12.8 Hz, 4H), 4.31-4.15 (m, 2H), 3.30-3.20 (m, 2H), 3.19-3.08 (m, 4H), 3.07-2.88 (m, 4H), 2.85-2.66 (m, 3H), 2.59 (br s, 3H), 2.44 (s, 3H), 2.22-1.93 (m, 7H), 1.92-1.66 (m, 9H)

Example 149: Synthesis of 6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)-4-(6-(4-(isoxazole-3-carbonyl)piperazin-1-yl)pyridin-3-yl)pyrazolo[1,5-a]pyrazine-3-carbonitrile (Compound 116)

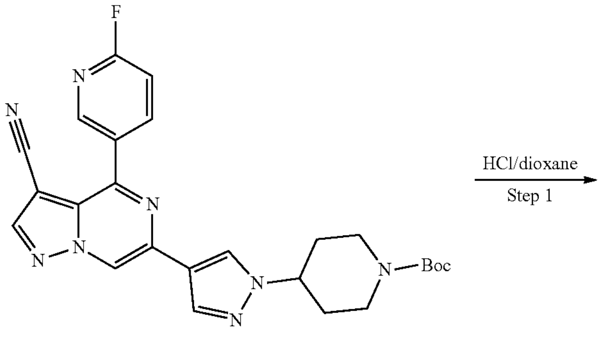

1

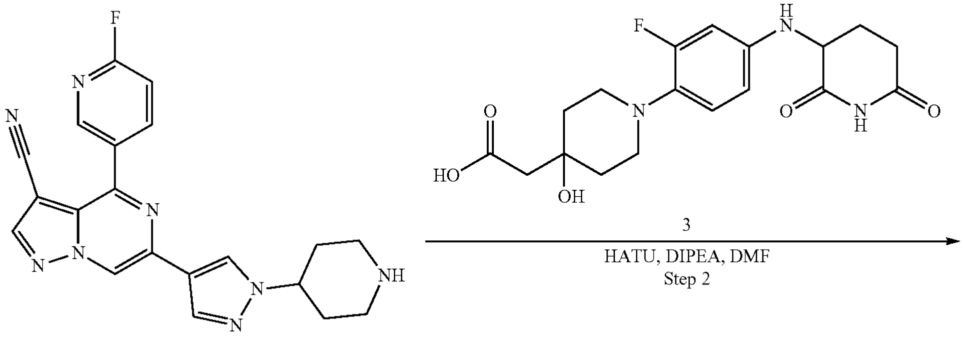

2

3

-continued

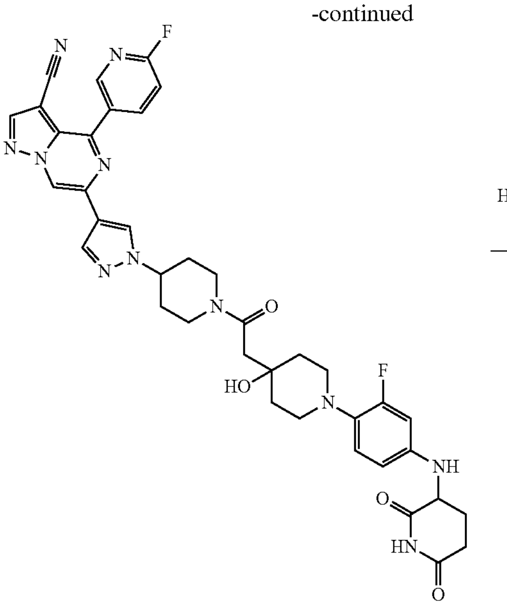

4

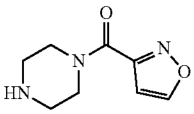

5

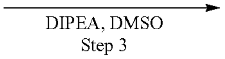

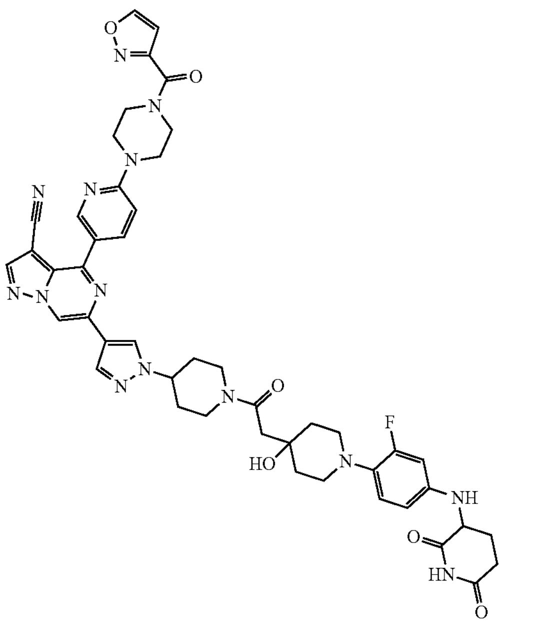

Compound 116

Step 1: To a solution of tert-butyl 4-(4-(3-cyano-4-(6-fluoropyridin-3-yl)pyrazolo[1,5-a]pyrazin-6-yl)-1H-pyrazol-1-yl)piperidine-1-carboxylate (1, 200 mg, 409.40 μmol) in DCM (1 mL) was added HCl/dioxane (4 M, 0.5 mL). After addition, the solution was stirred at 30° C. for 30 min. The solution was concentrated under vacuum. The residue was used for next step directly without purification. 4-(6-fluoro-3-pyridyl)-6-[1-(4-piperidyl)pyrazol-4-yl]pyrazolo[1,5-a]pyrazine-3-carbonitrile (2, 170 mg, 400.13 μmol, 98% yield, HCl salt) was obtained as a yellow solid.

Step 2: To a solution of 4-(6-fluoro-3-pyridyl)-6-[1-(4-piperidyl)pyrazol-4-yl]pyrazolo[1,5-a]pyrazine-3-carbonitrile (2, 174 mg, 409.55 μmol, HCl salt), 2-(1-(4-((2,6-dioxopiperidin-3-yl)amino)-2-fluorophenyl)-4-hydroxypiperidin-4-yl)acetic acid (3, 170.31 mg, 409.55 μmol, HCl salt) and DIPEA (158.79 mg, 1.23 mmol, 214.01 μL) in DMF (2 mL) was added HATU (233.58 mg, 614.32 μmol). After addition, the solution was stirred at 30° C. for 12h. The solution was poured into water (4 mL) to give a suspension. The suspension was washed with water (5 mL) and filtered under vacuum, and the filter cake was concentrated under vacuum. The residue was used for next step directly without purification. 6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)-4-(6-fluoropyridin-3-yl)pyrazolo[1,5-a]pyrazine-3-carbonitrile (4, 217 mg, 289.42 μmol, 71% yield) was obtained as a brown solid. LCMS ($ES^+$): m/z 750.3 $[M+H]^+$.

Step 3: To a solution of 6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)-4-(6-fluoropyridin-3-yl)pyrazolo[1,5-a]pyrazine-3-carbonitrile (4, 50 mg, 66.69 µmol), isoxazol-3-yl(piperazin-1-yl)methanone (5, 15.97 mg, 73.36 µmol, HCl salt) in DMSO (0.5 mL) was added DIPEA (25.86 mg, 200.06 µmol, 34.85 µL). After addition, the solution was stirred at 90° C. for 12h. The solution was adjusted to pH<7 with FA. The residue was separated by Prep-HPLC (Shim-pack C18 150*25*10 um, water (0.225% FA)-ACN, 22%-44%, 25 ml/min, 11 min). 6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)-4-(6-(4-(isoxazole-3-carbonyl)piperazin-1-yl)pyridin-3-yl)pyrazolo[1,5-a]pyrazine-3-carbonitrile (Compound 116, 27.69 mg, 28.65 µmol, 43% yield, formic acid salt) was obtained as a yellow solid. LCMS ($ES^+$): m/z 911.9 $[M+H]^+$. $^1H$ NMR (400 MHz, DMSO-$d_6$) δ=10.83-10.67 (m, 1H), 9.35-9.27 (m, 1H), 9.17-9.08 (m, 1H), 8.86-8.80 (m, 1H), 8.75-8.68 (m, 1H), 8.54-8.46 (m, 1H), 8.18-8.16 (m, 1H), 8.12 (m, 1H), 7.05 (d, J=9.2 Hz, 1H), 6.91-6.81 (m, 2H), 6.52-6.45 (m, 1H), 6.44-6.38 (m, 1H), 5.81-5.71 (m, 1H), 4.94-4.85 (m, 1H), 4.63-4.45 (m, 2H), 4.33-4.08 (m, 2H), 3.86-3.78 (m, 4H), 3.76-3.70 (m, 4H), 2.97-2.80 (m, 5H), 2.78-2.68 (m, 2H), 2.62-2.54 (m, 3H), 2.55-2.53 (m, 1H), 2.15-2.02 (m, 3H), 1.98-1.84 (m, 2H), 1.82-1.63 (m, 5H)

Example 150: 4-[6-(4-benzyl-4-hydroxy-1-piperidyl)-3-pyridyl]-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazine-3-carbonitrile (Compound 117)

Compound 117 was Prepared Following the Synthesis of Compound 116

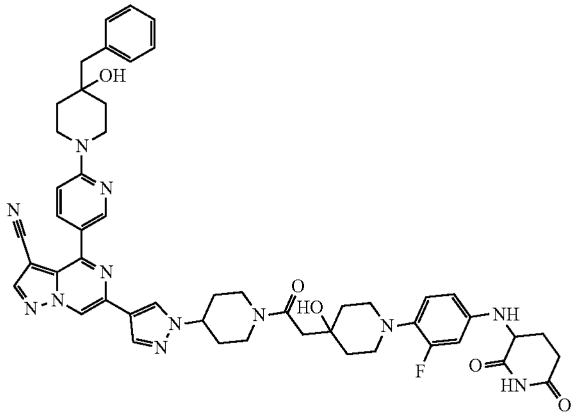 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC(O)(Cc5ccccc5)CC4)nc3)c12]

LCMS ($ES^+$): m/z 921.3 $[M+H]^+$

1H NMR (400 MHz, DMSO-$d_6$) δ=10.77 (br s, 1H), 9.27 (s, 1H), 8.81 (s, 1H), 8.65 (d, J=2.5 Hz, 1H), 8.49 (s, 1H), 8.45-8.40 (m, 1H), 8.17 (s, 1H), 8.03 (dd, J=2.5, 8.9 Hz, 1H), 7.34-7.13 (m, 6H), 6.98 (d, J=9.0 Hz, 1H), 6.85 (t, J=9.3 Hz, 1H), 6.49 (dd, J=2.4, 14.9 Hz, 1H), 6.41 (dd, J=2.3, 8.8 Hz, 1H), 5.77 (d, J=7.6 Hz, 1H), 4.90 (s, 1H), 4.63-4.44 (m, 3H), 4.30-4.10 (m, 4H), 3.24-3.16 (m, 1H), 2.96-2.81 (m, 5H), 2.78-2.66 (m, 4H), 2.62-2.56 (m, 1H), 2.61-2.53 (m, 2H), 2.17-2.03 (m, 3H), 2.01-1.91 (m, 1H), 1.86-1.62 (m, 6H), 1.57-1.42 (m, 4H).

Example 151: Synthesis of 1-(5-(3-cyano-6-(1-(1-((1-(4-((2,6-dioxopiperidin-3-yl)amino)-2-fluorophenyl)-4-hydroxypiperidin-4-yl)methyl)piperidin-4-yl)-1H-pyrazol-4-yl)pyrazolo[1,5-a]pyrazin-4-yl)pyridin-2-yl)-4-ethyl-N-isopropylpiperidine-4-carboxamide (Compound 118)

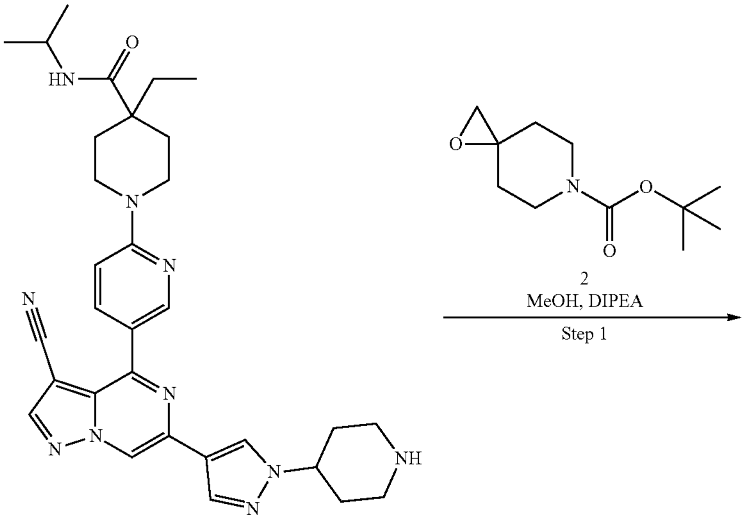

1

-continued
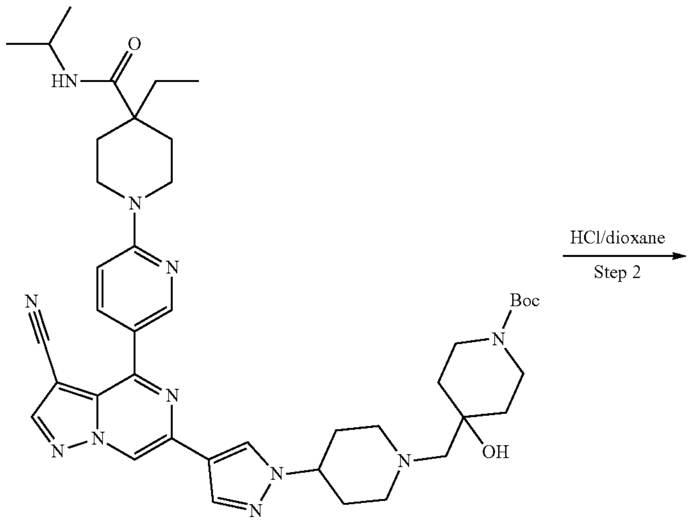
3
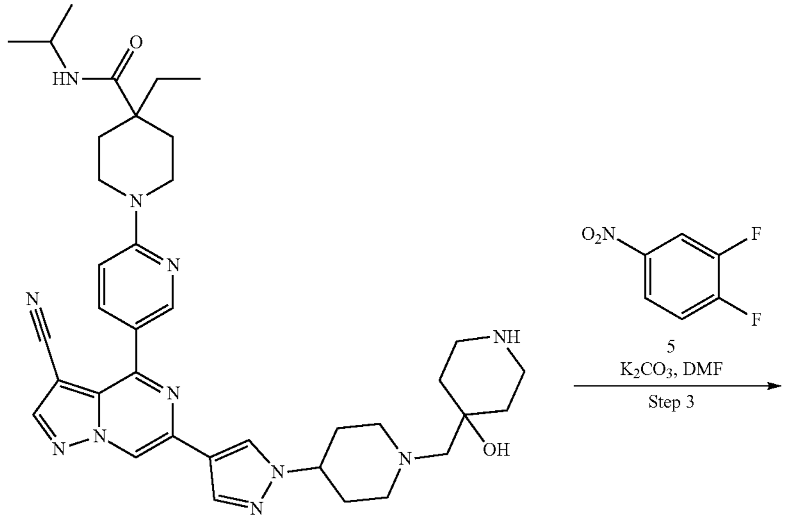
4
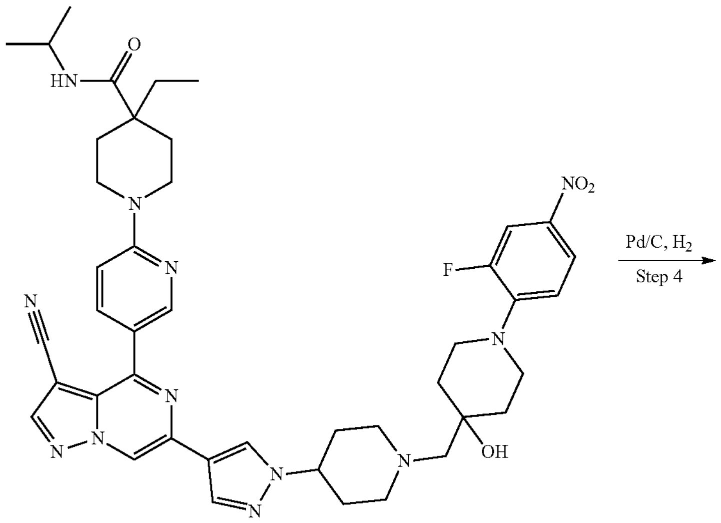
6

-continued

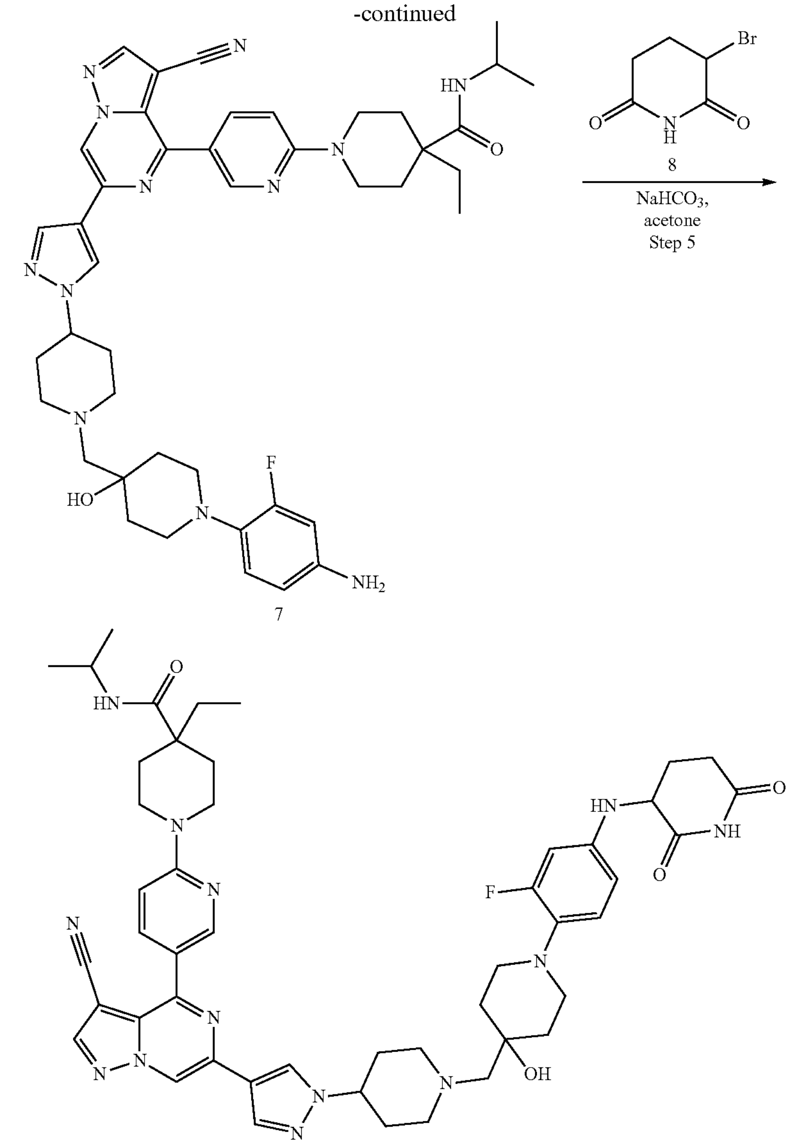

7

Compound 118

Step 1: To a solution of 1-[5-[3-cyano-6-[1-(4-piperidyl) pyrazol-4-yl]pyrazolo[1,5-a]pyrazin-4-yl]-2-pyridyl]-4-ethyl-N-isopropyl-piperidine-4-carboxamide (1, 300 mg, 497.38 μmol, HCl salt) and tert-butyl 1-oxa-6-azaspiro[2.5] octane-6-carboxylate (2, 137.90 mg, 646.60 μmol) in Methanol (3 mL) was added DIPEA (321.42 mg, 2.49 mmol, 433.17 μL). After addition, the solution was stirred at 90° C. for 12 hr. The reaction solution was poured into water (10 mL) to give a suspension. The suspension was filtered, and the filter cake was washed with water (3 mL) and concentrated in vacuum to afford tert-butyl 4-[[4-[4-[3-cyano-4-[6-[4-ethyl-4-(isopropylcarbamoyl)-1-piperidyl]-3-pyridyl] pyrazolo[1,5-a]pyrazin-6-yl]pyrazol-1-yl]-1-piperidyl] methyl]-4-hydroxy-piperidine-1-carboxylate (3, 370 mg, 441.17 μmol, 89% yield) as yellow solid. LCMS ($ES^+$): m/z 780.5 $[M+H]^+$.

Step 2: A solution of tert-butyl 4-[[4-[4-[3-cyano-4-[6-[4-ethyl-4-(isopropylcarbamoyl)-1-piperidyl]-3-pyridyl]pyrazolo[1,5-a]pyrazin-6-yl]pyrazol-1-yl]-1-piperidyl]methyl]-4-hydroxy-piperidine-1-carboxylate (3, 500 mg, 641.05 μmol) in HCl/dioxane (4 M, 5.00 mL) was stirred at 30° C. for 30 min. The reaction solution was concentrated in vacuum to afford 1-[5-[3-cyano-6-[1-[1-[(4-hydroxy-4-piperidyl)methyl]-4-piperidyl]pyrazol-4-yl]pyrazolo[1,5-a] pyrazin-4-yl]-2-pyridyl]-4-ethyl-N-isopropyl-piperidine-4-carboxamide (4, 460 mg, 608.74 μmol, 95% yield, HCl salt) as yellow solid. $^1H$ NMR (400 MHz, DMSO-$d_6$) δ=10.35-10.13 (m, 1H), 9.54-9.40 (m, 1H), 9.25-9.06 (m, 2H), 8.87 (s, 1H), 8.53 (d, J=2.0 Hz, 1H), 8.44 (s, 1H), 8.27 (dd, J=2.0, 9.6 Hz, 1H), 8.25-8.21 (m, 1H), 7.54 (d, J=8.0 Hz, 1H), 7.42 (br d, J=8.8 Hz, 1H), 3.84 (br s, 1H), 3.64-3.58 (m, 1H), 3.52-3.44 (m, 1H), 3.34-3.22 (m, 5H), 3.20-3.02 (m, 6H), 2.30 (br s, 1H), 2.26 (br d, J=13.2 Hz, 2H), 2.06-1.95 (m, 2H), 1.93-1.83 (m, 2H), 1.53 (q, J=7.2 Hz, 2H), 1.49-1.40 (m, 2H), 1.31 (d, J=6.4 Hz, 4H), 1.28 (d, J=6.4 Hz, 4H), 1.10 (d, J=6.4 Hz, 6H), 0.76 (t, J=7.2 Hz, 3H)

Step 3: To a solution of 1-[5-[3-cyano-6-[1-[1-[(4-hydroxy-4-piperidyl)methyl]-4-piperidyl]pyrazol-4-yl]pyrazolo[1,5-a]pyrazin-4-yl]-2-pyridyl]-4-ethyl-N-isopropyl-piperidine-4-carboxamide (4, 460 mg, 642.17 μmol, HCl salt)

and 1,2-difluoro-4-nitrobenzene (5, 153.25 mg, 963.26 μmol, 106.42 μL) in DMF (4 mL) was added $K_2CO_3$ (266.26 mg, 1.93 mmol, 116.27 μL). After addition, the solution was stirred at 110° C. for 4 hr. The reaction solution was poured into water (15 mL) to give a suspension. Then the suspension was filtered, the filter cake was washed with water (5 mL) and concentrated in vacuum. 1-(5-(3-cyano-6-(1-(1-((1-(2-fluoro-4-nitrophenyl)-4-hydroxypiperidin-4-yl)methyl)piperidin-4-yl)-1H-pyrazol-4-yl)pyrazolo[1,5-a]pyrazin-4-yl)pyridin-2-yl)-4-ethyl-N-isopropylpiperidine-4-carboxamide (6, 260 mg, 285.74 μmol, 45% yield) was obtained as yellow solid. LCMS ($ES^+$): m/z 819.4 $[M+H]^+$ Step 4: To a solution of 1-(5-(3-cyano-6-(1-(1-((1-(2-fluoro-4-nitrophenyl)-4-hydroxypiperidin-4-yl)methyl)piperidin-4-yl)-1H-pyrazol-4-yl)pyrazolo[1,5-a]pyrazin-4-yl)pyridin-2-yl)-4-ethyl-N-isopropylpiperidine-4-carboxamide (6, 200 mg, 244.22 μmol) in Methanol (2 mL) was added 10 wt. % Pd/C (33.33 mg, 2.74 mmol) under N2 atmosphere. The suspension was degassed and purged with $H_2$ three times. The mixture was stirred under $H_2$ (15 Psi) at 30 for 12 h. The reaction solution was filtered; the filtrate was concentrated in vacuum. 1-(5-(6-(1-(1-((1-(4-amino-2-fluorophenyl)-4-hydroxypiperidin-4-yl)methyl)piperidin-4-yl)-1H-pyrazol-4-yl)-3-cyanopyrazolo[1,5-a]pyrazin-4-yl)pyridin-2-yl)-4-ethyl-N-isopropylpiperidine-4-carboxamide (7, 180 mg, 205.33 μmol, 84% yield) was obtained as white solid.

Step 5: To a solution of 1-(5-(6-(1-(1-((1-(4-amino-2-fluorophenyl)-4-hydroxypiperidin-4-yl)methyl)piperidin-4-yl)-1H-pyrazol-4-yl)-3-cyanopyrazolo[1,5-a]pyrazin-4-yl)pyridin-2-yl)-4-ethyl-N-isopropylpiperidine-4-carboxamide (7, 58 mg, 73.51 μmol), 3-bromopiperidine-2,6-dione (8, 16.94 mg, 88.22 μmol) and TBAI (5.43 mg, 14.70 μmol) in acetone (0.1 mL) was added $NaHCO_3$ (12.35 mg, 147.03 μmol, 5.72 μL). After addition, the solution was stirred at 90° C. for 12 hr. The reaction solution was acidified with FA to pH=7 and concentrated in vacuum. The residue was purified by Prep-HPLC (Phenomenex luna C18 150*25 mm*10 um, water (0.225% FA)-ACN, 11%-41%, 25 ml/min, 10 min). 1-(5-(3-cyano-6-(1-(1-((1-(4-((2,6-dioxopiperidin-3-yl)amino)-2-fluorophenyl)-4-hydroxypiperidin-4-yl)methyl)piperidin-4-yl)-1H-pyrazol-4-yl)pyrazolo[1,5-a]pyrazin-4-yl)pyridin-2-yl)-4-ethyl-N-isopropylpiperidine-4-carboxamide (Compound 118, 12.85 mg, 13.57 μmol, 18% yield, formic acid salt) was obtained as yellow solid LCMS ($ES^+$): m/z 900.7 $[M+H]^+$ $^1H$ NMR (400 MHz, DMSO-$d_6$) δ=10.78 (s, 1H), 9.27 (s, 1H), 8.82 (s, 1H), 8.68 (d, J=2.4 Hz, 1H), 8.50 (s, 1H), 8.23 (s, 1H), 8.15 (s, 1H), 8.06 (dd, J=2.4, 8.8 Hz, 1H), 7.41 (d, J=8.0 Hz, 1H), 7.00 (d, J=9.2 Hz, 1H), 6.91-6.82 (m, 1H), 6.51 (dd, J=2.4, 15.2 Hz, 1H), 6.45-6.38 (m, 1H), 5.77 (d, J=7.6 Hz, 1H), 4.28-3.97 (m, 6H), 3.16-3.04 (m, 5H), 2.96-2.81 (m, 5H), 2.79-2.65 (m, 2H), 2.38-2.32 (m, 4H), 2.22-2.13 (m, 3H), 2.13-1.96 (m, 6H), 1.93-1.78 (m, 2H), 1.78-1.68 (m, 2H), 1.61-1.45 (m, 5H), 1.42-1.22 (m, 4H), 1.09 (d, J=6.4 Hz, 6H), 0.75 (t, J=7.2 Hz, 3H)

Example 152: Synthesis of 1-(5-(3-cyano-6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)pyrazolo[1,5-a]pyrazin-4-yl)-3-fluoropyridin-2-yl)-4-ethyl-N-isopropylpiperidine-4-carboxamide (Compound 119)

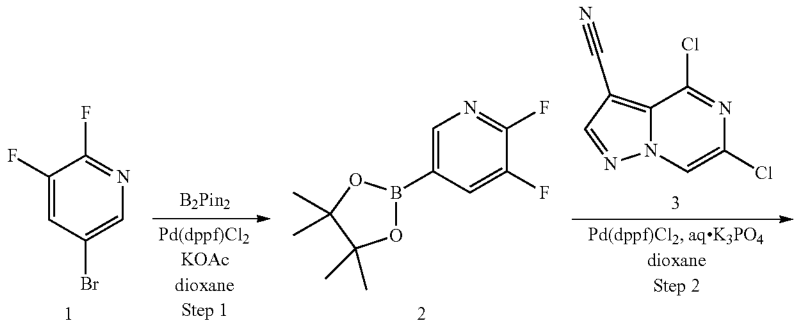

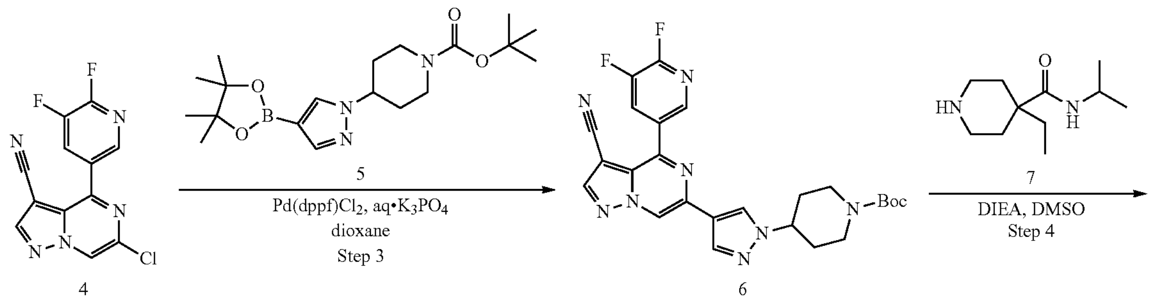

-continued
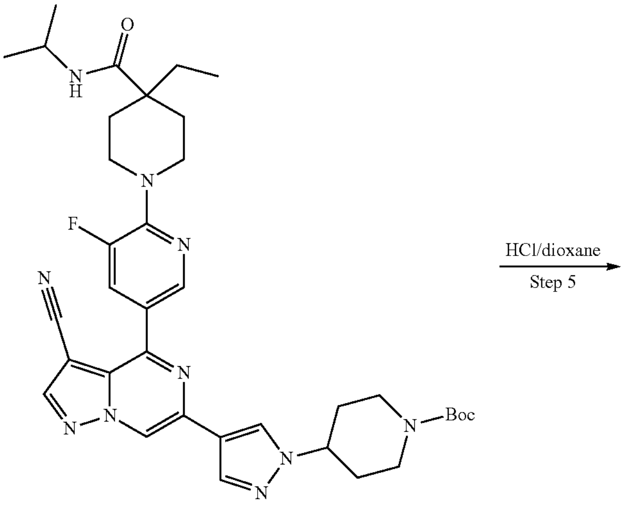
8
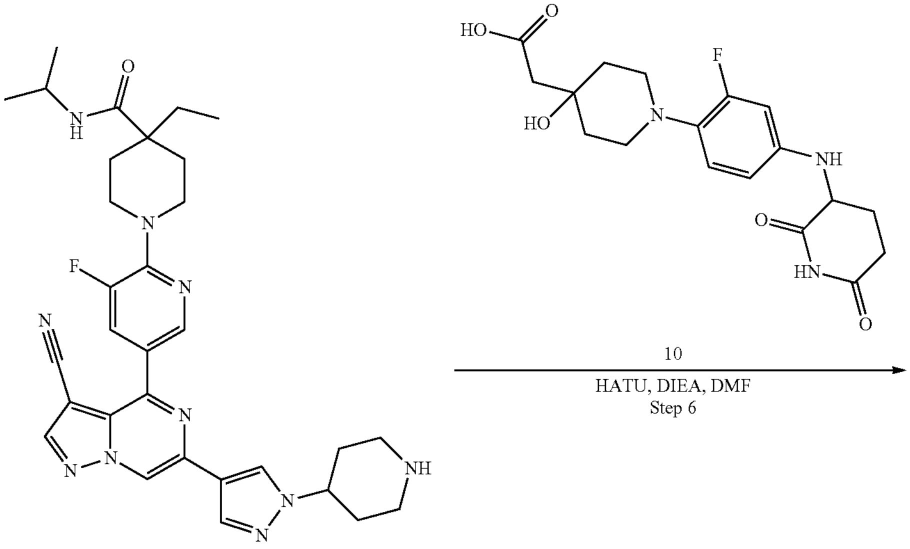
9
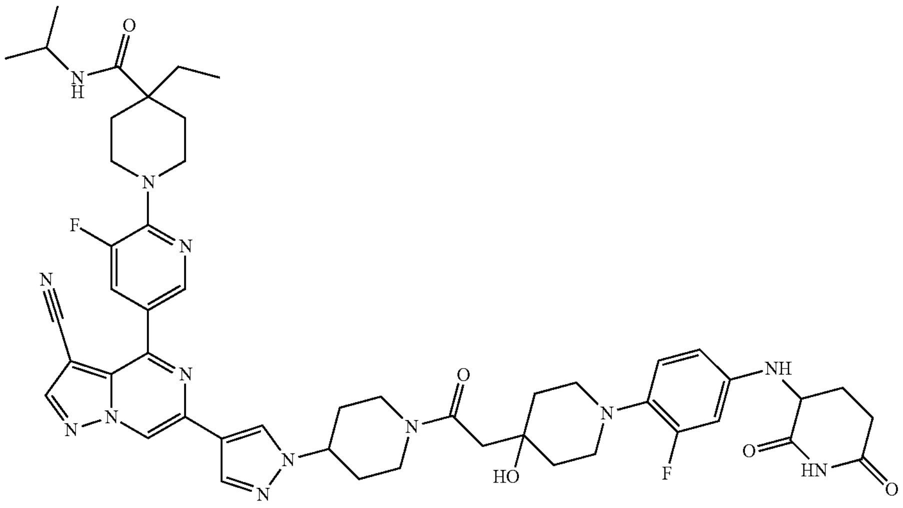
Compound 119

Step 1: To a solution of 5-bromo-2,3-difluoropyridine (1, 1 g, 5.16 mmol), $B_2Pin_2$ (2.62 g, 10.31 mmol) and KOAc (1.01 g, 10.31 mmol, 644.52 μL) in dioxane (20 mL) was added Pd(dppf)$Cl_2$—$CH_2Cl_2$ (210.50 mg, 257.76 μmol) at $N_2$ atmosphere. After addition, the solution was stirred at 90° C. for 12 h. The reaction mixture was concentrated under reduced pressure to remove dioxane. The residue was diluted with water (60 ml) and extracted with EA (60 ml×3). The combined organic layers were washed with brine (180 ml×2), dried over $Na_2SO_4$, filtered and concentrated under reduced pressure. The residue was purified by flash silica gel chromatography (12 g Silica Flash Column, Eluent of 0~15% EA/PE 20 mL/min) to afford 2,3-difluoro-5-(4,4,5,5-tetramethyl-1,3,2-dioxaborolan-2-yl)pyridine (2, 1.06 g, 4.20 mmol, 82% yield) as white solid. LCMS ($ES^+$): m/z 242.1 $[M+H]^+$ Step 2: To a solution of 2,3-difluoro-5-(4,4,5,5-tetramethyl-1,3,2-dioxaborolan-2-yl)pyridine (2, 1 g, 4.15 mmol), 4,6-dichloropyrazolo[1,5-a]pyrazine-3-carbonitrile (3, 883.76 mg, 4.15 mmol) and $K_3PO_4$ (2 M, 6.22 mL) in dioxane (20 mL) was added Pd(dppf)$Cl_2$—$CH_2Cl_2$ (169.40 mg, 207.43 μmol) at $N_2$ atmosphere. After addition, the solution was stirred at 70° C. for 12h. The reaction solution was poured into water (70 mL) to give a suspension. Then the suspension was filtered, the filter cake was washed with water (20 mL) and concentrated in vacuum to afford 6-chloro-4-(5,6-difluoropyridin-3-yl)pyrazolo[1,5-a]pyrazine-3-carbonitrile (4, 1.23 g, 4.22 mmol, 101% yield) as black solid Step 3: To a solution of 6-chloro-4-(5,6-difluoropyridin-3-yl)pyrazolo[1,5-a]pyrazine-3-carbonitrile (4, 600 mg, 2.06 mmol), tert-butyl 4-(4-(4,4,5,5-tetramethyl-1,3,2-dioxaborolan-2-yl)-1H-pyrazol-1-yl)piperidine-1-carboxylate (5, 853.81 mg, 2.26 mmol) and $K_3PO_4$ (2 M, 2.06 mL) in dioxane (8 mL) was added Pd(dppf)$Cl_2$—$CH_2Cl_2$ (84.00 mg, 102.87 μmol) at $N_2$ atmosphere. After addition, the solution was stirred at 70° C. for 12h. The reaction solution was poured into water (30 mL). The aqueous phase was extracted with EA (100 mL*3), the combined organic was washed with brine (200 mL*2), dried over $Na_2SO_4$ and concentrated in vacuum. The residue was purified by flash silica gel chromatography (12 g Silica Flash Column, Eluent of 0~50% EA/PE 20 mL/min) to afford tert-butyl 4-(4-(3-cyano-4-(5,6-difluoropyridin-3-yl)pyrazolo[1,5-a]pyrazin-6-yl)-1H-pyrazol-1-yl)piperidine-1-carboxylate (6, 720 mg, 1.41 mmol, 69% yield) as white solid. LCMS ($ES^+$): m/z 451.1 $[M+H-56]^+$ The Procedures for Steps 4-6 are Similar to Those of Steps 1-3 in Compound 89

1-(5-(3-cyano-6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)pyrazolo[1,5-a]pyrazin-4-yl)-3-fluoropyridin-2-yl)-4-ethyl-N-isopropylpiperidine-4-carboxamide. (Compound 119)

LCMS ($ES^+$): m/z 946.6 $[M+H]^+$ $^1$H NMR (400 MHz, DMSO-$d_6$) δ=10.80 (s, 1H), 9.37 (s, 1H), 8.86 (s, 1H), 8.59-8.47 (m, 2H), 8.20 (s, 1H), 8.14 (s, 1H), 8.01 (dd, J=2.0, 14.4 Hz, 1H), 7.40 (d, J=7.8 Hz, 1H), 7.13-6.70 (m, 1H), 6.65-6.31 (m, 2H), 4.65-4.45 (m, 2H), 4.37-4.09 (m, 2H), 4.07-3.91 (m, 3H), 3.29-3.20 (m, 3H), 3.14 (br t, J=11.6 Hz, 2H), 3.03-2.66 (m, 5H), 2.64-2.56 (m, 2H), 2.20 (m, 2H), 2.16-2.05 (m, 3H), 2.01-1.65 (m, 7H), 1.56-1.39 (m, 4H), 1.10 (d, J=6.4 Hz, 6H), 0.75 (t, J=7.6 Hz, 3H)

Example 153: 1-[5-[6-[1-[1-[2-[1-[2-chloro-4-[(2,6-dioxo-3-piperidyl)amino]phenyl]-4-hydroxy-4-piperidyl]acetyl]-4-piperidyl]pyrazol-4-yl]-3-cyano-pyrazolo[1,5-a]pyrazin-4-yl]-3-fluoro-2-pyridyl]-4-ethyl-N-isopropyl-piperidine-4-carboxamide (Compound 120)

Compound 120 was Prepared Following the Synthesis of Compound 119

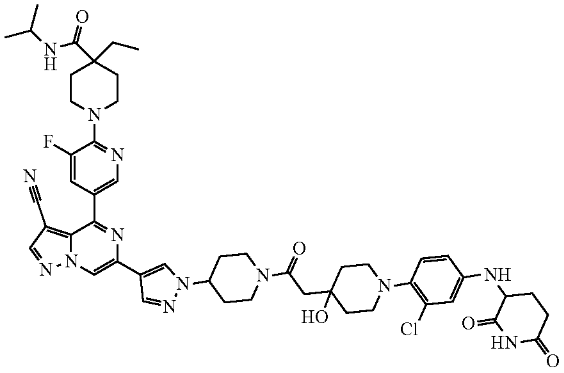 [SMILES: CCC1(C(=O)NC(C)C)CCN(c2ncc(-c3nc(-c4cnn(C5CCN(C(=O)CC6(O)CCN(c7ccc(NC8CCC(=O)NC8=O)cc7Cl)CC6)CC5)c4)cn4ncc(C#N)c34)cc2F)CC1]

LCMS ($ES^+$): m/z 962.5 $[M+H]^+$ $^1$H NMR (400 MHz, DMSO-$d_6$) δ=10.78 (s, 1H), 9.36 (s, 1H), 8.85 (s, 1H), 8.54 (d, J=9.2 Hz, 2H), 8.21 (br s, 1H), 8.20 (s, 1H), 8.01 (dd, J=2.0, 14.4 Hz, 1H), 7.40 (d, J=7.6 Hz, 1H), 6.98 (d, J=8.8 Hz, 1H), 6.75 (d, J=2.4 Hz, 1H), 6.60 (dd, J=2.4, 8.8 Hz, 1H), 5.84 (d, J=7.6 Hz, 1H), 4.93 (s, 1H), 4.65-4.47 (m, 2H), 4.34-4.24 (m, 1H), 4.19 (br d, J=12.4 Hz, 1H), 4.07-3.95 (m, 3H), 3.28-3.20 (m, 2H), 3.14 (m, 2H), 2.96-2.86 (m, 2H), 2.86-2.66 (m, 4H), 2.59 (s, 2H), 2.20 (m, 2H), 2.15-2.03 (m, 3H), 2.02-1.90 (m, 1H), 1.89-1.64 (m, 6H), 1.56-1.39 (m, 4H), 1.09 (d, J=6.4 Hz, 6H), 0.75 (t, J=7.2 Hz, 3H)

1-(4-(3-Cyano-6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)pyrazolo[1,5-a]pyrazin-4-yl)phenyl)-4-ethyl-N-isopropylpiperidine-4-carboxamide (Compound 121)
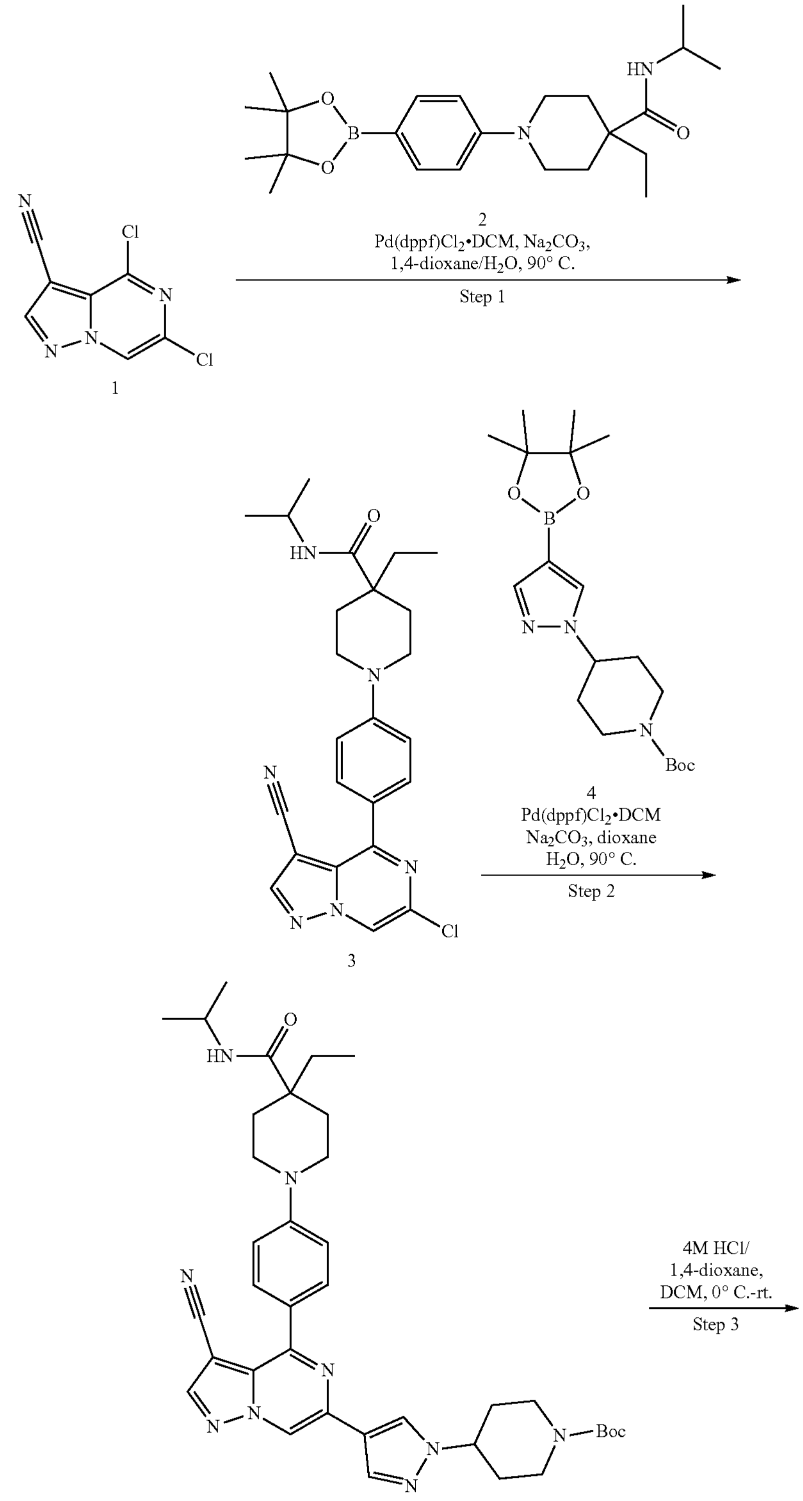
5

-continued

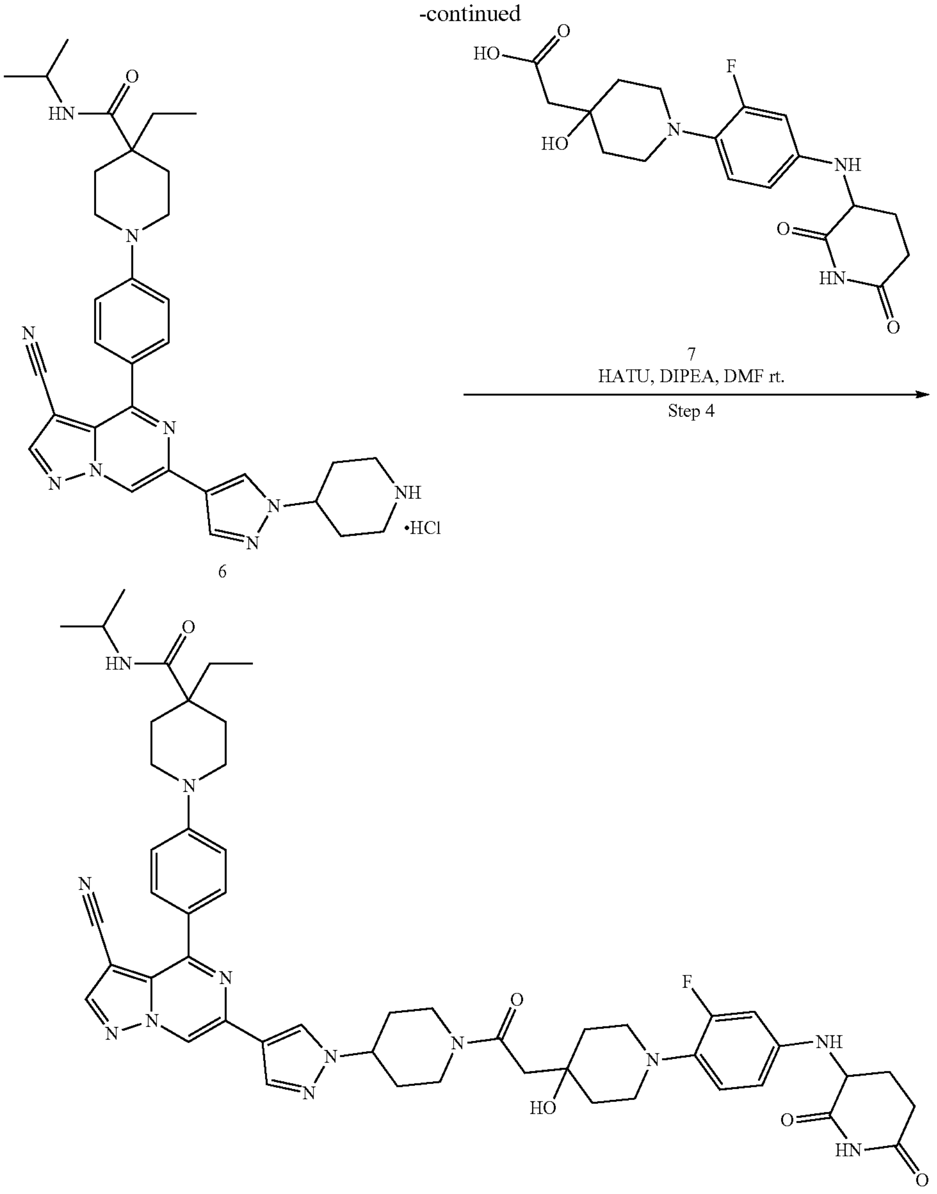

6

7

Compound 121

Step 1: Into a 50 mL sealed-tube containing a well stirred solution of 4-ethyl-N-isopropyl-1-[4-(4,4,5,5-tetramethyl-1,3,2-dioxaborolan-2-yl)phenyl]piperidine-4-carboxamide (2, 0.51 g, 1.27 mmol) and 4,6-dichloropyrazolo[1,5-a]pyrazine-3-carbonitrile (1, 271.36 mg, 1.27 mmol) in 1,4-dioxane (5 mL) and water (1 mL) was added Sodium bicarbonate (428.05 mg, 5.10 mmol) and the resulting mixture was degassed by bubbling nitrogen gas for 10 minutes. Subsequently, Pd(dppf)$Cl_2$ DCM (51.99 mg, 0.063 mmol) was added and the mixture was stirred heated at 100° C. under closed condition. The reaction was monitored by LCMS and found complete after 2 h. The reaction mixture was filtered through a pad of Celite and the Celite bed was washed with EtOAc (10 mL). The filtrate was concentrated under reduced pressure to get a crude mass. The crude was purified by silica-gel (230-400 mesh, 50 g) column with 30-100% EtOAc/pet ether while the desired product was eluting at 40-50% of the mobile phase to afford 1-[4-(6-chloro-3-cyano-pyrazolo[1,5-a]pyrazin-4-yl)phenyl]-4-ethyl-N-isopropyl-piperidine-4-carboxamide (3, 70 mg, 0.149 mmol, 12% yield) as a yellow liquid. LCMS ($ES^+$): m/z 451.2 $[M+H]^+$.

Step 2: Into a 25 mL sealed tube containing a well-stirred solution of 1-[4-(6-chloro-3-cyano-pyrazolo[1,5-a]pyrazin-4-yl)phenyl]-4-ethyl-N-isopropyl-piperidine-4-carboxamide (3, 110 mg, 0.243 mmol) and tert-butyl 4-[4-(4,4,5,5-tetramethyl-1,3,2-dioxaborolan-2-yl)pyrazol-1-yl] piperidine-1-carboxylate (4, 119.64 mg, 0.317 mmol) in 1,4-dioxane (2 mL) and water (0.5 mL) was added sodium carbonate (77.56 mg, 0.731 mmol) and the resulting mixture was degassed by bubbling nitrogen gas for 10 minutes. Subsequently, Pd(dppf)$Cl_2$ DCM (19.92 mg, 0.024 mmol) was added and the mixture was stirred at 90° C. under closed condition. The reaction was monitored by UPLC and found complete after 6 h. The reaction mixture was diluted with EtOAc (5 mL), filtered through a pad of Celite bed and Celite bed was washed with EtOAc (5 mL). The filtrate was concentrated under reduced pressure to get a crude mass. The crude was purified by flash silica-gel column (230-400 mesh) with 0-100% EtOAc/pet ether while the desired product was eluting at 70-80% of the mobile phase to afford tert-butyl 4-[4-[3-cyano-4-[4-[4-ethyl-4-(isopropylcarbamoyl)-1-piperidyl]phenyl]pyrazolo[1,5-a]pyrazin-6-yl]pyrazol-1-yl]piperidine-1-carboxylate (5, 70 mg, 0.059 mmol, 25% yield) as a yellow solid. LCMS (ES$^+$): m/z 666.2 $[M+H]^+$.

Step 3: Into a 50 mL single-necked round-bottomed flask containing a well-stirred solution of tert-butyl 4-[4-[3-cyano-4-[4-[4-ethyl-4-(isopropylcarbamoyl)-1-piperidyl]phenyl]pyrazolo[1,5-a]pyrazin-6-yl]pyrazol-1-yl]piperidine-1-carboxylate (5, 70 mg, 0.105 mmol) in anhydrous DCM (3 mL) was added 4N HCl in 1,4-dioxane (1 mL, 0.105 mmol) dropwise at ambient temperature under nitrogen atmosphere. The resulting mixture was stirred at ambient temperature. The reaction was monitored by UPLC and found complete after 2 h. Excess solvent was removed under reduced pressure to afford a crude mass. The crude mass was triturated with MTBE (50 mL) and solid thus crashed out was filtered to afford 1-[4-[3-cyano-6-[1-(4-piperidyl)pyrazol-4-yl]pyrazolo[1,5-a]pyrazin-4-yl]phenyl]-4-ethyl-N-isopropyl-piperidine-4-carboxamide hydrochloride (6, 65 mg, 0.093 mmol, 89% yield) as a yellow solid. LCMS (ES$^+$): m/z 566.2 $[M+H]^+$.

Step 4: Into a 50 mL single-necked round-bottomed flask containing a well-stirred solution of 1-[4-[3-cyano-6-[1-(4-piperidyl)pyrazol-4-yl]pyrazolo[1,5-a]pyrazin-4-yl]phenyl]-4-ethyl-N-isopropyl-piperidine-4-carboxamide hydrochloride (6, 65 mg, 0.107 mmol) and 2-[1-[4-[(2,6-dioxo-3-piperidyl)amino]-2-fluoro-phenyl]-4-hydroxy-4-piperidyl]acetic acid hydrochloride (7, 58.35 mg, 0.140 mmol) in anhydrous DMF (2 mL) were added DIPEA (41.85 mg, 0.323 mmol, 0.056.41 mL) and HATU (61.56 mg, 0.161 mmol) at ambient temperature under nitrogen atmosphere. The resulting mixture was stirred at ambient temperature. The reaction was monitored by LCMS and found complete after 2 h. The reaction mixture was cooled to ambient temperature and slowly added to ice-cold $H_2O$ (20 mL) and solid thus obtained was filtered. The crude solid was purified by reverse phase column chromatography [Mobile Phase A: 0.1% ammonium acetate in water; Mobile phase B: Acetonitrile] to yield 1-(4-(3-cyano-6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)pyrazolo[1,5-a]pyrazin-4-yl)phenyl)-4-ethyl-N-isopropylpiperidine-4-carboxamide (Compound 121, 12 mg, 0.012 mmol, 12% yield) as a yellow solid. $^1$H NMR (400 MHz, DMSO-$d_6$). δ 10.79 (s, 1H), 9.27 (s, 1H), 8.82 (s, 1H), 8.48 (s, 1H), 8.17 (s, 1H), 7.79 (d, J=8.4 Hz, 2H), 7.40 (d, J=8 Hz, 1H), 7.09 (d, J=8.8 Hz, 2H), 6.86 (t, J=9.2 Hz, 1H), 6.50 (d, J=15.2 Hz, 1H), 6.42 (d, J=8.4 Hz, 1H), 5.79 (d, J=7.6 Hz, 1H), 4.91 (s, 1H), 4.56 (m, 2H), 4.26 (m, 2H), 4.00 (m, 1H), 3.67 (m, 2H), 3.25 (m, 2H), 2.97-2.87 (m, 6H), 2.55 (s, 2H), 2.21-2.18 (m, 3H), 2.10-2.08 (m, 5H), 1.75 (m, 6H), 1.45 (m, 4H), 1.08 (d, J=6.8 Hz, 6H) and 0.76 (t, J=7.20 Hz, 3H). LCMS (ES$^+$): m/z 927.4 $[M+H]^+$.

1-(5-(3-cyano-6-(1-((1r, 4r)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-isopropylpiperidine-4-carboxamide (Compound 122)

1-(5-(3-cyano-6-(1-((1S,4r)-4-(4-(4-(((S)-2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-isopropylpiperidine-4-carboxamide (Compound 123)

1-(5-(3-cyano-6-(1-((1R,4r)-4-(4-(4-(((R)-2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-isopropylpiperidine-4-carboxamide (Compound 124)

(Configurations are arbitrarily assigned)

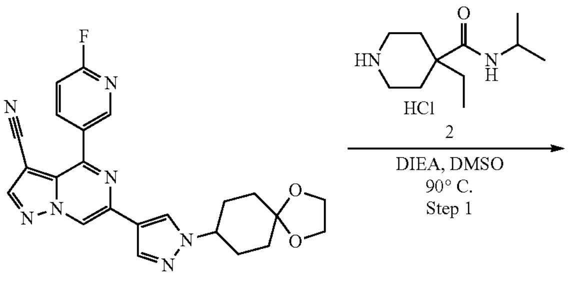

1

2

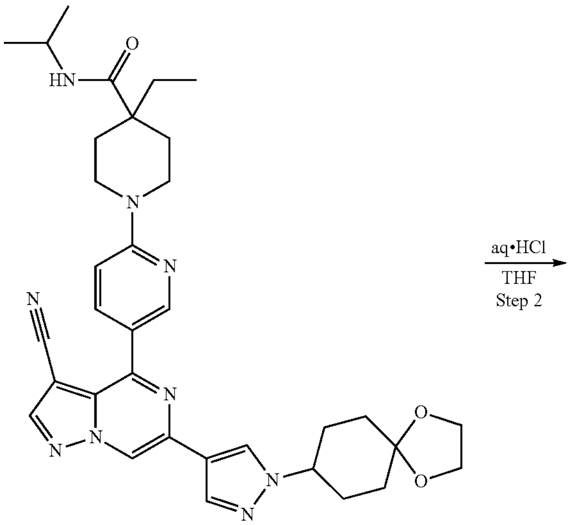

3

-continued
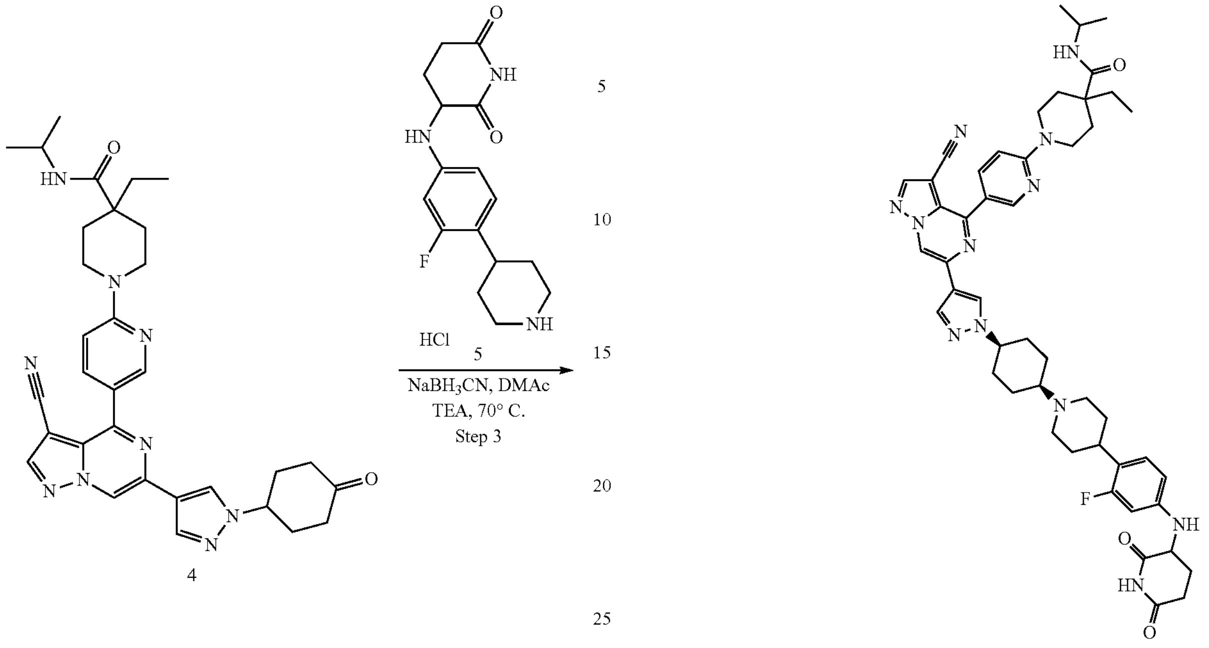
4
6
-continued
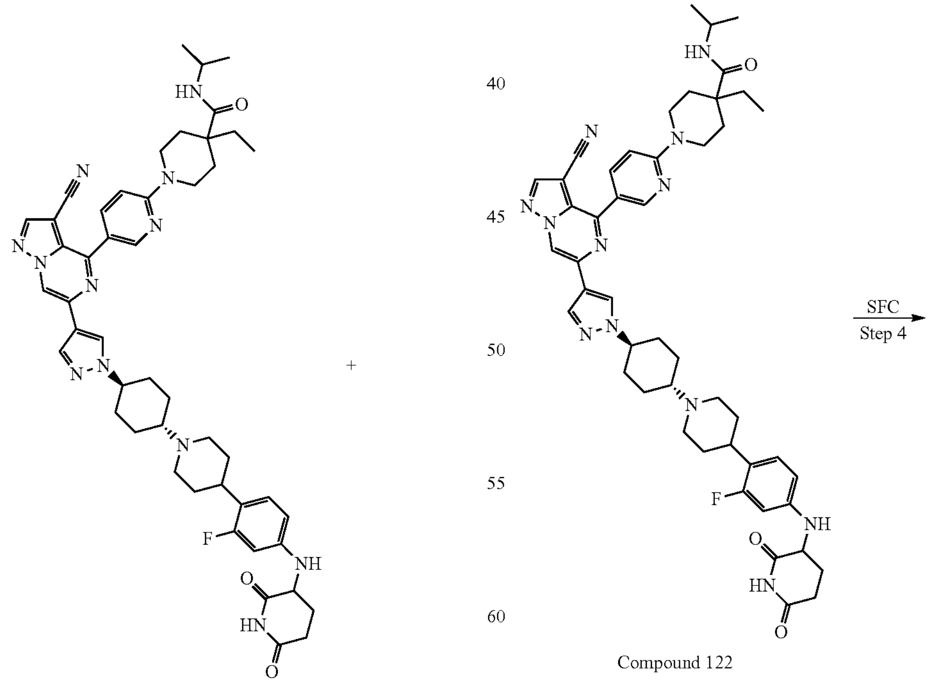
Compound 122
Compound 122

-continued

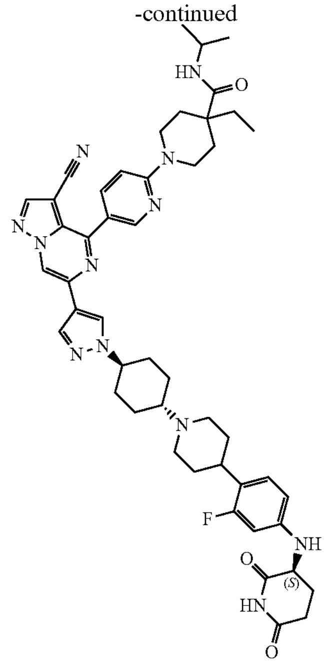

Compound 123

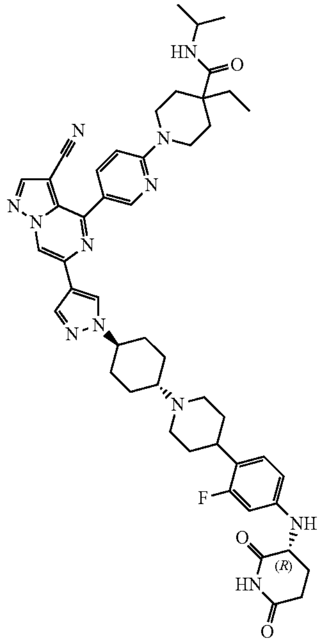

Compound 124

Step 1: To a solution of 4-ethyl-N-isopropyl-piperidine-4-carboxamide (2, 505.95 mg, 2.16 mmol, HCl salt) and 6-(1-(1,4-dioxaspiro[4.5]decan-8-yl)-1H-pyrazol-4-yl)-4-(6-fluoropyridin-3-yl)pyrazolo[1,5-a]pyrazine-3-carbonitrile (1, 800 mg, 1.80 mmol) in DMSO (5 mL) was added DIPEA (1.16 g, 8.98 mmol, 1.56 mL). After addition, the solution was stirred at 90° C. for 12 hr. The reaction solution was poured into water (20 mL) to give a suspension. Then the suspension was filtered, the filter cake was washed with water (10 mL) and concentrated in vacuum to afford 1-(5-(6-(1-(1,4-dioxaspiro[4.5]decan-8-yl)-1H-pyrazol-4-yl)-3-cyanopyrazolo[1,5-a]pyrazin-4-yl)pyridin-2-yl)-4-ethyl-N-isopropylpiperidine-4-carboxamide (3, 1.02 g, 1.64 mmol, 91% yield) as yellow solid. LCMS ($ES^+$): m/z 624.2 $[M+H]^+$ Step 2: To a solution of 1-(5-(6-(1-(1,4-dioxaspiro[4.5]decan-8-yl)-1H-pyrazol-4-yl)-3-cyanopyrazolo[1,5-a]pyrazin-4-yl)pyridin-2-yl)-4-ethyl-N-isopropylpiperidine-4-carboxamide (3, 1 g, 1.57 mmol) in THF (5 mL) was added aq. HCl (4 M, 5.00 mL). After addition, the solution was stirred at 20° C. for 12 hr. The reaction solution was poured into sat. $NaHCO_3$ (40 mL) to give a suspension. Then the suspension was filtered, the filter cake was washed with water (10 ml) and concentrated in vacuum to afford 1-(5-(3-cyano-6-(1-(4-oxocyclohexyl)-1H-pyrazol-4-yl)pyrazolo[1,5-a]pyrazin-4-yl)pyridin-2-yl)-4-ethyl-N-isopropylpiperidine-4-carboxamide HCl salt (4, 900 mg, 1.52 mmol, 97% yield) as yellow solid. LCMS ($ES^+$): m/z 580.2 $[M+H]^+$ Step 3: To a solution of 3-((3-fluoro-4-(piperidin-4-yl)phenyl)amino)piperidine-2,6-dione hydrochloride (5, 430.43 mg, 1.26 mmol) and 1-(5-(3-cyano-6-(1-(4-oxocyclohexyl)-1H-pyrazol-4-yl)pyrazolo[1,5-a]pyrazin-4-yl)pyridin-2-yl)-4-ethyl-N-isopropylpiperidine-4-carboxamide (4, 730 mg, 1.26 mmol) in DMAc (10 mL) was added TEA (637.14 mg, 6.30 mmol, 877.60 μL). After addition, the solution was stirred at 20° C. for 12 hr. Then $NaBH_3CN$ (791.36 mg, 12.59 mmol) was added into above solution and stirred at 50° C. for another 2 hr. The reaction solution was poured into water (40 mL) to give a suspension. Then the suspension was filtered, the filter cake was washed with water (10 mL) and concentrated in vacuum. The residue was purified by Prep-TLC (DCM: MeOH=10:1) and Prep-HPLC (Waters Xbridge 150*25 mm*5 um, water (10 mM NH4HCO3)-ACN, 38%-68%, 25 mL/min, 9 min) to afford 1-(5-(3-cyano-6-(1-((1r, 4r)-4-(4-(4-((2,6-dioxopiperidin-3-yl)amino)-2-fluorophenyl) piperidin-1-yl)cyclohexyl)-1H-pyrazol-4-yl)pyrazolo[1,5-a]pyrazin-4-yl)pyridin-2-yl)-4-ethyl-N-isopropylpiperidine-4-carboxamide (Compound 122, Early eluting isomer 1, 132.36 mg, 152.31 μmol, 12% yield) as yellow solid and 1-(5-(3-cyano-6-(1-((1s, 4s)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-isopropylpiperidine-4-carboxamide (6, Late eluting isomer 2, 154.69 mg, 178.00 μmol, 14% yield) as yellow solid.

Compound 122, Early eluting isomer 1: LCMS ($ES^+$): m/z 869.7 $[M+H]^+$ $^1H$ NMR (400 MHz, DMSO-$d_6$) δ=10.80 (s, 1H), 9.27 (s, 1H), 8.82 (s, 1H), 8.67 (d, J=2.4 Hz, 1H), 8.44 (s, 1H), 8.14 (s, 1H), 8.04 (dd, J=2.4, 8.8 Hz, 1H), 7.42 (d, J=8.0 Hz, 1H), 7.06-6.94 (m, 2H), 6.52-6.35 (m, 2H), 6.00 (d, J=7.6 Hz, 1H), 4.37-4.26 (m, 1H), 4.24-4.11 (m, 3H), 4.01 (qd, J=6.8, 13.6 Hz, 1H), 3.11 (br t, J=11.2 Hz, 2H), 2.93 (br d, J=10.0 Hz, 2H), 2.82-2.69 (m, 1H), 2.63-2.54 (m, 2H), 2.46-2.40 (m, 1H), 2.36-2.29 (m, 2H), 2.22-2.04 (m, 5H), 1.98-1.76 (m, 5H), 1.71-1.57 (m, 4H), 1.57-1.43 (m, 4H), 1.40-1.29 (m, 2H), 1.09 (d, J=6.4 Hz, 6H), 0.75 (t, J=7.6 Hz, 3H)

6, Late eluting isomer 2: LCMS ($ES^+$): m/z 869.4 $[M+H]^+$ $^1H$ NMR (400 MHz, DMSO-$d_6$) δ=10.79 (s, 1H), 9.33 (s, 1H), 8.82 (s, 1H), 8.67 (d, J=2.4 Hz, 1H), 8.49 (s, 1H), 8.16 (s, 1H), 8.04 (dd, J=2.4, 8.8 Hz, 1H), 7.41 (d, J=8.0 Hz, 1H), 7.07-6.92 (m, 2H), 6.50-6.36 (m, 2H), 5.99 (d, J=8.0 Hz, 1H), 4.37-4.26 (m, 2H), 4.20-4.11 (m, 2H), 4.06-3.96 (m, 1H), 3.17-3.01 (m, 4H), 2.73 (ddd, J=5.2, 12.0, 17.6 Hz, 1H), 2.58 (br d, J=4.2 Hz, 2H), 2.38-2.28 (m, 3H), 2.17 (br d, J=13.6 Hz, 2H), 2.12-1.98 (m, 3H), 1.92-1.78 (m, 5H), 1.71-1.55 (m, 6H), 1.54-1.46 (m, 2H), 1.40-1.30 (m, 2H), 1.09 (d, J=6.4 Hz, 6H), 0.75 (t, J=7.6 Hz, 3H)

Step 4: 1-(5-(3-cyano-6-(1-((1r, 4r)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-isopropylpiperidine-4-carboxamide (Compound 122, Early eluting isomer 1, 210 mg) was purified by Prep-SFC (DAICEL CHIRALPAK AD (250 mm*30 mm, 10 um, 0.1% NH3H2O IPA, 70%, 4.6, 130) to afford 1-(5-(3-cyano-6-(1-((1S,4r)-4-(4-(4-(((S)-2,6-dioxopiperidin-3-yl)amino)-2-fluorophenyl) piperidin-1-yl) cyclohexyl)-1H-pyrazol-4-yl)pyrazolo[1,5-a]pyrazin-4-yl) pyridin-2-yl)-4-ethyl-N-isopropylpiperidine-4-carboxamide formic acid salt (Compound 123, Early eluting isomer 1-1, 56.93 mg, 59.84 μmol, 24.76% yield) as yellow solid and 1-(5-(3-cyano-6-(1-((1R,4r)-4-(4-(4-(((R)-2,6-dioxopiperidin-3-yl)amino)-2-fluorophenyl)piperidin-1-yl) cyclohexyl)-1H-pyrazol-4-yl)pyrazolo[1,5-a]pyrazin-4-yl)pyridin-2-yl)-4-ethyl-N-isopropylpiperidine-4-carboxamide formic acid salt (Compound 124, Late eluting isomer 1-2, 65.23 mg, 70.22 μmol, 29% yield) as yellow solid.

Compound 123, Early Eluting Isomer 1-1:

LCMS ($ES^+$): m/z 869.6 $[M+H]^+$ $^1$H NMR (400 MHz, DMSO-$d_6$) δ=10.80 (s, 1H), 9.27 (s, 1H), 8.82 (s, 1H), 8.67 (d, J=2.4 Hz, 1H), 8.44 (s, 1H), 8.21 (s, 1H), 8.14 (s, 1H), 8.04 (dd, J=2.4, 8.8 Hz, 1H), 7.42 (br d, J=8.0 Hz, 1H), 7.07-6.91 (m, 2H), 6.54-6.37 (m, 2H), 6.01 (br d, J=7.6 Hz, 1H), 4.35-4.27 (m, 1H), 4.24-4.11 (m, 3H), 4.07-3.96 (m, 1H), 3.15-3.06 (m, 2H), 3.03-2.93 (m, 2H), 2.80-2.64 (m, 1H), 2.61-2.54 (m, 2H), 2.47-2.44 (m, 1H), 2.39 (br t, J=10.0 Hz, 3H), 2.20-2.06 (m, 5H), 1.98-1.90 (m, 2H), 1.90-1.78 (m, 3H), 1.73-1.60 (m, 4H), 1.57-1.45 (m, 4H), 1.40-1.30 (m, 2H), 1.09 (d, J=6.4 Hz, 6H), 0.75 (br t, J=7.2 Hz, 3H)

Compound 124, Late Eluting Isomer 1-2:

LCMS ($ES^+$): m/z 863.2 $[M+H]^+$ $^1$H NMR (400 MHz, DMSO-$d_6$) δ=10.80 (s, 1H), 9.27 (s, 1H), 8.82 (s, 1H), 8.67 (d, J=2.4 Hz, 1H), 8.44 (s, 1H), 8.21 (s, 1H), 8.14 (s, 1H), 8.04 (dd, J=2.4, 8.8 Hz, 1H), 7.42 (br d, J=8.0 Hz, 1H), 7.04-6.95 (m, 2H), 6.50-6.39 (m, 2H), 6.01 (br d, J=7.6 Hz, 1H), 4.35-4.27 (m, 1H), 4.24-4.11 (m, 3H), 4.01 (qd, J=6.8, 14.0 Hz, 1H), 3.11 (br t, J=11.2 Hz, 2H), 2.98 (br d, J=10.0 Hz, 2H), 2.80 (s, 1H), 2.60-2.54 (m, 2H), 2.47-2.44 (m, 1H), 2.39 (br t, J=9.6 Hz, 3H), 2.19-2.07 (m, 5H), 1.95 (br d, J=10.0 Hz, 2H), 1.89-1.78 (m, 3H), 1.71-1.61 (m, 4H), 1.56-1.46 (m, 4H), 1.35 (br t, J=10.4 Hz, 2H), 1.09 (d, J=6.4 Hz, 6H), 0.75 (br t, J=7.2 Hz, 3H)

Example 154: Synthesis of N-(1-(5-(3-Cyano-6-(1-((1s, 4s)-4-(4-(3-(2,4-dioxotetrahydropyrimidin-1(2H)-yl)-7-fluoro-1-methyl-1H-indazol-6-yl)piperazin-1-yl)cyclohexyl)-1H-pyrazol-4-yl)pyrazolo[1,5-a]pyrazin-4-yl)pyridin-2-yl)-4-ethylpiperidin-4-yl) isobutyramide (Compound 125)

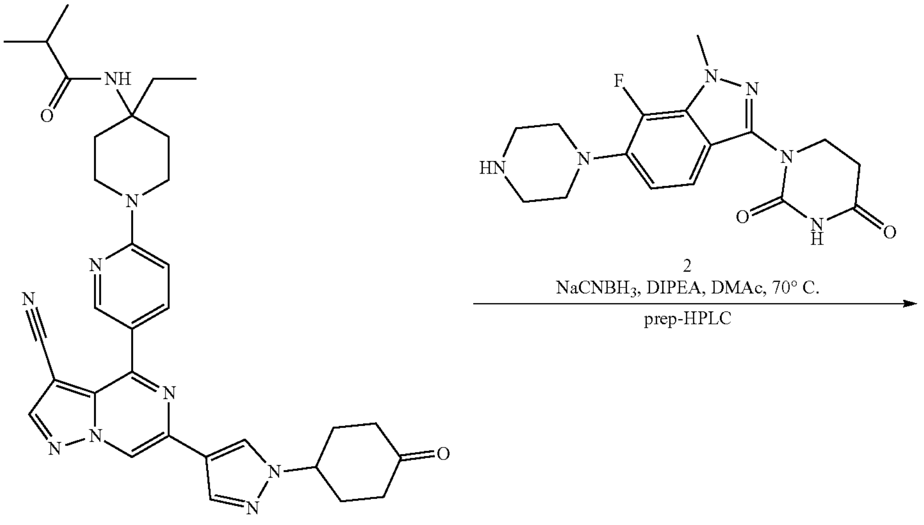

1

2

-continued

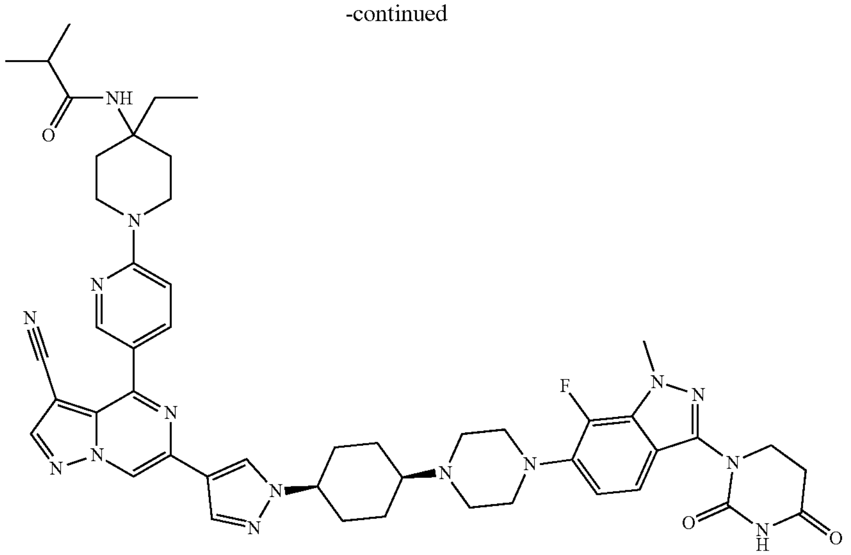

Compound 125

Into a 10 mL sealed tube containing a well-stirred solution of N-(1-(5-(3-cyano-6-(1-(4-oxocyclohexyl)-1H-pyrazol-4-yl)pyrazolo[1,5-a]pyrazin-4-yl)pyridin-2-yl)-4-ethylpiperidin-4-yl)isobutyramide (1, 100 mg, 0.172 mmol) and 1-(7-fluoro-1-methyl-6-(piperazin-1-yl)-1H-indazol-3-yl) dihydropyrimidine-2,4(1H,3H)-dione hydrochloride (2, 119 mg, 0.31 mmol) in anhydrous DMAc (2 mL) were added DIPEA (111 mg, 0.862 mmol, 0.15 mL) and Sodium cyanoborohydride (54 mg, 0.861 mmol) at ambient temperature under nitrogen atmosphere. The reaction mixture was stirred at 70° C. After completion of the reaction as indicated by UPLC (16 h later), the resulting reaction mixture was diluted with ice-cold water (10 mL) and the solid precipitated out was filtered and dried to afford a crude solid. The crude was purified by flash silica-gel (230-400 mesh) column with 5-7% MeOH/DCM to afford 140 mg of desired diastereomers. This diastereomeric mixture compound was purified by reverse phase prep-HPLC [Column: XBRIDGE OBD C18 (19×150 mm; 5 micron) column with Mobile phase: A: 0.1% $NH_4HCO_3$ in MQ-water; B: Acetonitrile and Flow rate: 15 mL/minutes to get N-(1-(5-(3-cyano-6-(1-((1s, 4s)-4-(4-(3-(2,4-dioxotetrahydropyrimidin-1(2H)-yl)-7-fluoro-1-methyl-1H-indazol-6-yl)piperazin-1-yl)cyclohexyl)-1H-pyrazol-4-yl)pyrazolo[1,5-a]pyrazin-4-yl)pyridin-2-yl)-4-ethylpiperidin-4-yl)isobutyramide (Compound 125, Early eluting isomer, 5 mg, 0.005 mmol) as a yellow solid. Yield-3.1%. $^1$H NMR (400 MHz, DMSO-$d_6$). δ 10.57 (s, 1H), 9.28 (s, 1H), 8.83 (s, 1H), 8.69 (d, J=2.4 Hz, 1H), 8.46 (s, 1H), 8.16 (s, 1H), 8.06 (dd, J=8.8, 2.4 Hz, 1H), 7.36 (d, J=8.8 Hz, 1H), 7.24 (s, 1H), 7.03 (d, J=8.8 Hz, 1H), 6.95 (t, J=7.2 Hz, 1H), 4.18-4.32 (m, 3H), 4.07 (s, 3H), 3.91 (t, J=6.8 Hz, 2H), 3.19-3.13 (m, 7H), 2.78-2.65 (m, 7H), 2.32-2.23 (m, 2H), 2.21-2.12 (m, 2H), 2.06-1.98 (m, 2H), 1.93-1.80 (m, 2H), 1.75-1.68 (m, 2H), 1.60-1.48 (m, 2H), 1.46-1.35 (m, 2H), 1.02 (d, J=6.8 Hz, 6H) and 0.77 (t, J=7.2 Hz, 3H). LCMS (ES$^+$): m/z 910.4 [M+H]+

1-(5-(3-cyano-6-(1-((1r, 4r)-4-(4-(4-((2,6-dioxopiperidin-3-yl)amino)phenyl)piperidin-1-yl)cyclohexyl)-1H-pyrazol-4-yl)pyrazolo[1,5-a]pyrazin-4-yl) pyridin-2-yl)-N-cyclobutyl-4-ethylpiperidine-4-carboxamide (Compound 126)

1-(5-(3-cyano-6-(1-((1S,4r)-4-(4-(4-(((S)-2,6-dioxopiperidin-3-yl)amino)phenyl)piperidin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 127)

1-(5-(3-cyano-6-(1-((1R,4r)-4-(4-(4-(((R)-2,6-dioxopiperidin-3-yl)amino)phenyl)piperidin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 128)

(Configurations are arbitrarily assigned)

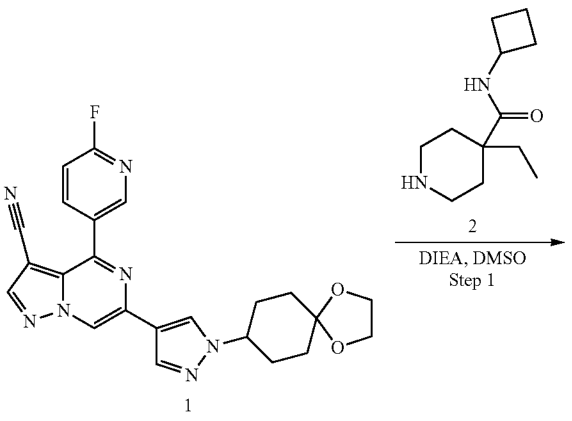

-continued
-continued
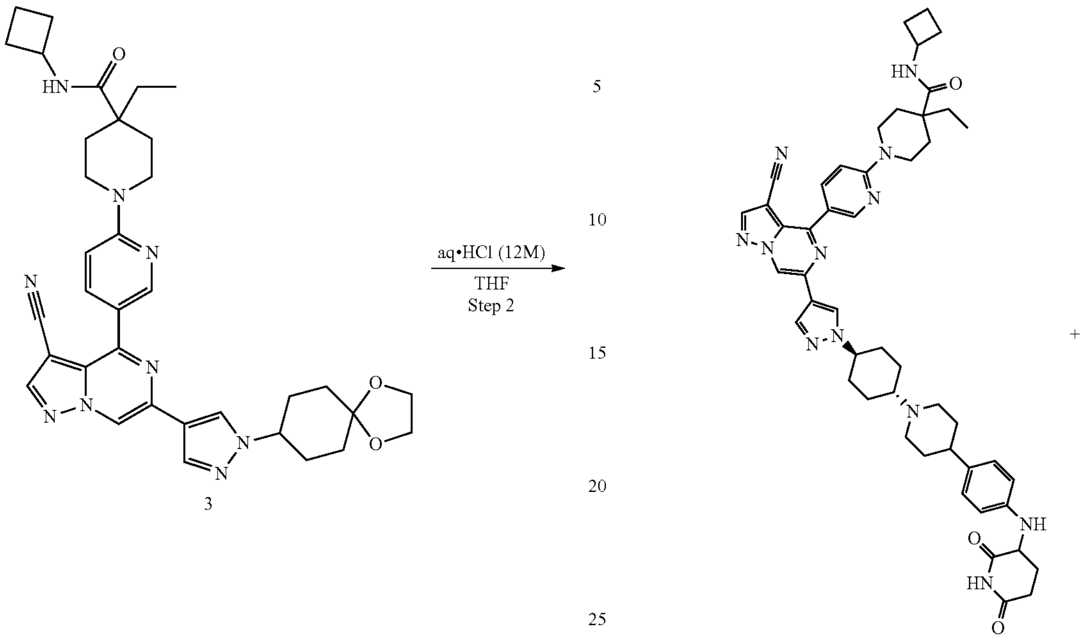
3
Compound 126
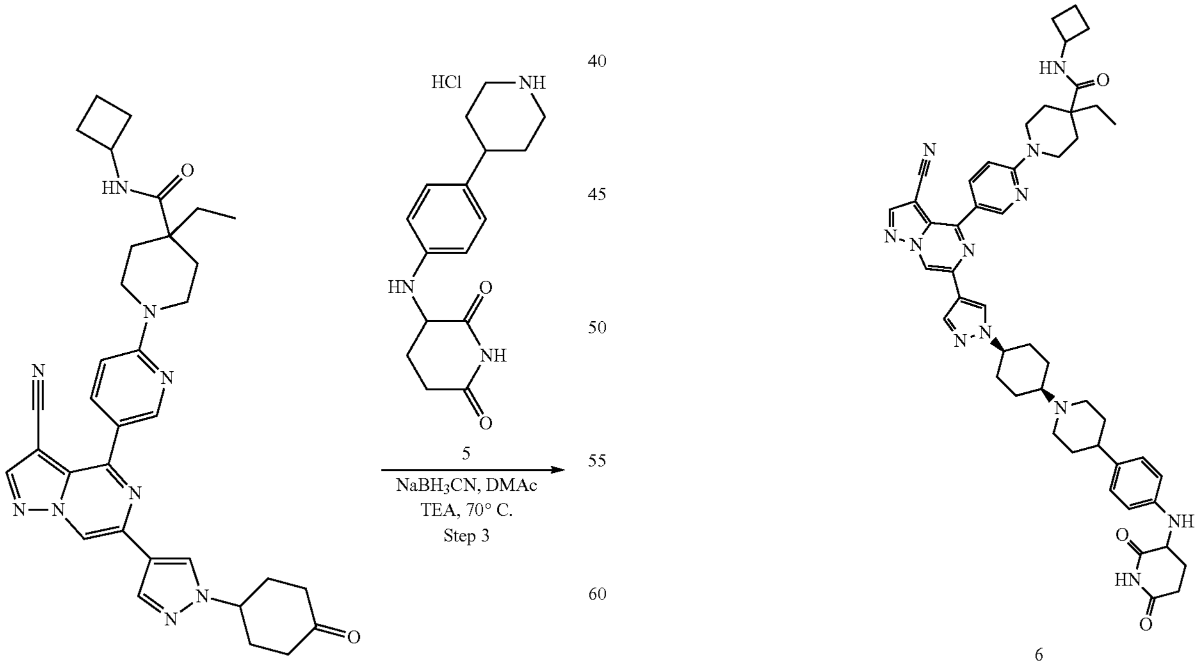
5
4
6

-continued

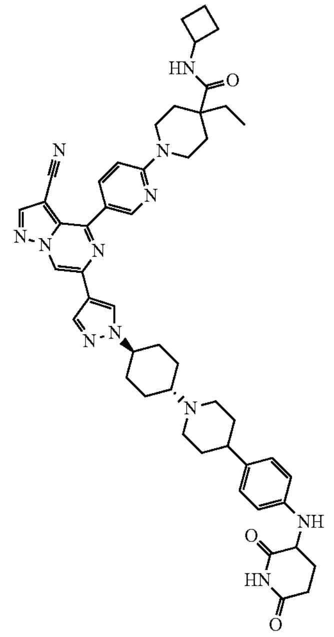

Compound 126

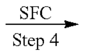

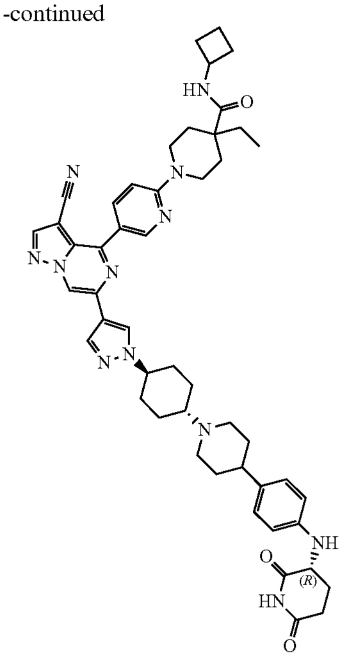

Compound 128

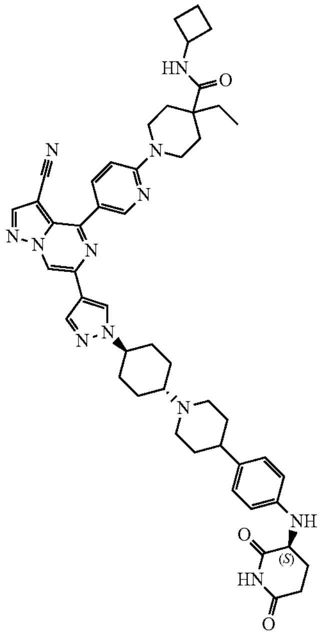

Compound 127

+

Step 1: To a solution of N-cyclobutyl-4-ethyl-piperidine-4-carboxamide (2, 531.84 mg, 2.16 mmol, HCl salt) and 6-(1-(1,4-dioxaspiro[4.5]decan-8-yl)-1H-pyrazol-4-yl)-4-(6-fluoropyridin-3-yl)pyrazolo[1,5-a]pyrazine-3-carbonitrile (1, 800 mg, 1.80 mmol) in DMSO (5 mL) was added DIPEA (1.16 g, 8.98 mmol, 1.56 mL). After addition, the solution was stirred at 90° C. for 12 hr. The reaction solution was poured into water (20 mL) to give a suspension. Then the suspension was filtered, the filter cake was washed with water (10 mL) and concentrated in vacuum to afford 1-[5-[3-cyano-6-[1-(1,4-dioxaspiro[4.5]decan-8-yl)pyrazol-4-yl]pyrazolo[1,5-a]pyrazin-4-yl]-2-pyridyl]-N-cyclobutyl-4-ethyl-piperidine-4-carboxamide (3, 1.04 g, 1.64 mmol, 91% yield) was obtained as yellow solid. LCMS ($ES^+$): m/z 636.2 $[M+H]^+$ Step 2: To a solution of 1-[5-[3-cyano-6-[1-(1,4-dioxaspiro[4.5]decan-8-yl)pyrazol-4-yl]pyrazolo[1,5-a]pyrazin-4-yl]-2-pyridyl]-N-cyclobutyl-4-ethyl-piperidine-4-carboxamide (3, 1 g, 1.57 mmol) in THF (5 mL) was added HCl (4 M, 5.00 mL). After addition, the solution was stirred at 20° C. for 12 hr. The reaction solution was poured into sat. $NaHCO_3$ (40 mL) to give a suspension. Then the suspension was filtered, the filter cake was washed with water (10 ml) and concentrated in vacuum to afford 1-[5-[3-cyano-6-[1-(4-oxocyclohexyl)pyrazol-4-yl]pyrazolo[1,5-a]pyrazin-4-yl]-2-pyridyl]-N-cyclobutyl-4-ethyl-piperidine-4-carboxamide (4, 900 mg, 1.52 mmol, 97% yield) as yellow solid. LCMS ($ES^+$): m/z 592.2 $[M+H]^+$ Step 3: To a solution of 3-[4-(4-piperidyl)anilino]piperidine-2,6-dione (5, 437.81 mg, 1.35 mmol, HCl salt) and 1-[5-[3-cyano-6-[1-(4-oxocyclohexyl)pyrazol-4-yl]pyrazolo[1,5-a]pyrazin-4-yl]-2-pyridyl]-N-cyclobutyl-4-ethyl-piperidine-4-carboxamide (4, 800 mg, 1.35 mmol) in DMAc (10 mL) was added TEA (410.43 mg, 4.06 mmol, 565.34 μL). After addition, the solution was stirred at 20° C. for 12 hr. Then sodium cyanoborohydride (849.64 mg, 13.52 mmol) was added into above solution and stirred at 50° C. for another 2 hr. The reaction solution was poured into water (40 mL) to give a suspension. Then the suspension was filtered, the filter cake was washed with water (10 mL) and concentrated in vacuum. The residue was purified by Prep-TLC (DCM: MeOH=10:1) and Prep-HPLC (Waters Xbridge 150*25 mm*5 um, water (10 mM $NH_4HCO_3$)-ACN, 38%-68%, 25 mL/min, 9 min) to afford 1-(5-(3-cyano-6-(1-((1r, 4r)-4-(4-(4-((2,6-dioxopiperidin-3-yl)amino)phenyl)piperidin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 126, Early eluting isomer 1, 89.04 mg, 101.74 μmol, 8% yield) as yellow solid and 1-(5-(3-cyano-6-(1-((1s, 4s)-4-(4-(4-((2,6-dioxopiperidin-3-yl)amino)phenyl)piperidin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (6, Late eluting isomer 2, 66.59 mg, 77.16 μmol, 6% yield) as yellow solid.

Compound 126, Early Eluting Isomer 1:

LCMS ($ES^+$): m/z 863.6 $[M+H]^+$

1H NMR (400 MHz, DMSO-$d_6$) δ=10.79 (br s, 1H), 9.26 (s, 1H), 8.82 (s, 1H), 8.67 (d, J=2.4 Hz, 1H), 8.43 (s, 1H), 8.13 (s, 1H), 8.04 (dd, J=2.4, 8.8 Hz, 1H), 7.80 (br d, J=7.2 Hz, 1H), 7.05-6.90 (m, 3H), 6.61 (br d, J=8.8 Hz, 2H), 5.65 (d, J=7.6 Hz, 1H), 4.36-4.22 (m, 2H), 4.22-4.08 (m, 3H), 3.11 (br t, J=11.2 Hz, 2H), 2.91 (br d, J=9.6 Hz, 2H), 2.81-2.69 (m, 1H), 2.63-2.54 (m, 1H), 2.43 (br t, J=11.2 Hz, 1H), 2.36-2.22 (m, 3H), 2.22-2.06 (m, 7H), 2.05-1.95 (m, 2H), 1.94-1.75 (m, 5H), 1.73-1.59 (m, 4H), 1.59-1.42 (m, 6H), 1.41-1.30 (m, 2H), 0.73 (t, J=7.6 Hz, 3H)

6, Late Eluting Isomer 2:

LCMS ($ES^+$): m/z 863.6 $[M+H]^+$

1H NMR (400 MHz, DMSO-$d_6$) δ=10.77 (s, 1H), 9.33 (s, 1H), 8.82 (s, 1H), 8.67 (d, J=2.4 Hz, 1H), 8.50 (s, 1H), 8.16 (s, 1H), 8.04 (dd, J=2.4, 8.8 Hz, 1H), 7.80 (br d, J=7.2 Hz, 1H), 7.05-6.92 (m, 3H), 6.60 (br d, J=8.4 Hz, 2H), 5.64 (d, J=7.2 Hz, 1H), 4.38-4.21 (m, 3H), 4.14 (br d, J=13.2 Hz, 2H), 3.17-3.00 (m, 4H), 2.80-2.69 (m, 1H), 2.62-2.55 (m, 1H), 2.30 (br d, J=4.4 Hz, 4H), 2.22-2.07 (m, 5H), 2.06-1.93 (m, 4H), 1.91-1.78 (m, 5H), 1.68 (br dd, J=10.8, 18.8 Hz, 3H), 1.63-1.55 (m, 4H), 1.55-1.46 (m, 3H), 1.41-1.31 (m, 2H), 0.73 (t, J=7.6 Hz, 3H)

Step 4: 1-(5-(3-cyano-6-(1-((1r, 4r)-4-(4-(4-((2,6-dioxopiperidin-3-yl)amino)phenyl)piperidin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 126, Early eluting isomer 1, 178 mg) was purified by Prep-SFC (DAICEL CHIRALPAK AD (250 mm*30 mm, 10 um, 0.1% NH3H2O IPA, 70%, 4.6, 130) to afford (Compound 127, Early eluting isomer 1-1, 62.89 mg, 68.21 μmol, 33% yield, formic acid salt) d as green solid and (Compound 128, Late eluting isomer 1-2, 59.27 mg, 62.59 μmol, 30% yield, formic acid salt) as green solid.

Note: Sample preparation: Add ACN and CH2CL2 40 ml into sample Instrument: Waters 80Q Mobile Phase: 70% IPA+ACN (0.1% $NH_3H_2O$) in Supercritical CO2 Flow Rate: 80 g/min Cycle Time: 4.6 min, total time: 130 min Single injection volume: 2.0 ml Back Pressure: 100 bar to keep the CO2 in Supercritical flow"

Compound 127, Early eluting isomer 1-1: LCMS ($ES^+$): m/z 863.2 $[M+H]^+$ $^1$H NMR (400 MHz, DMSO-$d_6$) δ=10.92-10.60 (m, 1H), 9.27 (s, 1H), 8.82 (s, 1H), 8.67 (d, J=2.0 Hz, 1H), 8.44 (s, 1H), 8.27 (s, 1H), 8.14 (s, 1H), 8.04 (dd, J=2.4, 9.2 Hz, 1H), 7.80 (br d, J=7.2 Hz, 1H), 6.98 (br dd, J=8.8, 14.0 Hz, 3H), 6.61 (br d, J=8.4 Hz, 2H), 5.65 (br d, J=7.2 Hz, 1H), 4.33-4.23 (m, 2H), 4.21-4.11 (m, 3H), 3.11 (br t, J=11.6 Hz, 2H), 3.00-2.92 (m, 2H), 2.75 (ddd, J=5.6, 12.0, 17.6 Hz, 1H), 2.60 (br d, J=4.4 Hz, 1H), 2.42-2.27 (m, 4H), 2.15 (br d, J=10.4 Hz, 7H), 2.02-1.91 (m, 4H), 1.89-1.78 (m, 3H), 1.71 (br d, J=13.2 Hz, 2H), 1.68-1.57 (m, 4H), 1.56-1.49 (m, 4H), 1.36 (br t, J=10.4 Hz, 2H), 0.73 (br t, J=7.6 Hz, 3H)

Compound 128, Late eluting isomer 1-2: LCMS ($ES^+$): m/z 863.2 $[M+H]^+$ $^1$H NMR (400 MHz, DMSO-$d_6$) δ=10.91-10.63 (m, 1H), 9.27 (s, 1H), 8.82 (s, 1H), 8.67 (d, J=2.0 Hz, 1H), 8.45 (s, 1H), 8.29 (br s, 1H), 8.14 (s, 1H), 8.05 (dd, J=2.0, 9.2 Hz, 1H), 7.80 (br d, J=7.2 Hz, 1H), 7.08-6.85 (m, 3H), 6.61 (br d, J=8.0 Hz, 2H), 5.65 (br d, J=7.6 Hz, 1H), 4.33-4.22 (m, 2H), 4.21-4.09 (m, 3H), 3.11 (br t, J=11.2 Hz, 2H), 2.95 (br d, J=10.4 Hz, 2H), 2.75 (ddd, J=5.6, 12.0, 17.6 Hz, 1H), 2.63-2.55 (m, 1H), 2.39-2.26 (m, 4H), 2.19-2.08 (m, 7H), 2.02-1.91 (m, 4H), 1.89-1.77 (m, 3H), 1.74-1.67 (m, 2H), 1.66-1.59 (m, 2H), 1.59-1.46 (m, 6H), 1.36 (br t, J=11.2 Hz, 2H), 0.74 (t, J=7.2 Hz, 3H)

Example 155: Synthesis of 1-[5-[3-cyano-6-[1-[4-[4-[1-[(3R)-2,6-dioxo-3-piperidyl]indolin-5-yl]-1-piperidyl]cyclohexyl]pyrazol-4-yl]pyrazolo[1,5-a]pyrazin-4-yl]-2-pyridyl]-N-cyclobutyl-4-ethyl-piperidine-4-carboxamide (Compound 129)

(Configurations are arbitrarily assigned)

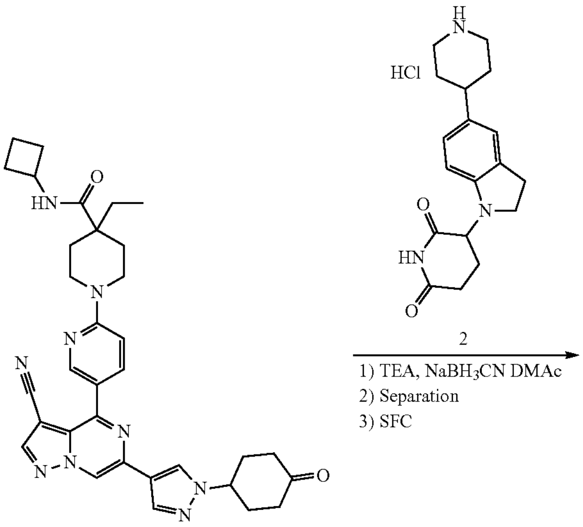

1

2

-continued

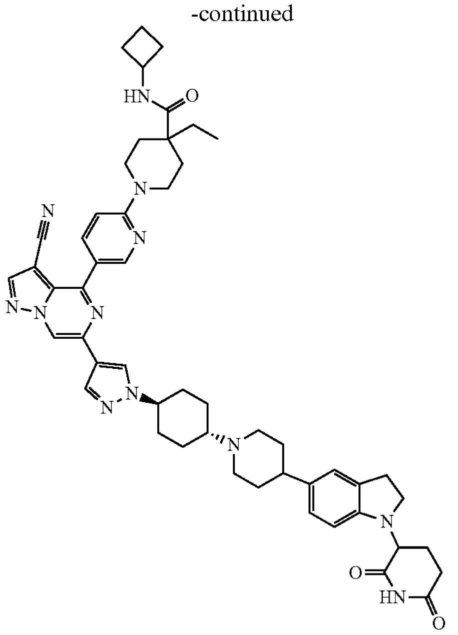

+

3

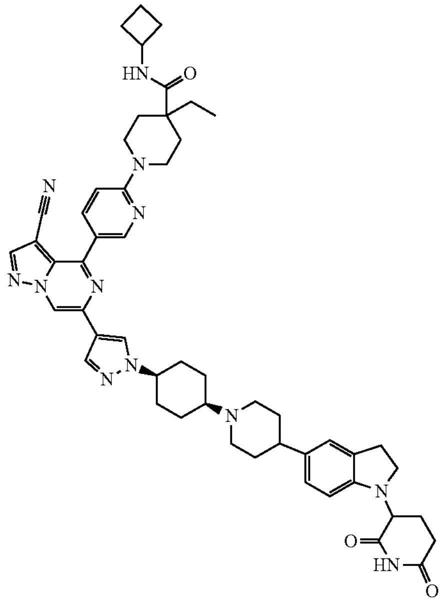

4

To a solution of 3-(5-(piperidin-4-yl) indolin-1-yl)piperidine-2,6-dione (2, 709.52 mg, 2.03 mmol, HCl salt), 1-(5-(3-cyano-6-(1-(4-oxocyclohexyl)-1H-pyrazol-4-yl)pyrazolo[1,5-a]pyrazin-4-yl)pyridin-2-yl)-N-cyclobutyl-4-ethylpiperidine-4-carboxamide (1, 1.2 g, 2.03 mmol) in DMAC (5 mL) was added TEA (1.03 g, 10.14 mmol, 1.41 mL). The mixture was stirred at 25° C. for 4h. Then $NaBH_3CN$ (1.27 g, 20.28 mmol) was added to the mixture. The reaction was stirred at 50° C. for 12h. The reaction mixture was poured into water (20 mL), filtered and filter cake was concentrated under pressure. The residue was purified by prep-NPLC (Column: Welch Ultimate XB-SiOH 250*50*10 um; Condition: Hexane-EtOH; B %: 25-60; Gradient Time (min): 20; 100% B Hold Time (min): 3; Flow Rate (ml/min): 140). The residue was purified by Prep-HPLC (Column: Waters Xbridge C18 150*50 mm*10 um;

Condition: water (10 mM $NH_4HCO_3$)-ACN; B % 45-75; 100% B Hold Time (min): 2; FlowRate (ml/min): 60). 1-[5-[3-cyano-6-[1-[4-[4-[1-(2,6-dioxo-3-piperidyl) indolin-5-yl]-1-piperidyl]cyclohexyl]pyrazol-4-yl]pyrazolo[1,5-a]pyrazin-4-yl]-2-pyridyl]-N-cyclobutyl-4-ethyl-piperidine-4-carboxamide (3, Early eluting isomer 1, 250 mg, 278.37 μmol, 13.73% yield) was obtained as yellow solid. LCMS ($ES^+$): m/z 889.6 $[M+H]^+$. 1-[5-[3-cyano-6-[1-[4-[4-[1-(2,6-dioxo-3-piperidyl) indolin-5-yl]-1-piperidyl]cyclohexyl]pyrazol-4-yl]pyrazolo[1,5-a]pyrazin-4-yl]-2-pyridyl]-N-cyclobutyl-4-ethyl-piperidine-4-carboxamide (4, Late eluting isomer 2, 379.93 mg, 405.95 μmol, 20% yield) was obtained as yellow solid. LCMS ($ES^+$): m/z 889.6 $[M+H]^+$

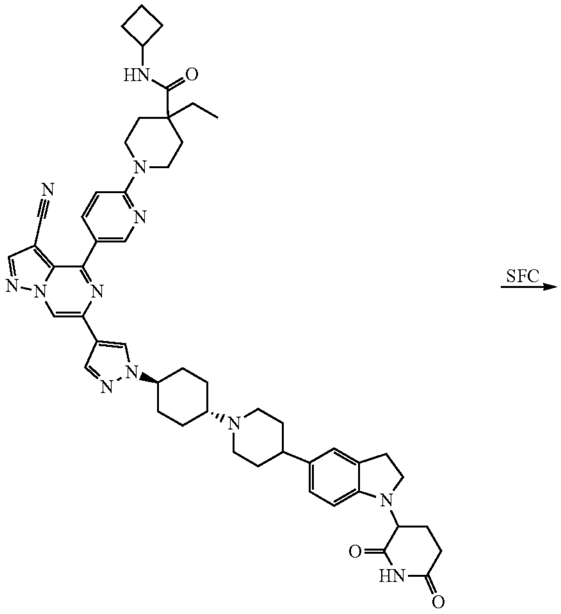

3

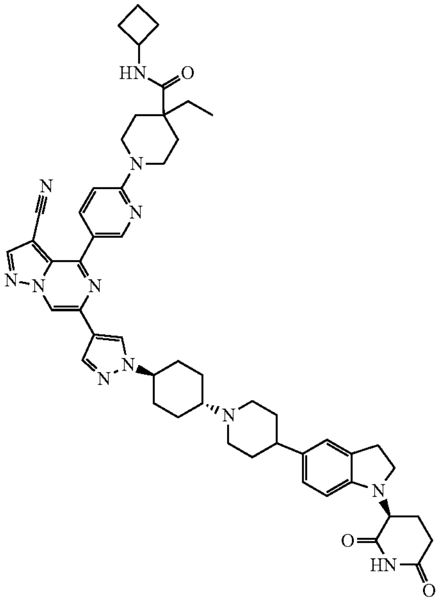

+

5

-continued

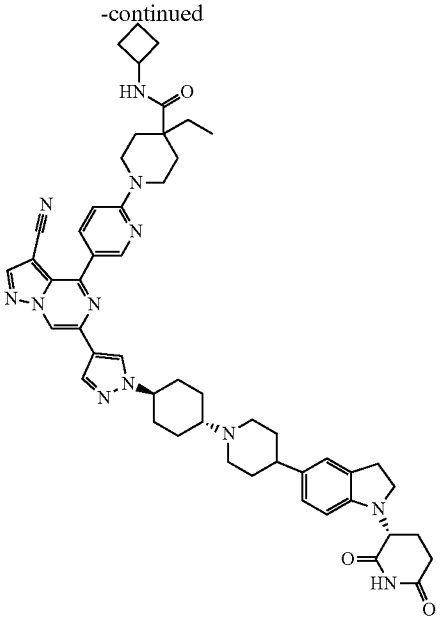

Compound 129

1-[5-[3-cyano-6-[1-[4-[4-[1-(2,6-dioxo-3-piperidyl) indolin-5-yl]-1-piperidyl]cyclohexyl]pyrazol-4-yl]pyrazolo[1,5-a]pyrazin-4-yl]-2-pyridyl]-N-cyclobutyl-4-ethyl-piperidine-4-carboxamide (3, Early eluting isomer 1, 250 mg, 278.37 μmol, 13.73% yield) was separated by SFC[Column: DAICEL CHIRALPAK AS (250 mm*30 mm, 10 um); Condition: 75% IPA+ACN (0.1% $NH_3 \cdot H_2O$) in Supercritical $CO_2$; Flow Rate: 80 mL/min; Cycle Time: 3 min, total time: 60 min; Single injection volume: 2.0 mL; Back Pressure: 100 bar to keep the $CO_2$ in Supercritical flow].

1-[5-[3-cyano-6-[1-[4-[4-[1-[(3S)-2,6-dioxo-3-piperidyl] indolin-5-yl]-1-piperidyl]cyclohexyl]pyrazol-4-yl]pyrazolo [1,5-a]pyrazin-4-yl]-2-pyridyl]-N-cyclobutyl-4-ethyl-piperidine-4-carboxamide (5, Early eluting isomer 1-1, 71.89 mg, 72.26 μmol, 26% yield, formic acid salt) was obtained as yellow solid. LCMS ($ES^+$): m/z 889.5 $[M+H]^+$. $^1H$ NMR (400 MHz, DMSO-$d_6$) δ=10.77 (s, 1H), 9.27 (s, 1H), 8.81 (s, 1H), 8.67 (d, J=2.4 Hz, 1H), 8.44 (s, 1H), 8.22-8.20 (m, 1H), 8.13 (s, 1H), 8.04 (dd, J=2.4, 8.8 Hz, 1H), 7.79 (d, J=7.6 Hz, 1H), 6.99 (d, J=9.2 Hz, 1H), 6.90 (s, 1H), 6.80 (br d, J=8.0 Hz, 1H), 6.39 (d, J=8.4 Hz, 1H), 4.57 (dd, J=4.8, 13.2 Hz, 1H), 4.36-4.24 (m, 1H), 4.23-4.07 (m, 3H), 3.42-3.36 (m, 1H), 3.29-3.22 (m, 2H), 3.15-3.05 (m, 2H), 2.98-2.91 (m, 2H), 2.90-2.72 (m, 2H), 2.61-2.52 (m, 1H), 2.47-2.41 (m, 1H), 2.38-2.27 (m, 3H), 2.21-2.09 (m, 7H), 2.04-1.88 (m, 5H), 1.86-1.76 (m, 2H), 1.75-1.67 (m, 2H), 1.67-1.56 (m, 3H), 1.56-1.44 (m, 5H), 1.41-1.30 (m, 2H), 0.73 (t, J=7.2 Hz, 3H)

1-[5-[3-cyano-6-[1-[4-[4-[1-[(3R)-2,6-dioxo-3-piperidyl] indolin-5-yl]-1-piperidyl]cyclohexyl]pyrazol-4-yl]pyrazolo [1,5-a]pyrazin-4-yl]-2-pyridyl]-N-cyclobutyl-4-ethyl-piperidine-4-carboxamide (Compound 129, Late eluting isomer 1-2, 60.29 mg, 63.18 μmol, 22% yield, formic acid salt) was obtained as green solid. LCMS ($ES^+$): m/z 889.5 $[M+H]^+$. $^1H$ NMR (400 MHz, DMSO-$d_6$) δ=10.77 (s, 1H), 9.27 (s, 1H), 8.82 (s, 1H), 8.67 (d, J=2.4 Hz, 1H), 8.44 (s, 1H), 8.17 (s, 1H), 8.13 (s, 1H), 8.07-8.01 (m, 1H), 7.82-7.74 (m, 1H), 7.04-6.94 (m, 1H), 6.93-6.87 (m, 1H), 6.84-6.77 (m, 1H), 6.44-6.34 (m, 1H), 4.63-4.52 (m, 1H), 4.36-4.24 (m, 1H), 4.23-4.07 (m, 3H), 3.42-3.36 (m, 1H), 3.29-3.21 (m, 2H), 3.16-3.05 (m, 2H), 3.01-2.92 (m, 2H), 2.91-2.72 (m, 2H), 2.62-2.54 (m, 2H), 2.39-2.30 (m, 3H), 2.21-2.09 (m, 7H), 2.05-1.88 (m, 5H), 1.87-1.79 (m, 2H), 1.76-1.69 (m, 2H), 1.67-1.55 (m, 4H), 1.54-1.45 (m, 4H), 1.41-1.30 (m, 2H), 0.73 (t, J=7.2 Hz, 3H)

1-[5-[6-[1-[4-[4-[2-chloro-4-[[(3S)-2,6-dioxo-3-piperidyl]amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (Compound 130)

1-[5-[6-[1-[4-[4-[2-chloro-4-[[(3R)-2,6-dioxo-3-piperidyl]amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (Compound 131)

(Configurations are arbitrarily assigned)

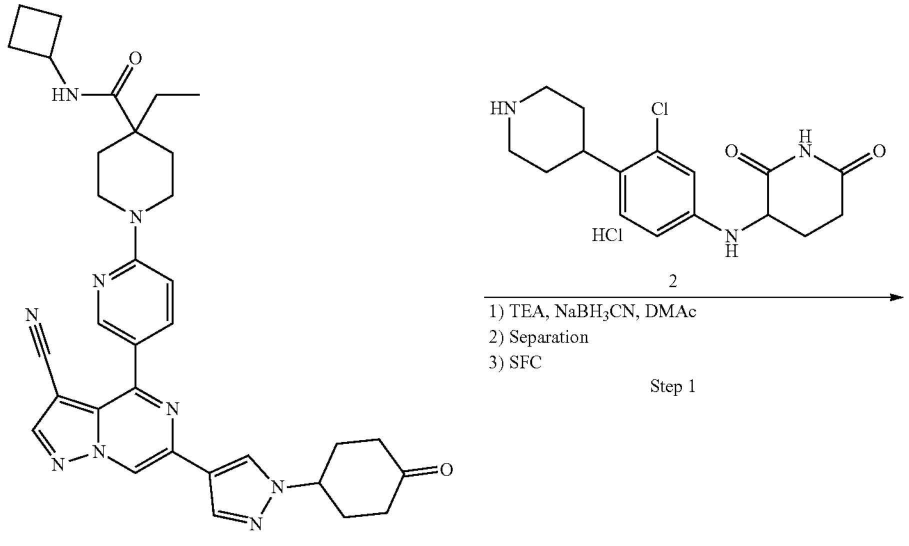

1

-continued
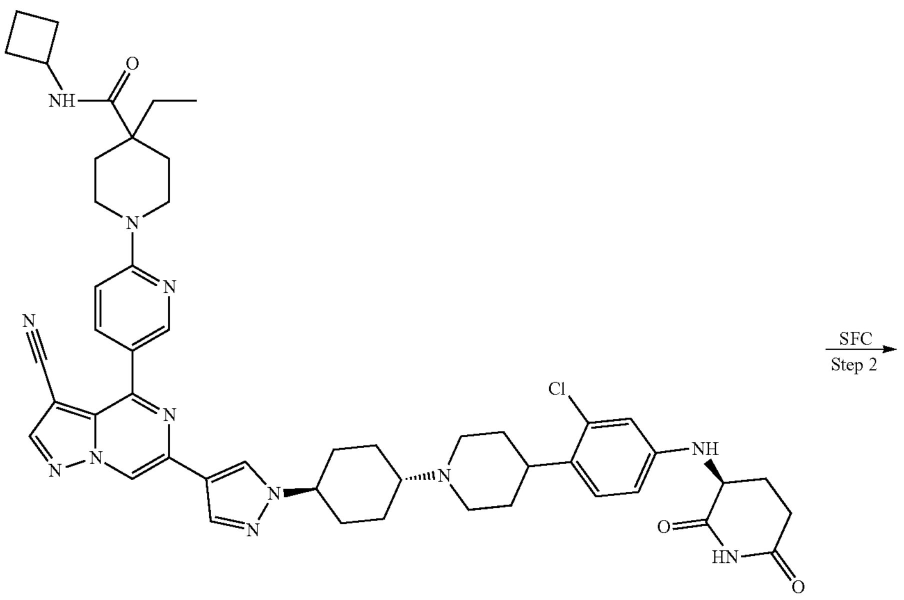
3
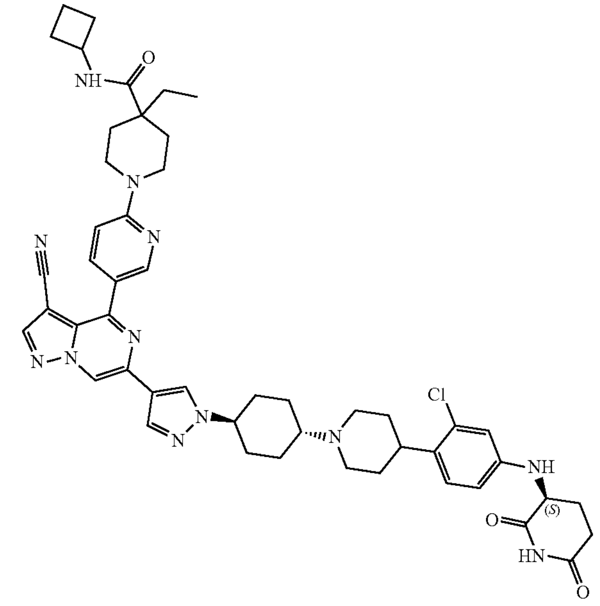
+
Compound 130

-continued

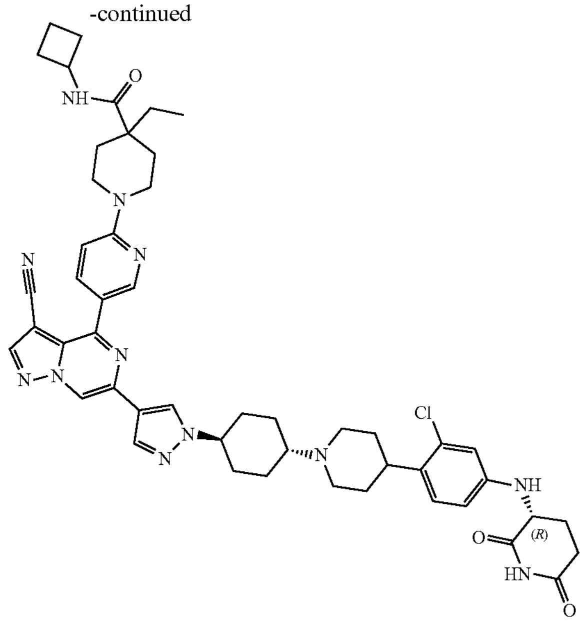

Compound 131

Step 1: To a solution of 3-[3-chloro-4-(4-piperidyl)anilino]piperidine-2,6-dione (2, 719.52 mg, 2.24 mmol) and 1-[5-[3-cyano-6-[1-(4-oxocyclohexyl)pyrazol-4-yl]pyrazolo[1,5-a]pyrazin-4-yl]-2-pyridyl]-N-cyclobutyl-4-ethyl-piperidine-4-carboxamide (1, 1.26 g, 2.13 mmol) in DMAc (10 mL) was added TEA (1.08 g, 10.65 mmol, 1.48 mL). After addition, the solution was stirred at 20° C. for 12 hr. Then $NaBH_3CN$ (1.34 g, 21.29 mmol) was added into above solution and stirred at 50° C. for another 2 hr. The reaction solution was dropped into water (30 mL) to give a suspension, then the suspension was filtered, and the filtered cake was concentrated with ACN to remove $H_2O$. The residue was purified by column chromatography ($SiO_2$, DCM: MeOH=100:1 to 10:1) and reversed phase flash chromatography (flow: 85 mL/min; gradient: from 1-70% water (0.1% $NH_3$H2O) in MeCN (add phase modifier if used) over 10 min; column: Welch Ultimate XB_C18 20-40 m; 120 A). 1-[5-[6-[1-[4-[4-[2-chloro-4-[(2,6-dioxo-3-piperidyl) amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (3, 300 mg, 331.92 μmol, 16% yield) was obtained as a green solid. LCMS ($ES^+$): m/z 897.5 $[M+H]^+$ Step 2: 1-[5-[6-[1-[4-[4-[2-chloro-4-[(2,6-dioxo-3-piperidyl)amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (3) was purified by SFC (ACSWH-PREP-SFC-A, REGIS (S, S), WHELK 01 (250 mm*25 mm, 10 um), 0.1% NH3H2O IPA, 70-70%, 80 ml/min, 6.5, 90 min).

1-[5-[6-[1-[4-[4-[2-chloro-4-[[(3S)-2,6-dioxo-3-piperidyl]amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (Compound 130, Early eluting isomer 1, 71.82 mg, 75.36 μmol, 23% yield, formic acid salt) was obtained as gray solid. LCMS ($ES^+$): m/z 897.6 $[M+H]^+$ $^1H$ NMR (400 MHz, DMSO-$d_6$) δ=10.79 (s, 1H), 9.27 (s, 1H), 8.82 (s, 1H), 8.67 (d, J=2.4 Hz, 1H), 8.44 (s, 1H), 8.22 (s, 1H), 8.14 (s, 1H), 8.04 (dd, J=2.4, 9.2 Hz, 1H), 7.79 (br d, J=7.6 Hz, 1H), 7.07 (d, J=8.8 Hz, 1H), 6.99 (br d, J=8.8 Hz, 1H), 6.71 (d, J=2.0 Hz, 1H), 6.62 (br d, J=8.4 Hz, 1H), 6.01 (br d, J=7.6 Hz, 1H), 4.38-4.24 (m, 2H), 4.23-4.09 (m, 3H), 3.11 (br t, J=11.6 Hz, 2H), 2.97 (br d, J=10.4 Hz, 2H), 2.79-2.70 (m, 2H), 2.59 (br d, J=4.4 Hz, 2H), 2.48-2.43 (m, 1H), 2.35 (br t, J=11.2 Hz, 2H), 2.18-2.13 (m, 5H), 2.08 (td, J=4.4, 8.8 Hz, 1H), 2.01-1.91 (m, 4H), 1.90-1.80 (m, 3H), 1.73-1.57 (m, 6H), 1.57-1.47 (m, 5H), 1.40-1.32 (m, 2H), 0.73 (br t, J=7.6 Hz, 3H)

1-[5-[6-[1-[4-[4-[2-chloro-4-[[(3R)-2,6-dioxo-3-piperidyl]amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (Compound 131, Late eluting isomer 2, 68.99 mg, 72.39 μmol, 22% yield, formic acid salt) was obtained as gray solid. LCMS ($ES^+$): m/z 897.6 $[M+H]^+$. $^1H$ NMR (400 MHz, DMSO-$d_6$) δ=10.79 (s, 1H), 9.26 (s, 1H), 8.81 (s, 1H), 8.67 (d, J=2.4 Hz, 1H), 8.43 (s, 1H), 8.25 (s, 1H), 8.13 (s, 1H), 8.04 (dd, J=2.4, 9.2 Hz, 1H), 7.79 (br d, J=7.2 Hz, 1H), 7.06 (br d, J=8.8 Hz, 1H), 6.98 (br d, J=9.2 Hz, 1H), 6.71 (d, J=2.0 Hz, 1H), 6.65-6.60 (m, 1H), 6.01 (br d, J=7.6 Hz, 1H), 4.37-4.24 (m, 2H), 4.22-4.08 (m, 3H), 3.11 (br t, J=11.6 Hz, 2H), 2.97 (br d, J=10.4 Hz, 2H), 2.80-2.69 (m, 2H), 2.62-2.54 (m, 2H), 2.36 (br t, J=10.8 Hz, 2H), 2.18-2.12 (m, 5H), 2.08 (td, J=4.4, 8.8 Hz, 1H), 2.02-1.91 (m, 4H), 1.90-1.76 (m, 4H), 1.74-1.58 (m, 6H), 1.57-1.45 (m, 5H), 1.40-1.31 (m, 2H), 0.73 (br t, J=7.6 Hz, 3H)

Example 156: Synthesis of 1-[5-[3-cyano-6-[1-[4-[4-[1-[(3R)-2,6-dioxo-3-piperidyl]indolin-5-yl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (Compound 132)

(Configurations are arbitrarily assigned)

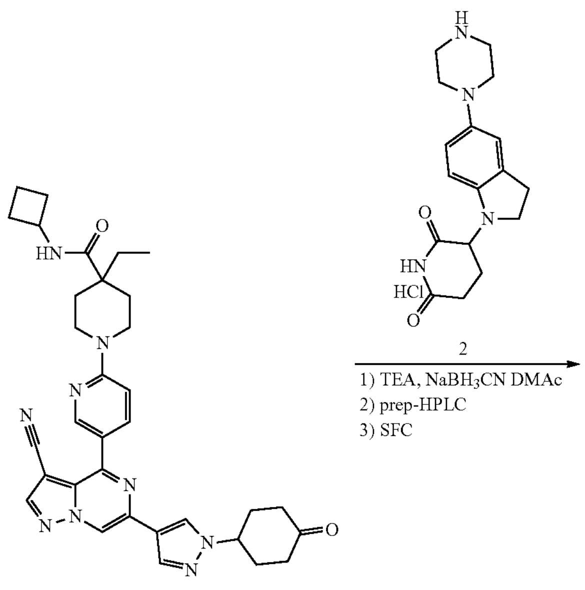

1

2

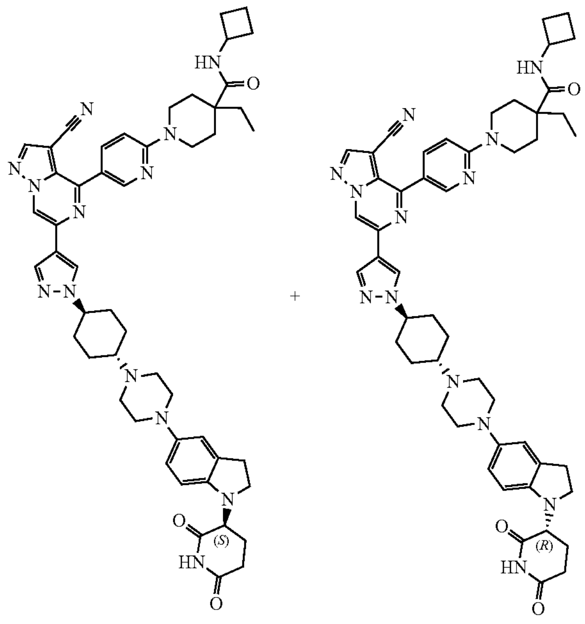

3

Compound 132

To a solution of 3-(5-(piperazin-1-yl) indolin-1-yl)piperidine-2,6-dione (2, 711.52 mg, 2.03 mmol, HCl salt) and 1-[5-[3-cyano-6-[1-(4-oxocyclohexyl)pyrazol-4-yl]pyrazolo[1,5-a]pyrazin-4-yl]-2-pyridyl]-N-cyclobutyl-4-ethyl-piperidine-4-carboxamide (1, 1.2 g, 2.03 mmol) in DMAC (12 mL) was added TEA (1.03 g, 10.14 mmol, 1.41 mL). After addition, the solution was stirred at 50° C. for 12 hr. Then sodium cyanoborohydride (1.27 g, 20.28 mmol) was added into above solution and stirred at 70° C. for another 12 hr. The reaction mixture was poured into water and filtered. The filter cake was dried in vacuum. The residue was purified by Prep-HPLC (ACSWH-GX-S Waters Xbridge C18 150*50 mm*10 um, water (10 mM $NH_4HCO_3$)-ACN, 43%-73%, 60 mL/min, 10 min). The residue was purified by Prep-HPLC (GX-A Waters Xbridge 150*25 mm*5 um, water (0.05% ammonia hydroxide v/v)-ACN, 40%-70%, 25 mL/min, 10 min). The residue was separated by SFC [Column: DAICEL CHIRALPAK AS (250 mm*30 mm, 10 um); Sample preparation: Add IPA and DCM 35 mL into sample Instrument: Waters 80Q Mobile Phase: 50% IPA+ACN (0.1% $NH_3 \cdot H_2O$) in Supercritical $CO_2$; Flow Rate: 80 g/min Cycle Time: 6.3 min, total time: 240 min Single injection volume: 0.8 ml Back Pressure: 100 bar to keep the $CO_2$ in Supercritical flow].

1-[5-[3-cyano-6-[1-[4-[4-[1-[(3S)-2,6-dioxo-3-piperidyl]indolin-5-yl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (3, Early eluting isomer 1, 50.2 mg, 51.56 μmol, 16% yield, formic acid salt) was obtained as green solid. LCMS ($ES^+$): m/z 890.5 $[M+H]^+$. $^1H$ NMR (400 MHz, DMSO-$d_6$) δ=10.75 (br s, 1H), 9.27 (s, 1H), 8.82 (s, 1H), 8.70-8.62 (m, 1H), 8.48-8.41 (m, 1H), 8.37 (s, 1H), 8.14 (s, 1H), 8.07-8.01 (m, 1H), 7.81-7.76 (m, 1H), 7.02-6.95 (m, 1H), 6.78-6.73 (m, 1H), 6.59-6.53 (m, 1H), 6.40-6.35 (m, 1H), 4.56-4.49 (m, 1H), 4.34-4.24 (m, 1H), 4.24-4.09 (m, 3H), 3.27-3.19 (m, 2H), 3.14-3.06 (m, 2H), 2.97-2.89 (m, 4H), 2.88-2.72 (m, 2H), 2.70-2.62 (m, 4H), 2.61-2.51 (m, 2H), 2.47-2.36 (m, 2H), 2.20-2.10 (m, 7H), 2.04-1.93 (m, 4H), 1.89-1.77 (m, 2H), 1.69-1.57 (m, 2H), 1.54-1.42 (m, 4H), 1.40-1.32 (m, 2H), 0.73 (t, J=7.2 Hz, 3H)

1-[5-[3-cyano-6-[1-[4-[4-[1-[(3R)-2,6-dioxo-3-piperidyl]indolin-5-yl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (Compound 132, Late eluting isomer 2, 55.64 mg, 56.27 μmol, 18% yield, formic acid salt) was obtained as green solid. LCMS ($ES^+$): m/z 890.5 $[M+H]^+$. $^1H$ NMR (400 MHz, DMSO-$d_6$) δ=10.84-10.65 (m, 1H), 9.32-9.23 (m, 1H), 8.84-8.79 (m, 1H), 8.71-8.63 (m, 1H), 8.47-8.41 (m, 1H), 8.38-8.30 (m, 1H), 8.17-8.11 (m, 1H), 8.08-8.00 (m, 1H), 7.84-7.73 (m, 1H), 7.02-6.96 (m, 1H), 6.79-6.72 (m, 1H), 6.61-6.51 (m, 1H), 6.42-6.35 (m, 1H), 4.56-4.46 (m, 1H), 4.35-4.24 (m, 1H), 4.24-4.09 (m, 3H), 3.27-3.20 (m, 2H), 3.15-3.04 (m, 3H), 2.98-2.87 (m, 4H), 2.85-2.72 (m, 1H), 2.71-2.60 (m, 4H), 2.59-2.51 (m, 2H), 2.46-2.36 (m, 2H), 2.22-2.09 (m, 7H), 2.04-1.93 (m, 4H), 1.88-1.77 (m, 2H), 1.68-1.57 (m, 2H), 1.55-1.42 (m, 4H), 1.41-1.30 (m, 2H), 0.73 (t, J=7.2 Hz, 3H)

1-[5-[6-[1-[4-[4-[2-chloro-4-[(2,6-dioxo-3-piperidyl) amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (Compound 133)

(Configurations are arbitrarily assigned)

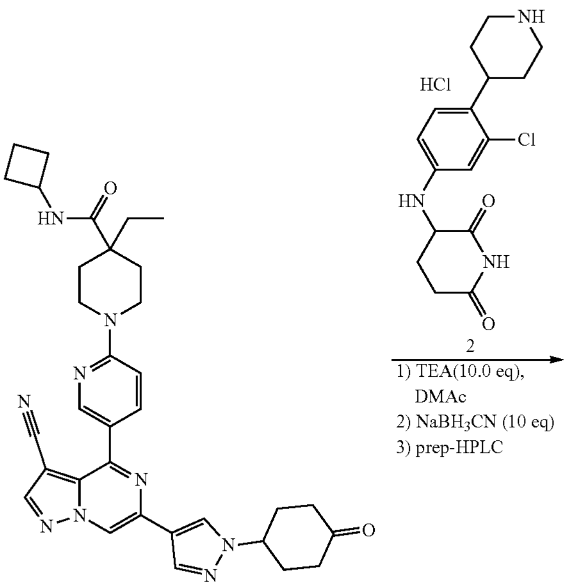

1

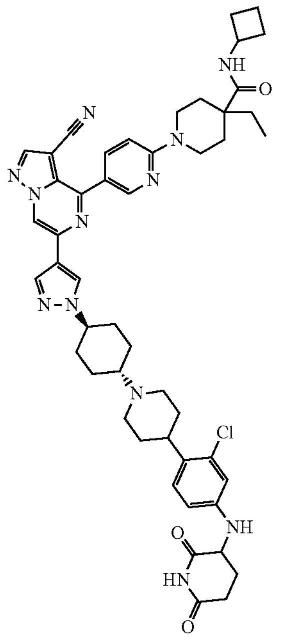

Compound 133

+

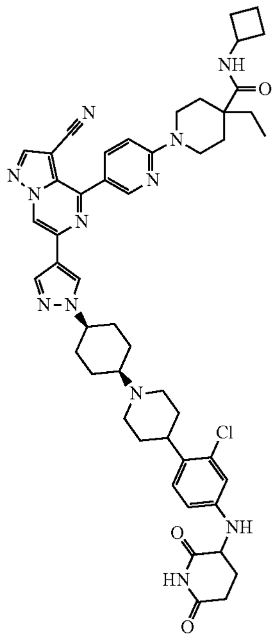

3

To a solution of 1-(5-(3-cyano-6-(1-(4-oxocyclohexyl)-1H-pyrazol-4-yl)pyrazolo[1,5-a]pyrazin-4-yl)pyridin-2-yl)-N-cyclobutyl-4-ethylpiperidine-4-carboxamide (1, 1.6 g, 2.70 mmol) and 3-(3-chloro-4-piperazin-1-yl-anilino)piperidine-2,6-dione (2, 872.84 mg, 2.70 mmol) in DMAc (13 mL) was added TEA (2.74 g, 27.04 mmol, 3.77 mL). After addition, the solution was stirred at 20° C. for 2 hr. Then sodium cyanoborohydride (1.70 g, 27.04 mmol) was added into above solution and stirred at 50° C. for another 12 hr. The reaction solution was dropped into water (30 mL) to give a suspension, then the suspension was filtered, and the filtered cake was concentrated with ACN to remove $H_2O$. The residue was purified by reversed phase flash chromatography (flow: 100 mL/min; gradient: from 100-25% water (0.1% formic $NH_3/H_2O$) in MeCN over 30 min; column: Welch Ultimate XB_C18 20-40 m; 120 A: The residue was purified by prep-HPLC (Phenomenex luna C18 150*25 mm*10 um, water (0.225% FA)-ACN, Begin B 20, End B 50, Gradient Time (min) 10). The residue was purified by prep-HPLC (Phenomenex luna C18 150*25 mm*10 um, water (0.225% FA)-ACN, Begin B 20, End B 50, Gradient Time (min) 10).

1-[5-[6-[1-[4-[4-[2-chloro-4-[(2,6-dioxo-3-piperidyl) amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (Compound 133, Early eluting isomer 1, 240.5 mg, 254.89 mol, 9% yield, formic acid salt) was obtained as a yellow solid. LCMS ($ES^+$): m/z 449.5 $[M+H]^+$. $^1H$ NMR (400 MHz, DMSO-$d_6$) δ=10.79 (s, 1H), 9.28 (s, 1H), 8.83 (s, 1H), 8.67 (d, J=2.4 Hz, 1H), 8.45 (s, 1H), 8.20 (0.684 FA), 8.15 (s, 1H), 8.05 (dd, J=2.4, 8.8 Hz, 1H), 7.80 (d, J=7.4 Hz, 1H), 7.08 (d, J=8.8 Hz, 1H), 7.00 (d, J=9.2 Hz, 1H), 6.71 (d, J=2.4 Hz, 1H), 6.62 (dd, J=2.0, 8.8 Hz, 1H), 6.01 (d, J=7.6 Hz, 1H), 4.38-4.27 (m, 2H), 4.24-4.10 (m, 3H), 3.11 (br t, J=10.8 Hz, 3H), 3.02-2.93 (m, 2H), 2.80-2.70 (m, 2H), 2.62-2.56 (m, 1H), 2.37-2.32 (m, 3H), 2.20-2.11 (m, 6H), 2.02-1.91 (m, 4H), 1.90-1.80 (m, 3H), 1.73-1.46 (m, 10H), 1.41-1.32 (m, 2H), 0.74 (t, J=7.2 Hz, 3H).

1-[5-[6-[1-[4-[4-[2-chloro-4-[(2,6-dioxo-3-piperidyl) amino]phenyl]-1-piperidyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (3, Late eluting isomer 2, 191.79 mg, 203.27 mol, 8% yield, formic acid salt) was obtained as a yellow solid. LCMS ($ES^+$): m/z 449.5 $[M+H]^+$. $^1H$ NMR (400 MHz, DMSO-$d_6$) δ=10.78 (s, 1H), 9.33 (s, 1H), 8.82 (s, 1H), 8.66 (d, J=2.4 Hz, 1H), 8.50 (s, 1H), 8.23-8.14 (m, 1H 0.847 FA), 8.04 (dd, J=2.4, 9.2 Hz, 1H), 7.79 (d, J=7.6 Hz, 1H), 7.06 (d, J=8.8 Hz, 1H), 6.99 (d, J=9.2 Hz, 1H), 6.70 (d, J=2.4 Hz, 1H), 6.60 (dd, J=2.4, 8.8 Hz, 1H), 6.00 (d, J=8.0 Hz, 1H), 4.40-4.24 (m, 3H), 4.13 (br d, J=13.2 Hz, 2H), 3.10 (br t, J=10.8 Hz, 5H), 2.80-2.65 (m, 3H), 2.36-2.26 (m, 3H), 2.18-2.11 (m, 5H), 2.01-1.93 (m, 2H), 1.91-1.78 (m, 5H), 1.76-1.55 (m, 9H), 1.50 (q, J=7.2 Hz, 2H), 1.41-1.29 (m, 2H), 0.73 (t, J=7.4 Hz, 3H).

1-(5-(3-cyano-6-(1-((1S,4r)-4-(4-(4-(((S)-2,6-dioxopiperidin-3-yl)amino)-2-fluoro-5-methoxyphenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 134)

1-(5-(3-cyano-6-(1-((1R,4r)-4-(4-(4-(((R)-2,6-dioxopiperidin-3-yl)amino)-2-fluoro-5-methoxyphenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 135)

(Configurations are arbitrarily assigned)

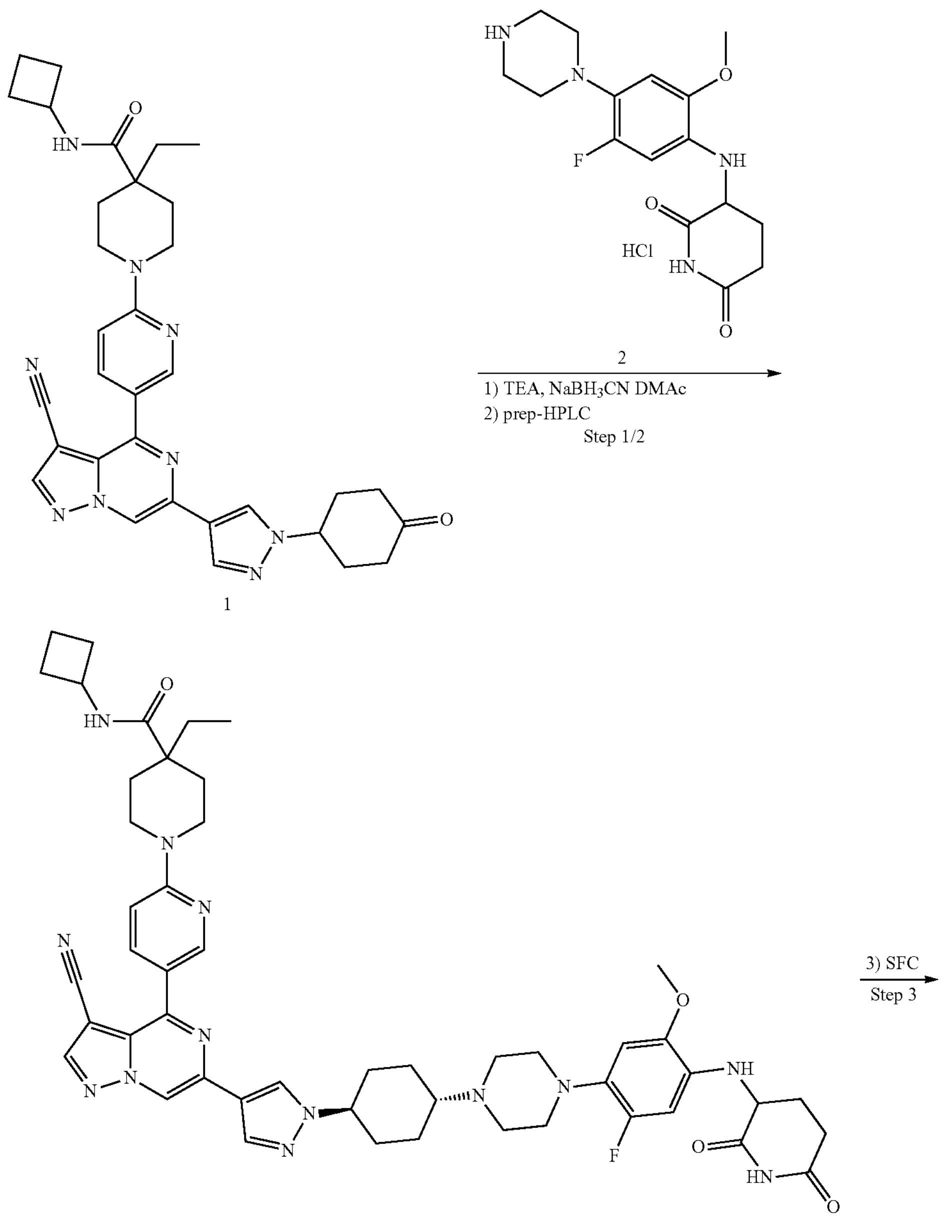

1

2

3

-continued

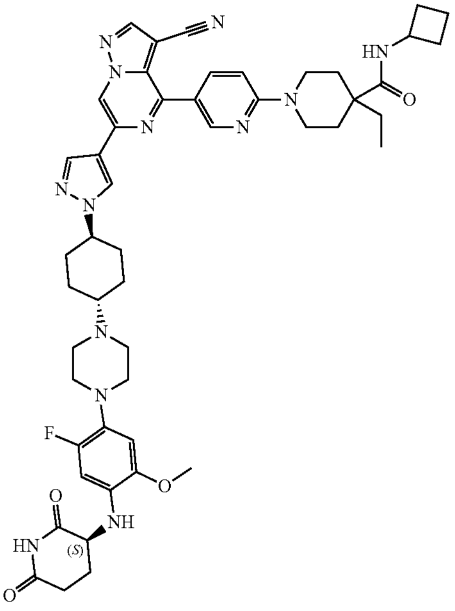

Compound 134

+

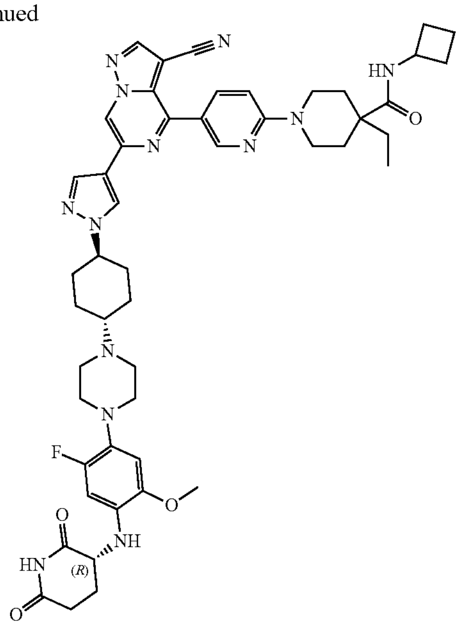

Compound 135

Step 1: To a solution of 3-((5-fluoro-2-methoxy-4-(piperazin-1-yl)phenyl)amino)piperidine-2,6-dione (2, 1.1 g, 2.95 mmol, HCl salt) in DMAC (10 mL) was added TEA (1.15 g, 11.35 mmol, 1.58 mL), the reaction mixture was stirred at 25° C. for 10 min, 1-[5-[3-cyano-6-[1-(4-oxocyclohexyl)pyrazol-4-yl]pyrazolo[1,5-a]pyrazin-4-yl]-2-pyridyl]-N-cyclobutyl-4-ethyl-piperidine-4-carboxamide (1, 1.34 g, 2.27 mmol) was added and stirred at 70° C. for 1 h, then $NaBH_3CN$ (427.88 mg, 6.81 mmol) was added and stirred at 70° C. for 12 h. The reaction mixture was purified by reverse phase column chromatography ($MeCN/H_2O$=1/1) and lyophilized. 1-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (1 g, 887.18 μmol, 39% yield, formic acid salt) was obtained as a yellow solid. LCMS ($ES^+$): m/z 912.5 $[M+H]^+$ Step 2: The product was purified by prep-HPLC (column: Waters Xbridge 150*25 mm*5 um; mobile phase: [water (10 mM NH4HCO3)-ACN]; B %: 49%-79%, 10 min). The desired fraction was collected and lyophilized. Compound 1-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (3, 200 mg, 217.09 μmol, 50% yield) was obtained as a yellow solid. LCMS ($ES^+$): m/z 912.5 $[M+H]^+$ Step 3: The product 1-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (3, 200 mg, 219.28 μmol) was purified by chiral separation (Sample preparation: Add IPA and $CH_2CL_2$ 40 ml into sample Instrument: Waters 80Q Mobile Phase: 70% IPA+ACN (0.1% $NH_3/H_2O$) in Supercritical CO2 Flow Rate: 70 g/min Cycle Time: 3.6 min, total time: 350 min Single injection volume: 1.0 ml Back Pressure: 100 bar to keep the CO2 in Supercritical flow") to give two peaks. 1-(5-(3-cyano-6-(1-((1S,4r)-4-(4-(4-(((S)-2,6-dioxopiperidin-3-yl)amino)-2-fluoro-5-methoxyphenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 134, Early eluting isomer 1, 31.14 mg, 33.80 μmol, 31% yield) was obtained as a yellow solid.

Compound 134, Early Eluting Isomer 1:

LCMS ($ES^+$): m/z 912.6 $[M+H]^+$.

$^1H$ NMR (400 MHz, DMSO-$d_6$) δ=10.85 (s, 1H), 9.27 (s, 1H), 8.82 (s, 1H), 8.67 (d, J=2.4 Hz, 1H), 8.44 (s, 1H), 8.14 (s, 1H), 8.04 (dd, J=2.4, 8.8 Hz, 1H), 7.79 (d, J=7.6 Hz, 1H), 6.99 (d, J=9.2 Hz, 1H), 6.66-6.49 (m, 2H), 5.09 (d, J=7.2 Hz, 1H), 4.33-4.07 (m, 5H), 3.79 (s, 3H), 3.30 (s, 1H), 3.10 (br t, J=11.2 Hz, 2H), 2.91 (br s, 4H), 2.85-2.75 (m, 1H), 2.71-2.63 (m, 4H), 2.55 (br d, J=3.2 Hz, 1H), 2.46-2.39 (m, 1H), 2.21-2.09 (m, 7H), 1.90 (br s, 5H), 1.88-1.77 (m, 2H), 1.69-1.57 (m, 2H), 1.56-1.41 (m, 4H), 1.41-1.30 (m, 2H), 0.73 (t, J=7.6 Hz, 3H)

1-(5-(3-cyano-6-(1-((1R,4r)-4-(4-(4-(((R)-2,6-dioxopiperidin-3-yl)amino)-2-fluoro-5-methoxyphenyl)piperazin-1-yl)cyclohexyl)-1H-pyrazol-4-yl)pyrazolo[1,5-a]pyrazin-4-yl)pyridine-2-yl)-N-cyclobutyl-4-ethylpiperidine-4-carboxamide (Compound 135, Late eluting isomer 2, 22.18 mg, 24.08 μmol, 21.96% yield) was obtained as a yellow solid.

Compound 135, Late Eluting Isomer 2:

LCMS ($ES^+$): m/z 912.6 $[M+H]^+$.

$^1H$ NMR (400 MHz, DMSO-$d_6$) δ=11.00-10.67 (m, 1H), 9.27 (s, 1H), 8.82 (s, 1H), 8.67 (d, J=2.4 Hz, 1H), 8.44 (s, 1H), 8.14 (s, 1H), 8.04 (dd, J=2.4, 9.2 Hz, 1H), 7.79 (d, J=7.2 Hz, 1H), 6.99 (d, J=8.8 Hz, 1H), 6.61 (d, J=8.0 Hz, 1H), 6.55 (d, J=14.4 Hz, 1H), 5.09 (d, J=7.2 Hz, 1H), 4.34-4.08 (m, 5H), 3.79 (s, 3H), 3.30 (br s, 1H), 3.10 (br t, J=11.2 Hz, 2H), 2.91 (br s, 4H), 2.85-2.74 (m, 1H), 2.66 (br s, 4H), 2.55 (br d, J=2.8 Hz, 1H), 2.43 (br t, J=11.6 Hz, 1H), 2.15 (br d, J=10.8 Hz, 7H), 2.03-1.90 (m, 5H), 1.87-1.76 (m, 2H), 1.69-1.56 (m, 2H), 1.55-1.42 (m, 4H), 1.41-1.29 (m, 2H), 0.73 (t, J=7.2 Hz, 3H)

1-(5-(3-cyano-6-(1-((1S,4r)-4-(4-(4-(((S)-2,6-dioxopiperidin-3-yl)amino)-2,6-difluorophenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 136)

1-(5-(3-cyano-6-(1-((1R,4r)-4-(4-(4-(((R)-2,6-dioxopiperidin-3-yl)amino)-2,6-difluorophenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 137)

(Configurations are arbitrarily assigned)

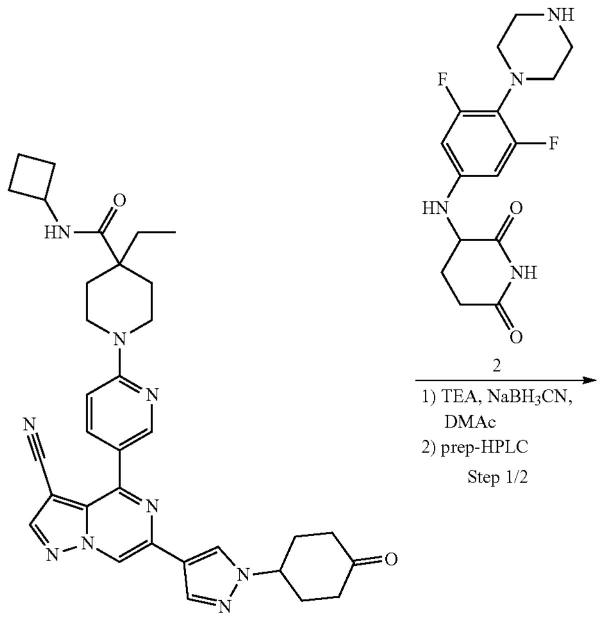

1

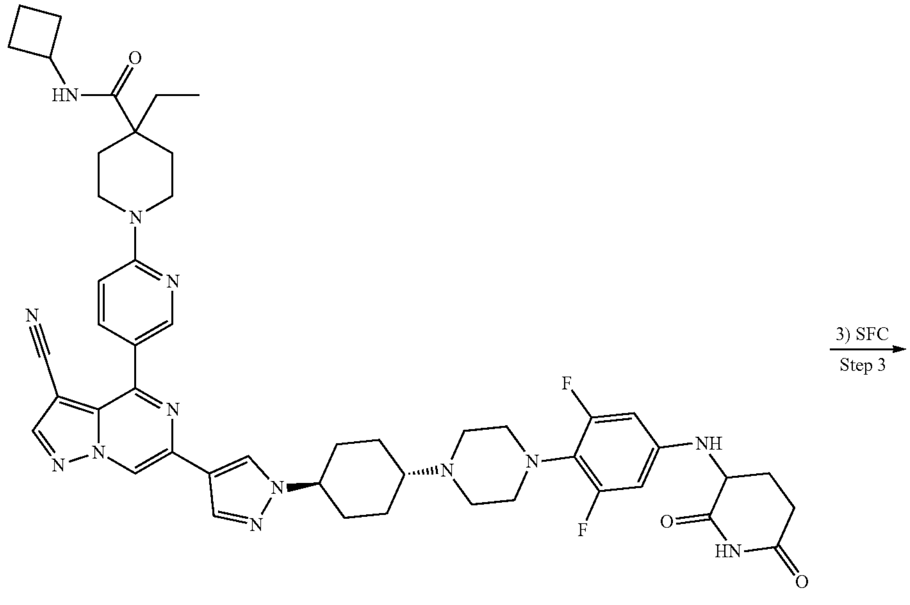

3

-continued

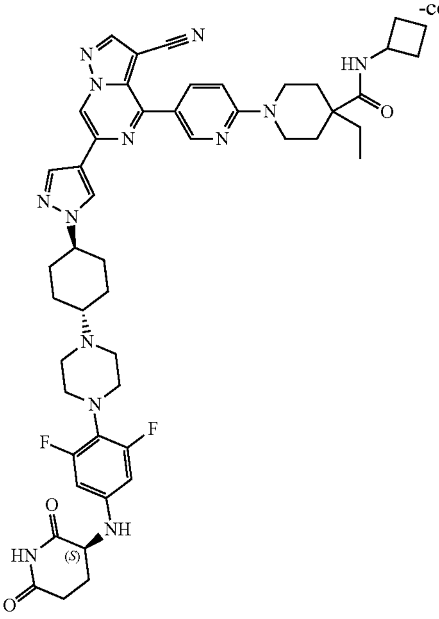

Compound 136

+

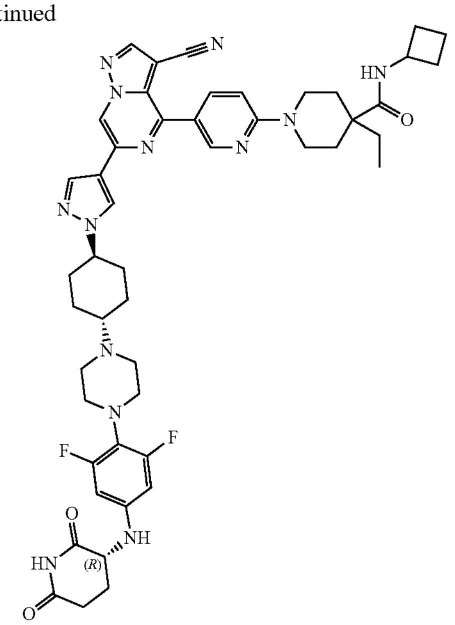

Compound 137

Step 1: To a solution of 3-(3,5-difluoro-4-piperazin-1-yl-anilino)piperidine-2,6-dione (2, 1.22 g, 3.38 mmol) in DMAc (10 mL) was added TEA (900.00 mg, 8.89 mmol, 1.24 mL), the reaction mixture was stirred at 25° C. for 10 min, 1-(5-(3-cyano-6-(1-(4-oxocyclohexyl)-1H-pyrazol-4-yl)pyrazolo[1,5-a]pyrazin-4-yl)pyridin-2-yl)-N-cyclobutyl-4-ethylpiperidine-4-carboxamide (1, 1 g, 1.69 mmol) was added and stirred at 70° C. for 1 h, $NaBH_3CN$ (250.00 mg, 3.98 mmol) was added and stirred at 70° C. for 16 h. The reaction mixture was purified by reverse phase column chromatography (flow: 100 mL/min; gradient: from 0-60% water (0.1% formic acid) in MeCN over 35 min; column: C18, 330 g) to give 1-[5-[3-cyano-6-[1-[4-[4-[4-[(2,6-dioxo-3-piperidyl)amino]-2,6-difluoro-phenyl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (880 mg, 938.64 μmol, 56% yield) as a yellow solid. LCMS ($ES^+$): m/z 909.9 $[M+H]^+$ Step 2: 1-[5-[3-cyano-6-[1-[4-[4-[4-[(2,6-dioxo-3-piperidyl)amino]-2,6-difluoro-phenyl]piperazin-1-yl]cyclohexyl]pyrazol-4-yl]pyrazolo[1,5-a]pyrazin-4-yl]-2-pyridyl]-N-cyclobutyl-4-ethyl-piperidine-4-carboxamide (9, 880 mg, 938.64 μmol) was purified by prep-HPLC (flow: 28 mL/min; gradient: from 48-78% MeCN in (water (10 mM $NH_4HCO_3$)-ACN) over 28 min; column: Waters Xbridge C18 150*50 mm*10 um) to give 1-(5-(3-cyano-6-(1-((1r,4r)-4-(4-(4-((2,6-dioxopiperidin-3-yl)amino)-2,6-difluoro-phenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (3, Early eluting isomer 1, 400 mg, 439.99 μmol, 45% yield) as a yellow solid. LCMS ($ES^+$): m/z 909.9 $[M+H]^+$ Step 3: 1-(5-(3-cyano-6-(1-((1r, 4r)-4-(4-(4-((2,6-dioxopiperidin-3-yl)amino)-2,6-difluorophenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (3, 400 mg, 439.99 μmol) was purified by SFC (Add $CH_3CN$:DCM (4:1) 40 ml into sample Instrument: Thar 80 SFC Mobile Phase: 70% IPA+CAN (0.1% $NH_3$/$H_2O$) in Supercritical $CO_2$ Flow Rate: 70 g/min Cycle Time: 3.8 min, total time: 50 min Single injection volume: 3.5 ml Back Pressure: 100 bar to keep the $CO_2$ in Supercritical flow).

1-(5-(3-cyano-6-(1-((1S,4r)-4-(4-(4-(((S)-2,6-dioxopiperidin-3-yl)amino)-2,6-difluorophenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 136, Early eluting isomer 1-1, 106.63 mg, 109.33 μmol) was obtained as yellow solid. LCMS ($ES^+$): m/z 900.6 $[M+H]^+$. $^1H$ NMR (400 MHz, DMSO-$d_6$) δ=10.81 (s, 1H), 9.27 (s, 1H), 8.82 (s, 1H), 8.66 (d, J=2.4 Hz, 1H), 8.44 (s, 1H), 8.31 (br s, 1H), 8.14 (s, 1H), 8.04 (dd, J=2.4, 8.8 Hz, 1H), 7.79 (br d, J=7.6 Hz, 1H), 6.99 (br d, J=9.2 Hz, 1H), 6.32 (br d, J=12.4 Hz, 2H), 6.25 (br d, J=7.6 Hz, 1H), 4.35-4.09 (m, 5H), 3.10 (br t, J=11.6 Hz, 2H), 2.96 (br s, 4H), 2.78-2.65 (m, 3H), 2.60 (br s, 6H), 2.42 (br s, 1H), 2.18-2.11 (m, 5H), 2.07-2.01 (m, 1H), 2.01-1.90 (m, 4H), 1.87-1.80 (m, 2H), 1.64 (br dd, J=6.8, 9.6 Hz, 2H), 1.55-1.43 (m, 4H), 1.41-1.30 (m, 2H), 0.73 (br t, J=7.6 Hz, 3H).

1-(5-(3-cyano-6-(1-((1R,4r)-4-(4-(4-(((R)-2,6-dioxopiperidin-3-yl)amino)-2,6-difluorophenyl)piperazin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 137, Late eluting isomer 1-2, 96.64 mg, 100.11 μmol) was obtained as yellow solid. LCMS ($ES^+$): m/z 900.6 $[M+H]^+$. $^1H$ NMR (400 MHz, DMSO-$d_6$) δ=10.81 (s, 1H), 9.27 (s, 1H), 8.82 (s, 1H), 8.67 (d, J=2.4 Hz, 1H), 8.44 (s, 1H), 8.30 (s, 1H), 8.14 (s, 1H), 8.04 (dd, J=2.4, 8.8 Hz, 1H), 7.79 (d, J=7.2 Hz, 1H), 6.99 (d, J=9.2 Hz, 1H), 6.33 (br d, J=12.4 Hz, 2H), 6.25 (br d, J=7.6 Hz, 1H), 4.36-4.10 (m, 5H), 3.11 (br t, J=11.2 Hz, 2H), 2.97 (s, 4H), 2.81-2.65 (m, 2H), 2.60 (br s, 4H), 2.48-2.36 (m, 2H), 2.23-2.10 (m, 6H), 2.10-2.04 (m, 1H), 1.96 (br dd, J=6.5, 9.2 Hz, 4H), 1.88-1.78 (m, 3H), 1.70-1.57 (m, 2H), 1.56-1.42 (m, 4H), 1.41-1.31 (m, 2H), 0.73 (t, J=7.2 Hz, 3H)

Example 157: Synthesis of 1-(5-(3-Cyano-6-(1-((1r,4r)-4-(4-(3-(2,4-dioxotetrahydropyrimidin-1(2H)-yl)-7-fluoro-1-methyl-1H-indazol-6-yl)piperidin-1-yl)cyclohexyl)-1H-pyrazol-4-yl)pyrazolo[1,5-a]pyrazin-4-yl)pyridin-2-yl)-N-cyclobutyl-4-ethylpiperidine-4-carboxamide (Compound 138)

(Configurations are arbitrarily assigned)

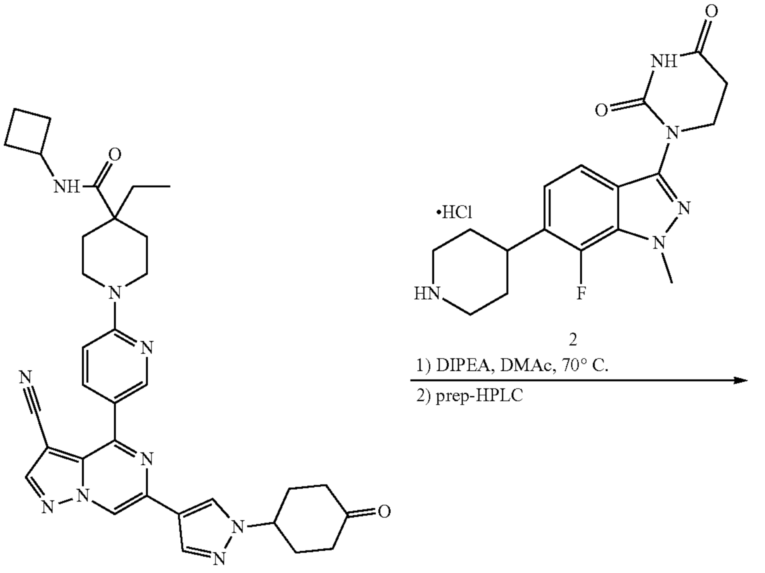

2

1

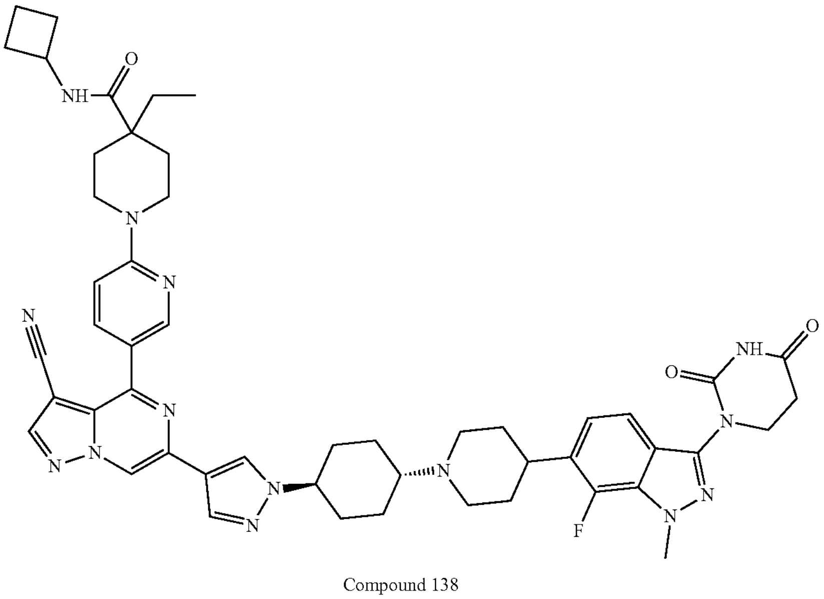

Compound 138

Into a 25 mL glass-capped vial containing a well stirred solution of 1-[5-[3-cyano-6-[1-(4-oxocyclohexyl)pyrazol-4-yl]pyrazolo[1,5-a]pyrazin-4-yl]-2-pyridyl]-N-cyclobutyl-4-ethyl-piperidine-4-carboxamide (1, 500 mg, 0.839 mmol) and 1-[7-fluoro-1-methyl-6-(4-piperidyl) indazol-3-yl]hexahydropyrimidine-2,4-dione hydrochloride (2, 555.22 mg, 1.43 mmol) in DMAc (10 mL) were added DIPEA (1.08 g, 8.39 mmol, 1.46 mL) and Sodium cyanoborohydride (210.92 mg, 3.36 mmol) at room temperature under nitrogen atmosphere. The resulting mixture was stirred at 70° C. The reaction was monitored by UPLC and found complete after 18 h. The reaction mixture was slowly added to ice-cold water (50 mL) and solid thus obtained was filtered. The crude solid was purified by reverse phase preparatory HPLC [Purification method: X-Bridge OBD C18 (19×150) 5 micron; Mobile phase A: 0.1% ammonium bicarbonate in water and Mobile phase B: Acetonitrile; RT=6.6 minutes] to afford 1-(5-(3-cyano-6-(1-((1r, 4r)-4-(4-(3-(2,4-dioxotetrahydropyrimidin-1(2H)-yl)-7-fluoro-1-methyl-1H-indazol-6-yl)piperidin-1-yl)cyclohexyl)-1H-pyrazol-4-yl)pyrazolo[1, 5-a]pyrazin-4-yl)pyridin-2-yl)-N-cyclobutyl-4-ethylpiperidine-4-carboxamide (Compound 138, Early eluting isomer, 40 mg, 0.043 mmol) as a light yellow solid. Yield-5.1%. $^1$H-NMR (400 MHz, DMSO-$d_6$); δ 10.59 (s, 1H), 9.28 (s, 1H), 8.82 (s, 1H), 8.68 (d, J=2.4 Hz, 1H), 8.46 (s, 1H), 8.15 (s, 1H), 8.05 (dd, J=8.8, 2.4 Hz, 1H), 7.78 (d, J=7.2 Hz, 1H), 7.41 (d, J=8.4 Hz, 1H), 7.08 (dd, J=8.4, 5.6 Hz, 1H), 7.00 (d, J=9.2 Hz, 1H), 4.30-4.12 (m, 4H), 4.11 (s, 3H), 3.916 (t, J=13.2 Hz, 2H), 3.15-3.04 (m, 5H), 2.77 (t, J=6.8 Hz, 2H), 2.18-2.16 (m, 7H), 2.01-1.97 (m, 5H), 1.87-1.78 (m, 7H), 1.66-1.61 (m, 2H), 1.57-1.51 (m, 4H), 1.37 (m, 2H) and 0.74 (t, J=7.60 Hz, 3H). LCMS (ES$^+$): m/z 921.3 [M+H]$^+$.

Example 158: Synthesis of 6-(1-((1S,4r)-4-(4-(4-(((S)-2,6-dioxopiperidin-3-yl)amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl)pyrazolo[1,5-a]pyrazine-3-carbonitrile (Compound 139)

6-(1-((1R,4r)-4-(4-(4-(((R)-2,6-dioxopiperidin-3-yl)amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl)pyrazolo[1,5-a]pyrazine-3-carbonitrile (Compound 140)

(Configurations are arbitrarily assigned)

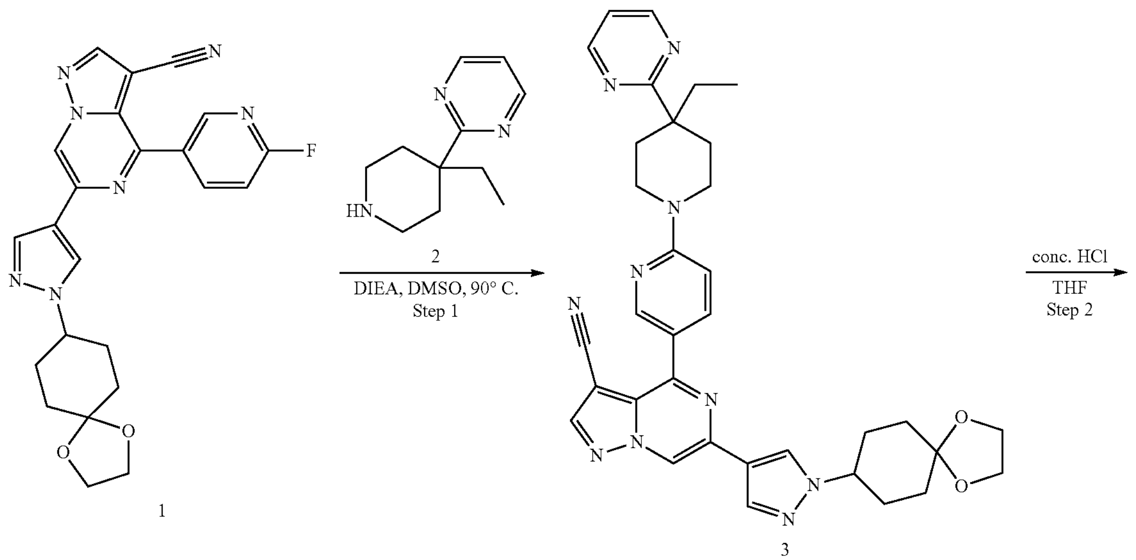

1

3

-continued
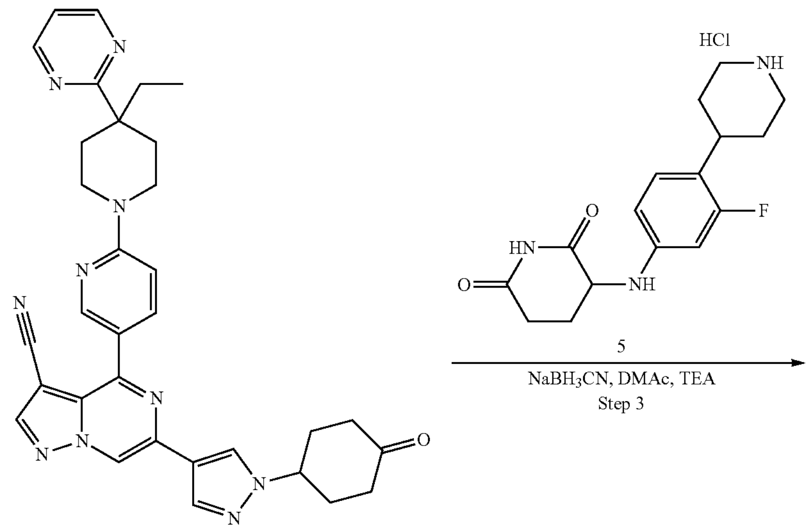
4
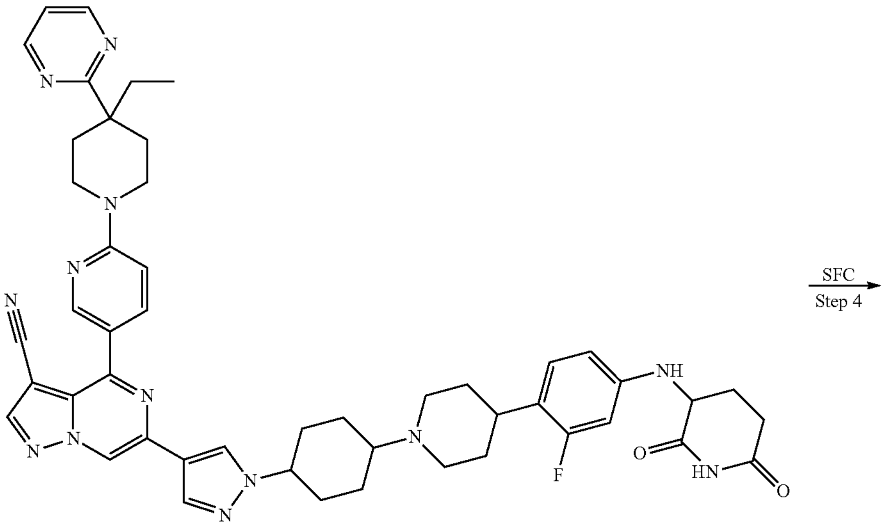
6

-continued

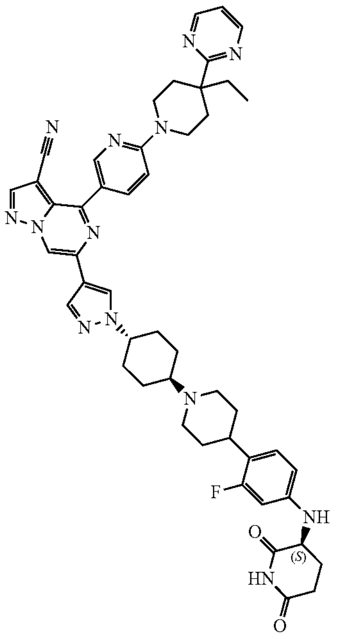

Compound 139

+

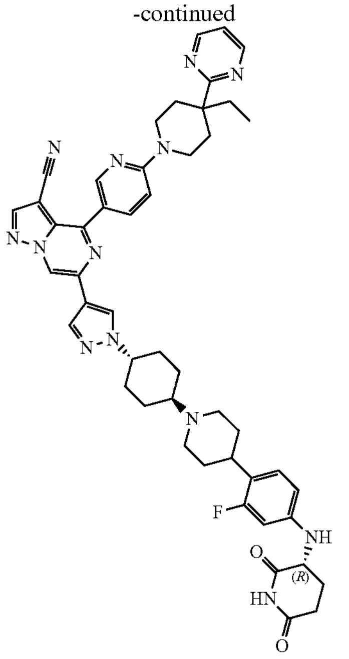

Compound 140

+

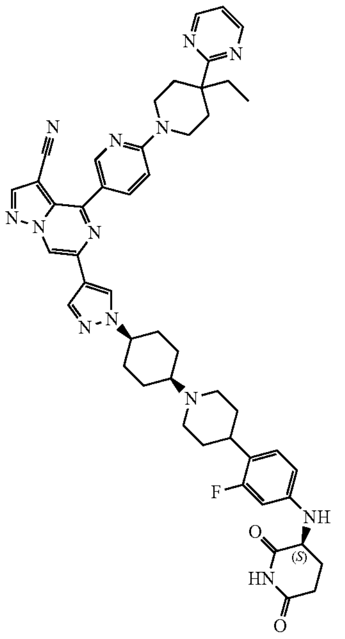

7

+

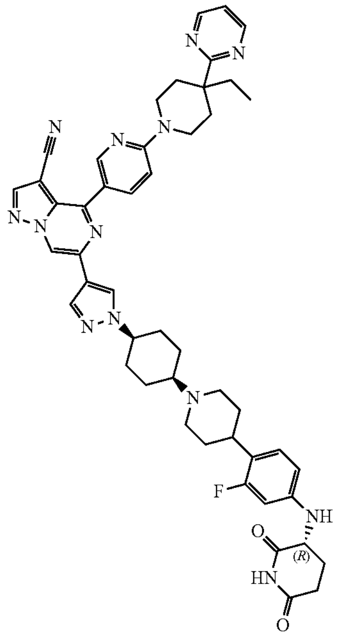

8

Step 1: To a solution of 2-(4-ethylpiperidin-4-yl)pyrimidine HCl salt (2, 899.79 mg, 3.95 mmol) and 6-(1-(1,4-dioxaspiro[4.5]decan-8-yl)-1H-pyrazol-4-yl)-4-(6-fluoropyridin-3-yl)pyrazolo[1,5-a]pyrazine-3-carbonitrile (1, 1.6 g, 3.59 mmol) in DMSO (16 mL) was added DIPEA (2.32 g, 17.96 mmol, 3.13 mL). After addition, the solution was stirred at 100° C. for 12h. The reaction was dropped into water (45 mL) to give a suspension, then the suspension was filtered and the filtered cake was washed with water and concentrated with ACN to remove water under vacuum. The reaction was used for next step directly without purification. 6-(1-(1,4-dioxaspiro[4.5]decan-8-yl)-1H-pyrazol-4-yl)-4-(6-(4-ethyl-4-(pyrimidin-2-yl)piperidin-1-yl)pyridin-3-yl) pyrazolo[1,5-a]pyrazine-3-carbonitrile (3, 1.8 g, 2.79 mmol, 78% yield) was obtained as a yellow. LCMS ($ES^+$): m/z 617.3 $[M+H]^+$ Step 2: To a solution of 6-(1-(1,4-dioxaspiro[4.5]decan-8-yl)-1H-pyrazol-4-yl)-4-(6-(4-ethyl-4-(pyrimidin-2-yl)piperidin-1-yl)pyridin-3-yl)pyrazolo[1,5-a]pyrazine-3-carbonitrile (3, 2 g, 3.24 mmol) in THF (15 mL) was added conc.HCl (12 M, 16 mL) at 0° C. After addition, the solution was stirred at 25° C. for 12h. The reaction was dropped into the aqueous of $Na_2CO_3$ (12 g) to give a suspension, then the suspension was filtered and the filtered cake was washed with water and concentrated with ACN to remove water under vacuum. The reaction was used for next step directly without purification. 4-(6-(4-ethyl-4-(pyrimidin-2-yl)piperidin-1-yl)pyridin-3-yl)-6-(1-(4-oxocyclohexyl)-1H-pyrazol-4-yl)pyrazolo[1,5-a]pyrazine-3-carbonitrile (4, 1.4 g, 2.28 mmol, 70% yield) was obtained as a yellow solid. LCMS ($ES^+$): m/z 573.2 $[M+H]^+$ Step 3: To a solution of 4-(6-(4-ethyl-4-(pyrimidin-2-yl) piperidin-1-yl)pyridin-3-yl)-6-(1-(4-oxocyclohexyl)-1H-pyrazol-4-yl)pyrazolo[1,5-a]pyrazine-3-carbonitrile (4, 1.3 g, 2.27 mmol) and 3-((3-fluoro-4-(piperidin-4-yl)phenyl) amino)piperidine-2,6-dione hydrochloride (5, 843.01 mg, 2.47 mmol, HCl salt) in DMAc (10 mL) was added sodium cyanoborohydride (1.43 g, 22.76 mmol). After addition, the solution was stirred at 20° C. for 12 hr. Then TEA (1.15 g, 11.35 mmol, 1.58 mL) was added into above solution and stirred at 50° C. for another 2 hr. The reaction solution was dropped into water (30 mL) to give a suspension, then the suspension was filtered and the filtered cake was concentrated with ACN to remove $H_2O$. The residue was purified by column chromatography ($SiO_2$, DCM: MeOH=100:1 to 10:1). 6-(1-(4-(4-(4-((2,6-dioxopiperidin-3-yl)amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl) pyrazolo[1,5-a]pyrazine-3-carbonitrile (6, lg, 1.16 mmol, 51% yield) was obtained as a yellow solid.

Step 4: 6-(1-(4-(4-(4-((2,6-dioxopiperidin-3-yl)amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl) pyrazolo[1,5-a]pyrazine-3-carbonitrile (1 g) was purified by Prep-SFC (Sample preparation: Add IPA and CH2CL2 150 ml into sample Instrument: Waters 80Q Mobile Phase: 65% IPA+ACN (0.1% $NH_3$H2O) in Supercritical CO2 Flow Rate: 80 g/min Cycle Time: 7.3 min, total time: 800 min Single injection volume: 1.3 ml Back Pressure: 100 bar to keep the $CO_2$ in Supercritical flow) to get Peak 1 (Compound 140 & 8) and Peak 2 (Compound 139 & 7). Then Peak 2 (Compound 139 & 7) was further purified by prep-SFC (Sample preparation: Add CH3CN:DCM (4:1) 40 mL into sample Instrument: Thar 80 SFC Mobile Phase: 70% EtOH+ACN (0.1% NH3 H2O) in Supercritical $CO_2$ Flow Rate: 70 g/min Cycle Time: 6.1 min, total time: 130 min Single injection volume: 2.0 ml Back Pressure: 100 bar to keep the CO2 in Supercritical flow). 6-(1-((1R,4s)-4-(4-(4-(((S)-2,6-dioxopiperidin-3-yl)amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl)pyrazolo[1,5-a] pyrazine-3-carbonitrile (7, Peak 2-1, 76.1 mg, 82.97 μmol, 7% yield, formic acid salt) was obtained as yellow solid.

6-(1-((1S,4r)-4-(4-(4-(((S)-2,6-dioxopiperidin-3-yl) amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl)pyrazolo[1,5-a]pyrazine-3-carbonitrile (Compound 139, Peak 2-2, 73.68 mg, 80.33 μmol, 7% yield, formic acid salt) was obtained as yellow solid.

7, Peak 2-1:

LCMS ($ES^+$): m/z 862.5 $[M+H]^+$ $^1$H NMR (400 MHz, DMSO-$d_6$) δ=10.80 (br s, 1H), 9.33 (s, 1H), 8.89-8.84 (m, 2H), 8.82 (s, 1H), 8.69-8.61 (m, 1H), 8.50 (s, 1H), 8.33 (br s, 1H), 8.31 (br s, 1H), 8.16 (s, 1H), 8.08-7.94 (m, 1H), 7.38 (t, J=4.8 Hz, 1H), 7.06-6.94 (m, 2H), 6.51-6.38 (m, 2H), 6.00 (d, J=7.2 Hz, 1H), 4.37-4.18 (m, 4H), 3.11-2.95 (m, 4H), 2.79-2.66 (m, 1H), 2.64-2.55 (m, 4H), 2.40-2.26 (m, 3H), 2.19-2.00 (m, 3H), 1.97-1.79 (m, 5H), 1.76-1.47 (m, 10H), 0.54 (t, J=7.2 Hz, 3H)

Compound 139, Peak 2-2:

LCMS ($ES^+$): m/z 862.5 $[M+H]^+$ $^1$H NMR (400 MHz, DMSO-$d_6$) δ=10.80 (s, 1H), 9.26 (s, 1H), 8.86 (d, J=4.8 Hz, 2H), 8.82 (s, 1H), 8.67 (d, J=2.4 Hz, 1H), 8.44 (s, 1H), 8.27 (s, 1H), 8.14 (s, 1H), 8.04 (dd, J=2.4, 8.8 Hz, 1H), 7.38 (t, J=4.8 Hz, 1H), 7.04-6.95 (m, 2H), 6.50-6.41 (m, 2H), 6.05-5.98 (m, 1H), 4.36-4.11 (m, 4H), 3.09-2.90 (m, 4H), 2.81-2.69 (m, 1H), 2.63-2.54 (m, 4H), 2.39-2.30 (m, 2H), 2.19-2.05 (m, 3H), 1.97-1.76 (m, 5H), 1.75-1.59 (m, 8H), 1.57-1.41 (m, 2H), 0.54 (t, J=7.2 Hz, 3H)

Peak 1 (Compound 140 & 8) was further purified by prep-SFC (Sample preparation: Add CH3CN:DCM (4:1) 40 mL into sample Instrument: Thar 80 SFC Mobile Phase: 70% EtOH+ACN (0.1% NH3H2O) in Supercritical $CO_2$ Flow Rate: 70 g/min Cycle Time: 6.1 min, total time: 130 min Single injection volume: 2.0 ml Back Pressure: 100 bar to keep the CO2 in Supercritical flow). 6-(1-((1R,4s)-4-(4-(4-(((S)-2,6-dioxopiperidin-3-yl)amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl) pyrazolo[1,5-a] pyrazine-3-carbonitrile FA salt (Compound 140, 76.1 mg, 82.97 μmol, 7% yield) was obtained as yellow solid. SFC showed the product was impure, The impure Compound 140 was purified by prep-SFC (Sample preparation: Add CH3CN:DCM (4:1) 40 ml into sample Instrument: Thar 80 SFC Mobile Phase: 70% IPA+ACN (0.1% $NH_3H_2O$) in Supercritical $CO_2$ Flow Rate: 70 g/min Cycle Time: 7.0 min, total time: 80 min Single injection volume: 4.0 ml Back Pressure: 100 bar to keep the $CO_2$ in Supercritical flow) to get 6-(1-((1R,4s)-4-(4-(4-(((S)-2,6-dioxopiperidin-3-yl) amino)-2-fluorophenyl)piperidin-1-yl)cyclohexyl)-1H-pyrazol-4-yl)-4-(6-(4-ethyl-4-(pyrimidin-2-yl)piperidin-1-yl)pyridin-3-yl)pyrazolo[1,5-a]pyrazine-3-carbonitrile FA salt (Compound 140, Peak 1-1, 66.82 mg, 72.85 μmol, 79% yield) was obtained as yellow solid. 6-(1-((1S,4s)-4-(4-(4-(((R)-2,6-dioxopiperidin-3-yl)amino)-2-fluorophenyl)piperidin-1-yl)cyclo hexyl)-1H-pyrazol-4-yl)-4-(6-(4-ethyl-4-(pyrimidin-2-yl)piperidin-1-yl)pyridin-3-yl)pyrazolo [1,5-a] pyrazine-3-carbonitrile (8, Peak 1-2, 97.1 mg, 111.52 μmol, 10% yield) was obtained as yellow solid.

Compound 140, Peak 1-1:

LCMS ($ES^+$): m/z 862.6 $[M+H]^+$ $^1$H NMR (400 MHz, DMSO-$d_6$) δ=10.80 (s, 1H), 9.27 (s, 1H), 8.89-8.80 (m, 3H), 8.67 (d, J=2.4 Hz, 1H), 8.44 (s, 1H), 8.26 (br s, 1H), 8.14 (s, 1H), 8.04 (dd, J=2.4, 8.8 Hz, 1H), 7.38 (t, J=4.8 Hz, 1H), 7.05-6.97 (m, 2H), 6.51-6.40 (m, 2H), 6.05-5.97 (m, 1H), 4.36-4.13 (m, 4H), 3.11-2.93 (m, 4H), 2.81-2.68 (m, 1H), 2.65-2.54 (m, 4H), 2.40-2.29 (m, 2H), 2.20-2.05 (m, 3H), 1.98-1.76 (m, 5H), 1.75-1.58 (m, 8H), 1.57-1.43 (m, 2H), 0.55 (t, J=7.2 Hz, 3H)

8, Peak 1-2:

LCMS ($ES^+$): m/z 862.5 $[M+H]^+$ $^1$H NMR (400 MHz, DMSO-$d_6$) δ=10.79 (s, 1H), 9.33 (s, 1H), 8.89-8.80 (m, 3H), 8.67 (d, J=2.4 Hz, 1H), 8.50 (s, 1H), 8.21 (s, 1H), 8.17 (s, 1H), 8.07-8.02 (m, J=2.5, 9.0 Hz, 1H), 7.38 (t, J=4.8 Hz, 1H), 7.03-6.96 (m, 2H), 6.47-6.40 (m, 2H), 6.00 (br d, J=7.6 Hz, 1H), 4.37-4.16 (m, 4H), 3.11-2.99 (m, 4H), 2.80-2.69 (m, 1H), 2.63-2.55 (m, 4H), 2.42-2.27 (m, 3H), 2.16-2.03 (m, 3H), 1.92-1.79 (m, 5H), 1.76-1.59 (m, 10H), 0.54 (t, J=7.2 Hz, 3H)

Example 159: Synthesis of 1-[5-[3-cyano-6-[1-[4-[4-[4-[[(3S)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]—N-cyclopentyl-4-ethyl-piperidine-4-carboxamide (Compound 141)

1-[5-[3-cyano-6-[1-[4-[4-[4-[[(3R)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-N-cyclopentyl-4-ethyl-piperidine-4-carboxamide (Compound 142)

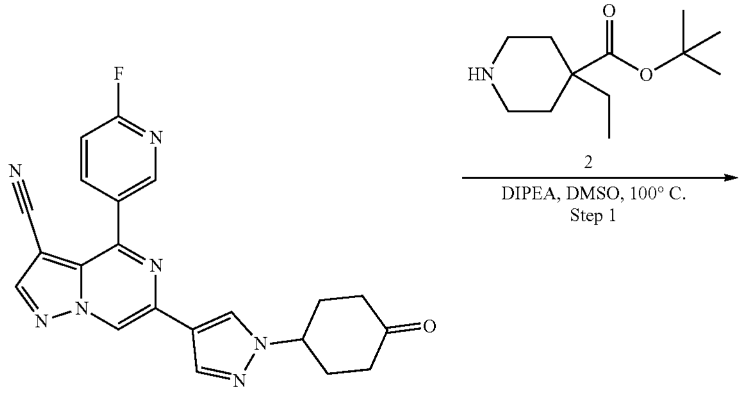

1

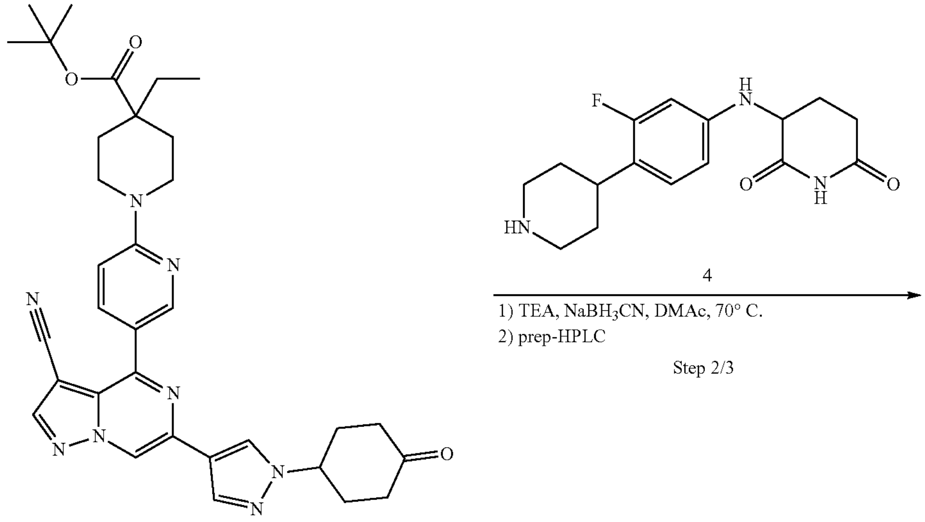

3

Step 1: To a solution of 4-(6-fluoropyridin-3-yl)-6-(1-(4-oxocyclohexyl)-1H-pyrazol-4-yl) pyrazolo[1,5-a]pyrazine-3-carbonitrile (1, 6.7 g, 13.00 mmol) in DMSO (20 mL) were added tert-butyl 4-ethylpiperidine-4-carboxylate (2, 2.77 g, 13.00 mmol) and DIPEA (5.04 g, 39.00 mmol, 6.79 mL). The mixture was stirred at 100° C. for 12 h. After being cooled to room temperature, the mixture was poured into the water (50 mL). During this period, yellow precipitate was formed. The precipitate was collected by filtration. The cake was concentrated in vacuo, and it was purified by silica gel column chromatography eluted with PE:EA=1:1 to give tert-butyl 1-(5-(3-cyano-6-(1-(4-oxocyclohexyl)-1H-pyrazol-4-yl)pyrazolo[1,5-a]pyrazin-4-yl)pyridin-2-yl)-4-ethylpiperidine-4-carboxylate (3, 4.5 g, 6.81 mmol, 52% yield) as a yellow solid. LCMS ($ES^+$): m/z 595.2 $[M+H]^+$ Step 2: To a solution of tert-butyl 1-(5-(3-cyano-6-(1-(4-oxocyclohexyl)-1H-pyrazol-4-yl)pyrazolo[1,5-a]pyrazin-4-yl)pyridin-2-yl)-4-ethylpiperidine-4-carboxylate (3, 600 mg, 1.01 mmol) in DMA (10 mL) were added 3-((3-fluoro-4-(piperidin-4-yl)phenyl)amino)piperidine-2,6-dione (4, 344.85 mg, 1.01 mmol, HCl salt), TEA (204.18 mg, 2.02 mmol, 281.24 µL) and $NaBH_3CN$ (126.80 mg, 2.02 mmol). The mixture was stirred at 70° C. for 12 h. The mixture was filtered, the filtrate was purified by reversed phase column (flow: 100 mL/min; gradient: from 0-60% water (0.1% formic acid) in MeCN over 35 min; column: C18, 330 g) to give tert-butyl 1-(5-(3-cyano-6-(1-(4-(4-(4-((2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethylpiperidine-4-carboxylate (300 mg, 322.38 µmol, 32% yield) as a yellow solid. LCMS ($ES^+$): m/z 884.5 $[M+H]^+$ Step 3: tert-butyl 1-[5-[3-cyano-6-[1-[4-[4-[4-[(2,6-dioxo-3-piperidyl)amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxylate (4.5 g, 5.09 mmol) was purified by prep-HPLC (flow: 60 mL/min; gradient: from 79-100% MeCN in water (10 mM $NH_4HCO_3$) over 10 min; column: Waters Xbridge C18 150*50 mm*10 um) to give tert-butyl 1-[5-[3-cyano-6-[1-[4-[4-[4-[(2,6-dioxo-3-piperidyl)amino]-2-fluoro-phenyl]-1-piperidyl] cyclohexyl]pyrazol-4-yl]pyrazolo[1,5-a]pyrazin-4-yl]-2-pyridyl]-4-ethyl-piperidine-4-carboxylate (5, Early eluting isomer 1, 2 g, 2.15 mmol, 42% yield) as a yellow solid. $^1H$ NMR (400 MHz, DMSO-$d_6$) δ=10.79 (s, 1H), 9.26 (s, 1H), 8.81 (s, 1H), 8.67 (d, J=2.4 Hz, 1H), 8.43 (s, 1H), 8.12 (s, 1H), 8.05 (dd, J=2.4, 8.9 Hz, 1H), 7.04-6.92 (m, 2H), 6.52-6.34 (m, 2H), 5.99 (d, J=7.6 Hz, 1H), 4.37-4.09 (m, 4H), 3.06 (t, J=11.6 Hz, 2H), 2.92 (d, J=10.4 Hz, 2H), 2.81-2.65 (m, 1H), 2.62-2.54 (m, 2H), 2.48-2.39 (m, 1H), 2.30 (t, J=10.0 Hz, 2H), 2.20-2.01 (m, 5H), 1.97-1.74 (m, 5H), 1.70-1.56 (m, 4H), 1.56-1.47 (m, 4H), 1.45 (s, 9H), 1.42-1.33 (m, 2H), 0.81 (t, J=7.6 Hz, 3H)

Step 4: The product of tert-butyl 1-[5-[3-cyano-6-[1-[4-[4-[4-[(2,6-dioxo-3-piperidyl)amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxylate (300 mg, 339.35 µmol) was purified by chiral separation (Add ACN and $CH_2Cl_2$ 50 ml into sample Instrument: Waters 80Q Mobile Phase: 60% IPA+ACN (0.1% $NH3{\cdot}H_2O$) in Supercritical $CO_2$ Flow Rate: 80 g/min Cycle Time: 3.9 min, total time: 50 min Single injection volume: 4.0 ml Back Pressure: 100 bar to keep the $CO_2$ in Supercritical flow) to give two peaks. The two peaks then were purified by Prep-HPLC (flow: 25 mL/min; gradient: from 29-59% MeCN in water (0.225% FA)-MeCN over 10 min; Phenomenex luna C18 150*25 mm*10 um tert-butyl 1-[5-[3-cyano-6-[1-[4-[4-[4-[[(3S)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxylate (6, Early eluting isomer 1-1, 113.9 mg, 121.24 µmol) as yellow solid. LCMS ($ES^+$): m/z 884.4 $[M+H]^+$ tert-butyl 1-[5-[3-cyano-6-[1-[4-[4-[4-[[(3R)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxylate (7, Late eluting isomer 1-2, 122.4 mg, 130.29 µmol) was also obtained as yellow solid. LCMS ($ES^+$): m/z 884.4 $[M+H]^+$

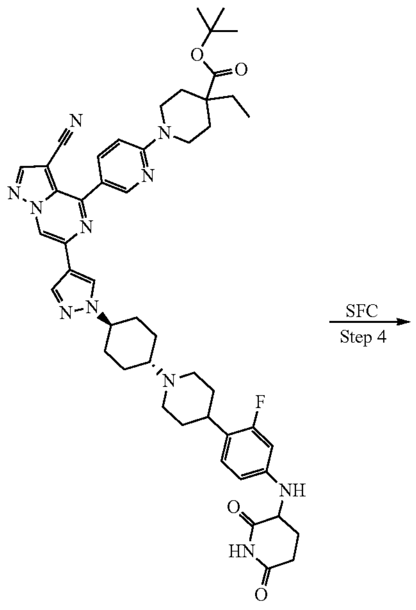

5

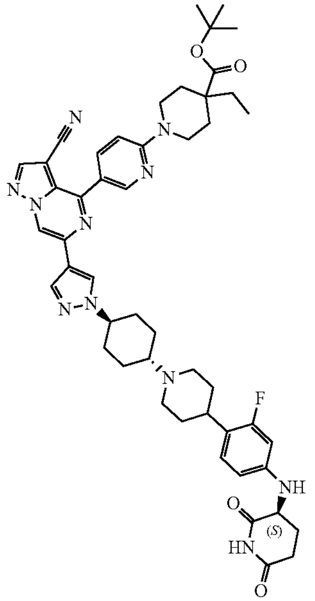

+

6

-continued

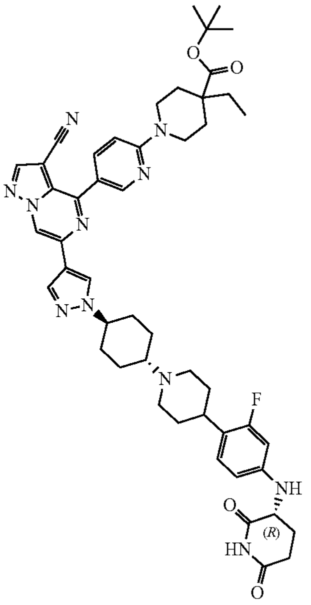

7

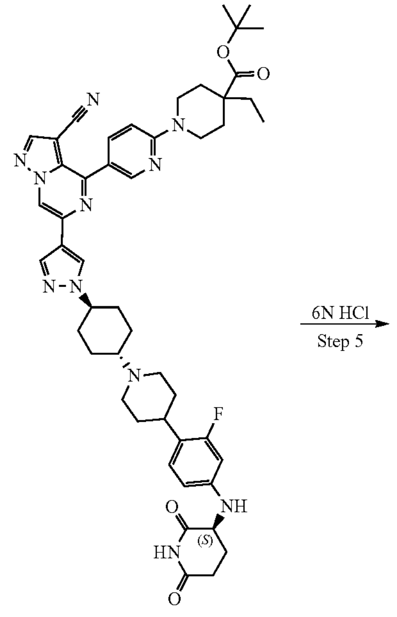

6

-continued

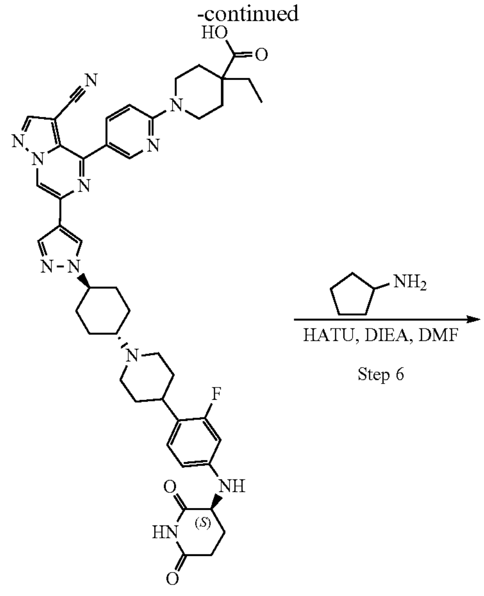

8

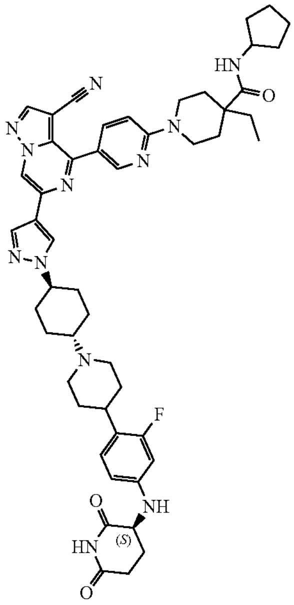

Compound 141

Step 5: A solution of tert-butyl 1-[5-[3-cyano-6-[1-[4-[4-[4-[[(3S)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxylate (6, Early eluting isomer 1-1, 700 mg, 791.81 μmol) in HCl (6 M, 5 mL) was stirred at 10° C. for 1 h. The mixture was filtered. The filtrated was purified by reversed phase column (flow: 100 mL/min; gradient: from 0-60% water (0.1% formic acid) in MeCN over 35 min; column: C18, 330 g) to give 1-[5-[3-cyano-6-[1-[4-[4-[4-[[(3S)-2,6-dioxo-3-piperidyl] amino]-2-fluoro-phenyl]-1-piperidyl] cyclohexyl]pyrazol-4-yl]pyrazolo[1,5-a]pyrazin-4-yl]-2-pyridyl]-4-ethyl-piperidine-4-carboxylic acid (8, 390 mg, 466.33 μmol, 59% yield) as a yellow solid. LCMS ($ES^+$): m/z 828.8 $[M+H]^+$ Step 6: To a solution of 1-[5-[3-cyano-6-[1-[4-[4-[4-[[(3S)-2,6-dioxo-3-piperidyl]amino]-2-fluoro-phenyl]-1-piperidyl]cyclohexyl]pyrazol-4-yl]pyrazolo[1,5-a]pyrazin-4- yl]-2-pyridyl]-4-ethyl-piperidine-4-carboxylic acid (8, 100 mg, 120.78 μmol) in DMF (2 mL) were added HATU (68.89 mg, 181.17 μmol), DIPEA (46.83 mg, 362.34 μmol, 63.11 μL) and cyclopentanamine (15.43 mg, 181.17 μmol, 17.88 μL). The mixture was stirred at 10° C. for 2 h. The mixture was filtered. The filtrated was purified by Prep-HPLC (flow: 25 mL/min; gradient: from 29-59% MeCN in water (0.225% FA)-MeCN over 10 min; Phenomenex luna C18 150*25 mm*10 um) to give 1-[5-[3-cyano-6-[1-[4-[4-[4-[[(3S)-2,6-dioxo-3-piperidyl]amino]-2-fluoro-phenyl]-1-piperidyl]cyclohexyl] pyrazol-4-yl]pyrazolo[1,5-a]pyrazin-4-yl]-2-pyridyl]-N-cyclopentyl-4-ethyl-piperidine-4-carboxamide (Compound 141, 99.59 mg, 104.76 μmol, 87% yield) as a yellow solid.

LCMS ($ES^+$): m/z 895.5 $[M+H]^+$ $^1H$ NMR (400 MHz, DMSO-$d_6$) δ=10.80 (s, 1H), 9.28 (s, 1H), 8.82 (s, 1H), 8.67 (d, J=2.4 Hz, 1H), 8.44 (s, 1H), 8.16 (s, 1H), 8.14 (s, 1H), 8.04 (dd, J=2.4, 8.8 Hz, 1H), 7.44 (d, J=7.2 Hz, 1H), 6.99 (d, J=9.2 Hz, 2H), 6.54-6.42 (m, 2H), 6.08 (d, J=7.6 Hz, 1H), 4.36-4.20 (m, 2H), 4.19-4.06 (m, 3H), 3.17-3.01 (m, 3H), 2.99-2.79 (m, 3H), 2.74 (ddd, J=5.2, 12.3, 17.6 Hz, 1H), 2.67-2.52 (m, 2H), 2.26-2.04 (m, 7H), 1.97-1.73 (m, 10H), 1.72-1.59 (m, 4H), 1.55-1.41 (m, 6H), 1.40-1.30 (m, 2H), 0.74 (t, J=7.6 Hz, 3H)

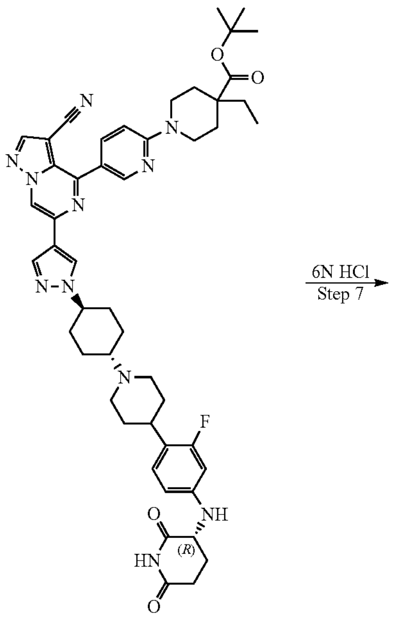

7

-continued

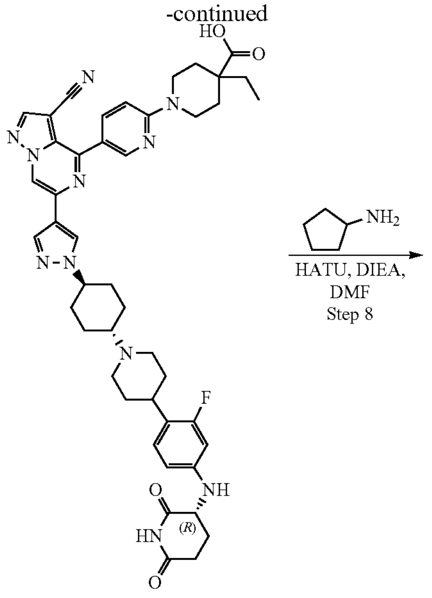

9

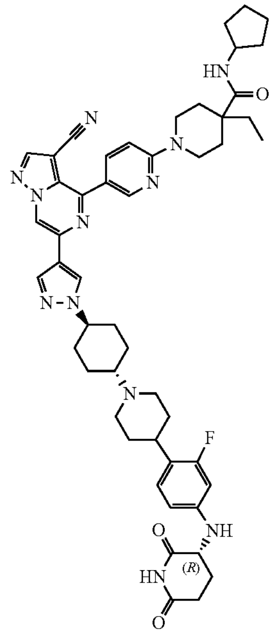

Compound 142

The procedures in steps 7 and 8 were similar to those of steps 5 and 6.

1-[5-[3-cyano-6-[1-[4-[4-[4-[[(3R)-2,6-dioxo-3-piperidyl]amino]-2-fluoro-phenyl]-1-piperidyl]cyclohexyl] pyrazol-4-yl]pyrazolo[1,5-a]pyrazin-4-yl]-2-pyridyl]-N-cyclopentyl-4-ethyl-piperidine-4-carboxamide. (Compound 142)

LCMS ($ES^+$): m/z 895.5 $[M+H]^+$ $^1H$ NMR (400 MHz, DMSO-$d_6$) δ=10.80 (s, 1H), 9.28 (s, 1H), 8.82 (s, 1H), 8.66 (d, J=2.4 Hz, 1H), 8.44 (s, 1H), 8.16 (s, 1H), 8.15 (s, 1H), 8.04 (dd, J=2.4, 8.8 Hz, 1H), 7.44 (d, J=7.6 Hz, 1H), 7.07-6.93 (m, 2H), 6.56-6.40 (m, 2H), 6.05 (d, J=7.6 Hz, 1H), 4.37-4.18 (m, 2H), 4.18-4.05 (m, 3H), 3.18 (d, J=10.0 Hz, 2H), 3.11 (t, J=11.2 Hz, 2H), 2.86-2.66 (m, 5H), 2.61-2.55 (m, 2H), 2.18 (d, J=12.0 Hz, 4H), 2.12-1.98 (m, 3H), 1.92-1.73 (m, 9H), 1.69-1.56 (m, 4H), 1.55-1.42 (m, 6H), 1.40-1.29 (m, 2H), 0.74 (t, J=7.6 Hz, 3H)

Example 160: Synthesis of 1-(5-(3-cyano-6-(1-((1R, 4r)-4-(4-(4-(((R)-2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-(tetrahydro-2H-pyran-4-yl)piperidine-4-carboxamide (Compound 143)

(Configurations are arbitrarily assigned)

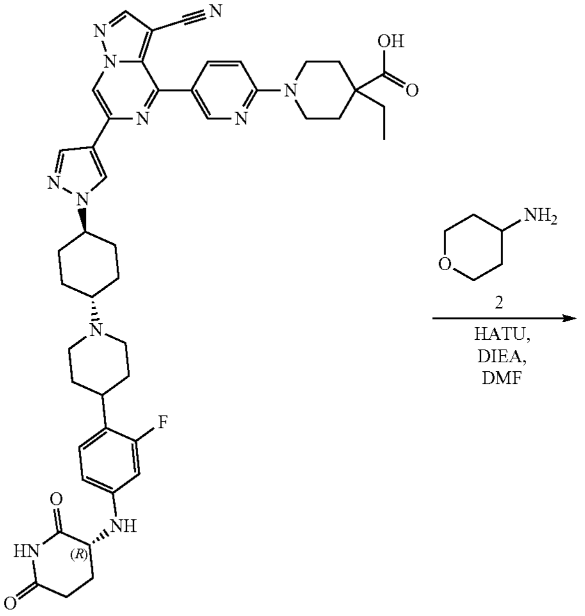

1

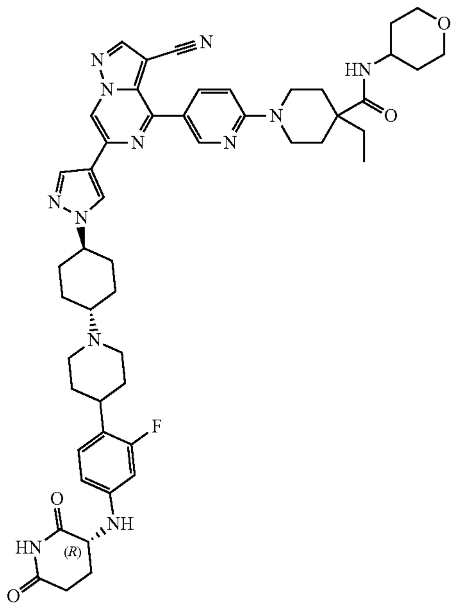

Compound 143

To a solution of 1-[5-[3-cyano-6-[1-[4-[4-[4-[[(3R)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxylic acid (1, 120 mg, 144.94 μmol) in DMF (2 mL) was added tetrahydropyran-4-amine (2, 21.99 mg, 217.41 μmol), HATU (110.22 mg, 289.87 μmol) and Diisopropylethylamine (56.20 mg, 434.81 μmol, 75.74 μL), the reaction mixture was stirred at 25° C. for 16 h. The residue was purified by prep-HPLC (flow: 25 mL/min; gradient: from 5-45% MeCN in water (0.225% FA) over 7 min; column: Phenomenex Gemini-NX C18 75*30 mm*3 um) to give 1-(5-(3-cyano-6-(1-((1R,4r)-4-(4-(4-(((R)-2,6-dioxopiperidin-3-yl)amino)-2-fluorophenyl)piperidin-1-yl)cyclohexyl)-1H-pyrazol-4-yl)pyrazolo[1,5-a]pyrazin-4-yl) pyridine-2-yl)-4-ethyl-N-(tetrahydro-2H-pyran-4-yl)piperidine-4-carboxamide (Compound 143, 77.68 mg, 80.35 μmol, 55% yield) as a yellow solid.

LCMS ($ES^+$): m/z 911.4 $[M+H]^+$ $^1H$ NMR (400 MHz, DMSO-$d_6$) δ=10.79 (d, J=2.0 Hz, 1H), 9.27 (d, J=3.2 Hz, 1H), 8.82 (d, J=3.6 Hz, 1H), 8.67 (br s, 1H), 8.44 (d, J=3.2 Hz, 1H), 8.16 (br s, 1H), 8.14 (d, J=3.6 Hz, 1H), 8.04 (d, J=8.4 Hz, 1H), 7.55-7.47 (m, 1H), 6.99 (d, J=6.8 Hz, 2H), 6.51-6.39 (m, 2H), 6.05-5.97 (m, 1H), 4.35-4.27 (m, 1H), 4.25-4.08 (m, 4H), 3.94-3.80 (m, 4H), 3.13-3.01 (m, 5H), 2.85-2.71 (m, 5H), 2.33 (br s, 1H), 2.17 (d, J=7.6 Hz, 5H), 2.09-2.04 (m, 1H), 2.00-1.94 (m, 2H), 1.92-1.77 (m, 5H), 1.65 (d, J=12.4 Hz, 4H), 1.53-1.48 (m, 4H), 1.40-1.32 (m, 2H), 0.78

0.72 (m, 3H)

Example 161: Synthesis of 1-(5-(3-cyano-6-(1-((1S, 4r)-4-(4-(4-(((S)-2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-(tetrahydro-2H-pyran-4-yl)piperidine-4-carboxamide (Compound 144)

(Configurations are arbitrarily assigned)

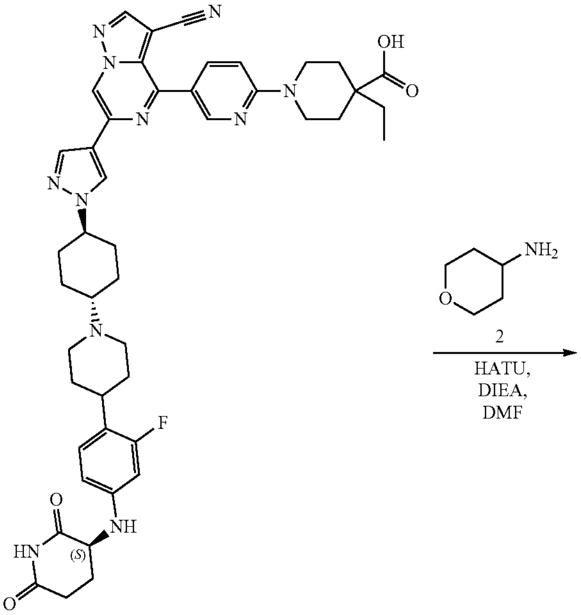

1

-continued

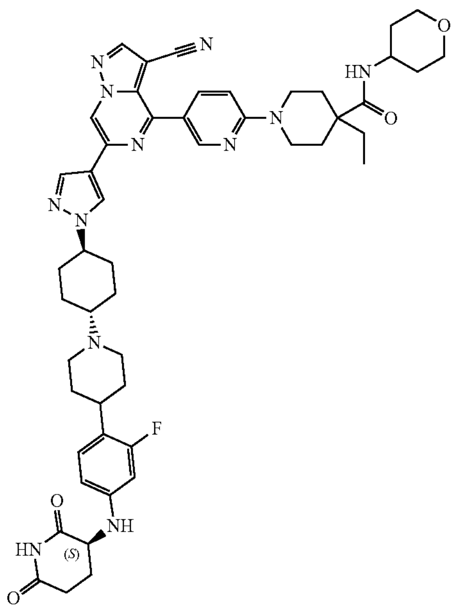

Compound 144

To a solution of 1-[5-[3-cyano-6-[1-[4-[4-[4-[[(3S)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxylic acid (1, 120.00 mg, 144.94 μmol) in DMF (2 mL) was added tetrahydropyran-4-amine (2, 21.99 mg, 217.41 μmol), HATU (110.22 mg, 289.87 μmol) and Diisopropylethylamine (56.20 mg, 434.81 μmol, 75.74 μL), the reaction mixture was stirred at 25° C. for 16 h. The residue was purified by prep-HPLC (flow: 25 mL/min; gradient: from 5-45% MeCN in water (0.225% FA) over 7 min; column: Phenomenex Gemini-NX C18 75*30 mm*3 um) to give 1-(5-(3-cyano-6-(1-((1S,4r)-4-(4-(4-(((S)-2,6-dioxopiperidin-3-yl)amino)-2-fluorophenyl)piperidin-1-yl)cyclohexyl)-1H-pyrazol-4-yl)pyrazolo[1,5-a]pyrazin-4-yl)pyridin-2-yl)-4-ethyl-N-(tetrahydro-2H-pyran-4-yl)piperidine-4-carboxamide (Compound 144, 79.14 mg, 81.86 μmol, 56% yield) as a yellow solid.

LCMS ($ES^+$): m/z 911.5 $[M+H]^+$ $^1H$ NMR (400 MHz, DMSO-$d_6$) δ=10.79 (s, 1H), 9.27 (s, 1H), 8.82 (s, 1H), 8.66 (d, J=2.4 Hz, 1H), 8.44 (s, 1H), 8.15 (s, 1H), 8.14 (s, 1H), 8.04 (dd, J=2.5, 9.0 Hz, 1H), 7.50 (d, J=7.8 Hz, 1H), 7.03-6.95 (m, 2H), 6.48-6.40 (m, 2H), 6.01 (d, J=7.2 Hz, 1H), 4.35-4.26 (m, 1H), 4.24-4.11 (m, 3H), 3.95-3.80 (m, 3H), 3.16-2.98 (m, 5H), 2.78-2.62 (m, 5H), 2.44 (br s, 2H), 2.34-2.31 (m, 1H), 2.22-2.12 (m, 4H), 2.11-2.04 (m, 1H), 1.96 (d, J=10.8 Hz, 2H), 1.91-1.76 (m, 4H), 1.70-1.61 (m, 5H), 1.55-1.48 (m, 5H), 1.41-1.31 (m, 2H), 0.75 (t, J=7.6 Hz, 3H)

Example 162: Synthesis of N-tert-butyl-1-[5-[3-cyano-6-[1-[4-[4-[4-[[(3S)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxamide (Compound 145)

N-tert-butyl-1-[5-[3-cyano-6-[1-[4-[4-[4-[[(3R)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxamide (Compound 146)

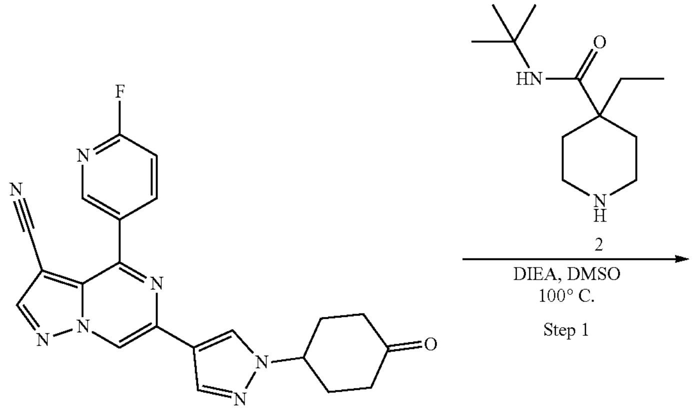

1

-continued

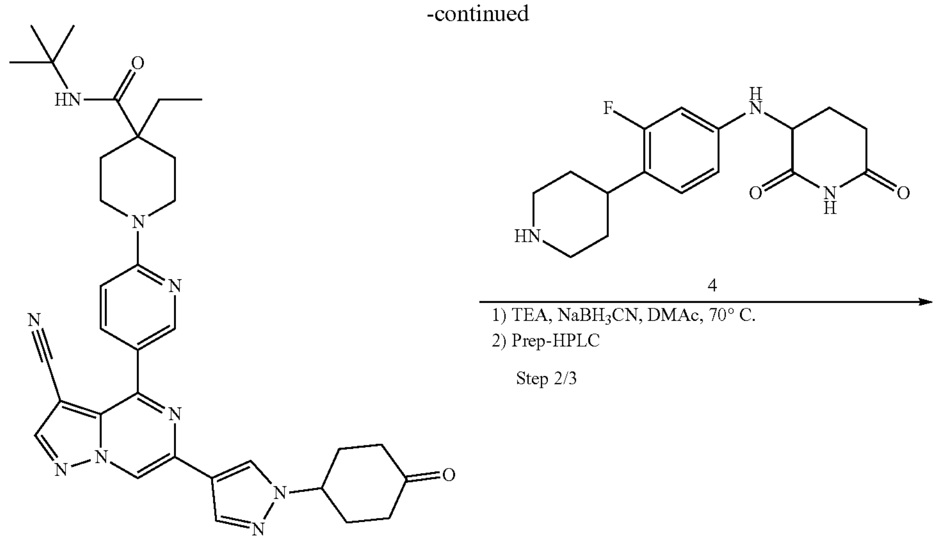

3

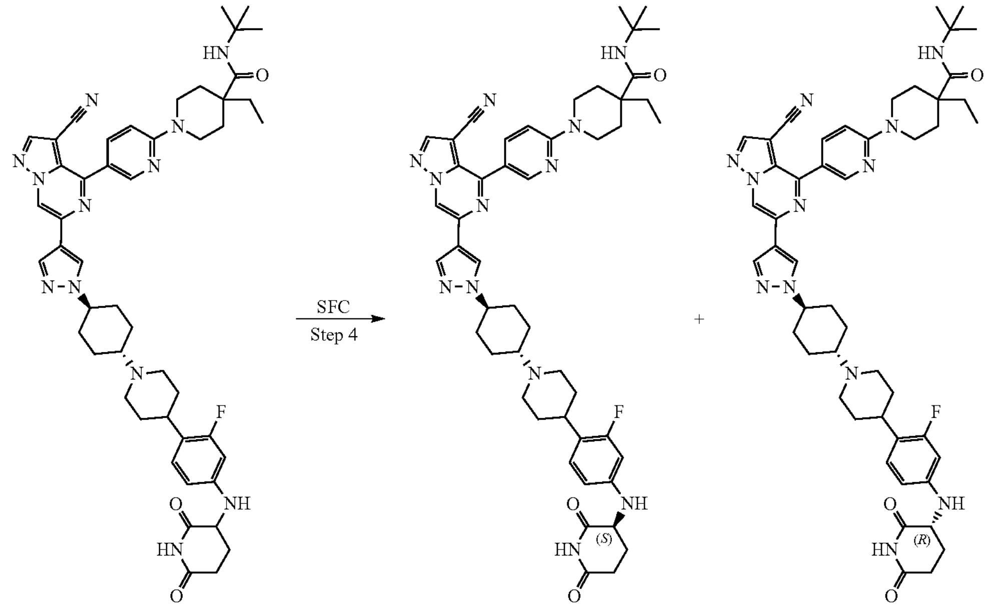

5 Compound 145 Compound 146

Step 1: To a solution of N-tert-butyl-4-ethyl-piperidine-4-carboxamide (2, 660 mg, 2.65 mmol, HCl salt) and 4-(6-fluoro-3-pyridyl)-6-[1-(4-oxocyclohexyl)pyrazol-4-yl]pyrazolo[1,5-a]pyrazine-3-carbonitrile (1, 1.37 g, 2.65 mmol, TFA salt) in DMSO (13.2 mL) was added DIPEA (1.04 g, 8.04 mmol, 1.4 mL). The mixture was stirred at 100° C. for 16 h. The mixture was cooled to 10° C. The mixture was poured into water (70 mL). Large yellow precipitate was carried out. The mixture was filtered, and the filter cake was washed with water (20 mL). The filter cake was dried in vacuo to give N-tert-butyl-1-[5-[3-cyano-6-[1-(4-oxocyclohexyl)pyrazol-4-yl]pyrazolo[1,5-a]pyrazin-4-yl]-2-pyridyl]-4-ethyl-piperidine-4-carboxamide (3, 1.65 g, 2.08 mmol, 79% yield) as a yellow solid. LCMS ($ES^+$): m/z 594.4 $[M+H]^+$ Step 2: To a solution of N-tert-butyl-1-[5-[3-cyano-6-[1-(4-oxocyclohexyl)pyrazol-4-yl]pyrazolo[1,5-a]pyrazin-4-yl]-2-pyridyl]-4-ethyl-piperidine-4-carboxamide (3, 550 mg, 694.77 μmol) and 3-[3-fluoro-4-(4-piperidyl)anilino]piperidine-2,6-dione (4, 476 mg, 1.39 mmol, HCl salt) in DMAc (10 mL) was added TEA (355.74 mg, 3.52 mmol, 490 μL). The mixture was stirred at 10° C. for 0.5 h. Then sodium cyanoborohydride (88 mg, 1.40 mmol) was added to the mixture. The resulting mixture was stirred at 70° C. for 16 h. The mixture was diluted with DMF (10 mL). The mixture was purified by reversed phase column (flow: 60 mL/min; gradient: from 38-46% water (0.1% formic acid) in MeCN over 48 min; column: Welch Ultimate XB-C18, 20-40 m, 100 Å, I.D. 95 mm*H 365 mm) to give N-tert-butyl-1-[5-[3-cyano-6-[1-[4-[4-[4-[(2,6-dioxo-3-piperidyl)amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxamide (600 mg, 468.82 mol, 67% yield) as a yellow solid. LCMS ($ES^+$): m/z 883.5 $[M+H]^+$ Step 3: The mixture was separated by prep-HPLC (flow: 60 mL/min; gradient: from 56-86% MeCN in water (10 mM $NH_4HCO_3$) over 10 min; column: Waters Xbridge C18 150×50 mm×10 μm) to give N-tert-butyl-1-[5-[3-cyano-6-[1-[4-[4-[4-[(2,6-dioxo-3-piperidyl)amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxamide (5, Early eluting isomer 1, 110 mg, 120.83 mol, 18% yield) as a yellow solid. LCMS ($ES^+$): m/z 883.4 $[M+H]^+$ Step 4: The mixture 5 (Early eluting isomer 1) was separated by chiral SFC (0.1% $NH_3H_2O$-IPA condition, column: DAICEL CHIRALPAK AS (250 mm×30 mm, 10 μm); B %: 50%-50%; 6.7 min, 55 min) to give two impure products. The crude product 1 was purified by Prep-HPLC (flow: 25 mL/min; gradient: from 18-48% MeCN in water (0.225% FA) over 10 min; column: Phenomenex Synergi C18 150×25 mm×10 μm) to give N-tert-butyl-1-[5-[3-cyano-6-[1-[4-[4-[4-[[(3S)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxamide (Compound 145, Early eluting isomer 1-1, 57.43 mg, 61.19 μmol, 49% yield, formic acid salt) as a yellow solid.

LCMS ($ES^+$): m/z 883.6 $[M+H]^+$ $^1H$ NMR (400 MHz, DMSO-$d_6$) δ=10.79 (s, 1H), 9.27 (s, 1H), 8.82 (s, 1H), 8.67 (d, J=2.4 Hz, 1H), 8.44 (s, 1H), 8.31 (s, 1H), 8.14 (s, 1H), 8.04 (dd, J=2.4, 8.8 Hz, 1H), 7.06-6.94 (m, 2H), 6.86 (s, 1H), 6.53-6.36 (m, 2H), 5.99 (d, J=7.6 Hz, 1H), 4.34-4.27 (m, 1H), 4.23-4.09 (m, 3H), 3.13 (t, J=11.2 Hz, 2H), 2.94 (d, J=10.6 Hz, 2H), 2.79-2.69 (m, 1H), 2.63-2.53 (m, 2H), 2.37-2.26 (m, 3H), 2.21-2.04 (m, 5H), 1.98-1.75 (m, 5H), 1.70-1.57 (m, 4H), 1.56-1.44 (m, 4H), 1.38-1.25 (m, 11H), 0.76 (t, J=7.6 Hz, 3H).

The crude product 2 was purified by Prep-HPLC (flow: 25 mL/min; gradient: from 18-48% MeCN in water (0.225% FA) over 10 min; column: Phenomenex Synergi C18 150×25 mm×10 μm) to give N-tert-butyl-1-[5-[3-cyano-6-[1-[4-[4-[4-[[(3R)-2,6-dioxo-3-piperidyl]amino]-2-fluoro-phenyl]-1-piperidyl]cyclohexyl]pyrazol-4-yl]pyrazolo[1,5-a]pyrazin-4-yl]-2-pyridyl]-4-ethyl-piperidine-4-carboxamide (Compound 146, Late eluting isomer 1-2, 60.79 mg, 64.78 μmol, 52% yield, formic acid salt) as a yellow solid.

LCMS ($ES^+$): m/z 883.6 $[M+H]^+$ $^1H$ NMR (400 MHz, DMSO-$d_6$) δ=10.79 (s, 1H), 9.27 (s, 1H), 8.82 (s, 1H), 8.67 (d, J=2.4 Hz, 1H), 8.44 (s, 1H), 8.31 (s, 1H), 8.14 (s, 1H), 8.04 (dd, J=2.4, 8.8 Hz, 1H), 7.03-6.96 (m, 2H), 6.86 (s, 1H), 6.49-6.39 (m, 2H), 5.99 (d, J=7.6 Hz, 1H), 4.30 (ddd, J=5.2, 6.8, 11.6 Hz, 1H), 4.22-4.10 (m, 3H), 3.13 (t, J=11.2 Hz, 2H), 2.94 (d, J=10.4 Hz, 2H), 2.79-2.68 (m, 1H), 2.61-2.53 (m, 2H), 2.37-2.28 (m, 3H), 2.21-2.04 (m, 5H), 1.97-1.74 (m, 5H), 1.72-1.57 (m, 4H), 1.56-1.44 (m, 4H), 1.38-1.24 (m, 11H), 0.76 (t, J=7.6 Hz, 3H).

Example 163: Synthesis of 6-(1-((1s, 4s)-4-(4-(4-((2,6-Dioxopiperidin-3-yl)amino)-2-fluorophenyl)piperazin-1-yl)cyclohexyl)-1H-pyrazol-4-yl)-4-(6-(4-methoxy-4-((6-methoxypyridin-3-yl)methyl)piperidin-1-yl)pyridin-3-yl)pyrazolo[1,5-a]pyrazine-3-carbonitrile (Compound 147)

(Configurations are arbitrarily assigned)

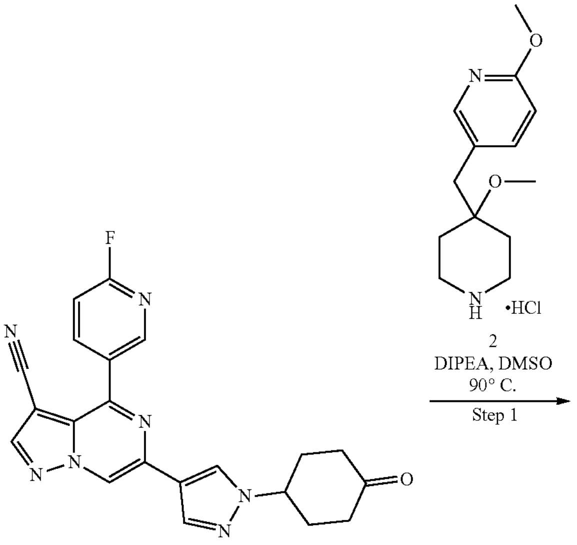

1

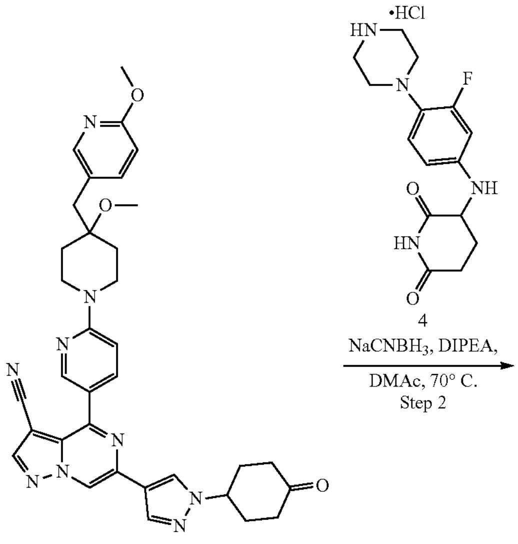

3

-continued

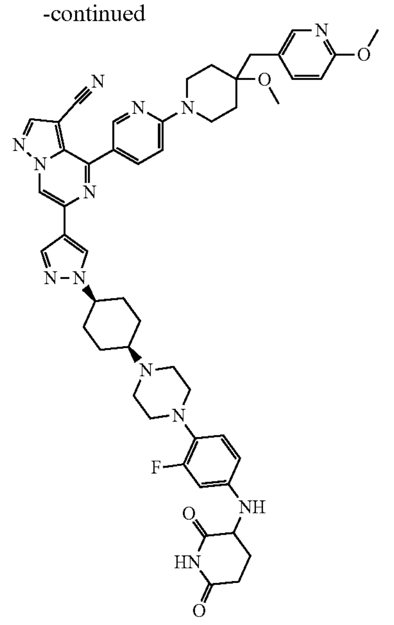

Compound 147

Step 1: Into a 50 mL sealed-tube containing a well-stirred solution of 2-methoxy-5-[(4-methoxy-4-piperidyl)methyl] pyridine hydrochloride (2, 191.33 mg, 0.701 mmol) and 4-(6-fluoro-3-pyridyl)-6-[1-(4-oxocyclohexyl)pyrazol-4-yl] pyrazolo[1,5-a]pyrazine-3-carbonitrile (1, 250 mg, 0.622 mmol) in anhydrous DMSO (5 mL) was added DIPEA (402.47 mg, 3.11 mmol, 0.542 mL) at ambient temperature under nitrogen atmosphere. The resulting reaction was heated at 90° C. under close condition. Progress of the reaction was monitored by LCMS and found complete after 16 h. The reaction mixture was cooled to room temperature. The reaction mixture was diluted with water (20 mL) and the product was extracted with DCM (2×60 mL). Organic phases were combined, dried (anhydrous $Na_2SO_4$), filtered and the filtrate was concentrated under reduced pressure to get a crude residue. The crude product was purified by flash silica-gel (230-400 mesh; 50 g SNAP) column with 0-100% EtOAc/pet ether while desired compound was eluting at 80-90% of the mobile phase to afford 4-[6-[4-methoxy-4-[(6-methoxy-3-pyridyl)methyl]-1-piperidyl]-3-pyridyl]-6-[1-(4-oxocyclohexyl)pyrazol-4-yl]pyrazolo[1,5-a]pyrazine-3-carbonitrile (3, 270 mg, 0.357 mmol, 57% yield) as a yellow solid. LCMS ($ES^+$): m/z 618.3 $[M+H]^+$.

Step 2: Into a 8 mL glass-vial containing a well-stirred solution of 3-(3-fluoro-4-piperazin-1-yl-anilino)piperidine-2,6-dione hydrochloride (4, 332.97 mg, 0.971 mmol) and 4-[6-[4-methoxy-4-[(6-methoxy-3-pyridyl)methyl]-1-piperidyl]-3-pyridyl]-6-[1-(4-oxocyclohexyl)pyrazol-4-yl]pyrazolo[1,5-a]pyrazine-3-carbonitrile (3, 200 mg, 0.323 mmol) in anhydrous DMAc (4 mL) were added Sodium cyanoborohydride (101.73 mg, 1.62 mmol) and DIPEA (209.23 mg, 1.62 mmol, 0.281 mL) at ambient temperature and the reaction mixture was heated to 70° C. for 16 h and the reaction mixture was cooled to ambient temperature. After complete consumption of the starting materials as indicated by UPLC and the reaction was quenched with ice-cold water (20 mL) and the solid precipitated out was filtered and dried to afford a crude solid (210 mg). The diastereomeric mixture was purified by reverse phase perp-HPLC [Column: XBRIDGE OBD C18 19×150 mm 5 micron; Mobile phase: A: 0.1% $NH_4HCO_3$ in MQ-water; B: Acetonitrile; Flow rate: 15 mL/minutes to get Compound 147 (Early eluting isomer) with RT=2.83 minutes. Desired fractions were combined and lyophilized to afford 6-(1-((1s, 4s)-4-(4-(4-((2,6-dioxopiperidin-3-yl)amino)-2-fluorophenyl)piperazin-1-yl) cyclohexyl)-1H-pyrazol-4-yl)-4-(6-(4-methoxy-4-((6-methoxypyridin-3-yl)methyl)piperidin-1-yl)pyridin-3-yl) pyrazolo[1,5-a]pyrazine-3-carbonitrile (43 mg, 0.045 mmol, 14% yield) as a yellow solid. $^1H$ NMR (400 MHz, DMSO-$d_6$). δ 10.76 (s, 1H), 9.29 (s, 1H), 8.83 (d, J=0.8 Hz, 1H), 8.68 (d, J=2.4 Hz, 1H), 8.46 (s, 1H), 8.15 (s, 1H), 8.06 (dd, J=9, 2 Hz, 1H), 7.98 (s, 1H), 7.53 (dd, J=8.4, 1.6 Hz, 1H), 7.02 (d, J=9.2 Hz, 1H), 6.84 (t, J=9.2 Hz, 1H), 6.76 (d, J=8.4 Hz, 1H), 6.52 (d, J=15.2 Hz, 1H), 6.43 (d, J=8 Hz, 1H), 5.81 (d, J=8 Hz, 1H), 4.32-4.16 (m, 4H), 3.83 (s, 3H), 3.20 (t, J=11.6 Hz, 2H), 2.87 (m, 4H), 2.77 (s, 3H), 2.72-2.65 (m, 5H), 2.55 (m, 1H), 2.52-2.42 (m, 2H), 2.22-2.02 (m, 4H), 1.98 (m, 2H), 1.95-1.75 (m, 3H), 1.70 (m, 2H) and 1.55-1.40 (m, 4H). LCMS ($ES^+$): m/z 908.3 $[M+H]^+$.

Example 164: Synthesis of 4-(6-(5H-Spiro[furo[3,4-b]pyridine-7,4'-piperidin]-1'-yl)pyridin-3-yl)-6-(1-((1r, 4r)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyrazine-3-carbonitrile (Compound 148)

(Configurations are arbitrarily assigned)

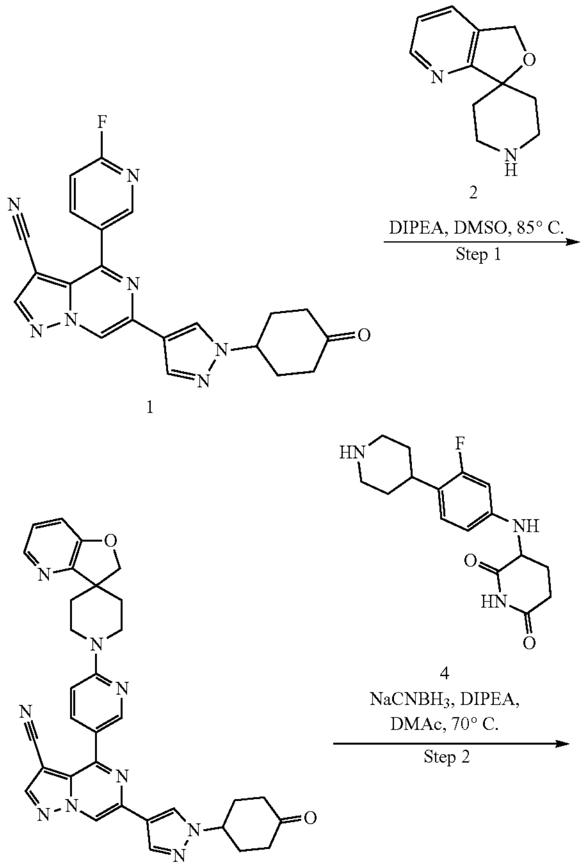

2

1

4

3

-continued

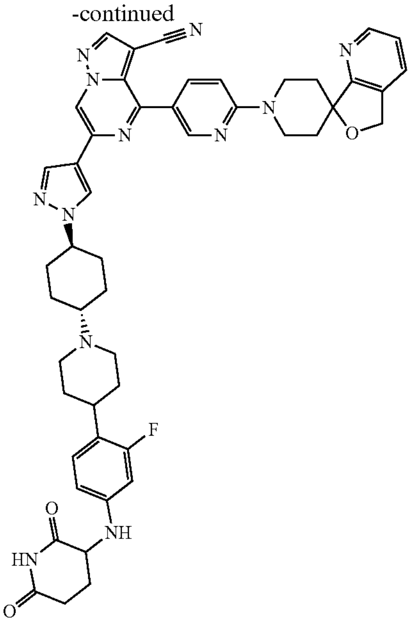

Compound 148

Step 1: Into a 100 mL sealed-tube containing a well-stirred solution of spiro[5H-furo[3,4-b]pyridine-7,4'-piperidine]·trifluoroacetic acid (2, 1.23 g, 4.04 mmol) and 6-[1-(1,4-dioxaspiro[4.5]decan-8-yl)pyrazol-4-yl]-4-(6-fluoro-3-pyridyl)pyrazolo[1,5-a]pyrazine-3-carbonitrile (1, 1.2 g, 2.69 mmol) in anhydrous DMSO (20 mL) was added DIPEA (4.45 g, 34.45 mmol, 6 mL) under nitrogen atmosphere. The reaction mixture was heated to 90° C. for 14 h. After completion of the reaction as indicated by UPLC, the reaction mixture was cooled and treated with water (50 mL) and solid precipitated out was filtered. The solid on the filter was dried under reduced pressure to afford a crude mass. The crude was purified by flash silica-gel (230-400 mesh) column with 50-100% EtOAc/pet ether, while desired compound eluting at 100% EtOAc to get 6-[1-(1,4-dioxaspiro[4.5]decan-8-yl)pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (3, 900 mg, 1.43 mmol, 53% yield) as an yellow solid. LCMS ($ES^+$): m/z 616.2 $[M+H]^+$.

Step 2: Into a 50 mL glass-vial containing a well-stirred solution of 6-[1-(4-oxocyclohexyl)pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (3, 380 mg, 0.664 mmol) and 3-[3-fluoro-4-(4-piperidyl)anilino]piperidine-2,6-dione·hydrochloride (4, 568.05 mg, 1.66 mmol) in anhydrous DMAc (5 mL) were added DIPEA (429.57 mg, 3.32 mmol, 0.557 mL) and Sodium cyanoborohydride (208.87 mg, 3.32 mmol) at ambient temperature and the reaction mixture was stirred at 70° C. for 16 h. After complete consumption of the starting material as indicated by UPLC, ice-cold water (20 mL) was added to the reaction mixture and solid precipitated out was filtered and dried to afford a crude mass (600 mg). The crude was purified by flash silica-gel (230-400 mesh) column with 0-15% MeOH/DCM, while desired compound was eluting at 10% to afford 320 mg of product with a diastereomeric mixture of 41.56% and 54.20%. The diastereomeric mixture (320 mg) was once again purified by perp-HPLC XBRIDGE OBD C18 (19×150 mm 5 micron) column; Mobile phase: A: 10 mm Ammonium bicarbonate in MQ-water; B: Acetonitrile; Flow rate: 15 mL/minutes to obtain:

Early eluting isomer: Fractions with RT=11.8 minutes were combined and lyophilized to afford 6-[1-[4-[4-[4-[(2,6-dioxo-3-piperidyl)amino]-2-fluoro-phenyl]-1-piperidyl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (Compound 148, 60 mg, 0.067 mmol, 10% yield) as a yellow solid. LCMS ($ES^+$): m/z 861.3 $[M+H]^+$. $^1H$ NMR (400 MHz, DMSO-$d_6$). δ 10.78 (s, 1H), 9.30 (s, 1H), 8.84 (s, 1H), 8.73 (d, J=2.4 Hz, 1H), 8.47 (s, 1H), 8.44 (d, J=3.6 Hz, 1H), 8.16 (s, 1H), 8.11 (dd, J=9.2, 2.4 Hz, 1H), 7.79 (d, J=7.6 Hz, 1H), 7.32 (dd, J=7.6, 5.2 Hz, 1H), 7.13 (d, J=8.8 Hz, 1H), 7.00 (t, J=8.4 Hz, 1H), 6.47-6.43 (m, 2H), 5.99 (d, J=7.6 Hz, 1H), 5.11 (s, 2H), 4.49 (m, 2H), 4.31-4.20 (m, 2H), 3.52-3.42 (m, 3H), 2.96-2.93 (m, 2H), 2.75-2.60 (m, 1H), 2.60 (m, 1H), 2.35 (m, 1H), 2.30-2.11 (m, 3H), 2.08-1.99 (m, 5H), 1.96-1.89 (m, 3H), 1.88-1.83 (m, 2H), 1.76-1.63 (m, 5H) and 1.56-1.50 (m, 2H).

Example 165: Synthesis of 6-[1-[4-[4-[2-fluoro-4-[[rac-(3R)-2,6-dioxo-3-piperidyl]amino]phenyl]-1-piperidyl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (Compound 149)

(Configurations are arbitrarily assigned)

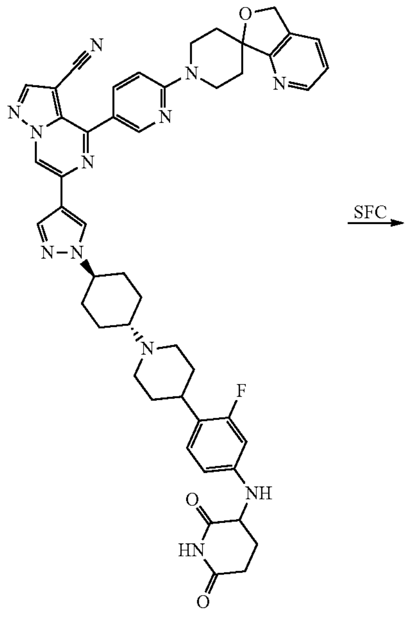

Compound 148

-continued

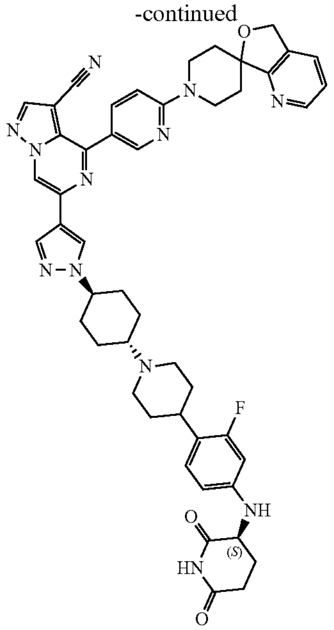

1

+

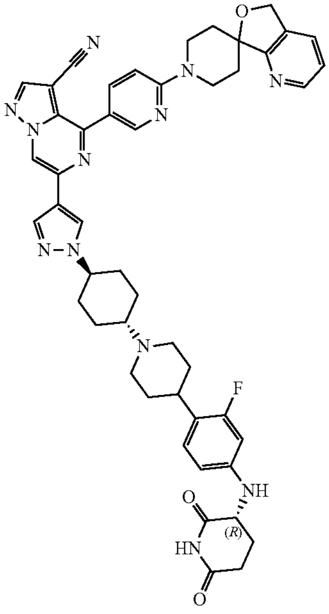

Compound 149

Compound 148 was separated by SFC [Column: DAICEL CHIRALPAK AS (250 mm*30 mm, 10 um); Condition: 75% IPA+ACN (0.1% $NH_3 \cdot H_2O$) in Supercritical $CO_2$; Flow Rate: 80 mL/min; Cycle Time: 3 min, total time: 60 min; Single injection volume: 2.0 ml; Back Pressure: 100 bar to keep the $CO_2$ in Supercritical flow]. Then the residue was purified by prep-HPLC ((column: 3_Phenomenex Luna C18 75*30 mm*3 um; mobile phase: [water (0.225% FA)-ACN]; B %: 14%-44%, 10 min).

6-[1-[4-[4-[2-fluoro-4-[[rac-(3R)-2,6-dioxo-3-piperidyl] amino]phenyl]-1-piperidyl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (Compound 149, Late eluting isomer, 73.38 mg, 80.90 mol, 23% yield, formic acid salt) was obtained as yellow solid. LCMS ($ES^+$): m/z 861.5 $[M+H]^+$. $^1H$ NMR (400 MHz, DMSO-$d_6$) δ=10.80 (s, 1H), 9.29 (s, 1H), 8.84 (s, 1H), 8.72 (d, J=2.4 Hz, 1H), 8.56-8.40 (m, 2H), 8.28 (br s, 0.731H), 8.20-8.07 (m, 2H), 7.79 (d, J=7.6 Hz, 1H), 7.31 (dd, J=4.8, 7.6 Hz, 1H), 7.12 (d, J=9.2 Hz, 1H), 7.04-6.95 (m, 1H), 6.50-6.39 (m, 2H), 6.00 (d, J=7.6 Hz, 1H), 5.10 (s, 2H), 4.48 (br d, J=13.2 Hz, 2H), 4.39-4.11 (m, 2H), 3.44 (br s, 2H), 3.11-2.89 (m, 2H), 2.80-2.60 (m, 2H), 2.39-2.29 (m, 2H), 2.28-1.37 (m, 20H).

Example 166: Synthesis of 4-(6-((1R,5S)-9-((4,4-Difluorocyclohexyl)methyl)-3-oxa-7,9-diazabicyclo[3.3.1]nonan-7-yl)pyridin-3-yl)-6-(1-((1s, 4s)-4-(4-(4-((2,6-dioxopiperidin-3-yl)amino)-fluorophenyl)piperazin-1-yl)cyclohexyl)-1H-pyrazol-4-yl)pyrazolo[1,5-a]pyrazine-3-carbonitrile (Compound 150)

(Configurations are arbitrarily assigned)

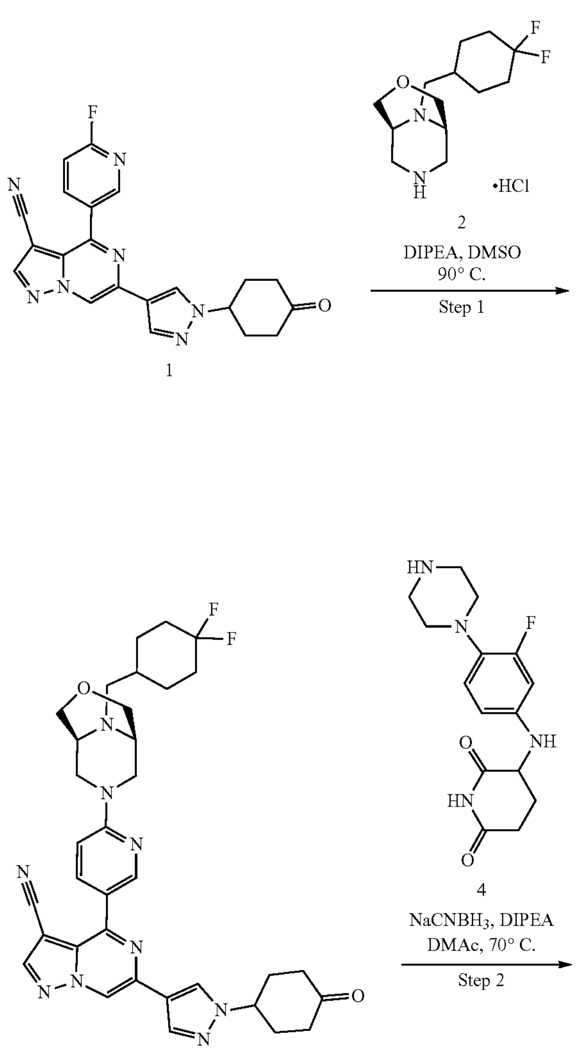

-continued

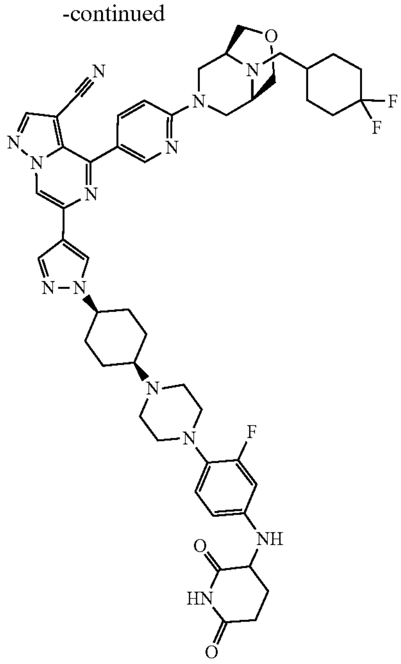

Compound 150

Step 1: Into a 25 mL sealed tube containing a well-stirred solution of 4-(6-fluoro-3-pyridyl)-6-[1-(4-oxocyclohexyl) pyrazol-4-yl]pyrazolo[1,5-a]pyrazine-3-carbonitrile (1, 400 mg, 0.996 mmol) and (1R,5S)-9-((4,4-difluorocyclohexyl) methyl)-3-oxa-7,9-diazabicyclo[3.3.1]nonane hydrochloride (2; 443.63 mg, 1.49 mmol) in dry DMSO (5 mL) was added DIPEA (643.97 mg, 4.98 mmol, 0.868 mL) under nitrogen atmosphere. The resulting reaction mixture was stirred at 90° C. for 16 h under nitrogen atmosphere. After completion of the reaction as monitored by TLC and UPLC, the reaction mixture was quenched with ice-water (10 mL) and extracted with EtOAc (2×50 mL). The organic phases were combined, dried (anhydrous $Na_2SO_4$), filtered and the filtrate was concentrated under reduced pressure to get a crude mass. The crude product was purified by flash silica-gel (230-400 mesh) column with 0-70% EtOAc/pet ether while desired compound eluting at 70-85% of the mobile phase to afford 4-(6-((1R,5S)-9-((4,4-difluorocyclohexyl) methyl)-3-oxa-7,9-diazabicyclo[3.3.1]nonan-7-yl)pyridin-3-yl)-6-(1-(4-oxocyclohexyl)-1H-pyrazol-4-yl)pyrazolo[1,5-a]pyrazine-3-carbonitrile (3, 330 mg, 0.447 mmol, 45% yield) as a yellow solid. LCMS ($ES^+$): m/z 642.2 $[M+H]^+$.

Step 2: Into a 25 mL sealed tube containing a well-stirred solution of 4-[6-[(1R,5S)-9-[(4,4-difluorocyclohexyl) methyl]-3-oxa-7,9-diazabicyclo[3.3.1]nonan-7-yl]-3-pyridyl]-6-[1-(4-oxocyclohexyl)pyrazol-4-yl]pyrazolo[1,5-a]pyrazine-3-carbonitrile (3, 150 mg, 0.233 mmol) and 3-(3-fluoro-4-piperazin-1-yl-anilino)piperidine-2,6-dione hydrochloride (4, 200.32 mg, 0.584 mmol) in anhydrous DMAc (4 mL) were added DIPEA (151.05 mg, 1.17 mmol, 0.203 mL) and Sodium cyanoborohydride (146.89 mg, 2.34 mmol) at ambient temperature and the reaction mixture was heated to 70° C. for 16 h and the reaction mixture was cooled to ambient temperature. After complete consumption of the starting material as indicated by UPLC and the reaction was diluted with ice-cold water (20 mL) and the solid precipitated out was filtered and the solid on the filter was dried to afford a crude solid. The crude solid was purified by flash silica-gel (230-400 mesh) column with 0-10% MeOH/DCM while desired compound was eluting at 5-7% of the mobile phase to afford 110 mg of diastereomeric mixture. This diastereomeric mixture was purified by reverse phase perp-HPLC [Column: XBRIDGE OBD C18 19×150 mm 5 micron; Mobile phase: A: 0.1% $NH_4HCO_3$ in MQ-water; B: Acetonitrile; Flow rate: 15 mL/minutes to afford 4-[6-[(1R,5S)-9-[(4,4-difluorocyclohexyl)methyl]-3-oxa-7,9-diazabicyclo[3.3.1]nonan-7-yl]-3-pyridyl]-6-[1-[4-[4-[4-[(2,6-dioxo-3-piperidyl)amino]-2-fluoro-phenyl]piperazin-1-yl] cyclohexyl]pyrazol-4-yl]pyrazolo[1,5-a]pyrazine-3-carbonitrile (Compound 150, Early eluting isomer, 30 mg, 0.031 mmol, 14% yield) as a yellow solid. $^1H$ NMR (400 MHz, DMSO-$d_6$). δ 10.79 (s, 1H), 9.27 (s, 1H), 8.83 (s, 1H), 8.71 (d, J=2.4 Hz, 1H), 8.46 (s, 1H), 8.15 (s, 1H), 8.08 (dd, J=2.4 Hz, 1H), 6.88 (d, J=9.6 Hz, 1H), 6.83 (d, J=9.6 Hz, 1H), 6.52 (dd, J=15, 2 Hz, 1H), 6.43 (dd, J=8.6, 2 Hz, 1H), 5.81 (d, J=7.6 Hz, 1H), 4.35-4.20 (m, 2H), 4.08 (d, J=10.8 Hz, 2H), 3.80 (m, 4H), 3.45 (d, J=9.6 Hz, 2H), 2.85 (m, 6H), 2.75 (m, 6H), 2.55 (m, 1H), 2.16 (m, 2H), 2.10 (m, 1H), 2.00 (m, 4H), 1.90-1.80 (m, 8H), 1.48 (m, 1H), 1.50 (m, 2H) and 1.15 (m, 2H). LCMS ($ES^+$): m/z 932.5 $[M+H]^+$.

Example 167: Synthesis of 6-(1-((1s, 4s)-4-(4-(4-((2,6-Dioxopiperidin-3-yl)amino)-2-fluorophenyl) piperazin-1-yl)cyclohexyl)-1H-pyrazol-4-yl)-4-(6-((1R,5S)-9-((5-fluoropyridin-2-yl)methyl)-3-oxa-7,9-diazabicyclo[3.3.1]nonan-7-yl)pyridin-3-yl) pyrazolo[1,5-a]pyrazine-3-carbonitrile (Compound 151)

(Configurations are arbitrarily assigned)

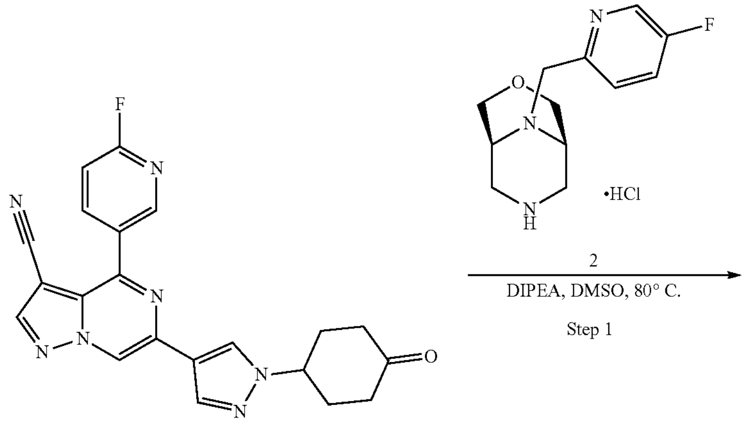

1

-continued

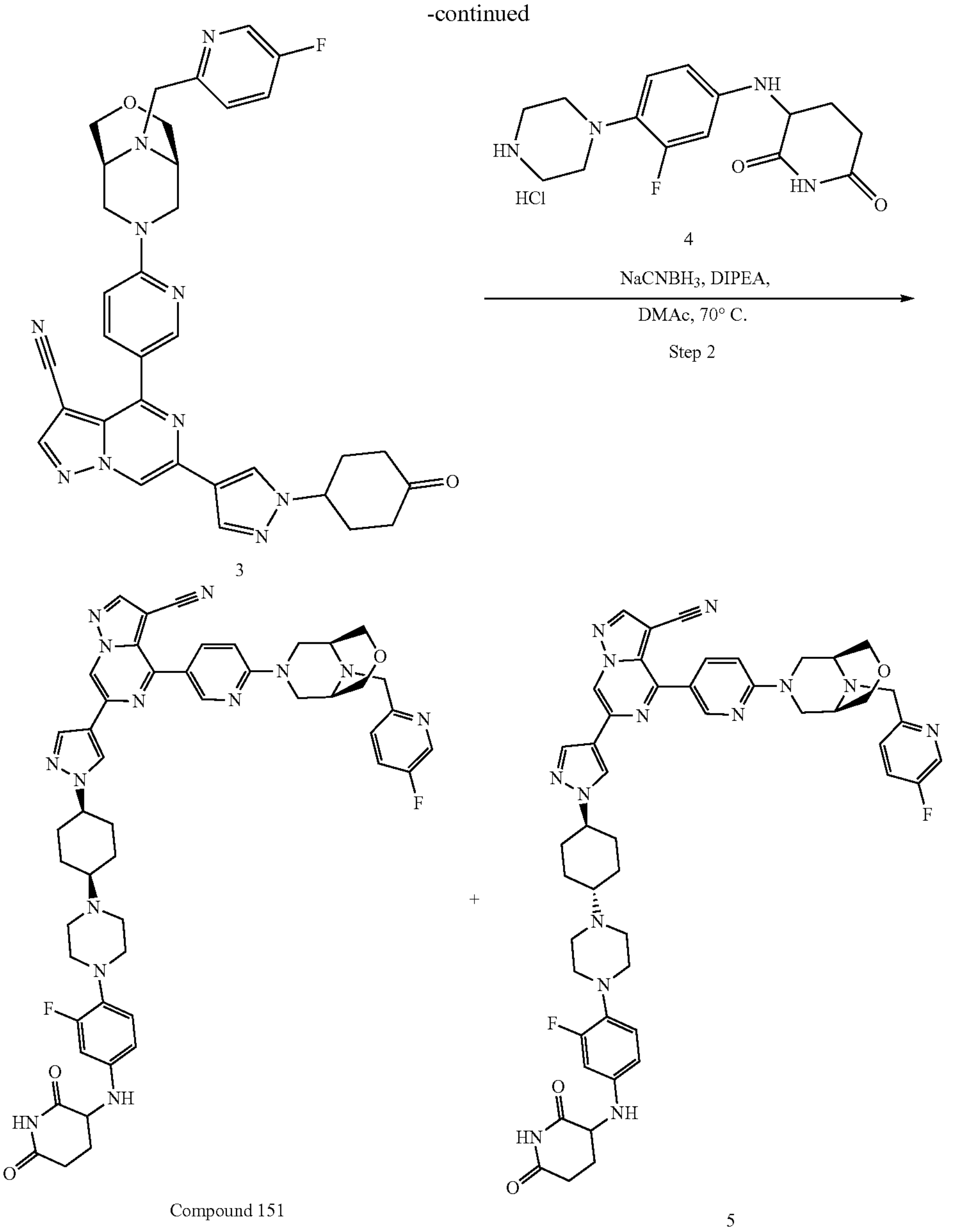

3

4

Compound 151

+

5

Step 1: Into a 50 mL sealed-tube containing a well-stirred solution of (1S,5R)-9-[(5-fluoro-2-pyridyl)methyl]-3-oxa-7,9-diazabicyclo[3.3.1]nonane hydrochloride (2, 147.78 mg, 0.539 mmol) and 4-(6-fluoro-3-pyridyl)-6-[1-(4-oxocyclohexyl)pyrazol-4-yl]pyrazolo[1,5-a]pyrazine-3-carbonitrile (1, 250 mg, 0.623 mmol) in anhydrous DMSO (4 mL) was added DIPEA (402.48 mg, 3.11 mmol, 0.542 mL) at ambient temperature. The resulting mixture was heated at 80° C. for 16 h and the reaction mixture was cooled to ambient temperature. The reaction mixture was quenched with water (15 mL) and the product was extracted with DCM (2×60 mL). The organic phases were combined, dried (anhydrous $Na_2SO_4$), filtered and the filtrate was concentrated under reduced pressure to get a crude residue. The crude product was purified by flash silica-gel (230-400 mesh; 25 g SNAP) column with 0-10% MeOH/DCM while desired compound eluting at 5-6% to afford 4-[6-[(1S,5R)-9-[(5-fluoro-2-pyridyl)methyl]-3-oxa-7,9-diazabicyclo[3.3.1]nonan-7-yl]-3-pyridyl]-6-[1-(4-oxocyclohexyl)pyrazol-4-yl]pyrazolo[1,5-a]pyrazine-3-carbonitrile (3, 140 mg, 0.213 mmol, 34% yield) as a yellow gummy oil. UPLC-MS ($ES^+$): m/z 619.7 $[M+H]^+$.

Step 2: Into a 25 mL sealed tube containing a well-stirred solution of 3-(3-fluoro-4-piperazin-1-yl-anilino)piperidine-2,6-dione hydrochloride (4, 216.10 mg, 0.63 mmol) and 4-[6-[(1S,5R)-9-[(5-fluoro-2-pyridyl)methyl]-3-oxa-7,9-diazabicyclo[3.3.1]nonan-7-yl]-3-pyridyl]-6-[1-(4-oxocyclohexyl)pyrazol-4-yl]pyrazolo[1,5-a]pyrazine-3-carbonitrile (3, 130 mg, 0.21 mmol) in anhydrous DMAc (3 mL) were added DIPEA (135.79 mg, 1.05 mmol, 0.183 mL) and sodium cyanoborohydride (66.03 mg, 1.05 mmol) at ambient temperature and the reaction mixture was heated to 70° C. for 16 h and the reaction mixture was cooled to ambient temperature. After complete consumption of the starting material as indicated by UPLC and the reaction was quenched with ice-cold water (20 mL) and the solid precipitated out was filtered and dried to afford a crude solid. The crude product was purified by flash silica-gel (230-400 mesh; 25 g SNAP) column with 0-10% MeOH/DCM while desired compound was eluting at 5-7% of the mobile phase to afford 110 mg of the desired diastereomers. The diastereomeric mixture was separated by reverse phase perp-HPLC [Column: XBRIDGE OBD C18 19×150 mm 5 micron; Mobile phase: A: 0.1% $NH_4HCO_3$ in MQ-water; B: Acetonitrile; Flow rate: 15 mL/minutes.

Prep HPLC fraction with RT=4.87 minutes was combined and lyophilized to afford 6-(1-((1s, 4s)-4-(4-(4-((2,6-dioxopiperidin-3-yl)amino)-2-fluorophenyl)piperazin-1-yl)cyclohexyl)-1H-pyrazol-4-yl)-4-(6-((1R,5S)-9-((5-fluoropyridin-2-yl)methyl)-3-oxa-7,9-diazabicyclo[3.3.1]nonan-7-yl)pyridin-3-yl)pyrazolo[1,5-a]pyrazine-3-carbonitrile (Compound 151, Early eluting isomer, 22 mg, 0.0238 mmol, 11% yield) as a yellow solid.

$^1$H NMR (400 MHz, DMSO-$d_6$). δ 10.79 (bs, 1H), 9.28 (s, 1H), 8.84 (s, 1H), 8.72 (d, J=2.4 Hz, 1H), 8.52 (d, J=3.2 Hz, 1H), 8.47 (s, 1H), 8.16 (s, 1H), 8.10 (dd, J=8.8, 2.4 Hz, 1H), 7.77-7.72 (m, 1H), 7.66 (dd, J=8.4, 4.8 Hz, 1H), 6.91 (d, J=9.2 Hz, 1H), 6.83 (t, J=9.6 Hz, 1H), 6.52 (dd, J=15, 2 Hz, 1H), 6.43 (d, J=8.8 Hz, 1H), 5.81 (d, J=7.2 Hz, 1H), 4.32-4.16 (m, 4H), 4.10 (s, 2H), 3.93-3.87 (m, 2H), 3.82-3.78 (m, 2H), 3.60-3.52 (m, 2H), 2.87 (m, 6H), 2.80-2.70 (m, 1H), 2.69-2.63 (m, 2H), 2.61-2.55 (m, 2H), 2.49-2.42 (m, 2H), 2.22-2.05 (m, 3H), 2.02-1.92 (m, 2H), 1.92-1.80 (m, 3H) and 1.55-1.40 (m, 2H). LCMS (ES$^+$): m/z 909.3 [M+H]$^+$.

Prep HPLC fractions with RT=7.02 minutes was combined and lyophilized to afford 6-(1-((1r, 4r)-4-(4-(4-((2,6-dioxopiperidin-3-yl)amino)-2-fluorophenyl)piperazin-1-yl)cyclohexyl)-1H-pyrazol-4-yl)-4-(6-((1R,5S)-9-((5-fluoropyridin-2-yl)methyl)-3-oxa-7,9-diazabicyclo[3.3.1]nonan-7-yl)pyridin-3-yl)pyrazolo[1,5-a]pyrazine-3-carbonitrile (5, Late eluting isomer, 27 mg, 0.029 mmol, 14% yield) as a yellow solid. $^1$H NMR (400 MHz, DMSO-$d_6$). δ 10.78 (s, 1H), 9.33 (s, 1H), 8.83 (s, 1H), 8.72 (d, J=2.4 Hz, 1H), 8.51 (d, J=2.8 Hz, 1H), 8.49 (s, 1H), 8.17 (s, 1H), 8.09 (dd, J=9.2, 2.4 Hz, 1H), 7.77-7.72 (m, 1H), 7.66 (dd, J=8.8, 4.8 Hz, 1H), 6.91 (d, J=9.2 Hz, 1H), 6.84 (t, J=9.6 Hz, 1H), 6.51 (dd, J=14.8, 2.4 Hz, 1H), 6.42 (dd, J=8.8, 2.4 Hz, 1H), 5.81 (d, J=7.2 Hz, 1H), 4.32-4.33 (m, 1H), 4.30-4.20 (m, 1H), 4.19-4.13 (m, 2H), 4.11 (s, 2H), 3.93-3.87 (m, 2H), 3.82-3.78 (m, 2H), 3.60-3.52 (m, 2H), 2.87 (m, 6H), 2.80-2.70 (m, 1H), 2.65-2.55 (m, 5H), 2.30-2.22 (m, 3H), 2.15-2.05 (m, 1H), 2.02-1.75 (m, 5H) and 1.68-1.55 (m, 2H). LCMS (ES$^+$): m/z 909.3 [M+H]$^+$.

Example 168: Synthesis of 6-(1-((1s, 4s)-4-(4-(3-(2,4-Dioxotetrahydropyrimidin-1(2H)-yl)-5-fluoro-1-methyl-1H-indazol-6-yl)piperazin-1-yl)cyclohexyl)-1H-pyrazol-4-yl)-4-(6-((1R,5S)-9-((6-methoxypyridin-3-yl)methyl)-3-oxa-7,9-diazabicyclo[3.3.1]nonan-7-yl)pyridin-3-yl)pyrazolo[1,5-a]pyrazine-3-carbonitrile (Compound 152)

6-(1-((1s, 4s)-4-(4-(3-(2,4-dioxotetrahydropyrimidin-1(2H)-yl)-5-fluoro-1-methyl-1H-indazol-6-yl)piperazin-1-yl)cyclohexyl)-1H-pyrazol-4-yl)-4-(6-((1R,5S)-9-((6-oxo-1,6-dihydropyridin-3-yl)methyl)-3-oxa-7,9-diazabicyclo[3.3.1]nonan-7-yl)pyridin-3-yl)pyrazolo[1,5-a]pyrazine-3-carbonitrile formic acid (Compound 153)

(Configurations are arbitrarily assigned)

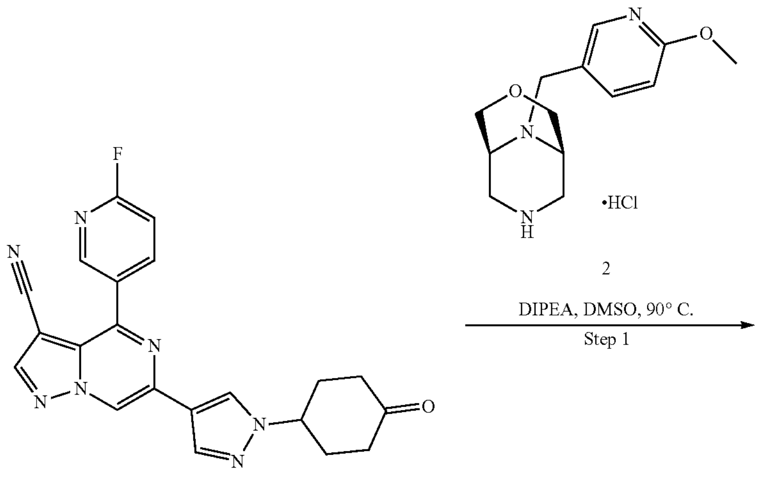

1

2

-continued

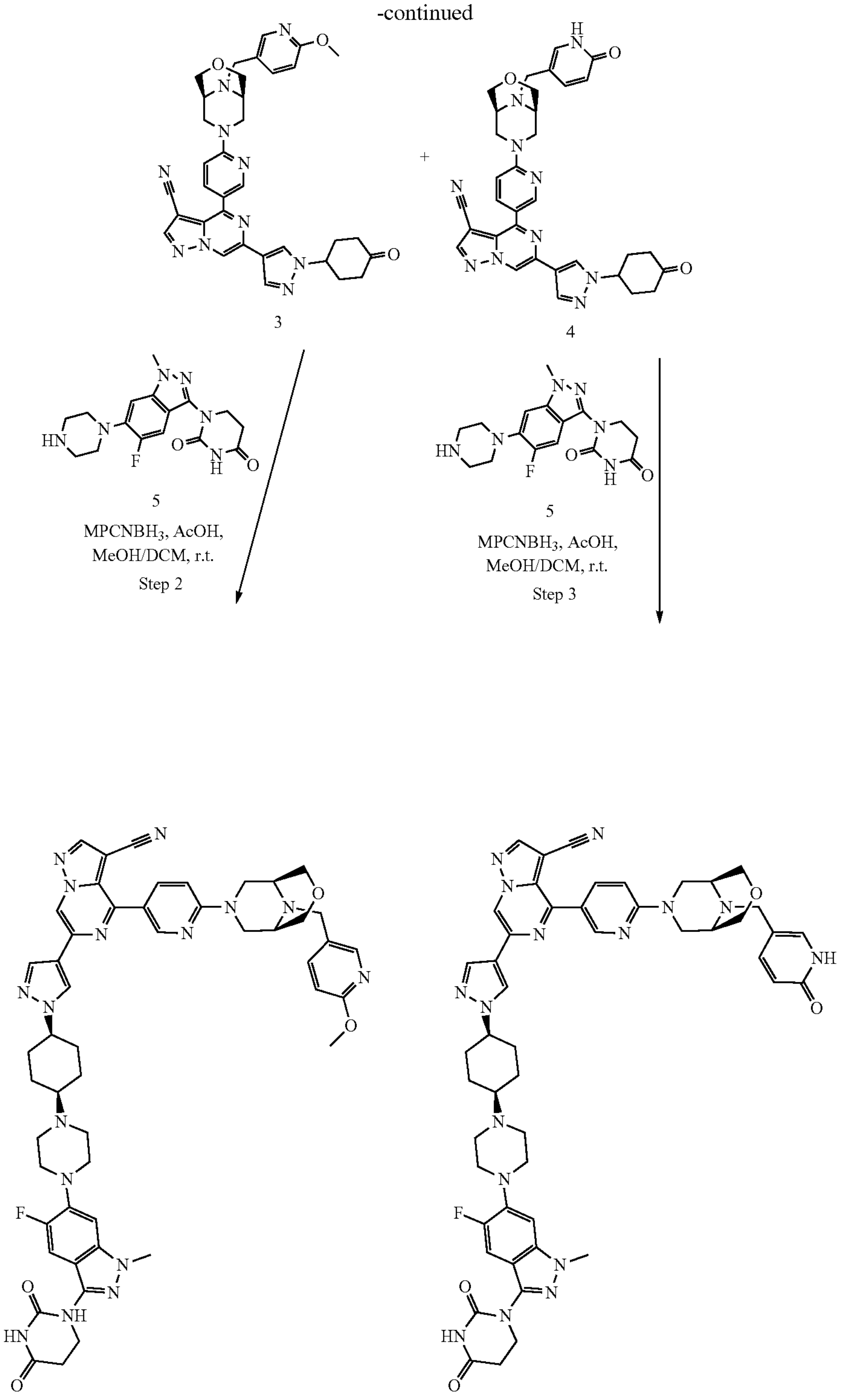

Compound 152

Compound 153

Step 1: Into a 50 mL sealed tube containing a well-stirred solution of (1S,5R)-9-[(6-methoxy-3-pyridyl)methyl]-3-oxa-7,9-diazabicyclo[3.3.1]nonane hydrochloride (2, 1.21 g, 4.24 mmol) and 4-(6-fluoro-3-pyridyl)-6-[1-(4-oxocyclohexyl)pyrazol-4-yl]pyrazolo[1,5-a]pyrazine-3-carbonitrile (1; 1.0 g, 2.49 mmol) in anhydrous DMSO (15 mL) was added DIPEA (3.22 g, 24.91 mmol, 4.34 mL) at ambient temperature under nitrogen atmosphere. Later the resulting mixture was heated with stirring at 90° C. for 12 h. After completion of the reaction as indicated by UPLC (12 h later), 33% of desired product 3 and 30% of undesired product 4 and 20% of unreacted starting material 5 was observed. The reaction mixture was allowed to attain room temperature and treated with ice-water (50.0 mL). Resulting solution was stirred for 15 minutes at room temperature, during which time desired product precipitated out. The solid product was filtered through a filter paper, solid on the filter was washed with water followed by pet ether and filtered solid was dried under vacuum to afford solid, which was purified by flash silica-gel (230-400 mesh, 25 g) column with 0-100% EtOAc/pet ether while desired compound was eluting at 85-95% of the mobile phase to afford 4-[6-[(1S, 5R)-9-[(6-methoxy-3-pyridyl)methyl]-3-oxa-7,9-diazabicyclo[3.3.1]nonan-7-yl]-3-pyridyl]-6-[1-(4-oxocyclohexyl) pyrazol-4-yl]pyrazolo[1,5-a]pyrazine-3-carbonitrile (3, 410 mg, 0.547 mmol, 22% yield) as a yellow-colored solid. UPLC-MS ($ES^+$): m/z 631.3 $[M+H]^+$.

Whereas elution of compound 4 was carried out with 0-20% MeOH/DCM, while desired compound was eluting at 10-15% of the mobile phase to afford 6-[1-(4-oxocyclohexyl)pyrazol-4-yl]-4-[6-[(1S,5R)-9-[(6-oxo-1H-pyridin-3-yl)methyl]-3-oxa-7,9-diazabicyclo[3.3.1]nonan-7-yl]-3-pyridyl]pyrazolo[1,5-a]pyrazine-3-carbonitrile (4, 130 mg, 0.190 mmol, 8% yield) as a yellow-colored solid. UPLC-MS ($ES^+$): m/z 617.2 $[M+H]^+$.

Step 2: Into a 25 mL glass-vial containing a well-stirred solution of 4-[6-[(1S,5R)-9-[(6-methoxy-3-pyridyl)methyl]-3-oxa-7,9-diazabicyclo[3.3.1]nonan-7-yl]-3-pyridyl]-6-[1-(4-oxocyclohexyl)pyrazol-4-yl]pyrazolo[1,5-a]pyrazine-3-carbonitrile (3, 250 mg, 0.396 mmol) and 1-(5-fluoro-1-methyl-6-piperazin-1-yl-indazol-3-yl) hexahydropyrimidine-2,4-dione (5, 219.67 mg, 0.634 mmol) in 1:1 anhydrous MeOH/DCM (8 mL) was added Acetic acid (315.00 mg, 5.25 mmol, 0.3 mL) at ambient temperature and the resulting mixture was stirred for 15 minutes then added MP-$CNBH_3$ (500 mg). The suspension was stirred at room temperature for 16 h. The progress of the reaction was monitored by LCMS. The reaction mixture was diluted with DCM (5 mL) and filtered, and the filtrate was concentrated under reduced pressure to afford a crude mass, which was purified by flash silica-gel (230-400 mesh, 10 g) column with 0-15% MeOH/DCM, while desired compound was eluting at 7-12% of the mobile phase to afford a mixture of diastereomers (150 mg) with 49.4 & 38.1%, respectively. Separation of diastereomers (150 mg) was carried out by prep HPLC purification following a method: Column: X-BRIDGE C8 (150×19) MM 5 MICRONS; Mobile phase: 10 mM Ammonium bicarbonate in water/ACN, Flow rate: 15 mL/minutes.

Early eluting isomer (cis-isomer): Fractions with RT=9.9 minutes were combined was lyophilized to afford 6-(1-((1s, 4s)-4-(4-(3-(2,4-Dioxotetrahydropyrimidin-1(2H)-yl)-5-fluoro-1-methyl-1H-indazol-6-yl)piperazin-1-yl)cyclohexyl)-1H-pyrazol-4-yl)-4-(6-((1R,5S)-9-((6-methoxypyridin-3-yl)methyl)-3-oxa-7,9-diazabicyclo[3.3.1]nonan-7-yl) pyridin-3-yl)pyrazolo[1,5-a]pyrazine-3-carbonitrile (Compound 152, 39.0 mg, 0.039.92 mmol, 10% yield) as a yellow fluffy solid. $^1$H NMR (400 MHz, DMSO-$d_6$). δ 10.53 (s, 1H), 9.28 (s, 1H), 8.84 (s, 1H), 8.73 (d, J=2.8 Hz, 1H), 8.47 (s, 1H), 8.18 (d, J=2 Hz, 1H), 8.16 (s, 1H), 8.10 (dd, J=9, 2.4 Hz, 1H), 7.77 (dd, J=8.4, 2.4 Hz, 1H), 7.36 (d, J=13.2 Hz, 1H), 7.10 (d, J=7.2 Hz, 1H), 6.91 (d, J=9.2, Hz, 1H), 6.83 (d, J=8.4 Hz, 1H), 4.15 (m, 1H), 4.12 (m, 2H), 3.96-3.90 (m, 5H), 3.87 (t, J=6.8 Hz, 2H), 3.81 (m, 4H), 3.78 (t, J=10.8 Hz, 3H), 3.54 (m, 2H), 3.10 (m, 4H), 2.82 (m, 2H), 2.76-2.73 (m, 7H), 2.19-2.17 (m, 2H), 2.08-2.00 (m, 2H), 1.88-1.85 (m, 2H) and 1.53-1.50 (m, 2H). LC-MS ($ES^+$): m/z 961.4 $[M+H]^+$.

Step 3: Into a 20 mL glass-vial containing a well-stirred solution of 6-[1-(4-oxocyclohexyl)pyrazol-4-yl]-4-[6-[(1S, 5R)-9-[(6-oxo-1H-pyridin-3-yl)methyl]-3-oxa-7,9-diazabicyclo[3.3.1]nonan-7-yl]-3-pyridyl]pyrazolo[1,5-a]pyrazine-3-carbonitrile (4, 130.0 mg, 0.210 mmol) and 1-(5-fluoro-1-methyl-6-piperazin-1-yl-indazol-3-yl) hexahydropyrimidine-2,4-dione (5, 87.62 mg, 0.252 mmol) in 1:1 anhydrous MeOH/DCM (4 mL) was added Acetic acid (0.15 mL, 2.62 mmol) at ambient temperature and the resulting mixture was stirred for 15 minutes, then added $MPCNBH_3$ (250 mg) and the resulting suspension was stirred at ambient temperature under nitrogen atmosphere. The progress of the reaction was monitored by LCMS and found complete after 16 h. The reaction mixture was diluted with DCM (5 mL) and filtered, and the filtrate was concentrated under reduced pressure to afford crude which was purified by prep HPLC purification following a method: Column: X-BRIDGE C8 (150×19) MM 5 MICRONS; Mobile phase: 10 mM Ammonium bicarbonate in water/ACN and Flow rate: 15 mL/minutes to afford semi-pure crude product.

The said semi-pure crude was re-purified by prep HPLC purification following a method: Column: X-BRIDGE C8 (150×19) MM 5 MICRONS; Mobile phase: HCOOH in water/ACN and Flow rate: 15 mL/minutes to obtain the desired compound.

Early eluting isomer (cis-isomer): Fractions with RT=9.9 minutes were combined and lyophilized to afford 6-(1-((1s, 4s)-4-(4-(3-(2,4-dioxotetrahydropyrimidin-1(2H)-yl)-5-fluoro-1-methyl-1H-indazol-6-yl)piperazin-1-yl)cyclohexyl)-1H-pyrazol-4-yl)-4-(6-((1R,5S)-9-((6-oxo-1,6-dihydropyridin-3-yl)methyl)-3-oxa-7,9-diazabicyclo[3.3.1] nonan-7-yl)pyridin-3-yl)pyrazolo[1,5-a]pyrazine-3-carbonitrile formic acid (Compound 153, 7 mg, 0.006 mmol, 3% yield) as a yellow fluffy solid. $^1$H NMR (400 MHz, DMSO-$d_6$). δ 11.42 (s, 1H), 10.53 (s, 1H), 9.23 (s, 1H), 9.23 (s, 1H), 8.80 (s, 1H), 8.69 (d, J=2.4 Hz, 1H), 8.44 (s, 1H), 8.14 (d, J=2 Hz, 1H), 8.08 (dd, J=8.8, 2.4 Hz, 1H), 7.55 (dd, J=9.4, 2.8 Hz, 1H), 7.35 (m, 2H), 7.10 (d, J=7.2 Hz, 1H), 6.89 (d, J=9.2 Hz, 1H), 6.37 (d, J=9.2 Hz, 1H), 4.23 (m, 1H), 4.11-4.08 (m, 2H), 3.94 (s, 3H), 3.89 (t, J=6.4 Hz, 2H), 3.83-3.79 (m, 4H), 3.76-3.71 (m, 2H), 3.50 (m, 2H), 3.16-3.12 (m, 4H), 2.82 (m, 5H), 2.74 (t, J=6.8 Hz, 2H), 2.55 (m, 2H), 2.16 (m, 2H), 2.04-2.02 (m, 2H), 1.87-1.84 (m, 2H), 1.54-1.51 (m, 2H). LC-MS ($ES^+$): m/z 947.3 $[M+H]^+$.

General method for desalting: CRBN-amine hydrochloride salt (280 mg, from C4T) was dissolved in 1:1 MeOH/DCM (6 mL) and Amberlyst A21 free base resin (600 mg) was added at room temperature and the suspension was stirred for 20 minutes while pH=7-8. Resin was filtered off, and the filtrate was concentrated under reduced pressure to afford 220 mg of amine free of salt.

Example 169: Synthesis of 6-[1-[4-[4-[4-[(2,6-dioxo-3-piperidyl)amino]-2-fluoro-phenyl]-1-piperidyl] cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 154)
(Configurations are arbitrarily assigned)
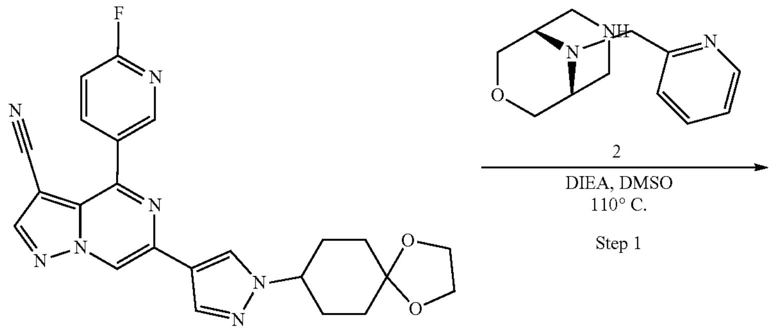
1
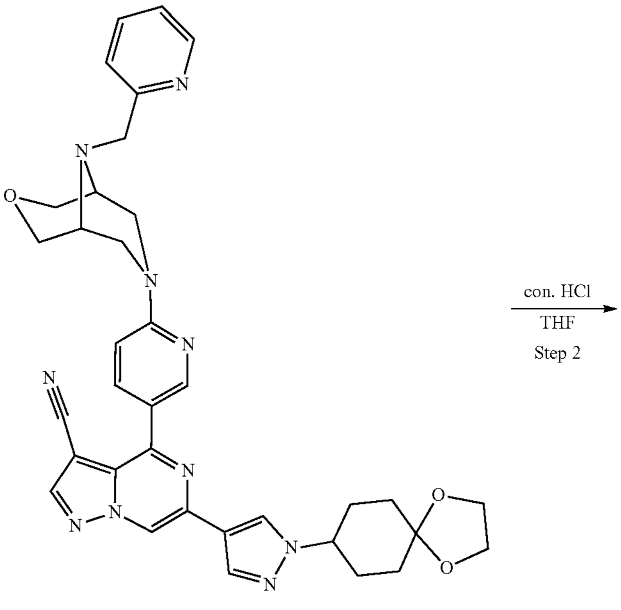
3

-continued

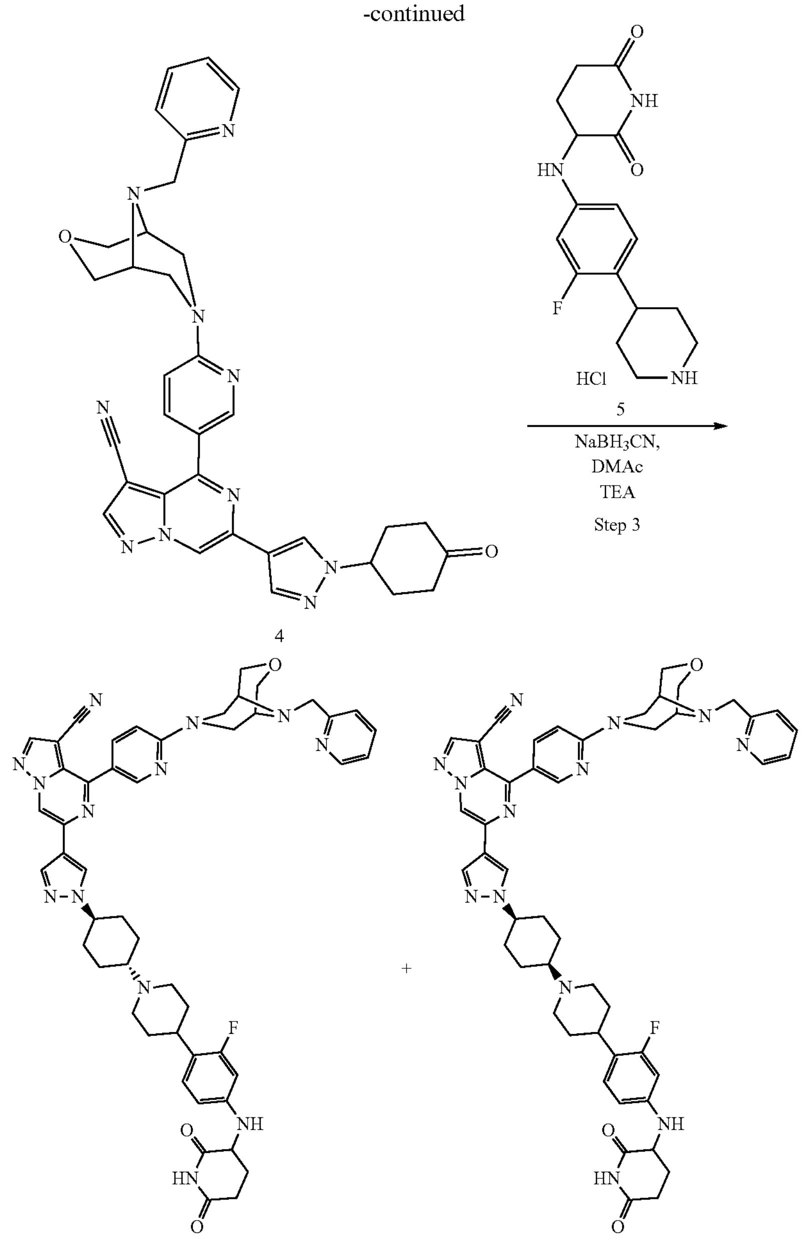

5

4

Compound 154

6

Step 1: To a solution of 6-(1-(1,4-dioxaspiro[4.5]decan-8-yl)-1H-pyrazol-4-yl)-4-(6-fluoropyridin-3-yl)pyrazolo[1,5-a]pyrazine-3-carbonitrile (1, 689 mg, 1.55 mmol) in DMSO (10 mL) was added 9-(pyridin-2-ylmethyl)-3-oxa-7,9-diazabicyclo[3.3.1]nonane (2, 680 mg, 2.66 mmol, HCl salt) and N-ethyl-N-isopropyl-propan-2-amine (999.54 mg, 7.73 mmol, 1.35 mL) at 20° C. After addition, the solution was stirred at 110° C. for 12 hr. The reaction mixture was poured into water (80 mL) to get the solid, then the solid was filtered. The filtered cake was dissolved in DCM: MeOH=10:1 (200 mL). The organic layer was washed with brine (40 mL), dried over Na2SO4, concentrated under reduced pressure to give a residue. The crude product was used for next step directly. 6-[1-(1,4-dioxaspiro[4.5]decan-8-yl)pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (3, 680 mg, 991.43 μmol, 64% yield) was obtained as a yellow solid. LCMS ($ES^+$): m/z 645.2 $[M+H]^+$ Step 2: To a solution of 6-[1-(1,4-dioxaspiro[4.5]decan-8-yl)pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (3, 820 mg, 1.27 mmol) in THF (10 mL) was added HCl (12 M, 7.45 mL) at −20° C. After addition, the solution was stirred at 20° C. for 1h. The reaction was dropped into the aqueous of $NaHCO_3$ to give a suspension, then the suspension was filtered and the filtered cake was dissolves in EtOAc (100 mL), the organic layer was washed with brine (30 mL), dried over $Na_2SO_4$ and filtered. The filtrate was concentrated to give a product. The crude product was used for next step directly. 6-[1-(4-oxocyclohexyl)pyrazol-4-yl]-4-[6-[9-(2-pyridylmethyl)-3- oxa-7,9-diazabicyclo[3.3.1] nonan-7-yl]-3-pyridyl]pyrazolo [1,5-a]pyrazine-3-carbonitrile (4, 587 mg, 908.83 μmol, 71% yield) was obtained as a yellow solid. LCMS ($ES^+$): m/z 601.2 $[M+H]^+$ Step 3: To a solution of 6-[1-(4-oxocyclohexyl)pyrazol-4-yl]-4-[6-[9-(2-pyridylmethyl)-3-oxa-7,9-diazabicyclo [3.3.1]nonan-7-yl]-3-pyridyl]pyrazolo[1,5-a]pyrazine-3-carbonitrile (4, 640 mg, 1.07 mmol) and 3-((3-fluoro-4-(piperidin-4-yl)phenyl)amino)piperidine-2,6-dione (5, 640 mg, 1.87 mmol, HCl salt) in DMAc (20 mL) was added TEA (929.28 mg, 9.18 mmol, 1.28 mL). After addition, the solution was stirred at 20° C. for 12 hr. Then sodium cyanoborohydride (669.56 mg, 10.65 mmol) was added into above solution and stirred at 70° C. for another 12 hr. The reaction was dropped into water (150 mL) to give a suspension, then the suspension was filtered and the filtered cake was dissolved in DCM:MeOH=10:1 (150 mL), then washed with brine (40 mL), dried over $Na_2SO_4$ and concentrated to get the residue. The residue was purified by Pre-TLC (DCM:MeOH=12:1). The purified product was purified by prep-HPLC (column: Waters Xbridge C18 150*50 mm*10 um, mobile phase: [water (10 mM NH4HCO3)-ACN]; B %: 31%-61%, Flowrate: 60 ml/min) to get the product. The purified product was purified by prep-HPLC (column: Waters Xbridge 150*25 mm*5 um, mobile phase: [water (0.05% ammonia hydroxide v/v)-ACN]; B %: 44%-74%, 10 min, Flowrate: 25 ml/min) to get the product. Compound 6-[1-[4-[4-[4-[(2,6-dioxo-3-piperidyl)amino]-2-fluoro-phenyl]-1-piperidyl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 154, Early eluting isomer, 80.47 mg, 89.51 μmol, 8% yield) was obtained as a yellow solid.

LCMS ($ES^+$): m/z 445.7 $[M+H]^+$ $^1H$ NMR (400 MHz, DMSO-$d_6$) δ=10.96-10.68 (m, 1H), 9.27 (s, 1H), 8.83 (s, 1H), 8.72 (d, J=2.0 Hz, 1H), 8.55-8.50 (m, 1H), 8.48-8.45 (m, 1H), 8.17-8.14 (m, 1H), 8.12-8.08 (m, 1H), 7.84-7.79 (m, 1H), 7.63-7.57 (m, 1H), 7.32-7.26 (m, 1H), 7.04-6.97 (m, 1H), 6.94-6.88 (m, 1H), 6.49-6.41 (m, 2H), 6.00 (d, J=7.6 Hz, 1H), 4.35-4.27 (m, 1H), 4.24-4.14 (m, 3H), 4.12-4.09 (m, 2H), 3.95-3.88 (m, 2H), 3.84-3.77 (m, 2H), 3.61-3.52 (m, 2H), 2.97-2.86 (m, 4H), 2.80-2.69 (m, 1H), 2.61-2.58 (m, 1H), 2.37-2.30 (m, 2H), 2.18-2.07 (m, 3H), 1.98-1.78 (m, 6H), 1.72-1.44 (m, 7H)

6-[1-[4-[4-[4-[(2,6-dioxo-3-piperidyl)amino]-2-fluoro-phenyl]-1-piperidyl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (6, 102.23 mg, 113.71 μmol, 11% yield) was obtained as a yellow solid.

LCMS ($ES^+$): m/z 445.7 $[M+H]^+$ $^1H$ NMR (400 MHz, DMSO-$d_6$) δ=10.78 (s, 1H), 9.34-9.30 (m, 1H), 8.85-8.81 (m, 1H), 8.73

8.70 (m, 1H), 8.54-8.47 (m, 2H), 8.18-8.15 (m, 1H), 8.09 (m, 1H), 7.83-7.77 (m, 1H), 7.60-7.55 (m, 1H), 7.31-7.25 (m, 1H), 7.03-6.96 (m, 1H), 6.91 (m, 1H), 6.46-6.40 (m, 2H), 6.01-5.96 (m, 1H), 4.37-4.26 (m, 2H), 4.16 (m, 2H), 4.10 (s, 2H), 3.93-3.88 (m, 2H), 3.80 (m, 2H), 3.59-3.52 (m, 2H), 3.08-3.02 (m, 2H), 2.89-2.85 (m, 2H), 2.75-2.65 (m, 1H), 2.60-2.54 (m, 2H), 2.34-2.27 (m, 3H), 2.10-1.99 (m, 3H), 1.90-1.79 (m, 5H), 1.69-1.52 (m, 6H)

Example 170: Synthesis of 6-[1-[4-[4-[4-[[(3S)-2,6-dioxo-3-piperidyl]amino]-2-fluoro-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 155)

6-[1-[4-[4-[4-[[(3R)-2,6-dioxo-3-piperidyl]amino]-2-fluoro-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 156)

(Configurations are arbitrarily assigned)

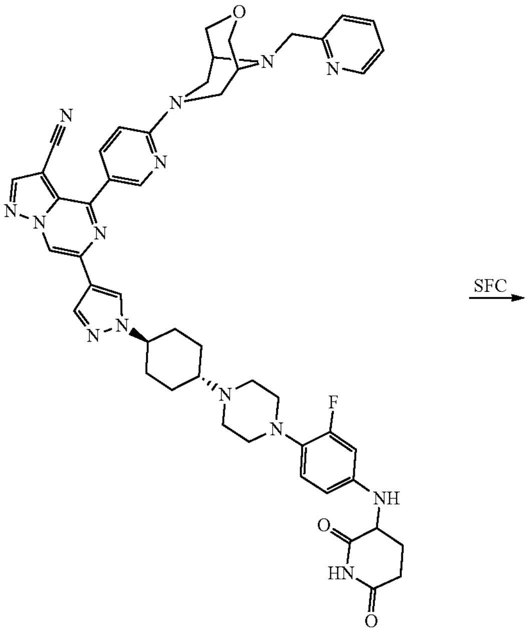

1

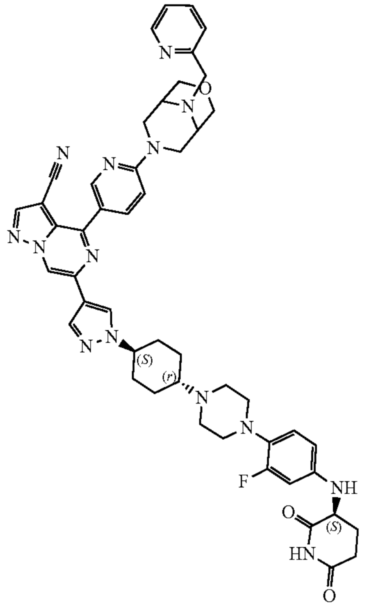

Compound 155

-continued

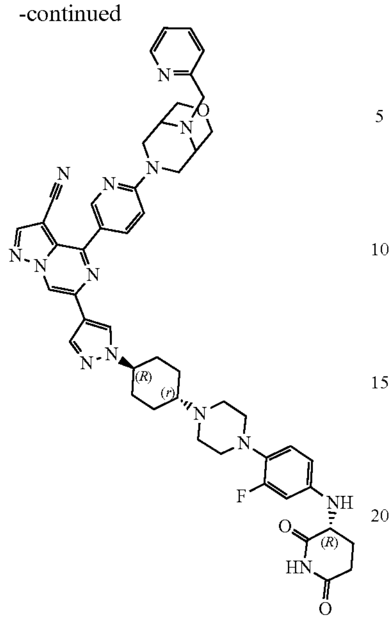

Compound 156

Compound 6-[1-[4-[4-[4-[(2,6-dioxo-3-piperidyl)amino]-2-fluoro-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (1, 1.1 g, 1.23 mmol) was purified by chiral separation (Add IPA and $CH_2Cl_2$ 150 ml into sample Instrument: Waters 80Q Mobile Phase: 75% IPA+ACN (Neu) in Supercritical $CO_2$ Flow Rate: 80 g/min Cycle Time: 5.5 min, total time: 400 min Single injection volume: 4.0 ml Back Pressure: 100 bar to keep the $CO_2$ in Supercritical flow) to give 6-[1-[4-[4-[4-[[(3S)-2,6-dioxo-3-piperidyl]amino]-2-fluoro-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 155, Early eluting isomer, 386.81 mg, 429.79 μmol) and 6-[1-[4-[4-[4-[[(3R)-2,6-dioxo-3-piperidyl]amino]-2-fluoro-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 156, Late eluting isomer, 343.11 mg, 381.23 μmol, 66% yield) as yellow products.

Compound 155, Early Eluting Isomer:

LCMS ($ES^+$): m/z 891.3 $[M+H]^+$ $^1$H NMR (400 MHz, DMSO-$d_6$) δ=10.79 (s, 1H), 9.28 (s, 1H), 8.84 (s, 1H), 8.72 (d, J=2.4 Hz, 1H), 8.52 (d, J=4.8 Hz, 1H), 8.47 (s, 1H), 8.17 (s, 1H), 8.10 (dd, J=2.4, 9.2 Hz, 1H), 7.82 (dt, J=1.6, 7.6 Hz, 1H), 7.60 (d, J=7.6 Hz, 1H), 7.29 (dd, J=5.6, 6.8 Hz, 1H), 6.92 (d, J=9.2 Hz, 1H), 6.85 (t, J=9.6 Hz, 1H), 6.53 (d, J=15.2 Hz, 1H), 6.47-6.40 (m, 1H), 5.95-5.75 (m, 1H), 4.36-4.14 (m, 4H), 4.11 (s, 2H), 3.96-3.87 (m, 2H), 3.81 (d, J=11.2 Hz, 2H), 3.57 (d, J=10.8 Hz, 2H), 3.06-2.80 (m, 7H), 2.79-2.64 (m, 4H), 2.62-2.55 (m, 2H), 2.24-2.14 (m, 2H), 2.13-1.95 (m, 3H), 1.86 (dq, J=3.6, 12.0 Hz, 3H), 1.63-1.41 (m, 2H)

Compound 156, Late Eluting Isomer:

LCMS ($ES^+$): m/z 891.2 $[M+H]^+$ $^1$H NMR (400 MHz, DMSO-$d_6$) δ=10.78 (s, 1H), 9.27 (s, 1H), 8.82 (s, 1H), 8.71 (d, J=2.4 Hz, 1H), 8.51 (d, J=4.8 Hz, 1H), 8.46 (s, 1H), 8.15 (s, 1H), 8.09 (dd, J=2.4, 9.2 Hz, 1H), 7.80 (dt, J=1.6, 7.6 Hz, 1H), 7.59 (d, J=7.6 Hz, 1H), 7.28

(dd, J=5.2, 6.8 Hz, 1H), 6.90 (d, J=9.2 Hz, 1H), 6.83 (t, J=9.2 Hz, 1H), 6.52 (dd, J=2.0, 15.2 Hz, 1H), 6.43 (d, J=8.8 Hz, 1H), 5.82 (d, J=6.8 Hz, 1H), 4.32-4.12 (m, 4H), 4.10 (s, 2H), 3.95-3.86 (m, 2H), 3.80 (d, J=10.8 Hz, 2H), 3.56 (d, J=10.4 Hz, 2H), 3.02-2.80 (m, 7H), 2.79-2.63 (m, 4H), 2.61-2.53 (m, 2H), 2.22-2.12 (m, 2H), 2.10-1.93 (m, 3H), 1.91-1.78 (m, 3H), 1.58-1.40 (m, 2H)

Example 171: Synthesis of 6-(1-((1r, 4r)-4-(4-(4-((2,6-dioxopiperidin-3-yl)amino)-2-fluorophenyl)piperazin-1-yl)cyclohexyl)-1H-pyrazol-4-yl)-4-(6-(9-(pyridin-2-ylmethyl)-3-oxa-7,9-diazabicyclo[3.3.1]nonan-7-yl)pyridin-3-yl)pyrazolo[1,5-a]pyrazine-3-carbonitrile (Compound 157)

(Configurations are arbitrarily assigned)

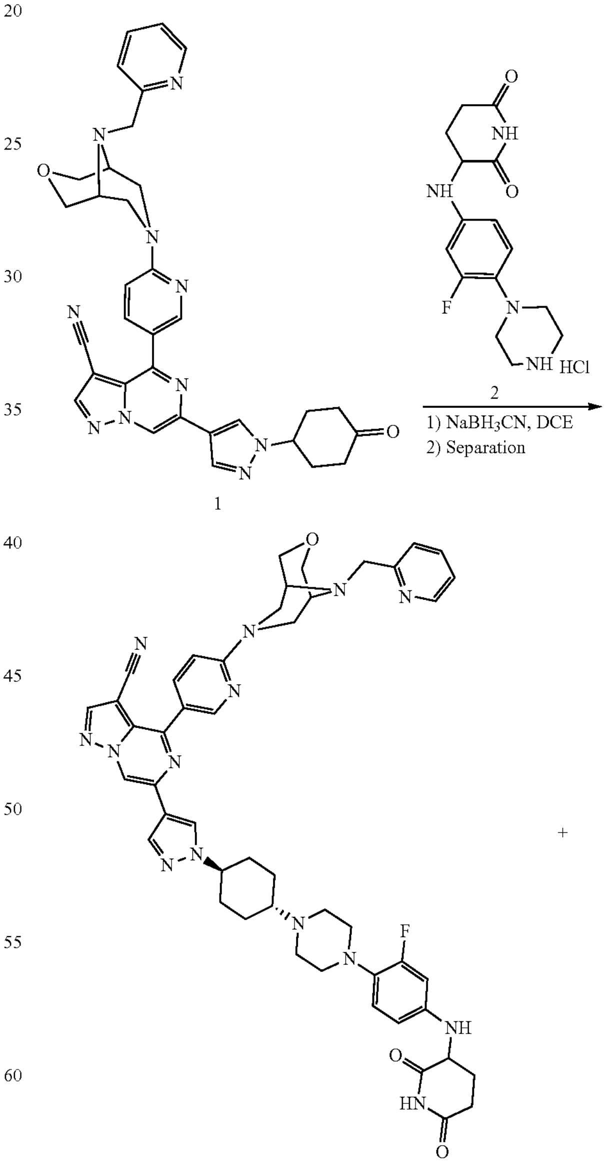

Compound 157

-continued

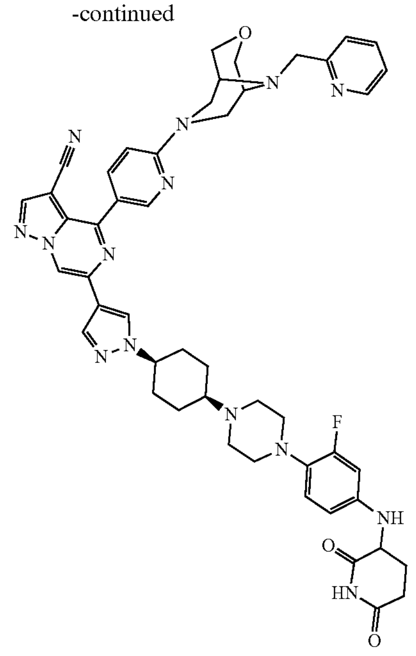

3

To a solution of 3-((3-fluoro-4-(piperazin-1-yl)phenyl) amino)piperidine-2,6-dione (2, 439.43 mg, 1.28 mmol, HCl salt) and 6-(1-(4-oxocyclohexyl)-1H-pyrazol-4-yl)-4-(6-((1R,5S)-9-(pyridin-2-ylmethyl)-3-oxa-7,9-diazabicyclo [3.3.1]nonan-7-yl)pyridin-3-yl)pyrazolo[1,5-a]pyrazine-3-carbonitrile (1, 700 mg, 1.17 mmol) in DMAc (10 mL) was added TEA (589.61 mg, 5.83 mmol, 812.14 μL). After addition, the solution was stirred at 50° C. for 12 hr. Then sodium cyanoborohydride (732.34 mg, 11.65 mmol) was added into above solution and stirred at 20° C. for another 2 hr. The reaction solution was poured into water (40 mL) to give a suspension. Then the suspension was filtered, the filter cake was washed with water (10 mL) and concentrated in vacuum. The residue was purified by Prep-TLC (DCM: MeOH=10:1) and Prep-HPLC (Waters Xbridge 150*25 mm*5 um, water (0.05% ammonia hydroxide v/v)-ACN, 34%-62%, 25 ml/min, min) to afford 6-(1-((1r, 4r)-4-(4-(4-((2,6-dioxopiperidin-3-yl)amino)-2-fluorophenyl)piperazin-1-yl)cyclohexyl)-1H-pyrazol-4-yl)-4-(6-(9-(pyridin-2-ylmethyl)-3-oxa-7,9-diazabicyclo[3.3.1]nonan-7-yl)pyridin-3-yl)pyrazolo[1,5-a]pyrazine-3-carbonitrile (Compound 157, Early eluting isomer, 71.64 mg, 80.40 μmol, 7% yield) as yellow solid and 6-(1-((1s, 4s)-4-(4-(4-((2,6-dioxopiperidin-3-yl)amino)-2-fluorophenyl)piperazin-1-yl)cyclohexyl)-1H-pyrazol-4-yl)-4-(6-(9-(pyridin-2-ylmethyl)-3-oxa-7,9-diazabicyclo[3.3.1]nonan-7-yl)pyridin-3-yl)pyrazolo[1,5-a] pyrazine-3-carbonitrile (3, Late eluting isomer, 92.46 mg, 103.21 μmol, 9% yield) as yellow solids.

Compound 157, Early Eluting Isomer:

LCMS ($ES^+$): m/z 891.6 $[M+H]^+$ $^1H$ NMR (400 MHz, DMSO-$d_6$) δ=10.80 (s, 1H), 9.27 (s, 1H), 8.84 (s, 1H), 8.73 (d, J=2.4 Hz, 1H), 8.52 (d, J=4.0 Hz, 1H), 8.47 (s, 1H), 8.16 (s, 1H), 8.10 (dd, J=2.4, 8.8 Hz, 1H), 7.82 (dt, J=1.6, 7.6 Hz, 1H), 7.60 (d, J=7.6 Hz, 1H), 7.29 (dd, J=5.2, 6.8 Hz, 1H), 6.92 (d, J=9.2 Hz, 1H), 6.84 (t, J=9.2 Hz, 1H), 6.52 (dd, J=2.0, 15.2 Hz, 1H), 6.47-6.38 (m, 1H), 5.81 (d, J=7.6 Hz, 1H), 4.31-4.14 (m, 4H), 4.13-4.09 (m, 2H), 3.96-3.88 (m, 2H), 3.85-3.78 (m, 2H), 3.57 (br d, J=10.4 Hz, 2H), 2.88 (br d, J=4.4 Hz, 6H), 2.80-2.69 (m, 1H), 2.69-2.62 (m, 4H), 2.62-2.54 (m, 1H), 2.46-2.39 (m, 1H), 2.22-2.07 (m, 3H), 1.98 (br d, J=10.8 Hz, 2H), 1.92-1.79 (m, 3H), 1.56-1.41 (m, 2H)

3, Late Eluting Isomer:

LCMS ($ES^+$): m/z 891.6 $[M+H]^+$

1H NMR (400 MHz, DMSO-$d_6$) δ=10.79 (s, 1H), 9.33 (s, 1H), 8.82 (s, 1H), 8.72 (br s, 1H), 8.56-8.45 (m, 2H), 8.18 (s, 1H), 8.14-8.06 (m, 1H), 7.82 (br t, J=7.2 Hz, 1H), 7.60 (br d, J=7.6 Hz, 1H), 7.35-7.24 (m, 1H), 6.98-6.88 (m, 1H), 6.88-6.79 (m, 1H), 6.52 (br d, J=15.6 Hz, 1H), 6.47-6.38 (m, 1H), 5.86-5.74 (m, 1H), 4.39 (br s, 4H), 4.11 (s, 2H), 3.96-3.88 (m, 2H), 3.85-3.77 (m, 2H), 3.61-3.53 (m, 2H), 2.89 (br s, 6H), 2.80-2.67 (m, 2H), 2.64-2.57 (m, 4H), 2.35-2.22 (m, 3H), 1.98-1.78 (m, 5H), 1.70-1.56 (m, 2H)

Example 172: Synthesis of 4-(6-((1R,5S)-9-(3,3-Dimethylbutanoyl)-3-oxa-7,9-diazabicyclo[3.3.1] nonan-7-yl)pyridin-3-yl)-6-(1-((1s, 4s)-4-(4-(4-((2,6-dioxopiperidin-3-yl)amino)-2-fluorophenyl) piperazin-1-yl)cyclohexyl)-1H-pyrazol-4-yl) pyrazolo[1,5-a]pyrazine-3-carbonitrile (Compound 158)

(Configurations are arbitrarily assigned)

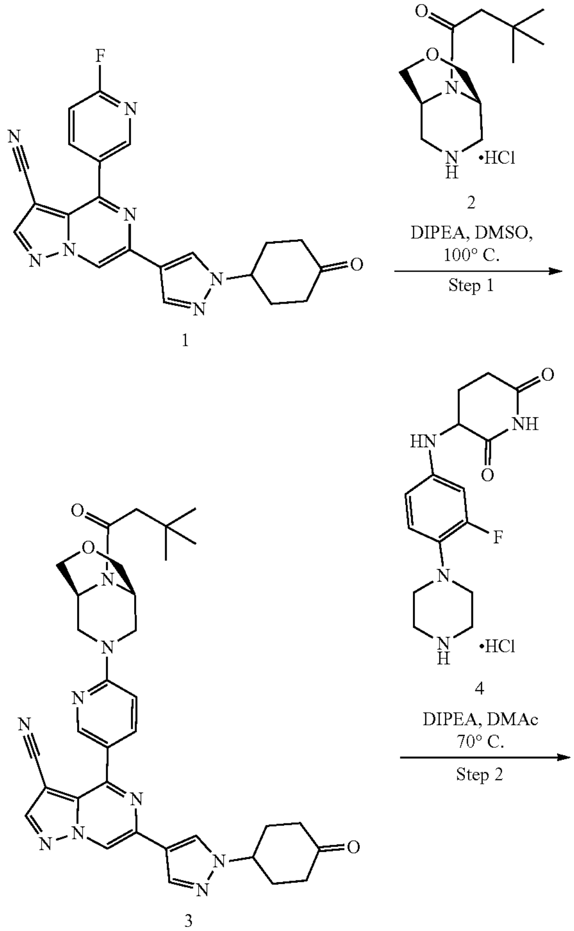

1 2 3 4

-continued

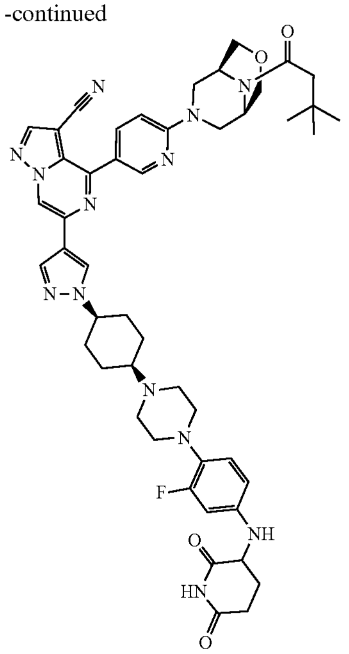

Compound 158

Step 1: Into a 10 mL single-necked round-bottomed flask containing a well stirred solution of 1-((1R,5S)-3-oxa-7,9-diazabicyclo[3.3.1]nonan-9-yl)-3,3-dimethylbutan-1-one hydrochloride (2, 145.18 mg, 0.552 mmol) and 4-(6-fluoro-3-pyridyl)-6-[1-(4-oxocyclohexyl)pyrazol-4-yl]pyrazolo[1,5-a]pyrazine-3-carbonitrile (1, 220 mg, 0.460 mmol) in anhydrous DMSO (5 mL) was added DIPEA (297.51 mg, 2.30 mmol, 400.9 mL). The resulting mixture was stirred at 100° C. The progress of reaction was monitored by UPLC and found complete after 16 h. The reaction mixture was slowly added to ice-cold water (30 mL) and solid thus obtained was filtered. The crude solid was purified by flash silica-gel (230-400 mesh) column with 50-100% EtOAc/pet ether while desired compound was eluting at 95-100% to afford 4-(6-((1R,5S)-9-(3,3-dimethylbutanoyl)-3-oxa-7,9-diazabicyclo[3.3.1]nonan-7-yl)pyridin-3-yl)-6-(1-(4-oxocyclohexyl)-1H-pyrazol-4-yl)pyrazolo[1,5-a]pyrazine-3-carbonitrile (3, 140 mg, 0.173 mmol, 38% yield) as a light brown solid. LCMS ($ES^+$): m/z 608.2 $[M+H]^+$.

Step 2: Into a 25 mL single-necked round-bottomed flask containing a well stirred solution of 4-(6-((1R,5S)-9-(3,3-dimethylbutanoyl)-3-oxa-7,9-diazabicyclo[3.3.1]nonan-7-yl)pyridin-3-yl)-6-(1-(4-oxocyclohexyl)-1H-pyrazol-4-yl)pyrazolo[1,5-a]pyrazine-3-carbonitrile (3, 120 mg, 0.148 mmol) and 3-(3-fluoro-4-piperazin-1-yl-anilino)piperidine-2,6-dione hydrochloride (4, 225.63 mg, 0.592 mmol) in DMAc (4 mL) were added DIPEA (191.41 mg, 1.48 mmol, 0.257 mL) and Sodium cyanoborohydride (37.23 mg, 0.592 mmol). The resulting mixture was stirred at 70° C. for 16 h. The progress of reaction was monitored by UPLC and found complete after 16 h. The reaction mixture was cooled to ambient temperature and slowly added to ice-cold water (30 mL) and solid thus obtained was filtered. The crude solid was purified by reverse phase preparatory HPLC [Purification method: X-Bridge OBD C18 (19×150) 5 micron; Mobile phase A: 0.1% ammonium bicarbonate in water and Mobile phase B: Acetonitrile; RT=5.9 minutes] to afford 4-(6-((1R,5S)-9-(3,3-Dimethylbutanoyl)-3-oxa-7,9-diazabicyclo[3.3.1]nonan-7-yl)pyridin-3-yl)-6-(1-((1s, 4s)-4-(4-(4-((2,6-dioxopiperidin-3-yl)amino)-2-fluorophenyl)piperazin-1-yl)cyclohexyl)-1H-pyrazol-4-yl)pyrazolo[1,5-a]pyrazine-3-carbonitrile (Compound 158, Early eluting isomer, 15 mg, 0.015 mmol, 11% yield) as a light yellow solid. $^1$H NMR (400 MHz, DMSO-$d_6$). δ 10.78 (s, 1H), 9.28 (s, 1H), 8.83 (s, 1H), 8.70 (d, J=2.4 Hz, 1H), 8.46 (s, 1H), 8.15 (s, 1H), 8.09 (dd, J=8.8, 2.4 Hz, 1H), 6.96 (d, J=9.2 Hz, 1H), 6.84 (t, J=9.6 Hz, 1H), 6.52 (dd, J=15.2, 2.4 Hz, 1H), 6.43 (dd, J=8.8, 2 Hz, 1H), 5.80 (d, J=7.6 Hz, 1H), 4.62-4.55 (m, 3H), 4.39-4.15 (m, 3H), δ 3.95 (dd, J=11.2, 4.4 Hz, 2H), 3.67 (d, J=11.2 Hz, 1H), 3.59 (d, J=11.2 Hz, 1H), 3.32-3.27 (m, 1H), 3.21-3.12 (m, 1H), 2.92-2.79 (m, 4H), 2.74-2.67 (m, 5H), 2.61-2.53 (m, 1H), 2.50-2.43 (m, 1H), 2.38-2.26 (m, 2H), 2.17-2.08 (m, 3H), 2.14-1.97 (m, 2H), 1.86-1.83 (m, 3H), 1.49-1.47 (m, 2H) and 1.05 (s, 9H). LCMS ($ES^+$): m/z 898.3 $[M+H]^+$.

Example 173: Synthesis of tert-butyl (1R,5S)-7-[5-[3-cyano-6-[1-[4-[4-[4-[(2,6-dioxo-3-piperidyl)amino]-2-fluoro-phenyl]piperazin-1-yl]cyclohexyl]pyrazol-4-yl]pyrazolo[1,5-a]pyrazin-4-yl]-2-pyridyl]-3-oxa-7,9-diazabicyclo[3.3.1]nonane-9-carboxylate (Compound 159)

(Configurations are arbitrarily assigned)

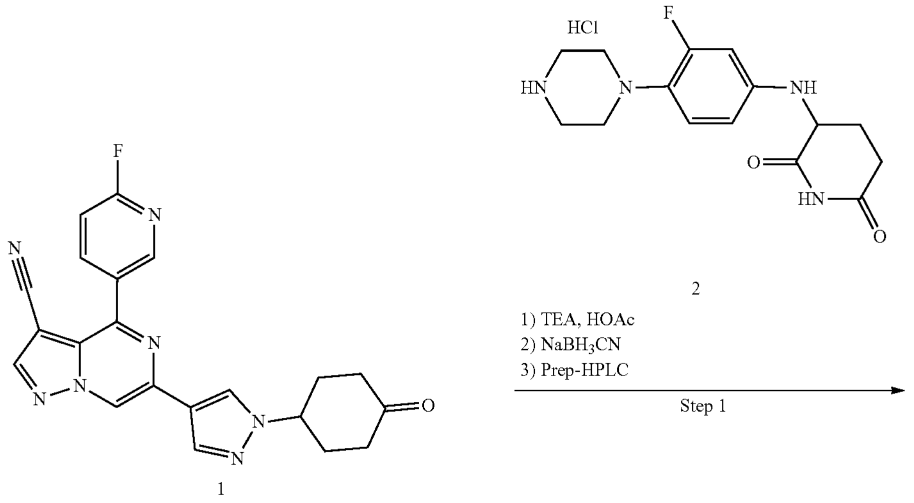

-continued

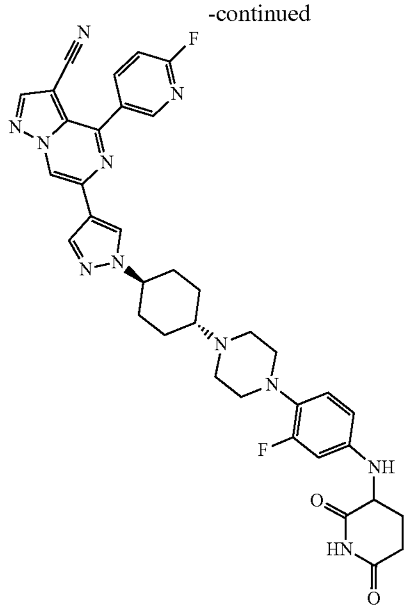

3

+

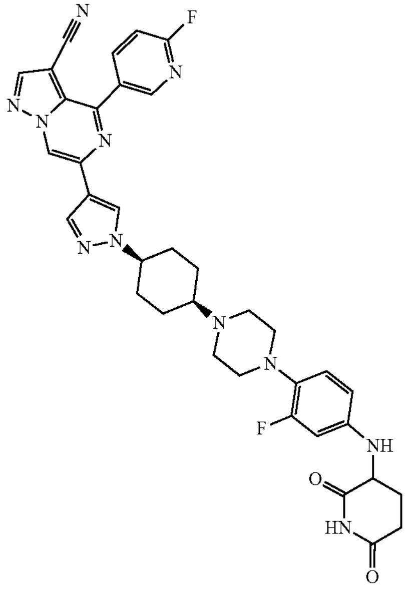

4

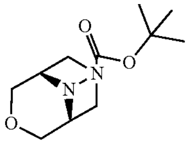

5

DIEA, DMSO

Step 2

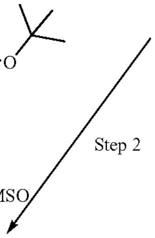

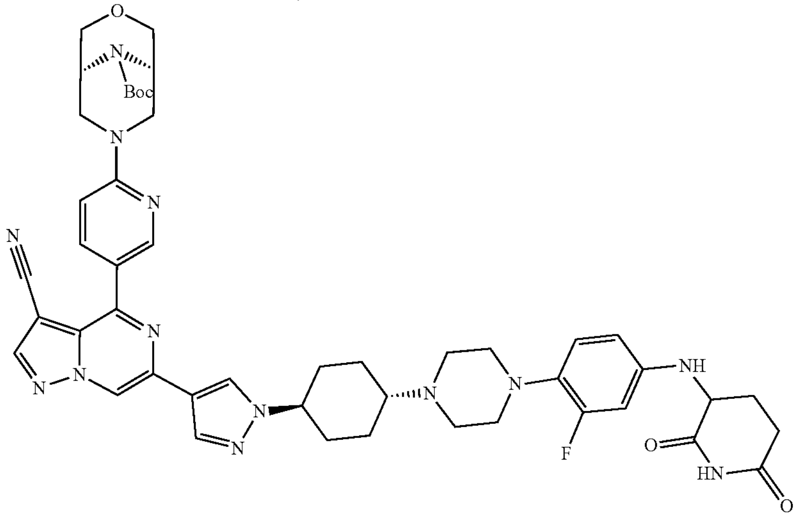

Compound 159

Step 1: To a solution of 3-((3-fluoro-4-(piperazin-1-yl) phenyl)amino)piperidine-2,6-dione (2, 5.62 g, 16.39 mmol, HCl salt) in DMAc (50 mL) was added TEA (6.38 g, 63.06 mmol, 8.79 mL) and 4-(6-fluoropyridin-3-yl)-6-(1-(4-oxo-cyclohexyl)-1H-pyrazol-4-yl)pyrazolo[1,5-a]pyrazine-3 carbonitrile (1, 6.5 g, 12.61 mmol, TFA salt). The mixture was stirred at 60° C. for 1 h. Then $NaBH_3CN$ (2.38 g, 37.83 mmol) was added. The mixture was stirred at 60° C. for 12 h. The mixture was filtered. The filtrate was purified by reversed phase column (C18, 330 g; condition: water/acetonitrile=1/0 to 0/1, 0.1% formic acid). The mixture of trans & cis isomers (5 g, 7.08 mmol, 56.17% yield) was obtained as a yellow solid. Then this mixture was purified by Prep-HPLC (column: Waters Xbridge C18 250*50 mm*10 um; flow: 100 mL/min; gradient: from 25-55% MeCN in water (10 mM $NH_4HCO_3$) over 18 min;) to give two peaks. 6-[1-[4-[4-[4-[(2,6-dioxo-3-piperidyl)amino]-2-fluoro-phenyl]piperazin-1-yl]cyclohexyl]pyrazol-4-yl]-4-(6-fluoro-3-pyridyl)pyrazolo[1,5-a]pyrazine-3-carbonitrile (3, Early eluting isomer, 1.4 g, 1.92 mmol, 27% yield) was obtained as a yellow solid. 6-[1-[4-[4-[4-[(2,6-dioxo-3-piperidyl) amino]-2-fluoro-phenyl]piperazin-1-yl]cyclohexyl]pyrazol- 4-yl]-4-(6-fluoro-3-pyridyl)pyrazolo[1,5-a]pyrazine-3-carbonitrile (4, Late eluting isomer, 500 mg, 650.54 μmol, 9% yield) was obtained as a yellow solid, Early eluting isomer: LCMS (ES$^+$): m/z 692.5 [M+H]$^+$ Late eluting isomer: LCMS (ES$^+$): m/z 692.1 [M+H]$^+$ Step 2: To a solution of tert-butyl (1S,5R)-3-oxa-7,9-diazabicyclo[3.3.1]nonane-9-carboxylate (47.52 mg, 208.17 μmol), 6-[1-[4-[4-[4-[(2,6-dioxo-3-piperidyl)amino]-2-fluoro-phenyl]piperazin-1-yl]cyclohexyl]pyrazol-4-yl]-4-(6-fluoro-3-pyridyl)pyrazolo[1,5-a]pyrazine-3-carbonitrile (3, Early eluting isomer, 120 mg, 173.48 μmol) in DMSO (1.5 mL) was added diisopropyl ethyl amine (112.10 mg, 867.39 μmol, 151.08 μL) dropwise. After addition, the mixture was kept at 100° C. for 12 hrs. The reaction mixture was acidified to pH<7 mixed HCOOH and then filtered. The filtrate was diluted with CH3CN (2 mL). The crude product was purified by Prep-HPLC (column: Phenomenex luna C18 150*25 mm*10 um; mobile phase: water (0.225% FA)-ACN; B %: 21%-51%, 10 min). tert-butyl (1R,5S)-7-[5-[3-cyano-6-[1-[4-[4-[4-[(2,6-dioxo-3-piperidyl)amino]-2-fluoro-phenyl]piperazin-1-yl]cyclohexyl]pyrazol-4-yl]pyrazolo[1,5-a]pyrazin-4-yl]-2-pyridyl]-3-oxa-7,9-diazabicyclo[3.3.1]nonane-9-carboxylate (Compound 159, 125.99 mg, 129.18 μmol, 74% yield, formic acid salt) was obtained as a white powder.

LCMS (ES$^+$): m/z 900.6 [M+H]$^+$ $^1$H NMR (400 MHz, DMSO-d$_6$) δ=10.79 (s, 1H), 9.28 (s, 1H), 8.83 (s, 1H), 8.69 (d, 1H), 8.46 (s, 1H), 8.16-8.14 (m, 1H), 8.11-8.06 (m, 1H), 6.98-6.92 (m, 1H), 6.87-6.79 (m, 1H), 6.55-6.48 (m, 1H), 6.46-6.40 (m, 1H), 5.86-5.79 (m, 1H), 4.59-4.47 (m, 2H), 4.31-4.15 (m, 2H), 4.09-4.00 (m, 2H), 3.95-3.86 (m, 2H), 3.68-3.60 (m, 2H), 3.26-3.19 (m, 2H), 2.87 (br s, 3H), 2.75-2.65 (m, 5H), 2.62-2.57 (m, 2H), 2.20-2.04 (m, 4H), 2.03-1.93 (m, 2H), 1.91-1.76 (m, 4H), 1.55-1.48 (m, 1H), 1.46 (s, 9H)

Example 174: Synthesis of 6-[1-[4-[4-[4-[(2,6-dioxo-3-piperidyl)amino]-2-fluoro-phenyl]piperazin-1-yl]cyclohexyl]pyrazol-4-yl]-4-[6-[(1R,5S)-7-[(6-methoxy-3-pyridyl)methyl]-3-oxa-7,9-diazabicyclo[3.3.1]nonan-9-yl]-3-pyridyl]pyrazolo[1,5-a]pyrazine-3-carbonitrile (Compound 160)

(Configurations are arbitrarily assigned)

Compound 160 was Prepared Following the Synthesis of Compound 159

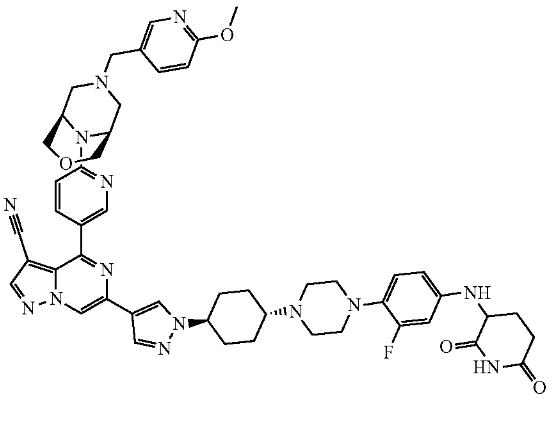 [SMILES: COc1ccc(CN2C[C@H]3COC[C@@H](C2)N3c2ccc(-c3nc(-c4cnn([C@H]5CC[C@H](N6CCN(c7ccc(NC8CCC(=O)NC8=O)cc7F)CC6)CC5)c4)cn4ncc(C#N)c34)cn2)cn1]

LCMS (ES$^+$): m/z 921.6 [M+H]$^+$ $^1$H NMR (400 MHz, DMSO-d$_6$) δ=10.79 (s, 1H), 9.30 (s, 1H), 8.84 (s, 1H), 8.70 (d, J=2.4 Hz, 1H), 8.47 (s, 1H), 8.17 (d, J=10.6 Hz, 2H), 8.13-8.05 (m, 2H), 7.67 (dd, J=2.4, 8.4 Hz, 1H), 7.03 (d, J=8.8 Hz, 1H), 6.88-6.77 (m, 2H), 6.52 (dd, J=2.4, 15.2 Hz, 1H), 6.43 (d, J=8.8 Hz, 1H), 5.81 (d, J=7.6 Hz, 1H), 4.76-4.42 (m, 2H), 4.30-4.16 (m, 2H), 3.90 (d, J=11.0 Hz, 2H), 3.84 (s, 3H), 3.77 (d, J=10.4 Hz, 2H), 3.38 (s, 2H), 2.95 (d, J=11.0 Hz, 2H), 2.87 (br s, 4H), 2.79-2.58 (m, 8H), 2.43 (d, J=8.8 Hz, 4H), 2.20-2.06 (m, 3H), 2.02-1.93 (m, 2H), 1.91-1.79 (m, 3H), 1.54-1.42 (m, 2H)

Example 175: Synthesis of 6-[1-[4-[4-[4-[(2,6-dioxo-3-piperidyl)amino]-2,5-difluoro-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 161)

(Configurations are arbitrarily assigned)

Compound 161 was Prepared Following the Synthesis of Compound 159

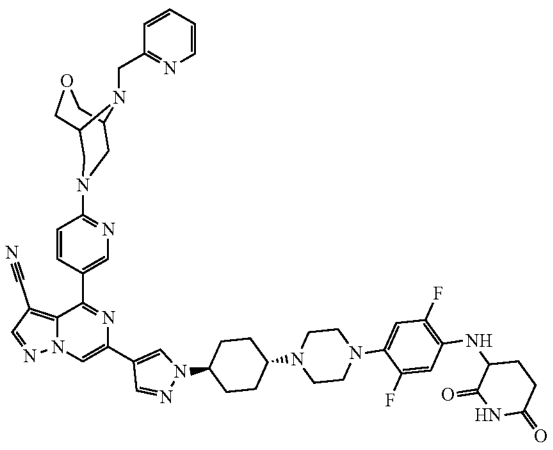 [SMILES: N#Cc1cnn2cc(-c3cnn([C@H]4CC[C@H](N5CCN(c6cc(F)c(NC7CCC(=O)NC7=O)cc6F)CC5)CC4)c3)nc(-c3ccc(N4CC5COCC(C4)N5Cc4ccccn4)nc3)c12]

LCMS (ES$^+$): m/z 909.2 [M+H]$^+$ $^1$H NMR (400 MHz, DMSO-d$_6$) δ=10.81 (s, 1H), 9.27 (s, 1H), 8.83 (s, 1H), 8.72 (d, J=2.4 Hz, 1H), 8.55-8.50 (m, 1H), 8.46 (s, 1H), 8.17 (br s, 1H), 8.15 (s, 1H), 8.10 (dd, J=2.4, 9.0 Hz, 1H), 7.81 (dt, J=1.8, 7.6 Hz, 1H), 7.60 (d, J=8.0 Hz, 1H), 7.29 (dd, J=5.2, 6.8 Hz, 1H), 6.91 (d, J=9.0 Hz, 1H), 6.85 (dd, J=8.4, 13.2 Hz, 1H), 6.74 (dd, J=8.4, 14.6 Hz, 1H), 5.50 (d, J=7.8 Hz, 1H), 4.43-4.28 (m, 1H), 4.27-4.12 (m, 3H), 4.11 (s, 2H), 3.99-3.86 (m, 2H), 3.81 (d, J=10.9 Hz, 2H), 3.57 (d, J=10.4 Hz, 2H), 2.88 (br s, 6H), 2.80-2.64 (m, 5H), 2.59 (d, J=3.4 Hz, 1H), 2.48-2.40 (m, 1H), 2.16 (d, J=10.8 Hz, 2H), 2.09-1.93 (m, 4H), 1.90-1.77 (m, 2H), 1.54-1.41 (m, 2H)

Example 176: Synthesis of 6-[1-[4-[4-[4-[(2,6-dioxo-3-piperidyl)amino]-2,5-difluoro-phenyl]piperazin-1-yl]cyclohexyl]pyrazol-4-yl]-4-[6-[9-[(6-methoxy-3-pyridyl)methyl]-3-oxa-7,9-diazabicyclo[3.3.1]nonan-7-yl]-3-pyridyl]pyrazolo[1,5-a]pyrazine-3-carbonitrile (Compound 162)

(Configurations are arbitrarily assigned)

Compound 162 was Prepared Following the Synthesis of Compound 159

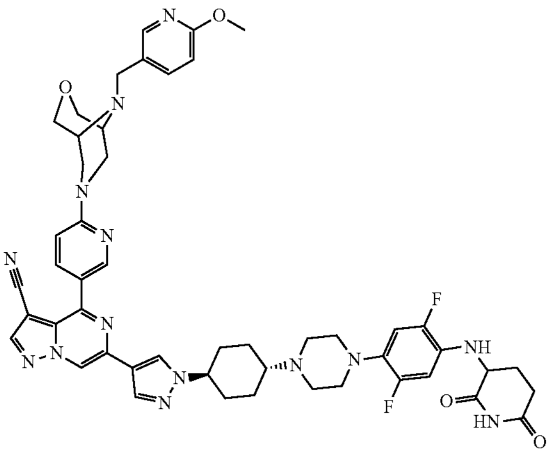 [SMILES: COc1ccc(CN2C3COCC2CN(c2ccc(-c4nc(-c5cnn([C@H]6CC[C@H](N7CCN(c8cc(F)c(NC9CCC(=O)NC9=O)cc8F)CC7)CC6)c5)cn5ncc(C#N)c45)cn2)C3)cn1]

LCMS ($ES^+$): m/z 939.2 $[M+H]^+$ $^1$H NMR (400 MHz, DMSO-$d_6$) δ=10.80 (s, 1H), 9.26 (s, 1H), 8.82 (s, 1H), 8.71 (d, J=2.4 Hz, 1H), 8.45 (s, 1H), 8.17 (d, J=2.0 Hz, 1H), 8.16 (s, 1H), 8.15 (s, 1H), 8.09 (dd, J=2.4, 8.9 Hz, 1H), 7.76 (dd, J=2.4, 8.5 Hz, 1H), 6.93-6.79 (m, 3H), 6.74 (dd, J=8.3, 14.5 Hz, 1H), 5.49 (d, J=8.4 Hz, 1H), 4.41-4.28 (m, 1H), 4.26-4.02 (m, 3H), 3.93 (s, 2H), 3.87-3.73 (m, 7H), 3.53 (d, J=10.0 Hz, 2H), 2.87 (br s, 4H), 2.81 (br s, 2H), 2.77-2.62 (m, 5H), 2.60-2.53 (m, 1H), 2.47-2.38 (m, 1H), 2.15 (d, J=10.8 Hz, 2H), 2.08-1.91 (m, 4H), 1.90-1.76 (m, 2H), 1.54-1.38 (m, 2H)

Example 177: Synthesis of tert-butyl 7-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-3-oxa-7,9-diazabicyclo[3.3.1]nonane-9-carboxylate (Compound 163)

(Configurations are arbitrarily assigned)

Compound 163 was Prepared Following the Synthesis of Compound 159

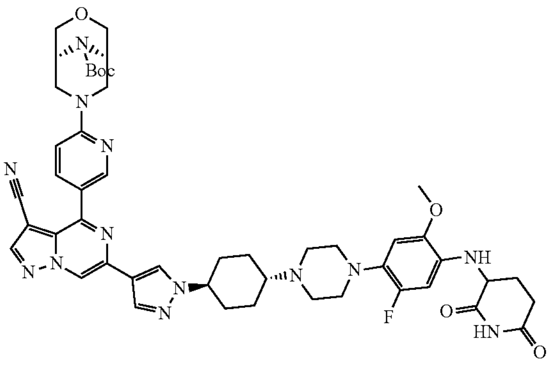 [SMILES: COc1cc(N2CCN([C@H]3CC[C@H](n4cc(-c5cn6ncc(C#N)c6c(-c6ccc(N7C[C@H]8COC[C@@H](C7)N8C(=O)OC(C)(C)C)nc6)n5)cn4)CC3)CC2)c(F)cc1NC1CCC(=O)NC1=O]

LCMS ($ES^+$): m/z 930.7 [M+H]P $^1$H NMR (400 MHz, DMSO-$d_6$) δ=10.87 (s, 1H), 9.29 (s, 1H), 8.84 (s, 1H), 8.71-8.68 (m, 1H), 8.46 (s, 1H), 8.16 (s, 1H), 8.11-8.06 (m, 1H), 6.95 (d, J=9.2 Hz, 1H), 6.61 (d, J=8.4 Hz, 1H), 6.56 (d, J=14.4 Hz, 1H), 5.15-5.08 (m, 1H), 4.59-4.48 (m, 2H), 4.31-4.16 (m, 2H), 4.12-4.00 (m, 2H), 3.96-3.86 (m, 2H), 3.80 (s, 3H), 3.70-3.60 (m, 2H), 3.27-3.20 (m, 2H), 3.04-2.87 (m, 4H), 2.86-2.65 (m, 5H), 2.59-2.52 (m, 2H), 2.22-2.08 (m, 3H), 2.05-1.77 (m, 5H), 1.57-1.42 (m, 11H).

Example 178: Synthesis of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[(1R,5S)-9-[(4-fluorophenyl)methyl]-3-oxa-7,9-diazabicyclo[3.3.1]nonan-7-yl]-3-pyridyl]pyrazolo[1,5-a]pyrazine-3-carbonitrile (Compound 164)

(Configurations are arbitrarily assigned)

Compound 164 was Prepared Following the Synthesis of Compound 159

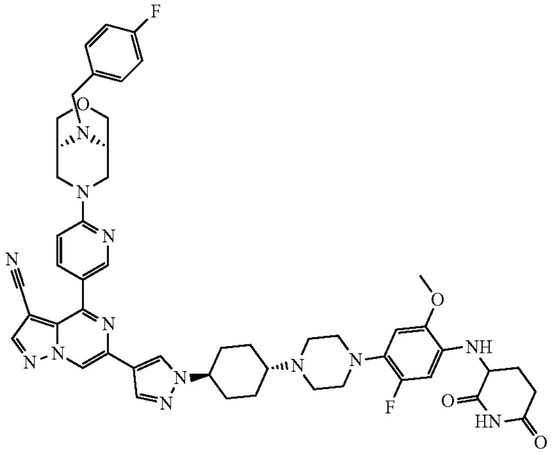 [SMILES: COc1cc(N2CCN([C@H]3CC[C@H](n4cc(-c5cn6ncc(C#N)c6c(-c6ccc(N7C[C@H]8COC[C@@H](C7)N8Cc7ccc(F)cc7)nc6)n5)cn4)CC3)CC2)c(F)cc1NC1CCC(=O)NC1=O]

LCMS ($ES^+$): m/z 938.1 $[M+H]^+$ $^1$H NMR (400 MHz, DMSO-$d_6$) δ=10.86 (s, 1H), 9.26 (s, 1H), 8.82 (s, 1H), 8.71 (d, J=2.4 Hz, 1H), 8.44 (s, 1H), 8.20 (s, 1H), 8.14 (s, 1H), 8.08 (dd, J=2.4, 8.8 Hz, 1H), 7.51-7.43 (m, 2H), 7.16 (t, J=8.8 Hz, 2H), 6.88 (d, J=9.2 Hz, 1H), 6.63-6.51 (m, 2H), 5.09 (br d, J=6.4 Hz, 1H), 4.30-4.06 (m, 4H), 4.00-3.93 (m, 2H), 3.89-3.82 (m, 2H), 3.81-3.75 (m, 5H), 3.53-3.50 (m, 2H), 2.96-2.86 (m, 4H), 2.86-2.75 (m, 3H), 2.70-2.61 (m, 4H), 2.58-2.54 (m, 1H), 2.47-2.41 (m, 1H), 2.19-2.08 (m, 3H), 2.00-1.76 (m, 5H), 1.54-1.39 (m, 2H).

6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[9-[(6-methoxy-3-pyridyl)methyl]-3-oxa-7,9-diazabicyclo[3.3.1]nonan-7-yl]-3-pyridyl]pyrazolo[1,5-a]pyrazine-3-carbonitrile (Compound 165)

(Configurations are arbitrarily assigned)

Compound 165 was Prepared Following the Synthesis of Compound 159

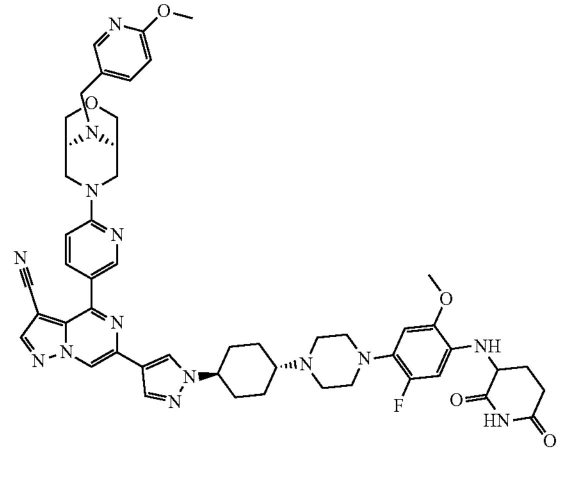 [SMILES: COc1ccc(CN2[C@@H]3COC[C@H]2CN(c2ccc(-c4nc(-c5cnn([C@H]6CC[C@H](N7CCN(c8cc(OC)c(NC9CCC(=O)NC9=O)cc8F)CC7)CC6)c5)cn5ncc(C#N)c45)cn2)C3)cn1]

LCMS ($ES^+$): m/z 951.3 $[M+H]^+$

1H NMR (400 MHz, DMSO-$d_6$) δ=10.86 (br s, 1H), 9.27 (s, 1H), 8.83 (s, 1H), 8.72 (d, J=2.4 Hz, 1H), 8.46 (s, 1H), 8.39 (s, 0.52H), 8.24-8.14 (m, 2H), 8.10 (dd, J=2.4, 8.8 Hz, 1H), 7.77 (dd, J=2.4, 8.4 Hz, 1H), 6.90 (d, J=9.2 Hz, 1H), 6.83 (d, J=8.4 Hz, 1H), 6.62 (d, J=8.4 Hz, 1H), 6.55 (d, J=14.4 Hz, 1H), 5.09 (br d, J=6.4 Hz, 1H), 4.31-4.06 (m, 4H), 3.94 (s, 2H), 3.89-3.75 (m, 10H), 3.52 (br d, J=2.8 Hz, 2H), 3.00-2.88 (m, 4H), 2.82 (br s, 3H), 2.68 (br d, J=1.6 Hz, 4H), 2.56 (br d, J=3.2 Hz, 1H), 2.41 (br d, J=4.8 Hz, 1H), 2.24-2.08 (m, 3H), 2.02-1.80 (m, 5H), 1.48 (br d, J=11.6 Hz, 2H)

Example 179: Synthesis of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[(1R,5S)-9-(tetrahydropyran-4-ylmethyl)-3-oxa-7,9-diazabicyclo[3.3.1]nonan-7-yl]-3-pyridyl]pyrazolo[1,5-a]pyrazine-3-carbonitrile (Compound 166)

(Configurations are arbitrarily assigned)

Compound 166 was Prepared Following the Synthesis of Compound 159

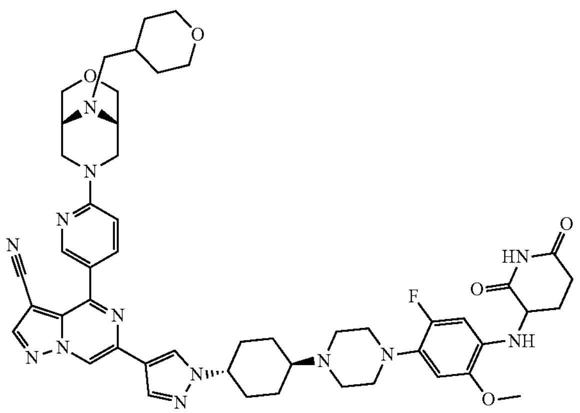 [SMILES: COc1cc(N2CCN([C@H]3CC[C@H](n4cc(-c5cn6ncc(C#N)c6c(-c6ccc(N7C[C@H]8COC[C@@H](C7)N8CC7CCOCC7)nc6)n5)cn4)CC3)CC2)c(F)cc1NC1CCC(=O)NC1=O]

LCMS ($ES^+$): m/z 928.2 $[M+H]^+$ $^1$H NMR (400 MHz, DMSO-$d_6$) δ=10.86 (s, 1H), 9.27 (s, 1H), 8.83 (s, 1H), 8.71 (d, J=2.8 Hz, 1H), 8.46 (s, 1H), 8.22 (s, 1H), 8.15 (s, 1H), 8.08 (dd, J=2.4, 8.9 Hz, 1H), 6.88 (d, J=9.2 Hz, 1H), 6.65-6.52 (m, 2H), 5.10 (d, J=6.4 Hz, 1H), 4.32-4.15 (m, 2H), 4.08 (d, J=12.0 Hz, 2H), 3.90-3.73 (m, 9H), 3.45 (d, J=10.4 Hz, 2H), 3.30 (t, J=10.8 Hz, 2H), 2.92 (br s, 4H), 2.86-2.74 (m, 3H), 2.72-2.59 (m, 6H), 2.59-2.54 (m, 1H), 2.45-2.40 (m, 1H), 2.21-2.08 (m, 3H), 2.04-1.78 (m, 5H), 1.77-1.60 (m, 3H), 1.57-1.39 (m, 2H), 1.24-1.11 (m, 2H)

Example 180: Synthesis of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[6-[(6-methoxy-3-pyridyl)methyl]-3,6-diazabicyclo[3.1.1]heptan-3-yl]-3-pyridyl]pyrazolo[1,5-a]pyrazine-3-carbonitrile (Compound 167)

(Configurations are arbitrarily assigned)

Compound 167 was Prepared Following the Synthesis of Compound 159

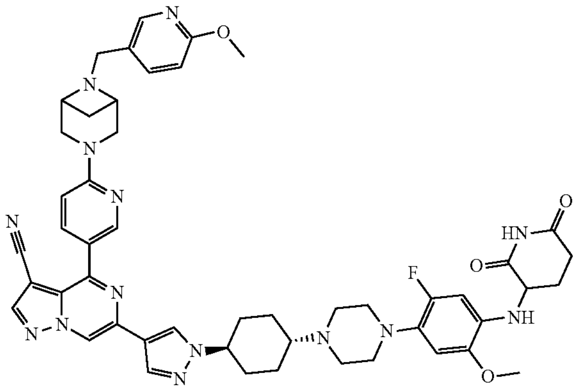 [SMILES: COc1ccc(CN2C3CC2CN(c2ccc(-c4nc(-c5cnn([C@H]6CC[C@H](N7CCN(c8cc(OC)c(NC9CCC(=O)NC9=O)cc8F)CC7)CC6)c5)cn5ncc(C#N)c45)cn2)C3)cn1]

LCMS ($ES^+$): m/z 921.4 $[M+H]^+$ $^1$H NMR (400 MHz, DMSO-$d_6$) δ=10.87 (s, 1H), 9.30 (s, 1H), 8.85 (s, 1H), 8.78 (d, J=2.5 Hz, 1H), 8.47 (s, 1H), 8.30 (s, 1H), 8.21-8.13 (m, 2H), 8.09 (d, J=2.4 Hz, 1H), 7.70 (dd, J=2.4, 8.8 Hz, 1H), 6.87 (d, J=8.8 Hz, 1H), 6.78 (d, J=8.8 Hz, 1H), 6.61 (d, J=8.8 Hz, 1H), 6.55 (d, J=14.4 Hz, 1H), 5.10 (br d, J=6.4 Hz, 1H), 4.30-4.19 (m, 2H), 3.83 (s, 3H), 3.79 (s, 3H), 3.78 (br s, 1H), 3.69 (br d, J=5.6 Hz, 1H), 3.63 (br d, J=12.0 Hz, 2H), 3.53 (s, 2H), 2.92 (br s, 4H), 2.84-2.75 (m, 1H), 2.67 (br s, 4H), 2.59-2.53 (m, 2H), 2.47-2.39 (m, 2H), 2.21-2.08 (m, 3H), 2.02-1.78 (m, 5H), 1.61 (br d, J=8.0 Hz, 1H), 1.56-1.42 (m, 2H), 1.06 (t, J=7.2 Hz, 1H)

3-chloro-N-[[(1S,5R)-3-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-3-azabicyclo[3.1.0]hexan-6-yl]methyl]pyridine-2-carboxamide (Compound 168)
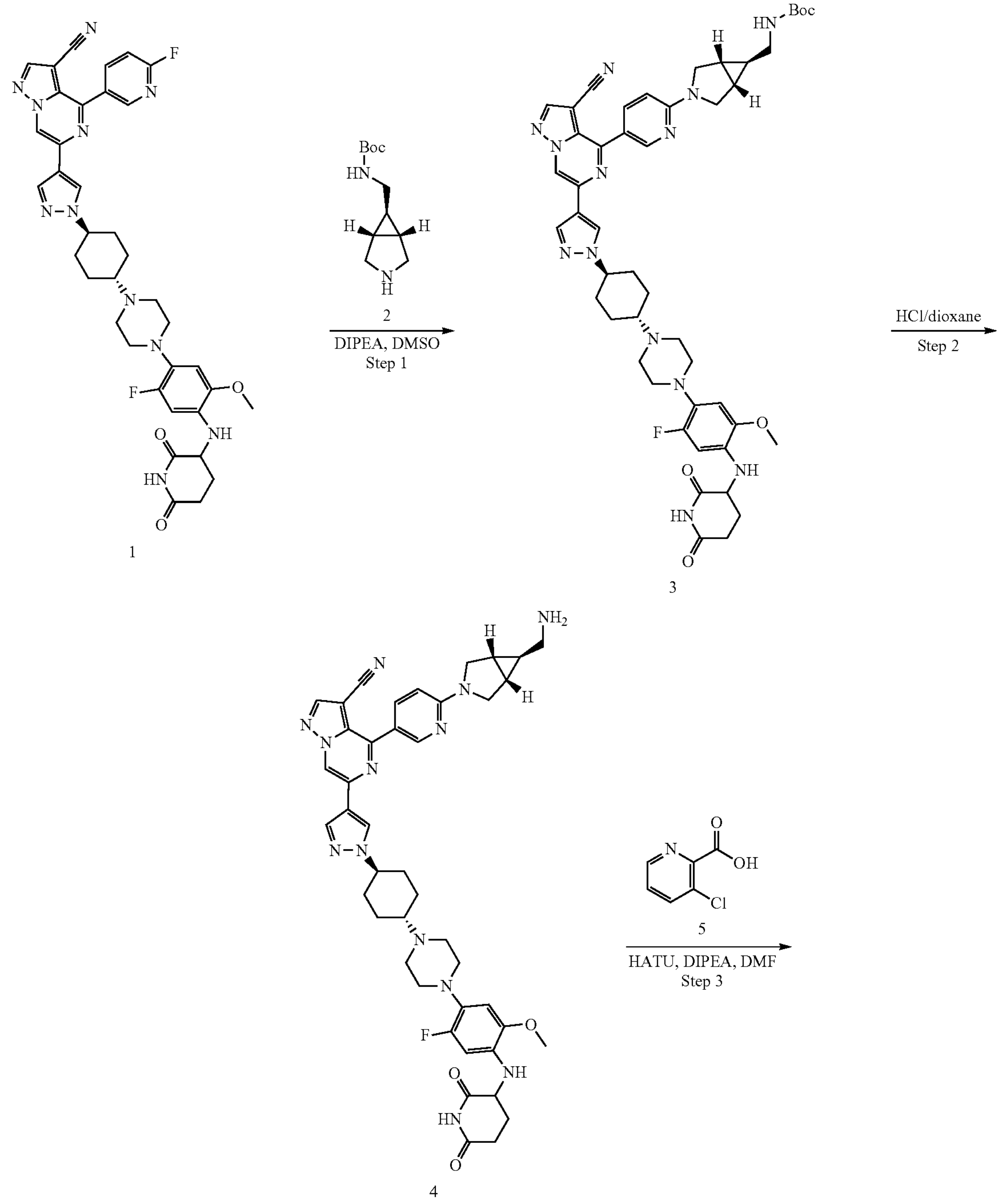

-continued

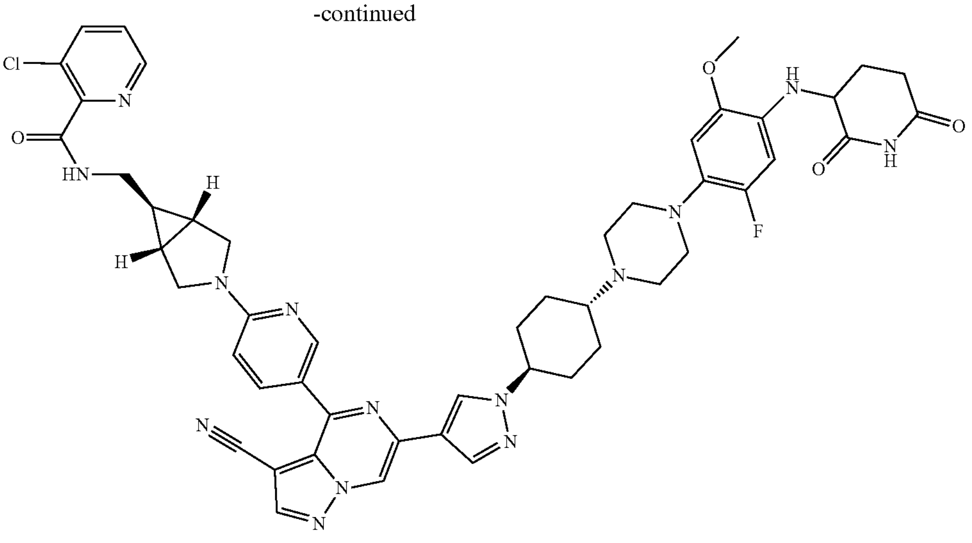

Compound 168

Step 1: To a solution of 6-[1-[4-[4-[4-[(2,6-dioxo-3-piperidyl)amino]-2-fluoro-5-methoxy-phenyl]piperazin-1-yl] cyclohexyl]pyrazol-4-yl]-4-(6-fluoro-3-pyridyl)pyrazolo[1,5-a]pyrazine-3-carbonitrile (1, 100 mg, 138.55 μmol) and DIPEA (53.72 mg, 415.65 μmol, 72.40 μL) in DMSO (1 mL) was added tert-butyl N-[[(1R,5S)-3-azabicyclo[3.1.0]hexan-6-yl]methyl]carbamate (2, 58.83 mg, 277.10 μmol), then the mixture was stirred at 100° C. for 12 h. The reaction mixture was poured into water (5 mL) and filtered. The filter cake was dried under vacuum to obtain tert-butyl N-[[(1S,5R)-3-[5-[3-cyano-6-[1-[4-[4-[4-[(2,6-dioxo-3-piperidyl)amino]-2-fluoro-5-methoxy-phenyl]piperazin-1-yl]cyclohexyl] pyrazol-4-yl]pyrazolo[1,5-a]pyrazin-4-yl]-2-pyridyl]-3-azabicyclo[3.1.0]hexan-6-yl]methyl]carbamate (3, 115 mg, 114.24 μmol, 82% yield) as gray solid. LCMS ($ES^+$): m/z 914.7 $[M+H]^+$ Step 2: The solution of tert-butyl N-[[(1S,5R)-3-[5-[3-cyano-6-[1-[4-[4-[4-[(2,6-dioxo-3-piperidyl) amino]-2-fluoro-5-methoxy-phenyl]piperazin-1-yl]cyclohexyl]pyrazol-4-yl]pyrazolo[1,5-a] pyrazin-4-yl]-2-pyridyl]-3-azabicyclo[3.1.0]hexan-6-yl]methyl]carbamate (3, 60 mg, 65.64 μmol) in HCl/dioxane (4 M, 49.23 μL) was stirred at 20° C. for 1 h. The reaction mixture was concentrated to obtain 4-[6-[(1S,5R)-6-(aminomethyl)-3-azabicyclo[3.1.0] hexan-3-yl]-3-pyridyl]-6-[1-[4-[4-[4-[(2,6-dioxo-3-piperidyl)amino]-2-fluoro-5-methoxy-phenyl]piperazin-1-yl] cyclohexyl]pyrazol-4-yl]pyrazolo[1,5-a]pyrazine-3-carbonitrile (4, 55 mg, 64.03 μmol, 98% yield, HCl salt) as a gray solid. LCMS ($ES^+$): m/z 814.4 $[M+H]^+$ Step 3: To the solution of 4-[6-[(1S,5R)-6-(aminomethyl)-3-azabicyclo[3.1.0]hexan-3-yl]-3-pyridyl]-6-[1-[4-[4-[4-[(2,6-dioxo-3-piperidyl)amino]-2-fluoro-5-methoxy-phenyl]piperazin-1-yl] cyclohexyl] pyrazol-4-yl]pyrazolo[1,5-a]pyrazine-3-carbonitrile (4, 55 mg, 64.68 μmol, HCl salt), 3-chloropyridine-2-carboxylic acid (5, 12.23 mg, 77.61 μmol) and DIPEA (25.08 mg, 194.03 μmol, 33.80 μL) in DMF (0.5 mL) was added HATU (49.44 mg, 129.35 μmol). Then the solution was stirred at 20° C. for 12 h. The reaction mixture was concentrated under vacuum. The residue was purified by HPLC (Instrument: ACSWH-GX-Q; Column: Phenomenex Synergi C18 150*25 mm*10 um; Condition: water (0.225% FA)-CAN; Begin B: 8%; End B: 41%; Gradient Time (min): 11; FlowRate (ml/min): 25) to obtain 3-chloro-N-[[(1S,5R)-3-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-3-azabicyclo[3.1.0]hexan-6-yl]methyl] pyridine-2-carboxamide (Compound 168, 26.95 mg, 26.37 μmol, 41% yield, formic acid salt) as a yellow solid.

LCMS ($ES^+$): m/z 954.0 $[M+H]^+$ $^1H$ NMR (400 MHz, DMSO-$d_6$) δ=10.85 (s, 1H), 9.26 (s, 1H), 8.81 (s, 1H), 8.80-8.75 (m, 1H), 8.65 (d, J=2.4 Hz, 1H), 8.58-8.55 (m, 1H), 8.44 (s, 1H), 8.14 (s, 1H), 8.06-8.01 (m, 2H), 7.57-7.52 (m, 1H), 6.66-6.59 (m, 2H), 6.58-6.51 (m, 1H), 5.09 (d, J=6.8 Hz, 1H), 4.30-4.16 (m, 2H), 3.82-3.74 (m, 5H), 3.53-3.48 (m, 2H), 3.28-3.26 (m, 2H), 2.95-2.89 (m, 4H), 2.85-2.74 (m, 1H), 2.70-2.64 (m, 4H), 2.57-2.54 (m, 1H), 2.45-2.40 (m, 1H), 2.19-2.10 (m, 3H), 2.00-1.94 (m, 2H), 1.93-1.87 (m, 1H), 1.87-1.80 (m, 2H), 1.79-1.75 (m, 2H), 1.54-1.42 (m, 2H), 0.99-0.88 (m, 1H)

4-[6-[(1R,5S)-9-(2,6-difluorobenzoyl)-3-oxa-7,9-diazabicyclo[3.3.1]nonan-7-yl]-3-pyridyl]-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazine-3-carbonitrile (Compound 169)

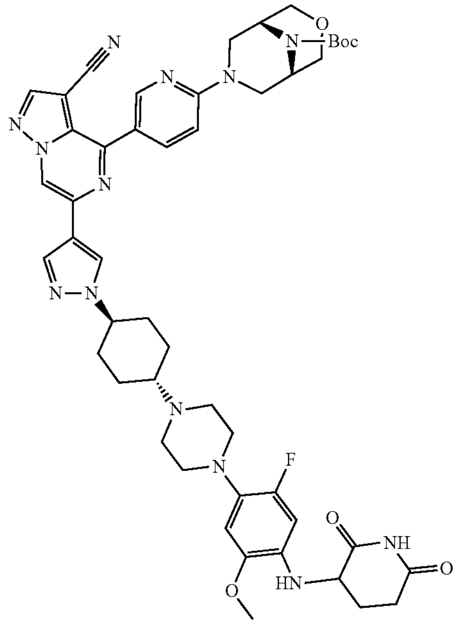

1

HCl/
dioxane
Step 1

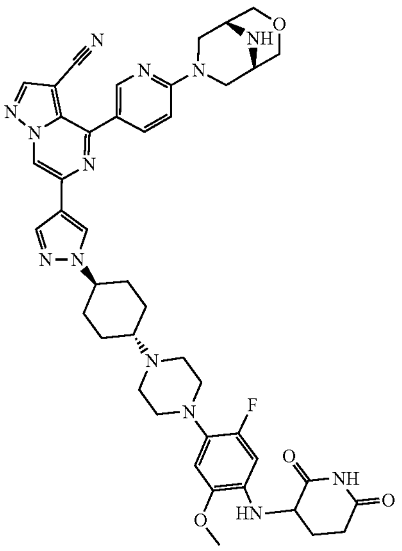

2

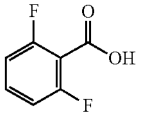

3

HATU, DIPEA,
DMF
Step 2

-continued

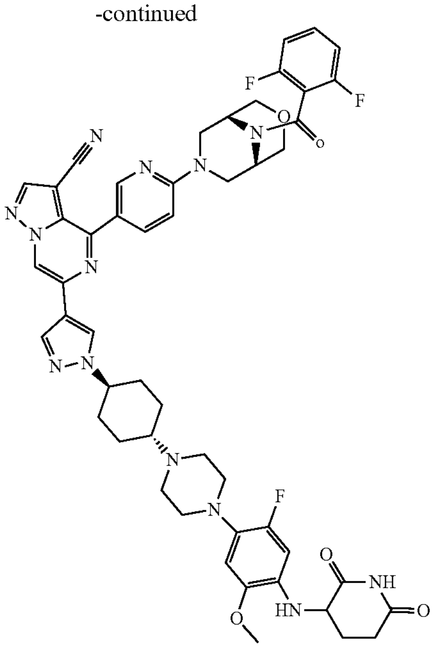

Compound 169

The starting compound tert-butyl (1R,5S)-7-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-3-oxa-7,9-diazabicyclo[3.3.1]nonane-9-carboxylate was prepared following the synthesis of Compound 159

Step 1: To a solution of tert-butyl (1R,5S)-7-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-3-oxa-7,9-diazabicyclo[3.3.1]nonane-9-carboxylate (1, 350 mg, 376.33 μmol) in DCM (3 mL) was added HCl/dioxane (4 M, 3 mL) at 20° C., the reaction was stirred at 20° C. for 2h. The reaction was concentrated under reduced pressure to get a residue. The crude residue was used for the next step directly without purification. 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[(1R,5S)-3-oxa-7,9-diazabicyclo[3.3.1]nonan-7-yl]-3-pyridyl]pyrazolo[1,5-a]pyrazine-3-carbonitrile (2, 326 mg, 312.31 μmol, 83% yield, HCl salt) was obtained as green solid. LCMS ($ES^+$): m/z 830.4 $[M+H]^+$ Step 2: To a solution of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[(1R,5S)-3-oxa-7,9-diazabicyclo [3.3.1]nonan-7-yl]-3-pyridyl]pyrazolo[1,5-a]pyrazine-3-carbonitrile (2, 320 mg, 369.35 μmol, HCl salt) and 2,6-difluorobenzoic acid (3, 58.40 mg, 369.35 μmol) in DMF (3 mL) was added HATU (210.66 mg, 554.03 μmol) and DIPEA (143.20 mg, 1.11 mmol, 193.00 μL). The mixture was stirred at 20° C. for 12h. The reaction mixture was concentrated under reduced pressure. The reaction was purified by Prep-HPLC (Column: Phenomenex luna C18 150*25 mm*10 um; Condition: water (0.225% FA)-ACN; B %: 23-53; Gradient Time (min) 10; 100% B Hold Time (min) 2; FlowRate (ml/min) 25). 4-[6-[(1R,5S)-9-(2,6-difluorobenzoyl)-3-oxa-7,9-diazabicyclo[3.3.1]nonan-7-yl]-3-pyridyl]-6-[1-[4-[4-[4-[(2,6-dioxo-3-piperidyl)amino]-2-fluoro-5-methoxy-phenyl]piperazin-1-yl]cyclohexyl]

pyrazol-4-yl]pyrazolo[1,5-a]pyrazine-3-carbonitrile (Compound 169, 152.32 mg, 146.92 μmol, 40% yield, formic acid salt) was obtained as brown solid.

LCMS ($ES^+$): m/z 970.1 $[M+H]^+$ $^1H$ NMR (400 MHz, DMSO-$d_6$) δ=10.86 (s, 1H), 9.29 (s, 1H), 8.83 (s, 1H), 8.69 (d, J=2.0 Hz, 1H), 8.46 (s, 1H), 8.17-8.15 (m, 1H), 8.14-8.13 (m, 1H), 8.12-8.07 (m, 1H), 7.67-7.56 (m, 1H), 7.34-7.25 (m, 2H), 7.01-6.93 (m, 1H), 6.65-6.52 (m, 2H), 5.18-5.10 (m, 1H), 4.78-4.68 (m, 2H), 4.65-4.57 (m, 1H), 4.30-4.20 (m, 2H), 4.10-4.04 (m, 1H), 3.96-3.91 (m, 1H), 3.82-3.77 (m, 3H), 3.75-3.69 (m, 1H), 3.68-3.65 (m, 1H), 3.63-3.58 (m, 1H), 3.32-3.28 (m, 2H), 3.20-3.14 (m, 2H), 3.08-3.00 (m, 4H), 2.97-2.91 (m, 2H), 2.85-2.75 (m, 2H), 2.56 (br s, 1H), 2.21-2.07 (m, 5H), 1.96-1.81 (m, 3H), 1.65-1.50 (m, 2H)

3-Chloro-N-(1-(5-(3-cyano-6-(1-((1s, 4s)-4-(4-(3-(2, 4-dioxotetrahydropyrimidin-1(2H)-yl)-7-fluoro-1-methyl-1H-indazol-6-yl)piperazin-1-yl)cyclohexyl)-1H-pyrazol-4-yl)pyrazolo[1,5-a]pyrazin-4-yl) pyridin-2-yl)-4-ethylpiperidin-4-yl)picolinamide (Compound 170)

(Configurations are arbitrarily assigned)

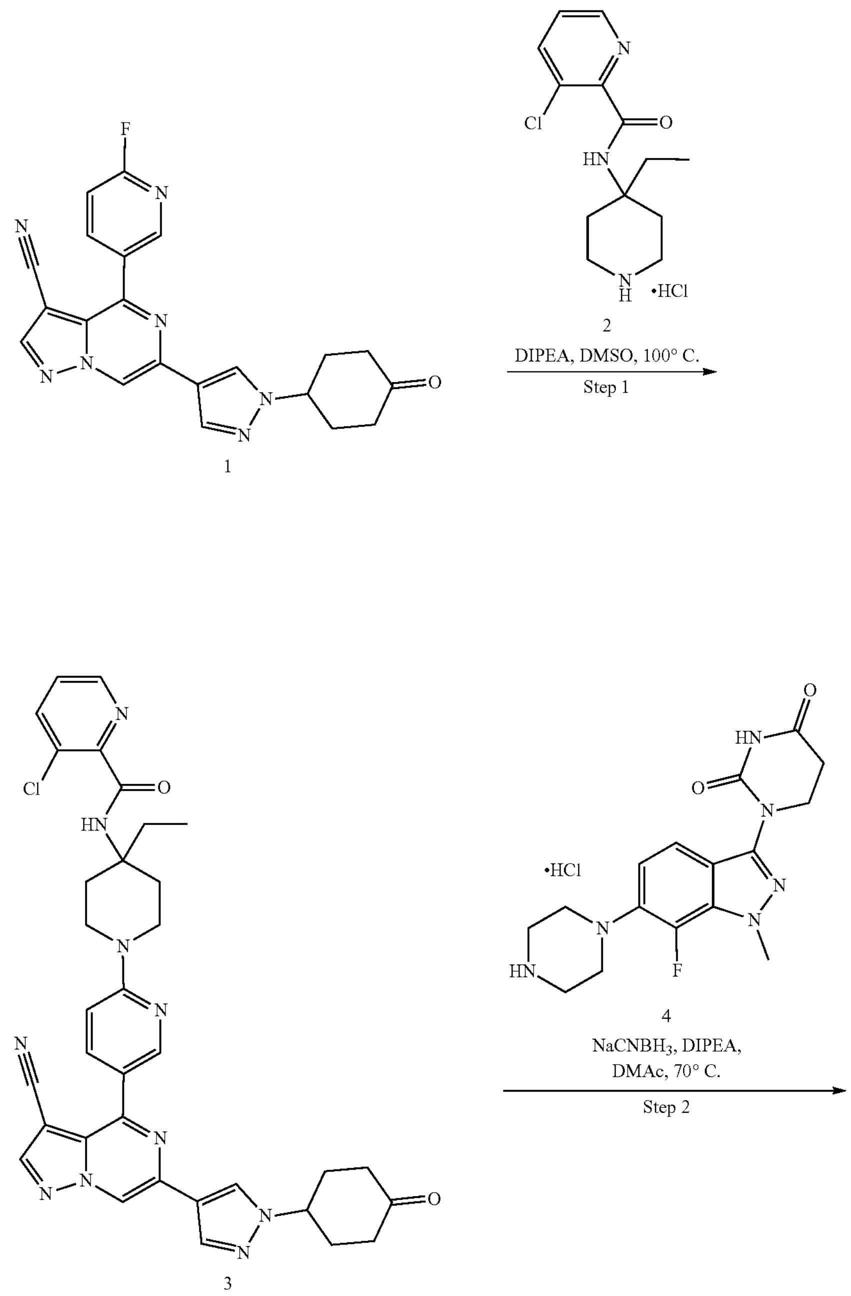

-continued

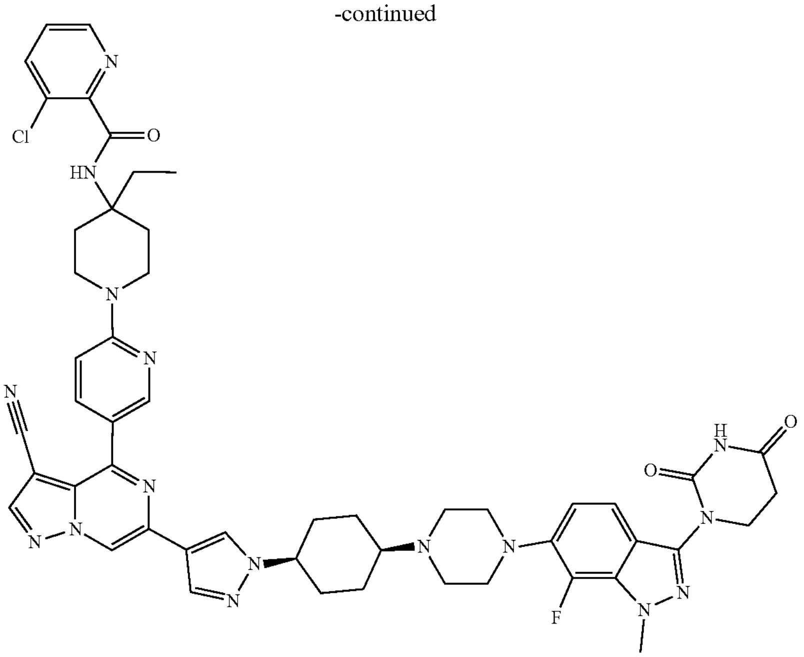

Compound 170

Step 1: Into a 25 mL sealed tube containing a well-stirred solution of 3-chloro-N-(4-ethyl-4-piperidyl)pyridine-2-carboxamide hydrochloride (2, 295 mg, 0.921 mmol) and 4-(6-fluoro-3-pyridyl)-6-[1-(4-oxocyclohexyl)pyrazol-4-yl]pyrazolo[1,5-a]pyrazine-3-carbonitrile (1, 420.20 mg, 0.921 mmol) in anhydrous DMSO (6 mL) was added diisopropylethylamine (1.60 mL, 9.21 mmol) at ambient temperature under nitrogen atmosphere. The resulting mixture was stirred at 100° C. The progress of reaction was monitored by UPLC and found complete after 16 h. The reaction mixture was quenched slowly with ice-cold water (30 mL) and solid thus obtained was filtered. The crude solid was purified by flash silica-gel (230-400 mesh) column with 50-100% EtOAc/pet ether while desired compound was eluting at 95-100% of the mobile phase to afford 3-chloro-N-[1-[5-[3-cyano-6-[1-(4-oxocyclohexyl)pyrazol-4-yl]pyrazolo[1,5-a]pyrazin-4-yl]-2-pyridyl]-4-ethyl-4-piperidyl]pyridine-2-carboxamide (3, 390 mg, 0.567 mmol, 62% yield) as a yellow solid. LCMS ($ES^+$): m/z 649.4 $[M+H]^+$.

Step 2: Into a 25 mL single-necked round-bottomed flask containing a well-stirred solution of 3-chloro-N-[1-[5-[3-cyano-6-[1-(4-oxocyclohexyl)pyrazol-4-yl]pyrazolo[1,5-a]pyrazin-4-yl]-2-pyridyl]-4-ethyl-4-piperidyl]pyridine-2-carboxamide (3, 175 mg, 0.253 mmol) and 1-(7-fluoro-1-methyl-6-piperazin-1-yl-indazol-3-yl)hexahydropyrimidine-2,4-dione hydrochloride (4, 218.00 mg, 0.506 mmol) in anhydrous DMAc (3 mL) were added diisopropylethylamine (0.441 mL, 2.53 mmol) and Sodium cyanoborohydride (79.62 mg, 1.27 mmol) at ambient temperature under nitrogen atmosphere. The resulting mixture was stirred at 70° C. The progress of reaction was monitored by UPLC and found complete after 16 h. The reaction mixture was cooled to ambient temperature and slowly added to ice-cold $H_2O$ (30 mL) and solid thus obtained was filtered. The crude solid was purified by reverse phase preparatory HPLC [Purification method: X-Bridge OBD C18 (19×150) 5 micron; Mobile phase A: 0.1% $NH_4HCO_3$ in $H_2O$ and Mobile phase B: Acetonitrile; RT=12.3 minutes] to afford 3-Chloro-N-(1-(5-(3-cyano-6-(1-((1s, 4s)-4-(4-(3-(2,4-dioxotetrahydropyrimidin-1(2H)-yl)-7-fluoro-1-methyl-1H-indazol-6-yl)piperazin-1-yl)cyclohexyl)-1H-pyrazol-4-yl)pyrazolo[1,5-a]pyrazin-4-yl)pyridin-2-yl)-4-ethylpiperidin-4-yl)picolinamide (Compound 170, Early eluting isomer, 38.5 mg, 0.038 mmol, 15% yield) as a yellow solid. $^1H$ NMR (400 MHz, DMSO-$d_6$). δ 10.57 (s, 1H), 9.29 (s, 1H), 8.83 (s, 1H), 8.70 (d, J=2.4 Hz, 1H), 8.55 (dd, J=4.6, 1.2 Hz, 1H), 8.47 (s, 1H), 8.19 (s, 1H), 8.15 (s, 1H), 8.07 (dd, J=8.8, 2.4 Hz, 1H), 8.02 (dd, J=8.2, 1.2 Hz, 1H), 7.51 (dd, J=8.2, 4.4 Hz, 1H), 7.36 (d, J=8.8 Hz, 1H), 7.06 (d, J=9.2 Hz, 1H), 6.93 (dd, J=8.8, 7.2 Hz, 1H), 4.25 (m, 3H), 4.07 (s, 3H), 3.91 (t, J=6.8 Hz, 2H), 3.22 (m, 2H), 3.13 (m, 4H), 2.77-2.74 (m, 5H), 2.56 (m, 2H), 2.38 (m, 2H), 2.15 (m, 2H), 1.95 (m, 2H), 1.85-1.84 (m, 4H), 1.51-1.50 (m, 4H) and 0.93 (t, J=7.6 Hz, 3H). LCMS ($ES^+$): m/z 979.3 $[M+H]^+$.

4-(6-(6-(2,6-Difluorobenzoyl)-3,6-diazabicyclo[3.1.1]heptan-3-yl)pyridin-3-yl)-6-(1-((1R,4s)-4-(4-(4-(((S)-2,6-dioxopiperidin-3-yl)amino)-2-fluorophenyl)piperazin-1-yl)cyclohexyl)-1H-pyrazol-4-yl)pyrazolo[1,5-a]pyrazine-3-carbonitrile (Compound 171)

4-(6-(6-(2,6-difluorobenzoyl)-3,6-diazabicyclo[3.1.1]heptan-3-yl)pyridin-3-yl)-6-(1-((1S,4s)-4-(4-(4-(((R)-2,6-dioxopiperidin-3-yl)amino)-2-fluorophenyl)piperazin-1-yl)cyclohexyl)-1H-pyrazol-4-yl)pyrazolo[1,5-a]pyrazine-3-carbonitrile (Compound 172)

(Configurations are arbitrarily assigned)

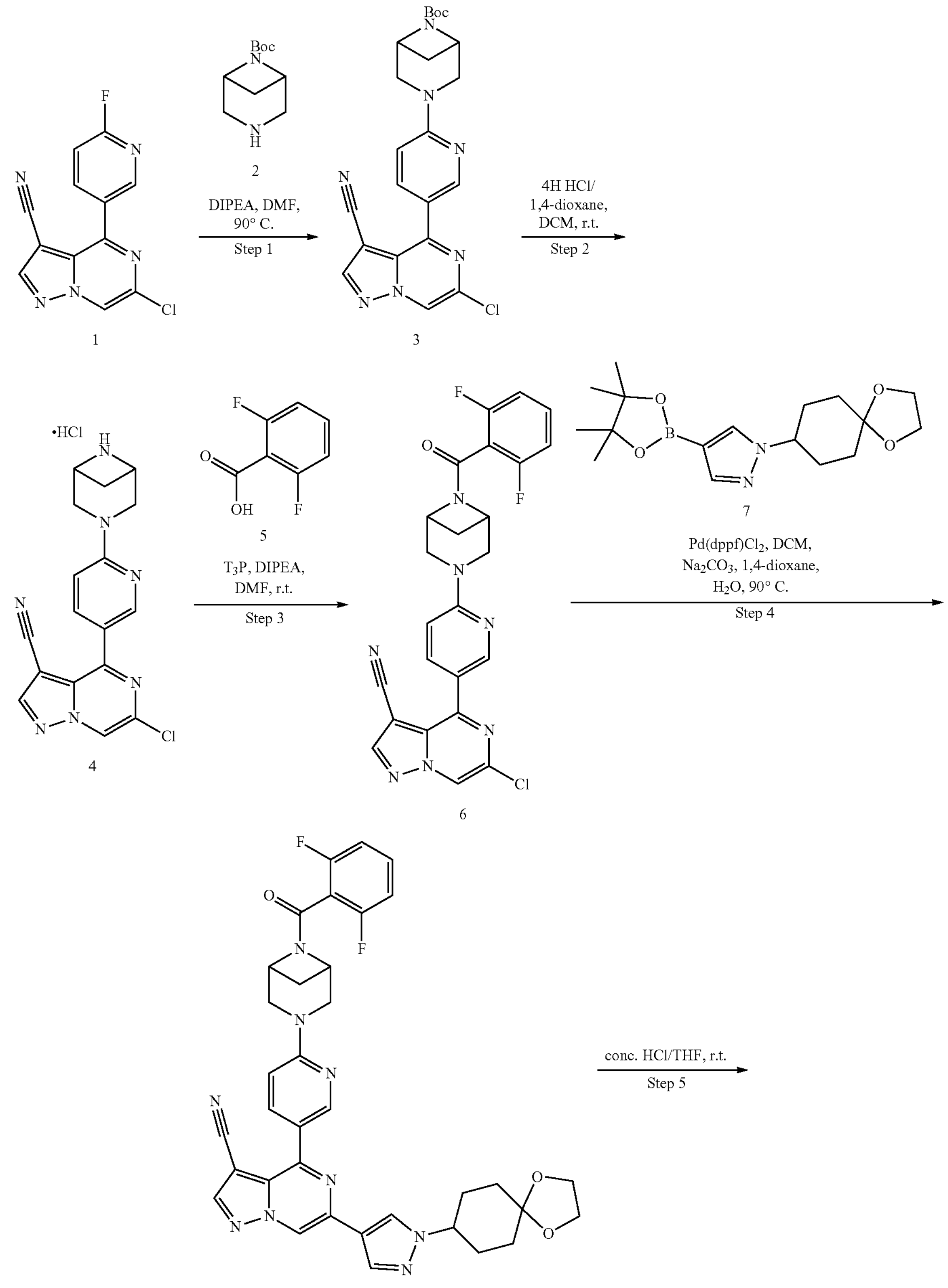
2
DIPEA, DMF,
90° C.
Step 1
1
3
4H HCl/
1,4-dioxane,
DCM, r.t.
Step 2
•HCl
4
5
$T_3P$, DIPEA,
DMF, r.t.
Step 3
6
7
Pd(dppf)$Cl_2$, DCM,
$Na_2CO_3$, 1,4-dioxane,
$H_2O$, 90° C.
Step 4
8
conc. HCl/THF, r.t.
Step 5

-continued

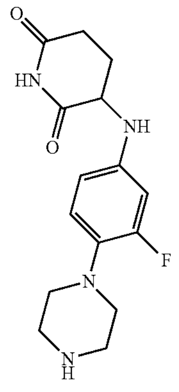

10

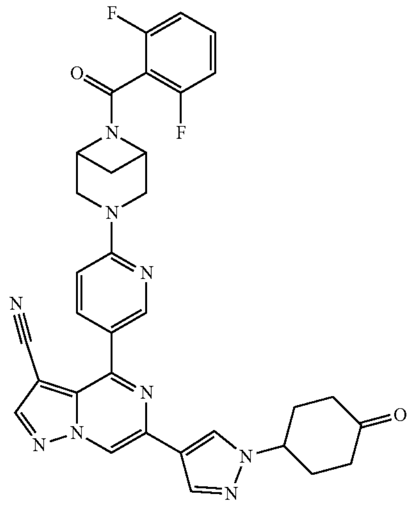

9

MP-CNBH$_3$, AcOH(cat),
4:1 MeOH/DMSO, r.t.
Step 6

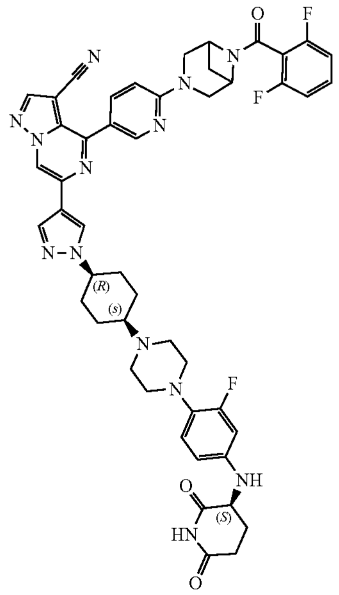

Compound 171

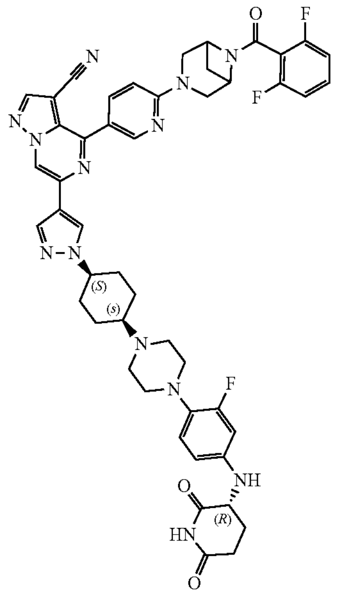

Compound 172

Step 1: Into a 100 mL sealed-tube containing a well-stirred solution of mixture of 6-chloro-4-(6-fluoro-3-pyridyl)pyrazolo[1,5-a]pyrazine-3-carbonitrile (1, 2.5 g, 9.14 mmol) and diisopropylethylamine (3.98 mL, 22.84 mmol) in anhydrous DMSO (20 mL) was added tert-Butyl 3,6-diazabicyclo[3.1.1]heptane-6-carboxylate (2, 2.17 g, 10.96 mmol) at ambient temperature. The reaction mixture was stirred at 90° C. under closed condition. After completion of the reaction as indicated by UPLC (16 h later), the reaction mixture was allowed to attain room temperature and treated with ice-water (30 mL). Resulting solution was stirred for 30 minutes at room temperature, during which time desired product precipitated out. The solid product was filtered through a filter paper, solid on the filter was washed with water and filtered solid was dried under vacuum for 16 h to afford tert-butyl 3-[5-(6-chloro-3-cyano-pyrazolo[1,5-a]pyrazin-4-yl)-2-pyridyl]-3,6-diazabicyclo[3.1.1]heptane-6-carboxylate (3, 3.5 g, 7.66 mmol, 84% yield) as an yellow-colored solid. LCMS (ES$^+$): m/z 452.0 $[M+H]^+$.

Step 2: Into a 100 mL single-necked round-bottomed flask containing a well-stirred solution of tert-butyl 3-[5-(6-chloro-3-cyano-pyrazolo[1,5-a]pyrazin-4-yl)-2-pyridyl]-3,6-diazabicyclo[3.1.1]heptane-6-carboxylate (3, 0.65 g, 1.44 mmol) in anhydrous DCM (10 mL) was added 4M HCl in 1,4-dioxane (8.00 g, 219.41 mmol, 10 mL) at ambient temperature under nitrogen atmosphere. The resulting solution was stirred for 2 h at ambient temperature. After completion of the starting material as indicated by LCMS (2 h later), excess solvent was removed from the reaction mixture under reduced pressure to get a crude mass. The crude product was washed with MTBE (10 mL) to get 6-chloro-4-[6-(3,6-diazabicyclo[3.1.1]heptan-3-yl)-3- pyridyl]pyrazolo[1,5-a]pyrazine-3-carbonitrile (4, 0.54 g, 1.33 mmol, 93% yield) as an yellow solid. LCMS ($ES^+$): m/z 352.2 $[M+H]^+$.

Step 3: Into a 100 mL single-necked round-bottomed flask containing a well-stirred solution of 6-chloro-4-[6-(3,6-diazabicyclo[3.1.1]heptan-3-yl)-3-pyridyl]pyrazolo[1,5-a]pyrazine-3-carbonitrile (4, 1.0 g, 2.84 mmol) in anhydrous DMF (10 mL) were added propylphosphonic anhydride solution ≥50 wt. % in EtOAc (2.71 g, 8.53 mmol) and DIPEA (1.84 g, 14.21 mmol, 2.48 mL) and the reaction mixture was stirred at room temperature for 5 minutes. Then, 2,6-difluorobenzoic acid (5, 0.539 g, 3.41 mmol) was added and the reaction mixture was stirred at ambient temperature for 3 h. The reaction was monitored by UPLC to observe the required product mass. Water (100 mL) was added to the reaction mixture and extracted with EtOAc (3×50 mL). Combined organic layer was successively washed with 10% aqueous $NaHCO_3$ solution, brine (50 mL), dried (anhydrous $Na_2SO_4$), filtered and the filtrate was concentrated under reduced pressure to afford 6-chloro-4-[6-[6-(2,6-difluorobenzoyl)-3,6-diazabicyclo[3.1.1]heptan-3-yl]-3-pyridyl]pyrazolo[1,5-a]pyrazine-3-carbonitrile (6, 0.9 g, 1.68 mmol, 59% yield) as a yellow solid. LCMS ($ES^+$): m/z 492.0 $[M+H]^+$.

Step 4: Into a 100 mL sealed-tube containing a well-stirred solution of 6-chloro-4-[6-[6-(2,6-difluorobenzoyl)-3,6-diazabicyclo[3.1.1]heptan-3-yl]-3-pyridyl]pyrazolo[1,5-a]pyrazine-3-carbonitrile (6, 0.9 g, 1.83 mmol) and 1-(1,4-dioxaspiro[4.5]decan-8-yl)-4-(4,4,5,5-tetramethyl-1,3,2-dioxaborolan-2-yl)pyrazole (7, 1.22 g, 3.66 mmol) in anhydrous 1,4-dioxane (10 mL) was added aqueous solution of sodium carbonate (0.193 g, 1.83 mmol) in water (3.5 mL) at ambient temperature and the resulting mixture was degassed by bubbling nitrogen gas into the reaction mixture for 10 minutes. Subsequently, $Pd(dppf)Cl_2 \cdot CH_2Cl_2$ (0.15 g, 0.183 mmol) was added, and the reaction mixture was heated to 90° C. under closed condition. After completion of the reaction as indicated by TLC (16 h later), the reaction mixture was allowed to attain room temperature and poured into water (100 mL) and aqueous phase was extracted with DCM (2×75 mL). Organic phases were combined and washed with brine (50 mL). Combined organic phase was dried (anhydrous $Na_2SO_4$), filtered and the filtrate was concentrated under reduced pressure to get 4-[6-[6-(2,6-difluorobenzoyl)-3,6-diazabicyclo[3.1.1]heptan-3-yl]-3-pyridyl]-6-[1-(1,4-dioxaspiro[4.5]decan-8-yl)pyrazol-4-yl]pyrazolo[1,5-a]pyrazine-3-carbonitrile (8, 0.9 g, 1.07 mmol, 59% yield) as a yellow solid LCMS ($ES^+$): m/z 664.2 $[M+H]^+$.

Step 5: Into a 250 mL single-necked round-bottomed flask containing a well-stirred solution of 4-[6-[6-(2,6-difluorobenzoyl)-3,6-diazabicyclo[3.1.1]heptan-3-yl]-3-pyridyl]-6-[1-(1,4-dioxaspiro[4.5]decan-8-yl)pyrazol-4-yl]pyrazolo[1,5-a]pyrazine-3-carbonitrile (8, 0.9 g, 1.36 mmol) in THF (10 mL) was added dropwise HCl, 36% w/w aq. soln. (7.20 g, 197.48 mmol, 9 mL) at 0° C. The resulting reaction mixture was stirred at ambient temperature. After completion of the reaction as monitored by UPLC (16 h later), excess acid was quenched with addition of 10% aqueous sodium bicarbonate solution (250 mL) slowly at 0° C. and solution pH was adjusted to 7-8 and extracted with DCM (2×75 mL). Combined organic layer was washed with brine (50 mL), dried (anhydrous $Na_2SO_4$), filtered and the filtrate was concentrated under reduced pressure to obtain a crude residue. The crude residue was purified by flash silica-gel (230-400 mesh) column with 0-100% EtOAc/pet ether while desired compound was eluting at 80-100% to afford 4-[6-[6-(2,6-difluorobenzoyl)-3,6-diazabicyclo[3.1.1]heptan-3-yl]-3-pyridyl]-6-[1-(4-oxocyclohexyl)pyrazol-4-yl]pyrazolo[1,5-a]pyrazine-3-carbonitrile (9, 0.7 g, 1.00 mmol, 74% yield) as a yellow solid. LCMS ($ES^+$): m/z 620.2 $[M+H]^+$.

Step 6: Into a 100 mL single-necked round-bottomed flask containing a well-stirred solution of 3-(3-fluoro-4-piperazin-1-yl-anilino)piperidine-2,6-dione (10, 692.14 mg, 2.26 mmol) and 4-[6-[6-(2,6-difluorobenzoyl)-3,6-diazabicyclo[3.1.1]heptan-3-yl]-3-pyridyl]-6-[1-(4-oxocyclohexyl)pyrazol-4-yl]pyrazolo[1,5-a]pyrazine-3-carbonitrile (9, 0.7 g, 1.13 mmol) in 1:1 anhydrous DMSO/MeOH (60 mL) was added Acetic acid (407.05 mg, 6.78 mmol, 0.387 mL) and the resulting mixture was stirred for 5 minutes at ambient temperature. MP-$CNBH_3$ (1.2 g) was added to the reaction mixture at ambient temperature and the reaction mixture was stirred under nitrogen atmosphere. The progress of the reaction was monitored by UPLC and found complete after 16 h. The reaction mixture was diluted with DCM (100 mL) and resin was filtered off. The filtrate was successively washed with water (100 mL) and brine (100 mL). The organic layer was dried (anhydrous $Na_2SO_4$), filtered and the filtrate concentrated under reduced pressure to get a crude mass. The crude mass was purified by flash silica-gel (230-400 mesh, 50 g) column with 10% MeOH/DCM while desired compound was eluting at 4-6% of the mobile phase to afford 530 mg of product with two peaks by LCMS with same mass with purity 39.5% and 45.8%, respectively.

The product 530 mg was purified by prep HPLC purification following a method: Column: Symmetry prep C18 (150×19) mm; 5 microns); Mobile phase: (10 mM Ammonium bicarbonate in water/ACN), Flow rate: 15 mL/minutes; while desired compound was eluting at 50% of the mobile phase and the fraction were lyophilized to afford (i) Early eluting isomer 1 (racemate): 145 mg with 98% product (LCMS) and (ii) Late eluting isomer 2 (racemate): 180 mg with 98% product (LCMS).

Early eluting isomer 1 (145 mg, racemate) was purified by Chiral HPLC SFC column following a method (The 145 mg of product was dissolved in DCM/THF): Column: Chiralpak AS-H (250×30) mm; 5 microns); Mobile phase: {$CO_2$: (0.1% Isopropyl amine IPA:ACN (1:1)) (65:45)}, Flow rate: 5 mL/minutes Compound 171 (Early eluting isomer 1-1) was eluting at RT=4.34 minutes. Desired fractions were combined and concentrated under reduced pressure at room temperature (Bath temperature 20° C.) and finally the mass thus obtained was lyophilized to afford 4-(6-(6-(2,6-difluorobenzoyl)-3,6-diazabicyclo[3.1.1]heptan-3-yl)pyridin-3-yl)-6-(1-((1R,4s)-4-(4-(4-(((S)-2,6-dioxopiperidin-3-yl)amino)-2-fluorophenyl)piperazin-1-yl)cyclohexyl)-1H-pyrazol-4-yl)pyrazolo[1,5-a]pyrazine-3-carbonitrile (Compound 171, 43 mg, 0.0454 mmol, 4% yield) as a yellow solid. $^1H$ NMR (400 MHz, DMSO-$d_6$). δ 10.78 (bs, 1H), 9.30 (s, 1H), 8.84 (s, 1H), 8.74 (d, J=2.4 Hz, 1H), 8.48 (s, 1H), 8.36 (s, 1H), 8.17 (s, 1H), 8.14 (dd, J=9, 2.4 Hz, 1H), 7.62-7.57 (m, 1H), 7.26-7.21 (m, 2H), 6.86-6.81 (m, 2H), 6.52 (dd, J=15, 2 Hz, 1H), 6.43 (dd, J=8.8, 2 Hz, 1H), 5.81 (d, J=7.6 Hz, 1H), 4.77-4.77 (m, 1H), 4.40 (s, 1H), 4.26-4.10 (m, 3H), 3.81-3.77 (m, 1H), 3.79-3.69 (m, 1H), 3.52-3.50 (m, 1H), 2.87-2.82 (m, 4H), 2.73-2.61 (m, 6H), 2.60-2.59 (m, 2H), 2.50-2.43 (m, 3H), 2.17-2.07 (m, 2H), 2.01-1.97 (m, 4H) and 1.49-1.47 (m, 2H). LCMS ($ES^+$): m/z 910.3 $[M+H]^+$.

Compound 172 (Early eluting isomer 1-2) eluted at RT=6.48 minutes. Desired fractions were combined and concentrated under reduced pressure at room temperature (Bath temperature 20° C.) and finally the mass thus obtained was lyophilized to afford 4-(6-(6-(2,6-difluorobenzoyl)-3,6- diazabicyclo[3.1.1]heptan-3-yl)pyridin-3-yl)-6-(1-((1S,4s)-4-(4-(4-(((R)-2,6-dioxopiperidin-3-yl)amino)-2-fluorophenyl)piperazin-1-yl)cyclohexyl)-1H-pyrazol-4-yl)pyrazolo[1,5-a]pyrazine-3-carbonitrile (Compound 172, 46 mg, 0.049 mmol, 4% yield) as a yellow solid. $^1$H NMR (400 MHz, DMSO-$d_6$). δ 10.78 (s, 1H), 9.30 (s, 1H), 8.84 (s, 1H), 8.74 (d, J=2.4 Hz, 1H), 8.48 (s, 1H), 8.17 (s, 1H), 8.14 (dd, J=9, 2.4 Hz, 1H), 7.63-7.56 (m, 1H), 7.26-7.21 (m, 2H), 6.86-6.81 (m, 2H), 6.52 (dd, J=15.2, 2.4 Hz, 1H), 6.43 (dd, J=8.8, 2 Hz, 1H), 5.80 (d, J=7.6 Hz, 1H), 4.77 (s, 1H), 4.40-4.34 (m, 2H), 4.21-4.09 (m, 2H), 3.84-3.71 (m, 2H), 3.56-3.53 (m, 1H), 2.89-2.82 (m, 5H), 2.68-2.57 (m, 1H), 2.55 (m, 2H), 2.34-2.25 (m, 4H), 2.11-2.06 (m, 2H), 1.90-1.78 (m, 7H) and 1.61-1.59 (m, 2H). LCMS ($ES^+$): m/z $[M+H]^+$.

Example 181: Synthesis of 1-(5-(3-cyano-6-(4-(4-(2-(1-(3-(2,4-dioxotetrahydropyrimidin-1(2H)-yl)-1-methyl-1H-indazol-6-yl)-4-hydroxypiperidin-4-yl)acetyl)piperazin-1-yl)phenyl)pyrazolo[1,5-a]pyrazin-4-yl)pyridin-2-yl)-4-ethyl-N-isopropylpiperidine-4-carboxamide (Compound 173)

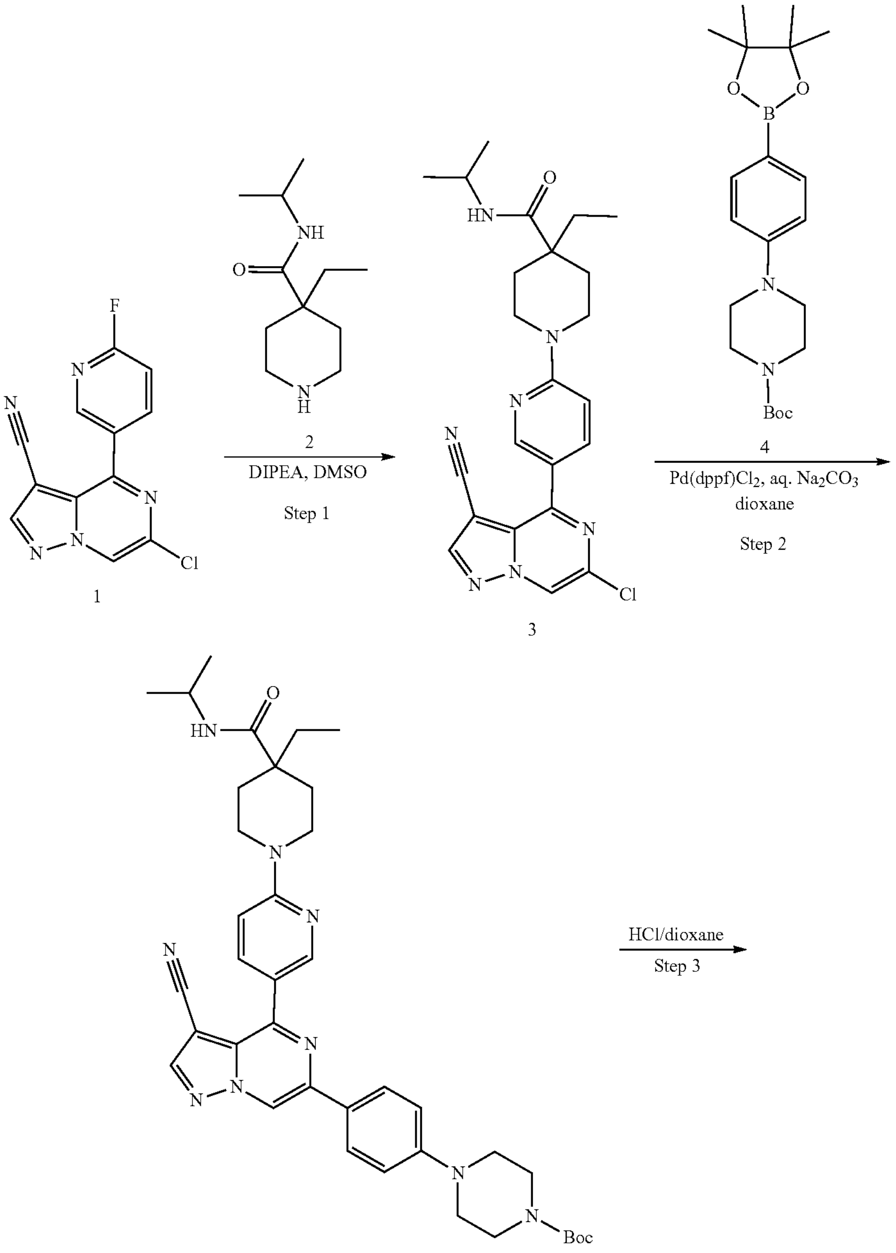

5

-continued

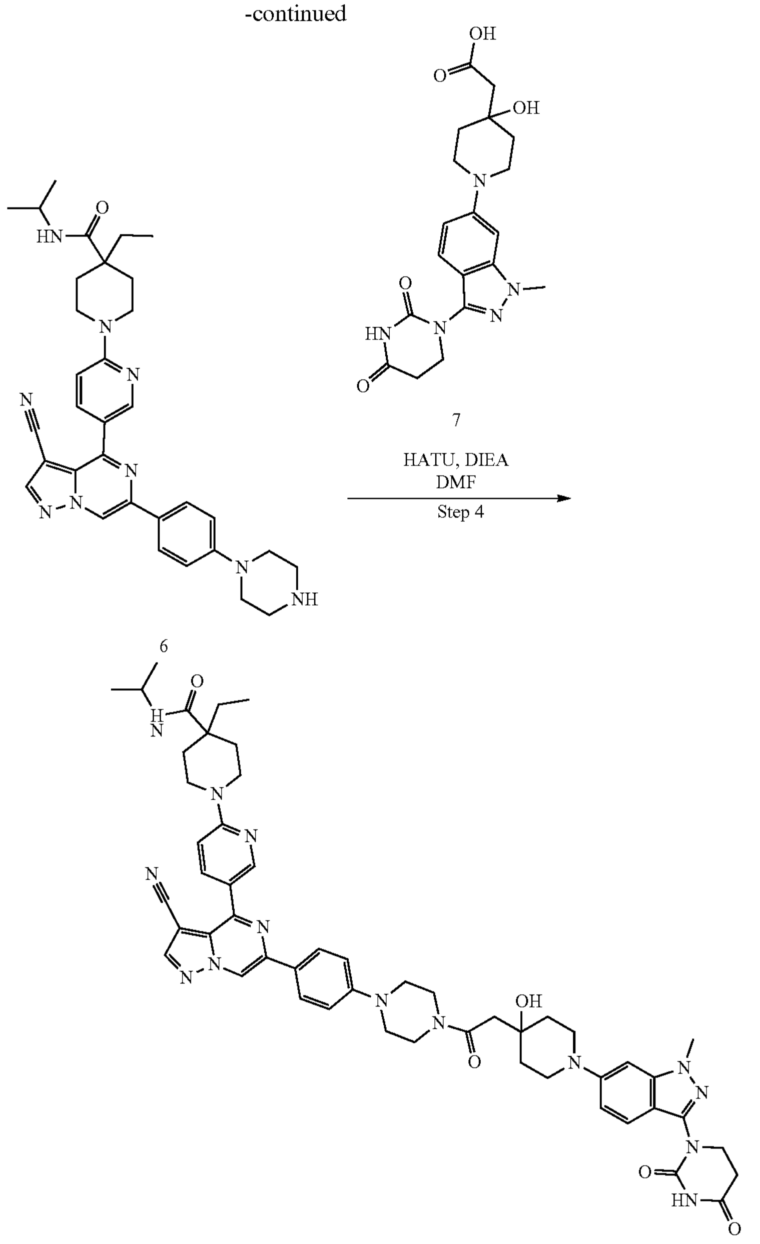

6

7

Compound 173

Step 1: In a 250 mL sealed-tube, a well-stirred solution of 4-ethyl-N-isopropyl-piperidine-4-carboxamide (2, 2.37 g, 10.09 mmol, HCl salt) and 6-chloro-4-(6-fluoro-3-pyridyl) pyrazolo[1,5-a]pyrazine-3-carbonitrile (1, 2.3 g, 8.40 mmol) in anhydrous DMSO (40 mL) was added DIPEA (5.43 g, 42.02 mmol, 7.32 mL) at ambient temperature. The resulting reaction was heated at 100° C. for 24 h before cooled to ambient temperature. The reaction mixture was quenched with water (100 mL) and the product was extracted with DCM (2×150 mL). The organic phases were combined, dried (anhydrous $Na_2SO_4$), filtered and the filtrate was concentrated under reduced pressure to get a crude residue. The crude product was purified by column chromatography (100 g, silica-gel column) with 0-70% EtOAc/pet ether to afford 1-[5-(6-chloro-3-cyano-pyrazolo[1,5-a]pyrazin-4-yl)-2-pyridyl]-4-ethyl-N-isopropyl-piperidine-4-carboxamide (3, 2.2 g, 4.48 mmol, 53% yield) as an yellow solid. LCMS ($ES^+$): m/z 452.2 $[M+H]^+$ Step 2: To a solution of tert-butyl 4-(4-(4,4,5,5-tetramethyl-1,3,2-dioxaborolan-2-yl)phenyl)piperazine-1-carboxylate (4, 1.29 g, 3.32 mmol), 1-(5-(6-chloro-3-cyanopyrazolo[1,5-a]pyrazin-4-yl)pyridin-2-yl)-4-ethyl-N-isopropylpiperidine-4-carboxamide (3, 1 g, 2.21 mmol) and Pd(dppf)$Cl_2$ (180.69 mg, 221.26 μmol) in dioxane (8 mL) was added potassium phosphate (2 M, 2.21 mL). After addition, the solution was stirred at 70° C. for 12 hr. The reaction solution was poured into water (30 mL) to give a suspension. The suspension was filtered, the filter cake was washed with water (10 mL), EtOAc (10 mL) and concentrated in vacuum. tert-butyl 4-(4-(3-cyano-4-(6-(4-ethyl-4-(isopropylcarbamoyl)piperidin-1-yl)pyridin-3-yl)pyrazolo

[1,5-a]pyrazin-6-yl)phenyl)piperazine-1-carboxylate (5, 810 mg, 1.08 mmol, 49% yield) was obtained as yellow solid. LCMS ($ES^+$): m/z 678.7 $[M+H]^+$ Step 3: To a solution of tert-butyl 4-(4-(3-cyano-4-(6-(4-ethyl-4-(isopropylcarbamoyl)piperidin-1-yl)pyridin-3-yl) pyrazolo[1,5-a]pyrazin-6-yl)phenyl)piperazine-1-carboxylate (5, 200 mg, 295.06 μmol) in DCM (4 mL) was added aq.HCl/dioxane (4 M, 2 mL). After addition, the solution was stirred at 25° C. for 30 min. The reaction solution was concentrated in vacuum to afford 1-(5-(3-cyano-6-(4-(piperazin-1-yl)phenyl)pyrazolo[1,5-a]pyrazin-4-yl)pyridin-2-yl)-4-ethyl-N-isopropylpiperidine-4-carboxamide HCl salt (6, 180 mg, 263.77 μmol, 89% yield) as yellow solid. LCMS ($ES^+$): m/z 578.3 $[M+H]^+$ Step 4: To a solution of 2-(1-(3-(2,4-dioxotetrahydropyrimidin-1(2H)-yl)-1-methyl-1H-indazol-6-yl)-4-hydroxypiperidin-4-yl)acetic acid (7, 50 mg, 114.19 μmol, HCl salt), 1-(5-(3-cyano-6-(4-(piperazin-1-yl)phenyl)pyrazolo[1,5-a] pyrazin-4-yl)pyridin-2-yl)-4-ethyl-N-isopropylpiperidine-4-carboxamide (6, 70.13 mg, 114.19 μmol, HCl salt) and HATU (65.13 mg, 171.28 μmol) in DMF (1 mL) was added DIPEA (59.03 mg, 456.75 μmol, 79.56 μL). After addition, the solution was stirred at 30° C. for 4 hr. The reaction solution was acidified with FA to pH=7 and concentrated in vacuum. The residue was purified by Prep-HPLC (3_Phenomenex Luna C18 75*30 mm*3 um, water (0.05% HCl)-ACN, 22%-42%, 25 ml/min, 6.5 min) to afford 1-(5-(3-cyano-6-(4-(4-(2-(1-(3-(2,4-dioxotetrahydropyrimidin-1 (2H)-yl)-1-methyl-1H-indazol-6-yl)-4-hydroxypiperidin-4-yl)acetyl)piperazin-1-yl)phenyl) pyrazolo[1,5-a]pyrazin-4-yl)pyridin-2-yl)-4-ethyl-N-isopropylpiperidine-4-carboxamide HCl salt (Compound 173, 47.41 mg, 47.05 μmol, 41% yield) as yellow solid. LCMS ($ES^+$): m/z 961.3 $[M+H]^+$. $^1H$ NMR (400 MHz, DMSO-$d_6$) δ=10.64 (s, 1H), 9.56 (s, 1H), 8.94 (s, 1H), 8.66 (d, J=2.4 Hz, 1H), 8.35-8.25 (m, 1H), 8.17 (d, J=8.8 Hz, 2H), 7.80-7.70 (m, 1H), 7.54 (d, J=8.0 Hz, 1H), 7.47-7.27 (m, 2H), 7.19 (br d, J=9.2 Hz, 2H), 4.24 (br d, J=13.6 Hz, 2H), 4.12-4.07 (m, 1H), 4.05 (s, 3H), 3.99 (br t, J=6.8 Hz, 3H), 3.64 (br d, J=5.6 Hz, 3H), 3.65 (br s, 2H), 3.43-3.34 (m, 4H), 3.30 (br d, J=11.2 Hz, 2H), 2.82 (t, J=6.8 Hz, 2H), 2.77-2.72 (m, 2H), 2.33-2.11 (m, 4H), 2.02-1.89 (m, 2H), 1.64-1.54 (m, 2H), 1.54-1.44 (m, 2H), 1.16 (d, J=6.8 Hz, 6H), 0.82 (t, J=7.2 Hz, 3H)

Example 182: Synthesis of 1-[5-[3-cyano-6-[4-[1-[2-[3-[4-[(2,6-dioxo-3-piperidyl)amino]-2-fluoro-phenyl]azetidin-1-yl]acetyl]-4-piperidyl]phenyl] pyrazolo[1,5-a]pyrazin-4-yl]-2-pyridyl]-4-ethyl-N-isopropyl-piperidine-4-carboxamide (Compound 174)

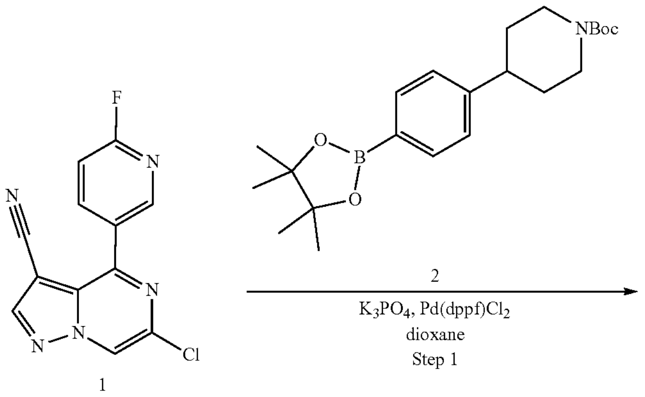

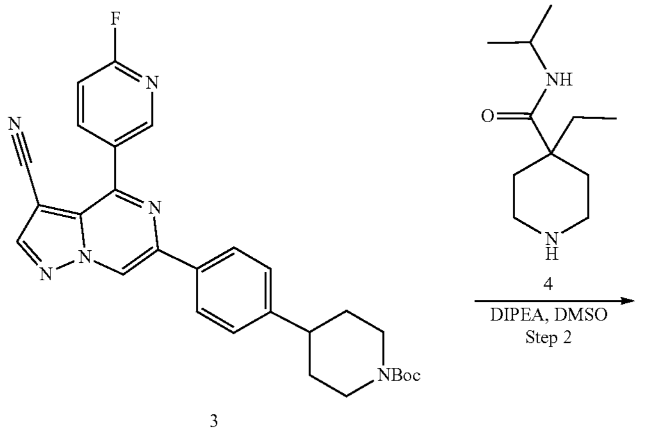

-continued
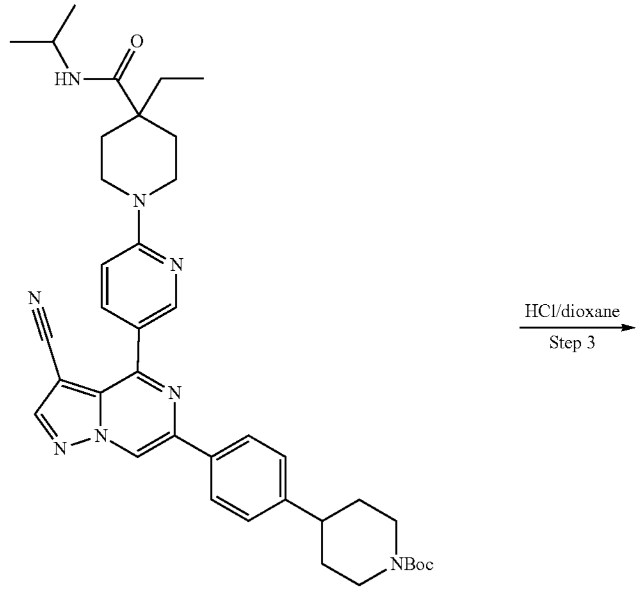
5
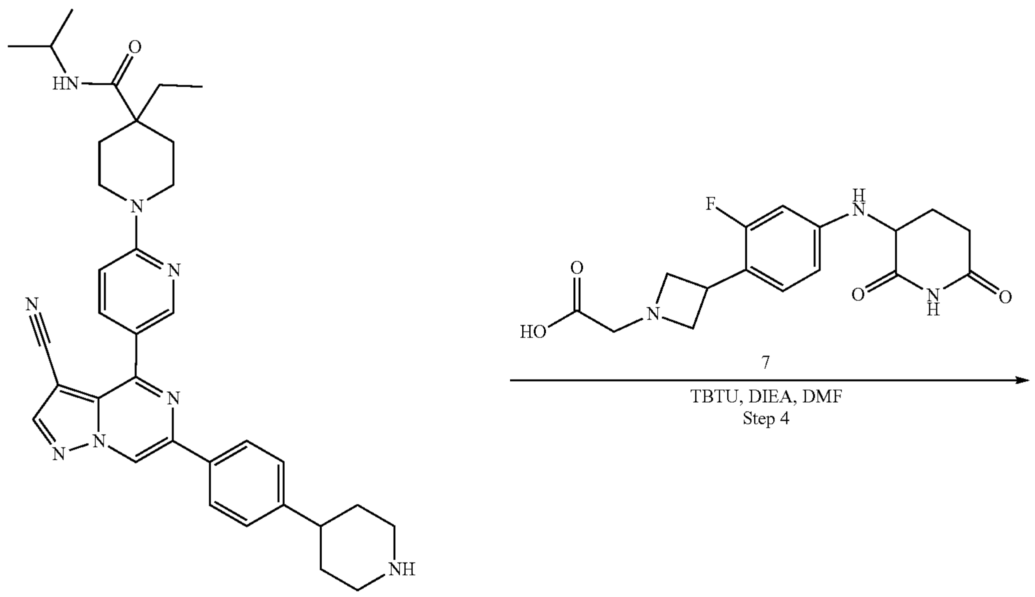
6
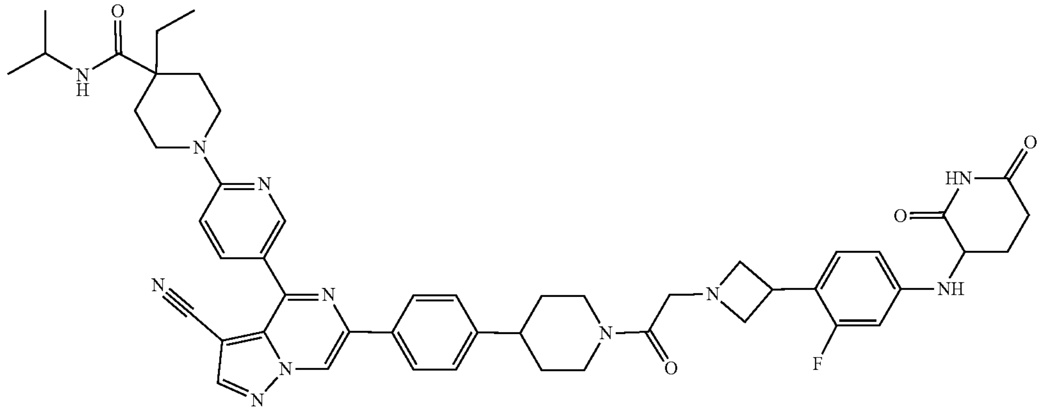
Compound 174

Step 1: Initially 6-chloro-4-(6-fluoro-3-pyridyl)pyrazolo[1,5-a]pyrazine-3-carbonitrile (1, 1.18 g, 4.30 mmol), tert-butyl 4-[4-(4,4,5,5-tetramethyl-1,3,2-dioxaborolan-2-yl)phenyl]piperidine-1-carboxylate (2, 2 g, 5.16 mmol) tripotassium phosphate (1.5 M, 5.74 mL) and Pd(dppf)C12*DCM (351.41 mg, 430.31 μmol) were added to a MW vial and sparged with Argon for 5 mins before being dissolved in dioxane (11.47 mL) and heated to 100° C. for 2 h. The reaction was monitored via LCMS. Upon reaction completion, the mixture was diluted with ethyl acetate and filtered through a celite frit. The filtrate was then washed with water (×2), brine (×1) before being dried over $Na_2SO_4$, filtered and concentrated to a crude residue which was then purified via Isco FCC (Hex:EA 1:0 to 0:1) to afford the product tert-butyl 4-[4-[3-cyano-4-(6-fluoro-3-pyridyl)pyrazolo[1,5-a]pyrazin-6-yl]phenyl]piperidine-1-carboxylate (3, 189 mg, 360.14 μmol, 8% yield) as a solid. LCMS ($ES^+$): m/z 399.3 $[M-Boc+H]^+$ Step 2: Initially tert-butyl 4-[4-[3-cyano-4-(6-fluoro-3-pyridyl)pyrazolo[1,5-a]pyrazin-6-yl]phenyl]piperidine-1-carboxylate (3, 129 mg, 258.75 μmol) and 4-ethyl-N-isopropyl-piperidine-4-carboxamide (4, 60.75 mg, 258.75 μmol, HCl salt) were suspended in DMSO (4.09 mL) before N-ethyl-N-isopropyl-propan-2-amine (167.20 mg, 1.29 mmol, 225.34 μL) was added dropwise and the mixture was stirred at 120° C. in the MW for 30 mins. Upon reaction completion the mixture was then diluted with water and extracted with EA (×3). The combined organic layers were then washed with Citric acid (10% aq w/v) solution, brine (×2) and dried over $Na_2SO_4$ before being concentrated to a yellow solid. LCMS/ELSD analysis shows pure material along with confirmation by NMR. tert-butyl 4-[4-[3-cyano-4-[6-[4-ethyl-4-(isopropylcarbamoyl)-1-piperidyl]-3-pyridyl]pyrazolo[1,5-a]pyrazin-6-yl]phenyl]piperidine-1-carboxylate (5, 109 mg, 152.99 μmol, 59% yield) LCMS ($ES^+$): m/z 677.7 $[M+H]^+$ Step 3: To a solution of tert-butyl 4-[4-[3-cyano-4-[6-[4-ethyl-4-(isopropylcarbamoyl)-1-piperidyl]-3-pyridyl]pyrazolo[1,5-a]pyrazin-6-yl]phenyl]piperidine-1-carboxylate (5, 1.67 g, 2.47 mmol) in dioxanes (50 mL) was added hydrogen chloride solution 4.0M in dioxane (4 M, 21.59 mL). The resulting solution was stirred at RT for 16 hr. At this time, the resulting solid was isolated by vacuum filtration, washing with MTBE, to afford the product 1-[5-[3-cyano-6-[4-(4-piperidyl)phenyl]pyrazolo[1,5-a]pyrazin-4-yl]-2-pyridyl]-4-ethyl-N-isopropyl-piperidine-4-carboxamide (6, 1.43 g, 2.10 mmol, 85% yield, HCl salt), which was used without further purification. LCMS ($ES^+$): m/z 577.6 $[M+H]^+$ Step 4: To a solution of 1-[5-[3-cyano-6-[4-(4-piperidyl)phenyl]pyrazolo[1,5-a]pyrazin-4-yl]-2-pyridyl]-4-ethyl-N-isopropyl-piperidine-4-carboxamide (6, 91.43 mg, 149.11 μmol, HCl salt), DIEA (45.26 mg, 447.32 μmol, 62.35 μL) and 2-[3-[4-[(2,6-dioxo-3-piperidyl)amino]-2-fluoro-phenyl]azetidin-1-yl]acetic acid (7, 50 mg, 149.11 μmol) in DMF (2 mL) was added TBTU (47.88 mg, 149.11 μmol) at 10° C. After addition, the solution was stirred at 20° C. for 6 hr. The reaction mixture was filtered and the filtrated was concentrated under reduced pressure to give a residue. The crude product was purified by prep-HPLC (column: 3_Phenomenex Luna C18 150*25 mm*10 um, mobile phase: [water (0.225%, FA)-ACN]; B %: 18%-38%, 10 min, Flowrate: 25 ml/min) to get the product. 1-[5-[3-cyano-6-[4-[1-[2-[3-[4-[(2,6-dioxo-3-piperidyl)amino]-2-fluoro-phenyl]azetidin-1-yl]acetyl]-4-piperidyl]phenyl]pyrazolo[1,5-a]pyrazin-4-yl]-2-pyridyl]-4-ethyl-N-isopropyl-piperidine-4-carboxamide (Compound 174, 26.07 mg, 27.45 μmol, 18% yield, formic acid salt) was obtained as yellow solid. LCMS ($ES^+$): m/z 894.6 $[M+H]^+$. $^1H$ NMR (400 MHz, DMSO-$d_6$) δ=10.79 (s, 1H), 9.51 (s, 1H), 8.88 (s, 1H), 8.70 (d, J=2.4 Hz, 1H), 8.18-8.13 (m, 2H), 8.05 (s, 1H), 7.45-7.37 (m, 3H), 7.17 (t, J=8.8 Hz, 1H), 7.02 (d, J=8.8 Hz, 1H), 6.61-6.35 (m, 2H), 6.08 (d, J=7.6 Hz, 1H), 4.59-4.46 (m, 1H), 4.36-4.29 (m, 1H), 4.23-4.15 (m, 2H), 4.09-3.96 (m, 2H), 3.76-3.62 (m, 4H), 3.20-3.06 (m, 6H), 2.94-2.61 (m, 4H), 2.25-2.15 (m, 2H), 2.13-2.03 (m, 1H), 1.95-1.79 (m, 3H), 1.73-1.60 (m, 1H), 1.57-1.44 (m, 3H), 1.41-1.32 (m, 2H), 1.09 (d, J=6.4 Hz, 6H), 0.76 (t, J=7.2 Hz, 3H)

Example 183: Synthesis of 6-[4-[1-[2-[1-[4-[(2,6-dioxo-3-piperidyl)amino]-2-fluoro-phenyl]-4-hydroxy-4-piperidyl]acetyl]-4-piperidyl]phenyl]-4-[6-[4-(isoxazole-3-carbonyl)piperazin-1-yl]-3-pyridyl]pyrazolo[1,5-a]pyrazine-3-carbonitrile (Compound 175)

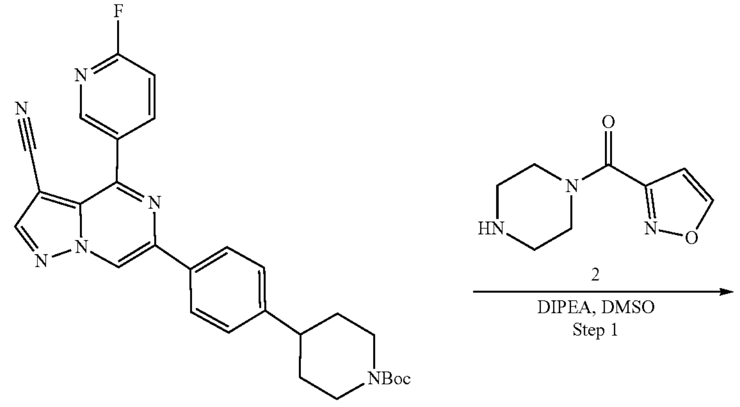

1

-continued
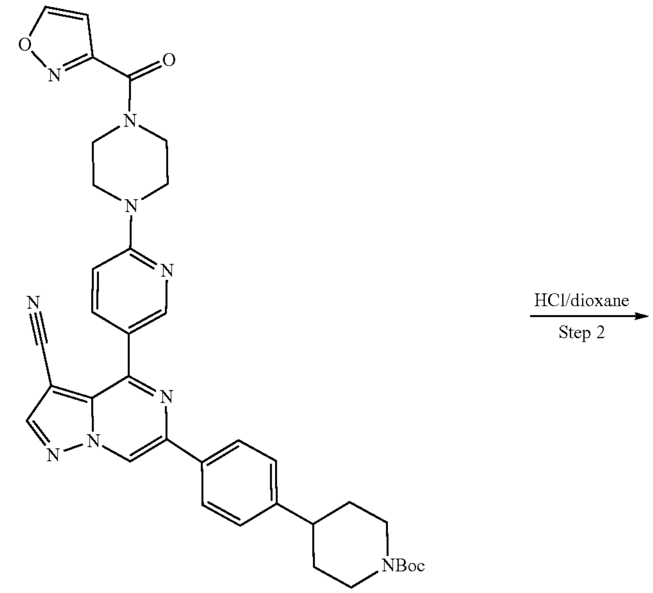
3
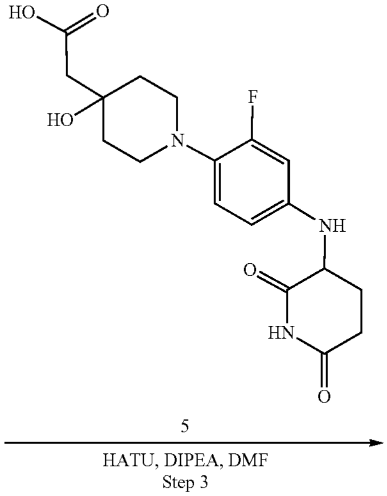
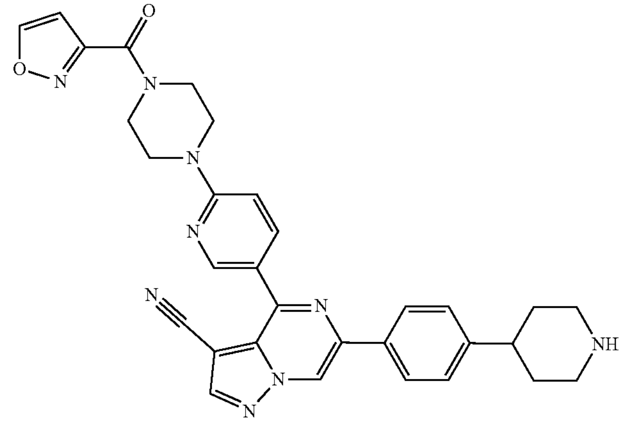
4
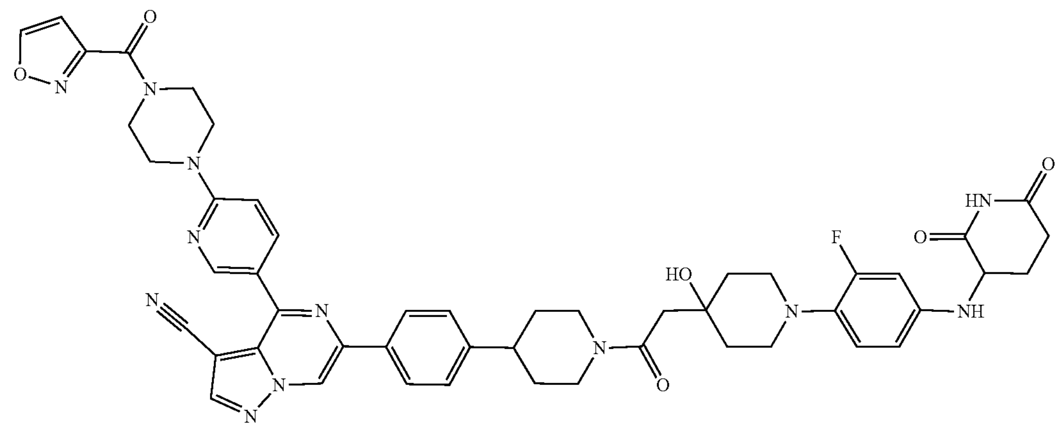
Compound 175

Step 1: To a solution of tert-butyl 4-(4-(3-cyano-4-(6-fluoropyridin-3-yl)pyrazolo[1,5-a]pyrazin-6-yl)phenyl)piperidine-1-carboxylate (1, 150 mg, 300.87 μmol), isoxazol-3-yl(piperazin-1-yl)methanone (2, 65.49 mg, 300.87 μmol, HCl salt) in DMSO (1 mL) was added DIPEA (116.66 mg, 902.62 μmol, 157.22 μL). After addition, the solution was stirred at 90° C. for 12h. After complete consumption of the reactant as confirmed by LCMS, the solution was poured into water (3 mL) to give a suspension. Then the suspension was filtered, the filter cake was washed with water (5*2 mL) and concentrated under vacuum to afford tert-butyl 4-[4-[3-cyano-4-[6-[4-(isoxazole-3-carbonyl)piperazin-1-yl]-3-pyridyl]pyrazolo[1,5-a]pyrazin-6-yl]phenyl]piperidine-1-carboxylate (3, 26 mg, 39.41 μmol, 13% yield) as a yellow solid. The residue was used for next step directly without purification. LCMS ($ES^+$): m/z 660.4 $[M+H]^+$ Step 2: To the reaction mixture of tert-butyl 4-[4-[3-cyano-4-[6-[4-(isoxazole-3-carbonyl)piperazin-1-yl]-3-pyridyl]pyrazolo[1,5-a]pyrazin-6-yl]phenyl]piperidine-1-carboxylate (3, 25 mg, 37.89 μmol) in DCM (0.5 mL) was added HCl/dioxane (4 M, 0.5 mL) at 0° C. Then the solution was stirred at 25° C. for 2 h. The reaction mixture was concentrated under vacuum to obtain 4-[6-[4-(isoxazole-3-carbonyl) piperazin-1-yl]-3-pyridyl]-6-[4-(4-piperidyl)phenyl] pyrazolo[1,5-a]pyrazine-3-carbonitrile (4, 22 mg, 36.10 μmol, 95% yield, HCl salt) as a light yellow solid. LCMS ($ES^+$): m/z 560.2 $[M+H]^+$ Step 3: The mixture of 4-[6-[4-(isoxazole-3-carbonyl) piperazin-1-yl]-3-pyridyl]-6-[4-(4-piperidyl) phenyl]pyrazolo[1,5-a]pyrazine-3-carbonitrile (4, 22 mg, 36.91 μmol, HCl salt), 2-[1-[4-[(2,6-dioxo-3-piperidyl)amino]-2-fluoro-phenyl]-4-hydroxy-4-piperidyl]acetic acid (5, 15.35 mg, 36.91 μmol, HCl salt), DIPEA (14.31 mg, 110.72 μmol, 19.29 μL) and N,N,N',N'-tetramethyl-1-(3-oxido-2,3-dihydrotriazolo[4,5-b]pyridin-3-ium-1-yl)methanediamine; hexafluorophosphate (21.16 mg, 55.36 μmol) in DMF (0.5 mL) was stirred at 25° C. for 14 h. LCMS showed the reactant 2 was consumed and the desired mass was given. The reaction mixture was concentrated under vacuum. The residue was purified by Prep-HPLC (Phenomenex Luna C18 150*25 mm*10 um, water (0.025% FA)-ACN, 23%-53%, 25 ml/min, 10 min) to obtain 6-[4-[1-[2-[1-[4-[(2,6-dioxo-3-piperidyl)amino]-2-fluoro-phenyl]-4-hydroxy-4-piperidyl]acetyl]-4-piperidyl]phenyl]-4-[6-[4-(isoxazole-3-carbonyl)piperazin-1-yl]-3-pyridyl]pyrazolo[1,5-a]pyrazine-3-carbonitrile (Compound 175, 14.21 mg, 14.52 μmol, 39% yield) as a green solid. LCMS ($ES^+$): m/z 921.5 $[M+H]^+$. $^1H$ NMR (400 MHz, DMSO-$d_6$): δ=10.78 (s, 1H), 9.54 (s, 1H), 9.14-9.11 (m, 1H), 8.90-8.88 (m, 1H), 8.75-8.72 (m, 1H), 8.18-8.13 (m, 3H), 7.45-7.39 (m, 2H), 7.10-7.05 (m, 1H), 6.90-6.80 (m, 2H), 6.56-6.46 (m, 1H), 6.45-6.37 (m, 1H), 5.84-5.71 (m, 1H), 5.04-4.92 (m, 1H), 4.71-4.59 (m, 1H), 4.32-4.14 (m, 2H), 3.88-3.80 (m, 4H), 3.77-3.72 (m, 4H), 3.22-3.08 (m, 2H), 2.93-2.84 (m, 4H), 2.76-2.66 (m, 2H), 2.59-2.56 (m, 2H), 2.15-2.05 (m, 1H), 1.89-1.82 (m, 3H), 1.78-1.62 (m, 5H), 1.57-1.48 (m, 1H).

Example 184: Synthesis of 4-(6-(6-benzyl-3,6-diazabicyclo[3.1.1]heptan-3-yl)pyridin-3-yl)-6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)pyrazolo[1,5-a]pyrazine-3-carbonitrile

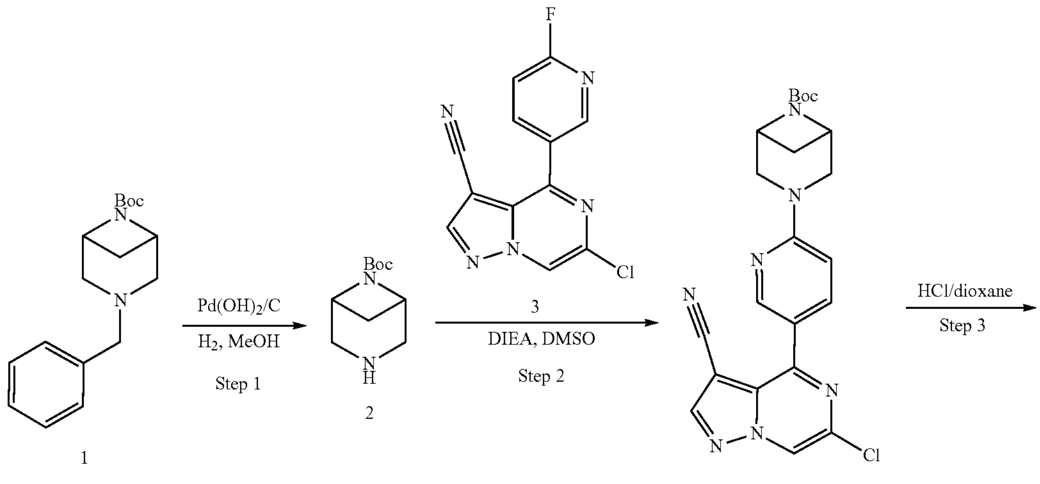

1 2 4

-continued
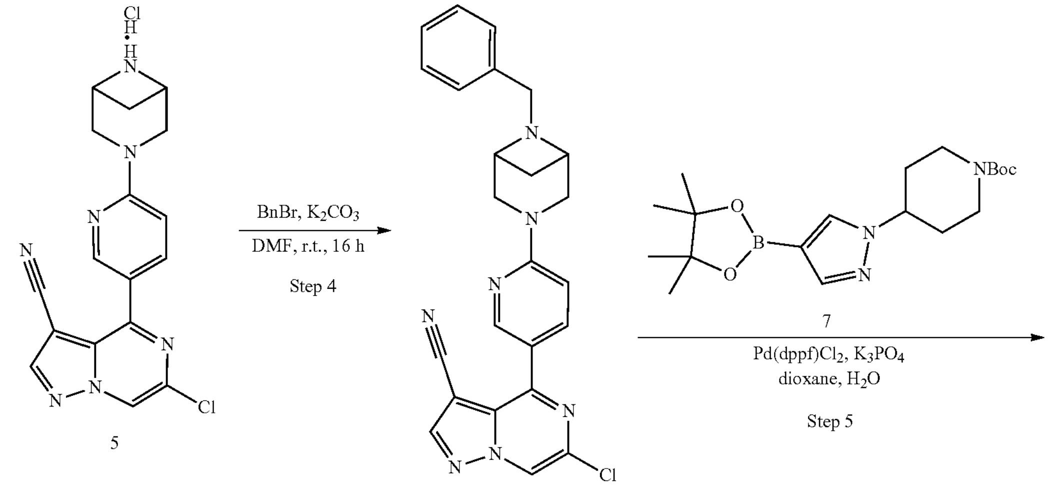
5
6
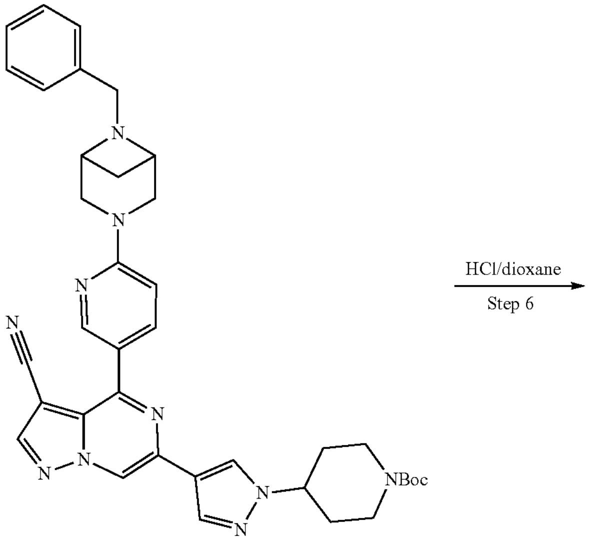
8
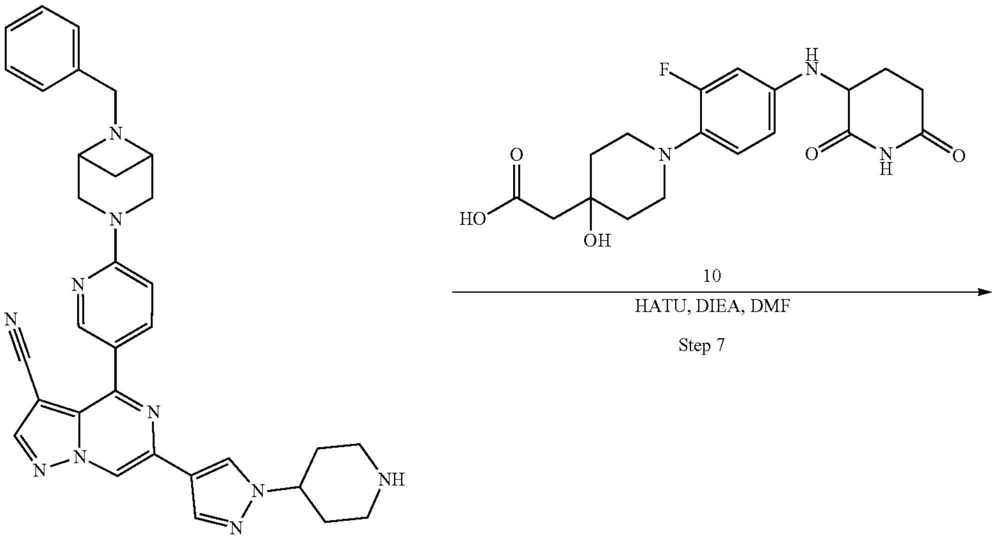
9

-continued

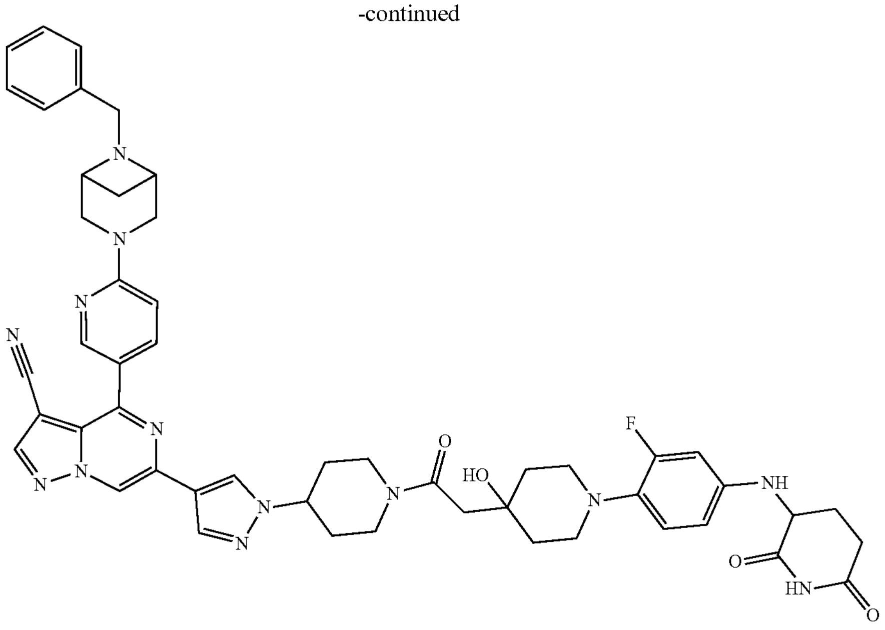

Compound 176

Step 1: To a solution of tert-butyl 3-benzyl-3,6-diazabicyclo[3.1.1]heptane-6-carboxylate (1, 1 g, 3.47 mmol) in MeOH (10 mL) was added 10 wt. % $Pd(OH)_2/C$ (100 mg) at 10° C. The suspension was degassed under vacuum and purged with $H_2$ for 3 times. The reaction mixture stirred under $H_2$ (15 psi) at 20° C. for 6 hours. The reaction mixture was concentrated under reduced pressure to give a residue. The crude product was used to next step directly. tert-butyl 3,6-diazabicyclo[3.1.1]heptane-6-carboxylate (2, 670 mg, 3.38 mmol, 97% yield) was obtained as a yellow oil. LCMS ($ES^+$): m/z 143.1 $[M+H]^+$ Step 2: To a solution of tert-butyl 3,6-diazabicyclo[3.1.1]heptane-6-carboxylate (2, 670 mg, 2.85 mmol, HCl salt) and 6-chloro-4-(6-fluoropyridin-3-yl)pyrazolo[1,5-a]pyrazine-3-carbonitrile (3, 742.07 mg, 2.71 mmol) in DMSO (10 mL) was added N-ethyl-N-isopropyl-propan-2-amine (1.88 g, 14.55 mmol, 2.53 mL) at 10° C. After addition, the solution was stirred at 100° C. for 6 hr. The reaction mixture was quenched by water (50 mL) then the mixture was filtered and the filtrated cake was concentrated under reduced pressure to give a residue, then the residue was washed by the solvent (PE:EA=5:1, 50 mL) to get the product. The crude product used to next step directly. tert-butyl 3-(5-(6-chloro-3-cyanopyrazolo[1,5-a]pyrazin-4-yl)pyridin-2-yl)-3,6-diazabicyclo[3.1.1]heptane-6-carboxylate (4, 870 mg, 1.83 mmol, 64% yield) was obtained as a yellow solid. LCMS ($ES^+$): m/z 452.1 $[M+H]^+$ Step 3: To a solution of tert-butyl 3-[5-(6-chloro-3-cyano-pyrazolo[1,5-a]pyrazin-4-yl)-2-pyridyl]-3,6-diazabicyclo[3.1.1]heptane-6-carboxylate (4, 870 mg, 1.93 mmol) in dioxane (20 mL) was added HCl/dioxane (4 M, 20 mL) at 20° C., and the mixture was stirred at 20° C. for 1 hr. The reaction was concentrated under reduced pressure to get a residue. The residue was used to next step directly. The compound 6-chloro-4-[6-(3,6-diazabicyclo[3.1.1]heptan-3-yl)-3-pyridyl]pyrazolo[1,5-a]pyrazine-3-carbonitrile (5, 760 mg, 1.96 mmol, 102% yield, HCl salt) was obtained as light-yellow solid. LCMS ($ES^+$): m/z 352.0 $[M+H]^+$ Step 4: To the solution of 6-chloro-4-[6-(3,6-diazabicyclo[3.1.1]heptan-3-yl)-3-pyridyl]pyrazolo[1,5-a]pyrazine-3-carbonitrile (5, 700 mg, 1.80 mmol, HCl salt) and benzyl bromide (510 mg, 2.98 mmol, 354.17 μL) in CH3CN (20 mL) was added DIPEA (2.97 g, 22.96 mmol, 4 mL) at 25° C. drop-wise. The reaction mixture was stirred at 90° C. for 12 hours. The reaction mixture was quenched by addition water 30 mL at 25° C. and extracted with EtOAc (20 mL*5). The combined organic layers were washed with brine (15 mL), dried with anhydrous $Na_2SO_4$, filtered and concentrated under reduced pressure to give a residue. The crude product was purified by Prep-TLC (PE:EA=1:1, $SiO_2$) to get the product. 4-[6-(6-benzyl-3,6-diazabicyclo[3.1.1]heptan-3-yl)-3-pyridyl]-6-chloro-pyrazolo[1,5-a]pyrazine-3-carbonitrile (6, 650 mg, 1.47 mmol, 82% yield) was obtained as yellow solid. $^1H$ NMR (400 MHz, DMSO-$d_6$) δ=9.34 (s, 1H), 8.92 (s, 1H), 8.70 (d, J=2.4 Hz, 1H), 8.10-8.03 (m, 1H), 7.37-7.30 (m, 4H), 7.25-7.19 (m, 1H), 6.88 (d, J=8.8 Hz, 1H), 3.84-3.66 (m, 5H), 3.61-3.53 (m, 3H), 2.61-2.54 (m, 1H), 1.66-1.56 (m, 1H)

Step 5: To a solution of 4-(6-(6-benzyl-3,6-diazabicyclo[3.1.1]heptan-3-yl)pyridin-3-yl)-6-chloropyrazolo[1,5-a]pyrazine-3-carbonitrile (6, 100 mg, 226.29 μmol), tert-butyl 4-(4-(4,4,5,5-tetramethyl-1,3,2-dioxaborolan-2-yl)-1H-pyrazol-1-yl)piperidine-1-carboxylate (7, 85.38 mg, 226.29 μmol) and $Pd(dppf)Cl_2$*DCM (36.96 mg, 45.26 μmol) in dioxane (1.5 mL) was added potassium dihydrogen phosphate (2 M, 0.3 mL) at 10° C., then the mixture was stirred at 70° C. for 2 hrs. The reaction mixture was diluted with EtOAc (100 mL). The organic layer was washed with brine (10 mL), dried over $Na_2SO_4$, filtered and concentrated. The crude product was purified by prep-TLC (PE:EA=2:1, SiO2, Rf=0.6) to get the product. tert-butyl 4-(4-(4-(6-(6-benzyl-3,6-diazabicyclo[3.1.1]heptan-3-yl)pyridin-3-yl)-3-cyano-pyrazolo[1,5-a]pyrazin-6-yl)-1H-pyrazol-1-yl)piperidine-1-carboxylate (8, 110 mg, 167.48 μmol, 74% yield) was obtained as yellow solid. $^1H$ NMR (400 MHz, DMSO-$d_6$) δ=9.30 (s, 1H), 8.85 (s, 1H), 8.78 (d, J=2.4 Hz, 1H), 8.52 (s, 1H), 8.22-8.11 (m, 2H), 7.40-7.29 (m, 4H), 7.26-7.18 (m, 1H), 6.87 (d, J=8.8 Hz, 1H), 4.53-4.38 (m, 1H), 4.16-4.05 (m, 2H), 3.87-3.69 (m, 4H), 3.65-3.50 (m, 4H), 3.04-2.84 (m, 2H), 2.10-2.04 (m, 3H), 1.90-1.78 (m, 2H), 1.66-1.60 (m, 1H), 1.43 (s, 9H)

Step 6: To a solution of tert-butyl 4-[4-[4-[6-(6-benzyl-3,6-diazabicyclo[3.1.1]heptan-3-yl)-3-pyridyl]-3-cyano-pyrazolo[1,5-a]pyrazin-6-yl]pyrazol-1-yl]piperidine-1-carboxylate (8, 96 mg, 146.17 μmol) in dioxane (2 mL) was added HCl/dioxane (4 M, 2 mL) at 10° C., then the mixture was stirred at 20° C. for 12 hrs. The reaction mixture was concentrated under vacuum. The crude product was used to next step directly. The 4-[6-(6-benzyl-3,6-diazabicyclo[3.1.1]heptan-3-yl)-3-pyridyl]-6-[1-(4-piperidyl)pyrazol-4-yl]pyrazolo[1,5-a]pyrazine-3-carbonitrile (9, 86 mg, 130.50 μmol, 89% yield, HCl salt) was obtained as blue solid. LCMS ($ES^+$): m/z 557.2 $[M+H]^+$ Step 7: To a solution of 4-(6-(6-benzyl-3,6-diazabicyclo[3.1.1]heptan-3-yl)pyridin-3-yl)-6-(1-(piperidin-4-yl)-1H-pyrazol-4-yl)pyrazolo[1,5-a]pyrazine-3-carbonitrile (9, 86 mg, 145.00 μmol, HCl salt), DIEA (58.69 mg, 579.98 μmol, 80.84 μL) and 2-(1-(4-((2,6-dioxopiperidin-3-yl)amino)-2-fluorophenyl)-4-hydroxypiperidin-4-yl)acetic acid (10, 66.01 mg, 173.99 μmol) in DMF (2 mL) was added HATU (82.70 mg, 217.49 μmol) at 10° C. After addition, the solution was stirred at 20° C. for 6 hr. The reaction mixture was filtered and concentrated under reduced pressure at 30° C. to give a residue. The crude product was purified by prep-HPCL to get the product (FA salt, 75 mg), then sat. $NaHCO_3$ (0.3 mL) was added into a solution of the product (FA salt, 75 mg) in DCM (2 mL) and $CH_3CN$ (1 mL), then the mixture was purified by Prep-TLC (DCM: MeOH: EtOH=100:10:1, $SiO_2$, Rf=0.40, plate 1) to get the product. 4-(6-(6-benzyl-3,6-diazabicyclo[3.1.1]heptan-3-yl)pyridin-3-yl)-6-(1-(1-(2-(1-(4-((2,6-dioxopiperidin-3-yl)amino)-2-fluorophenyl)-4-hydroxypiperidin-4-yl)acetyl)piperidin-4-yl)-1H-pyrazol-4-yl)pyrazolo[1,5-a]pyrazine-3-carbonitrile (Compound 176, 20.6 mg, 22.21 μmol, 15% yield) was obtained as a green solid.

LCMS ($ES^+$): m/z 918.2 $[M+H]^+$.

$^1$H NMR (400 MHz, DMSO-$d_6$) δ=10.79 (s, 1H), 9.31 (s, 1H), 8.85 (s, 1H), 8.77 (d, J=2.4 Hz, 1H), 8.52 (s, 1H), 8.24-8.07 (m, 2H), 7.41-7.28 (m, 4H), 7.23 (br d, J=7.2 Hz, 1H), 6.93-6.77 (m, 2H), 6.55-6.40 (m, 2H), 5.78 (d, J=7.6 Hz, 1H), 4.91 (s, 1H), 4.66-4.45 (m, 2H), 4.33-4.12 (m, 2H), 3.84-3.68 (m, 4H), 3.66-3.49 (m, 4H), 3.28-3.20 (br s, 1H), 2.95-2.69 (m, 6H), 2.63-2.55 (m, 4H), 2.16-2.05 (m, 3H), 2.03-1.92 (m, 1H), 1.90-1.60 (m, 7H)

Example 185: Synthesis of 4-(6-(6-benzyl-3,6-diazabicyclo[3.1.1]heptan-3-yl)pyridin-3-yl)-6-(4-(4-(2-(1-(4-((2,6-dioxopiperidin-3-yl)amino)-2-fluorophenyl)-4-hydroxypiperidin-4-yl)acetyl)piperazin-1-yl)phenyl)pyrazolo[1,5-a]pyrazine-3-carbonitrile (Compound 177)

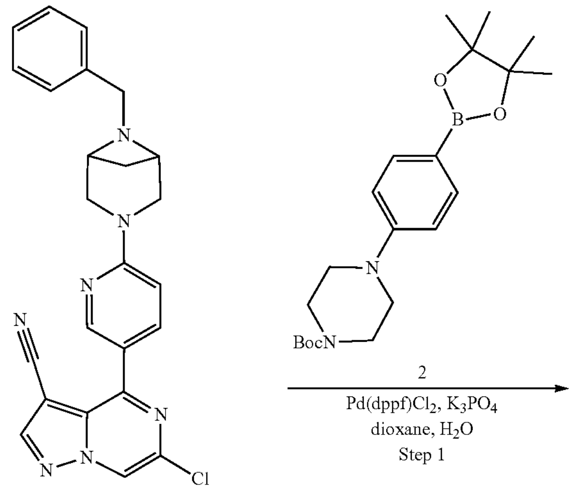

1

-continued
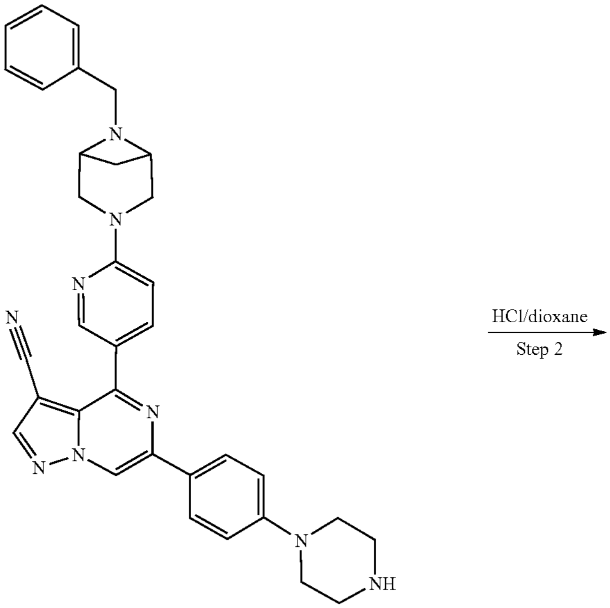
3
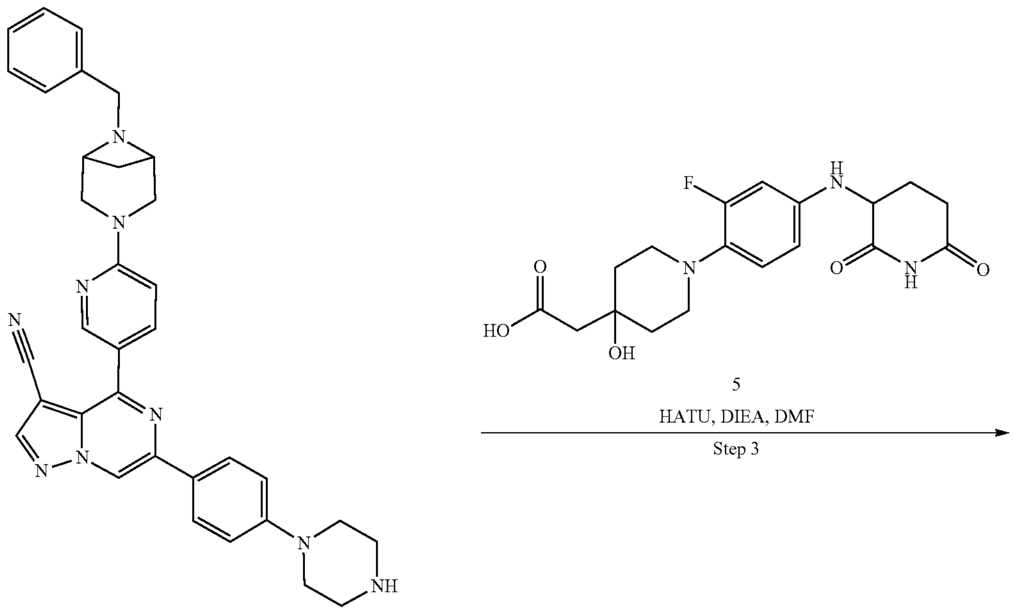
4

-continued

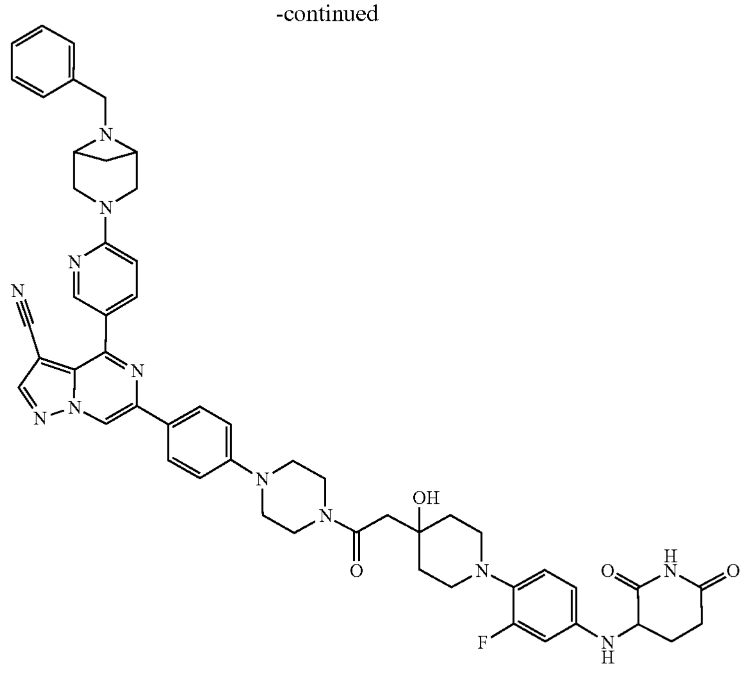

Compound 177

Step 1: To a solution of 4-(6-(6-benzyl-3,6-diazabicyclo[3.1.1]heptan-3-yl)pyridin-3-yl)-6-chloropyrazolo[1,5-a]pyrazine-3-carbonitrile (1, 100 mg, 226.29 μmol), tert-butyl 4-[4-(4,4,5,5-tetramethyl-1,3,2-dioxaborolan-2-yl)phenyl]piperazine-1-carboxylate (2, 87.87 mg, 226.29 μmol) and Pd(dppf)$Cl_2$*DCM (36.96 mg, 45.26 μmol) in dioxane (1.5 mL) was added potassium dihydrogen phosphate (2 M, 0.3 mL) at 10° C., then the mixture was stirred at 100° C. for 2 hrs, The reaction mixture was diluted with EtOAc (100 mL). The organic layer was washed with brine (10 mL), dried over $Na_2SO_4$, filtered and concentrated. The crude product was purified by prep-TLC (PE:EA=2:1, SiO2, Rf=0.6) to get the product. The tert-butyl 4-[4-[4-[6-(6-benzyl-3,6-diazabicyclo[3.1.1]heptan-3-yl)-3-pyridyl]-3-cyano-pyrazolo[1,5-a]pyrazin-6-yl]phenyl]piperazine-1-carboxylate (3, 110 mg, 125.19 μmol, 55% yield) was obtained as yellow solid. LCMS ($ES^+$): m/z 668.3 $[M+H]^+$ Step 2: To a solution of tert-butyl 4-[4-[4-[6-(6-benzyl-3,6-diazabicyclo[3.1.1]heptan-3-yl)-3-pyridyl]-3-cyano-pyrazolo[1,5-a]pyrazin-6-yl]phenyl]piperazine-1-carboxylate (3, 100 mg, 149.75 μmol) in DCM (1 mL) was added HCl/dioxane (4 M, 1.01 mL) at 25° C., then the mixture was stirred at 25° C. for 1 hrs. The reaction mixture was concentrated under vacuum. The crude product was used to next step directly. The 4-[6-(6-benzyl-3,6-diazabicyclo[3.1.1]heptan-3-yl)-3-pyridyl]-6-(4-piperazin-1-ylphenyl)pyrazolo[1,5-a]pyrazine-3-carbonitrile (4, 87 mg, 132.48 μmol, 88% yield, HCl salt) was obtained as blue solid. LCMS ($ES^+$): m/z 568.2 $[M+H]^+$ Step 3: To a solution of 2-(1-(4-((2,6-dioxopiperidin-3-yl)amino)-2-fluorophenyl)-4-hydroxypiperidin-4-yl)acetic acid (5, 60 mg, 144.29 μmol, HCl salt), HATU (90 mg, 236.70 μmol) and 4-[6-(6-benzyl-3,6-diazabicyclo[3.1.1]heptan-3-yl)-3-pyridyl]-6-(4-piperazin-1-ylphenyl)pyrazolo[1,5-a] pyrazine-3-carbonitrile (4, 89 mg, 147.32 μmol, HCl salt) in DMF (2 mL) was added DIEA (72.60 mg, 717.47 μmol, 0.1 mL) at 10° C. After addition, the solution was stirred at 20° C. for 6 hr. The reaction mixture was filtered and concentrated under reduced pressure at 25° C. to give a residue. The crude product was purified by prep-HPCL to the product (FA salt, 72 mg), then sat.$NaHCO_3$ (0.3 mL) was added into a solution of the product (FA salt 72 mg) in DCM (2 mL) and $CH_3CN$ (1 mL), then the mixture was purified by Prep-TLC (DCM:MeOH:EtOH=100:10:1, $SiO_2$, Rf=0.3) to get the product. 4-(6-(6-benzyl-3,6-diazabicyclo[3.1.1]heptan-3-yl)pyridin-3-yl)-6-(4-(4-(2-(1-(4-((2,6-dioxopiperidin-3-yl)amino)-2-fluorophenyl)-4-hydroxypiperidin-4-yl)acetyl)piperazin-1-yl)phenyl)pyrazolo[1,5-a]pyrazine-3-carbonitrile (Compound 177, 10.00 mg, 10.33 μmol, 7% yield) was obtained as a green solid. LCMS ($ES^+$): m/z 929.4 $[M+H]^+$. $^1$H NMR (400 MHz, DMSO-$d_6$) δ=10.78 (s, 1H), 9.43 (s, 1H), 8.86 (s, 1H), 8.79 (d, J=2.0 Hz, 1H), 8.28-8.06 (m, 4H), 7.40-7.27 (m, 4H), 7.25-7.19 (m, 1H), 7.11 (d, J=8.4 Hz, 2H), 6.94-6.79 (m, 2H), 6.54-6.36 (m, 2H), 5.83-5.73 (m, 1H), 4.94-4.80 (m, 1H), 4.30-4.19 (m, 1H), 3.79-3.65 (m, 8H), 3.60 (s, 2H), 2.93-2.83 (m, 4H), 2.77-2.67 (m, 2H), 2.63-2.55 (m, 4H), 2.36-2.32 (m, 1H), 2.12-2.04 (m, 1H), 1.92-1.59 (m, 7H)

Example 186: Synthesis of 4-(6-(6-((4,4-Difluorocyclohexyl)methyl)-3,6-diazabicyclo[3.1.1]heptan-3-yl)pyridin-3-yl)-6-(1-((1s, 4s)-4-(4-(4-((2,6-dioxopiperidin-3-yl)amino)-2-fluorophenyl)piperazin-1-yl)cyclohexyl)-1H-pyrazol-4-yl)pyrazolo[1,5-a]pyrazine-3-carbonitrile (Compound 178)

(Configurations are arbitrarily assigned)

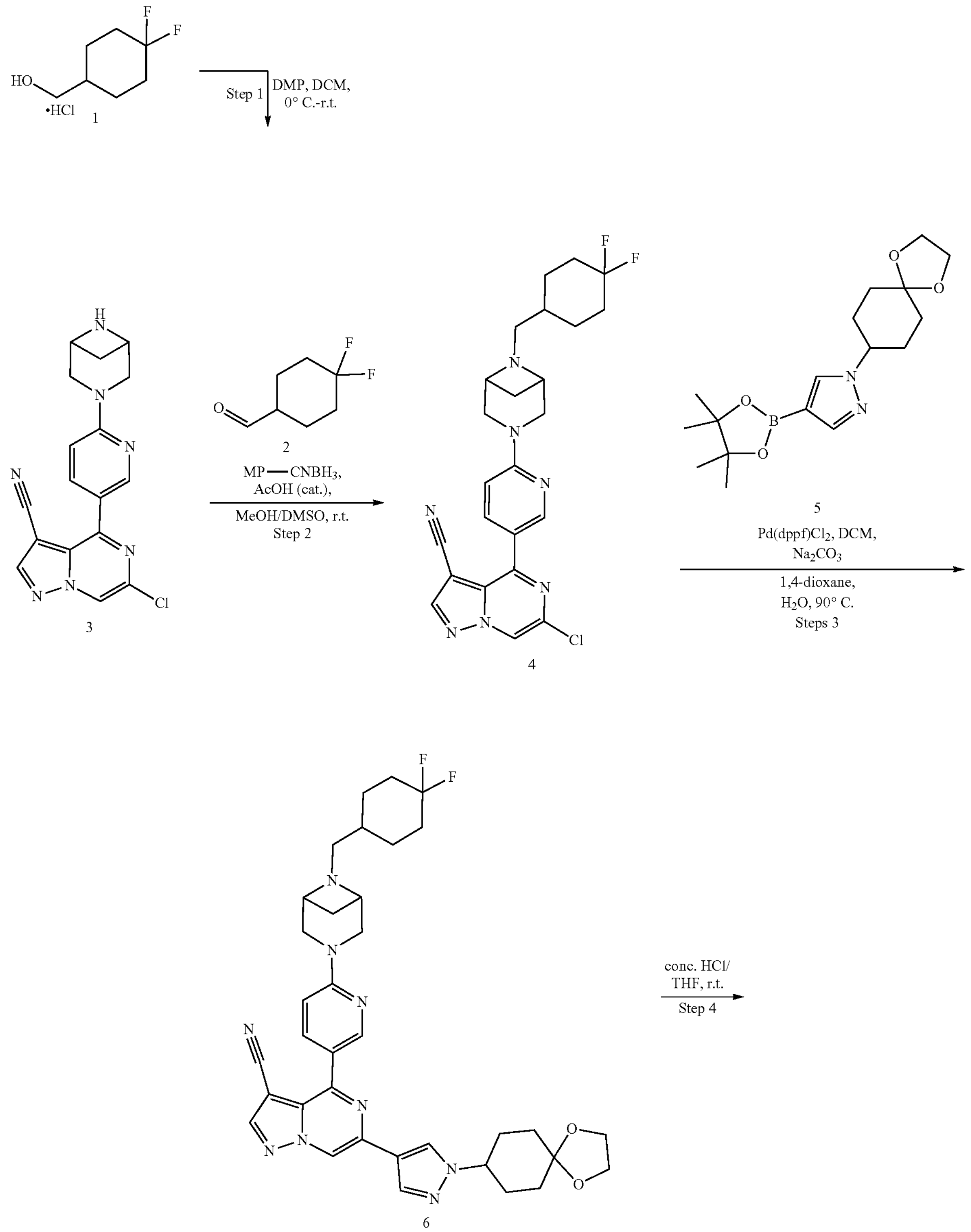
1
Step 1
DMP, DCM,
0° C.-r.t.
3
2
MP—CNBH3,
AcOH (cat.),
MeOH/DMSO, r.t.
Step 2
4
5
Pd(dppf)Cl2, DCM,
Na2CO3
1,4-dioxane,
H2O, 90° C.
Steps 3
6
conc. HCl/
THF, r.t.
Step 4

-continued

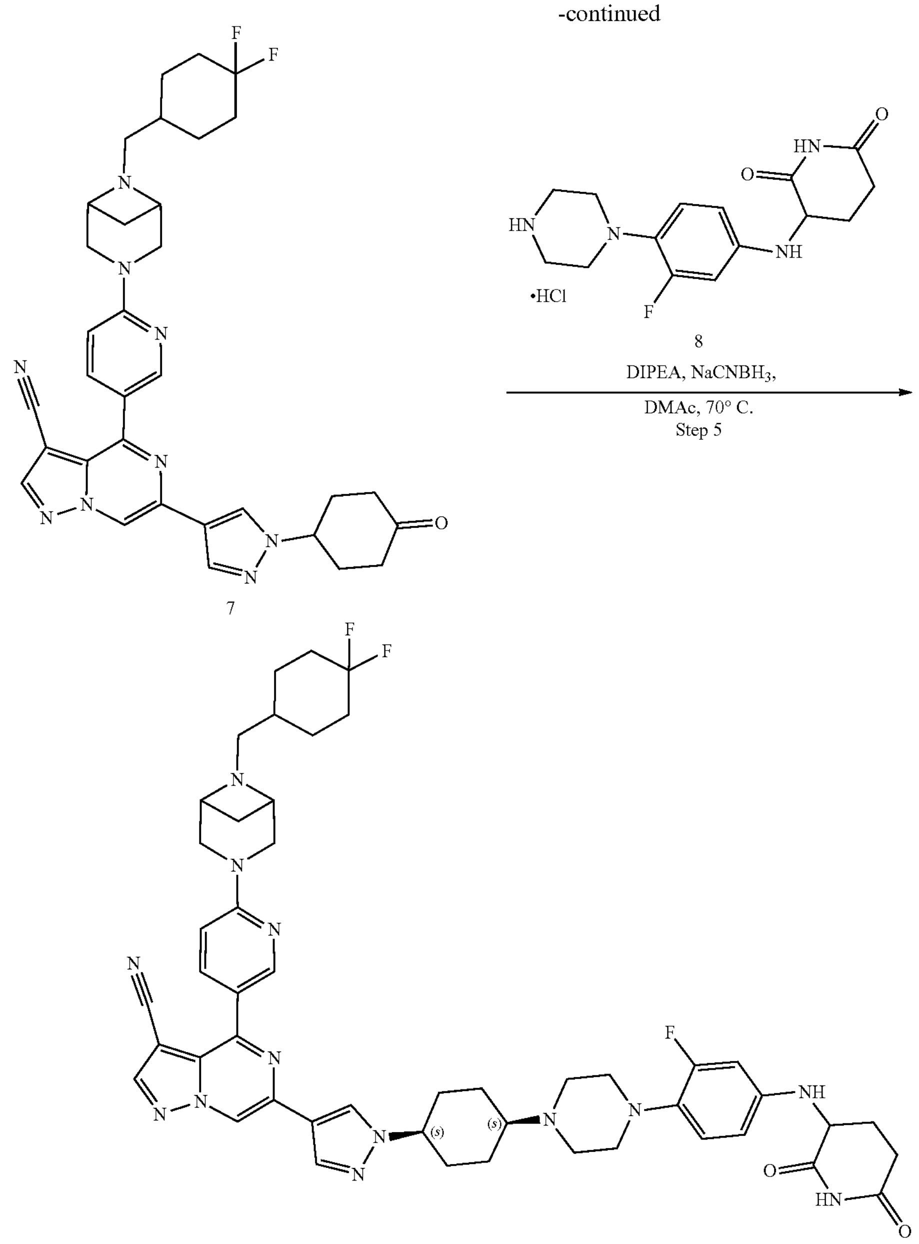

7

Compound 178

Step 1: Into a 50 mL single-necked round-bottomed flask containing a well-stirred solution of (4,4-difluorocyclohexyl)methanol (1, 0.5 g, 3.33 mmol) in anhydrous DCM (5 mL) was added Dess-Martin periodinane (2.82 g, 6.66 mmol) at 0° C. under nitrogen atmosphere. After completion of the addition, the reaction mixture was stirred under nitrogen atmosphere at ambient temperature for 5 h. After completion of the reaction as monitored by TLC, reaction mixture was filtered through a pad of Celite and Celite bed was washed with DCM (50 mL). Combined organic phase was concentrated under reduced pressure to obtain a crude colorless liquid. The crude liquid was purified by silica-gel (230-400 mesh) column with 0-50% EtOAc/pet ether while desired compound was eluting at 10-20% to afford 4,4-difluorocyclohexanecarbaldehyde (2, 0.2 g, 1.35 mmol, 41% yield) as a colorless liquid. $^{1}$H NMR (400 MHz, $CDCl_3$). δ 9.70 (s, 1H), 2.41-2.32 (m, 1H), 2.22-2.01 (m, 4H) and 1.97-1.80 (m, 4H).

Step 2: Into a 100 mL single-necked round-bottomed flask containing a well-stirred solution of 6-chloro-4-[6-(3,6-diazabicyclo[3.1.1]heptan-3-yl)-3-pyridyl]pyrazolo[1,5-a]pyrazine-3-carbonitrile (3, 0.8 g, 2.27 mmol) and 4,4-difluorocyclohexanecarbaldehyde (2, 404.28 mg, 2.73 mmol) in a mixture of anhydrous DMSO (3 mL) and MeOH (10 mL) was added Acetic acid (13.66 mg, 0.227 mmol, 0.013 mL) and the resulting mixture was stirred for 5 minutes at ambient temperature. MP-CNBH$_3$ resin (1.5 g, 2.27 mmol) was added to the reaction mixture at ambient temperature and the reaction mixture was stirred for 16 h. The progress of the reaction was monitored by UPLC, the reaction mixture was filtered through the cotton plug and cotton plug was washed with DCM and MeOH, diluted with water (30 mL) and the product was extracted with EtOAc (2×30 mL). Organic phases were combined, dried (anhydrous $Na_2SO_4$), filtered and the filtrate was concentrated under reduced pressure to get a crude residue. The crude product was purified by silica-gel (230-400 mesh) column with 0-15% MeOH/DCM while desired compound was eluting at 3-10% to afford 6-chloro-4-[6-[6-[(4,4-difluorocyclohexyl) methyl]-3,6-diazabicyclo[3.1.1]heptan-3-yl]-3-pyridyl] pyrazolo[1,5-a]pyrazine-3-carbonitrile (4, 0.5 g, 1.03 mmol, 45% yield) as a yellow solid. LCMS ($ES^+$): m/z 484.3 $[M+H]^+$.

Step 2: Into a 25 mL sealed-tube containing a well-stirred solution of 6-chloro-4-[6-[6-[(4,4-difluorocyclohexyl) methyl]-3,6-diazabicyclo[3.1.1]heptan-3-yl]-3-pyridyl] pyrazolo[1,5-a]pyrazine-3-carbonitrile (4, 0.2 g, 0.413 mmol) and 1-(1,4-dioxaspiro[4.5]decan-8-yl)-4-(4,4,5,5-tetramethyl-1,3,2-dioxaborolan-2-yl)pyrazole (5, 0.207 g, 0.619 mmol) in 1,4-dioxane (2.5 mL) was added solution of Sodium carbonate (0.131 g, 1.24 mmol) in water (0.5 mL) at ambient temperature and the resulting mixture was degassed by bubbling nitrogen gas into the reaction mixture for 10 minutes. Subsequently, $Pd(dppf)Cl_2$ $CH_2Cl_2$ (33.75 mg, 0.041 mmol) was added and the reaction mixture was heated to 90° C. for 16 h. After completion of the reaction as indicated by TLC, the reaction mixture was cooled to room temperature and poured into water (30 mL) and extracted with DCM (2×10 mL). Organic phases were combined and washed with brine (10 mL). Combined organic phase was dried (anhydrous $Na_2SO_4$), filtered and the filtrate was concentrated under reduced pressure to get 4-[6-[6-[(4,4-difluorocyclohexyl)methyl]-3,6-diazabicyclo [3.1.1]heptan-3-yl]-3-pyridyl]-6-[1-(1,4-dioxaspiro[4.5]decan-8-yl)pyrazol-4-yl]pyrazolo[1,5-a]pyrazine-3-carbonitrile (6, 0.4 g, 0.305 mmol, 74% yield) as a yellow solid. LCMS ($ES^+$): m/z 656.2 $[M+H]^+$.

Step 4: Into a 100 mL single-necked round-bottomed flask containing a well-stirred solution of 4-[6-[6-[(4,4-difluorocyclohexyl)methyl]-3,6-diazabicyclo[3.1.1]heptan-3-yl]-3-pyridyl]-6-[1-(1,4-dioxaspiro[4.5]decan-8-yl)pyrazol-4-yl] pyrazolo[1,5-a]pyrazine-3-carbonitrile (6, 0.4 g, 0.305 mmol) in THF (5 mL) was added dropwise HCl 36% w/w aq. soln. (0.8 g, 21.94 mmol, 1.0 mL) at 0° C. The resulting reaction mixture was stirred at ambient temperature for 2 h. After completion of the reaction as monitored by UPLC, excess acid was quenched with 10% sodium bicarbonate solution (50 mL) slowly at 0° C. and pH of the solution was adjusted to 7-8 and aqueous phase was extracted with DCM (2×30 mL). Combined organic phase was washed with brine (50 mL), dried (anhydrous $Na_2SO_4$), filtered and the filtrate was concentrated under reduced pressure to obtain a crude residue. The crude residue was purified by flash silica-gel (230-400 mesh) column with 0-100% EtOAc/pet ether while desired compound was eluting at 80-100% of the mobile phase to afford 4-[6-[6-[(4,4-difluorocyclohexyl)methyl]-3,6-diazabicyclo[3.1.1]heptan-3-yl]-3-pyridyl]-6-[1-(4-oxocyclohexyl)pyrazol-4-yl]pyrazolo[1,5-a]pyrazine-3-carbonitrile (7, 0.11 g, 0.140 mmol, 46% yield) as a yellow solid. UPLC-MS ($ES^+$): m/z 612.2 $[M+H]^+$.

Step 5: Into a 8 mL glass-vial containing a well-stirred solution of 3-(3-fluoro-4-piperazin-1-yl-anilino)piperidine-2,6-dione (8, 0.30 g, 0.876 mmol) and 4-[6-[6-[(4,4-difluorocyclohexyl)methyl]-3,6-diazabicyclo[3.1.1]heptan-3-yl]-3-pyridyl]-6-[1-(4-oxocyclohexyl)pyrazol-4-yl]pyrazolo[1,5-a]pyrazine-3-carbonitrile (7, 0.15 g, 0.245 mmol) in anhydrous DMAc (3 mL) were added Sodium cyanoborohydride (0.077 g, 1.23 mmol) and N,N-Diisopropylethylamine (0.158 g, 1.23 mmol, 0.213 mL) at ambient temperature and the reaction mixture was heated to 70° C. for 16 h and the reaction mixture was cooled to ambient temperature. After complete consumption of the starting material as indicated by UPLC, the reaction mixture was quenched with ice-cold water (20 mL) and extracted with DCM (2×15 mL). Combined organic phase was washed with brine (50 mL), dried (anhydrous $Na_2SO_4$), filtered and the filtrate was concentrated under reduced pressure to obtain a crude mass. The crude product was purified by flash silica-gel (230-400 mesh, 25 g) column with 10% MeOH/DCM while desired compound was eluting at 4-6% of the mobile phase to afford 160 mg of product with two peaks in LCMS with same mass (37.5% and 46.6%). The diastereomeric mixture (~160 mg) was purified by reverse phase perp-HPLC [Column: XBRIDGE OBD C18 19×150 mm 5 micron; Mobile phase: A: 0.1% $NH_4HCO_3$ in MQ-water; B: Acetonitrile; Flow rate: 15 mL/minutes.

Early eluting isomer (cis-isomer, arbitrarily assigned, RT=7.50 minutes)

The collected fraction was lyophilized to afford 4-(6-(6-((4,4-difluorocyclohexyl)methyl)-3,6-diazabicyclo[3.1.1] heptan-3-yl)pyridin-3-yl)-6-(1-((1s, 4s)-4-(4-(4-((2,6-dioxopiperidin-3-yl)amino)-2-fluorophenyl)piperazin-1-yl) cyclohexyl)-1H-pyrazol-4-yl)pyrazolo[1,5-a]pyrazine-3-carbonitrile (Compound 178, 16 mg, 0.017 mmol, 7% yield) as a yellow solid. $^1H$ NMR (400 MHz, DMSO-$d_6$). δ 10.79 (s, 1H), 9.29 (s, 1H), 8.85 (s, 1H), 8.75 (d, J=2.4 Hz, 1H), 8.46 (s, 1H), 8.16 (s, 1H), 8.13 (dd, J=8.8, 2.4 Hz, 1H), 6.83 (dd, J=13.8, 3.2 Hz, 2H), 6.52 (dd, J=15.2, 2 Hz, 1H), 6.43 (d, J=8.8 Hz, 1H), 5.81 (d, J=7.6 Hz, 1H), 4.28-4.18 (m, 2H), 3.70-3.33 (m, 6H), 2.87 (m, 4H), 2.68-2.67 (m, 1H), 2.65 (m, 4H), 2.51-2.50 (m, 2H), 2.24-2.23 (m, 2H), 2.17-2.10 (m, 3H), 2.07-1.97 (m, 4H), 1.84-1.58 (m, 8H), 1.58-1.47 (m, 4H) and 1.24-1.20 (m, 2H). LCMS ($ES^+$): m/z 902.3 $[M+H]^+$.

Example 187: Synthesis of 4-(6-(5H-Spiro[furo[3,4-b]pyridine-7,4'-piperidin]-1'-yl)pyridin-3-yl)-6-(1-((1S,4r)-4-(4-(4-(((S)-2,6-dioxopiperidin-3-yl)amino)-2-fluorophenyl)piperidin-1-yl)cyclohexyl)-1H-pyrazol-4-yl)pyrazolo[1,5-a]pyrazine-3-carbonitrile (Compound 179)

4-(6-(5H-spiro[furo[3,4-b]pyridine-7,4'-piperidin]-1'-yl)pyridin-3-yl)-6-(1-((1R,4r)-4-(4-(4-(((R)-2,6-dioxopiperidin-3-yl)amino)-2-fluorophenyl)piperidin-1-yl)cyclohexyl)-1H-pyrazol-4-yl)pyrazolo[1,5-a]pyrazine-3-carbonitrile (Compound 180)

(Configurations are arbitrarily assigned)

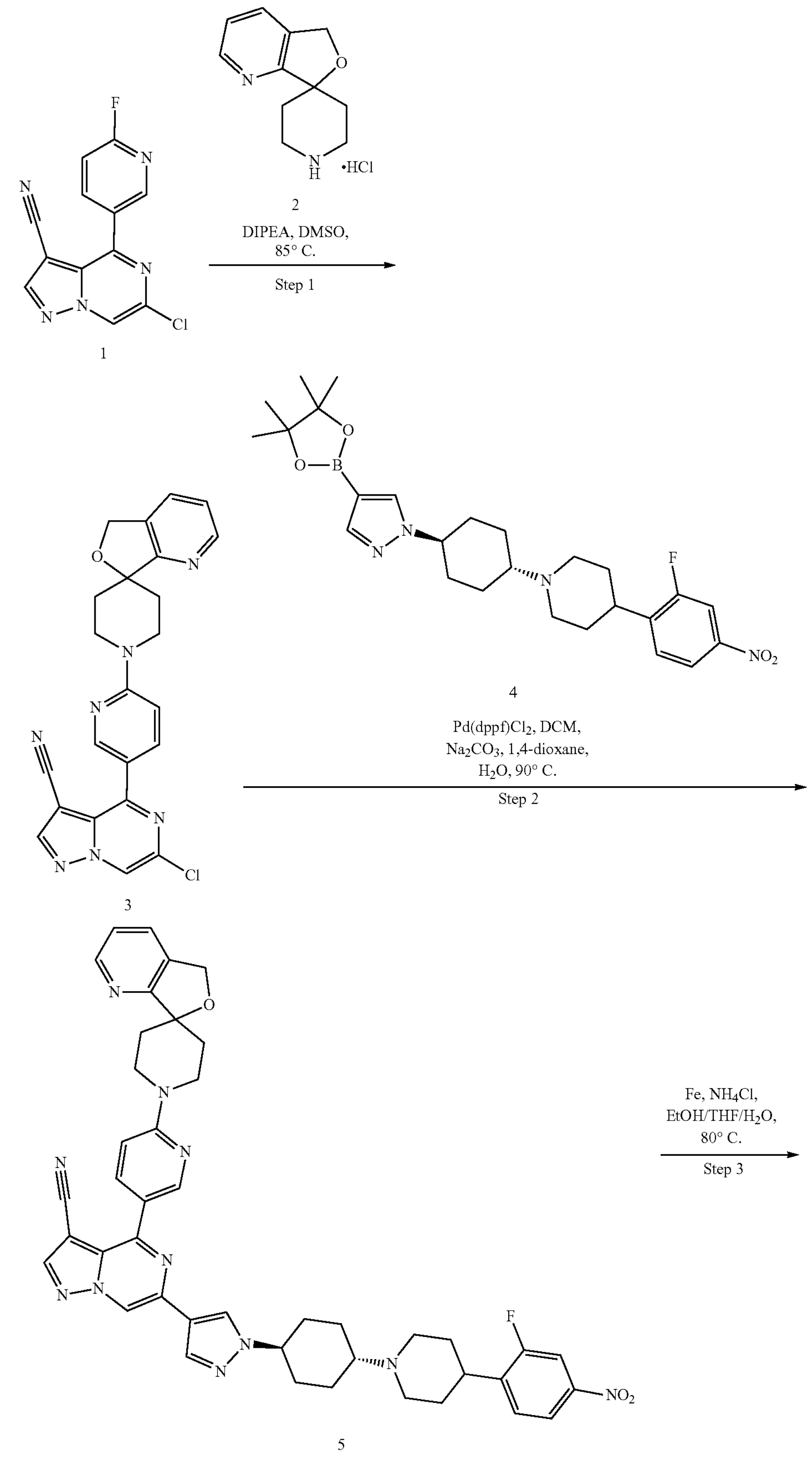
2
DIPEA, DMSO,
85° C.
Step 1
1
4
Pd(dppf)$Cl_2$, DCM,
$Na_2CO_3$, 1,4-dioxane,
$H_2O$, 90° C.
Step 2
3
Fe, $NH_4Cl$,
EtOH/THF/$H_2O$,
80° C.
Step 3
5

-continued
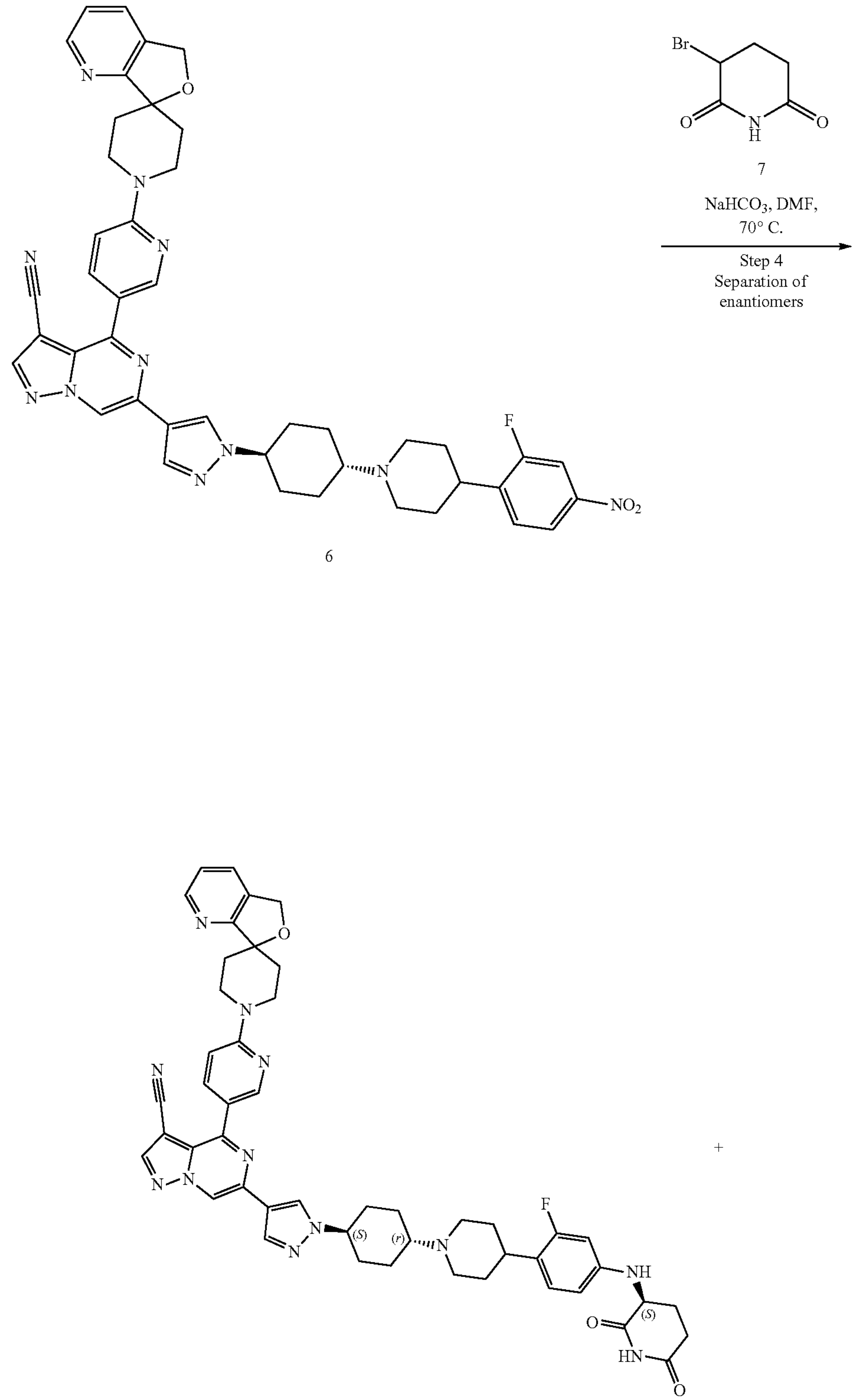
6
+
Compound 179

-continued

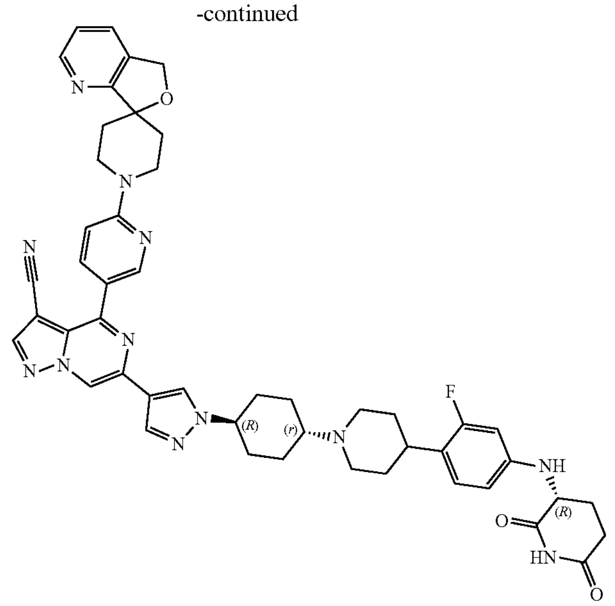

Compound 180

Step 1: Into a 50 mL sealed-tube containing a well-stirred solution of spiro[5H-furo[3,4-b]pyridine-7,4'-piperidine] (2, 833.90 mg, 2.74 mmol), trifluoroacetic acid (833.90 mg, 2.74 mmol) and 6-chloro-4-(6-fluoro-3-pyridyl)pyrazolo[1,5-a]pyrazine-3-carbonitrile (1, 500 mg, 1.83 mmol) in anhydrous DMSO (10 mL) was added DIPEA (1.89 g, 14.62 mmol, 2.55 mL) under nitrogen atmosphere. The reaction mixture was heated to 90° C. for 16 h. After completion of the reaction as indicated by UPLC, the reaction mixture was cooled and treated with water (50 mL) and solid precipitated out was filtered. The solid on the filter was dried under reduced pressure to afford a crude residue. The crude was purified by flash silica-gel (230-400 mesh) column with 0-100% EtOAc/pet ether while desired compound eluting at 60% to get 6-chloro-4-(6-spiro[5H-furo[3,4-b]pyridine-7,4'-piperidine]-1'-yl-3-pyridyl)pyrazolo[1,5-a]pyrazine-3-carbonitrile (3, 350 mg, 0.716.97 mmol, 39% yield) as a yellow solid. UP-LCMS ($ES^+$): m/z 444.6 $[M+H]^+$.

Step 2: Into a 250 mL sealed-tube containing a well-stirred solution of 6-chloro-4-(6-spiro[5H-furo[3,4-b]pyridine-7,4'-piperidine]-1'-yl-3-pyridyl)pyrazolo[1,5-a]pyrazine-3-carbonitrile (3, 627 mg, 1.41 mmol) and 4-(2-fluoro-4-nitro-phenyl)-1-[4-[4-(4,4,5,5-tetramethyl-1,3,2-dioxaborolan-2-yl)pyrazol-1-yl]cyclohexyl]piperidine (4, 1.06 g, 2.12 mmol) in 1,4-dioxane (25 mL) was added Sodium carbonate (299.43 mg, 2.83 mmol, 0.118 mL) in water (5 mL) at ambient temperature and the mixture was purged with nitrogen for 5 minutes, then Pd(dppf)$Cl_2$*DCM (115.35 mg, 0.141 mmol) was added to the sealed tube and the tube was closed. The reaction mixture was stirred at 90° C. for 16 h. The progress of the reaction was monitored by UPLC and TLC. After completion of the reaction as indicated by UPLC, the reaction mixture was diluted with EtOAc (25 mL) and filtered through a pad of Celite & sodium sulfate and the Celite pad was washed with EtOAc (2×25 mL) and the filtrate was concentrated under reduced pressure to afford a crude solid residue. The crude mass which was purified by reverse phase column chromatography by using C18 Redisep Rf Gold (160 g HP C18); Mobile phase: 0.1% Ammonium bicarbonate in MQ-water; B: Acetonitrile; Flow rate: 20 mL/minutes while compound eluting at 80% to get 6-[1-[4-[4-(2-fluoro-4-nitro-phenyl)-1-piperidyl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (5, 470 mg, 0.451 mmol, 32% yield) as a light yellow-colored solid LCMS ($ES^+$): m/z 780.5 $[M+H]^+$.

Step 3: Into a 50 mL single-necked round-bottomed flask containing a well-stirred suspension of 6-[1-[4-[4-(2-fluoro-4-nitro-phenyl)-1-piperidyl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (5, 570 mg, 0.730 mmol) in 1:1 EtOH/THF (20 mL) were added Iron powder (204.10 mg, 3.65 mmol) and Ammonium Chloride (195.48 mg, 3.65 mmol) in water (4 mL) at ambient temperature under nitrogen atmosphere. The resulting suspension was heated to 80° C. for 2 h and the reaction mixture was cooled to ambient temperature. After complete consumption of the starting material as indicated by UPLC, the reaction mixture was filtered through a pad of Celite and Celite bed was washed with DCM (20 mL). The combined filtrate was diluted with water (10 mL) and the product was extracted with DCM (2×50 mL). The organic phases were combined, dried (anhydrous $Na_2SO_4$), filtered and the filtrate was concentrated under reduced pressure to get 6-[1-[4-[4-(4-amino-2-fluoro-phenyl)-1-piperidyl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (6, 510 mg, 0.547 mmol, 75% yield) as a yellow solid. UP-LCMS ($ES^+$): m/z 750.6 $[M+H]^+$.

Step 4: Into a 50 mL sealed-tube containing a well-stirred solution of 6-[1-[4-[4-(4-amino-2-fluoro-phenyl)-1-piperidyl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (6, 300.0 mg, 0.4 mmol) and 3-bromopiperidine-2,6-dione (7, 153.63 mg, 0.8 mmol) in anhydrous DMF (5 mL) was added Sodium bicarbonate (100.8 mg, 1.2 mmol) at ambient temperature under nitrogen atmosphere. The reaction mixture was heated to 75° C. for 48 h. The reaction mixture was monitored by UPLC. The reaction mixture was quenched with water (5 mL) and the product was extracted with DCM (2×80 mL). The organic phases were combined, dried (anhydrous $Na_2SO_4$), filtered and the filtrate was concentrated under reduced pressure to get a crude residue. The crude product was purified by flash silica-gel (230-400 mesh) column with 0-15% MeOH/DCM while desired compound eluting at 10% to afford 230 mg of product with 56% purity. It was re-purified by reverse phase column chromatography [X-BRIDGE C18 (150×10) mm 5 MICRON; Mobile phase: 0.1% $NH_4HCO_3$ in-water, B: Acetonitrile; Flow rate: 15 mL/minutes] to afford racemic mixture of 133 mg as an yellow solid. The racemic mixture was purified by chiral SFC method: 133 mg of sample is dissolved in 5 mL of acetonitrile and injected 1.0 mL per injection. Instrument: PIC 175, Column: Chiralpak ASH (250*20) mm, 5, Mobile Phase: {$CO_2$: (0.1% Isopropyl amine in IPA:ACN) (50:50)}, Total Flow: 50 g/min. Back pressure: 120 bar, Wave length: 280 nm, Cycle time: 20.50 min.

Early eluting isomer: SFC fraction with RT=3.38 minutes was collected and concentrated under reduced pressure at 20° C. (Rota-vac bath temperature 20° C.) and finally the product mass was lyophilized to afford 4-(6-(5H-spiro[furo[3,4-b]pyridine-7,4'-piperidin]-1'-yl)pyridin-3-yl)-6-(1-((1S,4r)-4-(4-(4-(((S)-2,6-dioxopiperidin-3-yl)amino)-2-fluorophenyl)piperidin-1-yl)cyclohexyl)-1H-pyrazol-4-yl)pyrazolo[1,5-a]pyrazine-3-carbonitrile (Compound 179, 22 mg, 0.024 mmol, 6% yield) as an off-white solid. LCMS ($ES^+$): m/z 861.3 $[M+H]^+$. $^1H$ NMR (400 MHz, DMSO-$d_6$). δ 10.80 (s, 1H), 9.30 (s, 1H), 8.85 (s, 1H), 8.72 (d, J=2.8 Hz, 1H), 8.48 (s, 1H), 8.44 (d, J=3.6 Hz, 1H), 8.17 (s, 1H), 8.11 (dd, J=9, 2.8 Hz, 1H), 7.79 (dd, J=7.6, 1.2 Hz, 1H), 7.33-7.32 (dd, J=7.6, 4.8 Hz, 1H), 7.13 (d, J=8.8 Hz, 1H), 7.00 (t, J=8.8 Hz, 1H), 6.47-6.42 (m, 2H), 6.01 (d, J=7.6 Hz, 1H), 5.11 (s, 2H), 4.49 (d, J=12.8 Hz, 2H), 4.32 (m, 1H), 4.20 (m, 1H), 3.45 (t, J=11.6 Hz, 2H), 2.95-2.92 (m, 2H), 2.74-2.68 (m, 1H), 2.60 (m, 3H), 2.34-2.29 (m, 2H), 2.16-2.11 (m, 3H), 1.93-1.83 (m, 7H) and 1.75 (m, 2H), 1.65 (m, 4H) and 1.5 (m, 2H).

Late eluting isomer: SFC fraction with RT=5.09 minutes was collected and concentrated under reduced pressure at 20° C. (Rota-vac bath temperature 20° C.) and the product mass was lyophilized to afford 4-(6-(5H-spiro[furo[3,4-b]pyridine-7,4'-piperidin]-1'-yl)pyridin-3-yl)-6-(1-((1R,4r)-4-(4-(4-(((R)-2,6-dioxopiperidin-3-yl)amino)-2-fluorophenyl)piperidin-1-yl)cyclohexyl)-1H-pyrazol-4-yl)pyrazolo[1,5-a]pyrazine-3-carbonitrile (Compound 180; 12 mg, 0.013 mmol, 3% yield) as an off-white solid. $^1H$ NMR (400 MHz, DMSO-$d_6$). δ 10.80 (s, 1H), 9.30 (s, 1H), 8.85 (s, 1H), 8.72 (d, J=2.4 Hz, 1H), 8.48 (s, 1H), 8.44 (d, J=3.6 Hz, 1H), 8.16 (s, 1H), 8.11 (dd, J=9.2, 2.4 Hz, 0.6H), 7.79 (dd, J=7.8, 1.2 Hz, 1H), 7.33-7.30 (m, 1H), 7.13 (d, J=9.2 Hz, 1H), 7.02-6.98 (m, 1H), 6.47-6.42 (m, 2H), 6.01 (d, J=7.60 Hz, 1H), 5.11 (s, 2H), 4.49 (m, 2H), 4.31 (m, 1H), 4.30-4.20 (m, 1H), 3.43 (t, J=11.2 Hz, 2H), 2.94 (d, J=10.8 Hz, 2H), 2.62 (m, 1H), 2.60 (m, 3H), 2.34-2.29 (m, 2H), 2.17-2.14 (m, 3H), 1.99-1.92 m, 7H), 1.82-1.75 (m, 2H), 1.75-1.62 (m, 4H) and 1.59-1.52 (m, 2H). LCMS ($ES^+$): m/z 861.3 $[M+H]^+$.

Example 188: Synthesis of 1-(5-(3-Cyano-6-(1-((1r, 4r)-4-(2-(4-(4-((2,6-dioxopiperidin-3-yl)amino)-2-fluorophenyl)piperidin-1-yl)ethyl)cyclohexyl)-1H-pyrazol-4-yl)pyrazolo[1,5-a]pyrazin-4-yl)pyridin-2-yl)-4-ethyl-N-isopropylpiperidine-4-carboxamide (Compound 181)

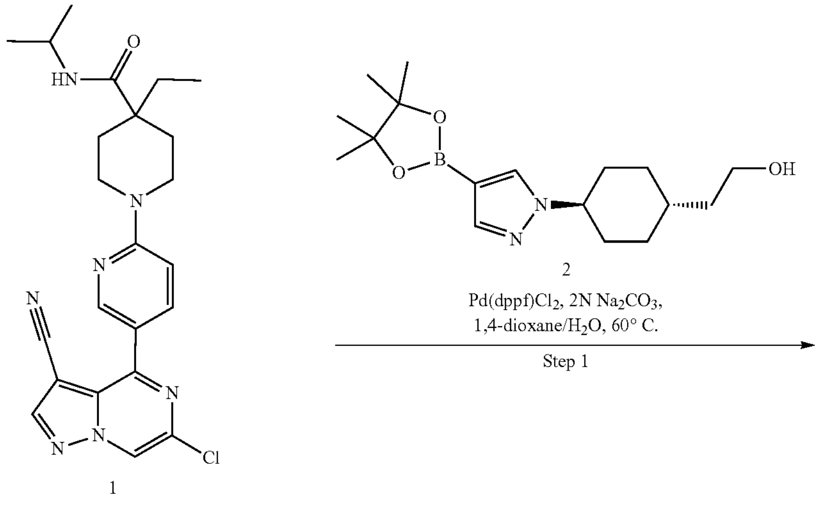

1

-continued
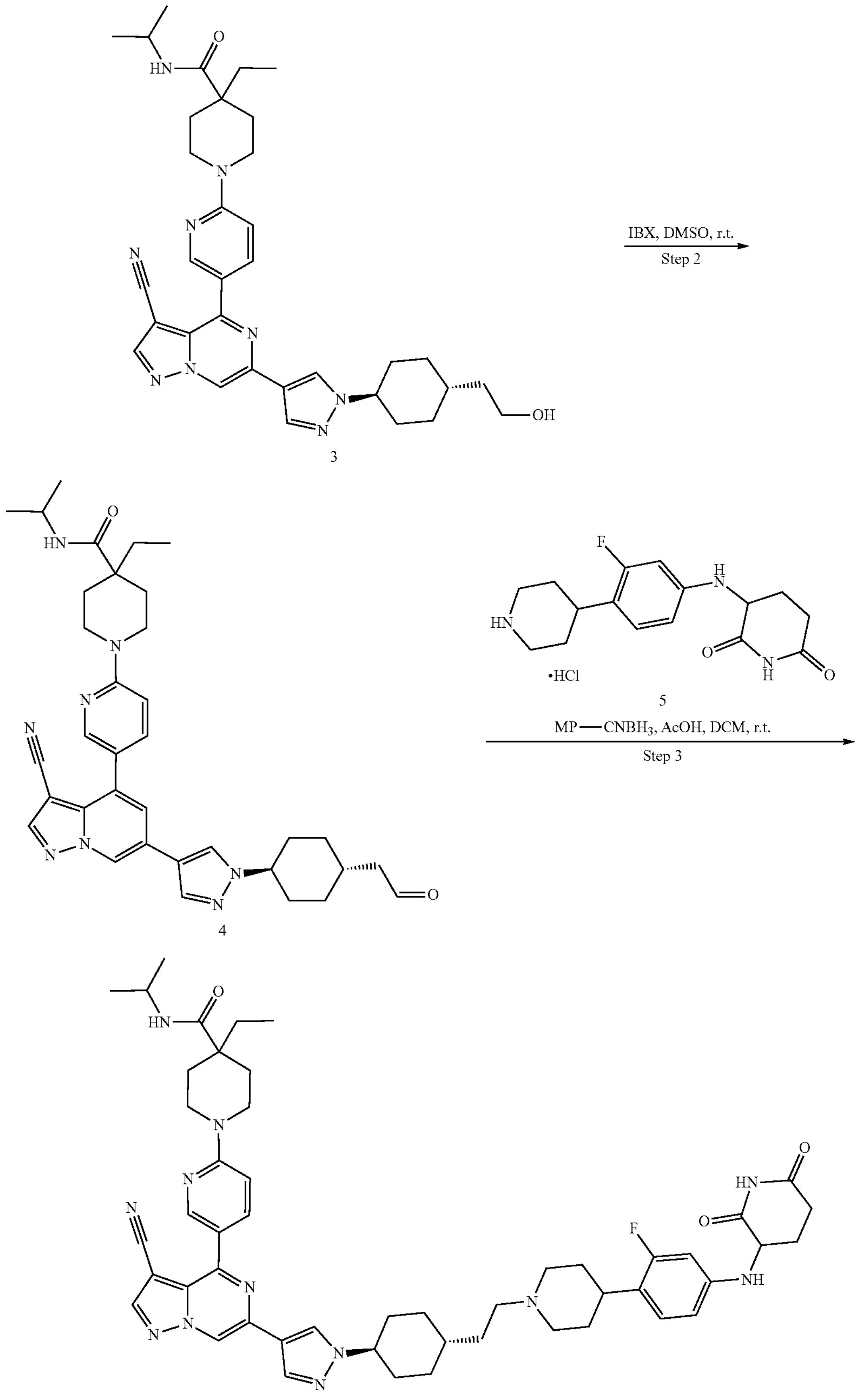
3
4
5
Compound 181

Step 1: Into 25 mL sealed tube, a well-stirred solution of 1-[5-(6-chloro-3-cyano-pyrazolo[1,5-a]pyrazin-4-yl)-2-pyridyl]-4-ethyl-N-isopropyl-piperidine-4-carboxamide (1, 200 mg, 0.442 mmol) and 2-((1r, 4r)-4-(4-(4,4,5,5-tetramethyl-1,3,2-dioxaborolan-2-yl)-1H-pyrazol-1-yl)cyclohexyl)ethan-1-ol (2, 141.71 mg, 0.442 mmol) in 1,4-dioxane (8.5 mL) was stirred at ambient temperature under nitrogen atmosphere. The resulting mixture was degassed by bubbling nitrogen gas into the reaction mixture for 5 minutes. Subsequently, $Pd(dppf)Cl_2 \cdot CH_2Cl_2$ (0.442 mmol) and sodium carbonate (46.90 mg, 0.442 mmol) in water (1.5 mL) were added. The resulting mixture was stirred at 90° C. for 3 h. After completion of the reaction as monitored by TLC, the reaction mixture was allowed to cool to room temperature. The reaction mixture was filtered through a pad of Celite and the Celite bed was washed with EtOAc (2×50 mL) to get crude product. The crude product was purified by flash column chromatography (230-400 mesh) with 0-100% EtOAc/pet ether, while desired compound eluting at 80-90% to get 1-(5-(3-cyano-6-(1-((1r, 4r)-4-(2-hydroxyethyl)cyclohexyl)-1H-pyrazol-4-yl)pyrazolo[1,5-a]pyrazin-4-yl)pyridin-2-yl)-4-ethyl-N-isopropylpiperidine-4-carboxamide (3, 225 mg, 0.287 mmol, 65% yield) as a black gummy liquid. LCMS ($ES^+$): m/z 610.2 $[M+H]^+$.

Step 2: Into a 50 mL single-necked round-bottomed flask containing a well-stirred of 1-(5-(3-cyano-6-(1-((1r, 4r)-4-(2-hydroxyethyl)cyclohexyl)-1H-pyrazol-4-yl)pyrazolo[1,5-a]pyrazin-4-yl)pyridin-2-yl)-4-ethyl-N-isopropylpiperidine-4-carboxamide (3, 150 mg, 0.246 mmol) in anhydrous DMSO (10 mL) was added 2-Iodoxybenzoic acid (68.88 mg, 0.246 mmol) at ambient temperature. The reaction mixture was stirred at ambient temperature for 2 h. The reaction was monitored by TLC and found complete after 2 h. After completion of the reaction, the reaction mixture was quenched with water (20 mL) and extracted with EtOAc (2×20 mL). Organic phases were combined and washed with sodium bicarbonate and then washed with brine (10 mL). Combined organic phases were dried over (anhydrous $Na_2SO_4$), filtered and the filtrate was concentrated under reduced pressure to get a crude mass. The crude mass was purified by flash silica-gel (230-400 mesh) column with 0-100% EtOAc/pet ether, while desired compound was eluting at 80-90% of the mobile phase to get 1-(5-(3-cyano-6-(1-((1r, 4r)-4-(2-oxoethyl)cyclohexyl)-1H-pyrazol-4-yl)pyrazolo[1,5-a]pyridin-4-yl)pyridin-2-yl)-4-ethyl-N-isopropylpiperidine-4-carboxamide (4, 80 mg, 0.095 mmol, 39% yield) as a yellow solid. LCMS ($ES^+$): m/z 608.2 $[M+H]^+$.

Step 3: Into a 20 mL glass-vial containing a well-stirred solution of 1-(5-(3-cyano-6-(1-((1r, 4r)-4-(2-oxoethyl)cyclohexyl)-1H-pyrazol-4-yl)pyrazolo[1,5-a]pyridin-4-yl)pyridin-2-yl)-4-ethyl-N-isopropylpiperidine-4-carboxamide (4, 130 mg, 0.214 mmol) in anhydrous DCM (5 mL) was added 3-[3-fluoro-4-(4-piperidyl)anilino]piperidine-2,6-dione hydrochloride (5, 65.42 mg, 0.191 mmol) and MP-$CNBH_3$ (80 mg, 0.214 mmol) and the resulting mixture was stirred for 30 minutes and then was added AcOH (0.021 mmol) at ambient temperature. The resulting mixture were stirred at ambient temperature for 2 h. After completion of the reaction as indicated by LCMS, reaction mixture was filtered through sintered funnel and the filtrate was concentrated under reduced pressure to get a crude slide. The crude solid was purified by reverse phase column chromatography by using C18 Redisep Rf Gold (HP C18; 30 g); Mobile phase: 0.1% HCOOH in MQ-water; B: Acetonitrile; Flow rate: 10 mL/minutes; while compound eluting at 45% of B to get 1-(5-(3-cyano-6-(1-((1r, 4r)-4-(2-(4-(4-((2,6-dioxopiperidin-3-yl)amino)-2-fluorophenyl)piperidin-1-yl)ethyl)cyclohexyl)-1H-pyrazol-4-yl)pyrazolo[1,5-a]pyrazin-4-yl)pyridin-2-yl)-4-ethyl-N-isopropylpiperidine-4-carboxamide (Compound 181, 6.66 mg, 0.006 mmol, 3% yield, formic acid salt) as an off-brown gum. $^1H$ NMR (400 MHz, DMSO-$d_6$). δ 10.80 (s, 1H), 9.28 (s, 1H), 8.83 (s, 1H), 8.67 (s, 1H), 8.46 (s, 1H), 8.25 (s, 1H), 8.14 (s, 1H), 8.05 (d, J=8.8 Hz, 1H), 7.42 (d, J=7.2 Hz, 1H), 7.00 (m, 2H), 6.44 (m, 2H), 6.01 (d, J=7.2 Hz, 1H), 4.31 (m, 1H), 4.28 (m, 1H), 4.09 (m, 1H), 3.11 (t, J=11.6 Hz, 2H), 2.99 (d, J=10.4 Hz, 2H), 2.68 (m, 1H), 2.35 (m, 2H), 2.20 (m, 3H), 2.16 (m, 4H), 2.00 (m, 1H), 1.88 (m, 7H), 1.65 (m, 4H), 1.50 (m, 3H), 1.40 (m, 6H), 1.16 (m, 1H), 1.10 (d, J=6.4 Hz, 6H) and 0.75 (t, J=7.6 Hz, 3H). LCMS ($ES^+$): m/z 897.2 $[M+H]^+$.

Example 189: Synthesis of 1-(5-(3-Cyano-6-(1-(2-(2-(1-(4-((2,6-dioxopiperidin-3-yl)amino)-2-fluorophenyl)-4-hydroxypiperidin-4-yl)acetyl)-2-azaspiro[3.5]nonan-7-yl)-1H-pyrazol-4-yl)pyrazolo[1,5-a]pyrazin-4-yl)pyridin-2-yl)-4-ethyl-N-isopropylpiperidine-4-carboxamide (Compound 182)

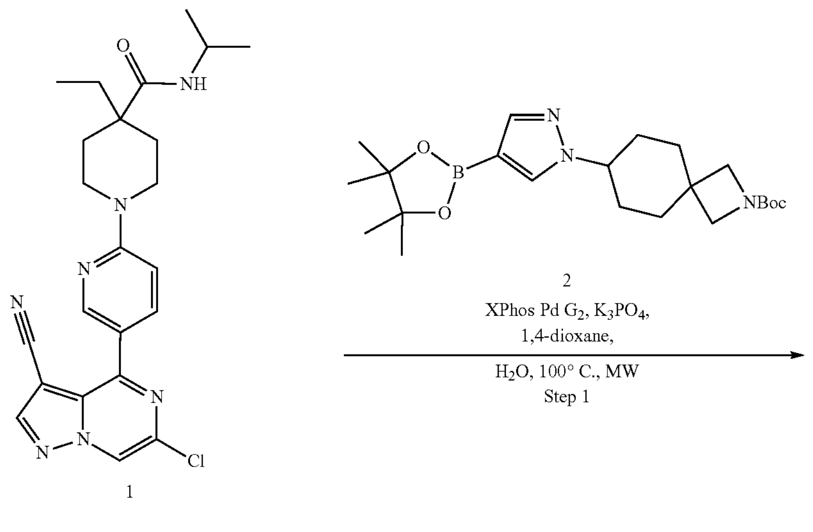

-continued
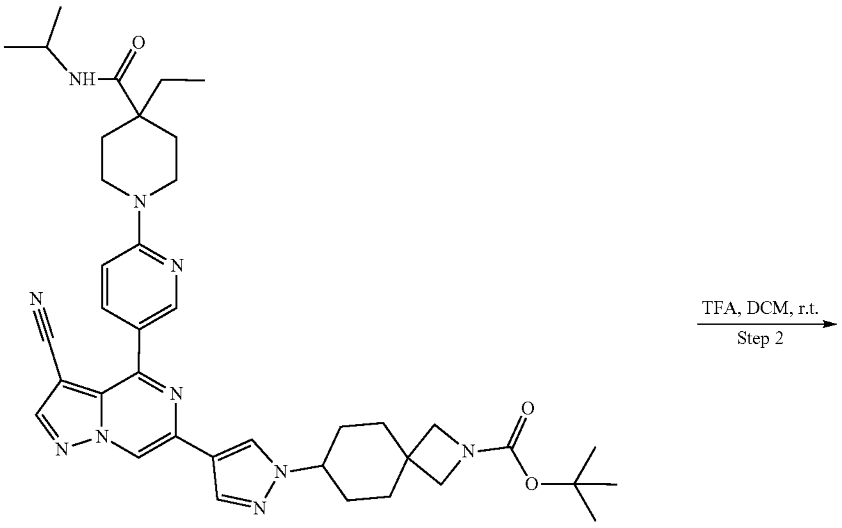
3
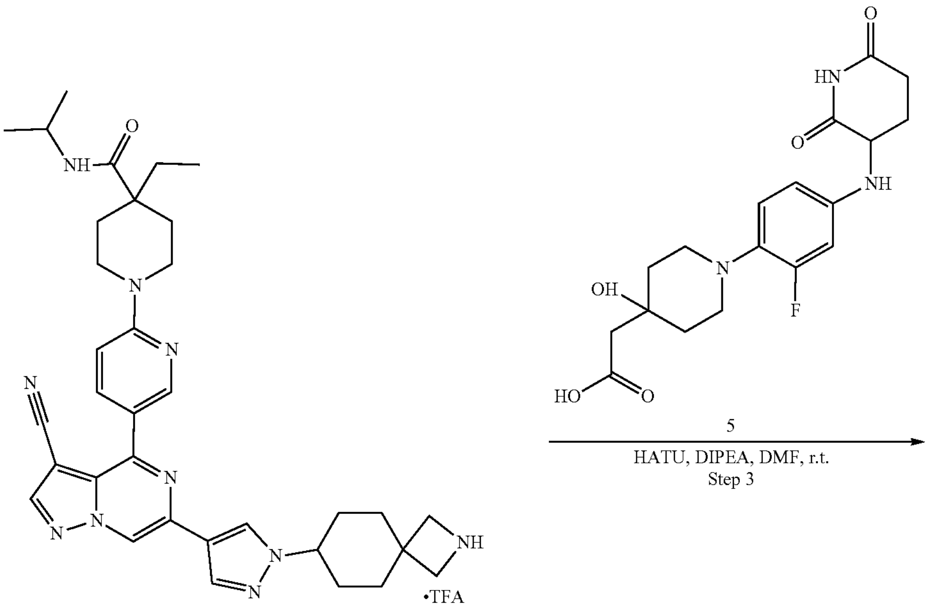
5
4

-continued

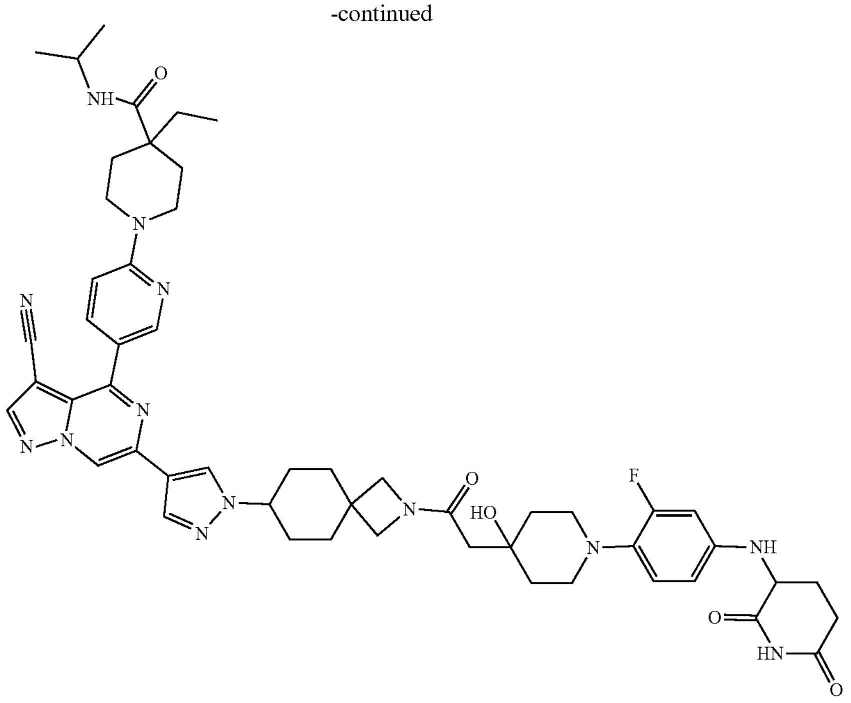

Compound 182

Step 1. Into a 30 mL microwave vial containing a well-stirred solution of 1-[5-(6-chloro-3-cyano-pyrazolo[1,5-a]pyrazin-4-yl)-2-pyridyl]-4-ethyl-N-isopropyl-piperidine-4-carboxamide (1, 180 mg, 0.398 mmol) in anhydrous 1,4-dioxane (10 mL) and Water (2 mL) were added tert-butyl 7-[4-(4,4,5,5-tetramethyl-1,3,2-dioxaborolan-2-yl)pyrazol-1-yl]-2-azaspiro[3.5]nonane-2-carboxylate (2, 249.33 mg, 0.597 mmol; commercially available) and potassium phosphate tribasic anhydrous (253.62 mg, 1.19 mmol) at ambient temperature under nitrogen atmosphere and the resulting mixture was degassed by bubbling nitrogen gas into the reaction mixture for 10 minutes. Subsequently, XPhos Pd G2 (31.34 mg, 0.039 mmol) was added to the reaction mixture and the reaction mixture was heated to 100° C. for 1 h in microwave. Progress of the reaction was monitored by UPLC. The reaction mixture was allowed to room temperature and quenched with water (20 mL) and the product was extracted with EtOAc (3×20 mL). The organic phases were combined, dried (anhydrous $Na_2SO_4$), filtered and the filtrate was concentrated under reduced pressure to get the crude residue. Crude residue was purified by silica-gel (230-400 mesh) column with 0-100% EtOAc/pet ether while desired compound was eluting at 80-85% of the mobile phase to afford tert-butyl 7-(4-(3-cyano-4-(6-(4-ethyl-4-(isopropylcarbamoyl)piperidin-1-yl)pyridin-3-yl)pyrazolo[1,5-a]pyrazin-6-yl)-1H-pyrazol-1-yl)-2-azaspiro[3.5]nonane-2-carboxylate (3, 70 mg, 0.061 mmol, 15% yield) as an off-white solid. LCMS ($ES^+$): m/z 707.4 $[M+H]^+$.

Step 2: Into a 25 mL single-necked round-bottomed flask containing a well-stirred solution of tert-butyl 7-(4-(3-cyano-4-(6-(4-ethyl-4-(isopropylcarbamoyl)piperidin-1-yl)pyridin-3-yl)pyrazolo[1,5-a]pyrazin-6-yl)-1H-pyrazol-1-yl)-2-azaspiro[3.5]nonane-2-carboxylate (3, 65 mg, 0.091 mmol) in anhydrous DCM (2 mL) was added Trifluoroacetic acid (740 mg, 6.49 mmol, 0.5 mL) at 0° C. under nitrogen atmosphere. The resulting mixture was stirred at ambient temperature for 2 h and the progress of the reaction was monitored by UPLC. After completion of the reaction, excess solvent was removed from the reaction mixture under reduced pressure to get the crude mass. The crude product was purified by reverse phase column chromatography [Reveleris C18 (30 g); Mobile phase: 0.1% TFA in MQ-water, B: Acetonitrile; Flow rate: 35 mL/minutes] while desired compound was eluting at 35-40% of B to afford 1-(5-(6-(1-(2-azaspiro[3.5]nonan-7-yl)-1H-pyrazol-4-yl)-3-cyanopyrazolo[1,5-a]pyrazin-4-yl)pyridin-2-yl)-4-ethyl-N-isopropylpiperidine-4-carboxamide trifluoroacetate (4, 60 mg, 0.071 mmol, 78% yield) as an off-white solid. LCMS ($ES^+$): m/z 607.5 $[M+H]^+$.

Step 3: Into a 5 mL single-necked round-bottomed flask containing a well-stirred solution of 2-[1-[4-[(2,6-dioxo-3-piperidyl)amino]-2-fluoro-phenyl]-4-hydroxy-4-piperidyl] acetic acid hydrochloride (5, 17.37 mg, 0.0417 mmol) in anhydrous DMF (1 mL) were added DIPEA (21.52 mg, 0.166 mmol, 29.00 µL) and HATU (21.39 mg, 0.0499 mmol) at ambient temperature under nitrogen atmosphere. The reaction mixture was stirred at ambient temperature for 15 minutes. Later, 1-(5-(6-(1-(2-azaspiro[3.5]nonan-7-yl)-1H-pyrazol-4-yl)-3-cyanopyrazolo[1,5-a]pyrazin-4-yl)pyridin-2-yl)-4-ethyl-N-isopropylpiperidine-4-carboxamide trifluoroacetate (4, 30 mg, 0.416 mmol) was added to the reaction mixture at ambient temperature. The resulting mixture was stirred at ambient temperature for 2 h. After complete consumption of the starting material as indicated by UPLC, water (5 mL) was added to the reaction mixture and extracted with DCM (3×5 mL). The organic phases were combined, dried (anhydrous $Na_2SO_4$), filtered and the filtrate was concentrated under reduced pressure to get the crude residue. NBK0618-31 reaction mixture was combined to the above crude residue and repurified by Prep HPLC following a method: Column: Xbridge C-8 20×150 m, 5 micron; Mobile Phase A: 0.1% Ammonium Acetate in milli-Q water; Mobile phase B: Acetonitrile to obtain 1-(5-(3-Cyano-6-(1-(2-(2-(1-(4-((2,6-dioxopiperidin-3-yl)amino)-2-fluorophenyl)-4-hydroxypiperidin-4-yl)acetyl)-2-azaspiro[3.5]nonan-7-yl)-1H-pyrazol-4-yl)pyrazolo[1,5-a]pyrazin-4-yl)pyridin-2-yl)-4-ethyl-N-isopropylpiperidine-4-carboxamide (Compound 182, 7.8 mg, 0.0078 mmol, 19% yield) as a yellow solid. $^1$H NMR (400 MHz, DMSO-$d_6$). δ 10.80 (s, 1H), 9.28 (s, 1H), 8.83 (s, 1H), 8.67 (d, J=2.8 Hz, 1H), 8.46 (d, J=4 Hz, 1H), 8.16 (s, 1H), 8.05 (dd, J=8.8, 2.4 Hz, 1H), 7.42 (d, J=8 Hz, 1H), 7.02 (d, J=8.8 Hz, 1H), 6.88 (m, 1H), 6.54-6.45 (m, 2H), 5.80-5.79 (m, 1H), 4.56-4.10 (m, 5H), 4.14-3.99 (m, 2H), 3.88 (s, 1H), 3.68 (s, 1H), 3.58 (s, 1H), 3.15 (t, J=22.4 Hz, 2H), 3.09-2.86 (m, 3H), 2.70-2.68 (m, 1H), 2.55 (m, 2H), 2.34-2.34 (bs, 2H), 2.27-2.16 (m, 2H), 2.19-2.00 (m, 5H), 1.84-1.80 (m, 5H), 1.70-1.67 (m, 4H), 1.77 (m, 2H), 1.36 (m, 2H), 1.09 (d, J=6.8 Hz, 6H) and 0.76 (t, J=7.6 Hz, 3H). LCMS (ES$^+$): m/z 968.0 [M+H]$^+$.

Example 190: Synthesis of 1-[5-[3-cyano-6-[1-[2-[2-[1-[4-[(2,6-dioxo-3-piperidyl)amino]-2-fluoro-phenyl]-4-hydroxy-4-piperidyl]acetyl]-2-azaspiro[3.3]heptan-6-yl]pyrazol-4-yl]pyrazolo[1,5-a]pyrazin-4-yl]-2-pyridyl]-4-ethyl-N-isopropyl-piperidine-4-carboxamide (Compound 183)

Compound 183 was Prepared Substantially Following the Synthesis of Compound 182

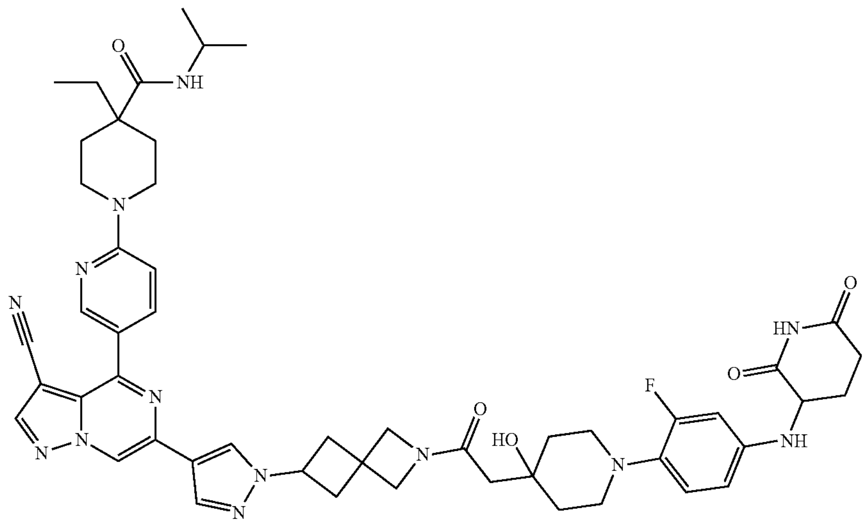 [SMILES: CCC1(C(=O)NC(C)C)CCN(c2ccc(-c3nc(-c4cnn(C5CC6(C5)CN(C(=O)CC5(O)CCN(c7ccc(NC8CCC(=O)NC8=O)cc7F)CC5)C6)c4)cn4ncc(C#N)c34)cn2)CC1]

[1,1'-Bis(diphenylphosphino)ferrocene]dichloropalladium(II) (1:1) (0.1 equiv.) and sodium bicarbonate (2 equiv.) were used in step 1 instead of XPhos Pd G2 and potassium phosphate tribasic anhydrous.

LCMS (ES$^+$): m/z 940.08 [M+H]$^+$.

$^1$H NMR (400 MHz, DMSO-$d_6$). δ 10.77 (s, 1H), 9.30 (s, 1H), 8.83 (s, 1H), 8.67 (d, J=2.4 Hz, 1H), 8.49 (d, J=4.8 Hz, 1H), 8.20 (s, 1H), 8.04 (dd, J=9.2, 2.4 Hz, 1H), 7.40 (d, J=8 Hz, 1H), 7.00 (d, J=8.8 Hz, 1H), 6.85 (t, J=8.8 Hz, 1H), 6.50 (d, J=15.2 Hz, 1H), 6.42 (d, J=8.8 Hz, 1H), 5.77 (d, J=7.6 Hz, 1H), 4.91-4.82 (m, 1H), 4.76 (s, 1H), 4.35-4.12 (m, 5H), 4.05-3.91 (m, 3H), 3.19-3.10 (m, 2H), 2.95-2.65 (m, 10H), 2.28-2.05 (m, 5H), 1.93-1.72 (m, 3H), 1.69-1.60 (m, 2H), 1.55-1.45 (m, 2H), 1.40-1.30 (m, 2H), 1.10 (d, J=6.8 Hz, 6H) and 0.76 (t, J=7.2 Hz, 3H).

Example 191: Synthesis of 1-[5-[3-cyano-6-[1-[1-[2-[1-[4-[(2,6-dioxo-3-piperidyl)amino]-2-fluoro-phenyl]-4-hydroxy-4-piperidyl]acetyl]azetidin-3-yl]pyrazol-4-yl]pyrazolo[1,5-a]pyrazin-4-yl]-2-pyridyl]-4-ethyl-N-isopropyl-piperidine-4-carboxamide (Compound 184)

Compound 184 was Prepared Substantially Following the Synthesis of Compound 182

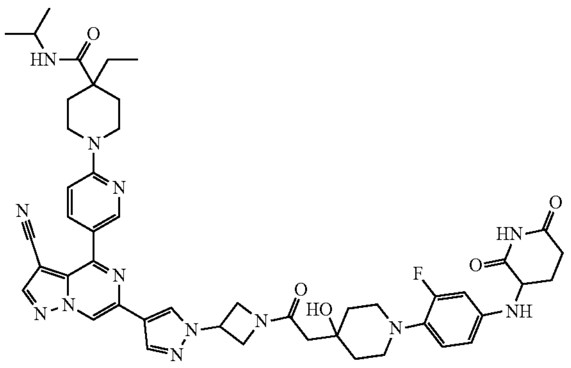 [SMILES: CCC1(C(=O)NC(C)C)CCN(c2ccc(-c3nc(-c4cnn(C5CN(C(=O)CC6(O)CCN(c7ccc(NC8CCC(=O)NC8=O)cc7F)CC6)C5)c4)cn4ncc(C#N)c34)cn2)CC1]

[1,1'-Bis(diphenylphosphino)ferrocene]dichloropalladium(II) (1:1) (0.1 equiv.) and cesium carbonate (2 equiv.) were used in step 1 instead of XPhos Pd G2 and potassium phosphate tribasic anhydrous.

LCMS (ES$^+$): m/z 900.0 [M+H]$^+$.

$^1$H NMR (400 MHz, DMSO-$d_6$). δ 10.79 (s, 1H), 9.33 (s, 1H), 8.84 (d, J=1.6 Hz, 1H), 8.67 (d, J=2 Hz, 1H), 8.61 (s, 1H), 8.31 (s, 1H), 8.05 (dd, J=9.2, 2.4 Hz, 1H), 7.42 (d, J=8 Hz, 1H), 7.00 (d, J=8.8 Hz, 1H), 6.86 (t, J=9.2 Hz, 1H), 6.50 (d, J=14.8 Hz, 1H), 6.42 (d, J=8.8 Hz, 1H), 5.78 (d, J=7.6 Hz, 1H), 5.40-5.31 (m, 1H), 4.76 (s, 1H), 4.72-4.61 (m, 1H), 4.55 (m, 1H), 4.45-4.35 (m, 1H), 4.31-4.12 (m, 4H), 4.08-3.96 (m, 1H), 3.16-3.05 (m, 2H), 2.95-2.81 (m, 4H), 2.78-2.70 (m, 1H), 2.38-2.25 (m, 2H), 2.21-2.11 (m, 4H), 1.93-

1.76 (m, 3H), 1.69-1.60 (m, 2H), 1.58-1.45 (m, 2H), 1.40-1.30 (m, 2H), 1.10 (d, J=6.8 Hz, 6H) and 0.76 (t, J=7.2 Hz, 3H).
Example 192: Synthesis of 6-(1-(1-(2-(1-(4-((2,6-dioxopiperidin-3-yl)amino)-2-fluorophenyl)piperidin-4-yl)acetyl)piperidin-4-yl)-1H-pyrazol-4-yl)-4-(6-(4-(3-methylbutanoyl)piperazin-1-yl)pyridin-3-yl)pyrazolo[1,5-a]pyrazine-3-carbonitrile (Compound 185)
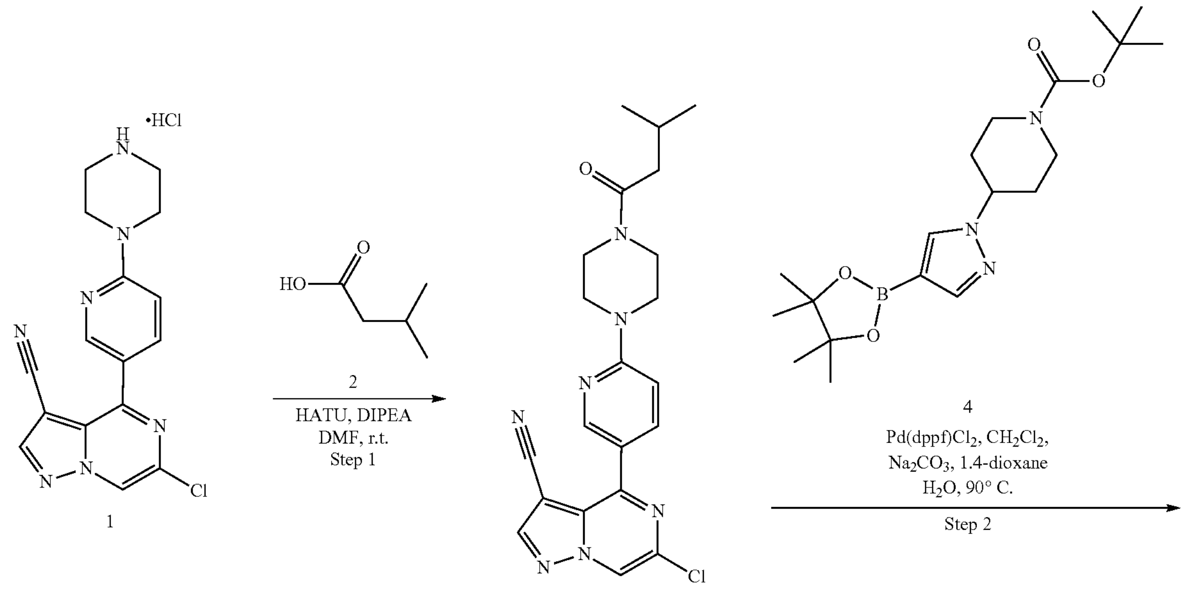
1
3
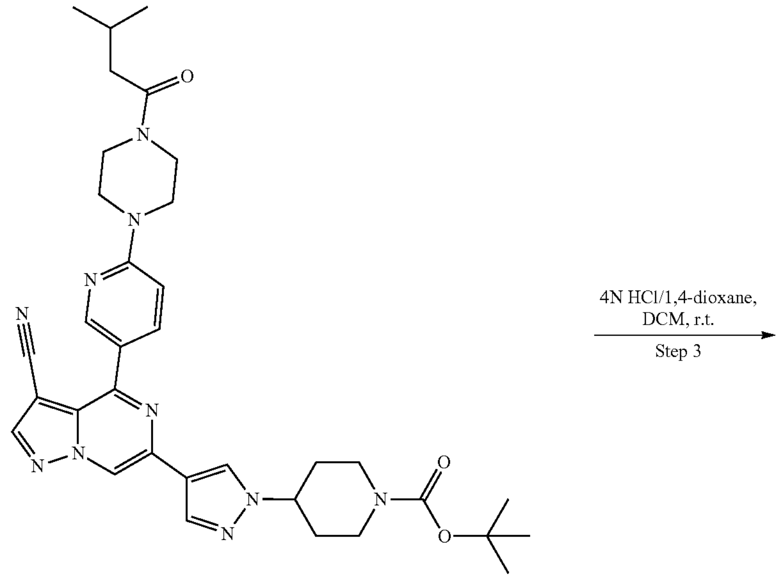
5

-continued

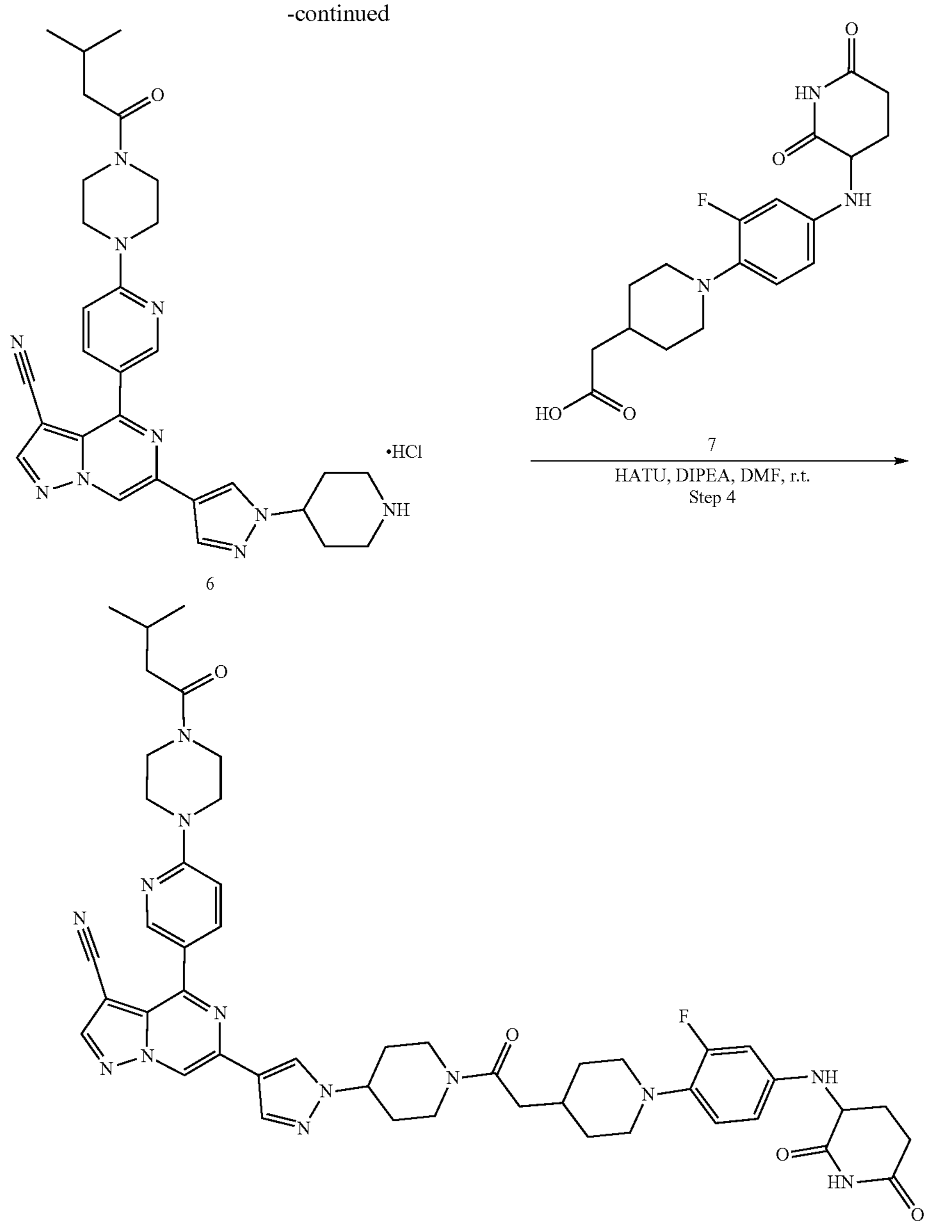

Compound 185

Step 1: Into a 50 mL single-necked round-bottomed flask containing a well-stirred solution of 6-chloro-4-(6-piperazin-1-yl-3-pyridyl)pyrazolo[1,5-a]pyrazine-3-carbonitrile hydrochloride (1, 100.03 mg, 0.294 mmol) and 3-methylbutanoic acid (2, 45.1 mg, 0.441 mmol) in anhydrous DMF (3 mL) were added DIPEA (190.23 mg, 1.47 mmol, 0.256 mL) and HATU (167.90 mg, 0.441 mmol) at ambient temperature under nitrogen atmosphere. The resulting mixture was stirred at ambient temperature for 16 h. The progress of the reaction was monitored by LCMS. After completion of the reaction, the reaction mixture was diluted with water (200 mL) and extracted with EtOAc (2×200 mL). Combined organic phase was was dried (anhydrous $Na_2SO_4$), filtered and the filtrate was concentrated under reduced pressure to get a crude mass. The crude mass was purified by flash silica-gel (230-400 mesh) column with 0-100% EtOAc/pet ether while desired compound eluting at 60-80% of the mobile phase to get 6-chloro-4-[6-[4-(3-methylbutanoyl)piperazin-1-yl]-3-pyridyl]pyrazolo[1,5-a]pyrazine-3-carbonitrile (3, 100 mg, 0.202 mmol, 69% yield) as a colorless gummy oil. LCMS ($ES^+$): m/z 424.2 $[M+H]^+$.

Step 2: A well-stirred solution of 6-chloro-4-[6-[4-(3-methylbutanoyl)piperazin-1-yl]-3-pyridyl]pyrazolo[1,5-a]pyrazine-3-carbonitrile (3, 100 mg, 0.235 mmol) and tert-butyl 4-[4-(4,4,5,5-tetramethyl-1,3,2-dioxaborolan-2-yl)pyrazol-1-yl]piperidine-1-carboxylate (4, 115.71 mg, 0.306 mmol) in 1,4-dioxane (15 mL) at ambient temperature under nitrogen atmosphere was taken in 50 mL sealed-tube reactor and the resulting mixture was degassed by bubbling nitrogen gas into the reaction mixture for 10 minutes. Subsequently, $Pd(dppf)Cl_2 \cdot CH_2Cl_2$ (0.02 mmol) followed by Sodium carbonate (75.01 mg, 0.707 mmol) in water (5 mL) were added. Resulting mixture was stirred at 90° C. for 4 h. After 4 h, reaction mixture was allowed to cool to room temperature.

Progress of the reaction was monitored by TLC. After completion, reaction mixture was filtered through a pad of Celite and Celite bed was washed with EtOAc to afford a crude mass. The crude mixture was purified by flash silica-gel (230-400 mesh) column with 0-100% EtOAc/pet ether and 0-5% MeOH/DCM as eluents while desired product was eluting at 80-85% of the mobile phase followed by 8-10% MeOH/DCM to obtain tert-butyl 4-[4-[3-cyano-4-[6-[4-(3-methylbutanoyl)piperazin-1-yl]-3-pyridyl]pyrazolo[1,5-a]pyrazin-6-yl]pyrazol-1-yl]piperidine-1-carboxylate (5, 127 mg, 0.129 mmol, 55% yield) as a green-colored solid. LCMS ($ES^+$): m/z 639.2 $[M+H]^+$.

Step 3: Into a 50 mL single-necked round-bottomed flask containing a well-stirred solution of tert-butyl 4-[4-[3-cyano-4-[6-[4-(3-methylbutanoyl)piperazin-1-yl]-3-pyridyl]pyrazolo[1,5-a]pyrazin-6-yl]pyrazol-1-yl]piperidine-1-carboxylate (5, 127 mg, 0.198 mmol) in anhydrous DCM (4 mL) was added 4N HCl in 1,4-dioxane (55.82 mg, 1.53 mmol) on cooling in ice under nitrogen atmosphere. The resulting mixture was stirred at ambient temperature for 3 h under nitrogen atmosphere. After completion of the reaction, excess solvent was removed from the reaction mixture under reduced pressure to get a crude mass. The crude product was washed with ether (50 mL) to get the 4-[6-[4-(3-methylbutanoyl)piperazin-1-yl]-3-pyridyl]-6-[1-(4-piperidyl)pyrazol-4-yl]pyrazolo[1,5-a]pyrazine-3-carbonitrile hydrochloride (6, 48 mg, 0.0492 mmol, 25% yield) as an off-white solid. LCMS ($ES^+$): m/z 539.2 $[M+H]^+$.

Step 4: Into a 50 mL single-necked round-bottomed flask containing a well-stirred solution of 4-[6-[4-(3-methylbutanoyl)piperazin-1-yl]-3-pyridyl]-6-[1-(4-piperidyl)pyrazol-4-yl]pyrazolo[1,5-a]pyrazine-3-carbonitrile hydrochloride (6, 48 mg, 0.083 mmol) and 2-[1-[4-[(2,6-dioxo-3-piperidyl)amino]-2-fluoro-phenyl]-4-piperidyl]acetic acid hydrochloride (7, 33.37 mg, 0.0834 mmol) in anhydrous DMF (2 mL) were added DIPEA (32.36 mg, 0.250 mmol, 0.043 mL) and HATU (47.60 mg, 0.125 mmol) under nitrogen atmosphere. The reaction mixture was stirred at ambient temperature for 2 h. Reaction was monitored by TLC and UPLC. After completion of the reaction, water (5 mL) was added to the reaction mixture, solid precipitated out was filtered and dried to afford a crude solid. The crude solid compound was purified by reverse phase column chromatography by using C18 Redisep Rf Gold (30 g HP C18); Mobile phase: 0.1% ammonium acetate in MQ-water; B: Acetonitrile; Flow rate: 15 mL/minutes to afford 6-(1-(1-(2-(1-(4-((2,6-dioxopiperidin-3-yl)amino)-2-fluorophenyl)piperidin-4-yl)acetyl)piperidin-4-yl)-1H-pyrazol-4-yl)-4-(6-(4-(3-methylbutanoyl)piperazin-1-yl)pyridin-3-yl)pyrazolo[1,5-a]pyrazine-3-carbonitrile (Compound 185, 6 mg, 0.007 mmol, 8% yield) as an off-white solid. $^1H$ NMR (400 MHz, DMSO-$d_6$). δ 10.77 (s, 1H), 9.31 (s, 1H), 8.84 (s, 1H), 8.72 (d, J=2.4 Hz, 1H), 8.51 (s, 1H), 8.18 (s, 1H), 8.12 (dd, J=8.8, 2.4 Hz, 1H), 7.04 (d, J=9.2 Hz, 1H), 6.85 (t, J=9.6 Hz, 1H), 6.50 (dd, J=15.2, 2.4 Hz, 1H), 6.42 (dd, J=8.8, 2.4 Hz, 1H), 5.78 (d, J=7.6 Hz, 1H), 4.52 (m, 2H), 4.25 (m, 1H), 4.05 (m, 1H), 3.72 (m, 2H), 3.65-3.63 (m, 7H), 3.20 (m, 2H), 3.11 (d, J=10.8 Hz, 2H), 2.68-2.67 (m, 1H), 2.60 (m, 3H), 2.35-2.33 (m, 3H), 2.27 (d, J=6.8 Hz, 2H), 2.10 (m, 5H), 1.95-1.75 (m, 3H), 1.35 (m, 2H) and 0.94 (d, J=6.4 Hz, 6H). LCMS ($ES^+$): m/z 884.4 $[M+H]^+$.

Example 193: Synthesis of 1-[5-[3-cyano-6-[1-[3-[[4-[4-[[(3S)-2,6-dioxo-3-piperidyl]amino]-2-fluoro-phenyl]piperazin-1-yl]methyl]-3-fluoro-cyclobutyl]pyrazol-4-yl]pyrazolo[1,5-a]pyrazin-4-yl]-2-pyridyl]-N-cyclobutyl-4-ethyl-piperidine-4-carboxamide (Compound 186)

1-[5-[3-cyano-6-[1-[3-[[4-[4-[[(3S)-2,6-dioxo-3-piperidyl]amino]-2-fluoro-phenyl]piperazin-1-yl]methyl]-3-fluoro-cyclobutyl]pyrazol-4-yl]pyrazolo[1,5-a]pyrazin-4-yl]-2-pyridyl]-N-cyclobutyl-4-ethyl-piperidine-4-carboxamide (Compound 187)

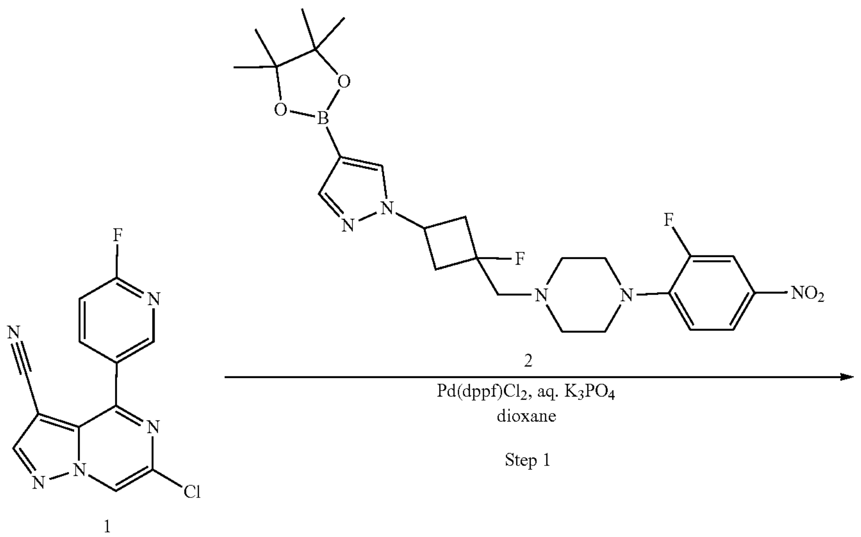

-continued
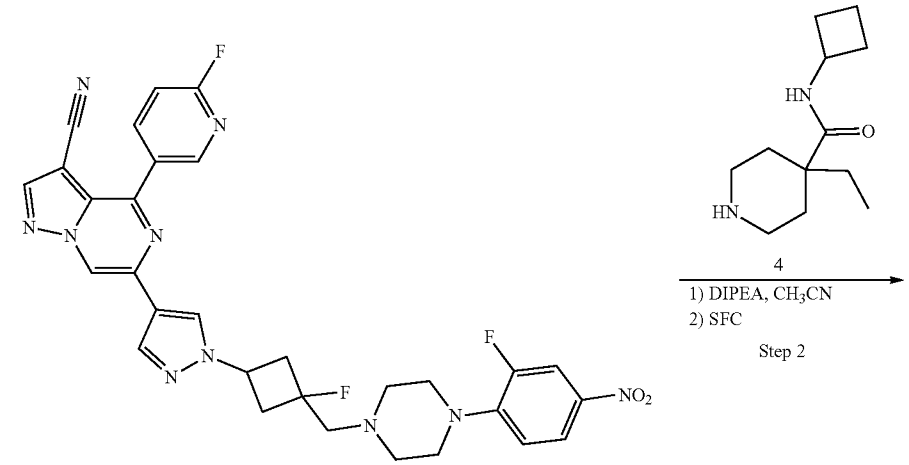
3
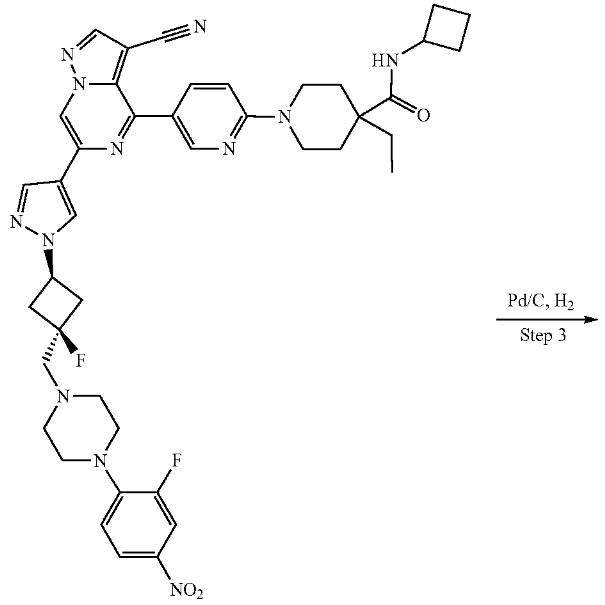
5

-continued

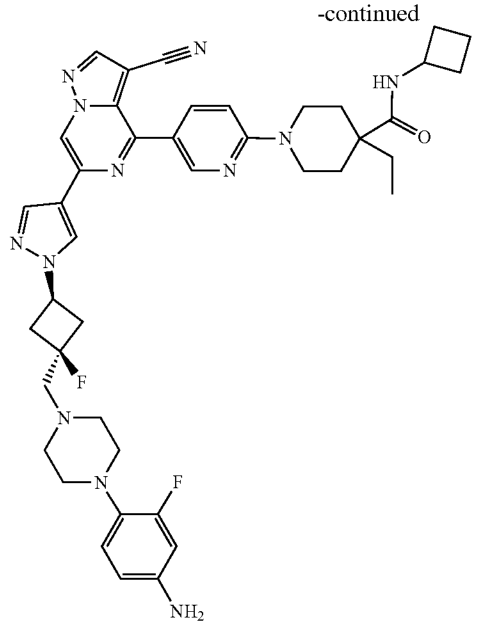

6

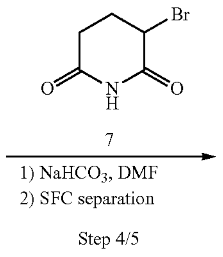

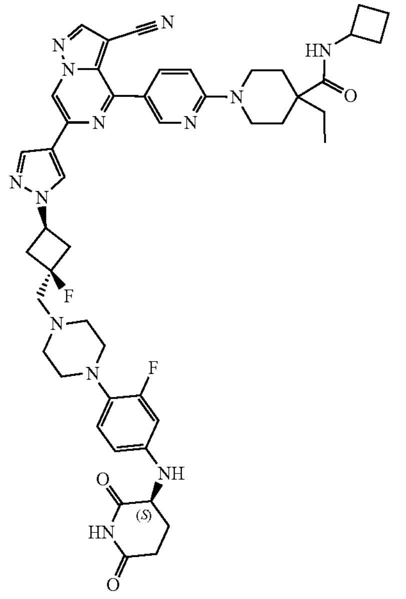

Compound 186

+

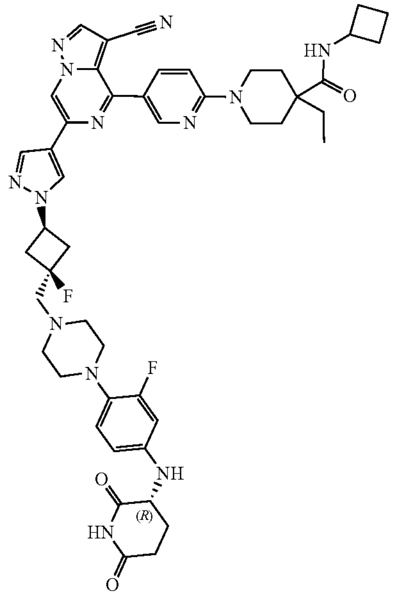

Compound 187

Step 1: To a solution of 1-((1-fluoro-3-(4-(4,4,5,5-tetramethyl-1,3,2-dioxaborolan-2-yl)-1H-pyrazol-1-yl)cyclobutyl)methyl)-4-(2-fluoro-4-nitrophenyl)piperazine (2, 800 mg, 1.59 mmol), 6-chloro-4-(6-fluoropyridin-3-yl)pyrazolo[1,5-a]pyrazine-3-carbonitrile (1, 434.93 mg, 1.59 mmol) and Pd(dppf)$Cl_2$*DCM (259.59 mg, 317.87 μmol) in dioxane (20 mL) was added aq.$K_3PO_4$ (2 M, 2.40 mL) at 10° C. under $N_2$, then the mixture was stirred at 70° C. for 12 hrs under $N_2$, The reaction mixture was diluted with EtOAc (100 mL). The organic layer was washed with brine (10 mL), dried over $Na_2SO_4$, filtered and concentrated. The crude product was purified by column chromatography (PE:EA=10:1-1:1-0:1 SiO2) to get the product. 6-(1-(3-fluoro-3-((4-(2-fluoro-4-nitrophenyl)piperazin-1-yl)methyl)cyclobutyl)-1H-pyrazol-4-yl)-4-(6-fluoropyridin-3-yl)pyrazolo[1,5-a]pyrazine-3-carbonitrile (3, 550 mg, 796.48 μmol, 50% yield) was obtained as yellow solid. LCMS ($ES^+$): m/z 615.1 $[M+H]^+$ Step 2: A solution of 6-[1-[3-fluoro-3-[[4-(2-fluoro-4-nitro-phenyl)piperazin-1-yl]methyl]cyclobutyl]pyrazol-4-yl]-4-(6-fluoro-3-pyridyl)pyrazolo[1,5-a]pyrazine-3-carbonitrile (3, 550 mg, 894.92 μmol) N-cyclobutyl-4-ethyl-piperidine-4-carboxamide (4, 225.86 mg, 1.07 mmol) and DIPEA (346.99 mg, 2.68 mmol, 467.64 μL) in $CH_3CN$ (3 mL) was stirred at 90° C. for 2 hour. After completion of the starting material, EtOAc (50 mL) was added to the reaction mixture. The reaction mixture was filtered and the combined filtrate was washed with brine (5 mL), dried (anhydrous $Na_2SO_4$), filtered and the filtrate was concentrated under reduced pressure to get the product. The residue was purified by column chromatography (SiO2, PE:EA=1:0-1:1-0:1) to get the product. Then the product was purified by prep-SFC (Sample preparation: DAICEL CHIRALCEL OJ (250 mm*30 mm, 10 um); Add MeOH: DCM (4:1) 30 mL into sample Instrument: Thar 80 SFC Mobile Phase: 60% MeOH (0.1% $NH_3H_2O$) in Supercritical CO2 Flow Rate: 70 g/min Cycle Time: 4.4 min, total time: 60 min Single injection volume: 2.5 ml Back Pressure: 100 bar to keep the CO2 in Supercritical flow) to get the product. The compound 1-[5-[3-cyano-6-[1-[3-fluoro-3-[[4-(2-fluoro-4-nitro-phenyl)piperazin-1-yl]methyl]cyclobutyl]pyrazol-4-yl]pyrazolo[1,5-a]pyrazin-4-yl]-2-pyridyl]-N-cyclobutyl-4-ethyl-piperidine-4-carboxamide (5, 350 mg, 430.49 μmol, 48% yield, 95% ee) was obtained as a yellow solid. LCMS ($ES^+$): m/z 805.3 $[M+H]^+$ Step 3: To a solution of 1-[5-[3-cyano-6-[1-[3-fluoro-3-[[4-(2-fluoro-4-nitro-phenyl)piperazin-1-yl]methyl]cyclobutyl]pyrazol-4-yl]pyrazolo[1,5-a]pyrazin-4-yl]-2-pyridyl]-N-cyclobutyl-4-ethyl-piperidine-4-carboxamide (5, 350.00 mg, 434.84 μmol) in DMF (20 mL) was added 10 wt. % Pd/C (55 mg, 45.29 μmol) under $N_2$. The suspension was degassed under vacuum and purged with $H_2$ several times. The mixture was stirred under $H_2$ (15 PSI) at 20° C. for 1 hr. The reaction mixture was filtered and the filtrated was concentrated to get the product. The product used to next step directly. The 1-[5-[6-[1-[3-[[4-(4-amino-2-fluoro-phenyl)piperazin-1-yl]methyl]-3-fluoro-cyclobutyl]pyrazol-4-yl]-3-cyano-pyrazolo[1,5-a]pyrazin-4-yl]-2-pyridyl]-N-cyclobutyl-4-ethyl-piperidine-4-carboxamide (6, 310 mg, 400.05 μmol, 92% yield) was obtained as yellow solid. LCMS ($ES^+$): m/z 775.1 $[M+H]^+$ Step 4: To a solution of 1-[5-[6-[1-[3-[[4-(4-amino-2-fluoro-phenyl)piperazin-1-yl]methyl]-3-fluoro-cyclobutyl]pyrazol-4-yl]-3-cyano-pyrazolo[1,5-a]pyrazin-4-yl]-2-pyridyl]-N-cyclobutyl-4-ethyl-piperidine-4-carboxamide (6, 310 mg, 400.05 μmol) and 3-bromopiperidine-2,6-dione (7, 115.22 mg, 600.07 μmol) in $CH_3CN$ (1 mL) was added $NaHCO_3$ (100.82 mg, 1.20 mmol) under $N_2$. The mixture was stirred at 90° C. for 12 hrs. The reaction mixture was filtered and the filtrated was concentrated to get the product. The crude product was purified by prep-HPLC ((Waters Xbridge C18 150*50 mm*10 um; water (10 mM NH4HCO3)-ACN; B %: 40%~70%, 100% B Hold Time (2 min), FlowRate (60 ml/min)) to get the product. The 1-[5-[3-cyano-6-[1-[3-[[4-[4-[(2,6-dioxo-3-piperidyl)amino]-2-fluoro-phenyl]piperazin-1-yl]methyl]-3-fluoro-cyclobutyl]pyrazol-4-yl]pyrazolo[1,5-a]pyrazin-4-yl]-2-pyridyl]-N-cyclobutyl-4-ethyl-piperidine-4-carboxamide (190 mg, 208.01 μmol, 52% yield) was obtained as yellow solid. LCMS ($ES^+$): m/z 886.2 $[M+H]^+$ Step 5: The crude product was purified by prep-SFC (Sample preparation: DAICEL CHIRALPAK AS (250 mm*30 mm, 10 um); Add ACN and CH2CL2 60 ml into sample Instrument: Waters 80Q Mobile Phase: 65% IPA+ACN (0.1% $NH_3H_2O$) in Supercritical CO2 Flow Rate: 80 g/min Cycle Time: 3 min; total time: 60 min Single injection volume: 3.0 ml Back Pressure: 100 bar to keep the CO2 in Supercritical flow) to get the products.

1-[5-[3-cyano-6-[1-[3-[[4-[4-[[(3S)-2,6-dioxo-3-piperidyl]amino]-2-fluoro-phenyl]piperazin-1-yl]methyl]-3-fluoro-cyclobutyl]pyrazol-4-yl]pyrazolo[1,5-a]pyrazin-4-yl]-2-pyridyl]-N-cyclobutyl-4-ethyl-piperidine-4-carboxamide (Compound 186, 38.21 mg, 40.59 μmol, 19% yield, formic acid salt) was obtained as yellow solid. LCMS ($ES^+$): m/z 886.1 $[M+H]^+$. $^1H$ NMR (400 MHz, DMSO-$d_6$) δ=10.89-10.66 (m, 1H), 9.31 (s, 1H), 8.83 (s, 1H), 8.72-8.63 (m, 1H), 8.56 (s, 1H), 8.24 (s, 1H), 8.08-8.00 (m, 1H), 7.84-7.72 (m, 1H), 7.06-6.95 (m, 1H), 6.91-6.79 (m, 1H), 6.60-6.48 (m, 1H), 6.47-6.38 (m, 1H), 5.81 (br d, J=7.6 Hz, 1H), 4.73-4.60 (m, 1H), 4.35-4.22 (m, 2H), 4.19-4.09 (m, 2H), 3.11 (t, J=11.2 Hz, 2H), 2.92-2.86 (m, 5H), 2.85-2.81 (m, 1H), 2.81-2.76 (m, 2H), 2.74-2.66 (m, 5H), 2.61-2.55 (m, 1H), 2.21-2.07 (m, 5H), 2.03-1.93 (m, 2H), 1.91-1.79 (m, 1H), 1.70-1.57 (m, 2H), 1.55-1.46 (m, 2H), 1.43-1.28 (m, 2H), 0.74 (t, J=7.2 Hz, 3H)

1-[5-[3-cyano-6-[1-[3-[[4-[4-[[(3R)-2,6-dioxo-3-piperidyl]amino]-2-fluoro-phenyl]piperazin-1-yl]methyl]-3-fluoro-cyclobutyl]pyrazol-4-yl]pyrazolo[1,5-a]pyrazin-4-yl]-2-pyridyl]-N-cyclobutyl-4-ethyl-piperidine-4-carboxamide (Compound 187, 33.33 mg, 35.40 μmol, 17% yield, formic acid salt) was obtained as yellow solid. LCMS ($ES^+$): m/z 886.1 [M+H]. $^1H$ NMR (400 MHz, DMSO-$d_6$) δ=10.83-10.74 (m, 1H), 9.32 (s, 1H), 8.83 (s, 1H), 8.67 (d, J=2.0 Hz, 1H), 8.53 (s, 1H), 8.24 (s, 1H), 8.07-8.01 (m, 1H), 7.79 (br d, J=7.2 Hz, 1H), 7.00 (d, J=8.8 Hz, 1H), 6.89-6.81 (m, 1H), 6.54-6.50 (m, 1H), 6.46-6.39 (m, 1H), 5.85-5.78 (m, 1H), 4.72-4.62 (m, 1H), 4.35-4.21 (m, 2H), 4.19-4.08 (m, 2H), 3.11 (t, J=11.3 Hz, 2H), 2.92-2.86 (m, 5H), 2.85-2.81 (m, 1H), 2.80-2.76 (m, 2H), 2.74-2.66 (m, 5H), 2.62-2.55 (m, 1H), 2.22-2.05 (m, 5H), 2.04-1.92 (m, 2H), 1.91-1.79 (m, 1H), 1.70-1.58 (m, 2H), 1.51 (q, J=7.2 Hz, 2H), 1.41-1.31 (m, 2H), 0.74 (br t, J=7.2 Hz, 3H)

Example 194: Synthesis of 1-[5-[3-cyano-6-[1-[3-[[4-[4-[[(3S)-2,6-dioxo-3-piperidyl]amino]-2-fluoro-phenyl]piperazin-1-yl]methyl]cyclobutyl]pyrazol-4-yl]pyrazolo[1,5-a]pyrazin-4-yl]-2-pyridyl]-N-cyclobutyl-4-ethyl-piperidine-4-carboxamide (Compound 188)

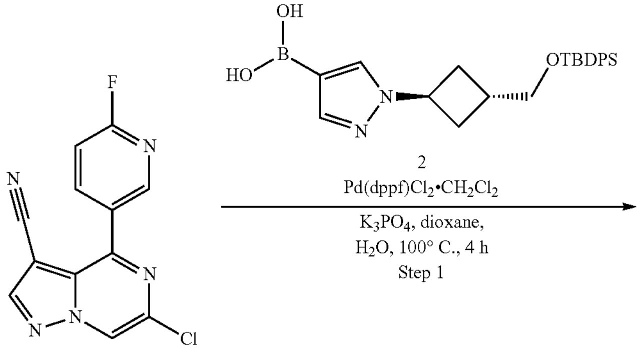

1

-continued
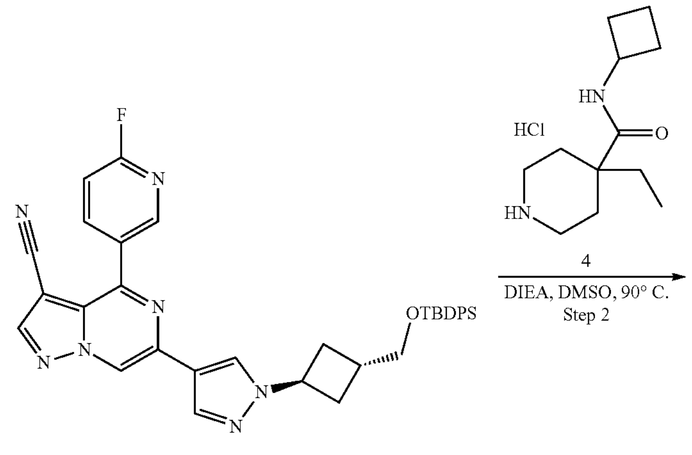
3
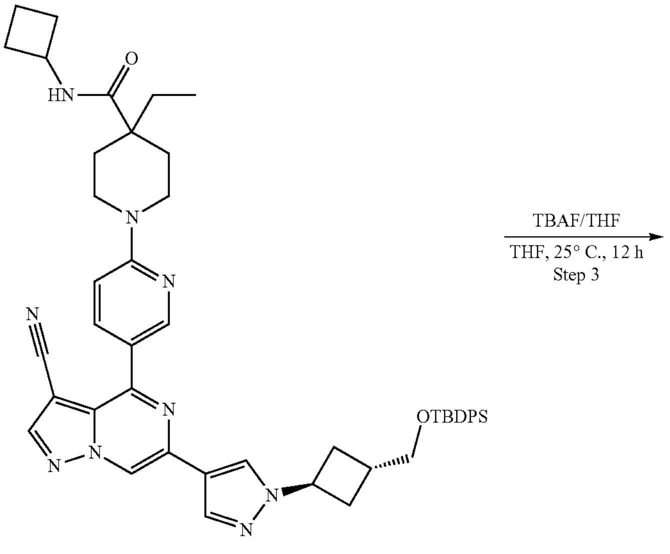
5
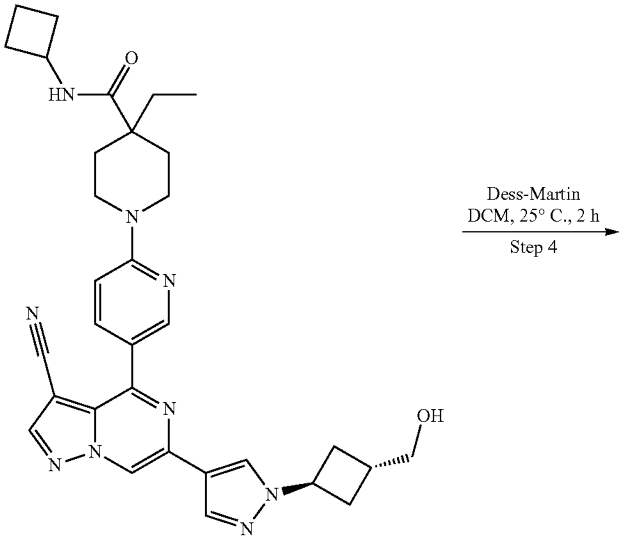
6

-continued

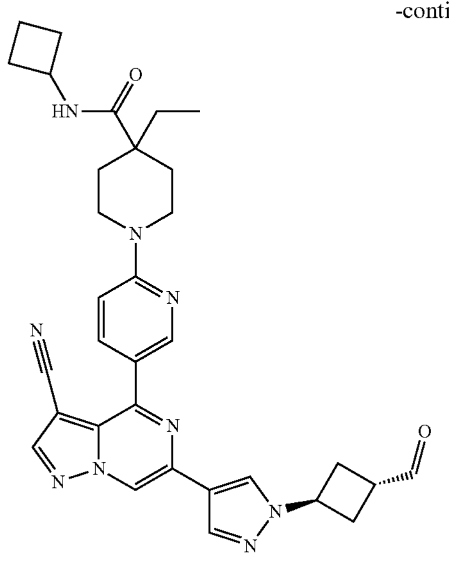

7

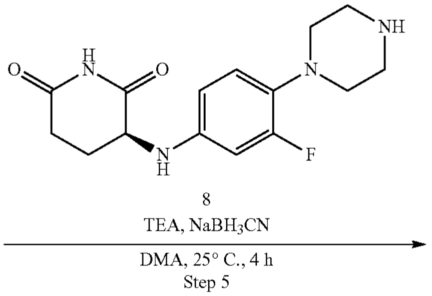

8

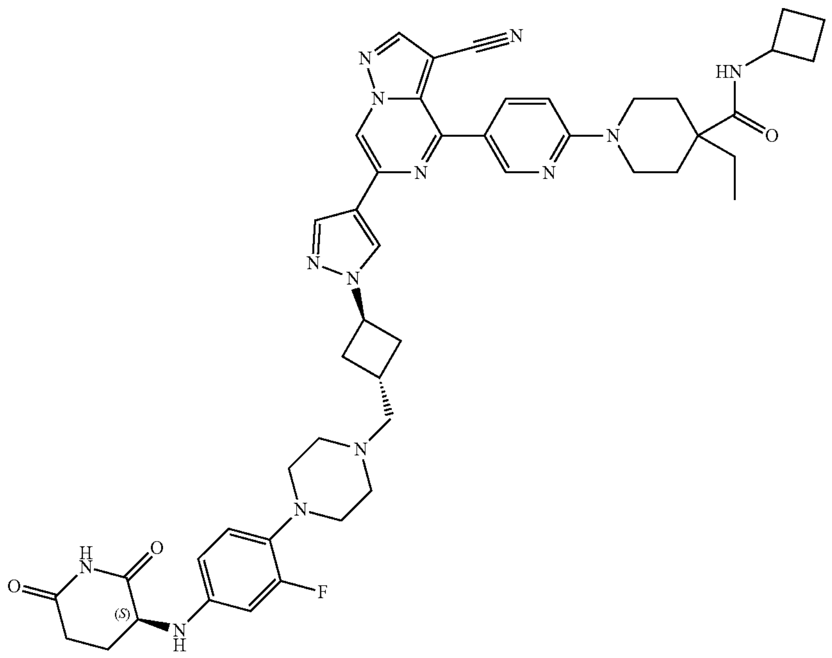

Compound 188

Step 1: To a solution of tert-butyl-diphenyl-[[3-[4-(4,4,5,5-tetramethyl-1,3,2-dioxaborolan-2-yl)pyrazol-1-yl]cyclobutyl]methoxy]silane(2, 1 g, 1.94 mmol) and 6-chloro-4-(6-fluoro-3-pyridyl)pyrazolo[1,5-a]pyrazine-3-carbonitrile (1, 423.81 mg, 1.55 mmol) in $H_2O$ (3.5 mL) and Dioxane (20 mL) was added $K_3PO_4$ (1.23 g, 5.81 mmol) and Pd(dppf)$Cl_2$ (141.65 mg, 193.59 µmol). The mixture was stirred at 100° C. for 4 h under $N_2$. The reaction mixture was poured into water (100 ml), extracted with Ethyl acetate (80 mL*2). The combined organic layers were washed with brine (30 mL*2), dried over $Na_2SO_4$, filtered and concentrated. The residue was purified by column chromatography ($SiO_2$, Petroleum ether/Ethyl acetate=20/1 to 3/1) to afford 6-[1-[3-[[tert-butyl(diphenyl)silyl]oxymethyl]cyclobutyl]pyrazol-4-yl]-4-(6-fluoro-3-pyridyl)pyrazolo[1,5-a]pyrazine-3-carbonitrile (3, 760 mg, 1.21 mmol, 63% yield) as a white solid. LCMS ($ES^+$): m/z 628.5 $[M+H]^+$ Step 2: To a solution of 6-[1-[3-[[tert-butyl(diphenyl)silyl]oxymethyl] cyclobutyl]pyrazol-4-yl]-4-(6-fluoro-3-pyridyl)pyrazolo[1,5-a]pyrazine-3-carbonitrile (3, 740 mg, 1.18 mmol) and N-cyclobutyl-4-ethyl-piperidine-4-carboxamide (4, 290.89 mg, 1.18 mmol) in DMSO (12 mL) was added DIPEA (457.04 mg, 3.54 mmol, 615.95 µL). The mixture was stirred at 90° C. for 4 h. The reaction mixture was poured into water (50 ml), extracted with Ethyl acetate (50 mL*2). The combined organic layers were washed with brine (20 mL*2), dried over $Na_2SO_4$, filtered and concentrated to afford 1-[5-[6-[1-[3-[[tert-butyl(diphenyl)silyl] oxymethyl]cyclobutyl] pyrazol-4-yl]-3-cyano-pyrazolo[1,5-a] pyrazin-4-yl]-2-pyridyl]-N-cyclobutyl-4-ethylpiperidine-4-carboxamide (5, 770 mg, 941.21 μmol, 80% yield) as yellow oil. LCMS ($ES^+$): m/z 818.7 $[M+H]^+$ Step 3: To a solution of 1-[5-[6-[1-[3-[[tert-butyl(diphenyl)silyl]oxymethyl]cyclobutyl]pyrazol-4-yl]-3-cyano-pyrazolo[1,5-a]pyrazin-4-yl]-2-pyridyl]-N-cyclobutyl-4-ethyl-piperidine-4-carboxamide (5, 770 mg, 941.21 μmol) in THF (8 mL) was added TBAF/THF (1 M, 941.21 μL). The mixture was stirred at 25° C. for 12 h. The reaction mixture was concentrated under reduced pressure. The residue was purified by column chromatography ($SiO_2$, Petroleum ether/Ethyl acetate=5/1 to 0/1) to afford 1-[5-[3-cyano-6-[1-[3-(hydroxymethyl)cyclobutyl] pyrazol-4-yl]pyrazolo[1,5-a]pyrazin-4-yl]-2-pyridyl]-N-cyclobutyl-4-ethyl-piperidine-4-carboxamide (6, 520 mg, 897.03 μmol, 95% yield) as a yellow solid. $^1H$ NMR (400 MHz, $CDCl_3$) δ=8.81 (d, J=2.0 Hz, 1H), 8.54 (s, 1H), 8.35 (s, 1H), 8.14-7.98 (m, 3H), 7.77-7.67 (m, 1H), 6.80 (d, J=8.8 Hz, 1H), 5.72 (d, J=6.8 Hz, 1H), 4.96 (t, J=7.6 Hz, 1H), 4.54-4.40 (m, 1H), 4.21-4.08 (m, 2H), 3.83 (s, 2H), 3.43-3.31 (m, 2H), 2.87-2.72 (m, 2H), 2.72-2.60 (m, 1H), 2.55-2.36 (m, 4H), 2.18-2.09 (m, 2H), 1.92-1.84 (m, 2H), 1.82-1.72 (m, 2H), 1.53 (s, 2H), 1.08-1.02 (m, 2H), 0.88 (t, J=7.2 Hz, 3H)

Step 4: To a solution of 1-[5-[3-cyano-6-[1-[3-(hydroxymethyl)cyclobutyl]pyrazol-4-yl]pyrazolo[1,5-a]pyrazin-4-yl]-2-pyridyl]-N-cyclobutyl-4-ethyl-piperidine-4-carboxamide (6, 200 mg, 345.01 μmol) in DCM (3 mL) was added Dess-Martin Periodinane (190.23 mg, 448.51 μmol). The mixture was stirred at 25° C. for 2 h. The reaction mixture was concentrated under reduced pressure to remove solvent. The residue was purified by column chromatography ($SiO_2$, Petroleum ether/Ethyl acetate=5/1 to 0/1) to afford 1-[5-[3-cyano-6-[1-(3-formylcyclobutyl) pyrazol-4-yl]pyrazolo[1,5-a]pyrazin-4-yl]-2-pyridyl]-N-cyclobutyl-4-ethyl-piperidine-4-carboxamide (7, 160 mg, 276.97 μmol, 80% yield) as a yellow solid. $^1H$ NMR (400 MHz, $CDCl_3$) δ=9.99 (s, 1H), 8.81 (d, J=2.0 Hz, 1H), 8.54 (s, 1H), 8.36 (s, 1H), 8.30 (t, J=8.4 Hz, 1H), 8.07-8.02 (m, 3H), 6.80 (d, J=9.2 Hz, 1H), 5.73 (d, J=7.2 Hz, 1H), 4.88 (t, J=8.0 Hz, 1H), 4.53-4.40 (m, 1H), 4.13 (d, J=13.6 Hz, 2H), 3.40-3.33 (m, 2H), 2.92-2.89 (m, 2H), 2.47-2.36 (m, 2H), 1.93-1.84 (m, 2H), 1.81-1.75 (m, 2H), 1.67-1.51 (m, 7H), 1.27 (s, 2H), 0.89 (t, J=7.6 Hz, 3H).

Step 5: To a solution of 1-[5-[3-cyano-6-[1-(3-formylcyclobutyl)pyrazol-4-yl]pyrazolo[1,5-a]pyrazin-4-yl]-2-pyridyl]-N-cyclobutyl-4-ethyl-piperidine-4-carboxamide (7, 160 mg, 276.97 μmol) and (3S)-3-(3-fluoro-4-piperazin-1-yl-anilino)piperidine-2,6-dione (8, 94.94 mg, 276.97 μmol) in DMA (3 mL) was added TEA (168.16 mg, 1.66 mmol, 231.63 μL) and $NaBH_3CN$ (52.35 mg, 830.91 μmol). The mixture was stirred at 25° C. for 4 h. The residue was purified by prep-HPLC (FA condition). column: Phenomenex luna C18 150*25 mm*10 um; mobile phase: water (0.225% FA)-ACN; B %: 13%-43%, 2 min to afford 1-[5-[3-cyano-6-[1-[3-[[4-[4-[[(3S)-2,6-dioxo-3-piperidyl]amino]-2-fluoro-phenyl]piperazin-1-yl]methyl]cyclobutyl]pyrazol-4-yl]pyrazolo[1,5-a]pyrazin-4-yl]-2-pyridyl]-N-cyclobutyl-4-ethyl-piperidine-4-carboxamide (Compound 188, 40.61 mg, 43.05 μmol, 16% yield) as a yellow solid. LCMS ($ES^+$): m/z 868.7 $[M+H]^+$. $^1H$ NMR (400 MHz, DMSO-$d_6$) δ=10.78 (s, 1H), 9.32-9.28 (m, 1H), 8.83 (s, 1H), 8.67 (d, J=2.8 Hz, 1H), 8.52 (s, 1H), 8.30 (s, 1H), 8.21-8.16 (m, 1H), 8.07-8.02 (m, 1H), 7.81 (d, J=7.2 Hz, 1H), 7.00 (d, J=9.2 Hz, 1H), 6.83 (t, J=9.2 Hz, 1H), 6.56-6.47 (m, 1H), 6.45-6.40 (m, 1H), 5.82 (d, J=7.6 Hz, 1H), 4.87-4.72 (m, 1H), 4.35-4.23 (m, 2H), 4.14 (d, J=13.2 Hz, 2H), 3.59 (s, 1H), 3.11 (t, J=11.2 Hz, 2H), 2.86 (s, 4H), 2.79-2.68 (m, 2H), 2.65-2.56 (m, 4H), 2.38-2.29 (m, 2H), 2.25-2.04 (m, 8H), 2.03-1.94 (m, 2H), 1.91-1.79 (m, 1H), 1.69-1.60 (m, 2H), 1.55-1.47 (m, 2H), 1.41-1.32 (m, 2H), 0.73 (t, J=7.2 Hz, 3H).

Example 195: Synthesis of 1-[5-[3-cyano-6-[1-[4-[[4-[4-[[(3S)-2,6-dioxo-3-piperidyl]amino]-2-fluoro-phenyl]piperazin-1-yl]methyl]cyclohexyl]pyrazol-4-yl]pyrazolo[1,5-a]pyrazin-4-yl]-2-pyridyl]-N-cyclobutyl-4-ethyl-piperidine-4-carboxamide (Compound 189)

1-[5-[3-cyano-6-[1-[4-[[4-[4-[[(3R)-2,6-dioxo-3-piperidyl]amino]-2-fluoro-phenyl]piperazin-1-yl]methyl]cyclohexyl]pyrazol-4-yl]pyrazolo[1,5-a]pyrazin-4-yl]-2-pyridyl]-N-cyclobutyl-4-ethyl-piperidine-4-carboxamide (Compound 190)

(Configurations are arbitrarily assigned)

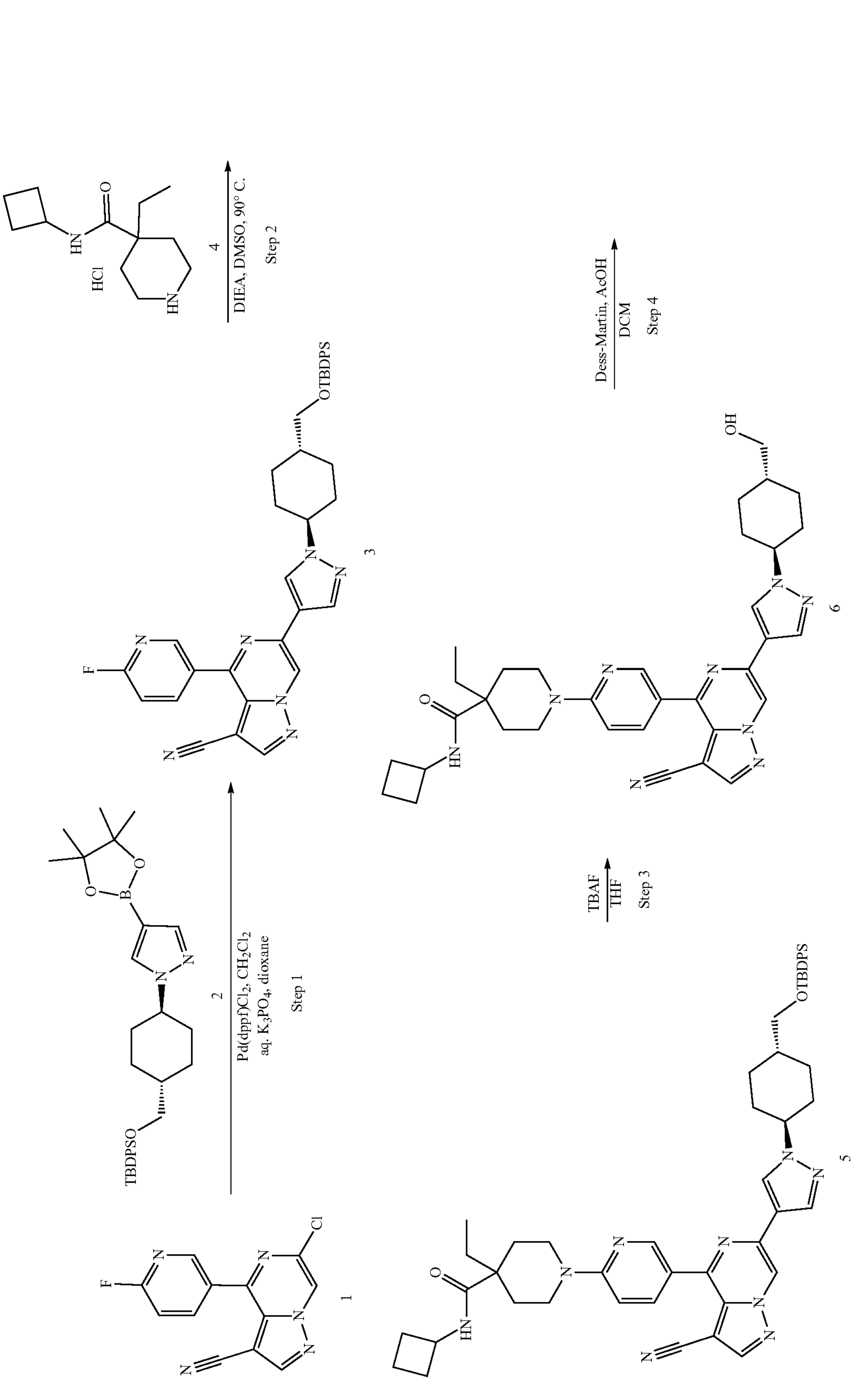
1
2
Pd(dppf)Cl2, CH2Cl2
aq. K3PO4, dioxane
Step 1
3
HCl
4
DIEA, DMSO, 90° C.
Step 2
5
TBAF
THF
Step 3
6
Dess-Martin, AcOH
DCM
Step 4

-continued
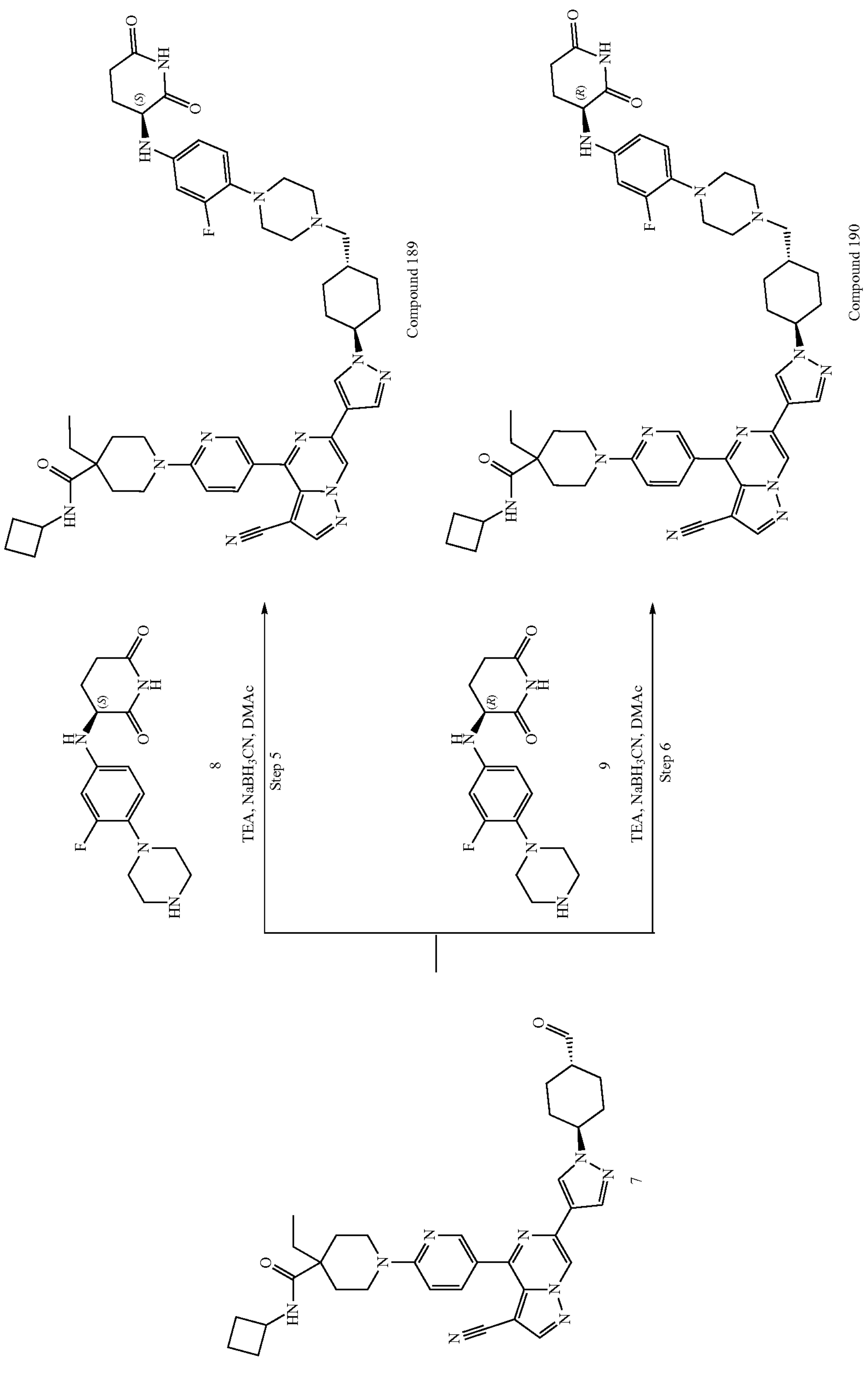
7
Compound 189
Compound 190

Step 1: To a solution of tert-butyl-diphenyl-[[4-[4-(4,4,5,5-tetramethyl-1,3,2-dioxaborolan-2-yl)pyrazol-1-yl]cyclohexyl]methoxy]silane (2, 230 mg, 422.32 μmol) and 6-chloro-4-(6-fluoro-3-pyridyl)pyrazolo[1,5-a]pyrazine-3-carbonitrile (1, 104.01 mg, 380.09 μmol) in dioxane (4 mL) and $H_2O$ (0.8 mL) was added potassium phosphate (268.93 mg, 1.27 mmol) and Pd(dppf)Cl2 (30.90 mg, 42.23 μmol). The mixture was stirred at 100° C. for 4 h under $N_2$. The reaction mixture was diluted with $H_2O$ (200 mL) and extracted with EtOAc (100 mL*2). The combined organic layers were washed with brine (200 mL*2), dried over $Na_2SO_4$, filtered and concentrated under reduced pressure. The residue was purified by flash silica gel chromatography (ISCO®; 12 g SepaFlash® Silica Flash Column, Eluent of 15-33% Ethyl acetate/Petroleum ether gradient @ 30 mL/min). 6-[1-[4-[[tert-butyl(diphenyl)silyl]oxymethyl]cyclohexyl]pyrazol-4-yl]-4-(6-fluoro-3-pyridyl)pyrazolo[1,5-a]pyrazine-3-carbonitrile (3, 140 mg, 213.47 μmol, 51% yield) was obtained as a yellow solid. LCMS ($ES^+$): m/z 656.3 $[M+H]^+$ Step 2: To a solution of 6-[1-[4-[[tert-butyl(diphenyl)silyl]oxymethyl]cyclohexyl]pyrazol-4-yl]-4-(6-fluoro-3-pyridyl)pyrazolo[1,5-a]pyrazine-3-carbonitrile (3, 120 mg, 182.97 μmol), N-cyclobutyl-4-ethyl-piperidine-4-carboxamide (4, 67.73 mg, 274.46 μmol, HCl salt) in DMSO (2 mL) was added Diisopropylethylamine (70.94 mg, 548.92 μmol, 95.61 μL). The mixture was stirred at 90° C. for 4 h. The reaction mixture was diluted with $H_2O$ (200 mL) and extracted with EtOAc (100 mL*2). The combined organic layers were washed with brine (200 mL*2), dried over $Na_2SO_4$, filtered and concentrated under reduced pressure. The crude product 1-[5-[6-[1-[4-[[tert-butyl(diphenyl)silyl]oxymethyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (5, 150 mg, 177.27 μmol, 97% yield) was used for the next step without further purification. LCMS ($ES^+$): m/z 846.6 $[M+H]^+$ Step 3: To a solution of 1-[5-[6-[1-[4-[[tert-butyl(diphenyl)silyl]oxymethyl]cyclohexyl]pyrazol-4-yl]-3-cyano-pyrazolo[1,5-a]pyrazin-4-yl]-2-pyridyl]-N-cyclobutyl-4-ethyl-piperidine-4-carboxamide (5, 150 mg, 177.27 μmol) in THF (2 mL) was added TBAF/THF (1 M, 177.27 μL). The mixture was stirred at 25° C. for 12 h. The reaction mixture was diluted with $H_2O$ (20 mL) and extracted with EtOAc (20 mL*2). The combined organic layers were washed with brine (20 mL*2), dried over $Na_2SO_4$, filtered and concentrated under reduced pressure. The residue was purified by flash silica gel chromatography (ISCO®; 12 g SepaFlash® Silica Flash Column, Eluent of 50-100% Ethyl acetate/Petroleum ether gradient @ 30 mL/min). 1-[5-[3-cyano-6-[1-[4-(hydroxymethyl)cyclohexyl]pyrazol-4-yl]pyrazolo[1,5-a]pyrazin-4-yl]-2-pyridyl]-N-cyclobutyl-4-ethyl-piperidine-4-carboxamide (6, 80 mg, 131.63 μmol, 74% yield) was obtained as a yellow solid. LCMS ($ES^+$): m/z 608.4 $[M+H]^+$ Step 4: To a solution of 1-[5-[3-cyano-6-[1-[4-(hydroxymethyl)cyclohexyl]pyrazol-4-yl]pyrazolo[1,5-a]pyrazin-4-yl]-2-pyridyl]-N-cyclobutyl-4-ethyl-piperidine-4-carboxamide (6, 30 mg, 49.36 μmol) in DCM (1 mL) was added Dess-Martin Periodinane (20.94 mg, 49.36 μmol) at 0° C. The mixture was stirred at 25° C. for 2 h. The reaction mixture was concentrated under reduced pressure to remove solvent. The residue was purified by flash silica gel chromatography (ISCO®; 12 g SepaFlash® Silica Flash Column, Eluent of 0-X % Ethyl acetate/Petroleum ether gradient @ 30 mL/min). 1-[5-[3-cyano-6-[1-(4-formylcyclohexyl)pyrazol-4-yl]pyrazolo[1,5-a]pyrazin-4-yl]-2-pyridyl]-N-cyclobutyl-4-ethyl-piperidine-4-carboxamide (7, total 100 mg) was obtained as a yellow solid. LCMS ($ES^+$): m/z 606.3 $[M+H]^+$ Step 5: To a solution of 1-[5-[3-cyano-6-[1-(4-formylcyclohexyl)pyrazol-4-yl]pyrazolo[1,5-a]pyrazin-4-yl]-2-pyridyl]-N-cyclobutyl-4-ethyl-piperidine-4-carboxamide (7, 80 mg, 132.07 μmol) and (3S)-3-(3-fluoro-4-piperazin-1-yl-anilino)piperidine-2,6-dione (8, 45.27 mg, 132.07 μmol, HCl salt) in DMF (1.5 mL) was added Triethylamine (80.19 mg, 792.43 μmol, 110.45 μL) and Sodium cyanoborohydride (24.90 mg, 396.22 μmol). The mixture was stirred at 25° C. for 2 h. The residue was purified by prep-HPLC (FA condition). 1-[5-[3-cyano-6-[1-[4-[[4-[4-[[(3S)-2,6-dioxo-3-piperidyl]amino]-2-fluoro-phenyl]piperazin-1-yl]methyl]cyclohexyl]pyrazol-4-yl]pyrazolo[1,5-a]pyrazin-4-yl]-2-pyridyl]-N-cyclobutyl-4-ethyl-piperidine-4-carboxamide (Compound 189, 29.36 mg, 29.92 μmol, 23% yield, formic acid) was obtained as a yellow solid. LCMS ($ES^+$): m/z 896.5 $[M+H]^+$. $^1H$ NMR (400 MHz, DMSO-$d_6$) δ=10.77 (s, 1H), 9.26 (s, 1H), 8.81 (s, 1H), 8.66 (s, 1H), 8.44 (s, 1H), 8.13 (s, 1H), 8.05-8.02 (m, 1H), 7.79-7.77 (m, 1H), 7.06-6.97 (d, 1H), 6.85-6.83 (m, 1H), 6.52-6.48 (m, 1H), 6.43-6.40 (m, 1H), 5.80-5.78 (m, 1H), 4.31-4.11 (m, 5H), 3.13-3.07 (m, 2H), 2.86 (s, 4H), 2.80-2.57 (m, 6H), 2.19-2.09 (m, 9H), 2.07-1.96 (m, 4H), 1.83-1.73 (m, 3H), 1.62-1.52 (m, 3H), 1.51-1.49 (m, 2H), 1.48-1.35 (m, 2H), 1.12-1.09 (m, 2H), 0.74-0.71 (m, 3H)

Step 6: To a solution of 1-[5-[3-cyano-6-[1-(4-formylcyclohexyl)pyrazol-4-yl]pyrazolo[1,5-a]pyrazin-4-yl]-2-pyridyl]-N-cyclobutyl-4-ethyl-piperidine-4-carboxamide (7, 100 mg, 165.09 μmol) and (3R)-3-(3-fluoro-4-piperazin-1-yl-anilino)piperidine-2,6-dione (9, 56.59 mg, 165.09 μmol, HCl salt) in DMF (2 mL) was added Triethylamine (100.23 mg, 990.54 μmol, 138.06 μL) and Sodium cyanoborohydride (31.12 mg, 495.27 μmol). The mixture was stirred at 25° C. for 2 h. The residue was purified by prep-HPLC (FA condition). 1-[5-[3-cyano-6-[1-[4-[[4-[4-[[(3R)-2,6-dioxo-3-piperidyl]amino]-2-fluoro-phenyl]piperazin-1-yl]methyl]cyclohexyl]pyrazol-4-yl]pyrazolo[1,5-a]pyrazin-4-yl]-2-pyridyl]-N-cyclobutyl-4-ethyl-piperidine-4-carboxamide (Compound 190, 33.08 mg, 35.11 μmol, 21% yield, formic acid) was obtained as a white solid. LCMS ($ES^+$): m/z 896.6 $[M+H]^+$. $^1H$ NMR (400 MHz, DMSO-$d_6$) δ=10.77 (s, 1H), 9.26 (s, 1H), 8.81 (s, 1H), 8.66 (s, 1H), 8.44 (s, 1H), 8.13 (s, 1H), 8.05-8.02 (m, 1H), 7.79-7.77 (m, 1H), 7.00-6.97 (d, 1H), 6.85-6.80 (m, 1H), 6.52-6.48 (m, 1H), 6.43-6.40 (m, 1H), 5.80-5.78 (m, 1H), 4.31-4.11 (m, 5H), 3.13-3.07 (m, 2H), 2.86 (s, 4H), 2.78-2.52 (m, 6H), 2.19-2.09 (m, 9H), 2.07-1.96 (m, 4H), 1.83-1.73 (m, 3H), 1.62-1.52 (m, 3H), 1.51-1.49 (m, 2H), 1.48-1.35 (m, 2H), 1.12-1.09 (m, 2H), 0.74-0.71 (m, 3H)

Example 196: Synthesis of 1-(5-(3-Cyano-6-(1-((S)-1'-(4-(((S)-2,6-dioxopiperidin-3-yl)amino)-2-fluorophenyl)-3',3'-difluoro-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (Compound 191)

1-(5-(3-cyano-6-(1-((R)-1'-(4-(((R)-2,6-dioxopiperidin-3-yl)amino)-2-fluorophenyl)-3',3'-difluoro-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (Compound 192)

(Configurations are arbitrarily assigned)

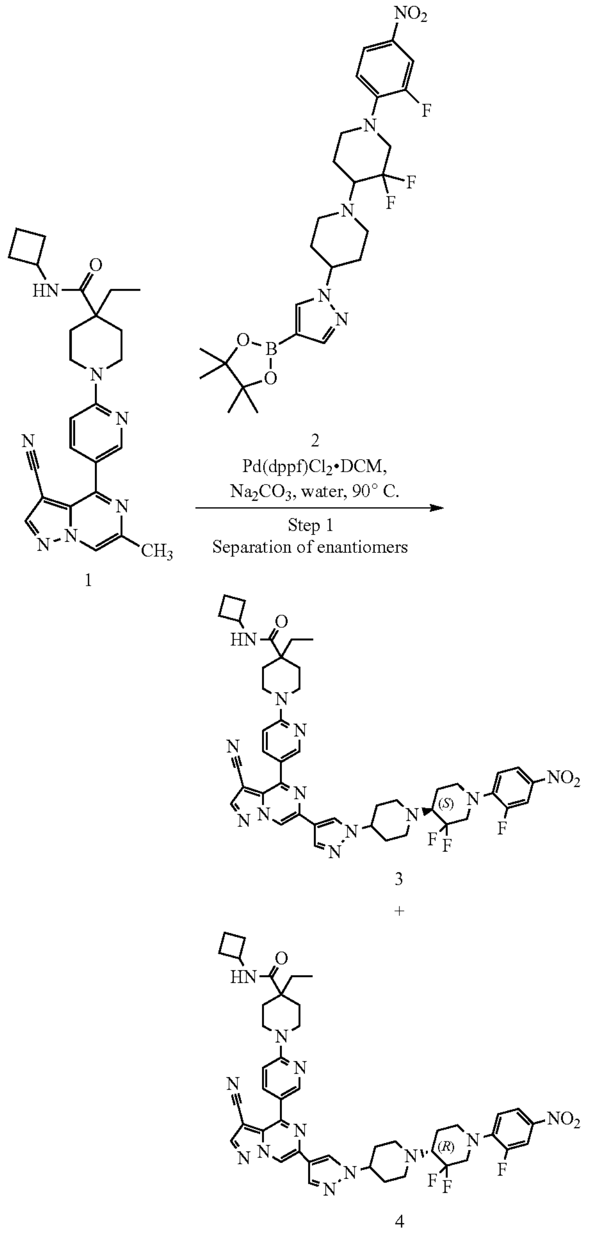

1 2 3 + 4

Step 1. Into a 25 mL three-necked round-bottomed flask, a well-stirred solution of 1-(5-(6-chloro-3-cyanopyrazolo[1,5-a]pyrazin-4-yl)pyridin-2-yl)-N-cyclobutyl-4-ethylpiperidine-4-carboxamide (1; 430.65 mg, 0.93 mmol) and 3',3'-difluoro-1'-(2-fluoro-4-nitrophenyl)-4-(4-(4,4,5,5-tetramethyl-1,3,2-dioxaborolan-2-yl)-1H-pyrazol-1-yl)-1,4'-bipiperidine (2, 496.93 mg, 0.93 mmol) in a mixture of 1,4-dioxane (7 mL) and water (3 mL) was degassed by bubbling nitrogen gas into the reaction mixture for 10 minutes. Subsequently, [1,1'-Bis(diphenylphosphino)ferrocene]dichloropalladium(II), complex with dichloromethane (151.60 mg, 0.19 mmol) and Sodium carbonate (295.14 mg, 2.78 mmol) were added to the reaction mixture and reaction mixture was heated at 90° C. After completion of the reaction as indicated by TLC (16 h later), the reaction mixture was cooled to room temperature and poured into water (10 mL) and extracted with EtOAc (2×25 mL). Organic phases were combined and washed with brine (25 mL). Combined organic phases were dried (anhydrous $Na_2SO_4$), filtered and the filtrate was concentrated under reduced pressure to get a crude residue, which was purified by flash silica-gel (230-400 mesh) column with 0-5% MeOH/DCM while desired compound eluting at 2-3% of the mobile phase to get mixture of isomers. Enantiomers were was separated by SFC chiral chromatography following the method: Chiracel OD-H; Co-solvent: 0.1% IPAm in IPA: ACN (1:1), injected volume: 15 μL; Flow rate: 5 mL/min; RT=3.37 minutes to afford (S)-1-(5-(3-cyano-6-(1-(3',3'-difluoro-1'-(2-fluoro-4-nitrophenyl)-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (3, Early eluting isomer 1, 130 mg, 0.15 mmol, 17% yield) as a yellow solid. LCMS ($ES^+$): m/z 837.3 $[M+H]^+$.

Isomer 2 was eluting at RT=6.27 minutes to afford (R)-1-(5-(3-cyano-6-(1-(3',3'-difluoro-1'-(2-fluoro-4-nitrophenyl)-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (4, Late eluting isomer 2, 150 mg, 0.162 mmol, 18% yield) as a yellow solid. LCMS ($ES^+$): m/z 837.3 $[M+H]^+$.

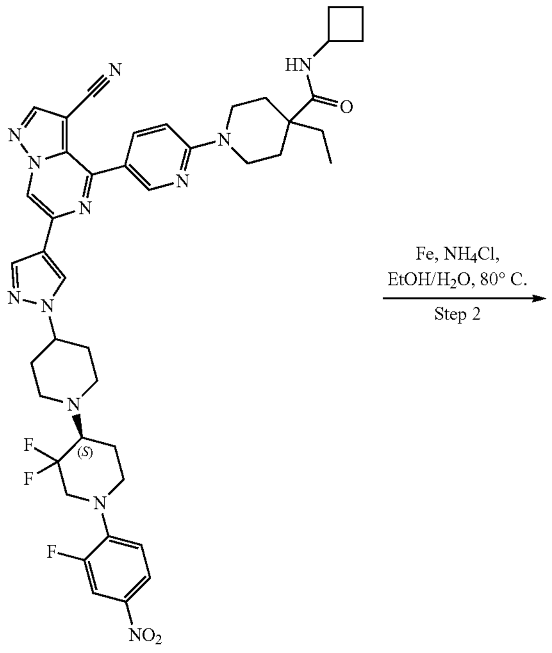

3

-continued
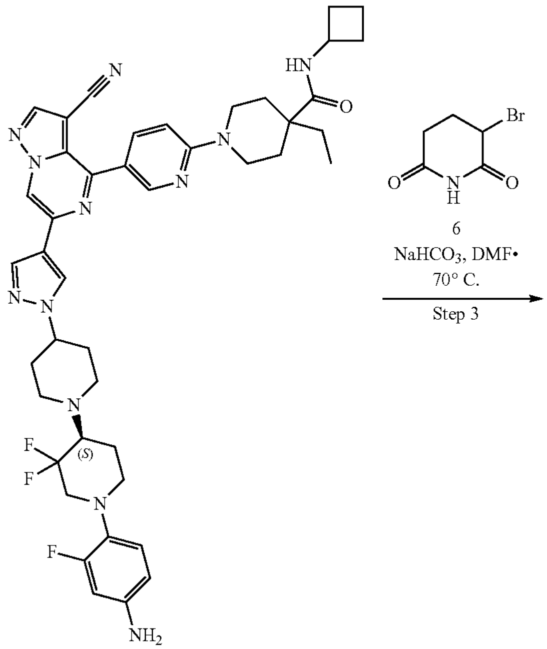
5
-continued
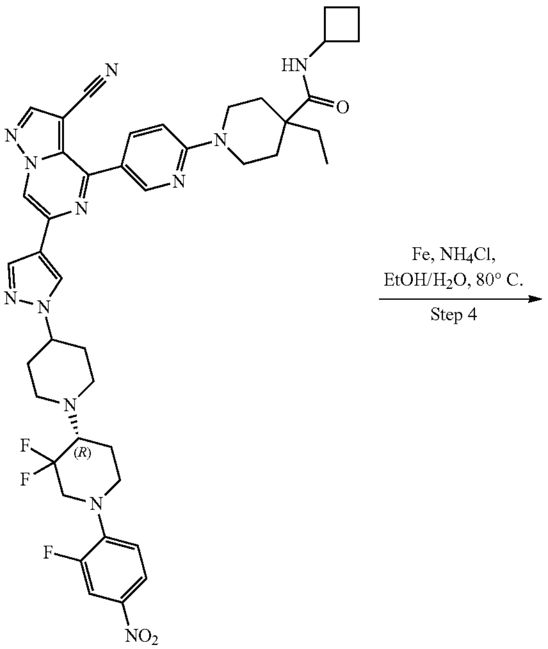
4
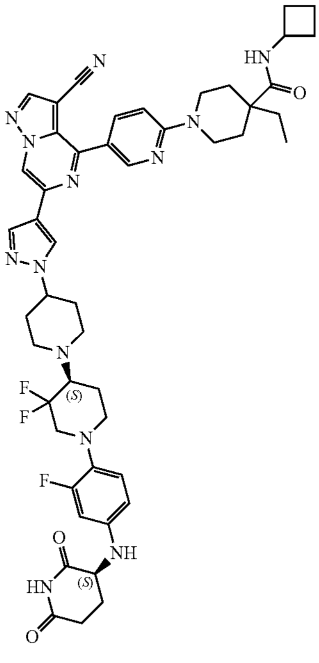
Compound 191
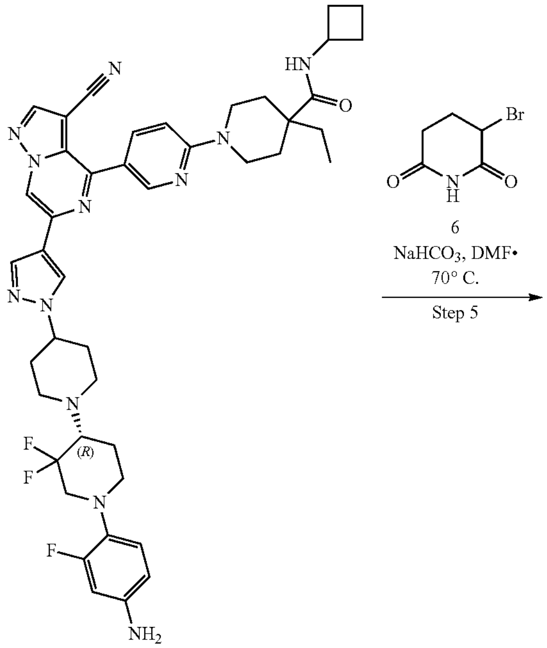
7

-continued

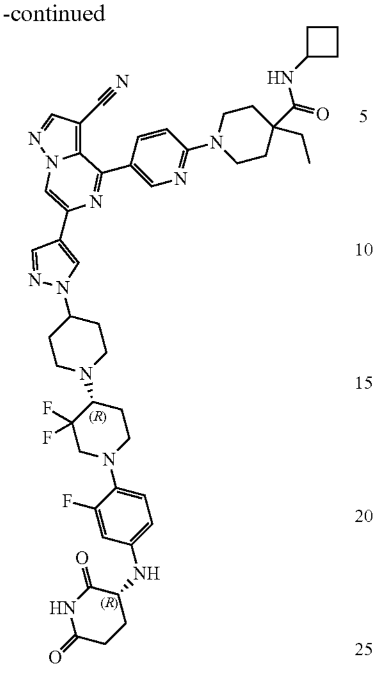

Compound 192

Step 2. Into a 100 mL single-necked round-bottomed flask containing a well-stirred suspension of (S)-1-(5-(3-cyano-6-(1-(3',3'-difluoro-1'-(2-fluoro-4-nitrophenyl)-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (3, Early eluting isomer 1, 130 mg, 0.16 mmol) in 1:1 THF/EtOH (10 mL) were added iron powder (43.37 mg, 0.78 mmol) and Ammonium Chloride (83.09 mg, 1.55 mmol) in water (2.5 mL) at ambient temperature. The resulting suspension was heated to 85° C. with stirring and progress of the reaction was monitored by UPLC-MS and found complete after 5 h. The reaction mixture was allowed to come to room temperature. The reaction mixture was filtered through a pad of Celite and Celite bed was washed with DCM (20 mL). Combined filtrate was diluted with water (10 mL) and the product was extracted with DCM (2×50 mL). The organic phases were combined, dried (anhydrous $Na_2SO_4$), filtered and the filtrate was concentrated under reduced pressure to get a crude mass. The crude mass was purified by flash silica-gel (230-400 mesh) with 0-10% MeOH/DCM while the desired product was eluting at 5% of the mobile phase to afford (S)-1-(5-(6-(1-(1'-(4-amino-2-fluorophenyl)-3',3'-difluoro-[1,4'-bipiperidin]-4-yl)-1H-pyrazol-4-yl)-3-cyanopyrazolo[1,5-a]pyrazin-4-yl)pyridin-2-yl)-N-cyclobutyl-4-ethylpiperidine-4-carboxamide (5, 110 mg, 0.12 mmol, 79% yield) as a yellow solid. LCMS ($ES^+$): m/z 807.3 $[M+H]^+$.

Step 3: Into a 10 mL sealed-tube containing a well-stirred solution of (S)-1-(5-(6-(1-(1'-(4-amino-2-fluorophenyl)-3',3'-difluoro-[1,4'-bipiperidin]-4-yl)-1H-pyrazol-4-yl)-3-cyanopyrazolo[1,5-a]pyrazin-4-yl)pyridin-2-yl)-N-cyclobutyl-4-ethylpiperidine-4-carboxamide (5, 100 mg, 0.12 mmol) and 3-bromopiperidine-2,6-dione (6, 237.95 mg, 1.24 mmol) in anhydrous DMF (4 mL) was added Sodium bicarbonate (31.23 mg, 0.37 mmol) at ambient temperature under nitrogen atmosphere. The reaction mixture was heated to 70° C. under closed condition for 24 h and the reaction mixture was cooled to ambient temperature. Additional amount of 3-bromopiperidine-2,6-dione (237.95 mg, 1.24 mmol) was added to the reaction mixture. The reaction mixture was heated to 70° C. for 24 h and the reaction mixture was cooled to ambient temperature. The progress of the reaction was monitored by LCMS. The reaction mixture was quenched with water (5 mL) and the product was extracted with DCM (2×30 mL). The organic phases were combined, dried (anhydrous $Na_2SO_4$), filtered and the filtrate was concentrated under reduced pressure to get a crude residue. The crude product was purified by reverse phase C18 Redisep Rf Gold (30 g HP C18) Mobile phase: 0.1% $NH_4OAc$ in MQ-water, B: Acetonitrile; Flow rate: 15 mL/minutes] while desired compound was eluting at 30% of B to afford 51 mg of product with 95.19% purity by LCMS. The enantiomers were separated by SFC chiral chromatography following the method: (R,R) Whelk 01; Co-solvent: 0.1% $^iPrNH_2$ in (1:1) IPA:ACN, Injected volume: 15 μL; Flow rate: 5 mL/minutes; RT=6.57 minutes to afford 1-(5-(3-cyano-6-(1-((S)-1'-(4-(((S)-2,6-dioxopiperidin-3-yl)amino)-2-fluorophenyl)-3',3'-difluoro-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (Compound 191, Early eluting isomer 1-1, 12 mg, 0.13 mmol, 10% yield) as a yellow solid. $^1H$ NMR (400 MHz, DMSO-$d_6$). δ 10.80 (s, 1H), 9.28 (s, 1H), 8.83 (s, 1H), 8.68 (d, J=2.4 Hz, 1H), 8.51 (s, 1H), 8.16 (s, 1H), 8.06 (dd, J=9, 2.4 Hz, 1H), 7.81 (d, J=7.2 Hz, 1H), 7.00 (d, J=9.2 Hz, 1H), 6.87 (t, J=9.6 Hz, 1H), 6.53 (dd, J=4.4, 1.5 Hz, 1H), 6.43 (dd, J=9.2, 1.6 Hz, 1H), 5.91 (d, J=8 Hz, 1H), 4.35-4.21 (m, 3H), 4.19-4.41 (m, 2H), 3.31-3.08 (m, 2H), 3.19-3.08 (m, 4H), 3.08-2.90 (m, 1H), 2.77-2.71 (m, 4H), 2.69-2.61 (m, 1H), 2.17-1.87 (m, 15H), 1.69-1.63 (m, 2H), 1.58-1.50 (m, 2H), 1.39-1.36 (m, 2H) and 0.74 (t, J=7.6 Hz, 3H). LCMS ($ES^+$): m/z 918.3 $[M+H]^+$.

Step 4. Into a 100 mL single-necked round-bottomed flask containing a well-stirred suspension of (R)-1-(5-(3-cyano-6-(1-(3',3'-difluoro-1'-(2-fluoro-4-nitrophenyl)-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (4, Late eluting isomer 2, 150 mg, 0.18 mmol) in 1:1 THF/EtOH (10 mL) were added Iron powder (50.05 mg, 0.89 mmol) and Ammonium Chloride (95.87 mg, 1.79 mmol) in water (2.5 mL) at ambient temperature. The resulting suspension was heated to 85° C. for 5 h and the reaction mixture was cooled to ambient temperature. After complete consumption of the starting material as indicated by UPLC-MS, the reaction mixture was filtered through a pad of Celite and Celite bed was washed with DCM (20 mL). Combined filtrate was diluted with water (10 mL) and the product was extracted with DCM (2×50 mL). The organic phases were combined, dried (anhydrous $Na_2SO_4$), filtered and the filtrate was concentrated under reduced pressure to get a crude mass. The crude mass was purified by flash silica-gel (230-400 mesh) with 0-10% MeOH/DCM while the desired product was eluting at 3% of the mobile phase to afford (R)-1-(5-(6-(1-(1'-(4-amino-2-fluorophenyl)-3',3'-difluoro-[1,4'-bipiperidin]-4-yl)-1H-pyrazol-4-yl)-3-cyanopyrazolo[1,5-a]pyrazin-4-yl)pyridin-2-yl)-N-cyclobutyl-4-ethylpiperidine-4-carboxamide (7, 70 mg, 0.076 mmol, 43% yield) as a yellow solid. LCMS ($ES^+$): m/z 807.3 $[M+H]^+$.

Step 5: Into a 10 mL sealed-tube containing a well-stirred solution of (R)-1-(5-(6-(1-(1'-(4-amino-2-fluorophenyl)-3',3'-difluoro-[1,4'-bipiperidin]-4-yl)-1H-pyrazol-4-yl)-3-cyanopyrazolo[1,5-a]pyrazin-4-yl)pyridin-2-yl)-N-cyclobutyl-4-ethylpiperidine-4-carboxamide (7, 70 mg, 0.87 mmol) and 3-bromopiperidine-2,6-dione (166.57 mg, 0.87 mmol) in anhydrous DMF (4 mL) was added Sodium bicarbonate (21.86 mg, 0.26 mmol) at ambient temperature under nitrogen atmosphere. The reaction mixture was heated to 70° C. for 24 h and the reaction mixture was cooled to ambient temperature. Additional amount of 3-bromopiperidine-2,6-dione (166.57 mg, 0.87 mmol) was added to the reaction mixture. The reaction mixture was heated to 70° C. for 24 h and the reaction mixture was cooled to ambient temperature. The progress of the reaction was monitored by LCMS. The reaction mixture was quenched with water (5 mL) and the product was extracted with DCM (2×30 mL). The organic phases were combined, dried (anhydrous $Na_2SO_4$), filtered and the filtrate was concentrated under reduced pressure to get a crude residue.

The crude residue was purified by reverse phase C18 Redisep Rf Gold (30 g HP C18) column; Mobile phase: 0.1% $NH_4OAc$ in MQ-water, B: Acetonitrile; Flow rate: 15 mL/minutes] while desired compound was eluting at 30% of B to afford 51 mg of product with 95.19% purity by LCMS. Enantiomers were separated by SFC chiral column following the method: (R,R) Whelk 01; Co-solvent: 0.1% $^i$PrNH$_2$ in (1:1) IPA:ACN, Injected volume: 15 μL; Flow rate: 5 mL/min; RT=7.36 minutes to afford 1-(5-(3-cyano-6-(1-((R)-1'-(4-(((R)-2,6-dioxopiperidin-3-yl)amino)-2-fluorophenyl)-3',3'-difluoro-[1,4'-bipiperidin]-4-yl)-1H-pyrazol-4-yl)pyrazolo[1,5-a]pyrazin-4-yl)pyridin-2-yl)-N-cyclobutyl-4-ethylpiperidine-4-carboxamide (Compound 192, Late eluting isomer 2-2, 3.9 mg, 0.41 mmol, 5% yield) as a yellow solid. $^1$H NMR (400 MHz, DMSO-$d_6$). δ 10.80 (s, 1H), 9.28 (s, 1H), 8.83 (s, 1H), 8.68 (d, J=2.8 Hz, 1H), 8.51 (s, 1H), 8.16 (s, 1H), 8.06 (dd, J=8.8, 2.4 Hz, 1H), 7.80 (d, J=7.2 Hz, 1H), 7.00 (d, J=9.2 Hz, 1H), 6.87 (t, J=9.6 Hz, 1H), 6.53 (dd, J=14.8, 2.4 Hz, 1H), 6.43 (d, J=8.4 Hz, 1H), 5.91 (d, J=7.6 Hz, 1H), 4.30-4.26 (m, 3H), 4.16-4.13 (m, 2H), 3.29-3.22 (m, 2H), 3.11-3.08 (m, 4H), 2.99-2.91 (m, 1H), 2.82-2.71 (m, 4H), 2.64-2.85 (m, 2H), 2.25-2.14 (m, 4H), 2.11-2.04 (m, 3H), 2.02-1.92 (m, 5H), 1.91-1.79 (m, 2H), 1.71-1.59 (m, 2H), 1.55-1.48 (m, 2H), 1.45-1.31 (m, 2H) and 0.75 (t, J=7.6 Hz, 3H). LCMS (ES$^+$): m/z 918.3 [M+H]$^+$.

Example 197: Synthesis of 1-(5-(3-cyano-6-(1-((1r,4r)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 87)

1-(5-(3-cyano-6-(1-((1S,4r)-4-(4-(4-(((S)-2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 194)

1-(5-(3-cyano-6-(1-((1R,4r)-4-(4-(4-(((R)-2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 195)

(Configurations are arbitrarily assigned)

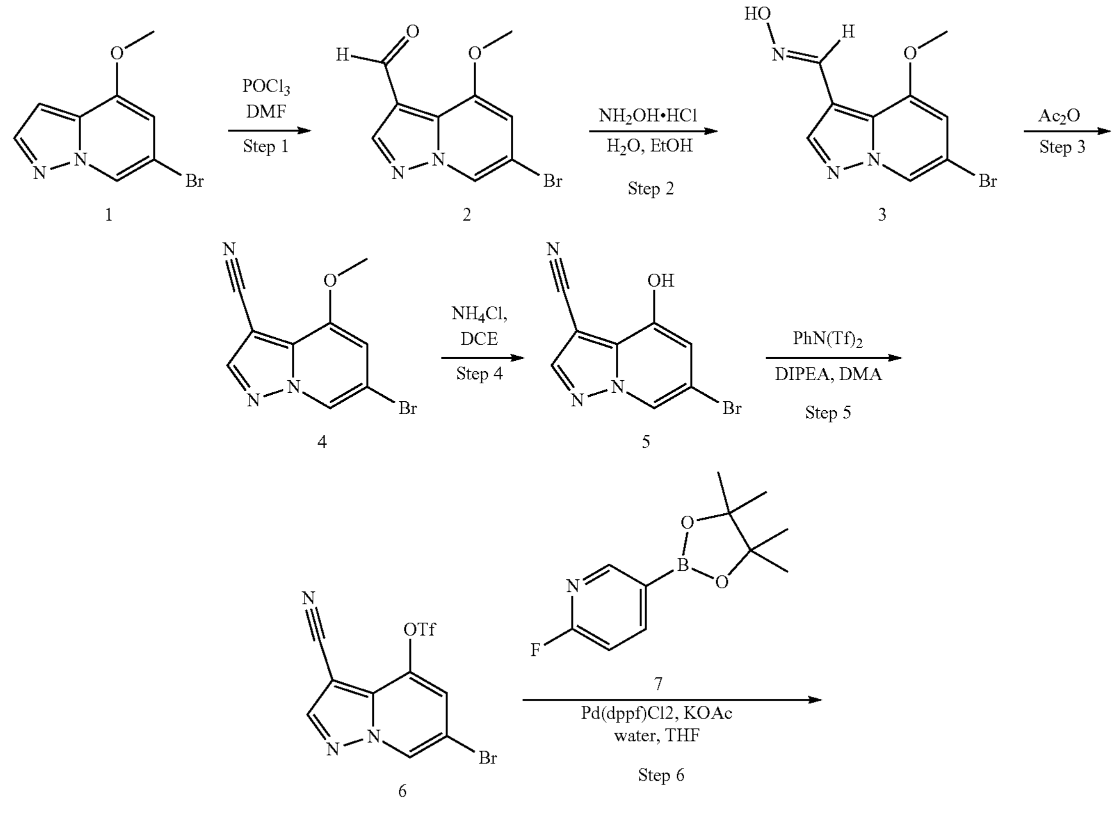

-continued
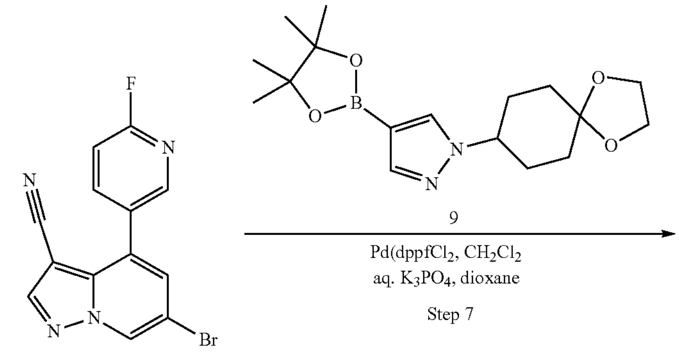
8
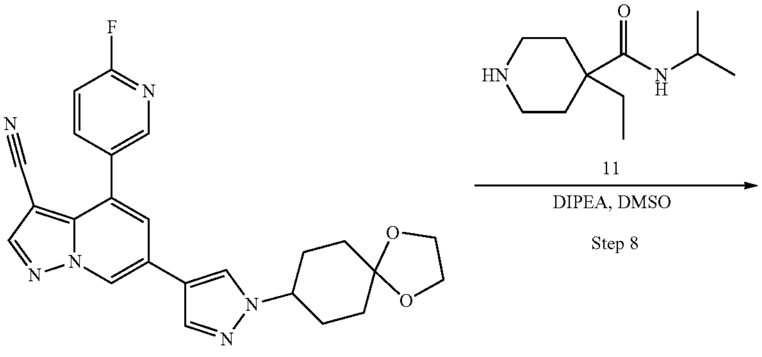
10
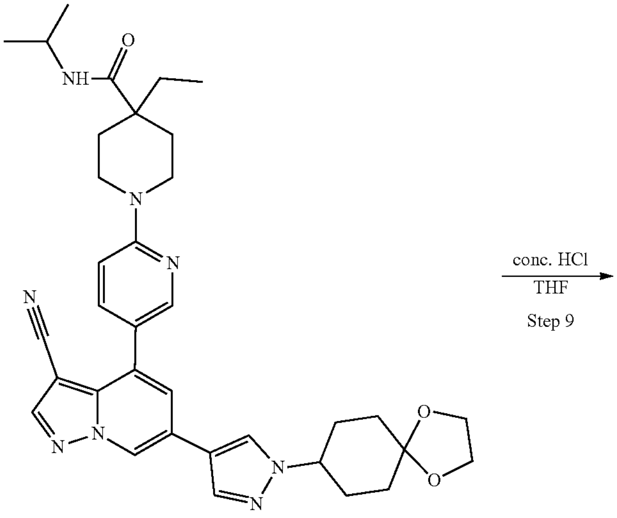
12

-continued
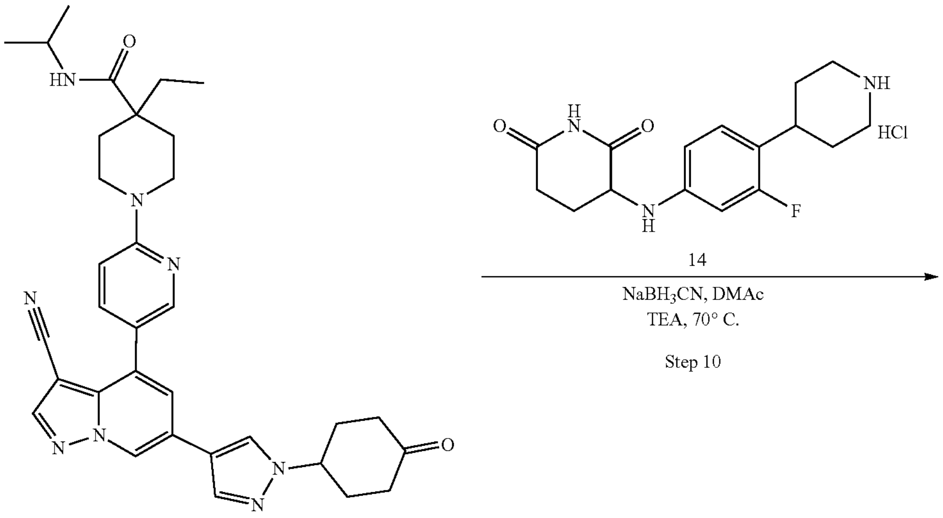
13
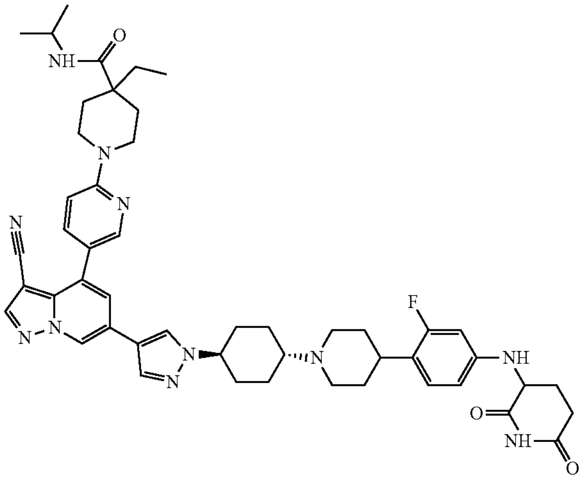
Compound 87
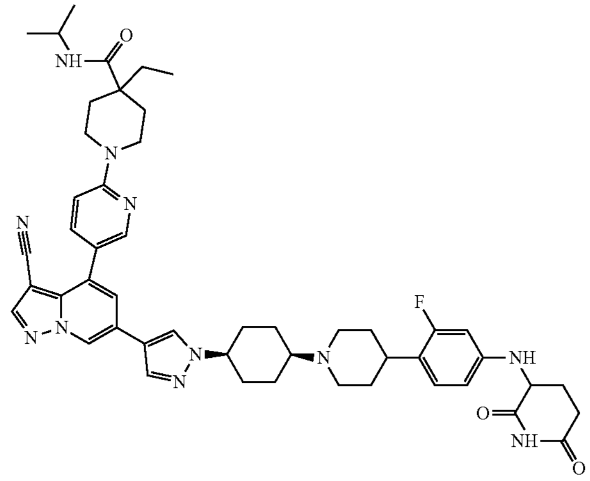
Compound 193
Step 11 SFC
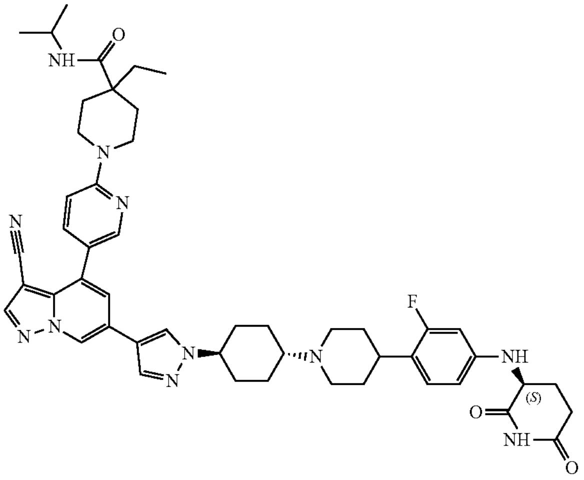
Compound 194
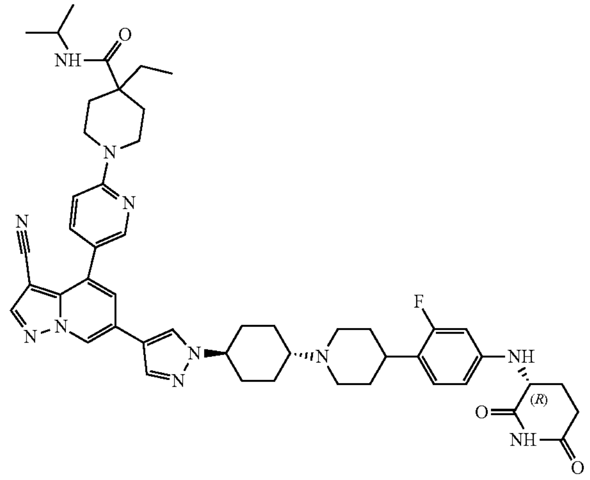
Compound 195

Step 1: Into a 1 L three-necked round-bottomed flask containing a well-stirred solution of 6-bromo-4-methoxy-pyrazolo[1,5-a]pyridine (1, 38 g, 167.36 mmol) in anhydrous DMF (400 mL) was added phosphorus oxychloride (76.98 g, 502.08 mmol) drop wise at 0° C. under nitrogen. After complete addition, the reaction mixture is allowed to room temperature and stirred for 5 h at ambient temperature under nitrogen. After completion of the reaction monitored by TLC and LCMS the reaction mixture was carefully quenched (reverse quenching) with cold water and adjust the PH 8 by using 50% NaOH solution. The precipitated solid was filtered through Buckner funnel and washed with pet ether, dried under vacuum to get 6-bromo-4-methoxy-pyrazolo[1,5-a]pyridine-3-carbaldehyde (2, 42 g, 158.14 mmol, 95% yield) as brown solid. LCMS ($ES^+$): m/z 256.9 $[M+2H]^+$.

Step 2: Into a 2 L three-necked round-bottomed flask containing a well-stirred solution of 6-bromo-4-methoxy-pyrazolo[1,5-a]pyridine-3-carbaldehyde (2, 42 g, 164.66 mmol) in ethanol (1 L) and water (300 mL) was added Hydroxylamine hydrochloride (57.21 g, 823.31 mmol, 34.26 mL) at ambient temperature. The reaction mixture was heated at 60° C. for 16 h.

After completion of the reaction monitored by TLC and LCMS the reaction mixture was concentrated under reduced pressure. The resulting crude product was neutralized to PH 7 by using saturated sodium bicarbonate solution. The precipitated solid was filtered off and washed with water and pet ether and dried over vacuum to get (3E)-6-bromo-4-methoxy-pyrazolo[1,5-a]pyridine-3-carbaldehyde oxime (3, 44 g, 160.71 mmol, 98% yield) as a brown solid. LCMS ($ES^+$): m/z 271.9 $[M+2H]^+$.

Step 3: Into a 2 L three-necked round-bottomed flask containing a well-stirred solution of (3E)-6-bromo-4-methoxy-pyrazolo[1,5-a]pyridine-3-carbaldehyde oxime (3, 44 g, 162.91 mmol) in Acetic anhydride (500 mL) was heated for 16 h at 120° C. temperature. Reaction was monitored by TLC and LCMS, after completion of reaction, the reaction mixture was concentrated under reduced pressure to remove Acetic Anhydride. The crude product was stirred with pet ether for 15 minutes and filtered to get a 6-bromo-4-methoxy-pyrazolo[1,5-a]pyridine-3-carbonitrile (4, 39 g, 141.72 mmol, 87% yield) as brown solid. LCMS ($ES^+$): m/z 251.1 $[M+H]^+$.

Step 4: Into a 2 L multi-neck round bottom flask, fitted with mechanical stirrer containing a well stirred solution of 6-bromo-4-methoxy-pyrazolo[1,5-a]pyridine-3-carbonitrile (4, 39 g, 154.72 mmol) in DCE (1 L) was added portion wise Aluminum chloride, Anhydrous (82.52 g, 618.88 mmol, 33.82 mL) at room temperature, after addition the reaction mixture was stirred at 90° C. for 4h. The progress of the reaction was monitored by UPLC. After completion of starting material, THF (200 ml) was added to the reaction mixture at 0° C. slowly and stirred for 30 minutes. Then added a solution of sodium sulfate decahydrate (200 g) at room temperature and stirred for 12h at room temperature. The reaction mixture was filtered on celite bed and washed with THE (2×500 ml). The filtrate was concentrated under reduced pressure to afford brown color solid. To the brown solid was added ethyl acetate (500 ml) and stirred for 1h, the organic layer was filtered and concentrated under reduced pressure to afford 6-bromo-4-hydroxy-pyrazolo[1,5-a]pyridine-3-carbonitrile (5, 36 g, 122.65 mmol, 79% yield) as brown solid. LCMS ($ES^+$): 10 m/z 235.9 $[M-H]^-$.

Step 5: Into a 2 L Three-necked round-bottomed flask containing a well-stirred solution of 6-bromo-4-hydroxy-pyrazolo[1,5-a]pyridine-3-carbonitrile (5, 22.5 g, 94.52 mmol) in DMA (600 mL) was added N-Phenylbis(trifluoromethanesulfonimide), 99% (40.52 g, 113.43 mmol) followed by DIPEA (36.65 g, 283.56 mmol, 49.39 mL) at 0° C. After addition, the reaction mixture was stirred at room temperature for 3 h. The progress of the reaction was monitored by UPLC. the reaction mixture was cooled to room temperature and poured into water (500 ml) and extracted with EtOAc (2×1000 ml). Organic phases were combined and washed with brine (200 ml). Combined organic phases were dried (anhydrous $Na_2SO_4$), filtered and the filtrate was concentrated under reduced pressure to get a crude residue, which was purified by flash silica-gel (230-400 mesh) column with 0-100% EtOAc/pet ether while desired compound eluting at 20-30% to afford (6-bromo-3-cyano-pyrazolo[1,5-a]pyridin-4-yl) trifluoromethanesulfonate (6, 17.7 g, 39.63 mmol, 42% yield) as brown solid. LCMS ($ES^+$): m/z 369.9 $[M+H]^+$.

Step 6: A 1 L multi necked round bottomed flask containing a well stirred solution of (6-bromo-3-cyano-pyrazolo[1,5-a]pyridin-4-yl) trifluoromethanesulfonate (6, 15 g, 40.53 mmol) and 2-fluoro-5-(4,4,5,5-tetramethyl-1,3,2-dioxaborolan-2-yl)pyridine (7, 9.04 g, 40.53 mmol) in THF (120 mL) was purged with nitrogen then added (1,1'-Bis(diphenylphosphino)ferrocene)palladium(II) dichloride (3.31 g, 4.05 mmol) and again purged with nitrogen then added drop wise a solution of Potassium Acetate (3.98 g, 40.53 mmol, 2.53 mL) in Water (20 mL) at 0° C. After addition, the reaction was stirred at room temperature under $N_2$ atmosphere for 24 h. The progress of the reaction was monitored by TLC and UPLC. After completion of the reaction, the reaction mixture was quenched with water (200 ml), suspension was filtered, dark gray color solid suspended in Methanol (100 ml) and stirred in room temperature for 30 minutes and filtered. The filter cake was washed with cold Methanol (50 ml) to obtain Pure 6-bromo-4-(6-fluoro-3-pyridyl)pyrazolo[1,5-a]pyridine-3-carbonitrile (8, 7.7 g, 23.78 mmol, 59% yield) as gray solid. LCMS ($ES^+$): m/z 317.0 $[M+H]^+$.

Step 7: To a solution of 1-(1,4-dioxaspiro[4.5]decan-8-yl)-4-(4,4,5,5-tetramethyl-1,3,2-dioxaborolan-2-yl)pyrazole (9, 1.5 g, 4.49 mmol), 6-bromo-4-(6-fluoro-3-pyridyl)pyrazolo[1,5-a]pyridine-3-carbonitrile (8, 1.42 g, 4.49 mmol) and $Pd(dppf)Cl_2{\cdot}CH_2Cl_2$ (366.51 mg, 448.81 μmol) in dioxane (18 mL) was added $K_3PO_4$ (2 M, 4.5 mL). After addition, the solution was stirred at 70° C. for 12 hr. The reaction solution was quenched with water (100 mL) and the mixture extracted with EtOAc (100 mL*3). The combined organic layers were washed with brine (200 mL), dried over $Na_2SO_4$, concentrated in vacuum to give a residue. The residue was purified by flash silica gel chromatography (40 g Silica Flash Column, Eluent of 0-76% EA/PE 60 mL/min) to afford 6-[1-(1,4-dioxaspiro[4.5]decan-8-yl)pyrazol-4-yl]-4-(6-fluoro-3-pyridyl)pyrazolo[1,5-a]pyridine-3-carbonitrile (10, 1.4 g, 3.15 mmol, 70% yield) as yellow solid. LCMS ($ES^+$): m/z 445.0 $[M+H]^+$ Step 8: To a solution of 6-[1-(1,4-dioxaspiro[4.5]decan-8-yl)pyrazol-4-yl]-4-(6-fluoro-3-pyridyl)pyrazolo[1,5-a]pyridine-3-carbonitrile (10, 1.2 g, 2.70 mmol) and 4-ethyl-N-isopropylpiperidine-4-carboxamide (11, 824.00 mg, 3.51 mmol, HCl salt) in DMSO (10 mL) was added DIPEA (1.40 g, 10.80 mmol, 1.88 mL). After addition, the solution was stirred at 90° C. for 12 hr. The reaction solution was poured into water (20 mL) to give a suspension. Then the suspension was filtered, the filter cake was washed with water (10 mL) and concentrated in vacuum to afford 1-[5-[3-cyano-6-[1-(1,4-dioxaspiro[4.5]decan-8-yl)pyrazol-4-yl]pyrazolo[1,5-a]pyridin-4-yl]-2-pyridyl]-4-ethyl-N-isopropyl-piperidine-4-carboxamide (12, 1.02 g, 1.64 mmol, 91% yield) as yellow solid. LCMS ($ES^+$): m/z 623.2 $[M+H]^+$ Step 9: To a solution of 1-[5-[3-cyano-6-[1-(1,4-dioxaspiro[4.5]decan-8-yl)pyrazol-4-yl]pyrazolo[1,5-a]pyridin-4-yl]-2-pyridyl]-4-ethyl-N-isopropyl-piperidine-4-carboxamide (12, 1.4 g, 2.25 mmol) in THF (5 mL) was added HCl (4 M, 5.00 mL). After addition, the solution was stirred at 20° C. for 12 hr. The reaction solution was poured into sat.$NaHCO_3$ (40 mL) to give a suspension. Then the suspension was filtered, the filter cake was washed with water (10 ml) and concentrated in vacuum to afford 1-[5-[3-cyano-6-[1-(4-oxocyclohexyl)pyrazol-4-yl]pyrazolo[1,5-a]pyrazin-4-yl]-2-pyridyl]-4-ethyl-N-isopropyl-piperidine-4-carboxamide (13, 1.2 g, 2.07 mmol, 92% yield) as yellow solid. LCMS ($ES^+$): m/z 579.4 $[M+H]^+$ Step 10: To a solution of 3-[3-fluoro-4-(4-piperidyl)anilino]piperidine-2,6-dione (14, 826.90 mg, 2.42 mmol, HCl salt) and 1-[5-[3-cyano-6-[1-(4-oxocyclohexyl)pyrazol-4-yl]pyrazolo[1,5-a]pyrazin-4-yl]-2-pyridyl]-4-ethyl-N-isopropyl-piperidine-4-carboxamide (13, 1.4 g, 2.42 mmol) in DMAc (14 mL) was added TEA (1.22 g, 12.10 mmol, 1.69 mL). After addition, the solution was stirred at 20° C. for 12 hr. Then sodium cyanoborohydride (1.52 g, 24.19 mmol) was added into above solution and stirred at 50° C. for another 2 hr. The reaction solution was poured into water (40 mL) to give a suspension. Then the suspension was filtered, the filter cake was washed with water (10 mL) and concentrated in vacuum. The residue was purified by Prep-TLC (DCM:MeOH=10:1) and Prep-HPLC (Waters Xbridge C18 150*50 mm*10 um, water (10 mM NH4HCO3)-ACN, 38%-68%, 25 ml/min, 9 min) and Prep-HPLC (Waters Xbridge C18 150*50 mm*10 um, water (10 mM NH4HCO3)-ACN, 38%-68%, 25 ml/min, 9 min) to afford 1-(5-(3-cyano-6-(1-((1r, 4r)-4-(4-(4-((2,6-dioxopiperidin-3-yl)amino)-2-fluorophenyl) piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 87, Early eluting isomer 1, 149.68 mg, 172.43 μmol, 7% yield) and 1-(5-(3-cyano-6-(1-((1s, 4s)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 193, Late eluting isomer 2, 116.42 mg, 134.12 μmol, 6% yield) as yellow solids.

Compound 87, Early Eluting Isomer 1:

LCMS ($ES^+$): m/z 868.6 $[M+H]^+$.

$^1H$ NMR (400 MHz, DMSO-$d_6$) δ=10.81 (br s, 1H), 9.24 (s, 1H), 8.65 (s, 1H), 8.53 (s, 1H), 8.37 (d, J=2.0 Hz, 1H), 8.14 (s, 1H), 7.86-7.74 (m, 2H), 7.41 (br d, J=7.6 Hz, 1H), 7.06-6.92 (m, 2H), 6.44 (br d, J=11.2 Hz, 2H), 6.01 (br d, J=7.6 Hz, 1H), 4.39-4.24 (m, 1H), 4.19-4.04 (m, 3H), 4.04-3.95 (m, 1H), 3.14-2.99 (m, 2H), 2.99-2.86 (m, 2H), 2.81-2.69 (m, 1H), 2.64-2.55 (m, 2H), 2.45-2.38 (m, 1H), 2.36-2.26 (m, 2H), 2.22-2.12 (m, 4H), 2.11-2.04 (m, 1H), 1.96-1.83 (m, 3H), 1.83-1.71 (m, 2H), 1.70-1.57 (m, 4H), 1.57-1.45 (m, 4H), 1.34 (br t, J=10.4 Hz, 2H), 1.09 (d, J=6.4 Hz, 6H), 0.75 (br t, J=7.2 Hz, 3H).

Compound 193, Late Eluting Isomer 2:

LCMS ($ES^+$): m/z 868.6 $[M+H]^+$.

$^1H$ NMR (400 MHz, DMSO-$d_6$) δ=10.81 (m, 1H), 9.29 (d, J=1.2 Hz, 1H), 8.65 (s, 1H), 8.58 (s, 1H), 8.38 (d, J=2.4 Hz, 1H), 8.18 (s, 1H), 7.88 (d, J=1.2 Hz, 1H), 7.80 (dd, J=2.4, 8.8 Hz, 1H), 7.39 (d, J=8.0 Hz, 1H), 7.05-6.92 (m, 2H), 6.50-6.37 (m, 2H), 5.99 (d, J=7.6 Hz, 1H), 4.35-4.25 (m, 2H), 4.09 (br d, J=13.2 Hz, 2H), 4.05-3.96 (m, 1H), 3.13-3.01 (m, 4H), 2.80-2.69 (m, 1H), 2.63-2.54 (m, 2H), 2.36-2.26 (m, 3H), 2.16 (br d, J=13.6 Hz, 2H), 2.11-1.99 (m, 3H), 1.93-1.78 (m, 5H), 1.71-1.57 (m, 6H), 1.50 (q, J=7.2 Hz, 2H), 1.40-1.31 (m, 2H), 1.09 (d, J=6.4 Hz, 6H), 0.76 (t, J=7.2 Hz, 3H)

Step 11: 1-(5-(3-cyano-6-(1-((1r, 4r)-4-(4-(4-((2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 87, Early eluting isomer 1, 54 mg) was purified by Prep-SFC (DAICEL CHIRALPAK AS (250 mm*30 mm, 10 um, 0.1% NH3H2O IPA, 60%, 4.6 min, 40 min) to afford 1-(5-(3-cyano-6-(1-((1S,4r)-4-(4-(4-(((S)-2,6-dioxopiperidin-3-yl)amino)-2-fluoro phenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 194, Early eluting isomer 1-1, 18.52 mg, 19.79 μmol, 32% yield) as a green solid and 1-(5-(3-cyano-6-(1-((1R,4r)-4-(4-(4-(((R)-2,6-dioxopiperidin-3-yl)amino)-2-fluorophenyl)piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide (Compound 195, Late eluting isomer 1-2, 14.89 mg, 16.18 μmol, 26% yield) as green solids.

Compound 194, Early Eluting Isomer 1-1:

LCMS ($ES^+$): m/z 868.7 $[M+H]^+$.

$^1H$ NMR (400 MHz, DMSO-$d_6$) δ=10.79 (s, 1H), 9.23 (s, 1H), 8.64 (s, 1H), 8.53 (s, 1H), 8.37 (d, J=2.0 Hz, 1H), 8.25 (s, 1H), 8.14 (s, 1H), 7.84-7.76 (m, 2H), 7.39 (br d, J=8.0 Hz, 1H), 7.07-6.87 (m, 2H), 6.52-6.39 (m, 2H), 6.00 (br d, J=7.6 Hz, 1H), 4.31 (ddd, J=5.4, 6.4, 11.5 Hz, 1H), 4.17-4.06 (m, 3H), 4.01 (br dd, J=7.2, 14.0 Hz, 1H), 3.11-3.05 (m, 2H), 2.97 (br d, J=10.0 Hz, 2H), 2.80-2.70 (m, 1H), 2.64-2.54 (m, 2H), 2.39-2.31 (m, 3H), 2.22-2.13 (m, 4H), 2.12-2.07 (m, 1H), 1.98-1.91 (m, 2H), 1.90-1.75 (m, 3H), 1.70-1.60 (m, 4H), 1.55-1.46 (m, 4H), 1.36 (br t, J=10.0 Hz, 2H), 1.09 (d, J=6.8 Hz, 6H), 0.76 (br t, J=7.2 Hz, 3H)

Compound 195, Late Eluting Isomer 1-2:

LCMS ($ES^+$): m/z 868.7 $[M+H]^+$ $^1H$ NMR (400 MHz, DMSO-$d_6$) δ=10.79 (s, 1H), 9.30-9.17 (m, 1H), 8.64 (s, 1H), 8.53 (s, 1H), 8.37 (d, J=2.4 Hz, 1H), 8.21 (s, 1H), 8.14 (s, 1H), 7.88-7.72 (m, 2H), 7.45-7.34 (m, 1H), 7.08-6.88 (m, 2H), 6.54-6.37 (m, 2H), 6.00 (br d, J=7.6 Hz, 1H), 4.38-4.27 (m, 1H), 4.17-4.04 (m, 3H), 4.04-3.96 (m, 1H), 3.07 (br t, J=11.2 Hz, 2H), 2.97 (br d, J=9.6 Hz, 2H), 2.75 (ddd, J=5.2, 12.0, 17.2 Hz, 1H), 2.65-2.57 (m, 2H), 2.47-2.41 (m, 1H), 2.41-2.32 (m, 2H), 2.16 (br d, J=10.0 Hz, 4H), 2.12-2.04 (m, 1H), 1.99-1.90 (m, 2H), 1.87 (br dd, J=4.0, 12.4 Hz, 1H), 1.83-1.72 (m, 2H), 1.71-1.60 (m, 4H), 1.57-1.46 (m, 4H), 1.35 (br t, J=10.4 Hz, 2H), 1.09 (d, J=6.8 Hz, 6H), 0.75 (t, J=7.2 Hz, 3H)

Example 198: Synthesis of 1-(5-(3-Cyano-6-(1-(2-(2-(4-(4-((2,6-dioxopiperidin-3-yl)amino)phenyl)piperidin-1-yl)acetyl)-2-azaspiro[3.5]nonan-7-yl)-1H-pyrazol-4-yl)pyrazolo[1,5-a]pyridin-4-yl)pyridin-2-yl)-N-isopropyl-4-m ethylpiperidine-4-carboxamide (Compound 196)
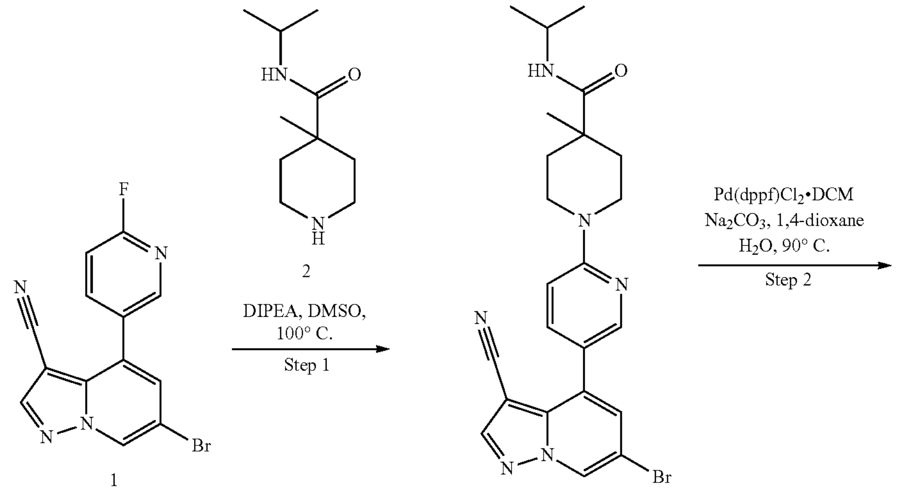
1 2 3
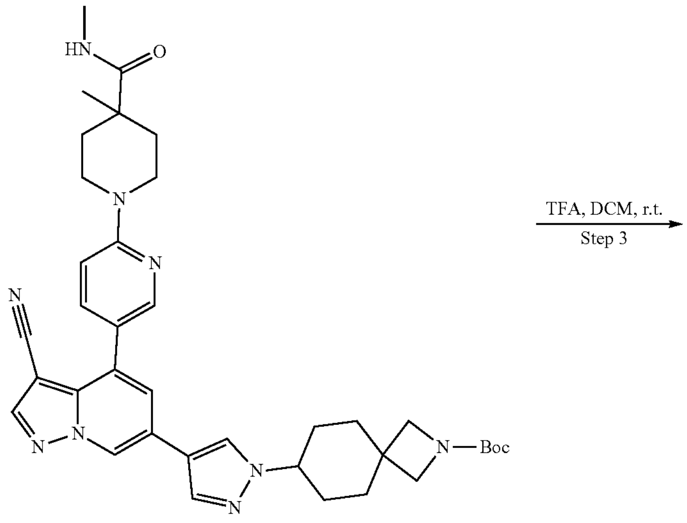
4

-continued

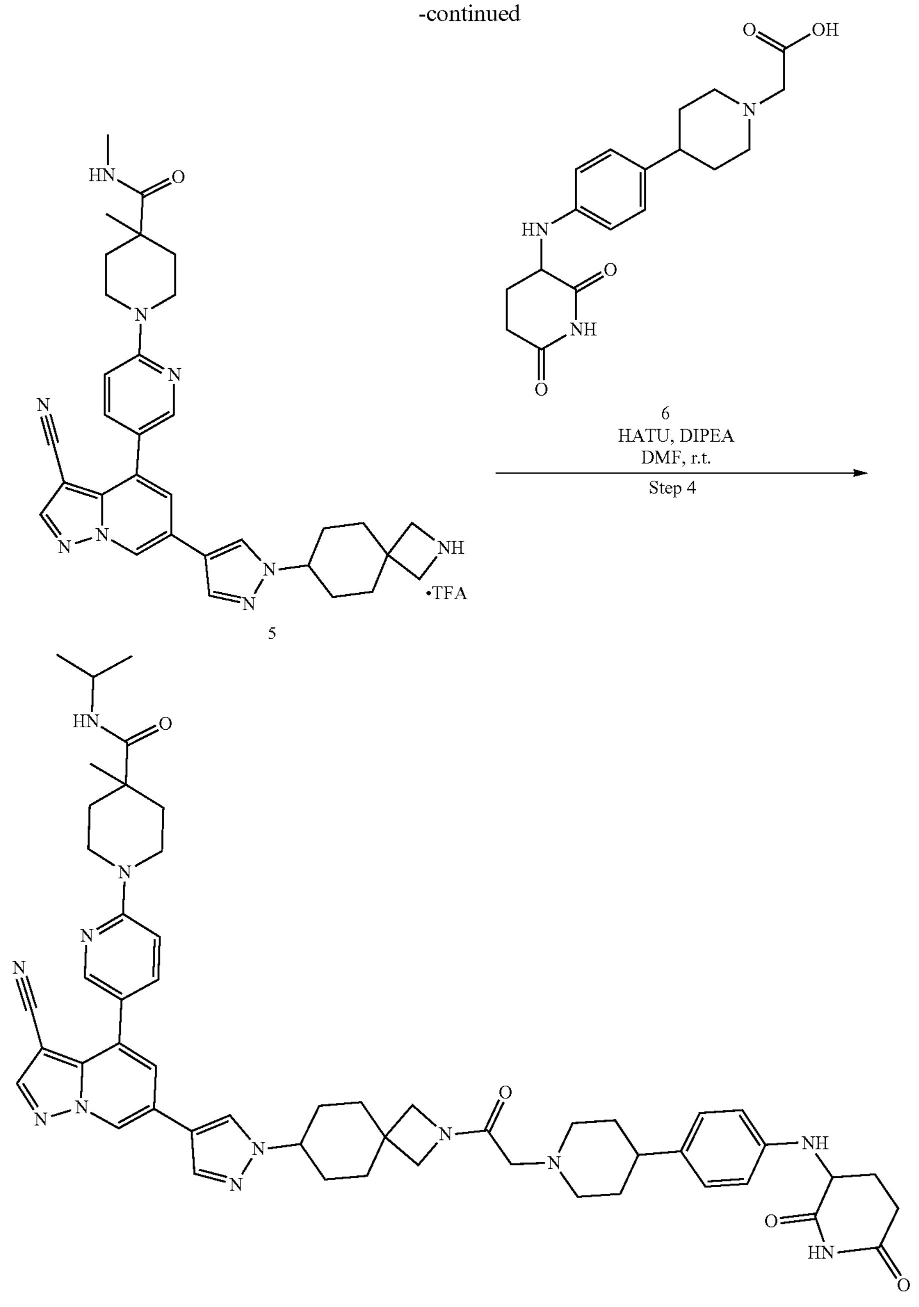

Compound 196

Step 1: Into a 100 mL sealed glass tube containing a well-stirred solution of N-isopropyl-4-methyl-piperidine-4-carboxamide hydrochloride (2, 696.08 mg, 3.15 mmol) and 6-bromo-4-(6-fluoro-3-pyridyl)pyrazolo[1,5-a]pyridine-3-carbonitrile (1, 1 g, 3.15 mmol) in anhydrous DMSO (20 mL) was added DIPEA (3.26 g, 25.23 mmol, 4.39 mL) under nitrogen atmosphere. The reaction mixture was heated to 100° C. for 16 h. After completion of the reaction as indicated by UPLC, the reaction mixture was cooled and treated with water (50 mL) and solid precipitated out was filtered. The filtered solid was dried under vacuum to afford a crude mass. The crude was purified by flash silica-gel (230-400 mesh) column with 20-100% EtOAc/pet ether while desired compound eluting at 70% of the mobile phase to afford 1-[5-(6-bromo-3-cyano-pyrazolo[1,5-a]pyridin-4-yl)-2-pyridyl]-N-isopropyl-4-methyl-piperidine-4-carboxamide (3, 800 mg, 1.59 mmol, 51% yield) as a white solid. LCMS ($ES^+$): m/z 481.1 $[M+H]^+$.

Step 2: Into a 50 mL sealed glass tube containing a well-stirred solution of 1-[5-(6-bromo-3-cyano-pyrazolo[1,5-a]pyridin-4-yl)-2-pyridyl]-N-isopropyl-4-methyl-piperidine-4-carboxamide (3, 350 mg, 0.727 mmol) and tert-butyl 7-[4-(4,4,5,5-tetramethyl-1,3,2-dioxaborolan-2-yl)pyrazol-1-yl]-2-azaspiro[3.5]nonane-2-carboxylate (364.13 mg, 0.872 mmol) in 1,4-dioxane (10 mL) was added Sodium carbonate (154.12 mg, 1.45 mmol) in water (2 mL) at ambient temperature and the mixture was purged with nitrogen, Subsequently, Pd(dppf)$Cl_2$·DCM (59.37 mg, 0.072 mmol) was added and reaction mixture was stirred at 90° C. for 10 h. The progress of the reaction was monitored by UPLC and TLC. After completion of the reaction as indicated by UPLC, the reaction mixture was diluted with EtOAc (25 mL) and filtered through a pad of Celite & sodium sulfate and Celite pad was washed with EtAOc (2×25 mL). Combined filtrate was concentrated under reduced pressure to afford a crude mass. The crude mass was purified by flash silica gel (230-400 mesh) column with 0-100% EtOAc/pet ether followed by 0-10% MeOH/DCM while the desired product was eluting at 4% of the mobile phase to afford tert-butyl 7-[4-[3-cyano-4-[6-[4-(isopropylcarbamoyl)-4-methyl-1-piperidyl]-3-pyridyl]pyrazolo[1,5-a]pyridin-6-yl]pyrazol-1-yl]-2-azaspiro[3.5]nonane-2-carboxylate (4, 280 mg, 0.250 mmol, 34% yield) as a light yellow solid. LCMS ($ES^+$): m/z 692.4 $[M+H]^+$.

Step 3: Into a 50 mL single-necked round-bottomed flask containing a well-stirred solution of tert-butyl 7-[4-[3-cyano-4-[6-[4-(isopropylcarbamoyl)-4-methyl-1-piperidyl]-3-pyridyl]pyrazolo[1,5-a]pyridin-6-yl]pyrazol-1-yl]-2-azaspiro[3.5]nonane-2-carboxylate (4, 280 mg, 0.404 mmol) in anhydrous DCM (5 mL) was added Trifluoroacetic acid (8.29 g, 72.69 mmol, 5.60 mL) at 0° C. and the resulting solution was stirred at ambient temperature for 2 h. Progress of the reaction was monitored by UPLC. Excess solvent was removed from the reaction mixture under reduced pressure to get a crude mass. Reaction crude was washed with diethyl ether (2×25 mL) to obtain [1-[5-[6-[1-(2-azaspiro[3.5]nonan-7-yl)pyrazol-4-yl]-3-cyano-pyrazolo[1,5-a]pyridin-4-yl]-2-pyridyl]-N-isopropyl-4-methyl-piperidine-4-carboxamide trifluoroacetate (5, 285 mg, 0.261 mmol, 65% yield) as a brown solid. LCMS ($ES^+$): m/z 592.4 $[M+H]^+$.

Step 4: Into a 50 mL single-necked round-bottomed flask containing a well-stirred solution of 2-[4-[4-[(2,6-dioxo-3-piperidyl)amino]phenyl]-1-piperidyl]acetic acid hydrochloride (6, 11; 48.94 mg, 0.128 mmol) and 1-[5-[6-[1-(2-azaspiro[3.5]nonan-7-yl)pyrazol-4-yl]-3-cyano-pyrazolo[1,5-a]pyridin-4-yl]-2-pyridyl]-N-isopropyl-4-methyl-piperidine-4-carboxamide trifluoroacetate (5, 100 mg, 0.141 mmol) in anhydrous DMF (2 mL) were added HATU (80.81 mg, 0.212 mmol) and DIPEA (54.94 mg, 0.425 mmol, 0.074 mL) at 0° C. and reaction mixture was stirred at ambient temperature for 2 h. Progress of reaction was monitored by UPLC. After complete consumption of the starting material as indicated by UPLC, water (5 mL) was added to the reaction mixture and solid precipitated out was filtered and dried to afford a crude solid. The crude solid compound was purified by reverse phase column chromatography by using C18 Redisep Rf Gold (30 g HP C18); Mobile phase: 0.1% ammonium acetate in MQ-water; B: Acetonitrile; Flow rate: 15 mL/minutes; while compound was eluting at 45% to afford 1-(5-(3-cyano-6-(1-(2-(2-(4-(4-((2,6-dioxopiperidin-3-yl)amino)phenyl)piperidin-1-yl)acetyl)-2-azaspiro[3.5]nonan-7-yl)-1H-pyrazol-4-yl)pyrazolo[1,5-a]pyridin-4-yl)pyridin-2-yl)-N-isopropyl-4-methylpiperidine-4-carboxamide (Compound 196, 25 mg, 0.027 mmol, 19% yield) as an off white solid. $^1H$ NMR (400 MHz, DMSO-$d_6$). δ 10.77 (s, 1H), 9.24 (s, 1H), 8.65 (s, 1H), 8.54 (s, 1H), 8.37 (s, 1H), 8.15 (s, 1H), 7.81-7.78 (m, 2H), 7.37 (d, J=8 Hz, 1H), 6.98-6.96 (m, 3H), 6.64 (d, J=8 Hz, 2H), 5.73 (s, 1H), 4.28-4.19 (m, 2H), 3.98-3.90 (m, 6H), 3.73-3.66 (m, 2H), 3.38 (m, 2H), 3.27-3.24 (m, 2H), 2.79-2.74 (m, 1H), 2.55 (m, 4H), 2.11-2.02 (m, 8H), 1.98-1.73 (m, 9H), 1.42-1.37 (m, 2H), 1.13 (s, 3H) and 1.07 (d, J=6.4 Hz, 6H). LCMS ($ES^+$): m/z 919.0 $[M+H]^+$.

Example 199: Synthesis of 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-(4-hydroxyphenyl)-1-piperidyl]-3-pyridyl]pyrazolo[1,5-a]pyridine-3-carbonitrile (Compound 197)

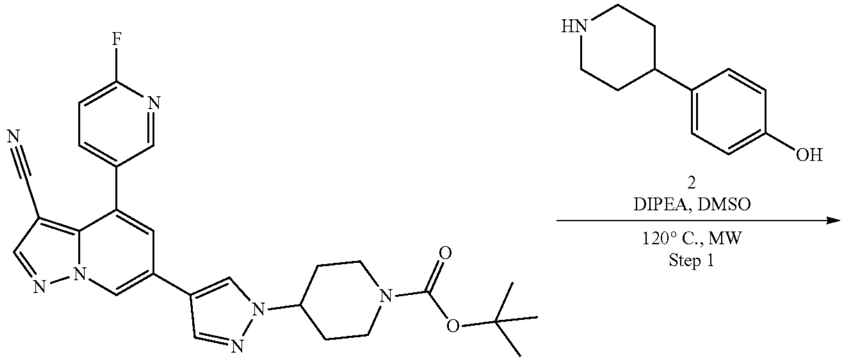

1

2

-continued
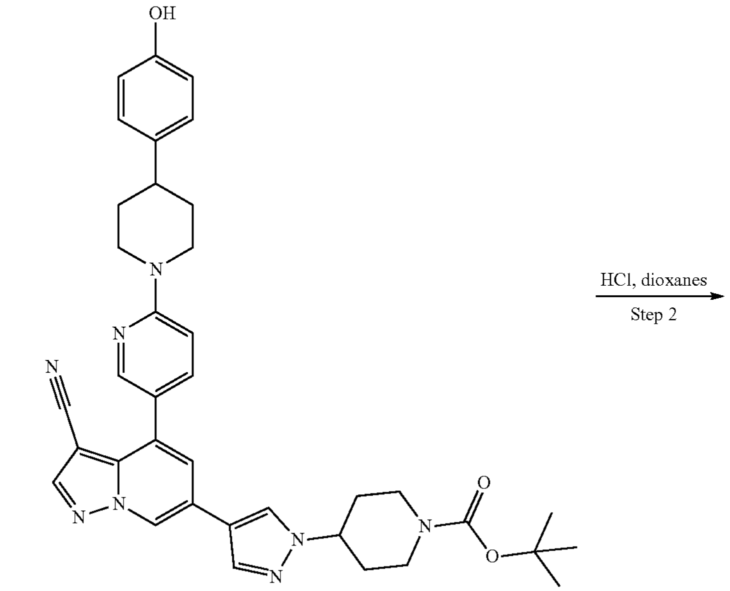
3
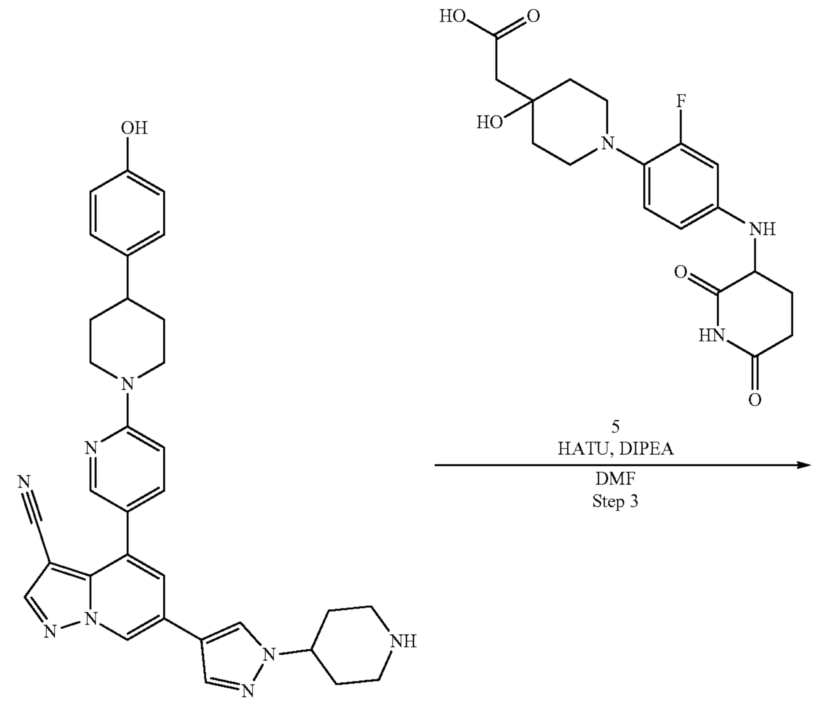
4
5

-continued

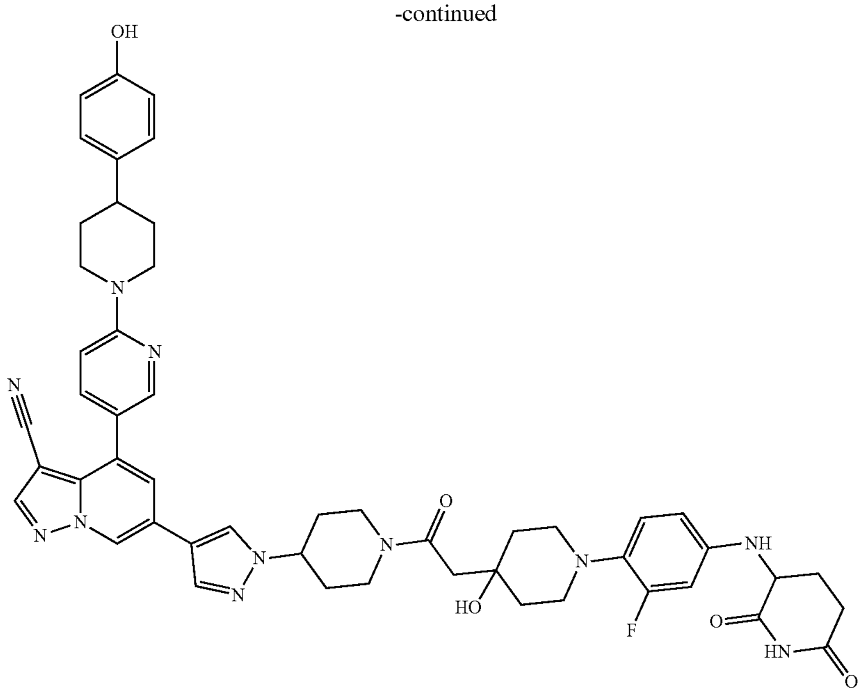

Compound 197

Step 1: Initially 4-(4-piperidyl)phenol (2, 528 mg, 2.98 mmol) and tert-butyl 4-[4-[3-cyano-4-(6-fluoro-3-pyridyl) pyrazolo[1,5-a]pyridin-6-yl]pyrazol-1-yl]piperidine-1-carboxylate (1, 1.45 g, 2.98 mmol) were added to a MW vial and the material was dissolved in DMSO (10.31 mL) before N-ethyl-N-isopropyl-propan-2-amine (1.93 g, 14.89 mmol, 2.59 mL) was added and the mixture was stirred at 120° C. in the MW for 30 mins. Upon reaction completion the mixture was then diluted with water and extracted with EA (×3). The combined organic layers were then washed with Citric acid (10% aq w/v) solution, brine (×2) and dried over $Na_2SO_4$ before being concentrated to a yellow solid. The crude material was then purified via Isco FCC (Hex/EA 1:0 to 0:1) to afford the product as a solid tert-butyl 4-[4-[3-cyano-4-[6-[4-(4-hydroxyphenyl)-1-piperidyl]-3-pyridyl] pyrazolo[1,5-a]pyridin-6-yl]pyrazol-1-yl]piperidine-1-carboxylate (3, 158 mg, 232.80 μmol, 8% yield). LCMS ($ES^+$): m/z 545.4 $[M+H]^+$ Step 2: Initially tert-butyl 4-[4-[3-cyano-4-[6-[4-(4-hydroxyphenyl)-1-piperidyl]-3-pyridyl]pyrazolo[1,5-a]pyridin-6-yl]pyrazol-1-yl]piperidine-1-carboxylate (3, 158 mg, 232.80 μmol, 7.81% yield) was taken and suspended in HCl in 1,4-dioxane (5 mL) and stirred for 2 hrs at room temperature. Upon reaction completion the mixture was concentrated down to dryness and co-evaporated with Hexanes to afford the product 4-(6-(4-(4-hydroxyphenyl)piperidin-1-yl)pyridin-3-yl)-6-(1-(piperidin-4-yl)-1H-pyrazol-4-yl) pyrazolo[1,5-a]pyridine-3-carbonitrile (4, 158 mg, 232.80 μmol, 8% yield). LCMS ($ES^+$): m/z 645.6 $[M+H]^+$ Step 3: Initially 2-[1-[4-[(2,6-dioxo-3-piperidyl)amino]-2-fluoro-phenyl]-4-hydroxy-4-piperidyl]acetic acid (5, 50 mg, 117.53 μmol, formic acid salt), 4-(6-(4-(4-hydroxyphenyl)piperidin-1-yl)pyridin-3-yl)-6-(1-(piperidin-4-yl)-1H-pyrazol-4-yl)pyrazolo[1,5-a]pyridine-3-carbonitrile (4, 68.42 mg, 117.53 μmol, HCl salt) and DIPEA (45.57 mg, 352.60 μmol, 61.42 μL) were dissolved in DMF (2 mL). HATU (53.63 mg, 141.04 μmol) was then added in one portion and stirred at room temperature for 2h. Upon reaction completion the mixture was immediately submitted to purification via Isco RP FCC (0.1% FA MeCN/Water) to afford the product 6-(1-(1-(2-(1-(4-((2,6-dioxopiperidin-3-yl)amino)-2-fluorophenyl)-4-hydroxypiperidin-4-yl)acetyl) piperidin-4-yl)-1H-pyrazol-4-yl)-4-(6-(4-(4-hydroxyphenyl)piperidin-1-yl)pyridin-3-yl)pyrazolo[1,5-a]pyridine-3-carbonitrile (Compound 197, 22 mg, 21.93 μmol, 19% yield, formic acid salt). LCMS ($ES^+$): m/z 906.8 $[M+H]^+$. $^1H$ NMR (400 MHz, DMSO-$d_6$) δ 10.71 (s, 1H), 9.18 (d, J=1.4 Hz, 1H), 9.09 (s, 1H), 8.58 (s, 1H), 8.50 (s, 1H), 8.32 (d, J=2.6 Hz, 1H), 8.11 (s, 1H), 7.79-7.71 (m, 2H), 6.96 (dd, J=13.2, 8.8 Hz, 3H), 6.79 (t, J=9.3 Hz, 1H), 6.65-6.59 (m, 2H), 6.49-6.39 (m, 1H), 6.34 (dd, J=8.7, 2.6 Hz, 1H), 5.70 (d, J=7.6 Hz, 1H), 4.82 (s, 1H), 4.48 (d, J=12.9 Hz, 3H), 4.40 (p, J=6.9 Hz, 1H), 4.18 (ddd, J=11.8, 7.2, 4.9 Hz, 1H), 4.10 (d, J=13.3 Hz, 1H), 3.17 (d, J=12.5 Hz, 1H), 2.96-2.57 (m, 8H), 2.54-2.45 (m, 3H), 2.14-1.94 (m, 3H), 1.88-1.41 (m, 10H).

Example 200: Synthesis of 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-(3-hydroxyphenyl)-1-piperidyl]-3-pyridyl] pyrazolo[1,5-a]pyridine-3-carbonitrile (Compound 198)

Compound 198 was Prepared Following the Synthesis of Compound 197

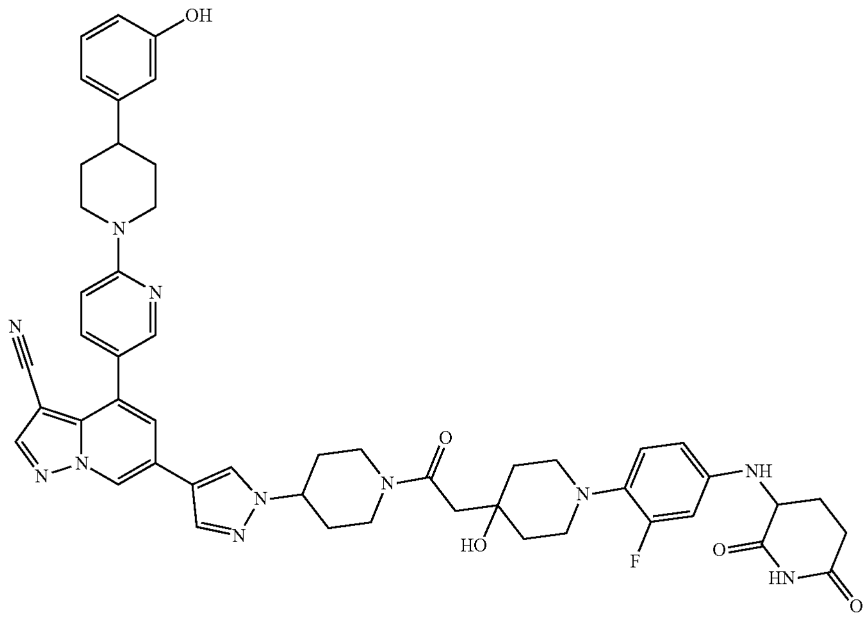 [SMILES: N#Cc1cnn2cc(-c3cnn(C4CCN(C(=O)CC5(O)CCN(c6ccc(NC7CCC(=O)NC7=O)cc6F)CC5)CC4)c3)cc(-c3ccc(N4CCC(c5cccc(O)c5)CC4)nc3)c12]

LCMS ($ES^+$): m/z 906.8 $[M+H]^+$.

$^1$H NMR (400 MHz, DMSO-$d_6$) δ 10.70 (s, 1H), 9.18 (d, J=1.8 Hz, 2H), 8.58 (s, 1H), 8.51 (s, 1H), 8.33 (d, J=2.5 Hz, 1H), 8.11 (s, 1H), 7.80-7.71 (m, 2H), 7.02 (t, J=7.8 Hz, 1H), 6.95 (d, J=9.0 Hz, 1H), 6.78 (t, J=9.3 Hz, 1H), 6.63-6.59 (m, 1H), 6.56 (d, J=1.9 Hz, 1H), 6.52 (dd, J=8.0, 2.4 Hz, 1H), 6.47-6.38 (m, 1H), 6.34 (dd, J=8.7, 2.5 Hz, 1H), 5.70 (d, J=7.6 Hz, 1H), 4.82 (s, 1H), 4.55-4.44 (m, 3H), 4.40 (dq, J=11.0, 5.5 Hz, 1H), 4.18 (ddd, J=11.8, 7.3, 4.7 Hz, 1H), 4.10 (d, J=13.3 Hz, 1H), 3.19 (t, J=12.6 Hz, 1H), 2.96-2.73 (m, 7H), 2.73-2.59 (m, 2H), 2.13-1.95 (m, 3H), 1.87-1.42 (m, 11H).

Example 201: Synthesis of 1-(5-(3-cyano-6-(1-(2-(1-(4-((2,6-dioxopiperidin-3-yl)amino)-2-fluorophenyl)piperidin-4-yl)-2-azaspiro[3.3]heptan-6-yl)-1H-pyrazol-4-yl)pyrazolo[1,5-a]pyridin-4-yl)pyridin-2-yl)-4-ethyl-N-isopropylpiperidine-4-carboxamide (Compound 199)

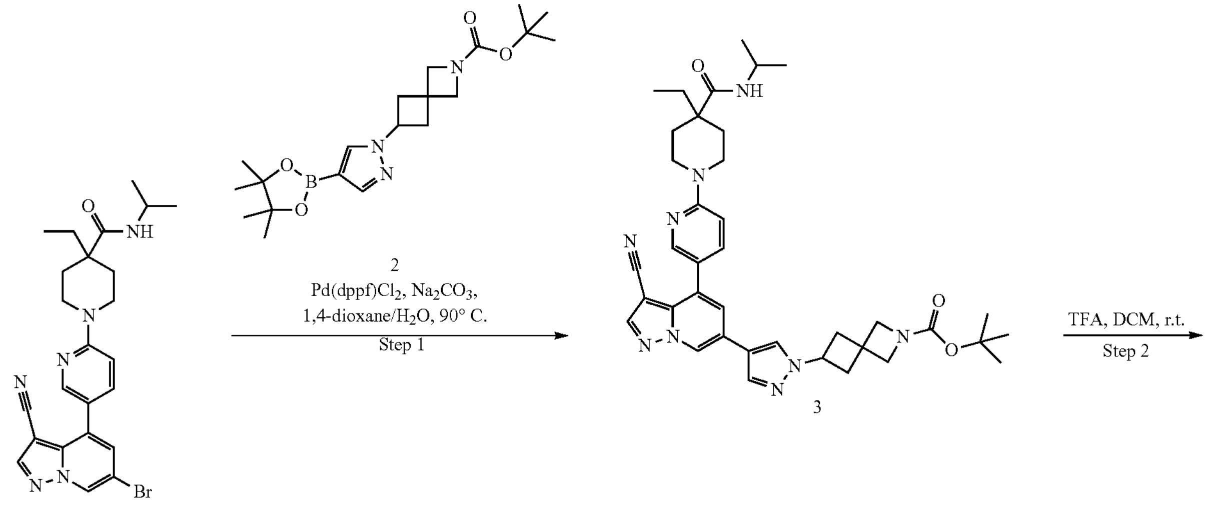

1

2

3

-continued

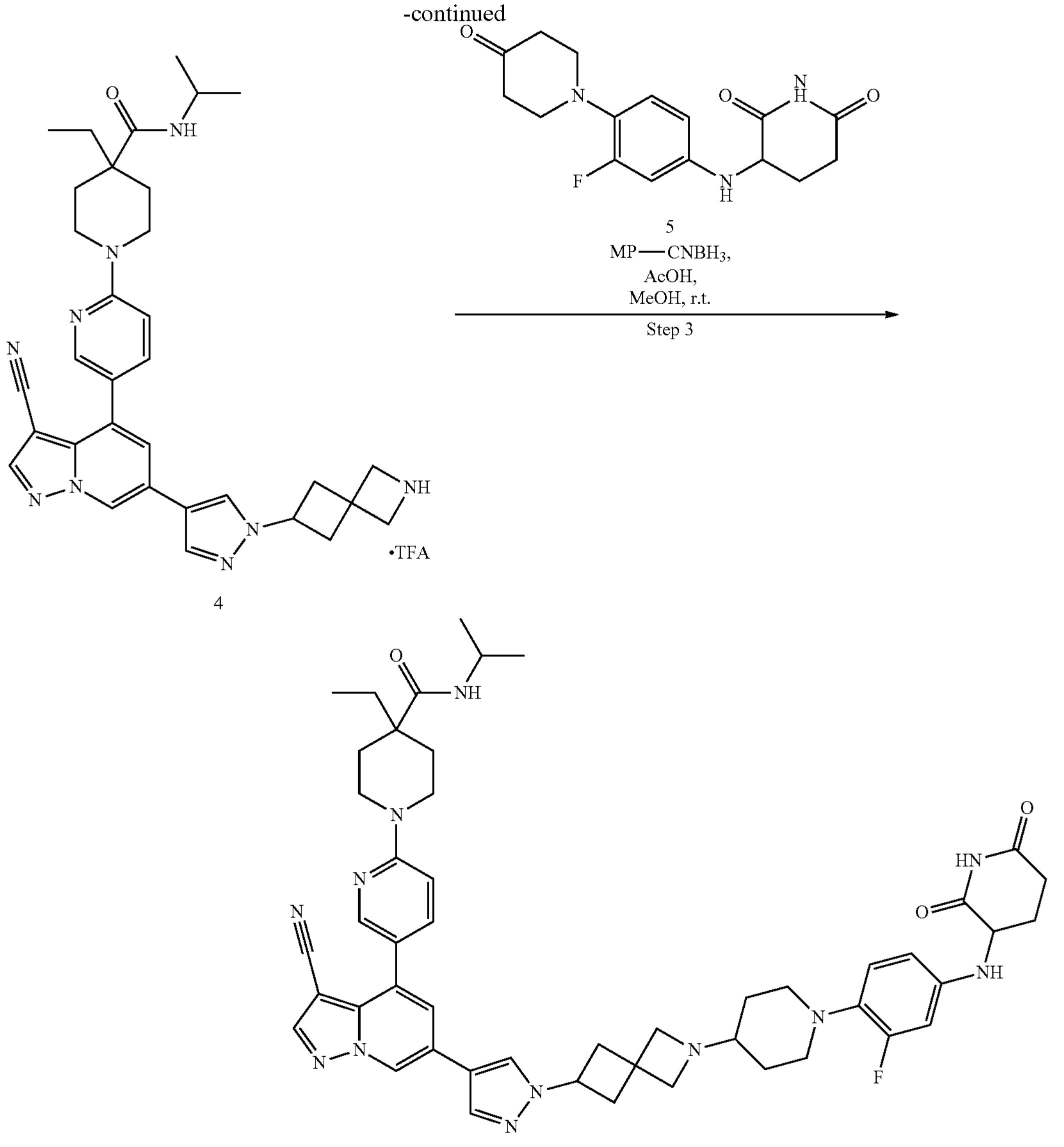

4

Compound 199

Step 1: Into a 10 mL sealed-tube reactor containing a well-stirred solution of 1-[5-(6-bromo-3-cyano-pyrazolo[1,5-a]pyridin-4-yl)-2-pyridyl]-4-ethyl-N-isopropyl-piperidine-4-carboxamide (1, 250 mg, 0.504 mmol) and tert-butyl 6-[4-(4,4,5,5-tetramethyl-1,3,2-dioxaborolan-2-yl)pyrazol-1-yl]-2-azaspiro[3.3]heptane-2-carboxylate (2, 294.67 mg, 0.756 mmol) in anhydrous 1,4-dioxane (2.5 mL) was added Sodium carbonate (160.46 mg, 1.51 mmol) in water (0.5 mL) at ambient temperature under nitrogen atmosphere and the resulting mixture was degassed by bubbling nitrogen gas for 10 minutes. Subsequently, Pd(dppf)$Cl_2$ (41.21 mg, 0.050 mmol) was added to the reaction mixture and reaction mixture was heated to 100° C. for 4 h. After completion of the reaction as indicated by TLC, the reaction mixture was cooled to room temperature and poured into water (20 mL) and extracted with EtOAc (2x30 mL). Organic phases were combined and washed with brine (20 mL). Combined organic phase was dried (anhydrous $Na_2SO_4$), filtered and the filtrate was concentrated under reduced pressure to get a crude residue. The crude residue was purified by flash silica-gel (230-400 mesh) column with 0-100% EtOAc/pet ether while desired compound was eluting at 45% of the mobile phase to afford tert-butyl 6-[4-[3-cyano-4-[6-[4-ethyl-4-(isopropylcarbamoyl)-1-piperidyl]-3-pyridyl]pyrazolo[1,5-a]pyridin-6-yl]pyrazol-1-yl]-2-azaspiro[3.3]heptane-2-carboxylate (3, 120 mg, 0.165 mmol, 33% yield) as an off-white solid. LCMS ($ES^+$): m/z 678.5 $[M+H]^+$.

Step 2: Into a 25 mL single-necked round-bottomed flask containing a well-stirred solution of tert-butyl 6-[4-[3-cyano-4-[6-[4-ethyl-4-(isopropylcarbamoyl)-1-piperidyl]-3-pyridyl]pyrazolo[1,5-a]pyridin-6-yl]pyrazol-1-yl]-2-azaspiro[3.3]heptane-2-carboxylate (3, 120 mg, 0.177 mmol) in anhydrous DCM (0.5 mL) under nitrogen atmosphere was added dropwise Trifluoroacetic acid (296.0 mg, 2.60 mmol, 0.2 mL) at 0° C. The reaction mixture was allowed to attain room temperature and stirred at ambient temperature for 2 h. After completion of the reaction as indicated by UPLC, the reaction mixture was concentrated under reduced pressure and co-distilled with DCM (2x10 mL) to afford 1-[5-[6-[1-(2-azaspiro[3.3]heptan-6-yl)pyrazol-4-yl]-3-cyano-pyrazolo[1,5-a]pyridin-4-yl]-2-pyridyl]-4-ethyl-N-isopropyl-piperidine-4-carboxamide trifluoroacetate (4, 120 mg, 0.073 mmol, 42% yield) as an off-white solid. LCMS ($ES^+$): m/z 578.3 $[M+H]^+$.

Step 3: Into a 8 mL glass-vial containing a well-stirred solution of 1-[5-[6-[1-(2-azaspiro[3.3]heptan-6-yl)pyrazol-4-yl]-3-cyano-pyrazolo[1,5-a]pyridin-4-yl]-2-pyridyl]-4-ethyl-N-isopropyl-piperidine-4-carboxamide trifluoroacetate (4, 110 mg, 0.159 mmol) in anhydrous MeOH (2 mL) were added 3-[3-fluoro-4-(4-oxo-1-piperidyl)anilino]piperidine-2,6-dione (5, 50.78 mg, 0.159 mmol) and acetic acid (23.87 mg, 0.397 mmol, 0.022 mL) followed by $MPCNBH_3$ (270 mg, 0.159 mmol) at ambient temperature. The resulting mixture was stirred at ambient temperature for 16 h. After completion of the reaction, reaction mixture was filtered through sintered funnel and the filtrate was concentrated under reduced pressure to get a crude mass. The crude mass was purified by prep-HPLC column: Xbridge C8 (20×150) MM 5 MICRONS; Mobile phase: 0.1% Ammonium acetate in milli-Q water/ACN; Flow rate: 15 mL\min; RT=11.2 minutes and the prep fraction was lyophilized to afford 1-(5-(3-cyano-6-(1-(2-(1-(4-((2,6-dioxopiperidin-3-yl)amino)-2-fluorophenyl)piperidin-4-yl)-2-azaspiro[3.3]heptan-6-yl)-1H-pyrazol-4-yl)pyrazolo[1,5-a]pyridin-4-yl)pyridin-2-yl)-4-ethyl-N-isopropylpiperidine-4-carboxamide (Compound 199, 10 mg, 0.011 mmol, 7% yield) as an off-white solid. $^1H$ NMR (400 MHz, DMSO-$d_6$). δ 10.78 (s, 1H), 9.25 (d, J=1.2 Hz, 1H), 8.65 (s, 1H), 8.56 (s, 1H), 8.37 (d, J=2.8 Hz, 1H), 8.17 (s, 1H), 7.82 (d, J=1.6 Hz, 1H), 7.79 (dd, J=8.8, 2.4 Hz, 1H), 7.40 (d, J=8 Hz, 1H), 6.96 (d, J=8.8 Hz, 1H), 6.83 (t, J=9.6 Hz, 1H), 6.50 (dd, J=15.2, 2.4 Hz, 1H), 6.41 (dd, J=8.6, 2.4 Hz, 1H), 5.79 (d, J=7.6 Hz, 1H), 4.76 (m, 1H), 4.25 (m, 1H), 4.08 (d, J=13.6 Hz, 2H), 4.03 (m, 1H), 3.40 (m, 1H), 3.25 (s, 2H), 3.15 (s, 2H), 3.10 (m, 4H), 2.70 (m, 1H), 2.60 (m, 6H), 2.16 (d, J=13.6 Hz, 2H), 2.07 (m, 2H), 1.85 (m, 1H), 1.70 (m, 2H), 1.50 (m, 2H), 1.30 (m, 4H), 1.09 (d, J=6.4 Hz, 6H) and 0.75 (t, J=7.6 Hz, 3H). LCMS ($ES^+$): m/z 881.0 $[M+H]^+$.

Example 202: Synthesis of 6-(1-((1s, 4s)-4-(4-(3-(2,4-Dioxotetrahydropyrimidin-1(2H)-yl)-5-fluoro-1-methyl-1H-indazol-6-yl)-3,3-difluoropiperidin-1-yl)cyclohexyl)-1H-pyrazol-4-yl)-4-(6-(6-((6-methoxypyridin-3-yl)methyl)-3,6-diazabicyclo[3.1.1]heptan-3-yl)pyridin-3-yl)pyrazolo[1,5-a]pyrazine-3-carbonitrile (Compound 200)

(Configurations are arbitrarily assigned)

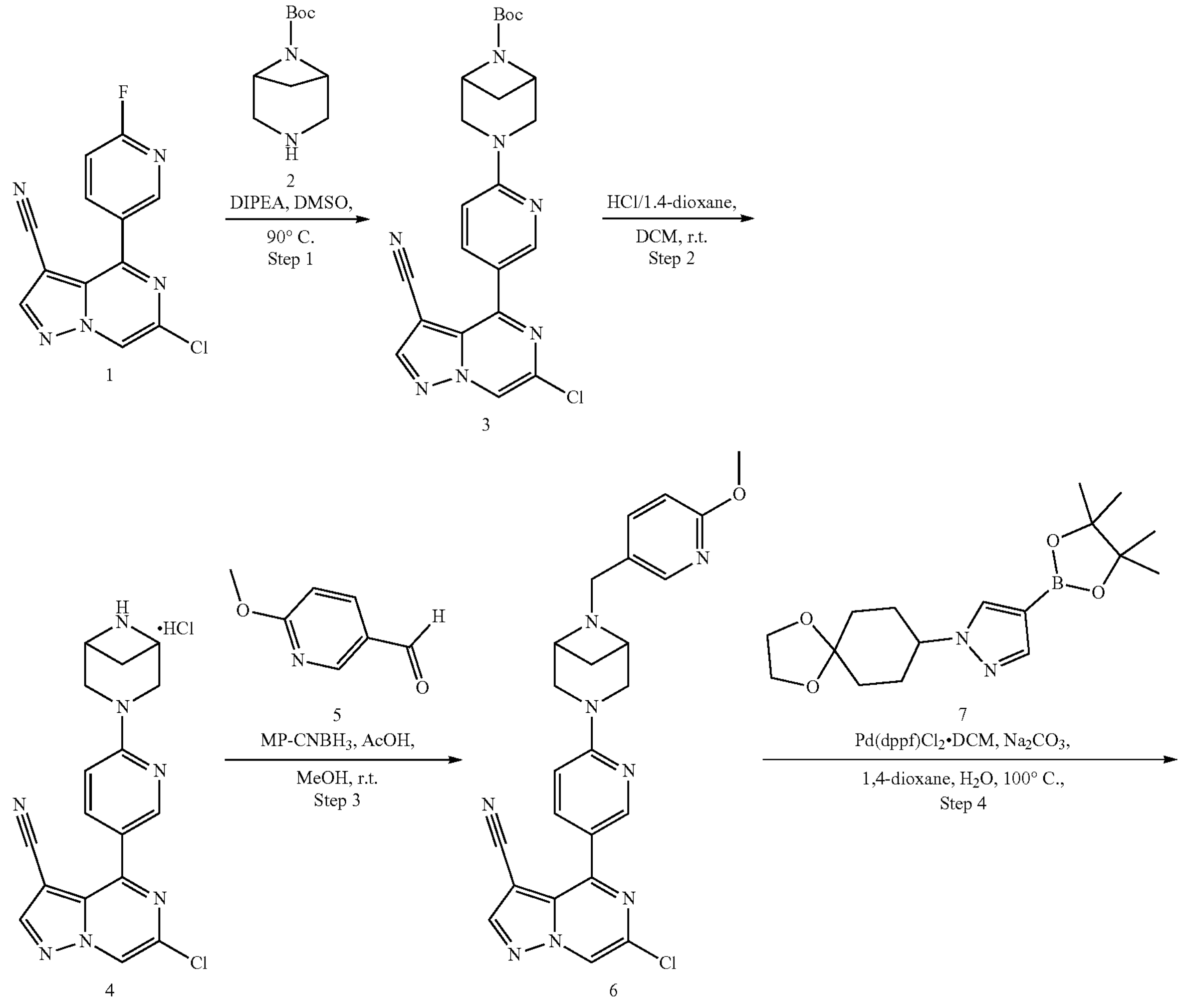

-continued
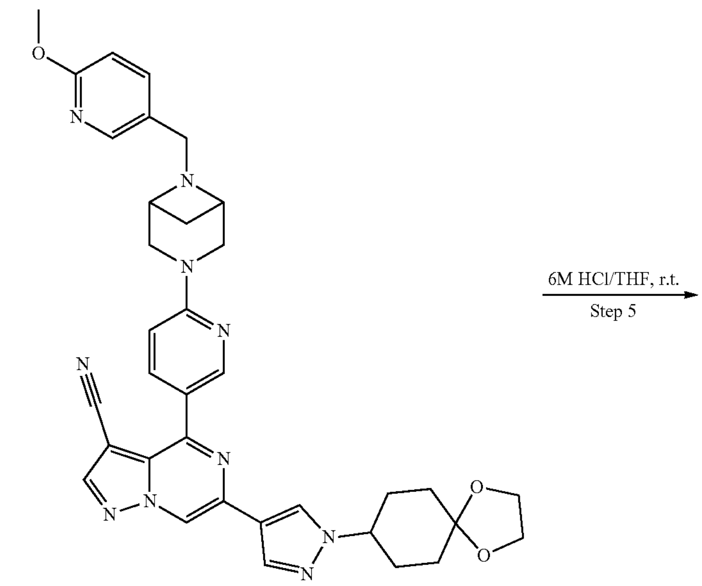
8
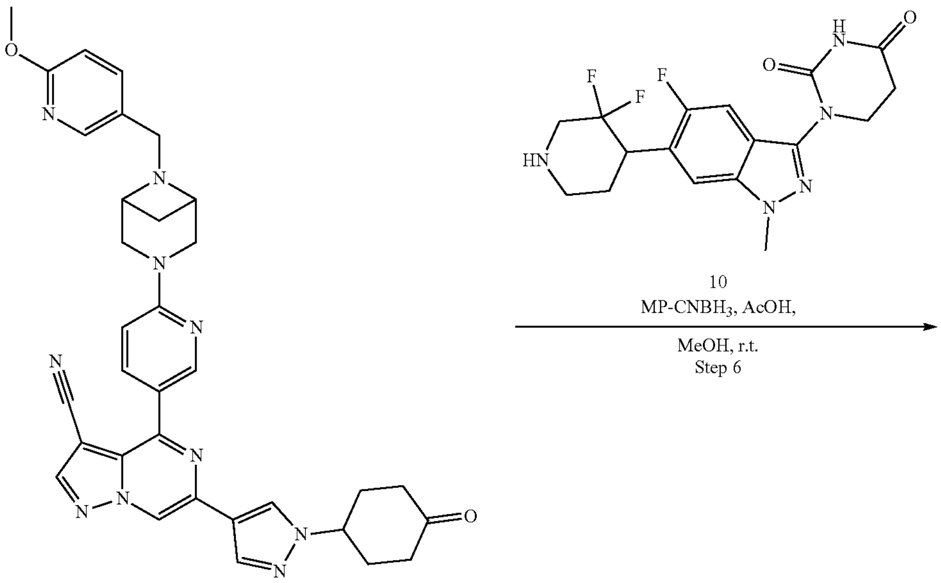
9

-continued

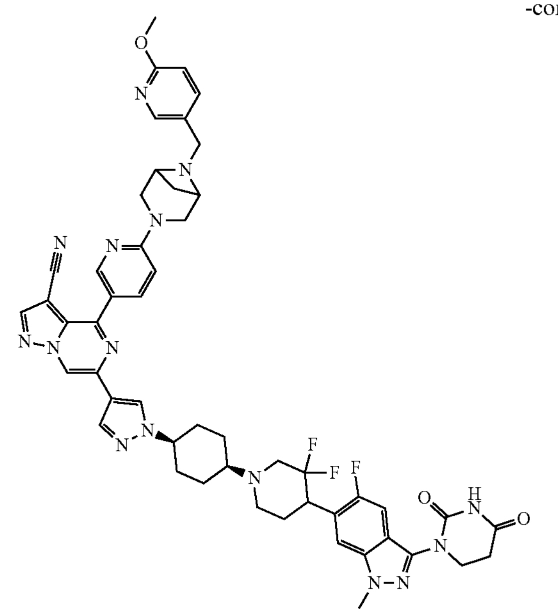

Compound 200

+

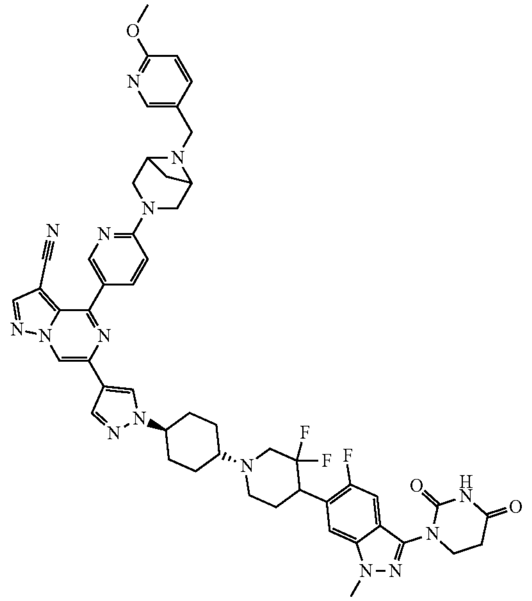

11

Step 1: Into a 250 mL sealed-tube containing a well-stirred solution of 6-chloro-4-(6-fluoro-3-pyridyl)pyrazolo[1,5-a]pyrazine-3-carbonitrile (1, 2.5 g, 9.14 mmol) and tert-butyl 3,6-diazabicyclo[3.1.1]heptane-6-carboxylate (2, 2.17 g, 10.96 mmol) in anhydrous DMSO (35 mL) was added DIPEA (5.90 g, 45.68 mmol, 7.96 mL) at ambient temperature. The resulting reaction was heated at 90° C. for 16 h and the reaction mixture was allowed to attain ambient temperature. The reaction mixture was quenched with water (100 mL) and the product was extracted with DCM (2×150 mL). The organic phases were combined, dried (anhydrous $Na_2SO_4$), filtered and the filtrate was concentrated under reduced pressure to get a crude residue. The crude product was purified by flash silica-gel (230-400 mesh; 100 g SNAP) column with 0-100% EtOAc/pet ether while desired compound was eluting at 70-80% of the mobile phase to afford tert-butyl 3-[5-(6-chloro-3-cyano-pyrazolo[1,5-a]pyrazin-4-yl)-2-pyridyl]-3,6-diazabicyclo[3.1.1]heptane-6-carboxylate (3, 3.9 g, 8.34 mmol, 91% yield) as a yellow solid. UPLC-MS ($ES^+$): m/z 452.5 $[M+H]^+$.

Step 2: Into a 250 mL single-necked round-bottomed flask containing a well-stirred solution of tert-butyl 3-[5-(6-chloro-3-cyano-pyrazolo[1,5-a]pyrazin-4-yl)-2-pyridyl]-3,6-diazabicyclo[3.1.1]heptane-6-carboxylate (3, 2 g, 4.43 mmol) in anhydrous DCM (30 mL) was added 4M HCl in 1,4-dioxane (20 mL) at ambient temperature under nitrogen atmosphere. The resulting mixture was stirred at ambient temperature for 2 h. After completion of the starting material as indicated by LCMS, excess solvent was removed from the reaction mixture under reduced pressure to get a crude mass. The crude product was washed with MTBE (50 mL) to get 6-chloro-4-[6-(3,6-diazabicyclo[3.1.1]heptan-3-yl)-3-pyridyl]pyrazolo[1,5-a]pyrazine-3-carbonitrile hydrochloride (4, 1.65 g, 4.04 mmol, 91% yield) as a yellow solid. UPLC-MS ($ES^+$): m/z 352.3 $[M+H]^+$.

Step 3: Into a 250 mL single-necked round-bottomed flask containing a well-stirred solution of 6-methoxypyridine-3-carbaldehyde (5, 584.73 mg, 4.26 mmol; CombiBlock) and 6-chloro-4-[6-(3,6-diazabicyclo[3.1.1]heptan-3-yl)-3-pyridyl]pyrazolo[1,5-a]pyrazine-3-carbonitrile hydrochloride (4, 1 g, 2.84 mmol) in a mixture of anhydrous MeOH (20 mL) and DCM (5 mL) was added Acetic acid (170.70 mg, 2.84 mmol, 0.627 mL) and the resulting mixture was stirred for 10 minutes at ambient temperature. MP-$CNBH_3$ (1.5 g, 2.84 mmol) was added to the reaction mixture at ambient temperature and the reaction mixture was stirred for 16 h. After complete consumption of the starting material as indicated by UPLC, the reaction mixture was filtered through a pad of Celite and Celite bed was washed with DCM (30 mL). Combined filtrate was concentrated under reduced pressure to get a crude residue. The crude product was purified by flash silica-gel (230-400 mesh; 50 g SNAP) column with 0-10% MeOH/DCM while desired compound was eluting at 3-5% of the mobile phase to afford 6-chloro-4-[6-[6-[(6-methoxy-3-pyridyl)methyl]-3,6-diazabicyclo[3.1.1]heptan-3-yl]-3-pyridyl]pyrazolo[1,5-a]pyrazine-3-carbonitrile (6, 1.1 g, 2.21 mmol, 78% yield) as an off white solid. UPLC-MS ($ES^+$): m/z 473.5 $[M+H]^+$.

Step 4: Into a 100 mL sealed-tube containing a well-stirred solution of 6-chloro-4-[6-[6-[(6-methoxy-3-pyridyl)methyl]-3,6-diazabicyclo[3.1.1]heptan-3-yl]-3-pyridyl]pyrazolo[1,5-a]pyrazine-3-carbonitrile (6, 300 mg, 0.634 mmol) and 1-(1,4-dioxaspiro[4.5]decan-8-yl)-4-(4,4,5,5-tetramethyl-1,3,2-dioxaborolan-2-yl)pyrazole (7, 318.01 mg, 0.951 mmol) in anhydrous 1,4-dioxane (6 mL) was added aqueous Sodium carbonate (2M, 0.951 mL) at ambient temperature under nitrogen atmosphere and the resulting mixture was degassed by bubbling nitrogen gas into the reaction mixture for 10 minutes. Subsequently, Pd(dppf)$Cl_2$.$CH_2Cl_2$ (51.80 mg, 0.063 mmol) was added to the reaction mixture and the reaction mixture was heated to 100° C. for 16 h. After completion of the reaction as indicated by UPLC, the reaction mixture was cooled to ambient temperature. The reaction mixture was diluted with water (20 mL) and the product was extracted with DCM (2×80 mL). The organic phases were combined, dried (anhydrous $Na_2SO_4$), filtered and the filtrate was concentrated under reduced pressure to get a crude residue. The crude product was purified by flash silica-gel (230-400 mesh; 50 g SNAP) with 0-10% MeOH/DCM while desired compound was eluting at 4-6% to afford 6-[1-(1,4-dioxaspiro[4.5]decan-8-yl)pyrazol-4-yl]-4-[6-[6-[(6-methoxy-3-pyridyl)methyl]-3,6-diazabicyclo[3.1.1]heptan-3-yl]-3-pyridyl]pyrazolo[1,5-a]pyrazine-3-carbonitrile (8, 320 mg, 0.471 mmol, 74% yield) as a yellow solid. UPLC-MS ($ES^+$): m/z 645.5 $[M+H]^+$.

Step 5: Into a 100 mL single-necked round-bottomed flask containing a well-stirred solution of 6-[1-(1,4-dioxaspiro[4.5]decan-8-yl)pyrazol-4-yl]-4-[6-[6-[(6-methoxy-3- pyridyl)methyl]-3,6-diazabicyclo[3.1.1]heptan-3-yl]-3-pyridyl]pyrazolo[1,5-a]pyrazine-3-carbonitrile (8, 320 mg, 0.496 mmol) in THF (8 mL) was added dropwise Hydrochloric acid, 6M aq. soln. (1.65 mL) at 0° C. After addition the reaction mixture was warmed to ambient temperature. The resulting mixture was stirred at ambient temperature for 1 h. After completion of the reaction as indicated by UPLC, excess acid was quenched by adding 10% sodium bicarbonate solution (100 mL) slowly at 0° C. and resulting mixture was stirred for 10 minutes while pH=7-8. Aqueous phase was extracted with DCM (2×80 mL). The combined organic phase was dried (anhydrous $Na_2SO_4$), filtered and the filtrate was concentrated under reduced pressure to obtain a crude residue. The crude residue was triturated with pet ether (10 mL) and solid thus formed was filtered, solid on the filter was dried under vacuum to afford 4-[6-[6-[(6-methoxy-3-pyridyl)methyl]-3,6-diazabicyclo[3.1.1]heptan-3-yl]-3-pyridyl]-6-[1-(4-oxocyclohexyl)pyrazol-4-yl]pyrazolo[1,5-a]pyrazine-3-carbonitrile (9, 295 mg, 0.456 mmol, 92% yield) as a yellow solid. UPLC-MS ($ES^+$): m/z 601.8 $[M+H]^+$.

Step 6: Into a 8 mL glass-vial, a well-stirred suspension of 1-[6-(3,3-difluoro-4-piperidyl)-5-fluoro-1-methyl-indazol-3-yl]hexahydropyrimidine-2,4-dione hydrochloride (10, 100 mg, 0.239 mmol) in MeOH (1 mL) was treated with amberlyst A21 free base resin (200 mg) and stirring was continued for 15 minutes. Subsequently, the suspension was filtered through filter paper and the filtrate was added to another 8 mL glass-vial containing 4-[6-[6-[(6-methoxy-3-pyridyl) methyl]-3,6-diazabicyclo[3.1.1]heptan-3-yl]-3-pyridyl]-6-[1-(4-oxocyclohexyl)pyrazol-4-yl]pyrazolo[1,5-a]pyrazine-3-carbonitrile (9, 143.77 mg, 0.239 mmol) in DCM (1 mL) and reaction mixture was stirred at ambient temperature for 5 minutes, then added Acetic acid (14.37 mg, 0.239 mmol, 0.013 mL) at ambient temperature. The resulting mixture was stirred at ambient temperature for 10 minutes, then MP-$CNBH_3$ (100 mg, 0.239 mmol) was added to the vial. The reaction mixture was stirred at ambient temperature for 16 h. The progress of the reaction was monitored by UPLC. The reaction mixture was diluted with DCM (5 mL) and filtered through a cotton plug, filtrate thus obtained was concentrated under reduced pressure to afford a crude solid, which was purified by prep HPLC purification following a method: Column: X-SELECT C18 (150×19 mm) 5 micron; Mobile phase: A: 0.1% $NH_4HCO_3$ in MQ-water; B: Acetonitrile; Flow rate: 15 mL/minutes; Fractions with RT=8.70 minutes were combined and lyophilized to afford 6-(1-((1s, 4s)-4-(4-(3-(2,4-Dioxotetrahydropyrimidin-1(2H)-yl)-5-fluoro-1-methyl-1H-indazol-6-yl)-3,3-difluoropiperidin-1-yl)cyclohexyl)-1H-pyrazol-4-yl)-4-(6-(6-((6-methoxypyridin-3-yl)methyl)-3,6-diazabicyclo[3.1.1]heptan-3-yl) pyridin-3-yl)pyrazolo[1,5-a]pyrazine-3-carbonitrile (Compound 200, Fast eluting isomer; 13 mg, 0.013 mmol, 5% yield) as a yellow fluffy solid. $^1H$ NMR (400 MHz, DMSO-$d_6$). δ 10.58 (s, 1H), 9.31 (s, 1H), 8.85 (s, 1H), 8.78 (d, J=2.4 Hz, 1H), 8.47 (s, 1H), 8.17 (s, 1H), 8.15 (s, 1H), 8.10 (s, 1H), 7.76 (d, J=5.2 Hz, 1H), 7.71 (d, J=8 Hz, 1H), 7.43 (d, J=10.4 Hz, 1H), 6.88 (d, J=8.8 Hz, 1H), 6.78 (d, J=8.4 Hz, 1H), 4.33-4.20 (m, 1H), 4.03 (s, 3H), 3.92 (t, J=6.8 Hz, 2H), 3.83 (s, 3H), 3.78 (m, 1H), 3.70 (m, 2H), 3.65-3.62 (m, 1H), 3.58-3.53 (m, 2H), 3.33 (m, 4H), 3.30-3.22 (m, 2H), 3.08-3.05 (m, 1H), 2.77 (t, J=6.8 Hz, 2H), 2.62-2.55 (m, 2H), 2.38-2.33 (m, 1H), 2.21-2.17 (m, 2H), 2.01.20-1.81 (m, 5H) and 1.63-1.50 (m, 3H). LCMS ($ES^+$): m/z 966.3 $[M+H]^+$.

Whereas fractions with RT=9.64 minutes were combined and lyophilized to afford 6-(1-((1r, 4r)-4-(4-(3-(2,4-dioxotetrahydropyrimidin-1(2H)-yl)-5-fluoro-1-methyl-1H-indazol-6-yl)-3,3-difluoropiperidin-1-yl)cyclohexyl)-1H-pyrazol-4-yl)-4-(6-(6-((6-methoxypyridin-3-yl)methyl)-3,6-diazabicyclo[3.1.1]heptan-3-yl)pyridin-3-yl)pyrazolo[1,5-a]pyrazine-3-carbonitrile (11; Late eluting isomer; 6 mg, 0.006 mmol, 3% yield) as a yellow solid. $^1H$ NMR (400 MHz, DMSO-$d_6$). δ 10.58 (s, 1H), 9.36 (s, 1H), 8.86 (s, 1H), 8.78 (d, J=2.4 Hz, 1H), 8.52 (s, 1H), 8.21 (s, 1H), 8.16 (dd, J=8.8, 2.4 Hz, 1H), 8.09 (s, 1H), 7.75 (d, J=5.2 Hz, 1H), 7.70 (d, J=8.8 Hz, 1H), 7.42 (d, J=10.4 Hz, 1H), 6.88 (d, J=8.8 Hz, 1H), 6.77 (d, J=8.4 Hz, 1H), 4.39-4.32 (m, 1H), 4.03 (s, 3H), 3.92 (t, J=6.8 Hz, 2H), 3.83 (s, 3H), 3.81-3.75 (m, 2H), 3.70-3.62 (m, 3H), 3.58-3.53 (m, 2H), 3.33 (m, 4H), 3.30-3.22 (m, 1H), 3.20-3.15 (m, 1H), 2.76 (t, J=6.8 Hz, 2H), 2.62-2.55 (m, 2H), 2.45-2.38 (m, 1H), 2.30-2.20 (m, 2H), 1.98-1.81 (m, 5H) and 1.73-1.60 (m, 3H). LCMS ($ES^+$): m/z 966.3 $[M+H]^+$.

Example 203: Synthesis of 6-(1-((1s, 4s)-4-(4-(4-((2,6-Dioxopiperidin-3-yl)amino)-2,6-difluorophenyl)piperazin-1-yl)cyclohexyl)-1H-pyrazol-4-yl)-4-(6-(4-((R)-2-methoxy-2-phenylacetyl)piperazin-1-yl) pyridin-3-yl)pyrazolo[1,5-a]pyrazine-3-carbonitrile (Compound 201)

(Configurations are arbitrarily assigned)

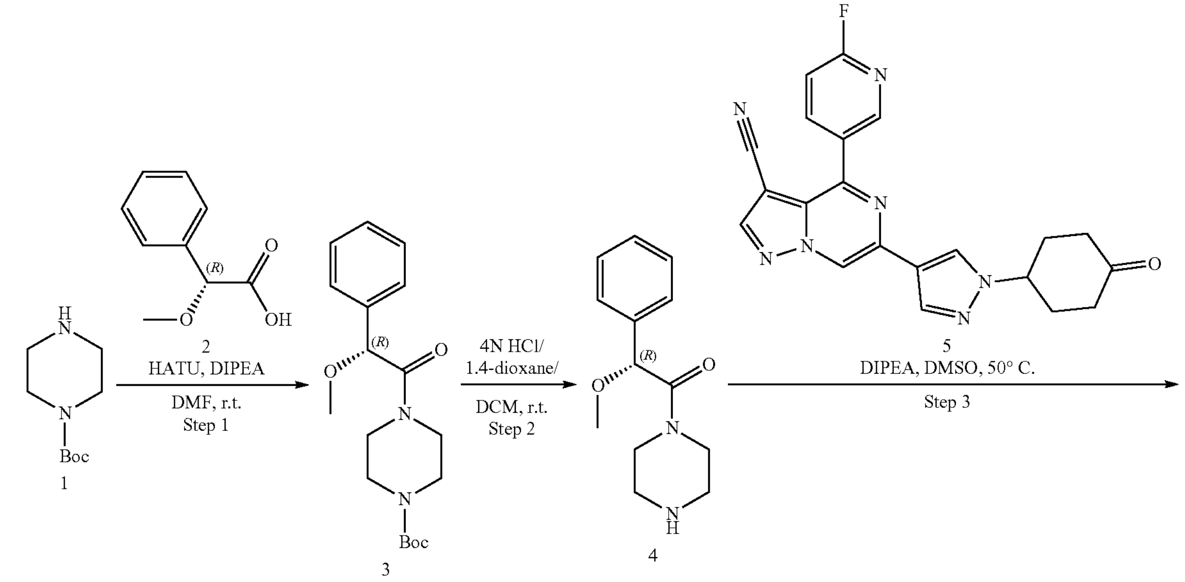

-continued
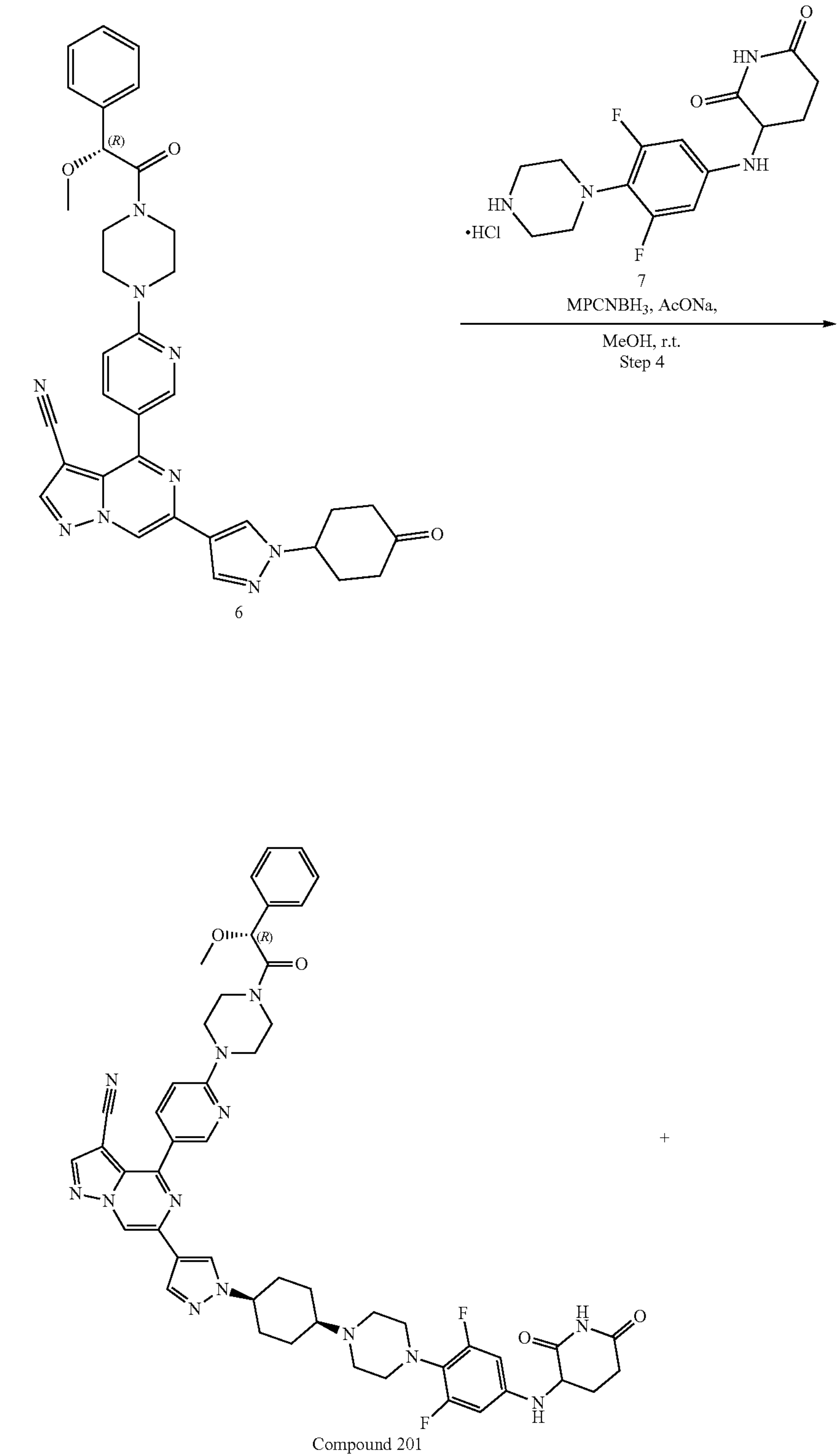
6
7
Compound 201

-continued

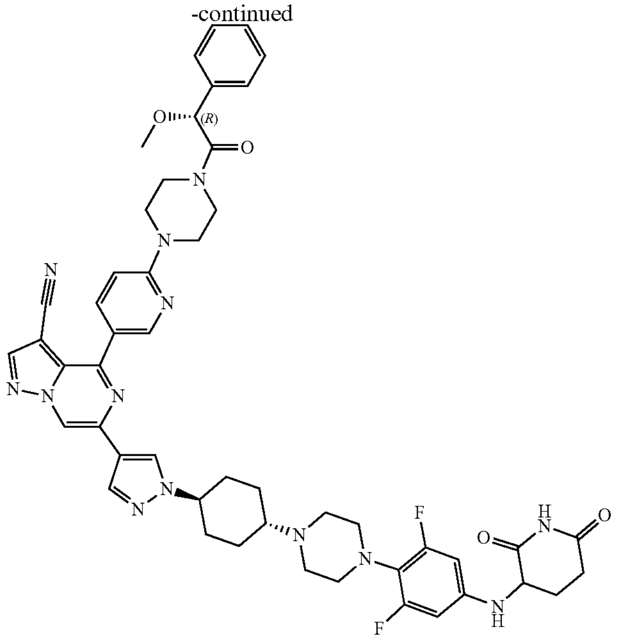

8

Step 1: Into a 100 mL single-necked round-bottomed flask containing a well-stirred solution of (2R)-2-methoxy-2-phenyl-acetic acid (2, 1.0 g, 6.02 mmol) and tert-butyl piperazine-1-carboxylate (1; 1.34 g, 7.22 mmol) in anhydrous DMF (10 mL) was added DIPEA (3.89 g, 30.09 mmol, 5.24 mL) and the resulting solution was stirred for 5 minutes at ambient temperature. Subsequently, HATU (2.75 g, 7.22 mmol) was added and stirring was continued at ambient temperature under nitrogen atmosphere. The reaction mixture was monitored by UPLC and found complete after 16 h. The reaction mixture was carefully added to ice-cold water (30 mL) and the aqueous layer was extracted with EtOAc (2×30 mL). Combined organic phase was washed successively with water (2×80 mL) and brine, dried (anhydrous $Na_2SO_4$), filtered and the filtrate was concentrated under reduced pressure to afford a crude mass. The crude was purified by flash silica-gel (230-400 mesh, 25 g) column with 0-100% EtOAc/pet ether while the desired product was eluting at 50-60% of the mobile phase to afford tert-butyl 4-[(2R)-2-methoxy-2-phenyl-acetyl]piperazine-1-carboxylate (3; 1.3 g, 3.87 mmol, 64% yield) as an off-white solid. LCMS ($ES^+$): m/z 335.6 $[M+H]^+$.

Step 2: Into a 100 mL single-necked round-bottomed flask containing a well-stirred solution of tert-butyl 4-[(2R)-2-methoxy-2-phenyl-acetyl]piperazine-1-carboxylate (3, 1.3 g, 3.89 mmol) in anhydrous DCM (16 mL) was added 4M HCl in 1,4-dioxane, 99% (10 mL) dropwise at ambient temperature under nitrogen atmosphere. The resulting mixture was stirred at ambient temperature under nitrogen atmosphere. The reaction was monitored by UPLC and found complete after 2 h. Excess solvent was removed under reduced pressure to afford a crude mass. The crude mass was triturated with pet ether (2×30 mL) and solid thus precipitated out was filtered to afford (2R)-2-methoxy-2-phenyl-1-piperazin-1-yl-ethanone hydrochloride (4; 1.0 g, 3.66 mmol, 94% yield) as an off-white solid. LCMS ($ES^+$): m/z 235.1 $[M+H]^+$.

Step 3: Into a 50 mL sealed-tube containing a well-stirred solution of (2R)-2-methoxy-2-phenyl-1-piperazin-1-yl-ethanone hydrochloride (4, 283.30 mg, 1.05 mmol) and 4-(6-fluoro-3-pyridyl)-6-[1-(4-oxocyclohexyl)pyrazol-4-yl]pyrazolo[1,5-a]pyrazine-3-carbonitrile (5, 300 mg, 0.747 mmol) in anhydrous DMSO (5 mL) was added DIPEA (482.96 mg, 3.74 mmol, 0.650 mL) under nitrogen atmosphere. The resulting mixture was stirred at 50° C. The reaction was monitored by UPLC and found complete after 14 h. The reaction mixture was cooled to room temperature and added slowly to ice-cold water (50 mL) and solid thus obtained was filtered. The crude solid was purified by flash silica-gel (230-400 mesh) column with 50-100% EtOAc/pet ether while desired compound was eluting at 100% of the mobile phase to afford 4-[6-[4-[(2R)-2-methoxy-2-phenyl-acetyl]piperazin-1-yl]-3-pyridyl]-6-[1-(4-oxocyclohexyl)pyrazol-4-yl]pyrazolo[1,5-a]pyrazine-3-carbonitrile (6, 200 mg, 0.270 mmol, 36% yield) as a yellow solid. LCMS ($ES^+$): m/z 616.3 $[M+H]^+$.

Step 4: Into a 10 mL glass-capped vial containing a well-stirred suspension of 4-[6-[4-[(2R)-2-methoxy-2-phenyl-acetyl]piperazin-1-yl]-3-pyridyl]-6-[1-(4-oxocyclohexyl)pyrazol-4-yl]pyrazolo[1,5-a]pyrazine-3-carbonitrile (6, 150 mg, 0.243 mmol,) and 3-(3,5-difluoro-4-piperazin-1-yl-anilino)piperidine-2,6-dione hydrochloride (7, 175.80 mg, 0.487 mmol) in anhydrous MeOH (5 mL) and DMSO (0.2 mL) was added Sodium acetate, anhydrous (99.93 mg, 1.22 mmol) at ambient temperature. The mixture was stirred at ambient temperature for 10 minutes. Subsequently, MP-$CNBH_3$ (200 mg, 0.243 mmol) was added and the resulting mixture was stirred at ambient temperature. The reaction was monitored by UPLC and found complete after 16 h. The reaction mixture was diluted with DCM (5 mL) and filtered through a pad of Celite and the Celite bed was washed with MeOH (10 mL). Combined filtrate was concentrated under reduced pressure to afford a crude solid. The crude solid was purified by prep HPLC [Column: X-SELECT C18(150×19) MM, 5 MICRONS; Mobile phase: (10 mM Ammonium bicarbonate in water/ACN)], Flow rate: 15 mL/minutes; the fractions with RT=13.9 minutes were combined and lyophilized to afford 6-(1-((1s, 4s)-4-(4-(4-((2,6-dioxopiperidin-3-yl)amino)-2,6-difluorophenyl)piperazin-1-yl)cyclohexyl)-1H-pyrazol-4-yl)-4-(6-(4-((R)-2-methoxy-2-phenylacetyl)piperazin-1-yl)pyridin-3-yl)pyrazolo[1,5-a]pyrazine-3-carbonitrile (Compound 201, Early eluting isomer; 25 mg, 0.026 mmol, 11% yield) as a yellow fluffy solid. $^1$H NMR (400 MHz, DMSO-$d_6$). δ 10.83 (s, 1H), 9.30 (s, 1H), 8.83 (s, 1H), 8.68 (d, J=2 Hz, 1H), 8.45 (s, 1H), 8.15 (s, 1H), 8.09 (d, J=8.8 Hz, 1H), 7.42-7.34 (m, 5H), 7.00 (d, J=9.2 Hz, 1H), 6.33 (d, J=12 Hz, 2H), 6.27 (d, J=6.4 Hz, 1H), 5.28 (s, 1H), 4.32-4.29 (m, 1H), 4.23-4.20 (m, 1H), 3.64 (s, 3H), 3.60 (m, 5H), 3.29 (m, 4H), 2.75-2.69 (m, 8H), 2.22-2.19 (m, 3H), 2.12 (m, 1H), 2.02-2.00 (m, 2H), 1.91-1.85 (m, 4H) and 1.53 (m, 2H). LCMS (ES$^+$): m/z 924.3 $[M+H]^+$.

Whereas fractions with RT=16.9 minutes were combined and lyophilized to afford 6-(1-((1r, 4r)-4-(4-(4-((2,6-dioxopiperidin-3-yl)amino)-2,6-difluorophenyl)piperazin-1-yl)cyclohexyl)-1H-pyrazol-4-yl)-4-(6-(4-((R)-2-methoxy-2-phenylacetyl)piperazin-1-yl)pyridin-3-yl)pyrazolo[1,5-a]pyrazine-3-carbonitrile (8, Late eluting isomer; 28 mg, 0.030 mmol, 12% yield) as a yellow solid. $^1$H NMR (400 MHz, DMSO-$d_6$). δ 10.82 (s, 1H), 9.36 (s, 1H), 8.83 (s, 1H), 8.68 (d, J=1.6 Hz, 1H), 8.49 (s, 1H), 8.16 (s, 1H), 8.09 (dd, J=9.2, 2 Hz, 1H), 7.42-7.34 (m, 5H), 7.00 (d, J=9.2 Hz, 1H), 6.33 (d, J=12 Hz, 2H), 6.26 (d, J=7.2 Hz, 1H), 5.28 (s, 1H), 4.31 (m, 2H), 3.66 (s, 3H), 3.60 (m, 5H), 3.00 (m, 4H), 2.74-2.71 (m, 2H), 2.55 (m, 4H), 2.34-2.33 (m, 4H), 2.14-2.11 (m, 2H), 1.90-1.86 (m, 6H) and 1.65 (m, 2H). LCMS (ES$^+$): m/z 924.3 $[M+H]^+$.

Example 204: Synthesis of 4-(6-(5H-spiro[furo[3,4-b]pyridine-7,4'-piperidin]-1'-yl)pyridin-3-yl)-6-(1-((1s, 4s)-4-(4-(4-((2,6-dioxopiperidin-3-yl)amino)-2,6-difluorophenyl)piperazin-1-yl)cyclohexyl)-1H-pyrazol-4-yl)pyrazolo[1,5-a]pyridine-3-carbonitrile (Compound 202)

(Configurations are arbitrarily assigned)

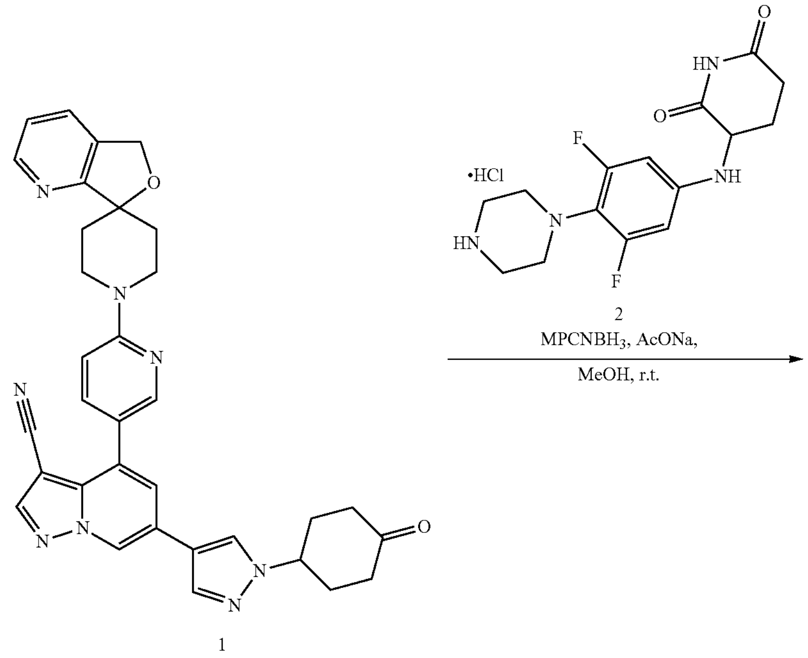

-continued

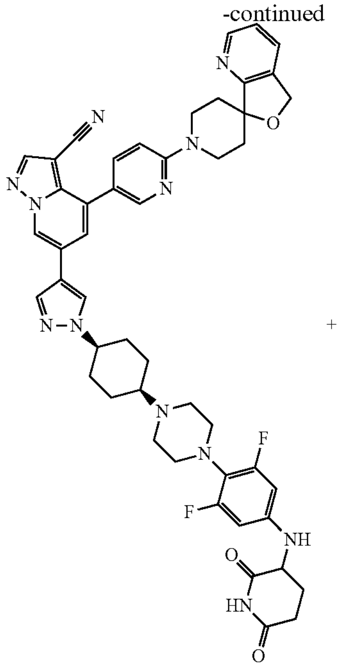

Compound 202

+

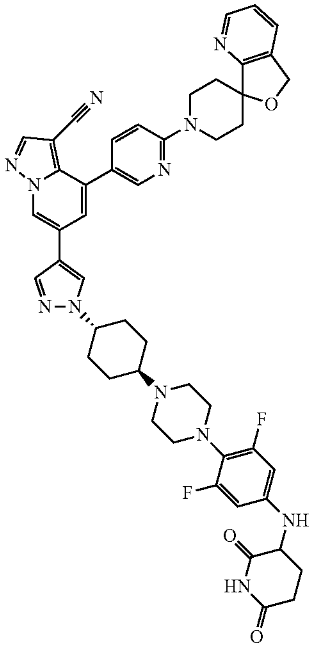

3

Into a 100 mL single-necked round-bottomed flask containing a well-stirred solution of 6-[1-(4-oxocyclohexyl)pyrazol-4-yl]-4-(6-spiro[5H-furo[3,4-b]pyridine-7,4'-piperidine]-1'-yl-3-pyridyl)pyrazolo[1,5-a]pyridine-3-carbonitrile (1, 150 mg, 0.262 mmol) and 3-(3,5-difluoro-4-piperazin-1-yl-anilino)piperidine-2,6-dione hydrochloride (2, 189.67 mg, 0.525 mmol) in a mixture of anhydrous DMSO (1.5 mL) and MeOH (8 mL) was added anhydrous Sodium acetate (107.81 mg, 1.31 mmol) at ambient temperature under nitrogen atmosphere. The resulting mixture was stirred at ambient temperature for 10 minutes. Subsequently, MP-$CNBH_3$ (200 mg) was added, and the mixture was stirred at ambient temperature. The reaction was monitored by UPLC and found complete after 16 h. The reaction mixture was diluted with DCM (5 mL) and filtered through a pad of Celite and the Celite bed was washed with MeOH (10 mL). Combined filtrate was concentrated under reduced pressure to afford a crude solid. The crude was purified by prep HPLC [Column: X-SELECT C18(150×19) MM 5 MICRONS; Mobile phase: (10 mM Ammonium bicarbonate in water/ACN), Flow rate: 15 mL/minutes; fractions with RT=11.4 minutes were combined and lyophilized to afford 4-(6-(5H-spiro[furo[3,4-b]pyridine-7,4'-piperidin]-1'-yl)pyridin-3-yl)-6-(1-((1s, 4s)-4-(4-(4-((2,6-dioxopiperidin-3-yl)amino)-2,6-difluorophenyl)piperazin-1-yl)cyclohexyl)-1H-pyrazol-4-yl)pyrazolo[1,5-a]pyridine-3-carbonitrile (Compound 202, Early eluting isomer; 8 mg, 0.08 mmol, 3% yield) as a yellow fluffy solid. $^1H$ NMR (400 MHz, DMSO-$d_6$). δ 10.82 (s, 1H), 9.25 (d, J=1.2 Hz, 1H), 8.67 (s, 1H), 8.57 (s, 1H), 8.44-8.42 (m, 2H), 8.16 (s, 1H), 7.88-7.84 (m, 2H), 7.79 (d, J=7.6 Hz, 1H), 7.31 (dd, J=7.6, 4.8 Hz, 1H), 7.09 (d, J=8.8 Hz, 1H), 6.35-6.31 (d, J=12.4 Hz, 2H), 6.26 (d, J=7.6 Hz, 1H), 5.10 (s, 2H), 4.41-4.38 (m, 2H), 4.28-4.26 (m, 1H), 4.16 (m, 1H), 3.51-3.44 (m, 2H), 3.07-3.01 (m, 4H), 2.75-2.72 (m, 1H), 2.61 (m, 4H), 2.46-2.43 (m, 2H), 2.34-2.21 (m, 2H), 2.14-2.11 (m, 1H), 2.05-2.02 (m, 4H), 1.92-1.82 (m, 5H) and 1.52-1.49 (m, 2H). LCMS ($ES^+$): m/z 879.3 $[M+H]^+$.

Whereas the fractions with RT=13.3 minutes were combined and lyophilized to afford 4-(6-(5H-spiro[furo[3,4-b]pyridine-7,4'-piperidin]-1'-yl)pyridin-3-yl)-6-(1-((1r, 4r)-4-(4-(4-((2,6-dioxopiperidin-3-yl)amino)-2,6-difluorophenyl)piperazin-1-yl)cyclohexyl)-1H-pyrazol-4-yl)pyrazolo[1,5-a]pyridine-3-carbonitrile (3, Late eluting isomer; 11 mg, 0.012 mmol, 5% yield) as a yellow solid. $^1H$ NMR (400 MHz, DMSO-$d_6$). δ 10.80 (s, 1H), 9.30 (d, J=1.2 Hz, 1H), 8.66 (s, 1H), 8.59 (s, 1H), 8.43 (d, J=2.4 Hz, 2H), 8.19 (s, 1H), 7.93 (d, J=1.2 Hz, 1H), 7.86 (dd, J=8.8, 2.8 Hz, 1H), 7.79 (d, J=6.4 Hz, 1H), 7.31 (dd, J=7.6, 4.8 Hz, 1H), 7.09 (d, J=8.8 Hz, 1H), 6.32 (d, J=12 Hz, 2H), 6.24 (d, J=8 Hz, 1H), 5.10 (s, 2H), 4.45-4.42 (m, 2H), 4.32-4.29 (m, 2H), 3.43-3.40 (m, 2H), 2.99 (m, 4H), 2.75 (m, 1H), 2.55 (m, 4H), 2.34-2.25 (m, 4H), 2.05 (m, 1H), 1.98-1.86 (m, 7H) and 1.73-1.61 (m, 4H). LCMS ($ES^+$): m/z 879.3 $[M+H]^+$.

Example 205: Synthesis of 6-(1-((1s, 4s)-4-(4-(4-((2,6-Dioxopiperidin-3-yl)amino)-2,6-difluorophenyl)piperazin-1-yl)cyclohexyl)-1H-pyrazol-4-yl)-4-(6-(4-((6-methoxypyridin-3-yl)amino)piperidin-1-yl)pyridin-3-yl)pyrazolo[1,5-a]pyrazine-3-carbonitrile (Compound 203)
(Configurations are arbitrarily assigned)
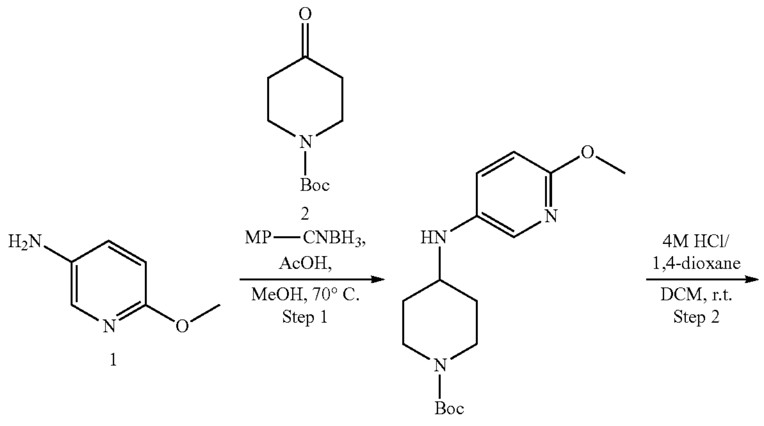
1
3
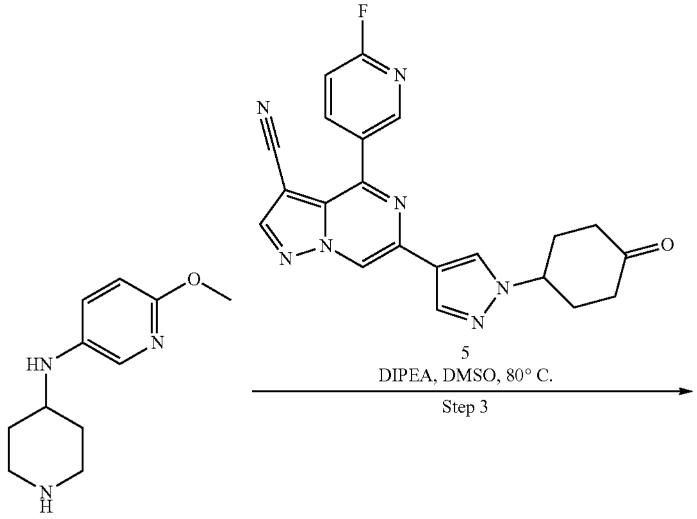
4

-continued
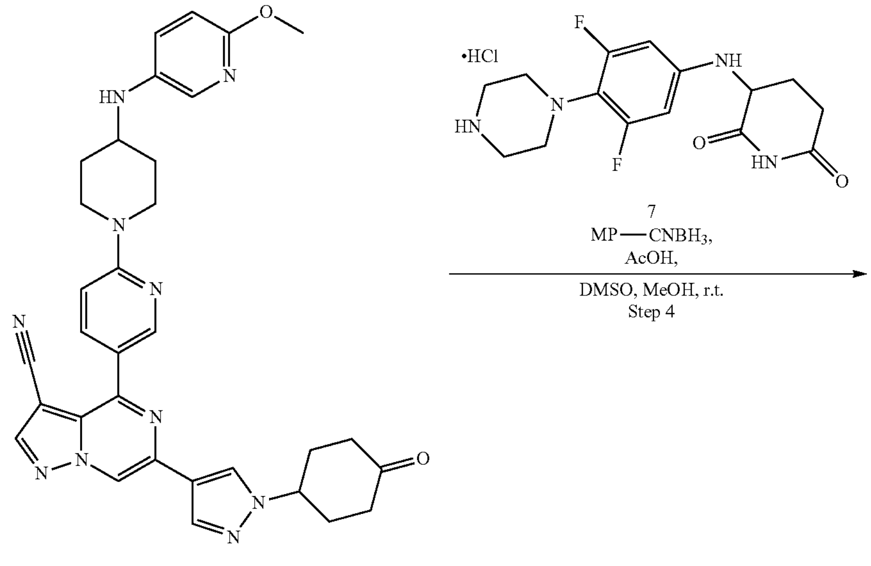
6
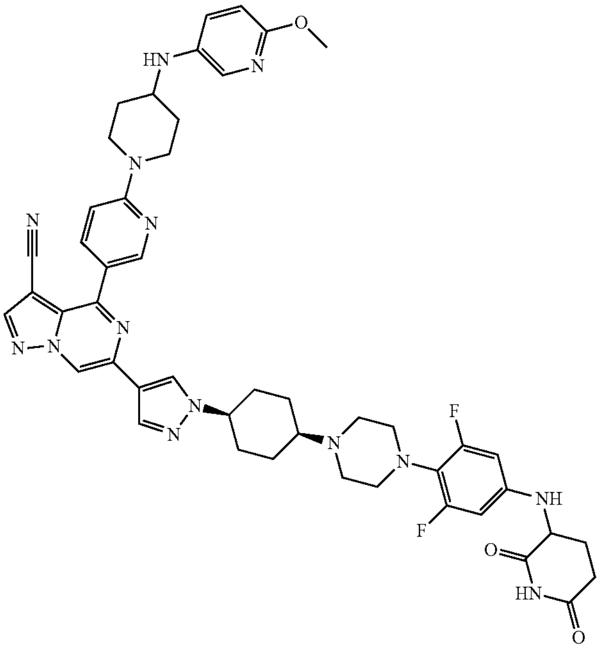
+
Compound 203

-continued

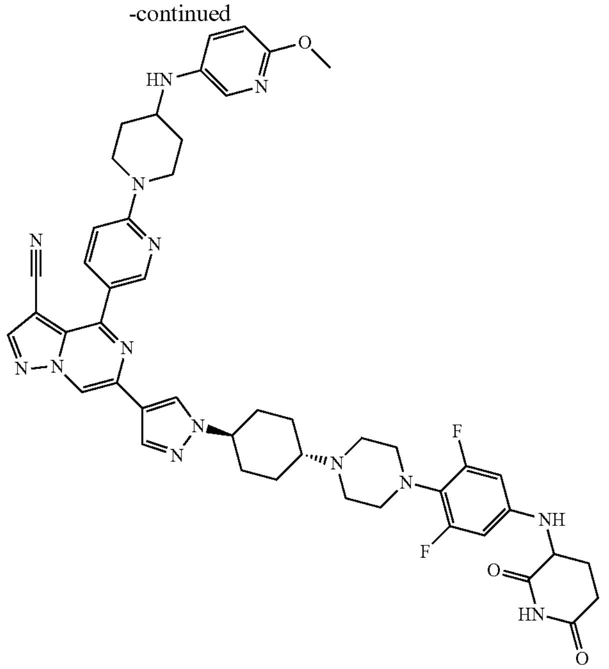

8

Step 1: Into a 8 mL glass-vial containing a well stirred solution of 6-methoxypyridin-3-amine (1, 623.05 mg, 5.02 mmol) and tert-butyl 4-oxopiperidine-1-carboxylate (2, 1 g, 5.02 mmol) in MeOH (10 mL) were added MP-$CNBH_3$ (2 g, 5.02 mmol) and AcOH (5.02 mmol, 2 mL) and the resulting mixture was stirred 70° C. for 16 h. After completion of the reaction as monitored by TLC, the reaction mixture was filtered, and the filtrate was concentrated under reduced pressure to get a crude mass. The crude product was purified by silica-gel (230-400 mesh, 50 g) column with 0-100% EtOAc/pet ether while desired compound was eluting at 70-85% to afford tert-butyl 4-[(6-methoxy-3-pyridyl)amino]piperidine-1-carboxylate (3, 1.2 g, 3.83 mmol, 76% yield) as a yellow semi-solid. LCMS ($ES^+$): m/z 308.3 $[M+H]^+$.

Step 2: Into a 25 mL single-necked round-bottomed flask containing a well-stirred solution of tert-butyl 4-[(6-methoxy-3-pyridyl)amino]piperidine-1-carboxylate (3, 1.2 g, 3.90 mmol) in anhydrous DCM (4 mL) was added 4N HCl in 1,4-dioxane (3 mL) at ambient temperature under nitrogen atmosphere. The resulting mixture was stirred at ambient temperature under nitrogen atmosphere and the reaction was monitored by UPLC and found complete after 2 h. After completion of the reaction, excess solvent was removed from the reaction mixture under reduced pressure to get a crude mass. The crude product was washed with methyl tert-butyl ether (10 mL) to get the 6-methoxy-N-(4-piperidyl)pyridin-3-amine hydrochloride (4, 900 mg, 2.51 mmol, 64% yield) as a brown solid. LCMS ($ES^+$): m/z 208.2 $[M+H]^+$.

Step 3: Into a 25 mL sealed tube containing a well-stirred solution of 6-methoxy-N-(4-piperidyl)pyridin-3-amine hydrochloride (4; 900 mg, 3.69 mmol) in dry DMSO (5 mL) were added DIPEA (954.46 mg, 7.39 mmol, 1.29 mL) and 4-(6-fluoro-3-pyridyl)-6-[1-(4-oxocyclohexyl)pyrazol-4-yl]pyrazolo[1,5-a]pyrazine-3-carbonitrile (5, 592.87 mg, 1.48 mmol). The resulting reaction mixture was stirred at 80° C. under closed condition. After completion of the reaction as monitored by TLC (16 h later), the reaction mixture was diluted with ice-water (10 mL) and extracted with EtOAc (2×15 mL). Organic phases were combined, dried (anhydrous $Na_2SO_4$), filtered and the filtrate was concentrated under reduced pressure to get a crude mass. The crude product was purified by silica-gel (230-400 mesh) column with 0-100% EtOAc/pet ether while desired compound was eluting at 70-85% of the mobile phase to afford 4-[6-[4-[(6-methoxy-3-pyridyl)amino]-1-piperidyl]-3-pyridyl]-6-[1-(4-oxocyclohexyl)pyrazol-4-yl]pyrazolo[1,5-a]pyrazine-3-carbonitrile (6, 800 mg, 1.29 mmol, 87% yield) as a green solid. LCMS ($ES^+$): m/z 589.3 $[M+H]^+$.

Step 4: Into a 8 mL glass-vial containing a well-stirred solution of 4-[6-[4-[(6-methoxy-3-pyridyl)amino]-1-piperidyl]-3-pyridyl]-6-[1-(4-oxocyclohexyl)pyrazol-4-yl]pyrazolo[1,5-a]pyrazine-3-carbonitrile (6, 150 mg, 0.254 mmol) and 3-(3,5-difluoro-4-piperazin-1-yl-anilino)piperidine-2,6-dione (7, 123.96 mg, 0.382 mmol) in a mixture of MeOH (3 mL) and DMSO (0.2 mL) was added AcOH (0.254 mmol, 0.05 mL) and the resulting mixture was stirred at ambient temperature for 20 minutes. Subsequently, MP-$CNBH_3$ (250 mg, 0.254 mmol) was to the vial and the stirring was continued at ambient temperature for 16 h. The reaction was monitored by UPLC to observe 11% and 13% desired product mass, respectively.

The suspended solid was filtered off and filtrate was concentrated under reduced pressure to obtain a crude mass. The crude product was purified by flash silica-gel (230-400 mesh) column with 0 to 10% MeOH/DCM while desired compound was eluting at 5-8% of the mobile phase to afford desired product with 89% purity−41%+43% diastereomers by UPLC. The crude material was purified by reverse phase preparatory HPLC [Purification method: X-Bridge OBD C18 (19×150) 5 micron; Mobile phase A: 0.1% ammonium bicarbonate in $H_2O$ and Mobile phase B: MeCN; the fractions as having eluted fast were combined and lyophilized to afford 6-[1-[4-[4-[4-[(2,6-dioxo-3-piperidyl)amino]-2,6-difluoro-phenyl]piperazin-1-yl]cyclohexyl]pyrazol-4-yl]-4-[6-[4-[(6-methoxy-3-pyridyl)amino]-1-piperidyl]-3-pyridyl] pyrazolo[1,5-a]pyrazine-3-carbonitrile (Compound 203, Early eluting isomer; 9.5 mg, 0.010 mmol, 4% yield) as a light yellow solid. $^1$H NMR (400 MHz, DMSO-$d_6$). δ 10.81 (s, 1H), 9.28 (s, 1H), 8.84 (s, 1H), 8.70 (d, J=2.8 Hz, 1H), 8.46 (s, 1H), 8.15 (s, 1H), 8.08 (dd, J=9, 2.4 Hz, 1H), 7.58 (d, J=2.8 Hz, 1H), 7.12 (dd, J=8.8, 2.8 Hz, 1H), 7.05 (d, J=8.8 Hz, 1H), 6.62 (d, J=8.8 Hz, 1H), 6.33 (d, J=12 Hz, 2H), 6.25 (d, J=7.6 Hz, 1H), 5.22 (d, J=8.4 Hz, 1H), 4.41-4.37 (m, 3H), 4.20 (m, 1H), 3.74 (s, 3H), 3.51 (m, 1H), 3.23-3.20 (m, 2H), 3.01-2.98 (m, 4H), 2.74 (m, 1H), 2.67-2.58 (m, 5H), 2.40 (m, 1H), 2.17-2.14 (m, 2H), 2.08-1.99 (m, 5H), 1.88-1.84 (m, 3H) and 1.39-1.36 (m, 4H). LCMS ($ES^+$): m/z 897.1 $[M+H]^+$.

Whereas fractions as having eluted late were combined and lyophilized to obtain 6-[1-[4-[4-[4-[(2,6-dioxo-3-piperidyl)amino]-2,6-difluoro-phenyl]piperazin-1-yl]cyclohexyl]pyrazol-4-yl]-4-[6-[4-[(6-methoxy-3-pyridyl)amino]-1-piperidyl]-3-pyridyl]pyrazolo[1,5-a]pyrazine-3-carbonitrile (8, Late eluting isomer; 10 mg, 0.010 mmol, 4% yield) as a light yellow solid. $^1$H NMR (400 MHz, DMSO-$d_6$). δ 10.80 (s, 1H), 9.34 (s, 1H), 8.83 (s, 1H), 8.70 (d, J=2.4 Hz, 1H), 8.50 (s, 1H), 8.17 (s, 1H), 8.08 (dd, J=9, 2.4 Hz, 1H), 7.58 (d, J=2.8 Hz, 1H), 7.12 (dd, J=8.8, 2.8 Hz, 1H), 7.06 (d, J=8.8 Hz, 1H), 6.62 (d, J=8.8 Hz, 1H), 6.32 (d, J=12.4 Hz, 2H), 6.24 (d, J=7.6 Hz, 1H), 5.22 (d, J=8.8 Hz, 1H), 4.41-4.31 (m, 4H), 3.74 (s, 3H), 3.51 (m, 1H), 3.23-3.20 (m, 2H), 3.20-3.00 (m, 4H), 2.73-2.70 (m, 1H), 2.69-2.67 (m, 5H), 2.34-2.34 (m, 3H), 2.28-2.00 (m, 3H), 1.89-1.84 (m, 5H), 1.70-1.59 (m, 2H) and 1.39-1.36 (m, 2H). LCMS ($ES^+$): m/z 897.1 $[M+H]^+$.

Example 206: Synthesis of 4-(6-(1-(4-Chloropyrimidin-2-yl)-1,7-diazaspiro[3.5]nonan-7-yl)pyridin-3-yl)-6-(1-((1s, 4s)-4-(4-(4-((2,6-dioxopiperidin-3-yl)amino)-2,6-difluorophenyl)piperazin-1-yl)cyclohexyl)-1H-pyrazol-4-yl)pyrazolo[1,5-a]pyrazine-3-carbonitrile (12) (Compound 204)

(Configurations are arbitrarily assigned)

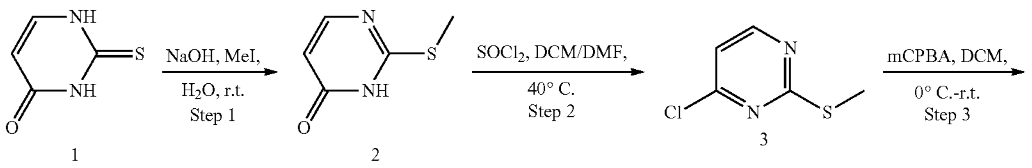

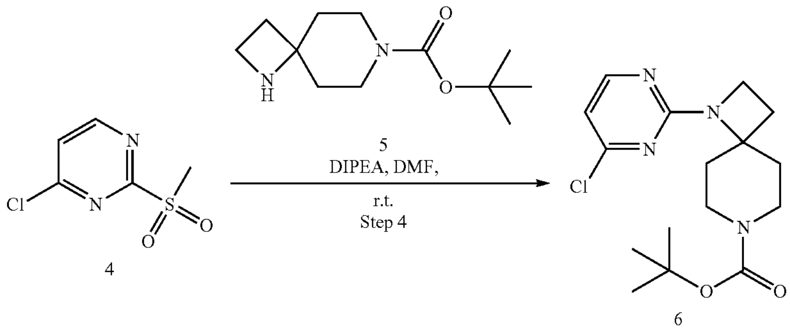

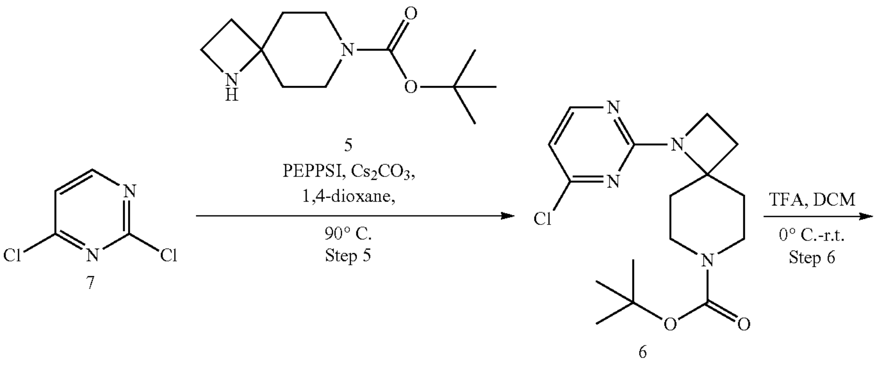

-continued
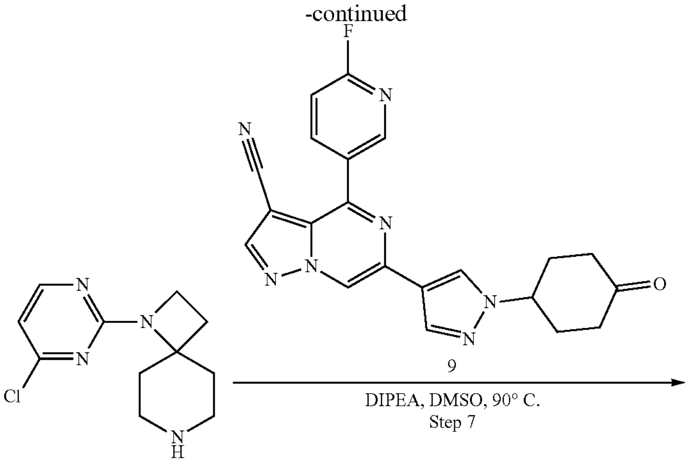
8
9
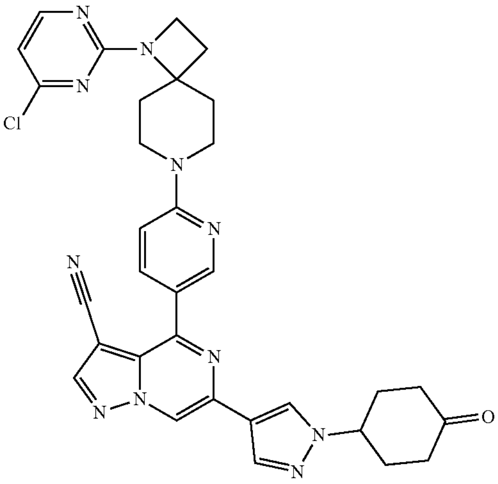
10
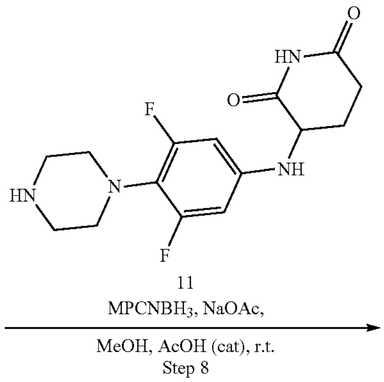
11
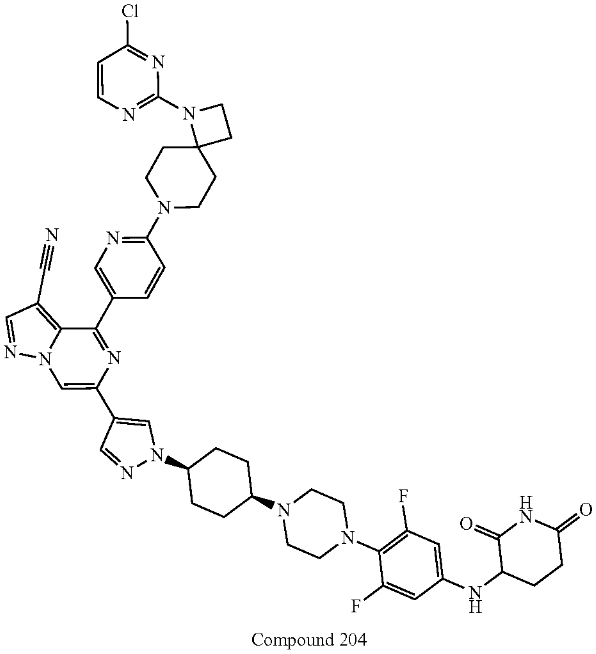
Compound 204

-continued

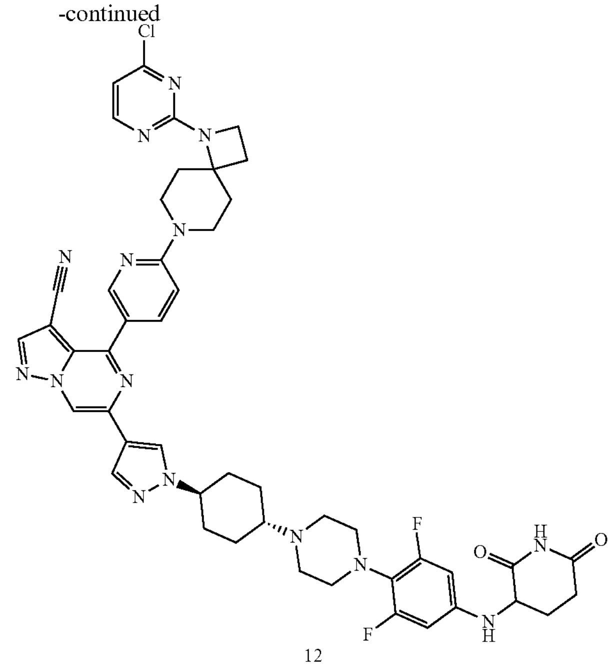

12

Step 1: Into a 250 mL single-necked round-bottomed flask containing a well-stirred solution of Sodium hydroxide, flake, 98% (3.12 g, 78.03 mmol) in water (30.63 mL) was added 2-thioxo-1H-pyrimidin-4-one (1, 5 g, 39.02 mmol) at 0° C. Methyl iodide (5.54 g, 39.02 mmol, 2.43 mL) was added and resulting mixture was stirred under nitrogen atmosphere at room temperature for 16 h. The progress of the reaction was monitored by UPLC. Upon completion, the reaction mixture was cooled to 0° C. and acidified with Glacial acetic acid until pH=2-3. The white solid precipitated out was filtered and dried under vacuum to afford 2-methylsulfanyl-1H-pyrimidin-6-one (2, 4.7 g, 33.06 mmol, 85% yield) as an off-white solid. LCMS ($ES^+$): m/z 143.0 $[M+H]^+$.

Step 2: Into a 250 mL three-necked round-bottomed flask containing a well stirred solution of 2-methylsulfanyl-1H-pyrimidin-6-one (2, 5.5 g, 38.68 mmol) in a mixture of anhydrous DCM (50 mL) and DMF (20 mL) was added thionyl chloride (2.76 g, 23.21 mmol, 1.68 mL) under nitrogen atmosphere. After completion of the addition, the reaction mixture was allowed to stir at 80° C. for 4 h under nitrogen atmosphere. The completion of reaction was monitored by UPLC. Reaction mixture was allowed to attain room temperature. The reaction mixture was concentrated under reduced pressure to afford a crude mass. The crude mass was dissolved into saturated Sodium bicarbonate solution (100 mL) and aqueous phase was extracted with DCM (2×250 mL). Combined organic phase was washed successively with $H_2O$ (2×500 mL) and brine (2×500 mL). Organic layer was dried (anhydrous $Na_2SO_4$), filtered and the filtrate was evaporated to dryness under reduced pressure to obtain crude 4-chloro-2-methylsulfanyl-pyrimidine (3, 5.2 g, 28.75 mmol, 74% yield) as a pale-yellow liquid. LCMS ($ES^+$): m/z 160.9 $[M+H]^+$.

Step 3: Into a 250 mL single-necked round-bottomed flask containing a well-stirred solution of 4-chloro-2-methylsulfanyl-pyrimidine (3, 3 g, 18.7 mmol, 2.17 mL) in anhydrous DCM (50 mL) was added 3-Chloroperoxybenzoic acid (6.45 g, 37.35 mmol) at 0° C. The resulting mixture was stirred at ambient temperature under nitrogen atmosphere for 2 h. Progress of the reaction was monitored by UPLC. After completion of the reaction as indicated by TLC, the reaction mixture was cooled to room temperature and poured into water (50 mL) and extracted with DCM (2×100 mL). Organic phases were combined and washed with aq saturated sodium bicarbonate (100 mL) and brine (100 mL). Combined organic phase was dried (anhydrous $Na_2SO_4$), filtered and the filtrate was concentrated under reduced pressure to get a crude residue, which was purified by flash silica-gel (230-400 mesh) column with 0-100% EtOAc/pet ether while desired compound was eluting at 25% EtOAc/pet ether to afford 4-chloro-2-methylsulfonyl-pyrimidine (4, 2.1 g, 10.68 mmol, 57% yield) as a white solid. $^1H$ NMR (400 MHz, DMSO-$d_6$). δ 9.08 (d, J=5.6 Hz, 1H), 8.09 (d, J=5.2 Hz, 1H) and 3.34 (s, 3H).

Step 4: Into a 100 mL single-necked round-bottomed flask containing a well-stirred solution of tert-butyl 1,7-diazaspiro[3.5]nonane-7-carboxylate (5, 200 mg, 0.884 mmol) and 4-chloro-2-methylsulfonyl-pyrimidine (4, 255.34 mg, 1.33 mmol) in anhydrous DMSO (2.5 mL) was added Cesium carbonate (431.90 mg, 1.33 mmol) at ambient temperature. The resulting mixture were heated at 90° C. for 2 h and progress of the reaction was monitored by UPLC. After completion of the reaction, reaction mixture was poured into water (20 mL) and the product was extracted with EtOAc (2×50 mL). The organic phases were combined, dried (anhydrous $Na_2SO_4$), filtered and the filtrate was concentrated under reduced pressure to get a crude residue. The crude product was purified by flash silica-gel (230-400 mesh) column with 0-100% EtOAc/pet ether while desired compound was eluting at 35% to afford tert-butyl 1-(4-chloropyrimidin-2-yl)-1,7-diazaspiro[3.5]nonane-7-carboxylate (6, 70 mg, 0.186 mmol, 21% yield) as an off-white solid. LCMS ($ES^+$): m/z 339.1 $[M+H]^+$.

Step 5: Into a 50 mL sealed-tube containing a well-stirred solution of 2,4-dichloropyrimidine (7, 400 mg, 2.68 mmol) and tert-butyl 1,7-diazaspiro[3.5]nonane-7-carboxylate (5, 405.1 mg, 1.79 mmol) in anhydrous 1,4-dioxane (10 mL) was added Cesium carbonate (1.46 g, 4.47 mmol) at ambient temperature under nitrogen atmosphere and the resulting mixture was degassed by bubbling nitrogen gas into the reaction mixture for 10 minutes. Subsequently, Pd-PEPPSI-iHeptCl (17.40 mg, 0.018 mmol) was added to the sealed tube and the resulting mixture was heated to 100° C. for 16 h. After complete consumption of the starting material as indicated by TLC, the reaction mixture was filtered through a pad of Celite and Celite bed was washed with DCM (30 mL). The combined filtrate was concentrated under reduced pressure to get a crude residue. The crude residue was purified by flash silica-gel (230-400 mesh, 50 g) column with 0-100% EtOAc/pet ether while desired compound was eluting at 35% of the mobile phase to afford tert-butyl 1-(4-chloropyrimidin-2-yl)-1,7-diazaspiro[3.5]nonane-7-carboxylate (6; 200 mg, 0.561 mmol, 31% yield) as an off white solid. LCMS ($ES^+$): m/z 283.2 $[M\text{-isobutene}+H]^+$.

Step 6: Into a 50 mL single-necked round-bottomed flask containing a well-stirred solution of tert-butyl 1-(4-chloropyrimidin-2-yl)-1,7-diazaspiro[3.5]nonane-7-carboxylate (6, 280 mg, 8.263 mmol) in anhydrous DCM (5 mL) was added Trifluoroacetic acid (471.13 mg, 4.13 mmol, 3.183 mmol) at 0° C. The resulting mixture was stirred at room temperature for 2 h and monitored by UPLC. Excess solvent was removed under reduced pressure to get a crude mass. Reaction crude was washed with MTBE (20 mL) to afford 1-(4-chloropyrimidin-2-yl)-1,7-diazaspiro[3.5]nonane trifluoroacetate (8; 230 mg, 6.247 mmol, 76% yield) as a light brown gummy liquid. UPLC-MS ($ES^+$): m/z 239.2 $[M+H]^+$.

Step 7: Into a 25 mL sealed tube containing a well-stirred solution of 1-(4-chloropyrimidin-2-yl)-1,7-diazaspiro[3.5]nonane trifluoroacetate (8, 200 mg, . . . mmol) and 4-(6-fluoro-3-pyridyl)-6-[1-(4-oxocyclohexyl)pyrazol-4-yl]pyrazolo[1,5-a]pyrazine-3-carbonitrile (9, 200 mg, 0.498 mmol) in anhydrous DMSO (2 mL) was added DIPEA (0.434 mL, 321.98 mg, 2.49 mmol) at ambient temperature. Later, the resulting mixture was heated with stirring at 90° C. for 16 h. After completion of the reaction as indicated by UPLC, the reaction mixture was allowed to attain room temperature and treated with ice-water (20 mL) and aqueous phase was extracted with EtOAc (2×20 mL). Combined the organic phase was dried (anhydrous $Na_2SO_4$), filtered and the filtrate was concentrated under reduced pressure to obtain a crude mass. The crude mass was purified by flash silica-gel (230-400 mesh) column with 0-100% EtOAc/pet ether while the desired compound was eluting at 90% EtOAc of the mobile phase to afford 4-[6-[1-(4-chloropyrimidin-2-yl)-1,7-diazaspiro[3.5]nonan-7-yl]-3-pyridyl]-6-[1-(4-oxocyclohexyl)pyrazol-4-yl]pyrazolo[1,5-a]pyrazine-3-carbonitrile (10; 110 mg, 0.164 mmol, 33% yield) as a light yellow solid. UPLC-MS ($ES^+$): m/z 620.2 $[M+H]^+$.

Step 8: Into a 25 mL single-necked round-bottomed flask containing a well-stirred solution of 4-[6-[1-(4-chloropyrimidin-2-yl)-1,7-diazaspiro[3.5]nonan-7-yl]-3-pyridyl]-6-[1-(4-oxocyclohexyl)pyrazol-4-yl]pyrazolo[1,5-a]pyrazine-3-carbonitrile (10, 100 mg, 0.161 mmol) and 3-(3,5-difluoro-4-piperazin-1-yl-anilino)piperidine-2,6-dione hydrochloride (11, 130.75 mg, 0.362 mmol) in anhydrous MeOH (2 mL) were added anhydrous Sodium acetate (66.15 mg, 0.806 mmol, 0.043 mL) and Acetic acid (0.968 mg, 0.016 mmol, 9.23e-1 μL) at ambient temperature and the resulting mixture was stirred for 10 minutes. MP-$CNBH_3$ (50.67 mg, 0.806 mmol) was added at ambient temperature under nitrogen atmosphere and stirring was continued for 16 h. After complete consumption of the starting material as indicated by UPLC and the reaction was quenched with ice-cold water (20 mL) and the solid precipitated out was filtered and dried to afford a crude solid mass. The crude solid was purified by flash silica-gel (230-400 mesh, 25 g) column with 0-10% MeOH/DCM while desired compound was eluting at 5-7% to afford 110 mg of diastereomers. The diastereomeric mixture was purified by reverse phase perp-HPLC [Column: XBRIDGE OBD C18 19×150 mm 5 micron; Mobile phase: A: 0.1% $NH_4HCO_3$ in MQ-water; B: Acetonitrile; Flow rate: 15 mL/minutes; Fractions with RT=12.7 minutes were combined and lyophilized to afford 4-(6-(1-(4-chloropyrimidin-2-yl)-1,7-diazaspiro[3.5]nonan-7-yl)pyridin-3-yl)-6-(1-((1s, 4s)-4-(4-(4-((2,6-dioxopiperidin-3-yl)amino)-2,6-difluorophenyl)piperazin-1-yl)cyclohexyl)-1H-pyrazol-4-yl)pyrazolo[1,5-a]pyrazine-3-carbonitrile (Compound 204, Early eluting isomer; 3.2 mg, 0.003 mmol, 2% yield) as a yellow solid. $^1H$ NMR (400 MHz, DMSO-$d_6$). δ 10.82 (s, 1H), 9.30 (s, 1H), 8.84 (s, 1H), 8.70 (s, 1H), 8.47 (s, 1H), 8.19 (m, 1H), 8.16 (s, 1H), 8.09 (d, J=8.4 Hz, 1H), 7.10 (d, J=8.4 Hz, 1H), 6.68 (s, 1H), 6.33 (d, J=12.4 Hz, 2H), 6.26 (d, J=7.6 Hz, 1H), 4.57 (d, J=12 Hz, 2H), 4.32 (s, 1H), 4.20 (t, J=11.2 Hz, 1H), 3.98 (s, 2H), 2.97 (s, 8H), 2.68 (m, 1H), 2.55 (m, 2H), 2.17-2.06 (m, 5H), 1.97-1.83 (m, 9H), 1.52-1.43 (m, 3H), 0.86 (s, 1H). LCMS ($ES^+$): m/z 928.3 $[M+H]^+$. Whereas fractions with RT=15.3 minutes were combined and lyophilized to afford 4-[6-[1-(4-chloropyrimidin-2-yl)-1,7-diazaspiro[3.5]nonan-7-yl]-3-pyridyl]-6-[1-[4-[4-[4-[(2,6-dioxo-3-piperidyl)amino]-2,6-difluoro-phenyl]piperazin-1-yl]cyclohexyl]pyrazol-4-yl]pyrazolo[1,5-a]pyrazine-3-carbonitrile (12, Late eluting isomer; 4.7 mg, 0.005 mmol, 3% yield) as a yellow solid. $^1H$ NMR (400 MHz, DMSO-$d_6$). δ 10.82 (s, 1H), 9.35 (s, 1H), 8.84 (s, 1H), 8.70 (s, 1H), 8.70 (s, 1H), 8.51 (s, 1H), 8.18 (s, 2H), 8.09 (d, J=8 Hz, 1H), 7.10 (d, J=9.2 Hz, 1H), 6.66 (s, 1H), 6.32 (d, J=12.4 Hz, 2H), 6.25 (d, J=8 Hz, 1H), 4.57 (d, J=13.2 Hz, 2H), 4.32 (m, 2H), 3.98 (m, 2H), 2.99 (s, 6H), 2.75 (m, 1H), 2.68-2.40 (m, 8H), 2.34-2.26 (m, 4H), 1.90-1.71 (m, 8H) and 1.63-1.52 (m, 2H). LCMS ($ES^+$): m/z 928.3 $[M+H]^+$.

Example 207: Synthesis of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile (Compound 205)
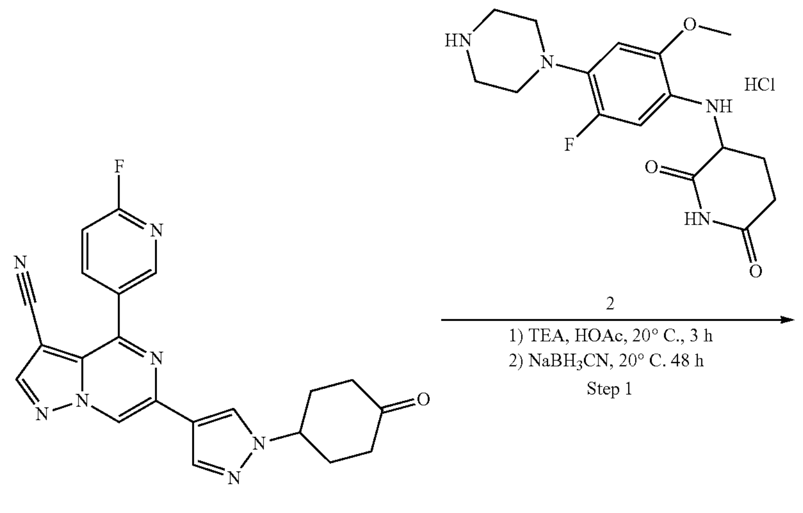
1
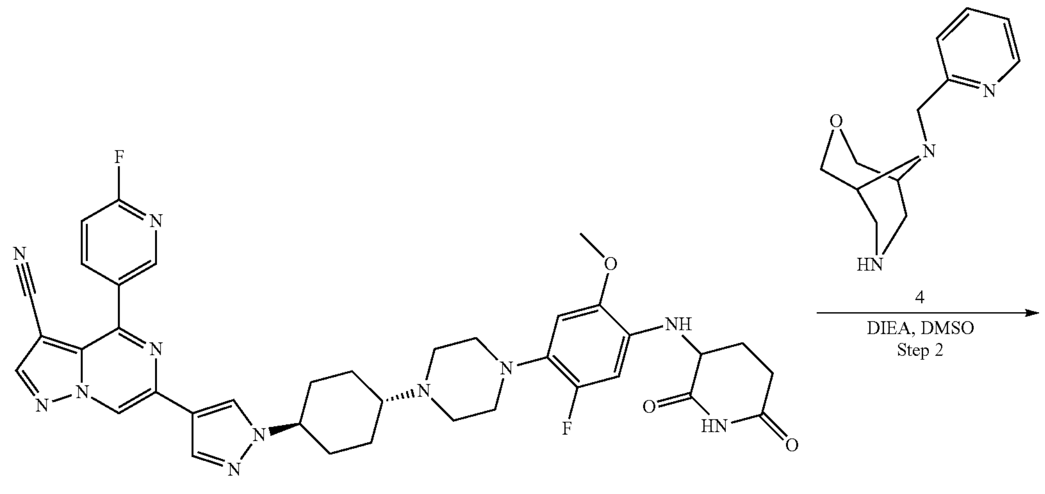
3

-continued

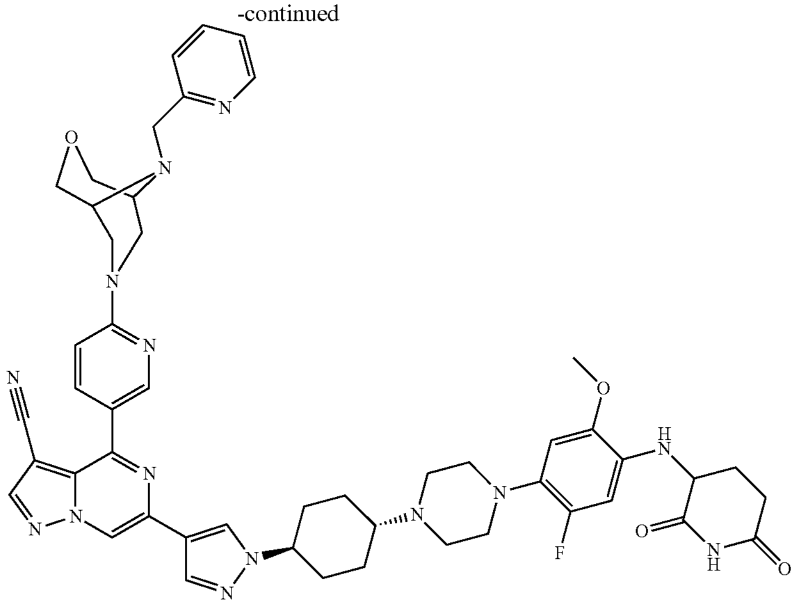

Compound 205

Step 1: To a solution of 4-(6-fluoro-3-pyridyl)-6-[1-(4-oxocyclohexyl)pyrazol-4-yl]pyrazolo[1,5-a]pyrazine-3-carbonitrile (1, 3 g, 7.47 mmol) and 3-((5-fluoro-2-methoxy-4-(piperazin-1-yl)phenyl)amino)piperidine-2,6-dione (2, 3.07 g, 8.22 mmol, HCl salt) in DMAc (60 mL) was added TEA (2.27 g, 22.42 mmol, 3.13 mL) and the mixture was stirred at 20° C. for 15 min. then AcOH (4.49 g, 74.74 mmol, 4.27 mL) was added into the mixture at 25° C., After addition, the solution was stirred at 20° C. for 2 hr. Then $NaBH_3CN$ (4.70 g, 74.74 mmol) was added into above solution and stirred at 20° C. for another 16 hr. The reaction solution was poured into water (240 mL) to give a suspension. Then the suspension was filtered, the filter cake was washed with water (100 mL) and concentrated in vacuum. The yellow residue was purified by column chromatography ($SiO_2$, DCM:MeOH=100:0-30:1-10:1) to get the product. The product was purified by flash silica gel chromatography (330 g Flash Column; Welch Ultimate XB_C18 20-40 m; MeCN/H2O (0.5%, NH3·H2O); 120 A; 65% 10 min; 100 ml/min, three batches) to get the product. 6-[1-[4-[4-[4-[(2,6-dioxo-3-piperidyl)amino]-2-fluoro-5-methoxy-phenyl]piperazin-1-yl]cyclohexyl]pyrazol-4-yl]-4-(6-fluoro-3-pyridyl)pyrazolo[1,5-a]pyrazine-3-carbonitrile (3, 910 mg, 1.26 mmol, 28% yield) was obtained as yellow solid. LCMS ($ES^+$): m/z 722 $[M+H]^+$.

Step 2: A solution of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-(6-fluoro-3-pyridyl)pyrazolo[1,5-a]pyrazine-3-carbonitrile (3, 100 mg, 138.55 μmol), 9-(pyridin-2-ylmethyl)-3-oxa-7,9-diazabicyclo[3.3.1]nonane (4, 30.38 mg, 118.80 μmol, HCl salt) and DIPEA (53.72 mg, 415.65 μmol, 72.40 μL) in DMSO (1 mL) was stirred at 120° C. for 2 hour. The mixture was adjusted to pH=5-6 with FA. The crude product was purified by prep-HPLC ((Phenomenex luna C18 150*25 mm*10 um; water (0.225% FA)-ACN; B %: 10%~40%, Gradient Time (10 min), 100% B Hold Time (2 min), FlowRate (25 ml/min)) to get the product. 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[9-(2-pyridylmethyl)-3-oxa-7,9-diazabicyclo[3.3.1]nonan-7-yl]-3-pyridyl]pyrazolo[1,5-a]pyrazine-3-carbonitrile formic acid salt (Compound 205, 3.81 mg, 3.90 μmol, 3% yield) was obtained as a brown solid.

LCMS ($ES^+$): m/z 921.6 $[M+H]^+$. $^1H$ NMR (400 MHz, DMSO-$d_6$) δ=10.91-10.83 (m, 1H), 9.29 (s, 1H), 8.84 (s, 1H), 8.72 (d, J=2.4 Hz, 1H), 8.54-8.50 (m, 1H), 8.48 (s, 1H), 8.20-8.16 (m, 1H), 8.15 (s, 1H), 8.12-8.08 (m, 1H), 7.85-7.79 (m, 1H), 7.63-7.57 (m, 1H), 7.31-7.26 (m, 1H), 6.92 (d, J=9.2 Hz, 1H), 6.64-6.55 (m, 2H), 5.21-5.09 (m, 1H), 4.33-4.23 (m, 2H), 4.21-4.14 (m, 2H), 4.11 (s, 2H), 3.95-3.87 (m, 3H), 3.84-3.78 (m, 5H), 3.62-3.53 (m, 3H), 3.21-3.05 (m, 5H), 2.89 (br s, 3H), 2.82-2.75 (m, 1H), 2.59-2.55 (m, 1H), 2.29-2.05 (m, 5H), 1.98-1.82 (m, 3H), 1.78-1.52 (m, 2H)

Example 208: Synthesis of 6-[1-[4-[4-[2-chloro-4-[(2,6-dioxo-3-piperidyl)amino]phenyl]-1-piperidyl]cyclohexyl]pyrazol-4-yl]-4-[6-[9-[(6-methoxy-3-pyridyl)methyl]-3-oxa-7,9-diazabicyclo[3.3.1]nonan-7-yl]-3-pyridyl]pyrazolo[1,5-a]pyrazine-3-carbonitrile (Compound 206)

Compound 206 was Prepared Following the Synthesis of Compound 205

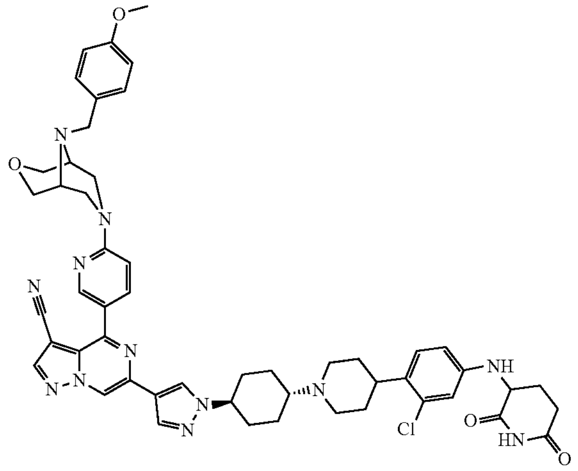 [SMILES: COc1ccc(CN2C3COCC2CN(c2ccc(-c4nc(-c5cnn([C@H]6CC[C@H](N7CCC(c8ccc(NC9CCC(=O)NC9=O)cc8Cl)CC7)CC6)c5)cn5ncc(C#N)c45)cn2)C3)cc1]

LCMS ($ES^+$): m/z 936.4 $[M+H]^+$.

$^1H$ NMR (400 MHz, DMSO-$d_6$) δ=10.78 (s, 1H), 9.26 (s, 1H), 8.82 (s, 1H), 8.71 (d, J=2.4 Hz, 1H), 8.45 (s, 1H), 8.21 (s, 1H), 8.17 (d, J=2.0 Hz, 1H), 8.15 (s, 1H), 8.09 (dd, J=2.4, 9.2 Hz, 1H), 7.76 (dd, J=2.4, 8.4 Hz, 1H), 7.07 (d, J=8.4 Hz, 1H), 6.89 (d, J=9.2 Hz, 1H), 6.82 (d, J=8.8 Hz, 1H), 6.71 (d, J=2.2 Hz, 1H), 6.62 (dd, J=2.0, 8.8 Hz, 1H), 6.01 (d, J=7.6 Hz, 1H), 4.37-4.30 (m, 1H), 4.23-4.06 (m, 3H), 3.93 (s, 2H), 3.84 (s, 5H), 3.81-3.75 (m, 2H), 3.55-3.50 (m, 2H), 2.99 (br d, J=10.4 Hz, 2H), 2.81 (br s, 2H), 2.77-2.70 (m, 2H), 2.43-2.30 (m, 3H), 2.20-2.11 (m, 2H), 2.10-2.03 (m, 1H), 1.99-1.79 (m, 6H), 1.75-1.66 (m, 2H), 1.64-1.44 (m, 4H).

Example 209: Synthesis of 1-[5-[3-cyano-6-[1-[4-[4-[4-[(2,6-dioxo-3-piperidyl)amino]-2-fluoro-phenyl]piperazin-1-yl]cyclohexyl]pyrazol-4-yl]pyrazolo[1,5-a]pyrazin-4-yl]-2-pyridyl]-4-ethyl-N-[(3-fluorocyclobutyl)methyl]piperidine-4-carboxamide (Compound 207)

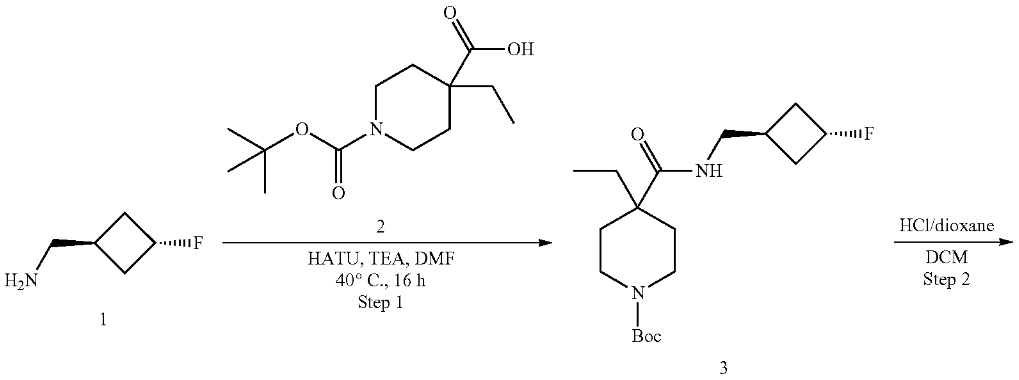

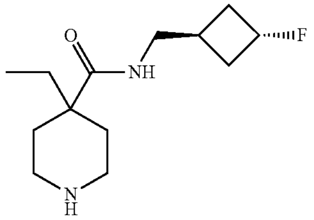

4

-continued

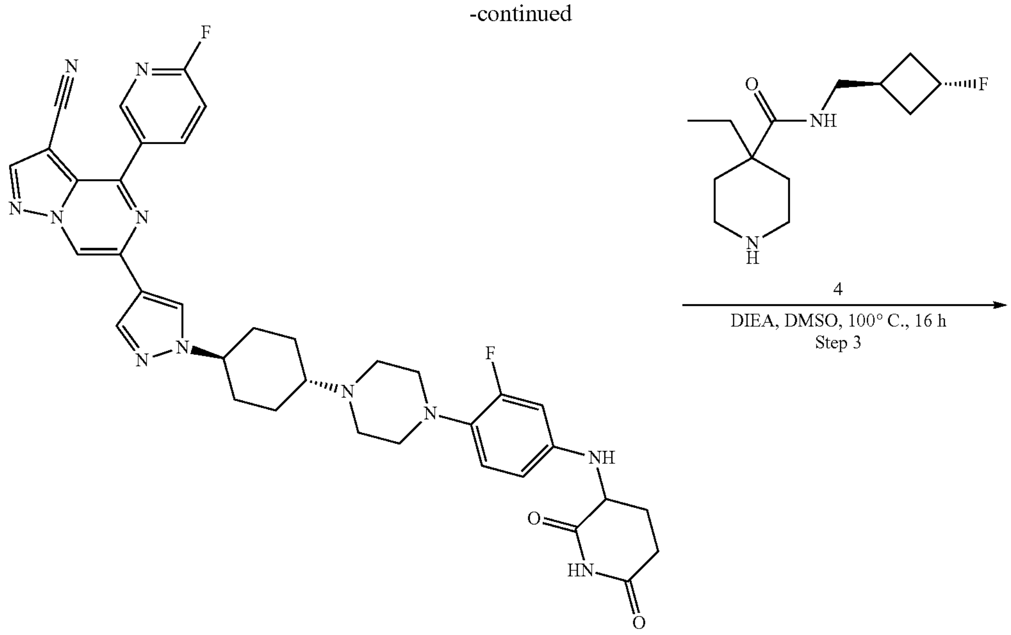

5

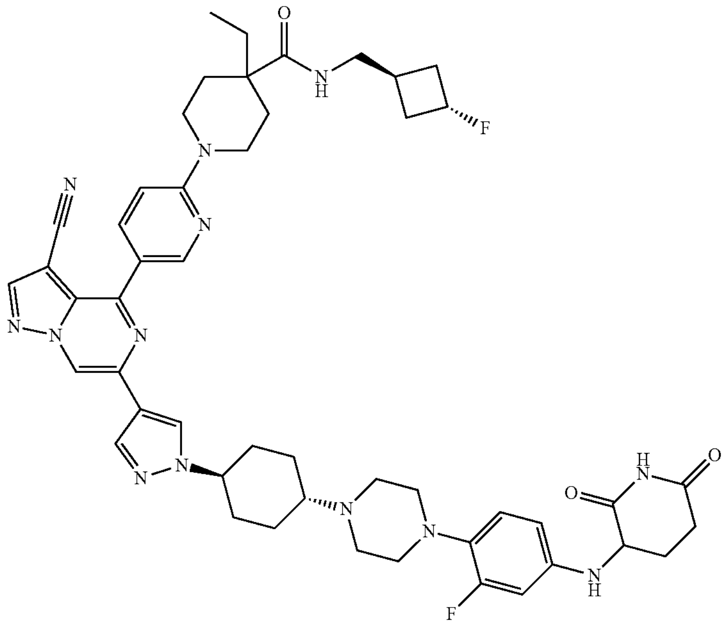

Compound 207

Step 1: To a solution of (3-fluorocyclobutyl)methanamine (1, 50.00 mg, 358.17 μmol, HCl salt) and 1-(tert-butoxycarbonyl)-4-ethylpiperidine-4-carboxylic acid (2, 110.60 mg, 429.80 μmol) in DMF (0.5 mL) was added HATU (204.28 mg, 537.25 μmol) and TEA (108.73 mg, 1.07 mmol, 149.77 μL). The mixture was stirred at 25° C. for 16 h. The reaction mixture was diluted with $H_2O$ (5 mL) and extracted with EtOAc (5 mL*3). The combined organic layers were washed with brine (5 mL*2), dried over $Na_2SO_4$, filtered, and concentrated under reduced pressure. The residue was purified by column chromatography ($SiO_2$, Petroleum ether/Ethyl acetate=100/1 to 1/1), (PE/EA=1/1, Rf=0.3). tert-butyl 4-ethyl-4-[(3-fluorocyclobutyl)methylcarbamoyl]piperidine-1-carboxylate (3, 60 mg, 148.93 mol, 42% yield) was obtained as a colorless oil. LCMS ($ES^+$): m/z 342.2 $[M+H]^+$.

Step 2: To a solution of tert-butyl 4-ethyl-4-[(3-fluorocyclobutyl) methylcarbamoyl]piperidine-1-carboxylate (3, 50.00 mg, 146.01 mol) in DCM (444.44 μL) was added HCl/Dioxane (4 M, 555.56 μL). The mixture was stirred at 25° C. for 0.5 h. The reaction mixture was concentrated under reduced pressure to remove solvent. 4-ethyl-N-[(3-fluorocyclobutyl)methyl]piperidine-4-carboxamide HCl salt (4, 38 mg, 136.17 μmol, 93% yield) was obtained as a white solid. LCMS ($ES^+$): m/z 243.1 $[M+H]^+$.

Step 3: To a solution of 4-ethyl-N-[(3-fluorocyclobutyl) methyl]piperidine-4-carboxamide (4, 10.51 mg, 37.70 μmol, HCl salt) in DMSO (1 mL) was added 6-[1-[4-[4-[4-[(2,6-dioxo-3-piperidyl)amino]-2-fluoro-phenyl]piperazin-1-yl] cyclohexyl]pyrazol-4-yl]-4-(6-fluoro-3-pyridyl)pyrazolo[1,5-a]pyrazine-3-carbonitrile (5, 30 mg, 43.37 mol) and N-ethyl-N-isopropyl-propan-2-amine (28.03 mg, 216.85 mol, 37.77 μL). The mixture was stirred at 100° C. for 16 h. The reaction solution was filtered. The residue was purified by Prep-HPLC (Phenomenex luna C18 150*25 mm*10 um, water (0.225% FA)-ACN, Begin B 13, End B 43, Gradient Time (min) 10). 1-[5-[3-cyano-6-[1-[4-[4-[4-[(2,6-dioxo-3-piperidyl)amino]-2-fluoro-phenyl]piperazine-1-yl]cyclohexyl]pyrazol-4-yl]pyrazolo[1,5-a]pyrazin-4-yl]-2-pyridyl]-4-ethyl-N-[(3-fluorocyclobutyl)methyl]piperidine-4-carboxamide (Compound 207, 10 mg, 10.93 mol, 25% yield) was obtained as a yellow solid.

LCMS ($ES^+$): m/z 457.8 $[M/2+H]^+$.

$^1H$ NMR (400 MHz, DMSO-$d_6$) δ=10.78 (s, 1H), 9.26 (s, 1H), 8.81 (s, 1H), 8.66 (d, J=2.4 Hz, 1H), 8.44 (s, 1H), 8.29 (s, 1H), 8.16-8.11 (m, 1H), 8.04 (dd, J=2.4, 8.8 Hz, 1H), 7.81 (br t, J=5.6 Hz, 1H), 6.99 (d, J=8.8 Hz, 1H), 6.86-6.77 (m, 1H), 6.55-6.47 (m, 1H), 6.42 (dd, J=1.6, 8.4 Hz, 1H), 5.80 (br d, J=7.6 Hz, 1H), 5.25-4.99 (m, 1H), 4.33-4.05 (m, 4H), 3.22-3.05 (m, 6H), 2.86 (br s, 4H), 2.70-2.62 (m, 4H), 2.46-2.37 (m, 3H), 2.25-2.05 (m, 6H), 2.01-1.74 (m, 6H), 1.52-1.33 (m, 6H), 0.80-0.68 (m, 3H).

Example 210: Synthesis of 6-[1-[4-[4-[3-(2,4-dioxohexahydropyrimidin-1-yl)-7-fluoro-1-methyl-indazol-6-yl]piperazin-1-yl]cyclohexyl]pyrazol-4-yl]-4-[6-[(1S,5R)-9-(2-pyridylmethyl)-3-oxa-7,9-diazabicyclo [3.3.1]nonan-7-yl]-3-pyridyl]pyrazolo [1,5-a]pyrazine-3-carbonitrile (Compound 208)

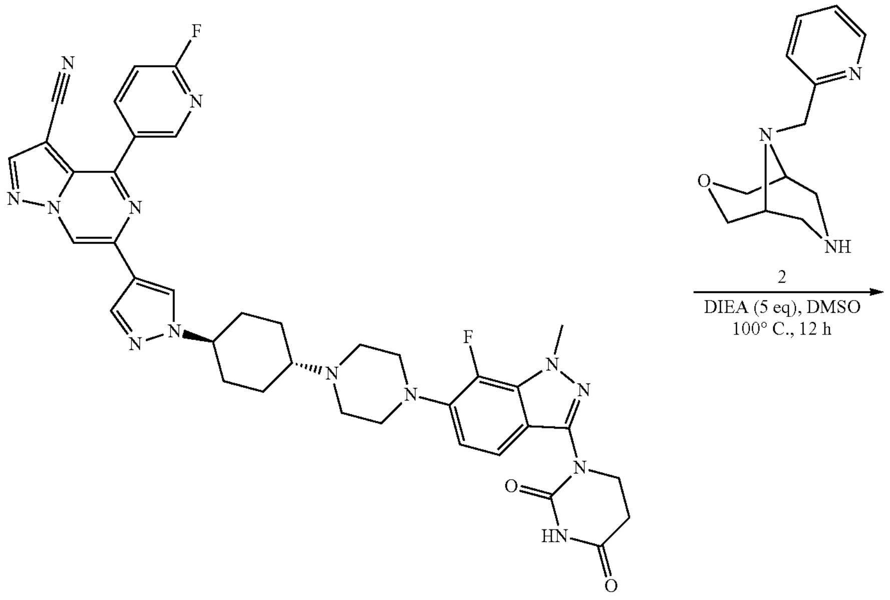

1

-continued

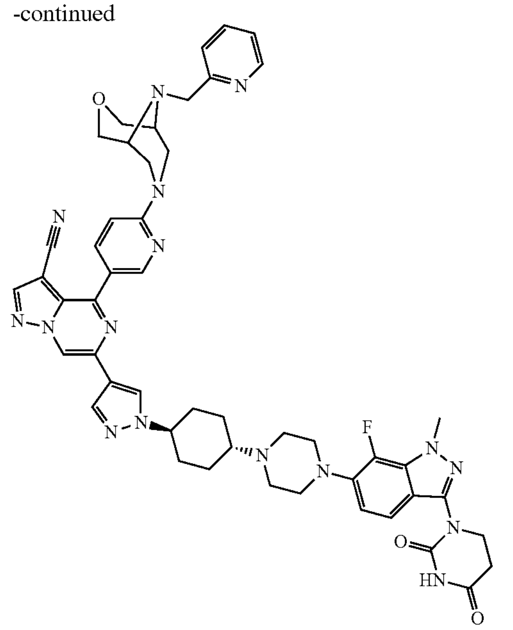

Compound 208

To a solution of 6-[1-[4-[4-[3-(2,4-dioxohexahydropyrimidin-1-yl)-7-fluoro-1-methyl-indazol-6-yl]piperazin-1-yl]cyclohexyl]pyrazol-4-yl]-4-(6-fluoro-3-pyridyl)pyrazolo[1,5-a]pyrazine-3-carbonitrile (1, 30 mg, 41.00 mol) in DMSO (2 mL) was added 9-(2-pyridylmethyl)-3-oxa-7,9-diazabicyclo[3.3.1]nonane (2, 20.97 mg, 81.99 mol, HCl salt) and DIPEA (26.49 mg, 204.99 mol, 35.70 μL). The mixture was stirred at 100° C. for 12 h. The mixture was filtered, the filtrate was purified by Prep-HPLC (column: Phenomenex luna C18 150*25 mm*10 um; mobile phase: [water (0.225% FA)-ACN]; B %: 4%-34%, 10 min) to give 6-[1-[4-[4-[3-(2,4-dioxohexahydropyrimidin-1-yl)-7-fluoro-1-methyl-indazol-6-yl]piperazin-1-yl]cyclohexyl]pyrazol-4-yl]-4-[6-[(1S,5R)-9-(2-pyridylmethyl)-3-oxa-7,9-diazabicyclo[3.3.1]nonan-7-yl]-3-pyridyl]pyrazolo[1,5-a]pyrazine-3-carbonitrile (Compound 208, 10.06 mg, 10.09 mol, 25% yield) as a yellow solid.

LCMS ($ES^+$): m/z 931.2 $[M+H]^+$.

$^1H$ NMR (400 MHz, DMSO-$d_6$) δ=10.80-10.45 (m, 1H), 9.27 (s, 1H), 8.83 (s, 1H), 8.72 (d, J=2.4 Hz, 1H), 8.52 (d, J=4.4 Hz, 1H), 8.47 (s, 1H), 8.36 (s, 1H), 8.16 (s, 1H), 8.10 (dd, J=2.0, 9.0 Hz, 1H), 7.86-7.78 (m, 1H), 7.60 (d, J=7.8 Hz, 1H), 7.36 (d, J=8.8 Hz, 1H), 7.31-7.24 (m, 1H), 6.99-6.86 (m, 2H), 4.32-4.13 (m, 4H), 4.11 (s, 2H), 4.06 (s, 3H), 3.91 (t, J=6.4 Hz, 4H), 3.81 (d, J=10.8 Hz, 2H), 3.58 (br s, 2H), 3.12 (br s, 4H), 2.89 (br s, 2H), 2.79-2.70 (m, 6H), 2.17 (d, J=11.6 Hz, 2H), 1.99 (d, J=9.8 Hz, 2H), 1.92-1.77 (m, 2H), 1.58-1.41 (m, 2H).

Example 211: Synthesis of N-[(3aR,6aS)-2-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-5-methyl-1,3,3a,4,6,6a-hexahydrocyclopenta[c]pyrrol-5-yl]-3-chloro-pyridine-2-carboxamide (Compound 209)

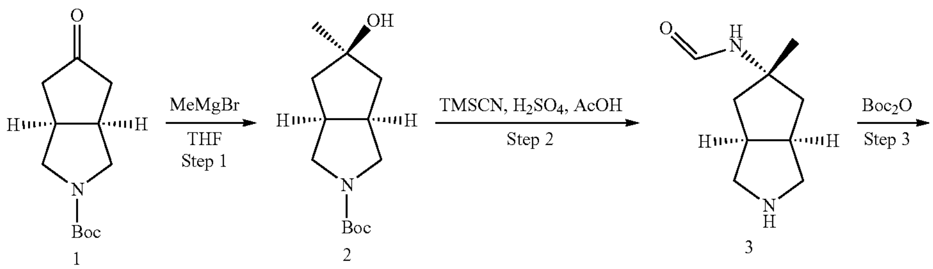

1 2 3

-continued
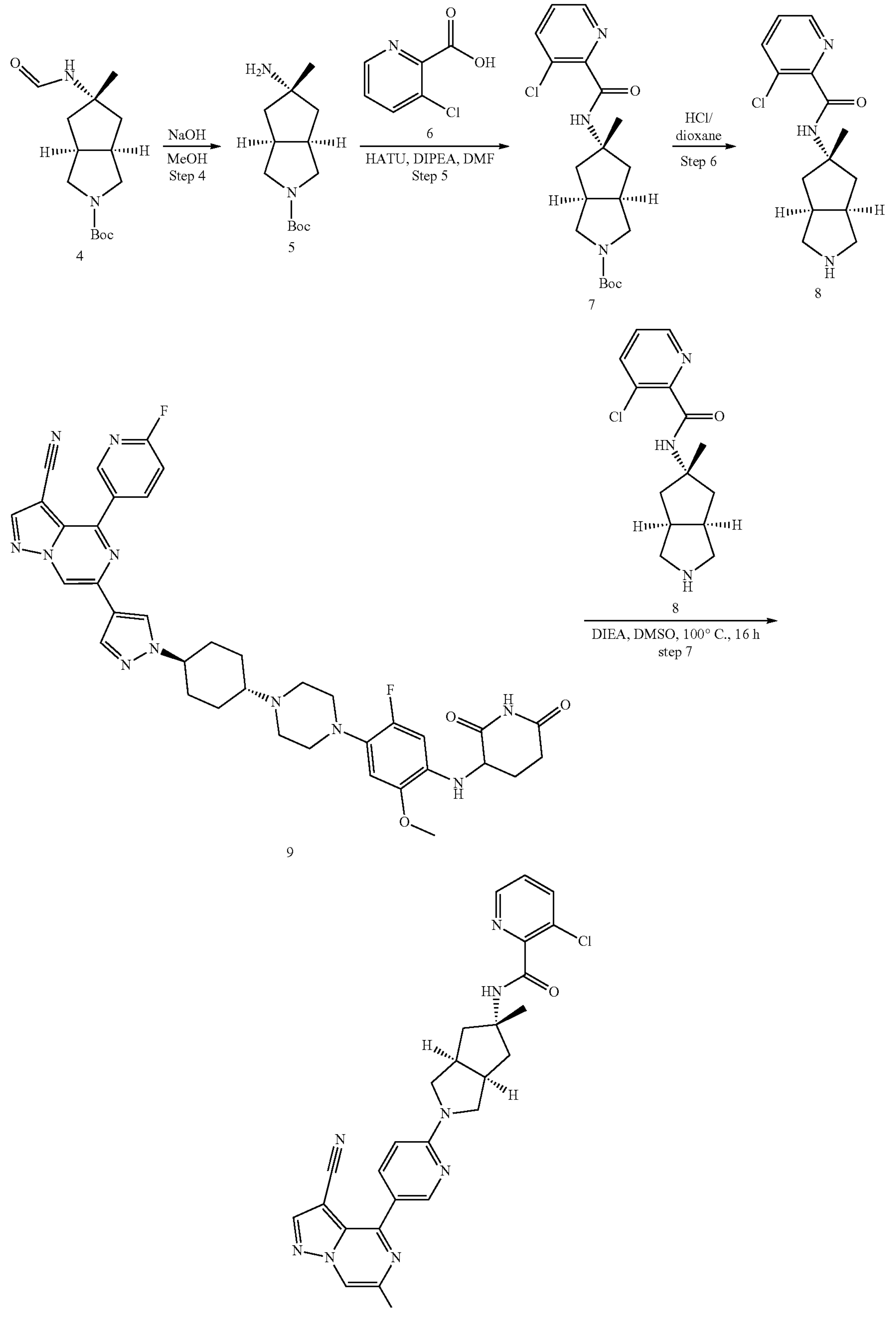
4 5 6 7 8 8 9

-continued

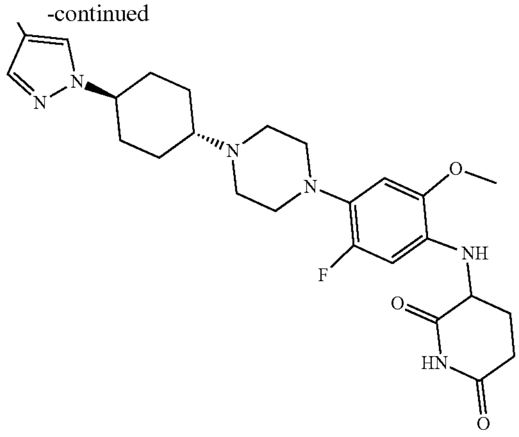

Compound 209

Step 1: To a solution of tert-butyl (3aS,6aR)-5-oxo-1,3,3a,4,6,6a-hexahydrocyclopenta[c]pyrrole-2-carboxylate (1, 1.75 g, 7.77 mmol) in dry THE (18 mL) was added methylmagnesium bromide (1 M, 19.42 mL) at −30° C. for 2h. The reaction was quenched by dropwise addition of MeOH (6 mL) and aq.HCl (1 N, 6 mL) at −30° C. The mixture was diluted with EtOAc (20 mL), washed by $H_2O$ (20×2 mL) and brine (10 mL), dried over anhydrous $Na_2SO_4$ filtered off and concentrated in vacuum. The residue was purified by flash silica gel chromatography (ISCO®; 20 g SepaFlash® Silica Flash Column, Eluent of 0-50% Ethyl acetate/Petroleum ether gradient @ 45 mL/min) to afford (3aR,5r, 6aS)-tert-butyl 5-hydroxy-5-methylhexahydrocyclopenta[c]pyrrole-2(1H)-carboxylate (2, 1.8 g, 6.34 mmol, 82% yield) as a yellow solid. $^1$H NMR (400 MHz, CHLOROFORM-d) δ=3.53-3.44 (m, 2H), 3.35 (dd, J=3.2, 11.2 Hz, 2H), 2.68 (br d, J=3.6 Hz, 2H), 1.98-1.89 (m, 2H), 1.67 (dd, J=4.8, 13.2 Hz, 2H), 1.46-1.44 (m, 9H), 1.32 (s, 3H)

Step 2: To a solution of (3aR,5r,6aS)-tert-butyl 5-hydroxy-5-methylhexahydrocyclopenta[c]pyrrole-2(1H)-carboxylate (2, 1.5 g, 6.22 mmol) and trimethylsilanecarbonitrile (1.85 g, 18.65 mmol) in AcOH (5 mL) was added conc.$H_2SO_4$ (609.63 mg, 6.22 mmol, 4 mL) at 0° C. The mixture was stirred at 20° C. for 2 h. The reaction mixture was cooled in ice-$H_2O$ bath, basified with aq.NaOH (5 N) until pH=8-9 to afford N-[(3aS,6aR)-5-methyl-2,3,3a, 4,6,6a-hexahydro-1H-cyclopenta[c]pyrrol-5-yl]formamide (3, 1 g, crude) as a yellow oil.

Step 3: To a solution of N-[(3aS,6aR)-5-methyl-2,3,3a,4,6,6a-hexahydro-1H-cyclopenta[c]pyrrol-5-yl]formamide (3, 1 g, 5.94 mmol) in previous reaction solution was added di-tert-butyl dicarbonate (1.43 g, 6.54 mmol, 1.50 mL), the mixture was stirred at 20° C. for 1 h. The reaction mixture was extracted with EtOAc (50 mL*3). The organic layers concentrated under reduced pressure to afford tert-butyl (3aS,6aR)-5-formamido-5-methyl-1,3,3a, 4,6,6a-hexahydrocyclopenta[c]pyrrole-2-carboxylate (4, 1.6 g, crude) as a yellow oil. LCMS ($ES^+$): m/z 213.1 [M+H-56]+

Step 4: To a solution of tert-butyl (3aS,6aR)-5-formamido-5-methyl-1,3,3a, 4,6,6a-hexahydrocyclopenta[c]pyrrole-2-carboxylate (4, 200 mg, 745.29 mol) in Ethanol (3 mL) was added aqueous NaOH (5 M, 3 mL). The mixture was stirred at 80° C. for 2 h. After cooling to rt, the mixture was concentrated in vacuum. Then the mixture was added EtOAc (50 mL). It was stirred at 25° C. for 10 min, the organic layer was filtered and concentrated under reduced pressure to afford tert-butyl (3aS,6aR)-5-amino-5-methyl-1,3,3a, 4,6,6a-hexahydrocyclopenta[c]pyrrole-2-carboxylate (5, 50 mg, crude) as a yellow oil.

Step 5: To a solution of tert-butyl (3aS,6aR)-5-amino-5-methyl-1,3,3a, 4,6,6a-hexahydrocyclopenta[c]pyrrole-2-carboxylate (5, 50 mg, 208.04 mol), 3-chloropicolinic acid (6, 32.78 mg, 208.04 mol) and HATU (118.65 mg, 312.06 mol) in DMF (5.28 mL) was added DIPEA (80.66 mg, 624.11 mol, 108.71 µL) at 20° C. The mixture was stirred at 40° C. for 2 h. After cooling to room temperature, the mixture was diluted with EtOAc (50 mL), washed by $H_2O$ (15 mL×2) and brine (15 mL), dried over anhydrous $Na_2SO_4$, and concentrated in vacuum. The residue was purified by flash silica gel chromatography (ISCO®; 4 g SepaFlash® Silica Flash Column, Eluent of 0-50% Ethyl acetate/Petroleum ether gradient @ 36 mL/min) to afford tert-butyl (3aS,6aR)-5-[(3-chloropyridine-2-carbonyl)amino]-5-methyl-1,3,3a, 4,6,6a-hexahydrocyclopenta[c]pyrrole-2-carboxylate (7, 60 mg, 134.25 mol, 65% yield) as a yellow oil.

$^1$H NMR (400 MHz, CHLOROFORM-d) δ=8.43-8.39 (m, 1H), 7.80 (dd, J=0.8, 8.2 Hz, 1H), 7.69 (s, 1H), 7.34 (dd, J=4.4, 8.2 Hz, 1H), 3.41 (br dd, J=7.2, 11.2 Hz, 2H), 3.27 (br d, J=10.8 Hz, 2H), 2.61 (br d, J=10.4 Hz, 2H), 2.51-2.36 (m, 2H), 1.59 (s, 3H), 1.54-1.48 (m, 2H), 1.45 (s, 9H).

Step 6: A mixture of tert-butyl (3aS,6aR)-5-[(3-chloropyridine-2-carbonyl)amino]-5-methyl-1,3,3a, 4,6,6a-hexahydrocyclopenta[c]pyrrole-2-carboxylate (7, 60 mg, 157.94 mol) in HCl/dioxane (4 M, 1 mL) was stirred at 20° C. for 1 h. The reaction mixture was concentrated under reduced pressure to afford N-[(3aS,6aR)-5-methyl-2,3,3a, 4,6,6a-hexahydro-1H-cyclopenta[c]pyrrol-5-yl]-3-chloro-pyridine-2-carboxamide HCl salt (8, 50 mg, 158.12 mol, 100% yield) as a white solid.

Step 7: To a solution of 6-[1-[4-[4-[4-[(2,6-dioxo-3-piperidyl)amino]-2-fluoro-5-methoxy-phenyl]piperazin-1-yl] cyclohexyl]pyrazol-4-yl]-4-(6-fluoro-3-pyridyl)pyrazolo[1,5-a]pyrazine-3-carbonitrile (9, 25 mg, 34.64 mol) in DMSO (1 mL) was added N-[(3aS,6aR)-5-methyl-2,3,3a, 4,6,6a-hexahydro-1H-cyclopenta[c]pyrrol-5-yl]-3-chloro-pyridine-2-carboxamide (8, 21.91 mg, 69.28 mol, HCl salt) and DIPEA (22.38 mg, 173.19 mol, 30.17 µL). The mixture was stirred at 100° C. for 16 h. The reaction mixture was purified by Prep-HPLC (column: Phenomenex Synergi C18 150*25 mm*10 um; mobile phase: [water (0.225% FA)-ACN]; B %: 14%-34%, 10 min) to afford N-[(3aR,6aS)-2-[5-[3-cyano- 6-[1-[4-[4-[4-[(2,6-dioxo-3-piperidyl)amino]-2-fluoro-5-methoxy-phenyl]piperazin-1-yl]cyclohexyl]pyrazol-4-yl] pyrazolo [1,5-a]pyrazin-4-yl]-2-pyridyl]-5-methyl-1,3,3a,4,6,6a-hexahydrocyclopenta[c]pyrrol-5-yl]-3-chloro-pyridine-2-carboxamide FA salt (Compound 209, 13.02 mg, 12.46 mol, 36% yield) as a yellow solid. LCMS ($ES^+$): m/z 981.1 $[M+H]^+$, 491.4 $[M12+H]^+$.

$^1H$ NMR (400 MHz, DMSO-$d_6$) δ=10.86 (s, 1H), 9.34-9.20 (m, 1H), 8.85-8.78 (m, 1H), 8.68 (d, J=2.4 Hz, 1H), 8.53 (dd, J=1.2, 4.8 Hz, 1H), 8.45 (s, 1H), 8.31 (s, 1H), 8.15 (s, 1H), 8.06 (dd, J=2.4, 8.8 Hz, 1H), 8.01 (dd, J=1.2, 8.4 Hz, 1H), 7.51 (dd, J=4.8, 8.4 Hz, 1H), 6.70 (d, J=9.2 Hz, 1H), 6.61 (d, J=8.0 Hz, 1H), 6.55 (d, J=14.4 Hz, 1H), 5.09 (br d, J=6.4 Hz, 1H), 4.34-4.09 (m, 2H), 3.84-3.74 (m, 3H), 3.68-3.47 (m, 5H), 3.02-2.87 (m, 6H), 2.67 (br d, J=1.6 Hz, 6H), 2.21-1.77 (m, 10H), 1.55-1.51 (m, 3H), 1.50-1.41 (m, 4H)

Example 212: Synthesis of 1-[5-[3-cyano-6-[1-[4-[4-[4-[(2,6-dioxo-3-piperidyl)amino]-2-fluoro-phenyl]piperazin-1-yl]cyclohexyl]pyrazol-4-yl]pyrazolo [1,5-a]pyrazin-4-yl]-2-pyridyl]-4-ethyl-N-[(3-fluorocyclobutyl)methyl]piperidine-4-carboxamide (Compound 210)

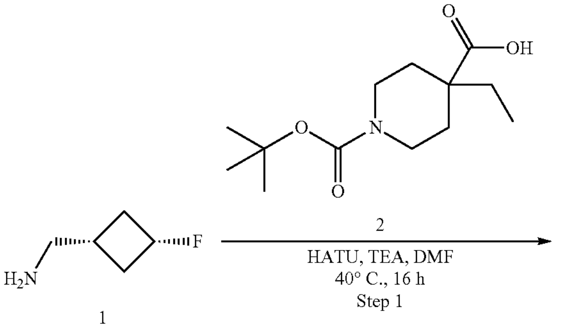

1

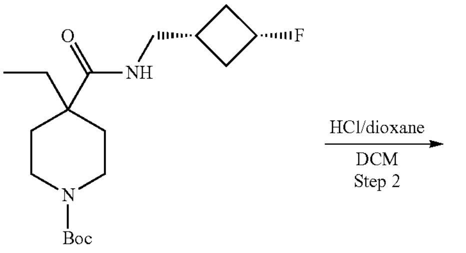

3

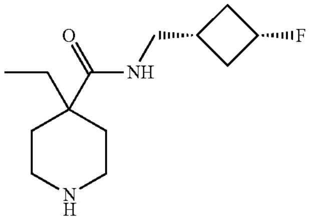

4

-continued

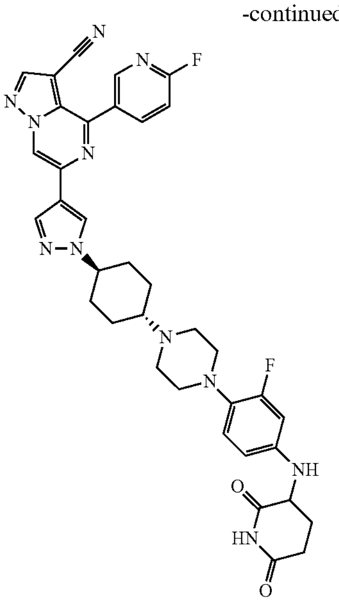

5

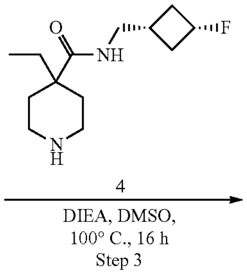

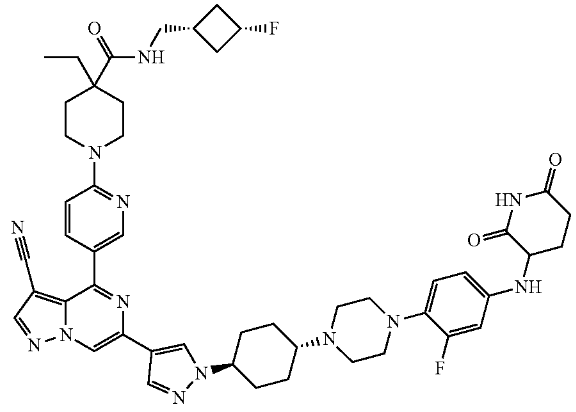

Compound 210

Step 1: To a solution of (3-fluorocyclobutyl)methanamine (1, 50 mg, 358.17 mol, HCl salt) and 1-(tert-butoxycarbonyl)-4-ethylpiperidine-4-carboxylic acid (2, 110.60 mg, 429.80 mol) in DMF (0.5 mL) was added N,N,N',N'-tetramethyl-1-(3-oxido-2,3-dihydrotriazolo[4,5-b]pyridin-3-ium-1-yl)methanediamine;hexafluorophosphate (205.36 mg, 537.26 mol) and N,N-diethylethanamine (108.73 mg, 1.07 mmol, 149.77 μL). The mixture was stirred at 40° C. for 16 hr. The residue was diluted with $H_2O$ (5 mL) and extracted with EtOAc (10 mL*3). The combined organic layers were washed with brine (5 mL*2), dried over $Na_2SO_4$, filtered and concentrated under reduced pressure. The residue was purified by column chromatography ($SiO_2$, Petroleum ether/Ethyl acetate=100/1 to 1/1, TLC: PE:EA=1:1 Product RF=0.3). tert-butyl 4-ethyl-4-[(3-fluorocyclobutyl)methylcarbamoyl]piperidine-1-carboxylate (3, 0.1 g, 292.02 mol, 81.53% yield) was obtained as a yellow oil. LCMS ($ES^+$): m/z 343.2 $[M+H]^+$.

Step 2: To a solution of tert-butyl 4-ethyl-4-[(3-fluorocyclobutyl)methylcarbamoyl]piperidine-1-carboxylate (3, 100 mg, 292.02 mol) in DCM (2.00 mL) was added HCl/Dioxane (4 M, 2.00 mL). The mixture was stirred at 25° C. for 0.5 h. The reaction mixture was concentrated under reduced pressure to remove solvent. 4-ethyl-N-[(3-fluorocyclobutyl)methyl]piperidine-4-carboxamide HCl salt (4, 78 mg, 279.78 mol, 96% yield) was obtained as a yellow solid. LCMS ($ES^+$): m/z 243.2 $[M+H]^+$.

Step 3: To a solution of 4-ethyl-N-[(3-fluorocyclobutyl)methyl]piperidine-4-carboxamide (4, 15 mg, 53.80 mol, HCl salt) and 6-[1-[4-[4-[4-[(2,6-dioxo-3-piperidyl)amino]-2-fluoro-phenyl]piperazin-1-yl]cyclohexyl]pyrazol-4-yl]-4-(6-fluoro-3-pyridyl)pyrazolo[1,5-a]pyrazine-3-carbonitrile (5, 37.22 mg, 53.80 mol) in DMSO (1 mL) was added N-ethyl-N-isopropyl-propan-2-amine (34.77 mg, 269.02 mol, 46.86 μL). The mixture was stirred at 100° C. for 16 h. The reaction solution was filtered. The residue was purified by prep-HPLC (Unisil 3-100° C.18 Ultra 150*50 mm*3 um, water (0.225% FA)-ACN, Begin B 10, End B 40, Gradient Time (min) 10). 1-[5-[3-cyano-6-[1-[4-[4-[4-[(2,6-dioxo-3-piperidyl)amino]-2-fluoro-phenyl]piperazin-1-yl]cyclohexyl]pyrazol-4-yl]pyrazolo[1,5-a]pyrazin-4-yl]-2-pyridyl]-4-ethyl-N-[(3-fluorocyclobutyl)methyl]piperidine-4-carboxamide FA salt (Compound 210, 15.35 mg, 15.94 mol, 30% yield) was obtained as a yellow solid.

LCMS ($ES^+$): m/z 457.8 $[M/2+H]^+$.

$^1$H NMR (400 MHz, DMSO-$d_6$) δ=10.77 (s, 1H), 9.27 (s, 1H), 8.81 (s, 1H), 8.67 (d, J=2.4 Hz, 1H), 8.45 (s, 1H), 8.38 (s, 1H), 8.15 (s, 1H), 8.14 (0.042 FA), 8.04 (dd, J=2.4, 8.8 Hz, 1H), 7.86-7.77 (m, 1H), 7.00 (d, J=9.2 Hz, 1H), 6.83 (t, J=9.2 Hz, 1H), 6.51 (dd, J=2.4, 15.2 Hz, 1H), 6.42 (dd, J=2.0, 8.8 Hz, 1H), 5.79 (d, J=7.6 Hz, 1H), 4.99-4.74 (m, 1H), 4.31-4.08 (m, 4H), 3.22-3.12 (m, 5H), 2.86 (br s, 4H), 2.69-2.62 (m, 4H), 2.37-2.28 (m, 3H), 2.20-2.04 (m, 6H), 2.00-1.80 (m, 8H), 1.52-1.35 (m, 6H), 0.75 (t, J=7.4 Hz, 3H).

Example 213: Synthesis of 6-[1-[4-[4-[4-[(2,6-dioxo-3-piperidyl)amino]-2,6-difluoro-phenyl]piperazin-1-yl]cyclohexyl]pyrazol-4-yl]-4-[6-[rac-(3S)-3-(2-pyridylmethoxy)pyrrolidin-1-yl]-3-pyridyl]pyrazolo[1,5-a]pyrazine-3-carbonitrile (Compound 211)

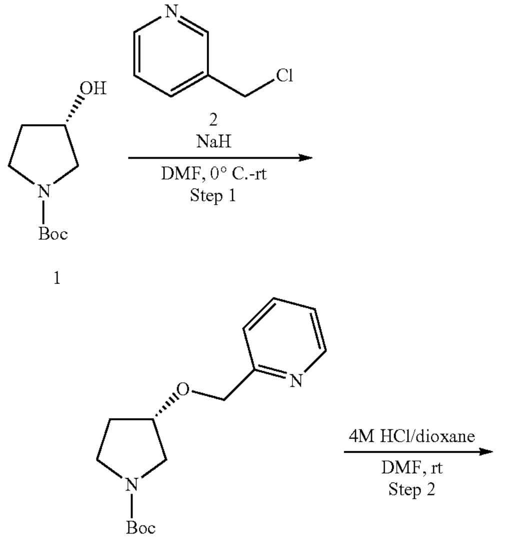

-continued

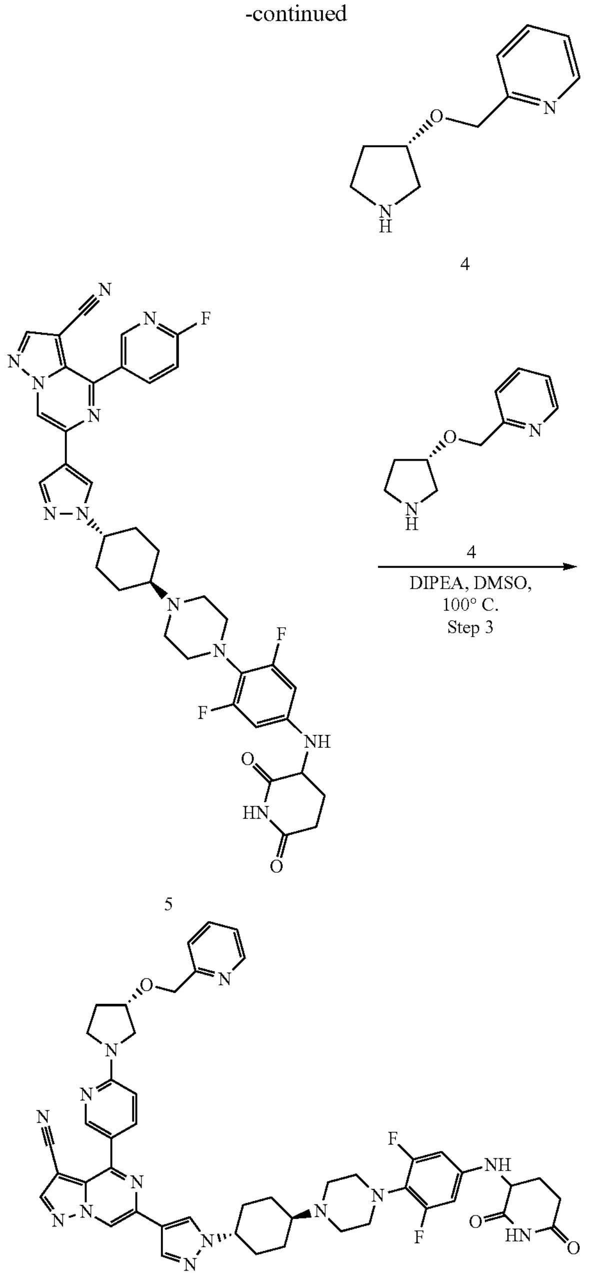

Compound 211

Step 1: A suspension of 2-(chloromethyl)pyridine (2, 2 g, 12.19 mmol, HCl salt) in DMF (10 mL) was added sodium hydride (488 mg, 12.20 mmol, 60% dispersion in mineral oil) at 0° C. The suspension was stirred at 0° C. for 0.25 h under $N_2$. Meanwhile, another suspension of tert-butyl rac-(3S)-3-hydroxypyrrolidine-1-carboxylate (1, 2.28 g, 12.19 mmol) in DMF (10 mL) was added sodium hydride (488 mg, 12.20 mmol, 60% dispersion in mineral oil) at 0° C. under $N_2$. The suspension was stirred at 0° C. for 0.25 h. After stirring, two suspensions were combined, the combined suspension was stirred at 15° C. for 2 h under $N_2$. The mixture was quenched with water (100 mL). The mixture was extracted with EtOAc (2×100 mL). The combined organic layer was washed with brine (2×50 mL), dried over $Na_2SO_4$, filtered and concentrated under reduced pressure. The crude product was purified by flash silica gel chromatography (ISCO®; 40 g SepaFlash® Silica Flash Column, Eluent of 17~44% Ethyl acetate/Petroleum ether gradient @ 60 mL/min) to give tert-butyl rac-(3S)-3-(2-pyridylmethoxy)pyrrolidine-1-carboxylate (3, 2.3 g, 8.18 mmol, 67% yield) as a light yellow liquid. LCMS ($ES^+$): m/z 279.2 $[M+H]^+$ Step 2: A mixture of tert-butyl rac-(3S)-3-(2-pyridylmethoxy)pyrrolidine-1-carboxylate (3, 200 mg, 718.53 mol) in DCM (2 mL) and HCl (4 M, 2.00 mL) was stirred at 15° C. for 1 h. The mixture was concentrated under reduced pressure to give 2-[[rac-(3S)-pyrrolidin-3-yl]oxymethyl]pyridine (4, 160 mg, 737.80 mol, crude, HCl salt) as an off-white solid. LCMS ($ES^+$): m/z 179.2 $[M+H]^+$ Step 3: To a solution of 6-[1-[4-[4-[4-[(2,6-dioxo-3-piperidyl)amino]-2,6-difluoro-phenyl]piperazin-1-yl]cyclohexyl]pyrazol-4-yl]-4-(6-fluoro-3-pyridyl)pyrazolo[1,5-a]pyrazine-3-carbonitrile (5, 50 mg, 70.45 mol) and 2-[[rac-(3S)-pyrrolidin-3-yl]oxymethyl]pyridine (4, 31.00 mg, 144.39 mol, HCl salt) in DMSO (1.00 mL) was added DIPEA (44.52 mg, 344.48 mol, 60.00 μL). The mixture was stirred at 100° C. for 16 h. The mixture was filtered. The filtrate was purified by Prep-HPLC (flow: 25 mL/min; gradient: from 10-33% MeCN in water (0.225% FA) over 10 min; column: Phenomenex Synergi C18 150×25 mm×10 μm) and lyophilized to give 6-[1-[4-[4-[4-[(2,6-dioxo-3-piperidyl)amino]-2,6-difluoro-phenyl]piperazin-1-yl]cyclohexyl]pyrazol-4-yl]-4-[6-[rac-(3S)-3-(2-pyridylmethoxy)pyrrolidin-1-yl]-3-pyridyl]pyrazolo[1,5-a]pyrazine-3-carbonitrile FA salt (Compound 211, 44.13 mg, 47.80 mol, 68% yield) as a yellow solid.

LCMS ($ES^+$): m/z 868.4 $[M+H]^+$ $^1H$ NMR (400 MHz, DMSO-$d_6$) δ=10.81 (s, 1H), 9.30-9.20 (m, 1H), 8.81 (s, 1H), 8.68 (d, J=2.4 Hz, 1H), 8.52 (d, J=4.4 Hz, 1H), 8.44 (s, 1H), 8.14 (s, 1H), 8.06 (dd, J=2.4, 8.8 Hz, 1H), 7.79 (dt, J=1.6, 7.6 Hz, 1H), 7.44 (d, J=7.6 Hz, 1H), 7.29 (dd, J=5.2, 6.8 Hz, 1H), 6.66 (d, J=8.8 Hz, 1H), 6.32 (d, J=12.0 Hz, 2H), 6.25 (d, J=8.0 Hz, 1H), 4.70-4.61 (m, 2H), 4.41 (s, 1H), 4.36-4.27 (m, 1H), 4.25-4.13 (m, 1H), 3.71-3.62 (m, 2H), 3.61-3.50 (m, 2H), 2.96 (s, 4H), 2.73 (ddd, J=5.2, 12.4, 17.6 Hz, 1H), 2.59 (s, 4H), 2.56-2.52 (m, 1H), 2.42 (t, J=11.2 Hz, 1H), 2.29-2.20 (m, 1H), 2.20-2.09 (m, 3H), 2.09-2.02 (m, 1H), 1.95 (bd, J=10.8 Hz, 2H), 1.89-1.75 (m, 3H), 1.55-1.38 (m, 2H).

Example 214: Synthesis of 6-[1-[4-[4-[4-[(2,6-dioxo-3-piperidyl)amino]-2,6-difluoro-phenyl]piperazin-1-yl]cyclohexyl] pyrazol-4-yl]-4-[6-[rac-(1R, 5S)-9-[(6-ethoxy-3-pyridyl)methyl]-3-oxa-7,9-diazabicyclo[3.3.1] nonan-7-yl]-3-pyridyl]pyrazolo [1,5-a]pyrazine-3-carbonitrile (Compound 212)

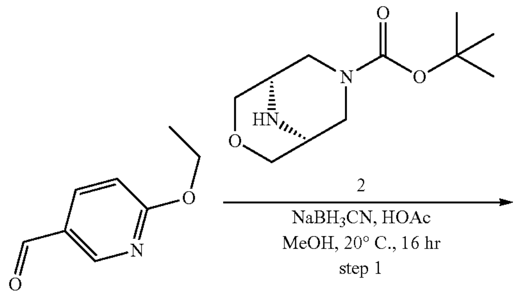

1

-continued

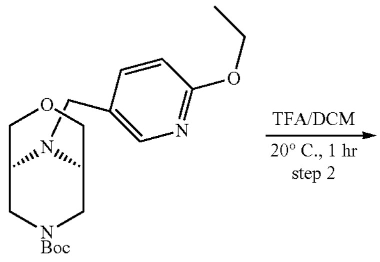

3

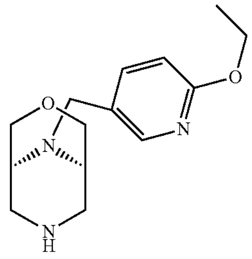

4

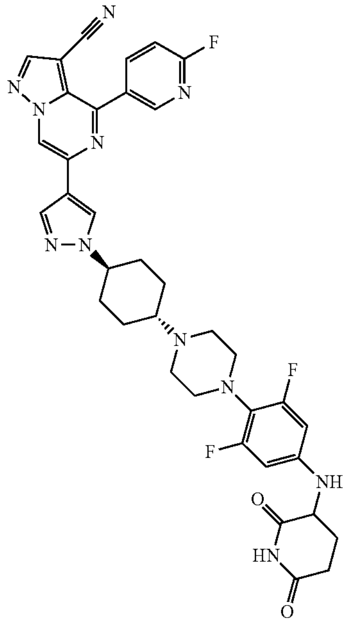

5

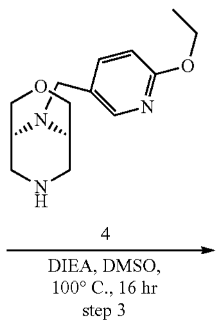

4

-continued

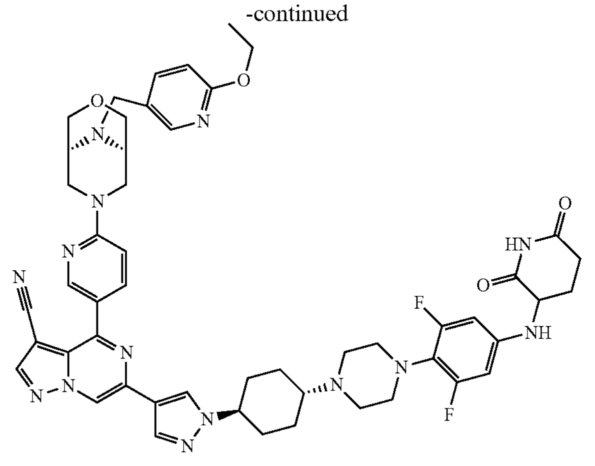

Compound 212

Step 1: To a solution of 6-ethoxypyridine-3-carbaldehyde (1, 148.99 mg, 985.60 μmol) in MeOH (1 mL) was added tert-butyl (1R,5S)-3-oxa-7,9-diazabicyclo[3.3.1]nonane-7-carboxylate (2, 150 mg, 657.07 mol) and AcOH (39.46 mg, 657.07 mol) and the mixture was stirred at 25° C. for 15 min, then $NaBH_3CN$ (123.87 mg, 1.97 mmol) was added into the mixture at 25° C. The solution was stirred at 40° C. for 16 hr. The reaction was added into water (50 mL) and extracted with EtOAc (20 mL×3). The combined organic phases was washed with water (20 mL) and concentrated in vacuum to give tert-butyl rac-(1R,5S)-9-[(6-ethoxy-3-pyridyl)methyl]-3-oxa-7,9-diazabicyclo[3.3.1]nonane-7-carboxylate (3, 150 mg, 412.71 mol, 63% yield) as yellow oil LCMS ($ES^+$): m/z 364.2 $[M+H]^+$ Step 2: To a solution of tert-butyl rac-(1R,5S)-9-[(6-ethoxy-3-pyridyl)methyl]-3-oxa-7,9-diazabicyclo[3.3.1] nonane-7-carboxylate (3, 50 mg, 137.57 mol) in DCM (1 mL) was added TFA (296.00 mg, 2.60 mmol, 0.2 mL) and the mixture was stirred at 20° C. for 1 hr. The reaction was concentrated to get rac-(1R,5S)-9-[(6-ethoxy-3-pyridyl) methyl]-3-oxa-7,9-diazabicyclo [3.3.1] nonane FA salt (4, 50 mg, 132.50 mol, 96% yield) as yellow oil, which was used directly. LCMS ($ES^+$): m/z 264.1 $[M+H]^+$ Step 3: To a solution of rac-(1R,5S)-9-[(6-ethoxy-3-pyridyl)methyl]-3-oxa-7,9-diazabicyclo[3.3.1] nonane (4, 20 mg, 53.00 mol, TFA) in DMSO (1 mL) was added DIPEA (68.50 mg, 530.00 mol, 92.31 μL) and 6-[1-[4-[4-[4-[(2,6-dioxo-3-piperidyl)amino]-2,6-difluoro-phenyl]piperazin-1-yl]cyclohexyl]pyrazol-4-yl]-4-(6-fluoro-3-pyridyl) pyrazolo[1,5-a]pyrazine-3-carbonitrile (5, 15 mg, 21.14 mol) and the mixture was stirred at 100° C. for 16 hr. The reaction mixture was quenched by aq.HCl (1M, 0.2 mL) and purified with Prep-HPLC (neutral condition: Waters Xbridge 150*25 mm*5 um) and lyophilized to give 6-[1-[4-[4-[4-[(2,6-dioxo-3-piperidyl)amino]-2,6-difluoro-phenyl]piperazin-1-yl]cyclohexyl]pyrazol-4-yl]-4-[6-[rac-(1R,5S)-9-[(6-ethoxy-3-pyridyl)methyl]-3-oxa-7,9-diazabicyclo[3.3.1] nonan-7-yl]-3-pyridyl]pyrazolo[1,5-a]pyrazine-3-carbonitrile (Compound 212, 9.09 mg, 8.89 mol, 17% yield) as light yellow solid LCMS ($ES^+$): m/z 953.4 $[M+H]^+$, 477.5 $[M/2+H]^+$ $^1H$ NMR (400 MHz, DMSO-$d_6$) δ=10.82 (s, 1H), 9.27 (s, 1H), 8.83 (s, 1H), 8.72 (s, 1H), 8.46 (s, 1H), 8.16 (s, 2H), 8.09 (dd, J=8.8 Hz and 2.4 Hz, 1H), 7.75 (dd, J=8.8 Hz and 2.4 Hz, 1H), 6.90 (d, J=8.8 Hz, 1H), 6.79 (d, J=8.8 Hz, 1H), 6.34-6.31 (m, 2H), 6.25 (d, J=8.0 Hz, 1H), 4.33-4.26 (m, 3H), 4.23-4.08 (m, 3H), 3.95-3.91 (m, 2H), 3.87-3.77 (m, 5H), 3.56-3.50 (m, 2H), 3.00-2.94 (m, 4H), 2.84-2.80 (m, 2H), 2.64-2.57 (m, 5H), 2.45-2.38 (m, 1H), 2.20-2.11 (m, 2H), 2.08 (s, 1H), 2.00-1.92 (m, 2H), 1.89-1.79 (m, 3H), 1.54-1.43 (m, 2H), 1.40-1.39 (m, 1H), 1.34-1.29 (m, 4H).

Example 215: Synthesis of 6-[1-[4-[4-[4-[(2,6-dioxo-3-piperidyl)amino]-2,6-difluoro-phenyl]piperazin-1-yl]cyclohexyl] pyrazol-4-yl]-4-[6-[rac-(1R, 5S)-9-[(6-isopropoxy-3-pyridyl)methyl]-3-oxa-7,9-diazabicyclo [3.3.1]nonan-7-yl]-3-pyridyl]pyrazolo [1,5-a]pyrazine-3-carbonitrile (Compound 213)

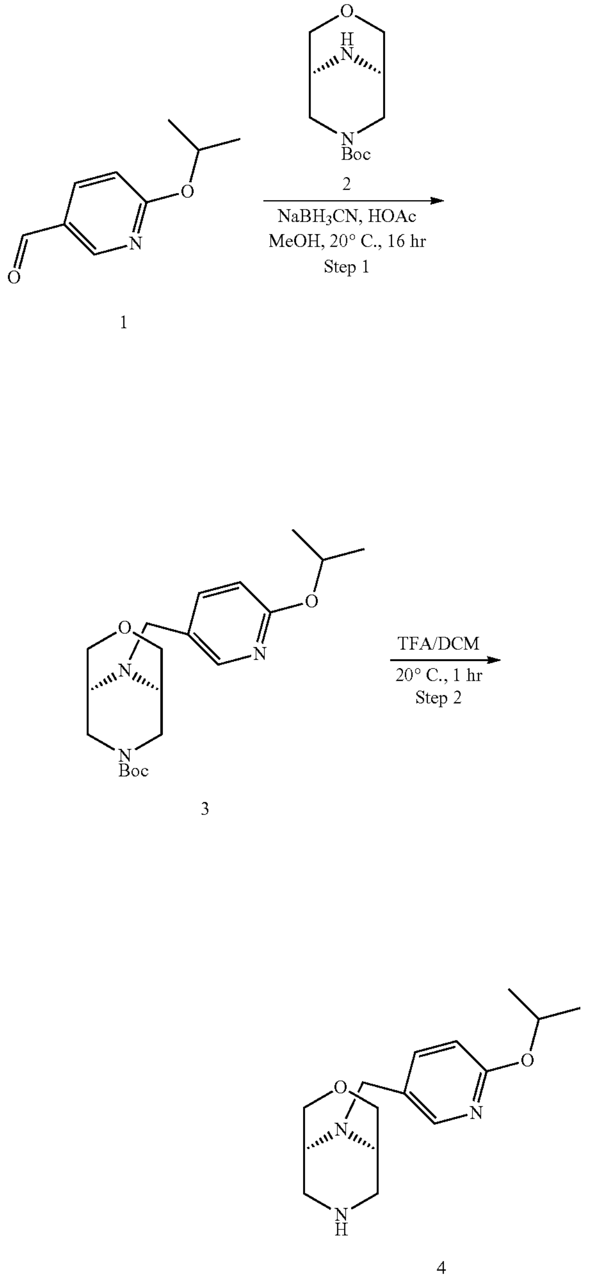

-continued

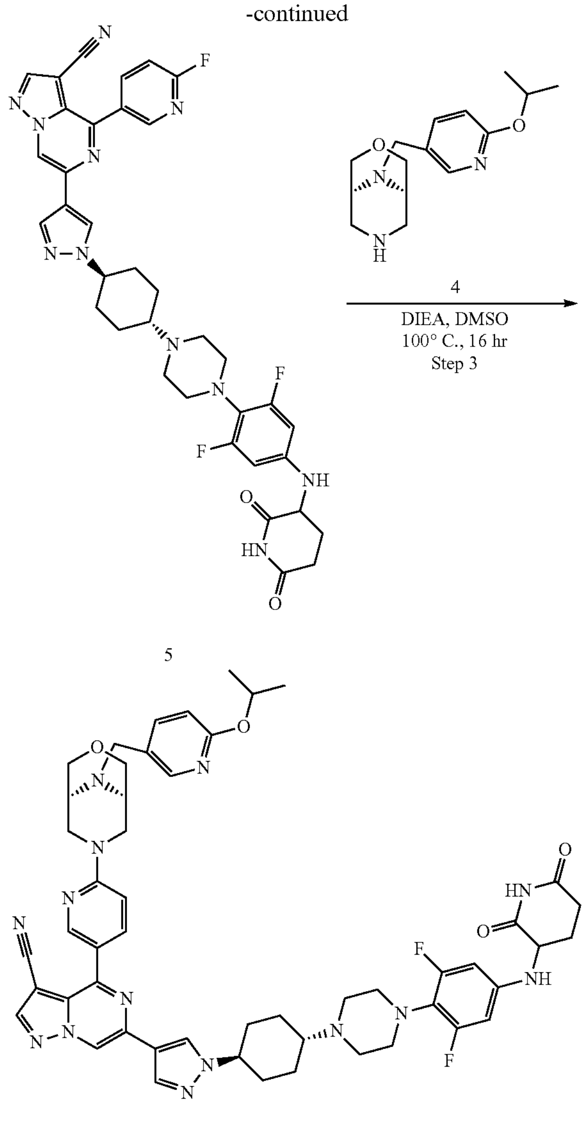

5

4

Compound 213

Step 1: To a solution of 6-isopropoxypyridine-3-carbaldehyde (1, 162.81 mg, 985.60 mol) in MeOH (2 mL) was added tert-butyl (1R,5S)-3-oxa-7,9-diazabicyclo[3.3.1] nonane-7-carboxylate (2, 150 mg, 657.07 mol) and AcOH (39.46 mg, 657.07 mol) and the mixture was stirred at 25° C. for 15 min, then $NaBH_3CN$ (123.87 mg, 1.97 mmol) was added into the mixture at 25° C. The solution was stirred at 40° C. for 16 hr. The reaction was added water 50 mL and extracted with EtOAc (20 ml×3). The combined organic phases was washed with water (20 mL) and concentrated in vacuum to give tert-butyl (1R,5S)-9-[(6-isopropoxy-3-pyridyl)methyl]-3-oxa-7,9-diazabicyclo[3.3.1] nonane-7-carboxylate (3, 160 mg, 423.87 mol, 65% yield) as yellow oil. LCMS ($ES^+$): m/z 378.2 $[M+H]^+$ Step 2: To a solution of tert-butyl rac-(1R,5S)-9-[(6-isopropoxy-3-pyridyl)methyl]-3-oxa-7,9-diazabicyclo [3.3.1]nonane-7-carboxylate (3, 50 mg, 132.46 mol) in DCM (0.8 mL) was added TFA (148.00 mg, 1.30 mmol, 0.1 mL) and the mixture was stirred at 20° C. for 1 hr. The reaction was concentrated to get rac-(1R,5S)-9-[(6-isopropoxy-3-pyridyl)methyl]-3-oxa-7,9-diazabicyclo [3.3.1] nonane FA salt (4, 50 mg, 127.75 mol, 96% yield) as yellow oil, which was used directly. LCMS ($ES^+$): m/z 278.3 $[M+H]^+$ Step 3: To a solution of rac-(1R,5S)-9-[(6-isopropoxy-3-pyridyl)methyl]-3-oxa-7,9-diazabicyclo[3.3.1]nonane (4, 25 mg, 90.14 mol) in DMSO (1 mL) was added DIPEA (116.49 mg, 901.35 mol, 157.00 μL) and 6-[1-[4-[4-[4-[(2,6-dioxo-3-piperidyl)amino]-2,6-difluoro-phenyl]piperazin-1-yl]cyclohexyl]pyrazol-4-yl]-4-(6-fluoro-3-pyridyl)pyrazolo[1,5-a]pyrazine-3-carbonitrile (5, 20 mg, 28.18 mol) and the mixture was stirred at 100° C. for 16 hr. The reaction mixture was quenched by aq. HCl (1M, 0.2 mL) and purified with Prep-HPLC (neutral condition: Waters Xbridge 150*25 mm*5 um) and lyophilized to give 6-[1-[4-[4-[4-[(2,6-dioxo-3-piperidyl)amino]-2,6-difluoro-phenyl]piperazin-1-yl] cyclohexyl]pyrazol-4-yl]-4-[6-[rac-(1R,5S)-9-[(6-isopropoxy-3-pyridyl)methyl]-3-oxa-7,9-diazabicyclo[3.3.1] nonan-7-yl]-3-pyridyl]pyrazolo[1,5-a]pyrazine-3-carbonitrile (Compound 213, 5.29 mg, 5.47 mol, 6% yield) as yellow solid.

LCMS ($ES^+$): m/z 967.6 $[M+H]^+$, 484.5 $[M/2+H]^+$ $^1H$ NMR (400 MHz, DMSO-$d_6$) δ=10.82 (s, 1H), 9.27 (s, 1H), 8.83 (s, 1H), 8.72 (s, 1H), 8.46 (s, 1H), 8.16 (s, 2H), 8.09 (dd, J=8.8 Hz and 2.4 Hz, 1H), 7.73 (dd, J=8.8 Hz and 2.4 Hz, 1H), 6.90 (d, J=8.8 Hz, 1H), 6.74 (d, J=8.8 Hz, 1H), 6.34-6.31 (m, 2H), 6.28-6.25 (m, 1H), 5.25-5.22 (m, 3H), 4.33-4.26 (m, 3H), 4.23-4.08 (m, 2), 3.95-3.91 (m, 4H), 3.87-3.77 (m, 2H), 3.56-3.50 (m, 2H), 3.00-2.94 (m, 4H), 2.84-2.80 (m, 2H), 2.64-2.57 (m, 1H), 2.45-2.38 (m, 2H), 2.20-2.11 (m, 2H), 2.08 (s, 1H), 2.00-1.92 (m, 2H), 1.89-1.79 (m, 3H), 1.54-1.43 (m, 2H), 1.40-1.39 (m, 6H), 1.34-1.29 (m, 2H), 1.28-1.25 (m, 1H).

Example 216: Synthesis of 4-[6-[6-[(4,4-difluorocyclohexyl)methyl]-3,6-diazabicyclo[3.1.1]heptan-3-yl]-3-pyridyl]-6-[1-[4-[4-[4-[(2,6-dioxo-3-piperidyl) amino]-2,6-difluoro-phenyl]piperazin-1-yl] cyclohexyl]pyrazol-4-yl]pyrazolo[1,5-a]pyrazine-3-carbonitrile (Compound 214)

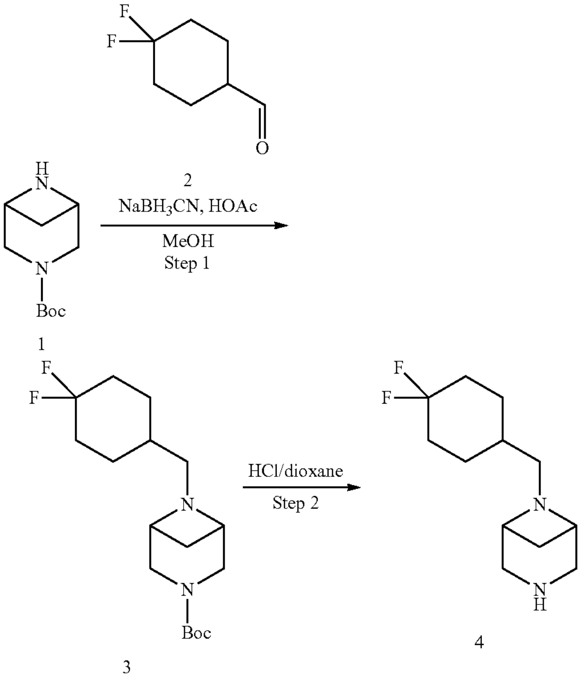

-continued

-continued

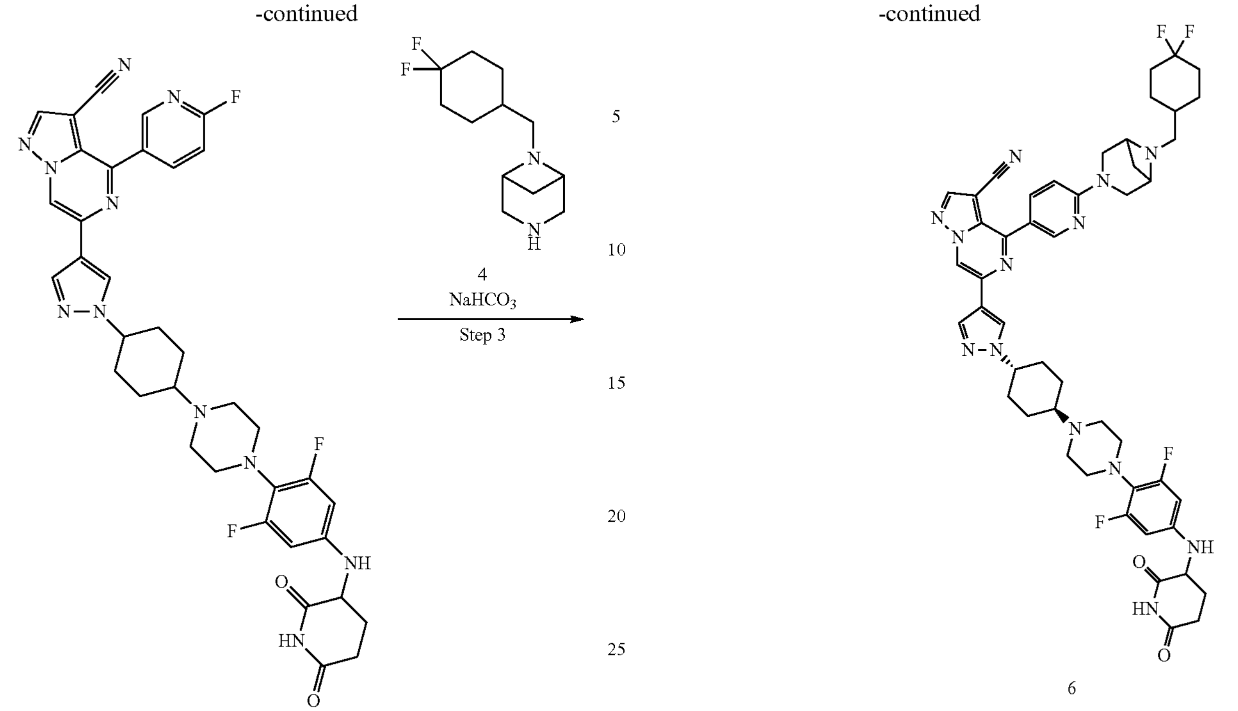

5

6

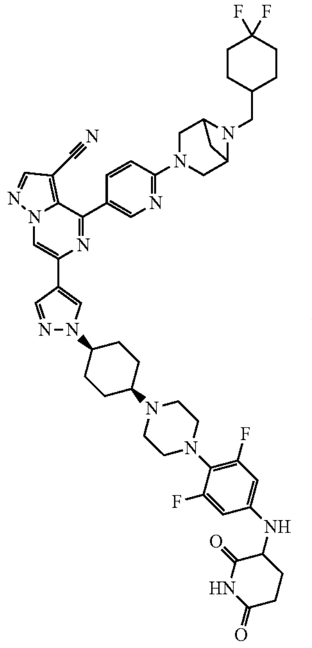

Compound 214

+

Step 1: To a solution of tert-butyl 3,6-diazabicyclo[3.1.1]heptane-3-carboxylate (1, 500 mg, 2.52 mmol) and 4,4-difluorocyclohexanecarbaldehyde (2, 373.62 mg, 2.52 mmol) in Methanol (5 mL) was added acetic acid (15.14 mg, 252.19 mol, 14.44 μL). The mixture was stirred at 20° C. for 2h. Then to the mixture was added sodium triacetoxyborohydride (1.07 g, 5.04 mmol), the mixture was stirred at 20° C. for 16h. The reaction mixture was concentrated under reduced pressure to remove solvent. The residue purified by flash silica gel column chromatography ($SiO_2$, Petroleum ether/Ethyl acetate=1/1 to 0/1) to afford tert-butyl 6-((4,4-difluorocyclohexyl)methyl)-3,6-diazabicyclo[3.1.1]heptane-3-carboxylate (3, 350 mg, 1.06 mmol, 42% yield) as a yellow oil.

$^1H$ NMR (400 MHz, CHLOROFORM-d) δ=3.77-3.61 (m, 2H), 3.59 (br d, J=11.2 Hz, 2H), 3.44-3.34 (m, 2H), 2.69-2.55 (m, 1H), 2.31 (br dd, J=6.8, 11.6 Hz, 2H), 2.11-2.07 (m, 2H), 1.90-1.56 (m, 2H), 1.82-1.53 (m, 4H), 1.51 (s, 9H), 1.33-1.23 (m, 2H)

Step 2: To a solution of tert-butyl 6-[(4,4-difluorocyclohexyl)methyl]-3,6-diazabicyclo[3.1.1]heptane-3-carboxylate (3, 400 mg, 1.21 mmol) in DCM (0.5 mL) was added HCl/dioxane (302.65 mol, 2 mL). The mixture was stirred at 20° C. for 0.5h. The reaction mixture was concentrated under reduced pressure to afford 6-[(4,4-difluorocyclohexyl)methyl]-3,6-diazabicyclo[3.1.1]heptane (4, 320 mg, 1.20 mmol, 99% yield, HCl salt) as an off-white solid.

Step 3: To a solution of 6-[(4,4-difluorocyclohexyl)methyl]-3,6-diazabicyclo[3.1.1]heptane (4, 320 mg, 1.20 mmol, HCl salt) and 6-[1-[4-[4-[4-[(2,6-dioxo-3-piperidyl)amino]-2,6-difluoro-phenyl]piperazin-1-yl]cyclohexyl]pyrazol-4-yl]-4-(6-fluoro-3-pyridyl)pyrazolo[1,5-a]pyrazine-3-carbonitrile (5, 568.89 mg, 801.57 mol) in DMSO (10 mL) was added sodium bicarbonate (335.91 mg, 4.00 mmol, 155.59 μL), the mixture was stirred at 80° C. for 16h. The reaction mixture was filtered. The residue was purified by Prep-HPLC (neutral condition) (column: Waters Xbridge 150*25 mm*5 um; mobile phase: [water (NH4HCO3)-ACN]; B %: 53%-83%, 8 min) to give 4-[6-[6-[(4,4-difluorocyclohexyl)methyl]-3,6-diazabicyclo[3.1.1]heptan-3-yl]-3-pyridyl]-6-[1-[4-[4-[4-[(2,6-dioxo-3-piperidyl)amino]-2,6-difluoro-phenyl]piperazin-1-yl]cyclohexyl]pyrazol-4-yl]pyrazolo[1,5-a]pyrazine-3-carbonitrile (6, 92.28 mg, 97.74 mol, 12% yield) as white solid.

LCMS (ES$^+$): m/z 920.5 [M+H]$^+$, 461.0 [M/2+H]$^+$, $^1$H NMR (400 MHz, DMSO-$d_6$) δ=10.82 (br d, J=4.0 Hz, 1H), 9.35 (s, 1H), 8.84 (s, 1H), 8.74 (d, J=2.8 Hz, 1H), 8.50 (s, 1H), 8.17 (s, 1H), 8.13 (dd, J=2.4, 8.8 Hz, 1H), 6.83 (d, J=9.0 Hz, 1H), 6.41-6.20 (m, 3H), 4.37-4.28 (m, 2H), 3.79-3.65 (m, 4H), 3.58-3.39 (m, 2H), 3.30 (s, 2H), 2.99 (br s, 4H), 2.80-2.64 (m, 2H), 2.32-2.21 (m, 5H), 2.13-1.39 (m, 18H), 1.20-1.04 (m, 3H)

The other peak was purified by Prep-HPLC (FA condition) (column: Phenomenex C18 75*30 mm*3 um; mobile phase: [water (FA)-ACN]; B %: 10%-40%, 9 min) to give product 4-[6-[6-[(4,4-difluorocyclohexyl)methyl]-3,6-diazabicyclo[3.1.1]heptan-3-yl]-3-pyridyl]-6-[1-[4-[4-[4-[(2,6-dioxo-3-piperidyl)amino]-2,6-difluoro-phenyl]piperazin-1-yl]cyclohexyl]pyrazol-4-yl]pyrazolo[1,5-a]pyrazine-3-carbonitrile FA salt (Compound 214, 68.38 mg, 68.77 mol, 9% yield) as yellow solid.

LCMS (ES$^+$): m/z 920.5 [M+H]$^+$, 461.0 [M/2+H]$^+$, $^1$H NMR (400 MHz, DMSO-$d_6$) δ=10.81 (s, 1H), 9.29 (s, 1H), 8.84 (s, 1H), 8.75 (d, J=2.4 Hz, 1H), 8.46 (s, 1H), 8.12 (d, J=2.4 Hz, 1H), 8.15 (d, J=4.8 Hz, 2H), 6.84 (d, J=8.8 Hz, 1H), 6.38-6.23 (m, 3H), 4.35-4.17 (m, 2H), 3.85-3.61 (m, 6H), 3.00 (br s, 4H), 2.79-2.73 (m, 1H), 2.61-2.55 (m, 4H), 2.32-2.24 (m, 2H), 2.19-2.14 (m, 2H), 2.13-2.02 (m, 2H), 2.00-1.96 (m, 3H), 1.88-1.79 (m, 6H), 1.75-1.68 (m, 1H), 1.61-1.38 (m, 5H), 1.25-1.10 (m, 3H)

Example 217: Synthesis of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[4-hydroxy-4-[(5-methoxy-2-pyridyl)methyl]-1-piperidyl]-3-pyridyl]pyrazolo[1,5-a]pyrazine-3-carbonitrile (Compound 215)

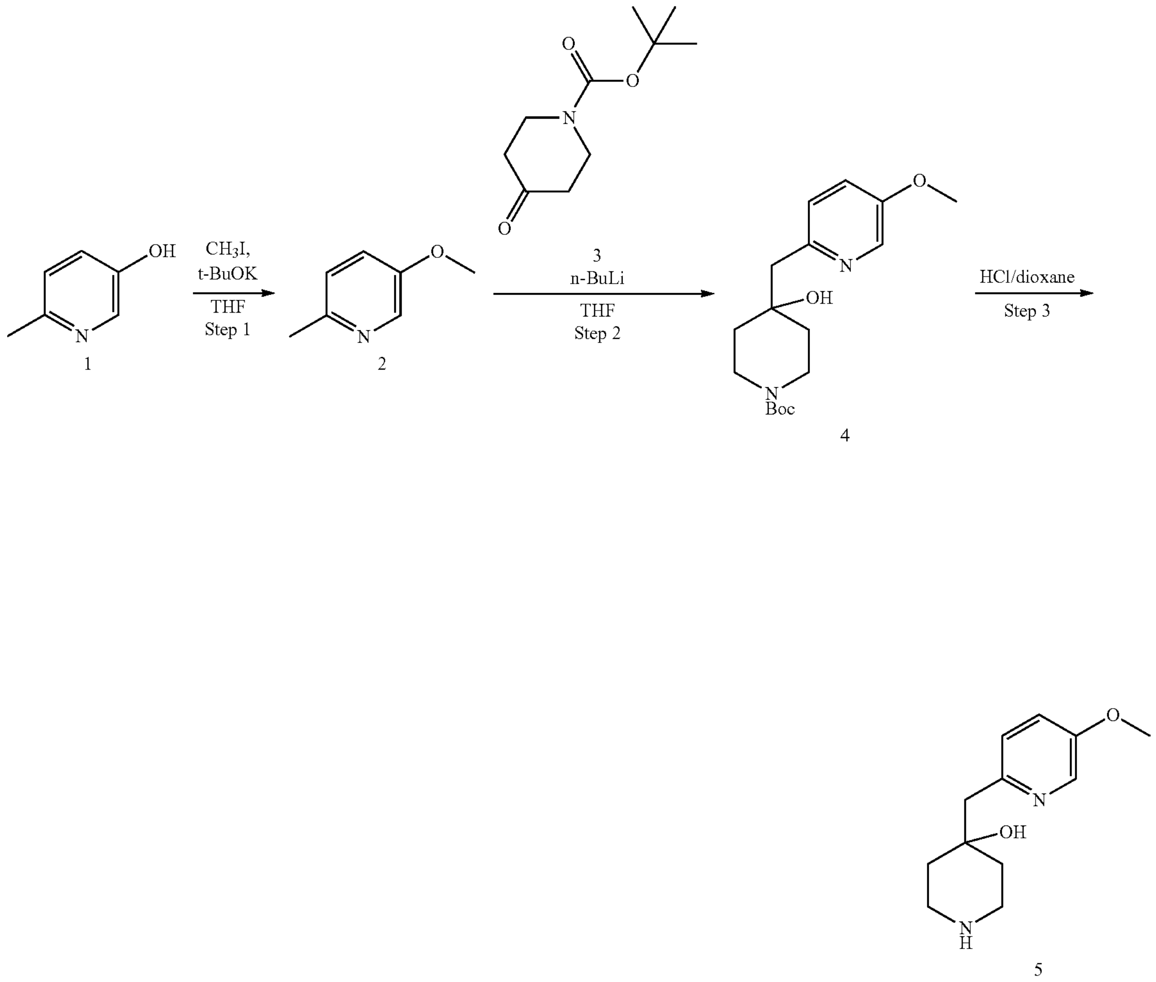

-continued

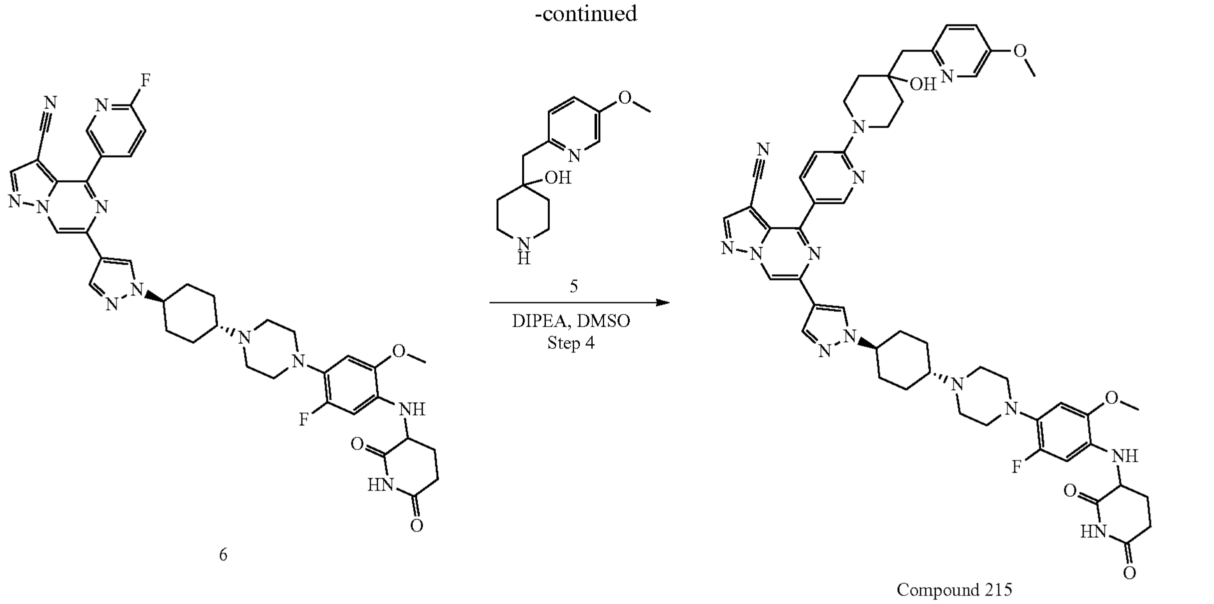

6

Compound 215

Step 1: To a solution of 6-methylpyridin-3-ol (1, 1 g, 9.16 mmol) in THF (30 mL) was added potassium; 2-methylpropan-2-olate (1.03 g, 9.16 mmol) at 10° C. Then iodomethane (1.43 g, 10.08 mmol, 627.53 μL) was added into above solution at 10° C. After addition, the solution was stirred at 10° C. for 12 hr. The reaction solution was poured into water (100 mL). The aqueous solution was extracted with EtOAc (50 mL*3), The combined organic layer was wash with brine (10 ml), dried over $Na_2SO_4$, filtered and concentrated in vacuum. The residue was purified by flash silica gel chromatography (12 g Silica Flash Column, Eluent of 0-50% Ethyl acetate/Petroleum ether gradient 40 mL/min, 40 min). 5-methoxy-2-methylpyridine (2, 410 mg, 3.30 mmol, 36% yield) was obtained as yellow oil. LCMS ($ES^+$): m/z 123.8 $[M+H]^+$ Step 2: Butyllithium (2.5 M, 1.17 mL) was added to 5-methoxy-2-methyl-pyridine (2, 300 mg, 2.44 mmol, 1.06 mL) in THF (10 mL) at −60° C. The mixture was stirred for 30 min and then the solution was slowed to stir at −5° C. for another 30 min. The reaction was cooled to −60° C. again and the solution of tert-butyl 4-oxopiperidine-1-carboxylate (3, 533.90 mg, 2.68 mmol) in THF (10 mL) was added and then the mixture was allowed to stir at −60° C. for 1 h. The reaction mixture was poured into sat.$NH_4Cl$ (25 mL) and extracted with EA (20 mL*2). The combined organic layer was washed with brine (50 mL), dried over $Na_2SO_4$, filtered and the filtrate was concentrated. The residue was purified by prep=TLC ($SiO_2$, PE:EA=1:2, Rf=0.4) to get the product. tert-butyl 4-hydroxy-4-[(5-methoxy-2-pyridyl)methyl]piperidine-1-carboxylate (4, 160 mg, 486.35 μmol, 20% yield) was obtained as a light yellow oil. LCMS ($ES^+$): m/z 323.1 $[M+H]^+$ Step 3: To a solution of tert-butyl 4-hydroxy-4-[(5-methoxy-2-pyridyl)methyl]piperidine-1-carboxylate (4, 150 mg, 465.26 μmol) in DCM (1 mL) was added HCl/Dioxane (4 M, 2 mL) dropwise at 25° C. After addition, the solution was stirred at 25° C. for 12 hr. The mixture was concentrated in vacuum to get the product. The crude product was washed with dioxane (1 mL) to get the product. Compound 4-[(5-methoxy-2-pyridyl)methyl]piperidin-4-ol (5, 110 mg, 382.62 mol, 82% yield, HCl salt) was obtained as a white solid. LCMS ($ES^+$): m/z 223.1 $[M+H]^+$ Step 4: To a solution of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-(6-fluoro-3-pyridyl)pyrazolo[1,5-a]pyrazine-3-carbonitrile (6, 50 mg, 69.28 μmol) and 4-((5-methoxypyridin-2-yl)methyl)piperidin-4-ol (5, 26.89 mg, 103.91 μmol, HCl salt) in DMSO (999.93 μL) was added DIPEA (35.81 mg, 277.10 μmol, 48.26 μL) at 20° C., then the mixture was stirred at 120° C. for 4 h. The reaction mixture was concentrated and adjust to pH=4-5 with FA, then the mixture was purified by prep-HPLC ((Unisil 3-100 C18 Ultra 150*50 mm*3 um; water (0.225% FA)-ACN; B %: 8%~38%, Gradient Time (10 min), 100% B Hold Time (2 min), FlowRate (25 ml/min)) to get the product. The 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[4-hydroxy-4-[(5-methoxy-2-pyridyl)methyl]-1-piperidyl]-3-pyridyl]pyrazolo[1,5-a]pyrazine-3-carbonitrile (Compound 215, 44.87 mg, 45.79 mol, 66% yield, TFA salt) was obtained as yellow solid.

LCMS ($ES^+$): m/z 924.6 $[M+H]^+$ $^1H$ NMR (400 MHz, DMSO-$d_6$) δ=10.87 (br s, 1H), 9.28 (s, 1H), 8.83 (s, 1H), 8.66 (d, J=2.0 Hz, 1H), 8.45 (s, 1H), 8.23 (s, 1H), 8.21 (d, J=2.8 Hz, 1H), 8.15 (s, 1H), 8.07-8.01 (m, 1H), 7.36-7.24 (m, 2H), 6.99 (br d, J=9.2 Hz, 1H), 6.64-6.52 (m, 2H), 5.10 (br d, J=6.4 Hz, 1H), 4.90 (br s, 1H), 4.30-4.07 (m, 4H), 3.81 (s, 3H), 3.80 (s, 3H), 3.37-3.34 (m, 2H), 2.98-2.89 (m, 4H), 2.86 (s, 2H), 2.82-2.75 (m, 1H), 2.72-2.64 (m, 4H), 2.59-2.55 (m, 1H), 2.45-2.39 (m, 1H), 2.20-2.11 (m, 3H), 2.02-1.91 (m, 3H), 1.88-1.78 (m, 2H), 1.60-1.44 (m, 6H)

Example 218: Synthesis of 1-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-N-isopropyl-4-[(5-methoxy-2-pyridyl)methyl]piperidine-4-carboxamide (Compound 216)
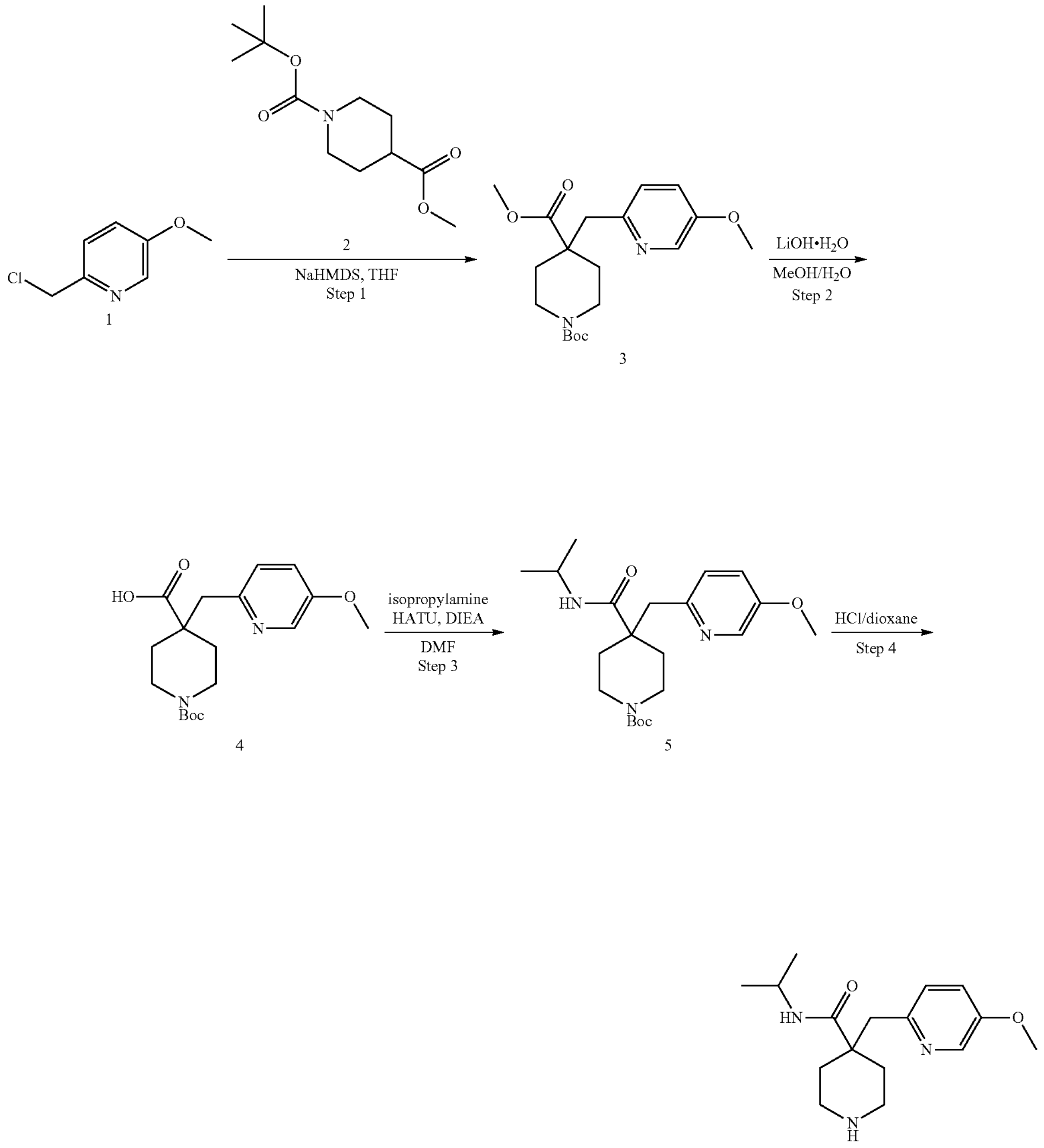
1 2 3 4 5 6

-continued

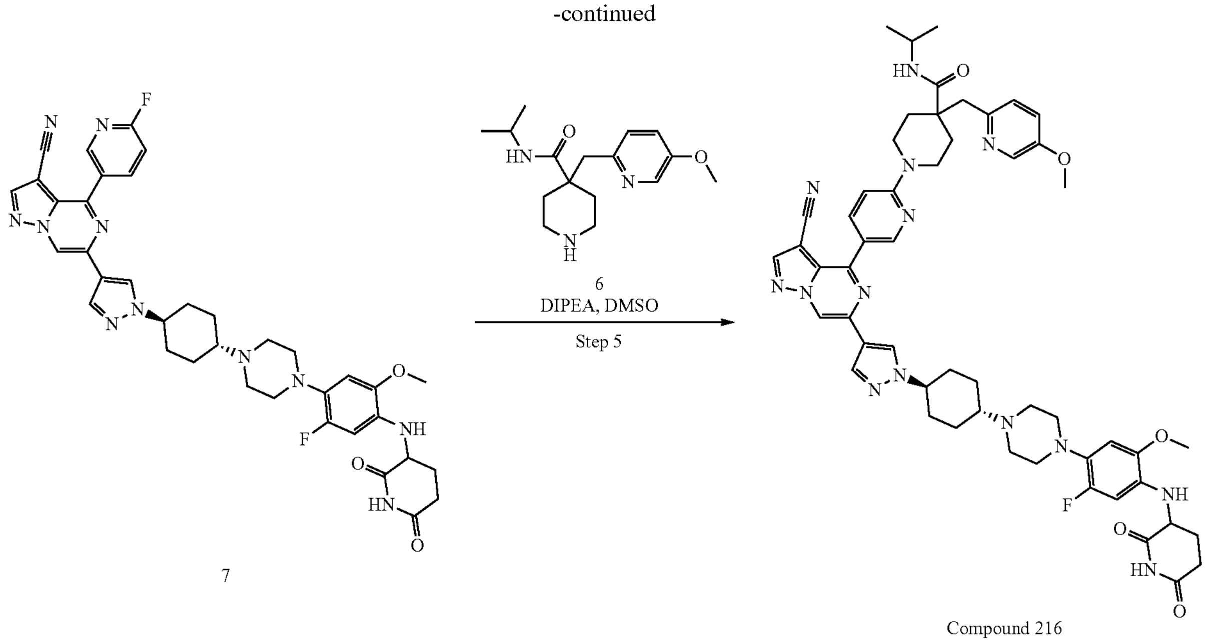

7

Compound 216

Step 1: To a solution of 01-tert-butyl 04-methyl piperidine-1,4-dicarboxylate (2, 500 mg, 2.06 mmol, 952.38 μL) in THF (10.03 mL) was added NaHMDS (2 M, 966.21 μL) dropwise at −50° C. Then 2-(chloromethyl)-5-methoxy-pyridine (1, 150 mg, 772.96 mol, HCl salt) was added into above solution at −50° C. After addition, the solution was stirred at −50° C. for 2 hr. The reaction solution was poured $NH_4Cl$ (aq. sat. 100 mL). The aqueous solution was extracted with EA (50 mL*3), The combined organic layer was wash with brine (50 ml*3), dried over $Na_2SO_4$, filtered and concentrated in vacuum. The residue was purified by prep-TLC (PE:EA=2:1, $SiO_2$, Rf=0.3) to get the product. 01-tert-butyl 04-methyl 4-[(5-methoxy-2-pyridyl)methyl]piperidine-1,4-dicarboxylate (3, 140 mg, 380.31 mol, 49% yield) was obtained as yellow oil. LCMS ($ES^+$): m/z 364.9 $[M+H]^+$ Step 2: To a solution of 01-tert-butyl 04-methyl 4-[(5-methoxy-2-pyridyl)methyl]piperidine-1,4-dicarboxylate (3, 150 mg, 411.60 mol) in MeOH (1 mL) was added $LiOH{\cdot}H_2O$ (4 M, 205.80 μL) dropwise at 10° C. After addition, the solution was stirred at 70° C. for 12 hr. The reaction solution was concentrated in vacuum to get the residue, then the residue was added into water (6 mL), and adjusted to pH=6-7 with aq. HCl (4M), the aqueous solution was extracted with EtOAc (5 mL*5), The combined organic layer were wash with brine (5 ml*3), dried over Na2SO4, filtered and concentrated in vacuum. The crude product was used to next step directly. 1-tert-butoxycarbonyl-4-[(5-methoxy-2-pyridyl)methyl]piperidine-4-carboxylic acid (4, 110 mg, 310.78 mol, 76% yield) was obtained as yellow solid. LCMS ($ES^+$): m/z 350.9 $[M+H]^+$ Step 3: To a solution of 1-tert-butoxycarbonyl-4-[(5-methoxy-2-pyridyl)methyl]piperidine-4-carboxylic acid (4, 110 mg, 313.92 mol) and propan-2-amine (37.11 mg, 627.84 mol, 53.71 μL) in DMF (10.78 mL) was added HATU (238.72 mg, 627.84 μmol) at 20° C. Then DIPEA (121.72 mg, 941.76 μmol, 164.04 μL) was added into above solution at 20° C. After addition, the solution was stirred at 20° C. for 12 hr. The reaction solution was poured into water (30 mL). The aqueous solution was extracted with EtOAc (15 mL*3), The combined organic layer was wash with brine (10 ml*3), dried over $Na_2SO_4$, filtered and concentrated in vacuum. The residue was purified by by prep-TLC (SiO2, PE:EA=0:1, Rf=0.5) to get the product. tert-butyl 4-(isopropylcarbamoyl)-4-[(5-methoxy-2-pyridyl)methyl]piperidine-1-carboxylate (5, 95 mg, 240.23 μmol, 77% yield) was obtained as colorless oil. LCMS ($ES^+$): m/z 392.2 $[M+H]^+$ Step 4: To a solution of tert-butyl 4-(isopropylcarbamoyl)-4-[(5-methoxy-2-pyridyl)methyl]piperidine-1-carboxylate (5, 95 mg, 242.65 μmol) in DCM (2 mL) was added HCl/Dioxane (4 M, 1 mL) dropwise at 25° C. After addition, the solution was stirred at 25° C. for 12 hr. The mixture was concentrated in vacuum to get the product. The crude product used to next step directly. Compound N-isopropyl-4-[(5-methoxy-2-pyridyl)methyl]piperidine-4-carboxamide (6, 75 mg, 205.89 μmol, 85% yield, HCl salt) was obtained as a white solid. LCMS ($ES^+$): m/z 291.9 $[M+H]^+$ Step 5: To a solution of 6-[1-[4-[4-[4-[(2,6-dioxo-3-piperidyl)amino]-2-fluoro-5-methoxy-phenyl]piperazin-1-yl]cyclohexyl]pyrazol-4-yl]-4-(6-fluoro-3-pyridyl)pyrazolo[1,5-a]pyrazine-3-carbonitrile (7, 50 mg, 69.28 μmol) and N-isopropyl-4-((5-methoxypyridin-2-yl)methyl)piperidine-4-carboxamide (6, 45.42 mg, 138.55 μmol, HCl salt) in DMSO (3 mL) was added DIPEA (35.81 mg, 277.10 μmol, 48.26 μL) at 20° C., then the mixture was stirred at 120° C. for 2 h. The reaction mixture was concentrated and adjust to pH=4-5 with FA, then the crude product was purified by prep-HPLC ((Phenomenex Luna C18 150*25 mm*10 um; water (0.225% FA)-ACN; B %: 9%~39%, Gradient Time (10 min), 100% B Hold Time (2 min), FlowRate (25 ml/min)) to get the product The 1-[5-[3-cyano-6-[1-[4-[4-[4-[(2,6-dioxo-3-piperidyl)amino]-2-fluoro-5-methoxy-phenyl]piperazin-1-yl]cyclohexyl]pyrazol-4-yl]pyrazolo[1,5-a]pyrazin-4-yl]-2-pyridyl]-N-isopropyl-4-[(5-methoxy-2-pyridyl)methyl]piperidine-4-carboxamide (Compound 216, 44.60 mg, 38.63 mol, 56% yield, formic acid salt) was obtained as yellow solid.

LCMS ($ES^+$): m/z 497.5 $[M/2+H]^+$ $^1H$ NMR (400 MHz, DMSO-$d_6$) δ=10.86 (s, 1H), 9.28 (s, 1H), 8.83 (s, 1H), 8.70-8.65 (m, 1H), 8.46 (s, 1H), 8.20-8.15

(m, 2H), 8.15 (s, 1H), 8.10-7.99 (m, 1H), 7.45 (d, J=8.0 Hz, 1H), 7.33-7.26 (m, 1H), 7.07 (d, J=8.6 Hz, 1H), 7.00 (br d, J=9.0 Hz, 1H), 6.64-6.52 (m, 2H), 5.11 (br d, J=6.8 Hz, 1H), 4.30-4.19 (m, 2H), 4.19-4.08 (m, 2H), 4.02-3.89 (m, 1H), 3.80 (d, J=2.0 Hz, 6H), 3.21-3.15 (m, 2H), 2.98-2.91 (m, 6H), 2.87-2.71 (m, 5H), 2.59-2.55 (m, 1H), 2.23-2.06 (m, 6H), 2.03-1.80 (m, 6H), 1.57-1.47 (m, 4H), 1.07 (d, J=6.4 Hz, 6H)

Example 219: Synthesis of 6-[1-[4-[4-[4-[(2,6-dioxo-3-piperidyl)amino]-2-fluoro-5-methoxy-phenyl] piperazin-1-yl] cyclohexyl]pyrazol-4-yl]-4-[6-[6-[(2-methylsulfonylphenyl)methyl]-3,6-diazabicyclo [3.1.1]heptan-3-yl]-3-pyridyl]pyrazolo[1,5-a]pyrazine-3-carbonitrile (Compound 217)

filtered and the filtrate was concentrated. The residue was purified by column chromatography ($SiO_2$, PE:EA=10:1-1:1) to obtain tert-butyl 6-[(2-methylsulfonylphenyl)methyl]-3,6-diazabicyclo[3.1.1]heptane-3-carboxylate (3, 301 mg, 808.20 mol, 80% yield) as a white solid. LCMS ($ES^+$): m/z 367.1 $[M+H]^+$ Step 2: The solution of tert-butyl 6-[(2-methylsulfonylphenyl)methyl]-3,6-diazabicyclo[3.1.1]heptane-3-carboxylate (3, 100 mg, 272.87 mol) in TFA (0.3 mL) and DCM (1 mL) was stirred at 15° C. for 1h. The reaction was concentrated under vacuum at 25° C. to obtain 6-[(2-methylsulfonylphenyl) methyl]-3,6-diazabicyclo[3.1.1]heptane (4, 100 mg, 241.86 mol, 89% yield, TFA salt) as colorless oil. LCMS ($ES^+$): m/z 267.1 $[M+H]^+$ Step 3: To a solution of 6-[(2-methylsulfonylphenyl) methyl]-3,6-diazabicyclo[3.1.1]heptane (4, 100.00 mg,

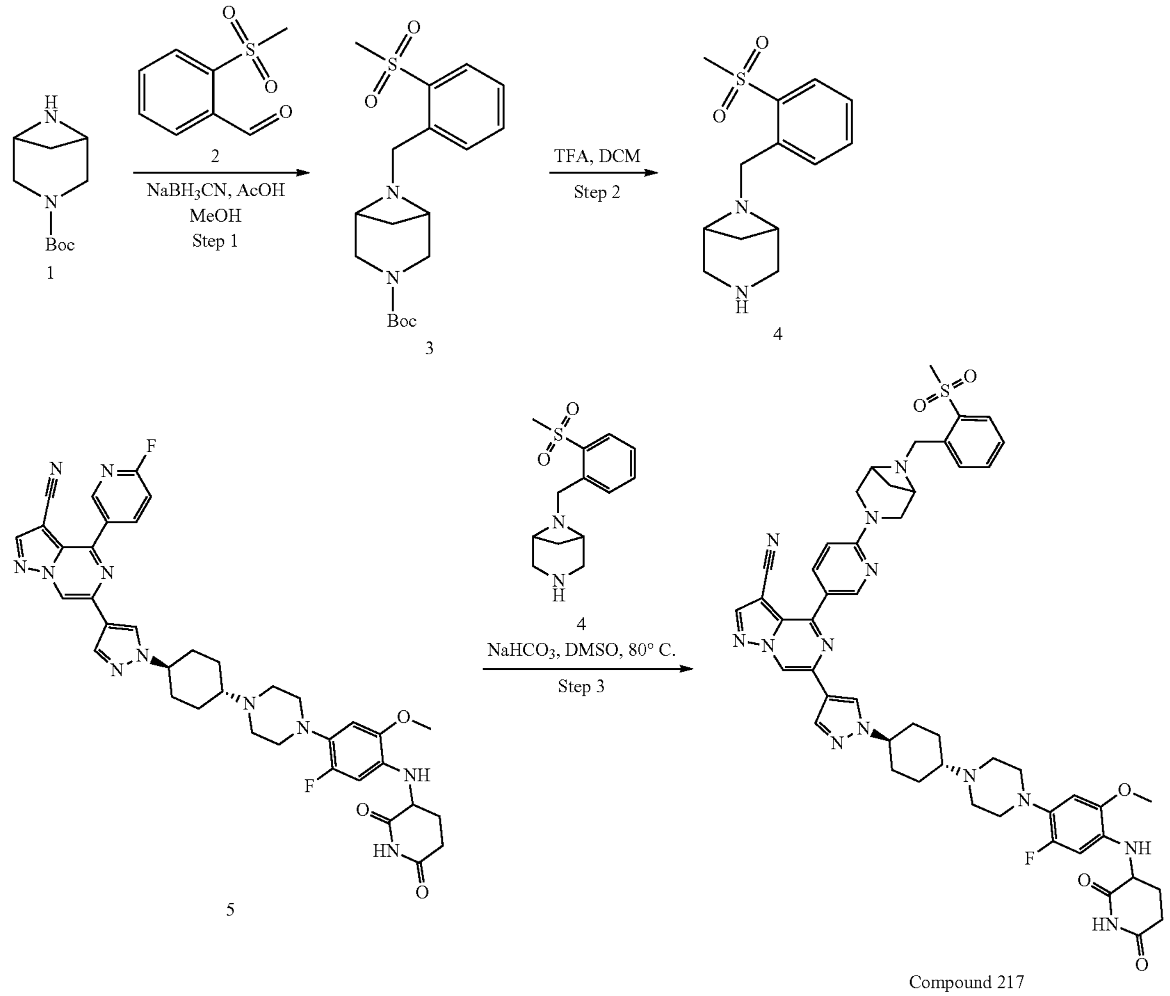

Compound 217

Step 1: To a solution of tert-butyl 3,6-diazabicyclo[3.1.1] heptane-3-carboxylate (1, 200 mg, 1.01 mmol) in Methanol (2 mL) was added 2-methylsulfonylbenzaldehyde (2, 185.83 mg, 1.01 mmol) and ACETIC ACID (6.06 mg, 100.88 mol, 5.77 µL). The mixture was stirred at 40° C. for 2 h. Then sodium cyanoborohydride (316.96 mg, 5.04 mmol) was added at 0° C., the solution was stirred at 20° C. for 16 h. The reaction mixture was poured into sat.$NH_4Cl$ (10 mL) and extracted with EA (5 mL*3). The combined organic layer was washed with brine (10 mL), dried over $Na_2SO_4$, 262.89 mol, TFA salt) in DMSO (1.03 mL) was added 6-[1-[4-[4-[4-[(2,6-dioxo-3-piperidyl)amino]-2-fluoro-5-methoxy-phenyl]piperazin-1-yl]cyclohexyl]pyrazol-4-yl]-4-(6-fluoro-3-pyridyl) pyrazolo [1,5-a]pyrazine-3-carbonitrile (5, 75.90 mg, 105.16 mol) and sodium bicarbonate (44.17 mg, 525.79 mol, 20.46 µL). The mixture was stirred at 90° C. for 12h. The reaction mixture was concentrated under reduced pressure. The reaction was purified by Prep-HPLC (Phenomenex Synergi C18 150*25 mm*10 um;

Condition: water (0.225% FA)-ACN; B %: 7-37; Gradient Time (min) 10; 100% B Hold Time (min) 2; Flow Rate (ml/min) 25) to obtain 6-[1-[4-[4-[4-[(2,6-dioxo-3-piperidyl)amino]-2-fluoro-5-methoxy-phenyl]piperazin-1-yl]cyclohexyl]pyrazol-4-yl]-4-[6-[6-[(2-methylsulfonylphenyl)methyl]-3,6-diazabicyclo[3.1.1]heptan-3-yl]-3-pyridyl]pyrazolo[1,5-a]pyrazine-3-carbonitrile (Compound 217, 33.64 mg, 32.81 mol, 31% yield, formic acid salt) as yellow solid.

LCMS ($ES^+$): m/z 968.6 $[M+H]^+$ $^1H$ NMR (400 MHz, DMSO-$d_6$) δ=10.85 (s, 1H), 9.30 (s, 1H), 8.84 (s, 1H), 8.77 (d, J=2.0 Hz, 1H), 8.47 (s, 1H), 8.19-8.14 (m, 2H), 7.99-7.93 (m, 1H), 7.75-7.65 (m, 2H), 7.59-7.50 (m, 1H), 6.88 (d, J=9.2 Hz, 1H), 6.65-6.52 (m, 2H), 5.19-5.11 (m, 1H), 4.32-4.20 (m, 2H), 4.10-3.98 (m, 2H), 3.94-3.83 (m, 2H), 3.80 (s, 3H), 3.78-3.72 (m, 2H), 3.70-3.57 (m, 2H), 3.34 (s, 3H), 3.15-2.89 (m, 8H), 2.87-2.71 (m, 2H), 2.61-2.52 (m, 2H), 2.27-2.04 (m, 5H), 2.01-1.78 (m, 3H), 1.73-1.48 (m, 3H).

Example 220: Synthesis of 6-[1-[4-[4-[2,6-difluoro-4-[[rac-(3R)-2,6-dioxo-3-piperidyl]amino]phenyl]piperazin-1-yl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (6) (Compound 218)

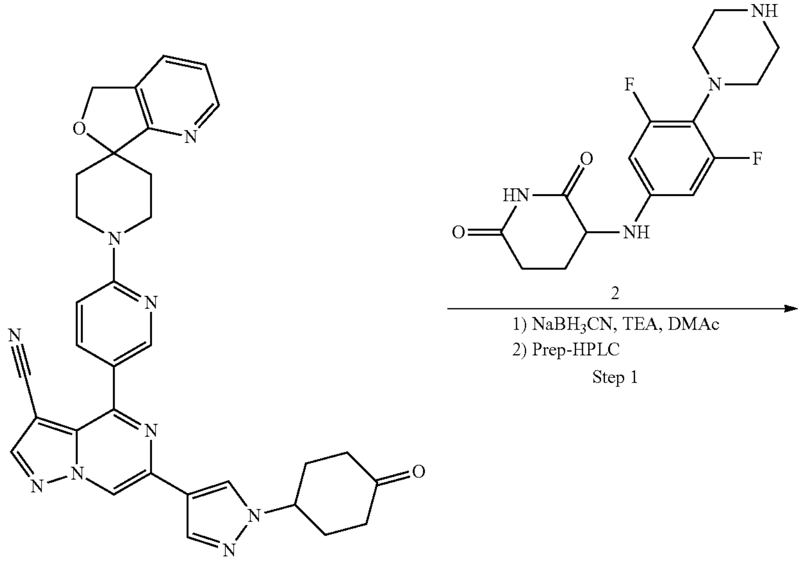

1

2

-continued

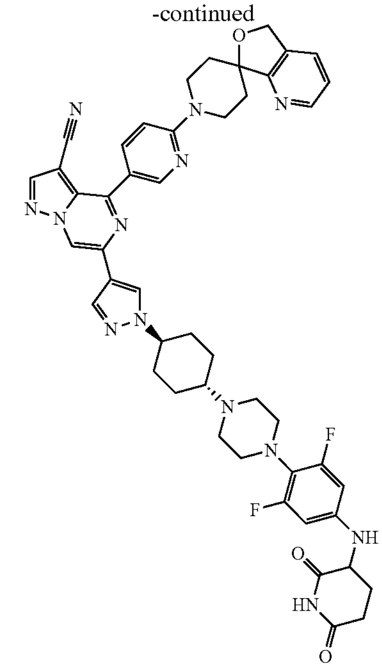

3

+

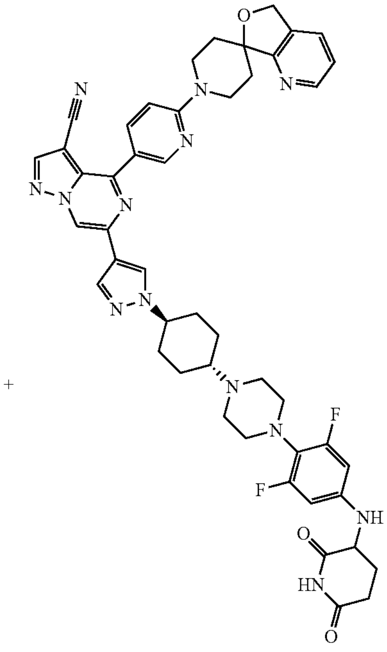

4

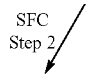

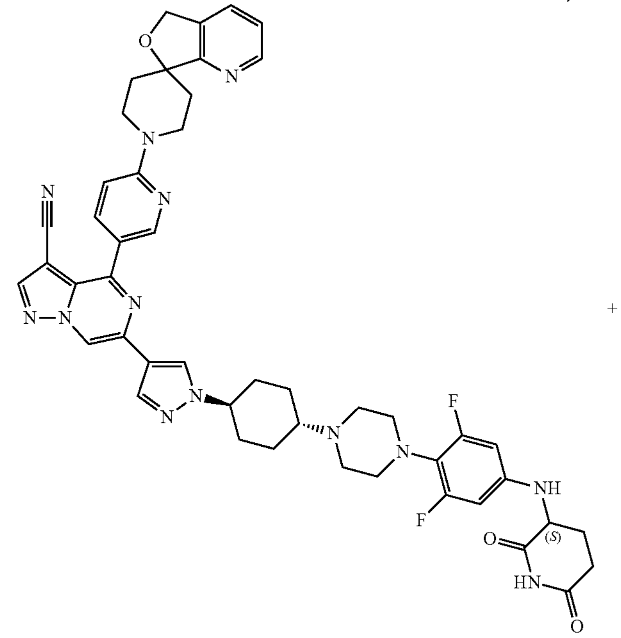

5

+

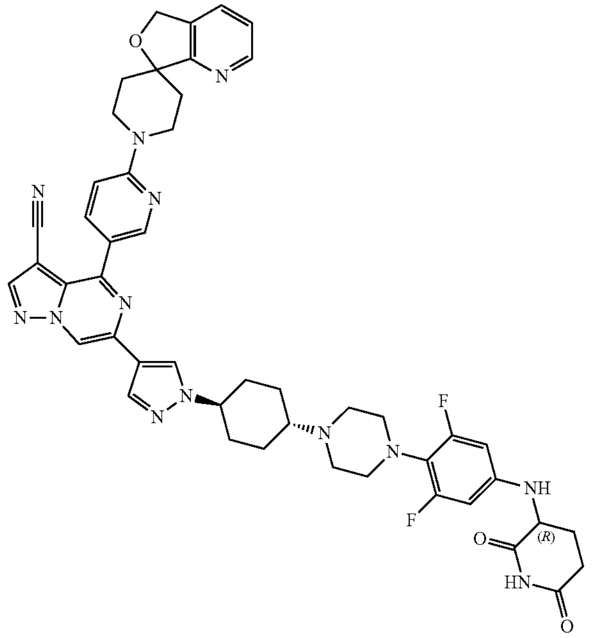

Compound 218

Step 1: To a solution of 4-(6-(5H-spiro[furo[3,4-b]pyridine-7,4'-piperidin]-1'-yl)pyridin-3-yl)-6-(1-(4-oxocyclohexyl)-1H-pyrazol-4-yl)pyrazolo[1,5-a]pyrazine-3-carbonitrile (1, 180 mg, 314.89 mol) and 3-[3,5-difluoro-4-(4-piperidyl)anilino]piperidine-2,6-dione (2, 169.94 mg, 472.33 mol, HCl salt) in DMAc (1.87 mL) was added TEA (159.32 mg, 1.57 mmol, 219.45 μL). The mixture was stirred at 50° C. for 2 h, then sodium cyanoborohydride (197.88 mg, 3.15 mmol) was added above, the mixture was stirred at 70° C. for 12 h. The reaction mixture was filtered and the filtrate was concentrated in vacuum. The residue was purified by prep-HPLC (column: 3_Phenomenex Luna C18 75*30 mm*3 um; mobile phase: [water (10 mM $NH_4HCO_3$)-ACN]; B %: 39%-69%, 9 min), thenlyophilization. Compound 6-[1-[4-[4-[4-[(2,6-dioxo-3-piperidyl)amino]-2,6-difluoro-phenyl] piperazin-1-yl] cyclohexyl]pyrazol-4-yl]-4-(6-spiro[5H-furo[3,4-b]pyridine-7,4'piperidine]-1'-yl-3-pyridyl)pyrazolo[1,5-a]pyrazine-3-carbonitrile (3, 60 mg, 65.46 mol, 20.79% yield) was obtained as a yellow solid. Compound 6-[1-[4-[4-[4-[(2,6-dioxo-3-piperidyl)amino]-2,6-difluoro-phenyl]piperazin-1-yl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (4, 60.67 mg, 68.95 mol, 22% yield) was obtained as a yellow solid. LCMS ($ES^+$): m/z 880.2 $[M+H]^+$ Step 2: The residue was separated by SFC[Column: DAICEL CHIRALPAK AS (250 mm*30 mm, 10 um); Condition: 75% IPA+ACN (0.1% NH3·H2O) in Supercritical $CO_2$; Flow Rate: 80 mL/min; Cycle Time: 3 min, total time: 60 min; Single injection volume: 2.0 ml; Back Pressure: 100 bar to keep the $CO_2$ in Supercritical flow]. Then the residue was purified by prep-HPLC (column: 3_Phenomenex Luna C18 75*30 mm*3 um; mobile phase: [water (0.225% FA)-ACN]; B %: 14%-44%, 10 min).

Compound 6-[1-[4-[4-[2,6-difluoro-4-[[rac-(3R)-2,6-dioxo-3-piperidyl]amino]phenyl]piperazin-1-yl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (Compound 218, 11.95 mg, 12.91 mol, 19% yield, formic acid salt) was obtained as yellow solid.

LCMS ($ES^+$): m/z 880.1 $[M+H]^+$

1H NMR (400 MHz, DMSO-$d_6$) δ=10.82 (br s, 1H), 9.29 (s, 1H), 8.83 (s, 1H), 8.71 (d, J=2.3 Hz, 1H), 8.50-8.39 (m, 2H), 8.23 (s, 1H), 8.16 (s, 1H), 8.10 (dd, J=2.4, 8.8 Hz, 1H), 7.78 (d, J=7.6 Hz, 1H), 7.31 (dd, J=4.8, 7.6 Hz, 1H), 7.11 (d, J=9.2 Hz, 1H), 6.41-6.20 (m, 3H), 5.10 (s, 2H), 4.48 (br d, J=13.0 Hz, 2H), 4.38-4.07 (m, 2H), 3.41 (br s, 2H), 2.97 (br s, 4H), 2.80-2.56 (m, 6H), 2.20-2.03 (m, 3H), 2.01-1.68 (m, 10H), 1.56-1.40 (m, 2H)

Compound 6-[1-[4-[4-[2,6-difluoro-4-[[rac-(3S)-2,6-dioxo-3-piperidyl]amino]phenyl]piperazin-1-yl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (5, 20 mg) was separated again by SFC[Column: DAICEL CHIRALPAK AS (250 mm*30 mm, 10 um); Condition: 75% IPA+ACN (0.1% NH3·H2O) in Supercritical $CO_2$; Flow Rate: 80 mL/min; Cycle Time: 3 min, total time: 60 min; Single injection volume: 2.0 ml; Back Pressure: 100 bar to keep the $CO_2$ in Supercritical flow]. Then the residue was purified by prep-HPLC ((column: 3_Phenomenex Luna C18 75*30 mm*3 um; mobile phase: [water (0.225% FA)-ACN]; B %: 14%-44%, 10 min). 6-[1-[4-[4-[2,6-difluoro-4-[[rac-(3S)-2,6-dioxo-3-piperidyl]amino]phenyl]piperazin-1-yl]cyclohexyl]pyrazol-4-yl]-4-(6-spiro[5H-furo[3,4-b]pyridine-7,4'-piperidine]-1'-yl-3-pyridyl)pyrazolo[1,5-a]pyrazine-3-carbonitrile (5, 7.34 mg, 7.93 mol, 35% yield, formic acid salt) was obtained as yellow solid.

LCMS ($ES^+$): m/z 880.5 $[M+H]^+$ $^1H$ NMR (400 MHz, $CDCl_3$) δ=8.83 (br s, 1H), 8.65-8.27 (m, 3H), 8.24-7.89 (m, 3H), 7.59 (br d, J=6.4 Hz, 1H), 7.20 (br s, 1H), 6.88 (br d, J=8.4 Hz, 1H), 6.18 (br d, J=6.4 Hz, 2H), 5.25-4.45 (m, 8H), 4.22 (br s, 1H), 4.00 (br s, 1H), 3.56 (br s, 1H), 3.29 (br s, 2H), 3.05-2.71 (m, 14H), 2.56-2.14 (m, 4H), 2.02-1.78 (m, 3H)

1H NMR (400 MHz, DMSO-$d_6$) δ=10.82 (s, 1H), 9.30 (s, 1H), 8.84 (s, 1H), 8.71 (d, J=2.4 Hz, 1H), 8.50-8.40 (m, 2H), 8.16 (s, 1.477H), 8.10 (dd, J=2.4, 8.8 Hz, 1H), 7.78 (d, J=7.6 Hz, 1H), 7.31 (dd, J=4.8, 7.6 Hz, 1H), 7.12 (d, J=9.2 Hz, 1H), 6.40-6.22 (m, 3H), 5.10 (s, 2H), 4.48 (br d, J=13.2 Hz, 2H), 4.37-4.13 (m, 2H), 3.40 (br s, 2H), 2.98 (br s, 4H), 2.79-2.56 (m, 6H), 2.20-2.02 (m, 3H), 2.01-1.66 (m, 10H), 1.48 (q, J=12.0 Hz, 2H)

Example 221: Synthesis of N-tert-butyl-1-[5-[3-cyano-6-[1-[4-[4-[2,6-difluoro-4-[[rac-(3R)-2,6-dioxo-3-piperidyl]amino] phenyl] piperazin-1-yl]cyclohexyl]pyrazol-4-yl]pyrazolo[1,5-a]pyrazin-4-yl]-2-pyridyl]-4-ethyl-piperidine-4-carboxamide (Compound 219)

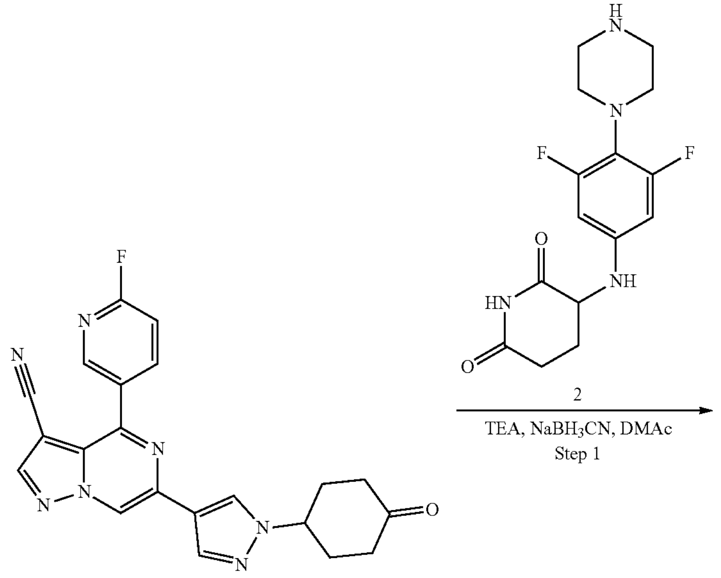

1

-continued
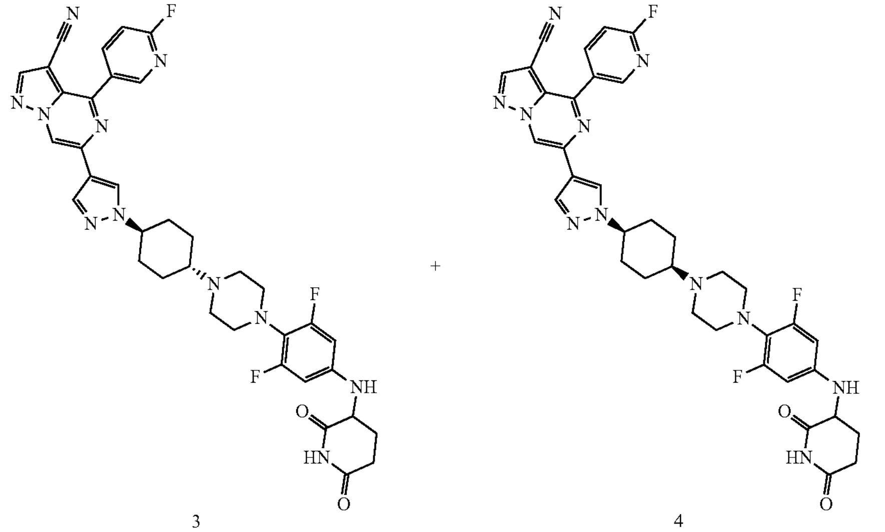
3 4
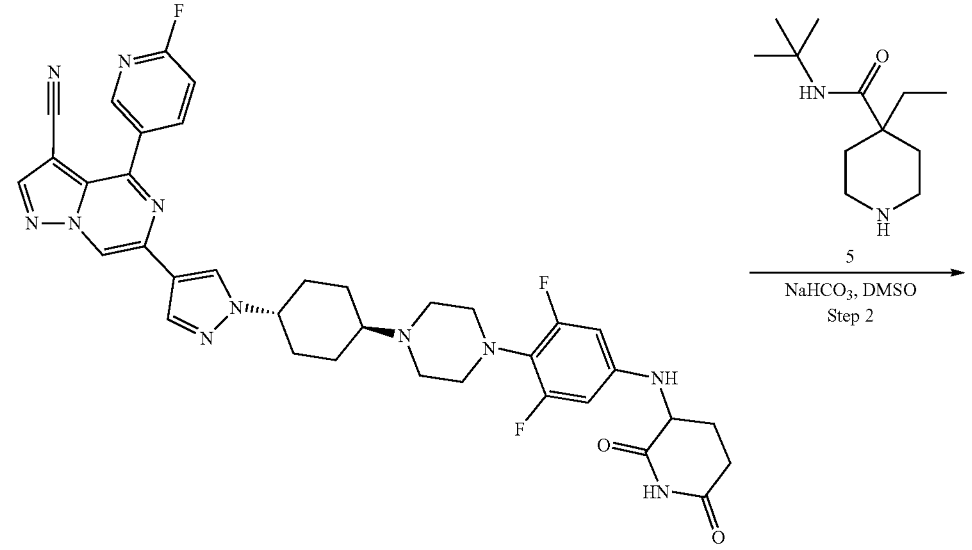
3
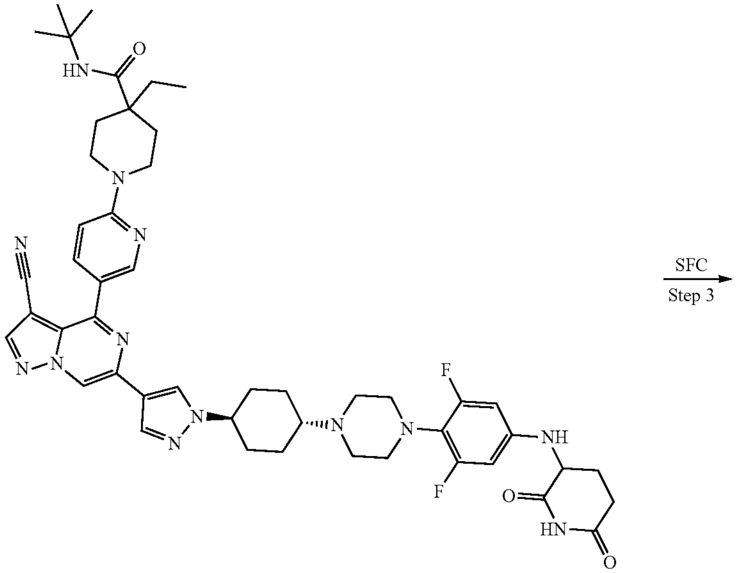
6

-continued

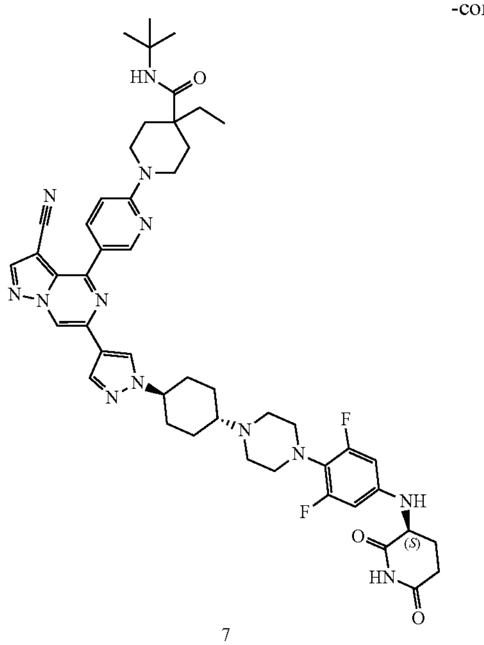

7

+

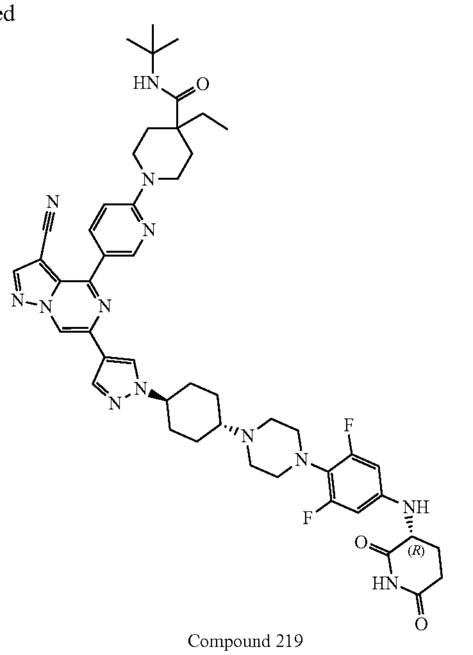

Compound 219

Step 1: To a solution of 3-(3,5-difluoro-4-piperazin-1-yl-anilino)piperidine-2,6-dione HCl salt (2, 1.66 g, 4.60 mmol, 021) and 4-(6-fluoropyridin-3-yl)-6-(1-(4-oxocyclohexyl)-1H-pyrazol-4-yl)pyrazolo[1,5-a]pyrazine-3-carbonitrile (1, 1.23 g, 3.07 mmol) in DMAc (40 mL) was added TEA (1.55 g, 15.34 mmol, 2.14 mL). The mixture was stirred at 50° C. for 2 h, then sodium cyanoborohydride (1.93 g, 30.67 mmol) was added above, the mixture was stirred at 70° C. for 12 h. The reaction mixture was filtered. The residue was purified by reversed phase flash chromatography (flow: 100 mL/min; gradient: from 5-40% water (0.1% formic acid) in MeCN (add phase modifier if used) over 30 min; column: 330 g Flash Column Welch Ultimate XB_C18 20-40 m; 120 A. Then it was purified by Prep-HPLC (neutral condition). 6-[1-[4-[4-[4-[(2,6-dioxo-3-piperidyl)amino]-2,6-difluoro-phenyl]piperazin-1-yl]cyclohexyl]pyrazol-4-yl]-4-(6-fluoro-3-pyridyl)pyrazolo[1,5-a]pyrazine-3-carbonitrile (3, 200 mg, 276.16 mol, 9% yield) was obtained as a yellow solid. LCMS ($ES^+$): m/z 710.5. $[M+H]^+$. 6-[1-[4-[4-[4-[(2, 6-dioxo-3-piperidyl)amino]-2,6-difluoro-phenyl]piperazin-1-yl]cyclohexyl]pyrazol-4-yl]-4-(6-fluoro-3-pyridyl)pyrazolo[1,5-a]pyrazine-3-carbonitrile (4, 130 mg, 166.69 mol, 5% yield) was obtained as a yellow solid. LCMS ($ES^+$): m/z 710.5 $[M+H]^+$.

Step 2: A solution of N-tert-butyl-4-ethyl-piperidine-4-carboxamide HCl salt (5, 35.90 mg, 169.08 mol) and 6-[1-[4-[4-[4-[(2,6-dioxo-3-piperidyl)amino]-2,6-difluoro-phenyl]piperazin-1-yl]cyclohexyl]pyrazol-4-yl]-4-(6-fluoro-3-pyridyl)pyrazolo[1,5-a]pyrazine-3-carbonitrile (3, 80 mg, 112.72 mol) in DMSO (1 mL) was added $NaHCO_3$ (94.69 mg, 1.13 mmol), the mixture was stirred at 100° C. for 12 hrs. The reaction mixture was poured into $H_2O$ (10 mL), then filtered and the filter cake was washed with EtOAc (3 mL), then concentrated in vacuum. The residue was purified by Prep-HPLC (column: 3_Phenomenex Luna C18 75*30 mm*3 um; mobile phase: [water (0.225% FA)-ACN]; B %: 19%-49%, 10 min), then lyophilization. N-tert-butyl-1-[5-[3-cyano-6-[1-[4-[4-[2,6-difluoro-4-[[rac-(3S)-2,6-dioxo-3-piperidyl]amino]phenyl]piperazin-1-yl]cyclohexyl]pyrazol-4-yl]pyrazolo[1,5-a]pyrazin-4-yl]-2-pyridyl]-4-ethyl-piperidine-4-carboxamide formic acid salt (6, 60 mg, 62.02 mol, 55% yield) was obtained as a yellow solid. LCMS ($ES^+$): m/z 451.6 $[M/2+H]^+$ Step 3: The residue was separated by SFC[Column: DAICEL CHIRALPAK AS (250 mm*30 mm, 10 um); Condition: 60% IPA+ACN 0.1% NH3·H2O PA in Supercritical CO2; Flow Rate: 70 mL/min; Cycle Time: 3 min, total time: 25 min; Single injection volume: 3.5 ml; Back Pressure: 100 bar to keep the CO2 in Supercritical flow]. Then the residue was purified by Prep-HPLC ((column: 3_Phenomenex Luna C18 75*30 mm*3 um; mobile phase: [water (0.225% FA)-ACN]; B %: 19%-49%, 10 min). N-tert-butyl-1-[5-[3-cyano-6-[1-[4-[4-[2,6-difluoro-4-[[rac-(3S)-2,6-dioxo-3-piperidyl]amino]phenyl]piperazin-1-yl] cyclohexyl]pyrazol-4-yl]pyrazolo[1,5-a]pyrazin-4-yl]-2-pyrid yl]-4-ethyl-piperidine-4-carboxamide formic acid salt (7, 25.1 mg, 26.47 mol, 40% yield) was obtained as yellow solid.

LCMS ($ES^+$): m/z 902.6 $[M+H]^+$ $^1$HNMR (400 MHz, DMSO-d6) δ=10.81 (s, 1H), 9.27 (s, 1H), 8.82 (s, 1H), 8.67 (d, J=2.4 Hz, 1H), 8.44 (s, 1H), 8.26 (s, 0.46H), 8.14 (s, 1H), 8.04 (dd, J=2.4, 8.8 Hz, 1H), 6.99 (d, J=9.2 Hz, 1H), 6.86 (s, 1H), 6.38-6.21 (m, 3H), 4.31 (ddd, J=4.8, 7.6, 12.0 Hz, 1H), 4.24-4.08 (m, 3H), 3.13 (br t, J=10.8 Hz, 2H), 2.96 (br s, 4H), 2.73 (ddd, J=5.2, 12.4, 17.6 Hz, 1H), 2.63-2.57 (m, 1H), 2.63-2.57 (m, 4H), 2.42 (br t, J=11.2 Hz, 2H), 2.20-2.02 (m, 5H), 1.99-1.76 (m, 5H), 1.56-1.41 (m, 4H), 1.38-1.31 (m, 2H), 1.30 (s, 9H), 0.76 (t, J=7.2 Hz, 3H)

N-tert-butyl-1-[5-[3-cyano-6-[1-[4-[4-[2,6-difluoro-4-[[rac-(3R)-2,6-dioxo-3-piperidyl]amino]phenyl]piperazin-1-yl]cyclohexyl]pyrazol-4-yl]pyrazolo[1,5-a]pyrazin-4-yl]-2-pyridyl]-4-ethyl-piperidine-4-carboxamide formic acid salt (Compound 219, 23.9 mg, 25.21 mol, 380 yield) was obtained as yellow solid.

LCMS ($ES^+$): m/z 902.5 $[M+H]^+$ $^1$HNMR (400 MHz, DMSO-d6) δ=10.81 (s, 1H), 9.27 (s, 1H), 8.82 (s, 1H), 8.67 (d, J=2.4 Hz, 1H), 8.44 (s, 1H), 8.27

(s, 0.546H), 8.14 (s, 1H), 8.04 (dd, J=2.4, 8.8 Hz, 1H), 6.99 (d, J=9.2 Hz, 1H), 6.86 (s, 1H), 6.43-6.14 (m, 3H), 4.31 (ddd, J=4.8, 7.6, 12.0 Hz, 1H), 4.24-4.09 (m, 3H), 3.13 (br t, J=11.2 Hz, 2H), 2.96 (br s, 4H), 2.79-2.67 (m, 1H), 2.60 (br s, 4H), 2.42 (br t, J=11.6 Hz, 2H), 2.21-2.02 (m, 5H), 2.00-1.76 (m, 5H), 1.58-1.40 (m, 4H), 1.38-1.31 (m, 2H), 1.30 (s, 9H), 0.76 (t, J=7.2 Hz, 3H)
Example 222: Compounds of the Present Invention
TABLE 1A
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 1 | 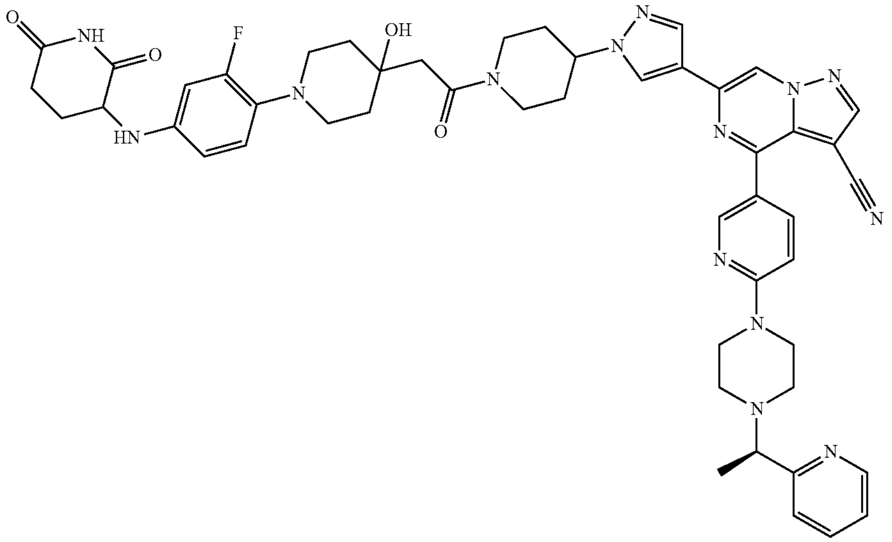 [SMILES: C[C@H](c1ccccn1)N1CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] | ++++ | +++ |
| 2 | 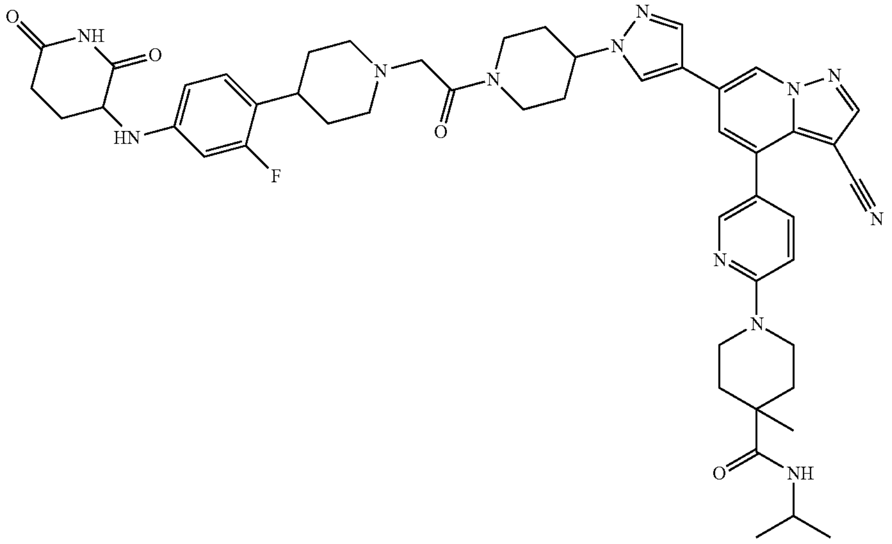 [SMILES: CC(C)NC(=O)C1(C)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | ++++ | +++ |

TABLE 1A-continued
Biological Data
| # | Compound Structure | HiBiT-Degradation 293T.165 RET(KD: 658-1114 G810R) 6.0 hours (DC50) [nM] | HiBiT-Degradation 293T.165 RET(KD: 658-1114 G810R) 6.0 hours (Emax) |
|---|---|---|---|
| 3 | 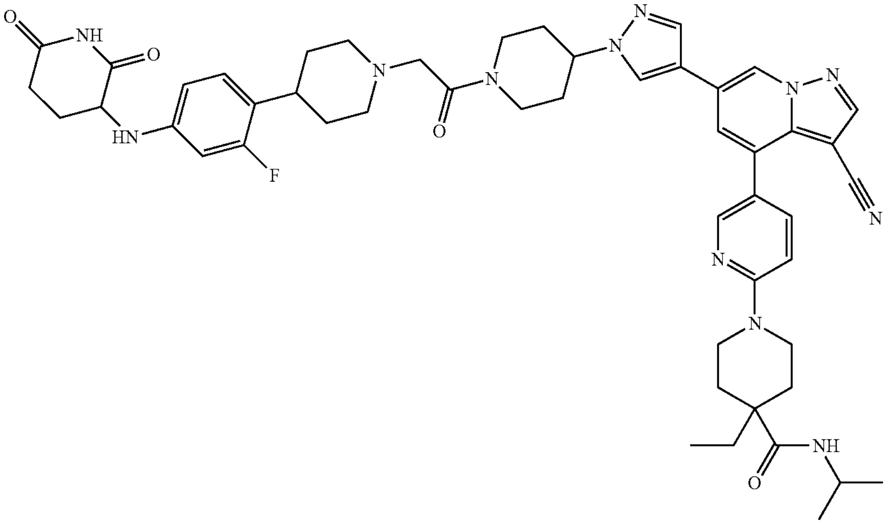 [SMILES: CCC1(C(=O)NC(C)C)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | ++++ | ++++ |
| 4 | 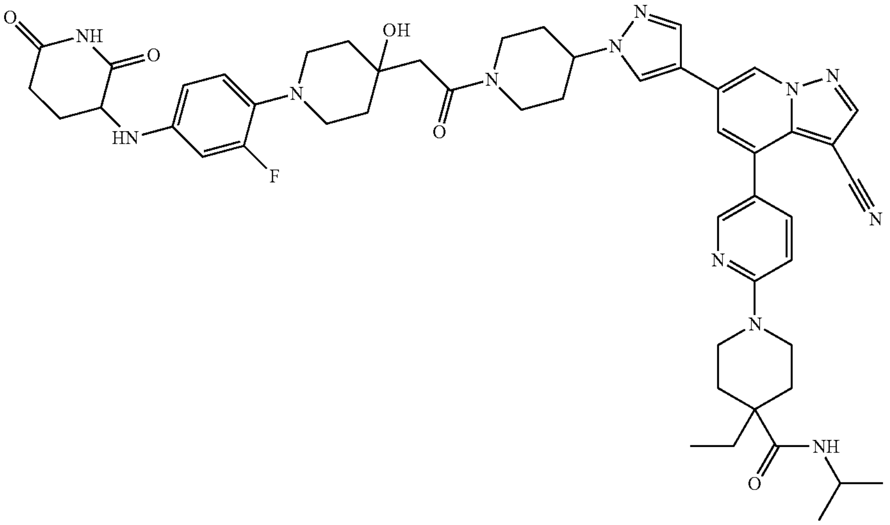 [SMILES: CCC1(C(=O)NC(C)C)CCN(c2ccc(-c3cc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] | ++++ | ++++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 5 | 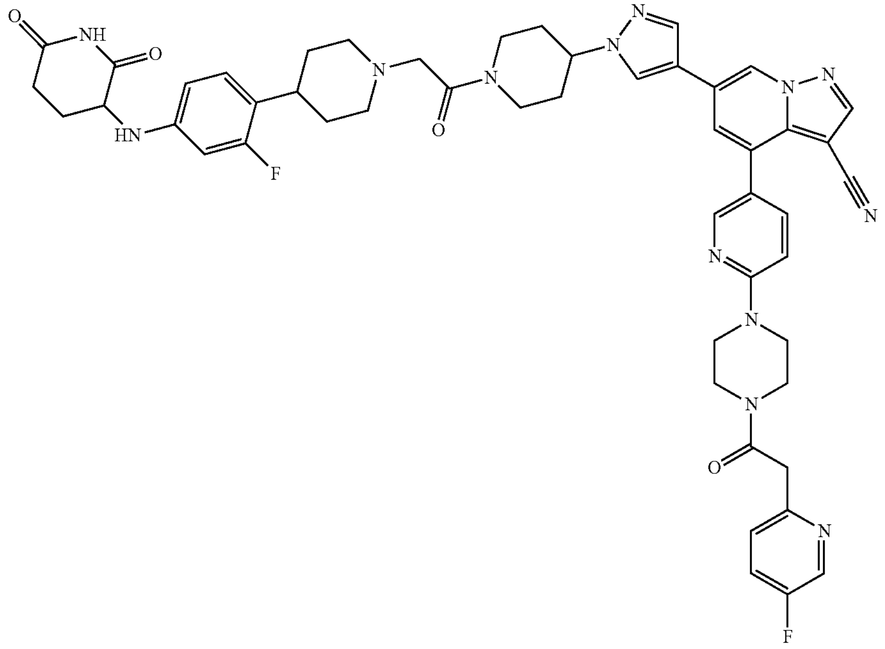 [SMILES: N#Cc1cnn2cc(-c3cnn(C4CCN(C(=O)CN5CCC(c6ccc(NC7CCC(=O)NC7=O)cc6F)CC5)CC4)c3)cc(-c3ccc(N4CCN(C(=O)Cc5ccc(F)cn5)CC4)nc3)c12] | ++++ | ++++ |
| 6 | 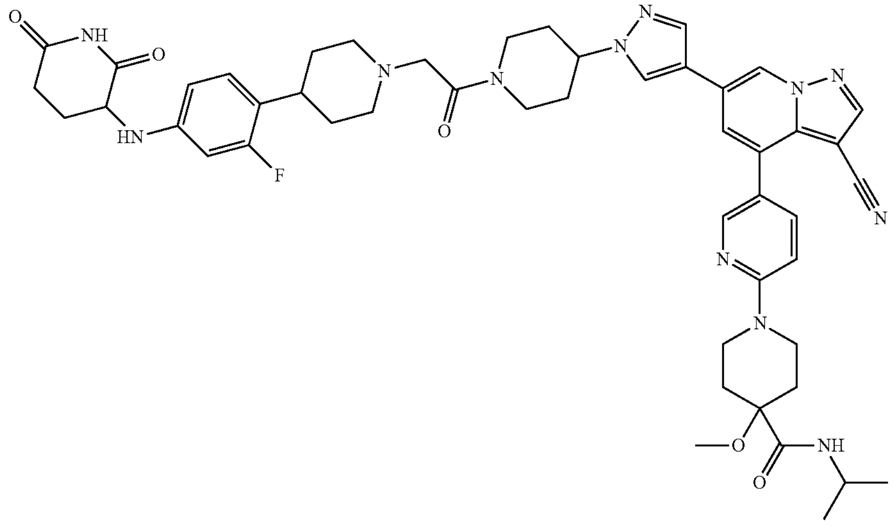 [SMILES: COC1(C(=O)NC(C)C)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | ++++ | +++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 7 | 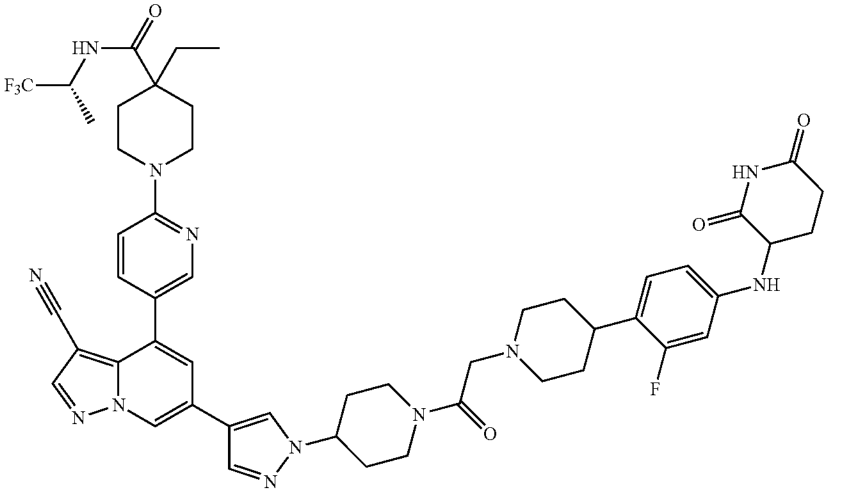 [SMILES: CCC1(C(=O)N[C@H](C)C(F)(F)F)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | ++ | +++ |
| 8 | 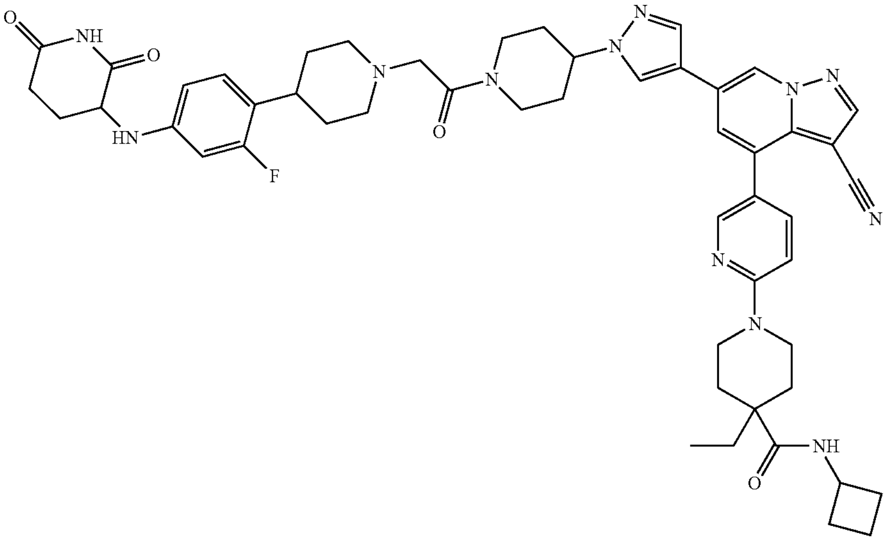 [SMILES: CCC1(C(=O)NC2CCC2)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | ++++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 9 | 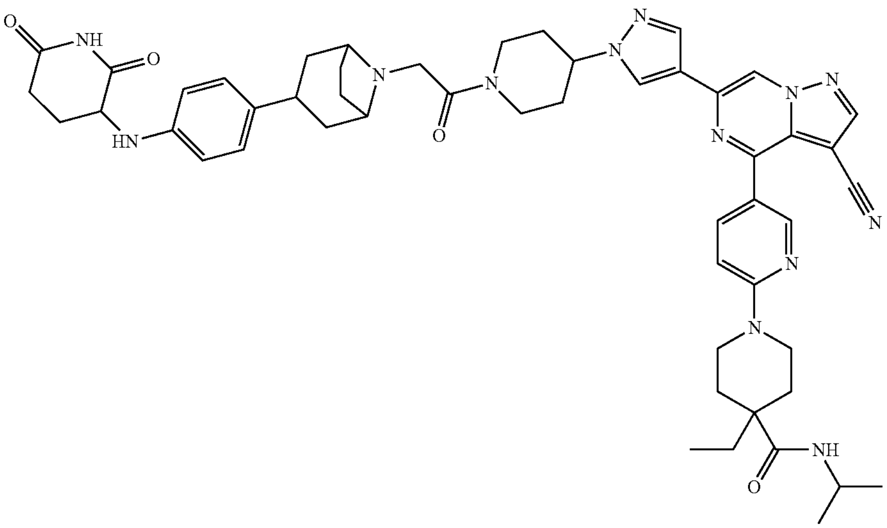 [SMILES: CCC1(C(=O)NC(C)C)CCN(c2ccc(-c3nc(-c4cnn(C5CCN(C(=O)CN6C7CCC6CC(c6ccc(NC8CCC(=O)NC8=O)cc6)C7)CC5)c4)cn4ncc(C#N)c34)cn2)CC1] | +++ | ++++ |
| 10 | 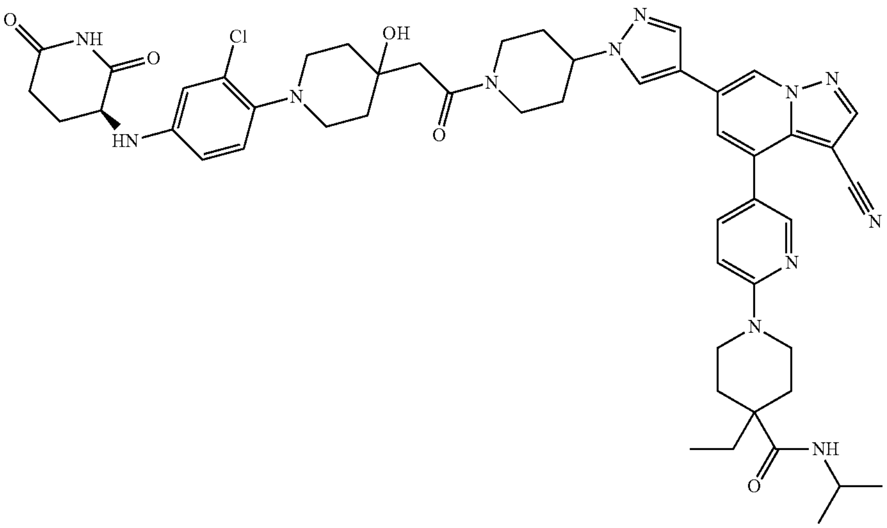 separated enantiomer, chirality arbitrarily assigned | ++++ | ++++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 11 | 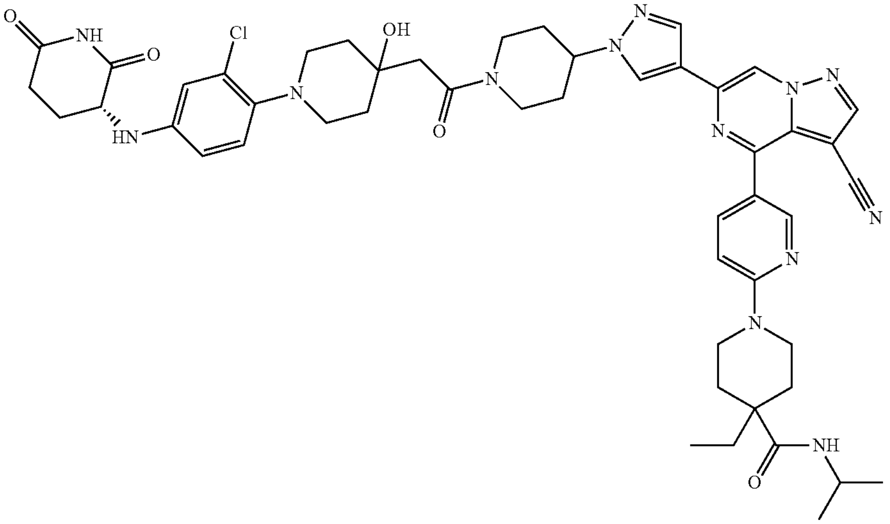 separated enantiomer, chirality arbitrarily assigned | ++++ | ++++ |
| 12 | 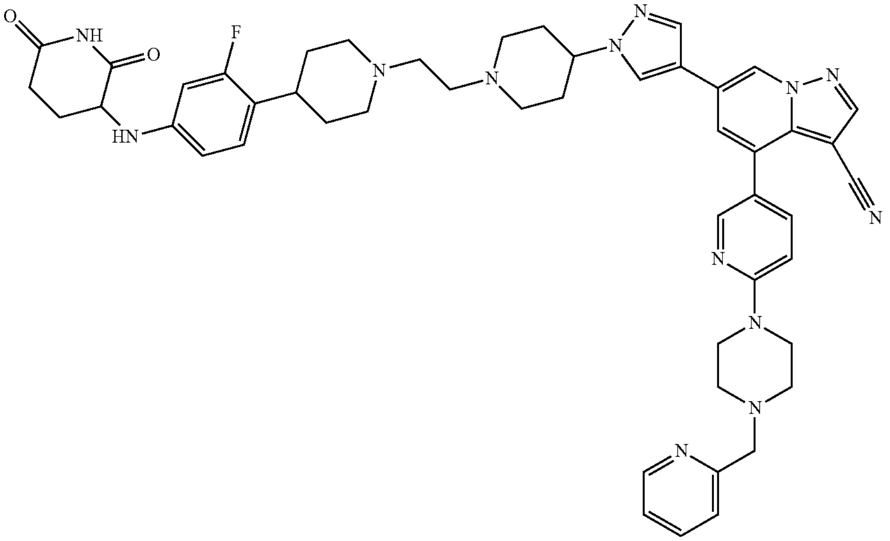 [SMILES: N#Cc1cnn2cc(-c3cnn(C4CCN(CCN5CCC(c6ccc(NC7CCC(=O)NC7=O)cc6F)CC5)CC4)c3)cc(-c3ccc(N4CCN(Cc5ccccn5)CC4)nc3)c12] | +++ | +++ |

TABLE 1A-continued
Biological Data
| Compound # | Structure | HiBiT-Degradation 293T.165 RET(KD: 658-1114 G810R) 6.0 hours (DC50) [nM] | 293T.165 RET(KD: 658-1114 G810R) 6.0 hours (Emax) |
|---|---|---|---|
| 13 | 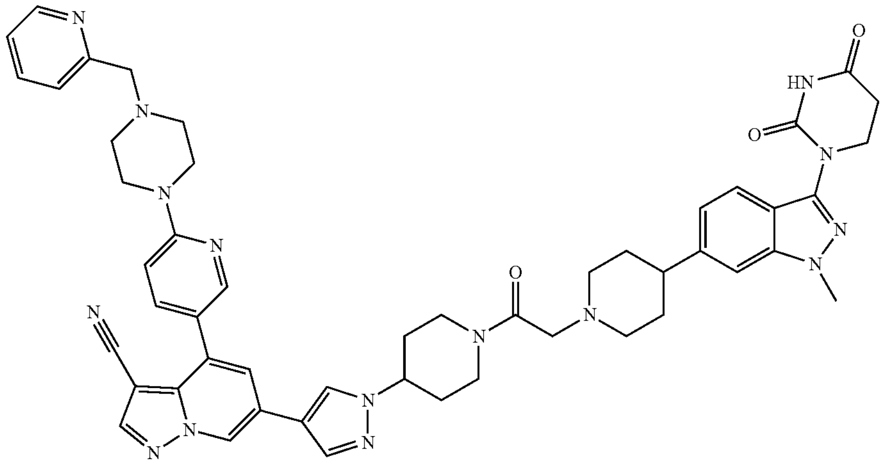 [SMILES: Cn1nc(N2CCC(=O)NC2=O)c2ccc(C3CCN(CC(=O)N4CCC(n5cc(-c6cc(-c7ccc(N8CCN(Cc9ccccn9)CC8)nc7)c7c(C#N)cnn7c6)cn5)CC4)CC3)cc21] | +++ | +++ |
| 14 | 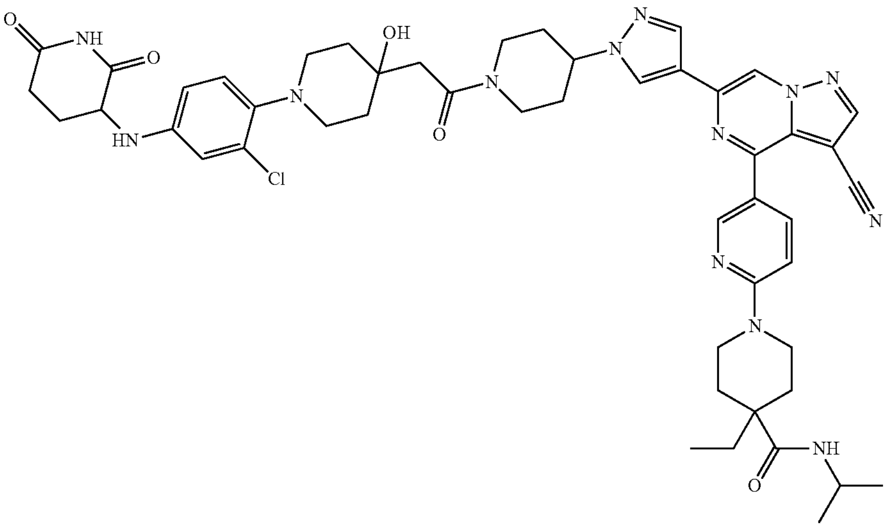 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7Cl)CC6)CC5)c4)cn4ncc(C#N)c34)cn2)CC1] | ++++ | ++++ |

TABLE 1A-continued
| Biological Data | | | |
|---|---|---|---|
| Compound | | HiBiT-Degradation 293T.165 RET(KD: 658-1114 G810R) 6.0 hours (DC50) | 293T.165 RET(KD: 658-1114 G810R) 6.0 hours |
| # | Structure | [nM] | (Emax) |
| 15 | 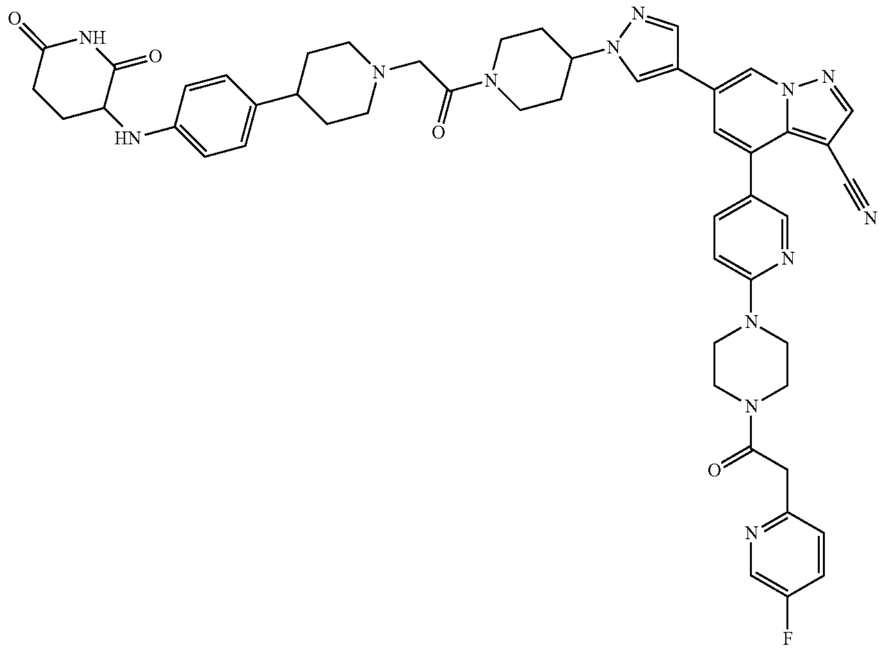 [SMILES: N#Cc1cnn2cc(-c3cnn(C4CCN(C(=O)CN5CCC(c6ccc(NC7CCC(=O)NC7=O)cc6)CC5)CC4)c3)cc(-c3ccc(N4CCN(C(=O)Cc5ccc(F)cn5)CC4)nc3)c12] | +++ | ++++ |
| 16 | 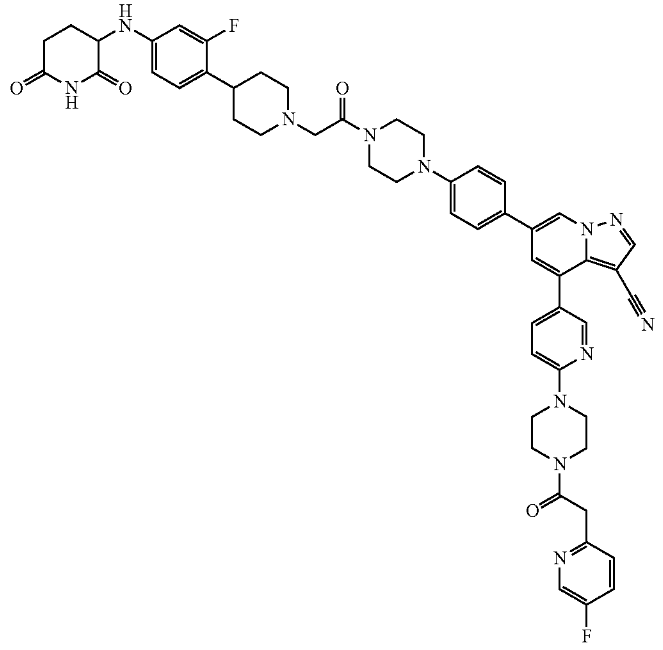 [SMILES: N#Cc1cnn2cc(-c3ccc(N4CCN(C(=O)CN5CCC(c6ccc(NC7CCC(=O)NC7=O)cc6F)CC5)CC4)cc3)cc(-c3ccc(N4CCN(C(=O)Cc5ccc(F)cn5)CC4)nc3)c12] | +++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 17 | 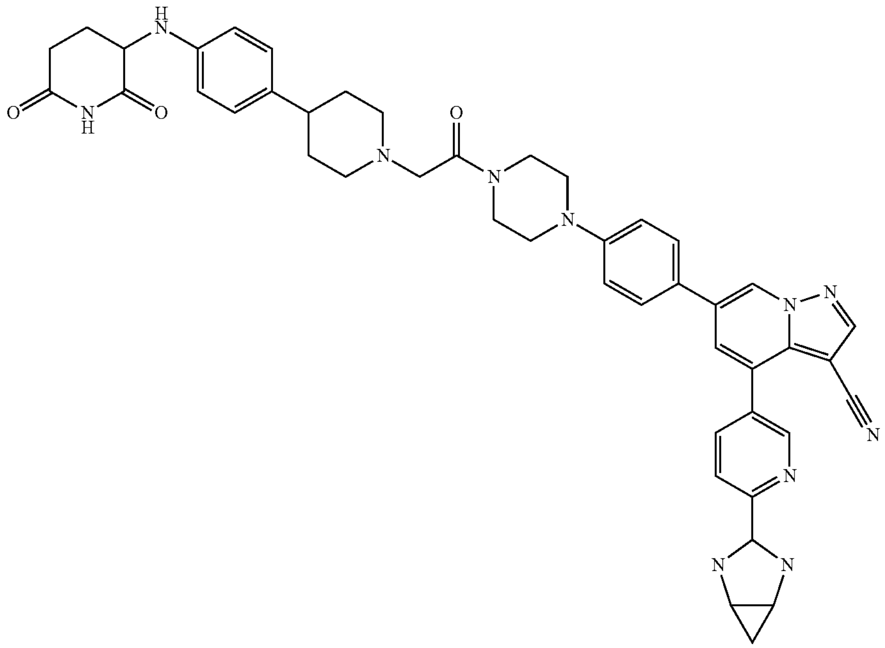 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(C4NC5CC5N4)nc3)c12] | ++++ | ++++ |

TABLE 1A-continued
| Biological Data | | | |
|---|---|---|---|
| Compound | | HiBiT-Degradation 293T.165 RET(KD: 658-1114 G810R) 6.0 hours (DC50) | HiBiT-Degradation 293T.165 RET(KD: 658-1114 G810R) 6.0 hours |
| # | Structure | [nM] | (Emax) |
| 18 | 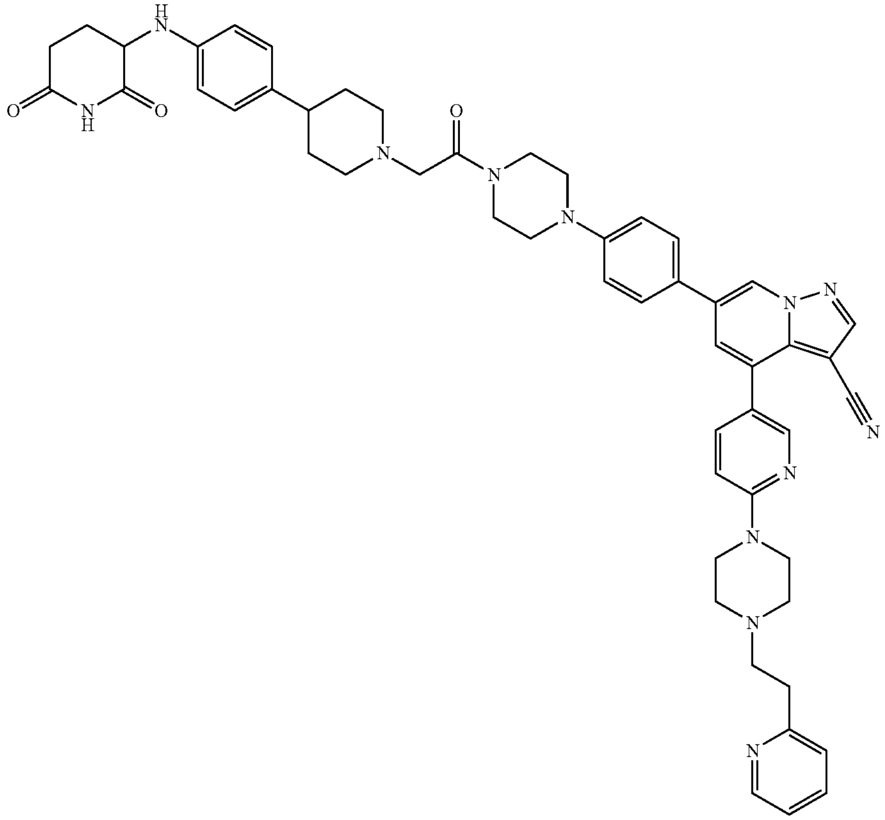 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(N4CCN(CCc5ccccn5)CC4)nc3)c12] | +++ | ++++ |

TABLE 1A-continued
| Biological Data | | | |
|---|---|---|---|
| Compound | | HiBiT-Degradation 293T.165 RET(KD: 658-1114 G810R) 6.0 hours (DC50) | HiBiT-Degradation 293T.165 RET(KD: 658-1114 G810R) 6.0 hours |
| # | Structure | [nM] | (Emax) |
| 19 | 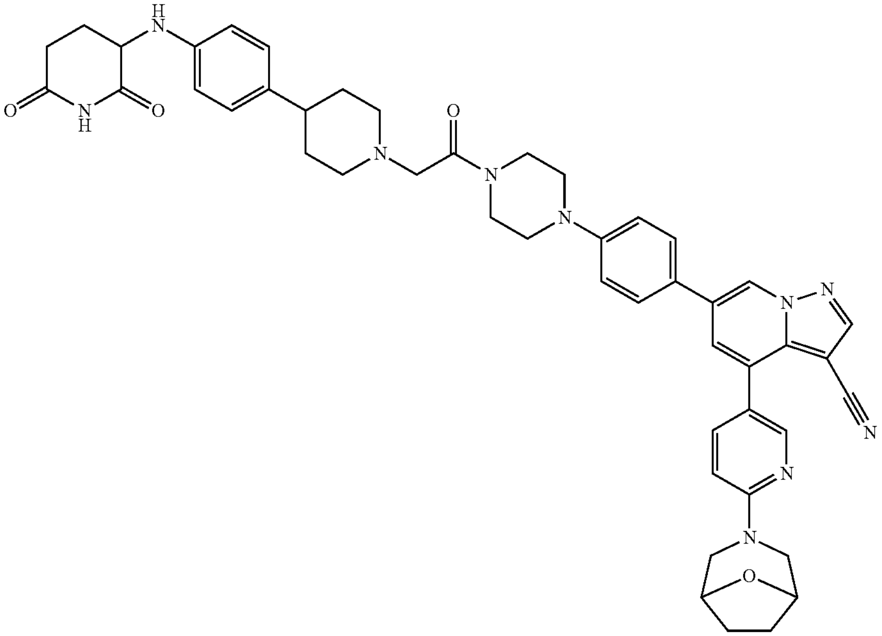 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(N4CC5CCC(C4)O5)nc3)c12] | +++ | +++ |
| 20 | 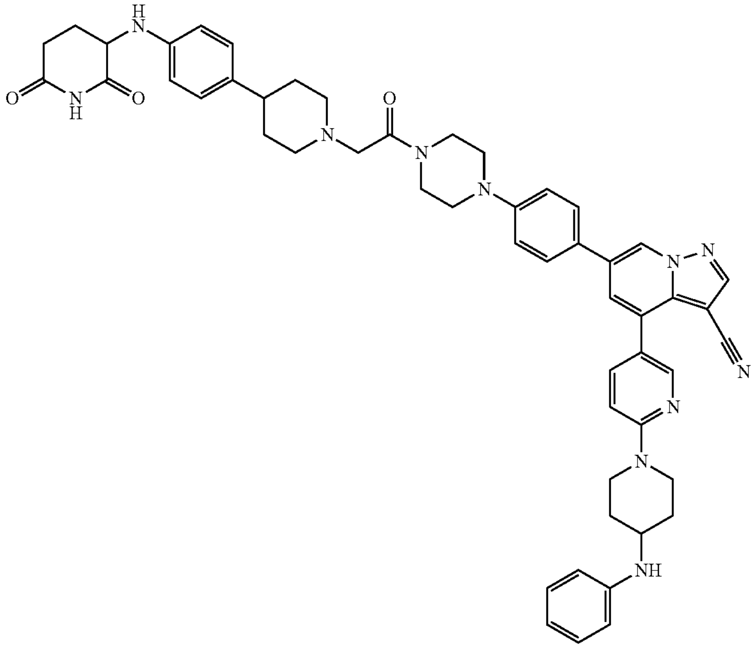 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(N4CCC(Nc5ccccc5)CC4)nc3)c12] | +++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 21 | 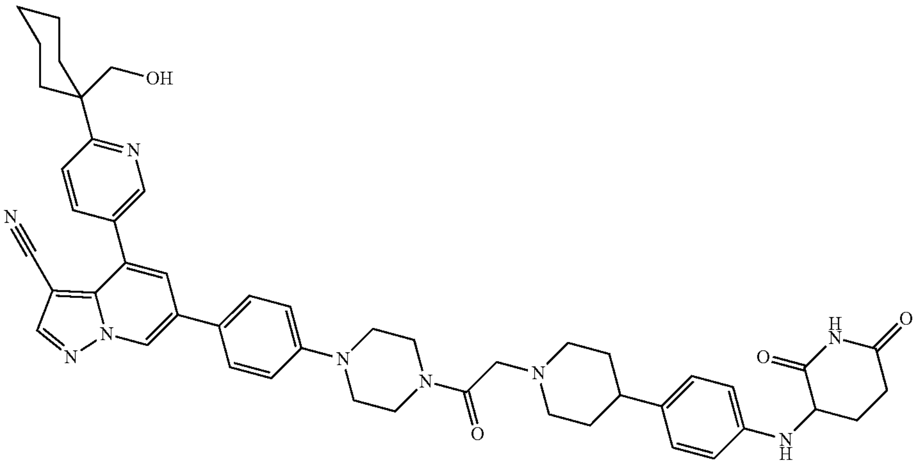 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(C4(CO)CCCCC4)nc3)c12] | ++ | +++ |
| 22 | 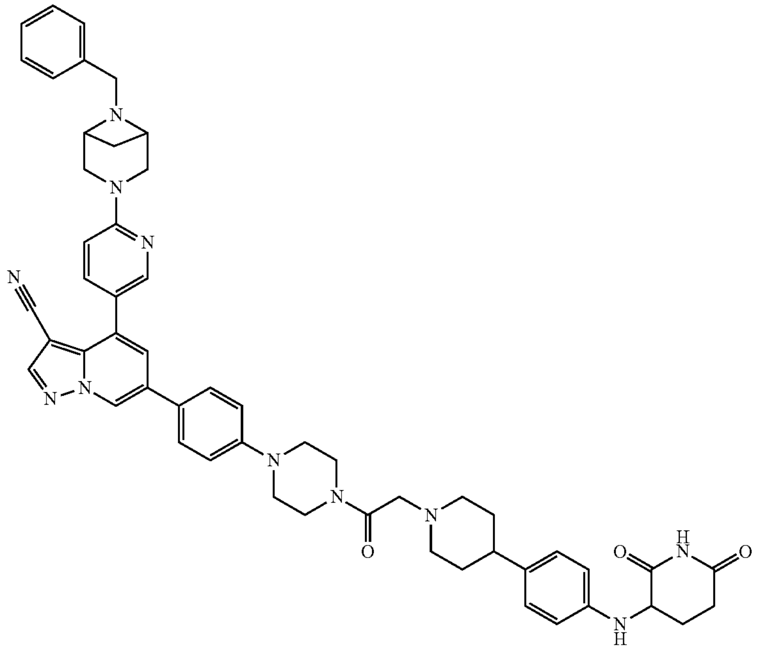 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(N4CC5CC(C4)N5Cc4ccccc4)nc3)c12] | +++ | ++++ |

TABLE 1A-continued
| Biological Data | | | |
|---|---|---|---|
| | | HiBiT-Degradation | |
| Compound | | 293T.165 RET(KD: 658-1114 G810R) 6.0 hours (DC50) | 293T.165 RET(KD: 658-1114 G810R) 6.0 hours |
| # | Structure | [nM] | (Emax) |
| 23 | 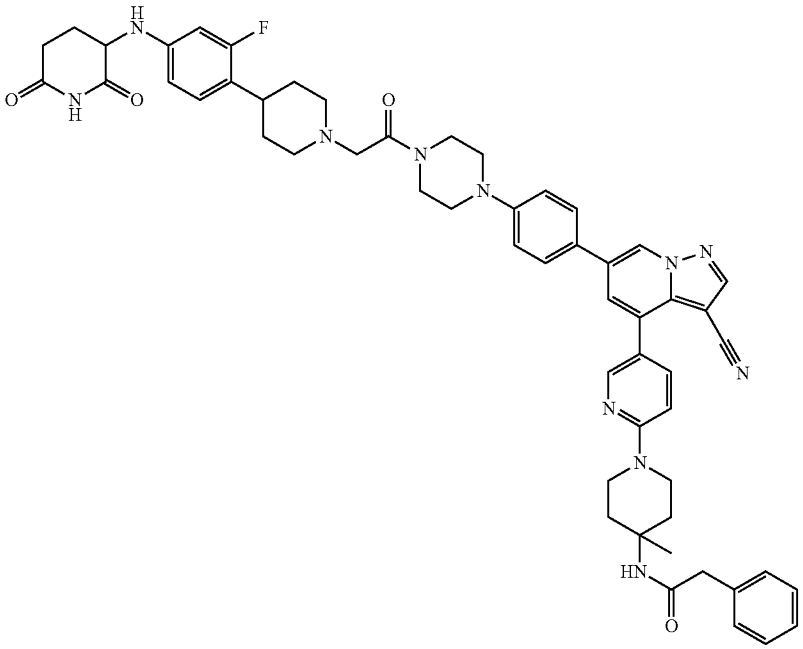 [SMILES: CC1(NC(=O)Cc2ccccc2)CCN(c2ccc(-c3cc(-c4ccc(N5CCN(C(=O)CN6CCC(c7ccc(NC8CCC(=O)NC8=O)cc7F)CC6)CC5)cc4)cn4ncc(C#N)c34)cn2)CC1] | +++ | ++++ |
| 24 | 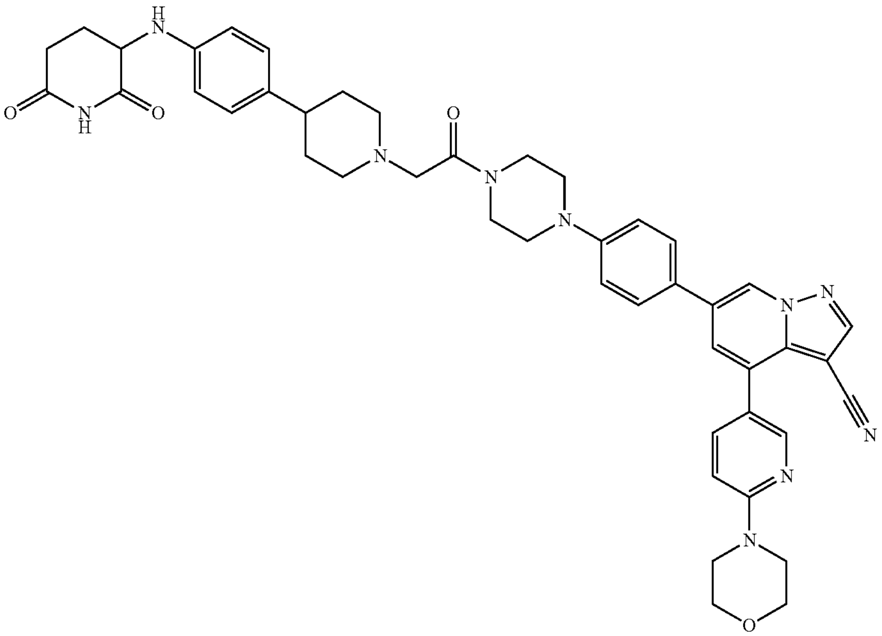 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(N4CCOCC4)nc3)c12] | +++ | +++ |

TABLE 1A-continued
Biological Data
| Compound # | Structure | HiBiT-Degradation 293T.165 RET(KD: 658-1114 G810R) 6.0 hours (DC50) [nM] | HiBiT-Degradation 293T.165 RET(KD: 658-1114 G810R) 6.0 hours (Emax) |
|---|---|---|---|
| 25 | 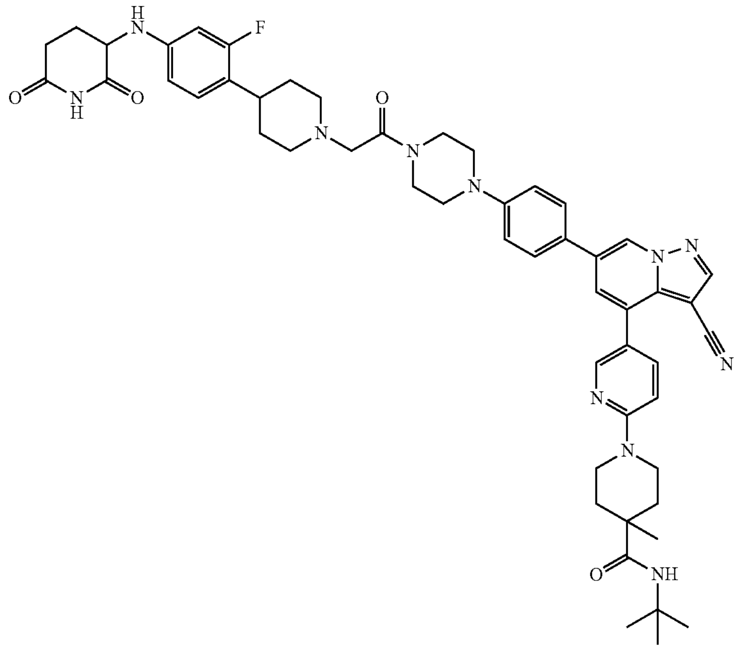 [SMILES: CC(C)(C)NC(=O)C1(C)CCN(c2ccc(-c3cc(-c4ccc(N5CCN(C(=O)CN6CCC(c7ccc(NC8CCC(=O)NC8=O)cc7F)CC6)CC5)cc4)cn4ncc(C#N)c34)cn2)CC1] | +++ | +++ |
| 26 | 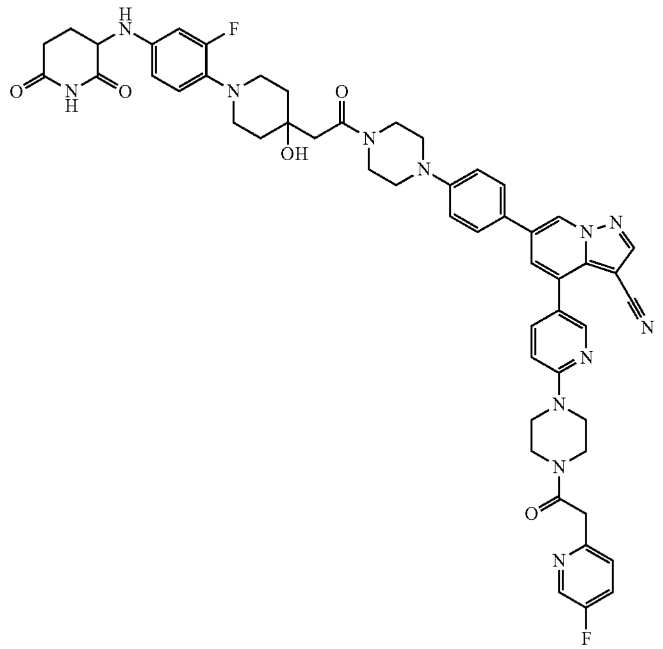 [SMILES: N#Cc1cnn2cc(-c3ccc(N4CCN(C(=O)CC5(O)CCN(c6ccc(NC7CCC(=O)NC7=O)cc6F)CC5)CC4)cc3)cc(-c3ccc(N4CCN(C(=O)Cc5ccc(F)cn5)CC4)nc3)c12] | ++++ | +++ |

TABLE 1A-continued
| Biological Data | | | |
|---|---|---|---|
| | Compound | HiBiT-Degradation 293T.165 RET(KD: 658-1114 G810R) 6.0 hours (DC50) | HiBiT-Degradation 293T.165 RET(KD: 658-1114 G810R) 6.0 hours |
| # | Structure | [nM] | (Emax) |
| 27 | 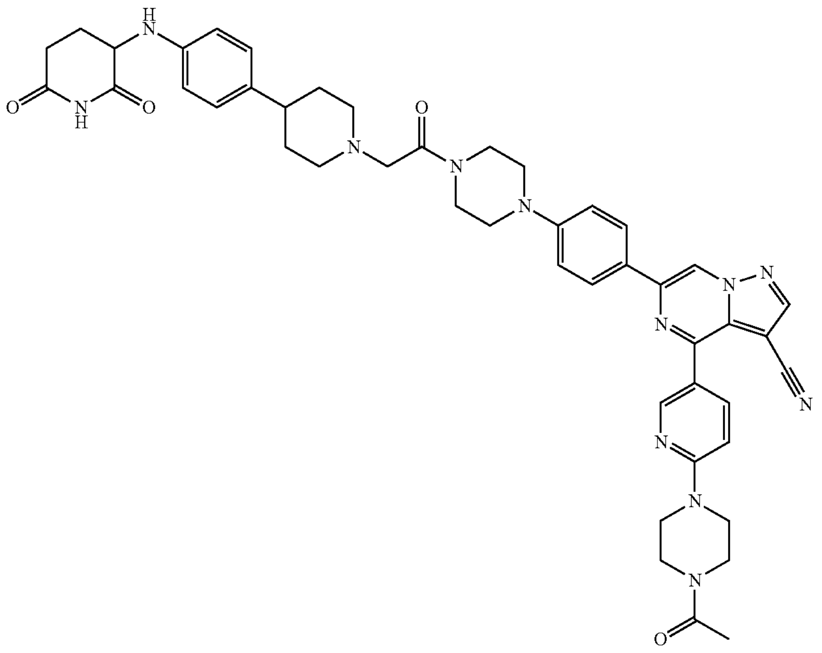 [SMILES: CC(=O)N1CCN(c2ccc(-c3nc(-c4ccc(N5CCN(C(=O)CN6CCC(c7ccc(NC8CCC(=O)NC8=O)cc7)CC6)CC5)cc4)cn4ncc(C#N)c34)cn2)CC1] | ++++ | ++++ |
| 28 | 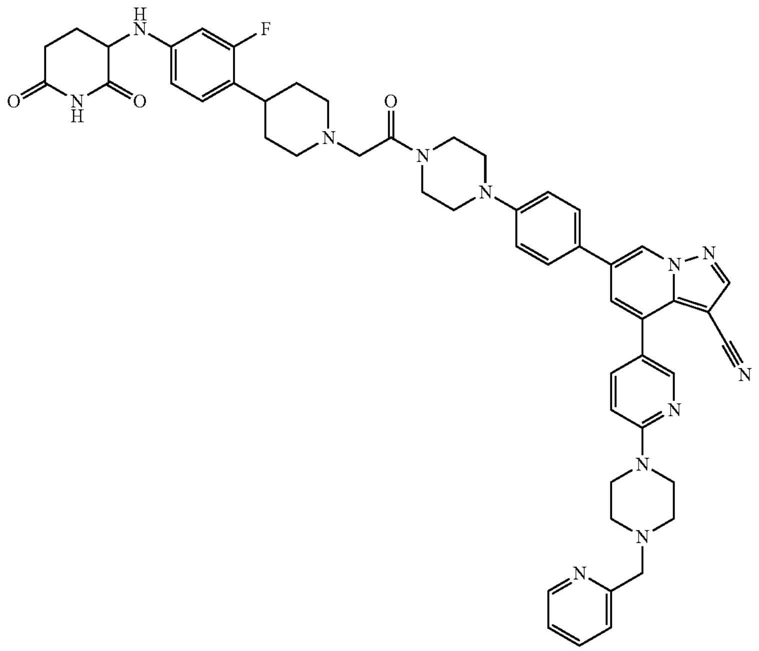 [SMILES: N#Cc1cnn2cc(-c3ccc(N4CCN(C(=O)CN5CCC(c6ccc(NC7CCC(=O)NC7=O)cc6F)CC5)CC4)cc3)cc(-c3ccc(N4CCN(Cc5ccccn5)CC4)nc3)c12] | +++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 29 | 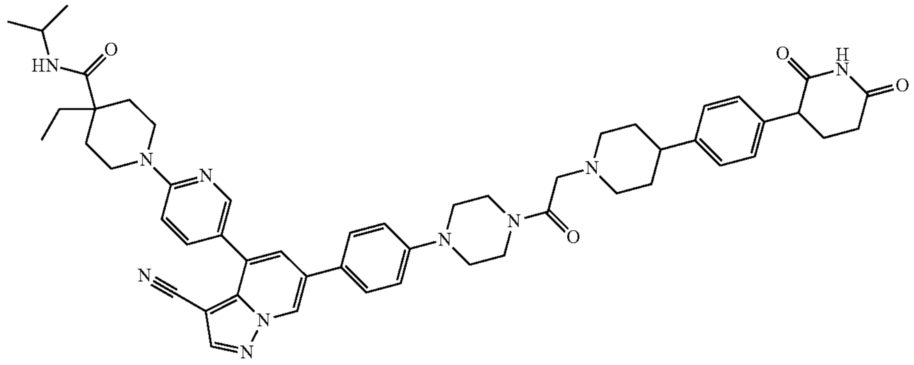 [SMILES: CCC1(C(=O)NC(C)C)CCN(c2ccc(-c3cc(-c4ccc(N5CCN(C(=O)CN6CCC(c7ccc(C8CCC(=O)NC8=O)cc7)CC6)CC5)cc4)cn4ncc(C#N)c34)cn2)CC1] | ++ | +++ |
| 30 | 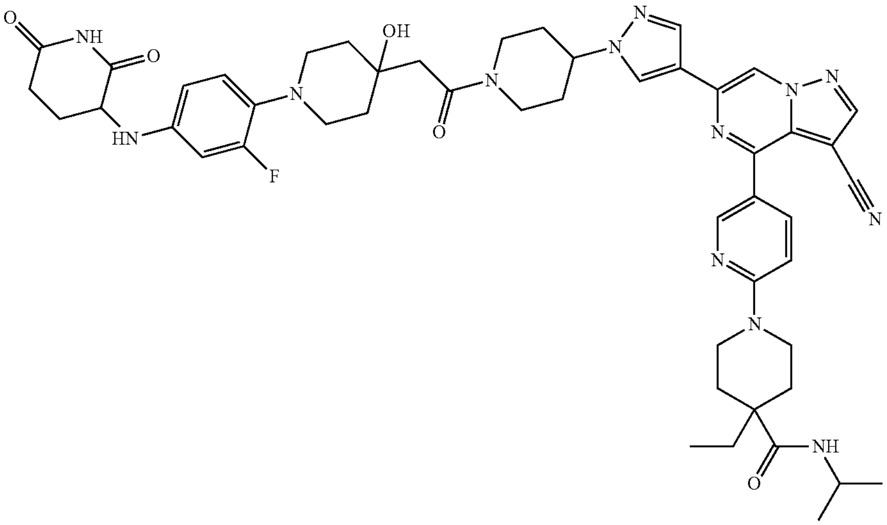 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] | ++++ | +++ |

TABLE 1A-continued
| Biological Data | | | |
|---|---|---|---|
| Compound | | HiBiT-Degradation 293T.165 RET(KD: 658-1114 G810R) 6.0 hours (DC50) | HiBiT-Degradation 293T.165 RET(KD: 658-1114 G810R) 6.0 hours |
| # | Structure | [nM] | (Emax) |
| 31 | 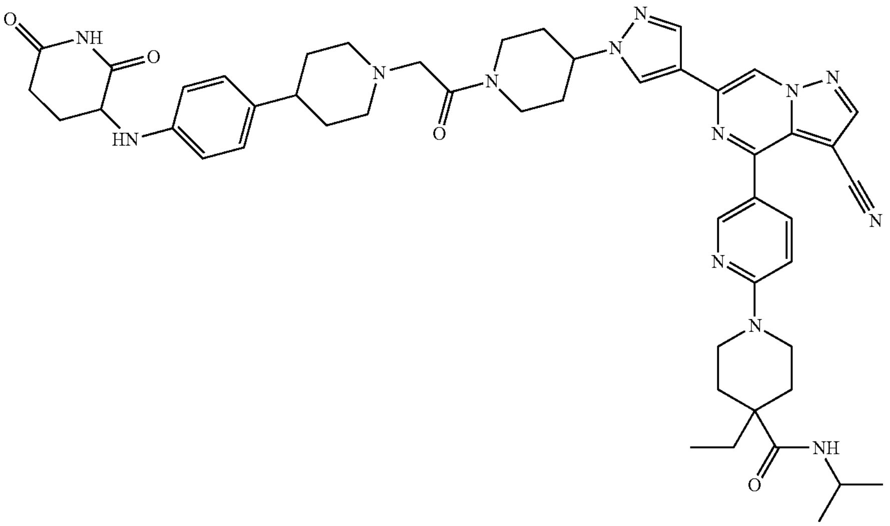 [SMILES: CCC1(C(=O)NC(C)C)CCN(c2ccc(-c3nc(-c4cnn(C5CCN(C(=O)CN6CCC(c7ccc(NC8CCC(=O)NC8=O)cc7)CC6)CC5)c4)cn4ncc(C#N)c34)cn2)CC1] | ++++ | ++++ |
| 32 | 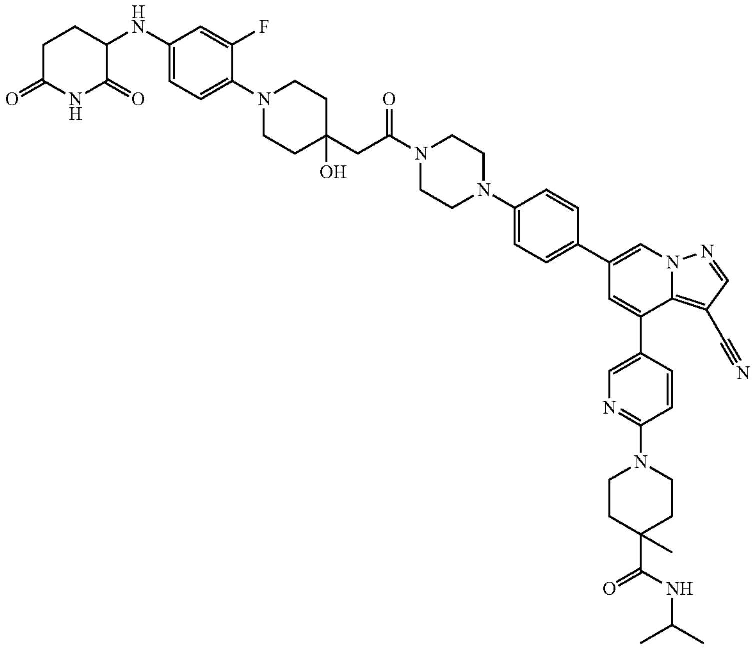 [SMILES: CC(C)NC(=O)C1(C)CCN(c2ccc(-c3cc(-c4ccc(N5CCN(C(=O)CC6(O)CCN(c7ccc(NC8CCC(=O)NC8=O)cc7F)CC6)CC5)cc4)cn4ncc(C#N)c34)cn2)CC1] | ++++ | +++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 33 | 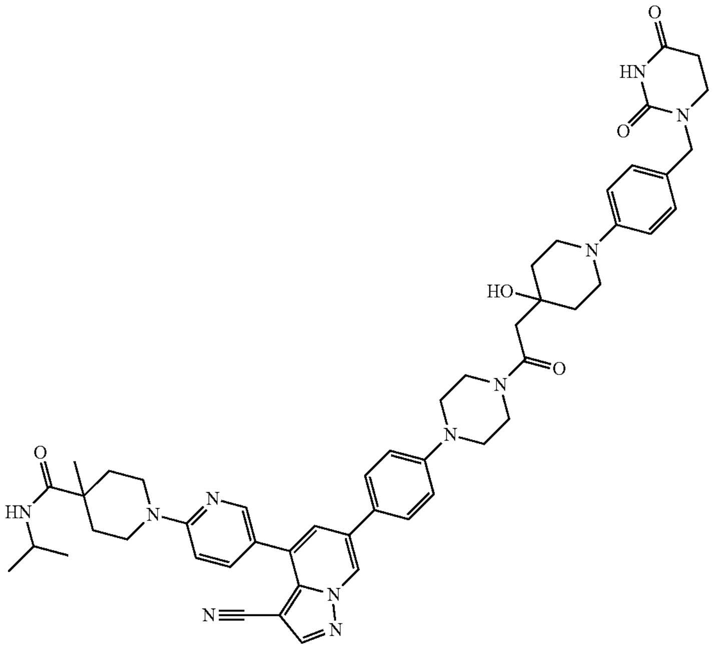 [SMILES: CC(C)NC(=O)C1(C)CCN(c2ccc(-c3cc(-c4ccc(N5CCN(C(=O)CC6(O)CCN(c7ccc(CN8CCC(=O)NC8=O)cc7)CC6)CC5)cc4)cn4ncc(C#N)c34)cn2)CC1] | + | ++ |
| 34 | 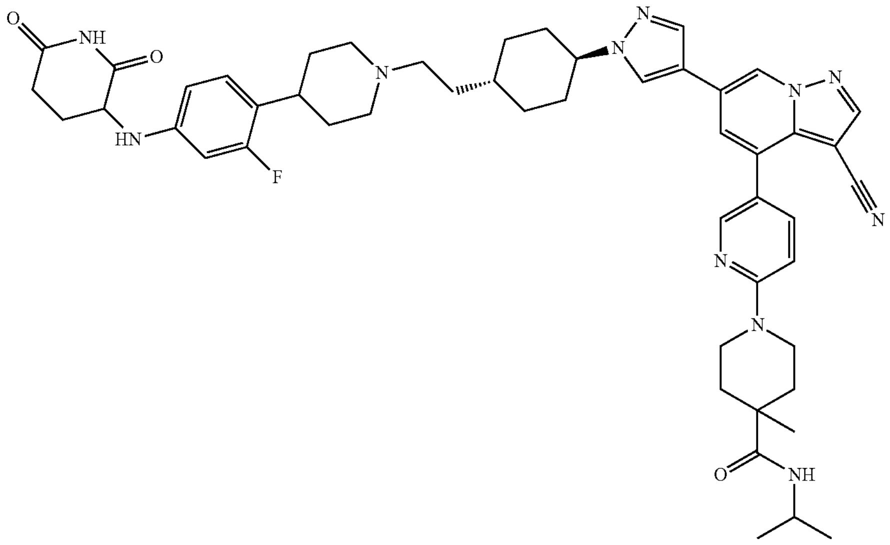 [SMILES: CC(C)NC(=O)C1(C)CCN(c2ccc(-c3cc(-c4cnn([C@H]5CC[C@H](CCN6CCC(c7ccc(NC8CCC(=O)NC8=O)cc7F)CC6)CC5)c4)cn4ncc(C#N)c34)cn2)CC1] | ++++ | ++++ |

TABLE 1A-continued
| Biological Data | | | |
|---|---|---|---|
| Compound | | HiBiT-Degradation 293T.165 RET(KD: 658-1114 G810R) 6.0 hours (DC50) | 293T.165 RET(KD: 658-1114 G810R) 6.0 hours |
| # | Structure | [nM] | (Emax) |
| 35 | 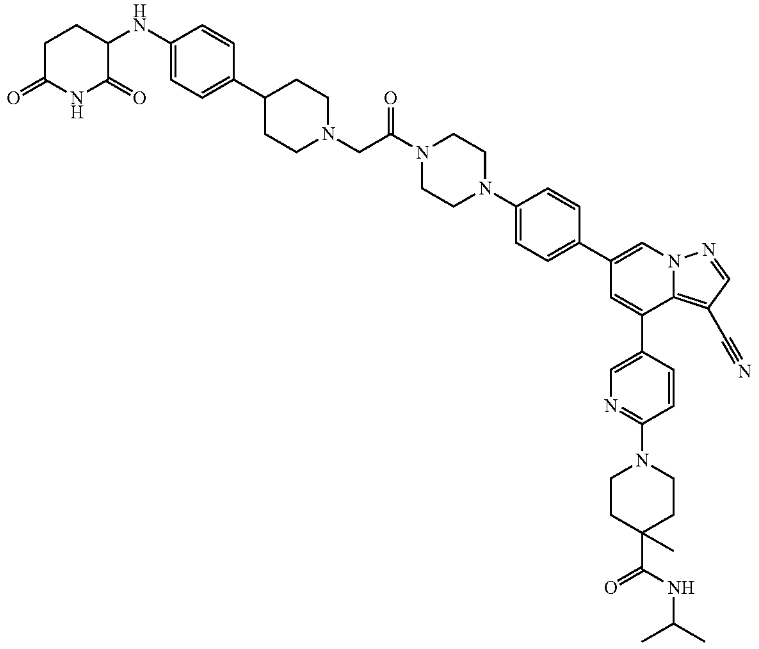 [SMILES: CC(C)NC(=O)C1(C)CCN(c2ccc(-c3cc(-c4ccc(N5CCN(C(=O)CN6CCC(c7ccc(NC8CCC(=O)NC8=O)cc7)CC6)CC5)cc4)cn4ncc(C#N)c34)cn2)CC1] | ++++ | ++++ |
| 36 | 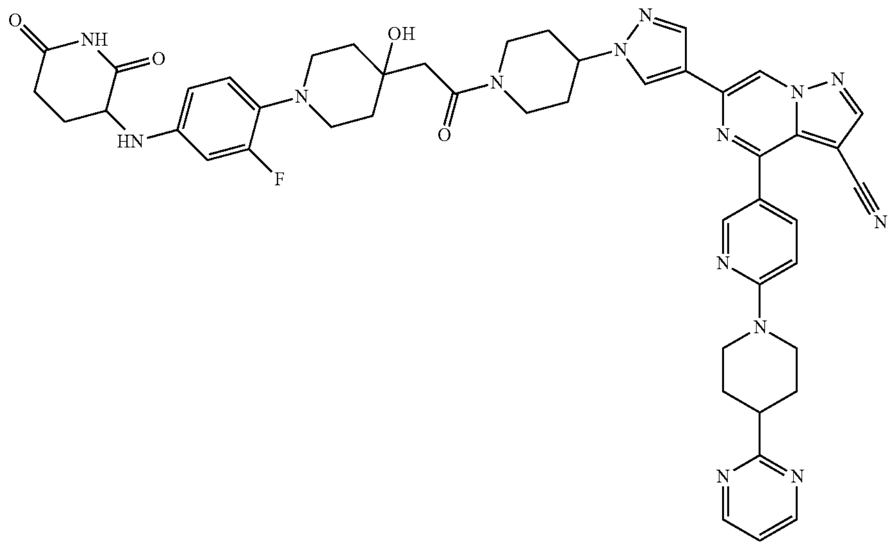 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC(c5ncccn5)CC4)nc3)c12] | ++++ | ++++ |

TABLE 1A-continued
| Biological Data | | | |
|---|---|---|---|
| Compound | | HiBiT-Degradation 293T.165 RET(KD: 658-1114 G810R) 6.0 hours (DC50) | 293T.165 RET(KD: 658-1114 G810R) 6.0 hours |
| # | Structure | [nM] | (Emax) |
| 37 | 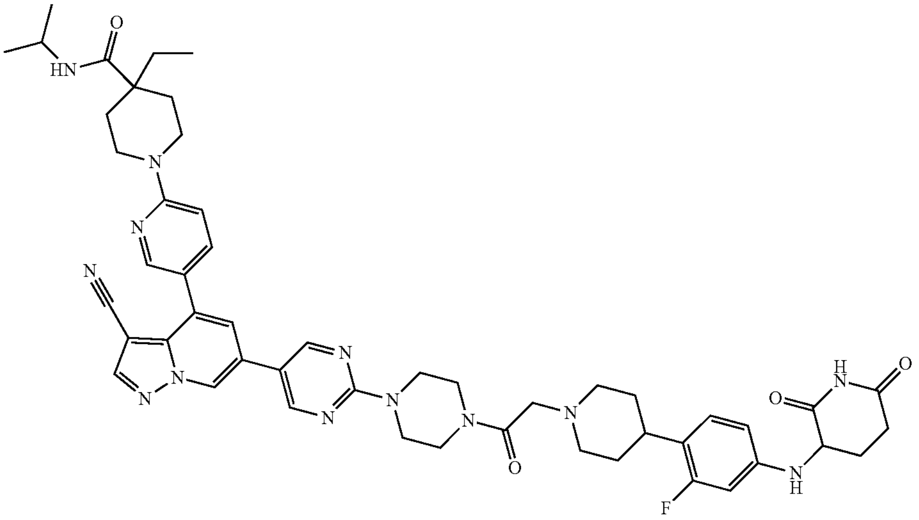 [SMILES: CCC1(C(=O)NC(C)C)CCN(c2ccc(-c3cc(-c4cnc(N5CCN(C(=O)CN6CCC(c7ccc(NC8CCC(=O)NC8=O)cc7F)CC6)CC5)nc4)cn4ncc(C#N)c34)cn2)CC1] | ++ | +++ |
| 38 | 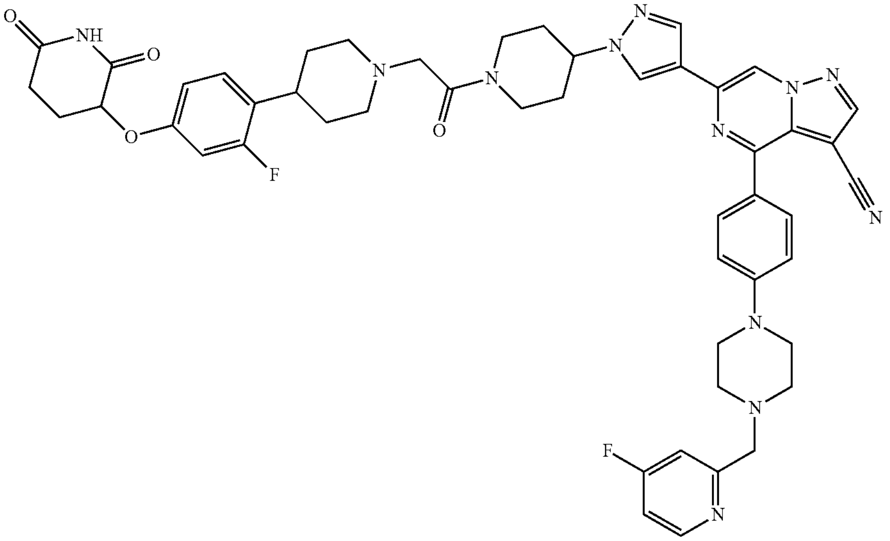 [SMILES: N#Cc1cnn2cc(-c3cnn(C4CCN(C(=O)CN5CCC(c6ccc(OC7CCC(=O)NC7=O)cc6F)CC5)CC4)c3)nc(-c3ccc(N4CCN(Cc5cc(F)ccn5)CC4)cc3)c12] | +++ | +++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 39 | 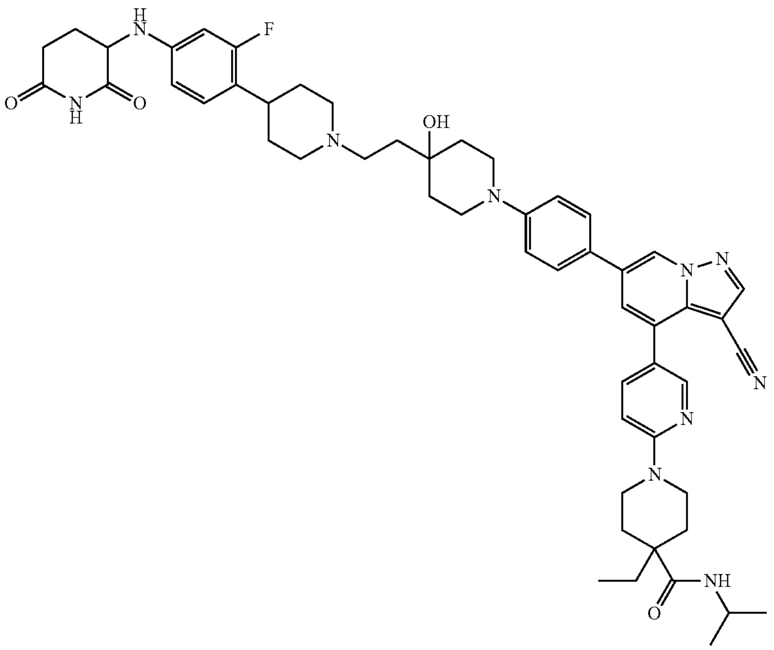 [SMILES: CCC1(C(=O)NC(C)C)CCN(c2ccc(-c3cc(-c4ccc(N5CCC(O)(CCN6CCC(c7ccc(NC8CCC(=O)NC8=O)cc7F)CC6)CC5)cc4)cn4ncc(C#N)c34)cn2)CC1] | ++++ | ++++ |
| 40 | 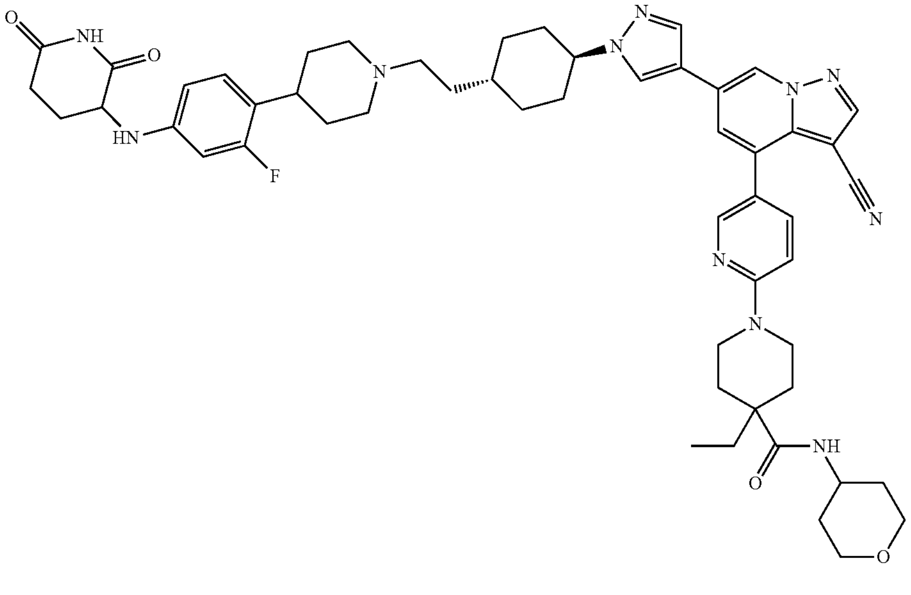 [SMILES: CCC1(C(=O)NC2CCOCC2)CCN(c2ccc(-c3cc(-c4cnn([C@H]5CC[C@H](CCN6CCC(c7ccc(NC8CCC(=O)NC8=O)cc7F)CC6)CC5)c4)cn4ncc(C#N)c34)cn2)CC1] | ++++ | ++++ |

TABLE 1A-continued
| Biological Data | | | |
|---|---|---|---|
| Compound | | HiBiT-Degradation 293T.165 RET(KD: 658-1114 G810R) 6.0 hours (DC50) | HiBiT-Degradation 293T.165 RET(KD: 658-1114 G810R) 6.0 hours |
| # | Structure | [nM] | (Emax) |
| 41 | 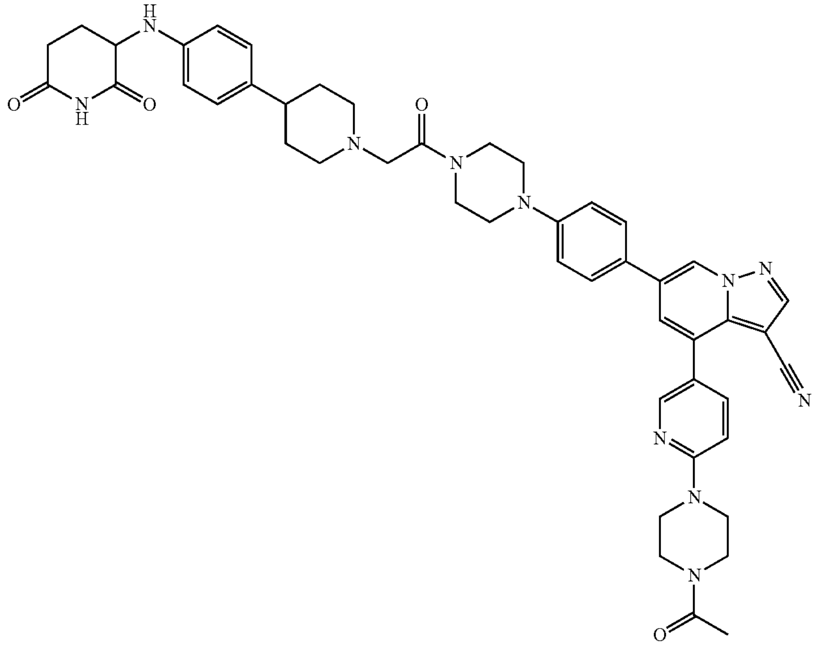 | +++ | +++ |
| 42 | 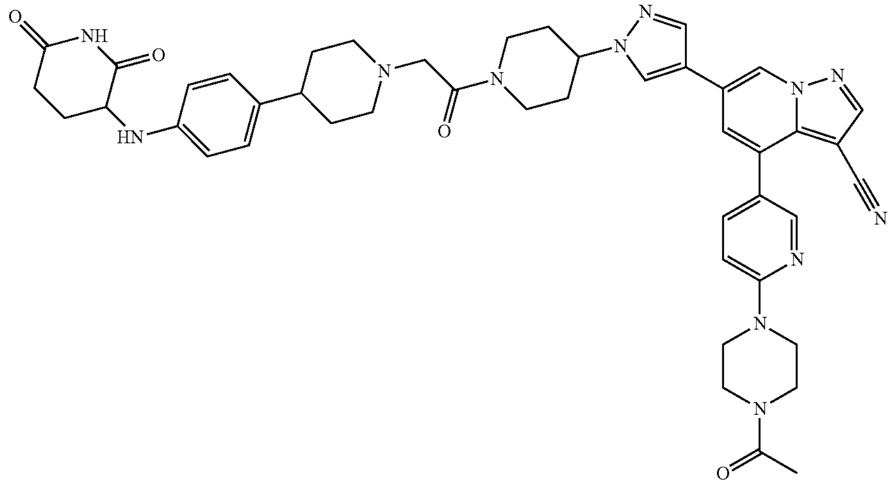 [SMILES: CC(=O)N1CCN(c2ccc(-c3cc(-c4cnn(C5CCN(C(=O)CN6CCC(c7ccc(NC8CCC(=O)NC8=O)cc7)CC6)CC5)c4)cn4ncc(C#N)c34)cn2)CC1] | +++ | +++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 43 | 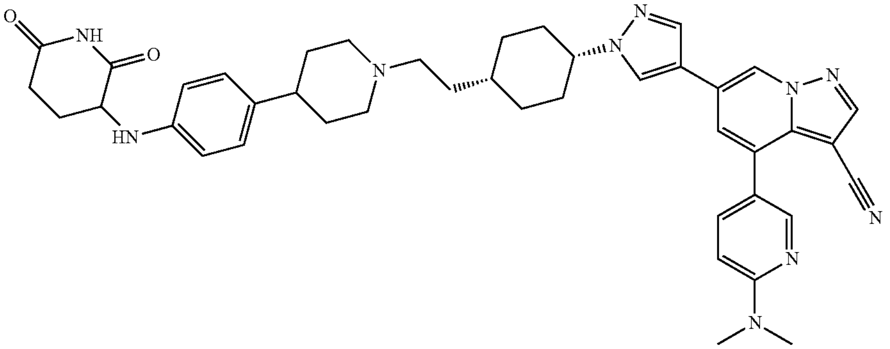 [SMILES: CN(C)c1ccc(-c2cc(-c3cnn([C@H]4CC[C@@H](CCN5CCC(c6ccc(NC7CCC(=O)NC7=O)cc6)CC5)CC4)c3)cn3ncc(C#N)c23)cn1] | +++ | +++ |
| 44 | 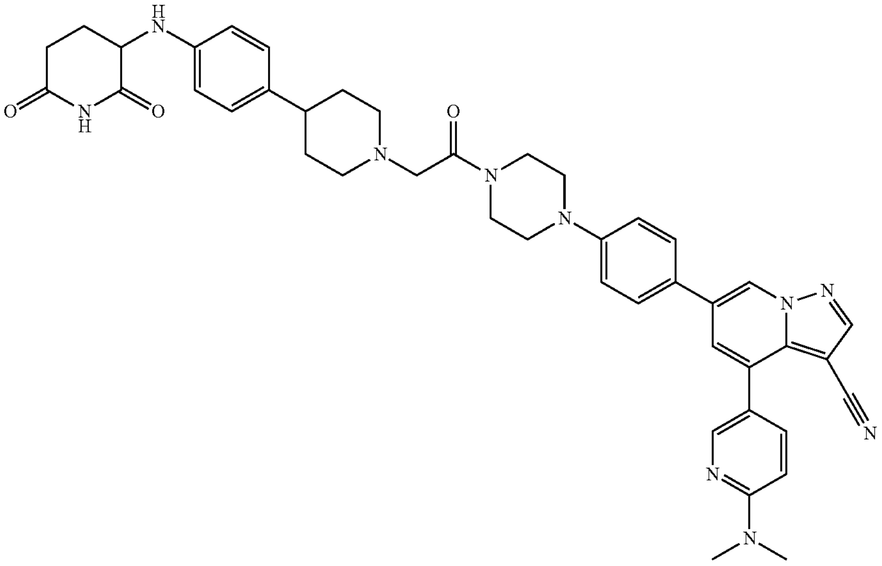 [SMILES: CN(C)c1ccc(-c2cc(-c3ccc(N4CCN(C(=O)CN5CCC(c6ccc(NC7CCC(=O)NC7=O)cc6)CC5)CC4)cc3)cn3ncc(C#N)c23)cn1] | +++ | +++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 45 | 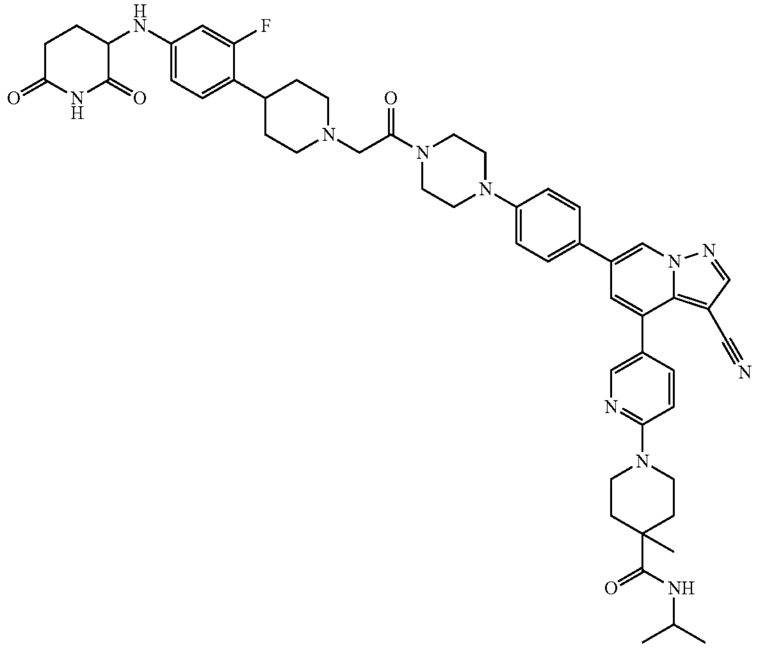 [SMILES: CC(C)NC(=O)C1(C)CCN(c2ccc(-c3cc(-c4ccc(N5CCN(C(=O)CN6CCC(c7ccc(NC8CCC(=O)NC8=O)cc7F)CC6)CC5)cc4)cn4ncc(C#N)c34)cn2)CC1] | +++ | ++++ |
| 46 | 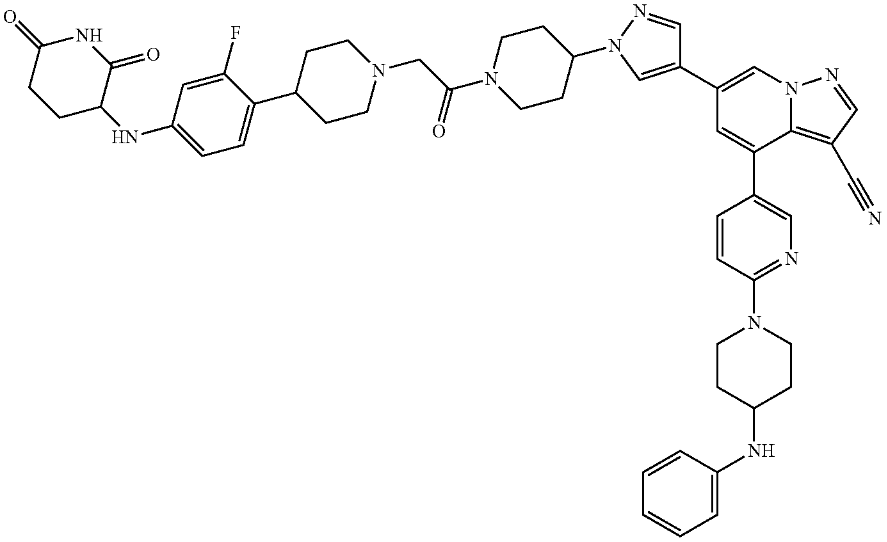 [SMILES: N#Cc1cnn2cc(-c3cnn(C4CCN(C(=O)CN5CCC(c6ccc(NC7CCC(=O)NC7=O)cc6F)CC5)CC4)c3)cc(-c3ccc(N4CCC(Nc5ccccc5)CC4)nc3)c12] | +++ | +++ |

TABLE 1A-continued
| Biological Data | | | |
|---|---|---|---|
| Compound | | HiBiT-Degradation 293T.165 RET(KD: 658-1114 G810R) 6.0 hours (DC50) [nM] | HiBiT-Degradation 293T.165 RET(KD: 658-1114 G810R) 6.0 hours (Emax) |
| # | Structure | | |
| 47 | 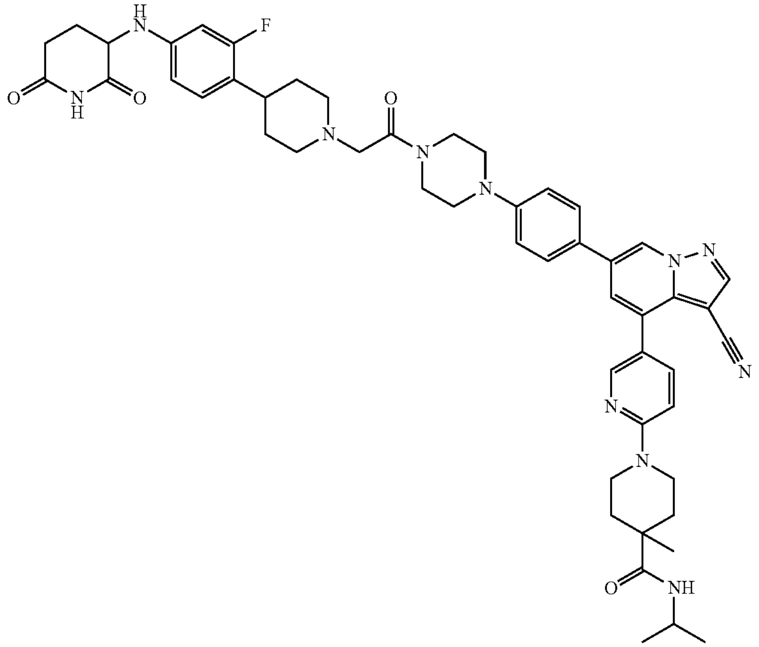 [SMILES: CC(C)NC(=O)C1(C)CCN(c2ccc(-c3cc(-c4ccc(N5CCN(C(=O)CN6CCC(c7ccc(NC8CCC(=O)NC8=O)cc7F)CC6)CC5)cc4)cn4ncc(C#N)c34)cn2)CC1] | +++ | ++++ |
| 48 | 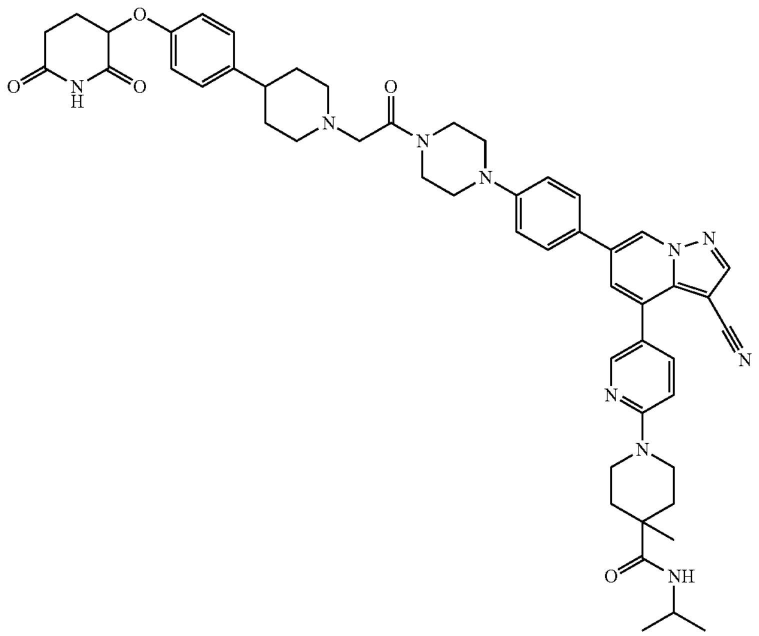 [SMILES: CC(C)NC(=O)C1(C)CCN(c2ccc(-c3cc(-c4ccc(N5CCN(C(=O)CN6CCC(c7ccc(OC8CCC(=O)NC8=O)cc7)CC6)CC5)cc4)cn4ncc(C#N)c34)cn2)CC1] | +++ | ++++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 49 | 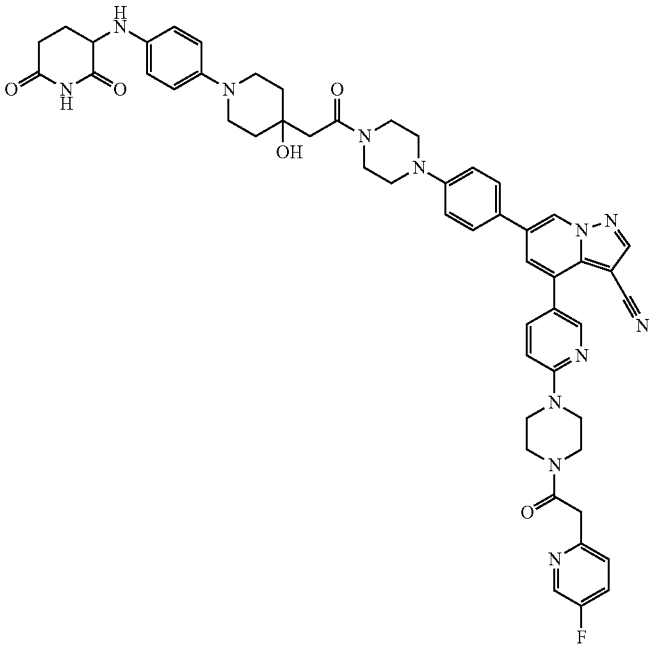 [SMILES: N#Cc1cnn2cc(-c3ccc(N4CCN(C(=O)CC5(O)CCN(c6ccc(NC7CCC(=O)NC7=O)cc6)CC5)CC4)cc3)cc(-c3ccc(N4CCN(C(=O)Cc5ccc(F)cn5)CC4)nc3)c12] | +++ | +++ |
| 50 | 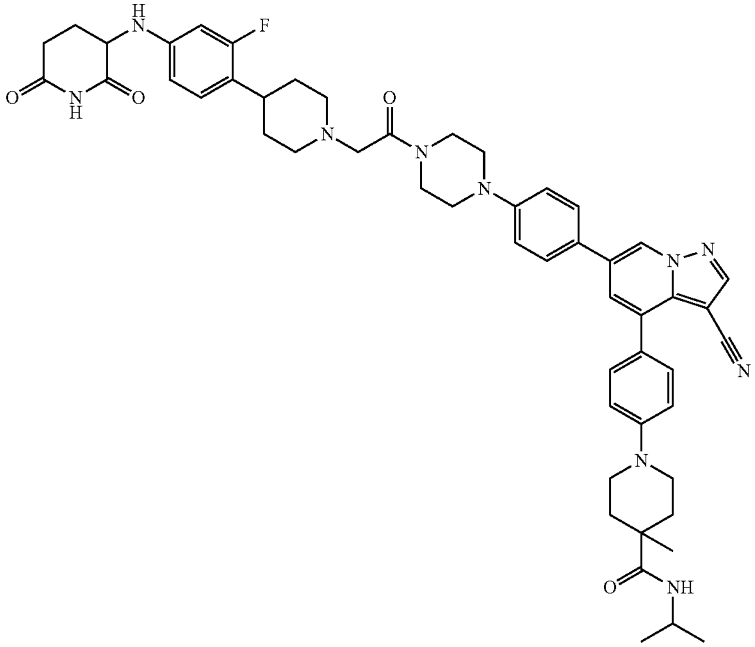 [SMILES: CC(C)NC(=O)C1(C)CCN(c2ccc(-c3cc(-c4ccc(N5CCN(C(=O)CN6CCC(c7ccc(NC8CCC(=O)NC8=O)cc7F)CC6)CC5)cc4)cn4ncc(C#N)c34)cc2)CC1] | +++ | ++++ |

TABLE 1A-continued
| Biological Data | | | |
|---|---|---|---|
| Compound | | HiBiT-Degradation 293T.165 RET(KD: 658-1114 G810R) 6.0 hours (DC50) | 293T.165 RET(KD: 658-1114 G810R) 6.0 hours |
| # | Structure | [nM] | (Emax) |
| 51 | 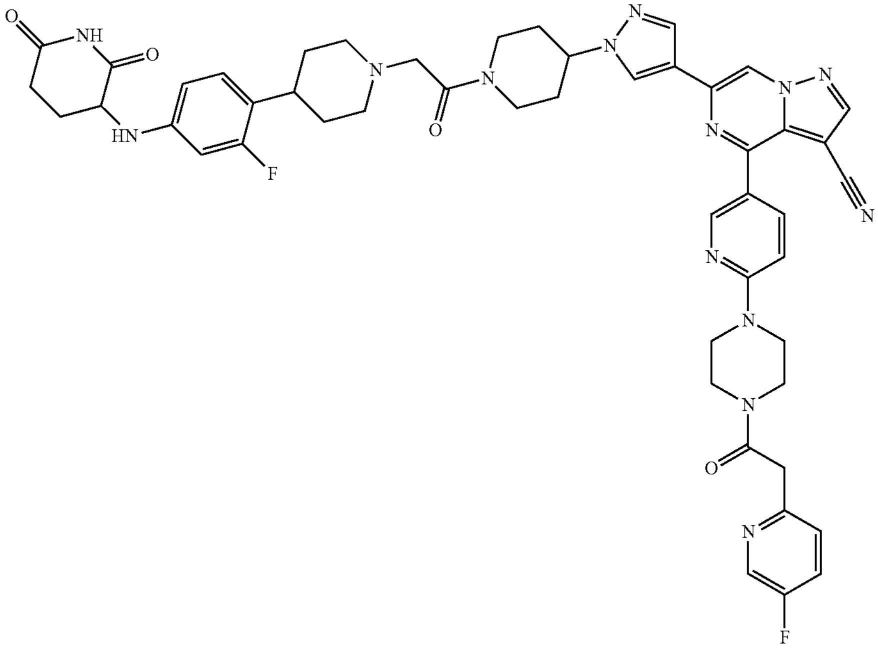 [SMILES: N#Cc1cnn2cc(-c3cnn(C4CCN(C(=O)CN5CCC(c6ccc(NC7CCC(=O)NC7=O)cc6F)CC5)CC4)c3)nc(-c3ccc(N4CCN(C(=O)Cc5ccc(F)cn5)CC4)nc3)c12] | +++ | +++ |
| 52 | 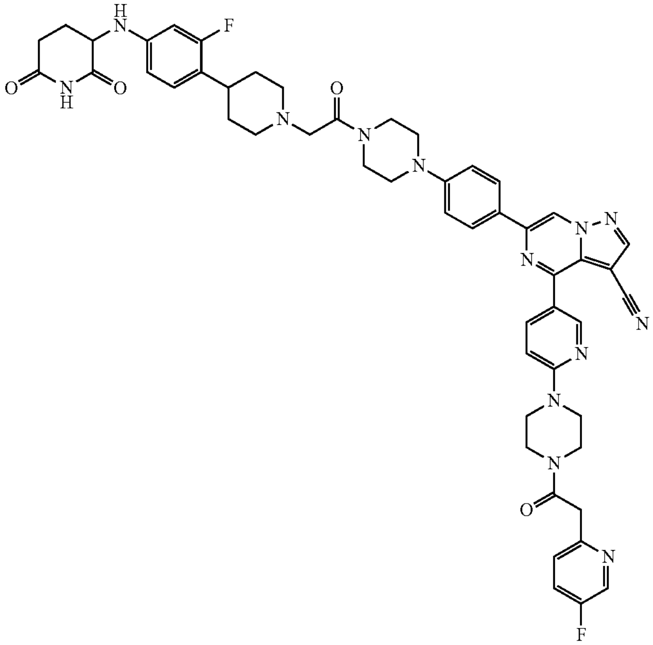 [SMILES: N#Cc1cnn2cc(-c3ccc(N4CCN(C(=O)CN5CCC(c6ccc(NC7CCC(=O)NC7=O)cc6F)CC5)CC4)cc3)nc(-c3ccc(N4CCN(C(=O)Cc5ccc(F)cn5)CC4)nc3)c12] | +++ | +++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 53 | 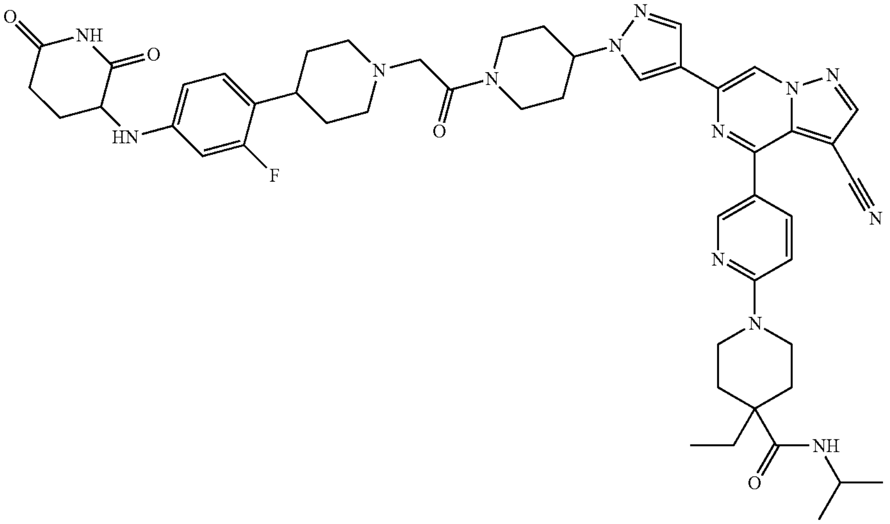 [SMILES: CCC1(C(=O)NC(C)C)CCN(c2ccc(-c3nc(-c4cnn(C5CCN(C(=O)CN6CCC(c7ccc(NC8CCC(=O)NC8=O)cc7F)CC6)CC5)c4)cn4ncc(C#N)c34)cn2)CC1] | ++++ | +++ |
| 54 | 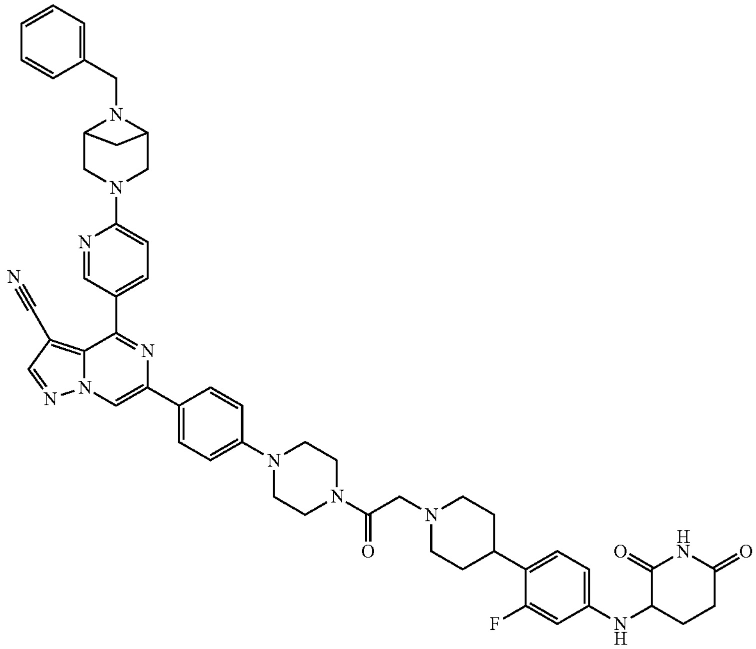 [SMILES: N#Cc1cnn2cc(-c3ccc(N4CCN(C(=O)CN5CCC(c6ccc(NC7CCC(=O)NC7=O)cc6F)CC5)CC4)cc3)nc(-c3ccc(N4CC5CC(C4)N5Cc4ccccc4)nc3)c12] | +++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 55 | 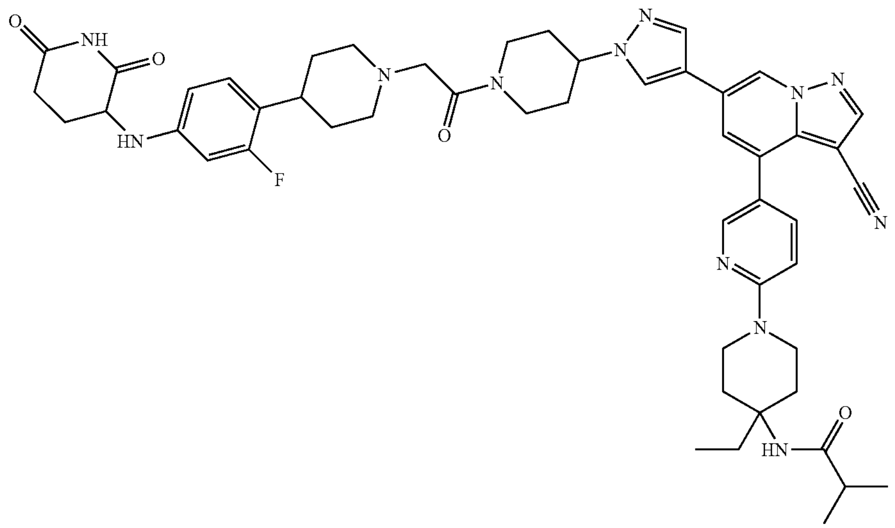 [SMILES: CCC1(NC(=O)C(C)C)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | ++++ | +++ |
| 56 | 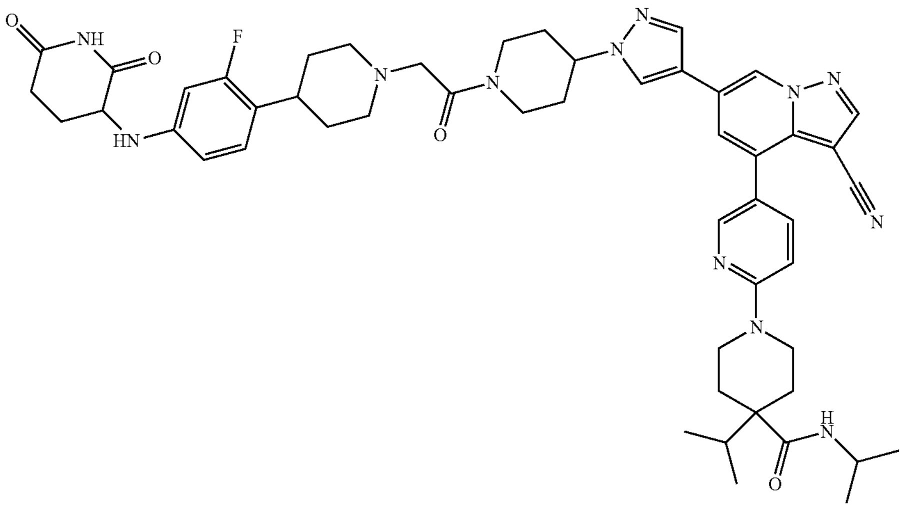 [SMILES: CC(C)NC(=O)C1(C(C)C)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | +++ | +++ |

TABLE 1A-continued
| Biological Data | | | |
|---|---|---|---|
| Compound | | HiBiT-Degradation 293T.165 RET(KD: 658-1114 G810R) 6.0 hours (DC50) | 293T.165 RET(KD: 658-1114 G810R) 6.0 hours |
| # | Structure | [nM] | (Emax) |
| 57 | 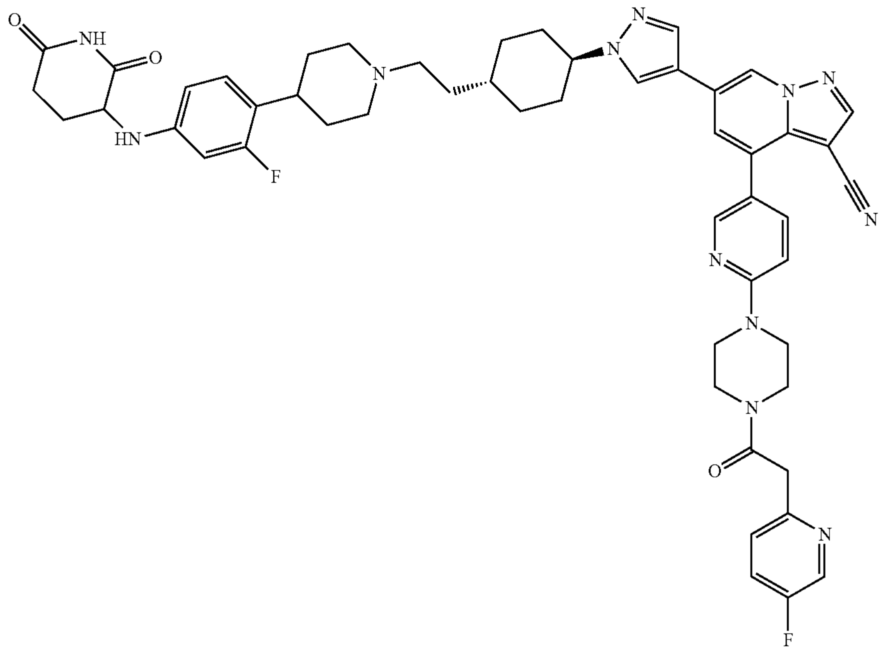 [SMILES: N#Cc1cnn2cc(-c3cnn([C@H]4CC[C@H](CCN5CCC(c6ccc(NC7CCC(=O)NC7=O)cc6F)CC5)CC4)c3)cc(-c3ccc(N4CCN(C(=O)Cc5ccc(F)cn5)CC4)nc3)c12] | ++++ | ++++ |
| 58 | 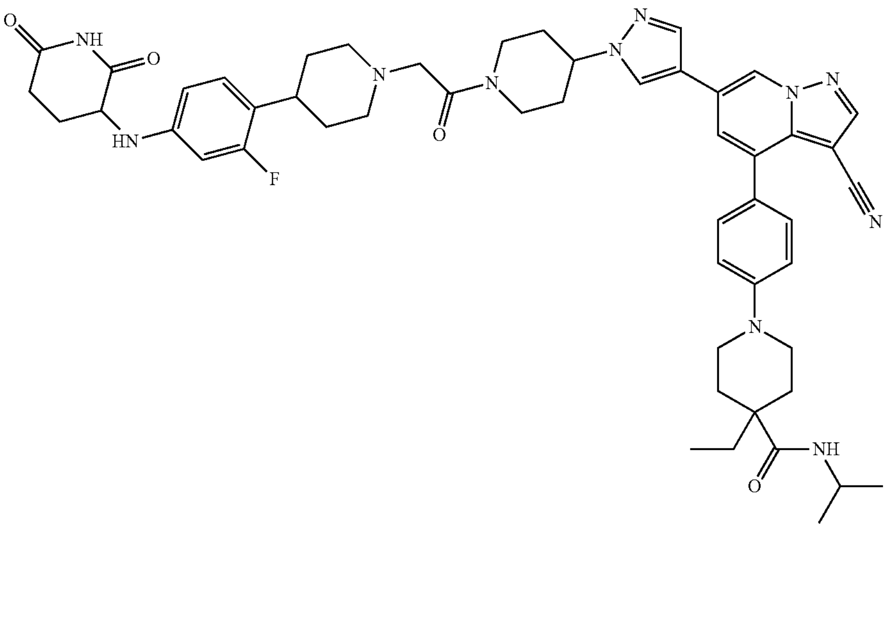 [SMILES: CCC1(C(=O)NC(C)C)CCN(c2ccc(-c3cc(-c4cnn(C5CCN(C(=O)CN6CCC(c7ccc(NC8CCC(=O)NC8=O)cc7F)CC6)CC5)c4)cn4ncc(C#N)c34)cc2)CC1] | ++++ | +++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 59 | 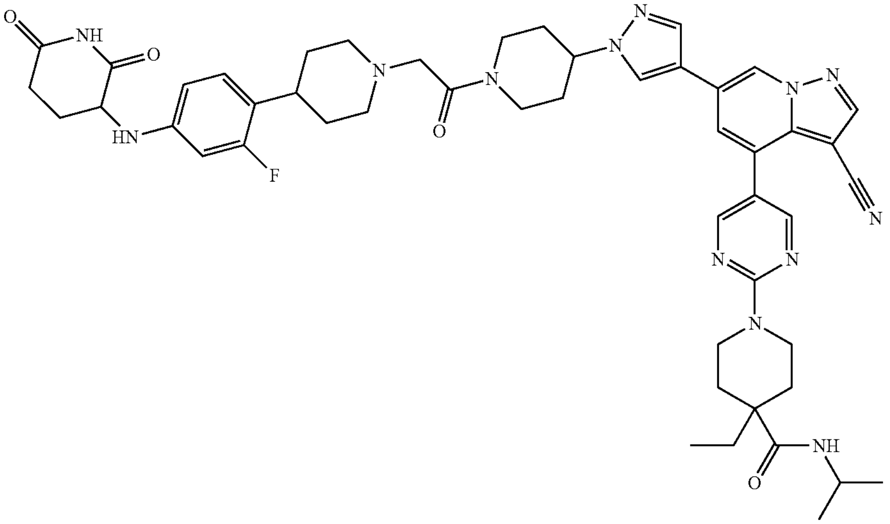 [SMILES: CCC1(C(=O)NC(C)C)CCN(c2ncc(-c3cc(-c4cnn(C5CCN(C(=O)CN6CCC(c7ccc(NC8CCC(=O)NC8=O)cc7F)CC6)CC5)c4)cn4ncc(C#N)c34)cn2)CC1] | +++ | +++ |
| 60 | 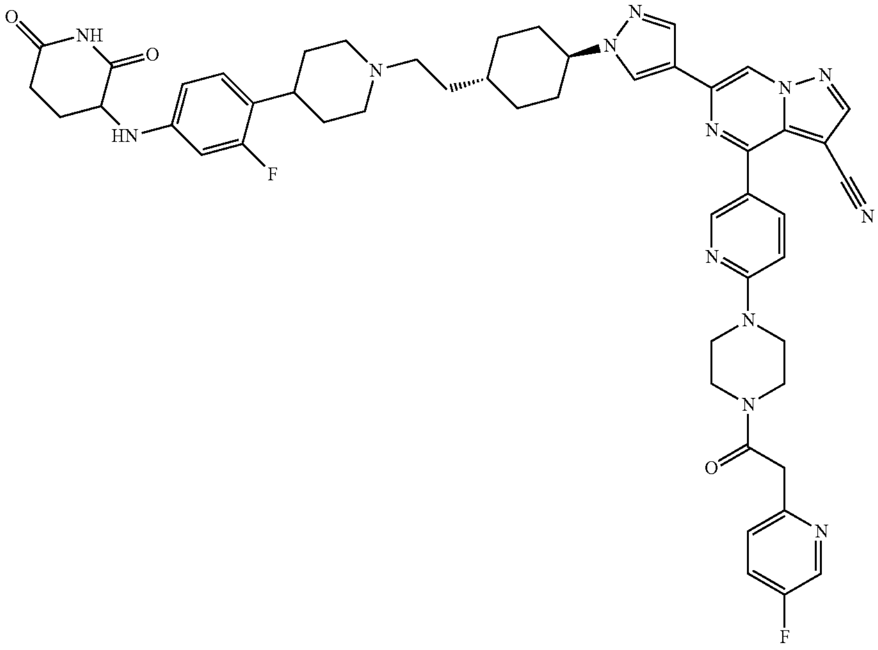 [SMILES: N#Cc1cnn2cc(-c3cnn([C@H]4CC[C@H](CCN5CCC(c6ccc(NC7CCC(=O)NC7=O)cc6F)CC5)CC4)c3)nc(-c3ccc(N4CCN(C(=O)Cc5ccc(F)cn5)CC4)nc3)c12] | ++++ | ++++ |

TABLE 1A-continued
Biological Data
| Compound | | HiBiT-Degradation | |
|---|---|---|---|
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 61 | 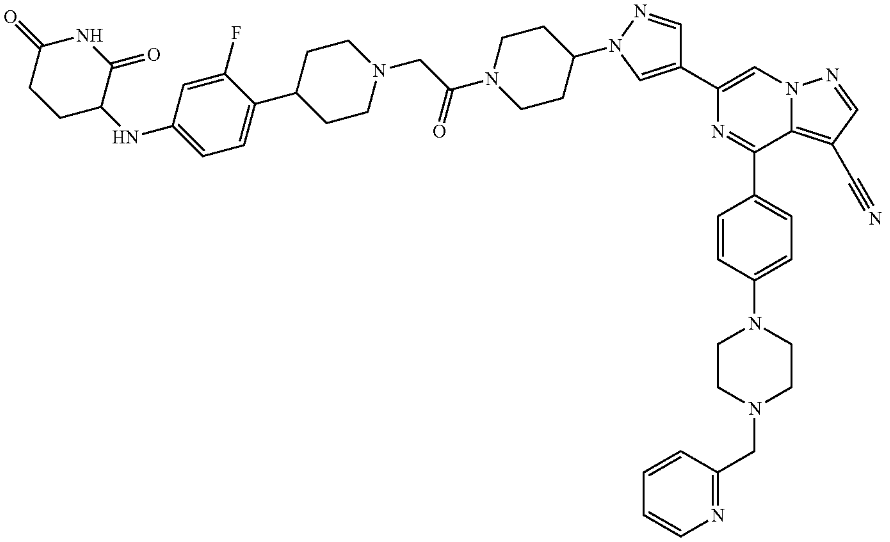 [SMILES: N#Cc1cnn2cc(-c3cnn(C4CCN(C(=O)CN5CCC(c6ccc(NC7CCC(=O)NC7=O)cc6F)CC5)CC4)c3)nc(-c3ccc(N4CCN(Cc5ccccn5)CC4)cc3)c12] | +++ | +++ |
| 62 | 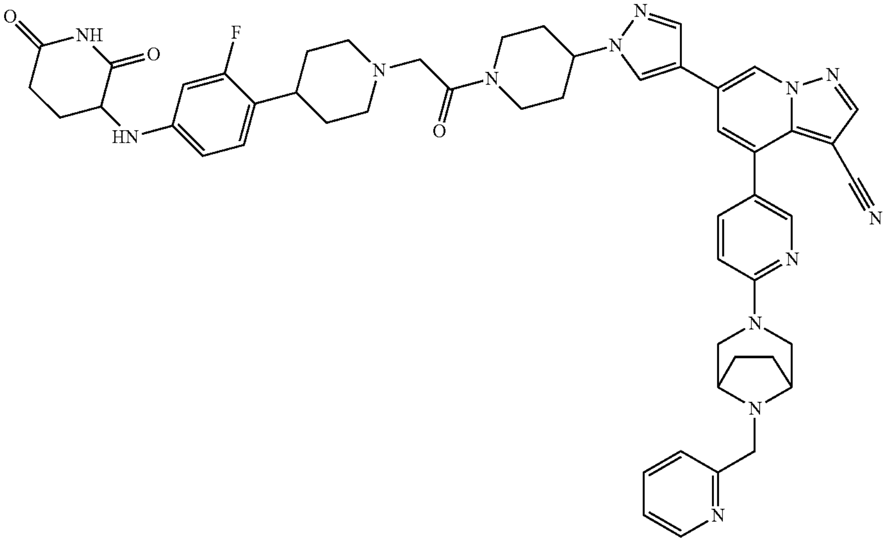 [SMILES: N#Cc1cnn2cc(-c3cnn(C4CCN(C(=O)CN5CCC(c6ccc(NC7CCC(=O)NC7=O)cc6F)CC5)CC4)c3)cc(-c3ccc(N4CC5CCC(C4)N5Cc4ccccn4)nc3)c12] | +++ | +++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 63 | 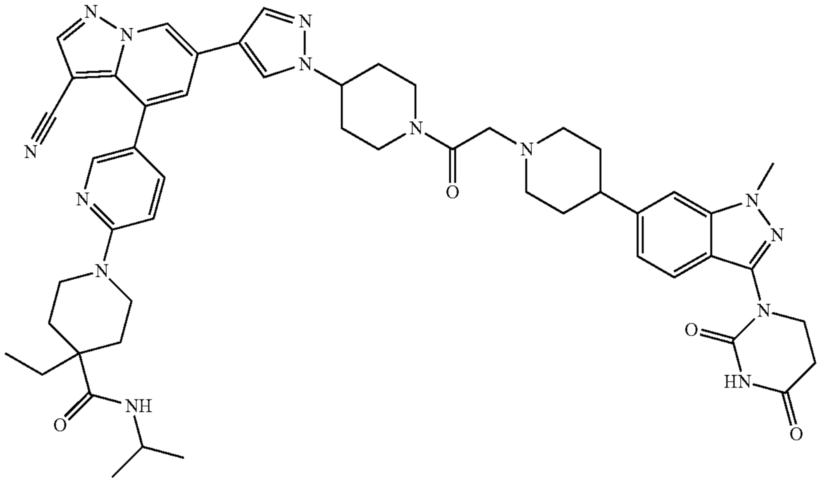 [SMILES: CCC1(C(=O)NC(C)C)CCN(c2ccc(-c3cc(-c4cnn(C5CCN(C(=O)CN6CCC(c7ccc8c(N9CCC(=O)NC9=O)nn(C)c8c7)CC6)CC5)c4)cn4ncc(C#N)c34)cn2)CC1] | +++ | ++++ |
| 64 | 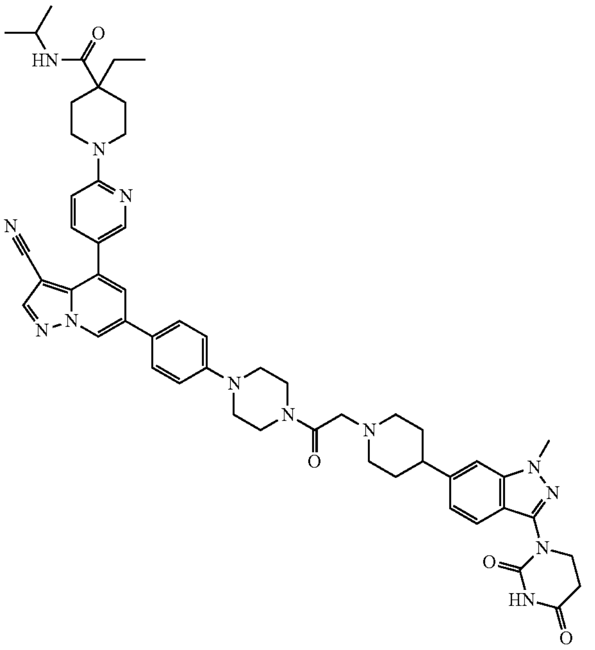 [SMILES: CCC1(C(=O)NC(C)C)CCN(c2ccc(-c3cc(-c4ccc(N5CCN(C(=O)CN6CCC(c7ccc8c(N9CCC(=O)NC9=O)nn(C)c8c7)CC6)CC5)cc4)cn4ncc(C#N)c34)cn2)CC1] | +++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 65 | 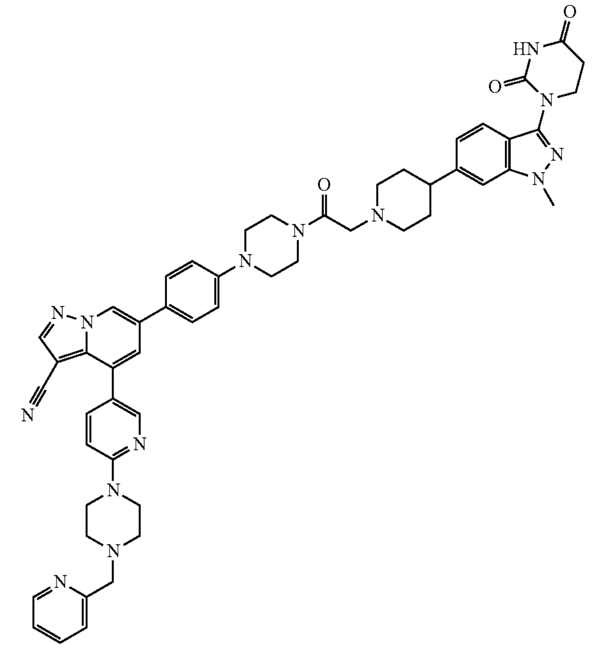 [SMILES: Cn1nc(N2CCC(=O)NC2=O)c2ccc(C3CCN(CC(=O)N4CCN(c5ccc(-c6cc(-c7ccc(N8CCN(Cc9ccccn9)CC8)nc7)c7c(C#N)cnn7c6)cc5)CC4)CC3)cc21] | +++ | +++ |
| 66 | 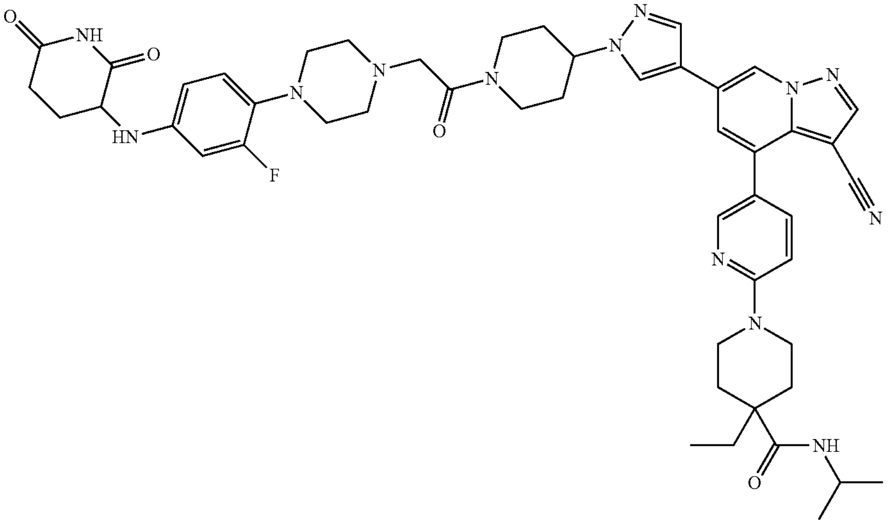 [SMILES: CCC1(C(=O)NC(C)C)CCN(c2ccc(-c3cc(-c4cnn(C5CCN(C(=O)CN6CCN(c7ccc(NC8CCC(=O)NC8=O)cc7F)CC6)CC5)c4)cn4ncc(C#N)c34)cn2)CC1] | ++++ | ++++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 67 | 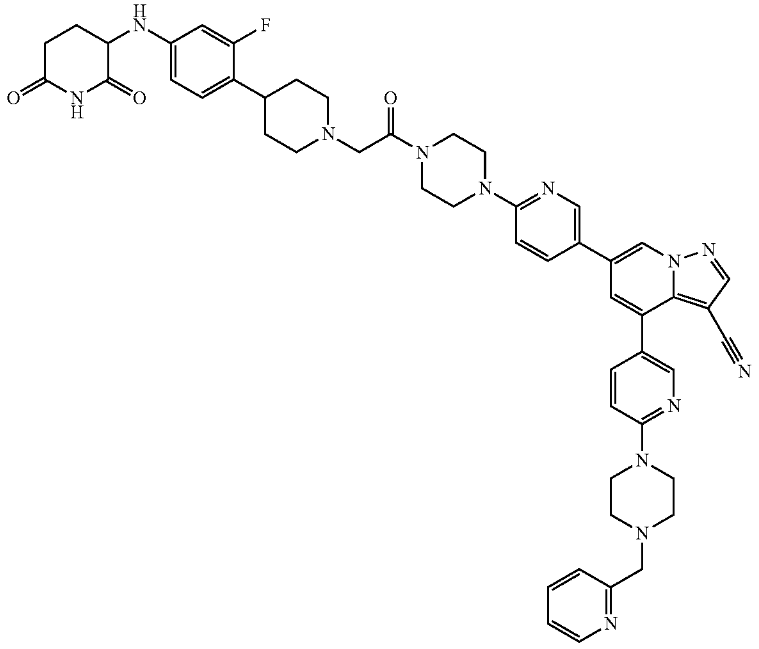 [SMILES: N#Cc1cnn2cc(-c3ccc(N4CCN(C(=O)CN5CCC(c6ccc(NC7CCC(=O)NC7=O)cc6F)CC5)CC4)nc3)cc(-c3ccc(N4CCN(Cc5ccccn5)CC4)nc3)c12] | +++ | +++ |
| 68 | 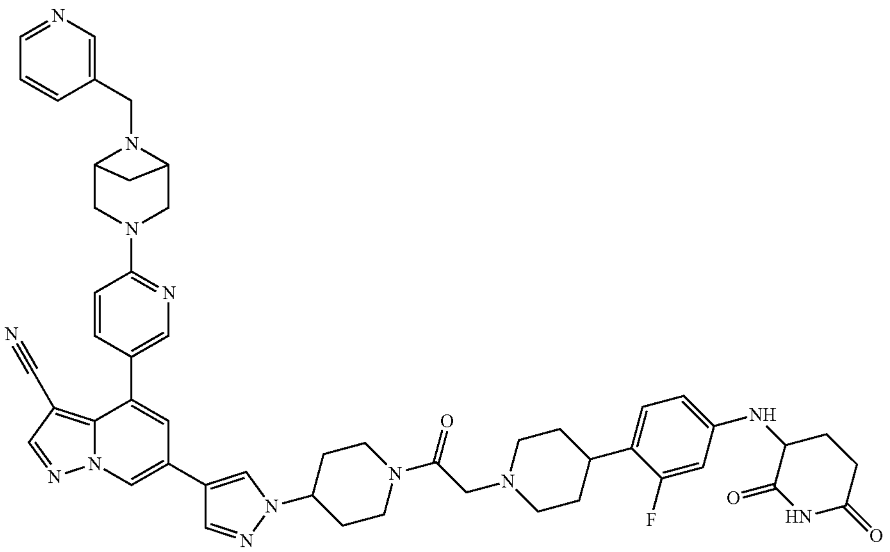 [SMILES: N#Cc1cnn2cc(-c3cnn(C4CCN(C(=O)CN5CCC(c6ccc(NC7CCC(=O)NC7=O)cc6F)CC5)CC4)c3)cc(-c3ccc(N4CC5CC(C4)N5Cc4cccnc4)nc3)c12] | ++++ | ++++ |

TABLE 1A-continued
Biological Data
| Compound # | Structure | HiBiT-Degradation 293T.165 RET(KD: 658-1114 G810R) 6.0 hours (DC50) [nM] | 293T.165 RET(KD: 658-1114 G810R) 6.0 hours (Emax) |
|---|---|---|---|
| 69 | 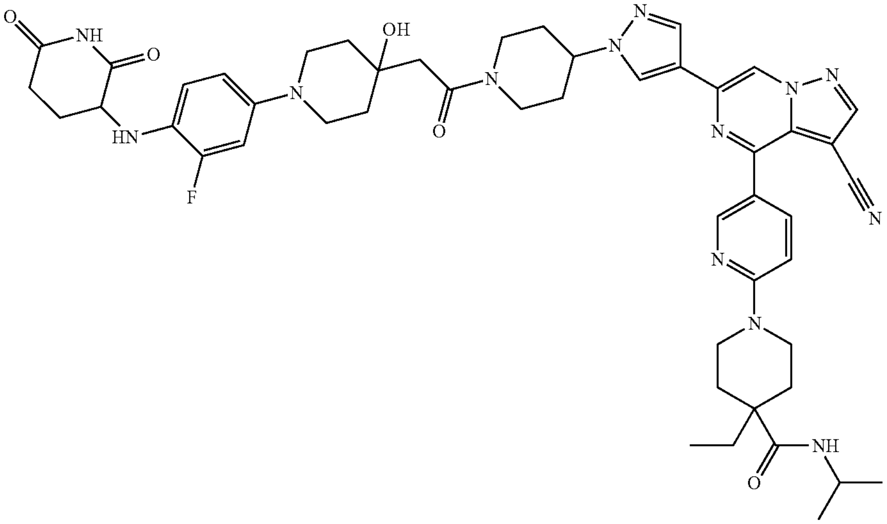 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)c(F)c7)CC6)CC5)c4)cn4ncc(C#N)c34)cn2)CC1] | +++ | +++ |
| 70 | 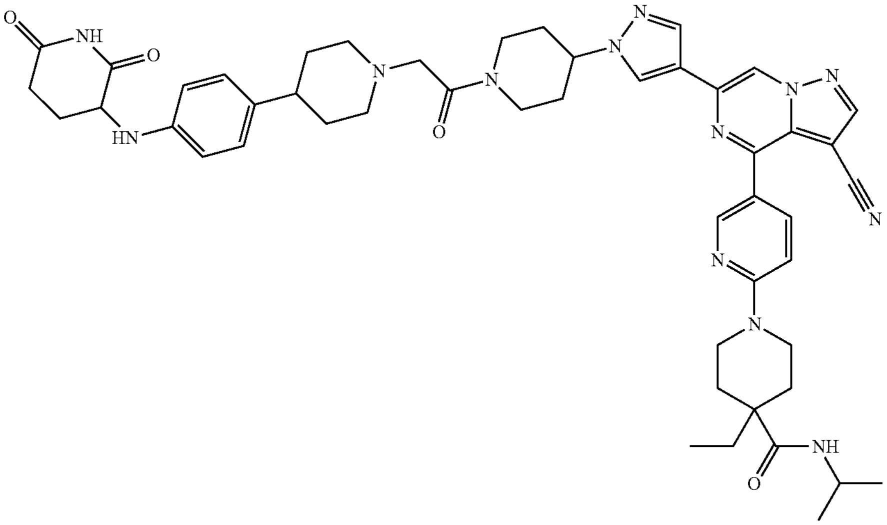 [SMILES: CCC1(C(=O)NC(C)C)CCN(c2ccc(-c3nc(-c4cnn(C5CCN(C(=O)CN6CCC(c7ccc(NC8CCC(=O)NC8=O)cc7)CC6)CC5)c4)cn4ncc(C#N)c34)cn2)CC1] | ++++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 71 | 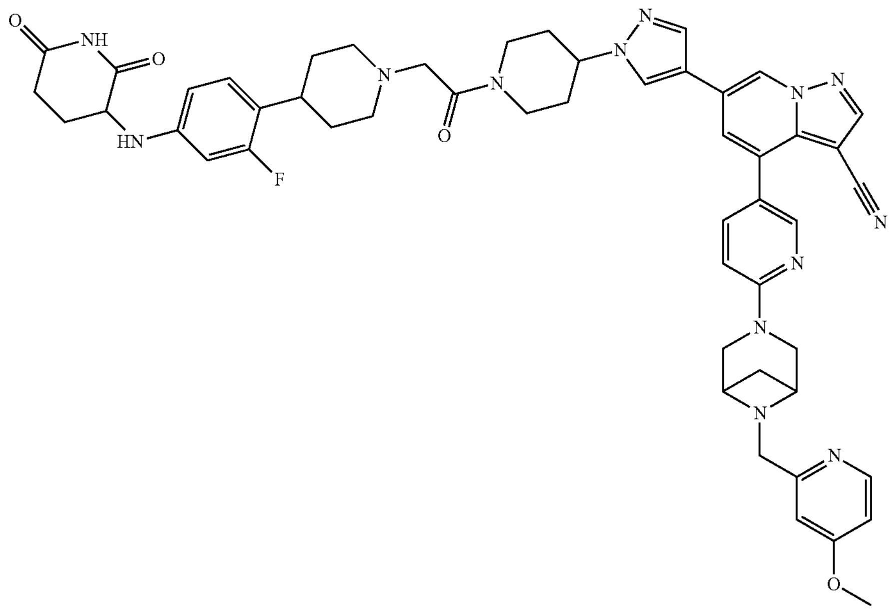 [SMILES: COc1ccnc(CN2C3CC2CN(c2ccc(-c4cc(-c5cnn(C6CCN(C(=O)CN7CCC(c8ccc(NC9CCC(=O)NC9=O)cc8F)CC7)CC6)c5)cn5ncc(C#N)c45)cn2)C3)c1] | +++ | ++++ |
| 72 | 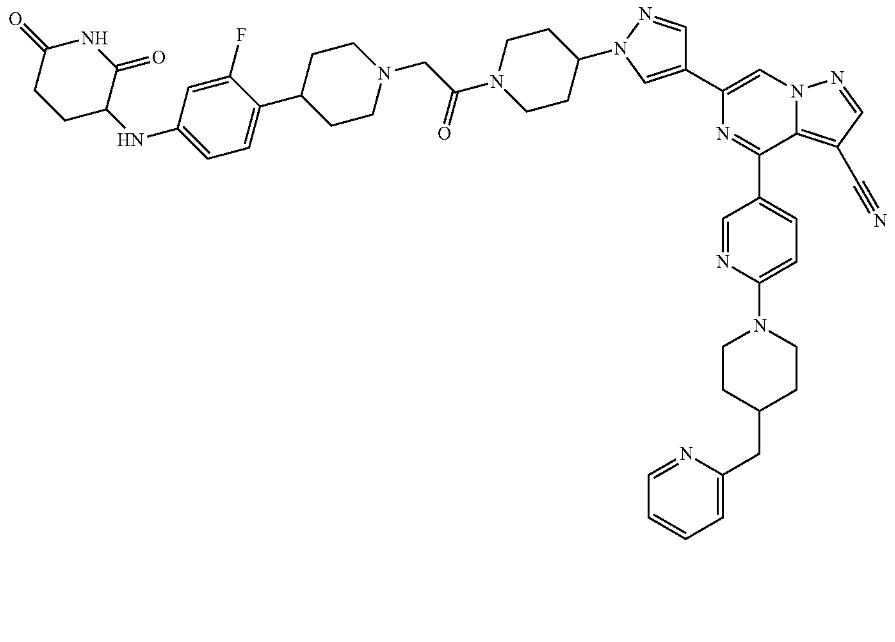 [SMILES: N#Cc1cnn2cc(-c3cnn(C4CCN(C(=O)CN5CCC(c6ccc(NC7CCC(=O)NC7=O)cc6F)CC5)CC4)c3)nc(-c3ccc(N4CCC(Cc5ccccn5)CC4)nc3)c12] | ++++ | +++ |

TABLE 1A-continued
Biological Data
| # | Compound Structure | HiBiT-Degradation 293T.165 RET(KD: 658-1114 G810R) 6.0 hours (DC50) [nM] | HiBiT-Degradation 293T.165 RET(KD: 658-1114 G810R) 6.0 hours (Emax) |
|---|---|---|---|
| 73 | 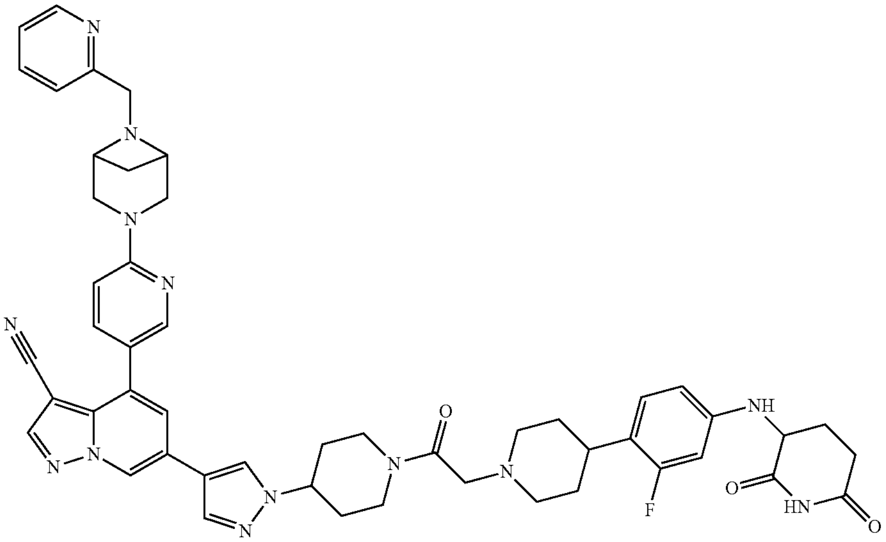 [SMILES: N#Cc1cnn2cc(-c3cnn(C4CCN(C(=O)CN5CCC(c6ccc(NC7CCC(=O)NC7=O)cc6F)CC5)CC4)c3)cc(-c3ccc(N4CC5CC(C4)N5Cc4ccccn4)nc3)c12] | ++++ | ++++ |
| 74 | 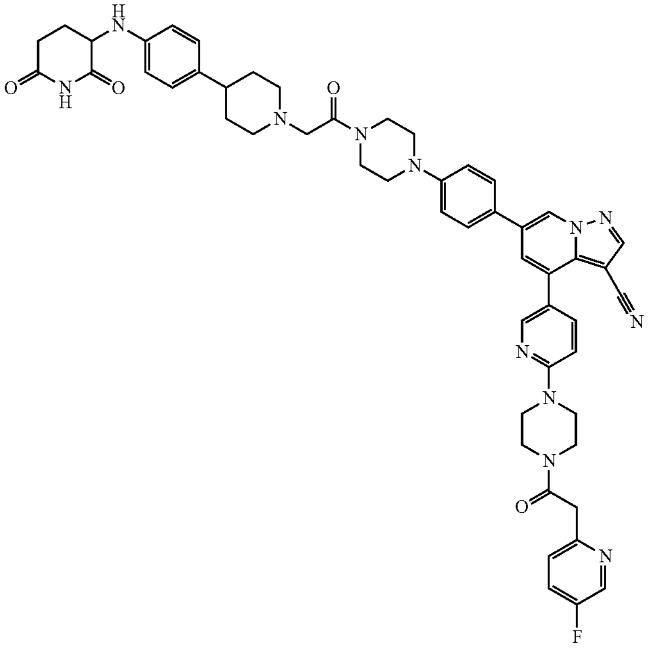 [SMILES: N#Cc1cnn2cc(-c3ccc(N4CCN(C(=O)CN5CCC(c6ccc(NC7CCC(=O)NC7=O)cc6)CC5)CC4)cc3)cc(-c3ccc(N4CCN(C(=O)Cc5ccc(F)cn5)CC4)nc3)c12] | ++++ | ++++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 75 | 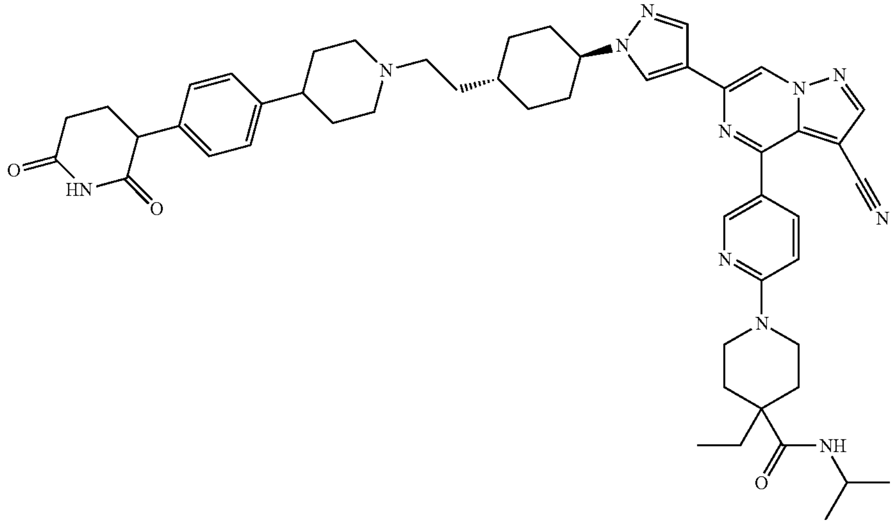 [SMILES: CCC1(C(=O)NC(C)C)CCN(c2ccc(-c3nc(-c4cnn([C@H]5CC[C@H](CCN6CCC(c7ccc(C8CCC(=O)NC8=O)cc7)CC6)CC5)c4)cn4ncc(C#N)c34)cn2)CC1] | +++ | ++++ |
| 76 | 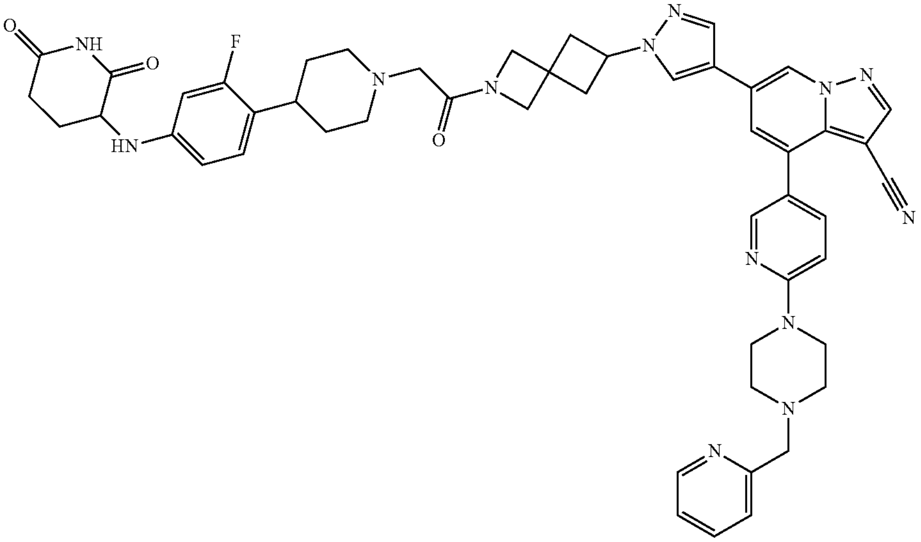 [SMILES: N#Cc1cnn2cc(-c3cnn(C4CC5(C4)CN(C(=O)CN4CCC(c6ccc(NC7CCC(=O)NC7=O)cc6F)CC4)C5)c3)cc(-c3ccc(N4CCN(Cc5ccccn5)CC4)nc3)c12] | +++ | ++++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 77 | 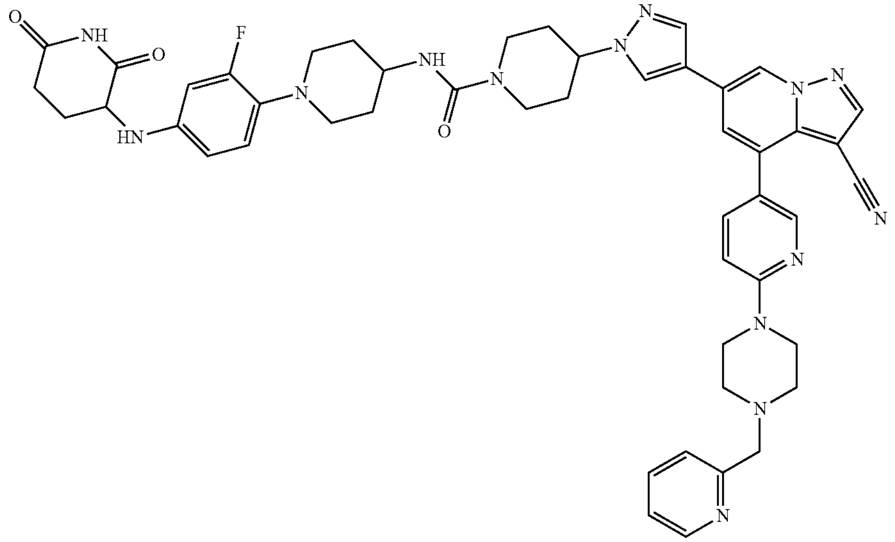 [SMILES: N#Cc1cnn2cc(-c3cnn(C4CCN(C(=O)NC5CCN(c6ccc(NC7CCC(=O)NC7=O)cc6F)CC5)CC4)c3)cc(-c3ccc(N4CCN(Cc5ccccn5)CC4)nc3)c12] | +++ | +++ |
| 78 | 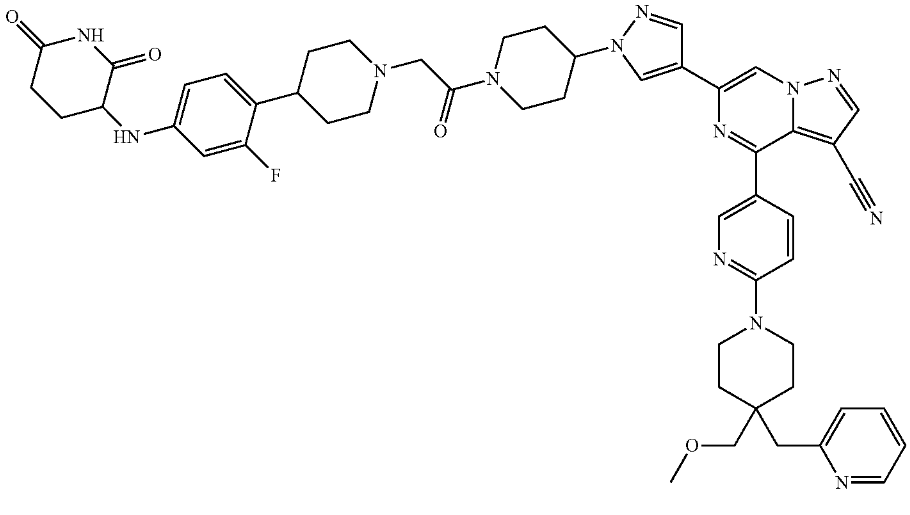 [SMILES: COCC1(Cc2ccccn2)CCN(c2ccc(-c3nc(-c4cnn(C5CCN(C(=O)CN6CCC(c7ccc(NC8CCC(=O)NC8=O)cc7F)CC6)CC5)c4)cn4ncc(C#N)c34)cn2)CC1] | +++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 79 | 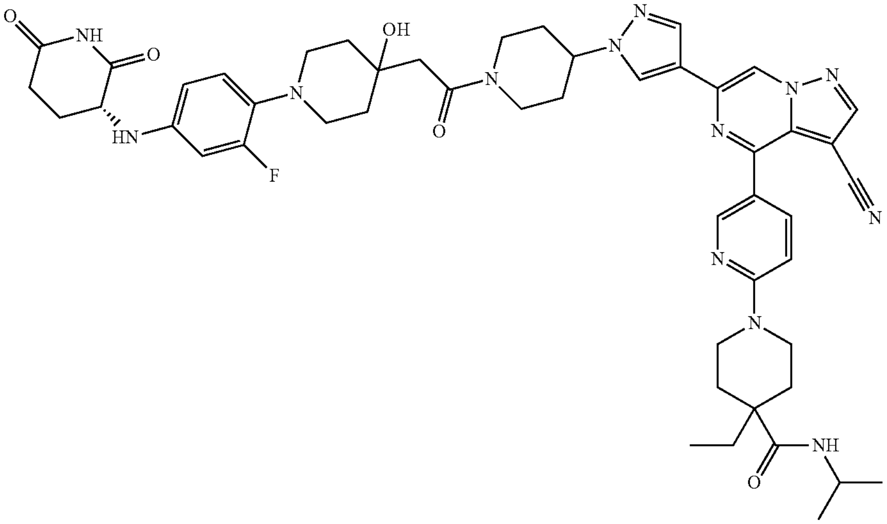 separated enantiomer, chirality arbitrarily assigned | ++++ | ++++ |
| 80 | 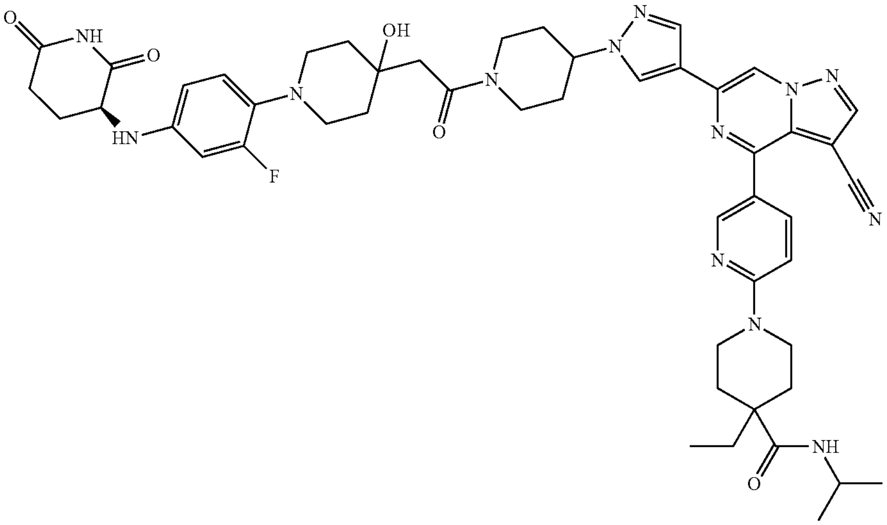 separated enantiomer, chirality arbitrarily assigned | ++++ | +++ |

TABLE 1A-continued
| Biological Data | | | |
|---|---|---|---|
| Compound | | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 81 | 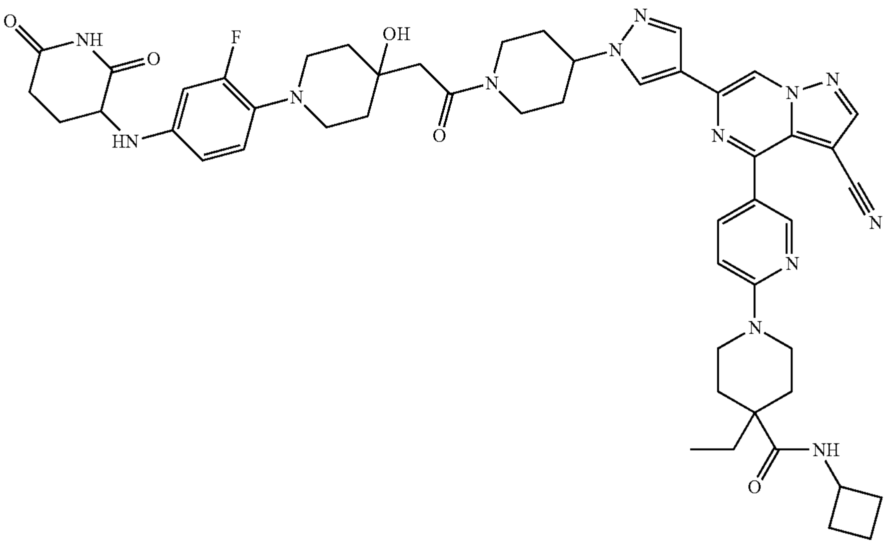 [SMILES: CCC1(C(=O)NC2CCC2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] | ++++ | ++++ |
| 82 | 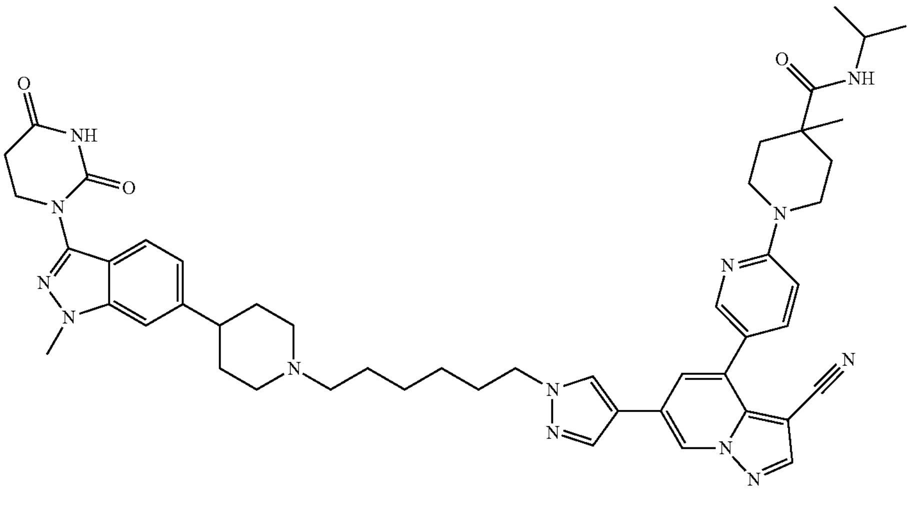 [SMILES: CC(C)NC(=O)C1(C)CCN(c2ccc(-c3cc(-c4cnn(CCCCCCN5CCC(c6ccc7c(N8CCC(=O)NC8=O)nn(C)c7c6)CC5)c4)cn4ncc(C#N)c34)cn2)CC1] | +++ | ++++ |

TABLE 1A-continued
| Biological Data | | | |
|---|---|---|---|
| Compound | | HiBiT-Degradation | |
| # | Structure | 293T.165 RET(KD: 658-1114 G810R) 6.0 hours (DC50) [nM] | 293T.165 RET(KD: 658-1114 G810R) 6.0 hours (Emax) |
| 83 | 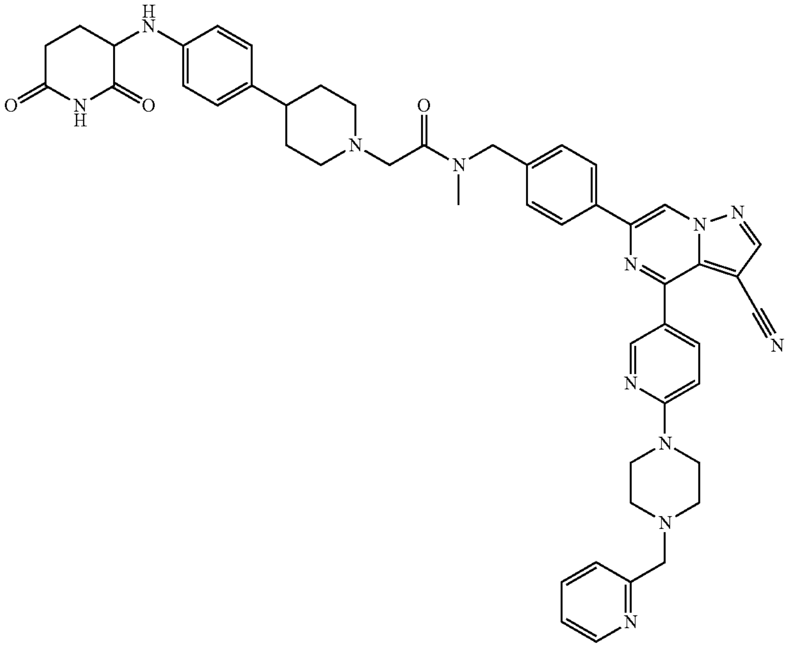 [SMILES: CN(Cc1ccc(-c2cn3ncc(C#N)c3c(-c3ccc(N4CCN(Cc5ccccn5)CC4)nc3)n2)cc1)C(=O)CN1CCC(c2ccc(NC3CCC(=O)NC3=O)cc2)CC1] | +++ | +++ |
| 84 | 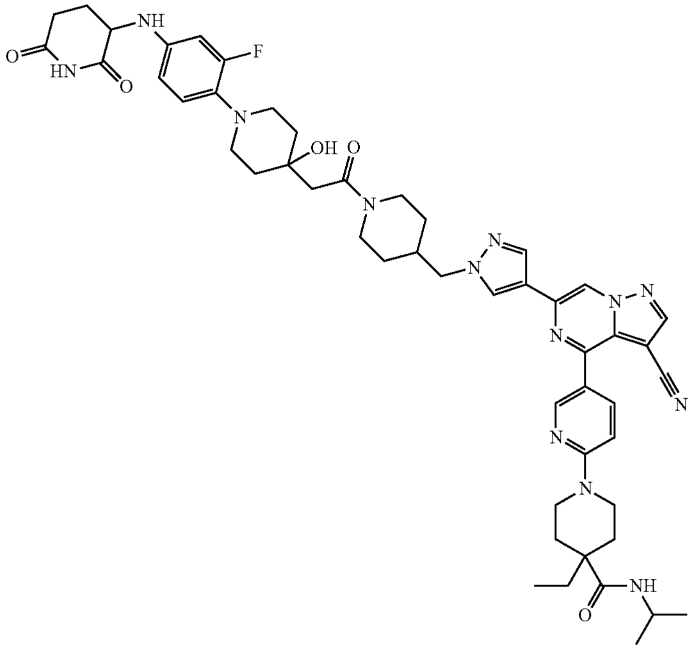 [SMILES: CCC1(C(=O)NC(C)C)CCN(c2ccc(-c3nc(-c4cnn(CC5CCN(C(=O)CC6(O)CCN(c7ccc(NC8CCC(=O)NC8=O)cc7F)CC6)CC5)c4)cn4ncc(C#N)c34)cn2)CC1] | +++ | ++++ |

TABLE 1A-continued
Biological Data
| Compound # | Structure | HiBiT-Degradation 293T.165 RET(KD: 658-1114 G810R) 6.0 hours (DC50) [nM] | HiBiT-Degradation 293T.165 RET(KD: 658-1114 G810R) 6.0 hours (Emax) |
|---|---|---|---|
| 85 | 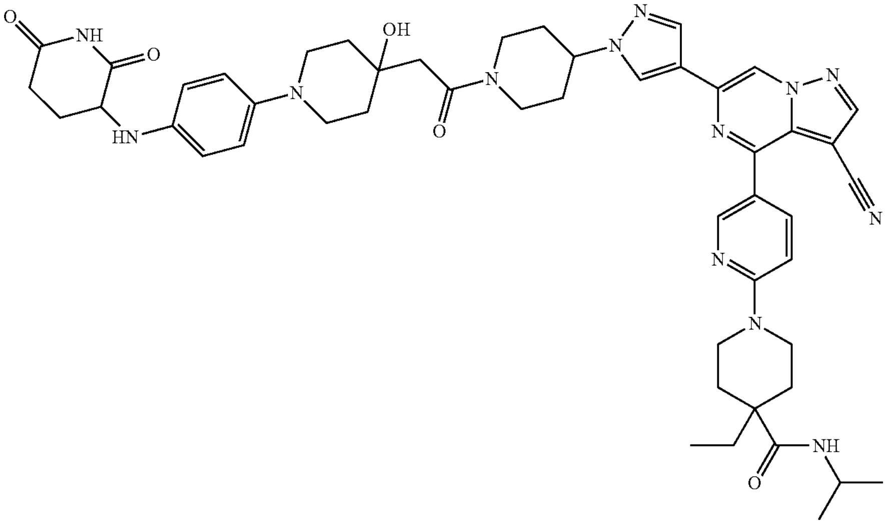 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7)CC6)CC5)c4)cn4ncc(C#N)c34)cn2)CC1] | +++ | +++ |
| 86 | 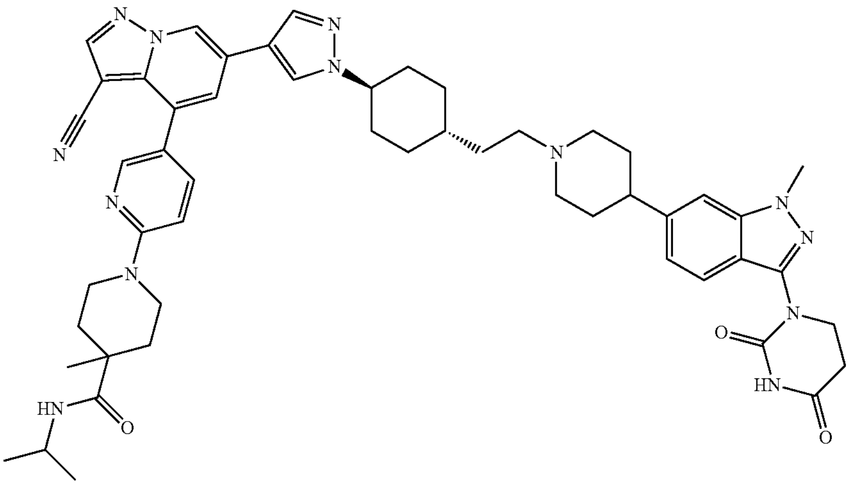 [SMILES: CC(C)NC(=O)C1(C)CCN(c2ccc(-c3cc(-c4cnn([C@H]5CC[C@H](CCN6CCC(c7ccc8c(N9CCC(=O)NC9=O)nn(C)c8c7)CC6)CC5)c4)cn4ncc(C#N)c34)cn2)CC1] | +++ | ++++ |

TABLE 1A-continued
| Biological Data | | | |
|---|---|---|---|
| | Compound | HiBiT-Degradation | |
| | | 293T.165 RET(KD: 658-1114 G810R) 6.0 hours (DC50) | 293T.165 RET(KD: 658-1114 G810R) 6.0 hours |
| # | Structure | [nM] | (Emax) |
| 87 | 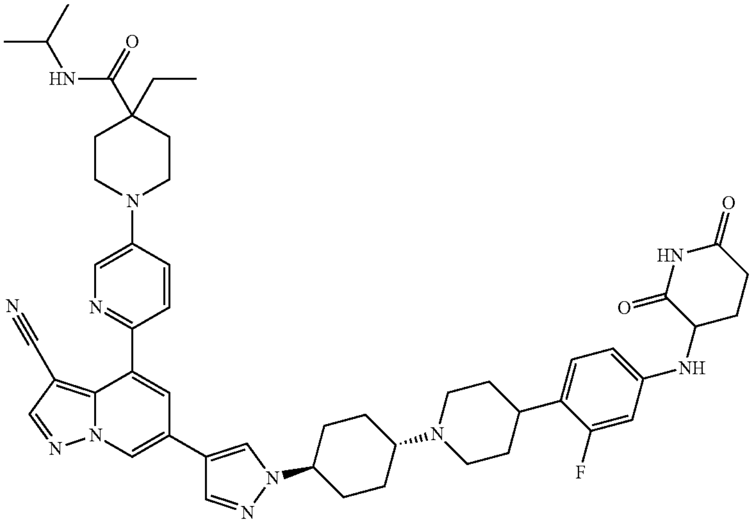 [SMILES: CCC1(C(=O)NC(C)C)CCN(c2ccc(-c3cc(-c4cnn([C@H]5CC[C@H](N6CCC(c7ccc(NC8CCC(=O)NC8=O)cc7F)CC6)CC5)c4)cn4ncc(C#N)c34)nc2)CC1] | ++++ | ++++ |
| 88 | 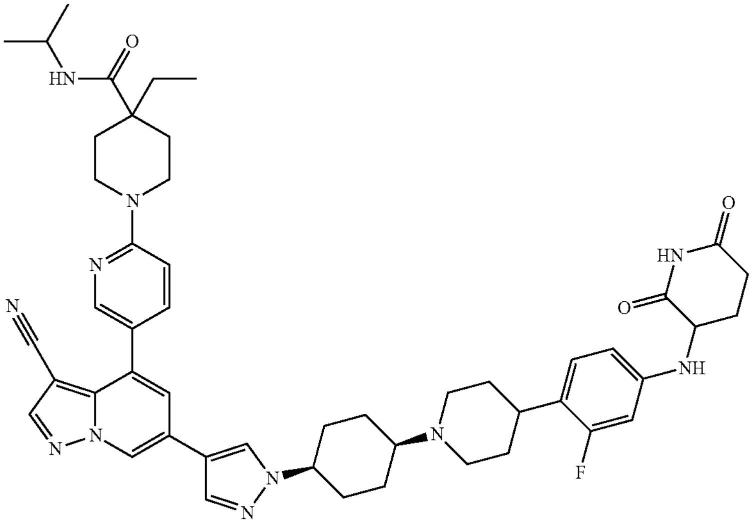 [SMILES: CCC1(C(=O)NC(C)C)CCN(c2ccc(-c3cc(-c4cnn([C@H]5CC[C@@H](N6CCC(c7ccc(NC8CCC(=O)NC8=O)cc7F)CC6)CC5)c4)cn4ncc(C#N)c34)cn2)CC1] | ++ | +++ |
As used in the table above for DC50 >= 1 um = +, <1 uM = ++, <100 nM = +++ and <50 nM = ++++.
For the Emax values >= 70% = +, <70% = ++, <50 % = +++, and <30% = ++++.

TABLE 1B
| Biological Data | |
|---|---|
| Cmpd # | Structure |
| 89 | 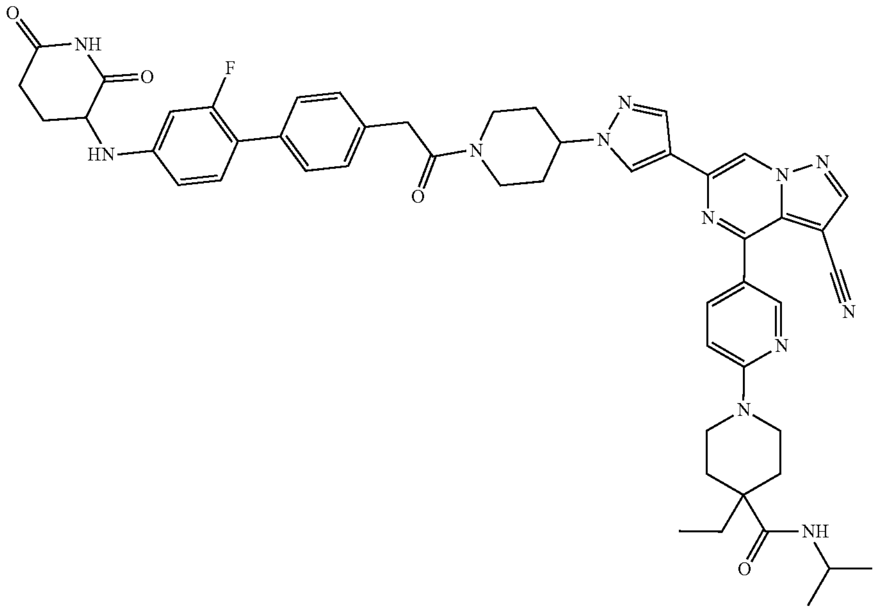 [SMILES: CCC1(C(=O)NC(C)C)CCN(c2ccc(-c3nc(-c4cnn(C5CCN(C(=O)Cc6ccc(-c7ccc(NC8CCC(=O)NC8=O)cc7F)cc6)CC5)c4)cn4ncc(C#N)c34)cn2)CC1] |
| 90 | 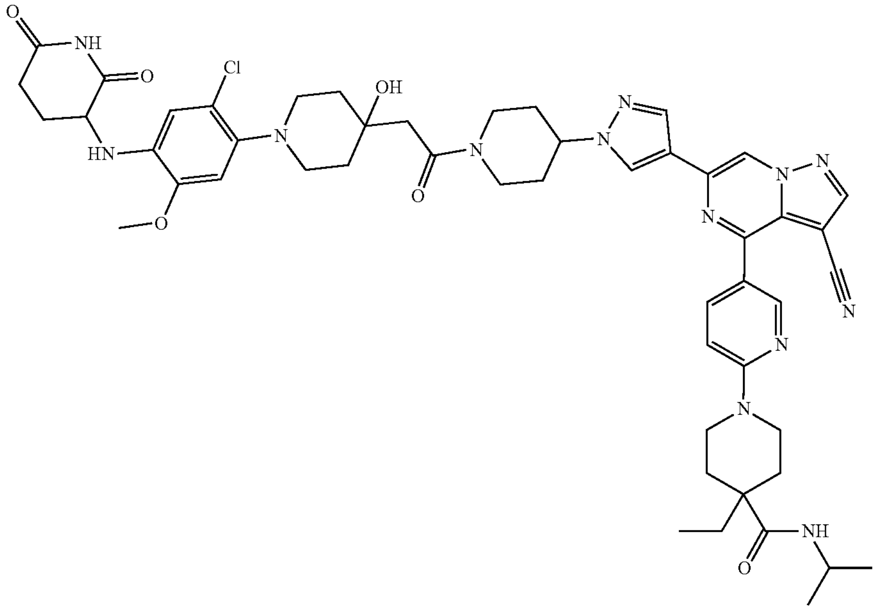 [SMILES: CCC1(C(=O)NC(C)C)CCN(c2ccc(-c3nc(-c4cnn(C5CCN(C(=O)CC6(O)CCN(c7cc(OC)c(NC8CCC(=O)NC8=O)cc7Cl)CC6)CC5)c4)cn4ncc(C#N)c34)cn2)CC1] |

TABLE 1B-continued
| Biological Data | |
|---|---|
| Cmpd # | Structure |
| 91 | 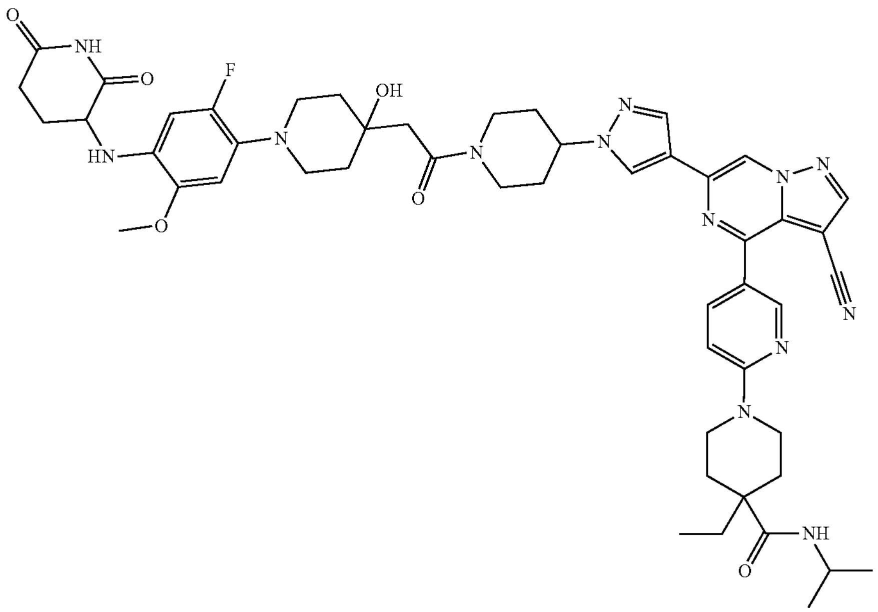 [SMILES: CCC1(C(=O)NC(C)C)CCN(c2ccc(-c3nc(-c4cnn(C5CCN(C(=O)CC6(O)CCN(c7cc(OC)c(NC8CCC(=O)NC8=O)cc7F)CC6)CC5)c4)cn4ncc(C#N)c34)cn2)CC1] |
| 92 | 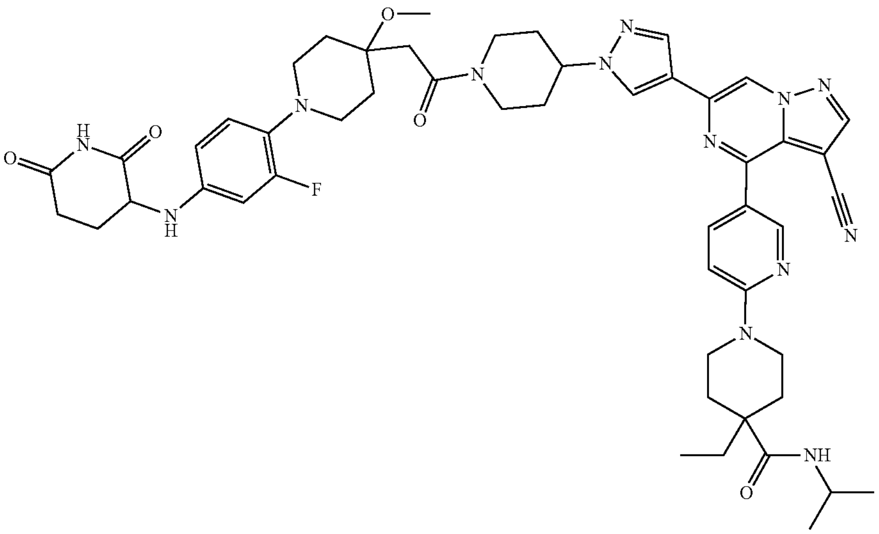 [SMILES: CCC1(C(=O)NC(C)C)CCN(c2ccc(-c3nc(-c4cnn(C5CCN(C(=O)CC6(OC)CCN(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 93 | 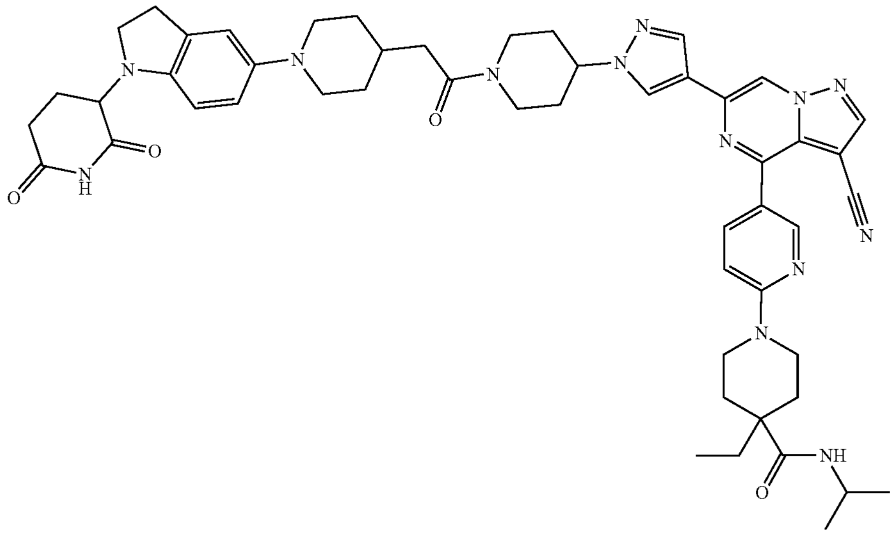 [SMILES: CCC1(C(=O)NC(C)C)CCN(c2ccc(-c3nc(-c4cnn(C5CCN(C(=O)CC6CCN(c7ccc8c(c7)CCN8C7CCC(=O)NC7=O)CC6)CC5)c4)cn4ncc(C#N)c34)cn2)CC1] |
| 94 | 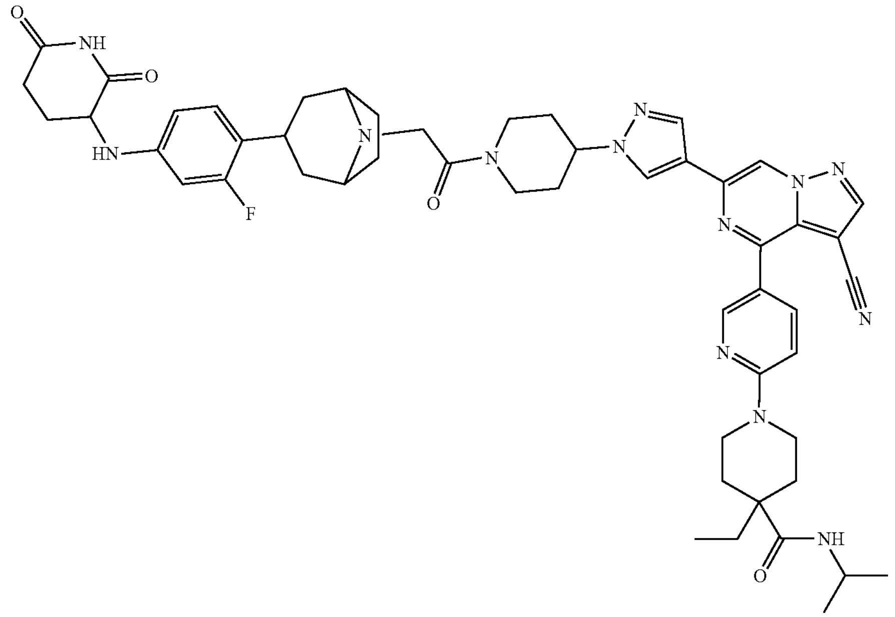 [SMILES: CCC1(C(=O)NC(C)C)CCN(c2ccc(-c3nc(-c4cnn(C5CCN(C(=O)CN6C7CCC6CC(c6ccc(NC8CCC(=O)NC8=O)cc6F)C7)CC5)c4)cn4ncc(C#N)c34)cn2)CC1] |

TABLE 1B-continued
| Biological Data | |
|---|---|
| Cmpd # | Structure |
| 95 | 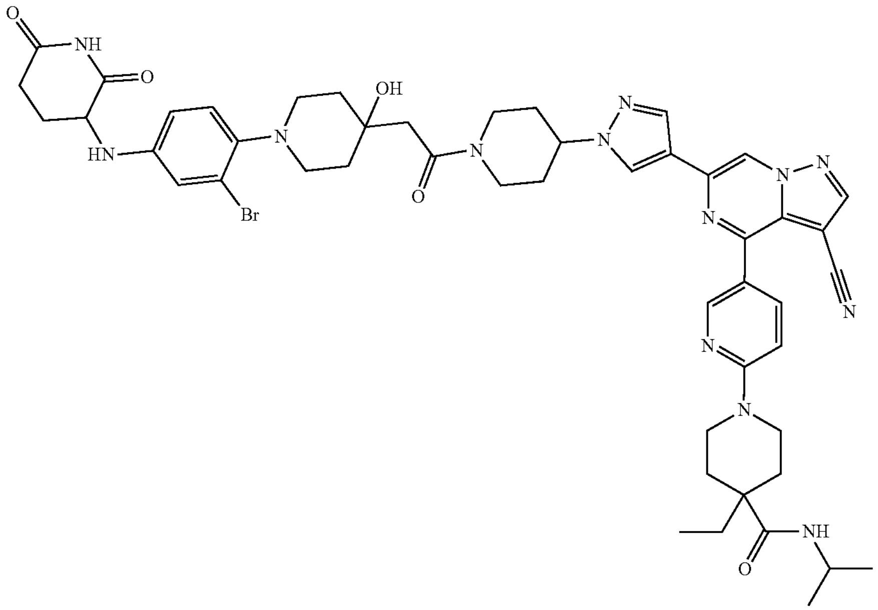 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7Br)CC6)CC5)c4)cn4ncc(C#N)c34)cn2)CC1] |
| 96 | 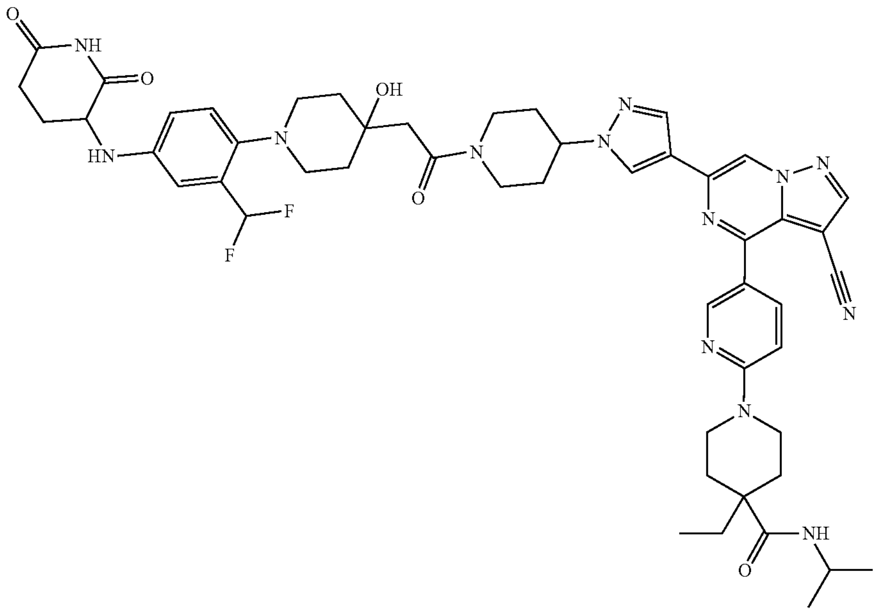 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7C(F)F)CC6)CC5)c4)cn4ncc(C#N)c34)cn2)CC1] |

TABLE 1B-continued
| Biological Data | |
|---|---|
| Cmpd # | Structure |
| 97 | 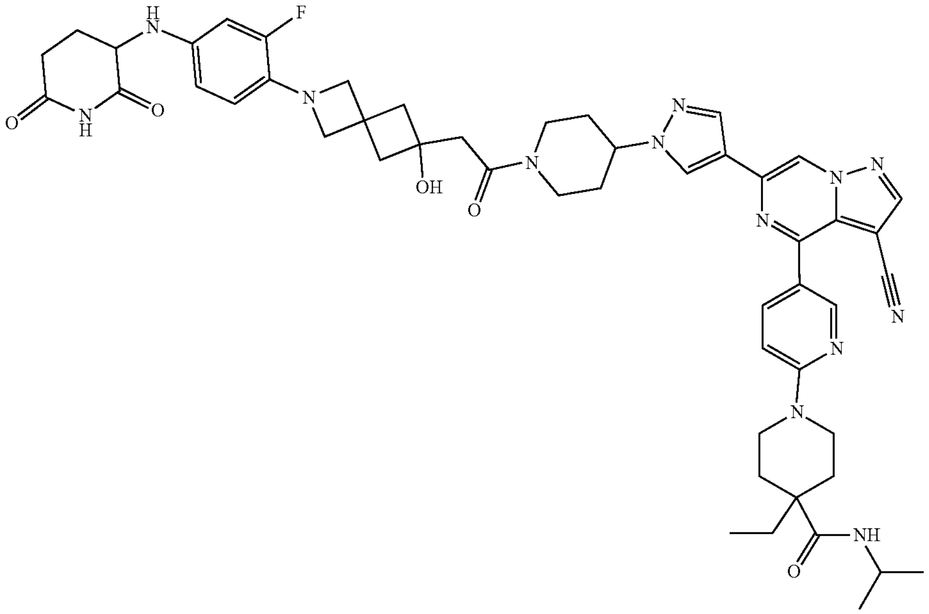 [SMILES: CCC1(C(=O)NC(C)C)CCN(c2ccc(-c3nc(-c4cnn(C5CCN(C(=O)CC6(O)CC7(CN(c8ccc(NC9CCC(=O)NC9=O)cc8F)C7)C6)CC5)c4)cn4ncc(C#N)c34)cn2)CC1] |
| 98 | 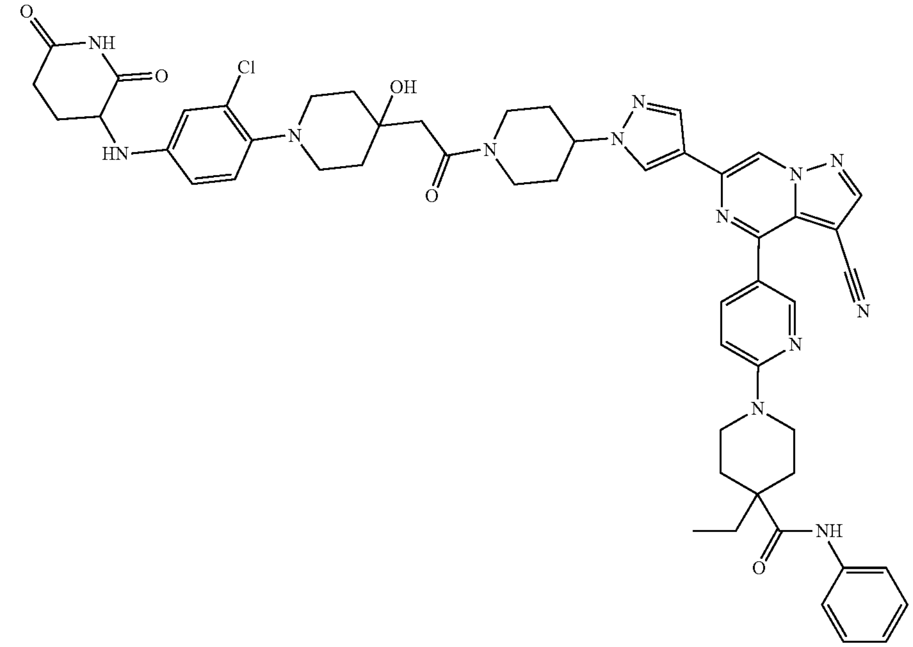 [SMILES: CCC1(C(=O)Nc2ccccc2)CCN(c2ccc(-c3nc(-c4cnn(C5CCN(C(=O)CC6(O)CCN(c7ccc(NC8CCC(=O)NC8=O)cc7Cl)CC6)CC5)c4)cn4ncc(C#N)c34)cn2)CC1] |

TABLE 1B-continued
| Biological Data | |
|---|---|
| Cmpd # | Structure |
| 99 | 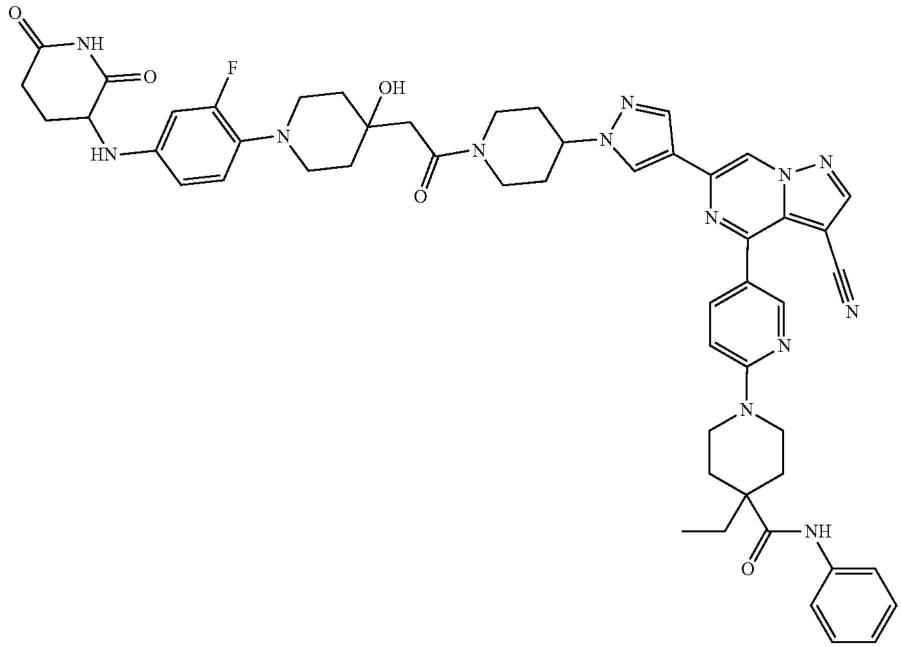 [SMILES: CCC1(C(=O)Nc2ccccc2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] |
| 100 | 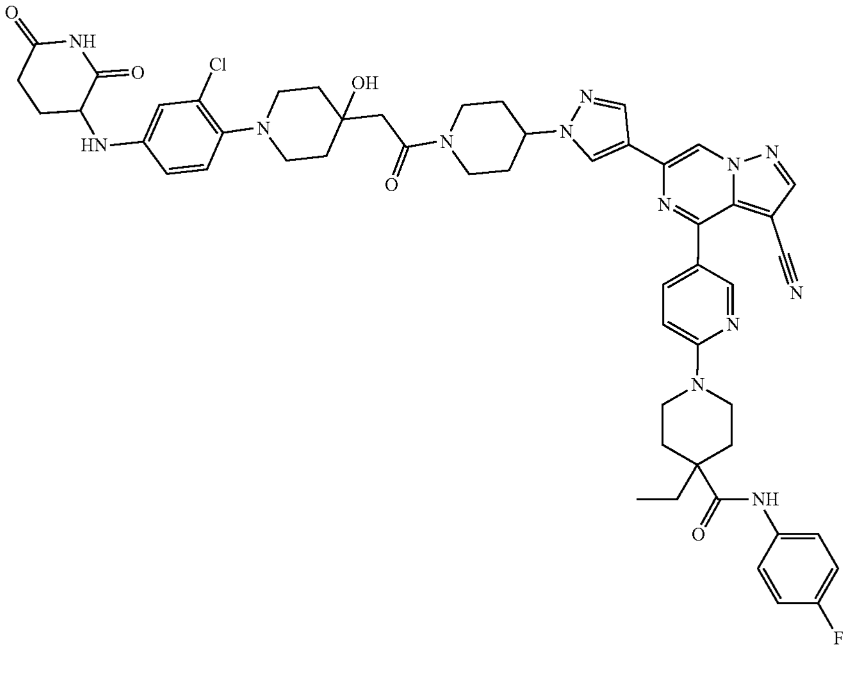 [SMILES: CCC1(C(=O)Nc2ccc(F)cc2)CCN(c2ccc(-c3nc(-c4cnn(C5CCN(C(=O)CC6(O)CCN(c7ccc(NC8CCC(=O)NC8=O)cc7Cl)CC6)CC5)c4)cn4ncc(C#N)c34)cn2)CC1] |

TABLE 1B-continued
| Biological Data | |
|---|---|
| Cmpd # | Structure |
| 101 | 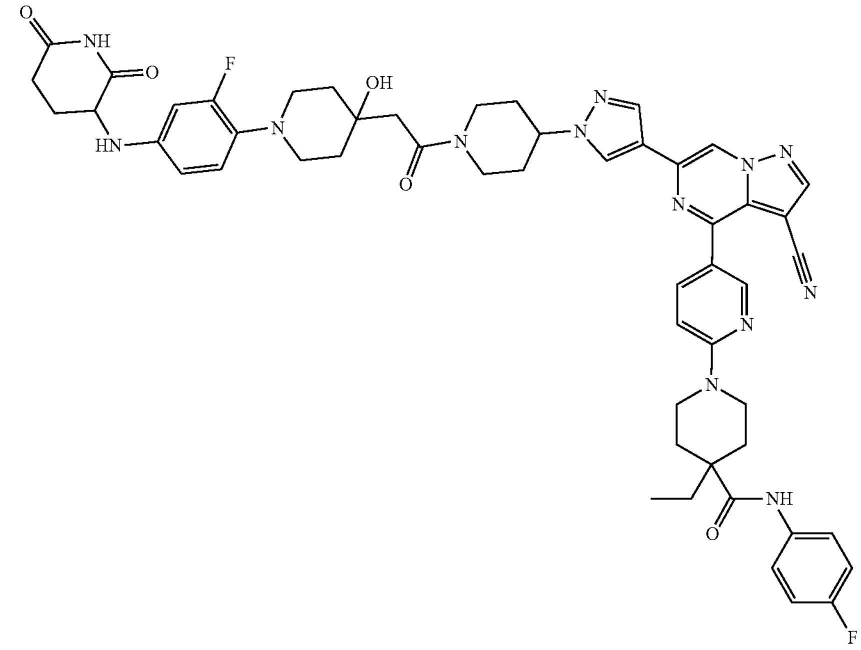 [SMILES: CCC1(C(=O)Nc2ccc(F)cc2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] |
| 102 | 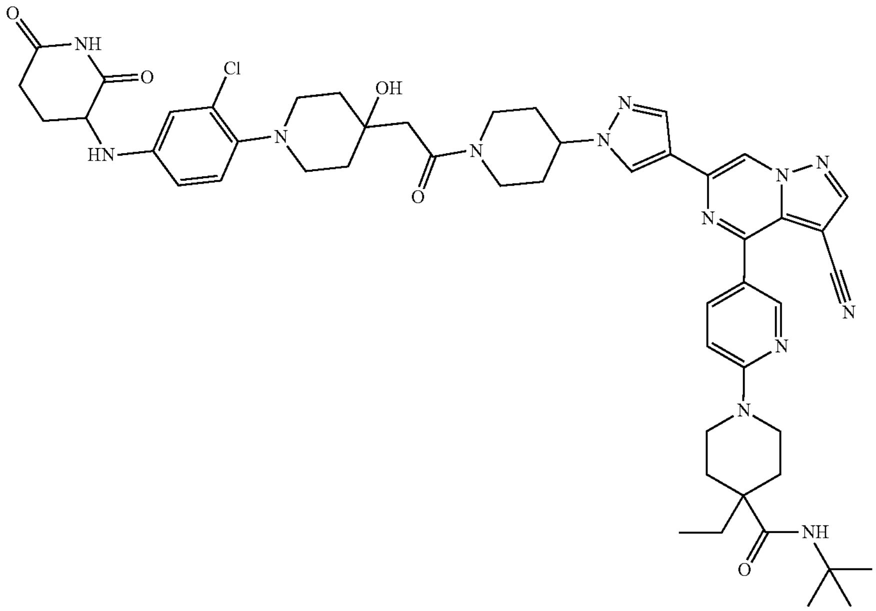 [SMILES: CCC1(C(=O)NC(C)(C)C)CCN(c2ccc(-c3nc(-c4cnn(C5CCN(C(=O)CC6(O)CCN(c7ccc(NC8CCC(=O)NC8=O)cc7Cl)CC6)CC5)c4)cn4ncc(C#N)c34)cn2)CC1] |

TABLE 1B-continued
| Biological Data | |
|---|---|
| Cmpd # | Structure |
| 103 | 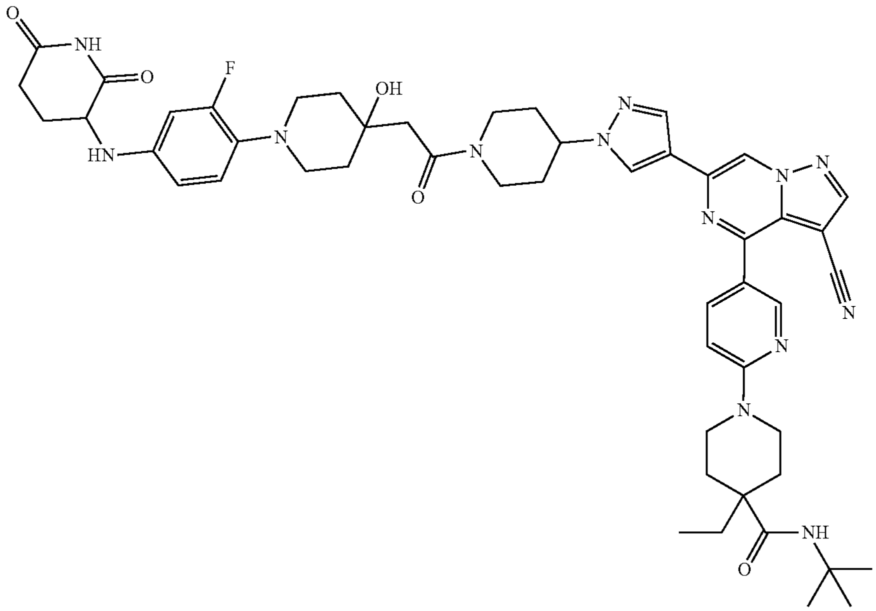 [SMILES: CCC1(C(=O)NC(C)(C)C)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] |
| 104 | 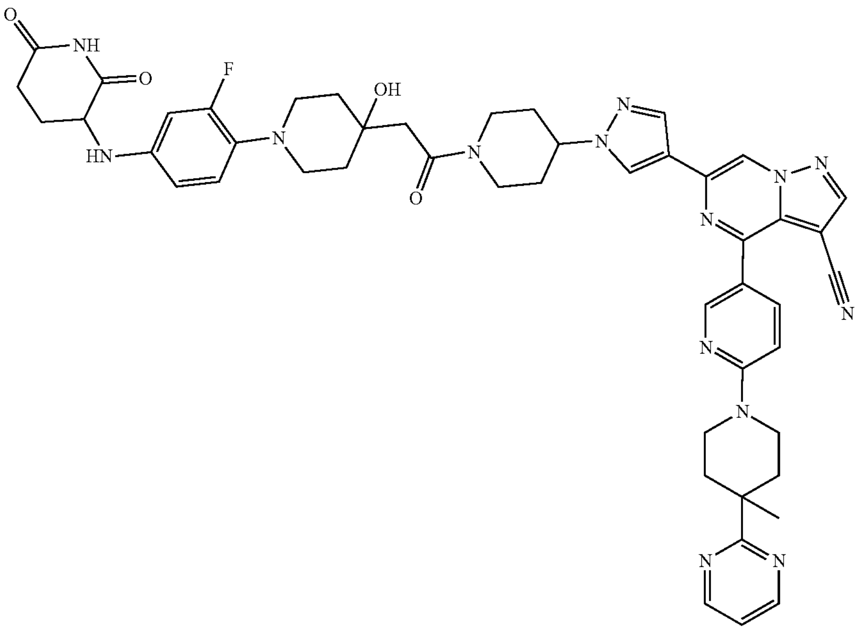 [SMILES: CC1(c2ncccn2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 105 | 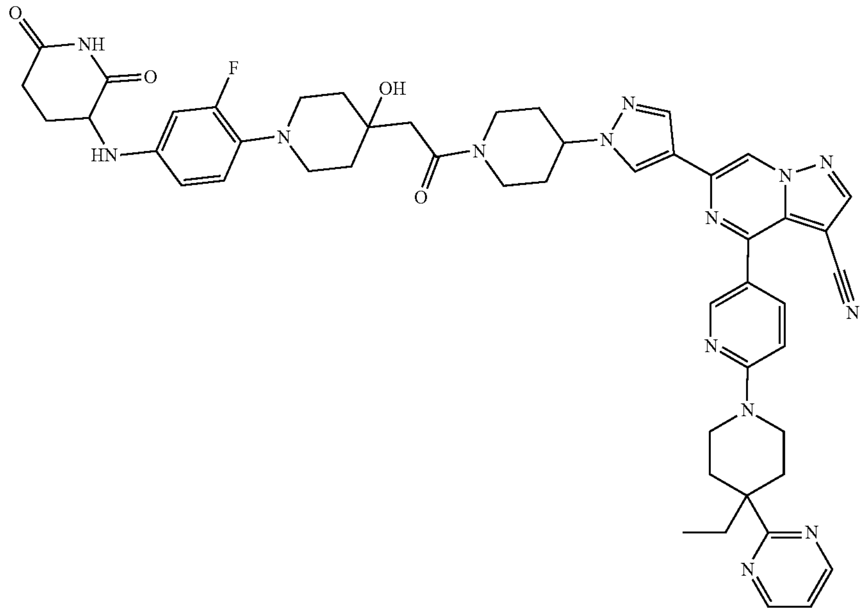 [SMILES: CCC1(c2ncccn2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] |
| 106 | 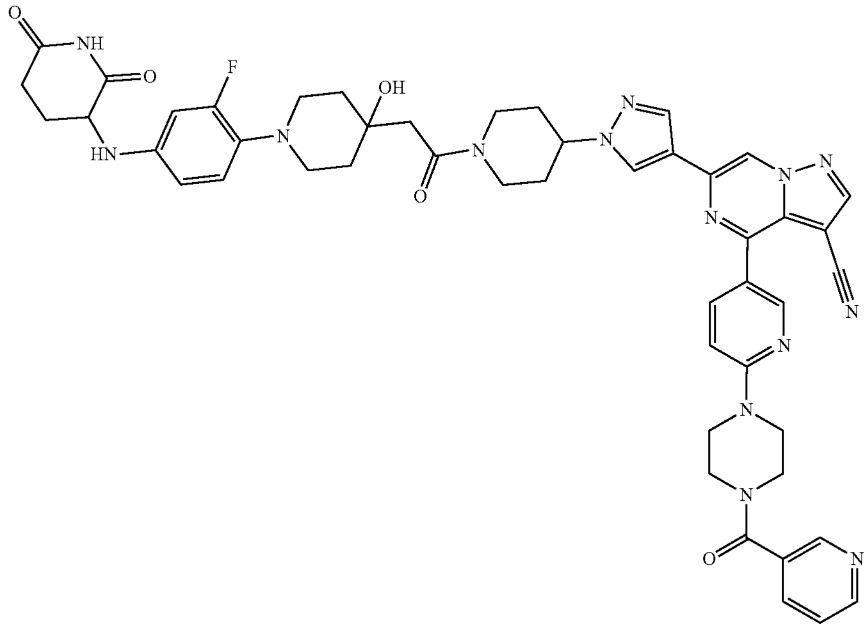 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCN(C(=O)c5cccnc5)CC4)nc3)c12] |

TABLE 1B-continued
| Biological Data | |
|---|---|
| Cmpd # | Structure |
| 107 | 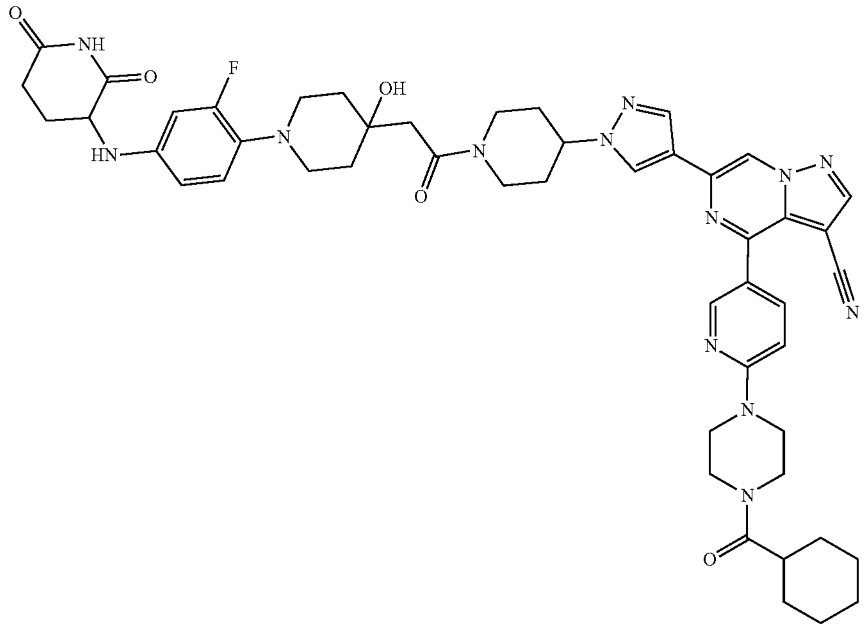 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCN(C(=O)C5CCCCC5)CC4)nc3)c12] |
| 108 | 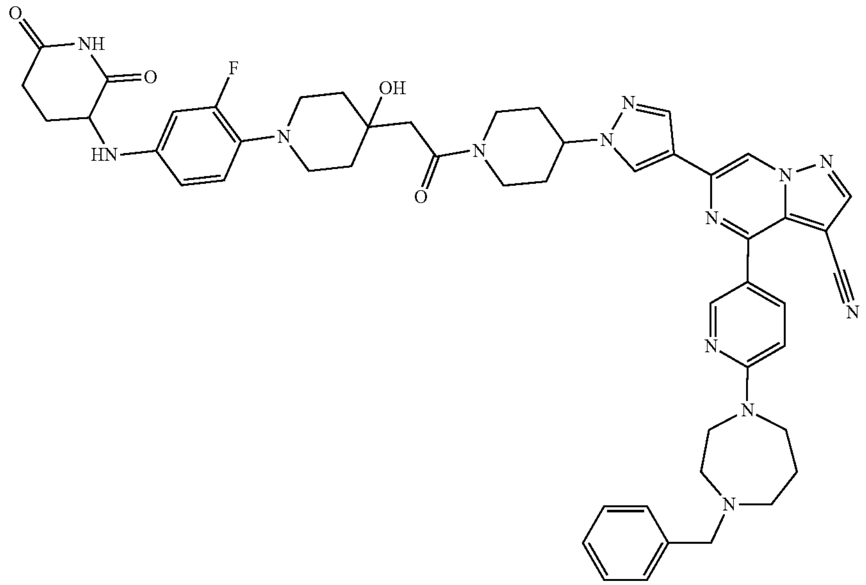 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCCN(Cc5ccccc5)CC4)nc3)c12] |

TABLE 1B-continued
| Biological Data | |
|---|---|
| Cmpd # | Structure |
| 109 | 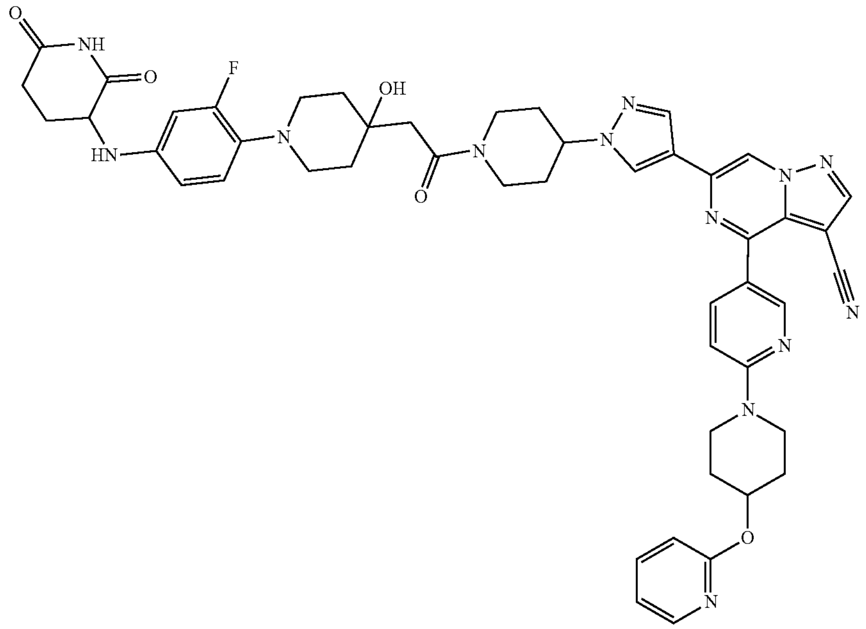 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC(Oc5ccccn5)CC4)nc3)c12] |
| 110 | 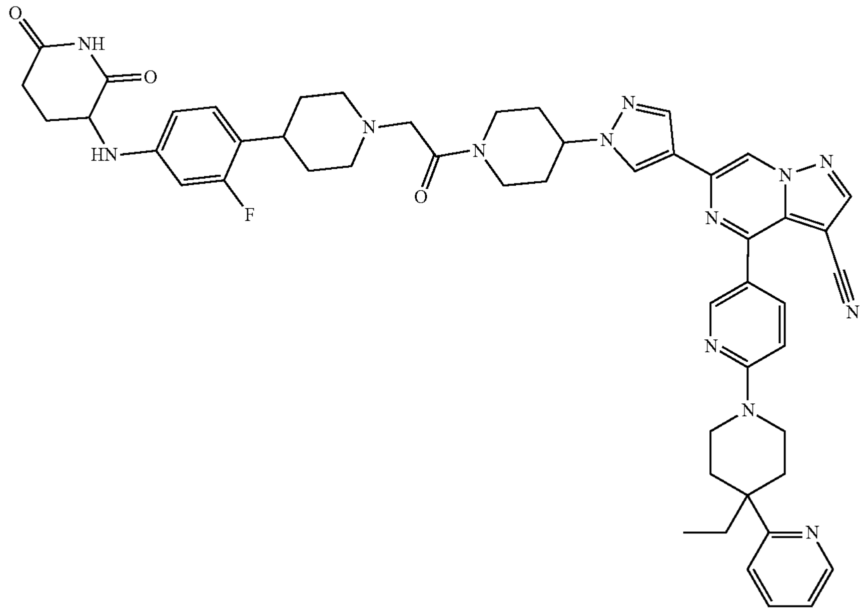 [SMILES: CCC1(c2ccccn2)CCN(c2ccc(-c3nc(-c4cnn(C5CCN(C(=O)CN6CCC(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 111 | 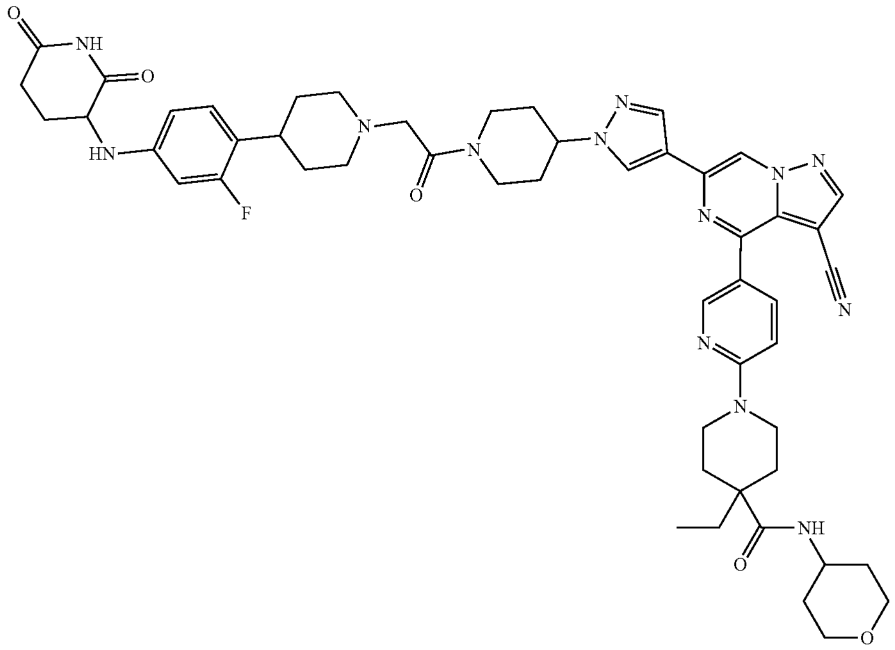 [SMILES: CCC1(C(=O)NC2CCOCC2)CCN(c2ccc(-c3nc(-c4cnn(C5CCN(C(=O)CN6CCC(c7ccc(NC8CCC(=O)NC8=O)cc7F)CC6)CC5)c4)cn4ncc(C#N)c34)cn2)CC1] |
| 112 | 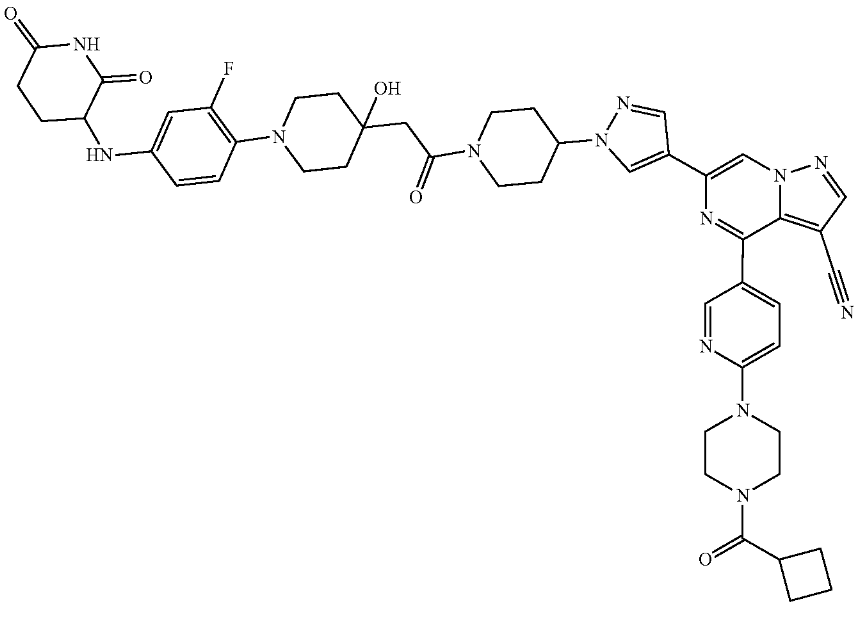 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCN(C(=O)C5CCC5)CC4)nc3)c12] |

TABLE 1B-continued
| Biological Data | |
|---|---|
| Cmpd # | Structure |
| 113 | 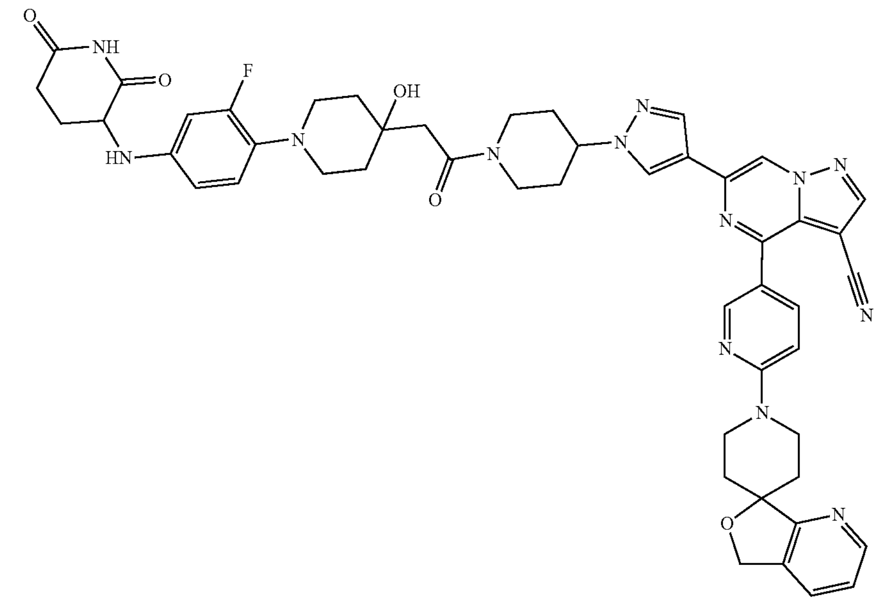 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC5(CC4)OCc4cccnc45)nc3)c12] |
| 114 | 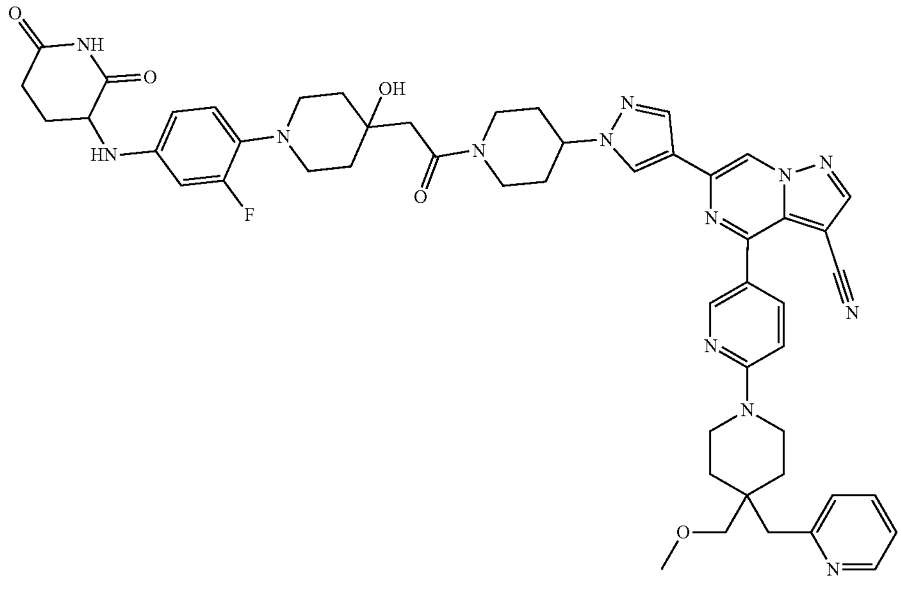 [SMILES: COCC1(Cc2ccccn2)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 115 | 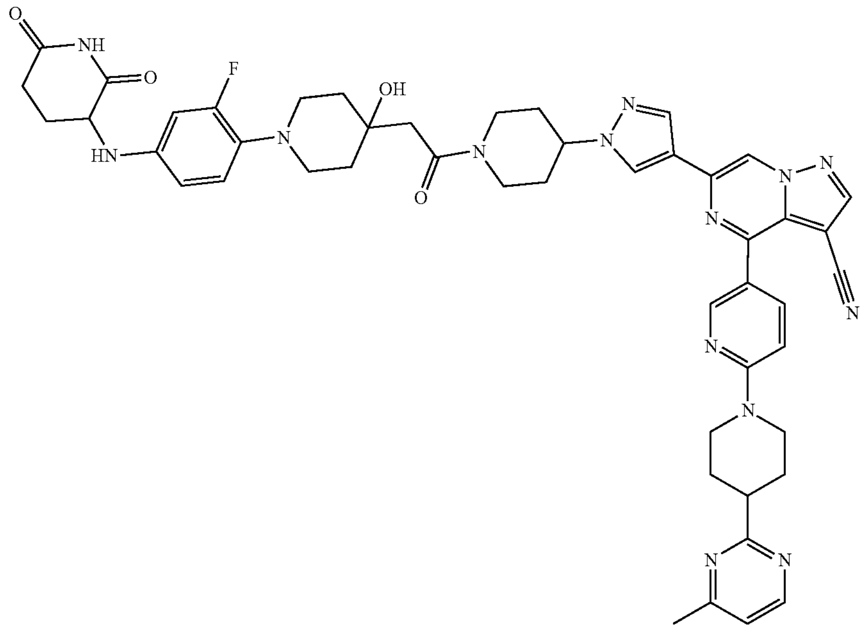 [SMILES: Cc1ccnc(C2CCN(c3ccc(-c4nc(-c5cnn(C6CCN(C(=O)CC7(O)CCN(c8ccc(NC9CCC(=O)NC9=O)cc8F)CC7)CC6)c5)cn5ncc(C#N)c45)cn3)CC2)n1] |
| 116 | 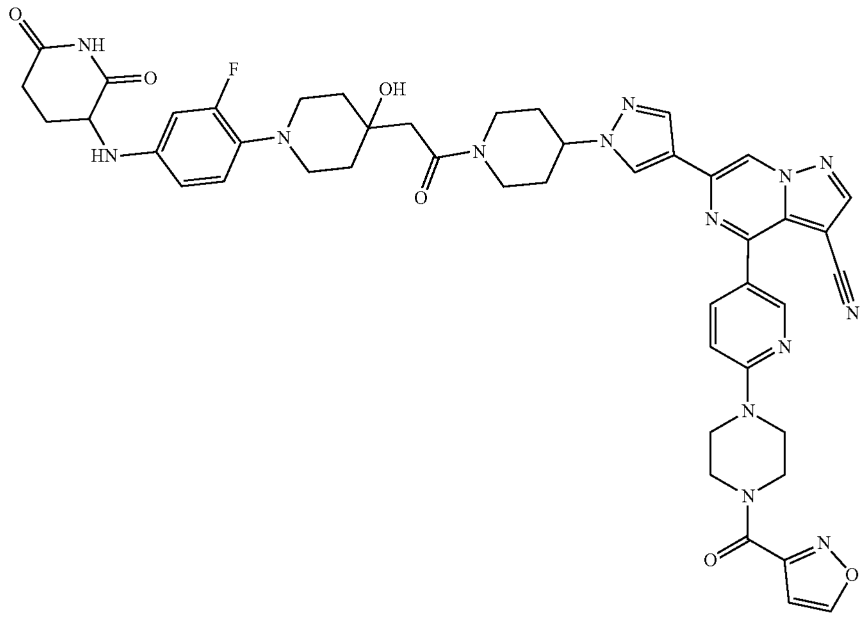 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCN(C(=O)c5ccon5)CC4)nc3)c12] |

TABLE 1B-continued
| Biological Data | |
|---|---|
| Cmpd # | Structure |
| 117 | 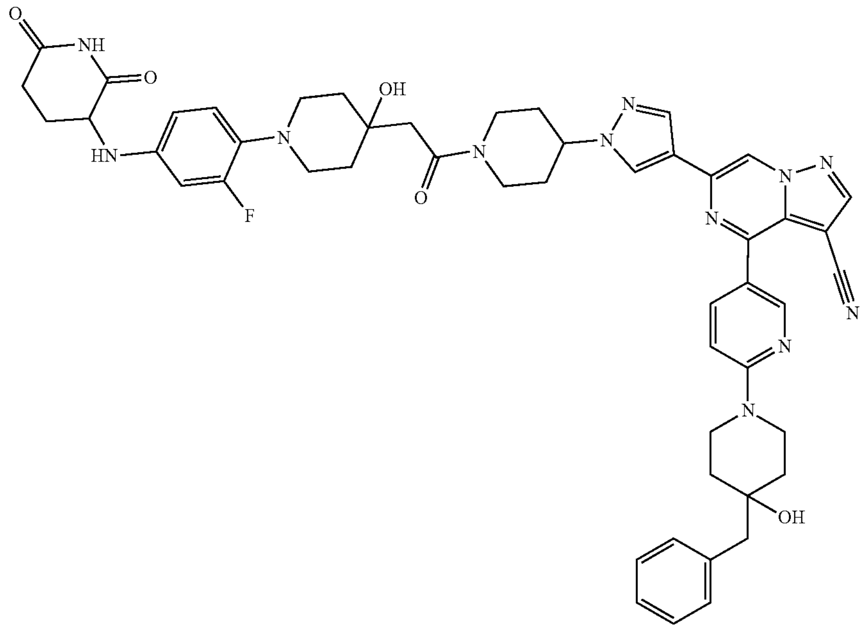 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC(O)(Cc5ccccc5)CC4)nc3)c12] |
| 118 | 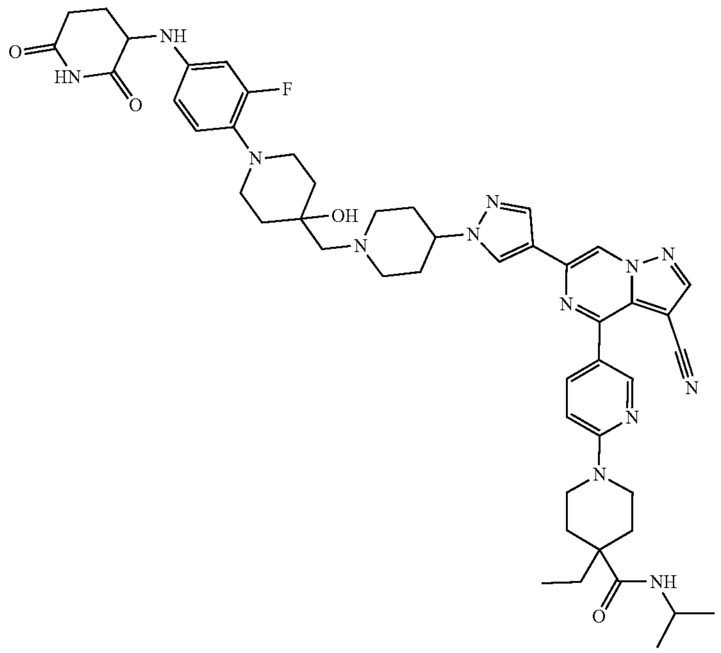 [SMILES: CCC1(C(=O)NC(C)C)CCN(c2ccc(-c3nc(-c4cnn(C5CCN(CC6(O)CCN(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 119 | 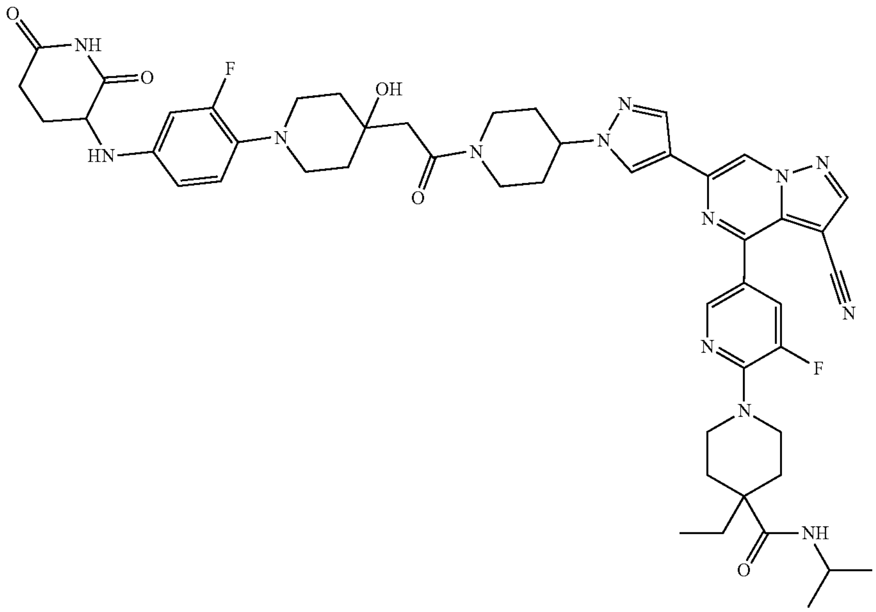 [SMILES: CCC1(C(=O)NC(C)C)CCN(c2ncc(-c3nc(-c4cnn(C5CCN(C(=O)CC6(O)CCN(c7ccc(NC8CCC(=O)NC8=O)cc7F)CC6)CC5)c4)cn4ncc(C#N)c34)cc2F)CC1] |
| 120 | 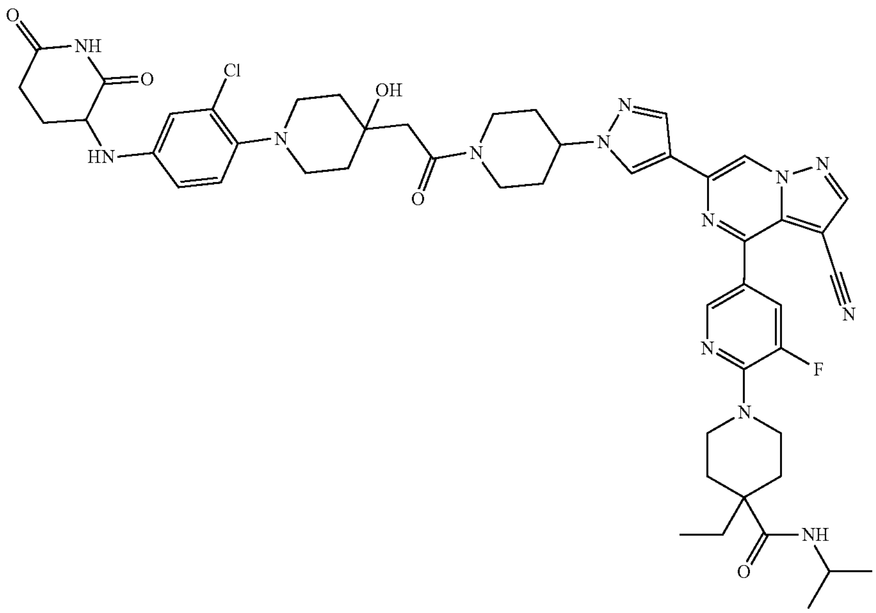 [SMILES: CCC1(C(=O)NC(C)C)CCN(c2ncc(-c3nc(-c4cnn(C5CCN(C(=O)CC6(O)CCN(c7ccc(NC8CCC(=O)NC8=O)cc7Cl)CC6)CC5)c4)cn4ncc(C#N)c34)cc2F)CC1] |

TABLE 1B-continued
| Biological Data | |
| --- | --- |
| Cmpd # | Structure |
| 121 | 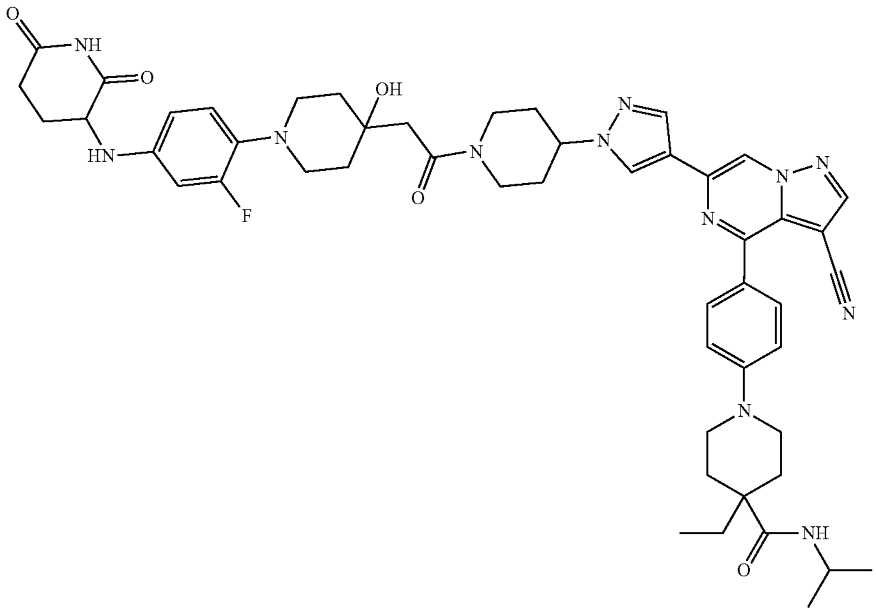 [SMILES: CCC1(C(=O)NC(C)C)CCN(c2ccc(-c3nc(-c4cnn(C5CCN(C(=O)CC6(O)CCN(c7ccc(NC8CCC(=O)NC8=O)cc7F)CC6)CC5)c4)cn4ncc(C#N)c34)cc2)CC1] |
| 122 | 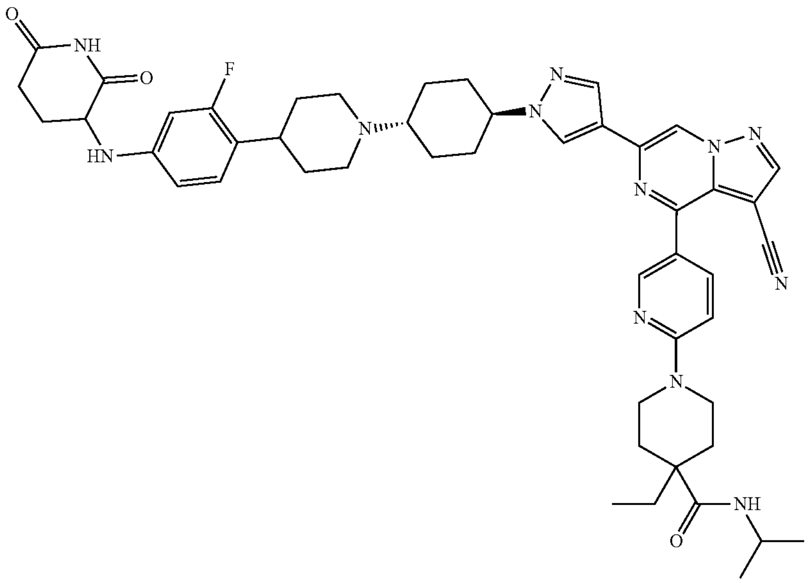 [SMILES: CCC1(C(=O)NC(C)C)CCN(c2ccc(-c3nc(-c4cnn([C@H]5CC[C@H](N6CCC(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 123 | 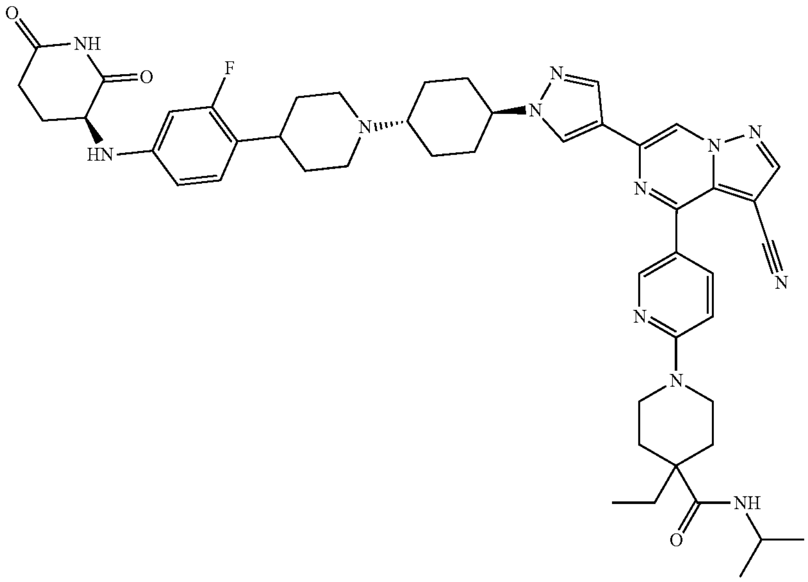 [SMILES: CCC1(C(=O)NC(C)C)CCN(c2ccc(-c3nc(-c4cnn([C@H]5CC[C@H](N6CCC(c7ccc(N[C@H]8CCC(=O)NC8=O)cc7F)CC6)CC5)c4)cn4ncc(C#N)c34)cn2)CC1] |
| 124 | 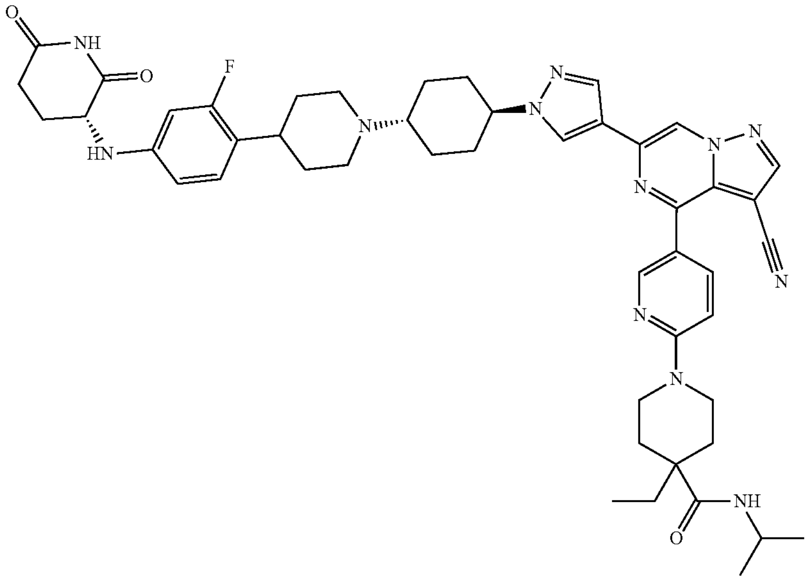 [SMILES: CCC1(C(=O)NC(C)C)CCN(c2ccc(-c3nc(-c4cnn([C@H]5CC[C@H](N6CCC(c7ccc(N[C@@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 125 | 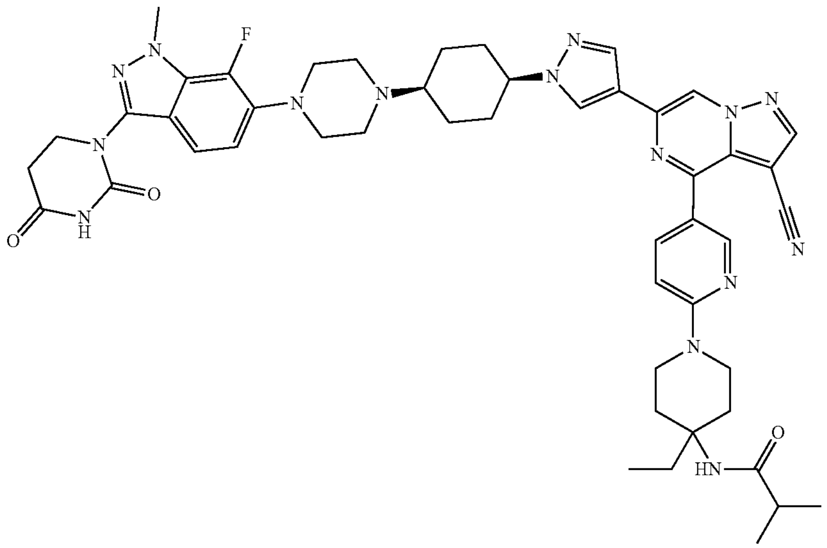 [SMILES: CCC1(NC(=O)C(C)C)CCN(c2ccc(-c3nc(-c4cnn([C@H]5CC[C@@H](N6CCN(c7ccc8c(N9CCC(=O)NC9=O)nn(C)c8c7F)CC6)CC5)c4)cn4ncc(C#N)c34)cn2)CC1] |
| 126 | 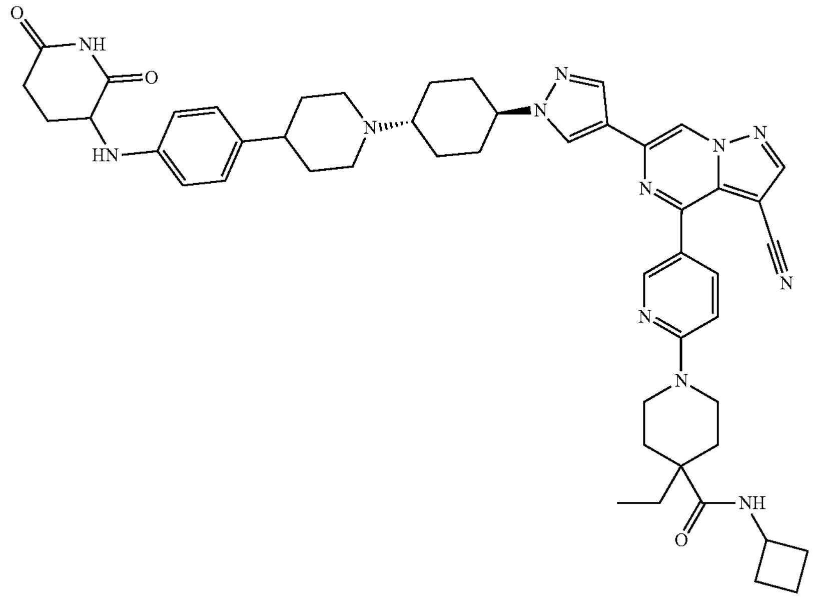 [SMILES: CCC1(C(=O)NC2CCC2)CCN(c2ccc(-c3nc(-c4cnn([C@H]5CC[C@H](N6CCC(c7ccc(NC8CCC(=O)NC8=O)cc7)CC6)CC5)c4)cn4ncc(C#N)c34)cn2)CC1] |

TABLE 1B-continued
| Biological Data | |
|---|---|
| Cmpd # | Structure |
| 127 | 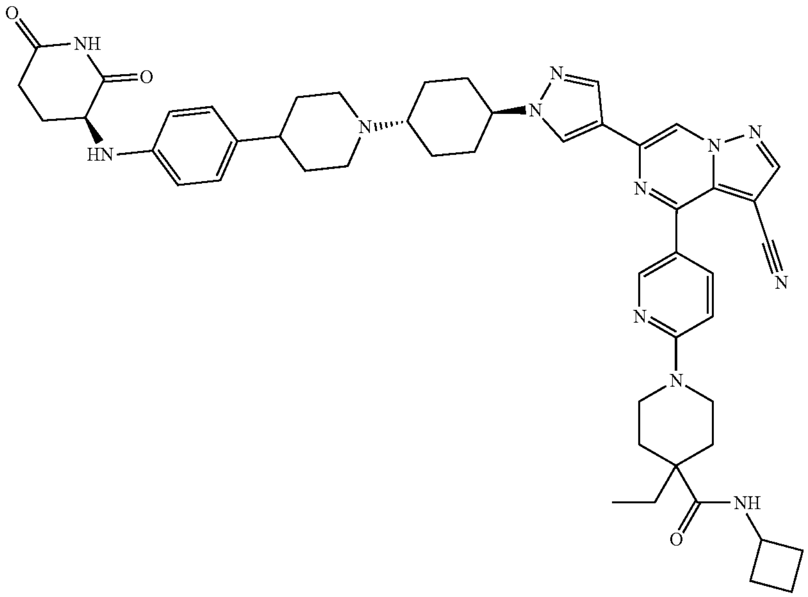 [SMILES: CCC1(C(=O)NC2CCC2)CCN(c2ccc(-c3nc(-c4cnn([C@H]5CC[C@H](N6CCC(c7ccc(N[C@H]8CCC(=O)NC8=O)cc7)CC6)CC5)c4)cn4ncc(C#N)c34)cn2)CC1] |
| 128 | 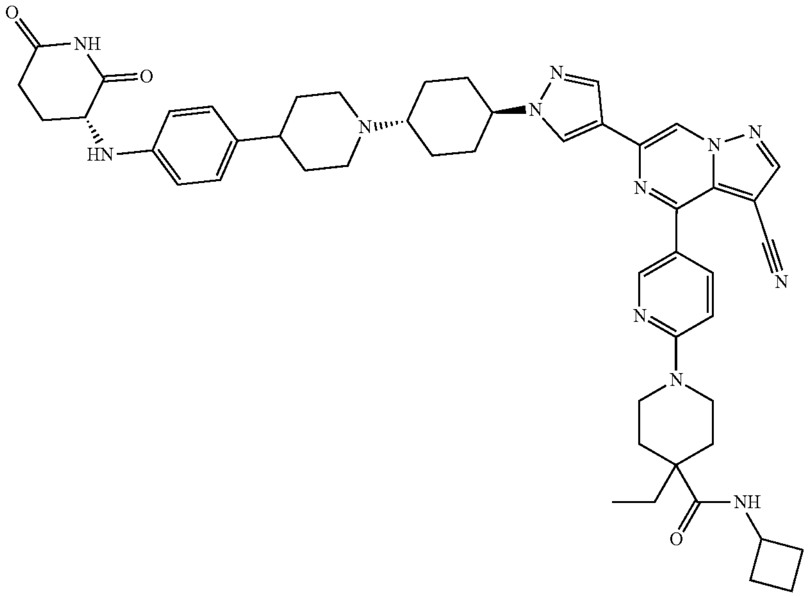 [SMILES: CCC1(C(=O)NC2CCC2)CCN(c2ccc(-c3nc(-c4cnn([C@H]5CC[C@H](N6CCC(c7ccc(N[C@@H]8CCC(=O)NC8=O)cc7)CC6)CC5)c4)cn4ncc(C#N)c34)cn2)CC1] |

TABLE 1B-continued
| Biological Data | |
|---|---|
| Cmpd # | Structure |
| 129 | 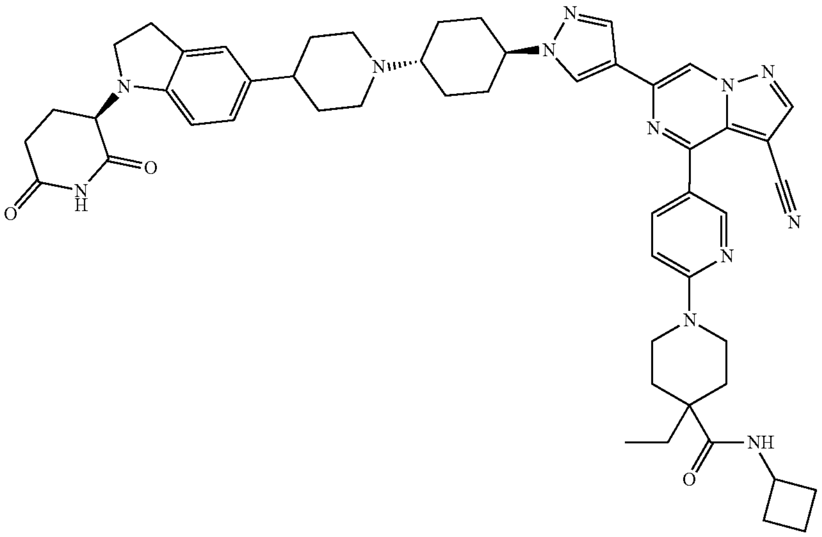 [SMILES: CCC1(C(=O)NC2CCC2)CCN(c2ccc(-c3nc(-c4cnn([C@H]5CC[C@H](N6CCC(c7ccc8c(c7)CCN8[C@@H]7CCC(=O)NC7=O)CC6)CC5)c4)cn4ncc(C#N)c34)cn2)CC1] |
| 130 | 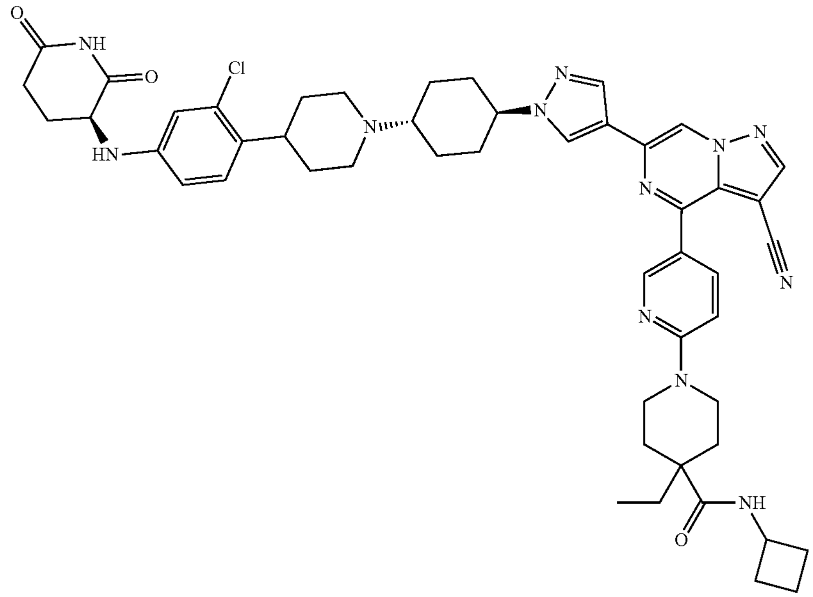 [SMILES: CCC1(C(=O)NC2CCC2)CCN(c2ccc(-c3nc(-c4cnn([C@H]5CC[C@H](N6CCC(c7ccc(N[C@H]8CCC(=O)NC8=O)cc7Cl)CC6)CC5)c4)cn4ncc(C#N)c34)cn2)CC1] |

TABLE 1B-continued
| Biological Data | |
|---|---|
| Cmpd # | Structure |
| 131 | 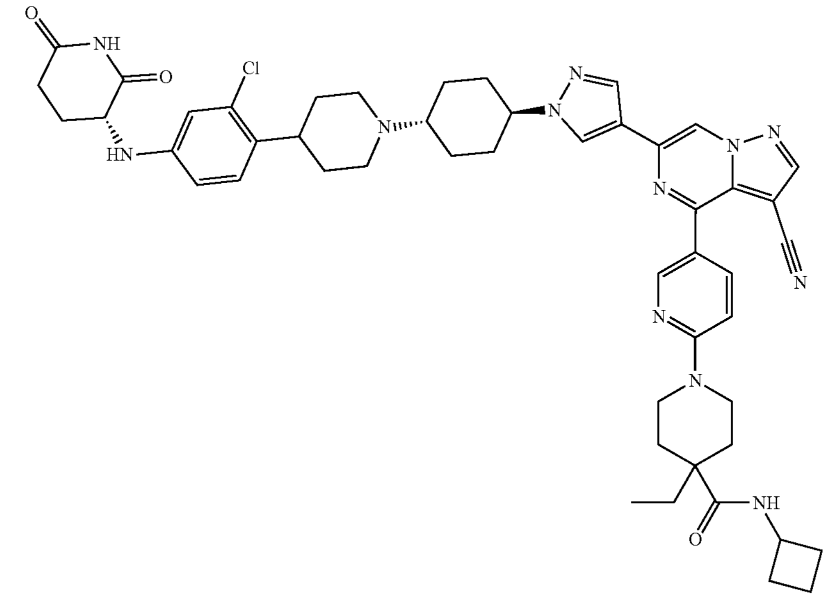 [SMILES: CCC1(C(=O)NC2CCC2)CCN(c2ccc(-c3nc(-c4cnn([C@H]5CC[C@H](N6CCC(c7ccc(N[C@@H]8CCC(=O)NC8=O)cc7Cl)CC6)CC5)c4)cn4ncc(C#N)c34)cn2)CC1] |
| 132 | 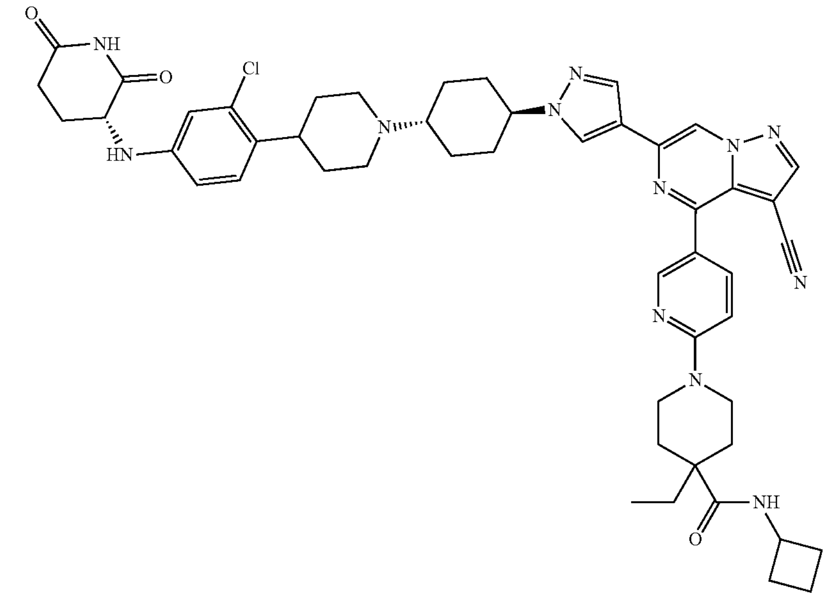 [SMILES: CCC1(C(=O)NC2CCC2)CCN(c2ccc(-c3nc(-c4cnn([C@H]5CC[C@H](N6CCC(c7ccc(N[C@@H]8CCC(=O)NC8=O)cc7Cl)CC6)CC5)c4)cn4ncc(C#N)c34)cn2)CC1] |

TABLE 1B-continued
| Biological Data | |
|---|---|
| Cmpd # | Structure |
| 133 | 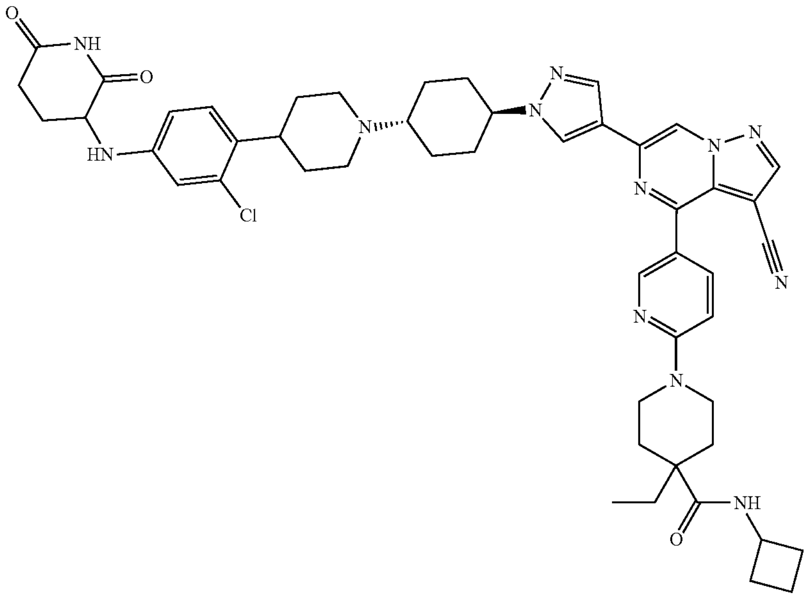 [SMILES: CCC1(C(=O)NC2CCC2)CCN(c2ccc(-c3nc(-c4cnn([C@H]5CC[C@H](N6CCC(c7ccc(NC8CCC(=O)NC8=O)cc7Cl)CC6)CC5)c4)cn4ncc(C#N)c34)cn2)CC1] |
| 134 | 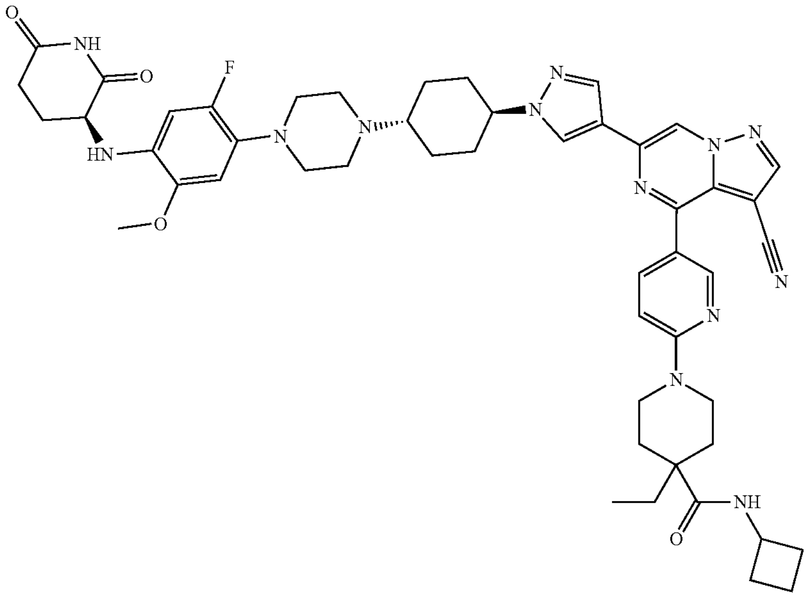 [SMILES: CCC1(C(=O)NC2CCC2)CCN(c2ccc(-c3nc(-c4cnn([C@H]5CC[C@H](N6CCN(c7cc(OC)c(N[C@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 135 | 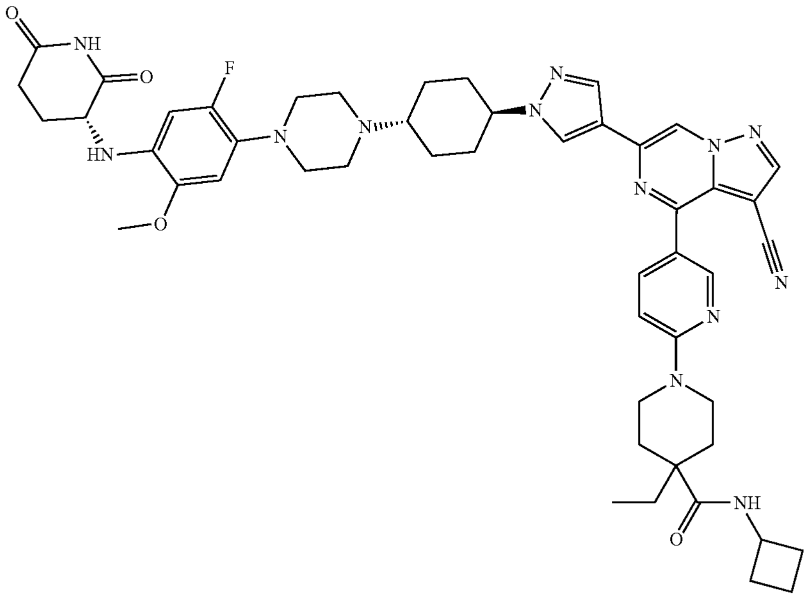 [SMILES: CCC1(C(=O)NC2CCC2)CCN(c2ccc(-c3nc(-c4cnn([C@H]5CC[C@H](N6CCN(c7cc(OC)c(N[C@@H]8CCC(=O)NC8=O)cc7F)CC6)CC5)c4)cn4ncc(C#N)c34)cn2)CC1] |
| 136 | 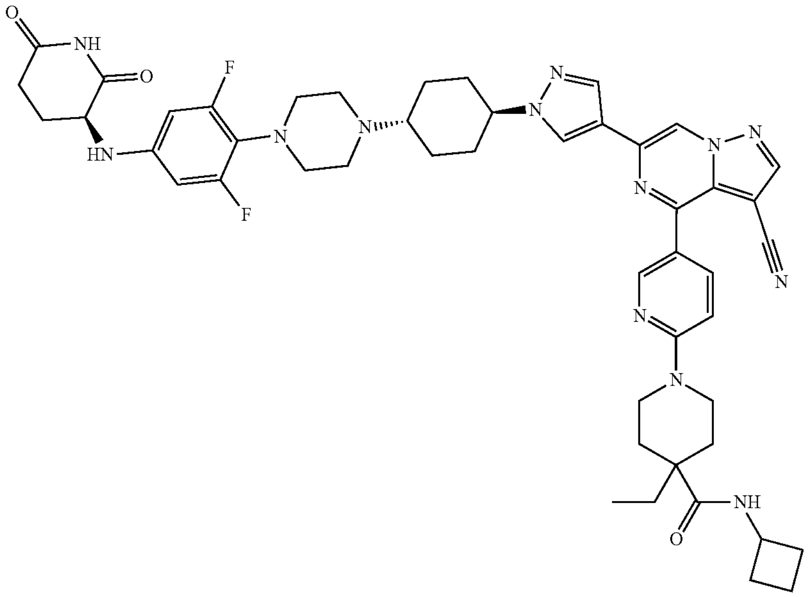 [SMILES: CCC1(C(=O)NC2CCC2)CCN(c2ccc(-c3nc(-c4cnn([C@H]5CC[C@H](N6CCN(c7c(F)cc(N[C@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 137 | 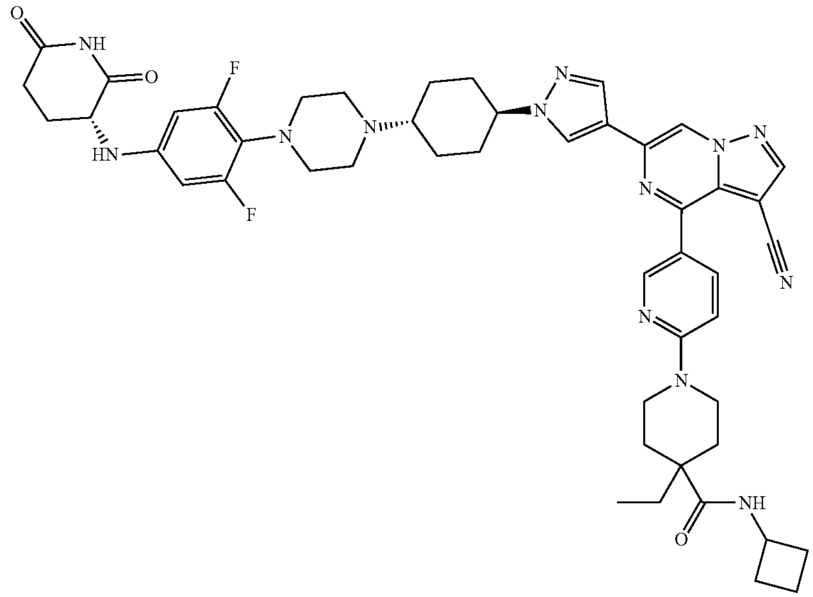 [SMILES: CCC1(C(=O)NC2CCC2)CCN(c2ccc(-c3nc(-c4cnn([C@H]5CC[C@H](N6CCN(c7c(F)cc(N[C@@H]8CCC(=O)NC8=O)cc7F)CC6)CC5)c4)cn4ncc(C#N)c34)cn2)CC1] |
| 138 | 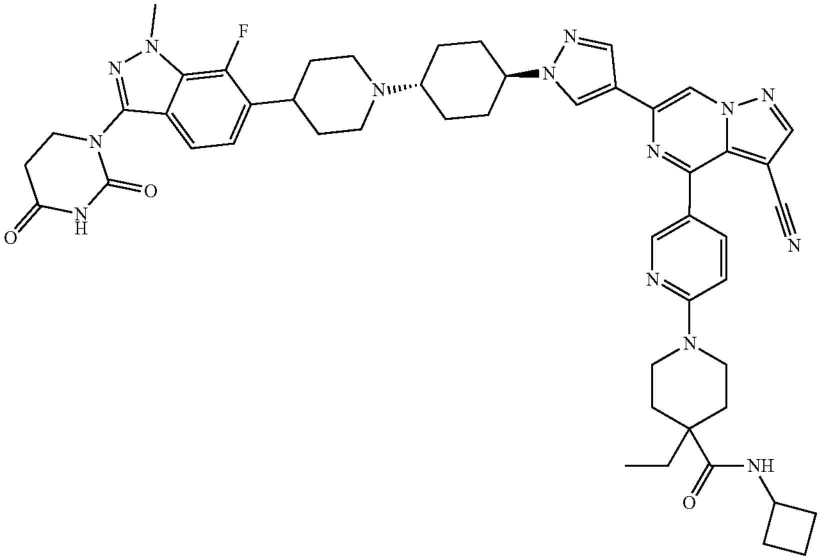 [SMILES: CCC1(C(=O)NC2CCC2)CCN(c2ccc(-c3nc(-c4cnn([C@H]5CC[C@H](N6CCC(c7ccc8c(N9CCC(=O)NC9=O)nn(C)c8c7F)CC6)CC5)c4)cn4ncc(C#N)c34)cn2)CC1] |

TABLE 1B-continued
| Biological Data | |
|---|---|
| Cmpd # | Structure |
| 139 | 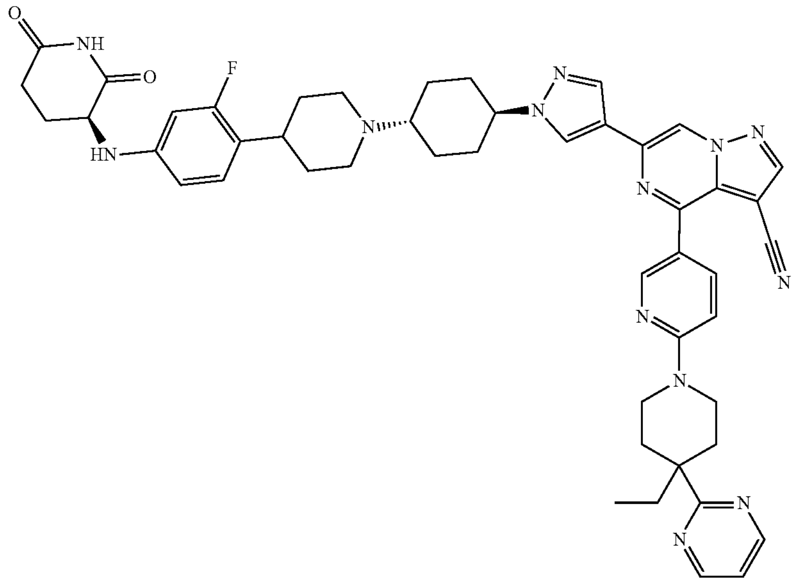 [SMILES: CCC1(c2ncccn2)CCN(c2ccc(-c3nc(-c4cnn([C@H]5CC[C@H](N6CCC(c7ccc(N[C@H]8CCC(=O)NC8=O)cc7F)CC6)CC5)c4)cn4ncc(C#N)c34)cn2)CC1] |
| 140 | 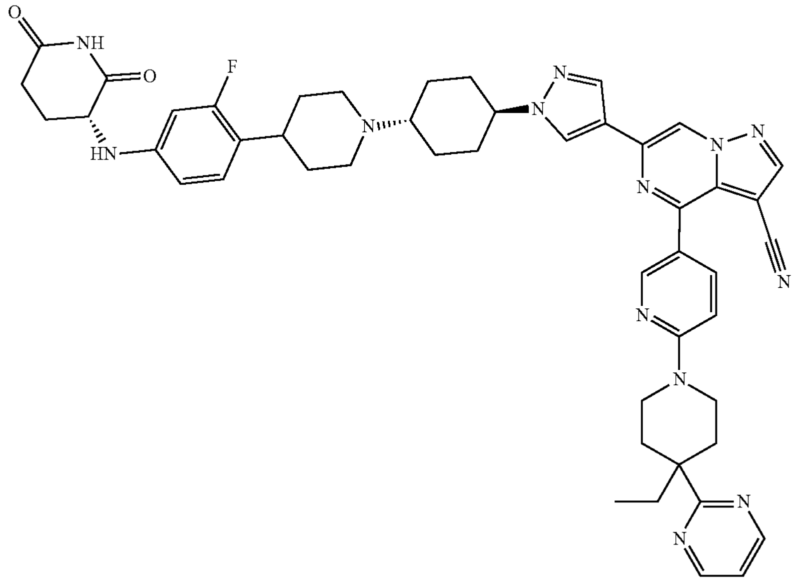 [SMILES: CCC1(c2ncccn2)CCN(c2ccc(-c3nc(-c4cnn([C@H]5CC[C@H](N6CCC(c7ccc(N[C@@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 141 | 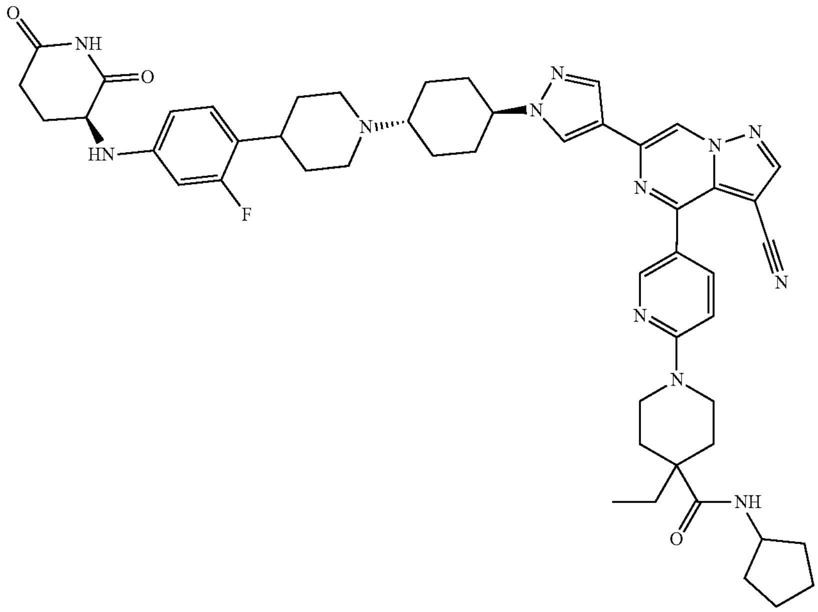 [SMILES: CCC1(C(=O)NC2CCCC2)CCN(c2ccc(-c3nc(-c4cnn([C@H]5CC[C@H](N6CCC(c7ccc(N[C@H]8CCC(=O)NC8=O)cc7F)CC6)CC5)c4)cn4ncc(C#N)c34)cn2)CC1] |
| 142 | 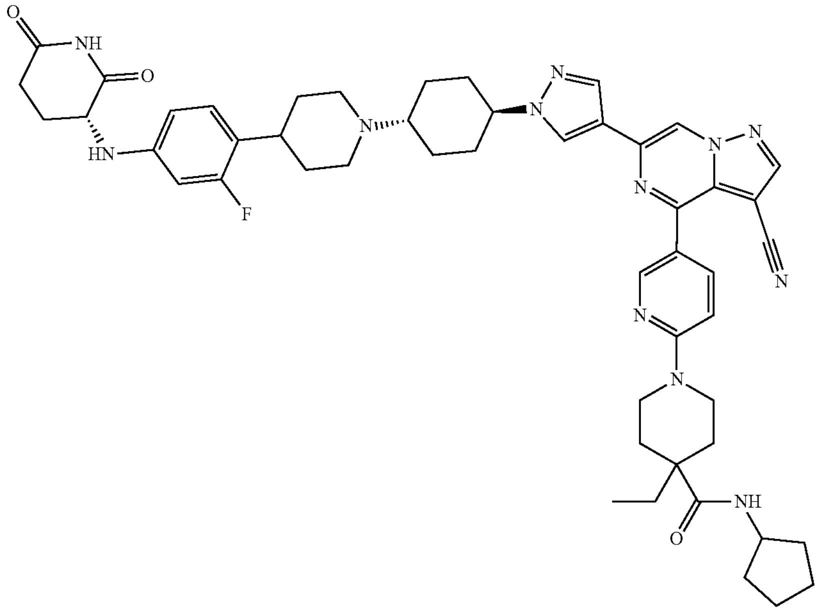 [SMILES: CCC1(C(=O)NC2CCCC2)CCN(c2ccc(-c3nc(-c4cnn([C@H]5CC[C@H](N6CCC(c7ccc(N[C@@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 143 | 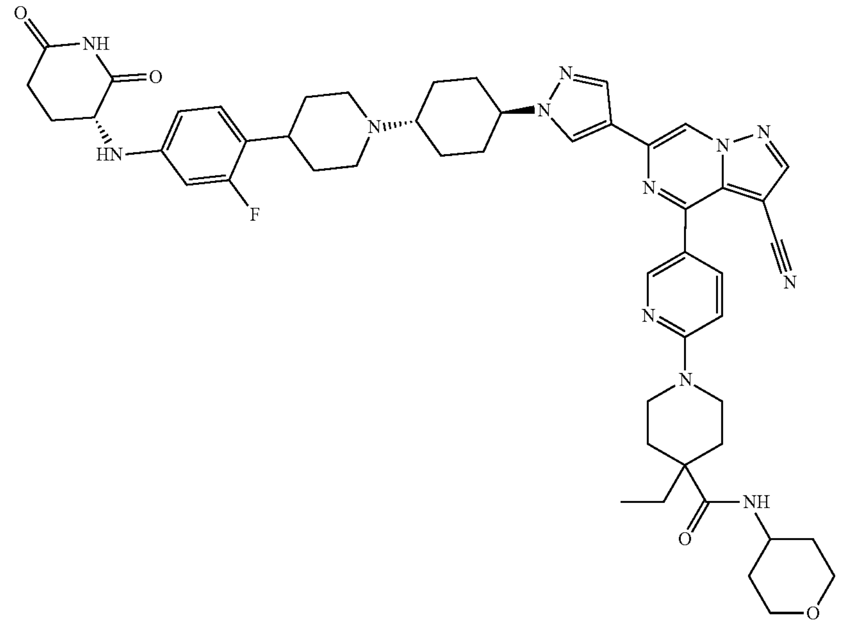 [SMILES: CCC1(C(=O)NC2CCOCC2)CCN(c2ccc(-c3nc(-c4cnn([C@H]5CC[C@H](N6CCC(c7ccc(N[C@@H]8CCC(=O)NC8=O)cc7F)CC6)CC5)c4)cn4ncc(C#N)c34)cn2)CC1] |
| 144 | 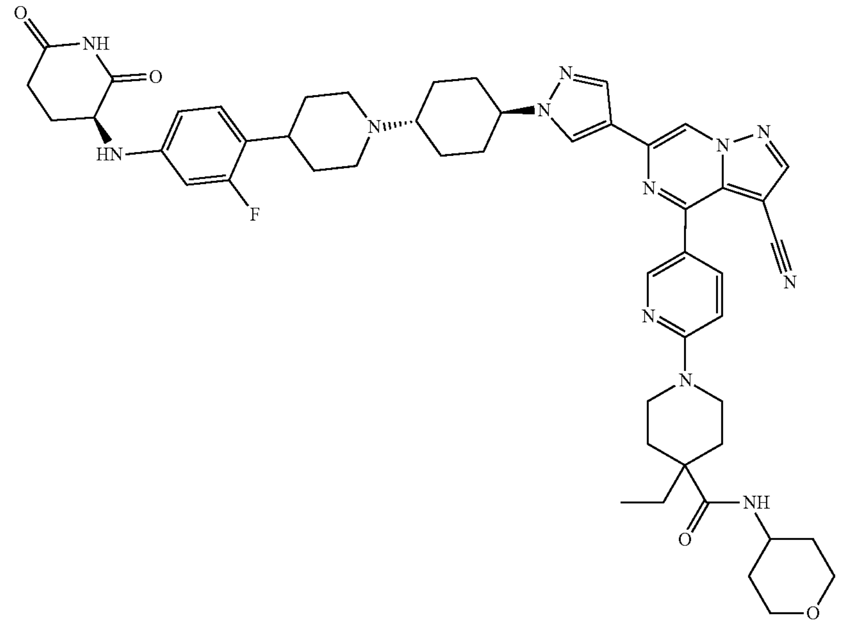 [SMILES: CCC1(C(=O)NC2CCOCC2)CCN(c2ccc(-c3nc(-c4cnn([C@H]5CC[C@H](N6CCC(c7ccc(N[C@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 145 | 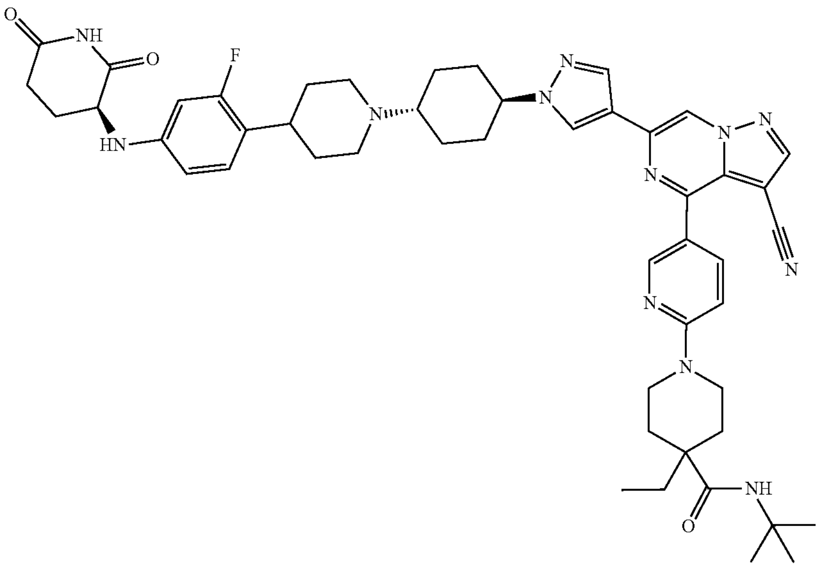 [SMILES: CCC1(C(=O)NC(C)(C)C)CCN(c2ccc(-c3nc(-c4cnn([C@H]5CC[C@H](N6CCC(c7ccc(N[C@H]8CCC(=O)NC8=O)cc7F)CC6)CC5)c4)cn4ncc(C#N)c34)cn2)CC1] |
| 146 | 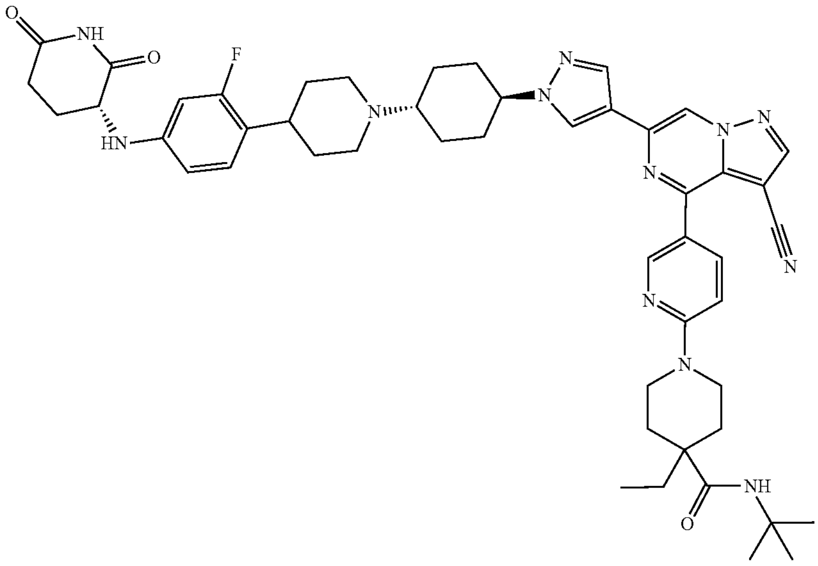 [SMILES: CCC1(C(=O)NC(C)(C)C)CCN(c2ccc(-c3nc(-c4cnn([C@H]5CC[C@H](N6CCC(c7ccc(N[C@@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 147 | 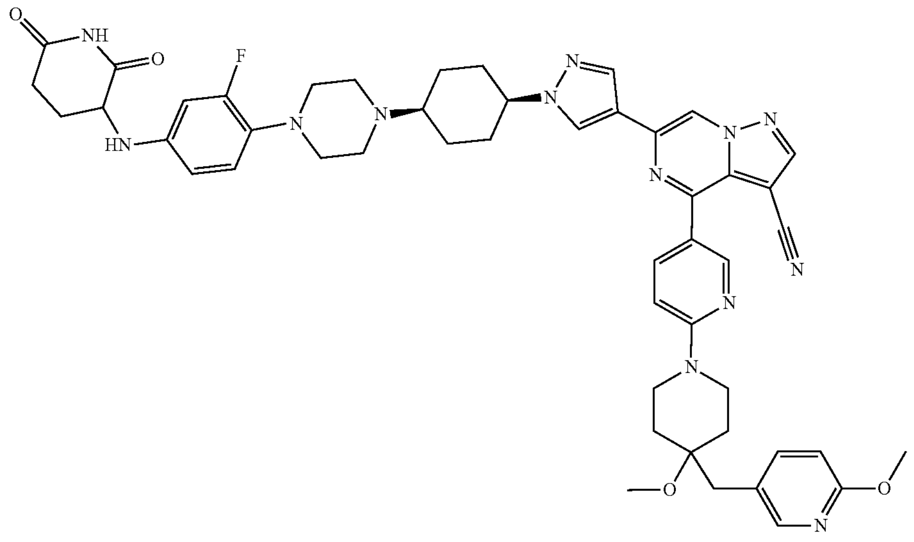 [SMILES: COc1ccc(CC2(OC)CCN(c3ccc(-c4nc(-c5cnn([C@H]6CC[C@@H](N7CCN(c8ccc(NC9CCC(=O)NC9=O)cc8F)CC7)CC6)c5)cn5ncc(C#N)c45)cn3)CC2)cn1] |
| 148 | 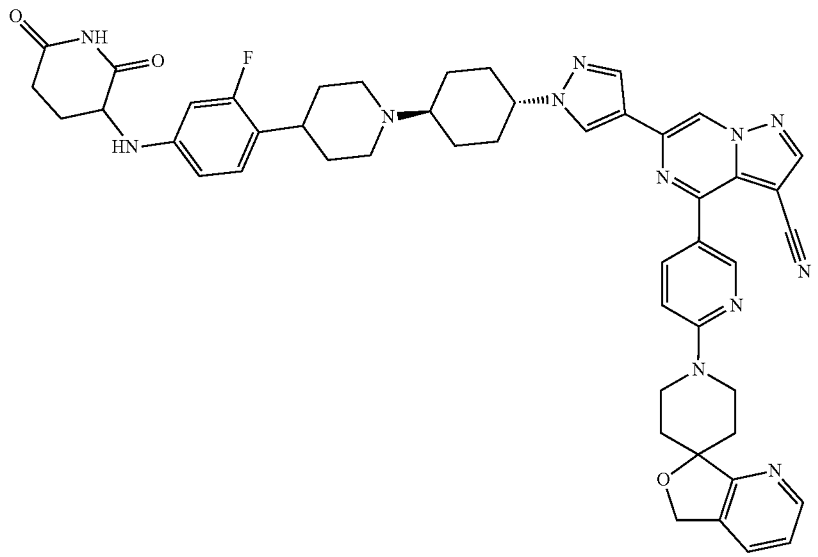 [SMILES: N#Cc1cnn2cc(-c3cnn([C@H]4CC[C@H](N5CCC(c6ccc(NC7CCC(=O)NC7=O)cc6F)CC5)CC4)c3)nc(-c3ccc(N4CCC5(CC4)OCc4cccnc45)nc3)c12] |

TABLE 1B-continued
| Biological Data | |
|---|---|
| Cmpd # | Structure |
| 149 | 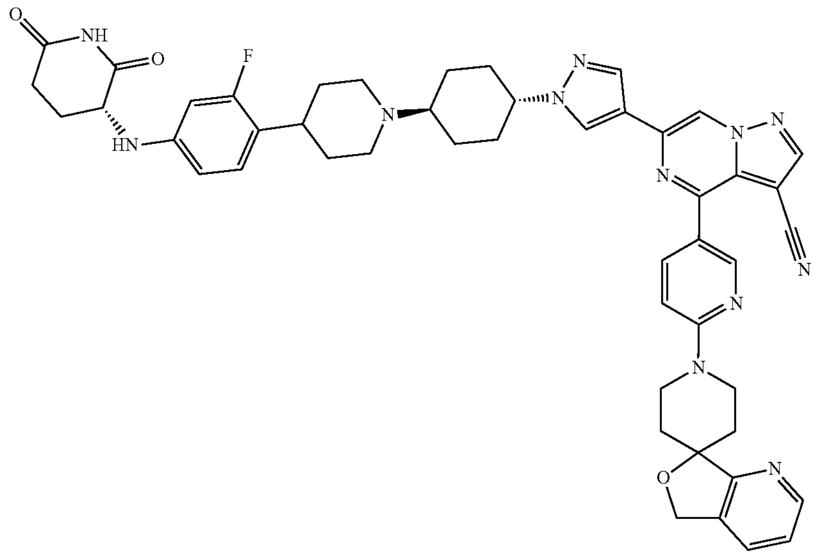 [SMILES: N#Cc1cnn2cc(-c3cnn([C@H]4CC[C@H](N5CCC(c6ccc(N[C@@H]7CCC(=O)NC7=O)cc6F)CC5)CC4)c3)nc(-c3ccc(N4CCC5(CC4)OCc4cccnc45)nc3)c12] |
| 150 | 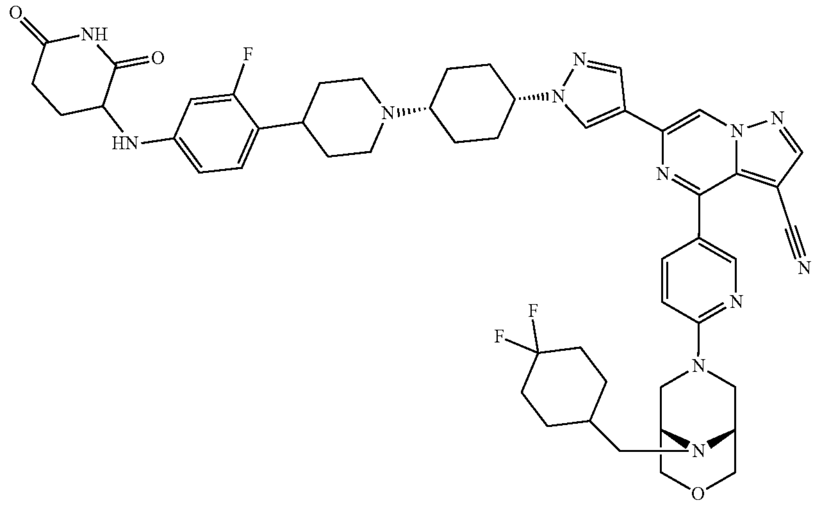 [SMILES: N#Cc1cnn2cc(-c3cnn([C@H]4CC[C@@H](N5CCC(c6ccc(NC7CCC(=O)NC7=O)cc6F)CC5)CC4)c3)nc(-c3ccc(N4C[C@H]5COC[C@@H](C4)N5CC4CCC(F)(F)CC4)nc3)c12] |

TABLE 1B-continued
| Biological Data | |
|---|---|
| Cmpd # | Structure |
| 151 | 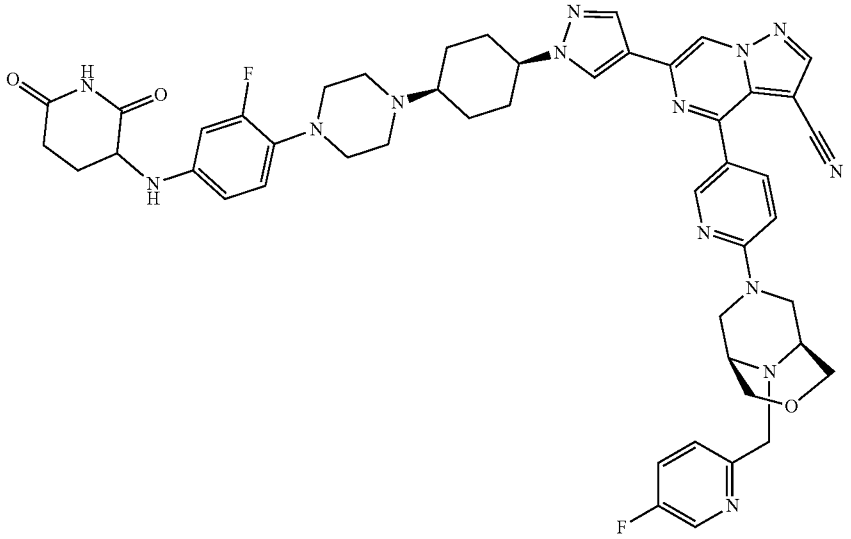 [SMILES: N#Cc1cnn2cc(-c3cnn([C@H]4CC[C@@H](N5CCN(c6ccc(NC7CCC(=O)NC7=O)cc6F)CC5)CC4)c3)nc(-c3ccc(N4C[C@H]5COC[C@@H](C4)N5Cc4ccc(F)cn4)nc3)c12] |
| 152 | 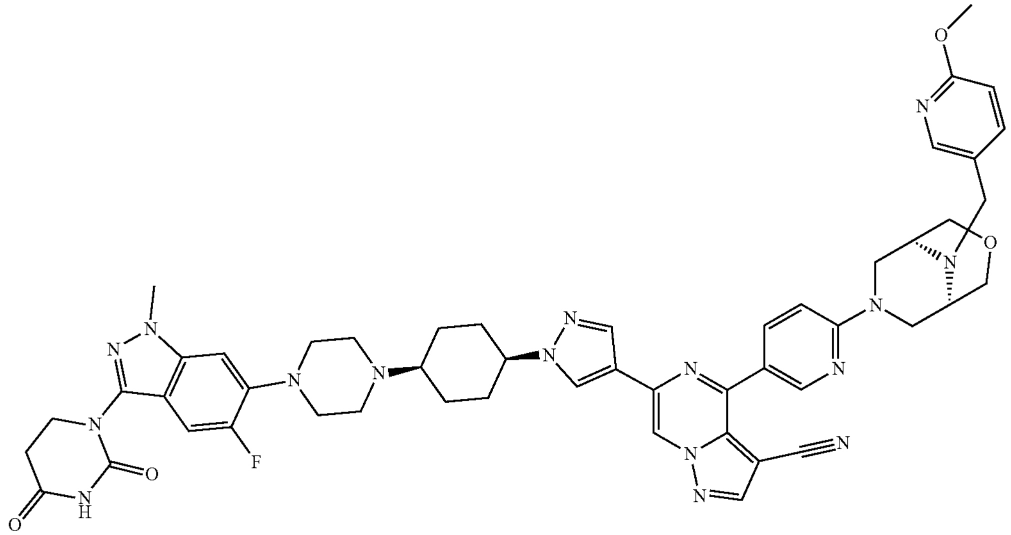 [SMILES: COc1ccc(CN2[C@@H]3COC[C@H]2CN(c2ccc(-c4nc(-c5cnn([C@H]6CC[C@@H](N7CCN(c8cc9c(cc8F)c(N8CCC(=O)NC8=O)nn9C)CC7)CC6)c5)cn5ncc(C#N)c45)cn2)C3)cn1] |
| 153 | 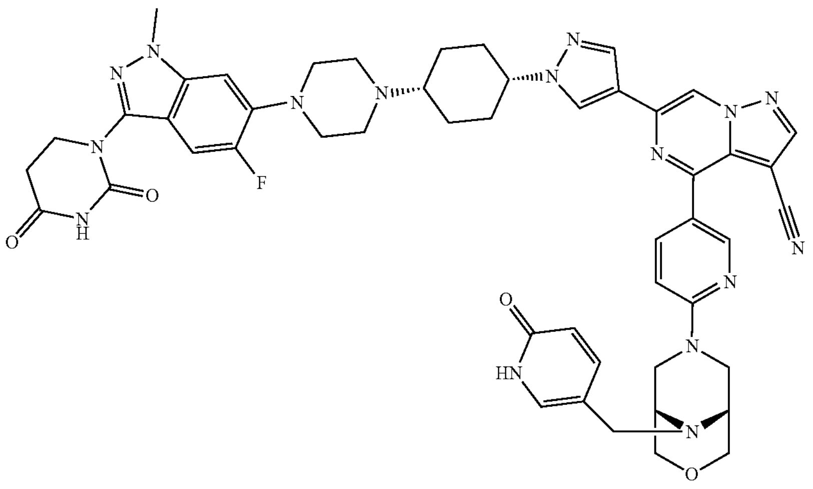 [SMILES: Cn1nc(N2CCC(=O)NC2=O)c2cc(F)c(N3CCN([C@H]4CC[C@@H](n5cc(-c6cn7ncc(C#N)c7c(-c7ccc(N8C[C@H]9COC[C@@H](C8)N9Cc8ccc(=O)[nH]c8)nc7)n6)cn5)CC4)CC3)cc21] |

TABLE 1B-continued
| Biological Data | |
|---|---|
| Cmpd # | Structure |
| 154 | 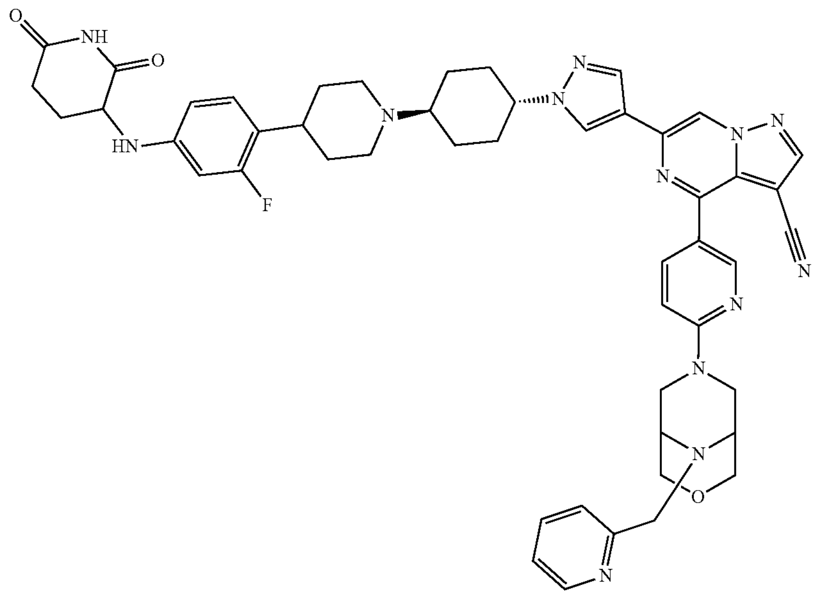 [SMILES: N#Cc1cnn2cc(-c3cnn([C@H]4CC[C@H](N5CCC(c6ccc(NC7CCC(=O)NC7=O)cc6F)CC5)CC4)c3)nc(-c3ccc(N4CC5COCC(C4)N5Cc4ccccn4)nc3)c12] |
| 155 | 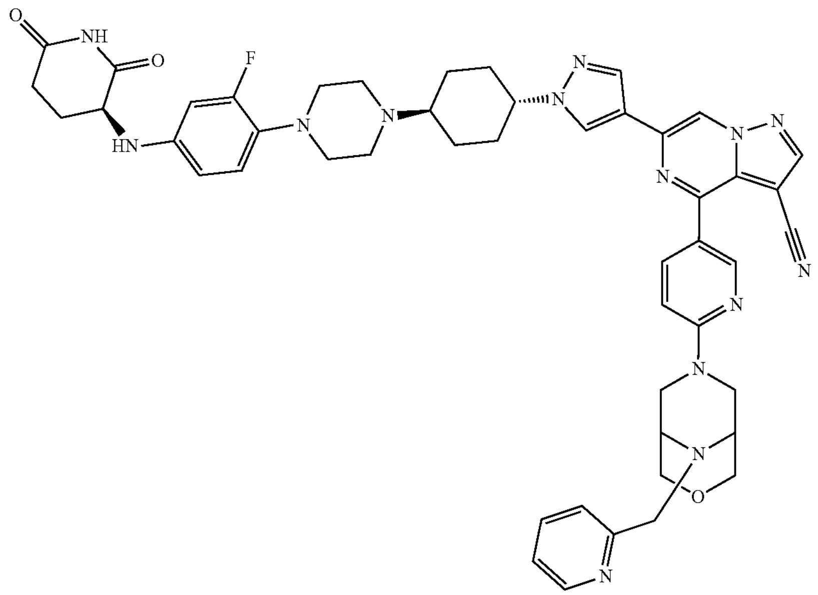 [SMILES: N#Cc1cnn2cc(-c3cnn([C@H]4CC[C@H](N5CCN(c6ccc(N[C@H]7CCC(=O)NC7=O)cc6F)CC5)CC4)c3)nc(-c3ccc(N4CC5COCC(C4)N5Cc4ccccn4)nc3)c12] |

TABLE 1B-continued
| Biological Data | |
|---|---|
| Cmpd # | Structure |
| 156 | 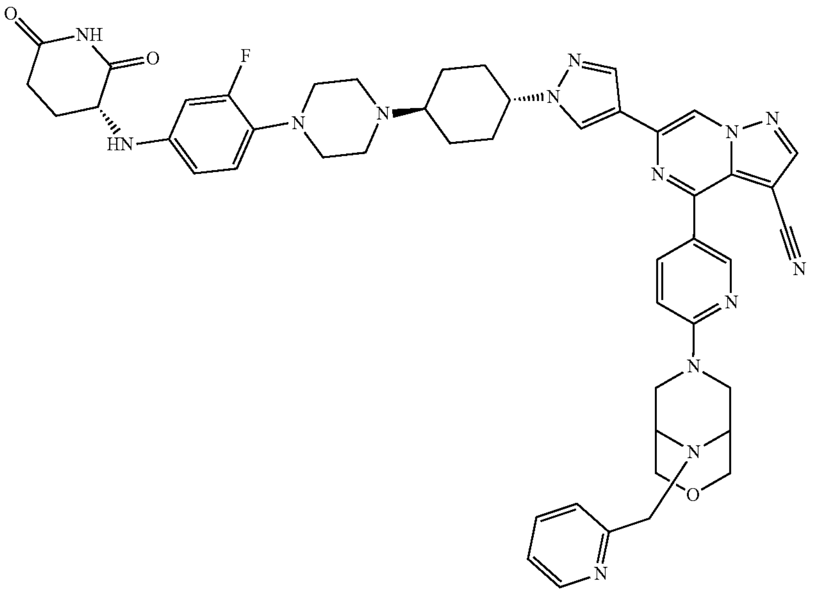 [SMILES: N#Cc1cnn2cc(-c3cnn([C@H]4CC[C@H](N5CCN(c6ccc(N[C@@H]7CCC(=O)NC7=O)cc6F)CC5)CC4)c3)nc(-c3ccc(N4CC5COCC(C4)N5Cc4ccccn4)nc3)c12] |
| 157 | 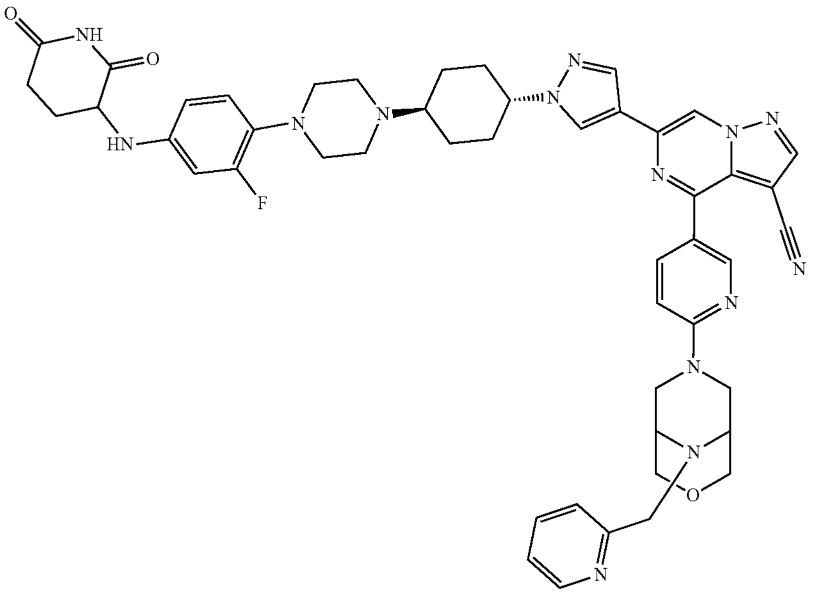 [SMILES: N#Cc1cnn2cc(-c3cnn([C@H]4CC[C@H](N5CCN(c6ccc(NC7CCC(=O)NC7=O)cc6F)CC5)CC4)c3)nc(-c3ccc(N4CC5COCC(C4)N5Cc4ccccn4)nc3)c12] |

TABLE 1B-continued
| Biological Data | |
|---|---|
| Cmpd # | Structure |
| 158 | 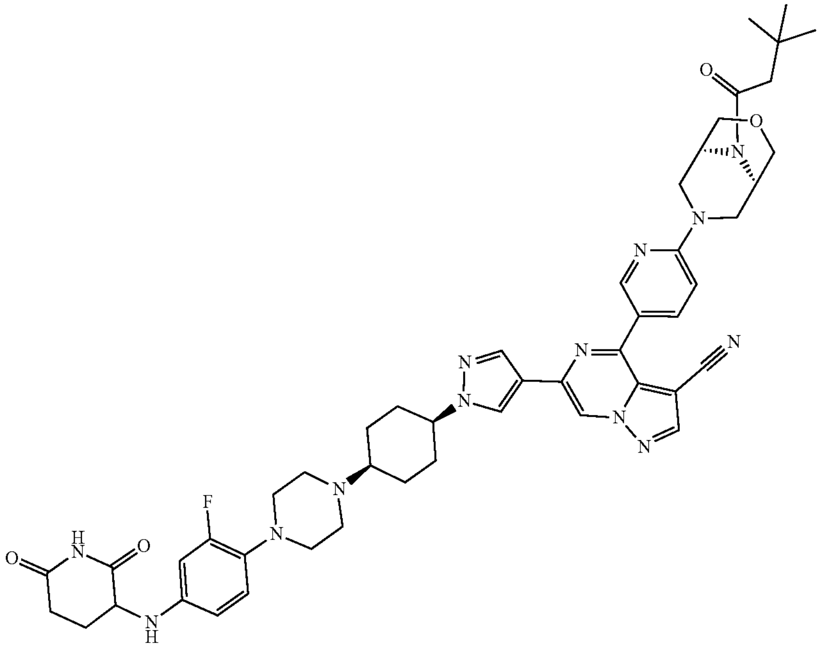 [SMILES: CC(C)(C)CC(=O)N1[C@@H]2COC[C@H]1CN(c1ccc(-c3nc(-c4cnn([C@H]5CC[C@@H](N6CCN(c7ccc(NC8CCC(=O)NC8=O)cc7F)CC6)CC5)c4)cn4ncc(C#N)c34)cn1)C2] |
| 159 | 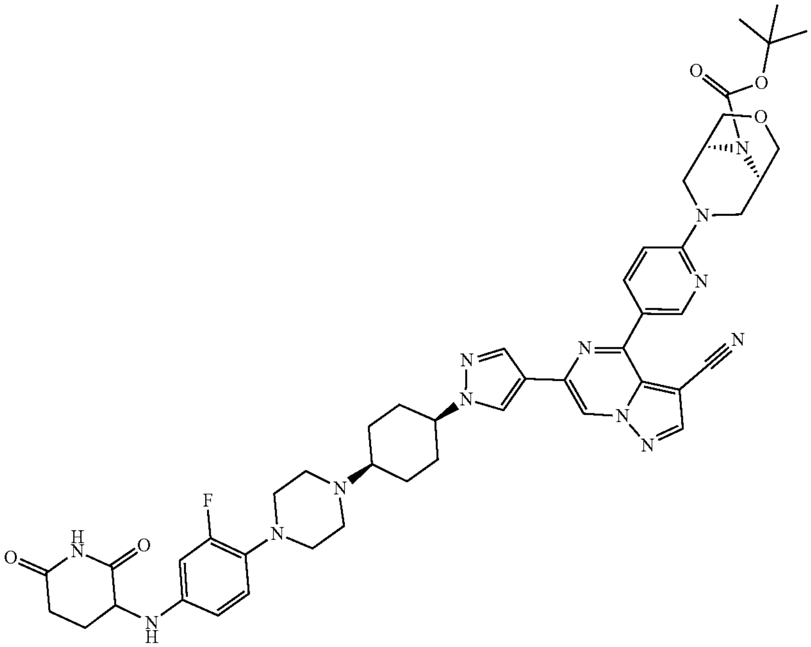 [SMILES: CC(C)(C)OC(=O)N1[C@@H]2COC[C@H]1CN(c1ccc(-c3nc(-c4cnn([C@H]5CC[C@@H](N6CCN(c7ccc(NC8CCC(=O)NC8=O)cc7F)CC6)CC5)c4)cn4ncc(C#N)c34)cn1)C2] |

TABLE 1B-continued
| Biological Data | |
|---|---|
| Cmpd # | Structure |
| 160 | 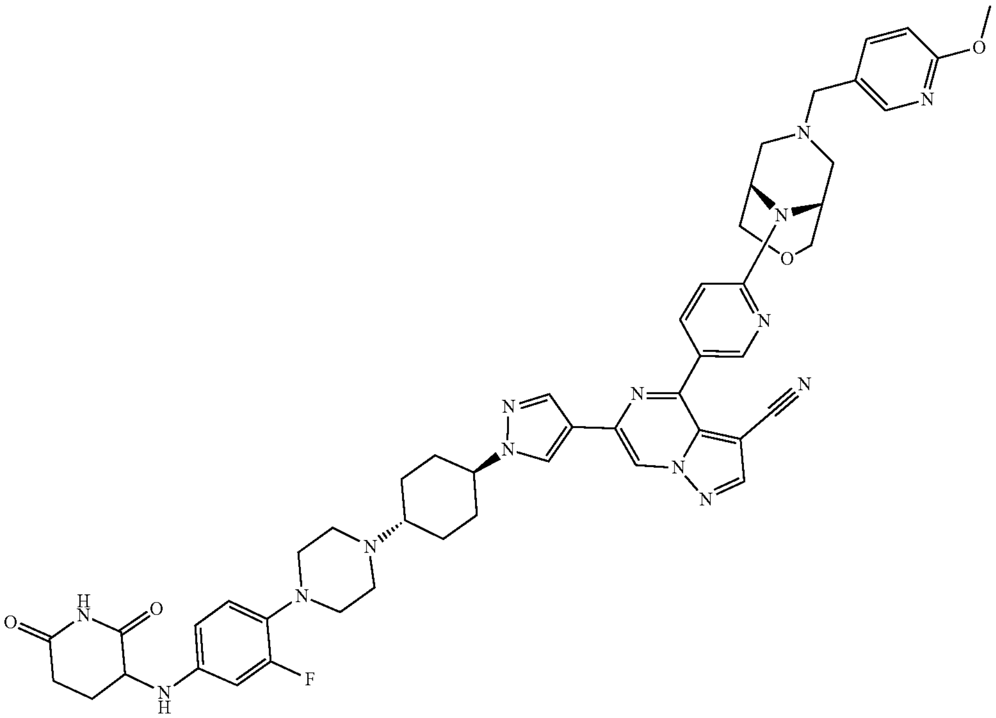 [SMILES: COc1ccc(CN2C[C@H]3COC[C@@H](C2)N3c2ccc(-c3nc(-c4cnn([C@H]5CC[C@H](N6CCN(c7ccc(NC8CCC(=O)NC8=O)cc7F)CC6)CC5)c4)cn4ncc(C#N)c34)cn2)cn1] |
| 161 | 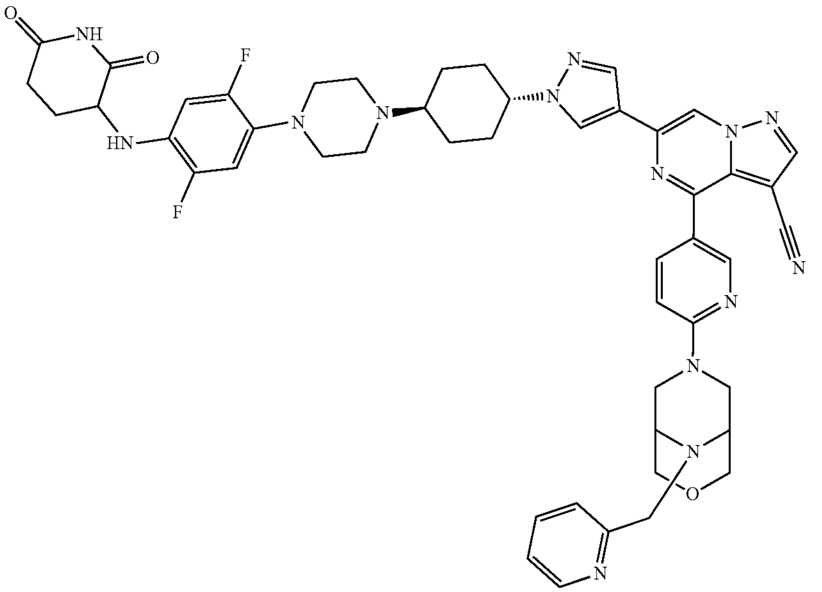 [SMILES: N#Cc1cnn2cc(-c3cnn([C@H]4CC[C@H](N5CCN(c6cc(F)c(NC7CCC(=O)NC7=O)cc6F)CC5)CC4)c3)nc(-c3ccc(N4CC5COCC(C4)N5Cc4ccccn4)nc3)c12] |

TABLE 1B-continued
| Biological Data | |
|---|---|
| Cmpd # | Structure |
| 162 | 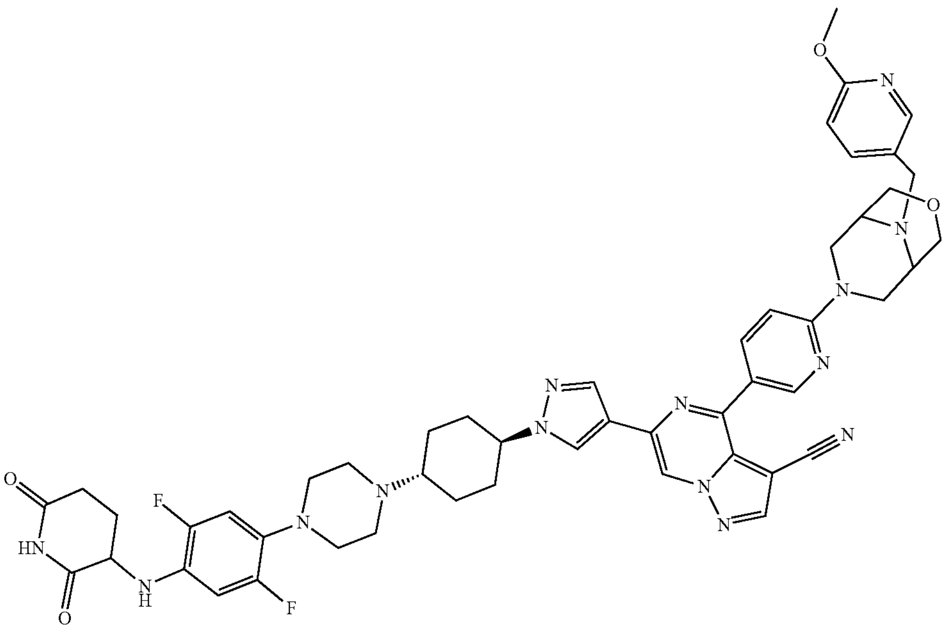 |
| 163 | 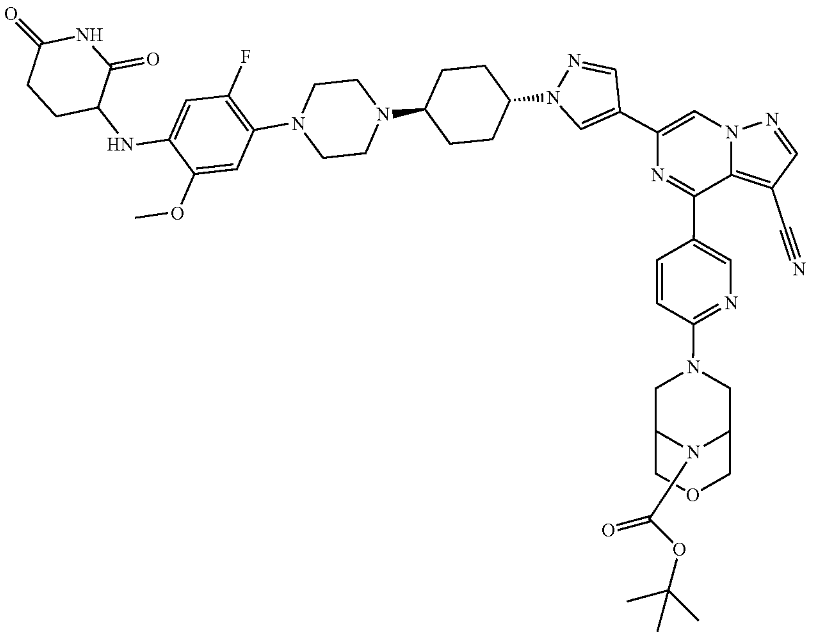 [SMILES: COc1cc(N2CCN([C@H]3CC[C@H](n4cc(-c5cn6ncc(C#N)c6c(-c6ccc(N7CC8COCC(C7)N8C(=O)OC(C)(C)C)nc6)n5)cn4)CC3)CC2)c(F)cc1NC1CCC(=O)NC1=O] |

TABLE 1B-continued
| Biological Data | |
|---|---|
| Cmpd # | Structure |
| 164 | 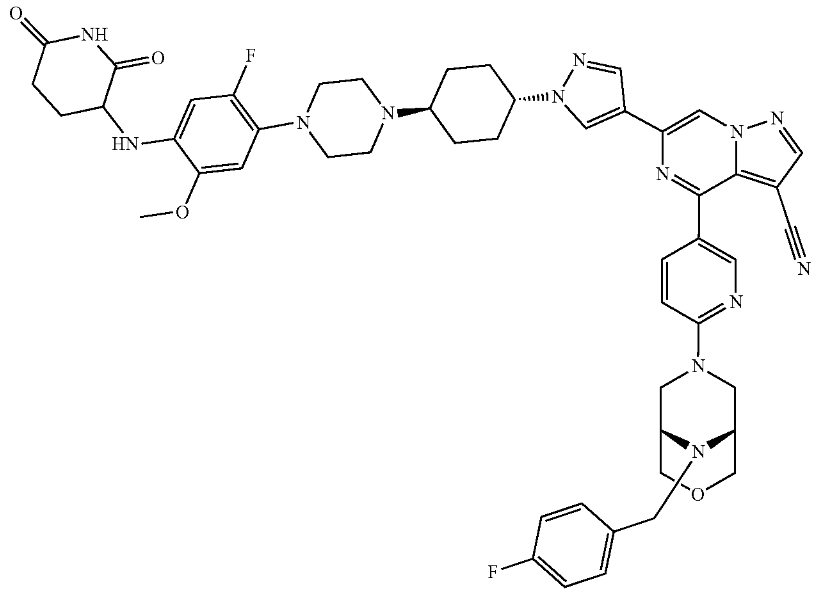 [SMILES: COc1cc(N2CCN([C@H]3CC[C@H](n4cc(-c5cn6ncc(C#N)c6c(-c6ccc(N7C[C@H]8COC[C@@H](C7)N8Cc7ccc(F)cc7)nc6)n5)cn4)CC3)CC2)c(F)cc1NC1CCC(=O)NC1=O] |
| 165 | 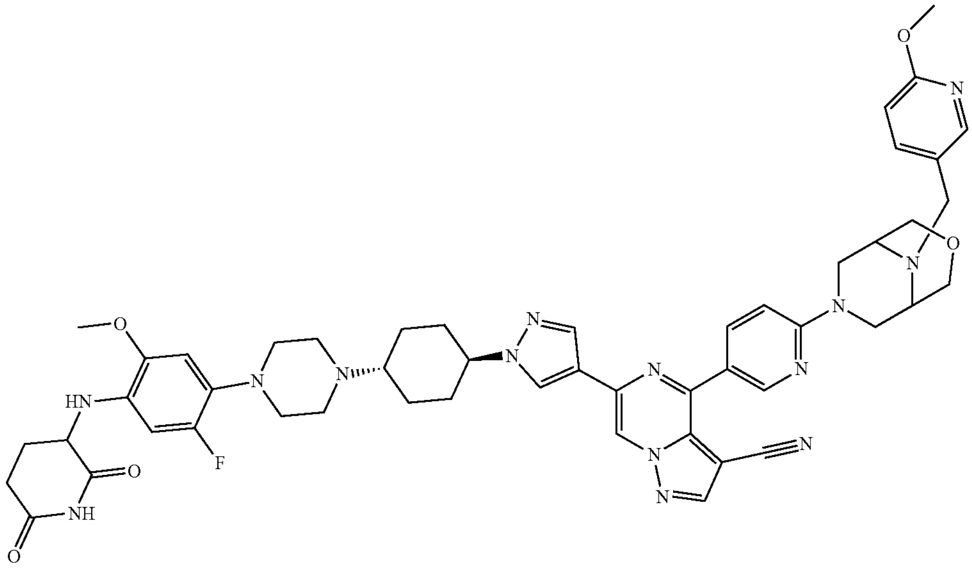 [SMILES: COc1ccc(CN2C3COCC2CN(c2ccc(-c4nc(-c5cnn([C@H]6CC[C@H](N7CCN(c8cc(OC)c(NC9CCC(=O)NC9=O)cc8F)CC7)CC6)c5)cn5ncc(C#N)c45)cn2)C3)cn1] |

TABLE 1B-continued
| Biological Data | |
|---|---|
| Cmpd # | Structure |
| 166 | 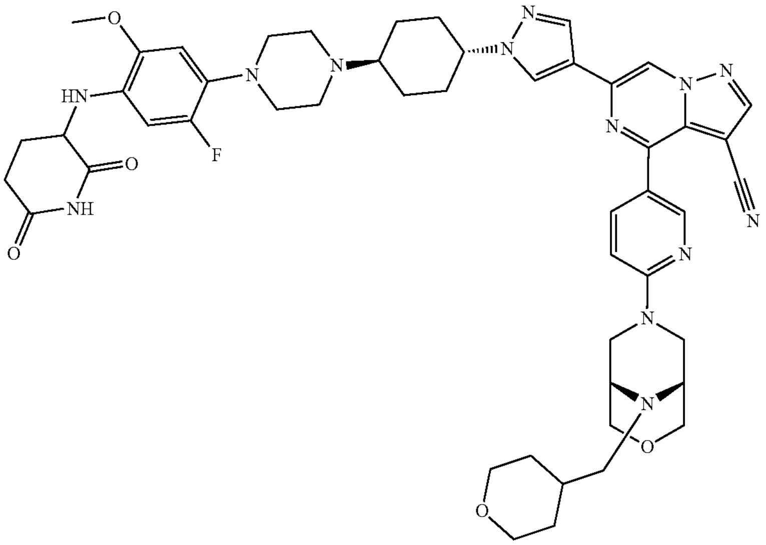 [SMILES: COc1cc(N2CCN([C@H]3CC[C@H](n4cc(-c5cn6ncc(C#N)c6c(-c6ccc(N7C[C@H]8COC[C@@H](C7)N8CC7CCOCC7)nc6)n5)cn4)CC3)CC2)c(F)cc1NC1CCC(=O)NC1=O] |
| 167 | 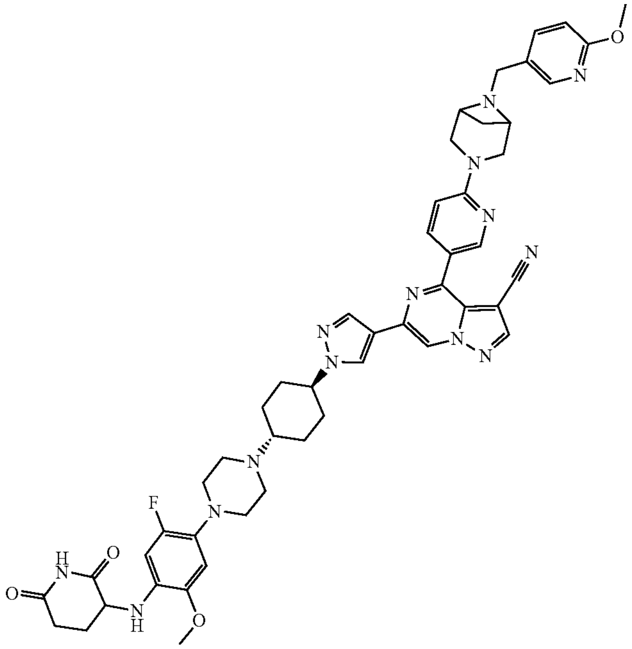 [SMILES: COc1ccc(CN2C3CC2CN(c2ccc(-c4nc(-c5cnn([C@H]6CC[C@H](N7CCN(c8cc(OC)c(NC9CCC(=O)NC9=O)cc8F)CC7)CC6)c5)cn5ncc(C#N)c45)cn2)C3)cn1] |

TABLE 1B-continued
| Biological Data | |
|---|---|
| Cmpd # | Structure |
| 168 | 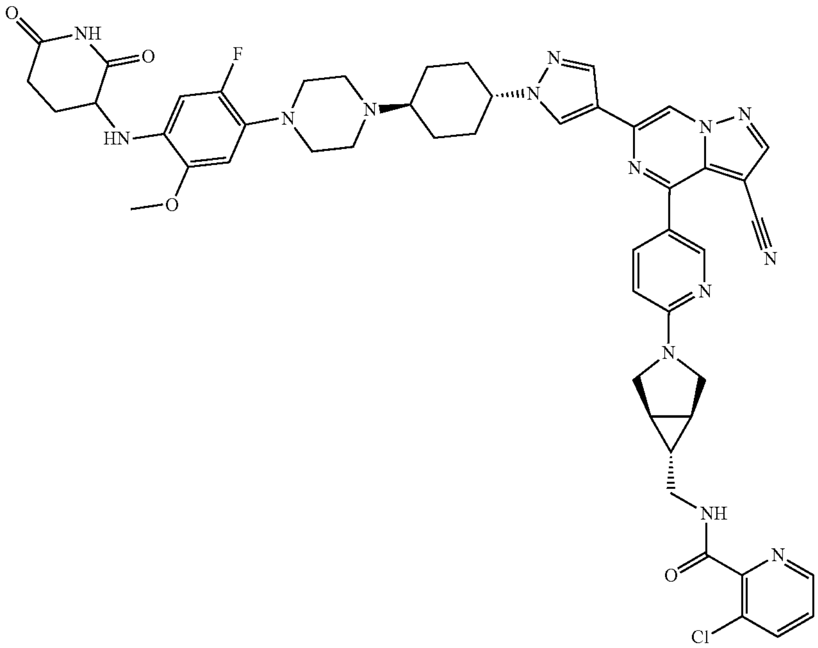 [SMILES: COc1cc(N2CCN([C@H]3CC[C@H](n4cc(-c5cn6ncc(C#N)c6c(-c6ccc(N7C[C@@H]8[C@@H](CNC(=O)c9ncccc9Cl)[C@@H]8C7)nc6)n5)cn4)CC3)CC2)c(F)cc1NC1CCC(=O)NC1=O] |
| 169 | 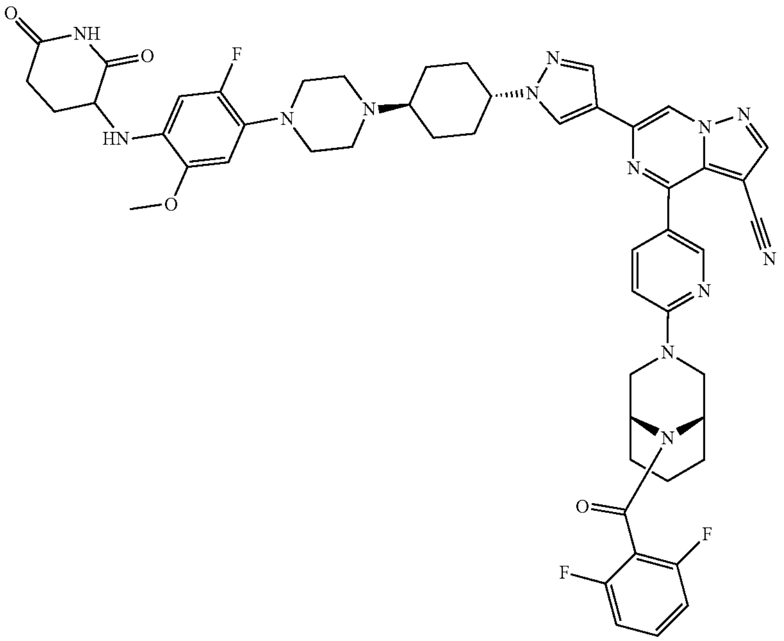 [SMILES: COc1cc(N2CCN([C@H]3CC[C@H](n4cc(-c5cn6ncc(C#N)c6c(-c6ccc(N7C[C@H]8CCC[C@@H](C7)N8C(=O)c7c(F)cccc7F)nc6)n5)cn4)CC3)CC2)c(F)cc1NC1CCC(=O)NC1=O] |

TABLE 1B-continued
| Biological Data | |
|---|---|
| Cmpd # | Structure |
| 170 | 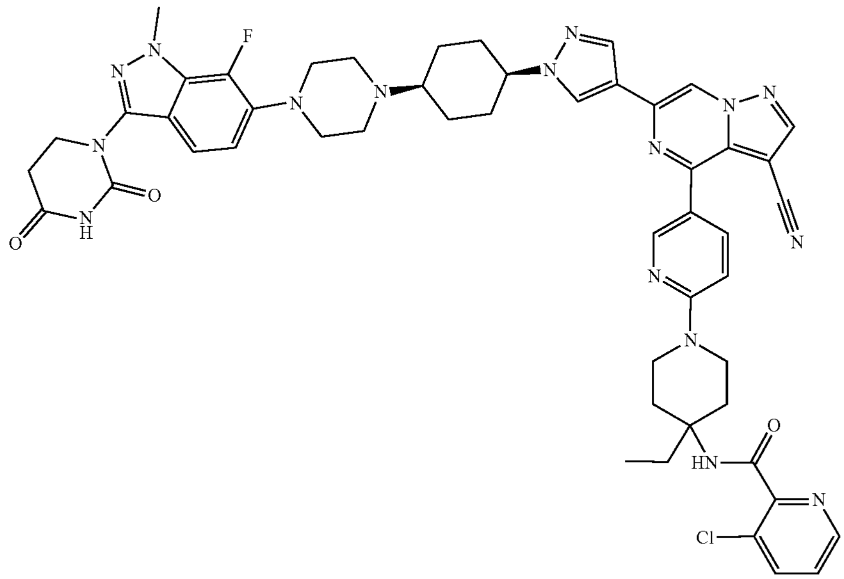 [SMILES: CCC1(NC(=O)c2ncccc2Cl)CCN(c2ccc(-c3nc(-c4cnn([C@H]5CC[C@@H](N6CCN(c7ccc8c(N9CCC(=O)NC9=O)nn(C)c8c7F)CC6)CC5)c4)cn4ncc(C#N)c34)cn2)CC1] |
| 171 | 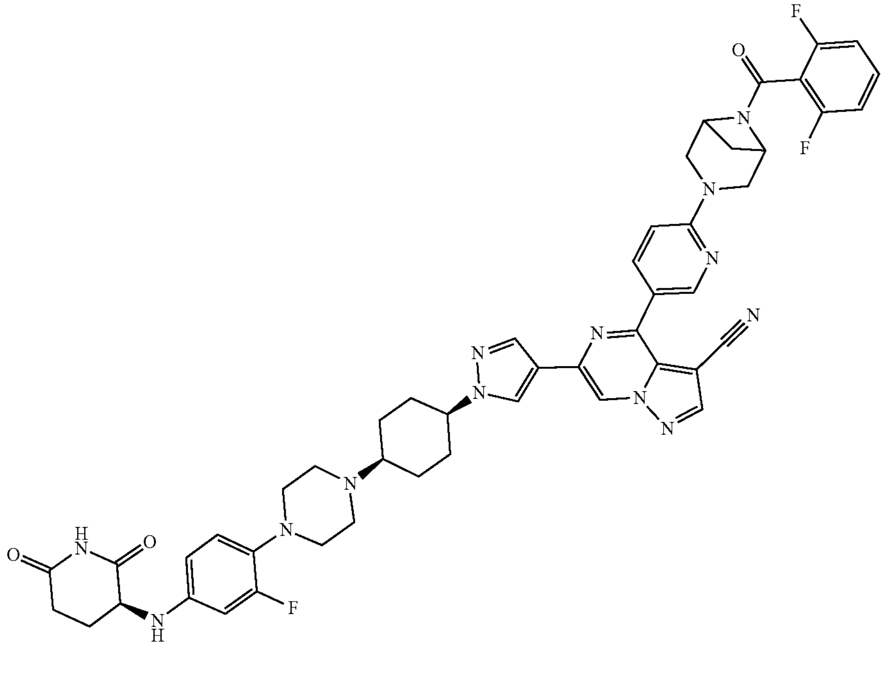 [SMILES: N#Cc1cnn2cc(-c3cnn([C@H]4CC[C@@H](N5CCN(c6ccc(N[C@H]7CCC(=O)NC7=O)cc6F)CC5)CC4)c3)nc(-c3ccc(N4CC5CC(C4)N5C(=O)c4c(F)cccc4F)nc3)c12] |

TABLE 1B-continued
| Biological Data | |
|---|---|
| Cmpd # | Structure |
| 172 | 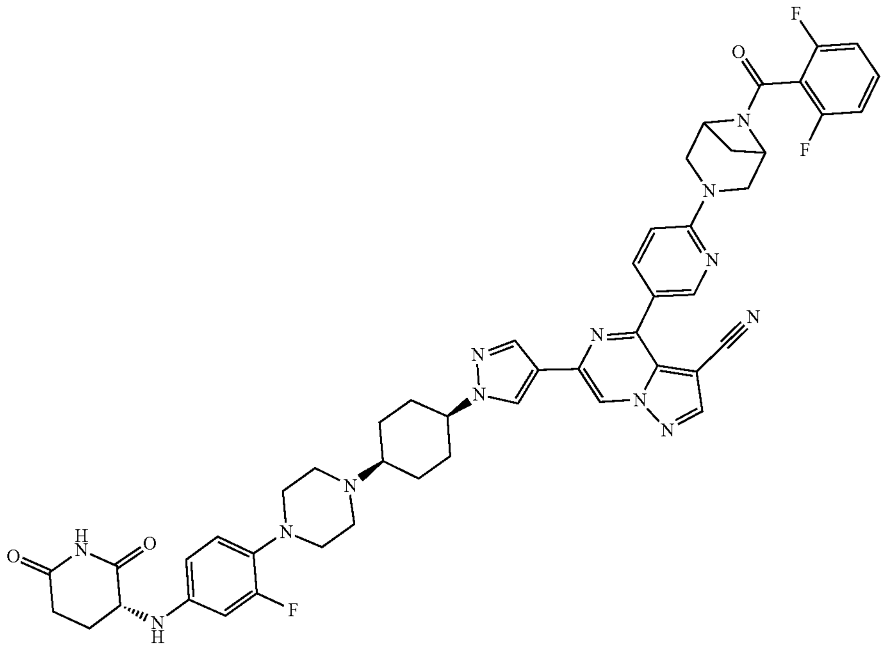 [SMILES: N#Cc1cnn2cc(-c3cnn([C@H]4CC[C@@H](N5CCN(c6ccc(N[C@@H]7CCC(=O)NC7=O)cc6F)CC5)CC4)c3)nc(-c3ccc(N4CC5CC(C4)N5C(=O)c4c(F)cccc4F)nc3)c12] |
| 173 | 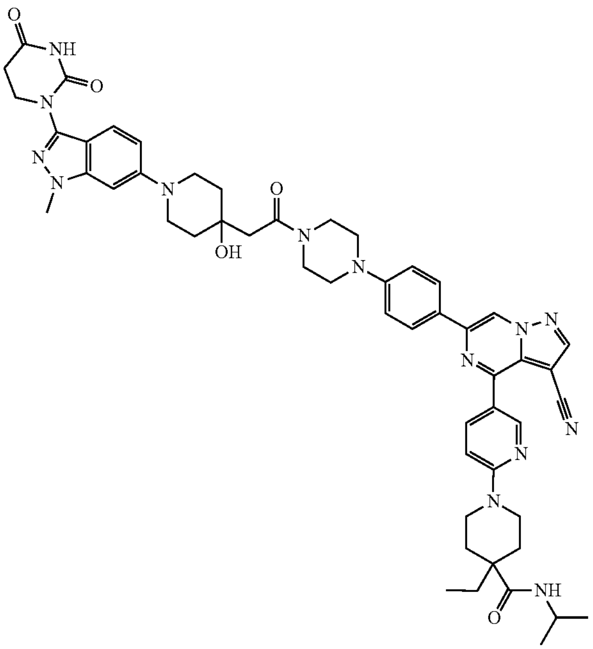 [SMILES: CCC1(C(=O)NC(C)C)CCN(c2ccc(-c3nc(-c4ccc(N5CCN(C(=O)CC6(O)CCN(c7ccc8c(N9CCC(=O)NC9=O)nn(C)c8c7)CC6)CC5)cc4)cn4ncc(C#N)c34)cn2)CC1] |

TABLE 1B-continued
| Biological Data | |
|---|---|
| Cmpd # | Structure |
| 174 | 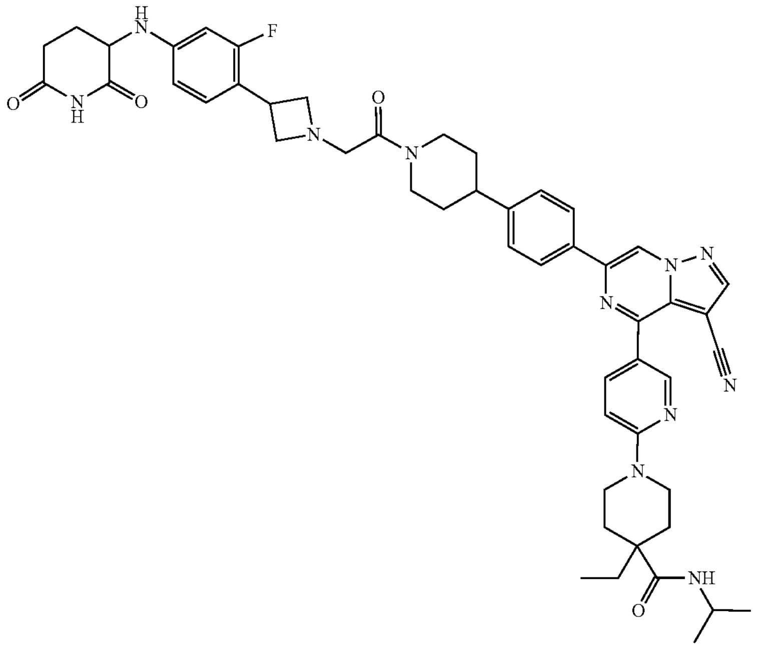 [SMILES: CCC1(C(=O)NC(C)C)CCN(c2ccc(-c3nc(-c4ccc(C5CCN(C(=O)CN6CC(c7ccc(NC8CCC(=O)NC8=O)cc7F)C6)CC5)cc4)cn4ncc(C#N)c34)cn2)CC1] |
| 175 | 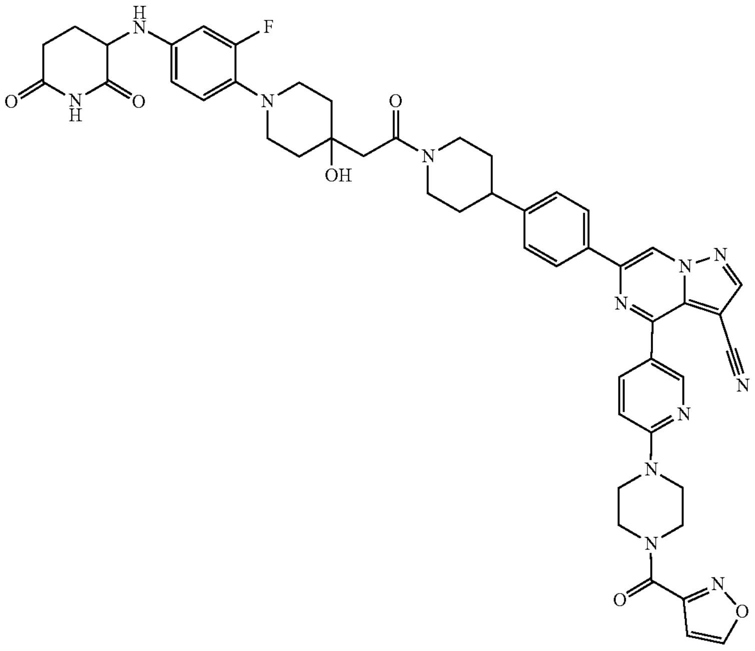 [SMILES: N#Cc1cnn2cc(-c3ccc(C4CCN(C(=O)CC5(O)CCN(c6ccc(NC7CCC(=O)NC7=O)cc6F)CC5)CC4)cc3)nc(-c3ccc(N4CCN(C(=O)c5ccon5)CC4)nc3)c12] |

TABLE 1B-continued
| Biological Data | |
|---|---|
| Cmpd # | Structure |
| 176 | 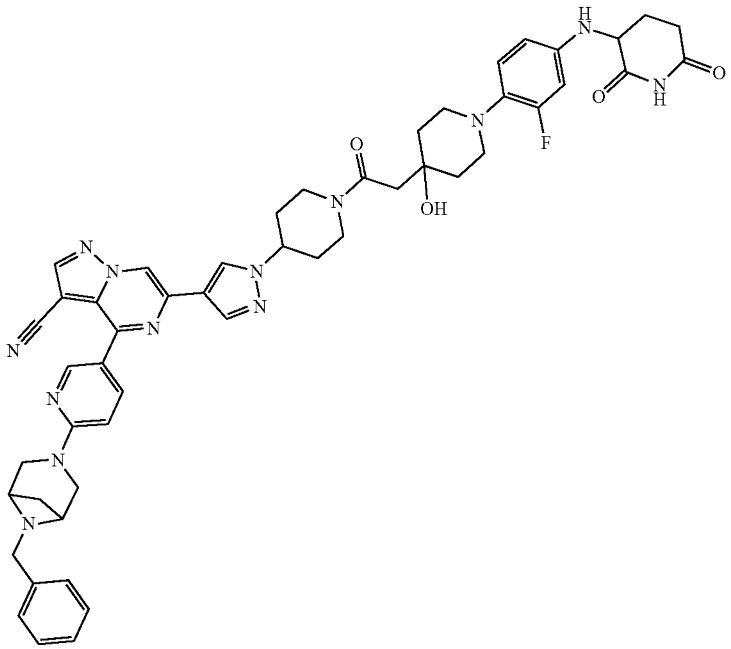 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CC5CC(C4)N5Cc4ccccc4)nc3)c12] |
| 177 | 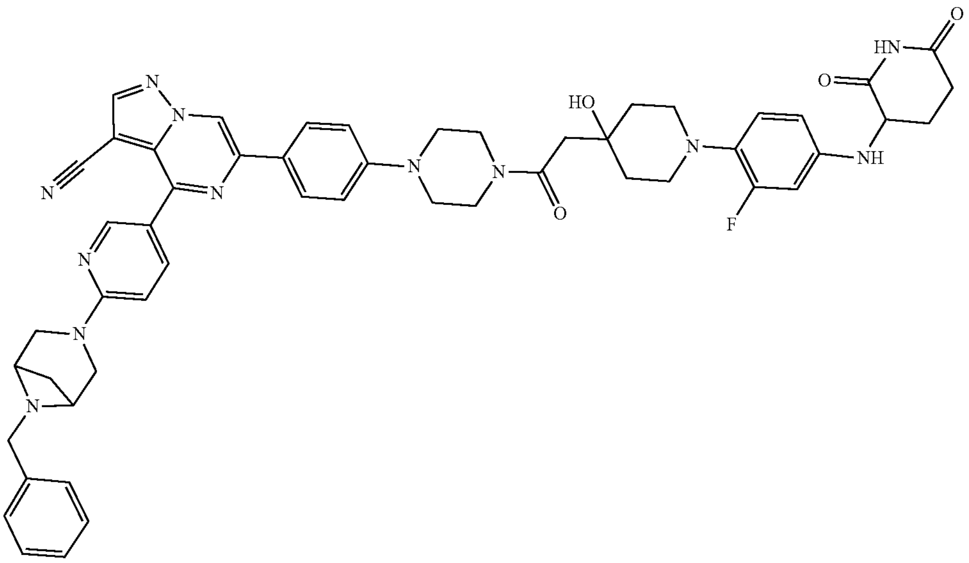 [SMILES: N#Cc1cnn2cc(-c3ccc(N4CCN(C(=O)CC5(O)CCN(c6ccc(NC7CCC(=O)NC7=O)cc6F)CC5)CC4)cc3)nc(-c3ccc(N4CC5CC(C4)N5Cc4ccccc4)nc3)c12] |

TABLE 1B-continued
| Biological Data | |
|---|---|
| Cmpd # | Structure |
| 178 | 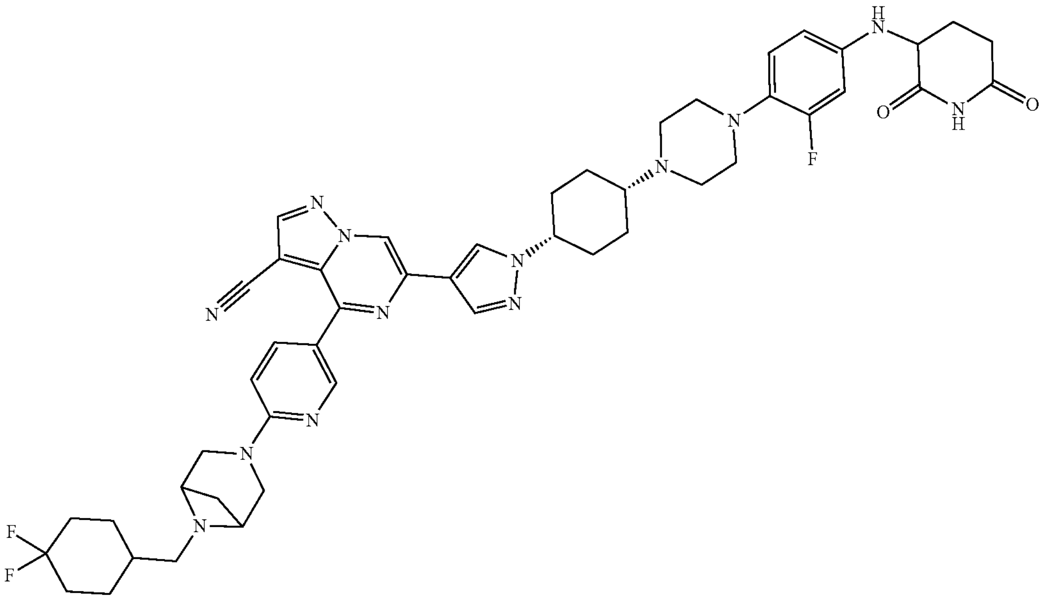 [SMILES: N#Cc1cnn2cc(-c3cnn([C@H]4CC[C@@H](N5CCN(c6ccc(NC7CCC(=O)NC7=O)cc6F)CC5)CC4)c3)nc(-c3ccc(N4CC5CC(C4)N5CC4CCC(F)(F)CC4)nc3)c12] |
| 179 | 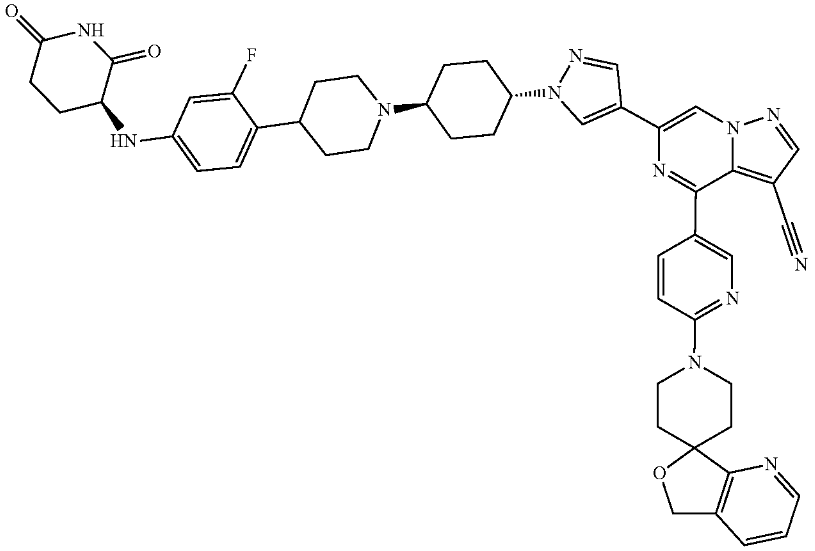 [SMILES: N#Cc1cnn2cc(-c3cnn([C@H]4CC[C@H](N5CCC(c6ccc(N[C@H]7CCC(=O)NC7=O)cc6F)CC5)CC4)c3)nc(-c3ccc(N4CCC5(CC4)OCc4cccnc45)nc3)c12] |

TABLE 1B-continued
| Biological Data | |
|---|---|
| Cmpd # | Structure |
| 180 | 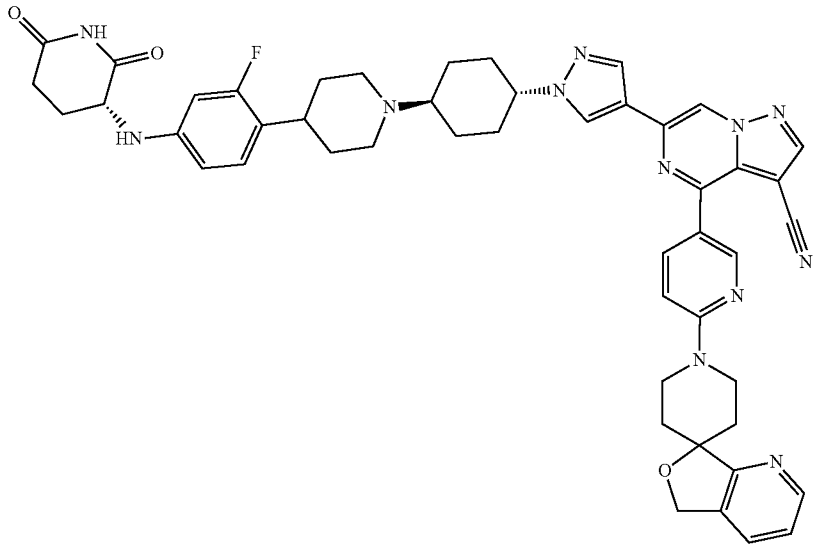 [SMILES: N#Cc1cnn2cc(-c3cnn([C@H]4CC[C@H](N5CCC(c6ccc(N[C@@H]7CCC(=O)NC7=O)cc6F)CC5)CC4)c3)nc(-c3ccc(N4CCC5(CC4)OCc4cccnc45)nc3)c12] |
| 181 | 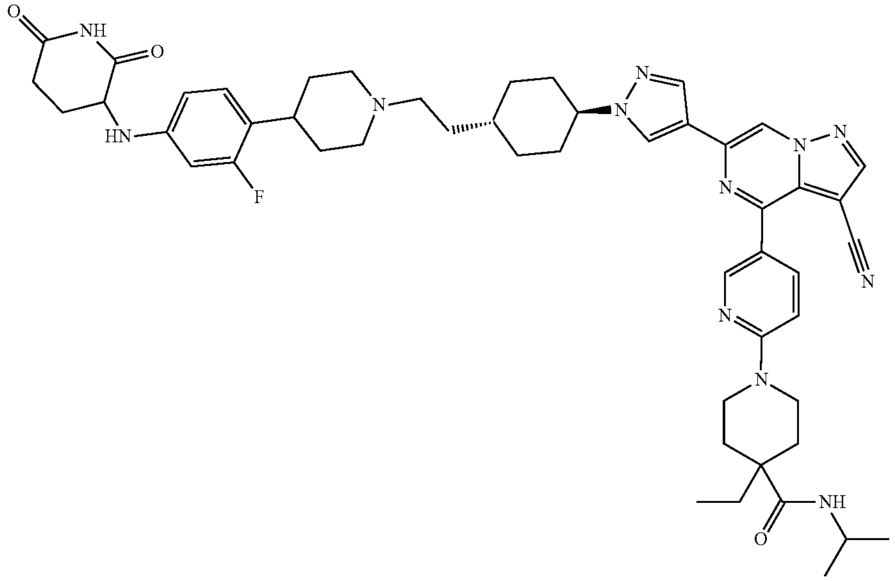 |

TABLE 1B-continued
| Biological Data | |
|---|---|
| Cmpd # | Structure |
| 182 | 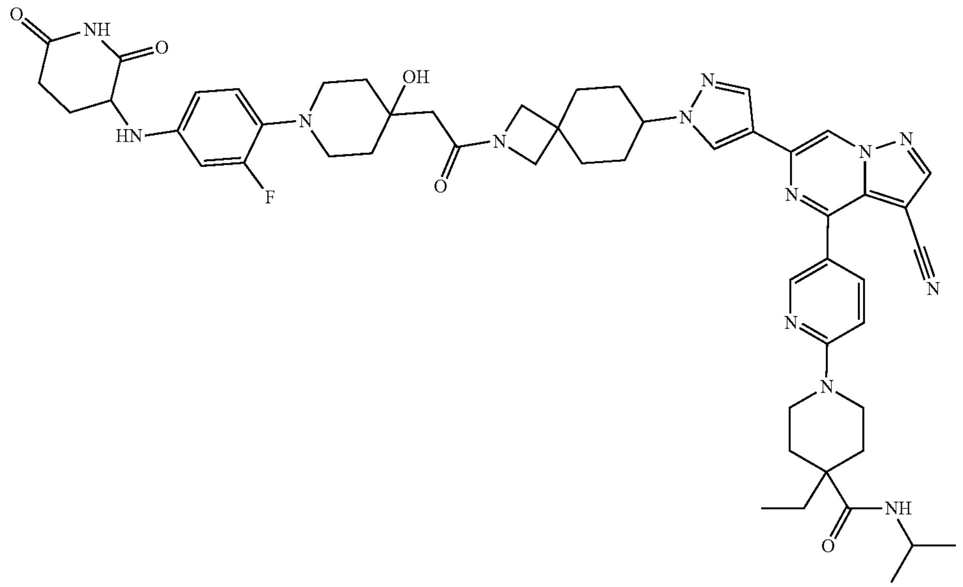 [SMILES: CCC1(C(=O)NC(C)C)CCN(c2ccc(-c3nc(-c4cnn(C5CCC6(CC5)CN(C(=O)CC5(O)CCN(c7ccc(NC8CCC(=O)NC8=O)cc7F)CC5)C6)c4)cn4ncc(C#N)c34)cn2)CC1] |
| 183 | 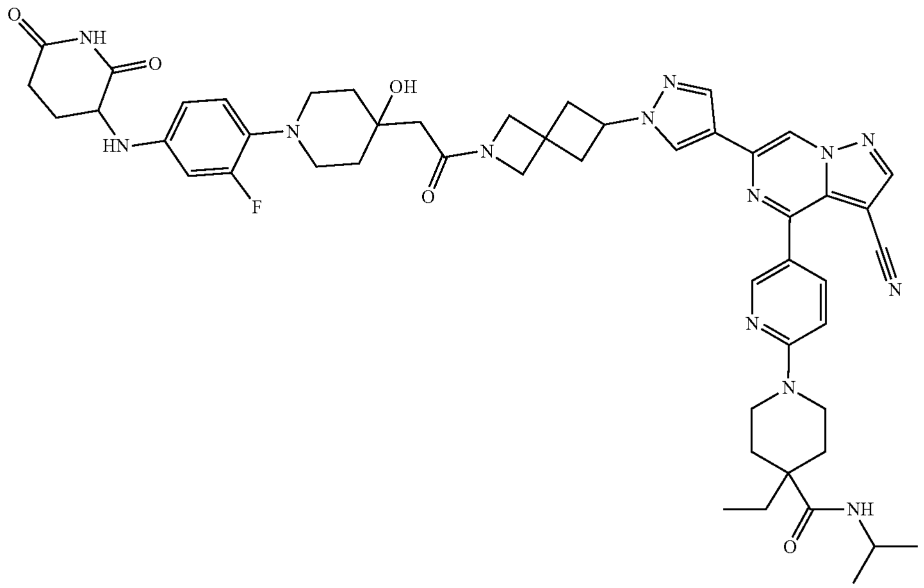 [SMILES: CCC1(C(=O)NC(C)C)CCN(c2ccc(-c3nc(-c4cnn(C5CC6(C5)CN(C(=O)CC5(O)CCN(c7ccc(NC8CCC(=O)NC8=O)cc7F)CC5)C6)c4)cn4ncc(C#N)c34)cn2)CC1] |

TABLE 1B-continued
| Biological Data | |
|---|---|
| Cmpd # | Structure |
| 184 | 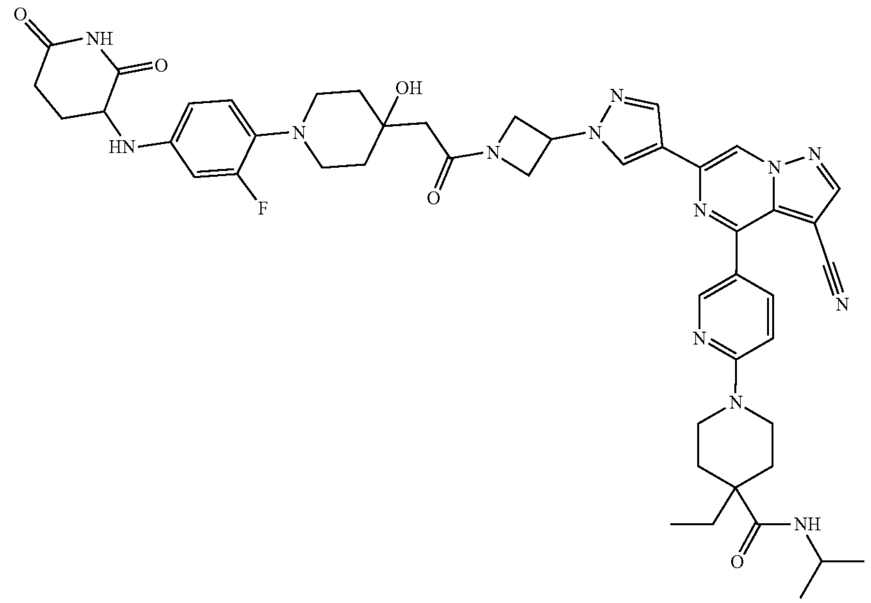 [SMILES: CCC1(C(=O)NC(C)C)CCN(c2ccc(-c3nc(-c4cnn(C5CN(C(=O)CC6(O)CCN(c7ccc(NC8CCC(=O)NC8=O)cc7F)CC6)C5)c4)cn4ncc(C#N)c34)cn2)CC1] |
| 185 | 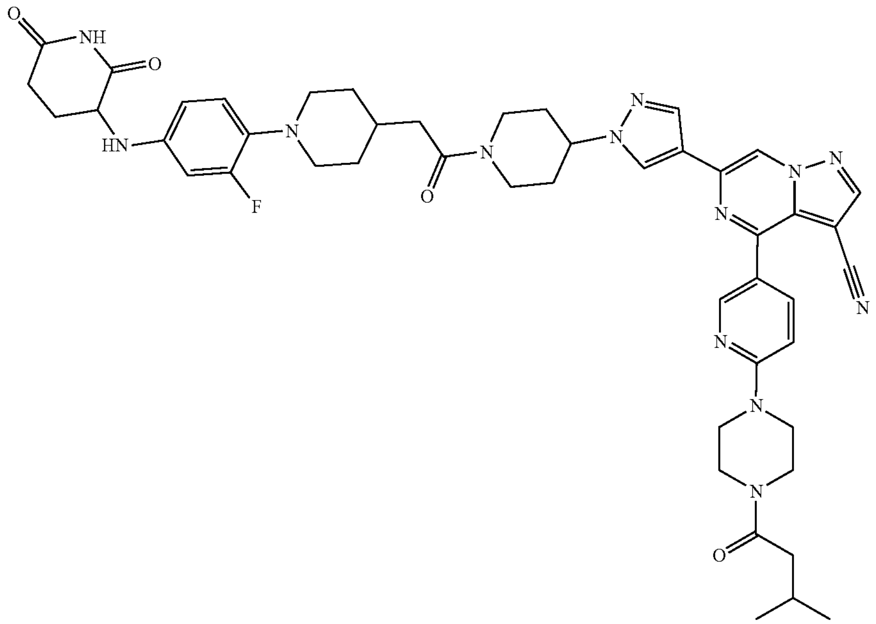 [SMILES: CC(C)CC(=O)N1CCN(c2ccc(-c3nc(-c4cnn(C5CCN(C(=O)CC6CCN(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 186 | 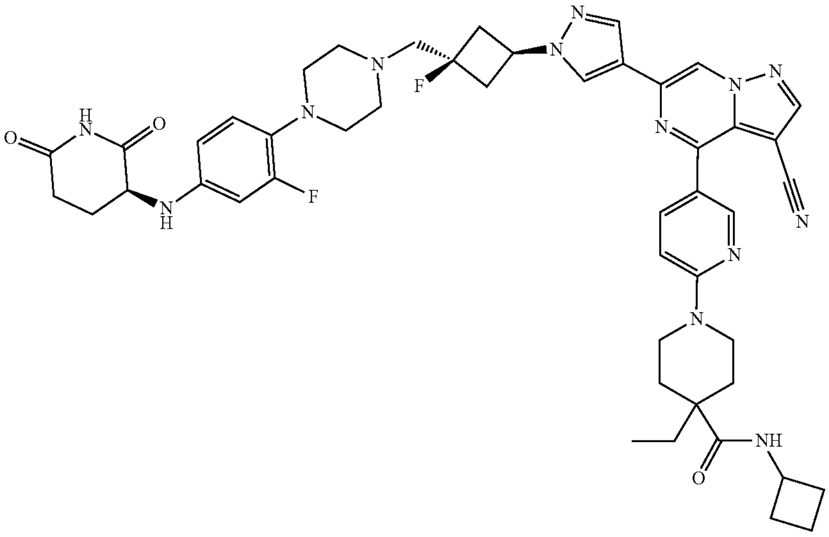 [SMILES: CCC1(C(=O)NC2CCC2)CCN(c2ccc(-c3nc(-c4cnn([C@H]5C[C@](F)(CN6CCN(c7ccc(N[C@H]8CCC(=O)NC8=O)cc7F)CC6)C5)c4)cn4ncc(C#N)c34)cn2)CC1] |
| 187 | 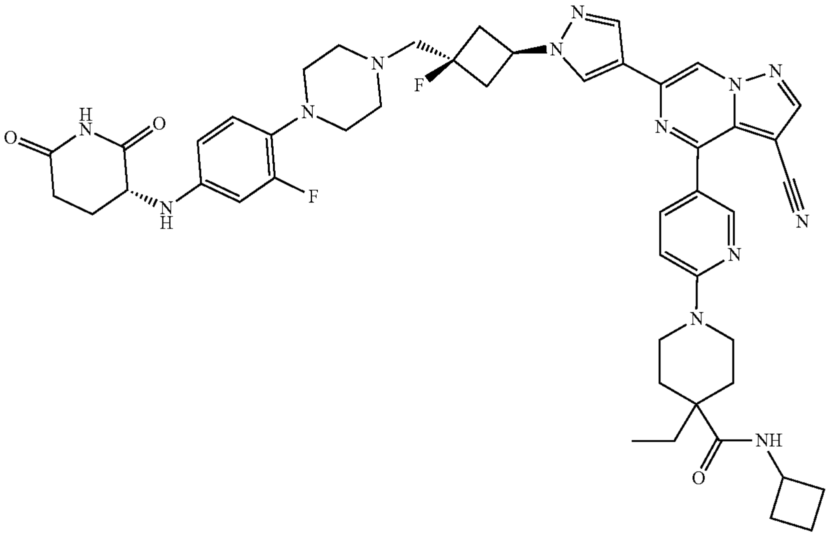 [SMILES: CCC1(C(=O)NC2CCC2)CCN(c2ccc(-c3nc(-c4cnn([C@H]5C[C@](F)(CN6CCN(c7ccc(N[C@@H]8CCC(=O)NC8=O)cc7F)CC6)C5)c4)cn4ncc(C#N)c34)cn2)CC1] |

TABLE 1B-continued
| Biological Data | |
|---|---|
| Cmpd # | Structure |
| 188 | 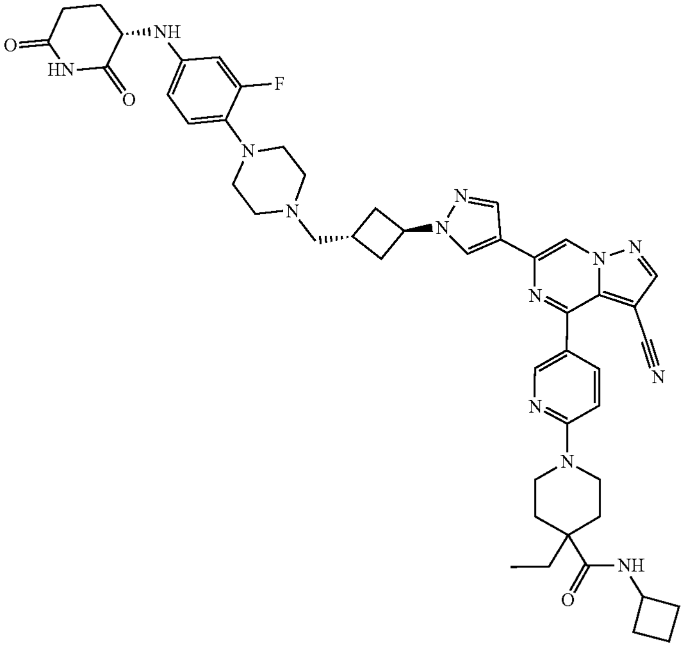 [SMILES: CCC1(C(=O)NC2CCC2)CCN(c2ccc(-c3nc(-c4cnn([C@H]5C[C@H](CN6CCN(c7ccc(N[C@H]8CCC(=O)NC8=O)cc7F)CC6)C5)c4)cn4ncc(C#N)c34)cn2)CC1] |
| 189 | 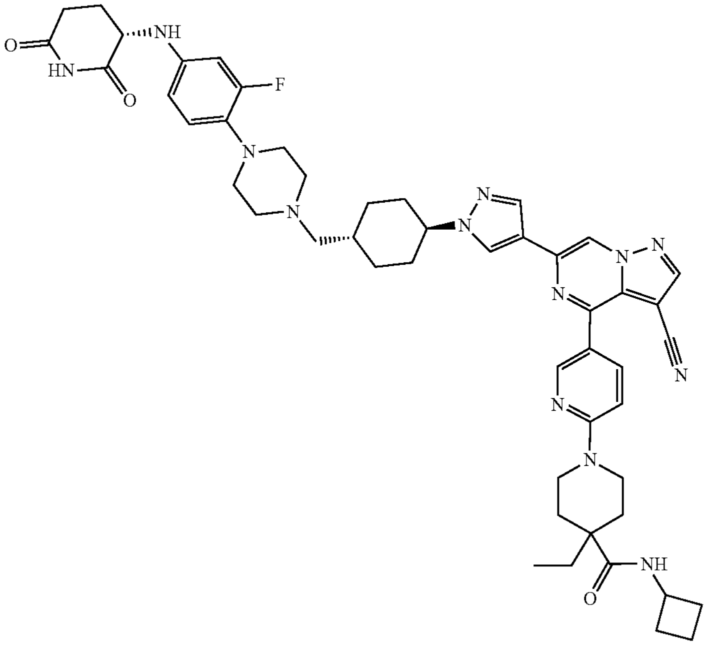 [SMILES: CCC1(C(=O)NC2CCC2)CCN(c2ccc(-c3nc(-c4cnn([C@H]5CC[C@H](CN6CCN(c7ccc(N[C@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 190 | 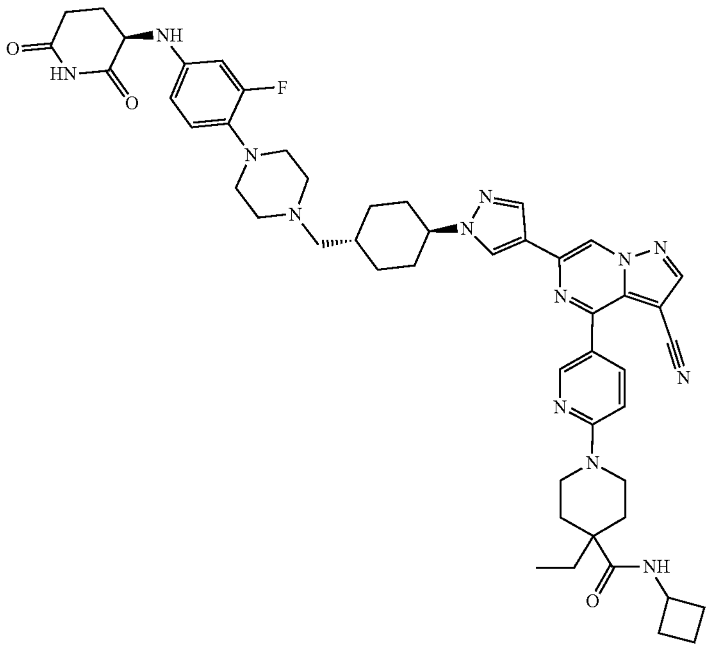 [SMILES: CCC1(C(=O)NC2CCC2)CCN(c2ccc(-c3nc(-c4cnn([C@H]5CC[C@H](CN6CCN(c7ccc(N[C@@H]8CCC(=O)NC8=O)cc7F)CC6)CC5)c4)cn4ncc(C#N)c34)cn2)CC1] |
| 191 | 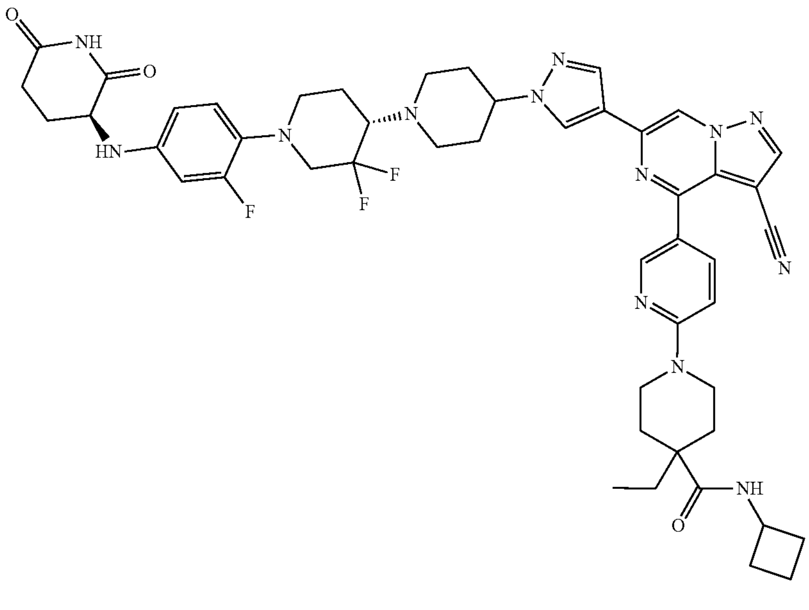 [SMILES: CCC1(C(=O)NC2CCC2)CCN(c2ccc(-c3nc(-c4cnn(C5CCN([C@H]6CCN(c7ccc(N[C@H]8CCC(=O)NC8=O)cc7F)CC6(F)F)CC5)c4)cn4ncc(C#N)c34)cn2)CC1] |

TABLE 1B-continued
| Biological Data | |
|---|---|
| Cmpd # | Structure |
| 192 | 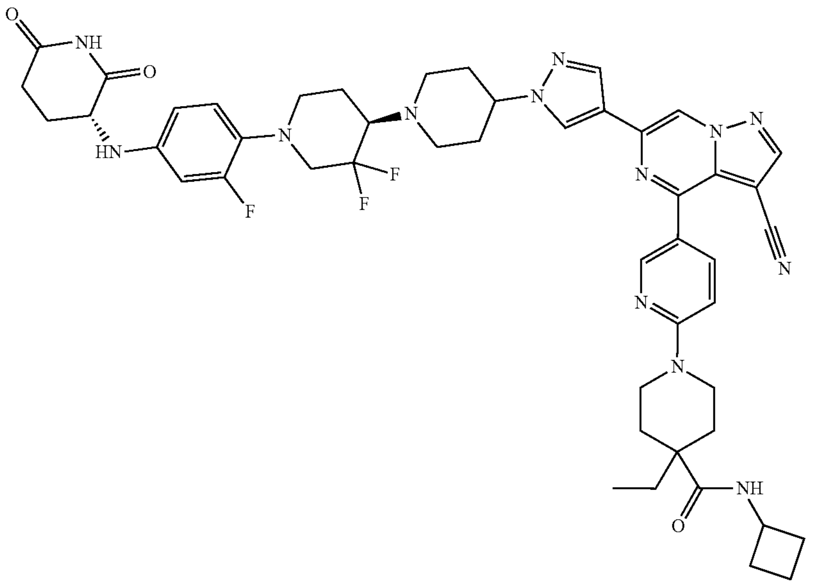 [SMILES: CCC1(C(=O)NC2CCC2)CCN(c2ccc(-c3nc(-c4cnn(C5CCN([C@@H]6CCN(c7ccc(N[C@@H]8CCC(=O)NC8=O)cc7F)CC6(F)F)CC5)c4)cn4ncc(C#N)c34)cn2)CC1] |
| 193 | 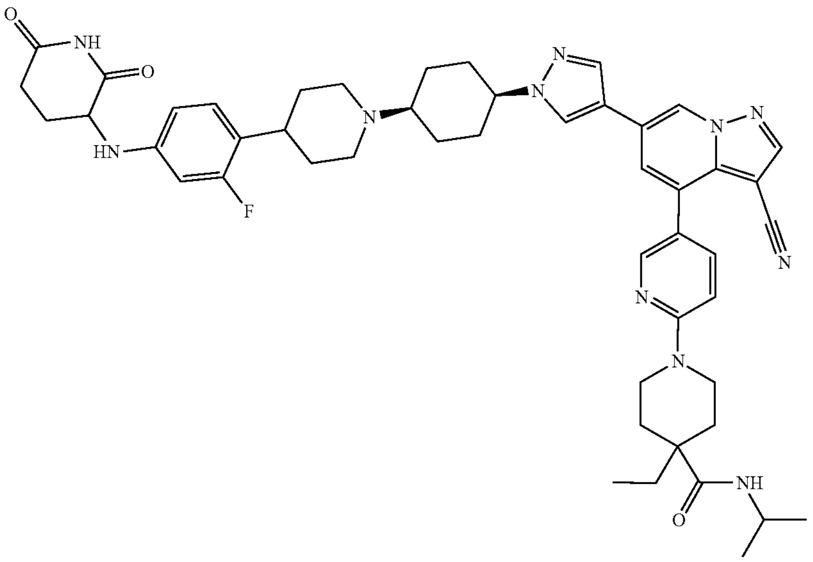 [SMILES: CCC1(C(=O)NC(C)C)CCN(c2ccc(-c3cc(-c4cnn([C@H]5CC[C@@H](N6CCC(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 194 | 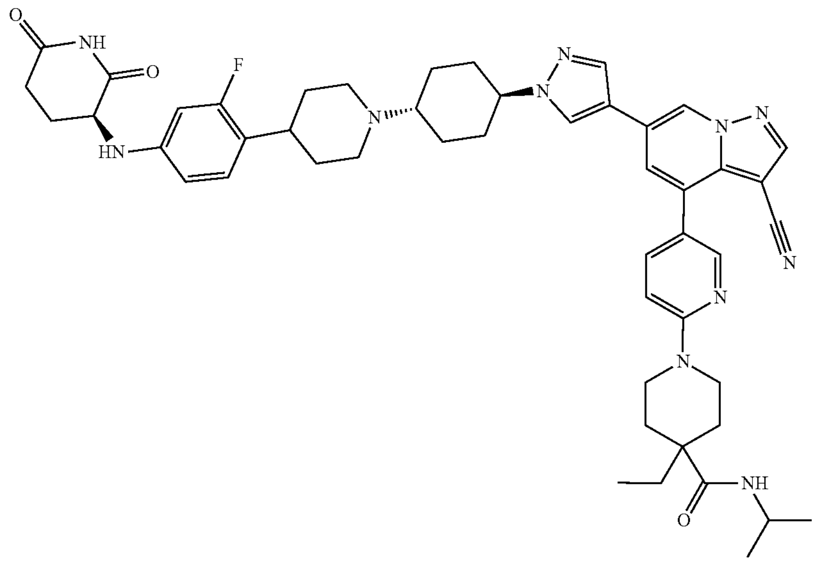 [SMILES: CCC1(C(=O)NC(C)C)CCN(c2ccc(-c3cc(-c4cnn([C@H]5CC[C@H](N6CCC(c7ccc(N[C@H]8CCC(=O)NC8=O)cc7F)CC6)CC5)c4)cn4ncc(C#N)c34)cn2)CC1] |
| 195 | 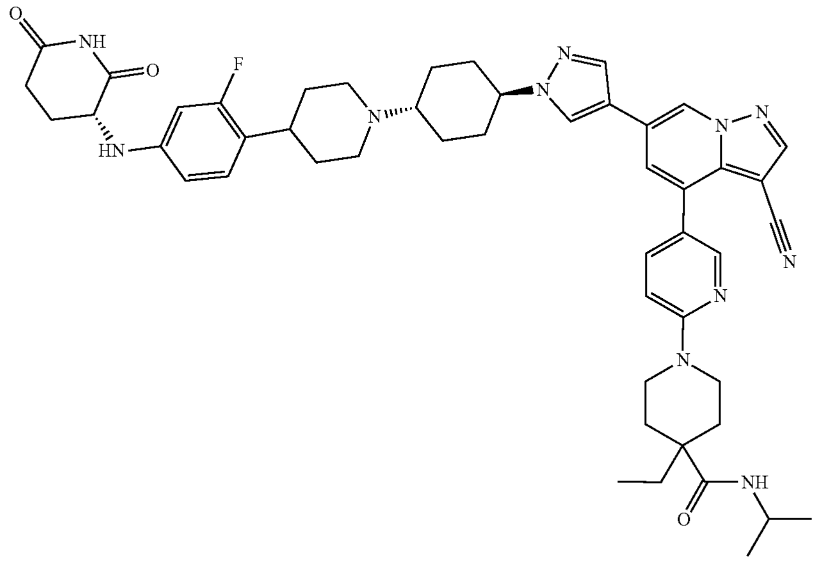 [SMILES: CCC1(C(=O)NC(C)C)CCN(c2ccc(-c3cc(-c4cnn([C@H]5CC[C@H](N6CCC(c7ccc(N[C@@H]8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 196 | 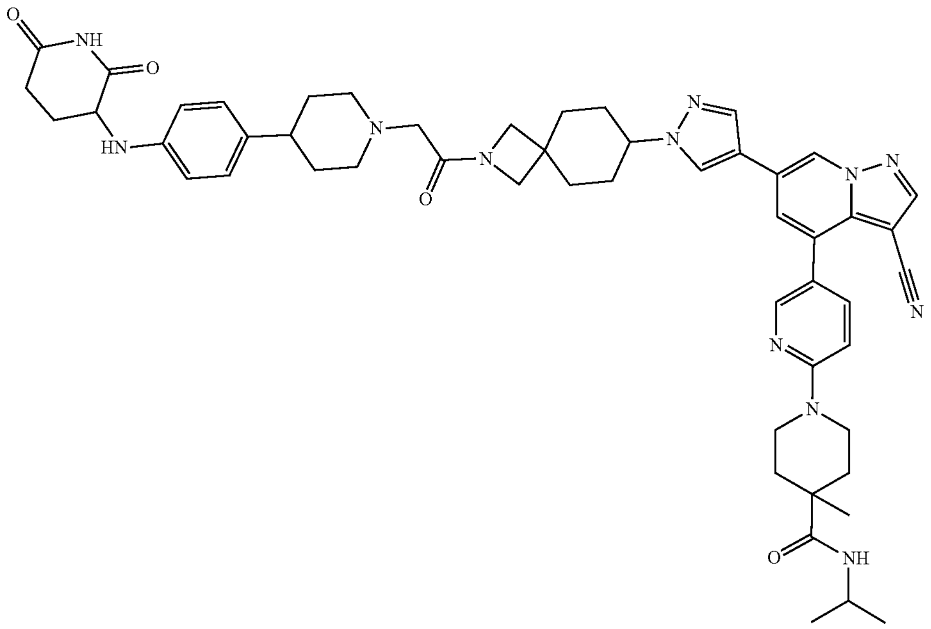 [SMILES: CC(C)NC(=O)C1(C)CCN(c2ccc(-c3cc(-c4cnn(C5CCC6(CC5)CN(C(=O)CN5CCC(c7ccc(NC8CCC(=O)NC8=O)cc7)CC5)C6)c4)cn4ncc(C#N)c34)cn2)CC1] |
| 197 | 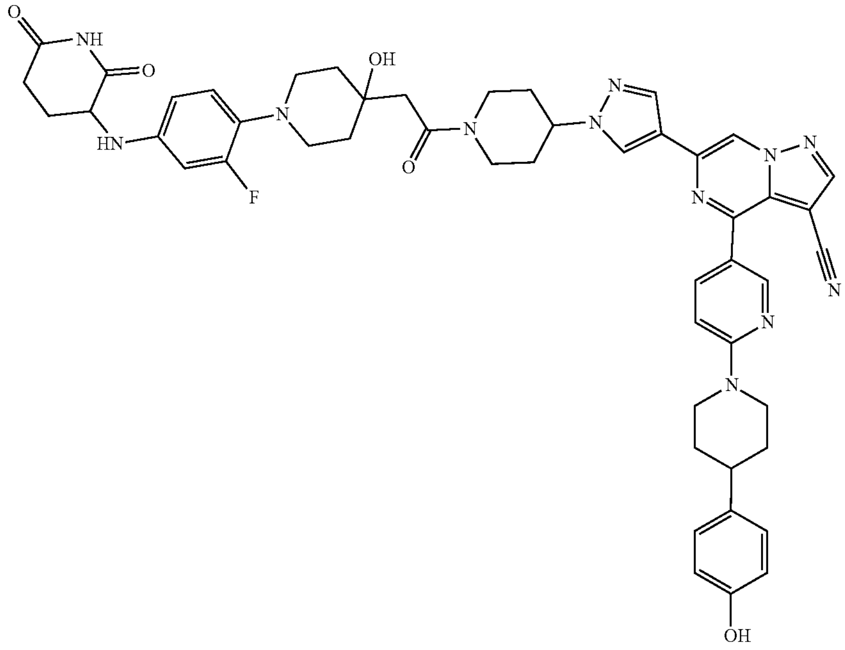 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC(c5ccc(O)cc5)CC4)nc3)c12] |

TABLE 1B-continued
| Biological Data | |
|---|---|
| Cmpd # | Structure |
| 198 | 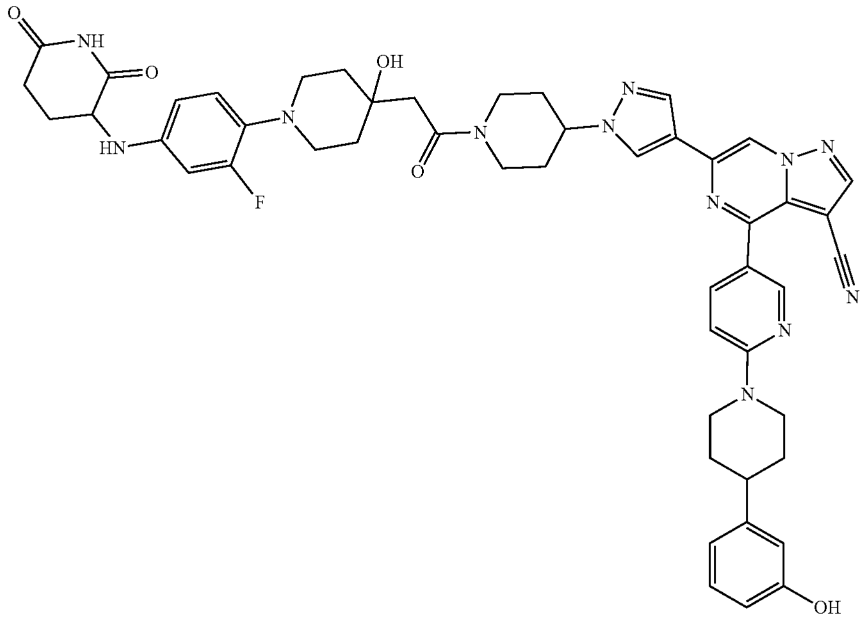 [SMILES: N#Cc1cnn2cc(-c3cnn(C4CCN(C(=O)CC5(O)CCN(c6ccc(NC7CCC(=O)NC7=O)cc6F)CC5)CC4)c3)nc(-c3ccc(N4CCC(c5cccc(O)c5)CC4)nc3)c12] |
| 199 | 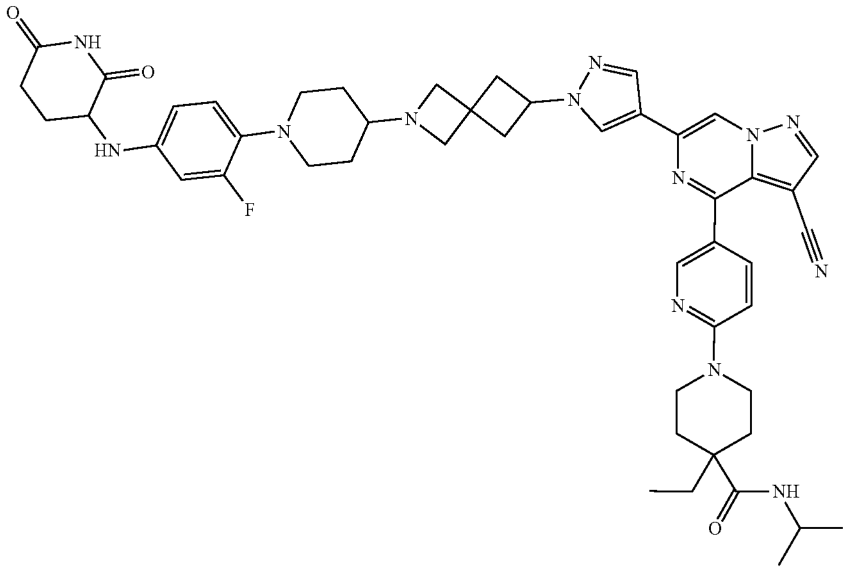 [SMILES: CCC1(C(=O)NC(C)C)CCN(c2ccc(-c3nc(-c4cnn(C5CC6(C5)CN(C5CCN(c7ccc(NC8CCC(=O)NC8=O)cc7F)CC5)C6)c4)cn4ncc(C#N)c34)cn2)CC1] |

TABLE 1B-continued
| Biological Data | |
|---|---|
| Cmpd # | Structure |
| 200 | 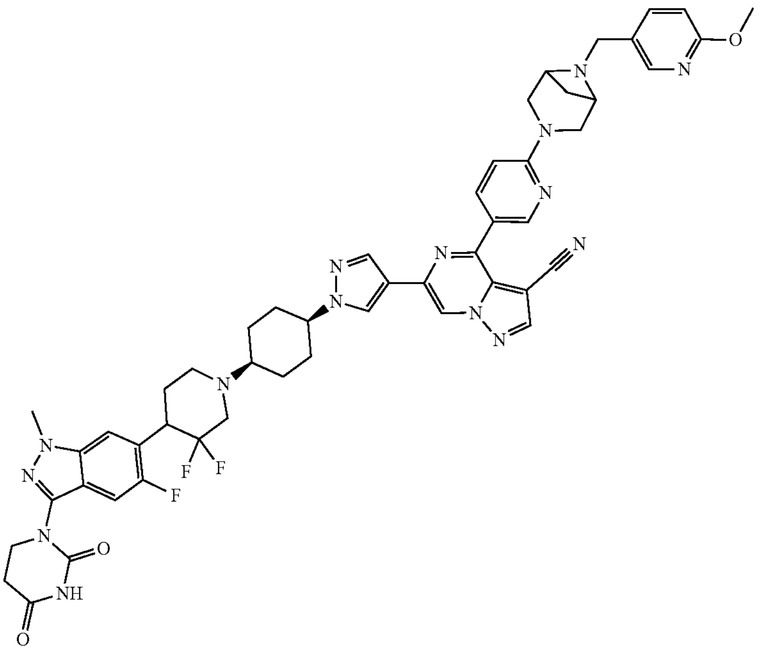 [SMILES: COc1ccc(CN2C3CC2CN(c2ccc(-c4nc(-c5cnn([C@H]6CC[C@@H](N7CCC(c8cc9c(cc8F)c(N8CCC(=O)NC8=O)nn9C)C(F)(F)C7)CC6)c5)cn5ncc(C#N)c45)cn2)C3)cn1] |
| 201 | 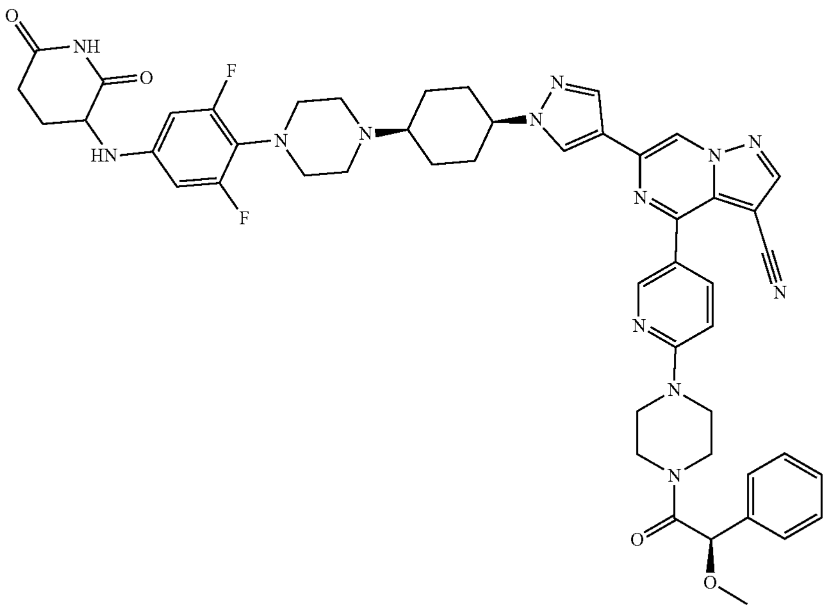 [SMILES: CO[C@@H](C(=O)N1CCN(c2ccc(-c3nc(-c4cnn([C@H]5CC[C@@H](N6CCN(c7c(F)cc(NC8CCC(=O)NC8=O)cc7F)CC6)CC5)c4)cn4ncc(C#N)c34)cn2)CC1)c1ccccc1] |

TABLE 1B-continued
| Biological Data | |
|---|---|
| Cmpd # | Structure |
| 202 | 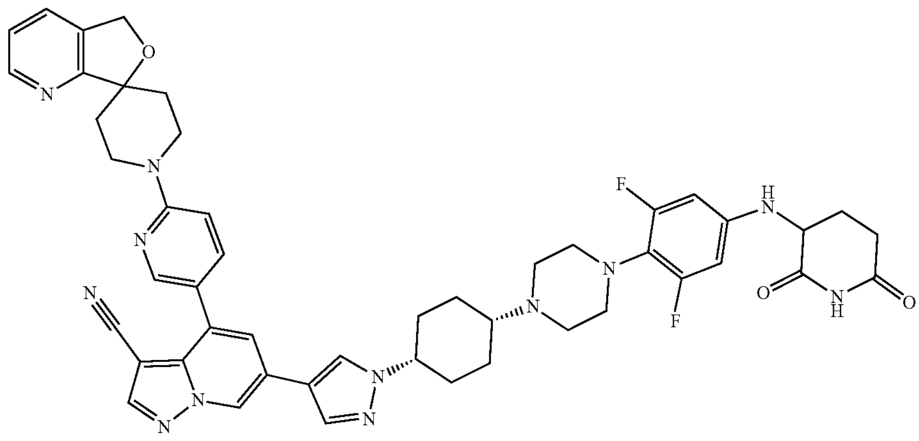 [SMILES: N#Cc1cnn2cc(-c3cnn([C@H]4CC[C@@H](N5CCN(c6c(F)cc(NC7CCC(=O)NC7=O)cc6F)CC5)CC4)c3)cc(-c3ccc(N4CCC5(CC4)OCc4cccnc45)nc3)c12] |
| 203 | 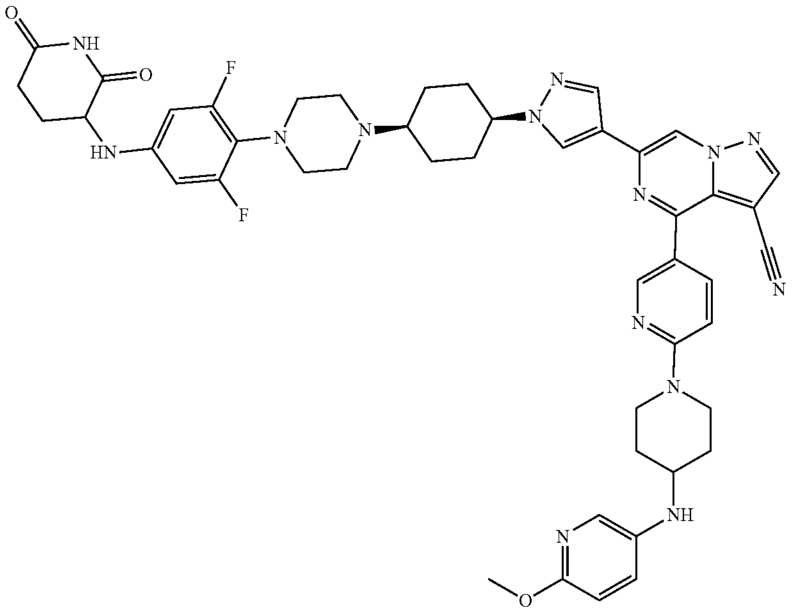 [SMILES: COc1ccc(NC2CCN(c3ccc(-c4nc(-c5cnn([C@H]6CC[C@@H](N7CCN(c8c(F)cc(NC9CCC(=O)NC9=O)cc8F)CC7)CC6)c5)cn5ncc(C#N)c45)cn3)CC2)cn1] |

TABLE 1B-continued
| Biological Data | |
|---|---|
| Cmpd # | Structure |
| 204 | 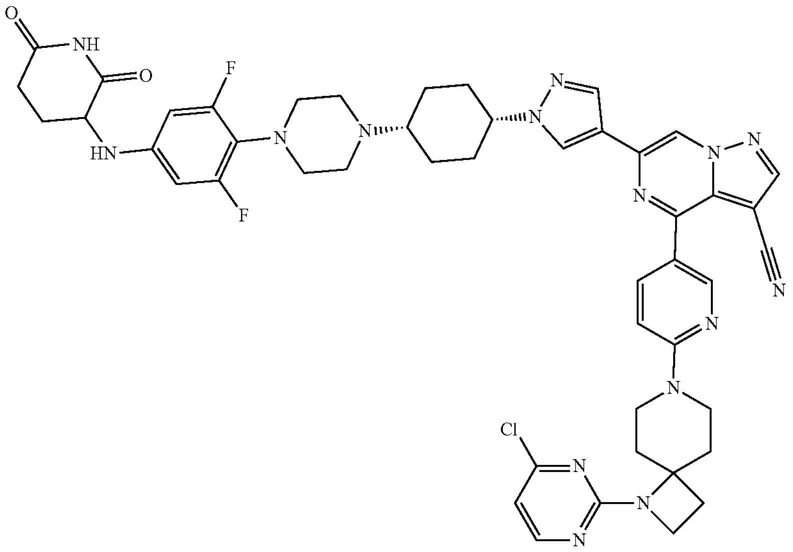 [SMILES: N#Cc1cnn2cc(-c3cnn([C@H]4CC[C@@H](N5CCN(c6c(F)cc(NC7CCC(=O)NC7=O)cc6F)CC5)CC4)c3)nc(-c3ccc(N4CCC5(CC4)CCN5c4nccc(Cl)n4)nc3)c12] |
| 205 | 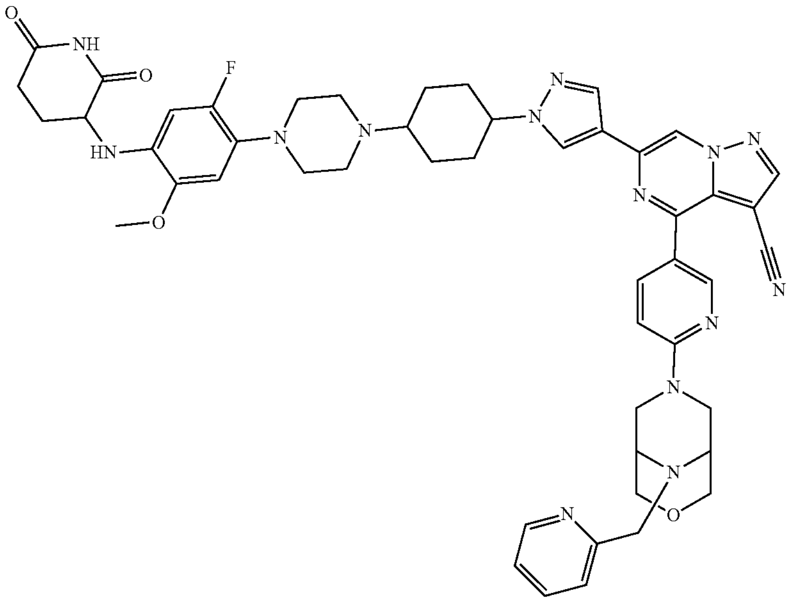 [SMILES: COc1cc(N2CCN(C3CCC(n4cc(-c5cn6ncc(C#N)c6c(-c6ccc(N7CC8COCC(C7)N8Cc7ccccn7)nc6)n5)cn4)CC3)CC2)c(F)cc1NC1CCC(=O)NC1=O] |

TABLE 1B-continued
| Biological Data | |
|---|---|
| Cmpd # | Structure |
| 206 | 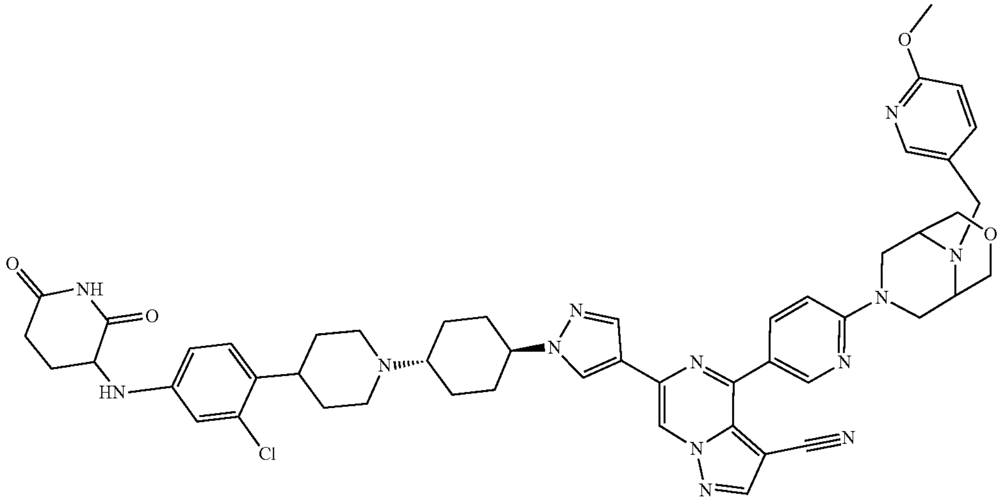 |
| 207 | 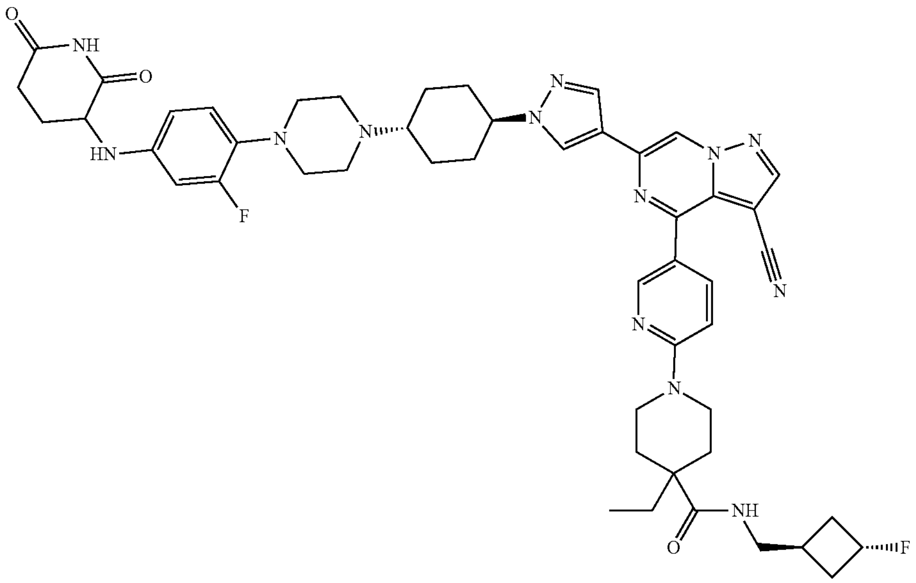 [SMILES: CCC1(C(=O)NC[C@H]2C[C@H](F)C2)CCN(c2ccc(-c3nc(-c4cnn([C@H]5CC[C@H](N6CCN(c7ccc(NC8CCC(=O)NC8=O)cc7F)CC6)CC5)c4)cn4ncc(C#N)c34)cn2)CC1] |

TABLE 1B-continued
| Biological Data | |
|---|---|
| Cmpd # | Structure |
| 208 | 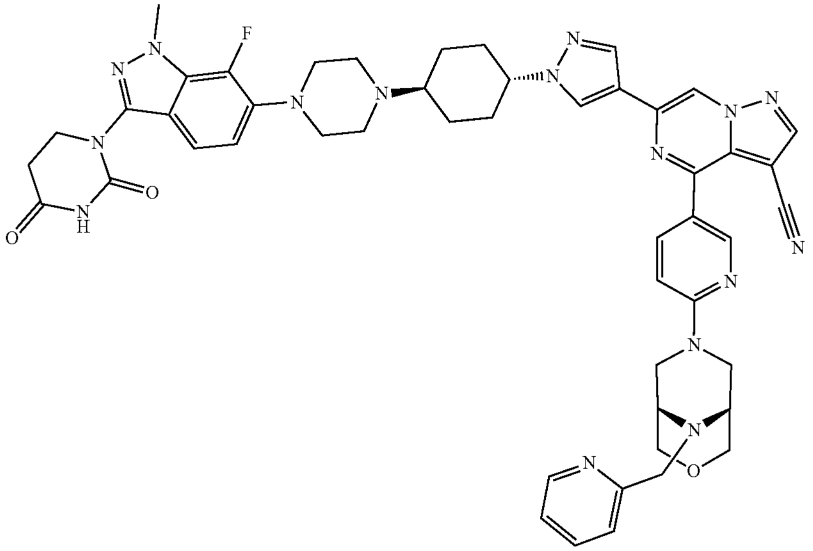 [SMILES: Cn1nc(N2CCC(=O)NC2=O)c2ccc(N3CCN([C@H]4CC[C@H](n5cc(-c6cn7ncc(C#N)c7c(-c7ccc(N8C[C@H]9COC[C@@H](C8)N9Cc8ccccn8)nc7)n6)cn5)CC4)CC3)c(F)c21] |
| 209 | 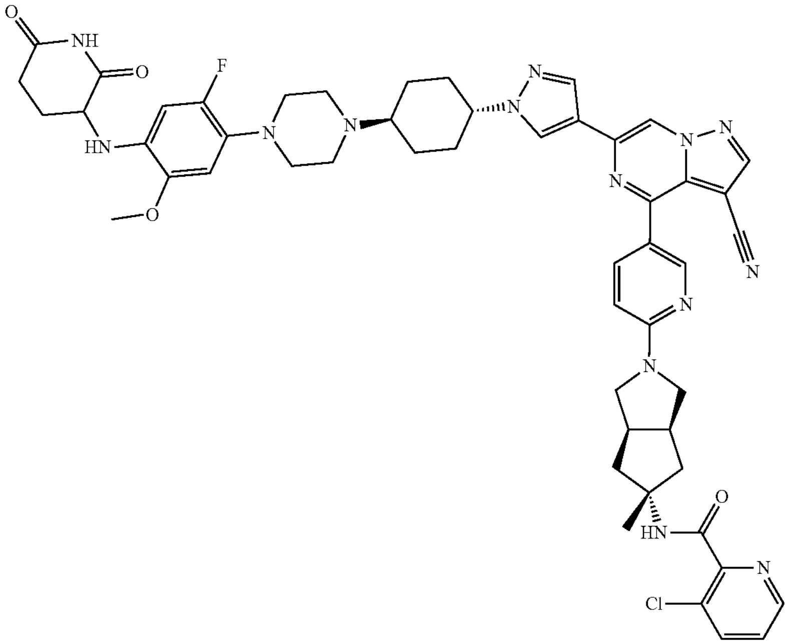 [SMILES: COc1cc(N2CCN([C@H]3CC[C@H](n4cc(-c5cn6ncc(C#N)c6c(-c6ccc(N7C[C@@H]8C[C@@](C)(NC(=O)c9ncccc9Cl)C[C@@H]8C7)nc6)n5)cn4)CC3)CC2)c(F)cc1NC1CCC(=O)NC1=O] |

TABLE 1B-continued
| Biological Data | |
|---|---|
| Cmpd # | Structure |
| 210 | 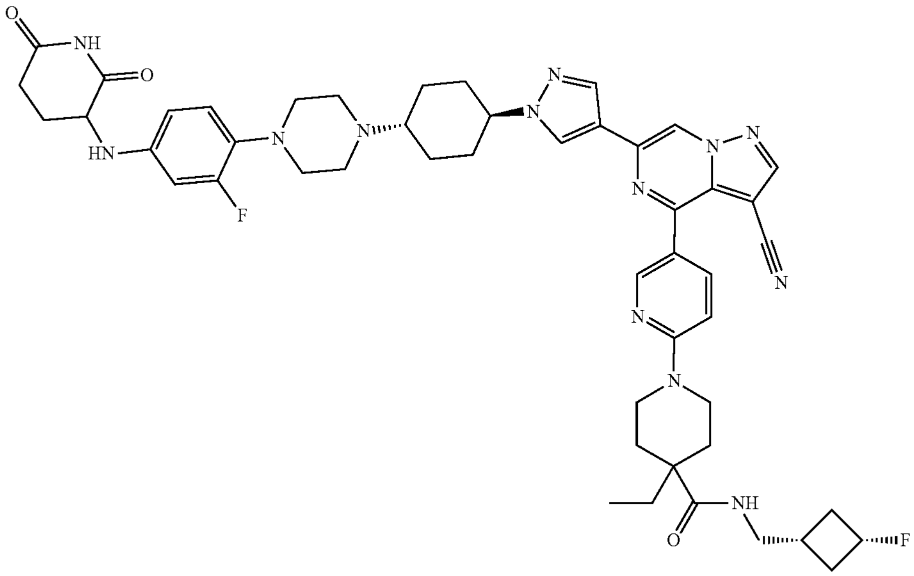 [SMILES: CCC1(C(=O)NC[C@H]2C[C@@H](F)C2)CCN(c2ccc(-c3nc(-c4cnn([C@H]5CC[C@H](N6CCN(c7ccc(NC8CCC(=O)NC8=O)cc7F)CC6)CC5)c4)cn4ncc(C#N)c34)cn2)CC1] |
| 211 | 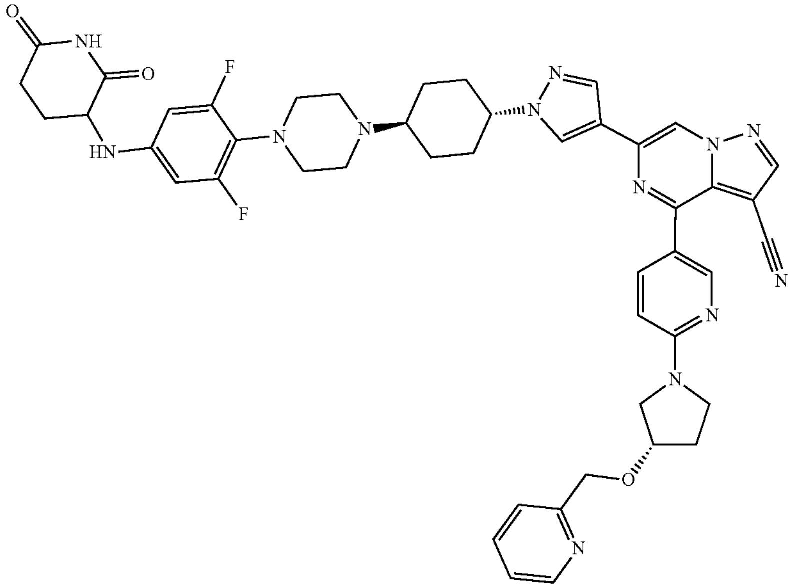 [SMILES: N#Cc1cnn2cc(-c3cnn([C@H]4CC[C@H](N5CCN(c6c(F)cc(NC7CCC(=O)NC7=O)cc6F)CC5)CC4)c3)nc(-c3ccc(N4CC[C@H](OCc5ccccn5)C4)nc3)c12] |

TABLE 1B-continued
| Biological Data | |
|---|---|
| Cmpd # | Structure |
| 212 | 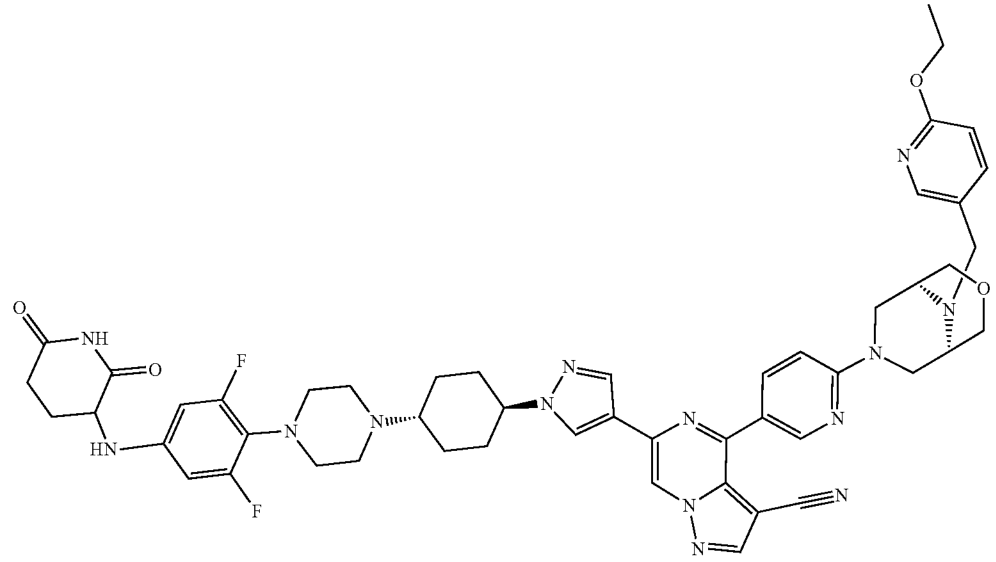 [SMILES: CCOc1ccc(CN2[C@@H]3COC[C@H]2CN(c2ccc(-c4nc(-c5cnn([C@H]6CC[C@H](N7CCN(c8c(F)cc(NC9CCC(=O)NC9=O)cc8F)CC7)CC6)c5)cn5ncc(C#N)c45)cn2)C3)cn1] |
| 213 | 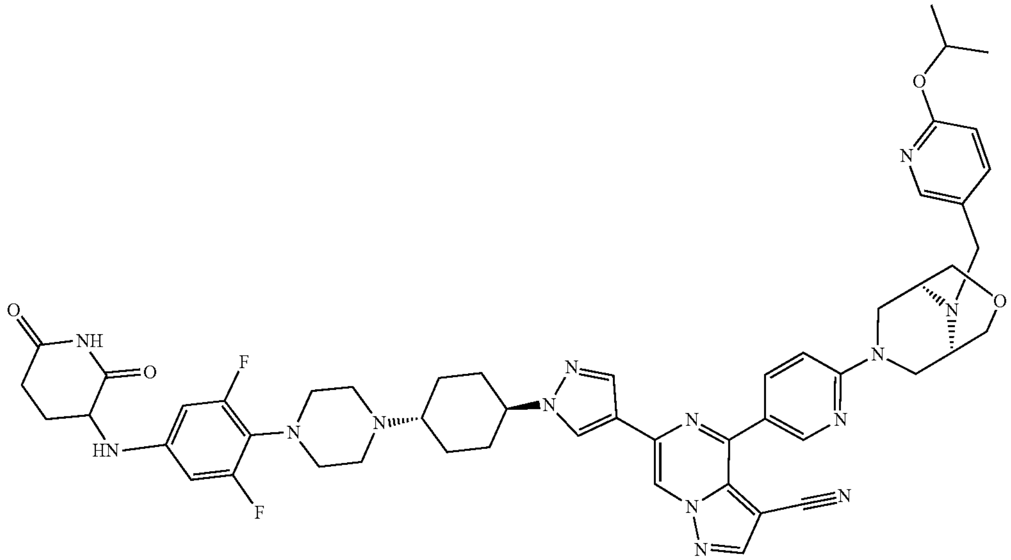 [SMILES: CC(C)Oc1ccc(CN2[C@@H]3COC[C@H]2CN(c2ccc(-c4nc(-c5cnn([C@H]6CC[C@H](N7CCN(c8c(F)cc(NC9CCC(=O)NC9=O)cc8F)CC7)CC6)c5)cn5ncc(C#N)c45)cn2)C3)cn1] |

TABLE 1B-continued
| Biological Data | |
|---|---|
| Cmpd # | Structure |
| 214 | 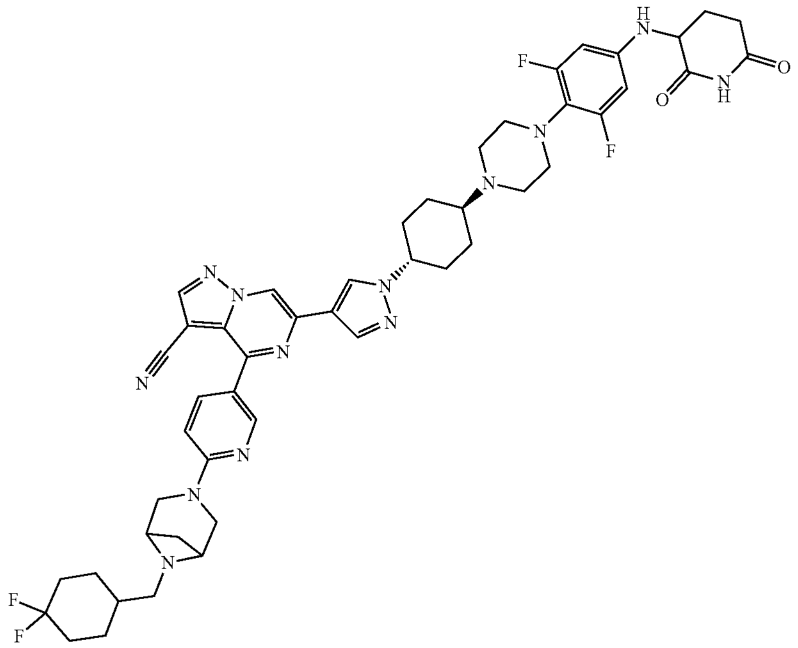 [SMILES: N#Cc1cnn2cc(-c3cnn([C@H]4CC[C@H](N5CCN(c6c(F)cc(NC7CCC(=O)NC7=O)cc6F)CC5)CC4)c3)nc(-c3ccc(N4CC5CC(C4)N5CC4CCC(F)(F)CC4)nc3)c12] |
| 215 | 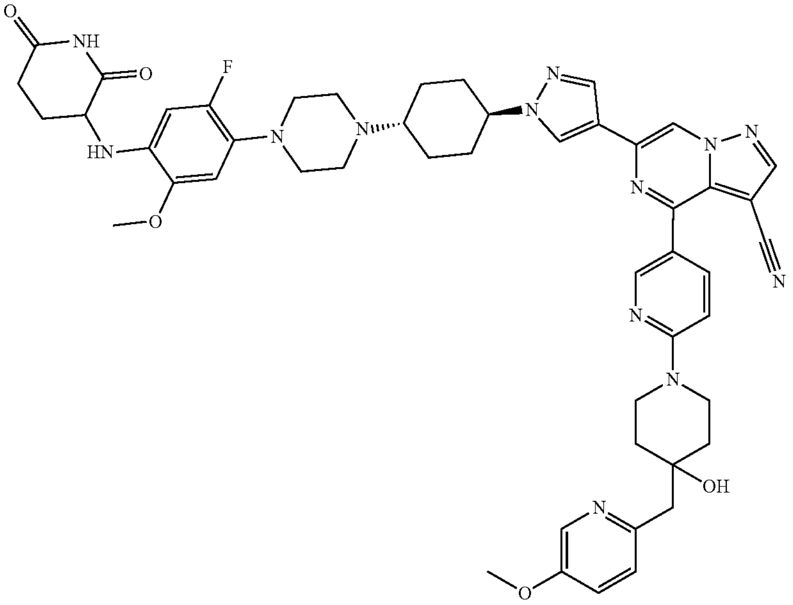 [SMILES: COc1ccc(CC2(O)CCN(c3ccc(-c4nc(-c5cnn([C@H]6CC[C@H](N7CCN(c8cc(OC)c(NC9CCC(=O)NC9=O)cc8F)CC7)CC6)c5)cn5ncc(C#N)c45)cn3)CC2)nc1] |

TABLE 1B-continued
| Biological Data | |
|---|---|
| Cmpd # | Structure |
| 216 | 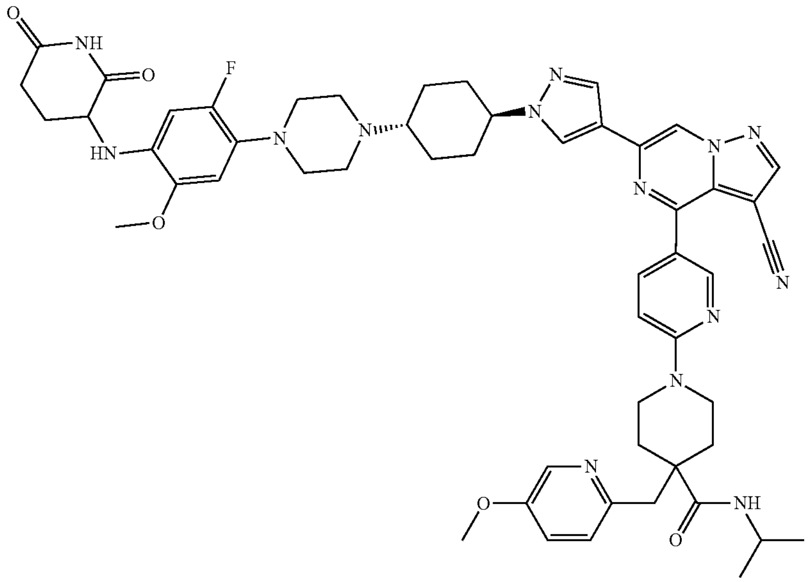 [SMILES: COc1ccc(CC2(C(=O)NC(C)C)CCN(c3ccc(-c4nc(-c5cnn([C@H]6CC[C@H](N7CCN(c8cc(OC)c(NC9CCC(=O)NC9=O)cc8F)CC7)CC6)c5)cn5ncc(C#N)c45)cn3)CC2)nc1] |
| 217 | 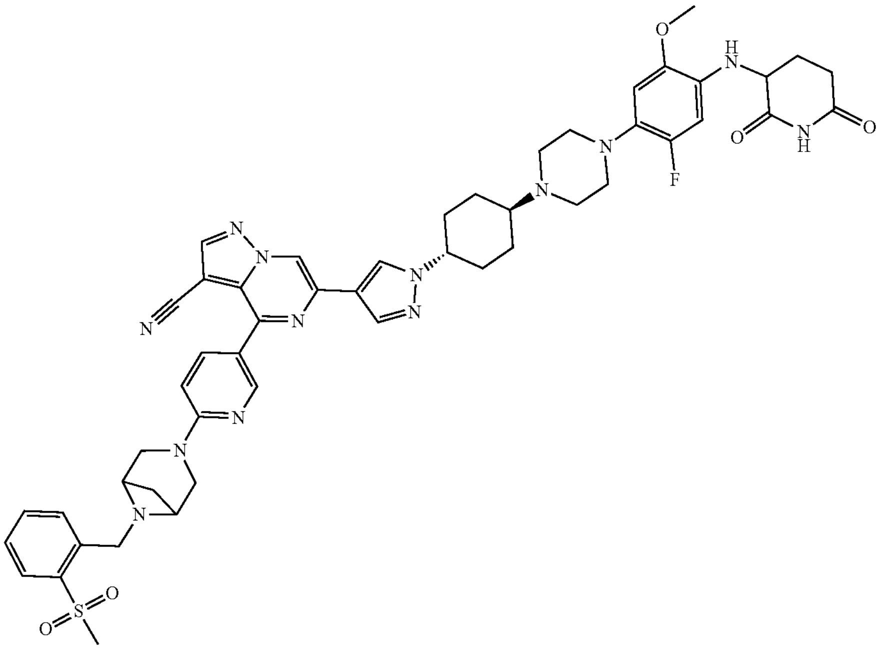 |

TABLE 1B-continued
| Biological Data | |
|---|---|
| Cmpd # | Structure |
| 218 | 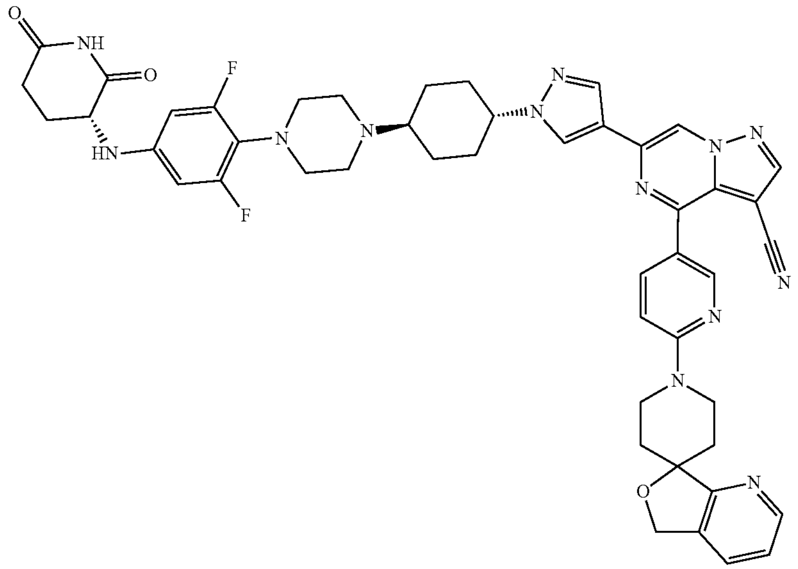 [SMILES: N#Cc1cnn2cc(-c3cnn([C@H]4CC[C@H](N5CCN(c6c(F)cc(N[C@@H]7CCC(=O)NC7=O)cc6F)CC5)CC4)c3)nc(-c3ccc(N4CCC5(CC4)OCc4cccnc45)nc3)c12] |
| 219 | 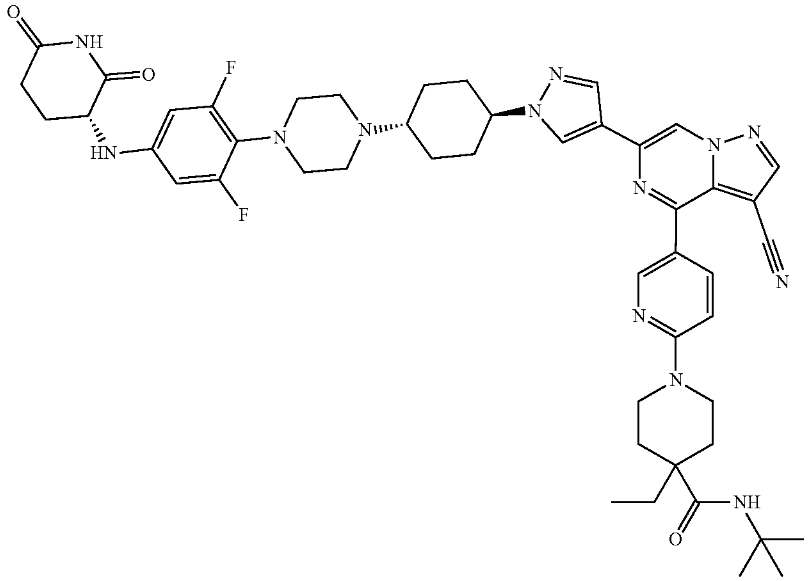 [SMILES: CCC1(C(=O)NC(C)(C)C)CCN(c2ccc(-c3nc(-c4cnn([C@H]5CC[C@H](N6CCN(c7c(F)cc(N[C@@H]8CCC(=O)NC8=O)cc7F)CC6)CC5)c4)cn4ncc(C#N)c34)cn2)CC1] |

TABLE 2A

| Biological Data | | | | | | | |
|---|---|---|---|---|---|---|---|
| | | HiBiT-Degradation | | | | | |
| Compound | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| 1 | 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-[4-[(1R)-1-(2-pyridyl)ethyl]piperazin-1-yl]-3-pyridyl]pyrazolo[1,5-a]pyrazine-3-carbonitrile | ++++ | ++++ | +++ | ++++ | ++++ | ++++ |
| 2 | 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-N-isopropyl-4-methyl-piperidine-4-carboxamide | ++++ | ++++ | +++ | ++++ | ++++ | ++++ |
| 3 | 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-4-ethyl-N-isopropyl-piperidine-4-carboxamide | ++++ | ++++ | ++++ | ++++ | ++++ | ++++ |
| 4 | 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyridin-4-yl]-2-pyridyl]-4-ethyl-N-isopropyl-piperidine-4-carboxamide | ++++ | ++++ | ++++ | ++++ | ++++ | ++++ |
| 5 | 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[4-[2-(5-fluoro-2-pyridyl)acetyl]piperazin-1-yl]-3-pyridyl]pyrazolo[l, | ++++ | ++++ | ++++ | ++++ | ++++ | ++++ |

TABLE 2A-continued

| Biological Data | | | | | | | |
|---|---|---|---|---|---|---|---|
| Compound | | HiBiT-Degradation | | | | | |
| | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | 5-a]pyridine-3-carbonitrile | | | | | | |
| 6 | 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-N-isopropyl-4-methoxy-piperidine-4-carboxamide | ++++ | ++++ | +++ | ++++ | ++++ | ++++ |
| 8 | 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-N-cyclobutyl-4-ethyl-piperidine-4-carboxamide | ++++ | ++++ | ++++ | ++++ | ++++ | ++++ |
| 9 | 1-[5-[3-cyano-6-[1-[1-[2-[3-[4-[(2,6-dioxo-3-piperidyl)amino]phenyl]-8-azabicyclo[3.2.1]octan-8-yl]acetyl]-4-piperidyl]pyrazol-4-yl]pyrazolo[1,5-a]pyrazin-4-yl]-2-pyridyl]-4-ethyl-N-isopropyl-piperidine-4-carboxamide | +++ | ++++ | ++++ | ++++ | ++++ | ++++ |
| 10 | 1-[5-[6-[1-[1-[2-[1-[2-chloro-4-[[(3S)-2,6-dioxo-3-piperidyl]amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-isopropyl-piperidine-4-carboxamide | ++++ | ++++ | ++++ | ++++ | ++++ | ++++ |
| 11 | 1-[5-[6-[1-[1-[2-[1-[2-chloro-4-[[(3R)-2,6-dioxo-3-piperidyl]amino]phenyl]-4-hydroxy-4-piperidyl]acetyl]-4-piperidyl]pyrazol-4-yl]-3-cyano- | ++++ | ++++ | ++++ | ++++ | ++++ | ++++ |

TABLE 2A-continued

| Biological Data | | | | | | | |
|---|---|---|---|---|---|---|---|
| Compound | | HiBiT-Degradation | | | | | |
| | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | pyrazolo[1,5-a]pyrazin-4-yl]-2-pyridyl]-4-ethyl-N-isopropyl-piperidine-4-carboxamide | | | | | | |
| 12 | 6-[1-[1-[2-[4-[4-[(2,6-dioxo-3-piperidyl)amino]-2-fluoro-phenyl]-1-piperidyl]ethyl]-4-piperidyl]pyrazol-4-yl]-4-[6-[4-(2-pyridylmethyl)piperazin-1-yl]-3-pyridyl]pyrazolo[1,5-a]pyridine-3-carbonitrile | +++ | ++++ | +++ | ++++ | ++++ | ++++ |
| 13 | 6-[1-[1-[2-[4-[3-(2,4-dioxohexahydropyrimidin-1-yl)-1-methyl-indazol-6-yl]-1-piperidyl]acetyl]-4-piperidyl]pyrazol-4-yl]-4-[6-[4-(2-pyridylmethyl)piperazin-1-yl]-3-pyridyl]pyrazolo[1,5-a]pyridine-3-carbonitrile | +++ | ++++ | +++ | ++++ | ++++ | ++++ |
| 14 | 1-[5-[6-[1-[1-[2-[1-[2-chloro-4-[(2,6-dioxo-3-piperidyl)amino]phenyl]-4-hydroxy-4-piperidyl]acetyl]-4-piperidyl]pyrazol-4-yl]-3-cyano-pyrazolo[1,5-a]pyrazin-4-yl]-2-pyridyl]-4-ethyl-N-isopropyl-piperidine-4-car | ++++ | ++++ | ++++ | ++++ | ++++ | ++++ |
| 15 | 6-[1-[1-[2-[4-[4-[(2,6-dioxo-3-piperidyl)amino]phenyl]-1-piperidyl]acetyl]-4-piperidyl]pyrazol-4-yl]-4-[6-[4-[2-(5-fluoro-2-pyridyl)acetyl]piperazin-1-yl]-3-pyridyl]pyrazolo[1,5-a]pyridine-3-carbonitrile | +++ | ++++ | ++++ | ++++ | ++++ | ++++ |
| 16 | 6-[4-[4-[2-[4-[4-[(2,6-dioxo-3-piperidyl)amino]-2-fluoro-phenyl]-1-piperidyl]acetyl]piperazin-1-yl]phenyl]-4-[6-[4- | +++ | ++++ | ++++ | ++++ | ++++ | ++++ |

TABLE 2A-continued

Biological Data

| Compound | | HiBiT-Degradation | | | | | |
|---|---|---|---|---|---|---|---|
| # | Name | 293T.165 RET(KD: 658-1114 G810R) 6.0 hours (DC50) [nM] | 293T.165 RET(KD: 658-1114 G810R) 6.0 hours (IP) [nM] | 293T.165 RET(KD: 658-1114 G810R) 6.0 hours (Emax) | 293T.144 RET (658-1114) 6.0 hours (DC50) [nM] | 293T.144 RET (658-1114) 6.0 hours (IP) [nM] | 293T.144 RET (658-1114) 6.0 hours (Emax) |
| | [2-(5-fluoro-2-pyridyl)acetyl] piperazin-1-yl]-3-pyridyl]pyrazolo[1,5-a]pyridine-3-carbonitrile | | | | | | |
| 17 | 4-[6-(3-azabicyclo[3.1.0] hexan-3-yl)-3-pyridyl]-6-[4-[4-[2-[4-[4-[(2,6-dioxo-3-piperidyl)amino] phenyl]-1-piperidyl]acetyl] piperazin-1-yl]phenyl]pyrazolo[1,5-a]pyridine-3-carbonitrile | ++++ | ++++ | ++++ | ++++ | ++++ | ++++ |
| 18 | 6-[4-[4-[2-[4-[4-[(2,6-dioxo-3-piperidyl)amino] phenyl]-1-piperidyl]acetyl] piperazin-1-yl]phenyl]-4-[6-[4-[2-(2-pyridyl)ethyl] piperazin-1-yl]-3-pyridyl]pyrazolo[1,5-a]pyridine-3-carbonitrile | +++ | ++++ | ++++ | ++++ | ++++ | ++++ |
| 19 | 6-[4-[4-[2-[4-[4-[(2,6-dioxo-3-piperidyl)amino] phenyl]-1-piperidyl]acetyl] piperazin-1-yl]phenyl]-4-[6-(8-oxa-3-azabicyclo[3.2.1] octan-3-yl)-3-pyridyl]pyrazolo[1,5-a]pyridine-3-carbonitrile | +++ | ++++ | +++ | ++++ | ++++ | ++++ |
| 20 | 4-[6-(4-anilino-1-piperidyl)-3-pyridyl]-6-[4-[4-[2-[4-[4-[(2,6-dioxo-3-piperidyl)amino] phenyl]-1-piperidyl]acetyl] piperazin-1-yl] phenyl]pyrazolo [1,5-a]pyridine-3-carbonitrile | +++ | +++ | ++++ | ++++ | ++++ | ++++ |
| 22 | 4-[6-(6-benzyl-3,6-diazabicyclo[3.1.1] heptan-3-yl)-3-pyridyl]-6-[4-[4-[2-[4-[4-[(2,6-dioxo-3-piperidyl)amino] phenyl]-1-piperidyl]acetyl] piperazin-1-yl]phenyl]pyrazolo | +++ | ++++ | ++++ | ++++ | ++++ | ++++ |

TABLE 2A-continued

| Biological Data | | | | | | | |
|---|---|---|---|---|---|---|---|
| Compound | | HiBiT-Degradation | | | | | |
| | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | [1,5-a]pyridine-3-carbonitrile | | | | | | |
| 23 | N-[1-[5-[3-cyano-6-[4-[4-[2-[4-[4-[(2,6-dioxo-3-piperidyl)amino]-2-fluoro-phenyl]-1-piperidyl]acetyl]piperazin-1-yl]phenyl]pyrazolo[1,5-a]pyridin-4-yl]-2-pyridyl]-4-methyl-4-piperidyl]-2-phenyl-acetamide | +++ | +++ | ++++ | ++++ | ++++ | ++++ |
| 24 | 6-[4-[4-[2-[4-[4-[(2,6-dioxo-3-piperidyl)amino]phenyl]-1-piperidyl]acetyl]piperazin-1-yl]phenyl]-4-(6-morpholino-3-pyridyl)pyrazolo[1,5-a]pyridine-3-carbonitrile | +++ | ++++ | +++ | ++++ | ++++ | ++++ |
| 25 | N-tert-butyl-1-[5-[3-cyano-6-[4-[4-[2-[4-[4-[(2,6-dioxo-3-piperidyl)amino]-2-fluoro-phenyl]-1-piperidyl]acetyl]piperazin-1-yl]phenyl]pyrazolo[1,5-a]pyridin-4-yl]-2-pyridyl]-4-methyl-piperidine-4-carboxamide | +++ | ++++ | +++ | ++++ | ++++ | ++++ |
| 26 | 6-[4-[4-[2-[1-[4-[(2,6-dioxo-3-piperidyl)amino]-2-fluoro-phenyl]-4-hydroxy-4-piperidyl]acetyl]piperazin-1-yl]phenyl]-4-[6-[4-[2-(5-fluoro-2-pyridyl)acetyl]piperazin-1-yl]-3-pyridyl]pyrazolo[1,5-a]pyridine-3-carbonitrile | ++++ | ++++ | +++ | ++++ | ++++ | ++++ |
| 27 | 4-[6-(4-acetylpiperazin-1-yl)-3-pyridyl]-6-[4-[4-[2-[4-[4-[(2,6-dioxo-3-piperidyl)amino]phenyl]-1-piperidyl]acetyl]piperazin-1-yl]phenyl]pyrazolo[1,5-a]pyrazine-3-carbonitrile | ++++ | ++++ | ++++ | ++++ | ++++ | ++++ |

TABLE 2A-continued

| Biological Data | | | | | | | |
|---|---|---|---|---|---|---|---|
| | | HiBiT-Degradation | | | | | |
| Compound | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| 28 | 6-[4-[4-[2-[4-[4-[(2,6-dioxo-3-piperidyl)amino]-2-fluoro-phenyl]-1-piperidyl]acetyl]piperazin-1-yl]phenyl]-4-[6-[4-(2-pyridylmethyl)piperazin-1-yl]-3-pyridyl]pyrazolo[1,5-a]pyridine-3-carbonitrile | +++ | ++++ | ++++ | ++++ | ++++ | ++++ |
| 30 | 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide | ++++ | ++++ | +++ | ++++ | ++++ | ++++ |
| 31 | 1-[5-[3-cyano-6-[1-[1-[2-[4-[4-[(2,6-dioxo-3-piperidyl)amino]phenyl]-1-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide | ++++ | ++++ | ++++ | ++++ | ++++ | ++++ |
| 32 | 1-[5-[3-cyano-6-[4-[4-[2-[1-[4-[(2,6-dioxo-3-piperidyl)amino]-2-fluoro-phenyl]-4-hydroxy-4-piperidyl]acetyl]piperazin-1-yl]phenyl]pyrazolo[1,5-a]pyridin-4-yl]-2-pyridyl]-N-isopropyl-4-methyl-piperidine-4-carboxamide | ++++ | ++++ | +++ | ++++ | ++++ | ++++ |
| 34 | 1-[5-[3-cyano-6-[1-[(1r,4r)-4-[2-[4-[4-[(2,6-dioxo-3-piperidyl)amino]-2-fluoro-phenyl]-1-piperidyl]ethyl]cyclohexyl]pyrazol-4-yl]pyrazolo[1,5-a]pyridin-4-yl]-2-pyridyl]-N-isopropyl-4- | ++++ | ++++ | ++++ | ++++ | ++++ | ++++ |

TABLE 2A-continued

| Biological Data | | | | | | | |
|---|---|---|---|---|---|---|---|
| | | HiBiT-Degradation | | | | | |
| Compound | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | methyl-piperidine-4-carboxamide | | | | | | |
| 35 | 1-[5-[3-cyano-6-[4-[4-[2-[4-[4-[(2,6-dioxo-3-piperidyl)amino] phenyl]-1-piperidyl]acetyl] piperazin-1-yl]phenyl]pyrazolo [1,5-a]pyridin-4-yl]-2-pyridyl]-N-isopropyl-4-methyl-piperidine-4-carboxamide | ++++ | ++++ | ++++ | ++++ | ++++ | ++++ |
| 36 | 6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]-4-[6-(4-pyrimidin-2-yl-1-piperidyl)-3-pyridyl]pyrazolo[1,5-a]pyrazine-3-carbonitrile | ++++ | ++++ | ++++ | ++++ | ++++ | ++++ |
| 38 | 6-[1-[1-[2-[4-[4-[(2,6-dioxo-3-piperidyl)oxy]-2-fluoro-phenyl]-1-piperidyl]acetyl]-4-piperidyl]pyrazol-4-yl]-4-[4-[4-[(4-fluoro-2-pyridyl)methyl] piperazin-1-yl] phenyl]pyrazolo [1,5-a]pyrazine-3-carbonitrile | +++ | ++++ | +++ | ++++ | ++++ | ++++ |
| 39 | 1-[5-[3-cyano-6-[4-[4-[2-[4-[4-[(2,6-dioxo-3-piperidyl)amino]-2-fluoro-phenyl]-1-piperidyl]ethyl]-4-hydroxy-1-piperidyl]phenyl] pyrazolo[1,5-a]pyridin-4-yl]-2-pyridyl]-4-ethyl-N-isopropyl-piperidine-4-carboxamide | ++++ | ++++ | ++++ | ++++ | ++++ | ++++ |
| 40 | 1-[5-[3-cyano-6-[1-[(1r,4r)-4-[2-[4-[4-[(2,6-dioxo-3-piperidyl)amino]-2-fluoro-phenyl]-1-piperidyl]ethyl] cyclohexyl]pyrazol-4-yl]pyrazolo[1,5-a]pyridin-4-yl]-2-pyridyl]-4-ethyl-N- | ++++ | ++++ | ++++ | ++++ | ++++ | ++++ |

TABLE 2A-continued

Biological Data

| Compound # | Name | HiBiT-Degradation 293T.165 RET(KD: 658-1114 G810R) 6.0 hours (DC50) [nM] | 293T.165 RET(KD: 658-1114 G810R) 6.0 hours (IP) [nM] | 293T.165 RET(KD: 658-1114 G810R) 6.0 hours (Emax) | 293T.144 RET (658-1114) 6.0 hours (DC50) [nM] | 293T.144 RET (658-1114) 6.0 hours (IP) [nM] | 293T.144 RET (658-1114) 6.0 hours (Emax) |
|---|---|---|---|---|---|---|---|
| | tetrahydropyran-4-yl-piperidine-4-carboxamide | | | | | | |
| 41 | 4-[6-(4-acetylpiperazin-1-yl)-3-pyridyl]-6-[4-[4-[2-[4-[4-[(2,6-dioxo-3-piperidyl)amino]phenyl]-1-piperidyl]acetyl]piperazin-1-yl]phenyl]pyrazolo[1,5-a]pyridine-3-carbonitrile | +++ | ++++ | +++ | ++++ | ++++ | ++++ |
| 42 | 4-[6-(4-acetylpiperazin-1-yl)-3-pyridyl]-6-[1-[1-[2-[4-[4-[(2,6-dioxo-3-piperidyl)amino]phenyl]-1-piperidyl]acetyl]-4-piperidyl]pyrazol-4-yl]pyrazolo[1,5-a]pyridine-3-carbonitrile | +++ | ++++ | +++ | ++++ | ++++ | ++++ |
| 43 | 4-[6-(dimethylamino)-3-pyridyl]-6-[1-[(1s,4s)-4-[2-[4-[4-[(2,6-dioxo-3-piperidyl)amino]phenyl]-1-piperidyl]ethyl]cyclohexyl]pyrazol-4-yl]pyrazolo[1,5-a]pyridine-3-carbonitrile | +++ | ++++ | +++ | ++++ | ++++ | ++++ |
| 44 | 4-[6-(dimethylamino)-3-pyridyl]-6-[4-[4-[2-[4-[4-[(2,6-dioxo-3-piperidyl)oxy]phenyl]-1-piperidyl]acetyl]piperazin-1-yl]phenyl]pyrazolo[1,5-a]pyridine-3-carbonitrile | +++ | ++++ | +++ | ++++ | ++++ | ++++ |
| 45 | 1-[5-[3-cyano-6-[4-[4-[2-[4-[4-[(2,6-dioxo-3-piperidyl)amino]-2-fluoro-phenyl]-1-piperidyl]acetyl]piperazin-1-yl]phenyl]pyrazolo[1,5-a]pyridin-4-yl]-2-pyridyl]-N-isopropyl-4-methyl-piperidine-4-carboxamide | +++ | ++++ | ++++ | ++++ | ++++ | ++++ |

TABLE 2A-continued

| Biological Data | | | | | | | |
|---|---|---|---|---|---|---|---|
| | | HiBiT-Degradation | | | | | |
| Compound | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| 46 | 4-[6-(4-anilino-1-piperidyl)-3-pyridyl]-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridine-3-carbonitrile | +++ | ++++ | +++ | ++++ | ++++ | ++++ |
| 47 | 1-[5-[3-cyano-6-[4-[4-[2-[4-[4-[(2,6-dioxo-3-piperidyl)oxy]-2-fluoro-phenyl]-1-piperidyl]acetyl]piperazin-1-yl]phenyl]pyrazolo[1,5-a]pyridin-4-yl]-2-pyridyl]-N-isopropyl-4-methyl-piperidine-4-carboxamide | +++ | ++++ | ++++ | ++++ | ++++ | ++++ |
| 48 | 1-[5-[3-cyano-6-[4-[4-[2-[4-[4-[(2,6-dioxo-3-piperidyl)oxy]phenyl]-1-piperidyl]acetyl]piperazin-1-yl]phenyl]pyrazolo[1,5-a]pyridin-4-yl]-2-pyridyl]-N-isopropyl-4-methyl-piperidine-4-carboxamide | +++ | ++++ | ++++ | ++++ | ++++ | ++++ |
| 49 | 6-[4-[4-[2-[1-[4-[(2,6-dioxo-3-piperidyl)amino]phenyl]-4-hydroxy-4-piperidyl]acetyl]piperazin-1-yl]phenyl]-4-[6-[4-[2-(5-fluoro-2-pyridyl)acetyl]piperazin-1-yl]-3-pyridyl]pyrazolo[1,5-a]pyridine-3-carbonitrile | +++ | ++++ | +++ | ++++ | ++++ | ++++ |
| 50 | 1-[4-[3-cyano-6-[4-[4-[2-[4-[4-[(2,6-dioxo-3-piperidyl)amino]-2-fluoro-phenyl]-1-piperidyl]acetyl]piperazin-1-yl]phenyl]pyrazolo[1,5-a]pyridin-4-yl]phenyl]-N-isopropyl-4-methyl-piperidine-4-carboxamide | +++ | ++++ | ++++ | ++++ | ++++ | ++++ |
| 51 | 6-[1-[1-[2-[4-[4-[(2,6-dioxo-3- | +++ | ++++ | +++ | ++++ | ++++ | ++++ |

TABLE 2A-continued

| Compound | | Biological Data HiBiT-Degradation 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
|---|---|---|---|---|---|---|---|
| # | Name | [nM] | [nM] | (Emax) | [nM] | [nM] | (Emax) |
| | piperidyl)amino]-2-fluoro-phenyl]-1-piperidyl]acetyl]-4-piperidyl]pyrazol-4-yl]-4-[6-[4-[2-(5-fluoro-2-pyridyl)acetyl]piperazin-1-yl]-3-pyridyl]pyrazolo[1,5-a]pyrazine-3-carbonitrile | | | | | | |
| 52 | 6-[4-[4-[2-[4-[4-[(2,6-dioxo-3-piperidyl)amino]-2-fluoro-phenyl]-1-piperidyl]acetyl]piperazin-1-yl]phenyl]-4-[6-[4-[2-(5-fluoro-2-pyridyl)acetyl]piperazin-1-yl]-3-pyridyl]pyrazolo[1,5-a]pyrazine-3-carbonitrile | +++ | ++++ | +++ | ++++ | ++++ | ++++ |
| 53 | 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide | ++++ | ++++ | +++ | ++++ | ++++ | ++++ |
| 54 | 4-[6-(6-benzyl-3,6-diazabicyclo[3.1.1]heptan-3-yl)-3-pyridyl]-6-[4-[4-[2-[4-[4-[(2,6-dioxo-3-piperidyl)amino]-2-fluoro-phenyl]-1-piperidyl]acetyl]piperazin-1-yl]phenyl]pyrazolo[1,5-a]pyrazine-3-carbonitrile | +++ | ++++ | ++++ | ++++ | ++++ | ++++ |
| 55 | N-[1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]-2-pyridyl]-4-ethyl-4-piperidyl]-2-methyl-propanamide | ++++ | ++++ | +++ | ++++ | ++++ | ++++ |
| 56 | 1-[5-[3-cyano-6-[1-[1-[2-[4-[4-[(2,6-dioxo-3- | +++ | ++++ | +++ | ++++ | ++++ | ++++ |

TABLE 2A-continued

| Biological Data | | | | | | | |
|---|---|---|---|---|---|---|---|
| | | HiBiT-Degradation | | | | | |
| Compound | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | piperidyl)amino]-2-fluoro-phenyl]-1-piperidyl]acetyl]-4-piperidyl]pyrazol-4-yl]pyrazolo[1,5-a]pyridin-4-yl]-2-pyridyl]-N,4-diisopropyl-piperidine-4-carboxamide | | | | | | |
| 57 | 6-[1-[(1r,4r)-4-[2-[4-[4-[(2,6-dioxo-3-piperidyl)amino]-2-fluoro-phenyl]-1-piperidyl]ethyl]cyclohexyl]pyrazol-4-yl]-4-[6-[4-[2-(5-fluoro-2-pyridyl)acetyl]piperazin-1-yl]-3-pyridyl]pyrazolo[1,5-a]pyridine-3-carbonitrile | ++++ | ++++ | ++++ | ++++ | ++++ | ++++ |
| 58 | 1-[4-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]phenyl]-4-ethyl-N-isopropyl-piperidine-4-carboxamide | ++++ | ++++ | +++ | ++++ | ++++ | ++++ |
| 59 | 1-[5-[3-cyano-6-[1-[1-[2-[4-[4-[(2,6-dioxo-3-piperidyl)amino]-2-fluoro-phenyl]-1-piperidyl]acetyl]-4-piperidyl]pyrazol-4-yl]pyrazolo[1,5-a]pyridin-4-yl]pyrimidin-2-yl]-4-ethyl-N-isopropyl-piperidine-4-carboxamide | +++ | ++++ | +++ | ++++ | ++++ | ++++ |
| 60 | 6-[1-[(1r,4r)-4-[2-[4-[4-[(2,6-dioxo-3-piperidyl)amino]-2-fluoro-phenyl]-1-piperidyl]ethyl]cyclohexyl]pyrazol-4-yl]-4-[6-[4-[2-(5-fluoro-2-pyridyl)acetyl]piperazin-1-yl]-3-pyridyl]pyrazolo[1,5-a]pyrazine-3-carbonitrile | ++++ | ++++ | ++++ | ++++ | ++++ | ++++ |
| 61 | 6-[1-[1-[2-[4-[4-[(2,6-dioxo-3- | +++ | ++++ | +++ | ++++ | ++++ | ++++ |

TABLE 2A-continued

| Biological Data | | | | | | | |
|---|---|---|---|---|---|---|---|
| Compound | | HiBiT-Degradation | | | | | |
| # | Name | 293T.165 RET(KD: 658-1114 G810R) 6.0 hours (DC50) [nM] | 293T.165 RET(KD: 658-1114 G810R) 6.0 hours (IP) [nM] | 293T.165 RET(KD: 658-1114 G810R) 6.0 hours (Emax) | 293T.144 RET (658-1114) 6.0 hours (DC50) [nM] | 293T.144 RET (658-1114) 6.0 hours (IP) [nM] | 293T.144 RET (658-1114) 6.0 hours (Emax) |
| | piperidyl)amino]-2-fluoro-phenyl]-1-piperidyl]acetyl]-4-piperidyl]pyrazol-4-yl]-4-[4-[4-(2-pyridylmethyl) piperazin-1-yl]phenyl]pyrazolo [1,5-a]pyrazine-3-carbonitrile | | | | | | |
| 62 | 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[8-(2-pyridylmethyl)-3,8-diazabicyclo[3.2.1] octan-3-yl]-3-pyridyl]pyrazolo[1,5-a]pyridine-3-carbonitrile | +++ | ++++ | +++ | ++++ | ++++ | ++++ |
| 63 | 1-[5-[3-cyano-6-[1-[1-[2-[4-[3-(2,4-dioxohexahydropyrimidin-1-yl)-1-methyl-indazol-6-yl]-1-piperidyl]acetyl]-4-piperidyl]pyrazol-4-yl]pyrazolo[1,5-a]pyridin-4-yl]-2-pyridyl]-4-ethyl-N-isopropyl-piperidine-4-carboxamide | +++ | ++++ | ++++ | ++++ | ++++ | ++++ |
| 64 | 1-[5-[3-cyano-6-[4-[4-[2-[4-[3-(2,4-dioxohexahydropyrimidin-1-yl)-1-methyl-indazol-6-yl]-1-piperidyl]acetyl] piperazin-1-yl]phenyl]pyrazolo [1,5-a]pyridin-4-yl]-2-pyridyl]-4-ethyl-N-isopropyl-piperidine-4-carboxamide | +++ | ++++ | ++++ | ++++ | ++++ | ++++ |
| 65 | 6-[4-[4-[2-[4-[3-(2,4-dioxohexahydropyrimidin-1-yl)-1-methyl-indazol-6-yl]-1-piperidyl]acetyl] piperazin-1-yl]phenyl]-4-[6-[4-(2-pyridylmethyl) piperazin-1-yl]-3- | +++ | +++ | +++ | ++++ | ++++ | ++++ |

TABLE 2A-continued

| Compound # | Compound Name | HiBiT-Degradation 293T.165 RET(KD: 658-1114 G810R) 6.0 hours (DC50) [nM] | 293T.165 RET(KD: 658-1114 G810R) 6.0 hours (IP) [nM] | 293T.165 RET(KD: 658-1114 G810R) 6.0 hours (Emax) | 293T.144 RET (658-1114) 6.0 hours (DC50) [nM] | 293T.144 RET (658-1114) 6.0 hours (IP) [nM] | 293T.144 RET (658-1114) 6.0 hours (Emax) |
|---|---|---|---|---|---|---|---|
| | pyridyl]pyrazolo[1,5-a]pyridine-3-carbonitrile | | | | | | |
| 66 | 1-[5-[3-cyano-6-[1-[1-[2-[4-[4-[(2,6-dioxo-3-piperidyl)amino]-2-fluoro-phenyl]piperazin-1-yl]acetyl]-4-piperidyl]pyrazol-4-yl]pyrazolo[1,5-a]pyridin-4-yl]-2-pyridyl]-4-ethyl-N-isopropyl-piperidine-4-carboxamide | ++++ | ++++ | ++++ | ++++ | ++++ | ++++ |
| 67 | 6-[6-[4-[2-[4-[4-[(2,6-dioxo-3-piperidyl)amino]-2-fluoro-phenyl]-1-piperidyl]acetyl]piperazin-1-yl]-3-pyridyl]-4-[6-[4-(2-pyridylmethyl)piperazin-1-yl]-3-pyridyl]pyrazolo[1,5-a]pyridine-3-carbonitrile | +++ | ++++ | +++ | ++++ | ++++ | ++++ |
| 68 | 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[6-(3-pyridylmethyl)-3,6-diazabicyclo[3.1.1]heptan-3-yl]-3-pyridyl]pyrazolo[1,5-a]pyridine-3-carbonitrile | ++++ | ++++ | ++++ | ++++ | ++++ | ++++ |
| 69 | 1-[5-[3-cyano-6-[1-[1-[2-[1-[4-[(2,6-dioxo-3-piperidyl)amino]-3-fluoro-phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide | +++ | ++++ | +++ | ++++ | ++++ | ++++ |
| 70 | 1-[5-[3-cyano-6-[1-[1-[2-[4-[4-[(2,6-dioxo-3-piperidyl)oxy]phenyl]-1-piperidyl]acetyl]-4-piperidyl]pyrazol-4-yl]pyrazolo[1,5-a]pyrazin-4-yl]-2- | ++++ | ++++ | ++++ | ++++ | ++++ | ++++ |

TABLE 2A-continued

| Biological Data | | | | | | | |
|---|---|---|---|---|---|---|---|
| | | HiBiT-Degradation | | | | | |
| Compound | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | pyridyl]-4-ethyl-N-isopropyl-piperidine-4-carboxamide | | | | | | |
| 71 | 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[6-[(4-methoxy-2-pyridyl)methyl]-3,6-diazabicyclo[3.1.1]heptan-3-yl]-3-pyridyl]pyrazolo[1,5-a]pyridine-3-carbonitrile | +++ | ++++ | ++++ | ++++ | ++++ | ++++ |
| 72 | 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[4-(2-pyridylmethyl)-1-piperidyl]-3-pyridyl]pyrazolo[1,5-a]pyrazine-3-carbonitrile | ++++ | ++++ | +++ | ++++ | ++++ | ++++ |
| 73 | 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[6-(2-pyridylmethyl)-3,6-diazabicyclo[3.1.1]heptan-3-yl]-3-pyridyl]pyrazolo[1,5-a]pyridine-3-carbonitrile | ++++ | ++++ | ++++ | ++++ | ++++ | ++++ |
| 74 | 6-[4-[4-[2-[4-[4-[(2,6-dioxo-3-piperidyl)amino]phenyl]-1-piperidyl]acetyl]piperazin-1-yl]phenyl]-4-[6-[4-[2-(5-fluoro-2-pyridyl)acetyl]piperazin-1-yl]-3-pyridyl]pyrazolo[1,5-a]pyridine-3-carbonitrile | ++++ | ++++ | ++++ | ++++ | ++++ | ++++ |
| 75 | 1-[5-[3-cyano-6-[1-[(1r,4r)-4-[2-[4-[4-(2,6-dioxo-3-piperidyl)phenyl]-1-piperidyl]ethyl]cyclohexyl]pyrazol-4-yl]pyrazolo[1,5- | +++ | ++++ | ++++ | ++++ | ++++ | ++++ |

TABLE 2A-continued

| Biological Data | | | | | | | |
|---|---|---|---|---|---|---|---|
| | | HiBiT-Degradation | | | | | |
| Compound | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | a]pyridin-4-yl]-2-pyridyl]-4-ethyl-N-isopropyl-piperidine-4-carboxamide | | | | | | |
| 76 | 6-[1-[2-[2-[4-[4-[(2,6-dioxo-3-piperidyl)amino]-2-fluoro-phenyl]-1-piperidyl]acetyl]-2-azaspiro[3.3]heptan-6-yl]pyrazol-4-yl]-4-[6-[4-(2-pyridylmethyl) piperazin-1-yl]-3-pyridyl]pyrazolo[1,5-a]pyridine-3-carbonitrile | +++ | +++ | ++++ | ++++ | ++++ | ++++ |
| 77 | 4-[4-[3-cyano-4-[6-[4-(2-pyridylmethyl) piperazin-1-yl]-3-pyridyl]pyrazolo[1,5-a]pyridin-6-yl]pyrazol-1-yl]-N-[1-[4-[(2,6-dioxo-3-piperidyl)amino]-2-fluoro-phenyl]-4-piperidyl]piperidine-1-carboxamide | +++ | ++++ | +++ | ++++ | ++++ | ++++ |
| 78 | 6-[1-[1-[2-[4-[4-[(2,6-dioxo-3-piperidyl)amino]-2-fluoro-phenyl]-1-piperidyl]acetyl]-4-piperidyl]pyrazol-4-yl]-4-[6-[4-(methoxymethyl)-4-(2-pyridylmethyl)-1-piperidyl]-3-pyridyl]pyrazolo[1,5-a]pyrazine-3-carbonitrile | +++ | ++++ | ++++ | ++++ | ++++ | ++++ |
| 79 | 1-[5-[3-cyano-6-[1-[1-[2-[1-[4-[[(3R)-2,6-dioxo-3-piperidyl]amino]-2-fluoro-phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide | ++++ | ++++ | ++++ | ++++ | ++++ | ++++ |
| 80 | 1-[5-[3-cyano-6-[1-[1-[2-[1-[4-[[(3S)-2,6-dioxo-3-piperidyl]amino]-2-fluoro-phenyl]-4-hydroxy-4-piperidyl]acetyl]-4- | ++++ | ++++ | +++ | ++++ | ++++ | ++++ |

TABLE 2A-continued

| Biological Data | | | | | | | |
|---|---|---|---|---|---|---|---|
| Compound | | HiBiT-Degradation | | | | | |
| | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | piperidyl]pyrazol-4-yl]pyrazolo[1,5-a]pyrazin-4-yl]-2-pyridyl]-4-ethyl-N-isopropyl-piperidine-4-carboxamide | | | | | | |
| 81 | 1-[5-[3-cyano-6-[1-[1-[2-[1-[4-[(2,6-dioxo-3-piperidyl)amino]-2-fluoro-phenyl]-4-hydroxy-4-piperidyl]acetyl]-4-piperidyl]pyrazol-4-yl]pyrazolo[1,5-a]pyrazin-4-yl]-2-pyridyl]-N-cyclobutyl-4-ethyl-piperidine-4-carboxamide | ++++ | ++++ | ++++ | ++++ | ++++ | ++++ |
| 82 | 1-[5-[3-cyano-6-[1-[6-[4-[3-(2,4-dioxohexahydropyrimidin-1-yl)-1-methyl-indazol-6-yl]-1-piperidyl]hexyl] pyrazol-4-yl]pyrazolo[1,5-a]pyridin-4-yl]-2-pyridyl]-N-isopropyl-4-methyl-piperidine-4-carboxamide | +++ | ++++ | ++++ | ++++ | ++++ | ++++ |
| 83 | N-[[4-[3-cyano-4-[6-[4-(2-pyridylmethyl) piperazin-1-yl]-3-pyridyl]pyrazolo[1,5-a]pyrazin-6-yl]phenyl]methyl]-2-[4-[4-[(2,6-dioxo-3-piperidyl)amino] phenyl]-1-piperidyl]-N-methyl-acetamide | +++ | ++++ | +++ | ++++ | ++++ | ++++ |
| 84 | 1-[5-[3-cyano-6-[1-[[1-[2-[1-[4-[(2,6-dioxo-3-piperidyl)amino]-2-fluoro-phenyl]-4-hydroxy-4-piperidyl]acetyl]-4-piperidyl]methyl] pyrazol-4-yl]pyrazolo[1,5-a]pyrazin-4-yl]-2-pyridyl]-4-ethyl-N-isopropyl-piperidine-4-carboxamide | +++ | ++++ | ++++ | ++++ | ++++ | ++++ |
| 85 | 1-[5-[3-cyano-6-[1-[1-[2-[1-[4-[(2,6- | +++ | ++++ | +++ | ++++ | ++++ | ++++ |

TABLE 2A-continued

| Biological Data | | | | | | | |
|---|---|---|---|---|---|---|---|
| Compound | | HiBiT-Degradation | | | | | |
| | | 293T.165 RET(KD: 658-1114 G810R) 6.0 hours (DC50) | 293T.165 RET(KD: 658-1114 G810R) 6.0 hours (IP) | 293T.165 RET(KD: 658-1114 G810R) 6.0 hours | 293T.144 RET (658-1114) 6.0 hours (DC50) | 293T.144 RET (658-1114) 6.0 hours (IP) | 293T.144 RET (658-1114) 6.0 hours |
| # | Name | [nM] | [nM] | (Emax) | [nM] | [nM] | (Emax) |
| | dioxo-3-piperidyl)amino] phenyl]-4-hydroxy-4-piperidyl]acetyl]-4-piperidyl]pyrazol-4-yl]pyrazolo[1,5-a]pyrazin-4-yl]-2-pyridyl]-4-ethyl-N-isopropyl-piperidine-4-carboxamide | | | | | | |
| 86 | 1-[5-[3-cyano-6-[1-[(1r,4r)-4-[2-[4-[3-(2,4-dioxohexahydropyrimidin-1-yl)-1-methyl-indazol-6-1]-1-piperidyl]ethyl] cyclohexyl]pyrazol-4-yl]pyrazolo[1,5-a]pyridin-4-yl]-2-pyridyl]-N-isopropyl-4-methyl-piperidine-4-carboxamide | +++ | ++++ | ++++ | ++++ | ++++ | ++++ |
| 87 | 1-(5-(3-cyano-6-(1-((1r,4r)-4-(4-(4-((2,6-dioxopiperidin-3-yl)amino)-2-fluorophenyl) piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide | ++++ | ++++ | ++++ | ++++ | ++++ | ++++ |
| 88 | 1-(5-(3-cyano-6-(1-((1s,4s)-4-(4-(4-(2,6-dioxopiperidin-3-yl)amino)-2-fluorophenyl) piperidin-1-yl)cyclohexyl)-1H-pyrazol-4-yl)pyrazolo[1,5-a]pyridin-4-yl)pyridin-2-yl)-4-ethyl-N-isopropylpiperidine-4-carboxamide | ++ | ++++ | +++ | ++++ | ++++ | ++++ |

As used in the table above for DC50 and IP values >= 1 uM = +, <1 uM = ++, <100 nM = +++ and < 50 nM = ++++.
For the Emax values >= 70% = +, <70% = + <50% = +++, and < 30% = ++++.

TABLE 2A

| Cmpd # | Biological Data<br>HiBiT-Degradation<br>293T.165 RET(KD: 658-1114 G810R) 6.0 hours (DC50) [nM] | 293T.165 RET(KD: 658-1114 G810R) 6.0 hours (IP) [nM] | 293T.165 RET(KD: 658-1114 G810R) 6.0 hours (Emax) | 293T.144 RET (658-1114) 6.0 hours (DC50) [nM] | 293T.144 RET (658-1114) 6.0 hours (IP) [nM] | 293T.144 RET (658-1114) 6.0 hours (Emax) |
|---|---|---|---|---|---|---|
| 89 | +++ | ++++ | +++ | ++++ | ++++ | ++++ |
| 90 | ++++ | ++++ | ++++ | ++++ | ++++ | ++++ |
| 91 | ++++ | ++++ | ++++ | ++++ | ++++ | ++++ |
| 92 | +++ | ++++ | ++++ | ++++ | ++++ | ++++ |
| 93 | +++ | ++++ | +++ | ++++ | ++++ | ++++ |
| 94 | ++++ | ++++ | ++++ | ++++ | ++++ | ++++ |
| 95 | ++++ | ++++ | ++++ | ++++ | ++++ | ++++ |
| 96 | +++ | +++ | +++ | ++++ | ++++ | ++++ |
| 97 | +++ | ++++ | +++ | ++++ | ++++ | ++++ |
| 98 | +++ | ++++ | ++++ | ++++ | ++++ | ++++ |
| 99 | ++++ | ++++ | ++++ | ++++ | ++++ | ++++ |
| 100 | +++ | ++++ | ++++ | ++++ | ++++ | ++++ |
| 101 | ++++ | ++++ | ++++ | ++++ | ++++ | ++++ |
| 102 | ++++ | ++++ | ++++ | ++++ | ++++ | ++++ |
| 103 | ++++ | ++++ | ++++ | ++++ | ++++ | ++++ |
| 104 | ++++ | ++++ | ++++ | ++++ | ++++ | ++++ |
| 105 | ++++ | ++++ | +++ | ++++ | ++++ | ++++ |
| 106 | +++ | ++++ | +++ | ++++ | ++++ | ++++ |
| 107 | +++ | ++++ | ++++ | ++++ | ++++ | ++++ |
| 108 | ++++ | ++++ | ++++ | ++++ | ++++ | ++++ |
| 109 | ++++ | ++++ | ++++ | ++++ | ++++ | ++++ |
| 110 | +++ | +++ | ++++ | ++++ | ++++ | ++++ |
| 111 | ++++ | ++++ | ++++ | ++++ | ++++ | ++++ |
| 112 | ++++ | ++++ | +++ | ++++ | ++++ | ++++ |
| 113 | ++++ | ++++ | ++++ | ++++ | ++++ | ++++ |
| 114 | ++++ | ++++ | ++++ | ++++ | ++++ | ++++ |
| 115 | ++++ | ++++ | ++++ | ++++ | ++++ | ++++ |
| 116 | ++++ | ++++ | ++++ | ++++ | ++++ | ++++ |
| 117 | ++++ | ++++ | ++++ | ++++ | ++++ | ++++ |
| 118 | ++++ | ++++ | ++++ | ++++ | ++++ | ++++ |
| 119 | +++ | ++++ | +++ | ++++ | ++++ | ++++ |
| 120 | +++ | ++++ | +++ | ++++ | ++++ | ++++ |
| 121 | ++++ | ++++ | ++++ | ++++ | ++++ | ++++ |
| 122 | ++++ | ++++ | ++++ | ++++ | ++++ | ++++ |
| 123 | ++++ | ++++ | ++++ | ++++ | ++++ | ++++ |
| 124 | ++++ | ++++ | ++++ | ++++ | ++++ | ++++ |
| 125 | ++++ | ++++ | ++++ | ++++ | ++++ | ++++ |
| 126 | ++++ | ++++ | ++++ | ++++ | ++++ | ++++ |
| 127 | ++++ | ++++ | ++++ | ++++ | ++++ | ++++ |
| 128 | ++++ | ++++ | ++++ | ++++ | ++++ | ++++ |
| 129 | ++++ | ++++ | ++++ | ++++ | ++++ | ++++ |
| 130 | ++++ | ++++ | ++++ | ++++ | ++++ | ++++ |
| 131 | ++++ | ++++ | ++++ | ++++ | ++++ | ++++ |
| 132 | +++ | ++++ | +++ | ++++ | ++++ | ++++ |
| 133 | ++++ | ++++ | ++++ | ++++ | ++++ | ++++ |
| 134 | ++++ | ++++ | ++++ | ++++ | ++++ | ++++ |
| 135 | ++++ | ++++ | ++++ | ++++ | ++++ | ++++ |
| 136 | ++++ | ++++ | ++++ | ++++ | ++++ | ++++ |
| 137 | ++++ | ++++ | ++++ | ++++ | ++++ | ++++ |
| 138 | +++ | ++++ | ++++ | ++++ | ++++ | ++++ |
| 139 | ++++ | ++++ | ++++ | ++++ | ++++ | ++++ |
| 140 | +++ | ++++ | +++ | ++++ | ++++ | ++++ |
| 141 | ++++ | ++++ | ++++ | ++++ | ++++ | ++++ |
| 142 | ++++ | ++++ | ++++ | ++++ | ++++ | ++++ |
| 143 | ++++ | ++++ | ++++ | ++++ | ++++ | ++++ |
| 144 | ++++ | ++++ | ++++ | ++++ | ++++ | ++++ |
| 145 | ++++ | ++++ | ++++ | ++++ | ++++ | ++++ |
| 146 | ++++ | ++++ | ++++ | ++++ | ++++ | ++++ |
| 147 | +++ | ++++ | ++++ | ++++ | ++++ | ++++ |
| 148 | ++++ | ++++ | ++++ | ++++ | ++++ | ++++ |
| 149 | ++++ | ++++ | ++++ | ++++ | ++++ | ++++ |
| 150 | +++ | ++++ | ++++ | ++++ | ++++ | ++++ |
| 151 | ++++ | ++++ | ++++ | ++++ | ++++ | ++++ |
| 152 | ++++ | ++++ | ++++ | ++++ | ++++ | ++++ |
| 153 | +++ | ++++ | ++++ | ++++ | ++++ | ++++ |
| 154 | ++++ | ++++ | ++++ | ++++ | ++++ | ++++ |
| 155 | ++++ | ++++ | ++++ | ++++ | ++++ | ++++ |
| 156 | ++++ | ++++ | ++++ | ++++ | ++++ | ++++ |
| 157 | ++++ | ++++ | ++++ | ++++ | ++++ | ++++ |

TABLE 2A-continued

| Biological Data | | | | | | |
|---|---|---|---|---|---|---|
| | HiBiT-Degradation | | | | | |
| Cmpd # | 293T.165 RET(KD: 658-1114 G810R) 6.0 hours (DC50) [nM] | 293T.165 RET(KD: 658-1114 G810R) 6.0 hours (IP) [nM] | 293T.165 RET(KD: 658-1114 G810R) 6.0 hours (Emax) | 293T.144 RET (658-1114) 6.0 hours (DC50) [nM] | 293T.144 RET (658-1114) 6.0 hours (IP) [nM] | 293T.144 RET (658-1114) 6.0 hours (Emax) |
| 158 | ++++ | ++++ | ++++ | ++++ | ++++ | ++++ |
| 159 | ++++ | ++++ | ++++ | ++++ | ++++ | ++++ |
| 160 | ++++ | ++++ | ++++ | ++++ | ++++ | ++++ |
| 161 | ++++ | ++++ | ++++ | ++++ | ++++ | ++++ |
| 162 | +++ | ++++ | ++++ | ++++ | ++++ | ++++ |
| 163 | +++ | ++++ | ++++ | ++++ | ++++ | ++++ |
| 164 | +++ | +++ | ++++ | ++++ | ++++ | ++++ |
| 165 | +++ | +++ | ++++ | ++++ | ++++ | ++++ |
| 166 | +++ | ++++ | ++++ | ++++ | ++++ | ++++ |
| 167 | ++++ | ++++ | ++++ | ++++ | ++++ | ++++ |
| 168 | +++ | ++++ | ++++ | ++++ | ++++ | ++++ |
| 169 | ++++ | ++++ | ++++ | ++++ | ++++ | ++++ |
| 170 | +++ | ++++ | ++++ | ++++ | ++++ | ++++ |
| 171 | ++++ | ++++ | ++++ | ++++ | ++++ | ++++ |
| 172 | ++++ | ++++ | ++++ | ++++ | ++++ | ++++ |
| 173 | +++ | +++ | +++ | ++++ | ++++ | ++++ |
| 174 | +++ | ++++ | +++ | ++++ | ++++ | ++++ |
| 175 | +++ | ++++ | +++ | ++++ | ++++ | ++++ |
| 176 | ++++ | ++++ | ++++ | ++++ | ++++ | ++++ |
| 177 | +++ | ++++ | ++++ | ++++ | ++++ | ++++ |
| 178 | ++++ | ++++ | ++++ | ++++ | ++++ | ++++ |
| 179 | ++++ | ++++ | ++++ | ++++ | ++++ | ++++ |
| 180 | ++++ | ++++ | ++++ | ++++ | ++++ | ++++ |
| 181 | ++++ | ++++ | ++++ | ++++ | ++++ | ++++ |
| 182 | ++++ | ++++ | +++ | ++++ | ++++ | ++++ |
| 183 | ++++ | ++++ | ++++ | ++++ | ++++ | ++++ |
| 184 | ++++ | ++++ | ++++ | ++++ | ++++ | ++++ |
| 185 | +++ | ++++ | +++ | ++++ | ++++ | ++++ |
| 186 | ++++ | ++++ | +++ | ++++ | ++++ | +++ |
| 187 | ++++ | ++++ | ++++ | ++++ | ++++ | ++++ |
| 188 | ++++ | ++++ | +++ | ++++ | ++++ | ++++ |
| 189 | +++ | ++++ | ++++ | ++++ | ++++ | ++++ |
| 190 | +++ | ++++ | ++++ | ++++ | ++++ | ++++ |
| 191 | +++ | +++ | ++++ | ++++ | ++++ | ++++ |
| 192 | +++ | +++ | ++++ | ++++ | ++++ | ++++ |
| 194 | ++++ | ++++ | ++++ | ++++ | ++++ | ++++ |
| 195 | ++++ | ++++ | ++++ | ++++ | ++++ | ++++ |
| 196 | +++ | ++++ | ++++ | ++++ | ++++ | ++++ |
| 197 | ++++ | ++++ | ++++ | ++++ | ++++ | ++++ |
| 198 | ++++ | ++++ | ++++ | ++++ | ++++ | ++++ |
| 199 | ++++ | +++ | ++++ | ++++ | ++++ | ++++ |
| 200 | ++++ | ++++ | +++ | ++++ | ++++ | ++++ |
| 201 | ++++ | ++++ | ++++ | ++++ | ++++ | ++++ |
| 202 | ++++ | ++++ | ++++ | ++++ | ++++ | ++++ |
| 203 | ++++ | ++++ | ++++ | ++++ | ++++ | ++++ |
| 204 | +++ | +++ | ++++ | ++++ | ++++ | ++++ |
| 205 | +++ | +++ | ++++ | ++++ | ++++ | ++++ |
| 206 | +++ | ++++ | ++++ | ++++ | ++++ | ++++ |
| 207 | ++++ | ++++ | ++++ | ++++ | ++++ | ++++ |
| 208 | +++ | ++++ | ++++ | ++++ | ++++ | ++++ |
| 209 | +++ | ++++ | ++++ | ++++ | ++++ | ++++ |
| 210 | +++ | ++++ | ++++ | ++++ | ++++ | ++++ |
| 211 | ++++ | ++++ | ++++ | ++++ | ++++ | ++++ |
| 212 | +++ | +++ | ++++ | ++++ | ++++ | ++++ |
| 213 | +++ | +++ | ++++ | ++++ | ++++ | ++++ |
| 214 | +++ | +++ | ++++ | ++++ | ++++ | ++++ |
| 215 | ++++ | ++++ | ++++ | ++++ | ++++ | ++++ |
| 216 | +++ | +++ | ++++ | ++++ | ++++ | ++++ |
| 217 | +++ | ++++ | ++++ | ++++ | ++++ | ++++ |
| 218 | ++++ | ++++ | ++++ | ++++ | ++++ | ++++ |
| 219 | ++++ | +++ | ++++ | ++++ | ++++ | ++++ |

As used in the table above for $DC_{50}$ and IP values >= 1 uM = +, <1 uM = ++, <100 nM = +++ and <50 nM = ++++.
For the Emax values >= 70% = +, <70% = ++, <50% = +++ and <30% = ++++.

Example 223: RET Wild-Type and G810R Degradation Assay

Materials

Dulbecco's modified Eagle medium (DMEM) no-phenol red media and fetal bovine serum (FBS) were purchased from Gibco (Grand Island, NY, USA). Cell lines ectopically expressing wild-type or G810R RET kinase domain fused with a HiBiT tag were generated in-house (293T. 144 and 293T. 165, respectively). Cell culture flasks and 384-well microplates were acquired from VWR (Radnor, PA, USA). The Nano-Glo® HiBiT Lytic Assay System was purchased from Promega (Madison, WI, USA).

Methods

RET wild-type (WT) and G810R degradation were assessed using the Nano-Glo® HiBiT Lytic assay (Promega, Medison, WI, USA). To determine the effect of degraders on protein levels, cells were plated in 384-well plates and treated with compounds of interest in duplicates for 6 hours using an 11-point half-log dilution series, with the highest dose set at 10 μM. Cell lysis and addition of the Nano-Glo® HiBiT Lytic Assay reagents was then performed. Luminescence signal was measured using an EnVision™ Multimode plate reader (Perkin Elmer, Santa Clara, CA, USA). The half-maximal degradation concentration (DC50) and % remaining protein (Emax) was then derived from the dose-response curves.

Example 224: Cell Viability Assays

Materials

RPMI 1640 media, Ham's F-12 media, F-12K media, cell culture flasks, and 384-well microplates were purchased from VWR. Fetal bovine serum (FBS) was purchased from Life Technologies and CellTiter-Glo® was purchased from Promega. The LC-2/ad cell line was purchased from Sigma Aldrich, the TT cell line from ATCC, and the Ba/F3 parental cell line from DSMZ. Ba/F3 cell lines ectopically expressing RET fusions and/or mutations were engineered: KIF5B-RET WT, KIF5B-RET V804L, KIF5B-RET V804M, KIF5B-RET G810R, KIF5B-RET G810C, KIF5B-RET G810S, KIF5B-RET L730I, KIF5B-RET Y806N, and RET M918T.

Methods

Cell viability was assessed based on the quantification of ATP using the CellTiter-Glo® assay (Promega, Medison, WI, USA). To determine the effect of compounds on cell viability, cells were plated in 384-well plates using appropriate media (LC-2/ad: RPMI+HAMS F12+10% FBS; TT: F-12K+10% FBS; Ba/F3: RPMI 1640+10% FBS) and treated with compounds of interest using a 10-point half-log dilution series, in duplicate, with the highest dose set at 1 mM. LC-2/ad and TT cells were incubated for 120 hours while Ba/F3 cells were incubated for 72 hours. Addition of the CellTiter-Glo® reagent was then performed. Luminescence signals were measured using an EnVision™ Multimode plate reader (Perkin Elmer, Santa Clara, CA, USA). For data normalization, cells untreated with the test compounds at Time=72 or 120 hours were set to 100% (equivalent to maximal cell growth after 72 or 120 hours); cells untreated with the test compounds at Time=0 hours were set to 0% (equivalent to cytostasis); and media-only wells were set to −100% (equivalent to complete cytotoxicity). The half-maximal inhibition of cell growth (GI50) is computed from where the fitted curve crosses 50% while the half-maximal lethal dose (LD50) is computed from where the fitted curve crosses −50%.

The results are summarized in FIG. 1 and FIG. 2.

Figure 3:
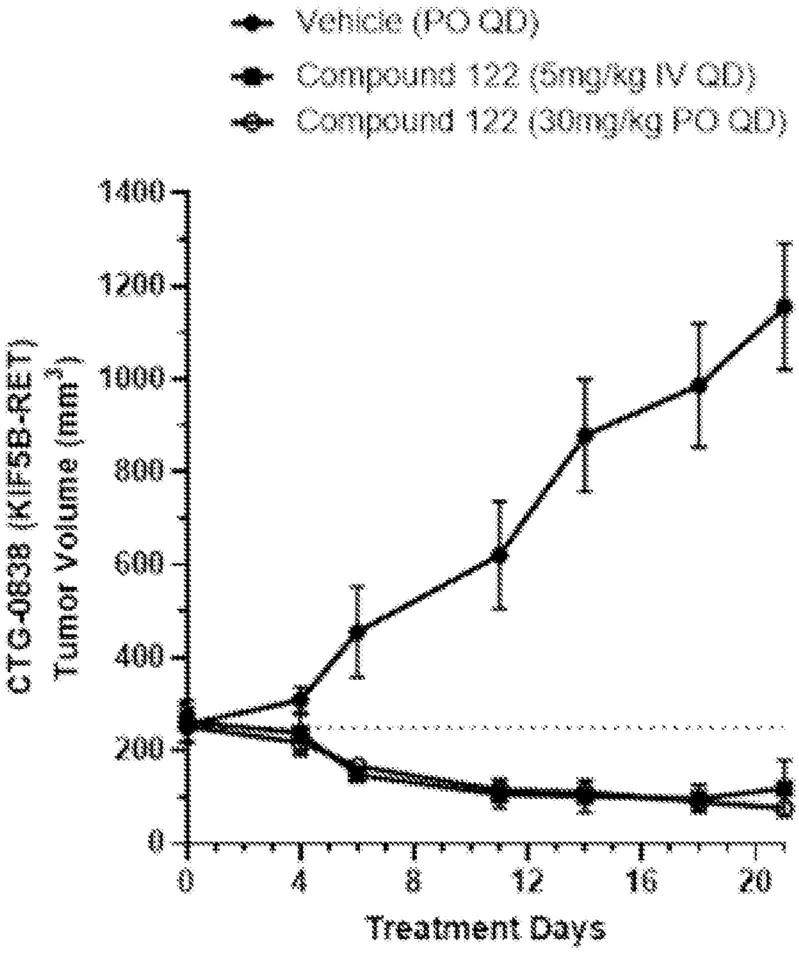
FIG. 3 is a line graph demonstrating the in vivo efficacy of Compound 122 in the treatment of female Athymic Nude-Foxn1nu (immune-compromised) mice bearing CTG-0838 NSCLC PDX tumors. Mice were treated once a day with the vehicle control or Compound 122 dosed intravenously at 5 mg/kg/day or orally at 30 mg/kg/day for 21 days. The x-axis is the time measured in days and the y-axis is CTG-0838 tumor volume measured in $mm^3$. The experimental procedure is provided in Example 225.
Figure 4:
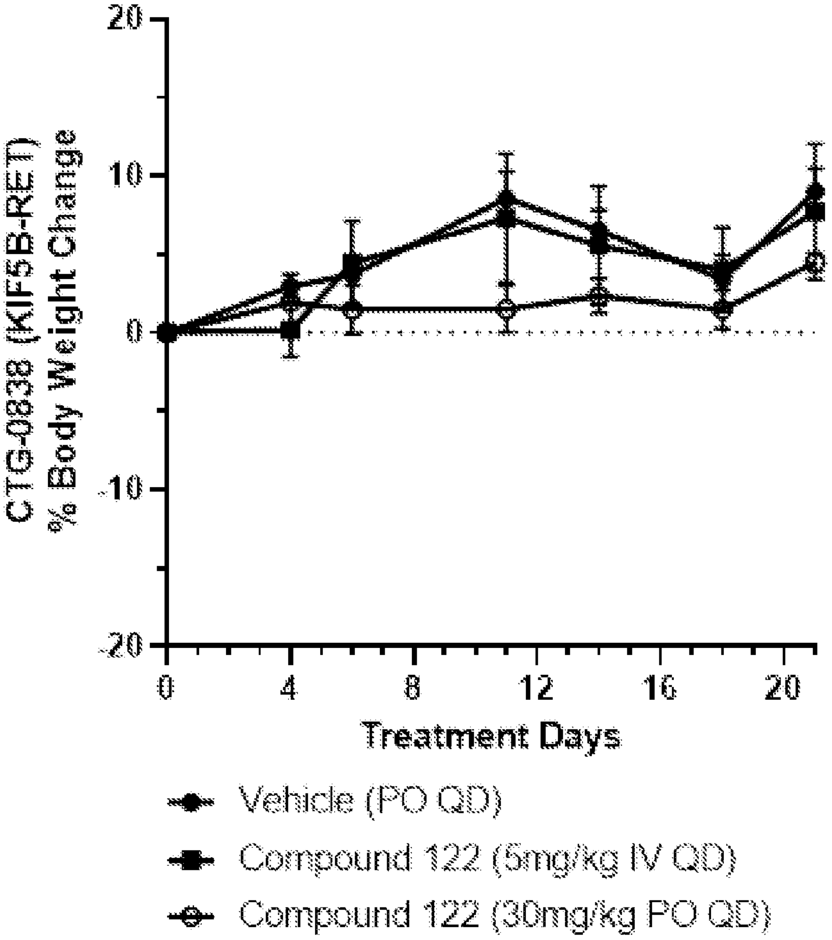
FIG. 4 is a line graph demonstrating the weight change caused by Compound 122 in the treatment of female Athymic Nude-Foxn1nu (immune-compromised) mice bearing CTG-0838 NSCLC PDX tumors. Mice were treated once a day with the vehicle control or Compound 122 dosed intravenously at 5 mg/kg/day or orally at 30 mg/kg/day for 21 days. The x-axis is the time measured in days and the y-axis is percent body weight change. The experimental procedure is provided in Example 225.

Example 225: Antitumor Efficacy of Compound 122 in CTG-0838 Patient Derived Xenograft (PDX) NSCLC Model CTG-0838 is a non-small cell lung cancer PDX model harboring the KIF5B-RET fusion. Mice bearing CTG-0838 tumors were treated once a day with Compound 122 at 5 mg/kg IV or 30 mg/kg PO for 21 days results in 116% and 119% TGI, respectively (FIG. 3). No body weight loss was observed after 21 days of daily treatment with Compound 122 (FIG. 4).

Experimentals

For PDX model CTG-0838, tumors were first grown in stock mice, then tumor fragments were harvested and inoculated into the left flank of female Athymic Nude-Foxn1nu mice for tumor development. Tumor volume and body weight were measured on designated days. Tumor volume was measured in two dimensions using a digital caliper, and volume ($mm^3$) was calculated using the formula: $V=0.52\ a \times b^2$ where a and b are the long and short diameters of the tumor in mm, respectively. Once tumors reached an average volume of 200-300 $mm^3$, the animals were divided randomly into groups of 3, stratified to result in about equal average tumor sizes in each treatment group, and dosing was initiated on Day 0.

Compound 122 was administered once a day intravenously (IV) at 5 mg/kg or orally (PO) at 30 mg/kg for 21 days. Compound 122 was formulated in 40% PEG400 and 60% of 10% hydroxypropyl beta cyclodextrin (HPPCD) in double distilled water, which was also used for the vehicle group. Body weight and tumor volume were measured on a 2× weekly schedule. Data are represented as MTV±SEM.

Figure 5:
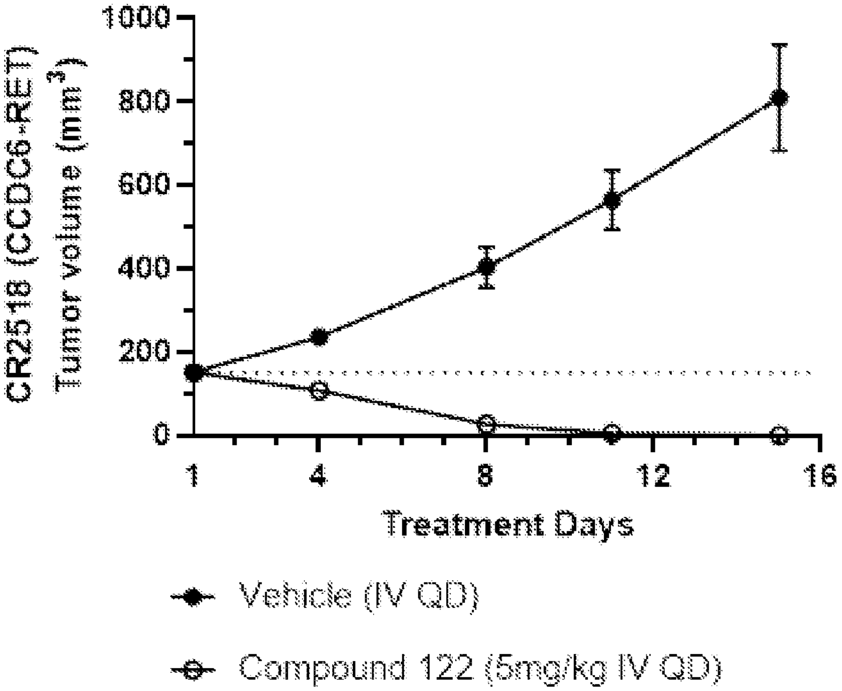
FIG. 5 is a line graph demonstrating the in vivo efficacy of Compound 122 in the treatment of female BALB/c Nude mice bearing $CR^{2518}$ CRC PDX tumors. Mice were treated once a day with the vehicle control or Compound 122 dosed intravenously at 5 mg/kg/day for 14 days. The x-axis is the time measured in days and the y-axis is $CR^{2518}$ tumor volume measured in $mm^3$. The experimental procedure is provided in Example 226.
Figure 6:
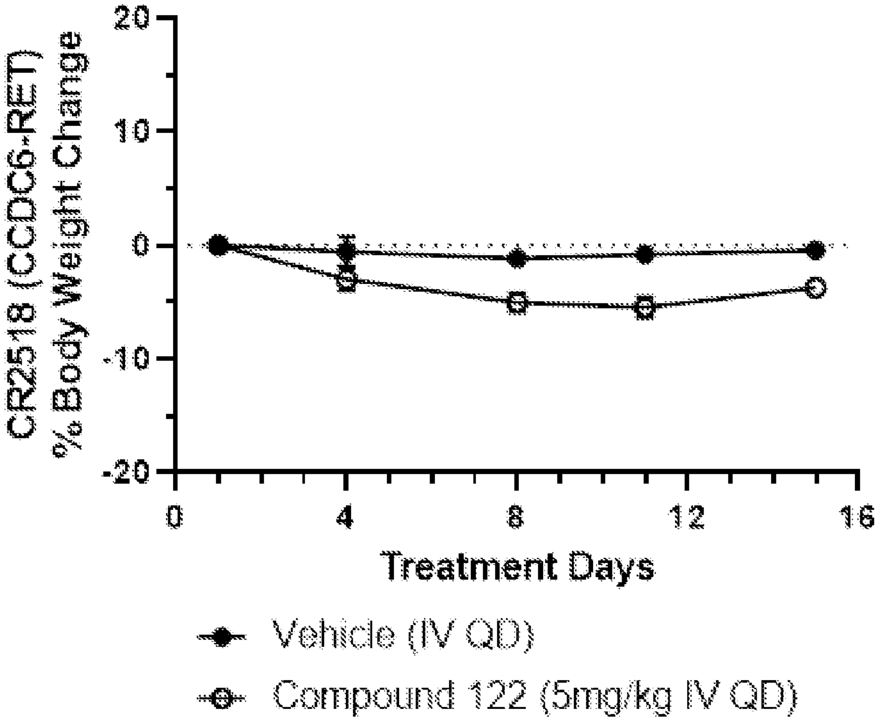
FIG. 6 is a line graph demonstrating the change in body weight caused by Compound 122 in the treatment of female BALB/c Nude mice bearing $CR^{2518}$ CRC PDX tumors. Mice were treated once a day with the vehicle control or Compound 122 dosed intravenously at 5 mg/kg/day for 14 days. The x-axis is the time measured in days and the y-axis is percent body weight change. The experimental procedure is provided in Example 226.

Example 226: Antitumor Efficacy of Compound 122 in $CR^{2518}$ Patient Derived Xenograft (PDX) CRC Model $CR^{2518}$ is a colorectal cancer PDX model harboring the CCDC6-RET fusion. Mice bearing $CR^{2518}$ tumors treated once a day with Compound 122 at 5 mg/kg IV for 14 days results in complete regression (see FIG. 5). No body weight loss was observed after 14 days of daily treatment with Compound 122 (see FIG. 6).

Experimentals

For PDX model $CR^{2518}$, tumors were first grown in stock mice, then tumor fragments were harvested and inoculated into the right flank of female BALB/c nude mice for tumor development. Tumor volume and body weight were measured twice weekly. Tumor volume was measured in two dimensions using calipers, and volume ($mm^3$) was calculated using the formula: $V=0.5\ a \times b^2$ where a and b are the long and short diameters of the tumor in mm, respectively. Once tumors reached an average volume of 150 $mm^3$, the animals were divided randomly into groups of 5, stratified to result in about equal average tumor sizes in each treatment group, and dosing was initiated on Day 1

Compound 122 was administered once a day intravenously (IV) at 5 mg/kg for 14 days. Compound 122 was formulated in 40% PEG400 and 60% of 10% hydroxypropyl beta cyclodextrin (HPPCD) in double distilled water, which was also used for the vehicle group. Body weight and tumor volume were measured on a 2× weekly schedule. Data are represented as MTV±SEM.

Figure 7:
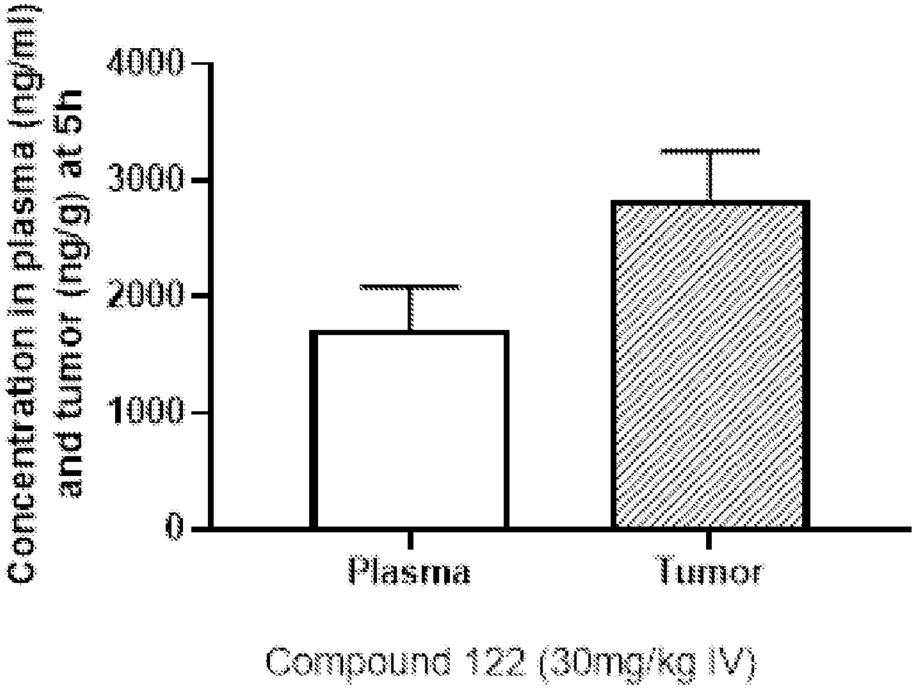
FIG. 7 is a bar graph of Compound 122 concentration in plasma and brain tumor following a single intravenous (IV) dose at 30 mg/kg. The experimental procedure is provided in Example 227.
Figure 8:
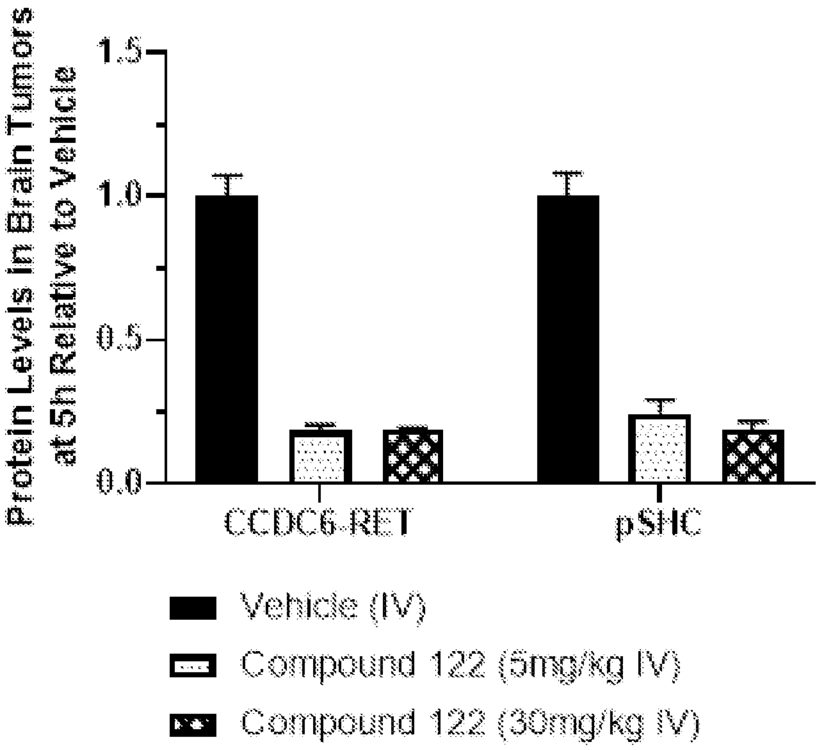
FIG. 8 is a bar graph of RET and phospho-SHC protein levels at five hours in brain tumors following a single intravenous (IV) dose at 5 mg/kg or 30 mg/kg of Compound 122. The experimental procedure is provided in Example 227.
Figure 9:
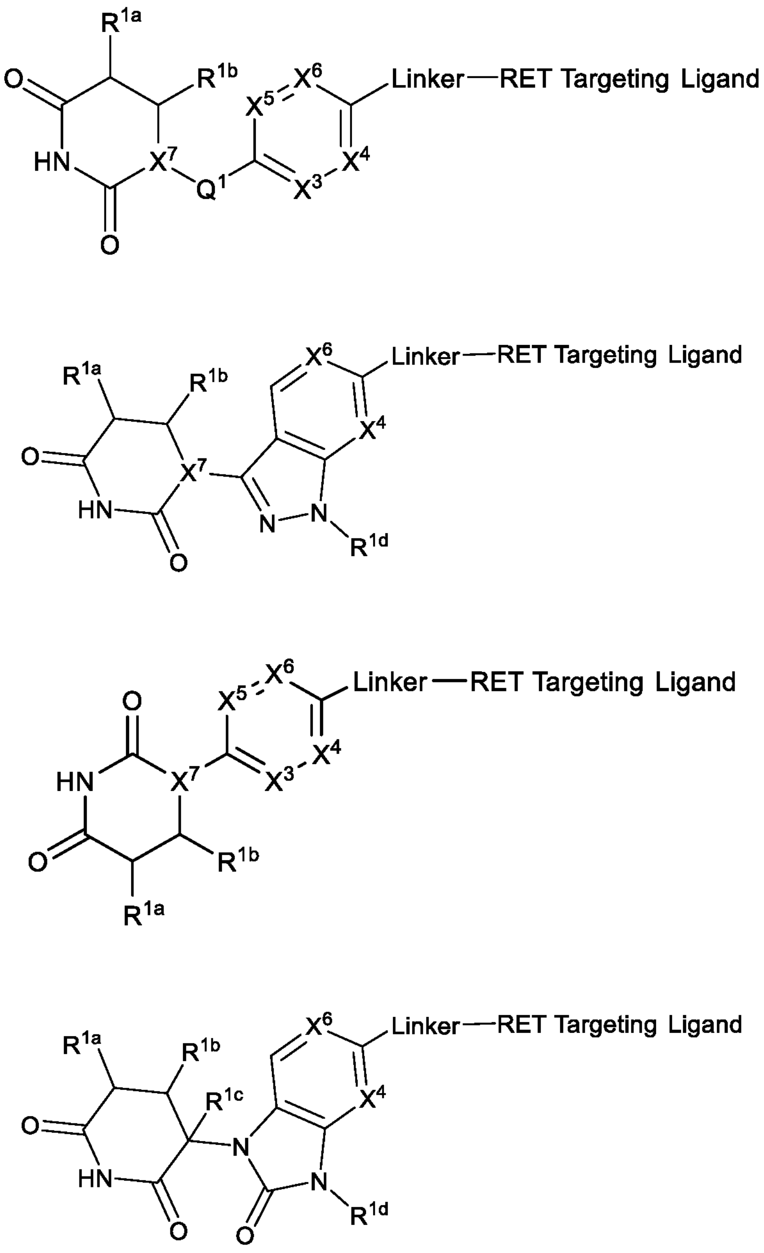
FIG. 9 depicts representative chemical formulas of the present invention wherein the variables are defined herein.

Example 227: Compound 122 Leads to RET Degradation in Brain Tumors Harboring the CCDC6-RET Fusion $CR^{2518}$ is a colorectal cancer PDX model harboring the CCDC6-RET fusion. A single IV dose of Compound 122 at 30 mg/kg administered to mice bearing $CR^{2518}$ brain tumors results in plasma concentration of 1716 ng/ml and brain tumor concentration of 2839 ng/g at 5 hours (FIG. 7). Additionally, a single IV dose of Compound 122 at 5 mg/kg or 30 mg/kg results in about 75-80% reduction in RET and phospho-SHC protein levels in brain tumors at 5 hours (FIG. 8).

Experimentals

For intracranial PDX model $CR^{2518}$, tumors were first grown in stock mice, then tumor fragments were harvested and digested for cell suspension preparation. $5\times10^5$ $CR^{2518}$ cells in 4 µl PBS were injected intracranially over 5 min, 2.5 mm intraparenchymally, 2 mm lateral from and 0.5 mm anterior to the bregma for tumor development in female BALB/c nude mice. With the appearance of clinical signs (body weight loss, inactivity), mice were randomized into groups of 3, stratified to result in about equal average body weight, and dosing was initiated on Day 0.

Compound 122 was formulated in 40% PEG400 and 60% of 10% hydroxypropyl beta cyclodextrin (HPPCD) in double distilled water, which was also used for the vehicle group. A single intravenous (IV) dose of Compound 122 was administered at 5 mg/kg or 30 mg/kg prior to collection of plasma and brain tumor at 5h. Tumor volume was measured in two dimensions using calipers, and volume ($mm^3$) was calculated using the formula: $V=0.5\ a\times b^2$ where a and b are the long and short diameters of the tumor in mm, respectively.

3 tumors and plasma samples were collected per each time point sampled. For pharmacokinetic analysis, plasma and tumor samples were injected into LC/MS/MS system for quantitative analysis. For pharmacodynamic analysis by western blot, brain tumors were mechanically homogenized, and protein extracted using RIPA buffer (Sigma) supplemented with protease and phosphatase inhibitor cocktails. Protein concentration was quantified using a Pierce™ BCA Protein Assay Kit, samples were reduced, and equal protein amounts were then loaded onto a western blot gel for analysis. Tumors were analyzed for RET (C31B4) at 1:1000 (CST, 3223), phospho-SHC (Tyr239/240) at 1:1000 (CST, 2434), GAPDH (D4C6R) at 1:2000 (CST, 97166). Immunoblots were imaged using the OdysseyCLX Imager (LI-COR Biosciences) and the intensity of the bands was measured using Image Studio software. Protein expression was quantitated in relation to the reference protein, GAPDH, to control for total protein concentration. The data was then normalized to the amount of target in the Compound 122 treated samples in comparison to the vehicle control samples. Data is represented as Mean±SEM.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the appended claims. Additionally, those skilled in the art will recognize, or be able to ascertain using no more than routine experimentation, many equivalents to the specific embodiments and methods described herein. Such equivalents are intended to be encompassed by the scope of the present application.

We claim:

1. A compound of Formula:

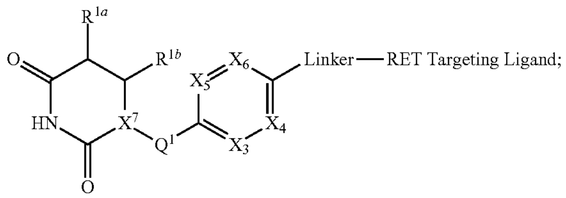

or a pharmaceutically acceptable salt thereof;

wherein $R^{1a}$ is hydrogen;

$R^{1b}$ is hydrogen;

$X^7$ is CH;

$Q^1$ is NH;

$X^3$, $X^4$, $X^5$, and $X^6$ are selected from the group consisting of CH and $CR^3$;

$R^3$ is independently at each occurrence selected from the group consisting of hydrogen, hydroxyl, $C_1$-$C_4$alkoxy, $C_1$-$C_4$alkyl, $C_1$-$C_4$haloalkyl, fluorine, and chlorine;

RET Targeting Ligand is selected from

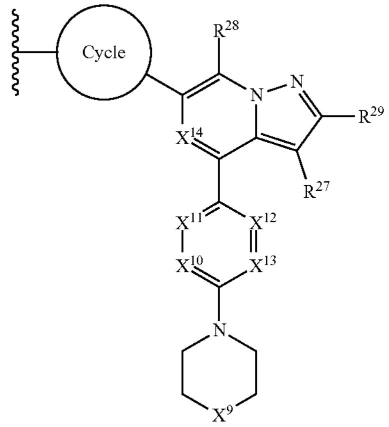

and

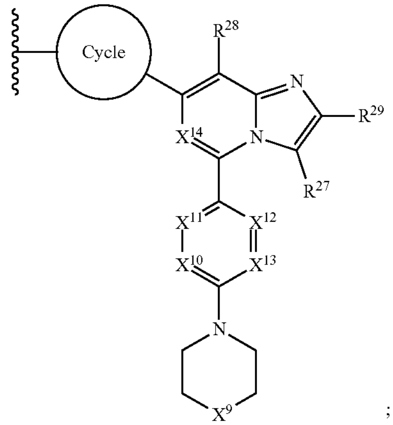

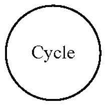

;

is a 5 or 6 membered heteroaryl, 6 membered heterocycle, or phenyl;

$X^9$ is $NR^4$, $CR^4R^{11}$, or O;

$X^{10}$ is CH or N;

$X^{11}$ and $X^{12}$ are CH;

$X^{13}$ is N, CH, or CR;

$X^{14}$ is $CR^{27}$ or N;

each $R^4$ is independently selected from the group consisting of hydrogen, $C_1$-$C_4$alkyl, $C_2$-$C_4$alkenyl, $C_2$-$C_4$alkynyl, $C_1$-$C_4$haloalkyl, —C(O)$R^5$, 5 or 6 membered heteroaryl, phenyl, and 4-8 membered heterocycle, and —$C_1$-$C_4$alkyl-C(O)$R^5$, each of which $C_1$-$C_4$alkyl, $C_2$-$C_4$alkenyl, $C_2$-$C_4$alkynyl, $C_1$-$C_4$haloalkyl, 5 or 6 membered heteroaryl, phenyl, and 4-8 membered heterocycle, is optionally substituted with 0, 1, 2, or 3 substituents independently selected from $R^8$;

$R^5$ is hydrogen, $C_1$-$C_4$alkyl, $C_2$-$C_4$alkenyl, $C_2$-$C_4$alkynyl, $C_1$-$C_4$haloalkyl, 5 or 6 membered heteroaryl, phenyl, 4-8 membered heterocycle, —$OR^6$, or-$NR^6R^7$, each of which $C_1$-$C_4$alkyl, $C_2$-$C_4$alkenyl, $C_2$-$C_4$alkynyl, $C_1$-$C_4$haloalkyl, 5 or 6 membered heteroaryl, phenyl, and 4-8 membered heterocycle, is optionally substituted with 0, 1, 2, or 3 substituents independently selected from $R^9$;

$R^6$ and $R^7$ are independently selected at each instance from the group consisting of hydrogen, $C_1$-$C_4$alkyl, $C_2$-$C_4$alkenyl, $C_2$-$C_4$alkynyl, $C_1$-$C_4$haloalkyl, 5 or 6 membered heteroaryl, phenyl, 4-8 membered heterocycle, and benzyl, each of which $R^6$ and $R^7$ groups other than hydrogen is optionally substituted with 0, 1, 2, or 3 substituents independently selected from $R^{10}$;

$R^8$ is independently at each occurrence selected from the group consisting of hydrogen, $C_1$-$C_4$haloalkyl, $C_1$-$C_4$alkyl, halogen, —$OR^6$, —$NR^6R^7$, —OC(O)$R^5$, —$NR^6$C(O)$R^5$, —C(O)$R^5$, and -$C_1$-$C_4$alkyl-C(O)$R^5$;

$R^9$ is independently at each occurrence selected from the group consisting of hydrogen, phenyl, benzyl, 5 or 6 membered heteroaryl, 4-8 membered heterocycle, $C_1$-$C_4$haloalkyl, $C_1$-$C_4$alkyl, halogen, —$OR^6$, —$NR^6R^7$, —C(O)$OR^6$, —C(O)$NR^6R^7$, -alkyl-C(O)$OR^6$, and -alkyl-C(O)$NR^6R^7$, each of which phenyl, benzyl, 5 or 6 membered heteroaryl, and 4-8 membered heterocycle, is optionally substituted with 0, 1, 2, or 3 substituents selected from —$S(O)_2$alkyl, $C_1$-$C_4$haloalkyl, $C_1$-$C_4$alkyl, halogen, —$OR^6$, —$NR^6R^7$, —C(O)$OR^6$, —C(O)$NR^6R^7$, -$C_1$-$C_4$alkyl-C(O)$OR^6$, and -$C_1$-$C_4$alkyl-C(O)$NR^6R^7$;

$R^{10}$ is independently at each occurrence selected from the group consisting of $C_1$-$C_4$alkyl, $C_2$-$C_4$alkenyl, $C_2$-$C_4$alkynyl, $C_1$-$C_4$haloalkyl, and halogen;

$R^{11}$ is hydrogen, $C_1$-$C_4$alkyl, $C_2$-$C_4$alkenyl, $C_2$-$C_4$alkynyl, $C_1$-$C_4$haloalkyl, 5 or 6 membered phenyl, heteroaryl, 4-8 membered heterocycle, -$C_1$-$C_4$alkyl-$OR^6$, —OC(O)$R^6$, —$OR^6$, -$C_1$-$C_4$alkyl-$NR^6R^7$, —$NR^6$C(O)$R^7$ or-$NR^6R^7$;

R is halogen;

$R^{27}$ is hydrogen or cyano;

$R^{28}$ and $R^{29}$ are hydrogen;

Linker is of Formula (LI)

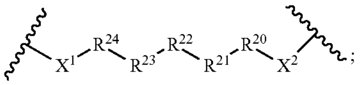

;

$X^1$ and $X^2$ are independently at each occurrence selected from bond, 4-8 membered heterocycle, $NR^2$, $C(R^2)_2$, O, C(O), and S;

$R^2$ is independently at each occurrence selected from the group consisting of hydrogen, $C_1$-$C_4$alkyl, 4-8 membered heterocycle, phenyl, 5 or 6 membered heteroaryl, —C(O) $C_1$-$C_4$alkyl;

$R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —$SO_2$—, —S(O)—, —C(S)-, —C(O)$NR^2$—, —$NR^2$C(O)—, —O—, —S—, —$NR^2$—, —C($R^{40}R^{40}$)—, —P(O)($OR^{26}$)O—, —P(O)($OR^{26}$)—, bicycle, $C_2$-Calkene, $C_2$-$C_4$alkyne, $C_1$-$C_4$haloalkyl, $C_1$-$C_4$alkoxy, phenyl, naphthyl, 4-8 membered heterocycle, 5 or 6 membered heteroaryl; each of which is optionally substituted with 1, 2, 3, or 4 substituents independently selected from $R^{40}$;

$R^{26}$ is independently at each occurrence selected from the group consisting of hydrogen, $C_1$-$C_4$alkyl, benzyl, $C_2$-$C_4$alkene, $C_2$-$C_4$alkyne, phenyl, 5 or 6 membered heteroaryl, and 4-8 membered heterocycle; and $R^{40}$ is independently at each occurrence selected from the group consisting of hydrogen, $C_1$-$C_4$alkyl, $C_2$-$C_4$alkene, $C_2$-$C_4$alkyne, fluoro, bromo, chloro, hydroxyl, alkoxy, amino, cyano, —NH($C_1$-$C_4$alkyl), —N($C_1$-$C_4$alkyl)$_2$, —$NHSO_2$($C_1$-$C_4$alkyl), —$NHSO_2$ (phenyl, 5 or 6 membered heteroaryl or 4-8 membered heterocycle), —N($C_1$-$C_4$alkyl) $SO_2$ (phenyl, 5 or 6 membered heteroaryl or 4-8 membered heterocycle), $C_1$-$C_4$haloalkyl, phenyl, 5 or 6 membered heteroaryl, and 4-8 membered heterocycle.

2. The compound of claim 1, wherein $X^1$ is bond and $R^{24}$ is

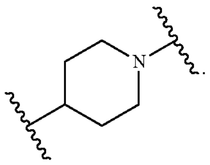 [SMILES: *C1CCN(*)CC1]

3. The compound of claim 1, wherein $X^1$ is bond and $R^{24}$ is

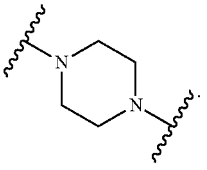 [SMILES: *N1CCN(*)CC1]

4. The compound of claim 1, wherein $X^1$ is bond and $R^{24}$ is

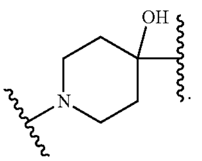 [SMILES: *N1CCC(*)(O)CC1]

5. The compound of claim 1, wherein
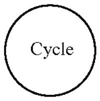
is a 5 or 6 membered heteroaryl.
6. The compound of claim 1, wherein
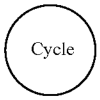
is
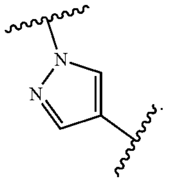
7. The compound of claim 1, wherein
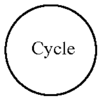
is
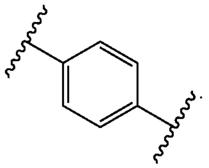
8. The compound of claim 1, wherein $X^6$ is CF.
9. The compound of claim 8, wherein $X^5$ is CH.
10. The compound of claim 9, wherein $X^4$ is CH.
11. The compound of claim 10, wherein $X^3$ is CH.
12. The compound of claim 1, wherein the RET Targeting Ligand is
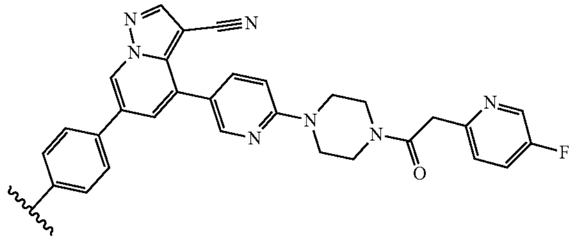
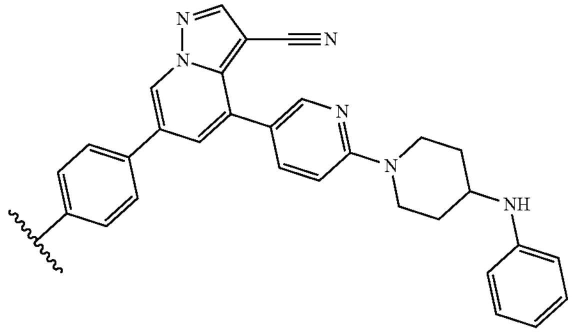
-continued
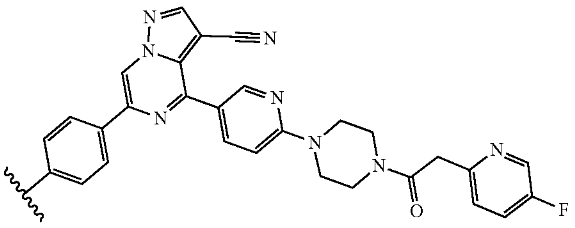
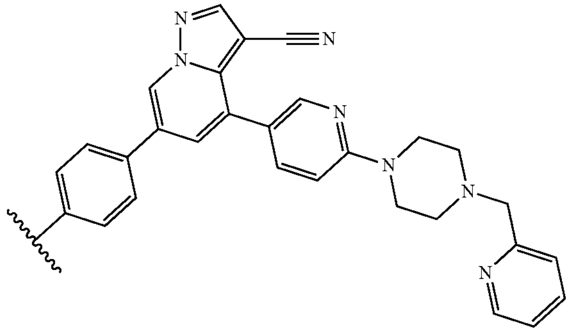
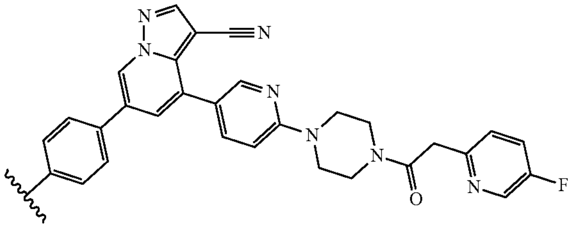
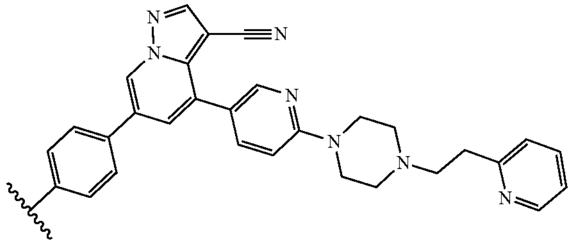
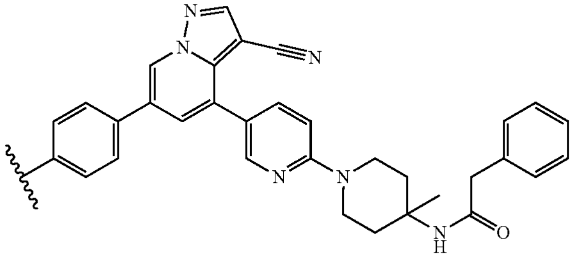
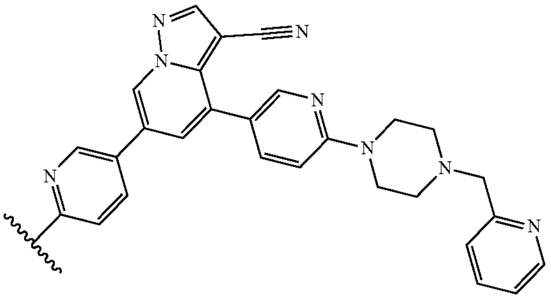
or -continued
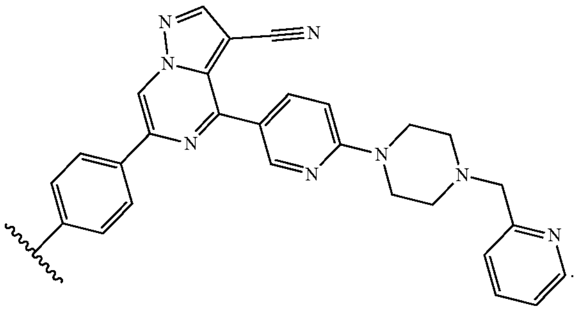
13. The compound of claim 1, wherein the RET Targeting Ligand is
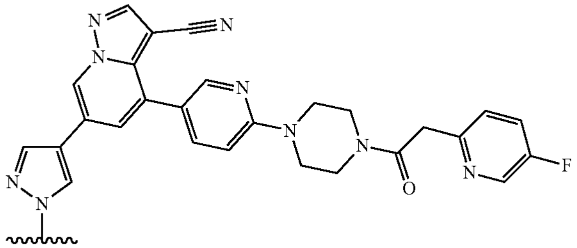
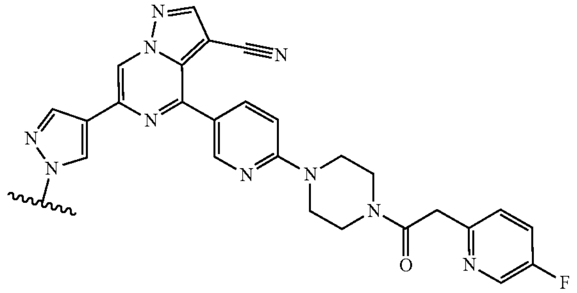
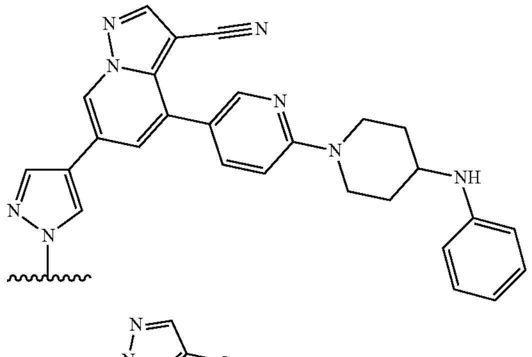
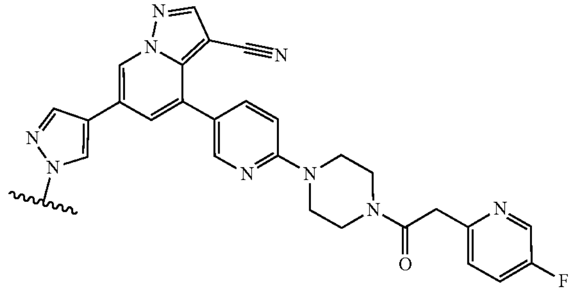
-continued
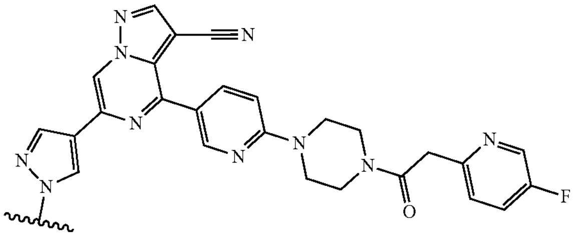
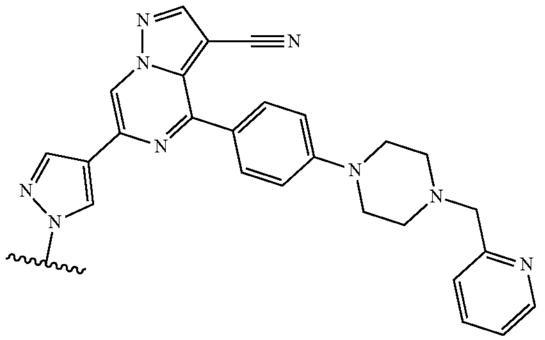
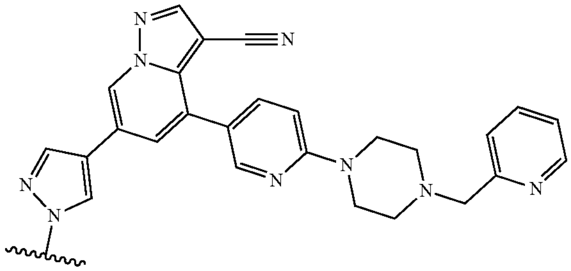
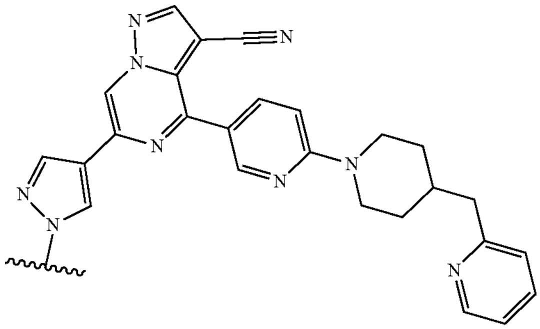
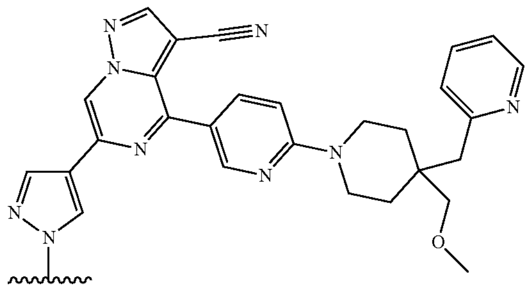

-continued

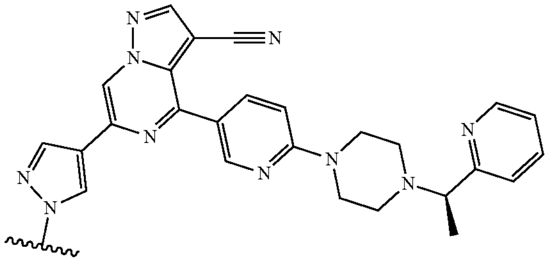

or

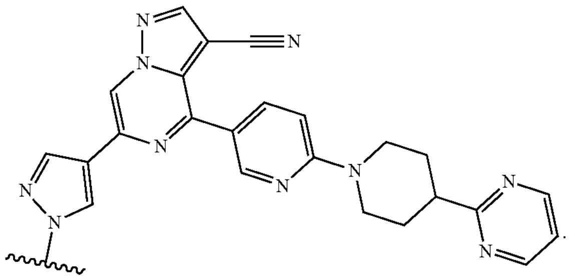

14. The compound of claim 1, wherein the RET Targeting Ligand is:

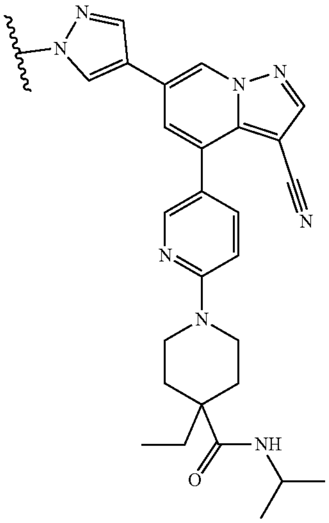

or

-continued

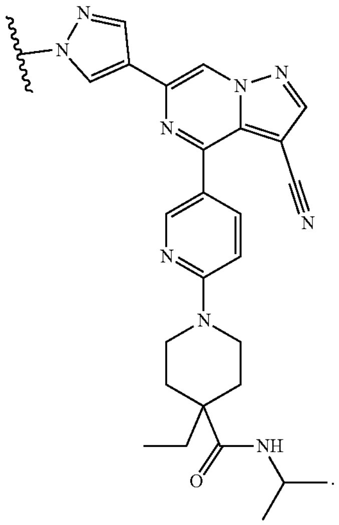

15. The compound of claim 1, wherein Linker is of formula

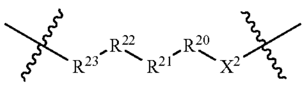

or

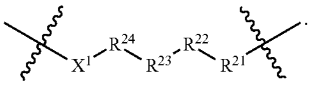

16. The compound of claim 15, wherein $X^1$ is bond.

17. The compound of claim 15, wherein $X^1$ is $NR^2$.

18. The compound of claim 15, wherein $X^1$ is C(O).

19. The compound of claim 15, wherein $X^2$ is bond.

20. The compound of claim 15, wherein $X^2$ is $NR^2$.

21. The compound of claim 15, wherein $X^2$ is C(O).

22. The compound of claim 1, wherein Linker is of formula

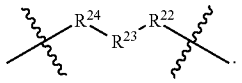

23. The compound of claim 1, wherein Linker is of formula

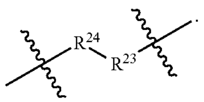

24. The compound of claim 1 of structure:

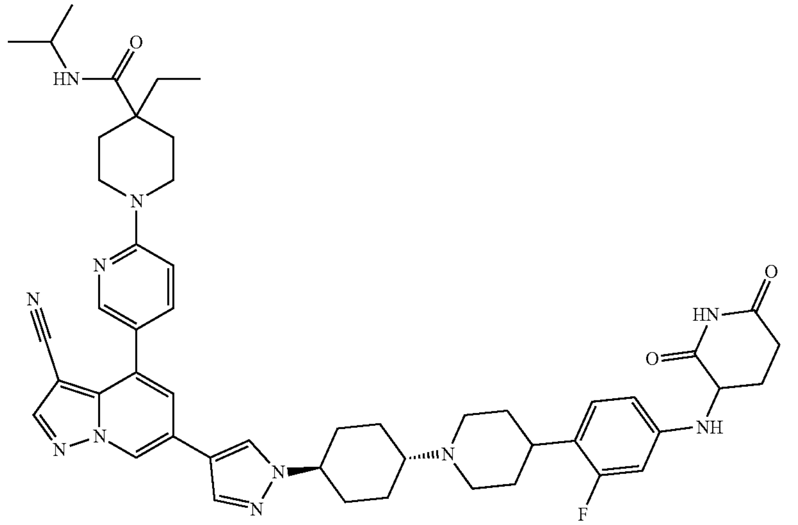 [SMILES: CCC1(C(=O)NC(C)C)CCN(c2ccc(-c3cc(-c4cnn([C@H]5CC[C@H](N6CCC(c7ccc(NC8CCC(=O)NC8=O)cc7F)CC6)CC5)c4)cn4ncc(C#N)c34)cn2)CC1]

or a pharmaceutically acceptable salt thereof.

25. The compound of claim 1 of structure:

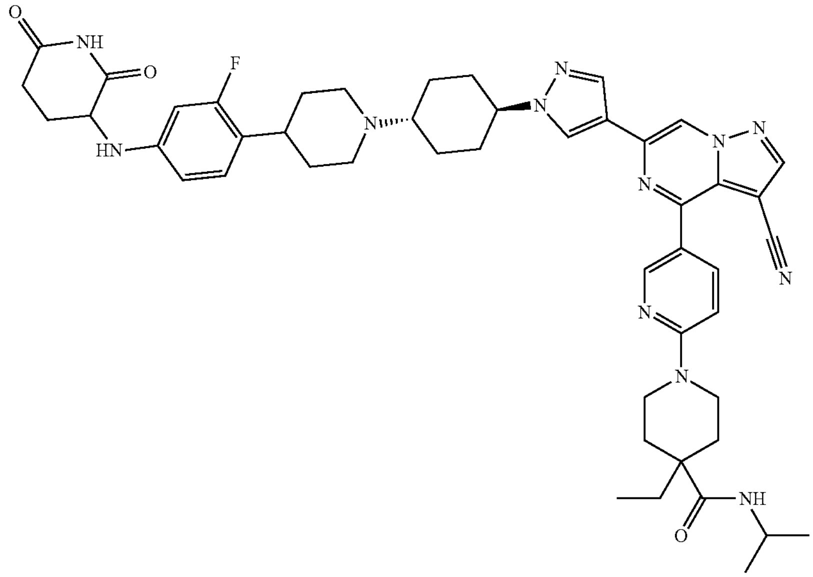 [SMILES: CCC1(C(=O)NC(C)C)CCN(c2ccc(-c3nc(-c4cnn([C@H]5CC[C@H](N6CCC(c7ccc(NC8CCC(=O)NC8=O)cc7F)CC6)CC5)c4)cn4ncc(C#N)c34)cn2)CC1]

or a pharmaceutically acceptable salt thereof.

26. A pharmaceutical composition comprising a compound of claim 1 or a pharmaceutically acceptable salt thereof, and a pharmaceutically acceptable excipient.

27. The pharmaceutical composition of claim 26, wherein the compound of claim 1 is:

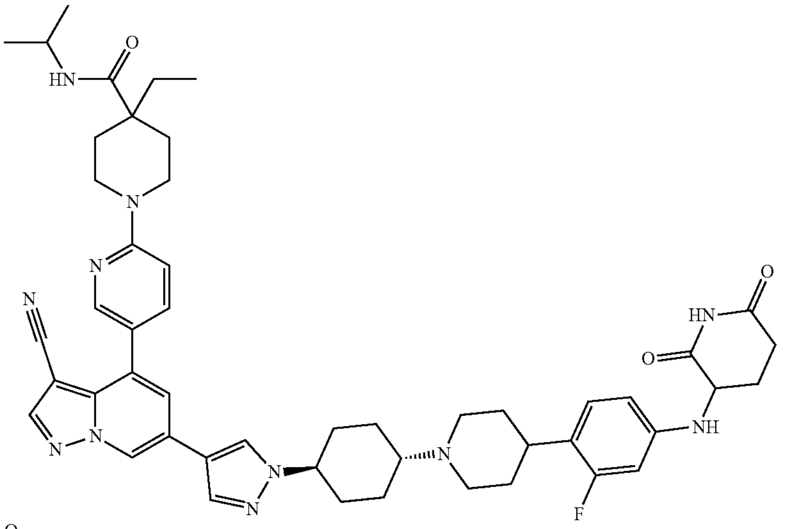
or
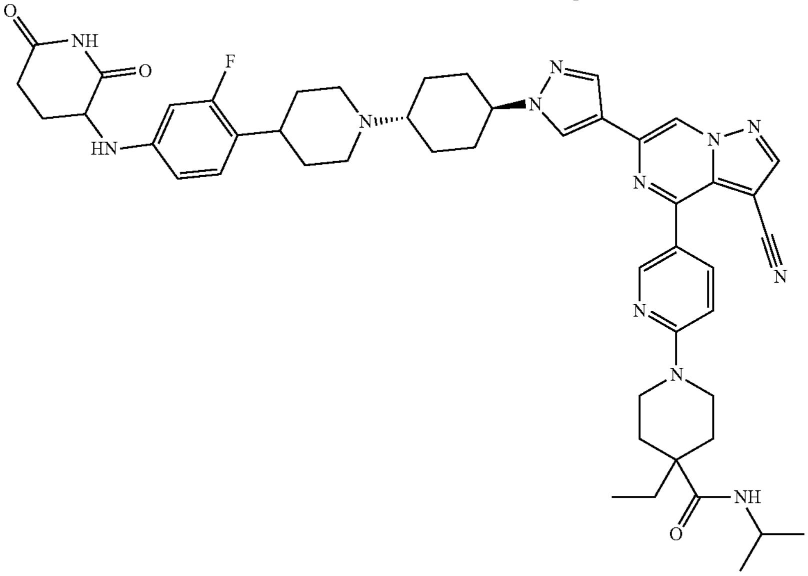
or a pharmaceutically acceptable salt thereof.
* * * * *